United States Patent
Johnson et al.

(10) Patent No.: US 9,593,097 B2
(45) Date of Patent: Mar. 14, 2017

(54) AXL INHIBITORS

(71) Applicant: Pfizer Inc., New York, NY (US)

(72) Inventors: Ted William Johnson, Carlsbad, CA (US); Paul Francis Richardson, San Diego, CA (US); Michael Raymond Collins, San Diego, CA (US); Daniel Tyler Richter, San Diego, CA (US); Benjamin Joseph Burke, San Diego, CA (US); Sacha Ninkovic, La Jolla, CA (US); Ketan Satish Gajiwala, San Diego, CA (US); Maria Angelica Linton, San Diego, CA (US); Phuong Thi Quy Le, San Diego, CA (US); Jacqui Elizabeth Hoffman, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/968,405

(22) Filed: Dec. 14, 2015

(65) Prior Publication Data

US 2016/0176850 A1    Jun. 23, 2016

Related U.S. Application Data

(60) Provisional application No. 62/093,844, filed on Dec. 18, 2014.

(51) Int. Cl.
| | |
|---|---|
| *C07D 401/14* | (2006.01) |
| *C07D 403/14* | (2006.01) |
| *A61K 31/53* | (2006.01) |
| *A61K 31/506* | (2006.01) |
| *A61K 31/4523* | (2006.01) |
| *A61P 35/00* | (2006.01) |
| *C07D 405/14* | (2006.01) |
| *C07D 471/04* | (2006.01) |
| *C07D 487/04* | (2006.01) |

(52) U.S. Cl.
CPC ........ *C07D 401/14* (2013.01); *A61K 31/4523* (2013.01); *A61K 31/506* (2013.01); *A61K 31/53* (2013.01); *C07D 403/14* (2013.01); *C07D 405/14* (2013.01); *C07D 471/04* (2013.01); *C07D 487/04* (2013.01)

(58) Field of Classification Search
CPC .. C07D 251/48; C07D 403/14; C07D 401/14; A61K 31/53; A61K 31/506; A61K 31/4523
USPC .......................... 544/205, 206; 514/245, 269
See application file for complete search history.

(56) References Cited

U.S. PATENT DOCUMENTS

| | | |
|---|---|---|
| 5,587,458 A | 12/1996 | King et al. |
| 5,747,498 A | 5/1998 | Schnur et al. |
| 5,792,783 A | 8/1998 | Tang et al. |
| 5,834,504 A | 11/1998 | Tang et al. |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,020 A | 3/1999 | Tang et al. |
| 6,071,935 A | 6/2000 | Lyssikatos |
| 6,080,769 A | 6/2000 | Lyssikatos et al. |
| 6,106,864 A | 8/2000 | Dolan et al. |
| 6,586,447 B1 | 7/2003 | Lyssikatos et al. |
| 6,682,736 B1 | 1/2004 | Hanson et al. |
| 2006/0223801 A1 | 10/2006 | Green et al. |

FOREIGN PATENT DOCUMENTS

| | | |
|---|---|---|
| EP | 0239362 A2 | 9/1987 |
| EP | 0606046 A1 | 7/1994 |
| EP | 0780386 A1 | 6/1997 |
| EP | 0818442 A2 | 1/1998 |
| EP | 0931788 A2 | 7/1999 |
| EP | 1004578 A2 | 5/2000 |
| GB | 9912961.1 | 6/1999 |
| WO | 90/05719 A1 | 5/1990 |
| WO | 91/11172 A1 | 8/1991 |
| WO | 94/02518 A1 | 2/1994 |
| WO | 95/19970 A1 | 7/1995 |

(Continued)

OTHER PUBLICATIONS

Cecil Textbook of Medicine, edited by Bennet, J.C., and Plum F., 20th edition,vol. 1, 1004-1010, 1996.*

(Continued)

*Primary Examiner* — Venkataraman Balasubramanian
(74) *Attorney, Agent, or Firm* — David Rubin

(57) ABSTRACT

Compounds of the general formula (I):

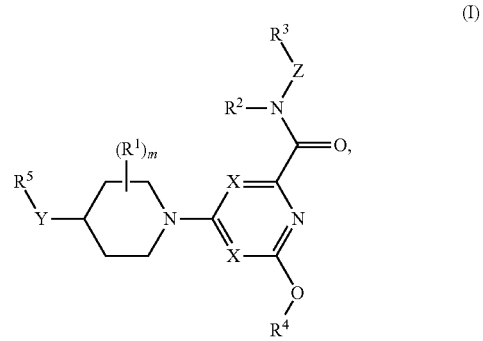

processes for the preparation of these compounds, compositions containing these compounds, and the uses of these compounds.

13 Claims, No Drawings

(56) References Cited

FOREIGN PATENT DOCUMENTS

| WO | 95/21613 | A1 | 8/1995 |
|----|----------|----|--------|
| WO | 95/27583 | A1 | 9/1996 |
| WO | 96/33172 | A1 | 10/1996 |
| WO | 97/13760 | A1 | 4/1997 |
| WO | 97/22596 | A1 | 6/1997 |
| WO | 97/32856 | A1 | 9/1997 |
| WO | 98/02434 | A1 | 1/1998 |
| WO | 98/02437 | A1 | 1/1998 |
| WO | 98/02438 | A1 | 1/1998 |
| WO | 98/03516 | A1 | 1/1998 |
| WO | 98/07697 | A1 | 2/1998 |
| WO | 98/14451 | A1 | 4/1998 |
| WO | 98/30566 | A1 | 7/1998 |
| WO | 98/33768 | A1 | 8/1998 |
| WO | 98/34915 | A1 | 8/1998 |
| WO | 98/34918 | A1 | 8/1998 |
| WO | 98/50356 | A1 | 11/1998 |
| WO | 98/54093 | A1 | 12/1998 |
| WO | 98/55148 | A1 | 12/1998 |
| WO | 9907675 |    | 2/1999 |
| WO | 99/10349 | A1 | 3/1999 |
| WO | 99/16755 | A1 | 4/1999 |
| WO | 99/24440 | A1 | 5/1999 |
| WO | 99/29667 | A1 | 6/1999 |
| WO | 99/35132 | A1 | 7/1999 |
| WO | 99/35146 | A1 | 7/1999 |
| WO | 99/52889 | A1 | 10/1999 |
| WO | 99/52910 | A1 | 10/1999 |
| WO | 99/61422 | A1 | 12/1999 |
| WO | 9962890  | A1 | 12/1999 |
| WO | 00/35298 | A1 | 6/2000 |
| WO | 00/37107 | A2 | 6/2000 |
| WO | 00/38665 | A2 | 7/2000 |
| WO | 00/38715 | A2 | 7/2000 |
| WO | 00/38716 | A1 | 7/2000 |
| WO | 00/38717 | A2 | 7/2000 |
| WO | 00/38718 | A  | 7/2000 |
| WO | 00/38719 | A1 | 7/2000 |
| WO | 00/38730 | A2 | 7/2000 |
| WO | 00/38786 | A2 | 7/2000 |
| WO | 2007056151 | A2 | 5/2007 |
| WO | 2011141474 | A1 | 11/2011 |

OTHER PUBLICATIONS

Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Berclaz et al., "Estrogen dependent expression of the receptor tyrosine kinase axl in normal and malignant human breast", Annals of Oncology, 2001, 819-824, (12).
Byers et al., "An Epithelial-Mesenchymal Transition Gene Signature Predicts Resistance to EGFR and PI3K Inhibitors and Identifies Axl as a Therapeutic Target for Overcoming EGFR Inhibitor Resistance", Clinical Cancer Research, 2012, 279-290, 19(1).
Chung et al., "Expression of the Proto-Oncogene Axl in Renal Cell Carcinoma", DNA & Cell Biology, 2003, 533-540, 22(8).
Cohen et al., "Delayed Apoptotic Cell Clearance and Lupus-like Autoimmunity in Mice Lacking the c-mer Membrane Tyrosine Kinase", Journal of Experimental Medicine, 2002, 135-140, 196(1).
Craven et al., "Receptor Tyrosine Kinases Expressed in Metastatic Colon Cancer", Int. J. Cancer, 1995, 791-797, 60.
Finnin et al., Transdermal Penetration Enhancers: Applications, Limitations, and Potential, Journal of Pharmaceutical Sciences, 1999, 955-958, 88(10).
Haleblian "Characterization of Habits and Crystalline Modification of Solids and Their Pharmaceutical Applications", Journal of Pharmaceutical Sciences, 1975, 1269-1288, 64(8).
Hutterer et al., "Axl and Growth Arrest-Specific Gene 6 Are Frequently Overexpressed in Human Gliomas and Predict Poor Prognosis in Patients with Glioblastoma Multiforme", Clinical Cancer Research, 2008, 130-138, 14(1).
Ito et al., "Expression of the Axl Receptor Tyrosine Kinase in Human Thyroid Carcinoma", Thyroid, 1999, 563-567, 9(6).
Lemke et al., "Macrophage regulation by Tyro 3 family receptors", Current Opinion in Immunology, 2003, 31-36, 15.
Li et al., "Axl as potential therapeutic target in cancer: role of Axl in tumor growth, metastasis and angiogenesis", Oncogene, 2009, 3442-3455, 28.
Liang et al., "Fast-dissolving intraoral drug delivery systems", Expert Opinion on Therapeutic Patents, 2001, 981-986, 11(6).
Linger et al., TAM Receptor Tyrosine Kinases: Biologic Functions, Signaling, and Potential Therapeutic Targeting in Human Cancer, Advances in Cancer Research, 2008, 35-38, 100.
Linger et al., "Taking aim at Mer and Axl receptor tyrosine kinases as novel therapeutic targets in solid tumors", Expert Opinion on Therapeutic Targets, 2010, 1073-1090, 14(10).
Liu et al., "Transforming genes in chronic myelogenous leukemia", Proc. Natl. Acad. Sci., 1988, 1952-1956, 85.
Neel et al., "Secrets of Drug Resistance in NSCLC Exposed by New Molecular Definition of EMT", Clinical Cancer Research, 2013, 3-5, 19(1).
O'Bryan et al., "axl, a Transforming Gene Isolated from Primary Human Myeloid Leukemia Cells, Encodes a Novel Receptor Tyrosine Kinase", Molecular and Cellular Biology, 1991, 5016-5031, 11(10).
Shieh et al., "Expression of Axl in Lung Adenocarcinoma and Correlation with Tumor Progression", Neoplasia, 2005, 1058-1064, 7(12).
Smit et al., "Epithelial-mesenchymal transition and senescence: two cancer-related processes are crossing paths", Aging, 2010, 735-741, 2(10).
Stitt et al., The Anticoagulation Factor Protein S and Its Relative, Gas6, Are Ligands for the Tyro 3/Axl Family of Receptor Tyrosine Kinases, Cell, 1995, 661-670, 80(4).
Sun et al., "Coexpression of Gas6/Axl in Human Ovarian Cancers", Oncology, 2004, 450-457, 66.
Thiery et al., "Epithelial-Mesenchymal Transitions in Development and Disease", Cell, 2009, 871-890, 139(5).
Zhang et al., "AXL is a Potential Target for Therapeutic Intervention in Breast Cancer Progression", Cancer Research, 2008, 1905-1915, 68(6).
Zhang et al., "Activation of the AXL kinase causes resistance to EGFR-targeted therapy in lung cancer", Nature Genetics, 2012, 852-860, 44(8).
Nemoto et al., "Overexpression of Protein Tyrosine Kinases in Human Esophageal Cancer", Pathobiology, 1997, 195-203, 65(4).
Wu et al., "Clinical Significance of AXL Kinase Family in Gastric Cancer", Anticancer Research, 2002, 1071-1078, 22.
U.S. Appl. No. 60/117,341, "Heteroaromatic Bicyclic Derivatives Useful as Anticancer Agents".
U.S. Appl. No. 60/117,346, "Substituted Bicyclic Derivatives Useful as Anticancer Agents".
U.S. Appl. No. 60/200,834, "Substituted Quinolin-2-One Derivatives Useful as Antiproliferative Agents".
U.S. Appl. No. 60/168,207, "Quinoline Derivatives Useful for Inhibiting Farnesyl Protein Transferase".
U.S. Appl. No. 60/177,718, "Anticancer Compound and Enantiomer Separation Method Useful for Synthesizing Said Compound".
U.S. Appl. No. 60/168,217, "Novel Benzoimidazole Derivatives Useful as Antiproliferative Agents".
U.S. Appl. No. 60/170,119, "Quinoline Derivatives Useful for Inhibiting Farnesyl Protein Transferase".
U.S. Appl. No. 09/384,339, "Quinolin-2-One Derivatives Useful as Anticancer Agents".
U.S. Appl. No. 09/501,163, "Heteroaryl-Substituted Quinolin-2-One Derivatives Useful as Anticancer Agents".
U.S. Appl. No. 09/383,755, "Alkynyl-Substituted Quinolin-2-One Derivatives Useful as Anticancer Agents".

(56) References Cited

OTHER PUBLICATIONS

U.S. Appl. No. 09/454,058, "Novel Derivatives of 2-(2Oxo-Ethylidene)-Imidazolidin-4-One, and Compositions and Methods for Inhibiting Abnormal Cell Growth Comprising Said Derivatives".
U.S. Appl. No. 60/148,464, "Selective Inhibition of Aggrecanase in Osteoarthritis Treatment".
Mikhailichenko, sym-Triazines. 7.Hydrolysis and Cyclization of 1,3,5-TYriazine Series Mononitriles, Chemistry of Heterocyclic Compounds, 2006, 642-647, 42(5).
International Search Report and the Written Opinion of the International Searching Authority, PCT/IB2015/059360, dated Mar. 31, 2016.

\* cited by examiner

AXL INHIBITORS

FIELD OF THE INVENTION

This invention relates to compounds of general formula (I):

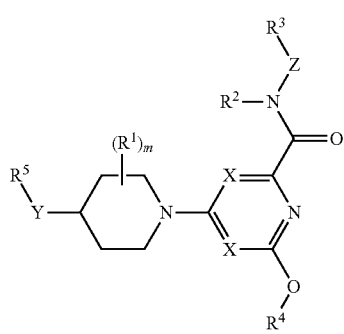

in which m, X, Y, Z, $R^1$, $R^2$, $R^3$, $R^4$ and $R^5$ have the meanings indicated below, and to processes for the preparation of, compositions containing and the uses of such compounds.

BACKGROUND

AXL is a membrane bound receptor tyrosine kinase and is the founding member of the TAM (Tyro3, AXL, Mer) family that is characterized both by their two immunoglobulin-like domains and the dual fibronectin repeats found in their extracellular domain and by their related tyrosine kinase domains found in their cytoplasmic domain. (Linger, R. M. et al., TAM receptor tyrosine kinases: biologic functions, signaling, and potential therapeutic targeting in human cancer. *Advances in cancer research* 2008, 100, 35-83.) Extracellular signaling mediated by TAM receptor tyrosine kinases has been implicated in a variety of normal cell functions such as cell survival, migration and adhesion. There are two known ligands for the TAM family, GAS6 (growth arrest specific-6) and protein S. Gas 6 binding to AXL results in receptor dimerization and AXL auto-phosphorylation. (Stitt, T. N. et al., The anticoagulation factor protein S and its relative, Gas6, are ligands for the Tyro 3/Axl family of receptor tyrosine kinases. *Cell* 1995, 80 (4), 661-70.) Also, the extracellular domain can be shed, though the function of the soluble TAM extracellular domains is unknown. Mouse knockouts of TAM family members have confirmed that they play roles in innate immunity, inflammation, phagocytosis and cell differentiation. (Cohen, P. L. et al., Delayed apoptotic cell clearance and lupus-like autoimmunity in mice lacking the c-mer membrane tyrosine kinase. *The Journal of experimental medicine* 2002, 196 (1), 135-40; and Lemke, G. et al., Macrophage regulation by Tyro 3 family receptors. *Current opinion in immunology* 2003, 15 (1), 31-6.) AXL is ubiquitously expressed, having been detected in a wide variety of organs and cells, including cell lines of epithelia, mesenchymal and hematopoietic origins, as well as non-transformed cells. (O'Bryan, J. P. et al., Axl, a transforming gene isolated from primary human myeloid leukemia cells, encodes a novel receptor tyrosine kinase. *Molecular and cellular biology* 1991, 11 (10), 5016-31.)

There is extensive literature implicating the dysregulation of AXL and other TAM family members in the development of cancer. AXL (short for "anexelekto" which means uncontrolled) was first discovered as the transforming oncogene in two chronic myelogenous leukemia (CML) patients. (Liu, E. et al., Transforming genes in chronic myelogenous leukemia. *Proceedings of the National Academy of Sciences of the United States of America* 1988, 85 (6), 1952-6.) AXL has been implicated in a wide range of cellular functions potentially important in cancer development, ranging from cell survival, angiogenesis, metastasis and immunity. (Li, Y. et al., Axl as a potential therapeutic target in cancer: role of Axl in tumor growth, metastasis and angiogenesis. *Oncogene* 2009, 28 (39), 3442-55; and Linger, R. M. et al., Taking aim at Mer and Axl receptor tyrosine kinases as novel therapeutic targets in solid tumors. *Expert opinion on therapeutic targets* 2010, 14 (10), 1073-90.)

Overexpression of AXL is associated with poor prognosis and increased invasiveness of human cancers and has been reported in breast (Berclaz, G. et al., Estrogen dependent expression of the receptor tyrosine kinase axl in normal and malignant human breast. *Annals of oncology: official journal of the European Society for Medical Oncology/ESMO* 2001, 12 (6), 819-24; and Zhang, Y. X. et al., AXL is a potential target for therapeutic intervention in breast cancer progression. *Cancer research* 2008, 68 (6), 1905-15), colon (Craven, R. J. et al., Receptor tyrosine kinases expressed in metastatic colon cancer. *International journal of cancer. Journal international du cancer* 1995, 60 (6), 791-7), esophageal (Nemoto, T. et al, Overexpression of protein tyrosine kinases in human esophageal cancer. *Pathobiology: journal of immunopathology, molecular and cellular biology* 1997, 65 (4), 195-203), thyroid (Ito, T. et al, Expression of the Axl receptor tyrosine kinase in human thyroid carcinoma. *Thyroid: official journal of the American Thyroid Association* 1999, 9 (6), 563-7), ovarian (Sun, W. et al., Coexpression of Gas6/Axl in human ovarian cancers. *Oncology* 2004, 66 (6), 450-7), gastric (Wu, C. W. et al., Clinical significance of AXL kinase family in gastric cancer. *Anticancer research* 2002, 22 (2B), 1071-8), renal (Chung, B. I. et al., Expression of the proto-oncogene Axl in renal cell carcinoma. *DNA and cell biology* 2003, 22 (8), 533-40), glioma (Hutterer, M. et al., Axl and growth arrest-specific gene 6 are frequently overexpressed in human gliomas and predict poor prognosis in patients with glioblastoma multiforme. *Clinical cancer research: an official journal of the American Association for Cancer Research* 2008, 14 (1), 130-8) and lung cancers (Shieh, Y. S. et al., Expression of axl in lung adenocarcinoma and correlation with tumor progression. *Neoplasia* 2005, 7 (12), 1058-64.)

AXL over-expression is closely associated with epithelial-mesenchymal transition (EMT) which is the process by which epithelial cells become motile and invasive and that often is a key characteristic of late stage metastatic tumors. (Byers, L. A. et al., An epithelial-mesenchymal transition gene signature predicts resistance to EGFR and PI3K inhibitors and identifies AXL as a therapeutic target for overcoming EGFR inhibitor resistance. *Clinical cancer research: an official journal of the American Association for Cancer Research* 2013, 19 (1), 279-90.) EMT also confers resistance to oncogene mediated senescence which is a key step in tumor development. (Smit, M. A. et al., Epithelial-mesenchymal transition and senescence: two cancer-related processes are crossing paths. *Aging* 2010, 2 (10), 735-41; and Thiery, J. P. et al., Epithelial-mesenchymal transitions in development and disease. *Cell* 2009, 139 (5), 871-90. Furthermore, AXL has also been implicated in playing a role in resistance to both chemotherapy and targeted therapies. (Neel, D. S. et al, Secrets of drug resistance in NSCLC exposed by new molecular definition of EMT. *Clinical cancer research: an official journal of the American Association for Cancer Research* 2013, 19 (1), 3-5; and Zhang, Z. et al., Activation of the AXL kinase causes resistance to EGFR-targeted therapy in lung cancer. Nature genetics 2012, 44 (8), 852-60.)

AXL potentially plays an important role in many diverse key tumorigenic mechanisms but as a result it has not been clear how to genetically select patients or when to treat during the development of cancer with an AXL inhibitor, for instance when during their tumor development is AXL function is actually required, and in which patients should an AXL-based therapeutic be used. These two fundamental unanswered questions have held up the development of AXL inhibitors for the treatment of cancer. Indeed finding a key AXL dependent functions and relevant preclinical models where AXL drives tumor cell survival has been a major challenge.

SUMMARY

The recent finding of the up-regulation of the AXL protein and the resulting activation of AXL kinase activity causing resistance to EGFR inhibitor-based therapy in NSCLC has provided a potential patient population to use AXL-based therapeutics. In this invention we disclose the discovery of potent, selective small molecule inhibitors of AXL. Each of the embodiments of the compounds of the present invention described below can be combined with any other embodiment of the compounds of the present invention described herein not inconsistent with the embodiment with which it is combined. Furthermore, each of the embodiments below describing the invention envisions within its scope pharmaceutically acceptable salts of the compounds of the invention. Accordingly, the phrase "or a pharmaceutically acceptable salt thereof" is implicit in the description of all compounds described herein.

In one embodiment of the invention there is provided a compound of formula (I):

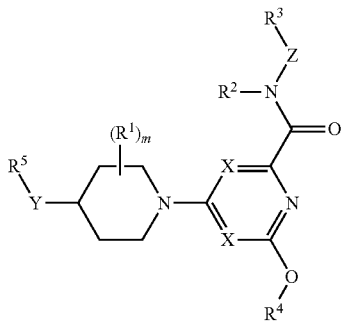

(I)

wherein:
each X is N or $CR^6$, where at least one X is N, where each $R^6$ is independently selected from the group consisting of hydrogen, halogen, $(C_1-C_8)$alkyl, $(C_1-C_8)$haloalkyl, $—(C_1-C_4)$alkylene-$R^7$, $—OR^7$, $—CN$, $—NO_2$ and $—NR^7R^7$, where each $R^7$ is independently selected from the group consisting of hydrogen and $(C_1-C_8)$alkyl, and where each said $(C_1-C_8)$alkyl in $R^6$ is optionally substituted by one or more substituents independently selected from the group consisting of halogen, hydroxyl and $(C_1-C_8)$alkoxy;

Y is $Y^1-Y^2$ or $Y^2-Y^1$, where $Y^1$ is absent or is selected from the group consisting of $(C_1-C_8)$alkylene, $(C_2-C_8)$alkenylene, $(C_1-C_8)$haloalkylene, $(C_1-C_8)$heteroalkylene, and $(C_2-C_8)$heteroalkenylene, where $Y^1$ is optionally substituted with one or more $R^8$ where each $R^8$ is independently selected from the group consisting of halogen, $(C_1-C_{10})$alkyl, $—CN$, $=O$, $—R^9—OR^9$, $—SR^9$ and $—NO_2$, and where each $R^9$ is independently selected from the group consisting of hydrogen, $(C_1-C_8)$alkyl, $(C_3-C_{10})$cycloalkyl, 3-12 membered heterocyclyl, $(C_6-C_{12})$aryl and 5-12 membered heteroaryl, and where $Y^2$ is absent or oxygen;

Z is $Z^1-Z^2$, where each of $Z^1$ and $Z^2$ is independently absent or selected from the group consisting of $(C_1-C_8)$alkylene, $(C_2-C_8)$alkenylene, $(C_3-C_{10})$cycloalkyl, 3-12 membered heterocyclyl and $(C_1-C_8)$heteroalkylene, where Z is optionally independently substituted with one or more $R^{10}$ where each $R^{10}$ is independently selected from the group consisting of halogen, $(C_1-C_8)$alkyl, $—CN$, $=O$, $—OR^{11}$ and $—NO_2$, and where each $R^{11}$ is independently selected from the group consisting of hydrogen, $(C_1-C_8)$alkyl, $(C_3-C_{10})$cycloalkyl, 3-12 membered heterocyclyl, $(C_6-C_{12})$aryl and 5-12 membered heteroaryl;

each $R^1$ is independently selected from the group consisting of hydrogen, halogen, $(C_1-C_8)$alkyl, $(C_2-C_8)$alkenyl, $(C_1-C_8)$alkynyl, $(C_1-C_8)$haloalkyl, $—(C_1-C_4$alkyl)$R^7$, $—OR^7$, $—CN$, $—C(O)R^7$, $—CO_2R^7$, $—C(O)NR^7R^7$, $—SR^7$, $—SOR^7$, $—SO_2R^7$, $—SO_2NR^7R^7$, $—NO_2$, $—NR^7R^7$, $—NR^7C(O)R^7$, $—NR^7C(O)NR^7R^7$, $—NR^7C(O)OR^7—NR^7SO_2R^7$, $—NR^7SO_2NR^7R^7$, $—OC(O)R^7$ and $—OC(O)NR^7R^7$; where any set of two $R^1$ on the same or different piperidine carbons optionally join to form a spirocyclic, fused or bridged ring system comprising 1-4 non-piperadine members and 1-2 heteroatoms selected from N, O and S, and where any set of two $R^1$ on adjacent piperidine carbons optionally join to form a carbon-carbon bond; $R^2$ and $R^3$ are each independently selected from the group consisting of hydrogen, halogen, $(C_1-C_8)$alkyl, $(C_1-C_8)$haloalkyl, $(C_3-C_{10})$cycloalkyl, 3-12 membered heterocyclyl, $—OR^{13}$, $—NR^{14}R^{14}$, $—C(O)NR^{14}R^{14}$, $—SO_2NR^{14}R^{14}$, $—NR^{14}SO_2R^{14}$, $—SO_2R^{14}$, $(C_6-C_{12})$aryl and 5-12 membered heteroaryl, where each $R^{13}$ is independently selected from the group consisting of hydrogen, $(C_1-C_4)$alkyl, $(C_1-C_4)$haloalkyl, $(C_3-C_{10})$cycloalkyl, 3-12 membered heterocyclyl, $(C_6-C_{12})$aryl and 5-12 membered heteroaryl, where each $R^{14}$ is independently selected from the group consisting of hydrogen, $(C_1-C_8)$alkyl, $(C_3-C_{10})$cycloalkyl, 3-12 membered heterocyclyl, $(C_6-C_{12})$aryl and 5-12 membered heteroaryl, or two $R^{14}$ together with the N atom to which they are attached to form a 3-12 membered heterocyclyl or 5-12 membered heteroaryl, each optionally containing 1, 2 or 3 additional heteroatoms selected from O, N and S, and where $R^2$, $R^3$ or both $R^2$ and $R^3$ is optionally substituted with one or more substituents independently selected from halogen, $(C_1-C_8)$alkyl, hydroxyl, $(C_1-C_4)$alkoxy, $—CN$, $NH_2$, $NH(C_1-C_4$alkyl), $N(C_1-C_4$alkyl)$_2$, $(C_3-C_{10})$cycloalkyl, 3-12 membered heterocyclyl, $(C_6-C_{12})$aryl and 5-12 membered heteroaryl;

or $R^2$ and $R^3$ join to form a heterocyclic ring selected from azetidinyl, pyrrolidinyl, piperidinyl, piperazinyl, piperadinonyl, piperazinonyl and morpholinyl, optionally substituted with one or more substituents independently selected from the group consisting of $R^{15}$ and $(C_1-C_4)$ alkylene-R$^{15}$, where R$^{15}$ is independently selected from the group consisting of halogen, (C$_1$-C$_4$)alkyl, (C$_1$-C$_4$)haloalkyl, hydroxyl, (C$_1$-C$_4$)alkoxy, CN, NH$_2$, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$)aryl and 5-12 membered heteroaryl;

R$^4$ is selected from the group consisting of (C$_1$-C$_8$)alkyl, (C$_1$-C$_8$)haloalkyl, (C$_3$-C$_{10}$)cycloalkyl, 3-12 membered heterocyclyl and —C(O)NR$^{14}$R$^{14}$, where R$^4$ is optionally substituted with one or more R$^{12}$ independently selected from halogen, hydroxyl, (C$_1$-C$_4$)alkoxy, —CN, NH$_2$, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$)aryl and 5-12 membered heteroaryl, and where, when R$^{12}$ is (C$_1$-C$_4$)alkoxy, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$)aryl or 5-12 membered heteroaryl, it is optionally substituted by one or more substituents independently selected from halogen, hydroxyl, (C$_1$-C$_4$)alkoxy, —CN, NH$_2$, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$)aryl and 5-12 membered heteroaryl;

R$^5$ is a mono- or bi-cyclic aryl or a mono- or bi-cyclic heteroaryl, optionally substituted with one or more substituents independently selected from the group consisting of (C$_1$-C$_8$)alkyl, (C$_1$-C$_8$)haloalkyl, (C$_3$-C$_{10}$)cycloalkyl, 3-12 membered heterocyclyl, —OR$^{13}$, —NR$^{14}$R$^{14}$, —C(O)NR$^{14}$R$^{14}$, —SO$_2$NR$^{14}$R$^{14}$, —SO$_2$R$^{14}$, —NR$^{14}$SO$_2$R$^{14}$, CN, mono- or bi-cyclic aryl and mono- or bi-cyclic heteroaryl, said one or more optional substituents being further optionally substituted with one or more substituents selected from the group consisting of (C$_1$-C$_8$)alkyl, halogen, (C$_1$-C$_8$)alkylene-OH, (C$_1$-C$_8$)haloalkyl, (C$_3$-C$_{10}$)cycloalkyl, 3-12 membered heterocyclyl, —OR$^{13}$, —NR$^{14}$R$^{14}$, —C(O)NR$^{14}$R$^{14}$, —SO$_2$NR$^{14}$R$^{14}$, —SO$_2$R$^{14}$, —NR$^{14}$SO$_2$R$^{14}$ and CN; and m is 1-9, or a pharmaceutically acceptable salt thereof.

In another embodiment of the invention there is provided a compound of formula (II):

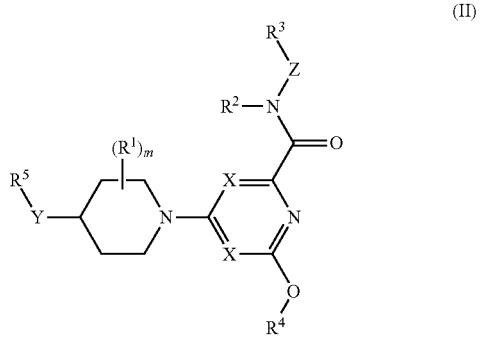

(II)

wherein:

each X is N or CR$^6$, where at least one X is N, and where each R$^6$ is independently selected from the group consisting of hydrogen, halogen and (C$_1$-C$_8$)alkyl;

Y is Y$^1$-Y$^2$ or Y$^2$-Y$^1$, where Y$^1$ is absent or is selected from the group consisting of (C$_1$-C$_8$)alkylene and (C$_1$-C$_8$)haloalkylene, where Y$^1$ is optionally substituted with one or more R$^8$ where each R$^8$ is independently selected from the group consisting of halogen, (C$_1$-C$_{10}$)alkyl and —CN, and where Y$^2$ is absent or oxygen; Z is Z$^1$-Z$^2$, where each of Z$^1$ and Z$^2$ is independently absent or selected from the group consisting of (C$_1$-C$_8$)alkylene, (C$_3$-C$_{10}$)cycloalkyl and 3-12 membered heterocyclyl, where Z is optionally substituted with one or more R$^{10}$ where each R$^{10}$ is independently selected from the group consisting of halogen, (C$_1$-C$_8$)alkyl and —CN; each R$^1$ is independently selected from the group consisting of hydrogen, halogen, (C$_1$-C$_8$)alkyl, (C$_1$-C$_8$)haloalkyl, —(C$_1$-C$_4$alkyl)R$^7$, —OR$^7$ and —CN; R$^2$ and R$^3$ are each independently selected from the group consisting of hydrogen, (C$_1$-C$_8$)alkyl, (C$_1$-C$_8$)haloalkyl, (C$_3$-C$_{10}$)cycloalkyl, 3-12 membered heterocyclyl, —OR$^{13}$ and —SO$_2$R$^{14}$, where each R$^{13}$ is independently selected from the group consisting of hydrogen, (C$_1$-C$_4$)alkyl and (C$_1$-C$_4$)haloalkyl, where each R$^{14}$ is independently selected from the group consisting of hydrogen and (C$_1$-C$_8$)alkyl, and where R$^2$, R$^3$ or both R$^2$ and R$^3$ is optionally substituted with one or more substituents independently selected from halogen, (C$_1$-C$_8$)alkyl, hydroxyl, (C$_1$-C$_4$)alkoxy, —CN, NH$_2$, NH(C$_1$-C$_4$alkyl), N(C$_1$-C$_4$alkyl)$_2$;

or R$^2$ and R$^3$ join to form a heterocyclic ring selected from azetidinyl, pyrrolidinyl, piperidinyl, piperazinyl, piperadinonyl, piperazinonyl and morpholinyl, optionally substituted with one or more substituents independently selected from the group consisting of R$^{15}$ and (C$_1$-C$_4$)alkylene-R$^{15}$, where R$^{15}$ is independently selected from the group consisting of halogen, (C$_1$-C$_4$)alkyl, (C$_1$-C$_4$)haloalkyl, hydroxyl, (C$_1$-C$_4$)alkoxy, CN, NH$_2$, NH(C$_1$-C$_4$alkyl), N(C$_1$-C$_4$alkyl)$_2$ and (C$_3$-C$_{10}$)cycloalkyl;

R$^4$ is selected from the group consisting of (C$_1$-C$_8$)alkyl and (C$_1$-C$_8$)haloalkyl, where R$^4$ is optionally substituted with one or more R$^{12}$ independently selected from halogen, hydroxyl, (C$_1$-C$_4$)alkoxy, —CN, NH$_2$, NH(C$_1$-C$_4$alkyl), N(C$_1$-C$_4$alkyl)$_2$, (C$_3$-C$_{10}$)cycloalkyl, and 3-12 membered heterocyclyl, and where, when R$^{12}$ is (C$_1$-C$_4$)alkoxy, NH(C$_1$-C$_4$alkyl), N(C$_1$-C$_4$alkyl)$_2$, (C$_3$-C$_{10}$)cycloalkyl or 3-12 membered heterocyclyl, it is optionally substituted by one or more substituents independently selected from halogen, hydroxyl, (C$_1$-C$_4$)alkoxy, —CN, NH$_2$, NH(C$_1$-C$_4$alkyl) and N(C$_1$-C$_4$alkyl)$_2$;

R$^5$ is a mono- or bi-cyclic aryl or a mono- or bi-cyclic heteroaryl, optionally substituted with one or more substituents independently selected from the group consisting of (C$_1$-C$_8$)alkyl, C$_1$-C$_8$ haloalkyl, —OR$^{13}$, —NR$^{14}$R$^{14}$, —C(O)NR$^{14}$R$^{14}$, CN, mono- or bi-cyclic aryl and mono- or bi-cyclic heteroaryl, said one or more optional substituents being further optionally substituted with one or more substituents selected from the group consisting of (C$_1$-C$_8$)alkyl, (C$_1$-C$_8$)alkylene-OH, (C$_1$-C$_8$)haloalkyl, —OR$^{13}$, —NR$^{14}$R$^{14}$ and —SO$_2$R$^{14}$; and m is 1-9; or a pharmaceutically acceptable salt thereof.

In yet another embodiment of the invention there is provided a compound of formula (III):

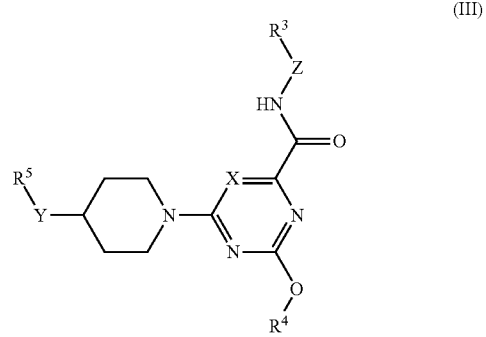

(III)

wherein:

X is N or CR$^6$, where R$^6$ is selected from the group consisting of hydrogen, halogen and (C$_1$-C$_8$)alkyl;

Y is absent or (C$_1$-C$_8$)alkylene;

Z is Z$^1$-Z$^2$, where each of Z$^1$ and Z$^2$ is independently absent or (C$_1$-C$_8$)alkylene, where Z is optionally substituted with one or more R$^{10}$ where each R$^{10}$ is independently selected from the group consisting of halogen and (C$_1$-C$_8$)alkyl;

R$^3$ is selected from the group consisting of hydrogen, (C$_1$-C$_8$)alkyl and —OR$^{13}$, where R$^{13}$ is selected from the group consisting of hydrogen and (C$_1$-C$_4$)alkyl;

R$^4$ is (C$_1$-C$_8$)alkyl optionally substituted by one or more R$^{12}$ independently selected from halogen, hydroxyl, (C$_1$-C$_4$) alkoxy, —(C$_3$-C$_{10}$)cycloalkyl, and 3-12 membered heterocyclyl, where one or more carbons on R$^{12}$, if present, are optionally substituted by one or more substituents independently selected from halogen, hydroxyl and (C$_1$-C$_4$)alkoxy; and R$^5$ is a mono- or bi-cyclic heteroaryl, optionally substituted with one or more substituents independently selected from the group consisting of (C$_1$-C$_8$)alkyl and —OR$^{13}$;

or a pharmaceutically acceptable salt thereof.

Additional embodiments of the invention include those wherein —Z—R$^3$ is straight or branched (C$_1$-C$_8$)alkylene-OH, or straight or branched (C$_1$-C$_8$)alkylene-O—(C$_1$-C$_4$)alkyl.

Additional embodiments of the invention include those wherein —R$^4$ is straight or branched C$_1$-C$_8$ alkyl substituted with hydroxyl, (C$_1$-C$_4$)alkoxy, (C$_3$-C$_{10}$)cycloalkyl or 3-12 membered heterocyclyl.

Additional embodiments of the invention include those wherein Y is absent or (C$_1$-C$_8$)alkylene, and R$^5$ is selected from pyrrolopyrimidine, pyrazolopyrimidine and pyridine, optionally substituted with one or more substituents independently selected from the group consisting of (C$_1$-C$_8$)alkyl, (C$_1$-C$_8$)haloalkyl, —OR$^{13}$, —NR$^{14}$R$^{14}$, mono- or bi-cyclic aryl and mono- or bi-cyclic heteroaryl, said aryl or heteroaryl being further optionally substituted with one or more substituents selected from the group consisting of (C$_1$-C$_8$)alkyl.

Additional embodiments of the invention include one of more of the compounds:

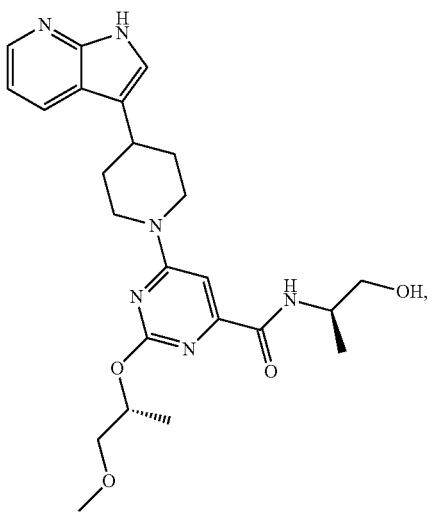

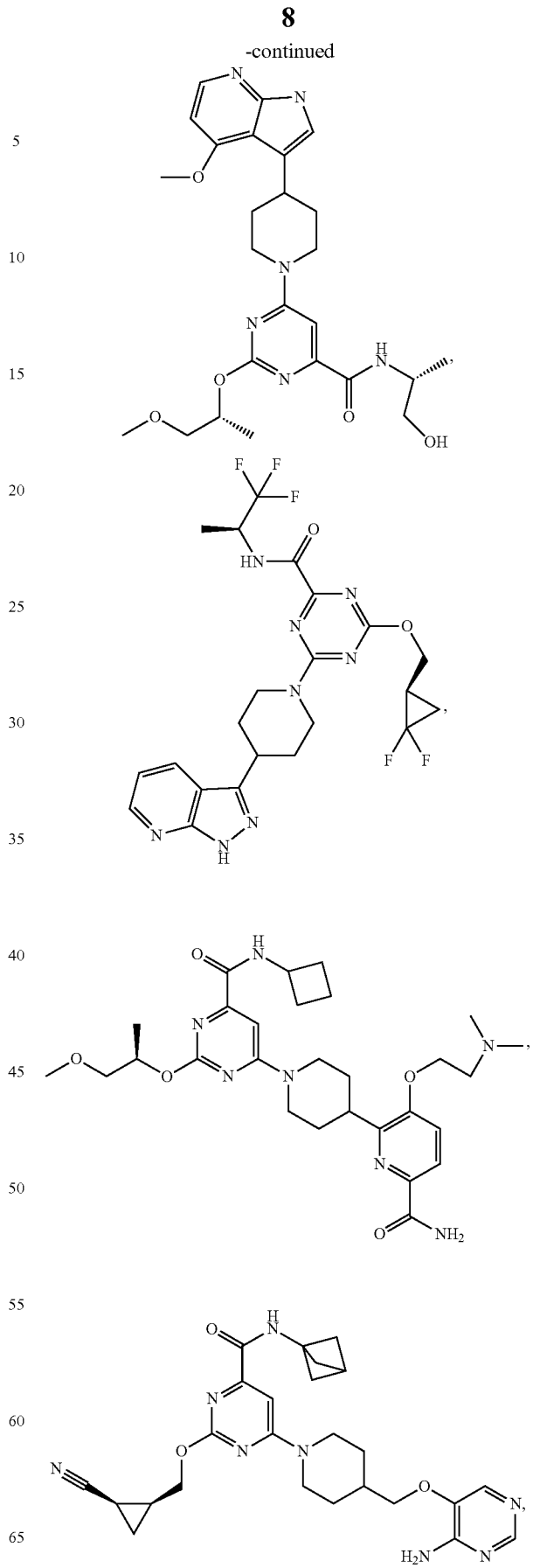

-continued

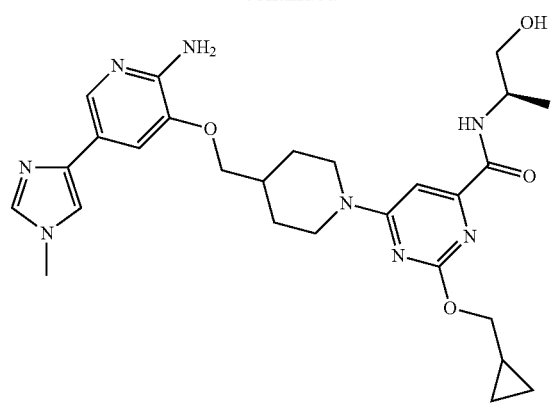

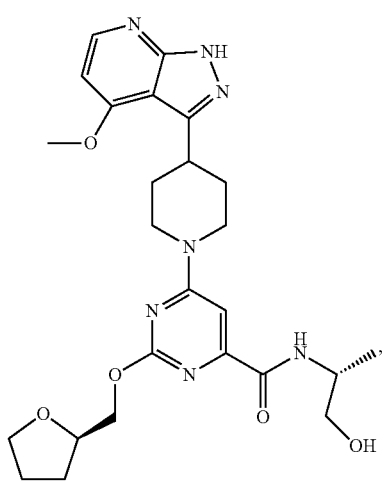

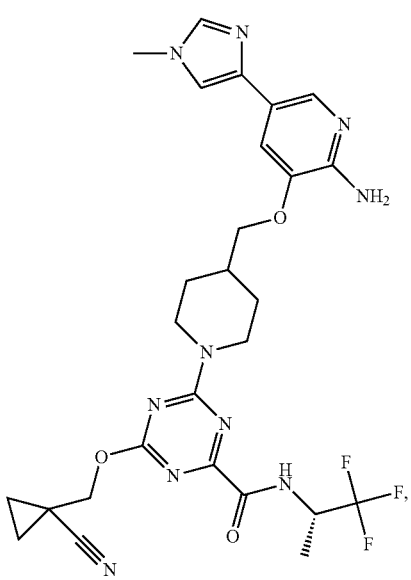

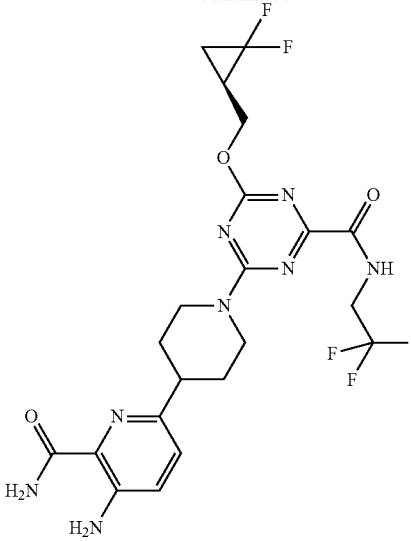

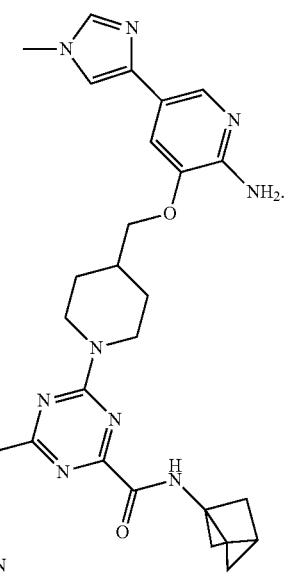

and or a pharmaceutically acceptable salt or salts thereof.

Additional embodiments of the invention include pharmaceutical composition comprising of a compound described herein or a pharmaceutically acceptable salt thereof, and a pharmaceutically acceptable carrier.

Additional embodiments of the invention include methods of treating abnormal cell growth in a mammal, the method comprising administering to the mammal a therapeutically effective amount of a compound described herein or a pharmaceutically acceptable salt thereof, and a pharmaceutically acceptable carrier.

Additional embodiments of the invention include such methods of treatment as are described herein, wherein the abnormal cell growth is cancer. In particular, such methods wherein the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

There is also provided an embodiment of the invention which is the use of a compound described herein, or a pharmaceutically acceptable salt thereof for the preparation of a medicament useful in the treatment of abnormal cell growth in a mammal, particularly wherein the abnormal cell growth is cancer, and more particularly wherein the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

In another embodiment, the invention provides a pharmaceutical composition comprising a compound of the invention or a pharmaceutically acceptable salt thereof, and a pharmaceutically acceptable carrier.

In another embodiment, the invention provides a method of treating abnormal cell growth in a mammal, including a human, the method comprising administering to the mammal a therapeutically effective amount of a compound of the invention or a pharmaceutically acceptable salt thereof. In another embodiment, the abnormal cell growth is cancer. In another embodiment, the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

In another embodiment, the invention provides a use of a compound according to the invention or a pharmaceutically acceptable salt thereof for the preparation of a medicament useful in the treatment of abnormal cell growth in a mammal, including a human. In another embodiment, the abnormal cell growth is cancer. In another embodiment, the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

In further specific embodiments of any of the inventive methods described herein, the method further comprises administering to the mammal an amount of one or more substances selected from anti-tumor agents, anti-angiogenesis agents, signal transduction inhibitors, and antiproliferative agents, which amounts are together effective in treating said abnormal cell growth. Such substances include those disclosed in PCT Publication Nos. WO 00/38715, WO 00/38716, WO 00/38717, WO 00/38718, WO 00/38719, WO 00/38730, WO 00/38665, WO 00/37107 and WO 00/38786, the disclosures of which are incorporated herein by reference in their entireties.

Examples of anti-tumor agents include mitotic inhibitors, for example vinca alkaloid derivatives such as vinblastine vinorelbine, vindescine and vincristine; colchines allochochine, halichondrine, N-benzoyltrimethyl-methyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example cis-platin, carboplatin oxiplatin, iproplatin, Ethyl ester of N-acetyl-DL-sarcosyl-L-leucine (Asaley or Asalex), 1,4-cyclohexadiene-1,4-dicarbamic acid, 2,5-bis(1-azirdinyl)-3,6-dioxo-, diethyl ester (diaziquone), 1,4-bis(methanesulfonyloxy)butane (bisulfan or leucosulfan) chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexyl-chloroethylnitrosourea, methylcyclohexyl-chloroethylnitrosourea 1-(2-chloroethyl)-3-(2,6-dioxo-3-piperidyl)-1-nitroso-urea, bis(2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, strptozoin, and temozolamide. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/

RNA antimetabolites, for example, L-alanosine, 5-azacytidine, acivicin, aminopterin and derivatives thereof such as N-[2-chloro-5-[[(2, 4-diamino-5-methyl-6-quinazolinyl)methyl]amino]benzoyl]-L-aspartic acid, N-[4-[[(2, 4-diamino-5-ethyl-6-quinazolinyl)methyl]amino]benzoyl]-L-aspartic acid, N-[2-chloro-4-[[(2, 4-diaminopteridinyl)methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents include MMP-2 (matrix-metalloprotienase 2) inhibitors, MMP-9 (matrix-metalloprotienase 9) inhibitors, and COX-II (cyclooxygenase II) inhibitors. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Examples of MMP inhibitors include AG-3340, RO 32-3555, RS 13-0830, and the following compounds: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo [3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1] octane-3-carboxylic acid hydroxyamide; 3-endo-3-[4-(4-fluoro-phenoxy)-benzenesulfonylamino]-8-oxa-bicyclo [3.2.1]octane-3-carboxylic acid hydroxyamide; 3-[4-(4-fluoro-phenoxy)-benzenesulfonylamino]-tetrahydro-furan-3-carboxylic acid hydroxyamide; and pharmaceutically acceptable salts, solvates and hydrates thereof.

Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined or co-administered with the composition. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody bevacizumab (Genentech, Inc. of South San Francisco, Calif.); and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with the composition. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); U.S. patent application Ser. No. 09/454,058 (filed Dec. 2, 1999); U.S. patent application Ser. No. 09/501,163 (filed Feb. 9, 2000); U.S. patent application Ser. No. 09/539,930 (filed Mar. 31, 2000); U.S. patent application Ser. No. 09/202,796 (filed May 22, 1997); U.S. patent application Ser. No. 09/384,339 (filed Aug. 26, 1999); and U.S. patent application Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

Compositions of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors. Specific CTLA4 antibodies that can be used in the present invention include those described in U.S. Pat. No. 6,682,736 which is herein incorporated by reference in its entirety.

Definitions

Unless otherwise stated, the following terms used in the specification and claims have the meanings discussed below. Variables defined in this section, such as R, X, n and the like, are for reference within this section only, and are not meant to have the save meaning as may be used outside of this definitions section. Further, many of the groups defined herein can be optionally substituted. The listing in this definitions section of typical substituents is exemplary and is not intended to limit the substituents defined elsewhere within this specification and claims.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like. "Alkenylene" refers to a di-valent form of alkenyl.

"Alkoxy" refers to —O-alkyl where alkyl is preferably $C_1$-$C_8$, $C_1$-$C_7$, $C_1$-$C_6$, $C_1$-$C_5$, $C_1$-$C_4$, $C_1$-$C_3$, $C_1$-$C_2$ or $C_1$ alkyl.

"Alkyl" refers to a saturated aliphatic hydrocarbon radical including straight chain and branched chain groups of 1 to 20 carbon atoms ("($C_1$-$C_{20}$)alkyl"), preferably 1 to 12 carbon atoms ("($C_1$-$C_{12}$)alkyl"), more preferably 1 to 8 carbon atoms ("($C_1$-$C_8$)alkyl"), or 1 to 6 carbon atoms ("($C_1$-$C_6$)alkyl"), or 1 to 4 carbon atoms ("($C_1$-$C_4$)alkyl"). Examples of alkyl groups include methyl, ethyl, propyl, 2-propyl, n-butyl, iso-butyl, tert-butyl, pentyl, neopentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are for example hydrogen, alkyl, cycloalkyl, aryl, carbonyl, acetyl, sulfonyl, trifluoromethanesulfonyl and, combined, a five- or six-member heteroalicyclic ring. "Haloalkyl" for instance ($C_1$-$C_8$)haloalkyl, refers to an alkyl having one or more, halogen substituents. "Alkylene" refers to a di-valent form of alkyl.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like. "Alkynylene" refers to a di-valent form of alkynyl.

"Amino" refers to an —$NR^xR^y$ group, wherein $R^x$ and $R^y$ are both hydrogen.

"($C_6$-$C_{12}$)aryl" refers to an all-carbon monocyclic or fused-ring polycyclic groups of 6 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^xR^y$, with $R^x$ and $R^y$ as defined above.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"Cyano" refers to a —C≡N group. Cyano may be expressed as CN.

"($C_3$-$C_{10}$)cycloalkyl" refers to a 3 to 10 member all-carbon monocyclic ring, a 3 to 10 member all-carbon bicyclic ring, an all-carbon 5-member/6-member or 6-member/6-member fused bicyclic ring, a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system, and a bridged all-carbon ring system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —$NR^xR^y$, with $R^x$ and $R^y$ as defined above. Illustrative examples of cycloalkyl are derived from, but not limited to, the following:

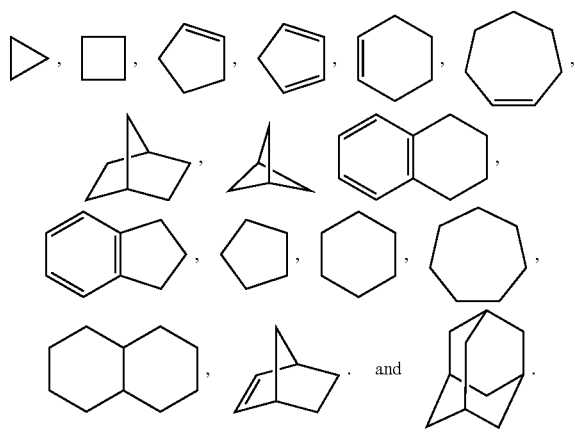

"Enantiomerically pure" as used herein, describes a compound that is present as a single enantiomer and which is described in terms of enantiomeric excess. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, "diastereomerically pure" as used herein, describes a compound that is present as a diastereomers and which is described in terms of enantiomeric excess. Preferably, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

"Halogen" or the prefix "halo" refers to fluoro, chloro, bromo and iodo. Preferably halogen refers to fluoro or chloro.

"Heteroalkyl" refers to a straight chain or branched chain alkyl group of 1 to 20 carbon atoms, preferably 1 to 12 carbon atoms, more preferably 1 to 8 carbon atoms, or 1 to 6 carbon atoms, or 1 to 4 carbon atoms, wherein one, two or three of which carbon atoms are replaced by a heteroatom selected from $NR^x$, O, and $S(O)_n$ (where n is 0, 1 or 2). Exemplary heteroalkyls include alkyl ethers, secondary and tertiary alkyl amines, amides, alkyl sulfides, and the like. The group may be a terminal group or a bridging group. As used herein, reference to the normal chain when used in the context of a bridging group refers to the direct chain of atoms linking the two terminal positions of the bridging group. As with "alkyl", typical substituent groups on "heteroalkyl" include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are for example hydrogen, alkyl, cycloalkyl, aryl, carbonyl, acetyl, sulfonyl, trifluoromethanesulfonyl and, combined, a five- or six-member heteroalicyclic ring. "Heteroalkenyl" refers to a heteroalkyl possessing one or more carbon-carbon double bonds. "Heteroalkylene" refers to a di-valent form of heteroalkyl. "Heteroalkenylene" refers to a di-valent form of heteroalkenyl.

"Heteroaryl" refers to a monocyclic or fused ring group of 5 to 12 carbon ring atoms containing one, two, three or four ring heteroatoms selected from $NR^x$, O, and $S(O)_n$ (where n is 0, 1 or 2) and, in addition, having a completely conjugated pi-electron system. Preferred heteroaryl groups include ($C_2$-$C_7$)heteroaryl in accordance with the definition above. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —$NR^xR^y$ with $R^x$ and $R^y$ as defined above. A pharmaceutically acceptable heteroaryl is one that is sufficiently stable to be attached to a compound of the invention, formulated into a pharmaceutical composition and subsequently administered to a patient in need thereof. Examples of typical monocyclic heteroaryl groups include, but are not limited to:

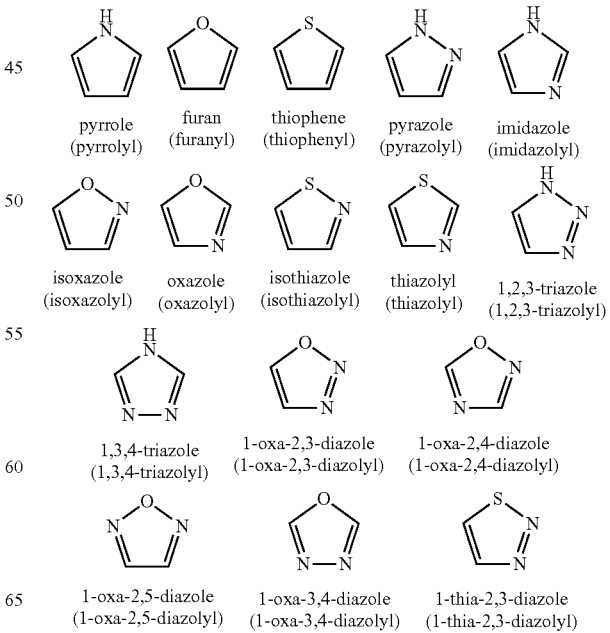

-continued
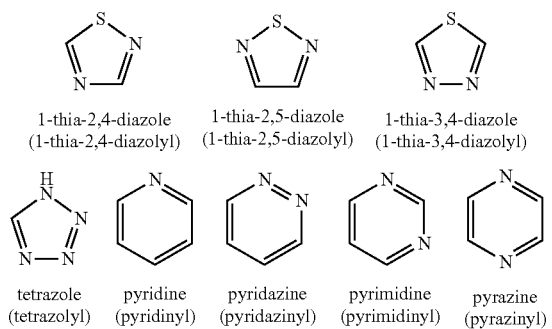
Examples of suitable fused ring heteroaryl groups include, but are not limited to:
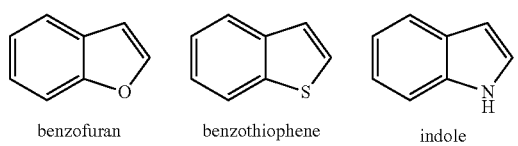
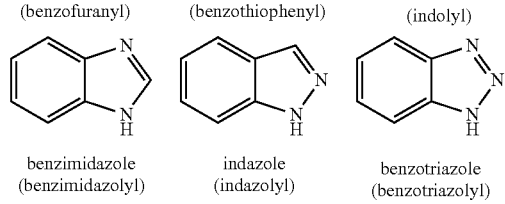
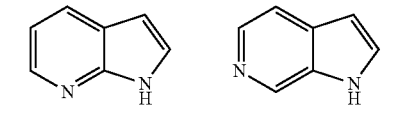
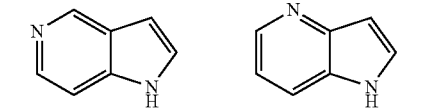
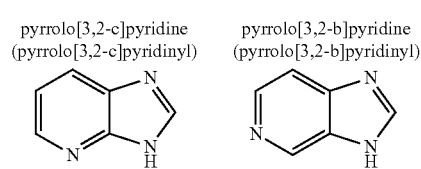
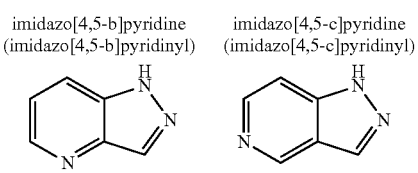
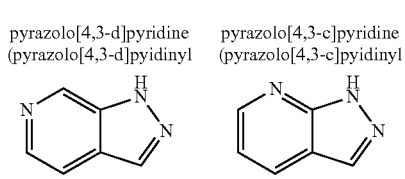
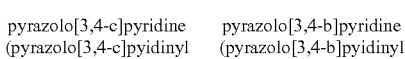
-continued
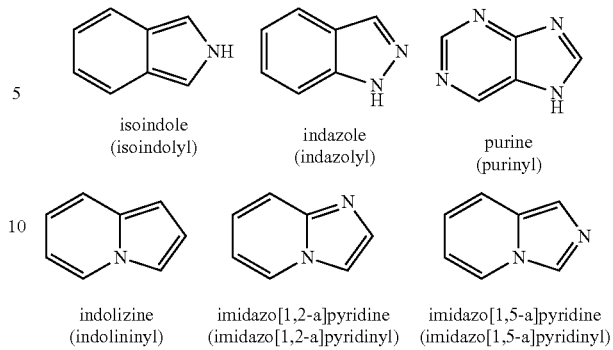
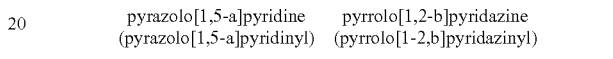
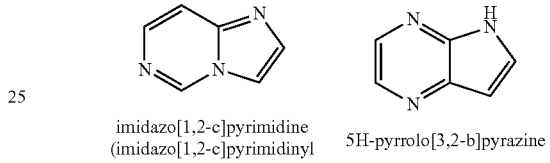
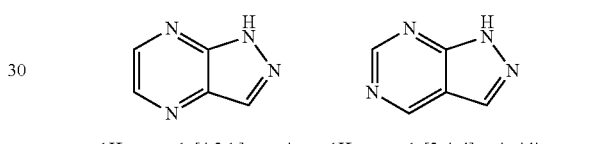
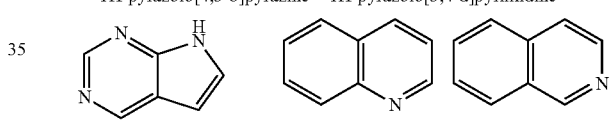
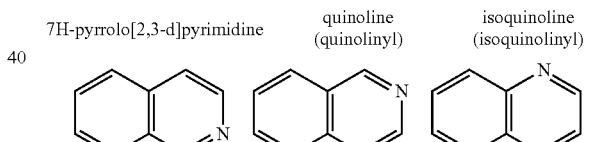
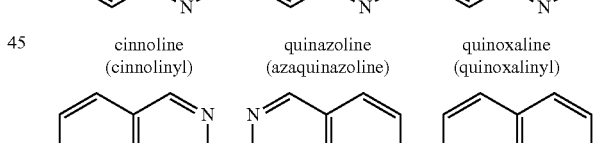
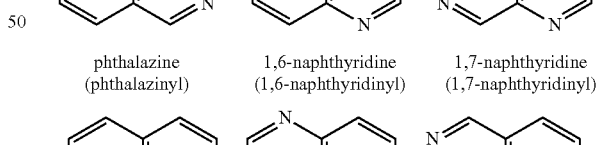
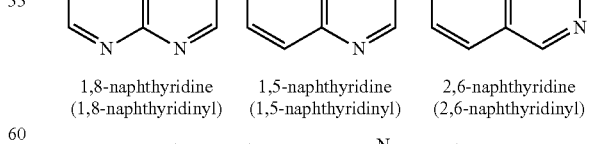

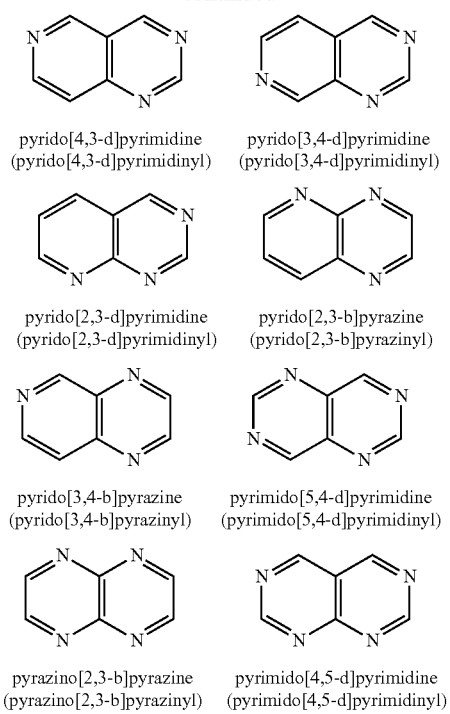

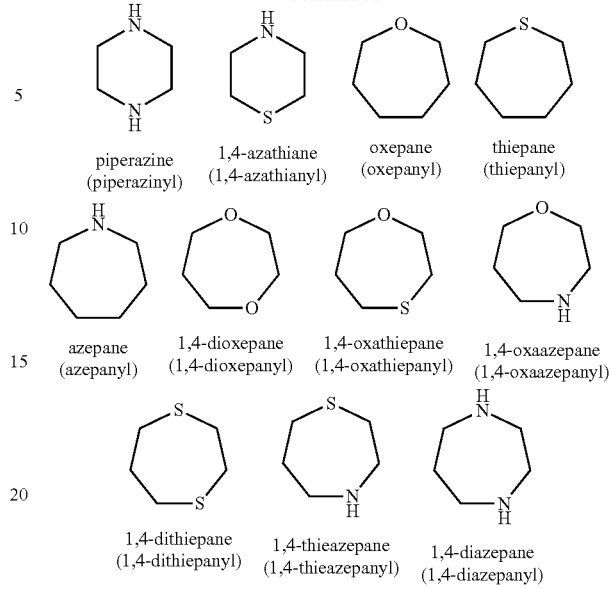

"Heterocyclyl" refers to a monocyclic or fused ring system having 3 to 12 ring atoms containing one, two, three or four ring heteroatoms selected from N, O, and $S(O)_n$ (where n is 0, 1 or 2), and 1-9 carbon atoms The rings may also have one or more double bonds. However, the rings do not have a completely conjugated pi-electron system. Preferred heterocycles include $(C_2-C_6)$heterocycles in accordance with the definition above. Examples of suitable saturated heteroalicyclic groups include, but are not limited to:

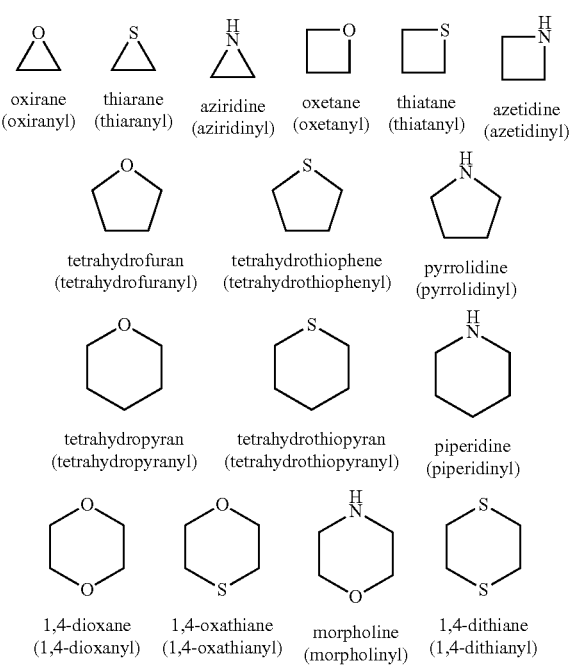

Examples of suitable partially unsaturated heteroalicyclic groups include, but are not limited to:

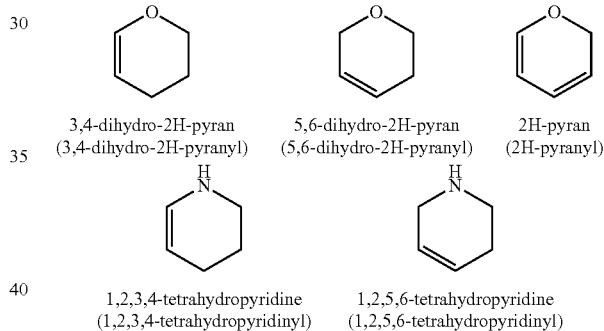

The heterocyclyl group is optionally substituted with one or two substituents independently selected from halo, lower alkyl, lower alkyl substituted with carboxy, ester hydroxy, or mono or dialkylamino. Moreover, the heterocycle may contain bridging, including bridging between non-adjacent carbons on the heterocycle, with the bridge containing 1-2 carbons and 0-1 heteroatoms selected from selected from $NR^x$, O, and $S(O)_n$ (where n is 0, 1 or 2).

"Hydroxy" or "hydroxyl" refers to an —OH group.

"In vitro" refers to procedures performed in an artificial environment such as, e.g., without limitation, in a test tube or culture medium.

"In vivo" refers to procedures performed within a living organism such as, without limitation, a mouse, rat or rabbit.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

"Organism" refers to any living entity comprised of at least one cell. A living organism can be as simple as, for example, a single eukariotic cell or as complex as a mammal, including a human being.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:
  (i) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or
  (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

"PK" refers to receptor protein tyrosine kinase (RTKs), non-receptor or "cellular" tyrosine kinase (CTKs) and serine-threonine kinases (STKs).

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:
  (1) reducing the size of the tumor;
  (2) inhibiting (that is, slowing to some extent, preferably stopping) tumor metastasis;
  (3) inhibiting to some extent (that is, slowing to some extent, preferably stopping) tumor growth, and
  (4) relieving to some extent (or, preferably, eliminating) one or more symptoms associated with the cancer.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

DETAILED DESCRIPTION

General schemes for synthesizing the compounds of the invention can be found in the Examples section herein.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts).

Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include:

(i) where the compound contains a carboxylic acid functionality —(COOH), an ester thereof, for example, replacement of the hydrogen with ($C_1$-$C_8$)alkyl;

(ii) where the compound contains an alcohol functionality (—OH), an ether thereof, for example, replacement of the hydrogen with ($C_1$-$C_6$)alkanoyloxymethyl; and (iii) where the compound contains a primary or secondary amino functionality (—$NH_2$ or —NHR where R≠H), an amide thereof, for example, replacement of one or both hydrogens with ($C_1$-$C_{10}$)alkanoyl.

Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon atoms can exist as two or more stereoisomers. Where the compounds according to this invention have at least one chiral center, they may accordingly exist as enantiomers. Where the compounds possess two or more chiral centers, they may additionally exist as diastereomers. Similarly, where a compound of the invention contains a cyclopropyl group or other cyclic group where chirality exists, and alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (H PLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention, or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864.

Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

General Synthetic Schemes

Unless stated otherwise, the variables in Schemes A-I have the same meanings as defined herein.

Scheme A:

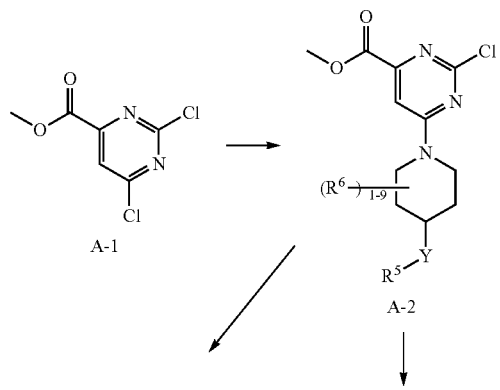

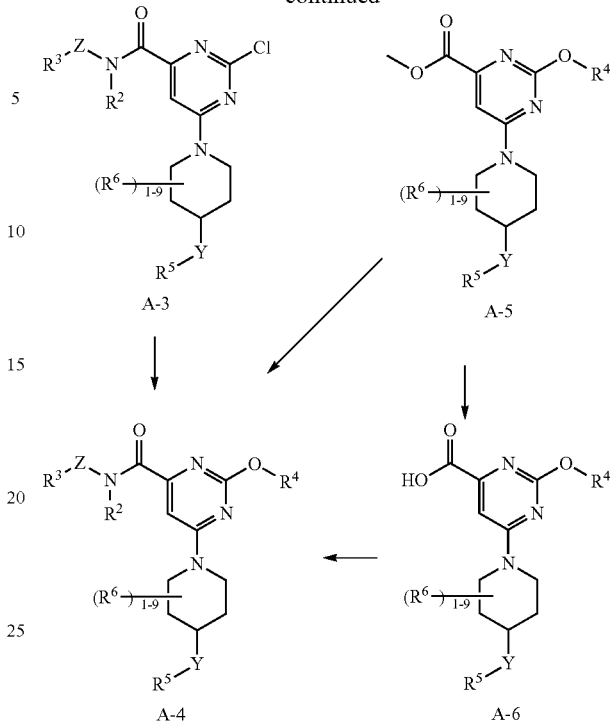

As exemplified in Scheme A, a functionalized piperidine is reacted with commercially available methyl-2,6-dichloropyrimidine-4-carboxylate (A-1) in the presence of a suitable base such as TEA or DIPEA in a reaction solvent such as MeOH to afford A-2. Typically, the reaction is heated either under oil bath or microwave conditions at temperatures ranging between 60 and 100° C. The desired 4-substituted derivative A-2 is purified from minor amounts of the corresponding regioisomer (5-10%) by silica gel chromatography or recrystallization. A-2 is stirred with an amine in the presence of a catalytic amount of a solvent such as methanol to effect amidation of the methyl ester to form the desired amide, A-3. Typically, the transformation of A-2 to A-3 is carried out at ambient temperature to prevent concomitant displacement of the 2-chloro substituent of A-2. Reaction of A-3 with an alcohol at elevated temperature in the presence of a base such as NaOMe, NaH, $K_3PO_4$ (with or without addition of a crown ether catalyst) or LiHMDS in a solvent such as MeOH or DMF affords A-4. The reaction is typically carried out at temperatures ranging from 60 to 120° C., and heating is provided either using a conventional oil bath or by microwave irradiation. Purification of A-4 is carried out by standard techniques such as column chromatography, crystallization or reverse phase HPLC. Alternatively the sequence of reactions can be altered with A-2 reacted with an alcohol at elevated temperature in the presence of a base such as NaOMe, NaH, $K_3PO_4$ (with or without addition of a crown ether catalyst) or LiHMDS in a solvent such as MeOH or DMF to affords A-5. The reaction is typically carried out at temperatures ranging from 60 to 120° C., and heating is provided either using a conventional oil bath or by microwave irradiation. Treatment of A-5 with an amine either under thermal conditions (typically at temperatures ranging between ambient and 60° C.), or in the presence of a catalytic amount of solvent such as methanol effects direct amidation of the methyl ester to afford A-4, which can be purified by the standard techniques described previously. Alternatively, hydrolysis of A-5 can be carried out under basic conditions to afford A-6. Typically, a base such as NaOH, LiOH, or KOH is utilized in a solvent system containing a combination of MeOH, THF and water. A-6 is condensed with an amine in the presence of a suitable coupling agent (such as HBTU, T3P or HATU) and a base (such as TEA or DIPEA) in a suitable solvent such as DMF to afford A-4, which can be purified by the standard techniques described previously herein. If necessary, separation of the enantiomers of A-4 may be carried out under standard methods known in the art such as chiral SFC or HPLC to afford single enantiomers of A-4.

nation of $POCl_3$ and $PCl_5$. Treatment of B-2 with a suitable amine in the presence of a base such as TEA or NaH in a solvent such as DCM or DMF affords the amide B-3. Conversion of B-2 to B-3 is typically carried out at temperatures ranging from 0 to 60° C. Selection of the base and temperature used for this transformation is dependent on the reactivity of the amine component. Treatment of B-3 with a functionalized piperidine in the presence of a suitable base such as TEA or DIPEA in a reaction solvent such as MeOH affords A-3. Typically, the reaction is heated either under oil bath or microwave conditions at temperatures ranging between 60 and 100° C. The desired 4-substituted derivative Scheme B:

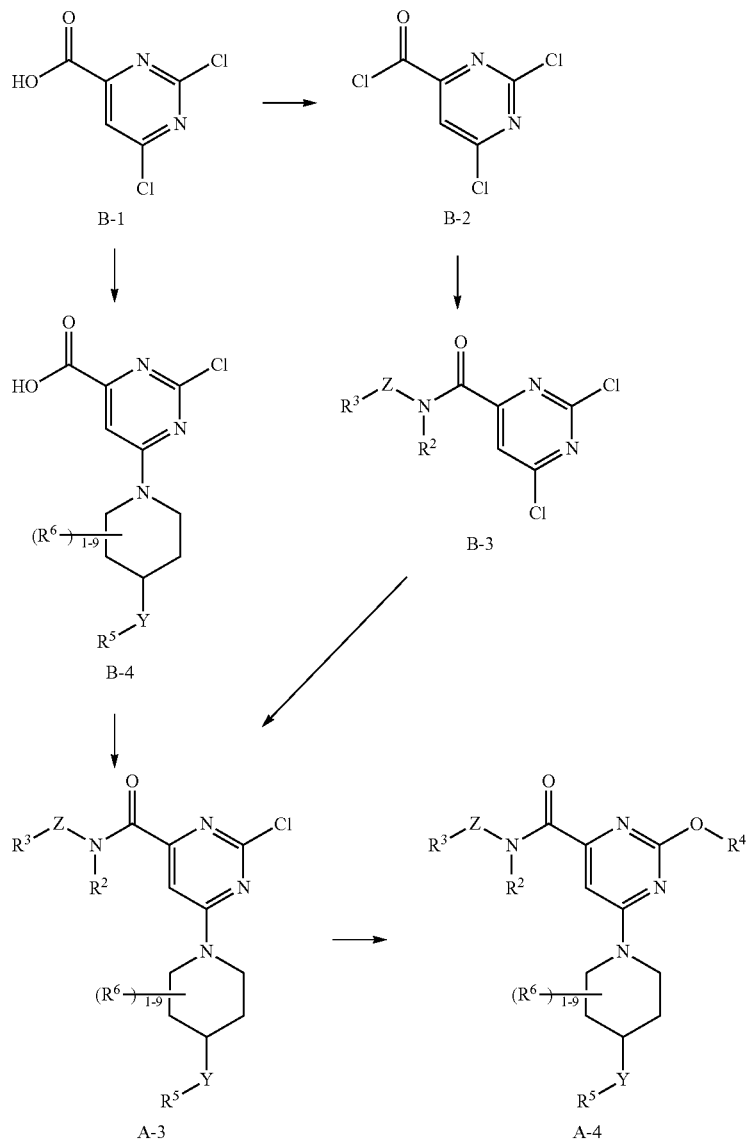

As exemplified in Scheme B, treatment of commercially available 2,6-dichloropyrimidine-4-carboxylic acid (B-1) with a suitable chlorinating agent such as $POCl_3$ or $SOCl_2$ either in the presence or absence of a catalytic amount of DMF provides after work-up and distillation the acid chloride B-2. Alternatively B-2 can be obtained from chlorination of commercially available orotic acid using a combi- A-3 is purified from minor amounts of the corresponding regioisomer (5-10%) by silica gel chromatography or recrystallization. Treatment of A-3 with an alcohol at elevated temperature in the presence of a base such as NaOMe, NaH, $K_3PO_4$ (with or without addition of a crown ether catalyst) or LiHMDS in a solvent such as MeOH or DMF affords A-4. The reaction is typically carried out at temperatures ranging from 60 to 120° C., and heating is provided either using a conventional oil bath or by microwave irradiation. Purification of A-4 is carried out by standard techniques such as column chromatography, crystallization or reverse phase HPLC. Alternatively the sequence of reactions can be altered with B-1 being reacted with a functionalized piperidine in the presence of a suitable base such as TEA or DIPEA in a reaction solvent such as MeOH to afford B-4. Typically, the reaction is heated either under oil bath or microwave conditions at temperatures ranging between 60 and 100° C. The desired 4-substituted derivative B-4 is purified from minor amounts of the corresponding regioisomer (5-10%) by silica gel chromatography or recrystallization. B-4 is condensed with an amine in the presence of a suitable coupling agent (such as HBTU, T3P or HATU) and a base (such as TEA or DIPEA) in a suitable solvent such as DMF to afford A-3, which is treated with an alcohol in an analogous manner to that described previously to afford A-4. If necessary, separation of the enantiomers of A-4 may be carried out under standard methods known in the art such as chiral SFC or HPLC to afford single enantiomers of A-4.

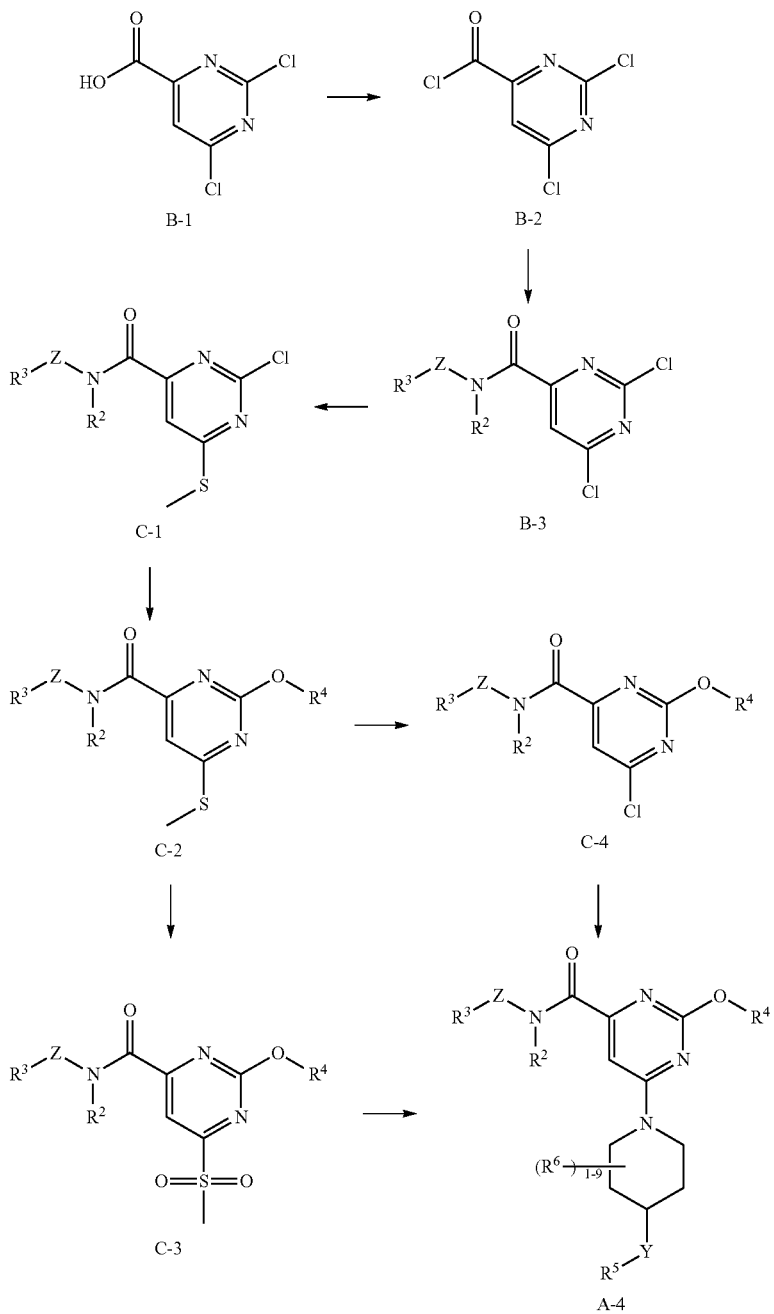

Scheme C:

As exemplified in Scheme C, treatment of commercially available 2,6-dichloropyrimidine-4-carboxylic acid (B-1) with a suitable chlorinating agent such as POCl$_3$ or SOCl$_2$ either in the presence or absence of a catalytic amount of DMF provides after work-up and distillation the acid chloride B-2. Treatment of B-2 with a suitable amine in the presence of a base such as TEA or NaH in a solvent such as DCM or DMF affords the amide B-3. Conversion of B-2 to B-3 is typically carried out at temperatures ranging from 0 to 60° C. Selection of the base and temperature used for this transformation is dependent on the reactivity of the amine component. Treatment of B-3 with NaSMe (either obtained commercially, or derived in situ from MeSH and a base such as NaH) in a solvent such as DMF or THF at temperatures ranging from 0 to 25° C. provided C-1, which was either used directly in the next step or purified by silica gel chromatography. Treatment of C-1 with an alcohol at elevated temperature in the presence of a base such as NaOMe, NaH, $K_3PO_4$ (with or without addition of a crown ether catalyst) or LiHMDS in a solvent such as MeOH or DMF affords C-2. The reaction is typically carried out at temperatures ranging from 60 to 120° C., and heating is provided either using a conventional oil bath or by microwave irradiation. Treatment of C-2 with an oxidizing agent such as oxone in a solvent system typically comprising of MeOH, THF and water affords sulfone C-3. The reaction is typically conducted at ambient temperature with C-3 being used directly without purification. Treatment of C-3 with a functionalized piperidine in the presence of a suitable base such as TEA or DIPEA in a reaction solvent such as MeOH affords A-4. Typically, the reaction is heated either under oil bath or microwave conditions at temperatures ranging between 60 and 100° C. Purification of A-4 is carried out by standard techniques such as column chromatography, crystallization, salt formation or reverse phase HPLC. Alternatively treatment of C-2 under an oxidative-halogenation type sequence using a reagent such as sulfuryl chloride in a solvent such as DCM or MeCN affords C-4 (for example, see *Tetrahedron Lett.*, 2010, 51, 4609). Similar treatment of C-4 with a functionalized piperidine in the presence of a suitable base such as TEA or DIPEA in a reaction solvent such as MeOH at temperatures typically ranging between 60 and 100° C. affords A-4, which can be purified using the standard techniques described above. If necessary, separation of the enantiomers of A-4 may be carried out under standard methods known in the art such as chiral SFC or HPLC to afford single enantiomers of A-4.

Scheme D:

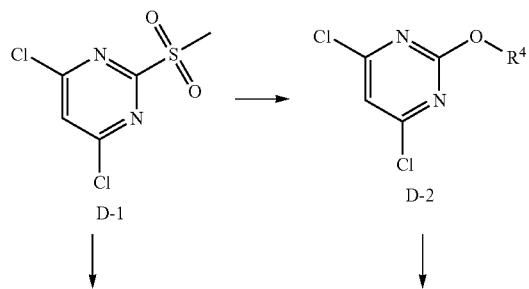

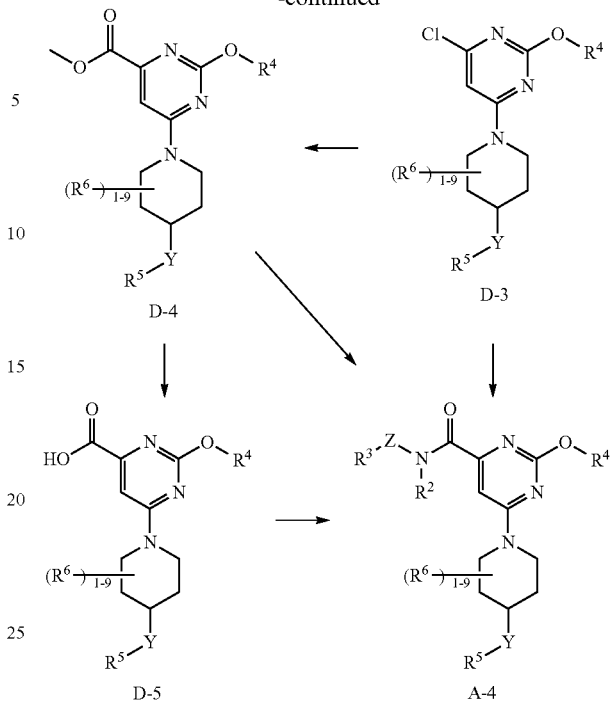

As exemplified in Scheme D, treatment of commercially available 4,6-dichloro-2-(methylsulfonyl)pyrimidine (D-1) with an alcohol at ambient temperature in the presence of a base such as LiHMDS in a solvent such as THF affords D-2. Typically, D-2 is telescoped directly into the next step, and treated with a functionalized piperidine in the presence of a suitable base such as LiHMDS, TEA or DIPEA in a reaction solvent such as MeOH, THF or MeCN to afford D-3. The conversion of D-2 to D-3 is typically carried out at temperatures ranging between 25 and 80° C. D-3 is treated with a suitable amine under standard carboamidation conditions to afford A-4. Typically for the conversion of D-3 to A-4, a palladium catalyst such as palladium acetate is used in combination with a ligand such as BINAP, DPE-Phos or DPPP. In addition, either excess amine is used or an additional base such as DIPEA or TEA is added to the system with the reaction typically being conducted in a solvent such as MeOH, toluene or MeCN. The reaction is carried out under a suitable pressure of CO (usually 2-8 bar) in a sealed pressure vessel at elevated temperature, which ranges between 60-80° C. Purification of A-4 is carried out by standard techniques such as column chromatography, crystallization, salt formation or reverse phase HPLC. Alternatively, D-3 is converted to D-4 under carbonylation conditions using MeOH as the nucleophile. For the conversion of D-3 to D-4, a palladium catalyst such as palladium acetate is used in combination with a ligand such as BINAP, DPE-Phos or DPPP. In addition, a base such as DIPEA or TEA is added to the system with the reaction typically being conducted in MeOH as the solvent, or MeOH in conjunction with a co-solvent such toluene or MeCN. The reaction is carried out under a suitable pressure of CO (usually 2-8 bar) in a sealed pressure vessel at elevated temperature, which ranges between 60-80° C. (for a review on the carbonylation of aryl halides, see *Angew. Chem. Int. Ed.*, 2009, 48, 4114). Treatment of D-4 with an amine either under thermal conditions (typically at temperatures ranging between ambient and 60° C.), or in the presence of a catalytic amount of solvent such as methanol effects direct amidation of the methyl ester to afford A-4, which can be purified by the standard techniques described previously. Alternatively, hydrolysis of D-4 can be carried out under basic conditions to afford D-5. Typically, a base such as NaOH, LiOH, or KOH is utilized in a solvent system containing a combination of MeOH, THF and water. D-5 is condensed with an amine in the presence of a suitable coupling agent (such as HBTU, T3P or HATU) and a base (such as TEA or DIPEA) in a suitable solvent such as DMF to afford A-4, which can be purified by the standard techniques described previously herein. If necessary, separation of the enantiomers of A-4 may be carried out under standard methods known in the art such as chiral SFC or HPLC to afford single enantiomers of A-4.

Scheme E:

such as MeCN affords E-4, which is often telescoped directly into the next step. Treatment of E-4 with an amine in the presence of an oxidant such as m-CPBA or peroxyacetic acid in a solvent such as MeCN (with or without additional DMSO to facilitate solubility) affords E-5, which can be purified by standard techniques such as column chromatography, crystallization, salt formation or reverse phase HPLC (for example of the use of malononitrile as a carbonyl synthon, see *Tetrahedron Lett.*, 2004, 45, 5909). If necessary, separation of the enantiomers of E-5 may be carried out under standard methods known in the art such as chiral SFC or HPLC to afford single enantiomers of E-5.

Scheme F:

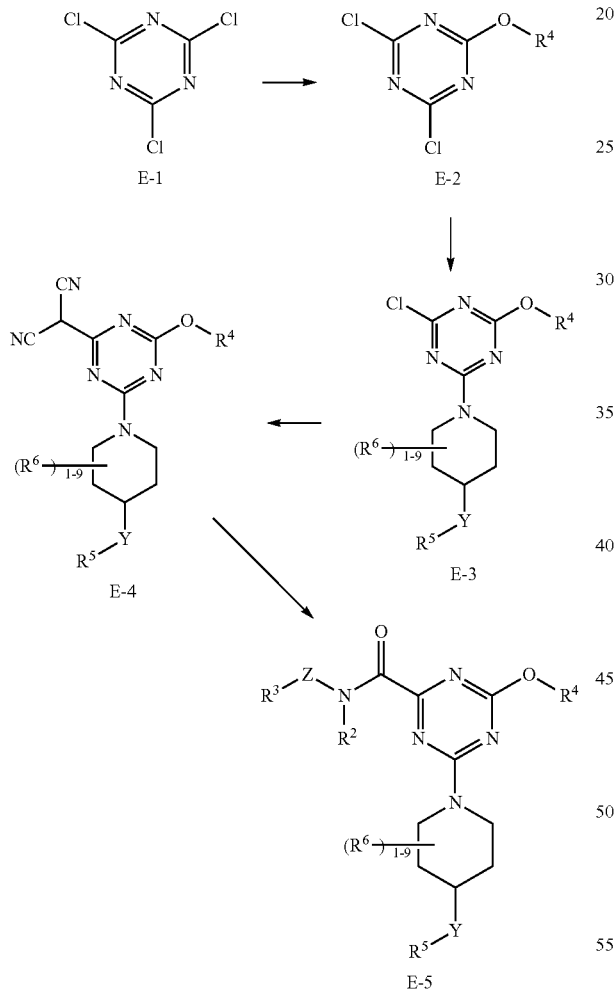

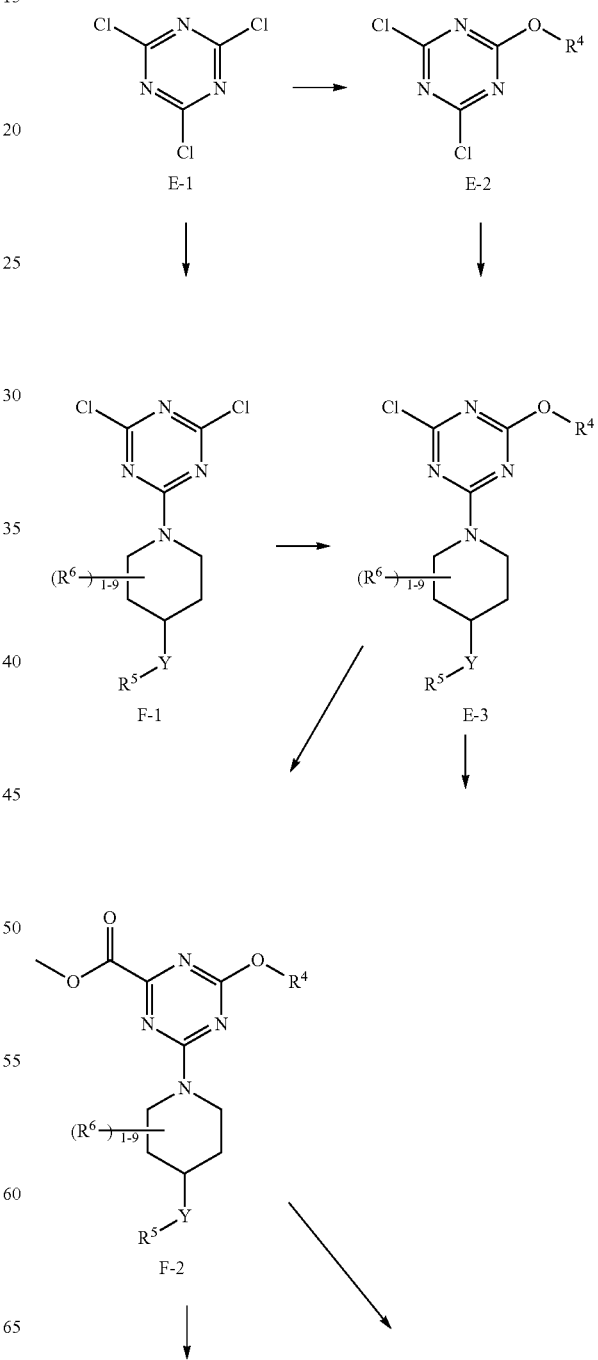

As exemplified in Scheme E, treatment of commercially available cyanuric chloride (E-1) with an alcohol at ambient temperature (0-25° C.) in the presence of a base such as LiHMDS in a solvent such as THF affords E-2. Typically, E-2 is telescoped directly into the next step, and treated with a functionalized piperidine in the presence of a suitable base such as LiHMDS, TEA or DIPEA in a reaction solvent such as MeOH, THF or MeCN to afford E-3. Treatment of E-3 with malononitrile and a base such as $K_2CO_3$ in a solvent

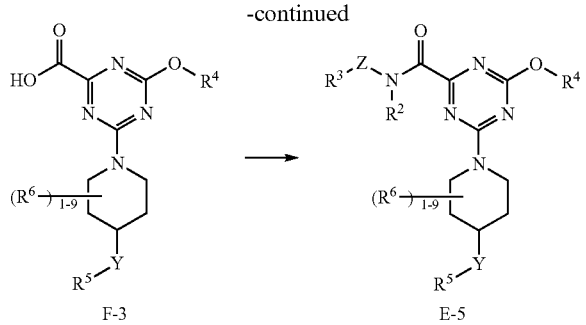

F-3 → E-5

As exemplified in Scheme F, treatment of commercially available cyanuric chloride (E-1) with an alcohol at ambient temperature (0-25° C.) in the presence of a base such as LiHMDS in a solvent such as THF affords E-2. Typically, E-2 is telescoped directly into the next step, and treated with a functionalized piperidine in the presence of a suitable base such as LiHMDS, TEA or DIPEA in a reaction solvent such as MeOH, THF or MeCN to afford E-3. Alternatively, the order of these two steps can be reversed to afford E-3. In this manner, treatment of commercially available cyanuric chloride (E-1) with a functionalized piperidine in the presence of a suitable base such as LiHMDS, TEA or DIPEA in a reaction solvent such as MeOH, THF or MeCN affords F-1. Typically, F-1 is telescoped directly into the next step, and treated with an alcohol at ambient temperature (0-25° C.) in the presence of a base such as LiHMDS in a solvent such as THF to affords E-3. E-3 is treated with a suitable amine under standard carboamidation conditions to afford E-5. Typically for the conversion of E-3 to E-5, a palladium catalyst such as palladium acetate is used in combination with a ligand such as BINAP, DPE-Phos or DPPP. In addition, either excess amine is used or an additional base such as DIPEA or TEA is added to the system with the reaction typically being conducted in a solvent such as MeOH, toluene or MeCN. The reaction is carried out under a suitable pressure of CO (usually 2-8 bar) in a sealed pressure vessel at elevated temperature, which ranges between 60-80° C. Temperature control is critical for this transformation to maximize the ratio of the desired product E-5 to that observed from direct SnAr displacement of the amine utilized. Purification of E-5 is carried out by standard techniques such as column chromatography, crystallization, salt formation or reverse phase HPLC. Alternatively, E-3 is converted to F-2 under carbonylation conditions using MeOH as the nucleophile. For the conversion of E-3 to F-2, a palladium catalyst such as palladium acetate is used in combination with a ligand such as BINAP, DPE-Phos or DPPP. In addition, a base such as DIPEA or TEA is added to the system with the reaction typically being conducted in MeOH as the solvent, or MeOH in conjunction with a co-solvent such toluene or MeCN. The reaction is carried out under a suitable pressure of CO (usually 2-8 bar) in a sealed pressure vessel at elevated temperature, which ranges between 60-80° C. Again, temperature control is critical to minimize the amount of direct methanol displacement observed (for a review on the carbonylation of aryl halides, see *Angew. Chem. Int. Ed.,* 2009, 48, 4114). Treatment of F-2 with an amine either under thermal conditions (typically at temperatures ranging between ambient and 60° C.), or in the presence of a catalytic amount of solvent such as methanol effects direct amidation of the methyl ester to afford E-5, which can be purified by the standard techniques described previously. Alternatively, hydrolysis of F-2 can be carried out under basic conditions to afford F-3. Typically, a base such as NaOH, LiOH, or KOH is utilized in a solvent system containing a combination of MeOH, THF and water. F-3 is condensed with an amine in the presence of a suitable coupling agent (such as HBTU, T3P or HATU) and a base (such as TEA or DIPEA) in a suitable solvent such as DMF to afford E-5, which can be purified by the standard techniques described previously herein. If necessary, separation of the enantiomers of E-5 may be carried out under standard methods known in the art such as chiral SFC or HPLC to afford single enantiomers of E-5.

Scheme G:

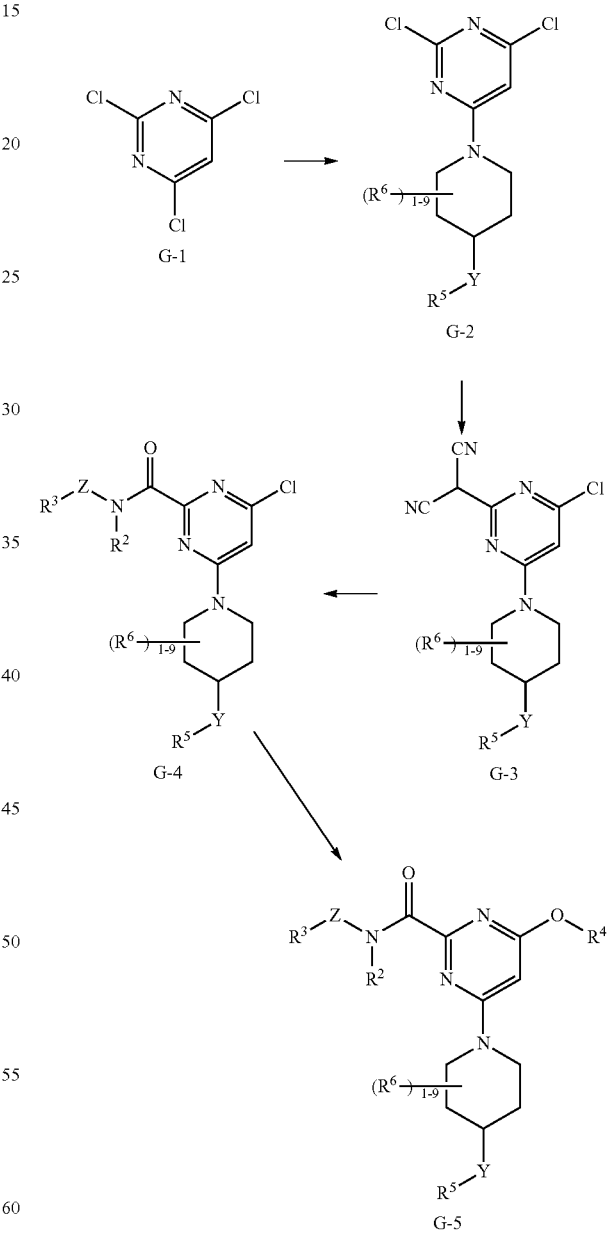

As exemplified in Scheme G, a functionalized piperidine is reacted with commercially available 2,4,6-trichloropyrimidine (G-1) in the presence of a suitable base such as TEA or DIPEA in a reaction solvent such as MeOH to afford G-2. Typically, the reaction is heated either under oil bath or microwave conditions at temperatures ranging between 60 and 100° C. The desired 4-substituted derivative G-2 is purified from minor amounts of the corresponding regioisomer (5-10%) by silica gel chromatography or recrystallization. Treatment of G-2 with malononitrile and a base such as $K_2CO_3$ in a solvent such as MeCN affords G-3, which is often telescoped directly into the next step. Treatment of G-3 with an amine in the presence of an oxidant such as m-CPBA or peroxyacetic acid in a solvent such as MeCN (with or without additional DMSO to facilitate solubility) affords G-4 (for example of the use of malonitrile as a carbonyl synthon, see *Tetrahedron Lett.*, 2004, 45, 5909). Reaction of G-4 with an alcohol at elevated temperature in the presence of a base such as NaOMe, NaH, $K_3PO_4$ (with or without addition of a crown ether catalyst) or LiHMDS in a solvent such as MeOH or DMF affords G-5. The reaction is typically carried out at temperatures ranging from 60 to 120° C., and heating is provided either using a conventional oil bath or by microwave irradiation. Purification of G-5 is carried out by standard techniques such as column chromatography, crystallization, salt formation or reverse phase HPLC. If necessary, separation of the enantiomers of G-5 may be carried out under standard methods known in the art such as chiral SFC or HPLC to afford single enantiomers of G-5.

Scheme H:

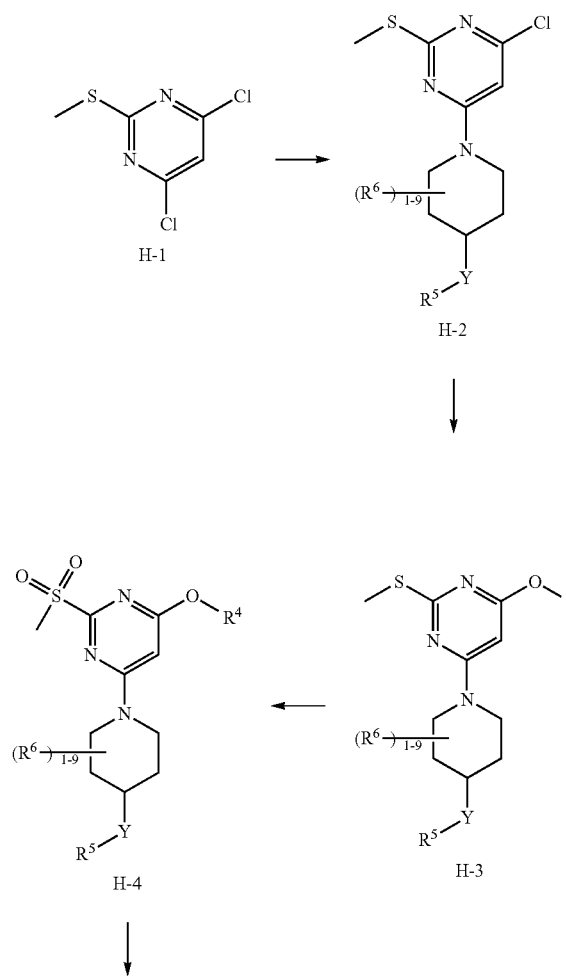

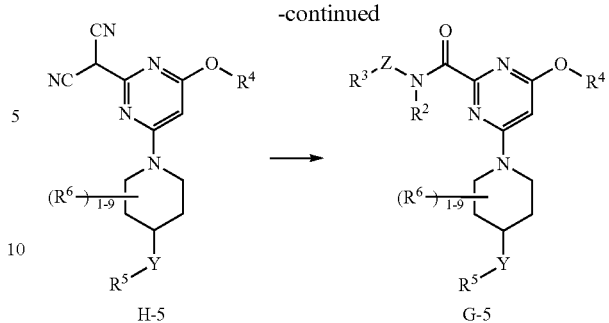

As exemplified in Scheme H, a functionalized piperidine is reacted with commercially available 4,6-dichloro-2-(thiomethyl)-pyrimidine (H-1) in the presence of a suitable base such as TEA or DIPEA in a reaction solvent such as MeOH to afford H-2. Typically, the reaction is heated either under oil bath or microwave conditions at temperatures ranging between 60 and 100° C. Reaction of H-2 with an alcohol at elevated temperature in the presence of a base such as NaOMe, NaH, $K_3PO_4$ (with or without addition of a crown ether catalyst) or LiHMDS in a solvent such as MeOH or DMF affords H-3. The reaction is typically carried out at temperatures ranging from 60 to 120° C., and heating is provided either using a conventional oil bath or by microwave irradiation. Treatment of H-3 with an oxidizing agent such as oxone in a solvent system typically comprising of MeOH, THF and water affords sulfone H-4. The reaction is typically conducted at ambient temperature with H-4 being used directly without purification. Treatment of H-4 with malononitrile and a base such as $K_2CO_3$ in a solvent such as MeCN affords G-3, which is often telescoped directly into the next step. Treatment of H-5 with an amine in the presence of an oxidant such as m-CPBA or peroxyacetic acid in a solvent such as MeCN (with or without additional DMSO to facilitate solubility) affords G-5 (for example of the use of malonitrile as a carbonyl synthon, see *Tetrahedron Lett.*, 2004, 45, 5909). Purification of G-5 is carried out by standard techniques such as column chromatography, crystallization, salt formation or reverse phase HPLC. If necessary, separation of the enantiomers of G-5 may be carried out under standard methods known in the art such as chiral SFC or HPLC to afford single enantiomers of G-5.

Scheme I:

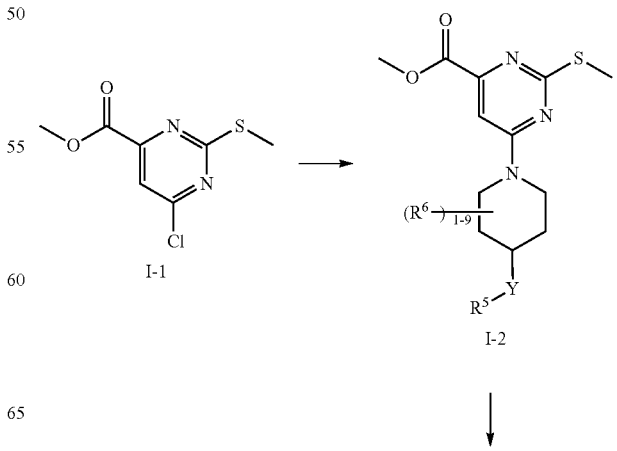

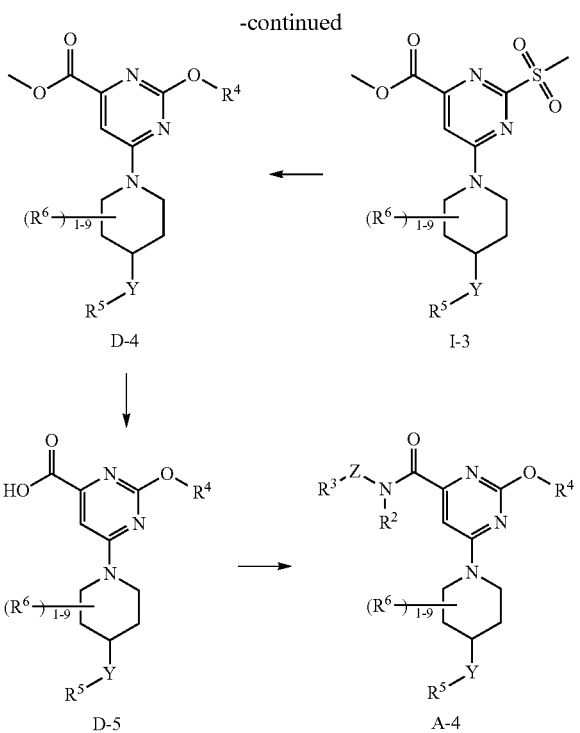

As exemplified in Scheme I, a functionalized piperidine is reacted with commercially available 4,6-dichloro-2-(thiomethyl)-pyrimidine (I-1) in the presence of a suitable base such as TEA or DIPEA in a reaction solvent such as MeOH to afford I-2. Typically, the reaction is heated either under oil bath or microwave conditions at temperatures ranging between 60 and 100° C. Reaction of I-2 with an oxidizing agent such as oxone in a solvent system typically comprising of MeOH, THF and water affords sulfone I-3. The reaction is typically conducted at ambient temperature with I-3 being used directly without purification. Reaction of I-3 with an alcohol at elevated temperature in the presence of a base such as NaOMe, NaH, $K_3PO_4$ (with or without addition of a crown ether catalyst) or LiHMDS in a solvent such as MeOH or DMF affords D-4. The reaction is typically carried out at temperatures ranging from 60 to 120° C., and heating is provided either using a conventional oil bath or by microwave irradiation. Hydrolysis of D-4 can be carried out under basic conditions to afford D-5. Typically, a base such as NaOH, LiOH, or KOH is utilized in a solvent system containing a combination of MeOH, THF and water. D-5 is condensed with an amine in the presence of a suitable coupling agent (such as HBTU, T3P or HATU) and a base (such as TEA or DIPEA) in a suitable solvent such as DMF to afford A-4, which can be purified by standard techniques such as column chromatography, crystallization, salt formation or reverse phase HPLC. If necessary, separation of the enantiomers of A-4 may be carried out under standard methods known in the art such as chiral SFC or HPLC to afford single enantiomers of A-4.

For some of the steps of the here above described process of preparation of the compounds of the invention, it may be necessary to protect potential reactive functions that are not wished to react, and to cleave said protecting groups in consequence. In such a case, any compatible protecting radical may be used. In particular methods of protection and deprotection such as those described by T. W. Greene (*Protective Groups in Organic Synthesis*, A. Wiley-Interscience Publication, 1981) or by P. J. Kocienski (*Protecting groups*, Georg Thieme Verlag, 1994), may be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

In the following examples, "Et" means ethyl, "Ac" means acetyl, "Me" means methyl, "Ms" means methanesulfonyl ($CH_3SO_2$), "iPr" means isopropyl, "Ph" means phenyl, "Boc" or "boc" means tert-butoxycarbonyl, "EtOAc" means ethyl acetate, "HOAc" means acetic acid, "TEA", "$NEt_3$" or "$Et_3N$" means triethylamine, "THF" means tetrahydrofuran, "DIC" means diisopropylcarbodiimide, "HOBt" means hydroxy benzotriazole, "MeOH" means methanol, "i-PrOAc" means isopropyl acetate, "KOAc" means potassium acetate, "DMSO" means dimethylsulfoxide, "AcCl" means acetyl chloride, "$CDCl_3$," means deuterated chloroform, "TBME" or "MTBE" means methyl t-butyl ether, "DMF" means dimethyl formamide, "$Ac_2O$" means acetic anhydride, "$Me_3SOI$" means trimethylsulfoxonium iodide, "DMAP" means 4-dimethylaminopyridine, "dppf" means diphenylphosphino ferrocene, "DME" means ethylene glycol dimethyl ether, "KHMDS" means potassium bis(trimethylsilyl)amide, "HOBT" means 1-hydroxybenzotriazole, "EDC" means 1-ethyl-3-(3-dimethylaminopropyl)-carbodiimide, "LiHMDS" means lithium bis(trimethylsilyl)amide, "TLC" means thin layer chromatography, "n-BuLi" means n-butyl lithium, "h", "hr" or "hrs" means hours, "min." or "mins." means minutes, "DCM" or "$CH_2Cl_2$" means methylene chloride, "SEMCl" means 2-(Trimethylsilyl)ethoxymethyl chloride, "SEM" means 2-(Trimethylsilyl)ethoxymethyl, "$Et_2O$" means diethyl ether, "LC-MS" means liquid chromatography-mass spectrometry, "rt" means room temperature, "conc." means concentrated, "NBS" means N-bromosuccinimide, "MeCN" or "$CH_3CN$" means acetonitrile, "brine" means saturated aqueous sodium chloride, "Bn" or "Bz" means benzyl, "Tos" means tosyl (i.e. 4-toluenesulfonyl), "LAH" means lithium aluminum hydride, "PPTS" means pyridinium p-toluenesulfonate, "PTSA" p-toluenesulfonic acid, means "DHP" means dihydropyran, "DMP" means 2,2-dimethoxy-propane, "TMS" means trimethylsilyl, "NMP" means N-methyl-2-pyrrolidone, "sat." means saturated, "HATU" means 2-(7-Aza-1H-benzotriazole-1-yl)-1,1,3,3-tetramethyluronium hexafluoro-phosphate, "18-crown-6" means 1,4,7,10,13,16-hexaoxacyclooctadecane, and "Si-thiol" means 3-mercaptopropyl silica gel.

EXAMPLES

The following abbreviations may be used herein: Ac (acetyl); AcOH (acetic acid); $Ac_2O$ (acetic anhydride); aq. (aqueous); Boc (tert-butoxycarbonyl); ca. (about or approximately); $CH_2Cl_2$ (dichloromethane); DAST (Diethylaminosulfur trifluoride); DEA (diethylamine); DIPEA or Hunig's base (N,N-diisopropylethylamine); DMA (dimethylacetamide); DMF (dimethylformamide); DMSO (dimethylsulphoxide); Et (ethyl); $Et_3N$ or TEA (triethylamine); EtOH (ethanol); EtOAc (ethyl acetate); $Et_2O$ (diethyl ether); HATU (2-(7-aza-1H-benzotriazole-1-yl)-1,1,3,3-tetramethyluronium hexafluorophosphate); HBTU (o-(benzotriazole-1-yl)-1,1,3,3-tetramethyluronium hexafluorophosphate); HPLC (high-performance liquid chromatography); hr (hour or hours, as appropriate); IPA (iso-propyl alcohol); LCMS (liquid chromatography-mass spectrometry); Me (methyl);

MeOH (methanol); MeCN (acetonitrile); min (minute or minutes, as appropriate); MsCl (methanesulfonyl chloride); N (normal); NMR (nuclear magnetic resonance); Pd/C (palladium on carbon); Pd$_2$(dba)$_3$ (tris(dibenzylideneacetone)dipalladium(0)); Pd(dppf)Cl$_2$ ([1,1'-bis(diphenylphosphino)ferrocene]dichloropalladium(II)); Ph (phenyl); Rt (retention time); sec (second or seconds, as appropriate); SEM (2-Trimethylsilylethoxymethoxy); SFC (supercritical fluid chromatography); Si-Thiol (silica 1-propanethiol); T3P (propylphosphonic anhydride); TBME (tert-butyl methyl ether); t-BuOH (2-methyl-2-propanol, tert-butanol or tert-butyl alcohol); THF (tetrahydrofuran); TLC (thin layer chromatography); and TMSCI (trimethylsilyl chloride).

Synthesis of Intermediates

Synthesis of 3-(piperidin-4-yl)-1H-pyrazolo[3,4-b]pyridine hydrochloride (I-11)

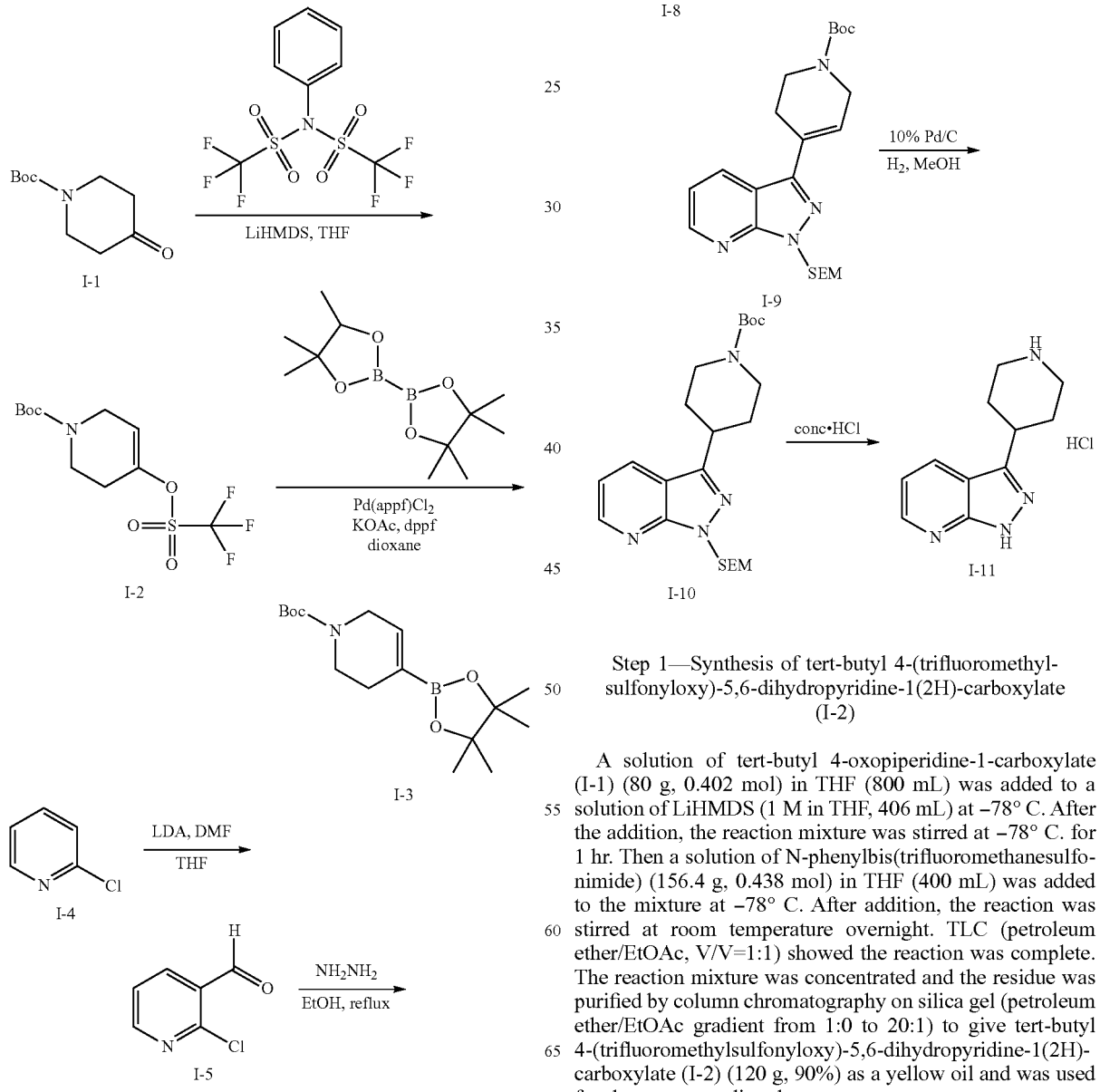

Step 1—Synthesis of tert-butyl 4-(trifluoromethylsulfonyloxy)-5,6-dihydropyridine-1(2H)-carboxylate (I-2)

A solution of tert-butyl 4-oxopiperidine-1-carboxylate (I-1) (80 g, 0.402 mol) in THF (800 mL) was added to a solution of LiHMDS (1 M in THF, 406 mL) at −78° C. After the addition, the reaction mixture was stirred at −78° C. for 1 hr. Then a solution of N-phenylbis(trifluoromethanesulfonimide) (156.4 g, 0.438 mol) in THF (400 mL) was added to the mixture at −78° C. After addition, the reaction was stirred at room temperature overnight. TLC (petroleum ether/EtOAc, V/V=1:1) showed the reaction was complete. The reaction mixture was concentrated and the residue was purified by column chromatography on silica gel (petroleum ether/EtOAc gradient from 1:0 to 20:1) to give tert-butyl 4-(trifluoromethylsulfonyloxy)-5,6-dihydropyridine-1(2H)-carboxylate (I-2) (120 g, 90%) as a yellow oil and was used for the next step directly.

Step 2—Synthesis of tert-butyl 4-(4,4,5,5-tetramethyl-1,3,2-dioxaborolan-2-yl)-5,6-dihydropyridine-1(2H)-carboxylate (I-3)

To a flask was added bis(pinacolato)diboron (101.28 g, 0.399 mol), KOAc (106.56 g, 1.087 mol), Pd(dppf)Cl$_2$·CH$_2$Cl$_2$ (8.88 g, 0.0109 mol) and dppf (6 g, 0.0109 mol) in 1,4-dioxane (1 L) and then degassed three times with N$_2$. A solution of tert-butyl 4-(trifluoromethylsulfonyloxy)-5,6-dihydropyridine-1(2H)-carboxylate (I-2) (120 g, 0.363 mol) in 1,4-dioxane (600 mL) was then added to the above mixture. After the addition, the reaction mixture was stirred at 80° C. overnight. TLC (petroleum ether/EtOAc=30:1) indicated the complete consumption of starting material. The reaction mixture was filtered and the filtrate was concentrated. The residue was purified by column chromatography on silica gel (petroleum ether/EtOAc 10:1) and recrystallized from EtOAc to give tert-butyl 4-(4,4,5,5-tetramethyl-1,3,2-dioxaborolan-2-yl)-5,6-dihydropyridine-1(2H)-carboxylate (I-3) (95 g, 85%) as a white solid.

Step 3—Synthesis of 2-chloronicotinaldehyde (I-5)

To a solution of diisopropylamine (35 g, 0.349 mol) in dry THF (300 mL) was added 2.5 M n-BuLi in hexane (140 mL, 0.349 mol) dropwise at 0° C. under N$_2$ atmosphere. After addition, the resulting mixture was stirred at 0° C. for 30 min and then cooled to −65° C. 2-chloropyridine (I-4) (36 g, 0.317 mol) was then added dropwise. The mixture was stirred at −65° C. for 2 hr at which time dry DMF (46 g, 0.634 mol) was added dropwise to the mixture at −65° C. After the addition, the reaction mixture was warmed to room temperature and stirred overnight. The mixture was quenched with H$_2$O (200 mL). The aqueous layer was extracted with EtOAc (200 mL). The combined organic layer was washed with brine (200 mL), dried over Na$_2$SO$_4$ and concentrated in vacuo to yield 2-chloronicotinaldehyde (I-5), which was used without further purification in the next step directly.

Step 4—Synthesis of 1H-pyrazolo[3,4-b]pyridine (I-6)

A stirred solution of 2-chloronicotinaldehyde (I-5) (5.1 g, 36 mmol) in EtOH (100 mL) and NH$_2$NH$_2$ (85% in H$_2$O, 50 mL) was heated to reflux for 24 hr. TLC (petroleum ether/EtOAc=1:1) showed the reaction was complete. The mixture was concentrated and separated between H$_2$O (100 mL) and EtOAc (200 mL). The aqueous layer was extracted with EtOAc (100 mL×2). The combined organic layers were washed with brine (100 mL), dried over Na$_2$SO$_4$ and concentrated in vacuo to give 1H-pyrazolo[3,4-b]pyridine (I-6) (4 g, 93%) as a yellow solid.

Step 5—Synthesis of 3-iodo-1H-pyrazolo[3,4-b]pyridine (I-7)

To a solution of 1H-pyrazolo[3,4-b]pyridine (I-6) (4 g, 34 mmol) in DMF (150 mL) was added KOH (7.6 g, 136 mmol) at 0° C. The mixture was stirred at room temperature for 30 min. To the resulting mixture was added iodine (15 g, 61 mmol) in portions at 0° C. and the mixture was stirred at room temperature overnight. TLC (petroleum ether/EtOAc=1:1) showed the reaction was complete. The reaction mixture was poured into ice water and extracted with CH$_2$Cl$_2$ (300 mL×2). The combined organic layers were washed with sat. aq.Na$_2$SO$_3$ (300 mL×2), brine (200 mL×3), dried over Na$_2$SO$_4$ and concentrated in vacuo to give 3-iodo-1H-pyrazolo[3,4-b]pyridine (I-7) (7 g, 84%) as a yellow solid.

Step 6—Synthesis of 3-iodo-1-((2-(trimethylsilyl)ethoxy)methyl)-1H-pyrazolo[3,4-b]pyridine (I-8)

To a solution of 3-iodo-1H-pyrazolo[3,4-b]pyridine (I-7) (7.2 g, 29 mmol) in DMF (250 mL) was added NaH (60%, 1.76 g, 44 mmol) in portions at 0° C. under N$_2$. The mixture was stirred at room temperature for 30 min. To the resulting mixture was added SEM-Cl (5.9 g, 35 mmol) dropwise at 0° C. and the mixture was stirred at room temperature overnight. TLC (petroleum ether/EtOAc=5:1) showed the reaction was complete. The reaction mixture was poured into water (300 mL) and extracted with Et$_2$O (400 mL×3). The combined organic layers were washed with brine (100 mL×3), dried over Na$_2$SO$_4$ and concentrated to give crude product, which was purified by column chromatography (petroleum ether/EtOAc 50:1) to give 3-iodo-1-((2-(trimethylsilyl)ethoxy)methyl)-1H-pyrazolo[3,4-b]pyridine (I-8) (7 g, 64%) as a white solid.

Step 7—Synthesis of tert-butyl 4-(1-((2-(trimethylsilyl)ethoxy)methyl)-1H-pyrazolo[3,4-b]pyridin-3-yl)-5,6-dihydropyridine-1(2H)-carboxylate (A-9)

To a mixture of 3-iodo-1-((2-(trimethylsilyl)ethoxy)methyl)-1H-pyrazolo[3,4-b]pyridine (I-8) (4.4 g, 11.56 mmol) and tert-butyl 4-(4,4,5,5-tetramethyl-1,3,2-dioxaborolan-2-yl)-5,6-dihydropyridine-1(2H)-carboxylate (I-3), (5 g, 16.18 mmol) in DME (100 mL) was added Cs$_2$CO$_3$ (11 g, 34.67 mmol), water (25 mL) and PdCl$_2$(dppf) (200 mg). The mixture was degassed by N$_2$ for three times and stirred under N$_2$ atmosphere at 80° C. overnight. TLC (petroleum ether/EtOAc=3:1) showed the reaction was complete. The mixture was cooled to room temperature, poured into water (200 mL) and extracted with EtOAc (100 mL×2). The combined organic layers were washed with brine (100 mL), dried over Na$_2$SO$_4$, concentrated and purified by column chromatography (petroleum ether/EtOAc 50:1) to give tert-butyl 4-(1-((2-(trimethylsilyl)ethoxy)methyl)-1H-pyrazolo[3,4-b]pyridin-3-yl)-5,6-dihydropyridine-1(2H)-carboxylate (I-9) (2 g, 40%) as a yellow solid.

Step 8—Synthesis of tert-butyl 4-(1-((2-(trimethylsilyl)ethoxy)methyl)-1H-pyrazolo[3,4-b]pyridin-3-yl)piperidine-1-carboxylate (I-10)

A mixture of tert-butyl 4-(1-((2-(trimethylsilyl)ethoxy)methyl)-1H-pyrazolo[3,4-b]pyridin-3-yl)-5,6-dihydropyridine-1(2H)-carboxylate (I-9) (2 g, 4.65 mmol) and 10% Pd/C (0.5 g) in MeOH (100 mL) was stirred under a H$_2$ balloon at 55° C. for 48 hr. LCMS showed starting material was consumed completely. The solution was filtered and concentrated in vacuo to a give crude oil, which was purified by column chromatography (petroleum ether/EtOAc 20:1) to give tert-butyl 4-(1-((2-(trimethylsilyl)ethoxy)methyl)-1H-pyrazolo[3,4-b]pyridin-3-yl)piperidine-1-carboxylate (I-10) (1 g, 50%) as a colorless oil.

Step 9—Synthesis of 3-(piperidin-4-yl)-1H-pyrazolo[3,4-b]pyridinehydrochloride (I-11)

A solution of tert-butyl 4-(1-((2-(trimethylsilyl)ethoxy)methyl)-1H-pyrazolo[3,4-b]pyridin-3-yl)piperidine-1-carboxylate (I-10) (1 g, 2.31 mmol) in conc. HCl (200 mL) was heated to reflux for 96 hr. The mixture was concentrated in vacuo to give 3-(piperidin-4-yl)-1H-pyrazolo[3,4-b]pyridinehydrochloride (I-11) (480 mg, yield 78%) as a yellow solid. $^1$H NMR (400 MHz, DMSO-d$_6$) δ ppm 9.10 (s, 2 H), 8.51 (d, 1 H), 8.40 (d, 1 H), 7.16-7.18 (m, 1 H), 3.38 (d, 3 H), 3.06 (s, 2 H), 2.13 (m, 4 H).

Synthesis of 6-(piperidin-4-yl)picolinamide dihydrochloride (I-17)

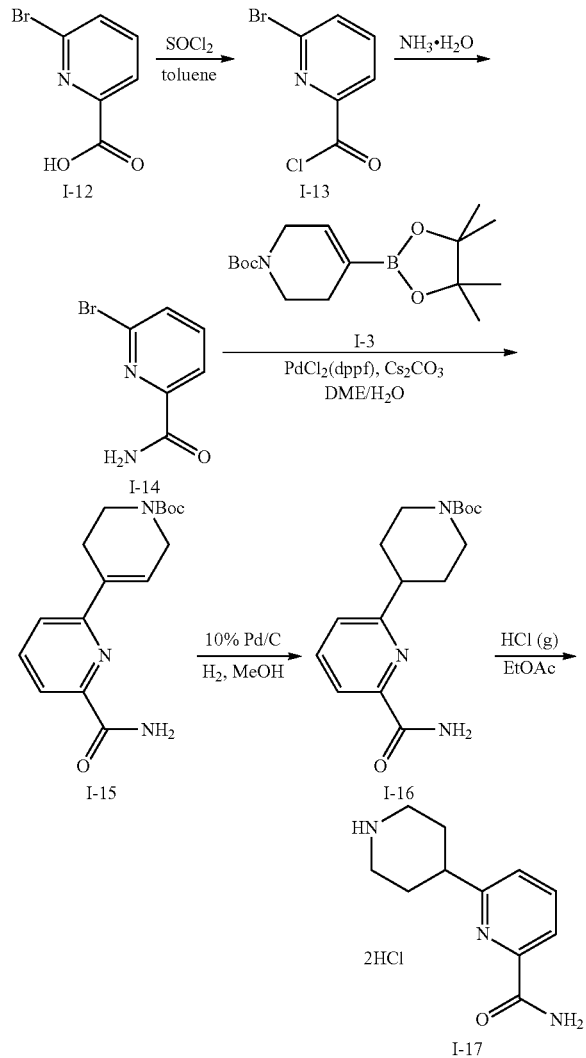

Step 1—Synthesis of 6-bromopicolinoyl chloride (I-13)

The reaction was done in two batches (2×49 g). To a stirred solution of 6-bromopicolinic acid (I-12) (49 g, 0.24 mol) in dry toluene (300 mL) was added SOCl$_2$ (100 mL) dropwise at room temperature. The mixture was heated to reflux for 2 hr. TLC (CH$_2$Cl$_2$:MeOH 10:1) showed the reaction was complete. The mixture was concentrated in vacuo to give 6-bromopicolinoyl chloride (I-13) as a yellow solid. Total yield for two batches 92 g (89%).

Step 2—Synthesis of 6-bromopicolinamide (I-14)

The reaction was done in 2 batches (2×46 g). To a stirred NH$_3$·H$_2$O (180 mL) was added a solution of 6-bromopicolinoyl chloride (I-13) (46 g, 0.21 mol) in THF (250 mL) dropwise at 0° C. After addition, the mixture was warmed to room temperature overnight. TLC (petroleum ether:EtOAc 2:1) showed the reaction was complete. The mixture was extracted with EtOAc (200 mL×3). The combined organic layers were washed with brine (400 mL), dried over Na$_2$SO$_4$ and filtered. The filtrate was concentrated in vacuo to give 6-bromopicolinamide (I-14) as a yellow solid. Total yield for two batches, 79 g (94%).

Step 3—Synthesis of tert-butyl 4-(6-carbamoylpyridin-2-yl)-5,6-dihydropyridine-1(2H)-carboxylate (I-15)

The reaction was done in 2 batches (2×25 g). To a stirred solution of 6-bromopicolinamide (I-14) (25 g, 0.124 mol) in a mixture of H$_2$O (124 mL) and dioxane (620 mL) was added tert-butyl 4-(4,4,5,5-tetramethyl-1,3,2-dioxaborolan-2-yl)-5,6-dihydropyridine-1(2H)-carboxylate (I-3) (42 g, 0.136 mol), CsCO$_3$ (122 g, 0.6 mol) and Pd(dppf)Cl$_2$ (2.5 g, 3 mmol) under a N$_2$ atmosphere at room temperature. After addition, the reaction was heated to reflux overnight. TLC (petroleum ether:EtOAc 2:1) showed the reaction was complete. The mixture was extracted with EtOAc (200 mL×3). The combined organic layers were washed with brine (400 mL), dried over Na$_2$SO$_4$ and concentrated in vacuo. The residue was purified by column chromatography on silica gel (from petroleum ether: EtOAc 5:1 to 2:1) to give tert-butyl 4-(6-carbamoylpyridin-2-yl)-5,6-dihydropyridine-1(2H)-carboxylate (I-15) as a white solid. Total yield for two batches, 74 g (90%).

Step 4—Synthesis of tert-butyl 4-(6-carbamoylpyridin-2-yl)piperidine-1-carboxylate (I-16)

The reaction was done in two batches (2×37 g). To a stirred solution of tert-butyl 4-(6-carbamoylpyridin-2-yl)-5,6-dihydropyridine-1(2H)-carboxylate (I-15) (37 g, 0.12 mol) in MeOH (500 mL) was added Pd/C (9.0 g, 10%) under H$_2$ balloon at room temperature. The mixture was stirred overnight at room temperature. LCMS showed the reaction was completed. The mixture was filtered, and the filtrate was concentrated in vacuo to give tert-butyl 4-(6-carbamoylpyridin-2-yl)piperidine-1-carboxylate (I-16) as a yellow oil. Total yield for two batches, 70 g (95%).

Step 5—Synthesis of 6-(piperidin-4-yl)picolinamide dihydrochloride (I-17)

To a stirred solution of tert-butyl 4-(6-carbamoylpyridin-2-yl)piperidine-1-carboxylate (I-16) (10 g, 0.033 mol) in EtOAc (300 mL) was added HCl (gas)/EtOAc (~5 N, 400 mL) dropwise at room temperature. After addition, the mixture was stirred for 1.5 hr. TLC (MeOH:CH$_2$Cl$_2$ 1:10) showed the reaction was complete. The reaction mixture was filtered to give 6-(piperidin-4-yl)picolinamide dihydrochloride (I-17) (50.03 g, 83%) as a white solid. $^1$H NMR (400 MHz, D$_2$O) δ ppm 8.08 (t, 1 H), 7.97 (d, 1 H), 7.66 (d, 1 H), 3.55 (d, 2 H), 3.14-3.27 (m, 3 H), 3.21 (d, 2 H) 2.03-2.10 (m, 2 H).

Synthesis of 3-amino-6-(piperidin-4-yl)picolinamide hydrochloride (I-24)

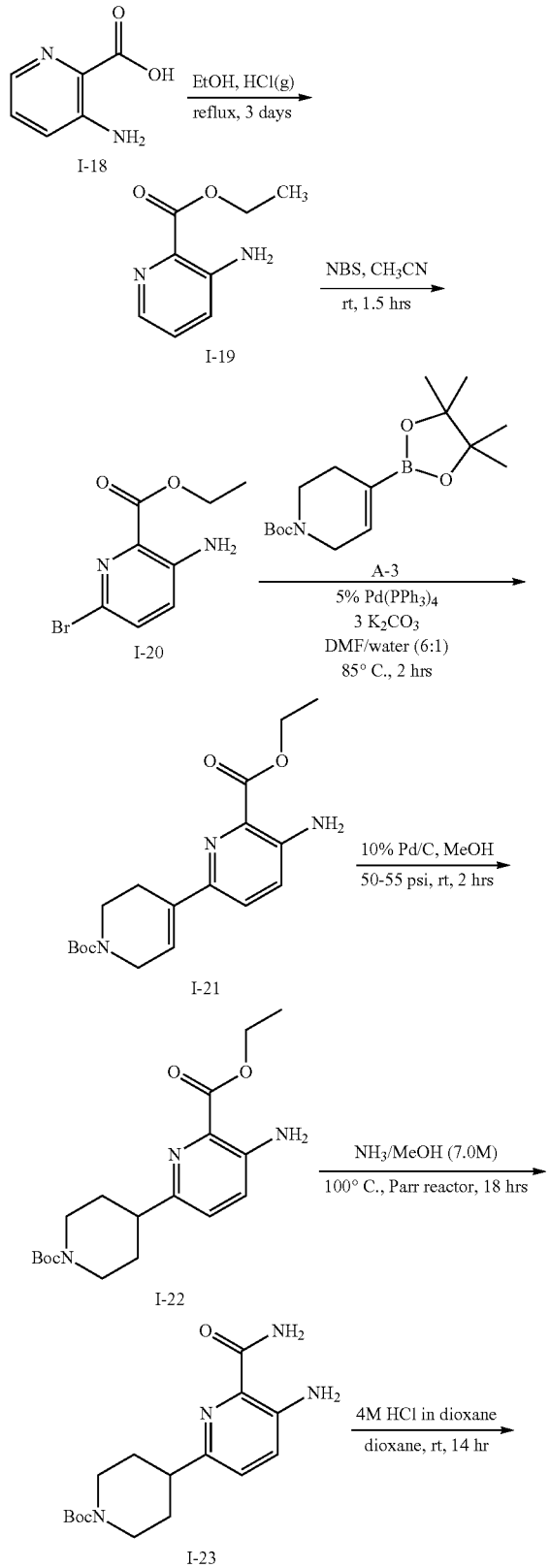

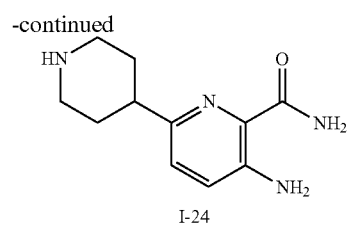

Step 1—Synthesis of ethyl 3-aminopicolinate (C-2)

A suspension of 3-aminopicolinic acid (I-18) (28 g, 200 mmoL, 1.0 eq) in EtOH (800 mL) at room temperature was bubbled with HCl (g) for 10 min. The reaction turned into a clear yellow solution. After being stirred at 100° C. for 1 day, LCMS indicated that about 50% of starting material remained. The reaction mixture was cooled to rt and bubbled with HCl (g) for 10 min. The mixture was then re-heated to 100° C. After being stirred at 100° C. for 1 day, LCMS indicated that about 50% of the starting material remained. The reaction mixture was cooled to rt and all solvents were removed under reduced pressure. The residue was resolved in EtOH (800 mL) and was bubbled with HCl (g) for 10 min. The resulting mixture was refluxed at 100° C. oil bath for 1 day. LCMS indicated about 70-75% conversion. The reaction mixture was cooled to rt and all solvents were removed under reduced pressure. The solid was dissolved in 250 mL water and the solution was quenched to pH=8-9 with saturated aq $Na_2CO_3$. A gas was generated and a white solid formed. The suspension was filtered, washed with water, and dried under vacuum at 65° C. to afford 22 g of ethyl 3-aminopicolinate (I-19) in 65% yield as a white solid. LCMS (APCI, M$^+$+1) 167.0; $^1$H NMR (300 MHz, DMSO-$d_6$) δ ppm 7.84 (dd, J=4.05, 1.60 Hz, 1 H), 7.23-7.30 (m, 1 H), 7.16-7.23 (m, 1 H), 6.65 (br. s., 2 H), 4.27 (q, J=7.10 Hz, 2 H), 1.30 (t, J=7.06 Hz, 3 H).

Step 2—Synthesis of ethyl 3-amino-6-bromopicolinate (I-20)

A mixture of ethyl 3-aminopicolinate (I-19) (21.3 g, 128 mmol, 1.0 eq), NBS (23 g, 129 mmol, 1.01 eq) in $CH_3CN$ (300 mL) was stirred at room temperature for 1.5 hr to reach completion. The reaction mixture was diluted with DCM (300 mL) and washed with water and $Na_2S_2O_3$. The organic layer was collected, dried over $MgSO_4$ and $Na_2SO_4$, filtered, and concentrated in vacuo to afford 29.5 g ethyl 3-amino-6-bromopicolinate (I-20) as a brown solid in 94% yield. LCMS (APCI, M$^+$+1) 245.0; $^1$H NMR (300 MHz, DMSO-$d_6$) δ ppm 7.44 (d, J=8.67 Hz, 1 H), 7.21 (d, J=8.85 Hz, 1 H), 6.87 (s, 2 H), 4.29 (q, J=7.03 Hz, 2 H), 1.31 (t, J=7.16 Hz, 3 H).

Step 3—Synthesis of ethyl 3-amino-6-(1-(tert-butoxycarbonyl)-1,2,3,6-tetrahydropyridin-4-yl)picolinate (I-21)

A mixture of ethyl 3-amino-6-bromopicolinate (I-20) (26 g, 110 mmol, 1.0 eq), 4-(4,4,5,5-tetramethyl-[1,3,2]dioxaborolan-2-yl)-3,6-dihydro-2H-pyridine-1-carboxylic acid tert-butyl ester (I-3) (37.7 g, 122 mmol, 1.15 eq), Pd(PPh$_3$)$_4$ (6.13 g, 5.30 mmol, 0.05 eq), $K_2CO_3$ (44 g, 318 mmol, 3.0 eq), DMF (300 mL) and water (50 mL) was heated to 85° C. under $N_2$. The reaction was stirred at 85° C. for 2 hr at which time Si-thiol was added and the suspension was stirred for 30 min. The reaction mixture was diluted with EtOAc and filtered through a short silica gel column. The filtrate was concentrated to afford crude product (I-21) used in the next step without further purification. LCMS (APCI, M⁺+1)=347.2.

Step 4—Synthesis of ethyl 3-amino-6-(1-(tert-butoxycarbonyl)piperidin-4-yl)picolinate (I-22)

A mixture of ethyl 3-amino-6-(1-(tert-butoxycarbonyl)-1,2,3,6-tetrahydropyridin-4-yl)picolinate (I-21) (25 g, 72 mmol, 1.0 eq) and Pd/C (10% on carbon, 10 mol %) in MeOH (200 mL) was hydrogenated under H$_2$ (50 psi) in Parr shaker. The reaction was stirred at 50-55 psi for 2 hr. The mixture was diluted with Et$_2$O, filtered through celite, and concentrated in vacuo to afford ethyl 3-amino-6-(1-(tert-butoxycarbonyl)piperidin-4-yl)picolinate (I-22) in quantitative yield. The crude product was taken to the next step without further purification. LCMS (APCI, M+1) 350.2.

Step 5—Synthesis of tert-butyl 4-(5-amino-6-carbamoylpyridin-2-yl)piperidine-1-carboxylate (I-23)

A mixture of ethyl 3-amino-6-(1-(tert-butoxycarbonyl)piperidin-4-yl)picolinate (I-22) (25 g, 72 mmol) and NH$_3$ solution (7.0 M in MeOH, 300 mL) was reacted at 100° C. in a Parr reactor for 18 hr. The reaction was cooled to rt and all solvent was removed in vacuo. The solid was triturated with EtOAc/heptane to afford 18 g tert-butyl 4-(5-amino-6-carbamoylpyridin-2-yl)piperidine-1-carboxylate (I-23) in 72% yield over three steps as a pale yellow solid. LCMS (APCI, M⁺+1) 321.2; $^1$H NMR (300 MHz, DMSO-d$_6$) δ ppm 7.82 (d, J=2.45 Hz, 1 H), 7.25 (d, J=2.64 Hz, 1 H), 7.12-7.19 (m, 1 H), 7.04-7.12 (m, 1 H), 6.66 (s, 2 H), 3.95-4.11 (m, 2 H), 2.60-2.89 (m, 3 H), 1.79 (d, J=11.11 Hz, 2 H), 1.54 (dd, J=12.53, 4.05 Hz, 2 H), 1.41 (s, 9 H).

Step 6—Synthesis of 3-amino-6-(piperidin-4-yl)picolinamide hydrochloride (I-24)

A mixture of tert-butyl 4-(5-amino-6-carbamoylpyridin-2-yl)piperidine-1-carboxylate (I-23) (8.0 g, 20 mmol, 1.0 eq), 4.0 M HCl in dioxane (15.6 mL, 62.4 mmol, 2.5 eq), dioxane (20 mL) was stirred at rt for 14 hr and a yellow suspension was obtained. The mixture was concentrated in vacuo to afford 6.0 g of 3-amino-6-(piperidin-4-yl)picolinamide hydrochloride (I-24) in 93% yield as a yellow solid. LCMS (APCI, M+1): 220.2; $^1$H NMR (300 MHz, DMSO-d$_6$) δ ppm 8.82-9.01 (m, 1 H), 8.49-8.76 (m, 1 H), 7.65-7.90 (m, 1 H), 7.31-7.51 (m, 1 H), 7.16 (d, J=3.58 Hz, 2 H), 3.23-3.41 (m, 2 H), 2.74-3.06 (m, 3 H), 1.77-2.11 (m, 4 H). One N—H proton was missing due to deuterium exchange.

Synthesis of 4-methyl-3-(piperidin-4-yl)-1H-pyrazolo[3,4-b]pyridine hydrochloride (I-34)

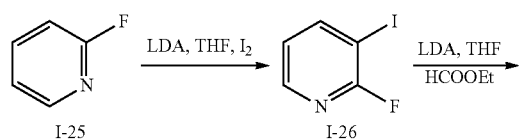

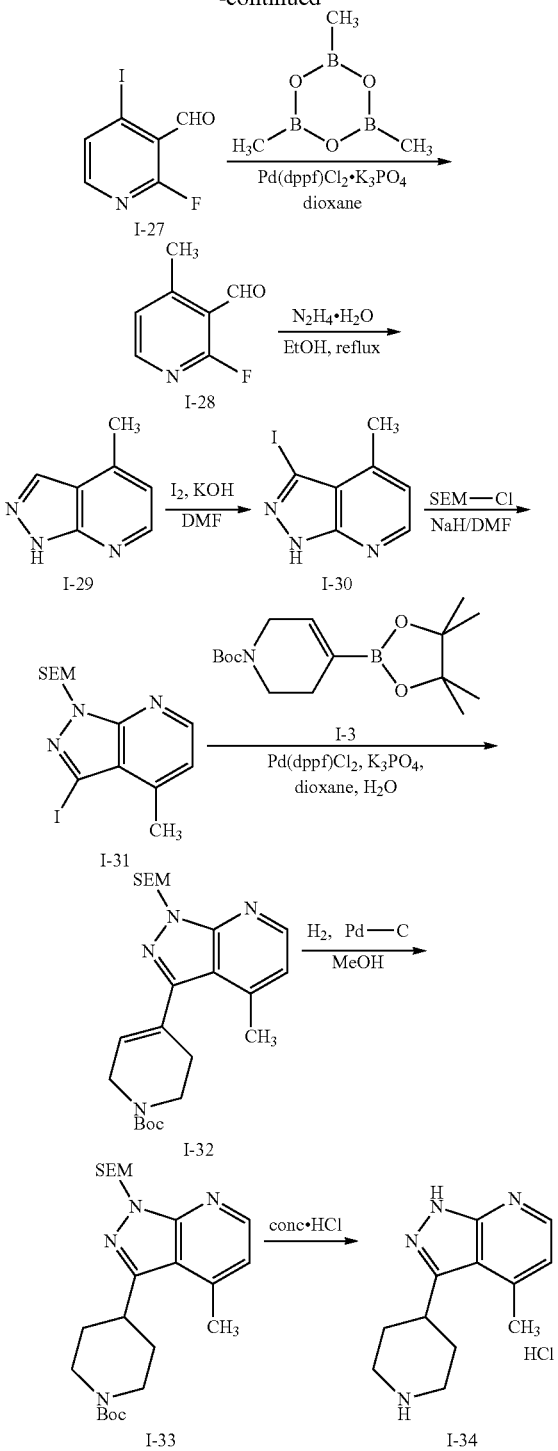

Step 1—Synthesis of 2-fluoro-3-iodopyridine (I-26)

To a solution of diisopropylamine (104 g, 1.03 mol) in dry THF (2.6 L) was added dropwise 2.5 M solution of n-BuLi in hexane (392 mL, 0.98 mol) at −30 to −40° C. under N$_2$. The resulting mixture was stirred at 0° C. for 35 min. The mixture was cooled to −70° C. and a solution of 2-fluoropyridine (I-25) (100 g, 1.03 mol) in dry THF (800 mL) was added. After stirring at −70° C. for 2 hr, the mixture was added to a solution of $I_2$ (261.6 g, 1.03 mol) in dry THF (800 mL) at −20° C. under $N_2$. After the reaction was complete, the mixture was quenched with ice water (4 L). The mixture was diluted with EtOAc (4 L) and washed with aq. $Na_2S_2O_3$ (500 mL) and brine (500 mL). The organic layer was dried over $Na_2SO_4$ and concentrated in vacuo. The residue was purified by distillation in vacuum to afford 2-fluoro-3-iodopyridine (I-26) (140 g, 61%) as a yellow solid.

Step 2—Synthesis of
2-fluoro-4-iodonicotinaldehyde (I-27)

To a solution of diisopropylamine (174.4 g, 1.73 mol) in dry THF (3 L) was added dropwise 2.5 M solution of n-BuLi in hexane (685 mL, 1.71 mol) at −10° C. The resulting mixture was stirred at 0° C. for 35 min. The mixture was cooled to −70° C. and a solution of 2-fluoro-3-iodopyridine (I-26) (350 g, 1.57 mol) in dry THF (1 L) was added. The mixture was stirred at −70° C. for 2 hr. HCOOEt (128 g, 1.73 mol) was added dropwise at −70° C. After the addition, the mixture was allowed to warm to room temperature and quenched with ice water (4 L). The mixture was diluted with EtOAc (4 L) and washed with brine (500 mL). The organic layer was dried over $Na_2SO_4$ and concentrated in vacuo. The residue was purified by silica gel chromatography eluted with petroleum:EtOAc=10:1 to afford 2-fluoro-4-iodonicotinaldehyde (I-27) (180 g, 46%) as a yellow solid. $^1$H NMR (400 MHz, $CDCl_3$) δ ppm 10.08 (s, 1 H), 7.91 (d, 1 H), 7.81 (d, 1 H).

Step 3—Synthesis of
2-fluoro-4-methylnicotinaldehyde (I-28)

A mixture of 2-fluoro-4-iodonicotinaldehyde (I-27) (75 g, 0.3 mol), 2,4,6-trimethyl-1,3,5,2,4,6-trioxatriborinane (188.3 g, 1.5 mol), $K_3PO_4$ (127.2 g, 0.6 mol) and Pd(dppf)$Cl_2CH_2Cl_2$ (4.9 g, 6 mmol) in dry dioxane (1.2 L) was degassed with $N_2$ for 4 times and then heated at reflux for 2 hr. The mixture was cooled and filtered. The filtrate was concentrated in vacuo and the residue was purified by silica gel chromatography eluted with petroleum ether:EtOAc=10:1 to afford 2-fluoro-4-methylnicotinaldehyde (I-28) (41.5 g, 99%) as a slight yellow oil.

Step 4—Synthesis of
4-methyl-1H-pyrazolo[3,4-b]pyridine (I-29)

A mixture of 2-fluoro-4-methylnicotinaldehyde (I-28) (83 g, 0.59 mol) and $N_2H_4 \cdot H_2O$ (85% in water, 810 mL) was heated at reflux for 6 hr. TLC (petroleum ether:EtOAc=3:1) showed the reaction was complete. The mixture was concentrated in vacuo to about 200 mL and poured into ice water (1 L) and extracted with EtOAc (500 mL×3). The extract was concentrated in vacuo to afford 4-methyl-1H-pyrazolo[3,4-b]pyridine (I-29) (70 g, 88%) as a white solid. $^1$H NMR (400 MHz, $CDCl_3$) δ ppm 12.45 (br. s., 1 H), 8.42 (d, 1 H), 8.07 (s, 1 H), 6.91 (d, 1 H), 2.59 (s, 3 H).

Step 5—Synthesis of
3-iodo-4-methyl-1H-pyrazolo[3,4-b]pyridine (I-30)

To a suspension of 4-methyl-1H-pyrazolo[3,4-b]pyridine (I-29) (44 g, 0.33 mol) in DMF (1 L) was added KOH (74 g, 1.32 mol) at 0° C. After addition, the mixture was stirred at room temperature for 30 min. $I_2$ (168 g, 0.66 mol) was added in portions at 0° C. The mixture was stirred at room temperature overnight. The mixture was poured into ice water (2 L) and extracted with EtOAc (1 L×6). The extract was washed with $Na_2S_2O_3$ aq (200 mL) and concentrated in vacuo to afford 3-iodo-4-methyl-1H-pyrazolo[3,4-b]pyridine (I-30) (66 g, 77%) as a yellow solid. $^1$H NMR (400 MHz, $CDCl_3$) δ ppm 10.14 (s, 1 H), 8.23 (d, 1 H), 7.12 (d, 1 H), 2.68 (s, 3 H).

Step 6—Synthesis of 3-iodo-4-methyl-1-((2-(trimethylsilyl)ethoxy)methyl)-1H-pyrazolo[3,4-b]pyridine (I-31)

To a solution of 3-iodo-4-methyl-1H-pyrazolo[3,4-b]pyridine (I-30) (45 g, 0.17 mol) in DMF (1.3 L) was added 60% NaH (10.5 g, 0.26 mol) in portions at 0° C. After stirring at 0° C. for 30 min, SEM-Cl (34.8 g, 0.21 mol) was added to the mixture at 0° C. After the addition, the mixture was warmed to room temperature and stirred for 2 hr. TLC (petroleum ether:EtOAc=3:1) showed the reaction was complete. The mixture was poured into ice water (1 L) and extracted with EtOAc (3×1 L). The extract was washed with brine (500 mL×2), dried over $Na_2SO_4$ and concentrated in vacuo. The residue was purified by silica gel chromatography eluted with petroleum ether:EtOAc=10:1 to afford 3-iodo-4-methyl-1-((2-(trimethylsilyl)ethoxy)methyl)-1H-pyrazolo[3,4-b]pyridine, (I-31) (45 g, 66%) as a slightly yellow solid. $^1$H NMR (400 MHz, $CDCl_3$) δ ppm 8.42 (d, 1 H), 6.94 (d, 1 H), 5.81 (s, 2 H), 3.66 (t, 2 H), 2.84 (s, 3 H), 0.94 (t, 2 H), −0.05 (s, 9 H).

Step 7—Synthesis of tert-butyl 4-(4-methyl-1-((2-(trimethylsilyl)ethoxy)methyl)-1H-pyrazolo[3,4-b]pyridin-3-yl)-5,6-dihydropyridine-1(2H)-carboxylate (I-32)

A mixture of 3-iodo-4-methyl-1-((2-(trimethylsilyl)ethoxy)methyl)-1H-pyrazolo[3,4-b]pyridine (I-31) (21 g, 53.8 mmol), tert-butyl 4-(4,4,5,5-tetramethyl-1,3,2-dioxaborolan-2-yl)-5,6-dihydropyridine-1(2H)-carboxylate (I-3) (19 g, 61.5 mmol), $K_3PO_4 \cdot 3H_2O$ (28.6 g, 107.6 mmol) and Pd(dppf)$Cl_2CH_2Cl_2$ (0.88 g, 1.1 mmol) in a mixture of dioxane (420 mL) and water (105 mL) was degassed with $N_2$ for 4 times and heated at reflux for 2 hr. TLC (petroleum ether:EtOAc=3:1) showed the reaction was complete. The mixture was diluted with EtOAc (1.5 L), washed with water (50 mL) and brine (500 mL×2). The organic layer was dried over $Na_2SO_4$ and concentrated in vacuo. The residue was purified by silica gel chromatography eluted with petroleum ether:EtOAc=4:1 to afford tert-butyl 4-(4-methyl-1-((2-(trimethylsilyl)ethoxy)methyl)-1H-pyrazolo[3,4-b]pyridin-3-yl)-5,6-dihydropyridine-1(2H)-carboxylate (I-32) (22.9 g, 95.8%) as a slight yellow oil. $^1$H NMR (400 MHz, $CDCl_3$) δ ppm 8.40 (d, 1 H), 6.92 (d, 1 H), 5.95 (br, 1 H), 5.82 (s, 2 H), 4.12 (m, 2 H), 3.69 (m, 4 H), 2.63 (m, 5 H), 1.50 (s, 9 H), 0.94 (t, 2 H), −0.07 (s, 9 H).

Step 8—Synthesis of tert-butyl 4-(4-methyl-1-((2-(trimethylsilyl)ethoxy)methyl)-1H-pyrazolo[3,4-b]pyridin-3-yl)piperidine-1-carboxylate (I-33)

A mixture of tert-butyl 4-(4-methyl-1-((2-(trimethylsilyl)ethoxy)methyl)-1H-pyrazolo[3,4-b]pyrindin-3-yl)-5,6-dihydropyridine-1(2H)-carboxylate (I-32) (22 g, 49.5 mmol) and Pd/C (3 g) in MeOH (400 mL) was degassed with $H_2$ for 4 times. The mixture was stirred at 50° C. under $H_2$ balloon for 3 hr. TLC (petroleum ether:EtOAc=8:1) showed the reaction was complete. The mixture was cooled to room temperature and filtered. The filtrate was concentrated in vacuo to afford tert-butyl 4-(4-methyl-1-((2-(trimethylsilyl)ethoxy)methyl)-1H-pyrazolo[3,4-b]pyridin-3-yl)piperidine-1-carboxylate (I-33) (22 g, 99%) as a slightly yellow oil. ¹H NMR (400 MHz, CDCl₃) δ ppm 8.36 (d, 1 H), 6.88 (d, 1 H), 5.78 (s, 2 H), 4.24 (br. s., 2 H), 3.63 (t, 2 H), 3.48 (m, 1 H), 2.90 (br. s., 2 H), 2.69 (s, 3 H), 1.96 (br. s., 4 H), 1.47 (s, 9 H), 0.92 (t, 2 H), −0.08 (s, 9 H).

Step 9—Synthesis of 4-methyl-3-(piperidin-4-yl)-1H-pyrazolo[3,4-b]pyridine hydrochloride (I-34)

A mixture of tert-butyl 4-(4-methyl-1-((2-(trimethylsilyl)ethoxy)methyl)-1H-pyrazolo[3,4-b]pyridin-3-yl)piperidine-1-carboxylate (I-33) (20 g, 45 mmol) and conc. HCl (300 mL) was heated to reflux overnight. TLC (CH₂Cl₂:MeOH=10:1) showed the reaction was not complete. The mixture was concentrated in vacuo to dryness. The residue was dissolved in concentrated HCl (300 mL) and heated to reflux overnight. TLC (CH₂Cl₂:MeOH=10:1) showed the reaction was not complete. The mixture was concentrated in vacuo to dryness. The residue was dissolved in conc. HCl (500 mL) and heated to reflux overnight. TLC (CH₂Cl₂:MeOH=10:1) showed the reaction was complete. Concentrated HCl was evaporated in vacuo. The residue was trituted with a mixture of CH₂Cl₂ (100 mL) and MeOH (5 mL). The solid formed was collected and dried in vacuo at 40° C. to afford 4-methyl-3-(piperidin-4-yl)-1H-pyrazolo[3,4-b]pyridine hydrochloride (I-34) (10 g, 80%) as a white solid. ¹H NMR (400 MHz, D₂O) δ ppm 8.46 (d, 1 H), 7.35 (d, 1 H), 3.76 (m, 1 H), 3.60 (d, 2H), 3.27 (t, 2 H), 2.89 (s, 3 H), 2.34 (d, 2 H), 2.15 (m, 2 H). MS: m/z 217.5 [M+H]⁺.

Synthesis of 3-piperidin-4-yl-1H-pyrrolo[2,3-b]pyridine (I-37)

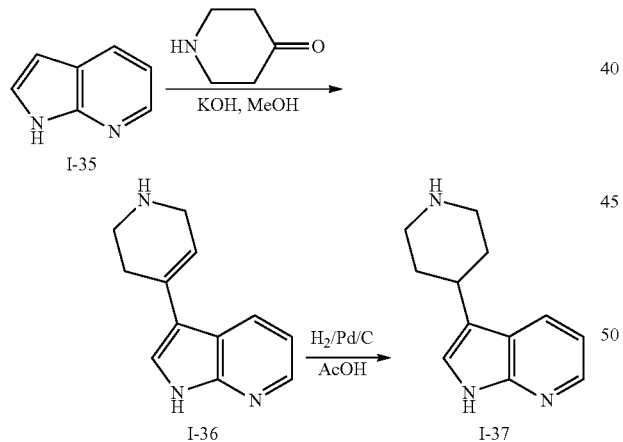

Step 1—Synthesis of 3-(1,2,3,6-tetrahydropyridin-4-yl)-1H-pyrrolo[2,3-b]pyridine (I-36)

A mixture of 7-azaindole (I-35) (1.5 g, 13 mmol) and 4-piperidone (3.12 g, 20.3 mmol) in methanol (35.3 mL) was treated with aq KOH (2 M, 25.4 mL). The resulting mixture was heated at 80° C. for 18 hr. The dark solution was concentrated to remove methanol, diluted with brine then extracted 5 times with EtOAc. The combined organics were washed with brine, dried over MgSO₄ and reduced to minimum volume in vacuo. The residue was triturated with TBME to obtain 1.9 g (75%) of 3-(1,2,3,6-tetrahydropyridin-4-yl)-1H-pyrrolo[2,3-b]pyridine (I-36) as a yellow solid. ¹H NMR (400 MHz, CDCl₃) δ ppm 9.23 (br. s., 1 H), 8.32 (dd, J=4.80, 1.26 Hz, 1 H), 8.21 (dd, J=7.96, 1.39 Hz, 1 H), 7.29 (s, 1 H), 7.12 (dd, J=7.83, 4.80 Hz, 1 H), 6.14-6.33 (m, 1 H), 3.60 (q, J=2.61 Hz, 2 H), 3.16 (t, J=5.81 Hz, 2 H), 2.46-2.57 (m, 2 H).

Step 2—Synthesis of 3-piperidin-4-yl-1H-pyrrolo[2,3-b]pyridine (I-37)

To a solution of 3-(1,2,3,6-tetrahydropyridin-4-yl)-1H-pyrrolo[2,3-b]pyridine (I-36) (4 g, 20 mmol) in EtOH (100 mL) and acetic acid (4 mL) was added 20% Palladium hydroxide on carbon (1.6 g). The mixture was sealed in the Parr hydrogenation apparatus and evacuated and charged with N₂ 3 times, evacuated and charged with H₂ 3 times. The apparatus was charged with H₂ to 100 psi and heated at 50° C. with stirring for 28 hr. The mixture was filtered through Celite and the filter cake rinsed with EtOH. The filtrate was reduced to minimum volume to give 5.7 g of the acetate salt of 3-piperidin-4-yl-1H-pyrrolo[2,3-b]pyridine as a tan solid (I-37) ¹H NMR (400 MHz, CDCl₃) δ ppm 10.17 (br. s., 1 H), 8.22 (d, J=4.29 Hz, 1 H), 8.06 (dd, J=7.83, 1.01 Hz, 1 H), 7.15 (s, 1 H), 7.10 (dd, J=7.83, 4.80 Hz, 1 H), 3.51 (d, J=12.63 Hz, 2 H), 2.87-3.14 (m, 3 H), 2.09-2.18 (m, 4 H, partially obscured by acetic acid).

Synthesis of 5-(2-(dimethylamino)ethoxy)-6-(piperidin-4-yl)picolinamide hydrochloride (I-42)

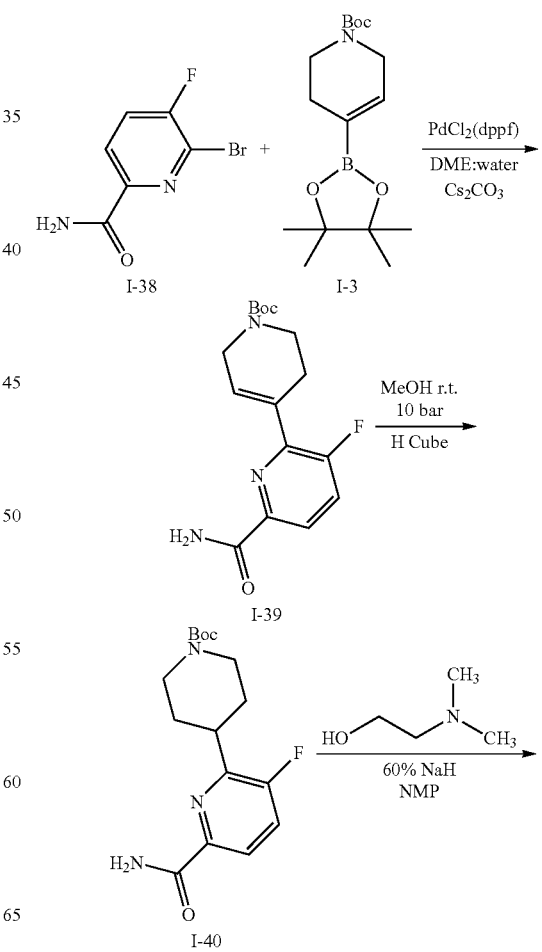

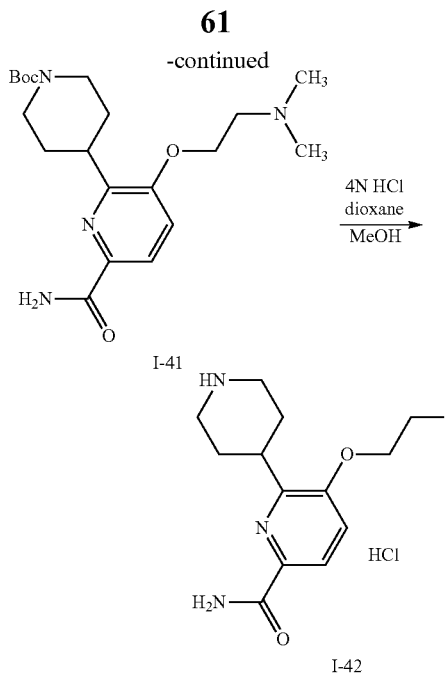

Step 1—Synthesis of tert-butyl 4-(6-carbamoyl-3-fluoropyridin-2-yl)-5,6-dihydropyridine-1(2H)-carboxylate (I-39)

6-bromo-5-fluoropicolinamide (I-38) (200 mg, 0.9 mmol) was combined with tert-butyl 4-(4,4,5,5-tetramethyl-1,3,2-dioxaborolan-2-yl)-5,6-dihydropyridine-1(2H)-carboxylate (I-3) (310 mg) and Pd(dppf)Cl$_2$ (74.3 mg, 0.09 mmol) and cesium carbonate (892 mg, 2.74 mmol) and water (1 mL) and 1,2-dimethoxyethane (10 mL). The reaction mixture was degassed three times. After the reaction mixture was stirred at r.t. overnight and heated at 100° C. for 45 mins, LCMS showed complete consumption of starting material. The reaction mixture was passed through Chem Elute and the column was washed with ethyl acetate. The eluent was concentrated and purified via 40 g column eluted with 0-100% EtOAc:heptanes to give tert-butyl 4-(6-carbamoyl-3-fluoropyridin-2-yl)-5,6-dihydropyridine-1(2H)-carboxylate (I-39) (220 mg, 75%). $^1$H NMR (400 MHz, CDCl$_3$) δ ppm 8.11 (dd, J=8.34, 3.54 Hz, 1 H), 7.65 (br. s., 1 H), 7.49-7.59 (m, 1 H), 6.65 (br. s., 1 H), 5.57 (br. s., 1 H), 4.18 (d, J=2.02 Hz, 2 H), 3.67 (t, J=5.68 Hz, 2 H), 2.72 (br. s., 2 H), 1.52 (s, 9 H).

Step 2—Synthesis of tert-butyl 4-(6-carbamoyl-3-fluoropyridin-2-yl)piperidine-1-carboxylate (I-40)

A solution of tert-butyl 4-(6-carbamoyl-3-fluoropyridin-2-yl)-5,6-dihydropyridine-1(2H)-carboxylate (I-39) (20 mg, 0.062 mmol) in 2.0 mL of MeOH was hydrogenated with the ThalesNano H Cube at room temperature and 10 bar H$_2$ pressure using a 10% Pd(OH)$_2$ cartridge. After the first pass, LCMS showed the desired product. The reaction mixture was concentrated to give tert-butyl 4-(6-carbamoyl-3-fluoropyridin-2-yl)piperidine-1-carboxylate; 20 mg (I-40) (quantitative yield).

Step 3—Synthesis of tert-butyl 4-(6-carbamoyl-3-(2-(dimethylamino)ethoxy)-pyridin-2-yl)piperidine-1-carboxylate (I-41)

To a dry flask was added 2-dimethylamino ethanol (110 mg, 0.31 mmol) and NMP 91.24 mL). To the reaction was added 60% NaH in mineral oil (49.5 mg, 1.24 mmol). After the reaction mixture was stirred at room temperature for 30 mins under nitrogen, tert-butyl 4-(6-carbamoyl-3-fluoropyridin-2-yl)piperidine-1-carboxylate (I-40) (100 mg, 0.31 mmol) was added. The reaction mixture was stirred at room temperature overnight then heated in microwave at 80° C. for 30 mins. LCMS showed completed conversion to the desired product. The crude reaction mixture was purified via reversed phase HPLC eluted with 0.1% acetic acid in acetonitrile and 0.1% acetic acid in water to give tert-butyl 4-(6-carbamoyl-3-(2-(dimethylamino)ethoxy)pyridin-2-yl)piperidine-1-carboxylate (I-41) as a white solid (85 mg. 70%). $^1$H NMR (400 MHz, CDCl$_3$) δ ppm 8.04 (d, J=8.59 Hz, 1 H), 7.72 (br. s., 1 H), 7.21 (d, J=8.59 Hz, 1 H), 5.42 (br. s., 1 H), 4.19-4.35 (m, 2 H), 4.15 (t, J=5.81 Hz, 2 H), 3.28 (s, 1 H), 2.83-2.93 (m, 2 H), 2.80 (t, J=5.81 Hz, 2 H), 2.37 (s, 6 H), 1.75-1.90 (m, 4 H), 1.49 (s, 9 H).

Step 4—Synthesis of 5-(2-(dimethylamino)ethoxy)-6-(piperidin-4-yl)picolinamide hydrochloride (I-42)

To a stirred solution of tert-butyl 4-(6-carbamoyl-3-(2-(dimethylamino)ethoxy)-pyridin-2-yl)piperidine-1-carboxylate (I-41) (75 mg, 0.19 mmol) in 10 mL of MeOH was added 1 mL of 4N HCl in dioxane at room temperature. After the reaction mixture was stirred at 50° C. for 2 hr, LCMS showed complete reaction. The reaction mixture was concentrated in vacuo to give 5-(2-(dimethylamino)ethoxy)-6-(piperidin-4-yl)picolinamide hydrochloride 56 mg (I-42) (quantitative yield) as a white solid.

Synthesis of 6-methoxy-4-(piperidin-4-yloxy)-1H-indazol-3-amine (I-46)

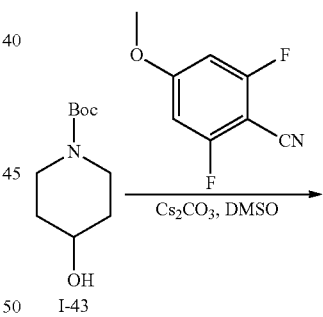

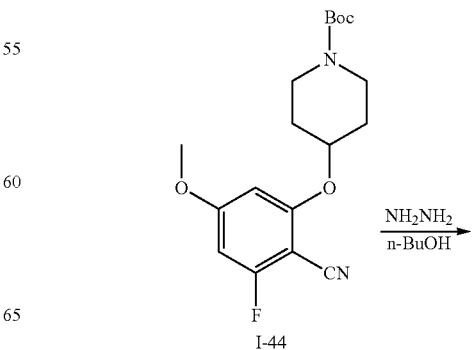

64

Synthesis of tert-butyl 4-{[(methylsulfonyl)oxy]methyl}piperidine-1-carboxylate (I-48)

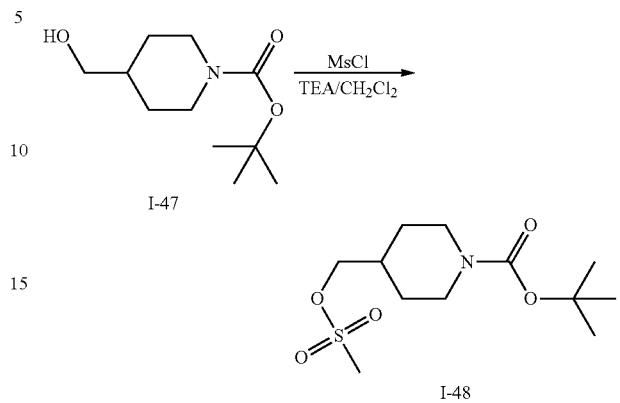

Step 1—Synthesis of tert-butyl 4-{[(methylsulfonyl)oxy]methyl}piperidine-1-carboxylate (I-48)

To a mixture of tert-butyl 4-(hydroxymethyl)piperidine-1-carboxylate (I-47) (100.0 g, 464 mmol) and TEA (94.0 g, 929 mmol) in dry $CH_2Cl_2$ (600 mL) was added in a dropwise manner MsCl (81.57 g, 712.1 mmol) at 0° C. under $N_2$. The resulting mixture was stirred at 0° C. for 3 hr. TLC (petroleum ether/EtOAc=1:1) showed the reaction was complete. The mixture was quenched with 150 mL of water, and the separated organic layer was washed with brine (100 mL). The organic layers were dried over $Na_2SO_4$ and concentrated in vacuo to dryness to give tert-butyl 4-{[(methylsulfonyl)oxy]methyl}piperidine-1-carboxylate (I-48) (143 g, >100%) as a colorless solid, which was used without further purification.

Synthesis of tert-butyl 4-(([2-amino-5-(4,4,5,5-tetramethyl-1,3,2-dioxaborolan-2-yl)pyridin-3-yl]oxy}methyl)piperidine-1-carboxylate (I-55)

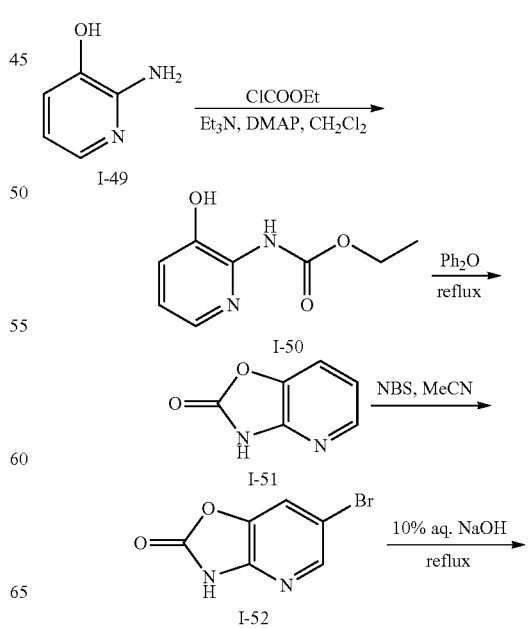

63

-continued

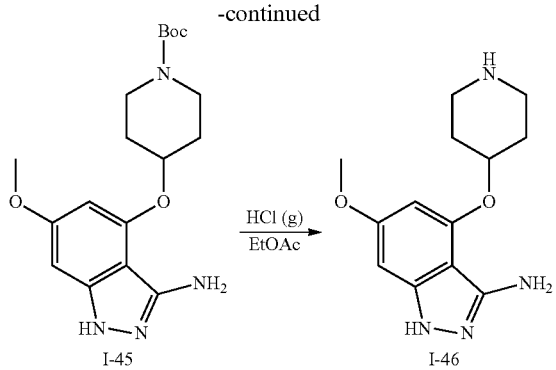

Step 1—Synthesis of tert-butyl 4-(2-cyano-3-fluoro-5-methoxyphenoxy)piperidine-1-carboxylate (I-44)

A solution of tert-butyl 4-hydroxypiperidine-1-carboxylate (I-43) (10 g, 0.049 mol), 2,6-difluoro-4-methoxybenzonitrile (8.4 g, 0.049 mol) and $Cs_2CO_3$ (47 g, 0.147 mol) in DMSO (20 mL) was stirred at 80° C. for 1 hr. TLC (petroleum ether/EtOAc=3/1) indicated the reaction was done. Brine (20 mL) was added and the reaction was extracted with EtOAc (2×100 mL). The combined organic layers were washed with brine (20 mL×3), dried over $Na_2SO_4$ and concentrated in vacuo. The residue was purified by silica gel chromatography (petroleum ether/EtOAc=3/1) to yield tert-butyl 4-(2-cyano-3-fluoro-5-methoxyphenoxy)piperidine-1-carbon/late (I-44) (9.5 g, 55%) as a yellow solid.

Step 2—Synthesis of tert-butyl 4-[(3-amino-6-methoxy-1H-indazol-4-yl)oxy]piperidine-1-carboxylate (I-45)

A solution of tert-butyl 4-(2-cyano-3-fluoro-5-methoxyphenoxy)piperidine-1-carboxylate (I-44) (9.5 g, 0.027 mol) and $NH_2NH_2 \cdot H_2O$ (2.71 g, 0.054 mol) in n-BuOH (50 mL) was heated at reflux overnight. TLC (petroleum ether/EtOAc=1/1) indicated the reaction was done. The mixture was concentrated and purified by silica gel chromatography (EtOAc) to yield tert-butyl 4-[(3-amino-6-methoxy-1H-indazol-4-yl)oxy]piperidine-1-carboxylate (I-45) (7 g, 72%) as a yellow solid.

Step 3—Synthesis of 6-methoxy-4-(piperidin-4-yloxy)-1H-indazol-3-amine (I-46)

A mixture of tert-butyl 4-[(3-amino-6-methoxy-1H-indazol-4-yl)oxy]piperidine-1-carboxylate (I-45) (7 g, 19.3 mmol) in HCl (g)/EtOAc (30 mL, ~4 N) was stirred at room temperature for 2 h. TLC (petroleum ether/EtOAc=1/2) indicated the reaction was complete. The precipitate was filtered, and dried under vacuum to yield 6-methoxy-4-(piperidin-4-yloxy)-1H-indazol-3-amine hydrochloride (I-46) (3.9 g, 60%) as a white solid. LCMS (APCI, M+1): 263.2; $^1H$ NMR (400 MHz, $D_2O$) δ ppm 6.34 (s, 1 H), 6.18 (s, 1 H), 4.76 (s, 1 H), 3.77 (s, 3 H), 3.37-3.40 (m, 2 H), 3.16-3.20 (m, 2 H), 2.21-2.25 (m, 2 H), 1.97-2.06 (m, 2 H).

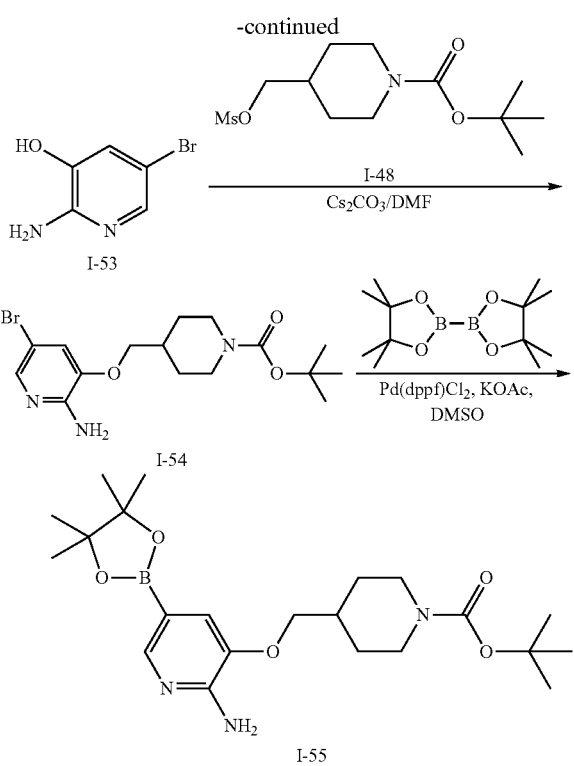

Step 1—Synthesis of ethyl (3-hydroxypyridin-2-yl)carbamate (I-50)

To a stirred solution of 3-hydroxy-2-aminopyridine (I-49) (100 g, 0.9 mol) in dry $CH_2Cl_2$ (1 L) were added TEA (182 g, 1.8 mol) and DMAP (7.3 g, 0.06 mol) at 0° C. Then ClCOOEt (100.4 g, 0.93 mol) was added in a dropwise manner. After the addition, the reaction mixture was stirred at room temperature overnight. TLC (EtOAc/hexane=1:1) indicated the reaction was complete. The reaction mixture was washed with water (3×100 m) and 3 N aqueous HCl (300 mL). The separated aqueous layer was neutralized to a pH~7 with $NaHCO_3$ powder and re-extracted with $CH_2Cl_2$ (3×1 L). The combined organic layers were washed with brine (0.8 L), dried over $Na_2SO_4$ and concentrated in vacuo to afford ethyl (3-hydroxypyridin-2-yl)carbamate (I-50) (106 g, 64%) as a yellow solid, which was used without further purification.

Step 2—Synthesis of [1,3]oxazolo[4,5-b]pyridin-2(3H)-one (I-51)

A solution of ethyl (3-hydroxypyridin-2-yl)carbamate (I-50) (106 g, 0.58 mol) in diphenyl ether (1 L) was stirred at reflux for 2 hr. TLC (EtOAc/hexane=1:1) indicated the reaction was complete. The mixture was allowed to cool to room temperature, and the precipitate formed was collected by filtration, washed with petroleum ether (0.5 L) and dried in vacuo to provide [1,3]oxazolo[4,5-b]pyridin-2(3H)-one (I-51) (68 g, 86%) as a yellow-green solid, which was used without further purification.

Step 3—Synthesis of 6-bromo[1,3]oxazolo[4,5-b]pyridin-2(3H)-one (I-52)

To a stirred suspension of [1,3]oxazolo[4,5-b]pyridin-2 (3H)-one (I-51) (34 g, 0.25 mol) in MeCN (0.35 L) was added NBS (47.6 g, 0.275 mol) in a portionwise manner at 0° C. After addition, the reaction mixture was stirred at room temperature for 3 h. TLC (EtOAc/hexane=1:1) indicated the reaction was complete. The precipitate was filtered, washed with cold MeCN (150 mL) and dried under vacuum to yield 6-bromo[1,3]oxazolo[4,5-b]pyridin-2(3H)-one (I-52) (45 g, 84%) as a yellow solid, which was used directly in the next step.

Step 4—Synthesis of 2-amino-5-bromopyridin-3-ol (I-53)

6-bromo[1,3]oxazolo[4,5-b]pyridin-2(3H)-one (I-52) (69 g, 0.3 mol) was added to 10% aqueous sodium hydroxide (600 mL) and the mixture was refluxed for 4 h. TLC (EtOAc/hexane=1:2) indicated the reaction was complete. The mixture was cooled to room temperature and acidified to pH~7 by dropwise addition of 10% HCl (300 mL). The precipitate formed was filtered, washed with water (100 mL) and dried undervacuum to afford 2-amino-5-bromopyridin-3-ol (I-53) (58 g, 73%) as a yellow solid, which was used without further purification.

Step 5—Synthesis of tert-butyl 4-{[(2-amino-5-bromopyridin-3-yl)oxy]methyl}piperidine-1-carboxylate (I-54)

To a mixture of tert-butyl 4-{[(methylsulfonyl)oxy]methyl}piperidine-1-carboxylate (I-48) (54.6 g, 186 mmol) and $Cs_2CO_3$ (110 g, 339 mmol) in DMF (400 mL) was added 2-amino-5-bromopyridin-3-ol (I-53) (32.0 g, 169.3 mol) at room temperature. The resulting mixture was stirred at 80° C. for 2 h. TLC (petroleum ether/EtOAc=1/1) showed the reaction was complete. The reaction mixture was cooled to room temperature and concentrated under high vacuum to dryness. The residue was diluted with 200 mL of water and extracted with $CH_2Cl_2$ (3×200 mL). The combined organic layers were washed with brine (100 mL), dried over $Na_2SO_4$. The mixture was concentrated under vacuum to give the crude product, which was purified by silica gel chromatography (petroleum ether/EtOAc=3/1 to 1/2) to give tert-butyl 4-{[(2-amino-5-bromopyridin-3-yl)oxy]methyl}piperidine-1-carboxylate (I-54) (59.0 g, 90%) as a white solid.

Step 6—Synthesis of tert-butyl 4-({[2-amino-5-(4,4,5,5-tetramethyl-1,3,2-dioxaborolan-2-yl)pyridin-3-yl]oxy}methyl)piperidine-1-carboxylate (I-55)

To a mixture of tert-butyl 4-{[(2-amino-5-bromopyridin-3-yl)oxy]methyl}piperidine-1-carboxylate (I-54) (20.00 g, 51.78 mmol), bis(pinacolato)diboron (13.1 g, 51.8 mmol), KOAc (12.7 g, 129 mmol) in anhydrous DMSO (200 mL) was added Pd(dppf)$Cl_2$ (5.68 g, 7.77 mmol). The mixture was thoroughly degassed before heating under nitrogen at 80° C. for 14 h.TLC (petroleum ether/EtOAc=1/1) indicated the reaction was complete. The mixture was cooled to room temperature and diluted with 300 mL of water and extracted with $CH_2Cl_2$ (3×200 mL). The combined organic layers were washed with brine (200 mL), dried over $Na_2SO_4$ and concentrated under vacuum to give crude compound, which was purified by silica gel chromatography (petroleum ether:EtOAc=1:1 to 0:1) to give tert-butyl 4-({[2-amino-5-(4,4,5,5-tetramethyl-1,3,2-dioxaborolan-2-yl)pyridin-3-yl]oxy}methyl)piperidine-1-carboxylate (I-55) (10.13 g, 48%) as a white solid. LCMS (APCI, M+1): 434.3; $^1$H NMR (400 MHz, $CDCl_3$) δ ppm 8.07 (s, 1 H), 7.18 (s, 1 H), 4.87 (s, 2

H), 4.17 (s, 2 H), 3.87-3.89 (d, 2 H), 2.76 (s, 2 H), 1.96 (s, 1 H), 1.83-1.88 (d, 2 H), 1.47 (s, 9 H), 1.34 (s, 12 H), 1.27-1.31 (m, 2 H).

Synthesis of 5-(1-methyl-1H-1,2,3-triazol-5-yl)-3-(piperidin-4-ylmethoxy)pyridin-2-amine (I-57)

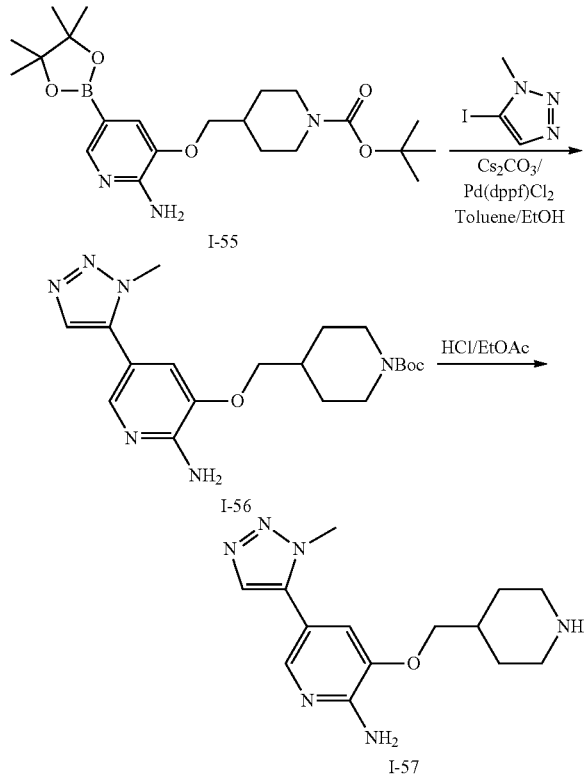

Step 1—Synthesis of tert-butyl 4-({[2-amino-5-(1-methyl-1H-1,2,3-triazol-5-yl)pyridin-3-yl]oxy}methyl)piperidine-1-carboxylate (I-56)

To a solution of tert-butyl 4-({[2-amino-5-(4,4,5,5-tetramethyl-1,3,2-dioxaborolan-2-yl)pyridin-3-yl]oxy}methyl)piperidine-1-carboxylate (I-55) (414 mg, 0.995 mmol), 5-iodo-1-methyl-1H-1,2,3-triazole (200 mg, 0.995 mmol) and Cs$_2$CO$_3$ (2N, 1 mL) in EtOH (6 mL) and toluene (2 mL) was added Pd(PPh$_3$)$_4$ (110 mg, 0.0995 mmol) under Ar. The reaction mixture was purged with Ar three times and stirred at 80° C. for 3 hr. TLC (petroleum ether:EtOAc=0:1) showed the reaction was complete. The reaction mixture was concentrated to give a crude product, which was purified by silica gel chromatography (eluting with EtOAc:MeOH=10:1) to give tert-butyl 4-({[2-amino-5-(1-methyl-1H-1,2,3-triazol-5-yl)pyridin-3-yl]oxy}methyl)piperidine-1-carboxylate (I-56) (310 mg, 84%) as a yellow solid, which was used directly in the next step.

Step 2—Synthesis of 5-(1-methyl-1H-1,2,3-triazol-5-yl)-3-(piperidin-4-ylmethoxy)pyridin-2-amine (I-57)

To a solution of tert-butyl 4-({[2-amino-5-(1-methyl-1H-1,2,3-triazol-5-yl)pyridin-3-yl]oxy}methyl)piperidine-1-carboxylate (I-56) (310 mg, 0.541 mmol) in CH$_2$Cl$_2$ (5 mL) was added HCl (g)/EtOAc (4N, 15 mL). The reaction mixture was stirred at room temperature for 3 hr. TLC (CH$_2$Cl$_2$:MeOH=10:1) showed the reaction was completed. The reaction mixture was concentrated to give crude 5-(1-methyl-1H-1,2,3-triazol-5-yl)-3-(piperidin-4-ylmethoxy)pyridin-2-amine (I-57), which was used directly for the next step without further purification.

Synthesis of 5-(1-methyl-1H-1,2,3-triazol-4-yl)-3-(piperidin-4-ylmethoxy)pyridin-2-amine (I-59)

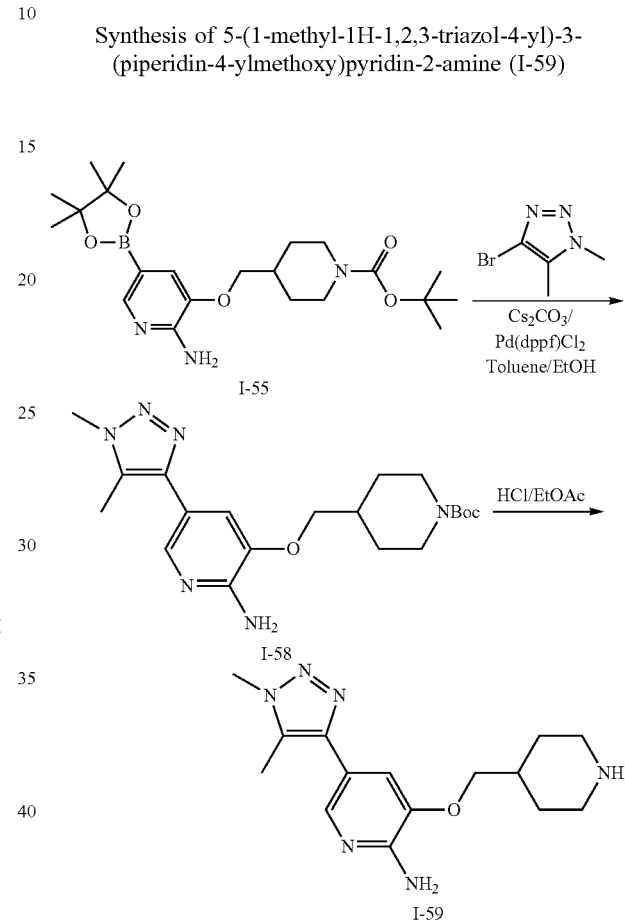

Step 1—Synthesis of tert-butyl 4-({[2-amino-5-(1,5-dimethyl-1H-1,2,3-triazol-4-yl)pyridin-3-yl]oxy}methyl)piperidine-1-carboxylate (I-58)

A mixture of tert-butyl 4-({[2-amino-5-(4,4,5,5-tetramethyl-1,3,2-dioxaborolan-2-yl)pyridin-3-yl]oxy}methyl)piperidine-1-carboxylate (I-55) (500 mg, 1.15 mmol), 4-bromo-1,5-dimethyl-1H-1,2,3-triazole (203 mg, 1.15 mmol), Cs$_2$CO$_3$ (2 M in water, 1.15 mL, 2.31 mmol) in toluene (1 mL) and EtOH (3 mL) was added Pd(PPh$_3$)$_4$ (20.3 mg, 0.115 mmol). The mixture was thoroughly degassed before heating under nitrogen at 90° C. for 14 hr. The mixture was concentrated under vacuum to dryness, and the residue purified by silica gel chromatography (petroleum ether/EtOAc=1/1 to 0/1) to give the tert-butyl 4-({[2-amino-5-(1,5-dimethyl-1H-1,2,3-triazol-4-yl)pyridin-3-yl]oxy}methyl)piperidine-1-carboxylate (I-58) (300 mg, 86%) as a yellow solid, which was use in next step without further purification.

Step 2—Synthesis of 5-(1-methyl-1H-1,2,3-triazol-4-yl)-3-(piperidin-4-ylmethoxy)pyridin-2-amine (I-59)

To a mixture of tert-butyl 4-({[2-amino-5-(1,5-dimethyl-1H-1,2,3-triazol-4-yl)pyridin-3-yl]oxy}methyl)piperidine-1-carboxylate (I-58) (400 mg, 0.994 mmol) in $CH_2Cl_2$ (10 mL) was added HCl (4 N, 3 mL, 10 mmol, in dioxane) at 0° C., and the reaction was stirred at room temperature for 18 hr. The reaction was concentrated under vacuum to dryness to give crude 5-(1-methyl-1H-1,2,3-triazol-4-yl)-3-(piperidin-4-ylmethoxy)pyridin-2-amine (I-59) (330 mg, crude), as a yellow solid, which was used directly in the next step.

Synthesis of 5-(1-methyl-1H-1,2,3-triazol-4-yl)-3-(piperidin-4-ylmethoxy)pyridin-2-amine (I-61)

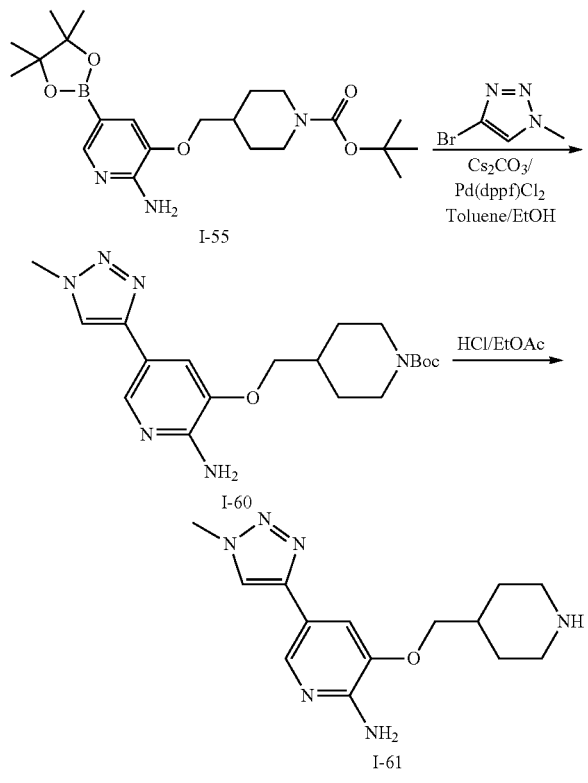

Step 1—Synthesis of tert-butyl 4-({[2-amino-5-(1-methyl-1H-1,2,3-triazol-4-yl)pyridin-3-yl]oxy}methyl)piperidine-1-carboxylate (I-60)

A mixture of tert-butyl 4-({[2-amino-5-(4,4,5,5-tetramethyl-1,3,2-dioxaborolan-2-yl)pyridin-3-yl]oxy}methyl)piperidine-1-carboxylate (I-55) (580 mg, 1.34 mmol), 4-bromo-1-methyl-1H-1,2,3-triazole (260 mg, 1.61 mmol), $Cs_2CO_3$ (2 N, 1.34 mL, 2.68 mmol) in toluene (2 mL) and EtOH (6 mL) was added $Pd(PPh_3)_4$ (30.9 mg, 0.0268 mmol). The mixture was thoroughly degassed before heating under nitrogen at 80° C. for 18 hr. TLC (EtOAc) indicated the reaction was completed. The mixture was concentrated under vacuum to dryness, and the residue purified by silica gel chromatography (petroleum ether/EtOAc=1/1 to 0/1) to give tert-butyl 4-({[2-amino-5-(1-methyl-1H-1,2,3-triazol-4-yl)pyridin-3-yl]oxy}methyl)piperidine-1-carboxylate (I-60) (503 mg, 97%) as a white solid.

Step 2—Synthesis of 5-(1-methyl-1H-1,2,3-triazol-4-yl)-3-(piperidin-4-ylmethoxy)pyridin-2-amine (I-61)

To a mixture of tert-butyl 4-({[2-amino-5-(1-methyl-1H-1,2,3-triazol-4-yl)pyridin-3-yl]oxy}methyl)piperidine-1-carboxylate (I-60) (569 mg, 1.46 mmol) in $CH_2Cl_2$ (10 mL) was added HCl (4 N, 10 mL, 40 mmol, in dioxane) at 0° C., and the reaction allowed to stir for 18 hr. LCMS indicated the reaction was complete. The reaction was concentrated under vacuum to dryness to give 5-(1-methyl-1H-1,2,3-triazol-4-yl)-3-(piperidin-4-ylmethoxy)pyridin-2-amine (I-61) (407 mg, 96%) as a white solid, which used directly in the next step without further purification.

Synthesis of 4-methoxy-3-(piperidin-4-yl)-1H-pyrazolo[3,4-b]pyridine (I-69)

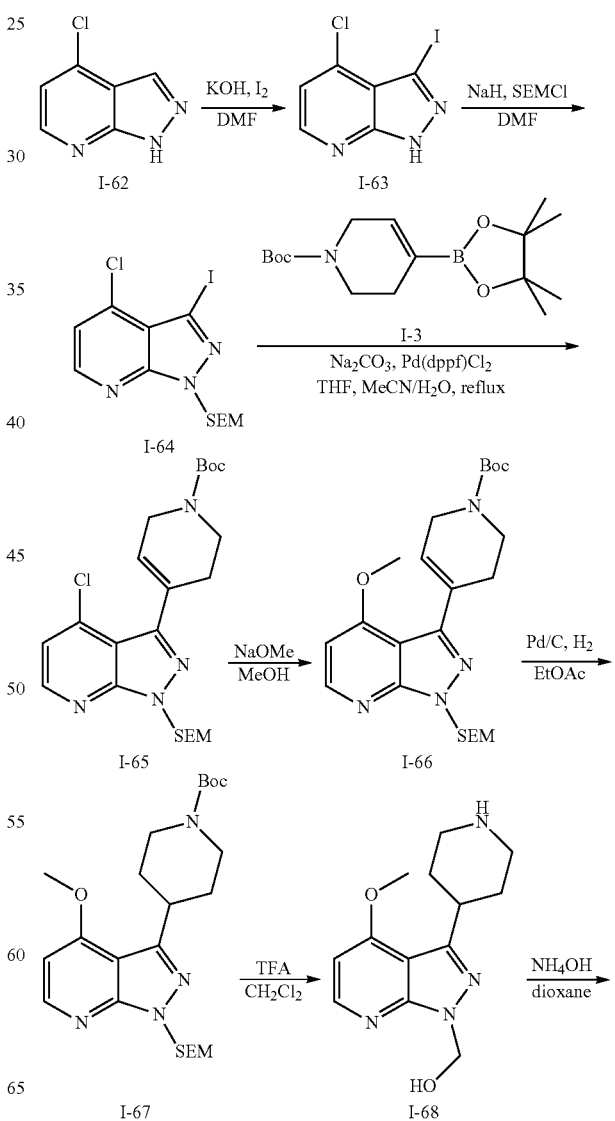

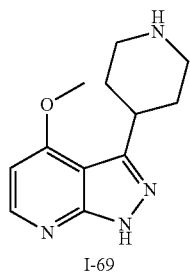

I-69

Step 1—Synthesis of 4-chloro-3-iodo-1H-pyrazolo[3,4-b]pyridine (I-63)

A mixture of 4-chloro-1H-pyrazolo[3,4-b]pyridine (I-62) (9 g, 58.6 mmol), KOH (9.86 g, 176 mmol) and I$_2$ (19.3 g, 76.2 mmol) in DMF (150 mL) was heated at 50° C. for 14 hr. TLC (petroleum ether/EtOAc=3:1) showed that 4-chloro-1H-pyrazolo[3,4-b]pyridine still remained. Then, I$_2$ (6.4 g, 25.2 mmol) was added to the mixture and the resulting mixture was heated at 50° C. for a further 15 hr. TLC (petroleum ether/EtOAc=3:1) showed all 4-chloro-1H-pyrazolo[3,4-b]pyridine had been consumed. The mixture was poured into ice-water (500 mL), extracted with EtOAc (900 mL). The organic extracts were washed with saturated Na$_2$SO$_3$ (500 mL), brine (500 mL), dried over Na$_2$SO$_4$ and concentrated to yield 4-chloro-3-iodo-1H-pyrazolo[3,4-b]pyridine (I-63) (16.4 g, 100%) as a yellow solid.

Step 2—Synthesis of -chloro-3-iodo-1-{[2-(trimethylsilyl)ethoxy]methyl}-1H-pyrazolo[3,4-b]pyridine (I-64)

To a stirred solution of 4-chloro-3-iodo-1H-pyrazolo[3,4-b]pyridine (I-63) (5 g, 17.89 mmol) in DMF (100 mL) was added NaH (60% in oil, 2.15 g, 53.7 mmol) at 0° C. The mixture was stirred at 0° C. for 60 min, and then SEMCl (3.28 g, 19.7 mmol) was added in a dropwise manner to the mixture. The resulting mixture was stirred at 0° C. for 2 hr. TLC (petroleum ether/EtOAc=3:1) showed the reaction was completed. The mixture was quenched by H$_2$O (150 mL) and extracted by EtOAc (2×100 mL). The combined organic layers were washed with brine (100 mL×5), dried over Na$_2$SO$_4$ and concentrated. The residue was purified by silica gelchromatography (petroleum ether/EtOAc=100:1~50:1) to yield 4-chloro-3-iodo-1-{[2-(trimethylsilyl)ethoxy]methyl}-1H-pyrazolo[3,4-b]pyridine (I-64) (5.11 g, 70%) as a white solid.

Step 3—Synthesis of tert-butyl 4-(4-chloro-1-{[2-(trimethylsilyl)ethoxy]methyl}-1H-pyrazolo[3,4-b]pyridin-3-yl)-3,6-dihydropyridine-1(2H)-carboxylate (I-65)

To a stirred mixture of 4-chloro-3-iodo-1-{[2-(trimethylsilyl)ethoxy]methy}-1H-pyrazolo[3,4-b]pyridine (I-64) (5.11 g, 12.47 mmol), tert-butyl 4-(4,4,5,5-tetramethyl-1,3,2-dioxaborolan-2-yl)-3,6-dihydropyridine-1(2H)-carboxylate (I-3) (4.24 g, 13.7 mmol) and Na$_2$CO$_3$ (2.64 g, 24.9 mmol) in a mixture of MeCN (75 mL), THF (75 mL) and H$_2$O (15 mL) was added Pd(dppf)Cl$_2$ (913 mg, 1.25 mmol) under N$_2$. The mixture was heated at reflux for 10 hr. TLC (petroleum ether/EtOAc=10:1) showed most of 4-chloro-3-iodo-1-{[2-(trimethylsilyl)ethoxy]methyl}- 1H-pyrazolo[3, 4-b]pyridine had been consumed. The mixture was concentrated to remove THF and MeCN. To the residue was added EtOAc (100 mL) and H$_2$O (100 mL). The aqueous layer was extracted with EtOAc (100 mL). The combined organic layers were washed with brine (2×100 mL), dried over Na$_2$SO$_4$ and concentrated. The residue was purified by silica gel chromatography (petroleum ether/EtOAc=10:1~6:1) to yield tert-butyl 4-(4-chloro-1-{[2-(trimethylsilyl)ethoxy]methyl}-1H-pyrazolo[3,4-b]pyridin-3-yl)-3,6-dihydropyridine-1(2H)-carboxylate (I-65) (3.9 g, 67%) as a yellow gum, and a second batch of crude tert-butyl 4-(4-chloro-1-{[2-(trimethylsilyl)ethoxy]methyl}-1H-pyrazolo[3,4-b]pyridin-3-yl)-3,6-dihydropyridine-1(2H)-carboxylate (0.7 g, ~70% purity) also as a yellow gum. $^1$H NMR (400 MHz, CDCl$_3$) δ ppm 8.42 (d, J=4.8 Hz, 1 H), 7.17 (d, J=4.8 Hz, 1 H), 6.15 (br. s., 1 H), 5.83 (s, 2 H), 4.14-4.16 (m, 2 H), 3.64-3.69 (m, 4 H), 2.66-2.68 (m, 3H), 1.50 (s, 9 H), 0.93 (t, J=8.2 Hz, 2 H), −0.03 (s, 9 H).

Step 4—Synthesis of tert-butyl 4-(4-methoxy-1-{[2-(trimethylsilyl)ethoxy]methyl}-1H-pyrazolo[3,4-b]pyridin-3-yl)-3,6-dihydropyridine-1(2H)-carboxylate (I-66)

Na (282 mg, 12.3 mmol) was added to dry MeOH (30 mL) and stirred at room temperature until the mixture turned clear. A solution of tert-butyl 4-(4-chloro-1-{[2-(trimethylsilyl)ethoxy]methyl}-1H-pyrazolo[3,4-b]pyridin-3-yl)-3,6-dihydropyridine-1(2H)-carboxylate (I-65) (1.9 g, 4.085 mmol) in MeOH (20 mL) was added to the solution. The mixture was heated at reflux for 3.5 hr. TLC (petroleum ether/EtOAc=3:1) showed the reaction was completed. The mixture was concentrated to remove MeOH. To the residue were added EtOAc (50 mL) and H$_2$O (50 mL). The organic layer was washed with brine (30 mL), dried over Na$_2$SO$_4$ and concentrated. The residue was purified by silica gel chromatography (petroleum ether/EtOAc=3:1) to yield tert-butyl 4-(4-methoxy-1-{[2-(trimethylsilyl)ethoxy]methyl}-1H-pyrazolo[3,4-b]pyridin-3-yl)-3,6-dihydropyridine-1 (2H)-carboxylate (I-66) (1.6 g, 85%) as a colorless syrup.

Step 5—Synthesis of tert-butyl 4-(4-methoxy-1-{[2-(trimethylsilyl)ethoxy]methyl}-1H-pyrazolo[3,4-b]pyridin-3-yl)piperidine-1-carboxylate (I-67)

A mixture of tert-butyl 4-(4-methoxy-1-{[2-(trimethylsilyl)ethoxy]methyl}-1H-pyrazolo[3,4-b]pyridin-3-yl)-3,6-dihydropyridine-1(2H)-carboxylate (I-66) (0.58 g, 1.26 mmol) and 10% Pd/C (174 mg) in EtOAc (20 mL) was hydrogenated under a H$_2$ balloon at room temperature overnight. TLC (petroleum ether/EtOAc=1:1) showed that tert-butyl 4-(4-methoxy-1-{[2-(trimethylsilyl)ethoxy]methyl}-1H-pyrazolo[3,4-b]pyridin-3-yl)-3,6-dihydropyridine-1 (2H)-carbon/late still remained. The mixture was filtered, and 10% Pd/C (174 mg) was added to the mixture and resulting mixture was hydrogenated under a H$_2$ balloon at 30° C. overnight. LCMS showed the reaction was completed. The mixture was filtered and the filtrate was concentrated to yield tert-butyl 4-(4-methoxy-1-{[2-(trimethylsilyl)ethoxy]methyl}-1H-pyrazolo[3,4-b]pyridin-3-yl) piperidine-1-carboxylate (I-67) (0.52 g, 89%) as a yellow gum, which was used in the next step directly.

Step 6—Synthesis of [4-methoxy-3-(piperidin-4-yl)-1H-pyrazolo[3,4-b]pyridin-1-yl]methanol (I-68)

To a stirred solution of tert-butyl 4-(4-methoxy-1-{[2-(trimethylsilyl)ethoxy]methyl}- 1H-pyrazolo[3,4-b]pyridin- 3-yl)piperidine-1-carboxylate (I-67) (0.52 g, 1.12 mmol) in CH$_2$Cl$_2$ (5 mL) was added TFA (5 mL) at 5° C. The mixture was stirred at room temperature overnight. TLC (petroleum ether/EtOAc=1:1) showed the reaction was completed. The mixture was concentrated to yield crude [4-methoxy-3-(piperidin-4-yl)-1H-pyrazolo[3,4-b]pyridin-1-yl]methanol (I-68) (~1.12 mmol, 100%) as yellow syrup, which was used in the next step directly.

Step 7—Synthesis of 4-methoxy-3-(piperidin-4-yl)-1H-pyrazolo[3,4-b]pyridine (I-69)

A mixture of [4-methoxy-3-(piperidin-4-yl)-1H-pyrazolo[3,4-b]pyridin-1-yl]methanol (I-68) (295 mg, 1.12 mmol) in dioxane (5 mL) and NH$_3$.H$_2$O (5 mL, 28%) was stirred at room temperature for 4 hr. LCMS showed the reaction was completed. The mixture was concentrated and purified by silica gel chromatography (CH$_2$Cl$_2$:MeOH=5:1) to yield crude 4-methoxy-3-(piperidin-4-yl)-1H-pyrazolo[3,4-b]pyridine (I-69) (260 mg, ~100%) as a yellow solid, which was used directly in the next step.

Synthesis of 2-(1-methyl-1H-pyrazol-4-yl)-7-(piperidin-4-yl)quinoxaline (I-77)

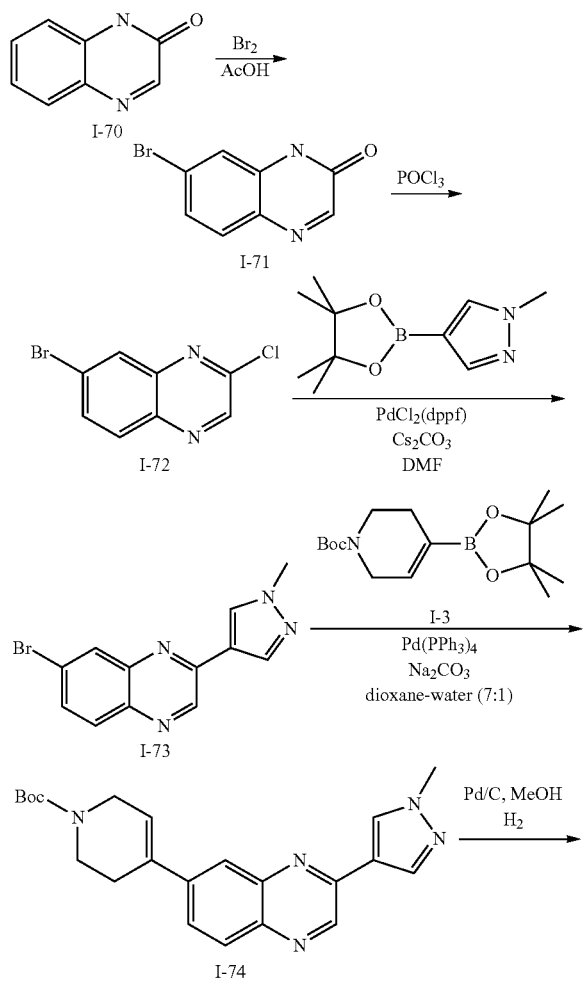

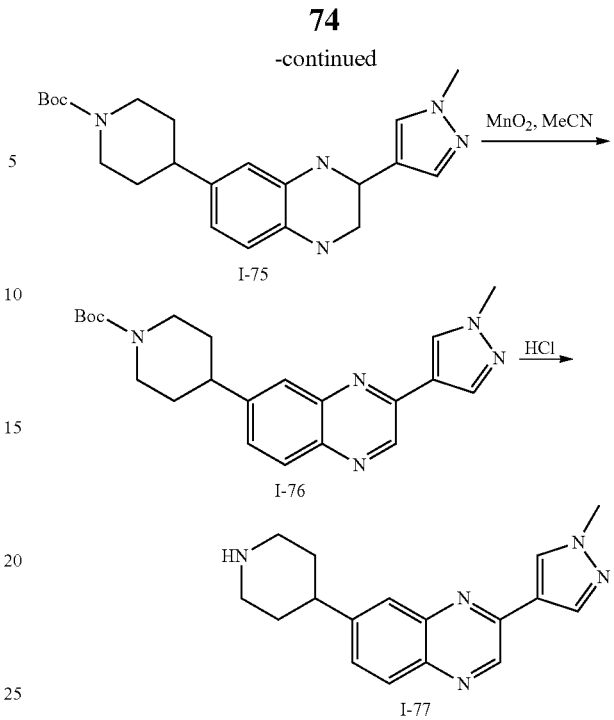

Step 1—Synthesis of 7-bromoquinoxalin-2(1H)-one (I-71)

To a cooled 0° C. solution of quinoxalin-2(1H)-one (I-70) (50 g, 342.2 mmol) in acetic acid (800 mL) was added in a dropwise manner a solution of bromine (32 mL) in acetic acid (200 mL) over a period of 30 min. Solids formed within the reaction upon addition of bromine, and the reaction was allowed to stir slowly for a further 90 min. The solid was filtered, washed with MeOH and ether, and dried under high vacuum to afford 7-bromoquinoxalin-2(1H)-one (I-71) (45 g, 58%) as a white solid. LCMS (APCI), m/z 224.1 [M+H]$^+$; $^1$H NMR (400 MHz, DMSO-d$_6$) δ ppm 12.46 (s, 1 H), 8.16-8.18 (m, 1 H), 7.69-7.72 (d, 1 H), 7.44-7.46 (m, 2 H).

Step 2—Synthesis of 7-bromo-2-chloroquinoxaline (I-72)

A stirred solution of 7-bromoquinoxalin-2(1H)-one (I-71) (50 g, 222.1 mmol) in POCl$_3$ (500 mL) was stirred and heated to reflux for 1 hr. The substrates took approximately 30 min to solubilize, and a further 30 min for the reaction to reach completion. The reaction was allowed to cool, and the excess POCl$_3$ removed under vacuum. The reaction residue was poured onto crushed ice, and neutralized with solid NaHCO3. The aqueous was extracted with EtOAc (3×250 mL). The organics were dried over Na$_2$SO$_4$, filtered, and concentrated to afford a yellowish solid, which was washed with 5% ether in hexanes to afford 7-bromo-2-chloroquinoxaline (I-72) (40 g, 70%) as a brownish solid. LCMS (APCI), m/z 242.1 [M+H]$^+$; $^1$H NMR (400 MHz, DMSO-d$_6$) δ ppm 9.04 (s, 1 H), 8.33 (d, J=2.0 Hz, 1 H), 8.03-8.11 (m, 2 H).

Step 3—Synthesis of 7-bromo-2-(1-methyl-1H-pyrazol-4-yl)quinoxaline (I-73)

To a mixture of 1-methyl-4-(4,4,5,5-tetramethyl-1,3,2-dioxaborolan-2-yl)-1H-pyrazole (8.54 g, 41.31 mmol), 7-bromo-2-chloroquinoxaline (I-72) (10 g, 41.31 mmol), and cesium carbonate (30 g, 103.26 mmol) in DMF was added Pd(dppf)Cl$_2$ (1.7 g, 2.08 mmol). The reaction was heated to 110 C for 16 hr before being allowed to cool. The reaction mixture was poured into water (250 mL), and extracted with EtOAc (3×300 mL). The combined organics were dried over Na2SO4, filtered and concentrated in vacuo to afford a residue that was purified by chromatography on silica gel (0-100% EtOAc in heptanes). Washing the solids obtained with ether afforded 7-bromo-2-(1-methyl-1H-pyrazol-4-yl)quinoxaline (I-73) (10 g, 84%) as a colorless solid. LCMS (APCI), m/z 289/291 [M+H]$^+$; $^1$H NMR (400 MHz, DMSO-d$_6$) δ ppm 9.33 (s, 1H), 8.63 (s, 1 H), 8.29 (s, 1 H), 8.18-8.19 (d, 1 H), 7.92-7.97 (m, 1 H), 7.85-7.88 (d, 1 H), 3.96 (s, 3 H).

Step 4—Synthesis of tert-butyl 4-[3-(1-methyl-1H-pyrazol-4-yl)quinoxalin-6-yl]-3,6-dihydropyridine-1(2H)-carboxylate (I-74)

To a mixture of 7-bromo-2-(1-methyl-1H-pyrazol-4-yl) quinoxaline (I-73) (7 6, 24.2 mmol), tert-butyl 4-(4,4,5,5-tetramethyl-1,3,2-dioxaborolan-2-yl)-3,6-dihydropyridine-1(2H)-carboxylate (I-3) (5 g, 24.2 mmol), and sodium carbonate (7.6 g, 72.64 mmol) in dioxane and water was added Pd(PPh$_3$)$_4$ (690 mg, 0.59 mmol). The reaction was heated to 100° C. for 12 hr before being allowed to cool. The reaction mixture was extracted with EtOAc (3×300 mL). The combined organics were dried over Na2SO4, filtered and concentrated in vacuo to afford a residue that was purified by chromatography on silica gel (0-5% MeOH in CH$_2$Cl$_2$) to afford tert-butyl 4-[3-(1-methyl-1H-pyrazol-4-yl)quinoxalin-6-yl]-3,6-dihydropyridine-1(2H)-carboxylate (I-74) (5 g, 53%) as a slightly yellow solid. LCMS (APCI), m/z 392.1 [M+H]$^+$; $^1$H NMR (400 MHz, DMSO-d$_6$) δ ppm 9.23 (s, 1H), 8.60 (s, 1 H), 8.26 (s, 1 H), 7.90-7.96 (m, 3 H), 6.51 (s, 1 H), 4.03 (s, 2 H), 3.95 (s, 3 H), 3.59-3.61 (m, 1 H), 2.63 (s, 2 H), 1.44 (s, 9 H).

Step 5—Synthesis of tert-butyl 4-[3-(1-methyl-1H-pyrazol-4-yl)-1,2,3,4-tetrahydroquinoxalin-6-yl]piperidine-1-carboxylate (I-75)

tert-Butyl 4-[3-(1-methyl-1H-pyrazol-4-yl)quinoxalin-6-yl]-3,6-dihydropyridine-1(2H)-carboxylate (I-74) (4.7 g, 12.02 mmol) was taken up in MeOH in a 500 mL Parr shaker vessel. The solution was degassed for 5 min followed by addition of Pd/C (2.5 g, 10%) under a nitrogen atmosphere. The reaction was agitated under 50 psi of hydrogen pressure for 16 hr. The reaction was filtered through a pad of celite, and the filtrate evaporated to dryness to afford tert-butyl 4-[3-(1-methyl-1 H-pyrazol-4-yl)-1,2,3,4-tetrahydroquinoxalin-6-yl]piperidine-1-carboxylate (I-75) (4.6 g), which was used in the next step without further purification. LCMS (APCI), m/z 396.1 [M+H]$^+$; $^1$H NMR (400 MHz, DMSO-d$_6$) δ ppm 7.39-7.57 (m, 1 H), 6.30-6.31 (d, 2 H), 6.22-6.24 (d, 2 H), 5.39 (s, 1 H), 5.29 (s, 1 H), 4.24-4.25 (d, 1 H), 3.95-4.02 (m, 2 H), 3.78 (s, 3 H), 3.25 (s, 1 H), 3.02-3.06 (m, 1 H), 2.73 (s, 2 H), 2.34-2.40 (m, 1 H), 1.63-1.66 (d, 2 H), 1.40 (s, 9 H).

Step 6—Synthesis of tert-butyl 4-[3-(1-methyl-1H-pyrazol-4-yl)quinoxalin-6-yl]piperidine-1-carboxylate (I-76)

To a solution of tert-butyl 4-[3-(1-methyl-1H-pyrazol-4-yl)-1,2,3,4-tetrahydroquinoxalin-6-yl]piperidine-1-carboxylate (I-75) (4.6 g, 11.64 mmol) in MeCN (50 mL) was added activated MnO$_2$ (10 g, 116.42 mmol). The reaction was allowed to stir for 3 hr before being filtered through a plug of Celite. Removal of the solvent in vacuo afforded tert-butyl 4-[3-(1-methyl-1H-pyrazol-4-yl)quinoxalin-6-yl]piperidine-1-carboxylate (I-76) (4.5 g), which was used directly in the next step without further purification. LCMS (APCI), m/z 394.2 [M+H]$^+$; $^1$H NMR (400 MHz, DMSO-d$_6$) δ ppm 9.23 (s, 1 H), 8.59 (s, 1 H), 8.25 (s, 1 H), 7.94-7.96 (d, 1 H), 7.78 (s, 1 H), 7.66-7.67 (d, 1 H), 4.13 (s, 2 H), 3.95 (s, 3 H), 2.87-2.95 (m, 3 H), 1.87-1.91 (m, 2 H), 1.51-1.63 (m, 2 H), 1.43 (s, 9 H).

Step 7—Synthesis of 2-(1-methyl-1H-pyrazol-4-yl)-7-(piperidin-4-yl)quinoxaline (I-77)

To a solution of tert-butyl 4-[3-(1-methyl-1H-pyrazol-4-yl)quinoxalin-6-yl]piperidine-1-carboxylate (I-76) (4.5 g, 11.45 mmol) in dioxane was added at ice-cold temperature a solution of 4N HCl in dioxane (20 mL). The reaction was stirred for 4 hr. Excess dioxane was removed in vacuo, and the yellow solids formed washed with ether, and dried under high vacuum to afford tert-butyl 4-[3-(1-methyl-1H-pyrazol-4-yl)quinoxalin-6-yl]piperidine-1-carboxylate (I-77) (4.1 g, 100%) as the hydrochloride salt, which was used without further purification. LCMS (APCI), m/z 294.4 [M+H]$^+$; $^1$H NMR (400 MHz, DMSO-d$_6$) δ ppm 9.26 (s, 1 H), 8.82 (br. s., 2 H), 8.62 (s, 1 H), 8.01 (s, 1 H), 7.78 (s, 1 H), 7.63-7.65 (d, 1 H), 3.95 (s, 3 H), 3.40-3.43 (m, 2 H), 3.06-3.11 (m, 3 H), 2.01-2.09 (m, 2 H), 1.92-1.98 (m, 2 H).

Synthesis of 4-(dimethylamino)-6-(piperidin-4-yl) pyridine-2-carboxamide (I-84)

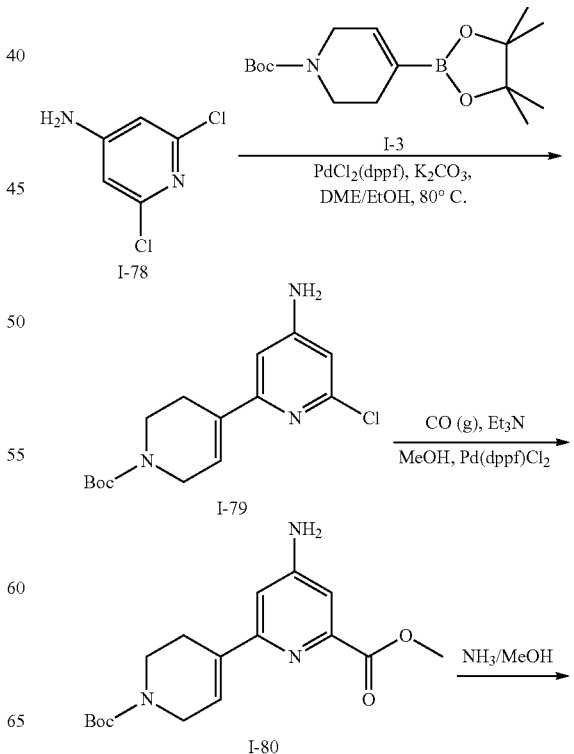

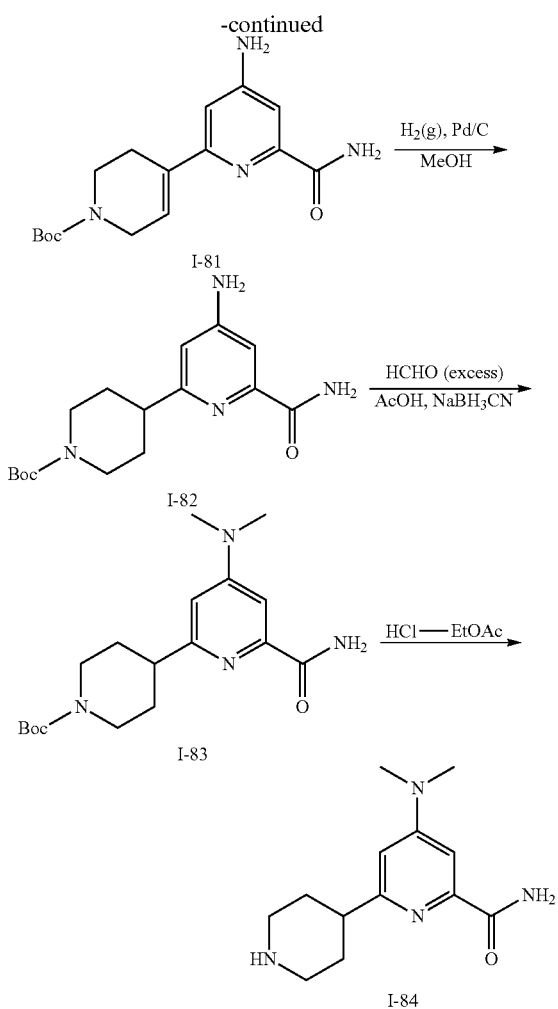

Step 1—Synthesis of tert-butyl 4-amino-6-chloro-3',6'-dihydro-2,4'-bipyridine-1'(2'H)-carboxylate (I-79)

To a mixture of 2,6-dichloropyridin-4-amine (I-78) (15 g, 92 mmol), tert-butyl 4-(4,4,5,5-tetramethyl-1,3,2-dioxaborolan-2-yl)-3,6-dihydropyridine-1(2H)-carboxylate (I-3) (28.44 g, 92 mmol) and Cs$_2$CO$_3$ (89 g, 276 mmol) in DME (270 mL) and H$_2$O (90 mL) was added Pd(dppf)Cl$_2$ (1.93 g, 2.76 mmol) at room temperature under N$_2$. The resulting mixture was heated at 80° C. for 12 hr. TLC (petroleum ether/EtOAc=3:1) showed most of 2,6-dichloropyridin-4-amine had been consumed. The mixture was partitioned between EtOAc (300 mL) and H$_2$O (50 mL). The organic layer was separated, washed with brine (25 mL) dried over Na$_2$SO$_4$, filtered and concentrated in vacuo to give the crude product, which was purified by silica gel chromatography (petroleum ether/EtOAc=5:1~2:1) to give tert-butyl 4-amino-6-chloro-3',6'-dihydro-2,4'-bipyridine-1'(2'H)-carboxylate (I-79) (6 g, 21%) as a white solid.

Step 2—Synthesis of 1'-tert-butyl 6-methyl 4-amino-3',6'-dihydro-2,4'-bipyridine-1',6(2'H)-dicarboxylate (I-80)

This reaction was run in three 2 g batches: To a solution of tert-butyl 4-amino-6-chloro-3',6'-dihydro-2,4'-bipyridine-1'(2'H)-carboxylate (I-79) (2 g, 6.48 mmol) in MeOH (30 mL) was added TEA (1.308 g, 12.96 mmol) and Pd(dppf)Cl$_2$ (0.136 g, 0.168 mmol) at room temperature. The resulting mixture was heated at 100° C. under CO pressure (2 MPa) for 12 hr. TLC (petroleum ether/EtOAc=1:1) showed most of tert-butyl 4-amino-6-chloro-3',6'-dihydro-2,4'-bipyridine-1'(2'H)-carboxylate was consumed. The mixture was concentrated in vacuo to give the crude product, which was purified by silica gel chromatography (petroleum ether/EtOAc=4:1 to 2:1) to give 1'-tert-butyl 6-methyl 4-amino-3',6'-dihydro-2,4'-bipyridine-1',6(2'H)-dicarboxylate (I-80) (7.5 g, 39%, three batches in total) as a white solid.

Step 3—Synthesis of tert-butyl 4-amino-6-carbamoyl-3',6'-dihydro-2,4'-bipyridine-1(2'H)-carboxylate (I-81)

To a solution of 1'-tert-butyl 6-methyl 4-amino-3',6'-dihydro-2,4'-bipyridine-1',6(2'H)-dicarboxylate (I-80) (2.5 g, 7.51 mmol) in MeOH (25 mL) was added NH$_3$-MeOH (4 M, 30 mL) at room temperature. The resulting mixture was sealed and heated at 80° C. for 12 hr. LCMS showed the reaction was complete. The mixture was concentrated in vacuo to give the crude product, which was purified by silica gel chromatography (petroleum ether/EtOAc=4:1 to CH$_2$Cl$_2$/MeOH=20:1) to give tert-butyl 4-amino-6-carbamoyl-3',6'-dihydro-2,4'-bipyridine-1'(2'H)-carboxylate (I-81) (2.4 g, 100%) as a white solid.

Step 4—Synthesis of tert-butyl 4-(4-amino-6-carbamoylpyridin-2-yl)piperidine-1-carboxylate (I-82)

To a solution of tert-butyl 4-amino-6-carbamoyl-3',6'-dihydro-2,4'-bipyridine-1'(2'H)-carboxylate (I-81) (2.4 g, 7.55 mmol) in MeOH (300 mL) was added 10% Pd/C (800 mg) at room temperature. The resulting mixture was stirred at room temperature under a balloon pressure of H$_2$ (15 Psi) for 12 h. LCMS showed the reaction was complete. The mixture was filtered through Celite, and washed with MeOH (100 mL). The filtrate was concentrated in vacuo to give tert-butyl 4-(4-amino-6-carbamoylpyridin-2-yl)piperidine-1-carboxylate (I-82) (2.2 g, 91%) as a white solid.

Step 5—Synthesis of tert-butyl 4-[6-carbamoyl-4-(dimethylamino)pyridin-2-yl]piperidine-1-carboxylate (I-83)

To a solution of tert-butyl 4-(4-amino-6-carbamoylpyridin-2-yl)piperidine-1-carboxylate (I-82) (0.2 g, 0.625 mmol) in MeOH (10 mL) was added TEA (63 mg, 0.625 mmol), AcOH (37.5 mg, 0.625 mmol) and HCHO (152 mg, 1.875 mmol) at room temperature, and the reaction stirred for 15 min. After 15 min, NaBH$_3$CN (114 mg, 1.875 mmol) was added to the mixture. The resulting mixture was stirred at room temperature overnight. TLC (CH$_2$Cl$_2$/MeOH=10:1) showed some of tert-butyl 4-(4-amino-6-carbamoylpyridin-2-yl)piperidine-1-carboxylate still remained. Another batch of HCHO (152 mg, 1.875 mmol) and NaBH$_3$CN (114 mg, 1.875 mmol) were added into the mixture. The resulting mixture was stirred at room temperature for 12 h. The mixture was concentrated in vacuo to give the crude product, which was purified by silica gel chromatography (CH$_2$Cl$_2$/MeOH=50:1~20:1) to give tert-butyl 4-[6-carbamoyl-4-(dimethylamino)pyridin-2-yl]piperidine-1-carboxylate (I-83) (0.13 g, 59%) as a colorless oil, which was used directly in the next step.

Step 6—Synthesis of 4-(dimethylamino)-6-(piperidin-4-yl)pyridine-2-carboxamide (I-84)

To a solution of tert-butyl 4-[6-carbamoyl-4-(dimethylamino)pyridin-2-yl]piperidine-1-carboxylate (I-83) (0.13 g, 0.374 mmol) in EtOAc (20 mL) was added HCl-EtOAc (4 M, 10 mL) at room temperature. The resulting mixture was stirred at room temperature overnight. The mixture was concentrated in vacuo to give 4-(dimethylamino)-6-(piperidin-4-yl)pyridine-2-carboxamide (I-84) (0.075 g, 80%) as a white solid, which was used without further purification.

Synthesis of tert-butyl 4-({[(4-methylphenyl)sulfonyl]oxy}methyl)piperidine-1-carboxylate (I-85)

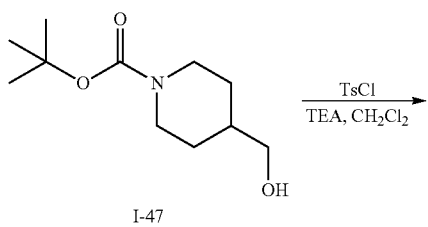

Step 1—Synthesis of tert-butyl 4-({[(4-methylphenyl)sulfonyl]oxy}methyl)piperidine-1-carboxylate To a stirred solution of tert-butyl 4-(hydroxymethyl)piperidine-1-carboxylate (I-47) (60 g, 46 mmol) and TEA (42.3 g, 418 mmol) in $CH_2Cl_2$ (300 mL) was added TsCl (55.8 g, 293 mmol) in portions at 0~5° C. The resulting mixture was stirred at 15° C. for 12 h. TLC (petroleum ether/EtOAc=3:1, Rf~0.7) showed that the reaction was completed. The reaction mixture was washed with saturated $NaHCO_3$ (3×300 mL) and brine (3×300 mL). The organic phase was dried over $Na_2SO_4$, filtered and concentrated in vacuo to give the crude product, which was stirred in petroleum ether (50 mL) for 10 min and then filtered, dried in vacuo to obtain tert-butyl 4-({[(4-methylphenyl)sulfonyl]oxy}methyl)piperidine-1-carboxylate (I-85) (80 g, 78%) as a white solid. $^1H$ NMR (400 MHz, $CDCl_3$) δ ppm 7.77 (d, J=8.0 Hz, 2 H), 7.34 (d, J=8.0 Hz, 2 H), 4.08 (br. s., 2 H), 3.84 (d, J=6.4 Hz, 2 H), 2.45 (s, 3 H), 1.81-1.83 (m, 1 H), 1.61-1.69 (m, 2 H), 1.43 (s, 9 H), 1.06-1.14 (m, 2 H).

Synthesis of 5-(piperidin-4-ylmethoxy)pyrimidin-4-amine (I-93)

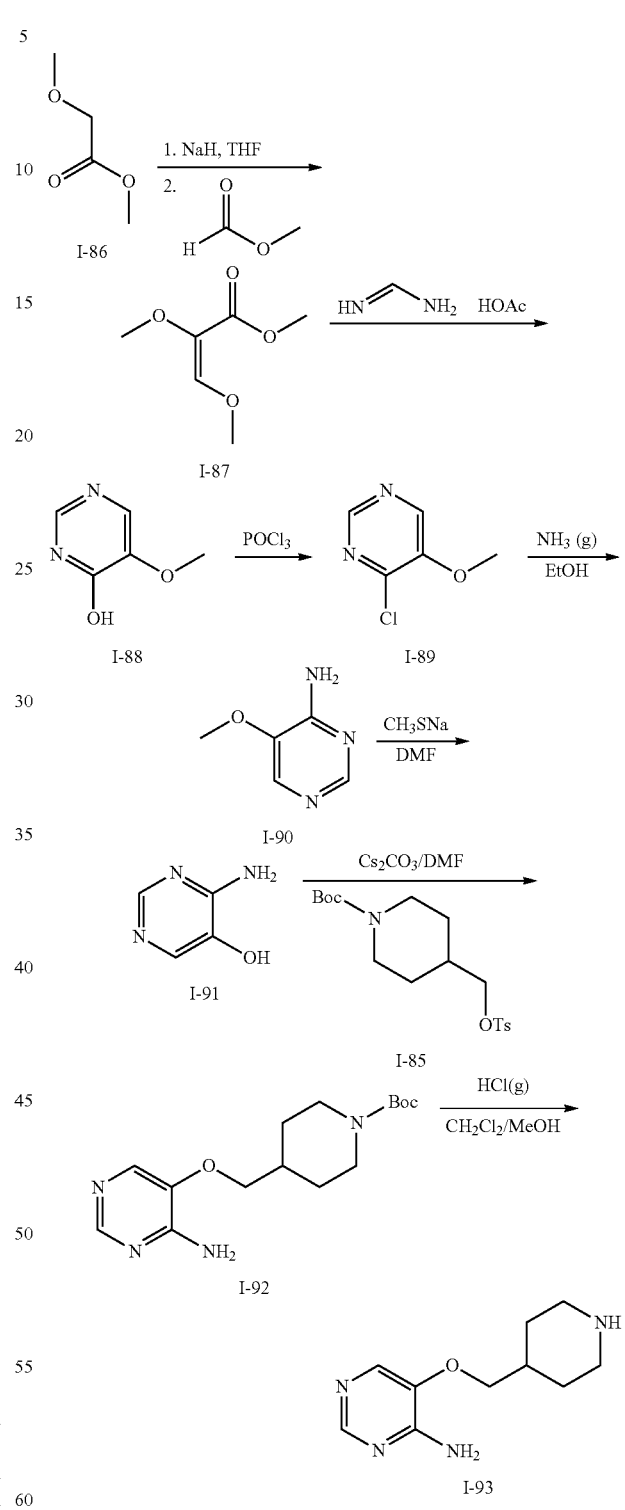

Step 1—Synthesis of methyl (2E)-2,3-dimethoxyprop-2-enoate (I-87)

Note, caution should be exercised due to the evolution of $H_2$ gas. To a mixture of methyl methoxyacetate (I-86) (249.6 g, 2.40 mol) and methyl formate (173 g, 2.88 mol) in anhydrous THF (3.5 L) was added NaH (134 g, 3.36 mol, 60% in oil) in portions over 1 h at 5~10° C. The resulting mixture was stirred at 15~20° C. for 12 h. The formation of a white solid was noted, TBME (1.5 L) was added and the resulting suspension was filtered. The filter cake was dried in air to give crude methyl (2E)-2,3-dimethoxyprop-2-enoate (I-87) (2.4 mol, 100%) as a white solid, which was used in the next step without further purification.

Step 2—Synthesis of 5-methoxypyrimidin-4-ol (I-88)

A mixture of methyl (2E)-2,3-dimethoxyprop-2-enoate (I-87) (351 g, 2.4 mol) and formamidine acetate (250 g, 2.4 mol) in EtOH (3 L) was stirred at room temperature for 12 h, and then refluxed for 24 h with air cooling (note potential issues of sublimation of formamidine acetate leading to condenser blockage). Water (500 mL) was added and the mixture was acidified with AcOH (750 mL) from pH=10 to 5. The mixture was concentrated in vacuo to give the residue, which was purified by silica gel chromatography ($CH_2Cl_2$/MeOH=50:1~10:1) to obtain 5-methoxypyrimidin-4-ol (I-88) (80 g, 26%) as an off-white solid. $^1$H NMR (400 MHz, DMSO-$d_6$) δ ppm 12.47 (br. s., 1 H), 7.81 (s, 1 H), 7.52 (s, 1 H), 3.70 (s, 3 H).

Step 3—Synthesis of 4-chloro-5-methoxypyrimidine (I-89)

A suspension of 5-methoxypyrimidin-4-ol (I-88) (57 g, 0.452 mol) in $POCl_3$ (540 mL) was heated at reflux for 6 hr. TLC ($CH_2Cl_2$/MeOH=10:1) showed the reaction was complete. Most of the $POCl_3$ was removed under reduced pressure, and the residue was poured into ice-water (2 L), basified with $K_2CO_3$ (250 g) to pH~7. The mixture was then extracted with EtOAc:TBME (3:1, 4×250 mL). The organic layers were combined, washed with brine (100 mL) and dried over $Na_2SO_4$, filtered and concentrated in vacuo to give 4-chloro-5-methoxypyrimidine (I-89) (38 g, 58%) as a yellow solid. $^1$H NMR (400 MHz, DMSO-$d_6$) δ ppm 8.63 (s, 1 H), 8.32 (s, 1 H), 4.02 (s, 3 H).

Step 4—Synthesis of 4-amino-5-methoxypyrimidine (I-90)

A suspension of 4-chloro-5-methoxypyrimidine (I-89) (40 g, 280 mmol) in $NH_3$ (g)/EtOH (4 M, 2000 mL) was poured into an autoclave at room temperature and stirred at 130° C. for 12 hr. TLC ($CH_2Cl_2$/MeOH=10:1) showed the reaction was complete. The mixture was cooled to room temperature and concentrated in vacuo to give a residue, to which was added $CH_2Cl_2$ (100 mL) and the resulting mixture was stirred at room temperature for 30 min. The resulting suspension was filtered to remove $NH_4Cl$ salt, and the filtrate was concentrated in vacuo to give the crude product. The crude product was stirred in a mixed solvent of EtOAc/$CH_2Cl_2$ (50 mL, 4:1) for 30 min, filtered and concentrated in vacuo to obtain 4-amino-5-methoxypyrimidine (I-90) (30 g, 87%) as a yellow solid. $^1$H NMR (400 MHz, DMSO-$d_6$) δ ppm 8.01 (s, 1 H), 7.81 (s, 1 H), 6.75 (br. s., 2 H), 3.81 (s, 3 H).

Step 5—Synthesis of 4-amino-5-hydroxypyrimidine (I-91)

To a solution of 4-amino-5-methoxypyrimidine (I-90) (40 g, 319.67 mmol) in anhydrous DMF (2500 mL) was added $CH_3SNa$ (40.3 g, 575 mmol, Aldrich 95% purity, powdered solid) at room temperature. The resulting mixture was heated at 120° C. for 12 hr. TLC ($CH_2Cl_2$/MeOH=10:1) showed the reaction was complete. The mixture was concentrated in vacuo to give a residue, to which was added AcOH (35 mL) and $H_2O$ (100 mL). The mixture was then evaporated in vacuo to give the crude product. The crude product was purified by silica gel chromatography ($CH_2Cl_2$/MeOH=50:1 to 5:1) to afford 4-amino-5-hydroxypyrimidine (I-91) (29 g, 82%) as a brown solid. This may contain some inorganic solids, but was used directly in the next step without further purification. $^1$H NMR (400 MHz, DMSO-$d_6$) δ ppm 7.90 (s, 1 H), 7.62 (s, 1 H), 6.46 (br. s., 2 H).

Step 6—Synthesis of tert-butyl 4-{[(4-aminopyrimidin-5-yl)oxy]methyl}piperidine-1-carboxylate (I-92)

To a mixture of tert-butyl 4-({[(4-methylphenyl)sulfonyl]oxy}methyl)piperidine-1-carboxylate (I-85) (66.5 g, 180.01 mmol) and 4-amino-5-hydroxypyrimidine (I-91) (20 g, 180.01 mol) in anhydrous DMF (1000 mL) was added $Cs_2CO_3$ (117 g, 360 mmol) at room temperature under a $N_2$ atmosphere. The resulting mixture was heated at 60° C. for 12 hr. TLC ($CH_2Cl_2$/MeOH=10:1) showed the reaction was complete. The mixture was cooled to 0° C., and $H_2O$ (350 mL) and $CH_2Cl_2$ (300 mL) were added. The organic layer was separated and the aqueous layer was extracted with $CH_2Cl_2$ (3×250 mL). The organic layers were combined, washed with $H_2O$ (4×150 mL), brine (2×100 mL), dried over $Na_2SO_4$ and concentrated in vacuo to give the crude product, which was stirred in a mixed solvent of petroleum ether/EtOAc (1:1, 150 mL) for 10 min and then filtered, dried in vacuo to give tert-butyl 4-{[(4-aminopyrimidin-5-yl)oxy]methyl}piperidine-1-carboxylate (I-92) (36 g, 65%) as a white solid.

Step 7—Synthesis of 5-(piperidin-4-ylmethoxy)pyrimidin-4-amine (I-93)

To a stirred solution of tert-butyl 4-{[(4-aminopyrimidin-5-yl)oxy]methyl}piperidine-1-carboxylate (I-92) (85 g, 275.64 mmol) in $CH_2Cl_2$ (1500 mL) and MeOH (200 mL) was added HCl (g)/EtOAc (4 M, 1000 mL) at room temperature. The resulting mixture was stirred at room temperature for 12 hr. The mixture was concentrated in vacuo to give the HCl salt of 5-(piperidin-4-ylmethoxy)pyrimidin-4-amine (I-93) (77 g, 99%) as a yellow solid. $^1$H NMR (400 MHz, $CD_3OD$) δ ppm 8.41 (s, 1 H), 7.93 (s, 1 H), 4.07 (d, J=6.4 Hz, 2 H), 3.46-3.49 (m, 2 H), 3.04-3.10 (m, 2 H), 2.19-2.31 (m, 1 H), 2.14-2.17 (m, 2 H), 1.61-1.70 (m, 2 H).

Synthesis of 7-(piperidin-4-yl)-5H-pyrrolo[2,3-b]pyrazine (I-100)

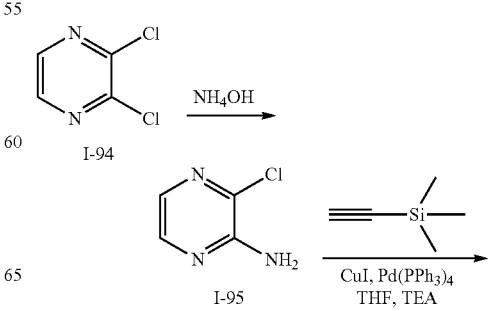

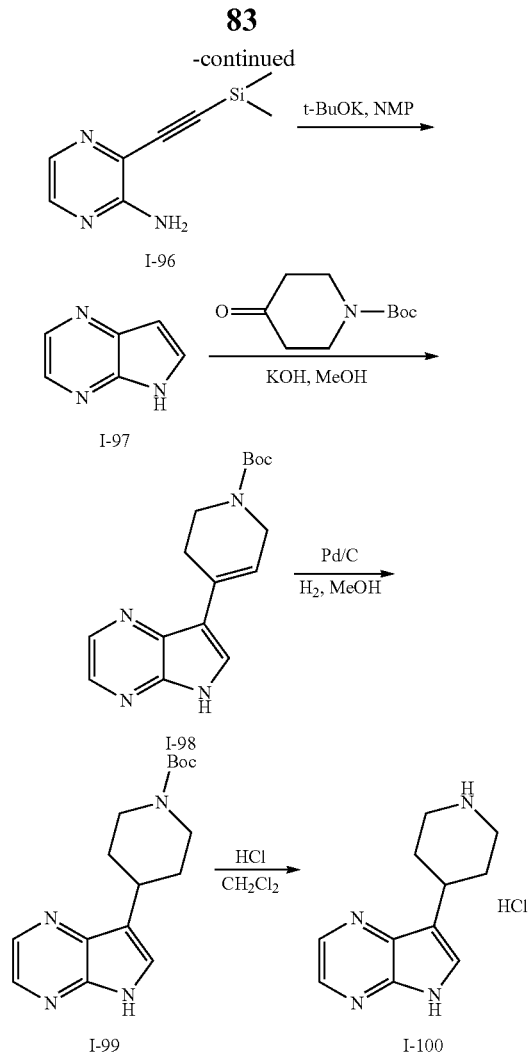

Step 3—Synthesis of 5H-pyrrolo[2,3-b]pyrazine (I-97)

To a solution of t-BuOK (24 g, 230 mmol) in dry NMP (30 mL) was added dropwise a solution of 3-[(trimethylsilyl)ethynyl]pyrazin-2-amine (I-96) (15 g, 78 mmol) in NMP (60 mL) over 10 min at 80° C. The mixture was stirred at 80° C. for 1.5 hr. TLC (petroleum ether:EtOAc=2:1) showed the reaction was complete. The reaction mixture was cooled to room temperature, and then diluted with EtOAc (500 mL) and water (100 mL). The EtOAc layer was washed with water (6×50 mL). The combined organic layers were dried ($Na_2SO_4$), filtered and concentrated under vacuum to give 5H-pyrrolo[2,3-b]pyrazine (I-97) (5 g, 54%) as a dark brown solid.

Step 4—Synthesis of tert-butyl 4-(5H-pyrrolo[2,3-b]pyrazin-7-yl)-3,6-dihydropyridine-1(2H)-carboxylate (I-98)

To a solution of 5H-pyrrolo[2,3-b]pyrazine (I-97) (4.3 g, 36.1 mmol) in MeOH (100 mL) was added tert-butyl 4-oxopiperidine-1-carboxylate (8.7 g, 43.3 mmol) and KOH (8.1 g, 144.4 mmol). The mixture was heated to 80° C. overnight. TLC (petroleum ether:EtOAc=1:1) showed the reaction was complete. The mixture was concentrated to give the crude product, which was purified by silica gel chromatography (petroleum ether:EtOAc=1:1) to give tert-butyl 4-(5H-pyrrolo[2,3-b]pyrazin-7-yl)-3,6-dihydropyridine-1(2H)-carboxylate (I-98) (8 g, 74%) as a yellow solid.

Step 5—Synthesis of tert-butyl 4-(5H-pyrrolo[2,3-b]pyrazin-7-yl)piperidine-1-carboxylate (I-99)

To a solution of tert-butyl 4-(5H-pyrrolo[2,3-b]pyrazin-7-yl)-3,6-dihydropyridine-1(2H)-carboxylate (I-98) (5 g, 16.7 mmol) in MeOH (150) was added 10% Pd/C (1.4 g) at room temperature. Then the mixture was stirred at 50° C. for 8 hr under a $H_2$ balloon. LCMS showed the reaction was complete. The mixture was filtered, and the filtrate was concentrated to give the crude product, which was purified by silica gel chromatography (0-100% EtOAc/petroleum ether) to give tert-butyl 4-(5H-pyrrolo[2,3-b]pyrazin-7-yl)piperidine-1-carboxylate (I-99) (3.4 g, 70%) as a yellow solid.

Step 6—Synthesis of 7-(piperidin-4-yl)-5H-pyrrolo[2,3-b]pyrazine (I-100)

To a solution of tert-butyl 4-(5H-pyrrolo[2,3-b]pyrazin-7-yl)piperidine-1-carboxylate (I-99) (3.4 g, 11.2 mmol) in $CH_2Cl_2$ (15 mL) was added HCl/EtOAc (4 N, 30 mL) at room temperature. Then the mixture was stirred at room temperature for 2 hr. LCMS showed the reaction was complete. The mixture was concentrated to give a crude product, which was washed with EtOAc (50 mL) and $CH_2Cl_2$ (50 mL) to give 7-(piperidin-4-yl)-5H-pyrrolo[2,3-b]pyrazine (I-100) (2.4 g, 90%) as a yellow solid. LCMS (APCI), m/z 203.3 $[M+H]^+$; 1H NMR (400 MHz, $CD_3OD$) δ ppm 8.73-8.74 (d, 1 H), 8.55-8.56 (d, 1 H), 8.26 (s, 1 H), 3.58-3.59 (m, 2 H), 3.44-3.45 (m, 1 H), 3.25-3.27 (m, 2 H), 2.34-2.38 (m, 2 H), 2.07-2.11 (m, 2 H).

Step 1—Synthesis of 2-amino-3-chloropyrazine (I-95)

A mixture of 2,3-dichloropyrazine (I-94) (45 g, 300 mmol) in $NH_3 \cdot H_2O$ (1000 mL) was stirred at 120° C. in a 2 L autoclave overnight. The mixture was filtered, and the filter cake was washed with water (400 mL) and $CH_2Cl_2$ (400 mL), and dried in vacuum to afford 2-amino-3-chloropyrazine (I-95) (36.85 g, 94%) as a gray solid, which was used directly without further purification.

Step 2—Synthesis of 3-[(trimethylsilyl)ethynyl]pyrazin-2-amine (I-96)

To a solution of 2-amino-3-chloropyrazine (I-95) (30 g, 250 mmol) in a mixture of THF (200 ml) and TEA (200 mL) was added CuI (1 g, 5.2 mmol), $Pd(PPh_3)_4$ (2 g, 1.7 mmol) and TMS-acetylene (30 mL, 480 mmol) at 0° C. under $N_2$. The reaction mixture was stirred at room temperature for two days. TLC (petroleum ether:EtOAc=2:1) showed the reaction was complete. The mixture was concentrated under vacuum to give the crude product, which was purified by silica gel chromatography (petroleum ether:EtOAc=30:1) to give 3-[(trimethylsilyl)ethynyl]pyrazin-2-amine (I-96) (14 g, 32%) as a faint yellow solid.

Synthesis of 5-amino-2-(piperidin-4-yl)pyrimidine-4-carboxamide (I-105)

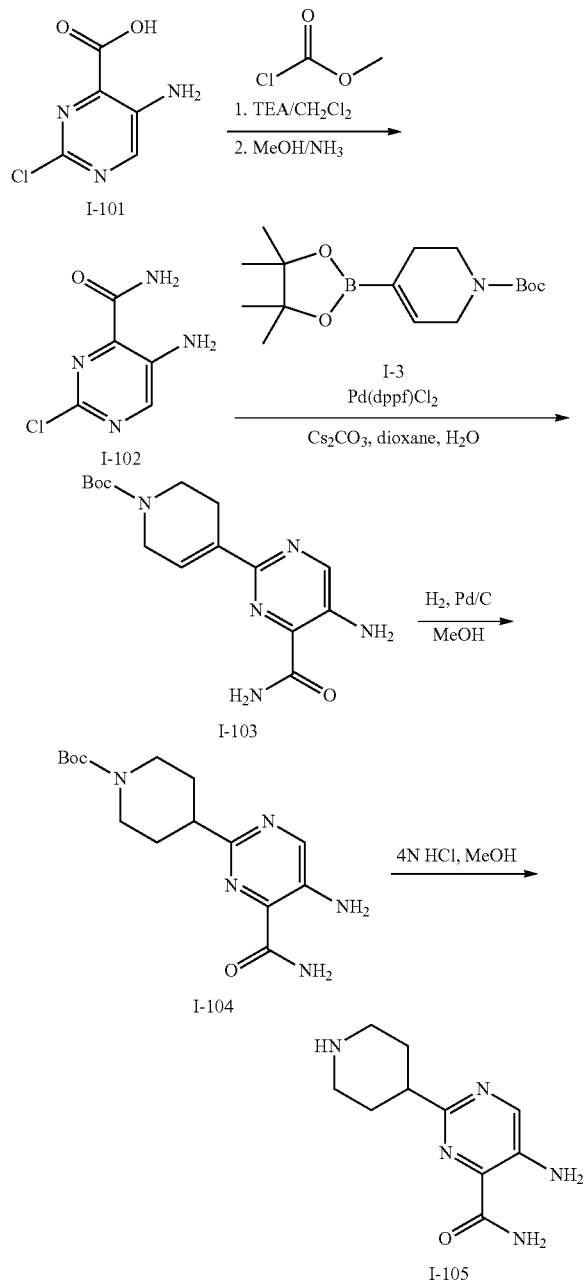

Step 1—Synthesis of 5-amino-2-chloropyrimidine-4-carboxamide (I-102)

To a cooled 0° C. solution of 5-amino-2-chloropyrimidine-4-carboxylic acid (I-101) (500 mg, 2.88 mmol) in CH$_2$Cl$_2$ (25 mL) was added TEA (1.2 mL, 8.64 mmol) followed by methyl chloroformate (0.45 mmol, 5.76 mmol). The reaction mixture was stirred at 0° C. for 30 min. After this time, NH$_3$ (20 mL, 7 N in MeOH, 140 mmol) was added, and the reaction stirred at room temperature for 5 days. The mixture was reduced to minimum volume, and the residue triturated with MeOH to afford 5-amino-2-chloropyrimidine-4-carboxamide (I-102) (334 mg, 67%) as a pale yellow solid. $^1$H NMR (400 MHz, CDCl$_3$) δ ppm 8.27 (s, 1 H), 7.66 (br. s., 1 H), 5.94 (br. s., 2 H), 5.53 (br. s., 1 H).

Step 2—Synthesis of tert-butyl 4-(5-amino-4-carbamoylpyrimidin-2-yl)-3,6-dihydropyridine-1(2H)-carboxylate (I-103)

A mixture of 5-amino-2-chloropyrimidine-4-carboxamide (I-102) (330 mg, 1.91 mmol), tert-butyl 4-(4,4,5,5-tetramethyl-1,3,2-dioxaborolan-2-yl)-3,6-dihydropyridine-1(2H)-carboxylate (828 mg, 2.68 mmol), and cesium carbonate (1.87 g, 5.74 mmol) was taken up in dioxane (25 mL) and degassed with nitrogen for 5 min. Pd(dppf)Cl$_2$ (78.4 mg, 0.096 mmol) was added, and the vessel sealed and heated to 80° C. for 18 hr. LCMS indicates complete conversion to the desired product (mass ion shows 264, which is product minus t-butyl). The mixture was partitioned between EtOAc (50 mL) and brine (50 mL). The aqueous layer was further extracted with EtOAc (2×50 mL). The combined organics were washed with brine, dried over MgSO4, filtered and concentrated to afford a residue, which was purified by chromatography over silica gel eluting with 20-100% EtOAc in heptanes to afford tert-butyl 4-(5-amino-4-carbamoylpyrimidin-2-yl)-3,6-dihydropyridine-1(2H)-carboxylate (I-103) as a pale yellow solid. $^1$H NMR (400 MHz, CDCl$_3$) δ ppm 8.34 (s, 1 H), 7.83 (br. s., 1 H), 6.94 (br. s., 1 H), 5.85 (br. s., 2 H), 5.48 (br. s., 1 H), 3.97-4.25 (m, 2 H), 3.64 (t, J=5.56 Hz, 2 H), 2.68 (br. s., 2 H), 1.50 (s, 9 H).

Step 3—Synthesis of tert-butyl 4-(5-amino-4-carbamoylpyrimidin-2-yl)piperidine-1-carboxylate (I-104)

To a solution of tert-butyl 4-(5-amino-4-carbamoylpyrimidin-2-yl)-3,6-dihydropyridine-1(2H)-carboxylate (I-103) (470 mg, 1.47 mmol) in MeOH (30 mL) was added Pd/C (100 mg, 10%). The reaction was place on a Parr shaker at 30 psi hydrogen pressure for 18 hr. A slight uptake in hydrogen was observed. Check LCMS and mass does not correlate either for product or starting material. Filter through microfiber filter paper washing with MeOH (10 mL). Strip to dryness to afford a foamy residue. Triturate with heptanes initially followed by ether to afford a free-flowing powder. Filter washing with heptanes/ether, and a collect second crop. Combine the solids to afford tert-butyl 4-(5-amino-4-carbamoylpyrimidin-2-yl)piperidine-1-carboxylate (I-104) (397 mg, 84%) as a colorless solid. LCMS (APCI), m/z 222.2 [M-Boc]$^+$; $^1$H NMR (400 MHz, DMSO-d$_6$) δ ppm 8.38 (s, 1 H), 8.02 (br. s., 1 H), 7.61 (br. s., 1 H), 6.66 (br. s., 2 H), 4.00 (d, J=12.8 Hz, 3 H), 2.75-2.93 (m, 2 H), 1.89 (d, J=10.7 Hz, 2 H), 1.61 (dd, J=12.3, 3.5 Hz, 2 H), 1.41 (s, 9 H).

Step 4—Synthesis of 5-amino-2-(piperidin-4-yl) pyrimidine-4-carboxamide (I-105)

To a solution of tert-butyl 4-(5-amino-4-carbamoylpyrimidin-2-yl)piperidine-1-carboxylate (I-104) (395 mg, 1.23 mmol) in MeOH (5 mL) was added HCl (5 mL, 4 N in dioxane, 20 mmol), and the reaction allowed to stir at room temperature for 18 hr. LCMS indicated the reaction was complete. The solvent was evaporated to minimum volume, and the residue dried under high vacuum to afford 5-amino-2-(piperidin-4-yl)pyrimidine-4-carboxamide (I-105) (364 mg, assume quantitative for bis-HCl salt) as the hydrochloride salt, which was used without further purification.

Synthesis of 5-(1-methyl-1H-imidazol-4-yl)-3-(piperidin-4-ylmethoxy)pyridin-2-amine (I-107)

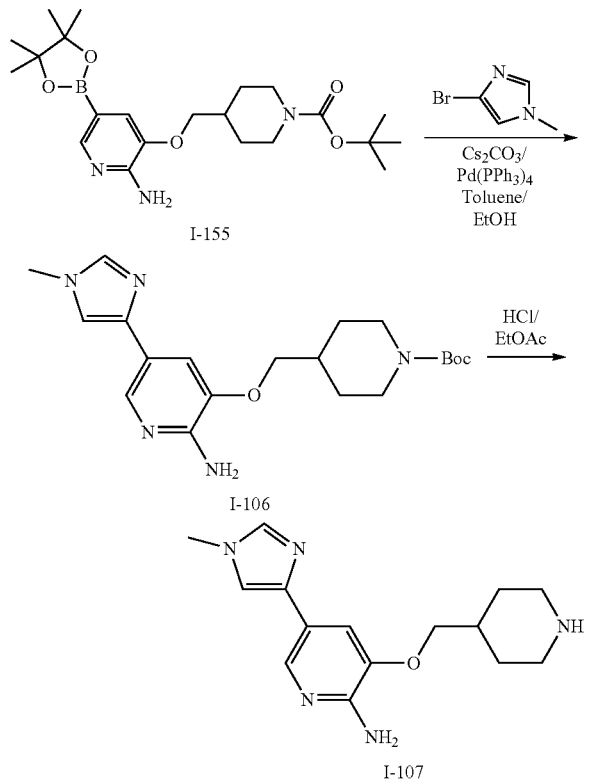

Step 1—Synthesis of tert-butyl 4-({[2-amino-5-(1-methyl-1H-imidazol-4-yl)pyridin-3-yl]oxy}methyl)piperidine-1-carboxylate (I-106)

To a suspension of tert-butyl 4-({[2-amino-5-(4,4,5,5-tetramethyl-1,3,2-dioxaborolan-2-yl)pyridin-3-yl]oxy}methyl)piperidine-1-carboxylate (I-55) (11.08 g, 27.2 mmol), 4-bromo-1-methyl-1H-imidazole (5.26 g, 32.7 mmol), $Cs_2CO_3$ (2 N in $H_2O$, 27.2 mL, 54.5 mmol) in toluene (50 mL) and EtOH (150 mL) was added $Pd(PPh_3)_4$ (4.72 g, 4.08 mmol). The mixture was thoroughly degassed with $N_2$ three times and the brown suspension was then stirred at 85° C. for 16 hr under $N_2$. LCMS showed the desired product by mass had formed. The reaction mixture was concentrated under vacuum to give a residue, which was diluted with $CH_2Cl_2$ (300 mL), washed with water (50 mL), brine (30 mL), dried over $Na_2SO_4$ and concentrated to give the crude product which was purified twice by silica gel chromatography (0 to 5% MeOH in $CH_2Cl_2$ followed by $CH_2Cl_2$/MeOH=1/0 to 20/1) to give tert-butyl 4-({[2-amino-5-(1-methyl-1H-imidazol-4-yl)pyridin-3-yl]oxy}methyl)piperidine-1-carboxylate (~5.9 g as a brown solid. ~90% purity). This material was diluted with EtOAc/$CH_2Cl_2$ (5:1, 60 mL) and heated to 60° C. until a clear solution was obtained. Cooling the solution to 25° C. with concomitant reduction of the volume under reduced pressure (~10 mL) lead to the appearance of a precipitate. The suspension was filtered, the filter cake was washed with EtOAc/petroleum ether (1:1, 10 mL) and dried under vacuum to give tert-butyl 4-({[2-amino-5-(1-methyl-1H-imidazol-4-yl)pyridin-3-yl]oxy}methyl)piperidine-1-carboxylate (I-106) (4.38 g, 42%) as a purple solid.

Step 2—Synthesis of 5-(1-methyl-1H-imidazol-4-yl)-3-(piperidin-4-ylmethoxy)pyridin-2-amine (I-107)

tert-Butyl 4-({[2-amino-5-(1-methyl-1H-imidazol-4-yl)pyridin-3-yl]oxy}methyl)piperidine-1-carboxylate (I-106) (10.6 g, 26.6 mmol) was dissolved in $CH_2Cl_2$/Methanol (66 mL). The yellow solution was cooled to 0° C. with an ice-bath and HCl (g) in EtOAC (50 mL, 4M) was slowly added in a dropwise manner over 5 min. Almost immediately a yellow precipitate appeared. After the addition was completed, the ice-bath was removed. The suspension was stirred at 25° C. for 20 hr. The light yellow suspension was then concentrated under vacuum to give the hydrochloride salt of 5-(1-methyl-1H-imidazol-4-yl)-3-(piperidin-4-ylmethoxy)pyridin-2-amine (I-107) (11.69 g, >100%) as a light yellow solid, which was used without further purification. LCMS (APCI), m/z 288.2 [M+H]$^+$; $^1$H NMR (400 MHz, $CD_3OD$) δ ppm 9.08 (s, 1 H), 8.12 (s, 1 H), 7.94 (s, 1 H), 7.84 (s, 1 H), 4.25-4.27 (d, 2 H), 4.03 (s, 3 H), 3.49-3.53 (d, 2 H), 3.12 (t, 2 H), 2.28-2.46 (m, 1 H), 2.14-2.27 (m, 2 H), 1.67-1.83 (m, 2 H).

Synthesis of 5-(1-methyl-1H-imidazol-5-yl)-3-(piperidin-4-ylmethoxy)pyridin-2-amine (I-109)

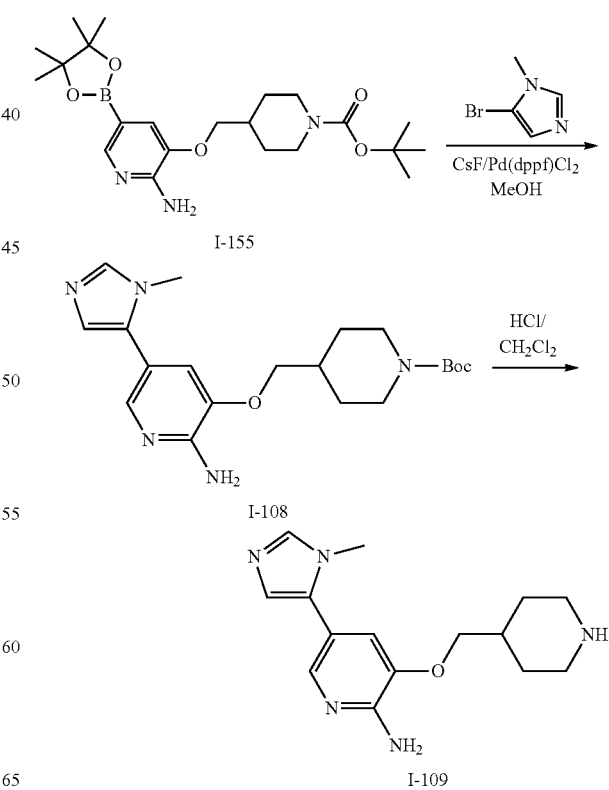

Step 1—Synthesis of tert-butyl 4-({[2-amino-5-(1-methyl-1H-imidazol-5-yl)pyridin-3-yl]oxy}methyl)piperidine-1-carboxylate (I-108)

To a suspension of tert-butyl 4-({[2-amino-5-(4,4,5,5-tetramethyl-1,3,2-dioxaborolan-2-yl)pyridin-3-yl]oxy}methyl)piperidine-1-carboxylate (I-55) (22 mg, 0.51 mmol), 5-bromo-1-methyl-1H-imidazole (124 mg, 0.77 mmol), CsF (273 mg, 1.80 mmol) in MeOH (8 mL) was added Pd(dppf)Cl$_2$ (21.2 mg, 0.026 mmol). The mixture was thoroughly degassed with N$_2$ three times and the brown suspension was then stirred at 85° C. for 16 hr under N$_2$. LCMS showed the desired product by mass had formed. The reaction mixture was concentrated under vacuum to give a residue, which was diluted with partitioned between EtOAc (20 mL) and H2O (10 mL). The aqueous was extracted with EtOAc (2×10 mL), and the combined organics dried over Na2SO4, filtered and concentrated to afford a residue, which was purified by reverse phase HPLC to afford tert-butyl 4-({[2-amino-5-(1-methyl-1H-imidazol-5-yl)pyridin-3-yl]oxy}methyl) piperidine-1-carboxylate (I-108) (97 mg, 49%) as a colorless solid. LCMS (APCI), m/z 388.2 [M+H]$^+$; $^1$H NMR (400 MHz, DMSO-d$_6$) δ ppm 7.62 (s, 1H), 7.58 (d, J=1.76 Hz, 1 H), 7.06 (d, J=1.76 Hz, 1 H), 6.90 (d, J=1.01 Hz, 1 H), 5.82 (s, 2 H), 3.97 (d, J=12.09 Hz, 3.87 (d, J=6.55 Hz, 2 H), 3.60 (s, 3 H), 2.67-2.79 (m, 2 H), 1.89-2.00 (m, 1 H), 1.80 (d, J=10.83 Hz, 2 H), 1.39 (s, 9 H), 1.17 (dd, J=12.21, 3.90 Hz, 1 H).

Step 2—Synthesis of 5-(1-methyl-1H-imidazol-5-yl)-3-(piperidin-4-ylmethoxy)pyridin-2-amine (I-109)

tert-butyl 4-({[2-amino-5-(1-methyl-1H-imidazol-5-yl)pyridin-3-yl]oxy}methyl)piperidine-1-carboxylate (I-108) (95 mg, 0.24 mmol) was dissolved in CH$_2$Cl$_2$ (3 mL). The yellow solution was cooled to 0° C. with an ice-bath and HCl (g) in dioxane (0.61 mL, 4M, 2.45 mmol) was slowly added in a dropwise manner. After the addition was completed, the ice-bath was removed. The suspension was stirred at 25° C. for 20 hr. The light yellow suspension was then concentrated under vacuum to give the hydrochloride salt of 5-(1-methyl-1H-imidazol-5-yl)-3-(piperidin-4-ylmethoxy)pyridin-2-amine (I-109) (88 mg, >100%) as a white solid, which was used without further purification. LCMS (APCI), m/z 288.3 [M+H]$^+$.

Synthesis of 3-(piperidin-4-yl)-1H-pyrazolo[3,4-d]pyrimidine (I-116)

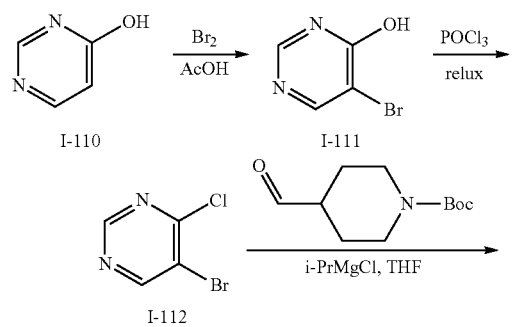

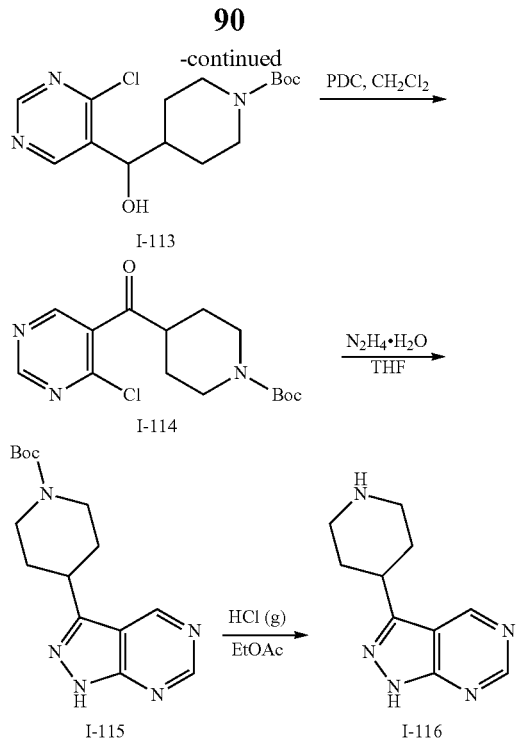

Step 1—Synthesis of 5-bromopyrimidin-4-ol (I-111)

To a solution of pyrimidin-4-ol (I-110) (50 g, 0.52 mol) in AcOH (800 mL) was added in a dropwise manner a solution of Br$_2$ (88 g, 0.55 mol) in AcOH (100 mL) over a period of 30 min at room temperature. Then the resulting mixture was stirred at room temperature overnight. The reaction mixture was filtered, and the cake was washed with petroleum ether (200 mL), and neutralized with saturated aq. NaHCO$_3$ (500 mL) carefully. The suspension was filtered, the cake was washed with H$_2$O (100 mL), dried under high vacuum to give 5-bromopyrimidin-4-ol (I-111) (45 g, 50%) as a pale white solid.

Step 2—Synthesis of 5-bromo-4-chloropyrimidine (I-112)

To a mixture of 5-bromopyrimidin-4-ol (I-111) (40 g, 0.22 mol) in POCl$_3$ (300 mL) was added in a dropwise manner DIPEA (29 g, 0.22 mol) at room temperature. Then the resulting mixture was heated to reflux for 3 hr. TLC (petroleum ether/EtOAc 1:1) showed the reaction was complete. Excess POCl$_3$ was removed through distillation under reduced pressure. The residue was poured into ice-water (300 mL) slowly with stirring. The mixture was extracted with EtOAc (2×300 mL), the combined organic layers were washed with water (300 mL), brine (300 mL), dried over Na$_2$SO$_4$ and concentrated under vacuum. The residue was purified by silica gel chromatography (petroleum ether/EtOAc from 20:1 to 10:1) to give 5-bromo-4-chloropyrimidine (I-112) (25 g, 60%) as a yellow oil.

Step 3—Synthesis of tert-butyl 4-[(4-chloropyrimidin-5-yl)(hydroxy)methyl]piperidine-1-carboxylate (I-113)

To a −30° C. solution of 5-bromo-4-chloropyrimidine (I-112) (13 g, 0.07 mol) in anhydrous THF (130 mL) was added in a dropwise manner a solution of i-PrMgCl (50 mL, 0.1 mol, 2M in THF). Then the resulting mixture was stirred at −30° C. for 30 min. A solution of tert-butyl 4-formylpiperidine-1-carboxylate (15 g, 0.07 mol) in THF (20 mL) was added to the above solution at −30° C. After the addition, the mixture was allowed to room temperature, and stirred for a further 4 hr. TLC (petroleum ether/EtOAc 3:1) showed the reaction was complete. Saturated aq. NH₄Cl (200 mL) was added to quench the reaction at 0° C. The mixture was extracted with EtOAc (2×200 mL). The organic layers were dried over Na₂SO₄ and concentrated under vacuum. The residue was purified by silica gel chromatography (petroleum ether/EtOAc from 10:1 to 3:1) to give tert-butyl 4-[(4-chloropyrimidin-5-yl)(hydroxy)methyl]piperidine-1-carboxylate (I-113) (13.7 g, 60%) as a pale white solid. ¹H NMR (400 MHz, CDCl₃) δ ppm 8.91 (s, 1 H), 8.83 (s, 1 H), 4.85-4.93 (m, 1 H), 4.14 (br. s., 2 H), 2.55-2.62 (m, 3 H), 1.83-1.92 (m, 1 H), 1.41-1.46 (m, 15 H).

Step 4—Synthesis of tert-butyl 4-[(4-chloropyrimidin-5-yl)carbonyl]piperidine-1-carboxylate (I-114)

To a mixture of tert-butyl 4-[(4-chloropyrimidin-5-yl)(hydroxy)methyl]piperidine-1-carboxylate (I-113) (4 g, 0.012 mol) in CH₂Cl₂ (150 mL) was added PDC (5.9 g, 0.016 mol) in portions. Then the mixture was stirred at room temperature for 14 hr. TLC (petroleum ether/EtOAc 2:1) showed the reaction was complete. The reaction mixture was filtered, and the filtrate was concentrated under vacuum at room temperature. The residue was purified by silica gel chromatography (petroleum ether/EtOAc from 6:1 to 3:1) to give tert-butyl 4-[(4-chloropyrimidin-5-yl)carbonyl]piperidine-1-carboxylate (I-114) (1.1 g, 28%) as a pale yellow oil.

Step 5—Synthesis of tert-butyl 4-(1H-pyrazolo[3,4-d]pyrimidin-3-yl)piperidine-1-carboxylate (I-115)

To a mixture of tert-butyl 4-[(4-chloropyrimidin-5-yl)carbonyl]piperidine-1-carboxylate (I-114) (1.5 g, 4.6 mmol) in THF (10 mL) was added N₂H₄.H₂O (0.25 g, 5.1 mmol). The resulting mixture was stirred at room temperature for 30 min. Then the reaction mixture was heated to 50° C. for another 30 min. TLC (petroleum ether/EtOAc 2:1) showed the reaction was complete. The reaction mixture was concentrated under high vacuum. The residue was dissolved with EtOAc (30 mL), and then washed with H₂O (10 mL), brine (10 mL), dried over Na₂SO₄ and concentrated under vacuum to give tert-butyl 4-(1H-pyrazolo[3,4-c]pyrimidin-3-yl)piperidine-1-carboxylate (I-115) (1.1 g, 78%) as a yellow solid, which was used in the next step without further purification.

Step 6—Synthesis of 3-(piperidin-4-yl)-1H-pyrazolo[3,4-d]pyrimidine (I-116)

To a ice-bath cooled solution of tert-butyl 4-(1H-pyrazolo[3,4-c]pyrimidin-3-yl)piperidine-1-carboxylate (I-115) (1.2 g, 3.9 mmol) in CH₂Cl₂ (10 mL) was added 4 M HCl/EtOAc (20 mL). Then the resulting mixture was stirred at room temperature overnight. The reaction mixture was concentrated under vacuum, and the residue was dissolved in H₂O (20 mL). The solution was washed with EtOAc (15 mL) and lyophilized under vacuum to give the hydrochloride salt 3-(piperidin-4-yl)-1H-pyrazolo[3,4-d]pyrimidine (I-116) (0.7 g, 87%) as a yellow solid. LCMS (APCI), m/z 204.1 [M+H]⁺; ¹H NMR (400 MHz, D₂O) δ ppm 9.55 (s, 1 H), 9.06 (s, 1 H), 3.50-3.54 (m, 2 H), 3.15-3.22 (m, 2 H), 2.31-2.35 (m, 2 H), 2.03-2.14 (m, 3 H).

Synthesis of 3-(piperidin-4-ylmethoxy)pyridin-2-amine (I-118)

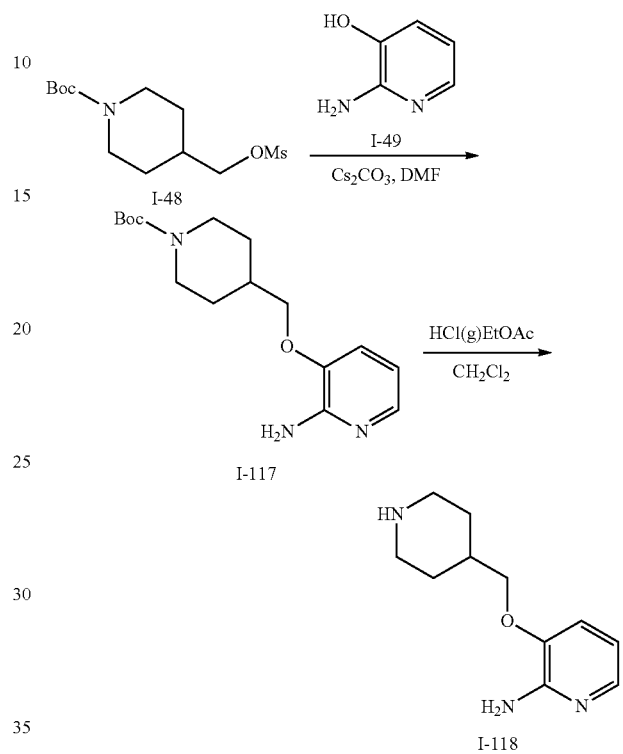

Step 1—Synthesis of tert-butyl 4-{[(2-aminopyridin-3-yl)oxy]methyl}piperidine-1-carboxylate (I-117)

A mixture of tert-butyl 4-{[(methylsulfonyl)oxy]methyl}piperidine-1-carboxylate (I-48) (12.08 g, 41.2 mmol), 2-aminopyridin-3-ol (I-49) (4.32 g, 39.2 mmol) and Cs₂CO₃ (25.5 g, 78.4 mmol) in DMF (120 m:) was stirred at 80° C. for 2 hr. TLC (CH₂Cl₂/MeOH=10/1) showed the reaction was complete. The reaction mixture was cooled to room temperature, and concentrated under vacuum to dryness. The residue was diluted with 100 mL of water and extracted with CH₂Cl₂ (3×100 mL). The combined organic layers were dried over Na₂SO₄, filtered and concentrated under vacuum to give the crude product. The crude product was washed with ethyl acetate (20 mL) to give tert-butyl 4-{[(2-aminopyridin-3-yl)oxy]methyl}piperidine-1-carboxylate (I-117) (9.37 g, 78%) as a yellow solid. ¹H NMR (400 MHz, CDCl₃) δ ppm 7.65-7.66 (m, 1 H), 6.81 (d, J=6.8 Hz, 1 H), 6.58-6.61 (m, 1 H), 4.62 (br. s., 2 H), 4.17 (br. s., 2 H), 3.82 (d, J=6.0 Hz, 2 H), 2.65-2.85 (m, 2 H), 1.97-2.01 (m, 1 H), 1.79-1.85 (m, 2 H), 1.46 (s, 9 H), 1.27-1.31 (m, 2 H).

Step 2—Synthesis of 3-(piperidin-4-ylmethoxy)pyridin-2-amine (I-118)

A solution of 4N HCl in EtOAc (45 mL) was added to a mixture of tert-butyl 4-{[(2-aminopyridin-3-yl)oxy]

methyl}piperidine-1-carboxylate (I-117) (9.37 g, 29.5 mmol) in CH$_2$Cl$_2$ (45 mL) at 0° C. The mixture was stirred at room temperature for 3 hr. LCMS showed the reaction was complete. The mixture was concentrated under vacuum, and the residue lyophilized to afford the hydrochloride salt of 3-(piperidin-4-ylmethoxy)pyridin-2-amine (I-118) (8.57 g, 95% yield) as a grey solid. LCMS (APCI), m/z 208.1 [M+H]$^+$; $^1$H NMR (400 MHz, CD$_3$OD) δ ppm 7.47-7.50 (m, 2 H), 6.88-6.91 (m, 1 H), 4.11 (d, J=6.4 Hz, 2 H), 3.49 (d, J=12.4 Hz, 2 H), 3.07-3.13 (m, 2 H), 2.25-2.35 (m, 1H), 2.18 (d, J=14.0 Hz, 2 H), 1.67-1.77 (m, 2 H).

Synthesis of 4-methoxy-3-(piperidin-4-yl)-1H-pyrrolo[2,3-b]pyridine (I-123)

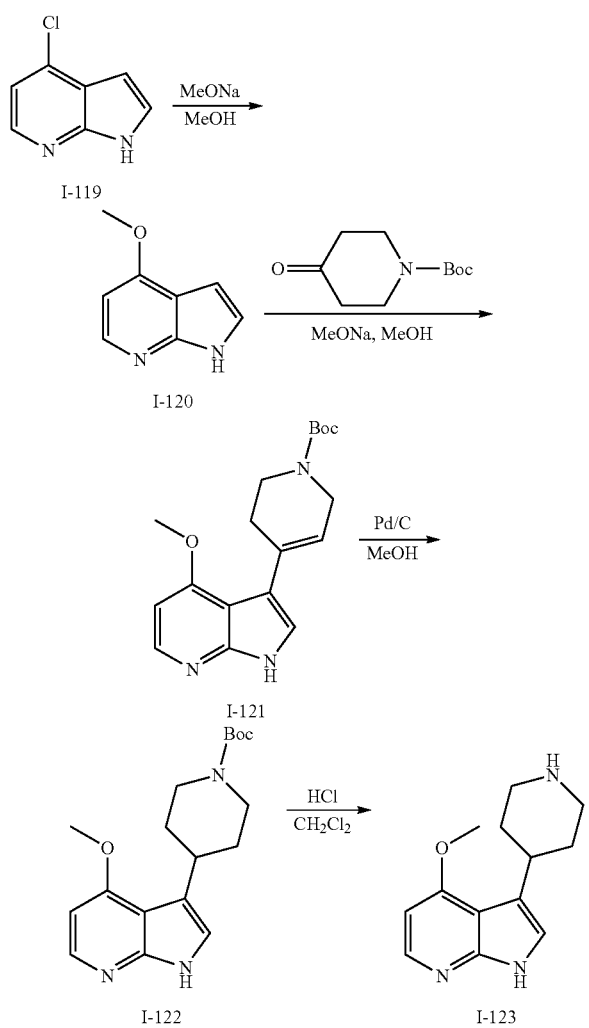

Step 1—Synthesis of 4-methoxy-1H-pyrrolo[2,3-b]pyridine (I-120)

To MeOH (600 mL) was added Na (22.6 g, 983 mmol.) in portions over 1 hr, and the mixture stirred to afford a clear solution. Then 4-chloro-1H-pyrrolo[2,3-b]pyridine (I-119) (50 g, 327.69 mmol) was added. The reaction mixture was stirred at 140° C. for 44 hr in a 1 L autoclave. Some yellow solids formed in the reaction mixture, and LCMS showed about 30% of starting material remained. The reaction mixture was concentrated under vacuum to remove MeOH. The residue was diluted into water (200 mL) and extracted with EtOAc/THF (2×300 mL/50 mL). The extracts were washed with saturated NH$_4$Cl (150 mL) and brine (150 mL). The extract was dried and concentrated to give a crude product, which was purified by silica gel chromatography (petroleum ether:EtOAc:THF=3:1:0.2 to 1:1:0.2) and recrystallized from petroleum ether/CH$_2$Cl$_2$/EtOH (600 mL/100 mL/10 mL) to give 4-methoxy-1H-pyrrolo[2,3-b]pyridine (I-120) (22 g, 45%) as a white solid.

Step 2—Synthesis of tert-butyl 4-(4-methoxy-1H-pyrrolo[2,3-b]pyridin-3-yl)-3,6-dihydropyridine-1 (2H)-carboxylate (I-121)

To MeOH (1.5 L) was added Na (57 g, 2.48 mol) in portions over 2 h, and the mixture stirred to afford a clear solution. 4-methoxy-1H-pyrrolo[2,3-b]pyridine (I-120) (64.4 g, 410 mmol) and tert-butyl 4-oxopiperidine-1-carboxylate (165.0 g, 826 mmol) was added to the NaOMe solution (1.5 L) at 25° C. The reaction mixture was stirred at 80° C. for 3 days. LCMS showed about 30% of starting material was remained. The reaction mixture was concentrated to remove MeOH. The residue was diluted into water (1.5 L) and extracted with EtOAc/THF (2×1.5 L/150 mL). The extracts were washed with brine (2×2 L). The extract was dried over Na$_2$SO$_4$, and concentrated to give a residue (300 g), which was purified by silica gel chromatography (petroleum ether:EtOAc:THF=3:1:0.15 to 1:1:0.15) to give tert-butyl 4-(4-methoxy-1H-pyrrolo[2,3-b]pyridin-3-yl)-3,6-dihydropyridine-1(2H)-carboxylate (I-121) (49 g, 35%) as a yellow solid.

Step 3—Synthesis of tert-butyl 4-(4-methoxy-1H-pyrrolo[2,3-b]pyridin-3-yl)piperidine-1-carboxylate (I-122)

To a light yellow suspension of tert-butyl 4-(4-methoxy-1H-pyrrolo[2,3-b]pyridin-3-yl)-3,6-dihydropyridine-1(2H)-carboxylate (I-121) (38 g, 110 mmol) in MeOH (800 mL)/THF (50 mL) was added 10% Pd/C (20 g, 50% H$_2$O) under an Ar atmosphere. The mixture was purged with Ar (15 psi) three times and H$_2$ (15 psi) three times. Then the reaction mixture was stirred under 30 psi of H$_2$ pressure and heated to 60° C. for 40 hr. LCMS showed that the reaction was complete. The mixture was filtered, and the filtrate was concentrated to give tert-butyl 4-(4-methoxy-1H-pyrrolo[2,3-b]pyridin-3-yl)piperidine-1-carboxylate (I-122) (37 g, 96%) as a grey solid.

Step 4—Synthesis of 4-methoxy-3-(piperidin-4-yl)-1H-pyrrolo[2,3-b]pyridine (I-123)

To a yellow solution of tert-butyl 4-(4-methoxy-1H-pyrrolo[2,3-b]pyridin-3-yl)piperidine-1-carboxylate (I-122) (37 g, 110 mmol) in CH$_2$Cl$_2$ (200 mL) was added 4 N HCl (g)/EtOAc (200 mL) in a dropwise manner maintaining the temperature between 10-20° C. A significant amount of solids were formed. The mixture was stirred at 20° C. for 2 hr. TLC (petroleum ether:EtOAc=2:3) showed that the reaction was complete. The mixture was filtered and the solid was dried under vacuum to give 4-methoxy-3-(piperidin-4-yl)-1H-pyrrolo[2,3-b]pyridine (I-123) (33.6 g, 100%) as a grey solid. LCMS (APCI), m/z 231.8 [M+H]$^+$; $^1$H NMR (400 MHz, CD$_3$OD) δ ppm 8.34-8.35 (d, 1 H), 7.35 (s, 1 H), 7.20-7.21 (d, 1 H), 4.28 (s, 3 H), 3.51-3.54 (d, 2 H), 3.36-3.42 (m, 1 H), 3.18-3.24 (t, 2 H), 2.27-2.31 (d, 2 H), 1.88-1.98 (m, 2 H).

Synthesis of N-(bicyclo[1.1.1]pent-1-yl)-2-chloro-6-{[(1S,2R)-2-cyanocyclopropyl]methoxy}pyrimidine-4-carboxamide (I-126)

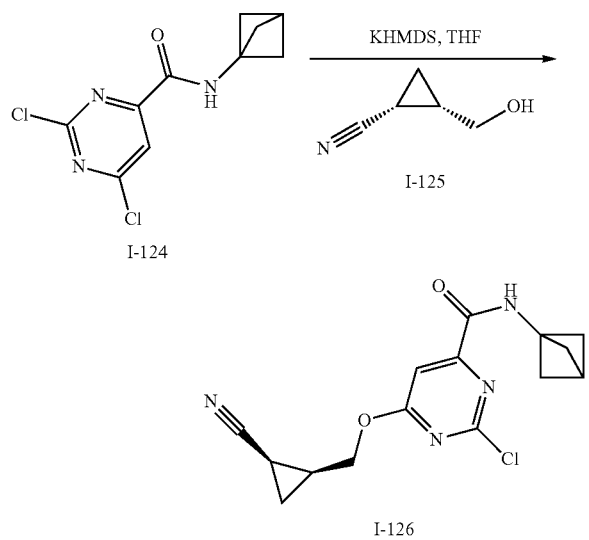

Step 1—Synthesis of N-(bicyclo[1.1.1]pent-1-yl)-2-chloro-6-{[(1S,2R)-2-cyanocyclopropyl]methoxy}pyrimidine-4-carboxamide (I-126)

To a solution of N-(bicyclo[1.1.1]pent-1-yl)-2,6-dichloropyrimidine-4-carboxamide (I-124) (55 mg, 0.21 mmol) in THF (23 mL) was added dropwise KHMDS (0.42 mL, 0.42 mmol, 1 M in THF) at −5~0° C. under a nitrogen atmosphere. After the addition, the mixture was stirred at −5~0° C. for 30 min before a solution of (1R,2S)-2-(hydroxymethyl)cyclopropanecarbonitrile (I-125) (41 mg, 0.42 mmol) in THF (2 mL) was then added in a dropwise manner to the reaction mixture at −5~0° C. After this addition, the mixture was warned to room temperature and stirred at room temperature for 14 hr. LCMS indicated the reaction was complete. The mixture was neutralized with AcOH (38 mg, 0.63 mmol) at room temperature. The resulting mixture was diluted with brine (10 mL) and H₂O (2 mL). The mixture was stirred at room temperature for 15 min. The organic layer was separated from the mixture and the aqueous layer was re-extracted with EtOAc (2×10 mL). The combined organic layers were dried over Na₂SO₄, filtered and concentrated. The residue was purified by chromatography on silica gel (petroleum ether/EtOAc=3:1) to give N-(bicyclo[1.1.1]pent-1-yl)-2-chloro-6-{[(1S,2R)-2-cyanocyclopropyl]methoxy}pyrimidine-4-carboxamide (I-126) (30 mg, 44.8%) as a colorless oil. $^1$H NMR (400 MHz, CDCl₃) δ ppm 8.07 (br. s. 1 H), 7.45 (s, 1 H), 4.65-4.71 (m, 1 H), 4.37-4.42 (m, 1 H), 2.51 (s, 1 H), 1.87-2.19 (m, 6 H), 1.73-1.87 (m, 1 H), 1.69-1.71 (m, 1 H), 1.36-1.38 (m, 1 H), 1.13-1.15 (m, 1 H).

Synthesis of 1-(hydroxymethyl)cyclopropanecarbonitrile (I-128)

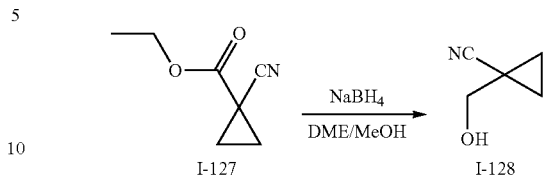

Step 1: Synthesis of 1-(hydroxymethyl)cyclopropanecarbonitrile (I-128)

To a solution of ethyl 1-cyanocyclopropanecarboxylate (I-127) (5 g, 36 mmol) in DME/MeOH (80 mL/8 mL) was added NaBH₄ (10.65 g, 0.288 mol) in a portionwise manner at 0~5° C. The mixture was stirred at room temperature for 4 hr. TLC (petroleum ether:EtOAc=1:1) showed the reaction was complete. The reaction mixture was diluted with saturated aq. NaHCO₃ (60 mL) and then extracted with 10% MeOH/CH₂Cl₂ (8×100 mL). The combined organic layers were dried over Na₂SO₄ and concentrated to give 1-(hydroxymethyl)cyclopropanecarbonitrile (I-128) (3 g, 85%) as a light yellow oil, which was used without further purification.

Synthesis of (1R,2S)-2-(hydroxymethyl)cyclopropanecarbonitrile (I-125)

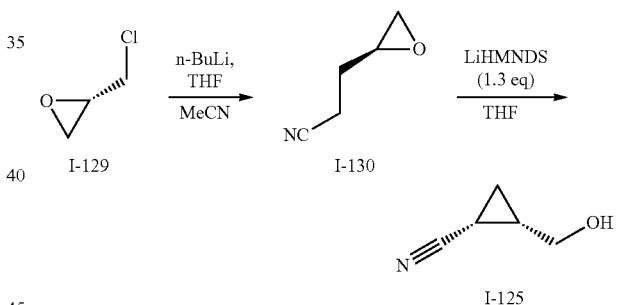

Step 1: Synthesis (S)-3-(oxiran-2-yl)propanenitrile (I-130)

To a mixture of (S)-2-(chloromethyl)oxirane (I-129) (100 g, 1.11 mol) in CH₃CN (340 mL) and THF (500 mL) was added n-BuLi (500 mL, 1.3 mol) in hexane dropwise at −65° C. The mixture was stirred at −65° C. for 4 hr and allowed to warm to room temperature. After stirring at room temperature overnight, NH₄Cl (150 mL) was added and the resulting mixture was extracted with EtOAc (3×250 mL). The combined organic phase was washed with brine (250 mL), dried with Na₂SO₄ and concentrated in vacuo. The residue was purified with column chromatography on silica gel (petroleum ether:EtOAc=10:1-4:1) to give (S)-3-(oxiran-2-yl)propanenitrile (I-130) (60 g, 56.2%) as a yellow oil.

Step 2—Synthesis of (1R,2S)-2-(hydroxymethyl)cyclopropanecarbonitrile (I-125)

To a mixture of (S)-3-(oxiran-2-yl)propanenitrile (I-130) (50 g, 0.52 mol) in THF (1.0 L) was added a solution of LiHMDS (1000 mL, 1.0 mol) in THF (1 M) under $N_2$ at −65° C., the resulting mixture was stirred at the same temperature for 2 hr, then warmed to room temperature. 200 mL of $H_2O$ was added at 0° C. to quench the reaction. The organic layer was separated and the aqueous layer was re-extracted with EtOAc (3×500 mL). The combined organic phase was concentrated and the residue was purified with column chromatography on silica gel (petroleum ether:ethyl acetate=4:1-1:1) to give (1R,2S)-2-(hydroxymethyl)-cyclopropanecarbonitrile (I-125) (6 g, 12%) as a yellow oil. $^1$H NMR (400 MHz, DMSO-$d_6$) δ ppm 4.76-4.78 (m, 1 H), 3.44-3.50 (m, 1 H), 3.22-3.26 (m, 1 H), 1.66-1.69 (m, 1 H), 1.33-1.39 (m, 1 H), 0.99-1.04 (m, 1 H), 0.75-0.77 (m, 1H).

Synthesis of [(2R)-5,5-dimethyltetrahydrofuran-2-yl]methanol (I-133)

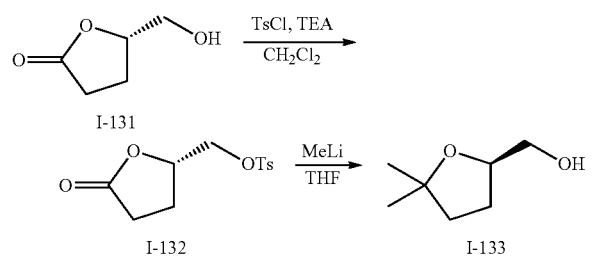

Step 1—Synthesis of [(2S)-5-oxotetrahydrofuran-2-yl]methyl 4-methylbenzenesulfonate (I-132)

To a light yellow solution of (5S)-5-(hydroxymethyl)dihydrofuran-2(3H)-one (I-131) (4.0 g, 34.45 mmol) and TEA (9.6 mL, 68.9 mmol) in $CH_2Cl_2$ (30 mL) was added TsCl (9850 mg, 51.7 mmol) in $CH_2Cl_2$ (15 mL) at 0° C. The solution turned to a gray suspension after stirring at 0° C. for 2 h. TLC (petroleum ether:EtOAc=1:2) showed that the starting material had been consumed. The reaction mixture was diluted with $CH_2Cl_2$ (100 mL), washed with aq. $NH_4Cl$ (3×100 mL), brine (100 mL), dried over anhydrous $Na_2SO_4$ and concentrated to give the crude product, which was purified silica gel chromatography (EtOAc:petroleum ether=0%-50%) to give [(2S)-5-oxotetrahydrofuran-2-yl]methyl 4-methylbenzenesulfonate (I-132) (7.5 g, 81%) as a white solid, which was used without further purification.

Step 2—Synthesis of [(2R)-5,5-dimethyltetrahydrofuran-2-yl]methanol (I-133)

To a solution of [(2S)-5-oxotetrahydrofuran-2-yl]methyl 4-methylbenzenesulfonate (I-132) (5.0 g, 18.5 mmol) in dry THF (90 mL) cooled to −90° C. was added dropwise a solution of methyllithium in diethyl ether (23.1 mL, 37.0 mmol, 1.6 M). The reaction mixture was stirred at −90° C. for 2 h. Then the reaction mixture was warmed up from −90° C. to 20° C. over 4 hr. TLC (petroleum ether:EtOAc=1:2) indicated that the starting material had been completely consumed with a new product formed. The reaction was quenched with saturated brine (100 mL). The reaction mixture turned to a yellow suspension, which turned clear upon addition of 1M HCl (30 mL). The reaction mixture was saturated with NaCl and extracted with EtOAc (4×80 mL). The combined organic layers were dried over anhydrous $Na_2SO_4$, filtered and concentrated to give the crude product, which was purified by silica gel chromatography (petroleum ether:EtOAc=0%-50%) to give [(2R)-5,5-dimethyltetrahydrofuran-2-yl]methanol (I-133) (620 mg, 25.7%) as a light yellow oil. $^1$H NMR (400 MHz, $CDCl_3$) δ ppm 4.08-4.11 (m, 1 H), 3.66-3.70 (m, 1 H), 3.47-3.50 (m, 1 H), 1.95-2.01 (m, 1 H), 1.73-1.81 (m, 3 H), 1.25-1.27 (d, 6 H).

Synthesis of [(1R)-2,2-difluorocyclopropyl]methanol (I-141) and [(1S)-2,2-difluorocyclopropyl]methanol (I-142)

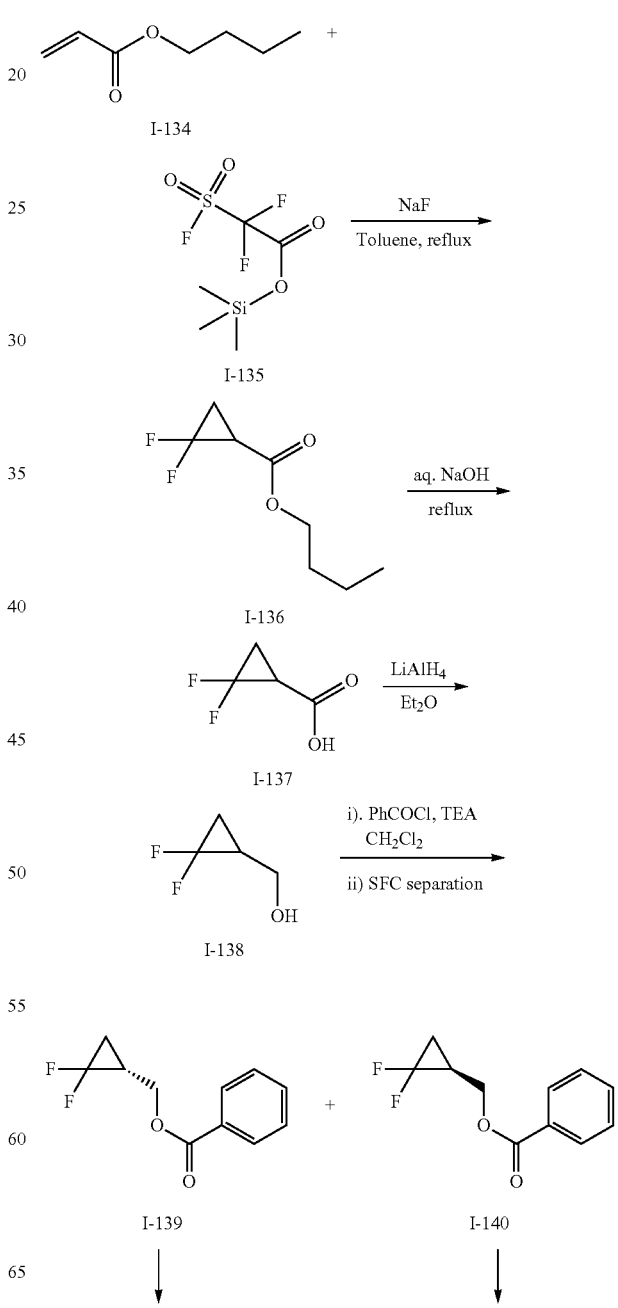

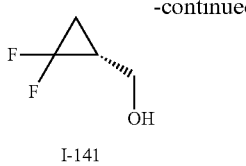
I-141

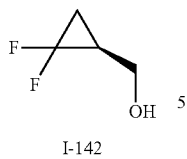
I-142

Step 1: Synthesis butyl 2,2-difluorocyclopropanecarboxylate (I-136)

A solution of butyl prop-2-enoate (80 g, 6.24 mol) and a catalytic amount of NaF (1.57 g, 375 mmol) in anhydrous toluene (800 mL) was degassed with nitrogen 3 times, and then refluxed for 1 hr. Then, trimethylsilyl difluoro(fluorosulfonyl)acetate (250 g, 9.99 mol) was added dropwise to the refluxing solution over a period of 40 mins. After the addition, the resulting pale colorless solution was refluxed under $N_2$ for a further 8 hr. The reaction solution was cooled to room temperature to afford a pale yellow solution. The solvent was removed under vacuum at ~45° C., The combined residue (~130 mL) was firstly distilled at 130° C. under atmospheric pressure to remove residual toluene, and then distilled under reduced pressure (~0.02 atm) at the same temperature to give butyl 2,2-difluorocyclopropanecarboxylate (I-136) (65 g, 59%) as a colorless oil. $^1$H NMR (400 MHz, $CDCl_3$) δ ppm 4.09-4.21 (m, 2 H), 2.36-2.47 (m, 1 H), 2.04-2.07 (m, 1 H), 1.60-1.66 (m, 3 H), 1.36-1.42 (m, 2 H), 0.94 (t, J=7.2 Hz, 3 H).

Step 2—Synthesis 2,2-difluorocyclopropanecarboxylic acid (I-137)

A colorless solution of butyl 2,2-difluorocyclopropanecarboxylate (I-136) (65.0 g, 330 mmol) in aq. NaOH (750 mL $H_2O$, 52.5 g NaOH) was refluxed for ~14 hr. A pale yellow solution was formed. The reaction solution was cooled to room temperature, and then concentrated in vacuo to ~250 mL volume. In an ice bath (~0-5° C.), the residue was adjusted to pH~3-4 using conc. aq. HCl (~70 mL). The resulting solution was extracted with EtOAc (2×500 mL). The combined organic layers were dried over $Na_2SO_4$ and concentrated under high vacuum to give 2,2-difluorocyclopropanecarboxylic acid (I-137) (30 g, 75%) as a yellow oil which gradually solidified on standing to give a pale yellow solid. $^1$H NMR (400 MHz, $CDCl_3$) δ ppm 10.78 (s, 1 H), 2.41-2.47 (m, 1 H), 2.05-2.08 (m, 1 H), 1.80-1.83 (m, 1 H).

Step 3—Synthesis (2,2-difluorocyclopropyl)methanol (I-138)

To a solution of 2,2-difluorocyclopropanecarboxylic acid (I-137) (1.00 g, 8.19 mmol) in anhydrous $Et_2O$ (30 mL) cooled with an ice-bath was added in a dropwise manner a solution of $LiAlH_4$ (12.3 mL, 1M in THF) over 20 min. After the addition, the resulting colorless suspension was allowed to warm to room temperature, and stirred for a further 18 hr. The reaction mixture was then cooled in an ice-bath, and then 2M NaOH (~1 mL) was added in a dropwise manner to quench the reaction followed by $H_2O$ (1 mL). The mixture was filtered, and rinsed with $Et_2O$ (2×10 mL). The filtrates was washed with brine (10 mL). The organic layer was dried over $Na_2SO_4$ and concentrated under vacuum at 5-10° C. to give (2,2-difluorocyclopropyl)methanol (I-138) (2.0 g, >100%, contaminated with residual THF) as a colorless oil. $^1$H NMR (400 MHz, $CDCl_3$) δ ppm 3.67-3.81 (m, 2 H), 1.83-1.87 (m, 1 H), 1.45-1.48 (m, 1 H), 1.14-1.18 (m, 1 H).

Step 4—Synthesis [(1R)-2,2-difluorocyclopropyl]methyl benzoate (I-139) and [(1S)-2,2-difluorocyclopropyl]methyl benzoate (I-140)

To a solution of (2,2-difluorocyclopropyl)methanol (I-138) (5.00 g, 46.3 mmol) in anhydrous $CH_2Cl_2$ (20 mL) was added TEA (1.12 g, 11.1 mmol) at 0° C. followed by a solution of benzoyl chloride (1.18 mL, 10.2 mmol) in $CH_2Cl_2$ (10 mL). The reaction mixture was stirred for 16 hr at room temperature. TLC (petroleum ether/EtOAc=10/1) indicated the reaction was complete. After quenching the reaction with saturated aq. $NaHCO_3$ (15 mL), the reaction mixture was extracted with $CH_2Cl_2$ (2×25 mL). The combined organic layers were washed with brine (15 mL), dried over $Na_2SO_4$ and concentrated under vacuum to dryness. The residue was purified by chromatography on silica gel (EtOAc/petroleum ether=0/100 to 1/24) to give racemic 2,2-difluorocyclopropyl]methyl benzoate (8.2 g, 84%) as a colorless oil. $^1$H NMR (400 MHz, DMSO-$d_6$) δ ppm 7.99 (d, J=8.0 Hz, 2 H), 7.70 (t, J=6.0 Hz, 1 H), 7.56 (t, J=8.0 Hz, 2 H), 4.46-4.50 (m, 1 H), 4.23-4.28 (m, 1 H), 2.25-2.26 (m, 1 H), 1.73-1.77 (m, 1 H), 1.54-1.59 (m, 1 H).

2,2-difluorocyclopropyl]methyl benzoate (18 g) was subjected to chiral separation by SFC to afford both enantiomers. The chiral separation by SFC was performed using a ChiralCel OJ-H (4.6 mm×250 mm column, 5 micron particle size), which was eluted with 1% IPA w. heptanes in $CO_2$ held at 100 bar. A flow rate of 1.0 mL/min gave $Rt_{(Peak\ 1)}$=9.80 min and $Rt_{(Peak\ 2)}$=10.32 min.

[(1R)-2,2-difluorocyclopropyl]methyl benzoate (I-139) (Peak 1): 6.05 g, ~95% ee. (+). LCMS (APCI), m/z 212.9 $[M+H]^+$. $[\alpha]_D$=+8.6° (c=0.6, MeOH, 22° C.).

[(1S)-2,2-difluorocyclopropyl]methyl benzoate (I-140) (Peak 2): 5.98 g, ~90% ee. (−). LCMS (APCI), m/z 212.9 $[M+H]^+$; $[\alpha]_D$=−8.4° (c=0.5, MeOH, 22° C.).

Step 5: Synthesis [(1R)-2,2-difluorocyclopropyl]methanol (I-141)

A light yellow solution of [(1R)-2,2-difluorocyclopropyl]methyl benzoate (I-139) (2.45 g, 11.56 mmol) (~95% ee (+)) in 10% NaOH/$H_2O$ (12.5 mL) was stirred at 80° C. for 2 hr. The reaction mixture was allowed to cool, and then extracted with $Et_2O$ (3×20 mL). The combined organic layers were washed with brine (30 mL), dried over $Na_2SO_4$ and concentrated in vacuo at 20° C. to give [(1R)-2,2-difluorocyclopropyl]methanol (I-141) (1.10 g, 88%) as a light yellow oil. $^1$H NMR (400 MHz, $CDCl_3$) δ ppm 3.76-3.78 (m, 1 H), 3.67-3.70 (m, 1 H), 1.89-1.92 (m, 1 H), 1.45-1.48 (m, 1 H), 1.14-1.18 (m, 1 H); $[\alpha]_D$=+13.3° (c=0.003, MeOH, 22° C.).

Step 6: Synthesis [(1S)-2,2-difluorocyclopropyl]methanol (I-142)

A light yellow solution of [(1S)-2,2-difluorocyclopropyl]methyl benzoate (I-140) (2.63 g, 12.39 mmol) (~90% ee, (−)) in 10% NaOH/$H_2O$ (13 mL) was stirred at 80° C. for 2 hr. The reaction mixture was allowed to cool, and then extracted with $Et_2O$ (3×20 mL). The combined organic layers were washed with brine (30 mL), dried over $Na_2SO_4$ and concentrated in vacuo at 20° C. to give [(1S)-2,2-difluorocyclopropyl]methanol (I-142)

(1.15 g, 86%) as a yellow oil. $^1$H NMR (400 MHz, CDCl$_3$) δ ppm 3.76-3.78 (m, 1 H), 3.65-3.69 (m, 1 H), 1.89-1.92 (m, 1 H), 1.45-1.48 (m, 1 H), 1.14-1.18 (m, 1 H); $[α]_D$=−10.3° (c=0.003, MeOH, 22° C.).

Synthesis of bicyclo[1.1.1]pentan-1-amine hydrochloride (I-146)

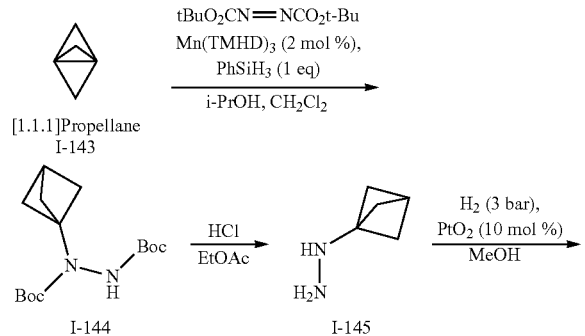

Step 1—Synthesis of di-tert-butyl 1-(bicyclo[1.1.1]pentan-1-yl)hydrazine-1,2-dicarboxylate (I-144)

A stirred solution of tris(2,2,6,6-tetramethyl-3,5-heptanedionato)-manganese(III) [Mn(TMHD)$_3$] (533 mg, 0.873 mmol) in 2-propanol (200 mL) was cooled to 0° C. To the cooled solution was added phenylsilane (4.87 g, 43.6 mmol), a solution of di-tert-butyl azodicarboxylate (15.40 g, 65.5 mmol) in CH$_2$Cl$_2$ (200 mL), and then [1.1.1] propellane (Org. Synth. 1998, 75, 98-105 and J. Am. Chem. Soc. 2001, 3484) (I-143) (ether/pentane solution, 2.89 g, 43.6 mmol, 90.0 mL, 0.485 M). The reaction mixture was maintained at 0° C. for 21 hr and then 20 mL of water was added followed by 50 mL of brine solution. The reaction mixture was allowed to stir 5 min and then an additional 100 mL of water and 100 mL of sat. brine solution (200 mL) was added. The mixture was then diluted with EtOAc (~400 mL) and extracted (3×100 mL) with EtOAc. The organic layers were combined, dried, and concentrated. The crude residue was subjected to flash chromatography (silica gel, 0-25% EtOAc/heptane) to give 12.87 g (99%) of di-tert-butyl 1-(bicyclo[1.1.1]pentan-1-yl)hydrazine-1,2-dicarboxylate (I-144) as a white solid. $^1$H NMR (400 MHz, CDCl$_3$) δ ppm 5.95-6.48 (m, 1 H), 2.38 (s, 1 H), 2.03 (s, 6 H), 1.46 (s, 18 H).

Step 2—Synthesis of bicyclo[1.1.1]pentan-1-ylhydrazine dihydrochloride (I-145)

To a stirred solution of di-tert-butyl 1-(bicyclo[1.1.1]pentan-1-yl)hydrazine-1,2-dicarboxylate (I-144) (11.03 g, 36.97 mmol) in ethyl acetate (200 mL) was added HCl (300 mL, 1.11 mol, 4M in dioxane) at room temperature. The reaction was stirred at rt and monitored by LCMS. After 18 hr the reaction was complete and the mixture was concentrated to give 5.99 g (95%) of crude bicyclo[1.1.1]pentan-1-ylhydrazine dihydrochloride (I-145) as a light yellow solid. $^1$H NMR (300 MHz, DMSO-d$_6$) δ ppm 8.57 (br. s., 5 H), 2.45 (s, 1 H), 1.83 (s, 6 H).

Step 3—Synthesis of bicyclo[1.1.1]pentan-1-amine hydrochloride (I-146)

To a slurry of platinum (IV) oxide (795 mg, 3.50 mmol) in MeOH (1 mL) was added a solution of the bicyclo[1.1.1]pentan-1-ylhydrazine dihydrochloride (I-145) (5.99 g, 35.0 mmol) in methanol (350 mL). The mixture was subjected to 3 bar of hydrogen at 25° C. for 24 hr. The mixture was then filtered through Whatman 1 filter paper and the filtrate concentrated. The crude residue was washed with ether and then triturated in 2-propanol:DCM (10:1). The mixture was filtered and the filtrate concentrated to give 3.35 g (80%) of bicyclo[1.1.1]pentan-1-amine hydrochloride (I-146) as an off-white solid. $^1$H NMR (300 MHz, DMSO-d$_6$) δ ppm 8.89 (br. s., 3 H), 2.58 (s, 1 H), 1.98 (s, 6 H).

Synthesis of 3,3-difluorobutan-2-amine (I-151)

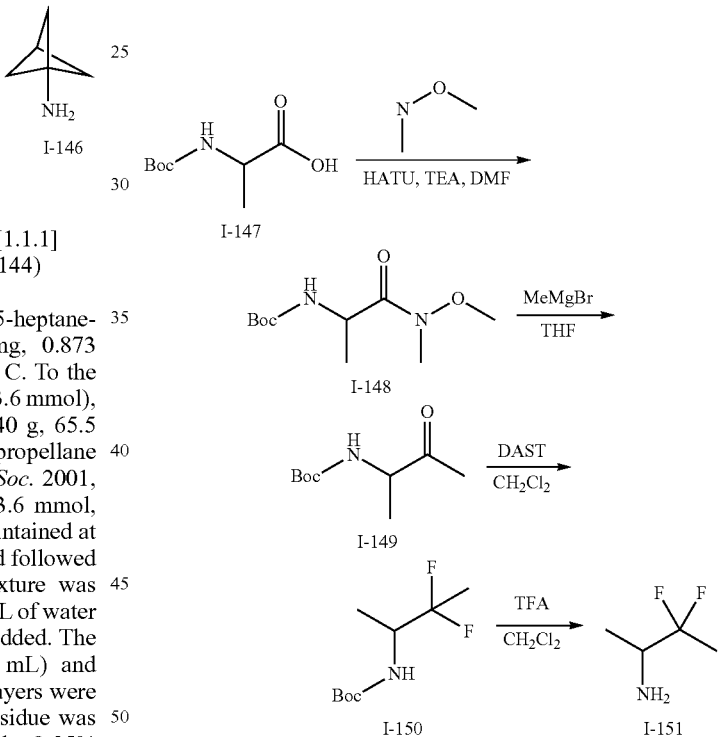

Step 1—Synthesis of N$^2$-(tert-butoxycarbonyl)-N-methoxy-N-methylalaninamide (I-148)

To a colorless solution of N-(tert-butoxycarbonyl)alanine (I-147) (5.0 g, 26.43 mmol) in DMF (100 mL) was added HATU (1.51 g, 39.6 mmol) and TEA (8.02 g, 79.3 mmol). The color is yellow. After stirring for 10 min at 25° C., compound N-methoxymethanamine hydrochloride (3.23 g, 52.9 mmol) was added at 0° C. The resulting yellow solution was stirred at 25° C. for 25 h. The reaction mixture turned to a yellow suspension. TLC (petroleum ether:EtOAc=1:1) showed the starting material was consumed and there was a new major spot. Water (60 mL) was added. The mixture was extracted with EtOAc (3×80 mL). The combined organic layers were washed with water (80 mL), aq. NH₄Cl (80 mL), aq. NaHCO₃ (80 mL), brine (80 mL) and then dried over anhydrous Na₂SO₄ and concentrated to give the crude product, which was purified by silica gel chromatography (petroleum ether:EtOAc=30% to 80%) to give N²-(tert-butoxycarbonyl)-N-methoxy-N-methylalaninamide (I-148) (5.0 g, 82%) as a white solid.

Step 2—Synthesis of tert-butyl (3-oxobutan-2-yl)carbamate (I-149)

To a colorless solution of N²-(tert-butoxycarbonyl)-N-methoxy-N-methylalaninamide (I-148) (3.0 g, 12.92 mmol) in dry THF (100 mL) was added MeMgBr (12 mL, 36 mmol, 3 M in Et₂O) in a dropwise manner at −15° C. over 20 min. The colorless solution turned to a light yellow suspension. After the addition, the reaction mixture was allowed to warm slowly to 25° C. and stirred for 20 hr. The reaction mixture was cooled to 0° C., quenched with aq. NH4Cl (50 mL), extracted with EtOAc (2×50 mL). The combined organic layers were washed with water (50 mL), brine (50 mL), dried over anhydrous Na₂SO₄ and concentrated to give crude product, which was purified by silica gel chromatography (EtOAc: petroleum ether=0%~20%) to give tert-butyl (3-oxobutan-2-yl)carbamate (I-149) (2.0 g, 83%) as a light yellow oil, which solidified within 30 min on standing.

Step 3—Synthesis of tert-butyl (3,3-difluorobutan-2-yl)carbamate (I-150)

To a colorless solution of tert-butyl (3-oxobutan-2-yl) carbamate (I-149) (600 mg, 3.2 mmol) in dry CH₂Cl₂ (30 mL) was added DAST (1.2 mL, 9.61 mmol, 1.2 g/mL) dropwise at 25° C. over 20 min. The colorless solution turned to a light yellow solution. After the addition, the reaction mixture was stirred at 25° C. for 20 hr. Further DAST (1.2 mL, 9.61 mmol, 1.2 g/mL) was added dropwise at 25° C. over 20 min, and the light brown solution was refluxed for 24 h. The reaction mixture was cooled to 20~25° C., quenched with saturated NaHCO₃ (60 mL), extracted with CH₂Cl₂ (50 mL×2). The combined organic layers were washed with brine (50 mL), dried over anhydrous Na₂SO₄ and concentrated to give the crude product (800 mg). The residue was purified by silica gel chromatography (EtOAc: petroleum ether=0%~5%) to give tert-butyl (3,3-difluorobutan-2-yl)carbamate (I-150) (270 mg, 40%) as a light yellow solid.

Step 4—Synthesis of 3,3-difluorobutan-2-amine (I-151)

To a clear solution of tert-butyl (3,3-difluorobutan-2-yl) carbamate (I-150) (100 mg, 0.478 mmol) in dry CH₂Cl₂ (3 mL) was added TFA (1.5 mL) at 0~5° C. The color changed to light yellow. The resulting light yellow solution was stirred at 25° C. for 2 hr. NMR showed that the starting material had been consumed. The solvent was evaporated to give 3,3-difluorobutan-2-amine (I-151) (170 mg, yield >100%, TFA salt) as a viscous yellow gum, which was used without further purification.

Synthesis Of Representative Examples

Example 1 (Scheme A)

Synthesis of N-ethyl-2-(2-fluoropropoxy)-6-{4-[3-(1-methyl-1H-pyrazol-4-yl)quinoxalin-6-yl]piperidin-1-yl}pyrimidine-4-carboxamide

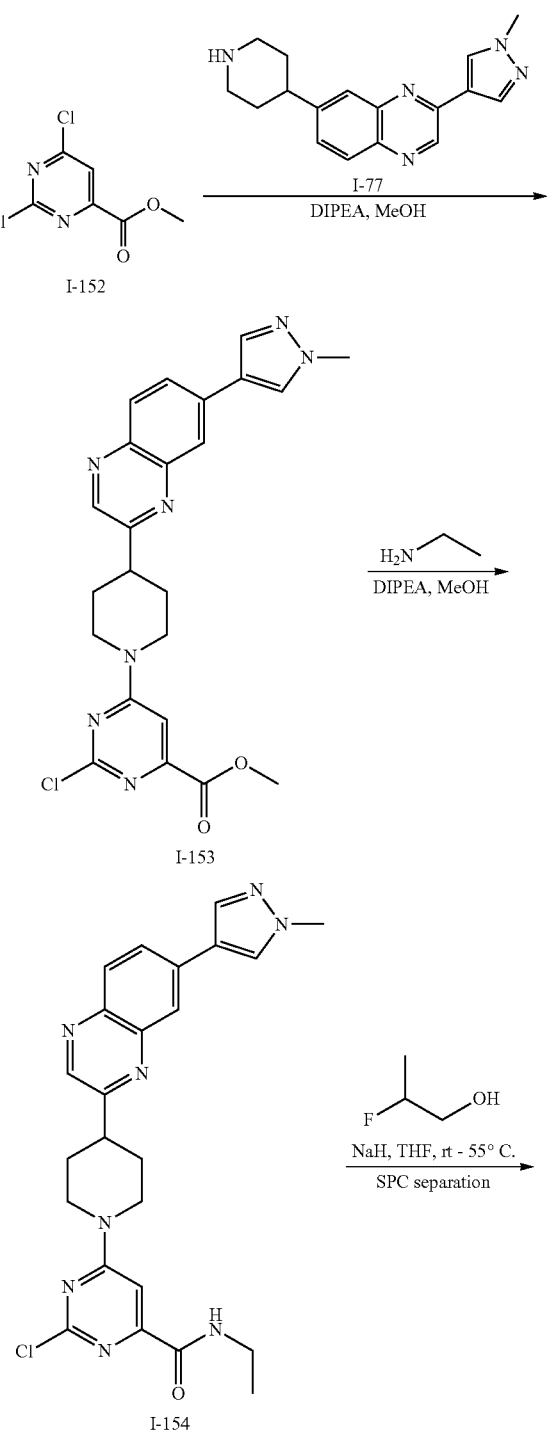

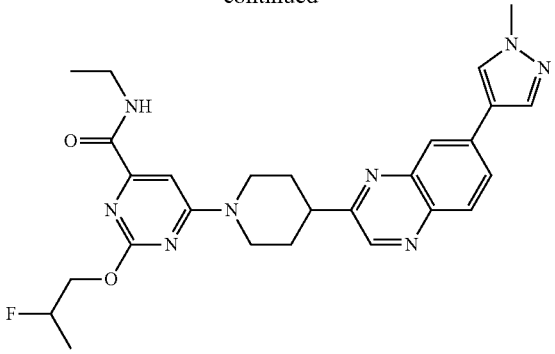

Example 1

Step 1—Synthesis of methyl 2-chloro-6-{4-[7-(1-methyl-1H-pyrazol-4-yl)quinoxalin-2-yl]piperidin-1-yl}pyrimidine-4-carboxylate (I-153)

To a solution of 2-(1-methyl-1H-pyrazol-4-yl)-7-(piperidin-4-yl)quinoxaline hydrochloride (I-77) (250 mg, 0.76 mmol) in MeOH (15 mL) was added methyl 2,6-dichloropyrimidine-4-carboxylate (I-152) (176 mg, 0.83 mmol) followed by DIPEA (588 mg, 0.79 mL, 4.55 mmol) at 0° C. The resulting mixture was stirred at room temperature for 18 hr. TLC (CH$_2$Cl$_2$/MeOH=10:1, R$_f$=0.5) showed the reaction was complete. The mixture was concentrated in vacuo to remove the majority of the solvent. The residue was triturated with CH$_2$Cl$_2$ to afford methyl 2-chloro-6-{4-[7-(1-methyl-1H-pyrazol-4-yl)quinoxalin-2-yl]piperidin-1-yl}pyrimidine-4-carboxylate (I-153) (183 mg, 52%) as a brownish solid. LCMS (APCI), m/z 464.2 [M+H]$^+$; $^1$H NMR (400 MHz, CDCl$_3$) δ ppm 9.02 (br. s., 1 H), 8.19 (s, 1 H), 8.14 (s, 1 H), 8.02 (d, J=8.7 Hz, 1 H), 7.84 (s, 1 H), 8.56 (d, J=8.5 Hz, 1 H), 4.02 (d, J=10.9 Hz, 6 H), 3.01-3.17 (m, 3 H), 2.17 (d, J=14.9 Hz, 2 H), 1.86 (d, J=12.8 Hz, 2 H), 1.56 (br. s., 10 H).

Step 2—Synthesis of 2-chloro-N-ethyl-6-{4-[7-(1-methyl-1H-pyrazol-4-yl)quinoxalin-2-yl]piperidin-1-yl}pyrimidine-4-carboxamide (I-154)

To a solution of methyl 2-chloro-6-{4-[7-(1-methyl-1H-pyrazol-4-yl)quinoxalin-2-yl]piperidin-1-yl}pyrimidine-4-carboxylate (I-153) (183 mg, 0.39 mmol) in MeOH (5 mL) was added DIPEA (255 mg, 0.34 mL, 1.97 mmol) and ethylamine (89 mg, 0.99 mL, 1.97 mmol). The reaction was allowed to stir at room temperature for 40 hr. LCMS showed complete conversion to desired product. The solvent was removed in vacuo to afford 2-chloro-N-ethyl-6-{4-[7-(1-methyl-1H-pyrazol-4-yl)quinoxalin-2-yl]piperidin-1-yl}pyrimidine-4-carboxamide (I-154) as a brown solid (188 mg, 100%), which was used without further purification. LCMS (APCI), m/z 477.2 [M+H]$^+$.

Step 3—N-ethyl-2-(2-fluoropropoxy)-6-{4-[3-(1-methyl-1H-pyrazol-4-yl)quinoxalin-6-yl]piperidin-1-yl}pyrimidine-4-carboxamide (Example 1)

To a solution of 2-fluoropropan-1-ol (154 mg, 1.97 mmol) in THF (3 mL) was added NaH (78.8 mg, 60% in mineral oil, 1.97 mmol). The mixture was allowed to stir at room temperature for 20 min. 2-chloro-N-ethyl-6-{4-[7-(1-methyl-1H-pyrazol-4-yl)quinoxalin-2-yl]piperidin-1-yl}pyrimidine-4-carboxamide (I-154) (188 mg, 0.39 mmol) in THF (3 mL) was then added, and the reaction mixture was heat at 55° C. for 30 min. LCMS indicated that the desired product had been formed. The reaction was quenched with water (10 mL), and the aqueous layer extracted with EtOAc (2×15 mL). The organic layers were washed with water (10 mL), dried over MgSO$_4$ and concentrated to afford the crude product, which was submitted to chiral separation.

200 mg was subjected to chiral separation by SFC to afford both enantiomers. The analytical chiral separation by SFC was performed using a Regis Whelk-O1 (R, R) (4.6 mm×250 mm column, 3 micron particle size), which was eluted with 35% MeOH (with 0.1% DEA) in CO$_2$ held at 140 bar. A flow rate of 2.5 mL/min gave Rt$_{(Peak\ 1)}$=15.77 min and Rt$_{(Peak\ 2)}$=17.38 min.

N-ethyl-2-(2-fluoropropoxy)-6-{4-[3-(1-methyl-1H-pyrazol-4-yl)quinoxalin-6-yl]piperidin-1-yl}pyrimidine-4-carboxamide (Example 1) (Peak 1): 35 mg, 99% ee. (−). LCMS (APCI), m/z 519.2 [M+H]$^+$; $^1$H NMR (400 MHz, CDCl$_3$) □ ppm 9.01 (s, 1 H), 8.18 (s, 1 H), 8.14 (s, 1 H), 8.01 (d, J=8.67 Hz, 1 H), 7.88 (br. s., 1 H), 7.83 (d, J=1.88 Hz, 1 H), 7.56 (dd, J=8.57, 1.98 Hz, 1 H), 7.18 (s, 1 H), 4.99 (td, J=6.50, 3.58 Hz, 1 H), 4.71 (br. s., 1 H), 4.30-4.57 (m, 2 H), 4.03 (s, 3 H), 3.41-3.55 (m, 2 H), 3.11 (d, J=12.81 Hz, 3 H), 2.12 (d, J=12.81 Hz, 2 H), 1.81-1.93 (m, 1 H), 1.77 (d, J=4.33 Hz, 1 H), 1.53 (d, J=6.40 Hz, 2 H), 1.41-1.48 (m, 2 H), 1.20-1.31 (m, 4 H).

Example 10 (Scheme A)

Synthesis of N-(bicyclo[1.1.1]pent-1-yl)-2-{[(1S,2R)-2-cyanocyclopropyl]methoxy}-6-[4-(1H-pyrazolo[3,4-b]pyridin-3-yl)piperidin-1-yl]Pyrimidine-4-carboxamide

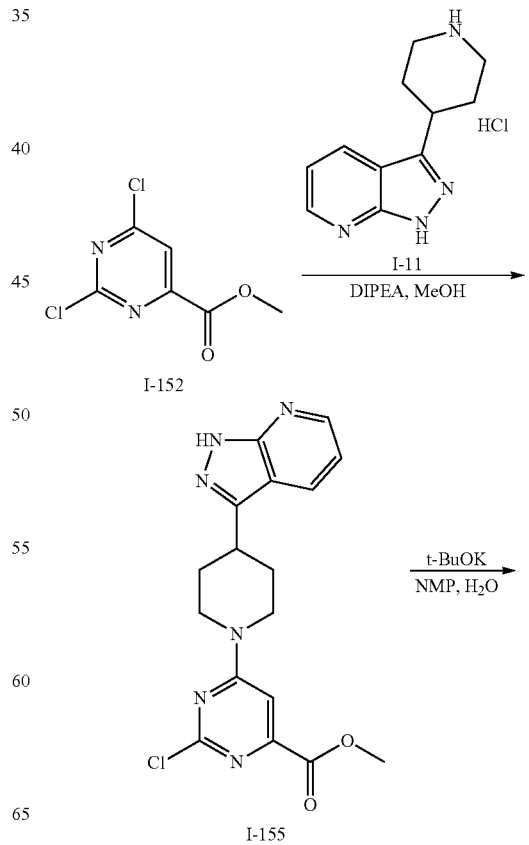

6-[4-(1H-pyrazolo[3,4-b]pyridin-3-yl)piperidin-1-yl]pyrimidine-4-carboxylate (I-155) (14 g, 83%) as a tan solid.

Step 2—Synthesis of 2-chloro-6-[4-(1H-pyrazolo[3,4-b]pyridin-3-yl)piperidin-1-yl]pyrimidine-4-carboxylic acid (I-156)

To a solution of methyl 2-chloro-6-[4-(1H-pyrazolo[3,4-b]pyridin-3-yl)piperidin-1-yl]pyrimidine-4-carboxylate (I-155) (28 g, 75.10 mmol) in NMP (390 mL) was added H₂O (2.7 g, 2.7 mL, 150.2 mmol) followed by a suspension of t-BuOK (16.8 g, 150.2 mmol) in THF (150 mL). The resulting mixture was stirred at room temperature for 30 min. TLC (CH₂Cl₂/MeOH=10:1, R$_f$=0.1) showed the reaction was complete. The mixture was filtered, and the filter cake was then dissolved in H₂O (500 mL). The suspension was then acidified with aq. HCl (2 N, 200 mL) to pH~4. The resulting suspension, was then filtered and dried in the vacuum oven to obtain 2-chloro-6-[4-(1H-pyrazolo[3,4-b]pyridin-3-yl)piperidin-1-yl]pyrimidine-4-carboxylic acid (I-156) (24 g, 89%) as a tan solid. ¹H NMR (400 MHz, CD₃OD/CDCl₃) δ ppm 8.46 (d, J=4.0 Hz, 1 H), 8.19 (d, J=7.6 Hz, 1 H), 7.55 (s, 1 H), 7.13-7.16 (m, 1 H), 4.51-4.61 (m, 2 H), 3.39-3.50 (m, 1 H), 3.31 (s, 2 H), 2.19 (d, J=12.4 Hz, 2 H), 1.99-2.02 (m, 2 H).

Step 3—Synthesis of N-(bicyclo[1.1.1]pent-1-yl)-2-chloro-6-[4-(1H-pyrazolo[3,4-b]pyridin-3-yl)piperidin-1-yl]pyrimidine-4-carboxamide (I-157)

To a mixture of 2-chloro-6-[4-(1H-pyrazolo[3,4-b]pyridin-3-yl)piperidin-1-yl]pyrimidine-4-carboxylic acid (I-156) (24 g, 67.04 mmol), bicyclo[1.1.1]pentan-1-amine hydrochloride (I-146) (8.82 g, 73.74 mmol) and HATU (30.57 g, 80.45 mmol) in DMF (360 mL) was added TEA (22.34 g, 30.77 mL, 221.23 mmol) at room temperature. The resulting mixture was stirred at room temperature for 12 hr. LCMS showed the reaction was complete. The mixture was then poured into aq. HCl (2 N, 2 L). The resulting suspension was filtered and the filter cake taken up and stirred in CH₂Cl₂ (400 mL) for 1 h. The suspension was filtered and dried in vacuo to afford N-(bicyclo[1.1.1]pent-1-yl)-2-chloro-6-[4-(1H-pyrazolo[3,4-b]pyridin-3-yl)piperidin-1-yl]pyrimidine-4-carboxamide (I-157) (18 g, 63%) as a brown solid. LCMS (ESI), m/z 424.0 [M+H]⁺; ¹H NMR (400 MHz, CDCl₃) δ ppm 8.58-8.59 (m, 1 H), 8.11-8.13 (m, 2 H), 7.34 (s, 1 H), 7.16 (dd, J=8.0, 4.4 Hz, 1 H), 4.57 (br. s., 2 H), 3.40-3.45 (m, 1 H), 3.30-3.31 (m, 2 H), 2.52 (s, 1 H), 2.20-2.23 (m, 8 H), 2.02-2.07 (m, 2 H).

Step 4—Synthesis of N-(bicyclo[1.1.1]pent-1-yl)-2-{[(1S,2R)-2-cyanocyclopropyl]methoxy}-6-[4-(1H-pyrazolo[3,4-b]pyridin-3-yl)piperidin-1-yl]pyrimidine-4-carboxamide (Example 10)

To a solution of N-(bicyclo[1.1.1]pent-1-yl)-2-chloro-6-[4-(1H-pyrazolo[3,4-b]pyridin-3-yl)piperidin-1-yl]pyrimidine-4-carboxamide (I-157) (11 g, 25.95 mmol) and (1R,2S)-2-(hydroxymethyl)cyclopropanecarbonitrile (I-125) (5.04 g, 51.90 mmol) in DMAc (64 mL) and MeCN (198 mL) was added 18-crown-6 (6.85 g, 25.95 mmol) at room temperature. The resulting mixture was then cooled in an ice-water bath (15-20° C.), while KHMDS (20.5 g, 0.104 mol) was added in several batches over 30 min. The resulting mixture was stirred at room temperature for 5 hr. TLC (petroleum ether/EtOAc=1:2, R$_f$=0.4) showed most of N-(bicyclo[1.1.1]pent-1-yl)-2- chloro-6-[4-(1H-pyrazolo[3,

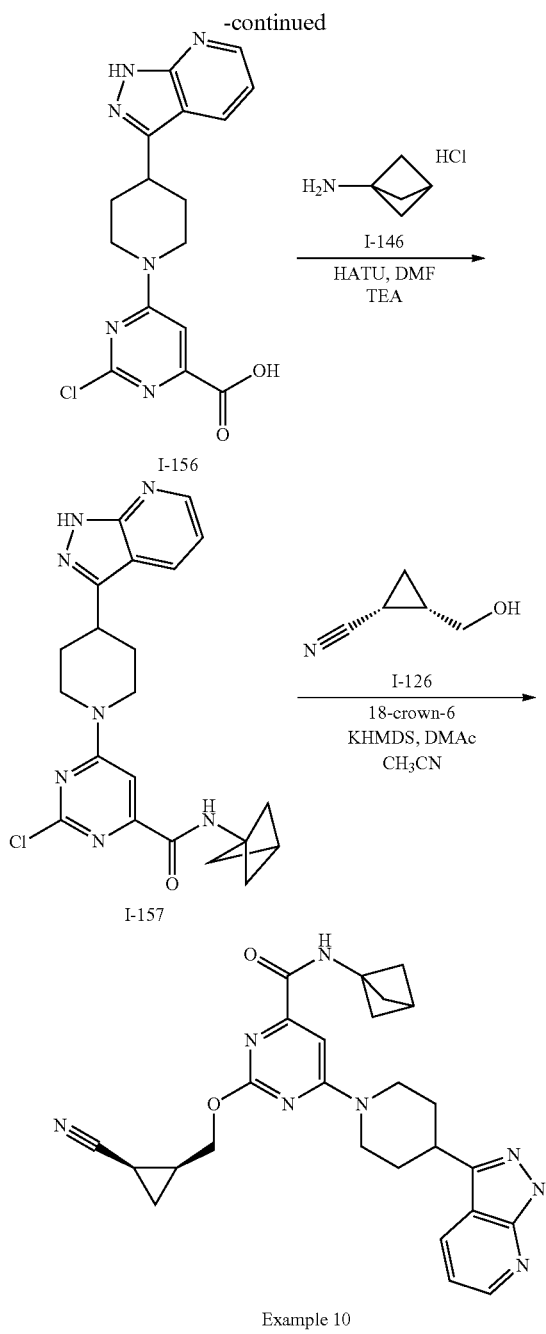

Example 10

Step 1—Synthesis of methyl 2-chloro-6-[4-(1H-pyrazolo[3,4-b]pyridin-3-yl)piperidin-1-yl]pyrimidine-4-carboxylate (I-155)

To a solution of 3-(piperidin-4-yl)-1H-pyrazolo[3,4-b]pyridine hydrochloride (I-11) (12 g, 45.11 mmol) in MeOH (340 mL) was added methyl 2,6-dichloropyrimidine-4-carboxylate (I-152) (9.33 g, 45.11 mmol) followed by DIPEA (29.10 g, 39 mL, 228 mmol) at 0° C. The resulting mixture was stirred at 0° C. for 1 hr. TLC (CH₂Cl₂/MeOH=10:1, R$_f$=0.5) showed the reaction was complete. The mixture was concentrated in vacuo to remove the majority of the solvent. The residue was then filtered, washed with MeOH (20 mL) and TBME (50 mL), dried in air to afford methyl 2-chloro- 4-b]pyridin-3-yl)piperidin-1-yl]pyrimidine-4-carboxamide was consumed. The mixture was slowly poured into aq. HCl (1 N, 2 L). The resulting suspension was extracted with EtOAc (3×500 mL). The organic layers were combined, washed with sat. NaHCO$_3$ (200 mL), H$_2$O (2×200 mL) and brine (100 mL), dried over Na$_2$SO$_4$ and concentrated in vacuo to give the crude product. The crude product was purified by column chromatography (petroleum ether/EtOAc=1:4 to neat EtOAc), and then re-purified by chiral SFC (Column: AD (300 mm×50 mm, 10 μm, mobile phase: 50% MeOH (w. NH$_3$)/H$_2$O 200 mL/min, wavelength: 220 nm) to afford N-(bicyclo[1.1.1]pent-1-yl)-2-{[(1S,2R)-2-cyanocyclopropyl]methoxy}-6-[4-(1H-pyrazolo[3,4-b]pyridin-3-yl)piperidin-1-yl]pyrimidine-4-carboxamide (Example 10) (3.06 g, 24%) as an off-white solid and the corresponding trans diastereomer (6.5 g). LCMS (ESI), m/z 485.2 [M+H]$^+$; 1 H NMR (400 MHz, CDCl$_3$) δ ppm 12.15 (br. s., 1 H), 8.47-8.48 (m, 1 H), 8.60-8.61 (m, 1 H), 8.21 (s, 1 H), 8.11-8.13 (m, 1 H), 7.13-7.16 (m, 2 H), 4.43-4.53 (m, 4 H), 3.40-3.45 (m, 1 H), 3.24 (t, J=11.4 Hz, 2 H), 2.49 (s, 1 H), 2.05-2.22 (m, 8 H), 2.00-2.10 (m, 2 H), 1.86-1.88 (m, 1 H), 1.67-1.69 (m, 1 H), 1.33-1.34 (m, 1 H), 1.13-1.15 (m, 1 H).

Example 26 (Scheme C)

Synthesis of 6-{4-[(3-amino-1,6-dimethyl-1H-indazol-4-yl)oxy]piperidin-1-yl}-N-ethyl-2-{[(2R)-1-methoxypropan-2-yl]oxy}pyrimidine-4-carboxamide

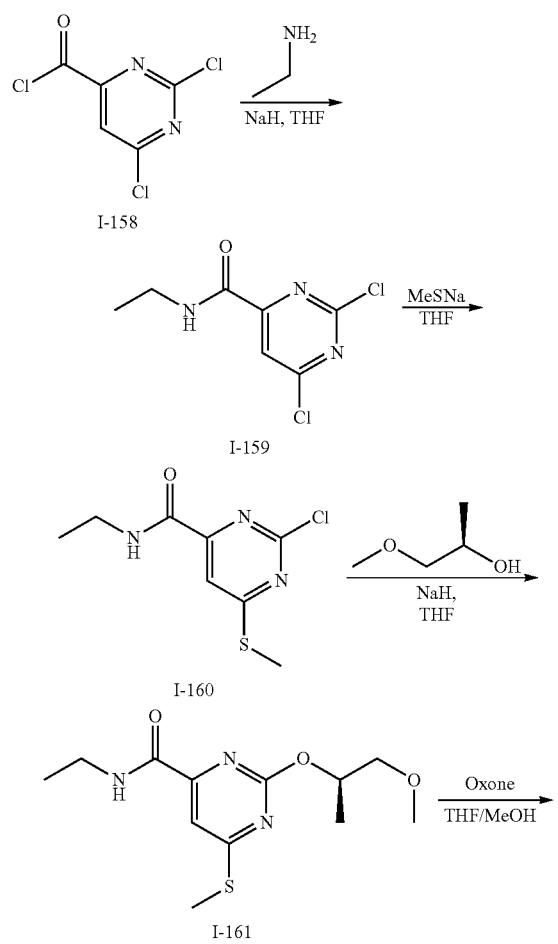

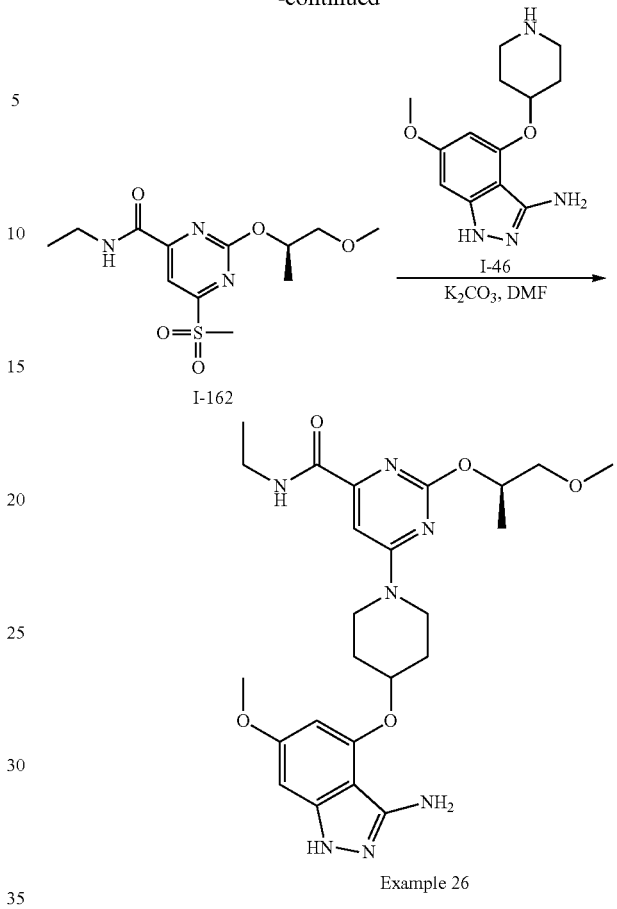

Step 1—Synthesis of 2,6-dichloro-N-ethylpyrimidine-4-carboxamide (I-159)

To a stirred solution of 2,6-dichloropyrimidine-4-carbonyl chloride (I-158) (3.1 g, 14.76 mmol) in dry THF (30 mL) was added NaH (60% in oil, 1.18 g, 29.52 mmol) followed by dropwise addition of ethylamine (0.66 g, 2 M in THF, 14.76 mmol) at 0° C. under a nitrogen atmosphere. After the addition was complete, the mixture was stirred at 0° C. for 1.5 hr. TLC (petroleum ether/EtOAc=8/1) indicated the reaction was complete. To the mixture acetic acid (1 mL) was added in a dropwise manner, and the reaction was quenched with H$_2$O (50 mL). The mixture was extracted with EtOAc (50 mL×2), and the combined organic layers washed with brine (100 mL), dried over Na$_2$SO$_4$ and concentrated. The residue was purified by column chromatography over silica gel eluting with petroleum ether/EtOAc (100% to 50/50) to yield 2,6-dichloro-N-ethylpyrimidine-4-carboxamide (I-159) (2.0 g, 62%) as yellow oil, which was used without further purification.

Step 2—Synthesis of 2-chloro-N-ethyl-6-(methylsulfanyl)pyrimidine-4-carboxamide (I-160)

To a stirred solution of 2,6-dichloro-N-ethylpyrimidine-4-carboxamide (I-159) (2.0 g, 9.13 mmol) in dry THF (50 mL) was added MeSNa (17% in solvent, 3.76 g, 9.13 mmol) at −20° C. under a nitrogen atmosphere. After the addition was complete, the mixture was allowed to warm to room temperature and stirred overnight. HPLC showed that the 2,6-dichloro-N-ethylpyrimidine-4-carboxamide had been consumed. H₂O (50 mL) was added to the mixture, which was extracted with EtOAc (50 mL). The organic layer was washed with brine (50 mL), dried over Na₂SO₄ and concentrated to yield crude 2-chloro-N-ethyl-6-(methylsulfanyl)pyrimidine-4-carboxamide (I-160) (1.7 g, 81%) as a yellow oil, which was used in the next step without further purification.

Step 3—Synthesis of N-ethyl-2-{[(2R)-1-methoxypropan-2-yl]oxy}-6-(methylsulfanyl)pyrimidine-4-carboxamide (I-161)

To a stirred solution of compound (2R)-1-methoxypropan-2-ol (0.9 g, 11.0 mmol) in anhydrous THF (30 mL) was added NaH (60% in oil, 0.88 g, 22.0 mmol) at 5° C.~10° C. under a nitrogen atmosphere. After being stirred at room temperature for 30 min, a solution of 2-chloro-N-ethyl-6-(methylsulfanyl)pyrimidine-4-carboxamide (I-160) (1.7 g, 7.36 mmol) in THF (10 mL) was added to the mixture. The resulting mixture was stirred at room temperature overnight. TLC (petroleum ether/EtOAc=3/1) indicated the reaction was complete. The mixture was quenched with H₂O (50 mL) and extracted with EtOAc (2×30 mL). The combined organic layers were washed with brine (100 mL), dried over Na₂SO₄ and concentrated. The residue was purified by column chromatography over silica gel eluting with petroleum ether/EtOAc (3/1) to yield N-ethyl-2-{[(2R)-1-methoxypropan-2-yl]oxy}-6-(methylsulfanyl)pyrimidine-4-carboxamide (I-161) (1.65 g, 78.6%) as yellow oil, which was used in the next step without further purification.

Step 4—Synthesis of N-ethyl-2-{[(2R)-1-methoxypropan-2-yl]oxy}-6-(methylsulfonyl)pyrimidine-4-carboxamide (I-162)

A mixture of N-ethyl-2-{[(2R)-1-methoxypropan-2-yl]oxy}-6-(methylsulfanyl)pyrimidine-4-carboxamide (I-161) (1.65 g, 5.79 mmol) and oxone (9.96 g, 16.2 mmol) in THF/MeOH/H₂O (1/1/1, 60 mL) was stirred at room temperature overnight. TLC (petroleum ether/EtOAc=3/1) indicated the reaction was complete. H₂O (50 mL) was added to the mixture, which was then extracted with EtOAc (50 mL×2). The combined organic layers were washed with brine (100 mL), dried over Na₂SO₄ and concentrated to yield crude N-ethyl-2-{[(2R)-1-methoxypropan-2-yl]oxy}-6-(methylsulfonyl)pyrimidine-4-carboxamide (I-162) (1.7 g, 92.6%) as a colorless oil, which was used directly in next step without further purification.

Step 5—Synthesis of 6-{4-[(3-amino-1,6-dimethyl-1H-indazol-4-yl)oxy]piperidin-1-yl}-N-ethyl-2-{[(2R)-1-methoxypropan-2-yl]oxy}pyrimidine-4-carboxamide (Example 26)

A mixture of N-ethyl-2-{[(2R)-1-methoxypropan-2-yl]oxy}-6-(methylsulfonyl)pyrimidine-4-carboxamide (I-162) (0.35 g, 1.1 mmol), 6-methoxy-4-(piperidin-4-yloxy)-1H-indazol-3-amine (I-46) (0.25 g, 0.75 mmol) and K₂CO₃ (0.3 g, 2.2 mmol) in dry DMF (3 mL) was stirred at room temperature overnight. LCMS indicated that the reaction was complete. H₂O (5 mL) was added to the mixture, which was extracted with EtOAc (2×10 mL). The combined organic layers were washed with brine (10 mL), dried over Na₂SO₄ and concentrated in vacuo. The residue was purified by preparative HPLC to give 6-{4-[(3-amino-1,6-dimethyl-1H-indazol-4-yl)oxy]piperidin-1-yl}-N-ethyl-2-{[(2R)-1-methoxypropan-2-yl]oxy}pyrimidine-4-carboxamide (Example 26) (0.16 g, 42%) as a white solid. LCMS (ESI), m/z 484.4 [M+H]⁺; ¹H NMR (400 MHz, CD₃OD) δ ppm 7.10 (s, 1 H), 6.65 (s, 1 H), 6.35 (s, 1 H), 5.40-5.44 (m, 1 H), 4.07 (s, 2 H), 3.78 (s, 2 H), 3.50-3.68 (m, 2 H), 3.41-3.46 (m, 5 H), 2.41 (s, 3 H), 2.46 (s, 2 H), 1.97 (s, 2 H), 1.36 (d, J=6.4 Hz, 3 H), 1.25 (t, J=7.6 Hz, 3 H).

Example 27 (Scheme C)

Synthesis of 6-{4-[6-carbamoyl-4-(dimethylamino)pyridin-2-yl]piperidin-1-yl}-2-{[(2R)-1-methoxypropan-2-yl]oxy}-N-(2,2,2-trifluoroethyl)pyrimidine-4-carboxamide

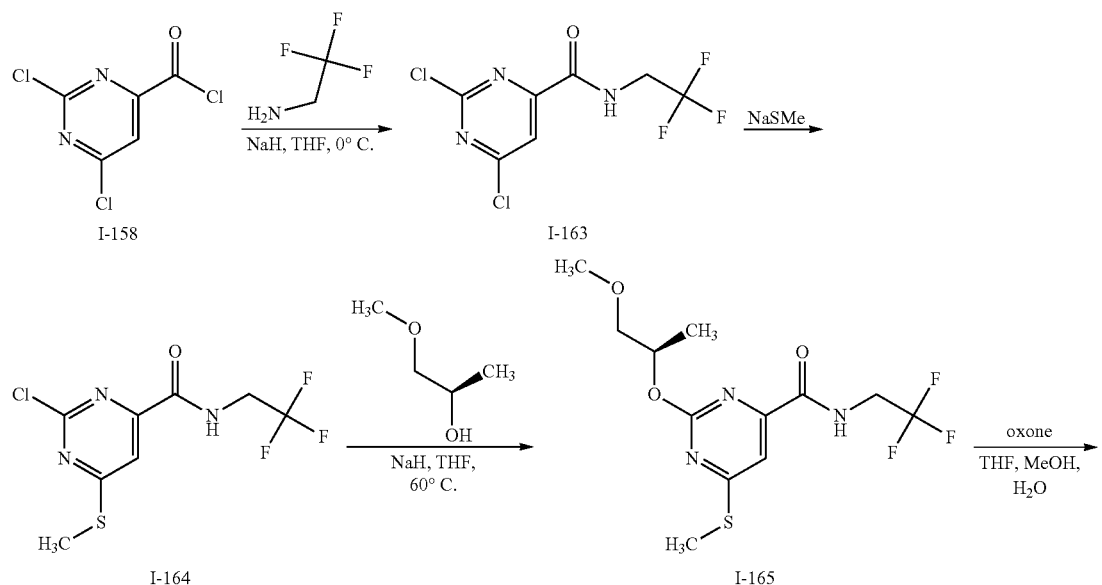

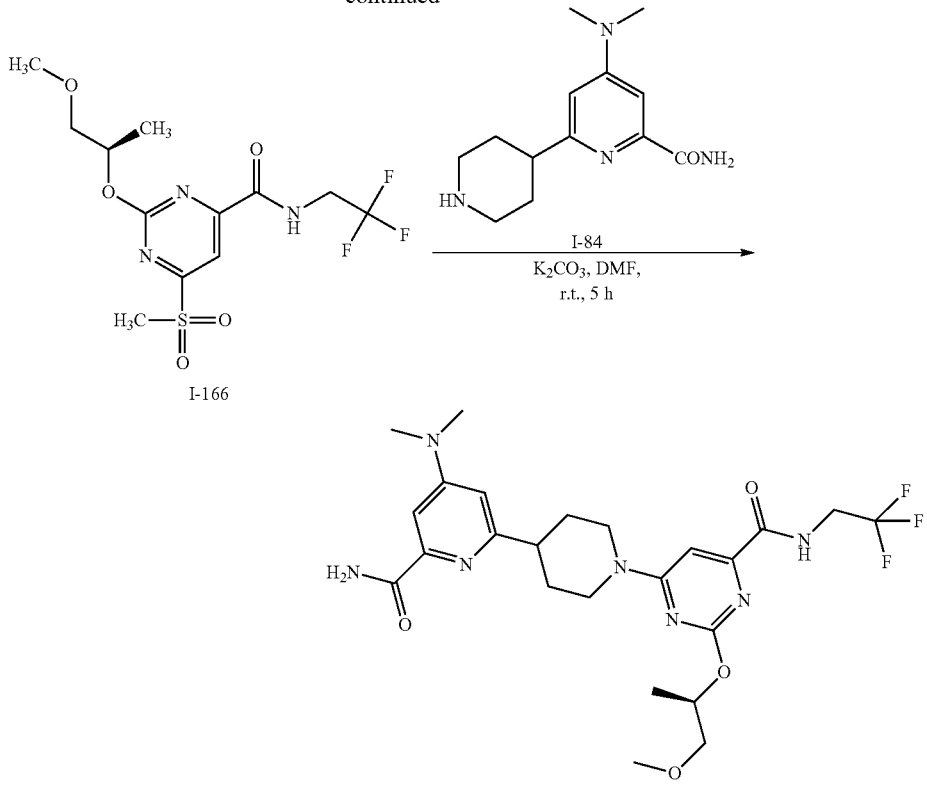

Example 27

Step 1—Synthesis of 2,6-dichloro-N-(2,2,2-trifluoroethyl)pyrimidine-4-carboxamide (I-163)

To a solution of 2,6-dichloropyrimidine-4-carbonyl chloride (I-158) (13 g, 61.5 mmol) and NaH (4.4 g, 60% dispersion in mineral oil, 110 mmol) in THF (100 mL) was added dropwise 2,2,2-trifluoroethanamine (5.5 g, 55 mmol) at 0° C. After the addition, the mixture was stirred at 0° C. for 1 hr. TLC (petroleum ether: EtOAc=5:1) indicated the complete consumption of the starting material. The reaction mixture was quenched with HOAc (3.5 g) and water (75 mL), extracted with EtOAc (3×50 mL). The combined organic layers were washed with brine (50 mL), dried over $Na_2SO_4$ and concentrated in vacuo to give the crude product, which was purified by silica gel chromatography (petroleum ether:EtOAc=10:1) to give 2,6-dichloro-N-(2,2,2-trifluoroethyl)pyrimidine-4-carboxamide (I-163) (13 g, 80%) as a yellow gum.

Step 2—Synthesis of 2-chloro-6-(methylthio)-N-(2,2,2-trifluoroethyl)-pyrimidine-4-carboxamide (I-164)

To a solution of 2,6-dichloro-N-(2,2,2-trifluoroethyl)pyrimidine-4-carboxamide (I-163) (13 g, 47.6 mmol) in THF (150 mL) was added dropwise aq. NaSMe (22 mL, 49 mmol) at −10° C. After addition, the reaction was stirred at −10° C. for 1 hr. HPLC indicated the complete consumption of starting material. The solution was concentrated in vacuo. The residue was extracted with TBME (3×100 mL). The combined organic layers were washed with brine (100 mL), dried over $Na_2SO_4$ and concentrated in vacuo to give the crude product, which was re-crystallized from petroleum ether to give 2-chloro-6-(methylthio)-N-(2,2,2-trifluoroethyl)pyrimidine-4-carboxamide (I-164) (8.8 g, 65%) as a white solid.

Step 3—Synthesis of (R)-2-(1-methoxypropan-2-yloxy)-6-(methylthio)-N-(2,2,2-trifluoroethyl)pyrimidine-4-carboxamide (I-165)

To a solution of R-(−)-1-methoxy-2-propanol (3.3 g, 36.8 mmol) in THF (100 mL) was added NaH (1.96 g, 60% dispersion in mineral oil, 49 mmol) at 0° C. 2-Chloro-6-(methylthio)-N-(2,2,2-trifluoroethyl)pyrimidine-4-carboxamide (I-164) (7 g, 24.5 mmol) was added to the solution. After addition, the reaction was heated to reflux overnight. TLC (petroleum ether:EtOAc=5:1) indicated complete consumption of the starting material. The solution was concentrated in vacuo. The residue was extracted with EtOAc (3×30 mL). The combined organic layers were washed with brine (50 mL), dried over $Na_2SO_4$ and concentrated in vacuo to give the crude product, which was purified by silica gel chromatography (petroleum ether:EtOAc=40:1-10:1) to give (R)-2-(1-methoxypropan-2-yloxy)-6-(methylthio)-N-(2,2,2-trifluoroethyl)pyrimidine-4-carboxamide (I-165) (5.0 g, 60.2%) as a light yellow gum.

Step 4—Synthesis of (R)-2-(1-methoxypropan-2-yloxy)-6-(methylsulfonyl)-N-(2,2,2-trifluoroethyl)pyrimidine-4-carboxamide (I-166)

To a solution of (R)-2-(1-methoxypropan-2-yloxy)-6-(methylthio)-N-(2,2,2-trifluoroethyl)pyrimidine-4-carboxamide (I-165) (3.6 g, 10.5 mmol) in THF (60 mL), MeOH (60 mL) and $H_2O$ (60 mL) was added oxone (18.1 g, 29.4 mmol) at 0° C. After addition, the mixture was stirred at room temperature for 3 hr. TLC (petroleum ether:EtOAc=1:1) indicated the complete consumption of starting material. The reaction mixture was extracted with CH$_2$Cl$_2$ (3×50 mL). The combined organic layers were washed with brine (75 mL), dried over Na$_2$SO$_4$ and concentrated in vacuo to give the crude product, which was purified by silica gel chromatography (petroleum ether:EtOAc=5:1) to give (R)-2-(1-methoxypropan-2-yloxy)-6-(methylsulfonyl)-N-(2,2,2-trifluoroethyl)pyrimidine-4-carboxamide (I-166) (3.4 g, 87%) as a white solid. $^1$H NMR (400 MHz, CDCl$_3$) δ 8.39 (s, 1 H), 8.08 (s, 1 H), 5.48-5.52 (m, 1 H), 4.09-4.18 (m, 2 H), 3.60-3.72 (m, 2 H), 3.42 (s, 3 H), 3.27 (s, 3 H), 1.48 (d, J=8.0 Hz, 3 H).

Step 5—Synthesis of (6-{4-[6-carbamoyl-4-(dimethylamino)pyridin-2-yl]piperidin-1-yl}-2-{[(2R)-1-methoxypropan-2-yl]oxy}-N-(2,2,2-trifluoroethyl)pyrimidine-4-carboxamide (Example 27)

To a stirred solution of 3-amino-6-(piperidin-4-yl)picolinamide (I-84) (75 mg, 0.34 mmol), and (R)-2-(1-methoxypropan-2-yloxy)-6-(methylsulfonyl)-N-(2,2,2-trifluoroethyl)pyrimidine-4-carboxamide (I-166) (86 mg, 0.34 mmol) in DMF (3 mL) was added potassium carbonate (129 mg, 9.36 mmol). The reaction mixture was stirred at room temperature for 2 hr. LCMS indicated the reaction was complete. Solids were filtered off, and the filtrate concentrated in vacuo. The residue was purified by reverse phase HPLC to give 6-{4-[6-carbamoyl-4-(dimethylamino)pyridin-2-yl]piperidin-1-yl}-2-{[(2R)-1-methoxypropan-2-yl]oxy}-N-(2,2,2-trifluoroethyl)pyrimidine-4-carboxamide as a white solid (Example 27) (23 mg, 18%). LCMS (APCI), m/z 540.3 [M+H]$^+$; $^1$H NMR (400 MHz, CD$_3$OD) δ ppm 7.21-7.29 (m, 1 H), 7.12 (s, 1 H), 6.62-6.65 (m, 1 H), 5.35-5.45 (m, 1 H), 4.10 (q, J=6.6 Hz, 2 H), 3.45-3.65 (m, 3 H), 3.39 (s, 3 H), 3.15-3.20 (m, 2 H), 3.06 (s, 3 H), 2.95-3.02 (m, 1 H), 1.95-2.05 (m, 2 H), 1.82-1.97 (m, 2 H), 1.35 (d, J=6.4 Hz, 3 H).

Example 29 (Scheme B)

Synthesis of 6-(4-{[(4-aminopyrimidin-5-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide

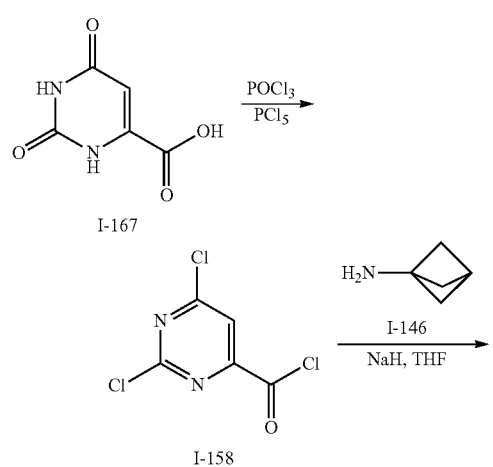

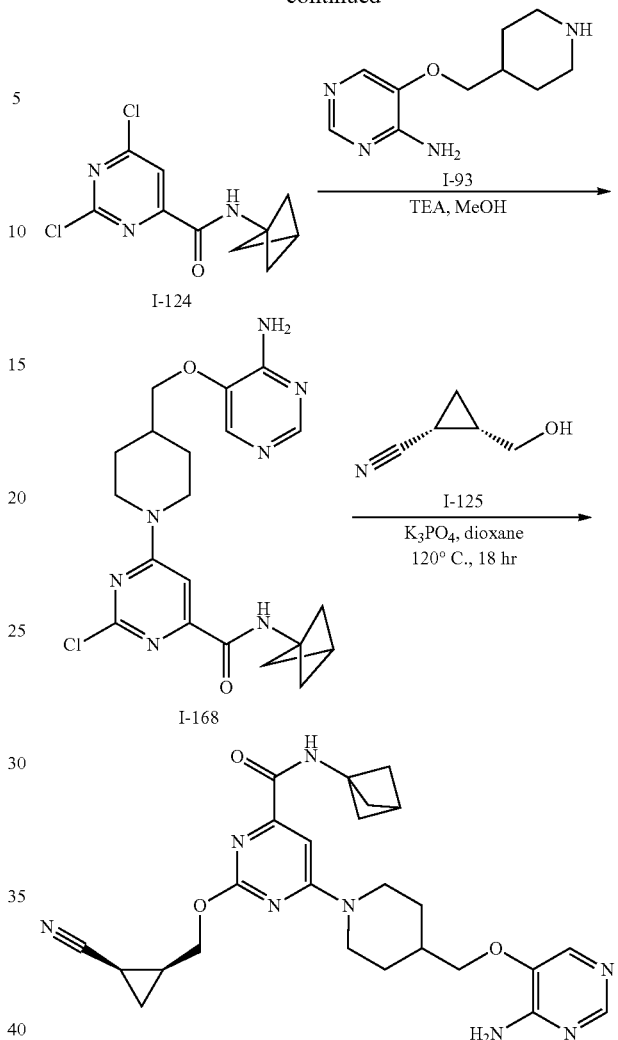

Example 29

Step 1—Synthesis of 2,6-dichloropyrimidine-4-carbonyl chloride (I-158)

To stirred POCl$_3$ (300 ml) was added in portions 2,6-dioxo-1,2,3,6-tetrahydropyrimidine-4-carboxylic acid (I-167) (60 g, 308 mmol) at room temperature. After the addition, PCl$_5$ (264 g, 1.27 mol) was added in portions to the mixture at room temperature. After this addition was complete, the reaction mixture was heated to reflux and stirred for 19 hr. LCMS indicated the reaction was complete (a sample was quenched with MeOH before LCMS analysis). The majority of the excess POCl$_3$ was removed by distillation, and the residue distilled under reduced pressure to give 2,6-dichloropyrimidine-4-carbonyl chloride (I-158) (b.p: 158~160° C./1 mm/Hg, 53 g, 45.5%, with ~70% of purity determined by TLC) as a yellow oil, which was used without further purification.

Step 2—Synthesis of N-(bicyclo[1.1.1]pent-1-yl)-2,6-dichloropyrimidine-4-carboxamide (I-124)

To a solution of bicyclo[1.1.1]pentan-1-amine (I-146) (4 g, 48.2 mmol) in dry THF (300 mL) was added in portions NaH (60% in oil, 5.8 g, 145 mmol) at 0° C. under a nitrogen atmosphere. After the addition was completed, the mixture was stirred at 0° C. for 30 min. 2,6-dichloropyrimidine-4-carbonyl chloride (I-158) (70% of purity, 21.8 g, 72.3 mmol) was added dropwise into the reaction mixture. Upon completion of the addition, the reaction mixture was stirred at room temperature for 2 hr. TLC (petroleum ether/EtOAc=10:1, $R_f$~0.6) indicated the reaction was complete. The mixture was quenched by adding AcOH (~40 mL) dropwise at 10° C. The reaction mixture was then filtered off, and washed with EtOAc (100 mL). The filtrate was concentrated. The residue was first neutralized (until no more bubbles formed) with saturated NaHCO$_3$, and then filtered off. The filtrate was extracted with EtOAc (3×200 mL). The combined organic layers were washed with brine (2×200 mL), dried over Na$_2$SO$_4$, and concentrated. The residue was purified by column chromatography on silica gel (petroleum ether to petroleum ether/EtOAc=300:1, $R_f$~0.6 in 10:1 petroleum ether/EtOAc) to give N-(bicyclo[1.1.1]pent-1-yl)-2,6-dichloropyrimidine-4-carboxamide (I-124) (6.5 g, 47%) as a yellow gum, which was used without further purification.

Step 3—Synthesis of 6-(4-{[(4-aminopyrimidin-5-yl)oxy]methyl}piperidin-1-yl)-N-(bicyclo[1.1.1]pent-1-yl)-2-chloropyrimidine-4-carboxamide (I-168)

To a mixture of 5-(piperidin-4-ylmethoxy)pyrimidin-4-amine (I-93) (7.98 g, 28.30 mmol, containing 2.04 eq HCl) and N-(bicyclo[1.1.1]pent-1-yl)-2,6-dichloropyrimidine-4-carboxamide (I-124) (7.3 g, 28.30 mmol) in MeOH (120 ml) was added Et$_3$N (14.29 g, 141.5 mmol) at room temperature. The resulting mixture was stirred at room temperature for 12 hr. TLC (CH$_2$Cl$_2$/MeOH=10:1, $R_f$=0.5) showed the reaction was complete. The mixture was concentrated in vacuo to give a residue, which was dissolved in CH$_2$Cl$_2$ (150 mL), and washed with H$_2$O (20 mL), brine (10 mL) and dried over Na$_2$SO$_4$, filtered and concentrated in vacuo to give the crude product. The crude product was stirred in EtOAc (50 mL) for 30 min and then filtered, dried in vacuo to give 6-(4-{[(4-aminopyrimidin-5-yl)oxy]methyl}piperidin-1-yl)-N-(bicyclo[1.1.1]pent-1-yl)-2-chloropyrimidine-4-carboxamide (I-168) (10 g, 82%) as a yellow solid, which was used without further purification.

Step 4—Synthesis of 6-(4-{[(4-aminopyrimidin-5-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide (Example 29)

This reaction was carried out in four batches with the batches being combined together for work-up and purification (2.6 g×4): To a mixture of 6-(4-{[(4-aminopyrimidin-5-yl)oxy]methyl}piperidin-1-yl)-N-(bicyclo[1.1.1]pent-1-yl)-2-chloropyrimidine-4-carboxamide (I-168) (2.6 g, 6.06 mmol) and (1R,2S)-2-(hydroxymethyl)cyclopropanecarbonitrile (1.2 g, 12.12 mmol) in anhydrous dioxane (50 mL) was added K$_3$PO$_4$ (3.85 g, 18.18 mmol) at room temperature under an argon atmosphere. The resulting mixture was stirred at 120° C. for 18 h. LCMS showed most of the 6-(4-{[(4-aminopyrimidin-5-yl)oxy]methyl}piperidin-1-yl)-N-(bicyclo[1.1.1]pent-1-yl)-2-chloropyrimidine-4-carboxamide had been consumed. The mixture was cooled to room temperature, and EtOAc (100 mL) and H$_2$O (30 mL) were added. The organic layer was separated and the aqueous layer was extracted with EtOAc (2×30 mL). The organic layers were combined and washed with brine (20 mL), dried over Na$_2$SO$_4$, filtered and concentrated in vacuo to give the crude product. The crude product was purified by column chromatography (on silica gel, CH$_2$Cl$_2$/MeOH=50:1 to 10:1, $R_f$=0.6 in 10:1 CH$_2$Cl$_2$/MeOH) and then re-purified by preparative HPLC under TFA-mediated condition (SYN-ERGI 250×50 10 μm, from 15% MeCN in water (0.1% TFA) to 45% MeCN in water (0.1% TFA) at a flow rate of 80 mIL/min) with the material obtained being basified with aq. NaHCO$_3$ and extracted with EtOAc to obtain 6-(4-{[(4-aminopyrimidin-5-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide (Example 29) (4.56 g, 38%) as a white solid. LCMS (ESI), m/z 491.0 [M+H]$^+$; (400 MHz, CDCl$_3$) δ ppm 8.24 (s, 1 H), 8.18 (s, 1 H), 7.81 (s, 1 H), 7.11 (s, 1 H), 5.13 (s, 2 H), 4.40-4.52 (m, 4 H), 3.92 (d, J=6.0 Hz, 2 H), 3.00 (m, 2 H), 2.49 (s, 1 H), 2.18 (s, 7 H), 1.93-1.96 (m, 2 H), 1.84-1.86 (m, 1 H), 1.68-1.75 (m, 2H), 1.32-1.40 (m, 3H), 1.12-1.17 (m, 1 H).

Example 30 (Scheme B)

Synthesis of N-(bicyclo[1.1.1]pent-1-yl)-2-{[(1S,2R)-2-cyanocyclopropyl]methoxy}-6-[4-(5H-pyrrolo[2,3-b]pyrazin-7-yl)piperidin-1-yl]pyrimidine-4-carboxamide

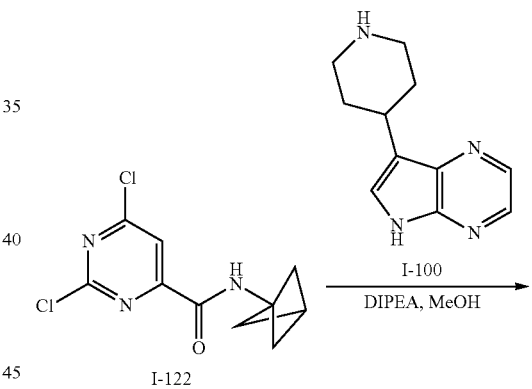

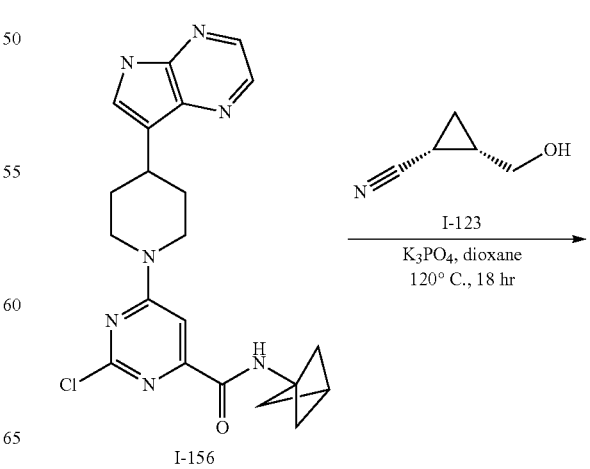

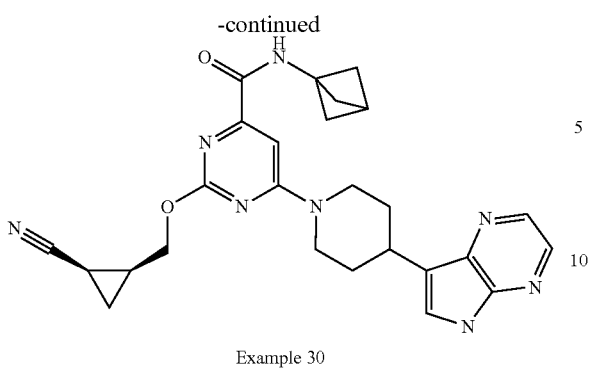

Example 30

Step 1—Synthesis of N-(bicyclo[1.1.1]pent-1-yl)-2-chloro-6-[4-(5H-pyrrolo[2,3-b]pyrazin-7-yl)piperidin-1-yl]pyrimidine-4-carboxamide (I-156)

To a mixture of 7-(piperidin-4-yl)-5H-pyrrolo[2,3-b]pyrazine hydrochloride (I-100) (138 mg, 0.58 mmol) and N-(bicyclo[1.1.1]pent-1-yl)-2,6-dichloropyrimidine-4-carboxamide (I-122) (149 mg, 0.58 mmol) in MeOH (5 ml) was added DIEPA (374 mg, 0.574 mL, 2.9 mmol) at room temperature. The resulting mixture was stirred at room temperature for 18 hr. LCMS showed the reaction was complete. The mixture was concentrated in vacuo to ~1 mL to give a suspension, which was filtered and washed with MeOH to afford 143 mg of a tan solid. NMR indicated the presence of DIEPA.HCl. The solids were triturated with MeOH to give N-(bicyclo[1.1.1]pent-1-yl)-2-chloro-6-[4-(5H-pyrrolo[2,3-b]pyrazin-7-yl)piperidin-1-yl]pyrimidine-4-carboxamide (I-156) (88 mg, 36%) as a tan solid, which was used without further purification.

LCMS (APCI), m/z 424.0 [M+H]$^+$; (400 MHz, CDCl$_3$) δ ppm 8.67 (br. s., 1 H), 8.44 (d, J=2.53 Hz, 1 H), 8.26 (d, J=2.53 Hz, 1 H), 8.12 (s, 1 H), 7.34 (d, J=2.78 Hz, 1 H), 7.32 (s, 1 H), 3.81-5.62 (br. m., 2 H), 3.38 (tt, J=11.84, 3.95 Hz, 1 H), 3.19 (br. s., 2 H), 2.51 (s, 1 H), 2.30 (d, J=12.88 Hz, 2 H), 2.20 (s, 6 H), 1.81 (qd, J=12.63, 4.04 Hz, 2 H).

Step 2—Synthesis of 6-(4-{[(4-aminopyrimidin-5-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide (Example 30)

To a mixture of N-(bicyclo[1.1.1]pent-1-yl)-2-chloro-6-[4-(5H-pyrrolo[2,3-b]pyrazin-7-yl)piperidin-1-yl]pyrimidine-4-carboxamide (I-156) (84 mg, 0.2 mmol) and (1R,2S)-2-(hydroxymethyl)cyclopropanecarbonitrile (I-123) (79 mg, 0.79 mmol) in anhydrous dioxane (50 mL) was added K$_3$PO$_4$ (168 mg, 0.79 mmol) at room temperature under an argon atmosphere. The resulting mixture was stirred at 120° C. for 36 hr. LCMS showed most of the N-(bicyclo[1.1.1]pent-1-yl)-2-chloro-6-[4-(5H-pyrrolo[2,3-b]pyrazin-7-yl)piperidin-1-yl]pyrimidine-4-carboxamide had been consumed. The mixture was dropped into dilute HCl (1 mL of 1 N HCl in 15 mL of H$_2$O), and the resulting precipitate collected by filtration. The precipitate was taken up in MeOH and purified by reverse phase preparative HPLC to afford N-(bicyclo[1.1.1]pent-1-yl)-2-{[(1S,2R)-2-cyanocyclopropyl]methoxy}-6-[4-(5H-pyrrolo[2,3-b]pyrazin-7-yl)piperidin-1-yl]pyrimidine-4-carboxamide (Example 30) (4.56 g, 38.4%) as a white solid. LCMS (APCI), m/z 485.2 [M+H]$^+$; (400 MHz, CDCl$_3$) δ ppm 8.49 (br. s., 1 H), 8.44 (d, J=2.78 Hz, 1 H), 8.25 (d, J=2.53 Hz, 1 H), 8.19 (s, 1 H), 7.33 (d, J=2.78 Hz, 1 H), 7.14 (s, 1 H), 4.28-5.13 (m, 4 H), 3.31-3.45 (m, 1 H), 3.18 (t, J=12.88 Hz, 2 H), 2.50 (s, 1 H), 2.28 (d, J=13.39 Hz, 2 H), 2.19 (s, 6 H), 1.73-1.94 (m, 3 H), 1.68 (td, J=8.34, 5.56 Hz, 1 H), 1.34 (td, J=8.53, 5.68 Hz, 1 H), 1.09-1.18 (m, 1 H).

Example 32 (Scheme B)

Synthesis of N-6-[4-(5-amino-4-carbamoylpyrimidin-2-yl)piperidin-1-yl]-N-(bicyclo[1.1.1]pent-1-yl)-2-{[(1S,2R)-2-cyanocyclopropyl]methoxy}pyrimidine-4-carboxamide

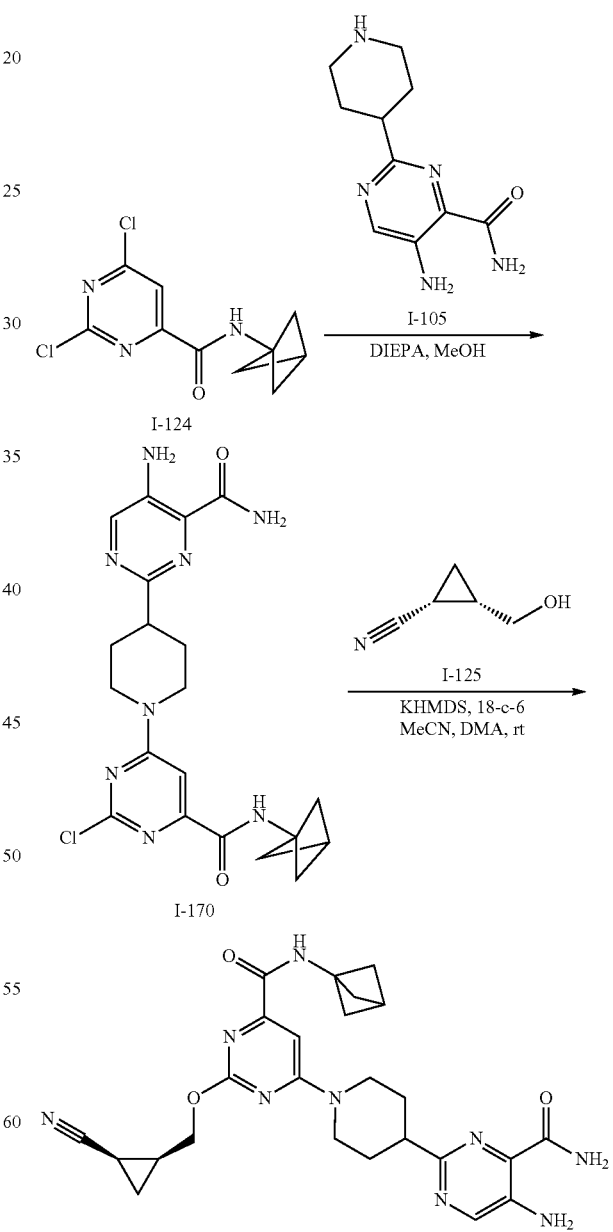

Example 32

Step 1—Synthesis of 6-[4-(5-amino-4-carbamoylpyrimidin-2-yl)piperidin-1-yl]-N-(bicyclo[1.1.1]pent-1-yl)-2-chloropyrimidine-4-carboxamide (I-170)

To a mixture of 5-amino-2-(piperidin-4-yl)pyrimidine-4-carboxamide hydrochloride (I-105) (350 mg, 1.19 mmol) and N-(bicyclo[1.1.1]pent-1-yl)-2,6-dichloropyrimidine-4-carboxamide (I-124) (307 mg, 1.19 mmol) in MeOH (10 ml) was added DIEPA (769 mg, 1.04 mL, 2.9 mmol) at room temperature. The resulting mixture was stirred at room temperature for 18 hr. LCMS showed the reaction was complete. The mixture was concentrated in vacuo to ~2 mL to give a suspension, which was filtered and washed with TBME to give 6-[4-(5-amino-4-carbamoylpyrimidin-2-yl)piperidin-1-yl]-N-(bicyclo[1.1.1]pent-1-yl)-2-chloropyrimidine-4-carboxamide (I-170) (309 mg, 57%) as a slightly brown solid, which was used without further purification. LCMS (APCI), m/z 443.0 [M+H]$^+$; (400 MHz, CDCl$_3$) δ ppm 8.32 (s, 1 H), 8.12 (br. s., 1 H), 7.78 (br. s., 1 H), 7.31 (s, 1 H), 5.78 (br. s., 2 H), 5.46 (br. s., 1 H), 3.86-5.24 (m, 2 H), 3.01-3.26 (m, 3 H), 2.51 (s, 1 H), 2.06-2.24 (m, 8 H), 1.75-1.91 (m, 2 H).

Step 2—Synthesis of N-6-[4-(5-amino-4-carbamoylpyrimidin-2-yl)piperidin-1-yl]-N-(bicyclo[1.1.1]pent-1-yl)-2-{[(1S,2R)-2-cyanocyclopropyl]methoxy}pyrimidine-4-carboxamide (Example 32)

A solution of the chloropyrimidine (I-170) (200 mg, 0.45 mmol) in DMAc (1.5 mL) was diluted with MeCN (3 mL). To the resulting tan suspension was added 18-crown-6 (120 mg, 0.45 mmol). KMDS (475 mg, 2.25 mmol) was added in a single portion. (1R,2S)-2-(hydroxymethyl)cyclopropanecarbonitrile (I-125) (88 mg, 0.91 mmol) was added and the mixture was sonicated until the mixture became a freely stirring suspension. The mixture was allowed to stir at ambient temp for 26 hr. After this time, LCMS indicated that the reaction was ~95% complete. The mixture was dropped into aq HCl (4 mL 1 N HCl in 50 mL water) and the resulting solids were collected by filtration. The solids were taken up in CH$_2$Cl$_2$ and initially purified by silica gel chromatography using a gradient of 20%-100% EtOAc/heptanes as eluent. The desired fractions were combined and reduced to minimum volume. The residue was dissolved in the minimal amount of acetonitrile and sonicated until the desired product crystallized out. The solids were collected by filtration to give N-6-[4-(5-amino-4-carbamoylpyrimidin-2-yl)piperidin-1-yl]-N-(bicyclo[1.1.1]pent-1-yl)-2-{[(1S,2R)-2-cyanocyclopropyl]methoxy}pyrimidine-4-carboxamide (Example 32) (78 mg, 34%) as a white solid. LCMS (APCI), m/z 504.2 [M+H]$^+$; (400 MHz, CDCl$_3$) δ ppm 8.32 (s, 1 H), 8.19 (s, 1 H), 7.80 (br. s., 1 H), 7.13 (s, 1 H), 5.77 (s, 2 H), 5.46 (br. s., 1 H), 4.30-5.04 (m, 4 H), 2.91-3.28 (m, 3 H), 2.50 (s, 1 H), 2.19 (s, 6 H), 2.07-2.15 (m, 2 H), 1.74-1.93 (m, 3 H), 1.68 (td, J=8.21, 5.56 Hz, 1 H), 1.34 (td, J=8.53, 5.68 Hz, 1 H), 1.14 (q, J=5.81 Hz, 1 H).

Example 35 (Scheme A)

Synthesis of 6-[4-(5-amino-6-carbamoylpyridin-2-yl)piperidin-1-yl]-2-(cyclopropylmethoxy)-N-[(2R)-1-hydroxypropan-2-yl]pyrimidine-4-carboxamide

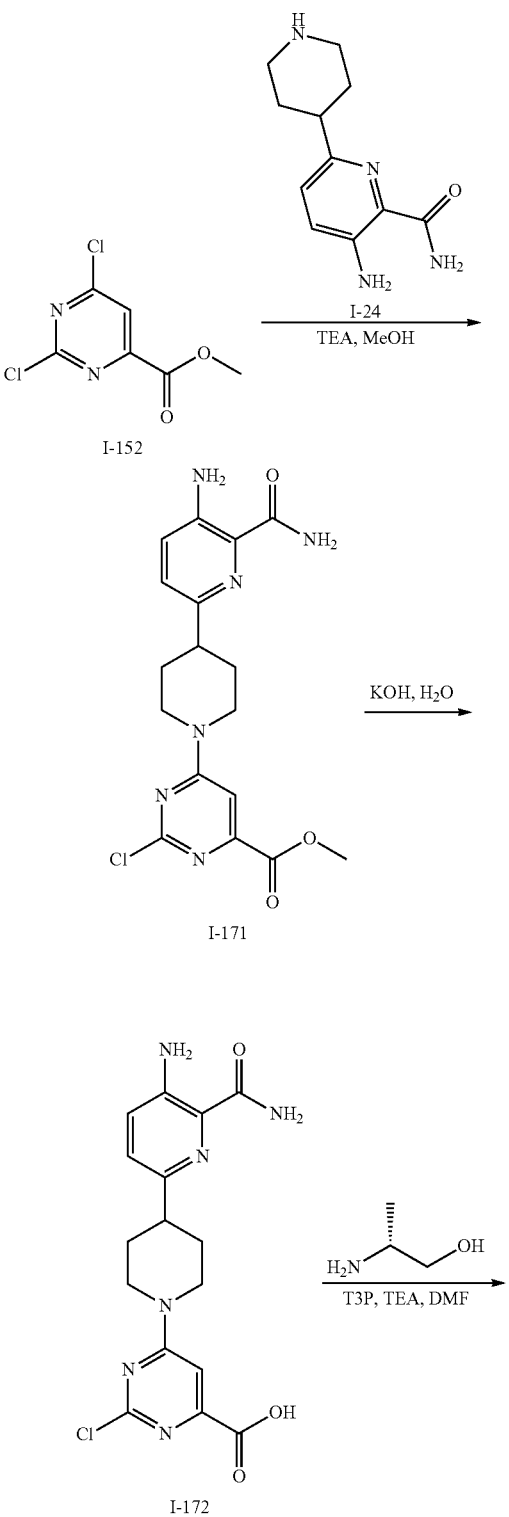

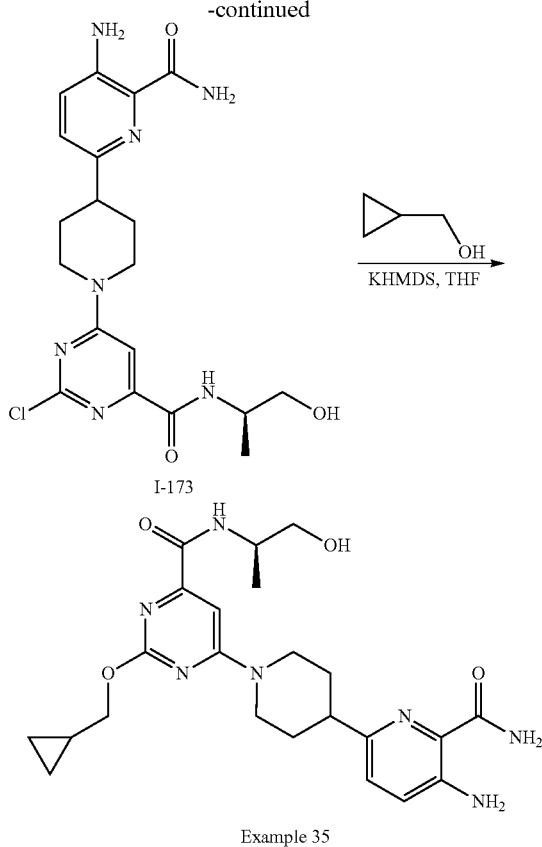

Example 35

Step 1—Synthesis of 6-[4-(5-amino-6-carbamoylpyridin-2-yl)piperidin-1-yl]-2-chloropyrimidine-4-carboxylic acid (I-171)

To a solution of 3-amino-6-(piperidin-4-yl)pyridine-2-carboxamide (I-24) (735 mg, 2.35 mmol) in MeOH (24.2 mL) was added methyl 2,6-dichloropyrimidine-4-carboxylate (I-152) (500 mg, 2.42 mmol) followed by TEA (1.22 g, 1.68 mL, 12.1 mmol) at 0° C. The resulting mixture was allowed to warm, and stirred at room temperature for 18 hr. To the mixture was added KOH (678 mg, 12.1 mmol) and water (12 mL). The reaction was allowed to stir for 2 hr. LCMS indicated the reaction was complete. The reaction was acidified to pH~4 with 1 N HCl, and the MeOH removed in vacuo. The solids were collected by filtration, and dried in the vacuum oven to afford 6-[4-(5-amino-6-carbamoylpyridin-2-yl)piperidin-1-yl]-2-chloropyrimidine-4-carboxylic acid (I-171) (575 mg, 63%) as a tan solid, which was used without further purification. LCMS (APCI), m/z 377.1 [M+H]$^+$.

Step 2—Synthesis of 6-[4-(5-amino-6-carbamoylpyridin-2-yl)piperidin-1-yl]-2-chloro-N-[(2R)-1-hydroxypropan-2-yl]pyrimidine-4-carboxamide (I-172)

To a flask containing 6-[4-(5-amino-6-carbamoylpyridin-2-yl)piperidin-1-yl]-2-chloropyrimidine-4-carboxylic acid (I-171) (700 mg, 1.86 mmol) and (2R)-2-aminopropan-1-ol (279 mg, 3.72 mmol) was added DMF (12.4 mL) followed by T3P (2.21 mL, 50% in DMF, 3.72 mmol) and TEA (940 mg, 1.30 mL, 9.29 mmol). The reaction was allowed to stir for 18 hr at room temperature. LCMS indicated the reaction was complete. The solids were removed by filtration, and the mother liquor concentrated. The residue was purified by silica gel chromatography eluting with 0-10% MeOH/CH$_2$Cl$_2$ to afford 6-[4-(5-amino-6-carbamoylpyridin-2-yl)piperidin-1-yl]-2-chloro-N-[(2R)-1-hydroxypropan-2-yl]pyrimidine-4-carboxamide (I-172) (206 mg, 26%) as a white solid. LCMS (APCI), m/z 434.2 [M+H]$^+$.

Step 3—Synthesis of 6-[4-(5-amino-6-carbamoylpyridin-2-yl)piperidin-1-yl]-2-(cyclopropylmethoxy)-N-[(2R)-1-hydroxypropan-2-yl]pyrimidine-4-carboxamide (Example 35)

To a mixture of 6-[4-(5-amino-6-carbamoylpyridin-2-yl)piperidin-1-yl]-2-chloro-N-[(2R)-1-hydroxpropan-2-yl]pyrimidine-4-carboxamide (I-172) (205 mg, 0.47 mmol) in THF (5 mL) was added in a portionwise manner solid KHMDS (753 mg, 3.78 mmol) to result in an orange suspension. To this was added, a solution of cyclopropylmethanol (102 mg, 1.42 mmol) in THF (2 mL), and the resulting solution heated to 50° C. for 18 hr. The reaction was allowed to cool, and neutralized with 1 N HCl. The mixture was diluted with EtOAc (25 mL), washed with water (10 mL), brine (10 mL), dried over MgSO4, filtered and concentrated in vacuo. The residue was initially purified by silica gel chromatography eluting with 0-5% MeOH/CH$_2$Cl$_2$ to give 84 mg of material, which was further purified by reverse phase HPLC to afford 6-[4-(5-amino-6-carbamoylpyridin-2-yl)piperidin-1-yl]-2-(cyclopropylmethoxy)-N-[(2R)-1-hydroxypropan-2-yl]pyrimidine-4-carboxamide (Example 35) (37 mg, 17%) as a white solid. LCMS (APCI), m/z 470.2 [M+H]$^+$; (400 MHz, DMSO-d$_6$) δ ppm 8.14 (d, J=8.6 Hz, 1 H), 7.82 (d, J=2.8 Hz, 1 H), 7.21 (d, J=2.8 Hz, 1 H), 7.15-7.20 (m, 1 H), 7.09 (d, J=8.6 Hz, 1 H), 6.98 (s, 1 H), 6.65 (s, 2 H), 4.84 (t, J=5.3 Hz, 1 H), 4.50 (br. s., 2 H), 4.11 (d, J=7.3 Hz, 2 H), 3.89-4.02 (m, 1 H), 3.43 (qd, J=5.5, 11.2 Hz, 2 H), 3.06 (t, J=12.2 Hz, 2 H), 2.88 (t, J=11.8 Hz, 1 H), 1.92 (dd, J=2.1, 12.7 Hz, 2H), 1.66 (dq, J=4.2, 12.5 Hz, 2 H), 1.17-1.27 (m, 1 H), 1.13 (d, J=6.8 Hz, 3H), 0.48-0.64 (m, 2 H), 0.27-0.38 (m, 2H).

Example 38 (Scheme D)

Synthesis of 6-(4-{6-carbamoyl-3-[2-(dimethylamino)ethoxy]pyridin-2-yl}piperidin-1-yl)-N-cyclobutyl-2-{[(2R)-1-methoxypropan-2-yl]oxy}pyrimidine-4-carboxamide

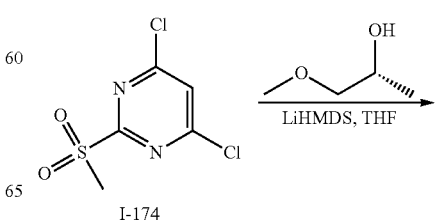

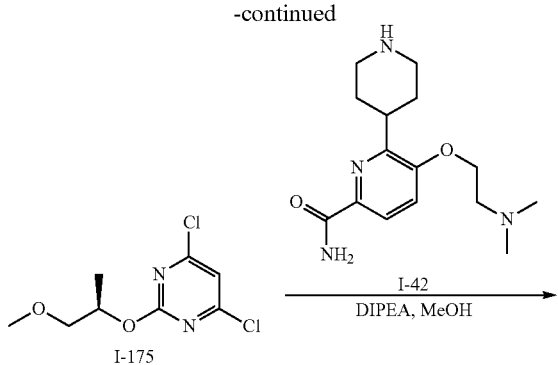

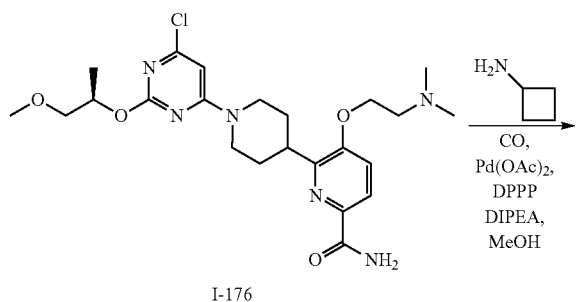

Example 38

Step 1—Synthesis of 4,6-dichloro-2-{[(2R)-1-methoxypropan-2-yl]oxy}pyrimidine (I-175)

A solution of 4,6-dichloro-2-(methylsulfonyl)pyrimidine (I-174) (200 mg, 0.881 mmol) and (2R)-1-methoxypropan-2-ol (79.4 mg, 0.881 mmol) in THF (5 mL) was cooled to 0° C. (5 min), and LiHMDS (0.969 mL, 1 M, THF) was added in a dropwise manner. The resultant suspension was allowed to stir at 0° C. for an additional 20 min. The ice-bath was removed and the mixture was allowed to warm to room temperature over 30 min. TLC (Petroleum ether:EtOAc=1:1) indicated the reaction was complete. The mixture was concentrated and taken up in EtOAc (8 mL), washed with saturated aq. $NH_4Cl$ (4 mL), and brine (4 mL). The organic layer was dried over $Na_2SO_4$, filtered and concentrated to give the crude 4,6-dichloro-2-{[(2R)-1-methoxypropan-2-yl]oxy}pyrimidine (I-175) (210 mg, 100%) as a yellow oil, which was used directly in the next step.

Step 2—Synthesis of 6-[1-(6-chloro-2-{[(2R)-1-methoxypropan-2-yl]oxy}pyrimidin-4-yl)piperidin-4-yl]-5-[2-(dimethylamino)ethoxy]pyridine-2-carboxamide (I-176)

To a solution of 4,6-dichloro-2-{[(2R)-1-methoxypropan-2-yl]oxy}pyrimidine (I-175) (209 mg, 0.882 mmol) and 5-[2-(dimethylamino)ethoxy]-6-(piperidin-4-yl)pyridine-2-carboxamide hydrochloride (I-42) (290 mg, 0.882 mmol) in MeOH (5 mL) was added slowly DIPEA (342 mg, 2.64 mmol). Then, the reaction mixture was stirred at room temperature for 2 hr. TLC (petroleum ether:EtOAc=1:1) showed the starting material was consumed. The mixture was concentrated in vacuo and diluted with EtOAc (10 mL) and washed with saturated aq. $NH_4Cl$ (2×10 mL), $H_2O$ (10 mL) and brine (10 mL), dried over $Na_2SO_4$ and concentrated. The residue was purified by silica gel chromatography (DCM:MeOH=1:0 to 10:1) to give 6-[1-(6-chloro-2-{[(2R)-1-methoxypropan-2-yl]oxy}pyrimidin-4-yl)piperidin-4-yl]-5-[2-(dimethylamino)ethoxy]pyridine-2-carboxamide (I-176) (300 mg, 69%) as a light yellow oil.

Step 3—Synthesis of 6-(4-{6-carbamoyl-3-[2-(dimethylamino)ethoxy]pyridin-2-yl}piperidin-1-yl)-N-cyclobutyl-2-{[(2R)-1-methoxypropan-2-yl]oxy}pyrimidine-4-carboxamide (Example 38)

A solution of 6-[1-(6-chloro-2-{[(2R)-1-methoxypropan-2-yl]oxy}pyrimidin-4-yl)piperidin-4-yl]-5-[2-(dimethylamino)ethoxy]pyridine-2-carboxamide (I-176) (310 mg, 0.629 mmol), cyclobutylamine (134 mg, 1.89 mmol), DIPEA (244 mg, 1.89 mmol) in MeOH (10 mL) was placed in a 50 mL stainless steel vessel, then $Pd(OAc)_2$ (14.1 mg, 0.0629 mmol) and DPPP (51.9 mg, 0.126 mmol) were added. Stirring was initiated (900 rpm) and the mixture was purged with Argon (2 Bar) three times and CO (1 MPa) three times. Then the reaction mixture was stirred under 1.5 MPa of CO pressure and heated to 100° C. for 18 hr. LCMS showed the starting material was consumed and 43% of the desired product was detected (220 nm). The mixture was filtered through a plug of celite and concentrated. The residue was purified with by silica gel chromatography (12 g HP Biotage column, 10% MeOH in $CH_2Cl_2$) to provide the crude product (300 mg, purity 79% by LCMS) as a light red oil, which was further purified by preparative HPLC. After preparative HPLC purification, the eluent was concentrated to remove the organic solvents. The residual aqueous solution was lyophilized to give 6-(4-{6-carbamoyl-3-[2-(dimethylamino)ethoxy]pyridin-2-yl}piperidin-1-yl)-N-cyclobutyl-2-{[(2R)-1-methoxypropan-2-yl]oxy}pyrimidine-4-carboxamide (Example 38) (125 mg, 36%) as a white solid. LCMS (ESI), m/z 556.3 [M+H]$^+$; $^1$H NMR (400 MHz, $CD_3OD$) δ ppm 8.01-8.05 (m, 2 H), 7.63 (d, J=4.0 Hz, 1 H), 7.22 (d, J=8.0 Hz, 1 H), 7.09 (s, 1 H), 5.48 (d, J=4.0 Hz, 1 H), 5.31-5.35 (m, 1 H), 5.51-5.53 (m, 3 H), 4.13 (t, J=5.6 Hz, 2 H), 3.66-3.69 (m, 1 H), 3.42-3.52 (m, 5 H), 3.09-3.11 (m, 2 H), 2.80 (t, J=5.6 Hz, 2 H), 2.36-2.38 (m, 8 H), 1.93-2.00 (m, 8 H, partially obscured by water), 1.40-1.38 (d, J=6.4 Hz, 3 H).

Example 55 (Scheme E)

Synthesis of 4-[4-(5-amino-6-carbamoylpyridin-2-yl)piperidin-1-yl]-6-{[(2R)-1-methoxypropan-2-yl]oxy}-N-(2,2,2-trifluoroethyl)-1,3,5-triazine-2-carboxamide

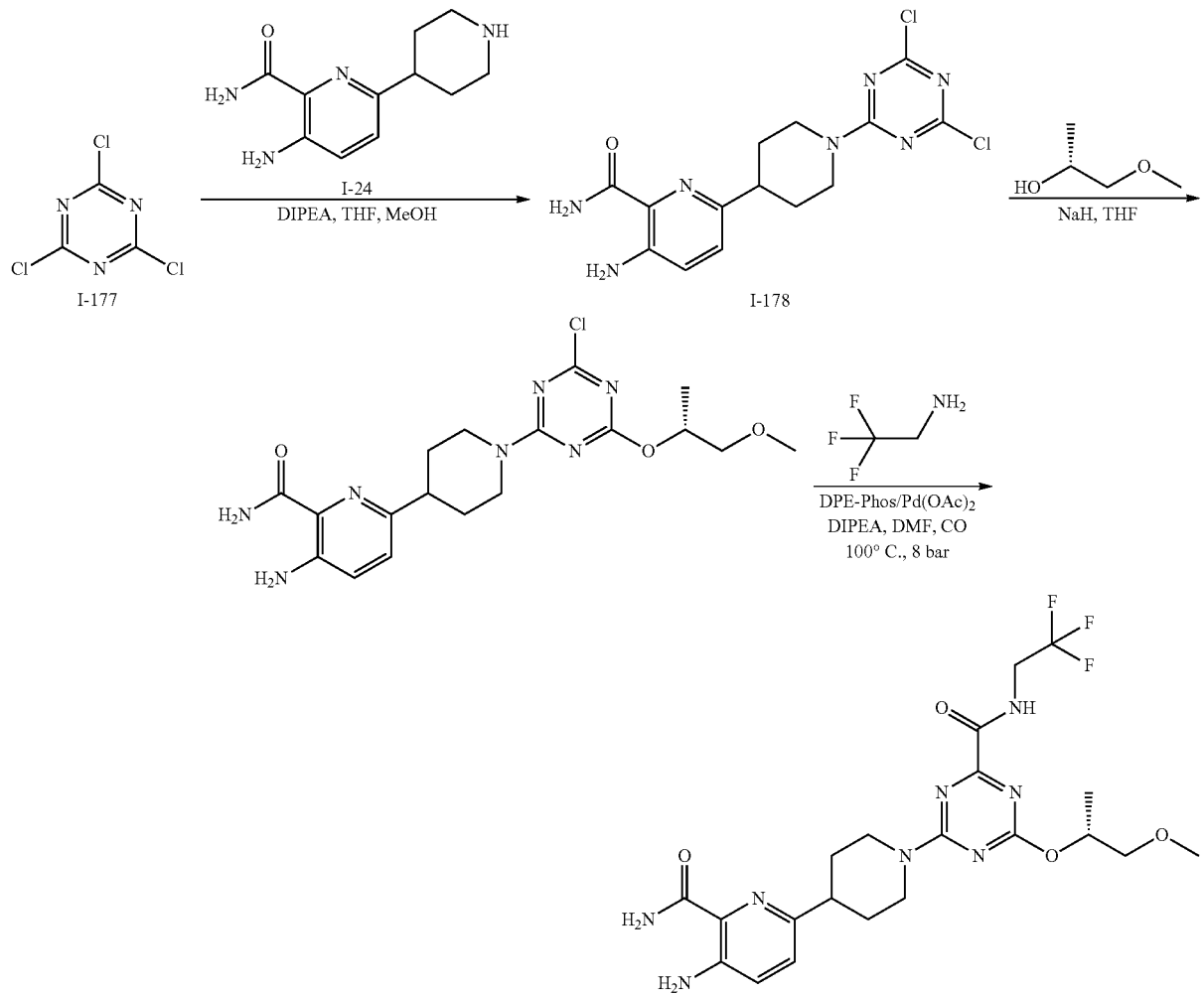

Example 55

Step 1—Synthesis of 3-amino-6-[1-(4,6-dichloro-1,3,5-triazin-2-yl)piperidin-4-yl]pyridine-2-carboxamide (I-178)

To a solution of cyanuric chloride (I-177) (500 mg, 2.71 mmol) in THF (27 mL) cooled with an ice bath was added in a portionwise manner 3-amino-6-(piperidin-4-yl)pyridine-2-carboxamide (I-24) (786 mg, 2.71 mmol) followed by DIPEA (1.4 g, 1.89 mL, 10.8 mmol). MeOH (2.5 mL) was added to aid solubilization resulting in a yellow reaction mixture. After 20 min at ice bath temperature, LCMS showed a mixture of the desired and bis-and tri-substituted products. The reaction was concentrated in vacuo, and purified by silica gel chromatography (0-100 EtOAc/heptanes) to afford 3-amino-6-[1-(4,6-dichloro-1,3,5-triazin-2-yl)piperidin-4-yl]pyridine-2-carboxamide (I-178) (620 mg, 62%) as a slightly yellow solid. LCMS (APCI), m/z 368.1 [M+H]$^+$; (400 MHz, DMSO-$d_6$) δ ppm 7.87 (br. s., 1 H), 7.25 (br. s., 1 H), 7.18 (d, J=8.56 Hz, 1 H), 7.10 (d, J=8.44 Hz, 1 H), 6.67 (s, 2 H), 4.61 (d, J=13.33 Hz, 2 H), 3.09-3.22 (m, 2 H), 2.90 (s, 1 H), 1.93 (d, J=10.76 Hz, 2 H), 1.74 (dd, J=12.53, 3.61 Hz, 2 H).

Step 2—Synthesis of 3-amino-6-[1-(4-chloro-6-{[(2R)-1-methoxypropan-2-yl]oxy}-1,3,5-triazin-2-yl)piperidin-4-yl]pyridine-2-carboxamide (I-179)

To a round bottom flask submerged in an ice bath was added the (2R)-1-methoxypropan-2-ol (98 mg, 1.1 mmol) followed by THF (12 ml) and NaH (92 mg, 60% in mineral oil, 2.17 mmol) under nitrogen. After being allowed to stir at ice bath temperature for 20 min, a suspension of 3-amino-6-[1-(4,6-dichloro-1,3,5-triazin-2-yl)piperidin-4-yl]pyridine-2-carboxamide (I-178) (400 mg, 1.09 mmol) in THF (12 mL) was added. After 10 min, LCMS indicated the reaction was complete. The reaction was quenched with saturated NaHCO₃ solution (0.5 mL), and concentrated in vacuo. The residue was purified by silica gel chromatography (0-100 EtOAc/heptanes) to afford 3-amino-6-[1-(4-chloro-6-{[(2R)-1-methoxypropan-2-yl]oxy}-1,3,5-triazin-2-yl)piperidin-4-yl]pyridine-2-carboxamide (I-179) (340 mg, 74%) as a white solid. LCMS (APCI), m/z 422.2 [M+H]⁺.

Step 3—Synthesis of 4-[4-(5-amino-6-carbamoylpyridin-2-yl)piperidin-1-yl]-6-{[(2R)-1-methoxypropan-2-yl]oxy}-N-(2,2,2-trifluoroethyl)-1,3,5-triazine-2-carboxamide (Example 55)

3-amino-6-[1-(4-chloro-6-{[(2R)-1-methoxypropan-2-yl]oxy}-1,3,5-triazin-2-yl)piperidin-4-yl]pyridine-2-carboxamide (I-179) (71 mg, 0.17 mmol), 2,2,2-trifluoroethylamine (46 mg, 0.34 mmol), DIPEA (0.11 g, 0.15 mL, 0.84 mmol) and DMA (2.5 mL) were combined in a 10 mL pressure vessel. To this solution was added DPE-Phos (18.3 mg, 0.034 mmol) and Pd(OAc)₂ (3.8 mg, 0.017 mmol). The vessel was sealed, and purged three times with nitrogen followed by CO. The vessel was then placed under 8 bar CO pressure, and heated to 100° C. for 4 hr. The reaction was allowed to cool, and the vessel opened. LCMS indicated a 3:1 mixture of the desired product to that resulting from direct displacement of the amine. The reaction was concentrated, and purified by SFC (4-Pyr-AXP column, 5-50% MeOH @ 18% min, 5.6 mL/min, 140 bar) to afford 4-[4-(5-amino-6-carbamoylpyridin-2-yl)piperidin-1-yl]-6-{[(2R)-1-methoxypropan-2-yl]oxy}-N-(2,2,2-trifluoroethyl)-1,3,5-triazine-2-carboxamide (Example 55) (7.8 mg, 9%) as a white solid. LCMS (APCI), m/z 513.1 [M+H]⁺; (700 MHz, DMSO-d₆) δ ppm 9.31 (t, J=6.66 Hz, 1 H), 7.87-7.96 (m, 1 H), 7.19 (d, J=8.54 Hz, 1 H), 7.06-7.12 (m, 2 H), 6.55 (br. s., 2 H), 5.37 (td, J=6.15, 4.10 Hz, 1 H), 4.92 (d, J=12.81 Hz, 1 H), 4.70 (d, J=12.13 Hz, 1 H), 3.42-3.53 (m, 2 H), 3.25 (s, 3 H), 3.05 (t, J=12.81 Hz, 2 H), 2.89 (t, J=11.70 Hz, 1 H), 1.86-1.95 (m, 2 H), 1.57-1.69 (m, 2 H), 1.23 (dd, J=6.41, 1.11 Hz, 3 H).

Example 64 (Scheme D)

Synthesis of N-[(2R)-1-hydroxypropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide

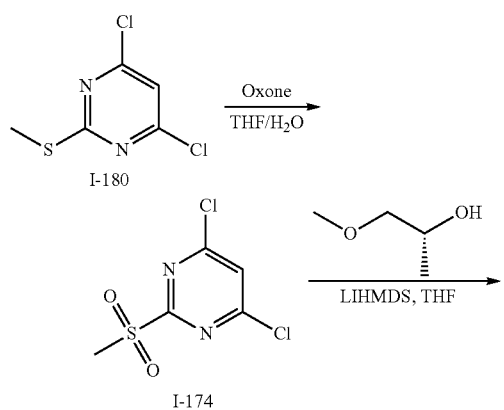

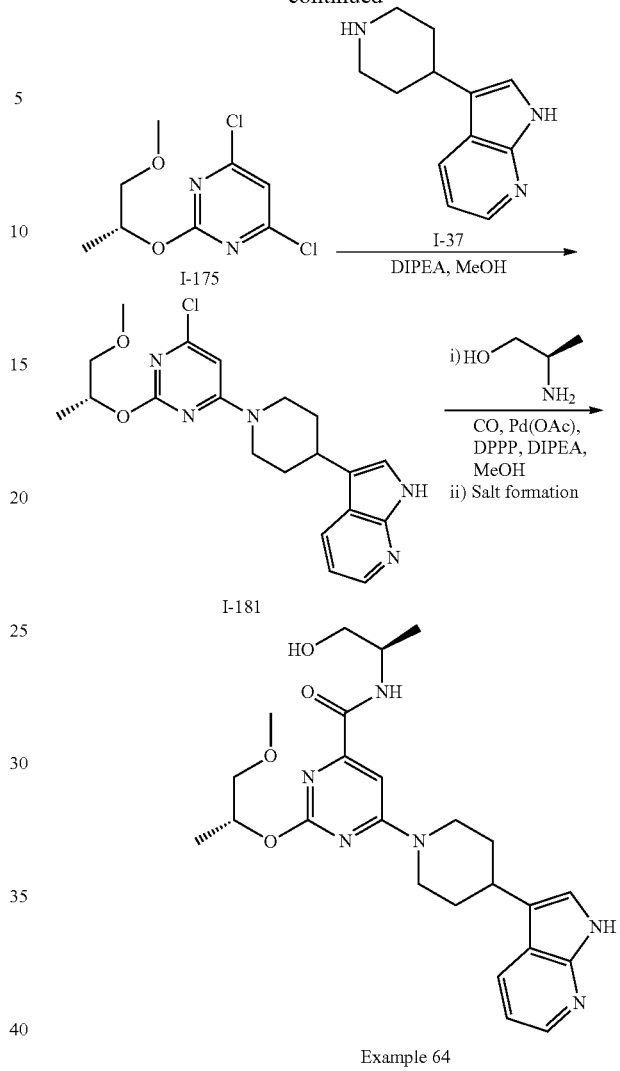

Example 64

Step 1—Synthesis of 4,6-dichloro-2-(methylsulfonyl)pyrimidine (I-174)

A mixture of 4,6-dichloro-2-(methylsulfanyl)pyrimidine (I-180) (20.0 g, 102.53 mmol) and oxone (189.0 g, 308 mmol) in THF (450 mL) and H₂O (150 mL) was stirred at room temperature for 16 hr. TLC (Petroleum ether:EtOAc=1:1) showed the starting material had been consumed. The reaction mixture was filtered and washed with THF (100 mL). The combined filtrate was concentrated, dissolved in EtOAc (500 mL) and washed with H₂O (2×300 mL) and brine (300 mL). The organic layer was dried over Na₂SO₄ and concentrated. The residue was purified by silica gel chromatography (petroleum ether:EtOAc=10:1 to pure EtOAc) to give 4,6-dichloro-2-(methylsulfonyl)pyrimidine (I-174) (20 g, 86%) as a white solid.

Step 2—Synthesis of 4,6-dichloro-2-{[(2R)-1-methoxypropan-2-yl]oxy}pyrimidine (I-175)

A solution of 4,6-dichloro-2-(methylsulfonyl)pyrimidine (I-174) (20.0 g, 88.08 mmol) and (2R)-1-methoxypropan-2-ol (7.94 g, 88.1 mmol) in THF (680 mL) was cooled to 0°

C. (10 min), and LiHMDS (96.9 mL, 1M in THF) was added in a dropwise manner over 30 min via an addition funnel. The resultant suspension was allowed to stir at 0° C. for an additional 20 min. The ice-bath was removed and the mixture was allowed to warm to room temperature over 30 min. TLC (petroleum ether:EtOAc=1:1) indicated the reaction was complete. The mixture was concentrated, taken up in EtOAc (800 mL), and washed with saturated aq. NH$_4$Cl (400 mL), and brine (400 mL). The organic layer was dried over Na$_2$SO$_4$, filtered and concentrated to give crude 3-[1-(6-chloro-2-{[(2R)-1-methoxypropan-2-yl]oxy}pyrimidin-4-yl)piperidin-4-yl]-1H-pyrrolo[2,3-b]pyridine (I-175) (23 g, 100%) as a yellow oil, which was used in the next step directly.

Step 3—Synthesis of 3-[1-(6-chloro-2-{[(2R)-1-methoxypropan-2-yl]oxy}pyrimidin-4-yl)piperidin-4-yl]-1H-pyrrolo[2,3-b]pyridine (I-181)

To a solution of 4,6-dichloro-2-{[(2R)-1-methoxypropan-2-yl]oxy}pyrimidine (I-175) (20.9 g, 88.155 mmol) and 3-(piperidin-4-yl)-1H-pyrrolo[2,3-b]pyridine hydrochloride (I-37) (21.4 g, 79.3 mmol) in MeOH (900 mL) was added slowly DIPEA (39.9 g, 309 mmol). The reaction mixture was stirred at room temperature for 2 hr. TLC (petroleum ether:EtOAc=1:1) showed the starting material had been consumed. The mixture was concentrated in vacuo, diluted with EtOAc (700 mL) and washed with saturated aq. NH$_4$Cl (2×700 mL), H$_2$O (700 mL) and brine (700 mL), dried over Na$_2$SO$_4$ and concentrated. The residue was purified by silica gel chromatography (petroleum ether:EtOAc=2:1 to 0:1) to give 3-[1-(6-chloro-2-{[(2R)-1-methoxypropan-2-yl]oxy}pyrimidin-4-yl)piperidin-4-yl]-1H-pyrrolo[2,3-b]pyridine (I-181) (23.0 g, 65%) as a light yellow solid, which was used without further purification.

Step 4—Synthesis of N-[(2R)-1-hydroxypropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide (Example 64)

A yellow solution of 3-[1-(6-chloro-2-{[(2R)-1-methoxypropan-2-yl]oxy}pyrimidin-4-yl)piperidin-4-yl]-1H-pyrrolo[2,3-b]pyridine (I-181) (10.0 g, 24.88 mmol), (2R)-2-aminopropan-1-ol (5.61 gg, 74.6 mmol), DIPEA (9.65 g, 74.6 mmol) in MeOH (180 mL) was placed in a 250 mL stainless steel vessel, and then Pd(OAc)$_2$ (559 mg, 2.49 mmol) and DPPP (2050 mg, 4.98 mmol) was added. Stirring was initiated (900 rpm) and the mixture was purged with argon (2 Bar) three times and CO (1 MPa) three times. The reaction mixture was the stirred under 1 MPa of CO pressure and heated to 100° C. for 18 hr. The vessel was opened to sample, and showed that there were some yellow solids present in the reaction mixture. TLC (EtOAc, R$_f$=0.2) showed the starting material was consumed and ~93% of the desired product was detected by LCMS. The mixture was filtered through a plug of celite and concentrated. The residue was initially purified by silica gel chromatography (10% MeOH in CH$_2$Cl$_2$) to provide the crude N-[(2R)-1-hydroxpropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide (10.0 g, purity 90.22%) as a light red solid, which was further purified by preparative HPLC. After preparative HPLC purification, the eluent was concentrated to remove the organic solvents. The residual aqueous solution was lyophilized to give N-[(2R)-1-hydroxypropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide (Example 64) (5.56 g, 48%) as a light yellow solid. LCMS (ESI), m/z 469.1 [M+H]$^+$; (400 MHz, CDCl$_3$) δ ppm 9.69 (s, 1 H), 8.30 (d, J=4.4 Hz, 1 H), 7.93-7.98 (m, 2 H), 7.06-7.11 (m, 3 H), 5.30-5.35 (m, 1 H), 4.58 (br. s., 2 H), 4.21-4.23 (m, 1 H), 3.65-3.72 (m, 3 H), 3.49-3.52 (m, 2 H), 3.41 (s, 3 H), 3.13-3.15 (m, 4 H), 2.14 (d, J=11.6 Hz, 2 H), 1.68-1.77 (m, 2 H), 1.38 (d, J=6.4 Hz, 3 H), 1.27 (d, J=6.4 Hz, 3 H).

Step 5—Synthesis of N-[(2R)-1-hydroxypropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide benzenesulfonate (Example 64)

Alternatively, after the carboamidation, the crude material can be precipitated from solution by precipitation from water after filtration through celite, and purified by salt formation as described herein.

Crude N-[(2R)-1-hydroxypropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide (25.5 g, 54.4 mmol) was dissolved in IPA (110 mL) and benzenesulfonic acid (8.78 g, 54.4 mmol) was added. The solution was heated to 65° C. before being allowed to cool slowly to room temperature overnight without stirring. The solids formed were slurried for 30 min, then filtered and rinsed with IPA (20 mL). The solids were collected by filtration, and dried under vacuum overnight to give N-[(2R)-1-hydroxypropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide benzenesulfonate (Example 64) (29 g, 85%) as a light yellow solid. (400 MHz, DMSO-d$_6$) δ ppm 11.99 (br. s., 1 H), 8.42 (d, J=7.70 Hz, 1 H), 8.31-8.37 (m, 1 H), 8.22 (d, J=8.56 Hz, 1 H), 7.57-7.64 (m, 2 H), 7.44 (d, J=2.08 Hz, 1 H), 7.24-7.37 (m, 4 H), 7.05 (s, 1 H), 5.30 (td, J=6.24, 4.16 Hz, 1 H), 4.57 (br. s., 1 H), 3.38-3.57 (m, 4 H), 3.30 (s, 3 H), 3.11-3.28 (m, 4 H), 2.09 (d, J=11.86 Hz, 2 H), 1.67 (qd, J=12.45, 3.61 Hz, 2 H), 1.27 (d, J=6.36 Hz, 3 H), 1.15 (d, J=6.72 Hz, 3 H).

Example 80 (Scheme B)

Synthesis of N-[(2R)-1-hydroxypropan-2-yl]-6-[4-(1H-pyrazolo[3,4-b]pyridin-3-yl)piperidin-1-yl]-2-[(2R)-tetrahydrofuran-2-ylmethoxy]pyrimidine-4-carboxamide

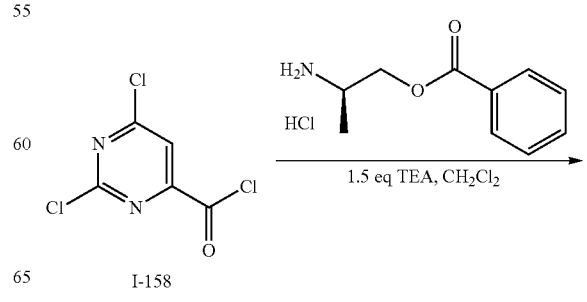

I-158

-continued

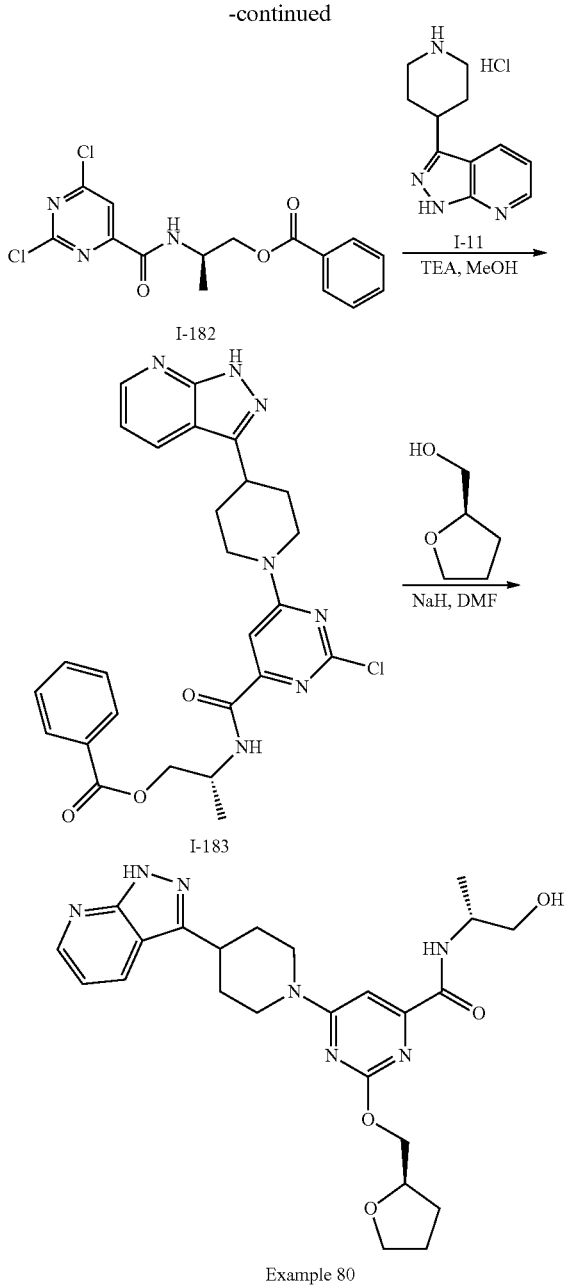

Step 1—Synthesis of (2R)-2-{[(2,6-dichloropyrimidin-4-yl)carbonyl]amino}propyl benzoate (I-182)

To a solution of 2,6-dichloropyrimidine-4-carbonyl chloride (I-158) (500 mg, 2.37 mmol), and TEA (718 mg, 7.11 mmol) in $CH_2Cl_2$ (30 mL) was added (2R)-2-aminopropyl benzoate hydrochloride (354 mg, 1.98 mmol) in portions at 0° C. under a nitrogen atmosphere, and the mixture was stirred at 0~10° C. for 1 hr. TLC (EtOAc) showed the reaction was completed. The mixture was quenched with $H_2O$ (20 mL) and extracted with $CH_2Cl_2$ (2×50 mL). The combined organic layers were washed with brine (3×30 mL), dried over $Na_2SO_4$ and concentrated. The residue was purified by silica gel chromatography (petroleum ether/EtOAc=6/1, Rf=0.4) to give (2R)-2-{[(2,6-dichloropyrimidin-4-yl)carbonyl]amino}propyl benzoate (I-182) (385 mg, 46%) as an oil, which was used without further purification.

Step 2—Synthesis of (2R)-2-[({2-chloro-6-[4-(1H-pyrazolo[3,4-b]pyridin-3-yl)piperidin-1-yl]pyrimidin-4-yl}carbonyl)amino]propyl benzoate (I-183)

To a solution of (2R)-2-{[(2,6-dichloropyrimidin-4-yl)carbonyl]amino}propyl benzoate (I-182) (342 mg, 0.97 mmol) and 3-(piperidin-4-yl)-1H-pyrazolo[3,4-b]pyridine hydrochloride (I-11) (232 mg, 0.97 mmol) in MeOH (10 mL) was added TEA (294 g, 2.91 mmol), and the mixture was stirred at room temperature for 1 hr. TLC (EtOAc) showed the reaction was completed. The mixture was concentrated to give to residue, which was purified by silica gel chromatography (petroleum ether/EtOAc 1/1, Rf~0.2) to give (2R)-2-[({2-chloro-6-[4-(1H-pyrazolo[3,4-b]pyridin-3-yl)piperidin-1-yl]pyrimidin-4-yl}carbonyl)amino]propyl benzoate (I-183) (370 mg, 73%) as a white solid, which was used directly in the next step.

Step 3—Synthesis of N-[(2R)-1-hydroxypropan-2-yl]-6-[4-(1H-pyrazolo[3,4-b]pyridin-3-yl)piperidin-1-yl]-2-[(2R)-tetrahydrofuran-2-ylmethoxy]pyrimidine-4-carboxamide (Example 80)

To a solution of (2R)-tetrahydrofuran-2-ylmethanol (58 mg, 0.57 mmol) in dry DMF (5 mL) was added NaH (23 mg, 60% in mineral oil, 0.57 mmol) under a $N_2$ atmosphere. After the addition, the reaction mixture was stirred at room temperature for 1 hr. Then, to the mixture was added (2R)-2-[({2-chloro-6-[4-(1H-pyrazolo[3,4-b]pyridin-3-yl)piperidin-1-yl]pyrimidin-4-yl}carbonyl)amino]propyl benzoate (I-183) (100 mg, 0.19 mmol). After the addition, the resulting mixture was heated at 50° C. for 4 hr. LCMS showed the reaction was completed. The mixture was cooled to room temperature and quenched with $H_2O$ (20 mL). The mixture was extracted with EtOAc (3×50 mL). The combined organic layers were washed with brine (4×50 mL), dried over $Na_2SO_4$ and concentrated to give the residue, which was purified by silica gel chromatography ($CH_2Cl_2$/MeOH=10/1, Rf~0.6) to give the crude product, which was further purified with preparative HPLC(Column: Phenomenex Gemini C18 250×21.2 mm, 8 µm. Mobile phase: from 20% MeCN (0.225% HCOOH) in water to 40% MeCN (0.225% HCOOH) in water. Wavelength: 220 nm) Lyophilization afforded N-[(2R)-1-hydroxypropan-2-yl]-6-[4-(1H-pyrazolo[3,4-b]pyridin-3-yl)piperidin-1-yl]-2-[(2R)-tetrahydrofuran-2-ylmethoxy]pyrimidine-4-carboxamide (Example 80) (20.1 mg, 22%) as a white solid. LCMS (APCI), m/z 482.2 [M+H]$^+$; (400 MHz, DMSO-$d_6$) δ ppm 13.29 (br. s., 1 H), 8.48-8.49 (m, 1 H), 8.31 (d, J=8.0 Hz, 1 H), 8.18 (d, J=8.8 Hz, 1 H), 7.13-7.16 (m, 1 H), 7.04 (s, 1 H), 4.89 (t, J=5.5 Hz, 1 H), 4.50 (br. s., 1 H), 4.26 (d, J=5.5 Hz, 2 H), 4.12-4.18 (m, 1 H), 4.03-4.04 (m, 1 H), 3.77-3.82 (m, 1 H), 3.65-3.70 (m, 1 H), 3.42-3.47 (m, 3 H), 3.16-3.23 (m, 2 H), 3.00 (br. s., 1 H), 2.12 (d, J=11 Hz, 2 H), 1.96-2.04 (m, 1 H), 1.81-1.88 (m, 4 H), 1.62-1.71 (m, 1 H), 1.15 (d, J=6.5 Hz, 3 H).

Example 92 (Scheme F)

Synthesis of 4-[4-({[2-amino-5-(1-methyl-1H-imidazol-4-yl)pyridin-3-yl]oxy}methyl)piperidin-1-yl]-{[(1S,2R)-2-cyanocyclopropyl]methoxy}-N-ethyl-1,3,5-triazine-2-carboxamide

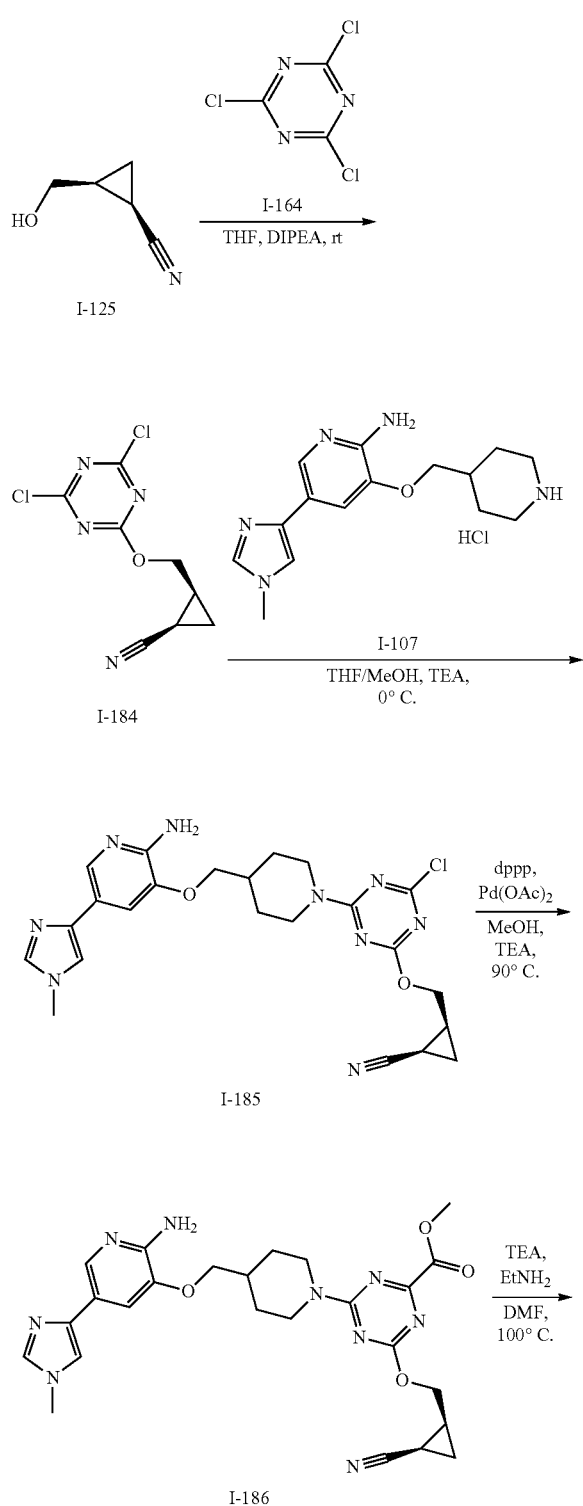

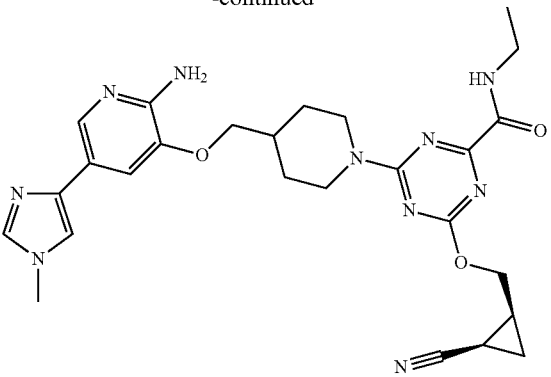

Example 92

Step 1—Synthesis of (1R,2S)-2-{[(4,6-dichloro-1,3,5-triazin-2-yl)oxy]methyl}cyclopropane carbonitrile (I-184)

A mixture of (1R,2S)-2-(hydroxymethyl)cyclopropanecarbonitrile (I-125) (1.06 g, 0.011 mol), cyanuric chloride (I-164) (2 g, 0.011 mol) and DIPEA (2.82 g, 0.022 mol) in THF (50 mL) was stirred at 0° C. for 1 hr, and then stirred at room temperature overnight. The solvent was evaporated and then purified by silica gel chromatography (Biotage. Petroleum ether:EtOAc=1:4) to give (1R,2S)-2-{[(4,6-dichloro-1,3,5-triazin-2-yl)oxy]methyl}cyclopropane carbonitrile (I-184) (400 mg, 15%) as white solid.

Step 2—Synthesis of (1R,2S)-2-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-185)

To a solution of (1R,2S)-2-{[(4,6-dichloro-1,3,5-triazin-2-yl)oxy]methyl}cyclopropane carbonitrile (I-184) (300 mg, 1.23 mmol) and 5-(1-methyl-1H-imidazol-4-yl)-3-(piperidin-4-ylmethoxy)pyridin-2-amine hydrochloride (I-107) (467 mg, 1.23 mmol) in THF (15 mL) and MeOH (5 mL) at 0° C. was added TEA (745 mg, 7.38 mmol). The mixture was stirred at 0° C. for 30 min. TLC ($CH_2Cl_2$:MeOH=15:1) showed the reaction was complete. The solvent was evaporated. The residue was purified by silica gel chromatography ($CH_2Cl_2$:MeOH=25:2) to give (1R,2S)-2-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-185) (560 mg, 92%) as gray solid, which was used without further purification.

Step 3—Synthesis of methyl 4-[4-({[2-amino-5-(1-methyl-1H-imidazol-4-yl)pyridin-3-yl]oxy}methyl)piperidin-1-yl]-6-{[(1S,2R)-2-cyanocyclopropyl]methoxy}-1,3,5-triazine-2-carboxylate (I-186)

A mixture of (1R,2S)-2-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-185) (300 mg, 0.6 mmol), DPPP (50 mg, 0.12 mmol), Pd(OAc)$_2$ (13.5 mg, 0.06 mmol) and TEA (121 mg, 1.2 mmol) in MeOH (30 mL) was stirred in a sealed tube under CO atmosphere (2 MPa) at 90~100° C. for 20 hr. TLC ($CH_2Cl_2$:MeOH=15:1) showed that the reaction was complete. The mixture was filtered and concentrated. The residue was purified by silica gel chromatography (MeOH:CH$_2$Cl$_2$=5% to 8%) to give methyl 4-[4-({[2-amino-5-(1-methyl-1H-imidazol-4-yl)pyridin-3-yl]oxy}methyl)piperidin-1-yl]-6-{[(1S,2R)-2-cyanocyclopropyl]methoxy}-1,3,5-triazine-2-carboxylate (I-186) (180 mg, 57%) as gray solid.

Step 4—Synthesis of 4-[4-({[2-amino-5-(1-methyl-1H-imidazol-4-yl)pyridin-3-yl]oxy}methyl)piperidin-1-yl]-6-{[(1S,2R)-2-cyanocyclopropyl]methoxy}-N-ethyl-1,3,5-triazine-2-carboxamide (Example 92)

A mixture of methyl 4-[4-({[2-amino-5-(1-methyl-1H-imidazol-4-yl)pyridin-3-yl]oxy}methyl)piperidin-1-yl]-6-{[(1S,2R)-2-cyanocyclopropyl]methoxy}-1,3,5-triazine-2-carboxylate (I-86) (50 mg, 0.096 mmol), ethylamine hydrochloride (34 mg, 0.289 mmol) and TEA (145 mg, 1.44 mmol) in DMF (1 mL) was stirred at 100° C. overnight. TLC (CH$_2$Cl$_2$:MeOH=15:1) showed that most of the starting material had been consumed. The solvent was evaporated. The residue was dissolved in CH$_2$Cl$_2$ (20 mL), washed with aq. NH$_4$Cl, brine, dried over Na$_2$SO$_4$ and concentrated. The residue was purified by silica gel chromatography (CH$_2$Cl$_2$:MeOH=10:1) to give 4-[4-({[2-amino-5-(1-methyl-1H-imidazol-4-yl)pyridin-3-yl]oxy}methyl)piperidin-1-yl]-6-{[(1S,2R)-2-cyanocyclopropyl]methoxy}-N-ethyl-1,3,5-triazine-2-carboxamide (Example 92) (7.6 mg, 15%) as yellow solid. LCMS (ESI), m/z 533.1 [M+H]$^+$; (400 MHz, CDCl$_3$) δ ppm 7.95 (s, 1 H), 7.61-7.72 (m, 1 H), 7.45 (s, 2 H), 7.10 (s, 1 H), 5.04-5.13 (m, 1 H), 4.81-4.90 (m, 1 H), 4.71 (s, 1 H), 4.56-4.61 (m, 1 H), 4.45-4.50 (m, 1 H), 3.96-3.97 (m, 2 H), 3.45-3.49 (m, 2 H), 2.96-3.06 (m, 1 H), 2.18-2.20 (m, 1 H), 1.80-1.97 (m, 2 H), 1.40-1.45 (m, 2 H), 1.20-1.35 (m, 6 H), 0.80-0.88 (m, 1 H).

Example 93 (Scheme F)

Synthesis of 4-[4-(5-amino-6-carbamoylpyridin-2-yl)piperidin-1-yl]-6-{[(1S,2R)-2-cyanocyclopropyl]methoxy}-N-[(2S)-1,1,1-trifluoropropan-2-yl]-1,3,5-triazine-2-carboxamide

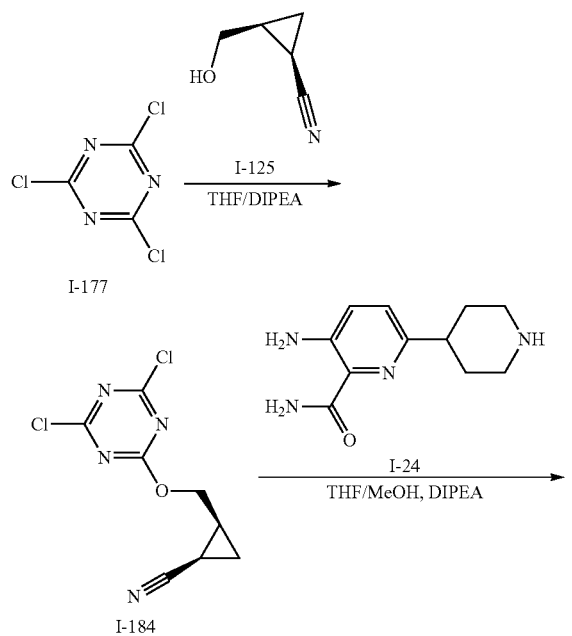

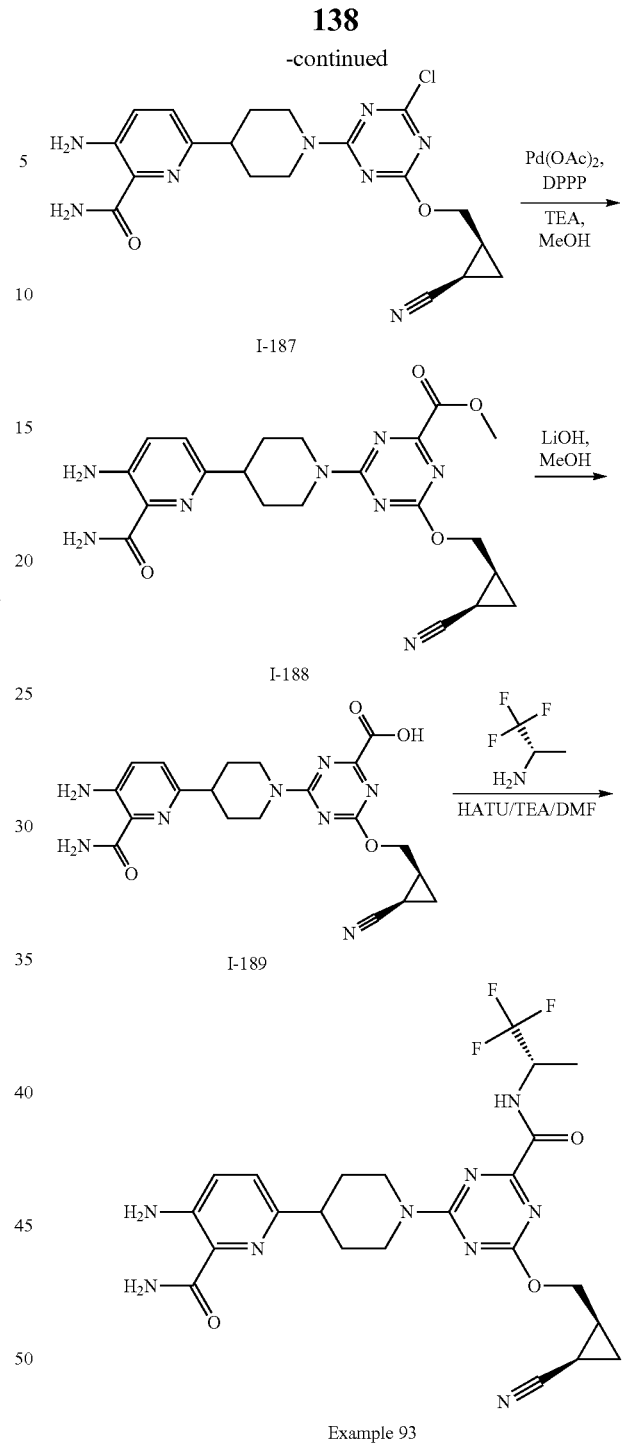

Example 93

Step 1—Synthesis of (1R,2S)-2-{[(4,6-dichloro-1,3,5-triazin-2-yl)oxy]methyl}cyclopropane carbonitrile (I-184)

To a solution of cyanuric chloride (I-167) (4.2 g, 0.022 mol) and DIPEA (3.3 g, 0.026 mol) in dry THF (30 mL) was added (1R,2S)-2-(hydroxymethyl)cyclopropanecarbonitrile (I-125) (2 g, 0.022 mol) at 0° C. The reaction was stirred at room temperature for 14 hr. TLC (petroleum ether:EtOAc=1:1) showed two new spots. The mixture was concentrated under vacuum to give a residue, which was purified by silica gel chromatography (petroleum ether:

EtOAc=1:1 R_f~0.5) to give (1R,2S)-2-{[(4,6-dichloro-1,3,5-triazin-2-yl)oxy]methyl}cyclopropane carbonitrile (I-184) (2 g, 38%) as a white solid, which was used directly in the next step.

Step 2—Synthesis of 3-amino-6-[1-(4-chloro-6-{[(1S,2R)-2-cyanocyclopropyl]methoxy}-1,3,5-triazin-2-yl)piperidin-4-yl]pyridine-2-carboxamide (I-187)

To a solution of (1R,2S)-2-{[(4,6-dichloro-1,3,5-triazin-2-yl)oxy]methyl}cyclopropane carbonitrile (I-184) (160.7 mg, 0.6557 mmol) and 3-amino-6-(piperidin-4-yl)pyridine-2-carboxamide (I-24) (144 mg, 0.656 mmol) in THF (30 mL) and MeOH (10 mL) was added DIPEA (339 mg, 2.62 mmol) at 0° C. The reaction was stirred at 0° C. for 30 min. TLC (EtOAc) indicated the reaction was completed. The mixture was concentrated and purified by silica gel chromatography (petroleum ether:EtOAc=1:1 to 0:1) to give 3-amino-6-[1-(4-chloro-6-{[(1S,2R)-2-cyanocyclopropyl]methoxy}-1,3,5-triazin-2-yl)piperidin-4-yl]pyridine-2-carboxamide (I-187) (255.5 mg, 91%) as a white solid, which was used directly in the next step.

Step 3—Synthesis of methyl 4-[4-(5-amino-6-carbamoylpyridin-2-yl)piperidin-1-yl]-6-{[(1S,2R)-2-cyanocyclopropyl]methoxy}-1,3,5-triazine-2-carboxylate (I-188)

A mixture of 3-amino-6-[1-(4-chloro-6-{[(1S,2R)-2-cyanocyclopropyl]methoxy}-1,3,5-triazin-2-yl)piperidin-4-yl]pyridine-2-carboxamide (I-187) (255.5 mg, 0.5957 mmol), DPPP (24.6 mg, 0.0596 mmol), Pd(OAc)$_2$ (13.4 mg, 0.0596) and TEA (121 mg, 1.19 mmol) in MeOH (15 mL) saturated with CO was stirred under 2 MPa at 90° C. for 12 hr. TLC (EtOAc) indicated the reaction was completed. The reaction mixture was filtered and washed with MeOH (5 mL). The organic layer was concentrated in vacuo to dryness to give a residue, which was purified by silica gel chromatography (EtOAc) to give the methyl 4-[4-(5-amino-6-carbamoylpyridin-2-yl)piperidin-1-yl]-6-{[(1S,2R)-2-cyanocyclopropyl]methoxy}-1,3,5-triazine-2-carboxylate (I-188) (210 mg, 78%) as a white solid, which was used directly in the next step.

Step 4—Synthesis of 4-[4-(5-amino-6-carbamoylpyridin-2-yl)piperidin-1-yl]-6-{[(1S,2R)-2-cyanocyclopropyl]methoxy}-1,3,5-triazine-2-carboxylic acid (I-189)

To a solution of methyl 4-[4-(5-amino-6-carbamoylpyridin-2-yl)piperidin-1-yl]-6- {[(1S,2R)-2-cyanocyclopropyl]methoxy}-1,3,5-triazine-2-carboxylate (I-188) (100 mg, 0.22 mmol) in MeOH (10 mL) was added aqueous LiOH (0.22 mL, 2 N, 0.44 mmol). The mixture was stirred at room temperature for 2.5 hr. LCMS showed the reaction was completed. The reaction mixture was then adjusted to pH=5 with 1N aqueous HCl. The solvent was evaporated to give crude 4-[4-(5-amino-6-carbamoylpyridin-2-yl)piperidin-1-yl]-6-{[(1S,2R)-2-cyanocyclopropyl]methoxy}-1,3,5-triazine-2-carboxylic acid (I-189), which was used in the next step directly without further purification.

Step 5—Synthesis of 4-[4-(5-amino-6-carbamoylpyridin-2-yl)piperidin-1-yl]-6-{[(1S,2R)-2-cyanocyclopropyl]methoxy}-N-[(2S)-1,1,1-trifluoropropan-2-yl]-1,3,5-triazine-2-carboxamide (Example 93)

To a solution of 4-[4-(5-amino-6-carbamoylpyridin-2-yl)piperidin-1-yl]-6-{[(1S,2R)-2-cyanocyclopropyl]methoxy}-1,3,5-triazine-2-carboxylic acid (I-189) (97 mg, 0.22 mmol) in anhydrous DMF (2 mL) was added HATU (84.1 mmg, 0.221 mmol) and Et$_3$N (56 mg, 0.553 mmol) at 0° C. (2S)-1,1,1-trifluoropropan-2-amine (50 mmg, 0.442 mmol) was added. After the addition, the mixture was stirred at room temperature for 16 hr. TLC showed the reaction was completed. The reaction mixture was poured into water (10 mL) and extracted with EtOAc (3×20 mL). The combined organic layers were washed with brine (10 mL) dried over Na$_2$SO$_4$ and purified by preparative HPLC to afford 4-[4-(5-amino-6-carbamoylpyridin-2-yl)piperidin-1-yl]-6-{[(1S,2R)-2-cyanocyclopropyl]methoxy}-N-[(2S)-1,1,1-trifluoropropan-2-yl]-1,3,5-triazine-2-carboxamide (Example 93) (15.4 mg, 13%) as a white solid. LCMS (APCI), m/z 534.1 [M+H]$^+$; (400 MHz, DMSO-d$_6$) δ ppm 9.06 (d, J=9.2 Hz, 1 H), 7.88 (s, 1 H), 7.21-7.25 (m, 2 H), 7.10 (d, J=8.4 Hz, 1 H), 6.68 (s, 2 H), 4.95 (d, J=13.6 Hz, 1 H), 4.69-4.80 (m, 3 H), 4.11-4.16 (m, 1 H), 3.09 (t, J=12.8 Hz, 2 H), 2.91 (t, J=10.7 Hz, 1 H), 1.81-2.01 (m, 4 H), 1.70-1.72 (m, 2 H), 1.38 (d, J=7.2 Hz, 3 H), 1.28-1.30 (m, 1 H), 1.17-1.19 (m, 1 H).

Example 98 (Scheme F)

Synthesis of 4-{[(1S,2R)-2-cyanocyclopropyl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide

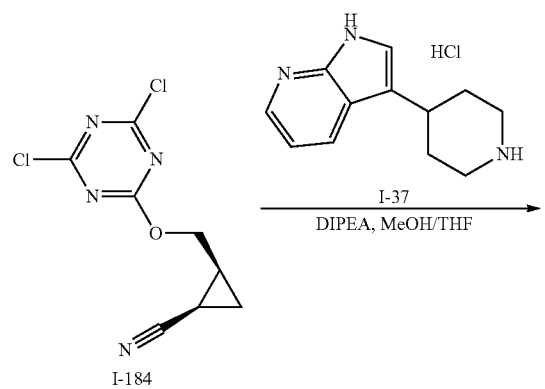

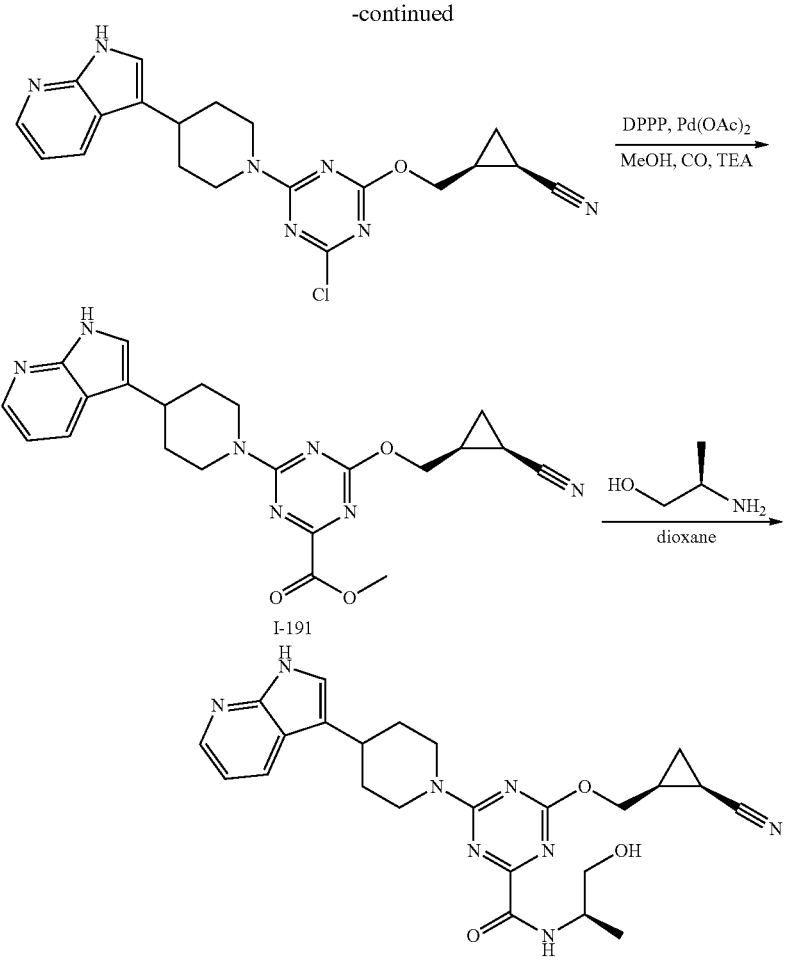

Example 98

Step 1—Synthesis of (1R,2S)-2-[({4-chloro-6-[4-(1H-pyrrolo[2,3-b]pyridin-3-yl)piperidin-1-yl]-1,3,5-triazin-2-yl}oxy)methyl]cyclopropanecarbonitrile (I-190)

To a solution of (1R,2S)-2-{[(4,6-dichloro-1,3,5-triazin-2-yl)oxy]methyl}cyclopropanecarbonitrile (I-184) (150 mg, 0.612 mmol) and 3-(piperidin-4-yl)-1H-pyrrolo[2,3-b]pyridine hydrochloride (I-37) (123 mg, 0.612 mmol) in THF (20 mL) and MeOH (5 mL) was added DIPEA (316 mg, 2.45 mmol) at 0° C. The reaction was stirred at 0° C. for 30 min. TLC (EtOAc) indicated the reaction was complete. The mixture was concentrated and purified by silica gel chromatography (petroleum ether:EtOAc=1:1 to 0:1) to give (1R,2S)-2-[({4-chloro-6-[4-(1H-pyrrolo[2,3-b]pyridin-3-yl)piperidin-1-yl]-1,3,5-triazin-2-yl}oxy)methyl]cyclopropane carbonitrile (I-190) (140 mg, 56%) as a white solid, which was used directly in the next step.

Step 2—Synthesis of Step 5: Synthesis of (1R,2S)-2-[({4-chloro-6-[4-(1H-pyrrolo[2,3-b]pyridin-3-yl)piperidin-1-yl]-1,3,5-triazin-2-yl}oxy)methyl]cyclopropanecarbonitrile (I-191)

A mixture of (1R,2S)-2-[({4-chloro-6-[4-(1H-pyrrolo[2,3-b]pyridin-3-yl)piperidin-1-yl]-1,3,5-triazin-2-yl}oxy)methyl]cyclopropanecarbonitrile (I-190) (100 mg, 0.244 mmol), DPPP (10.1 mg, 0.0244 mmol), Pd (OAc)2 (5.48 mg, 0.0244) and TEA (49.4 mg, 0.488 mmol) in MeOH (15 mL) was stirred under CO (2 MPa) at 90° C. for 12 hr. TLC (EtOAc) indicated the reaction was complete. The reaction mixture was filtered and washed with MeOH (5 mL). The organic layer was concentrated under vacuum to dryness to give a residue, which was purified by silica gel chromatography (EtOAc) to give the methyl 4-{[(1S,2R)-2-cyanocyclopropyl]methoxy}-6-[4-(1H-pyrrolo[2,3-b]pyridin-3-yl)piperidin-1-yl]-1,3,5-triazine-2-carboxylate (I-191) (83 mg, 78%) as a white solid, which was used directly in the next step.

Step 3—Synthesis of 4-{[(1S,2R)-2-cyanocyclopropyl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide (Example 98)

A mixture of methyl 4-{[(1S,2R)-2-cyanocyclopropyl]methoxy}-6-[4-(1H-pyrrolo[2,3-b]pyridin-3-yl)piperidin-1-yl]-1,3,5-triazine-2-carboxylate (I-191) (83 mg, 0.19 mmol) and (2R)-2-aminopropan-1-ol (43.1 mg, 0.574 mmol) in dioxane (1 mL) was stirred at 100° C. for 16 hr. TLC (EtOAc) showed the reaction was complete. The mixture was concentrated, and purified by preparative TLC (EtOAc) to give 4-{[(1S,2R)-2-cyanocyclopropyl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide (Example 98) (7.4 mg, 8%) as a white solid. LCMS (APCI), m/z 477.1 [M+H]+; (400 MHz, CD3OD) δ ppm 8.17 (d, J=4.8 Hz, 1 H), 8.11 (d, J=6.4 Hz, 1 H), 7.21 (s, 1 H), 7.09-7.12 (m, 1 H), 5.16 (d, J=10.8 Hz, 1 H), 4.97 (d, J=12.8 Hz, 1 H), 4.76-4.79 (m, 1 H), 4.32 (t, J=10.7 Hz, 1 H), 4.16 (d, J=6.8 Hz, 1 H), 3.64 (d, J=5.2 Hz, 2 H), 3.22 (t, J=12.8 Hz, 2 H), 2.20 (d, J=13.6 Hz, 2 H), 1.90-1.93 (m, 2 H), 1.79 (d, J=12.4 Hz, 2 H), 1.36 (d, J=6.8 Hz, 3 H), 1.27 (d, J=6.8 Hz, 3 H).

Example 101 (Scheme F)

Synthesis of N-[(2R)-1-hydroxypropan-2-yl]-4-{[(2R)-1-methoxypropan-2-yl]oxy}-6-[4-(1H-pyrrolo[2,3-b]pyridin-3-yl)piperidin-1-yl]-1,3,5-triazine-2-carboxamide

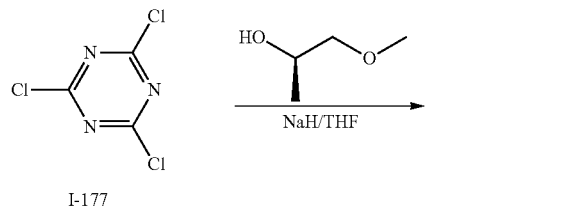

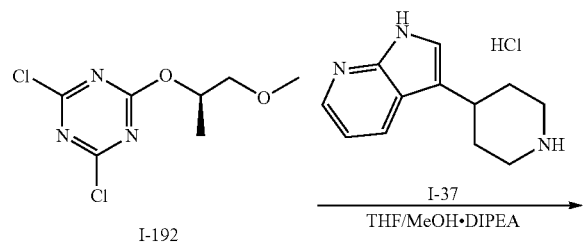

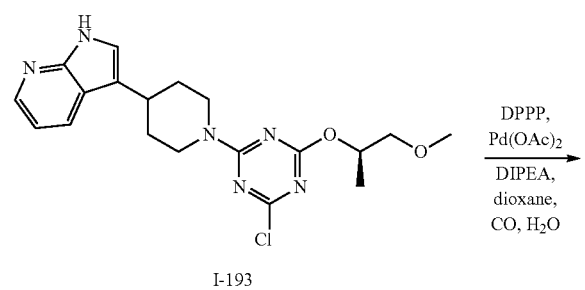

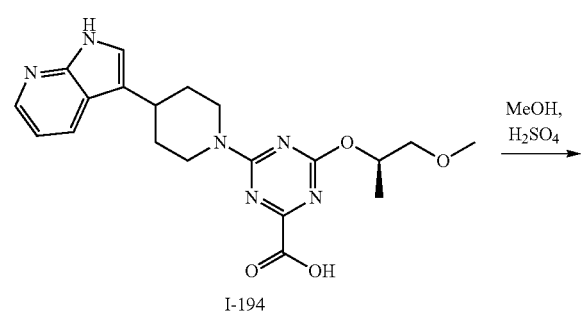

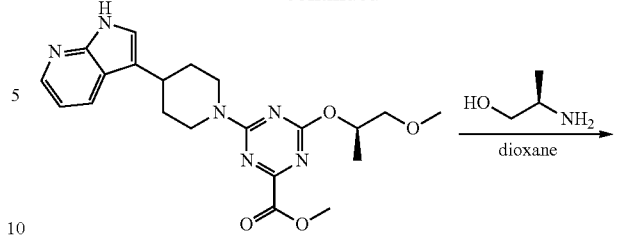

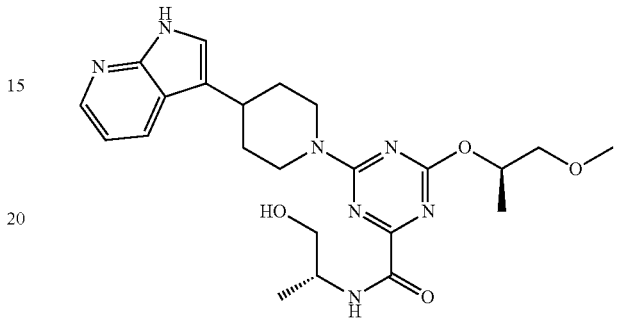

Example 101

Step 1—Synthesis of 4-{[(1S,2R)-2-cyanocyclopropyl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide (I-192)

To a mixture of (2R)-1-methoxypropan-2-ol (3 g, 33.29 mmol) in THF (20 mL) was added NaH (2.66 g, 60% in mineral oil, 66.6 mmol) in portions over a period of 10 min. After addition, the mixture was stirred at 0° C. for 1 hr. Then, cyanuric chloride (I-177) (6.14 g, 33.3 mmol) was added. After the addition, the reaction mixture was stirred at 0° C. for a further hr. TLC (petroleum ether/EtOAc=10/1) indicated the reaction was complete. The reaction mixture was poured into water (10 mL) and extracted with EtOAc (3×50 mL). The combined organic layers were washed with water (2×10 mL), brine (20 mL), dried over Na2SO4 and concentrated under vacuum to dryness to give a residue, which was purified by silica gel chromatography (petroleum ether/EtOAc=10/1 to 1/1) to give 2,4-dichloro-6-{[(2R)-1-methoxypropan-2-yl]oxy}-1,3,5-triazine (I-192) (1.1 g, 14%) as a colorless oil, which was used directly in the next step.

Step 2—Synthesis of 3-[1-(4-chloro-6-{[(2R)-1-methoxypropan-2-yl]oxy}-1,3,5-triazin-2-yl)piperidin-4-yl]-1H-pyrrolo[2,3-b]pyridine (I-193)

To a solution of 2,4-dichloro-6-{[(2R)-1-methoxypropan-2-yl]oxy}-1,3,5-triazine (I-192) (500 mg, 2.1 mmol) and 3-(piperidin-4-yl)-1H-pyrrolo[2,3-b]pyridine hydrochloride (I-37) (549 mg, 2.31 mmol) in THF (10 mL) and MeOH (2 mL) was added DIPEA (1090 mg, 8.40 mmol) at 0° C. The reaction was stirred at 0° C. for 30 min. LCMS showed the reaction was completed. The mixture was concentrated and purified, by silica gel chromatography (petroleum ether/EtOAc=1:1 to 0:1) to give 3-[1-(4-chloro-6-{[(2R)-1-methoxypropan-2-yl]oxy}-1,3,5-triazin- 2-yl)piperidin-4- yl]-1H-pyrrolo[2,3-b]pyridine (I-193) (600 mg, 71%) as a solid, which was used directly in the next step.

Step 3—Synthesis of 4-{[(2R)-1-methoxypropan-2-yl]oxy}-6-[4-(1H-pyrrolo[2,3-b]pyridin-3-yl)piperidin-1-yl]-1,3,5-triazine-2-carboxylic acid (I-194)

A mixture of 3-[1-(4-chloro-6-{[(2R)-1-methoxypropan-2-yl]oxy}-1,3,5-triazin-2-yl)piperidin-4-yl]-1H-pyrrolo[2,3-b]pyridine (I-193) (100 mg, 0.248 mmol), DPPP (15.4 mg, 0.0372 mmol), Pd(OAc)₂ (8.36 mg, 0.0372) and DIPEA (160 mg, 1.24 mmol) in dioxane (20 mL) and H₂O (4 mL) was stirred under CO (2 MPa) at 90° C. for 12 hr. LCMS indicated the reaction was completed. The reaction mixture was filtered, and washed with MeOH (5 mL). The organic layer was concentrated under vacuum to dryness to afford a residues, which was purified by silica gel chromatography (CH₂Cl₂/MeOH=15/1 to 10/1) to give 4-{[(2R)-1-methoxypropan-2-yl]oxy}-6-[4-(1H-pyrrolo[2,3-b]pyridin-3-yl)piperidin-1-yl]-1,3,5-triazine-2-carboxylic acid (I-194) (85 mg, 83%) as a white solid, which was used directly in the next step.

Step 4—Synthesis of 4 methyl 4-{[(2R)-1-methoxypropan-2-yl]oxy}-6-[4-(1H-pyrrolo[2,3-b]pyridin-3-yl)piperidin-1-yl]-1,3,5-triazine-2-carboxylate (I-195)

To a solution of 4-{[(2R)-1-methoxypropan-2-yl]oxy}-6-[4-(1H-pyrrolo[2,3-b]pyridin-3-yl)piperidin-1-yl]-1,3,5-triazine-2-carboxylic acid (I-194) (85 mg, 0.21 mmol) in MeOH (2 mL) was added H₂SO₄ (4.04 mg, 0.0412 mmol). The mixture was stirred at 65° C. for 1.5 hr. LCMS indicated that only 6% of starting material remained. The solvent was evaporated, and the residue was diluted with water (1 mL), adjusted to pH=8 with saturated sodium carbonate solution. The mixture was extracted with CH₂Cl₂/MeOH=10:1 (3×10 mL). The combined organic layers dried over Na₂SO₄, and concentrated to give methyl 4-{[(2R)-1-methoxypropan-2-yl]oxy}-6-[4-(1H-pyrrolo[2,3-b]pyridin-3-yl)piperidin-1-yl]-1,3,5-triazine-2-carboxylate (I-195) (61 mg), which was used in the next step directly without purification.

Step 5—Synthesis of N-[(2R)-1-hydroxypropan-2-yl]-4-{[(2R)-1-methoxypropan-2-yl]oxy}-6-[4-(1H-pyrrolo[2,3-b]pyridin-3-yl)piperidin-1-yl]-1,3,5-triazine-2-carboxamide (Example 101)

A mixture of methyl 4-{[(2R)-1-methoxypropan-2-yl]oxy}-6-[4-(1H-pyrrolo[2,3-b]pyridin-3-yl)piperidin-1-yl]-1,3,5-triazine-2-carboxylate (I-195) (61 mg, 0.14 mmol) and (2R)-2-aminopropan-1-ol (26.9 mg, 0.358 mmol) in dioxane (1 mL) was stirred at 100° C. for 16 hr. LCMS showed the reaction was complete. The mixture was concentrated, and purified by preparative HPLC to give N-[(2R)-1-hydroxypropan-2-yl]-4-{[(2R)-1-methoxypropan-2-yl]oxy}-6-[4-(1H-pyrrolo[2,3-b]pyridin-3-yl)piperidin-1-yl]-1,3,5-triazine-2-carboxamide (Example 101) (15.5 mg, 23%) as a white solid. LCMS (ESI), m/z 470.1 [M+H]⁺; (400 MHz, CD₃OD) δ ppm 8.18 (d, J=4.8 Hz, 1 H), 8.11 (d, J=6.4 Hz, 1 H), 7.22 (s, 1 H), 7.09-7.12 (m, 1 H), 5.46-5.50 (m, 1 H), 5.15 (d, J=10.8 Hz, 1 H), 4.92-4.96 (m, 1 H), 4.15-4.16 (m, 1 H), 3.57-3.65 (m, 4 H), 3.40 (s, 3 H), 3.19-3.25 (m, 3 H), 2.21 (d, J=13.6 Hz, 2 H), 1.76-1.79 (m, 2 H), 1.37 (d, J=6.8 Hz 3 H), 1.7 (d, J=6.8 Hz, 3 H).

Example 102 (Scheme D)

Synthesis of 2-[(1-cyanocyclopropyl)methoxy]-N-[(2R)-1-hydroxypropan-2-yl]-6-[4-(1H-pyrrolo[2,3-b]pyridin-3-yl)piperidin-1-yl]pyrimidine-4-carboxamide

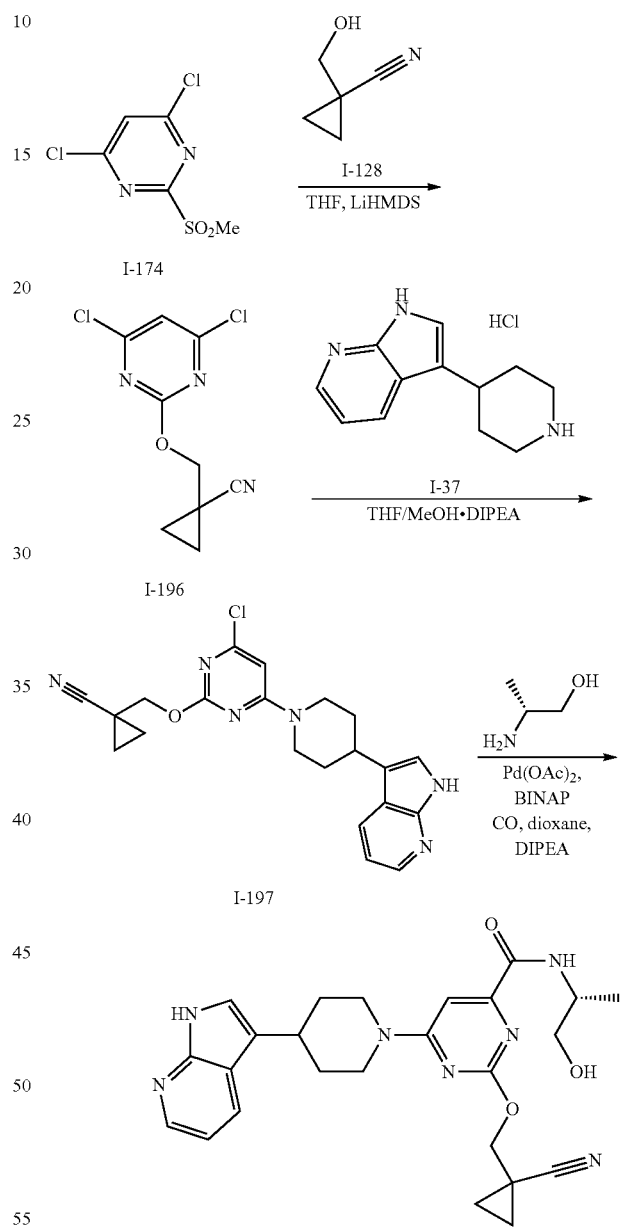

Example 102

Step 1—Synthesis of 1-{[(4,6-dichloropyrimidin-2-yl)oxy]methyl}cyclopropanecarbonitrile (I-196)

To a solution of 4,6-dichloro-2-(methylsulfonyl)pyrimidine (I-174) (15.9 g, 70 mmol) and 1-(hydroxymethyl)cyclopropanecarbonitrile (I-128) (7.0 g, 70 mmol) in THF (450 mL) was added LiHMDS (77 mL, 1 N, 1.1 eq) in a dropwise manner while keeping the internal temperature between −5~0° C. After stirring for 1 hr, the reaction mixture was allowed to warm to room temperature (20° C.) over 30 min. TLC (petroleum ether:EtOAc=1:1, $R_f$~0.6) showed the reaction was complete. The reaction mixture was concentrated, re-suspended in EtOAc (300 mL) and washed with saturated aqueous NH$_4$Cl solution (150 mL), brine (150 mL), dried over Na$_2$SO$_4$, and concentrated to give crude 1-{[(4,6-dichloropyrimidin-2-yl)oxy]methyl}cyclopropanecarbonitrile (I-196) (16.0 g), which was used directly in the next step without further purification.

Step 2—Synthesis of 1-[({4-chloro-6-[4-(1H-pyrrolo[2,3-b]pyridin-3-yl)piperidin-1-yl]pyrimidin-2-yl}oxy)methyl]cyclopropanecarbonitrile (I-197)

To a suspension of 1-{[(4,6-dichloropyrimidin-2-yl)oxy]methyl}cyclopropanecarbonitrile (I-196) (16 g, 66 mmol) and 3-(piperidin-4-yl)-1H-pyrrolo[2,3-b]pyridine hydrochloride (I-37) (17.7 g, 65.6 mmol) in MeOH (525 mL) was added DIPEA (42.4 g, 328 mmol) at room temperature (20° C.). After the addition of DIPEA, the reaction mixture became a clear yellow solution. The reaction mixture was stirred at room temperature (20° C.) for 3 hr while solid was generated slowly. TLC (EtOAc, $R_f$~0.2) showed the reaction was completes. The reaction mixture was concentrated to leave ~40 mL of MeOH. The reaction mixture was filtered and the filter cake washed with MeOH (30 mL) to give crude product (14.3 g, crude, 93.89% pure by HPLC). The crude product was re-crystallized from MeOH (50 mL) to give 1-[({4-chloro-6-[4-(1H-pyrrolo[2,3-b]pyridin-3-yl)piperidin-1-yl]pyrimidin-2-yl}oxy)methyl]cyclopropanecarbonitrile (I-197) (13.3 g, 50%) as a pale white solid. LCMS (APCI), m/z 408.1 [M+H]$^+$; (400 MHz, DMSO-d$_6$) δ ppm 11.36 (br. s., 1 H), 8.19 (d, J=3.2 Hz, 1 H), 8.02 (d, J=8.0 Hz, 1 H), 7.24 (s, 1 H), 7.01-7.04 (m, 1 H), 6.73 (s, 1 H), 4.51 (br. s., 2 H), 4.26 (s, 2 H), 3.11-3.18 (m, 3 H), 2.04 (d, J=12.8 Hz 2 H), 1.61-1.63 (m, 2 H), 1.34-1.37 (m, 2 H), 1.20-1.22 (m, 2 H).

Step 3—Synthesis of 2-[(1-cyanocyclopropyl)methoxy]-N-[(2R)-1-hydroxypropan-2-yl]-6-[4-(1H-pyrrolo[2,3-b]pyridin-3-yl)piperidin-1-yl]pyrimidine-4-carboxamide (Example 102)

A yellow suspension of 1-[({4-chloro-6-[4-(1H-pyrrolo[2,3-b]pyridin-3-yl)piperidin-1-yl]pyrimidin-2-yl}oxy)methyl]cyclopropanecarbonitrile (I-197) (3.5 g, 8.6 mmol), (2R)-2-aminopropan-1-ol (1.61 g, 21.4 mmol), DIPEA (3.32 g, 25.7 mmol) in dioxane (50 mL) was placed in a 100 mL stainless steel vessel. To the vessel was added Pd(OAc)$_2$ (120 mg, 0.535 mmol) and BINAP (666 mg, 1.07 mmol). Stirring was initiated, and the mixture was purged three times with Ar (2 bar) followed by three times with CO (1 MPa). Then, the reaction mixture was stirred under 18 Bar of CO pressure at 100° C. for 17 hr. The reaction mixture became an orange color, and showed some dark precipitate on being allowed to settle. TLC (EtOAc:MeOH=10:1, $R_f$~0.3) showed ~25% of the starting material still remained. Then the reaction mixture was filtered, and the filtrate concentrated to give crude product (3.6 g). The crude product was purified by silica gel chromatography eluting with EtOAc to give 5 g of crude material (86.8% pure by HPLC). This material was further purified by preparative HPLC (from 20% MeCN in water with 0.05% NH$_4$OH to 50% MeCN in water with 0.05% NH$_4$OH). After HPLC purification, the solution was concentrated to remove organic solvents. The residual aqueous solution was lyophilized to give 2-[(1-cyanocyclopropyl)methoxy]-N-[(2R)-1-hydroxypropan-2-yl]-6-[4-(1H-pyrrolo[2,3-b]pyridin-3-yl)piperidin-1-yl]pyrimidine-4-carboxamide (Example 102) (3.5 g, 50%) as a white solid. LCMS (APCI), m/z 476.2 [M+H]$^+$; (400 MHz, DMSO-d$_6$) δ ppm 11.36 (s, 1 H), 8.18-8.22 (m, 2 H), 8.01-8.03 (m, 1 H), 7.24 (d, J=5.6 Hz, 1 H), 7.03-7.06 (m, 2 H), 4.86-4.89 (m, 1 H), 4.70 (br. s., 1 H), 4.36 (s, 2 H), 3.98-4.00 (m, 1 H), 3.43-3.47 (m, 3 H), 3.13-3.40 (m, 3 H), 2.05-2.09 (m, 2 H), 1.62-1.65 (m, 2 H), 1.37-1.39 (m, 2 H), 1.22-1.24 (m, 2 H), 1.14-1.16 (m, 3 H).

Example 107 (Scheme F)

Synthesis of 4-(cyclopropylmethoxy)-N-[(2R)-1-hydroxypropan-2-yl]-6-[4-(1H-pyrazolo[3,4-b]pyridin-3-yl)piperidin-1-yl]-1,3,5-triazine-2-carboxamide

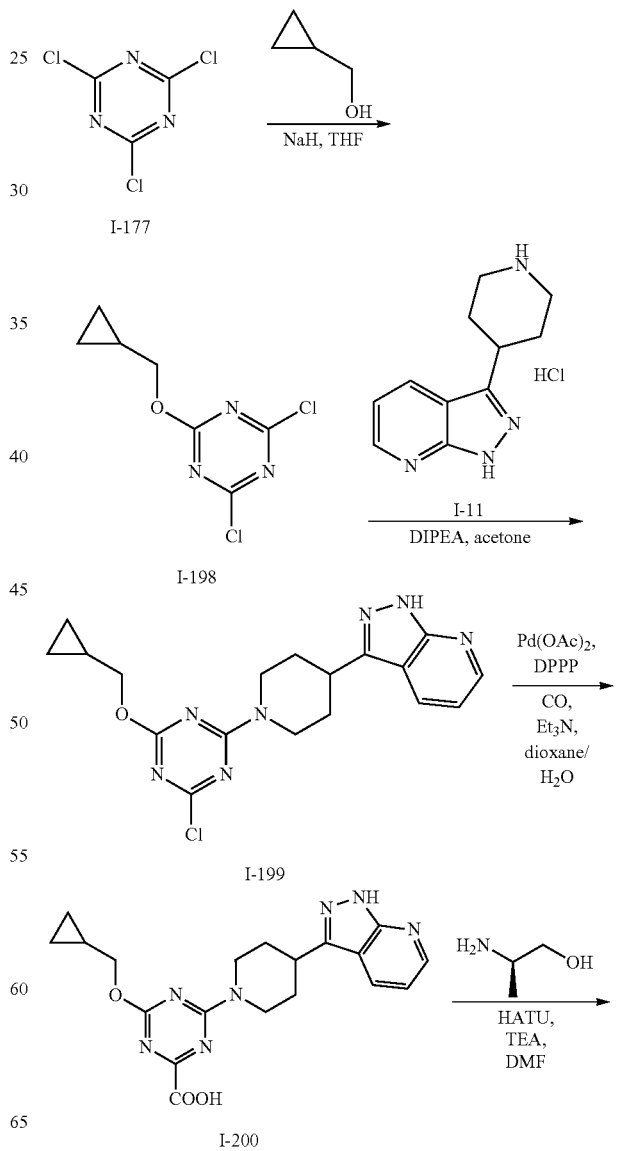

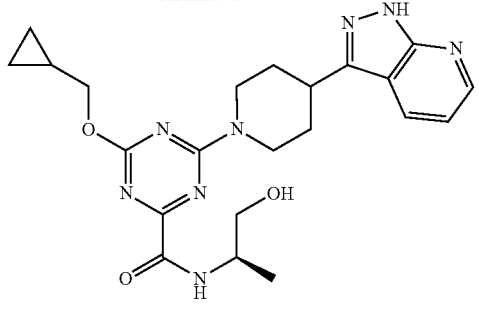

Example 107

Step 1—Synthesis of 2,4-dichloro-6-(cyclopropylmethoxy)-1,3,5-triazine (I-198)

To a solution of cyclopropylmethanol (0.4 g, 5.55 mmol) in anhydrous THF (30 mL) was added NaH (0.266 g, 60% in mineral oil, 6.66 mmol) at 0° C. The resulting mixture was stirred at room temperature for 30 min. The mixture was then cooled to 0° C. and cyanuric chloride (I-177) (0.93 g, 5.05 mmol) was added. The resulting mixture was stirred at room temperature for 12 hr. The mixture was quenched with ice-water (5 mL) and then extracted with EtOAc (3×10 mL). The organic layers were combined, washed with H$_2$O (5 mL), brine (5 mL), dried over Na$_2$SO$_4$ and concentrated in vacuo to give the crude product. The crude product was purified by column chromatography on silica gel (petroleum ether/EtOAc=10:1, R$_f$=0.7) to afford 2,4-dichloro-6-(cyclopropylmethoxy)-1,3,5-triazine (I-198) (0.5 g, 45%) as colorless oil, which was used without further purification.

Step 2—Synthesis of 3-{1-[4-chloro-6-(cyclopropylmethoxy)-1,3,5-triazin-2-yl]piperidin-4-yl}-1H-pyrazolo[3,4-b]pyridine (I-199)

To a mixture of 2,4-dichloro-6-(cyclopropylmethoxy)-1,3,5-triazine (I-198) (0.9 g, 4.091 mmol) and 3-(piperidin-4-yl)-1H-pyrazolo[3,4-b]pyridine hydrochloride (I-11) (0.906 g, 3.409 mmol) in acetone (60 mL) was added DIPEA (1.266 g, 1.71 mmol) at room temperature. The resulting mixture was stirred at −20° C. for 1 hr. TLC (petroleum ether/EtOAc=2:1, R$_f$=0.7) showed the reaction was complete. The mixture was concentrated in vacuo to give the crude product, which was purified by column chromatography on silica gel, (petroleum ether/EtOAc=2:1) to obtain 3-{1-[4-chloro-6-(cyclopropylmethoxy)-1,3,5-triazin-2-yl]piperidin-4-yl}-1H-pyrazolo[3,4-b]pyridine (I-199) (0.9 g, 68%) as a yellow solid, which was used without further purification.

Step 3—Synthesis of 4-(cyclopropylmethoxy)-6-[4-(1H-pyrazolo[3,4-b]pyridin-3-yl)piperidin-1-yl]-1,3,5-triazine-2-carboxylic acid (I-200)

To a mixture of 3-{1-[4-chloro-6-(cyclopropylmethoxy)-1,3,5-triazin-2-yl]piperidin-4-yl}-1H-pyrazolo[3,4-b]pyridine (I-199) (0.3 g, 0.779 mmol), DPPP (64 mg, 0.156 mmol) and Et$_3$N (0.393 g, 0.5 ml) in dioxane (45 mL) and H$_2$O (15 mL) was added Pd(OAc)$_2$ (17.5 mg, 0.0779 mmol) at room temperature. The resulting mixture was purged with CO three times and then heated at 80° C. under CO pressure (2.5 MPa) for 24 hr. TLC (petroleum ether/EtOAc=2:1) showed the reaction was complete. The mixture was diluted with EtOAc (50 mL). The organic layer was separated and the aqueous layer was extracted with EtOAc (2×10 mL). The organic layers were combined, washed with brine (10 mL), dried over Na$_2$SO$_4$, filtered and concentrated in vacuo to give the crude product. The crude product was purified by column chromatography on silica gel (petroleum ether/EtOAc=2:1 to CH$_2$Cl$_2$/MeOH=10:1, R$_f$=0.1 in CH$_2$Cl$_2$/MeOH=10:1) to obtain 4-(cyclopropylmethoxy)-6-[4-(1H-pyrazolo[3,4-b]pyridin-3-yl)piperidin-1-yl]-1,3,5-triazine-2-carboxylic acid (I-200) (0.28 g, 91%) as a yellow solid. $^1$H NMR (400 MHz, DMSO-d$_6$) δ ppm 13.28 (br. s., 1 H), 8.43 (s, 1 H), 8.31-8.32 (m, 1 H), 7.08-7.10 (m, 1 H), 4.61-4.72 (m, 2 H), 4.03-4.05 (m, 2 H), 2.93-2.96 (m, 4 H), 2.02-2.11 (m, 2 H), 1.71-1.80 (m, 2 H), 0.51-0.55 (m, 2 H), 0.31-0.33 (m, 2 H).

Step 4—Synthesis of 4-(cyclopropylmethoxy)-N-[(2R)-1-hydroxypropan-2-yl]-6-[4-(1H-pyrazolo[3,4-b]pyridin-3-yl)piperidin-1-yl]-1,3,5-triazine-2-carboxamide (Example 107)

To a mixture of 4-(cyclopropylmethoxy)-6-[4-(1H-pyrazolo[3,4-b]pyridin-3-yl)piperidin-1-yl]-1,3,5-triazine-2-carboxylic acid (I-200) (0.25 g, 0.634 mmol), (2R)-2-aminopropan-1-ol (0.057 g, 0.76 mmol) and HATU (0.28 g, 0.75 mmol) in DMF (10 mL) was added TEA (0.192 g, 0.26 mL) at 10° C. The resulting mixture was stirred at room temperature for 12 hr. LCMS showed the reaction was complete. The mixture was diluted with EtOAc (30 mL) and H$_2$O (20 mL). The organic layer was separated and the aqueous layer was extracted with EtOAc (2×10 mL). The organic layers were combined, washed with H$_2$O (3×8 mL), brine (8 mL), dried over Na$_2$SO$_4$, filtered and concentrated in vacuo to give the crude product. The crude product was purified by preparative TLC (CH$_2$Cl$_2$/MeOH=10:1, R$_f$=0.4) to afford 4-(cyclopropylmethoxy)-N-[(2R)-1-hydroxypropan-2-yl]-6-[4-(1H-pyrazolo[3,4-b]pyridin-3-yl)piperidin-1-yl]-1,3,5-triazine-2-carboxamide (Example 107) (25.5 mg, 9%) as a white solid. LCMS (APCI), m/z 453.1 [M+H]$^+$;

$^1$H NMR (400 MHz, DMSO-d$_6$) δ ppm 13.35 (s, 1 H), 8.47-8.48 (m, 1 H), 8.30-8.34 (m, 2 H), 7.12-7.15 (m, 1 H), 4.86-4.90 (m, 2 H), 4.72-4.75 (m, 1 H), 4.18-4.19 (m, 2 H), 3.85-3.95 (m, 2 H), 3.40-3.44 (m, 2 H), 3.21-3.23 (m, 2 H), 2.10-2.14 (m, 2 H), 1.80-1.83 (m, 2 H), 1.23-1.25 (m, 2 H), 1.11-1.13 (m, 3 H), 0.54-0.57 (m, 2 H), 0.33-0.37 (m, 2 H).

Example 108 (Scheme G)

Synthesis of N-cyclobutyl-4-{[(2R)-1-methoxypropan-2-yl]oxy}-6-[4-(1H-pyrazolo[3,4-b]pyridin-3-yl)piperidin-1-yl]pyrimidine-2-carboxamide

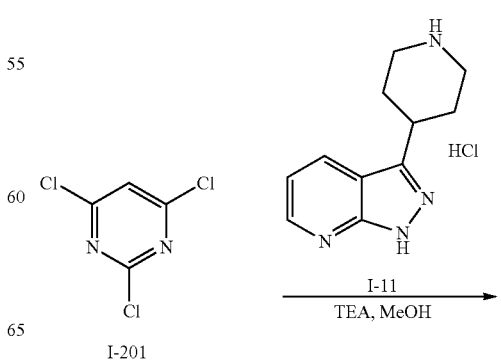

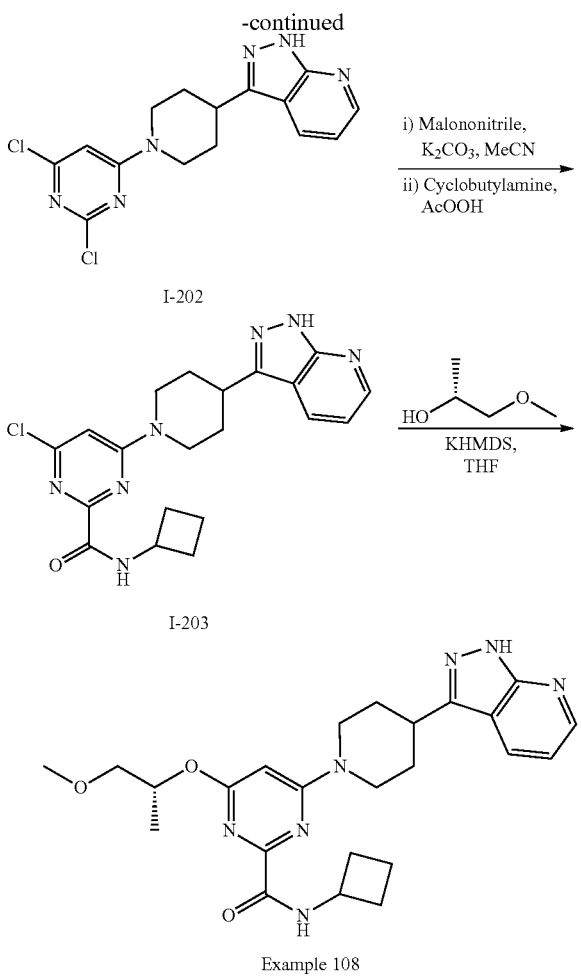

Example 108

Step 1—Synthesis of 3-[1-(2,6-dichloropyrimidin-4-yl)piperidin-4-yl]-1H-pyrazolo[3,4-b]pyridine (I-202)

To a mixture of 2,4,6-trichloropyrimidine (I-201) (750 mg, 4.09 mmol) and 3-(piperidin-4-yl)-1H-pyrazolo[3,4-b]pyridine hydrochloride (I-11) (1.12 g, 4.70 mmol) in MeOH (40.9 mL) was added TEA (2.07 g, 2.85 mL, 20.4 mmol). The reaction mixture was allowed to stir at room temperature for 4 hr. The solvents were removed in vacuo, and the residue slurried in 25% MeOH/H$_2$O. The solids were collected by filtration, and allowed to dry in the vacuum oven overnight to afford 3-[1-(2,6-dichloropyrimidin-4-yl)piperidin-4-yl]-1H-pyrazolo[3,4-b]pyridine (I-202) (1.28 g, 90%) as a brown solid. NMR indicated that this was a 3.2:1 ratio of regioisomers in favor of the desired material, and this was used in the next step without further purification. LCMS (APCI), m/z 349.1 [M+H]$^+$,

Step 2—Synthesis of 4-chloro-N-cyclobutyl-6-[4-(1H-pyrazolo[3,4-b]pyridin-3-yl)piperidin-1-yl]pyrimidine-2-carboxamide (I-203)

To a solution of malononitrile (170 mg, 2.58 mmol) in MeCN (4.3 mL) was added K$_2$CO$_3$ (712 mg, 5.15 mmol). Then, a mixture of the 3-[1-(2,6-dichloropyrimidin-4-yl)piperidin-4-yl]-1H-pyrazolo[3,4-b]pyridine (I-202) (3:1 mixture of regioisomers, 300 mg, 0.86 mmol) was added as a solution in DMSO (2.0 mL). The reaction mixture was heated to 50° C. for 18 hr. LCMS showed 3 peaks with the desired mass, and some starting material still remained. Malononitrile (57 mg, 0.86 mmol) and K$_2$CO$_3$ (237 mg, 1.72 mmol) was added, and the reaction heated to 60° C. for a further 4 hr. The reaction was a pretty thick mixture, and although the starting material had decreased, it could still be observed. MeCN (4 mL) and DMSO (4 ML) were added prior to adding cyclobutylamine hydrochloride (495 mg, 3.44 mmol) followed by the dropwise addition of peracetic acid (4.62 mL, 30% in AcOH, 6.87 mmol). Gas was evolved, and an exotherm was observed After ~30 min, LCMS showed the desired mass corresponding to the amide. The mixture was diluted with EtOAc (25 mL), washed with saturated NaHCO$_3$ (2×10 mL), saturated Na$_2$SO$_3$ (2×10 mL) and brine (10 mL). The organics were dried over MgSO$_4$, filtered and concentrated before being purified by silica gel chromatography (EtOAc/heptanes 0-100%) to afford 4-chloro-N-cyclobutyl-6-[4-(1H-pyrazolo[3,4-b]pyridin-3-yl)piperidin-1-yl]pyrimidine-2-carboxamide (I-203) (155 mg, 44%) as a colorless solid, and a single regioisomer. LCMS (APCI), m/z 412.1 [M+H]$^+$; $^1$H NMR (400 MHz, DMSO-d$_6$) δ ppm 13.26 (br. s., 1 H), 8.65 (d, J=7.6 Hz, 1 H), 8.48 (d, J=4.3 Hz, 1 H), 8.32 (d, J=7.8 Hz, 1 H), 7.14 (dd, J=8.1, 4.5 Hz, 1 H), 7.10 (s, 1 H), 4.56 (br. s., 2 H), 4.30-4.43 (m, 1 H), 3.44 (t, J=11.0 Hz, 1 H), 3.13-3.25 (m, 2 H), 2.05-2.24 (m, 6 H), 1.84 (dq, J=12.3, 3.3 Hz, 2 H), 1.57-1.71 (m, 2 H).

Step 3—Synthesis of N-cyclobutyl-4-{[(2R)-1-methoxypropan-2-yl]oxy}-6-[4-(1H-pyrazolo[3,4-b]pyridin-3-yl)piperidin-1-yl]pyrimidine-2-carboxamide (Example 108)

To a solution of 4-chloro-N-cyclobutyl-6-[4-(1H-pyrazolo[3,4-b]pyridin-3-yl)piperidin-1-yl]pyrimidine-2-carboxamide (I-203) (50 mg, 0.12 mmol) in THF (3 mL) was added (2R)-1-methoxypropan-2-ol (32.7 mg, 0.36 mmol) in THF (1 mL) followed by the portionwise addition of solid KHMDS (121 mg, 0.61 mmol) over 5 min. Upon completion of the addition, the reaction was heated to 50° C. for 18 hr. The reaction was diluted with EtOAc (10 mL), washed with saturated NH$_4$Cl solution (2×5 mL), brine (5 mL), and dried over MgSO$_4$. The reaction was filtered, concentrated, and the residue purified by SFC (ZymorSPHER HADP column 150×4.6 mm, 10-50% MeOH, 160 bar, 4.5 mL/min) to afford N-cyclobutyl-4-{[(2R)-1-methoxypropan-2-yl]oxy}-6-[4-(1H-pyrazolo[3,4-b]pyridin-3-yl)piperidin-1-yl]pyrimidine-2-carboxamide (Example 108) (5 mg, 9%) as a white solid. LCMS (APCI), m/z 466.3 [M+H]$^+$; $^1$H NMR (600 MHz, DMSO-d$_6$) δ ppm 8.56 (d, J=8.2 Hz, 1 H), 8.47 (dd, J=4.5, 1.0 Hz, 1 H), 8.30 (dd, J=8.0, 1.0 Hz, 1 H), 7.13 (dd, J=8.0, 4.5 Hz, 1 H), 6.17 (s, 1H), 5.42-5.51 (m, 1 H), 4.53 (br. s., 2 H), 4.37 (sxt, J=8.3 Hz, 1 H), 3.46-3.52 (m, 1 H), 3.34-3.46 (m, 2 H), 3.11 (t, J=11.9 Hz, 2 H), 2.55-2.52 (m, 3 H), 2.22-2.16 (m, 2 H), 2.13 (t, J=9.4 Hz, 2 H), 2.07 (d, J=11.4 Hz, 2 H), 1.74-1.86 (m, 2 H), 1.61-1.69 (m, 2 H), 1.23 (d, J=6.4 Hz, 3 H).

Example 110 (Scheme H)

Synthesis of N-(bicyclo[1.1.1]pent-1-yl)-4-{[(1S, 2R)-2-cyanocyclopropyl]methoxy}-6-[4-(1H-pyrazolo[3,4-b]pyridin-3-yl)piperidin-1-yl]pyrimidine-2-carboxamide

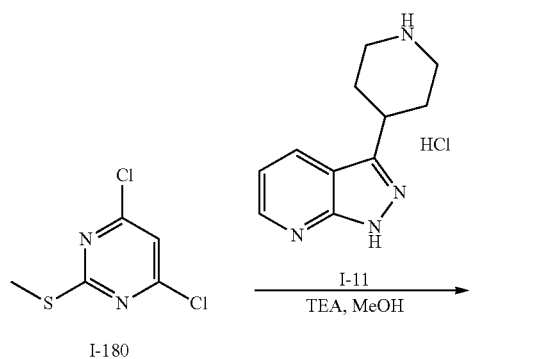

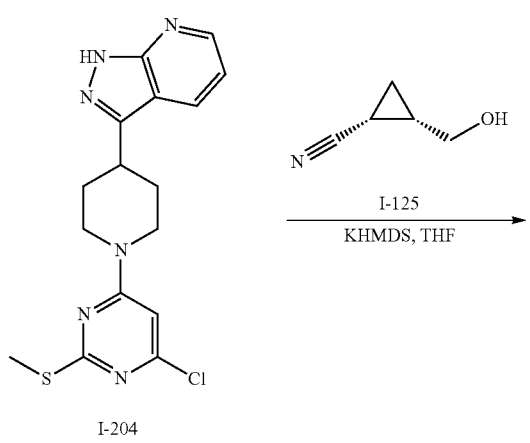

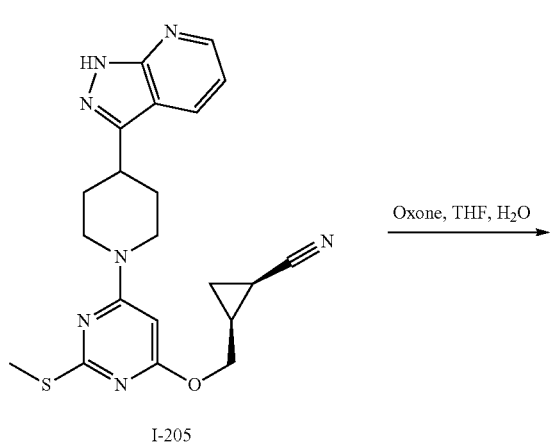

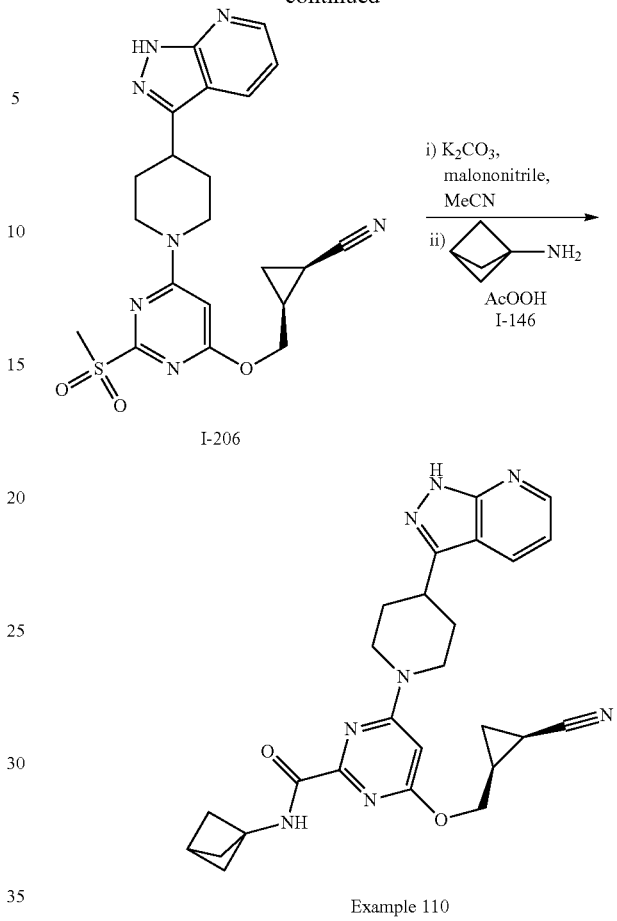

Example 110

Step 1—Synthesis of 3-{1-[6-chloro-2-(methylsulfanyl)pyrimidin-4-yl]piperidin-4-yl}-1H-pyrazolo[3,4-b]pyridine (I-204)

To a mixture of 4,6-dichloro-2-(methylsulfanyl)pyrimidine (I-180) (1.0 g, 5.1 mmol) and 3-(piperidin-4-yl)-1H-pyrazolo[3,4-b]pyridine hydrochloride (I-11) (1.41 g, 5.90 mmol, ground in a mortar and pestle) in MeOH (50.3 mL) was added TEA (3.57 mL, 25.6 mmol) to give a brown solution. The reaction was stirred for 18 h during which time a tan precipitate was observed to form. The reaction was diluted with EtOAc (200 mL), washed with water (100 mL), and saturated brine (100 mL). The combined aqueous extracts were washed with EtOAc (2×100 mL). The organics were dried over MgSO$_4$, filtered and concentrated to afford a tan solid, which was triturated with Et$_2$O/EtOAc. The solids were collected by filtration, and dried in a vacuum oven to afford 3-{1-[6-chloro-2-(methylsulfanyl)pyrimidin-4-yl]piperidin-4-yl}-1H-pyrazolo[3,4-b]pyridine (I-204) (1.59 g, 86%) as a tan solid. LCMS (APCI), m/z 361.2 [M+H]$^+$; $^1$H NMR (400 MHz, DMSO-d$_6$) δ ppm 13.25 (s, 1 H), 8.48 (dd, J=4.5, 1.5 Hz, 1 H), 8.31 (dd, J=8.1, 1.0 Hz, 1 H), 7.13 (dd, J=8.1, 4.3 Hz, 1 H), 6.73 (s, 1 H), 4.48 (br. s., 2 H), 3.35-3.47 (m, 1 H), 3.19 (t, J=11.5 Hz, 2 H), 2.44 (s, 3 H), 2.01-2.13 (m, 2 H), 1.70-1.88 (m, 2 H).

Step 2—Synthesis of (1R,2S)-2-[({2-(methylsulfanyl)-6-[4-(1H-pyrazolo[3,4-b]pyridin-3-yl)piperidin-1-yl]pyrimidin-4-yl}oxy)methyl]cyclopropanecarbonitrile (I-205)

To a mixture of 3-{1-[6-chloro-2-(methylsulfanyl)pyrimidin-4-yl]piperidin-4-yl}-1H-pyrazolo[3,4-b]pyridine (I-204) (750 mg, 2.08 mmol) in THF (20.8 mL) was added in a portionwise manner over 20 min solid KHMDS (1.45 g, 7.27 mmol) followed by (1R,2S)-2-(hydroxymethyl)cyclopropanecarbonitrile (I-125) (303 mg, 3.12 mmol). The reaction was heated to 50° C. for 18 hr. Analysis of the reaction proved difficult due to co-elution of the starting material and product on LCMS. The reaction mixture was neutralized with 1 N HCl, diluted with EtOAc (150 mL), and washed with brine (75 mL). The organic extracts were dried over MgSO$_4$, filtered and concentrated to afford a residue, which was purified by chromatography over silica gel eluting with 0-100% EtOAc/heptanes to afford recovered starting material (204 mg), and (1R,2S)-2-[({2-(methylsulfanyl)-6-[4-(1H-pyrazolo[3,4-b]pyridin-3-yl)piperidin-1-yl]pyrimidin-4-yl}oxy)methyl]cyclopropane carbonitrile (I-205) (383 mg, 44%) as a colorless solid. LCMS (APCI), m/z 422.1 [M+H]$^+$; $^1$H NMR (400 MHz, DMSO-d$_6$) δ ppm 13.25 (s, 1 H), 8.48 (dd, J=4.5, 1.3 Hz, 1 H), 8.30 (dd, J=8.1, 1.3 Hz, 1 H), 7.14 (dd, J=8.1, 4.3 Hz, 1 H), 5.93 (s, 1 H), 4.58 (dd, J=11.8, 5.5 Hz, 1 H), 4.44 (d, J=13.1 Hz, 2 H), 4.04 (dd, J=11.7, 8.9 Hz, 1 H), 3.39 (tdd, J=11.6, 7.7, 3.8 Hz, 1 H), 3.12 (t, J=11.6 Hz, 2 H), 2.45 (s, 3 H), 2.06 (d, J=10.8 Hz, 2 H), 1.96 (dt, J=8.2, 5.5 Hz, 1 H), 1.70-1.90 (m, 3 H), 1.27 (dt, J=8.5, 4.9 Hz, 1 H), 1.07-1.17 (m, 1 H).

Step 3—Synthesis of (1R,2S)-2-[({2-(methylsulfonyl)-6-[4-(1H-pyrazolo[3,4-b]pyridin-3-yl)piperidin-1-yl]pyrimidin-4-yl}oxy)methyl]cyclopropanecarbonitrile (I-206)

To a cooled solution of (1R,2S)-2-[({2-(methylsulfanyl)-6-[4-(1H-pyrazolo[3,4-b]pyridin-3-yl)piperidin-1-yl]pyrimidin-4-yl}oxy)methyl]cyclopropane carbonitrile (I-205) (200 mg, 0.474 mmol) in THF (3.2 mL) was added conc. HCl (45.6 µL, 0.474 mmol) followed by a mixture of oxone (589 mg, 0.948 mmol) in water (3.2 mL). The reaction was stirred for 30 min at 0° C. after which LCMS indicated that the main peak was the sulfoxide. The reaction was stirred for a further hr at 0° C., and then allowed to warm to room temperature over 30 min. LCMS indicated that the desired sulfone was the major product though impurities such as the N-oxide and the chlorinated version of the product were forming. The reaction was diluted with EtOAc (50 mL), washed with water (25 mL), saturated Na$_2$SO$_3$ (25 mL), and brine (25 mL), dried (MgSO$_4$), filtered and concentrated to afford a residue, which was purified by chromatography over silica gel eluting with 0-100% EtOAc/heptanes to afford (1R,2S)-2-[({2-(methylsulfonyl)-6-[4-(1H-pyrazolo[3,4-b]pyridin-3-yl)piperidin-1-yl]pyrimidin-4-yl}oxy)methyl]cyclopropane carbonitrile (I-206) (92 mg, 43%) as a colorless solid. LCMS (APCI), m/z 454.1 [M+H]$^+$; $^1$H NMR (400 MHz, DMSO-d$_6$) δ ppm 13.26 (s, 1 H), 8.48 (dd, J=4.5, 1.5 Hz, 1 H), 8.32 (dd, J=8.0, 1.4 Hz, 1 H), 7.14 (dd, J=8.0, 4.5 Hz, 1 H), 6.42 (s, 1 H), 4.65 (dd, J=11.8, 5.6 Hz, 1 H), 4.49 (d, J=12.7 Hz, 2 H), 4.11 (dd, J=11.7, 8.9 Hz, 1 H), 3.37-3.50 (m, 1 H), 3.31 (s, 3 H), 3.22 (t, J=11.9 Hz, 2 H), 2.10 (d, J=10.8 Hz, 2 H), 1.95-2.03 (m, 1 H), 1.73-1.93 (m, 3 H), 1.29 (dt, J=8.4, 5.0 Hz, 1 H), 1.13-1.19 (m, 1 H).

Step 4—Synthesis of N-(bicyclo[1.1.1]pent-1-yl)-4-{[(1S,2R)-2-cyanocyclopropyl]methoxy}-6-[4-(1H-pyrazolo[3,4-b]pyridin-3-yl)piperidin-1-yl]pyrimidine-2-carboxamide (Example 110)

A mixture of (1R,2S)-2-[({2-(methylsulfonyl)-6-[4-(1H-pyrazolo[3,4-b]pyridin-3-yl)piperidin-1-yl]pyrimidin-4-yl}oxy)methyl]cyclopropane carbonitrile (I-206) (48 mg, 0.11 mmol), malononitrile (21 mg, 0.318 mmol), K$_2$CO$_3$ (87.9 mg, 0.636 mmol) in MeCN (0.707 mL) was heated to 50° C. for 14 hr. LCMS indicated formation of the desired intermediate (M+H=440) as the major product. The reaction was allowed to cool to room temperature, and bicyclo[1.1.1]pentan-1-amine hydrochloride (I-146) (25.7 mg, 0.212 mmol) was added followed by the dropwise addition of peracetic acid (89.2 µL, 30% in acetic acid, 0.424 mmol) at room temperature. Gas evolution was observed, and the reaction allowed to stir for 4 hr. LCMS showed consumption of the intermediate, and appearance of the desired amide (M+H=485) as the major peak. The reaction was diluted with EtOAc (10 mL), washed with saturated NaHCO$_3$ (2×5 mL) and brine (5 mL), dried over MgSO$_4$, and concentrated to afford a residue which was purified by reverse phase HPLC to afford N-(bicyclo[1.1.1]pent-1-yl)-4-{[(1S,2R)-2-cyanocyclopropyl]methoxy}-6-[4-(1H-pyrazolo[3,4-b]pyridin-3-yl)piperidin-1-yl]pyrimidine-2-carboxamide (Example 110) (12.8 mg, 25%) as a colorless solid. LCMS (APCI), m/z 485.1 [M+H]$^+$; $^1$H NMR (600 MHz, DMSO-d$_6$) δ ppm 8.47 (dd, J=4.4, 1.5 Hz, 1 H), 8.30 (dd, J=8.0, 1.5 Hz, 1 H), 7.13 (dd, J=8.0, 4.4 Hz, 1 H), 6.27 (s, 1 H), 4.68 (dd, J=11.8, 5.5 Hz, 1 H), 4.55 (br. s., 2 H), 4.08 (dd, J=11.7, 9.1 Hz, 1 H), 3.12 (t, J=11.9 Hz, 2 H), 2.45 (s, 1 H), 2.07 (br. s., 9 H), 1.93-2.01 (m, 1 H), 1.74-1.89 (m, 3 H), 1.28 (dt, J=8.5, 5.0 Hz, 1 H), 1.13 (q, J=5.5 Hz, 1 H).

Example 117 (Scheme E)

Synthesis of 4-[4-({[2-amino-5-(1-methyl-1H-imidazol-4-yl)pyridin-3-yl]oxy}methyl)piperidin-1-yl]-N-(bicyclo[1.1.1]pent-1-yl)-6-[(1-cyanocyclopropyl)methoxy]-1,3,5-triazine-2-carboxamide

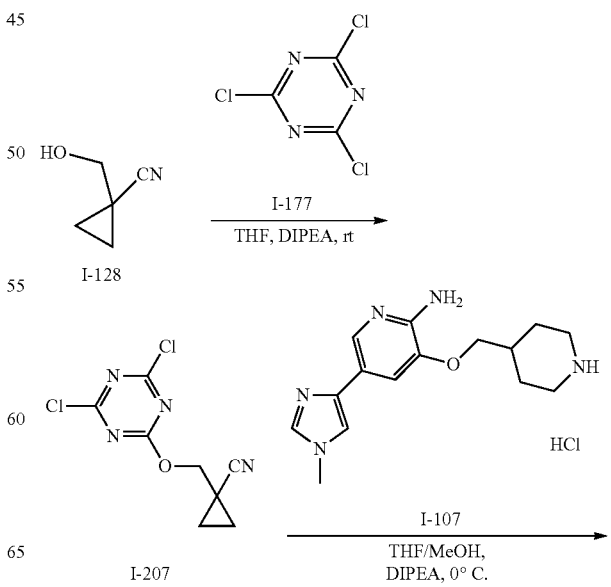

-continued

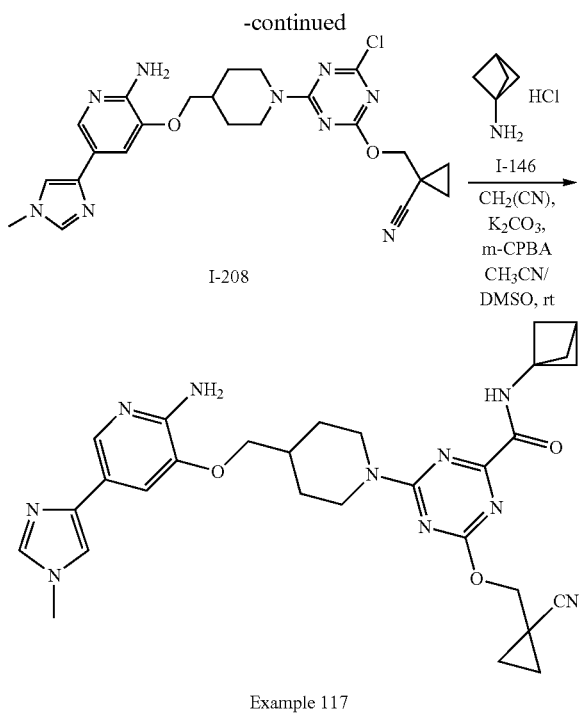

Step 1—Synthesis of 1-{[(4,6-dichloro-1,3,5-tri-azin-2-yl)oxy]methyl}cyclopropanecarbonitrile (I-207)

To a solution of cyanuric chloride (I-177) (7.43 g, 46.40 mmol), DIPEA (26.47 mL, 37.12 mmol) in THF (120 mL) at 0° C. was added over 2 hr in a dropwise manner a solution of 1-(hydroxymethyl)cyclopropanecarbonitrile (I-128) (3.0 g, 30.93 mmol) in THF (30 mL). The mixture was stirred at room temperature overnight. TLC (petroleum ether: EtOAc=1:1) showed the reaction was complete. The mixture was filtered and concentrated. The residue was purified by silica gel chromatography (petroleum ether:EtOAc=4:1 to 2:1) to give ~72% pure 1-{[(4,6-dichloro-1,3,5-triazin-2-yl)oxy]methyl}cyclopropane carbonitrile (I-207) (4.16 g, 55%) as white solid, which was used without further purification.

Step 2—Synthesis of 1-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-208)

To a solution of 1-{[(4,6-dichloro-1,3,5-triazin-2-yl)oxy]methyl}cyclopropanecarbonitrile (I-207) (420 mg, 72% of purity, 1.24 mmol) and 5-(1-methyl-1H-imidazol-4-yl)-3-(piperidin-4-ylmethoxy)pyridin-2-amine hydrochloride (I-107) (496 mg, 1.24 mmol) in THF (15 mL) and MeOH (5 mL) at 0° C. was added DIPEA (959 mg, 7.44 mmol). The mixture was stirred at 0° C. for 30 min. TLC (CH$_2$Cl$_2$: methanol=15:1) showed the reaction was complete. The solvent was evaporated. The residue was purified by silica gel chromatography (CH$_2$Cl$_2$:MeOH=25:2) to give 1-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-208) (400 mg, 65%) as a gray solid.

Step 3—Synthesis of 4-[4-({[2-amino-5-(1-methyl-1H-imidazol-4-yl)pyridin-3-yl]oxy}methyl)piperidin-1-yl]-N-(bicyclo[1.1.1]pent-1-yl)-6-[(1-cyanocyclopropyl)methoxy]-1,3,5-triazine-2-carboxamide (Example 117)

To a solution of malononitrile (27 mg 0.4 mmol) in MeCN (6 mL) was added K$_2$CO$_3$ (167 mg, 1.2 mmol), and the resulting mixture was stirred at room temperature for one hr. 1-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-208) (100 mg, 0.2 mmol) in DMSO (3 mL) was added, and the resulting mixture was stirred at room temperature for 16 hr. LCMS showed the starting material had been converted into the intermediate resulting from malononitrile displacement of the chloride. The mixture was cooled with an ice bath, and bicyclo[1.1.1]pentan-1-amine hydrochloride (I-146) (97.2 mg, 0.8 mmol) was added followed by m-CPBA (345 mg, 2 mmol) and MeCN (2 mL). The resulting mixture was stirred at room temperature for 2 hr. LCMS showed the reaction was complete. The reaction mixture was filtered and concentrated. The residue was purified by preparative HPLC to give after lyophilization 4-[4-({[2-amino-5-(1-methyl-1H-imidazol-4-yl)pyridin-3-yl]oxy}methyl)piperidin-1-yl]-N-(bicyclo[1.1.1]pent-1-yl)-6-[(1-cyanocyclopropyl)methoxy]-1,3,5-triazine-2-carboxamide (Example 117) (17.3 mg, 15%) as a yellow solid. LCMS (ESI), m/z 533.1 [M+H]$^+$; (400 MHz, CD$_3$OD) δ ppm 7.88 (s, 1 H), 7.74 (s, 1 H), 7.50 (s, 1 H), 7.44 (s, 1 H), 5.10-5.11 (br. s., 1 H), 4.44-4.50 (m, 2 H), 4.03-4.05 (m, 2 H), 3.78 (s, 3 H), 3.10-3.12 (m, 2 H), 2.50 (s, 1 H), 2.00-2.30 (m, 10 H), 1.35-1.45 (m, 4 H), 1.24 (s, 2 H).

Example 119 (Scheme E)

Synthesis of N-(bicyclo[1.1.1]pent-1-yl)-4-[(1-cyanocyclopropyl)methoxy]-6-[4-(1H-pyrazolo[3,4-d]pyrimidin-3-yl)piperidin-1-yl]-1,3,5-triazine-2-carboxamide

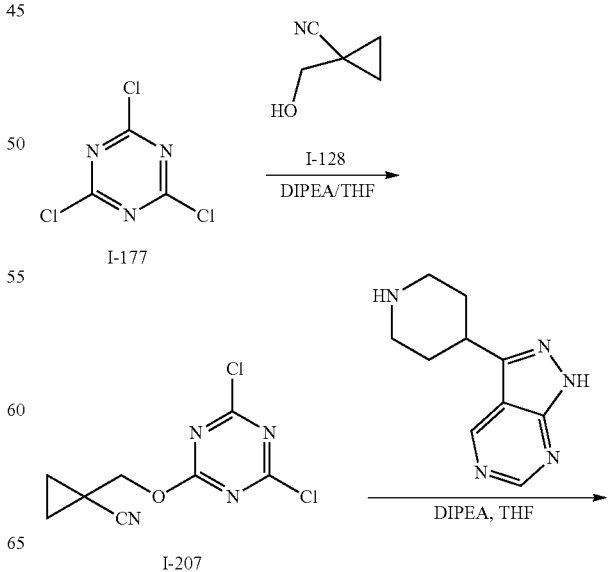

159

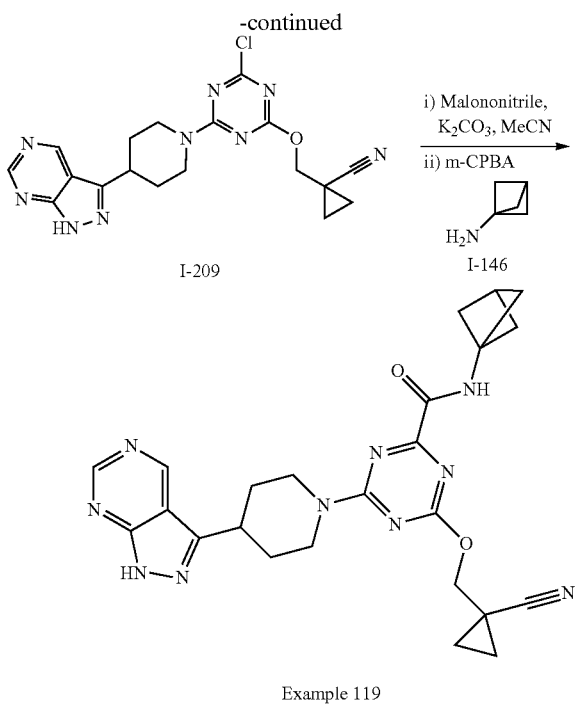

Example 119

Step 1—Synthesis of 1-{[(4,6-dichloro-1,3,5-triazin-2-yl)oxy]methyl}cyclopropanecarbonitrile (I-207)

To a solution of cyanuric chloride (I-177) (1 g, 5.5 mmol) and DIPEA (0.8 g, 6 mmol) in dry THF (20 mL) was added 1-(hydroxymethyl)cyclopropanecarbonitrile (I-128) (0.5 g, 5.5 mmol) at ice-bath temperature. The resulting mixture was stirred at room temperature for 14 hr. Two main spots were detected by TLC (petroleum ether/EtOAc 1:1). The reaction mixture was concentrated in vacuo. The residue was purified by silica gel chromatography (petroleum ether/EtOAc 1:1 $R_f$~0.4) to give 1-{[(4,6-dichloro-1,3,5-triazin-2-yl)oxy]methyl}cyclopropanecarbonitrile (I-207) (0.5 g, 40%) as colorless oil, which was used without further purification.

Step 2—Synthesis of 1-[({4-chloro-6-[4-(1H-pyrazolo[3,4-d]pyrimidin-3-yl)piperidin-1-yl]-1,3,5-triazin-2-yl}oxy)methyl]cyclopropanecarbonitrile (I-209)

To a solution of 1-{[(4,6-dichloro-1,3,5-triazin-2-yl)oxy]methyl}cyclopropanecarbonitrile (I-207) (0.2 g, 0.82 mmol), 3-(piperidin-4-yl)-1H-pyrazolo[3,4-d]pyrimidine hydrochloride (0.2 g, 0.84 mmol. commercial Matrix Chemical) and DIPEA (0.4 mL, 2.3 mmol) in THF (15 mL) cooled in an ice-bath was added MeOH (5 mL). After addition, the reaction mixture was stirred at the room temperature for ~30 min. TLC (EtOAc) showed the reaction was complete. The reaction mixture was concentrated in vacuo to give a residue, which was purified by silica gel chromatography (EtOAc $R_f$~0.5) to give 1-({4-chloro-6-[4-(1H-pyrazolo[3,4-d]pyrimidin-3-yl)piperidin-1-yl]-1,3,5-triazin-2-yl}oxy)methyl]cyclopropane carbonitrile (I-209) (0.3 g, 90%) as a white solid, which was used without further purification.

160

Step 3—Synthesis of N-(bicyclo[1.1.1]pent-1-yl)-4-[(1-cyanocyclopropyl)methoxy]-6-[4-(1H-pyrazolo[3,4-d]pyrimidin-3-yl)piperidin-1-yl]-1,3,5-triazine-2-carboxamide (Example 119)

To a solution of malononitrile (30 mg, 0.45 mmol) in MeCN (5 mL) was added $K_2CO_3$ (0.19 g, 1.4 mmol) and the reaction was then stirred at room temperature for 1 hr. Then 1-[({4-chloro-6-[4-(1H-pyrazolo[3,4-d]pyrimidin-3-yl)piperidin-1-yl]-1,3,5-triazin-2-yl}oxy)methyl]cyclopropanecarbonitrile (I-209) (80 mg, 0.19 mmol) was added to the above mixture, which was stirred at room temperature for a further 2 hr. The resulting mixture was cooled to 0-5° C., and bicyclo[1.1.1]pentan-1-amine (I-146) (100 mg, 0.84 mmol) and m-CPBA (0.2 g, 85%, 1 mmol) were added. After the addition, the resulting mixture was stirred at room temperature for 3 hr. The mixture was diluted with $H_2O$ (10 mL), and extracted with EtOAc (20 mL). The organic layer was dried over $Na_2SO_4$ and concentrated in vacuo to give a residue, which was purified preparative HPLC to give N-(bicyclo[1.1.1]pent-1-yl)-4-[(1-cyanocyclopropyl)methoxy]-6-[4-(1H-pyrazolo[3,4-d]pyrimidin-3-yl) piperidin-1-yl]-1,3,5-triazine-2-carboxamide (Example 119) (20 mg, 21%) as an off-white solid. LCMS (APCI), m/z 487.2 [M+H]$^+$; $^1$H NMR (400 MHz, $CD_3OD$) δ ppm 9.38 (s, 1 H), 8.93 (s, 1 H), 5.13-5.16 (m, 1 H), 4.45-4.63 (m, 3 H), 3.57-3.60 (m, 1 H), 3.20-3.23 (m, 1 H), 2.50 (s, 1 H), 2.21-2.28 (m, 8 H), 2.00-2.03 (m, 2 H), 1.38-1.41 (m, 2 H), 1.25-1.28 (m, 3 H).

Example 121 (Scheme E)

Synthesis of N-(bicyclo[1.1.1]pent-1-yl)-4-{[(1S,2R)-2-cyanocyclopropyl]methoxy}-6-[4-(5H-pyrrolo[2,3-b]pyrazin-7-yl)piperidin-1-yl]-1,3,5-triazine-2-carboxamide

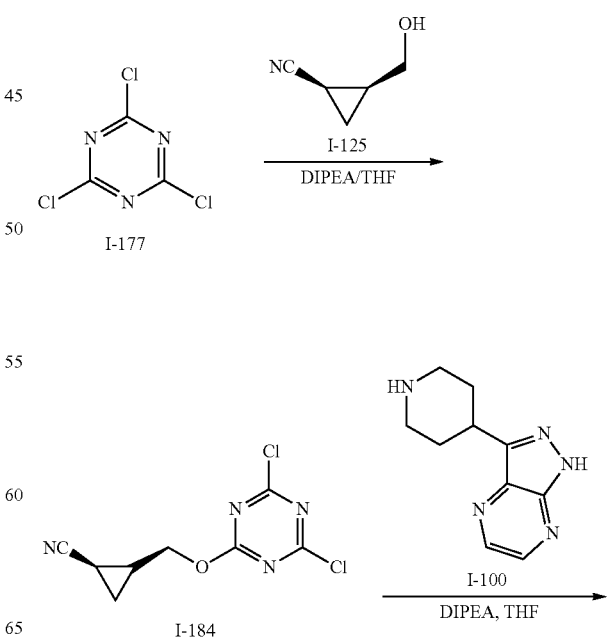

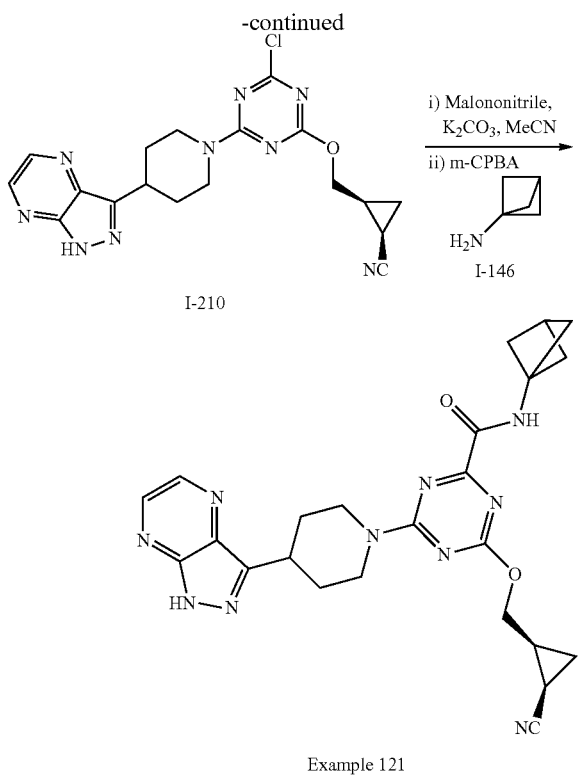

I-210

Example 121

Step 1—Synthesis of (1R,2S)-2-{[(4,6-dichloro-1,3,5-triazin-2-yl)oxy]methyl}cyclopropanecarbonitrile (I-184)

To a solution of cyanuric chloride (I-177) (5.3 g, 29 mmol) and (1R,2S)-2-(hydroxymethyl)cyclopropanecarbonitrile (I-125) (2.8 g, 29 mmol) in dry THF (40 mL) cooled in an ice-bath was added DIPEA (5 g, 36 mmol. The resulting mixture was stirred at room temperature for 14 hr. Two main spots were detected by TLC (petroleum ether/EtOAc 3:1). The reaction mixture was concentrated in vacuum. The residue was purified by silica gel chromatography (petroleum ether/EtOAc 3:1 $R_f$~0.3) to give (1R,2S)-2-{[(4,6-dichloro-1,3,5-triazin-2-yl)oxy]methyl}cyclopropanecarbonitrile (I-184) (4.8 g, 68%) as colorless oil, which was used without further purification.

Step 2—Synthesis of (1R,2S)-2-[({4-chloro-6-[4-(1H-pyrazolo[3,4-b]pyrazin-3-yl)piperidin-1-yl]-1,3,5-triazin-2-yl}oxy)methyl]cyclopropanecarbonitrile (I-210)

To a solution of (1R,2S)-2-{[(4,6-dichloro-1,3,5-triazin-2-yl)oxy]methyl}cyclopropanecarbonitrile (I-184) (0.2 g, 0.92 mmol), 3-(piperidin-4-yl)-1H-pyrazolo[3,4-b]pyrazine hydrochloride (I-100) (0.2 g, 0.84 mmol) and DIPEA (0.5 mL, 2.3 mmol) in THF (15 mL) cooled in an ice-bath was added MeOH (5 mL). After addition the reaction mixture was stirred at the temperature for ~30 min. TLC (EtOAc) showed the reaction was complete. The reaction mixture was concentrated in vacuo to give residue, which was purified by silica gel chromatography (EtOAc Rf~0.6) to give (1R,2S)-2-[({4-chloro-6-[4-(1H-pyrazolo[3,4-b]pyrazin-3-yl)piperidin-1-yl]-1,3,5- triazin-2-yl}oxy)methyl]cyclopropanecarbonitrile (I-210) (0.2 g, 58%) as a white solid, which was used without further purification.

Step 3—Synthesis of N-(bicyclo[1.1.1]pent-1-yl)-4-{[(1S,2R)-2-cyanocyclopropyl]methoxy}-6-[4-(5H-pyrrolo[2,3-b]pyrazin-7-yl)piperidin-1-yl]-1,3,5-triazine-2-carboxamide (Example 121)

To a solution of malononitrile (30 mg, 0.45 mmol) in MeCN (5 mL) was added K$_2$CO$_3$ (0.19 g, 1.4 mmol), and the reaction then stirred at room temperature for 1 hr. Then, (1R,2S)-2-[({4-chloro-6-[4-(1H-pyrazolo[3,4-b]pyrazin-3-yl)piperidin-1-yl]-1,3,5-triazin-2-yl}oxy)methyl]cyclopropanecarbonitrile (I-210) (80 mg, 0.19 mmol) and DMSO (1 mL) was added to the mixture, which was then stirred at room temperature for a further 2 hr. The resulting mixture was cooled to 0-5° C. and bicyclo[1.1.1]pentan-1-amine (I-146) (100 mg, 0.84 mmol) and m-CPBA (0.3 g, 85%, 1.5 mmol) were added. After the addition, the resulting mixture was stirred at room temperature for ~3 hr. The mixture was diluted with H$_2$O (10 mL) and extracted with EtOAc (20 mL). The organic layer was dried over Na$_2$SO$_4$ and concentrated in vacuo to give a residue, which was purified by preparative HPLC to give N-(bicyclo[1.1.1]pent-1-yl)-4-{[(1S,2R)-2-cyanocyclopropyl]methoxy}-6-[4-(5H-pyrrolo[2,3-b]pyrazin-7-yl)piperidin-1-yl]-1,3,5-triazine-2-carboxamide (Example 121) (25 mg, 27%) as an off-white solid. LCMS (APCI), m/z 486.2 [M+H]$^+$; $^1$H NMR (400 MHz, CD$_3$OD) δ ppm 8.35 (s, 1 H), 8.24 (s, 1 H), 7.61 (s, 1 H), 5.16-5.20 (m, 1 H), 4.56-4.62 (m, 2 H), 4.29-4.36 (m, 1 H), 3.19-3.25 (m, 1 H), 2.49 (s, 1 H), 1.95-2.21 (m, 8 H), 1.87-1.92 (m, 4 H), 1.34-1.37 (m, 2 H), 1.14-1.15 (m, 1 H).

Example 135 (Scheme E)

Synthesis of N-(bicyclo[1.1.1]pent-1-yl)-4-{[(1S,2R)-2-cyanocyclopropyl]methoxy}-6-[4-(4-methyl-1H-pyrazolo[3,4-b]pyridin-3-yl)piperidin-1-yl]-1,3,5-triazine-2-carboxamide

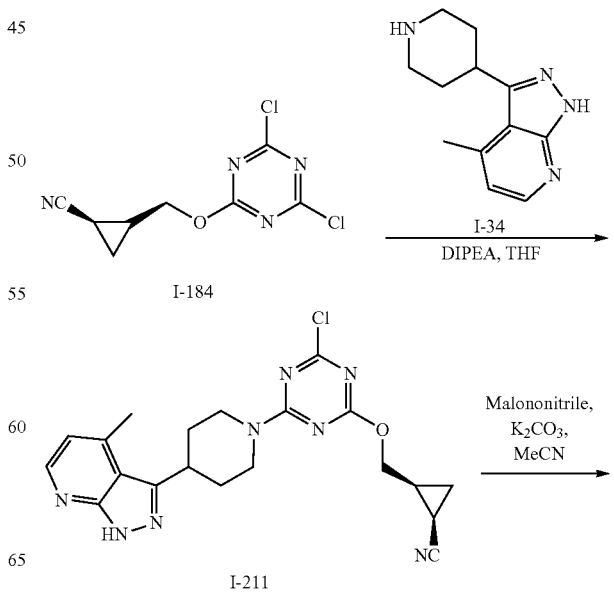

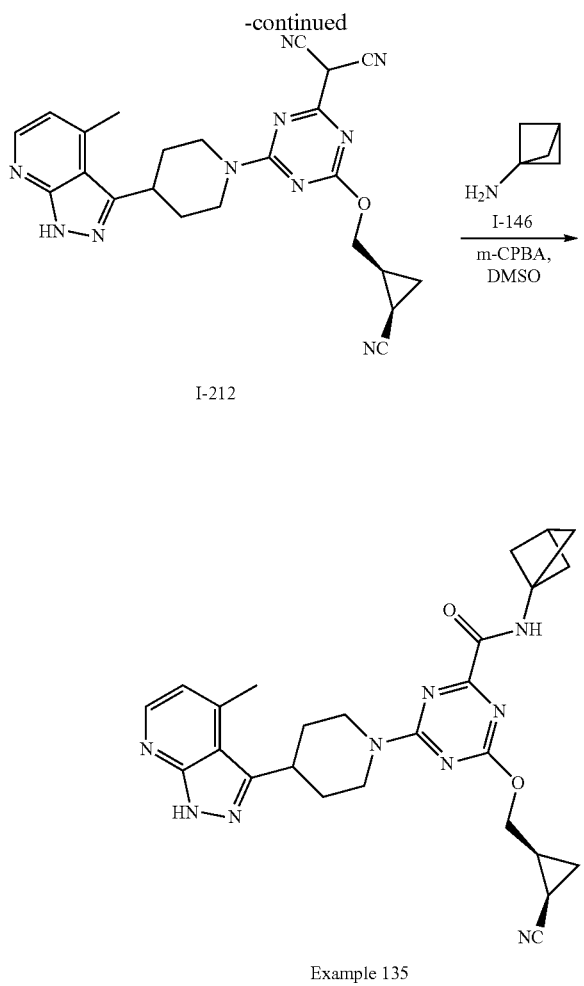

I-212

Example 135

Step 1—Synthesis of (1R,2S)-2-[({4-chloro-6-[4-(4-methyl-1H-pyrazolo[3,4-b]pyridin-3-yl)piperidin-1-yl]-1,3,5-triazin-2-yl}oxy)methyl]cyclopropanecarbonitrile (I-211)

To a mixture of (1R,2S)-2-{[(4,6-dichloro-1,3,5-triazin-2-yl)oxy]methyl}cyclopropanecarbonitrile (I-184) (424 mg, 1.73 mmol) and 4-methyl-3-(piperidin-4-yl)-1H-pyrazolo[3,4-b]pyridine hydrochloride (I-34) (500 mg, 1.73 mmol, 2 eq HCl)) in acetone (40 mL) was added DIPEA (1.12 g, 8.64 mmol) at −30° C. The resulting mixture was stirred at −30° C. for 2 hr. TLC (EtOAc, $R_f$=0.3) showed the reaction was complete. The mixture was concentrated in vacuo to give the crude product, which was purified by column chromatography (on silica gel, EtOAc/CH$_2$Cl$_2$=1:1) to give (1R,2S)-2-[({4-chloro-6-[4-(4-methyl-1H-pyrazolo[3,4-b]pyridin-3-yl)piperidin-1-yl]-1,3,5-triazin-2-yl}oxy)methyl]cyclopropanecarbonitrile (I-211) (0.7 g, 95%) as a white solid, which was used without further purification.

Step 2—Synthesis of (4-{[(1S,2R)-2-cyanocyclopropyl]methoxy}-6-[4-(4-methyl-1H-pyrazolo[3,4-b]pyridin-3-yl)piperidin-1-yl]-1,3,5-triazin-2-yl)propanedinitrile (I-212)

To a suspension of malononitrile (218 mg, 3.29 mmol) in MeCN (35 ml) was added K$_2$CO$_3$ (1.37 g, 9.88 mmol). The resulting mixture was stirred at room temperature for 1 hr. After 1 hr, (1R,2S)-2-[({4-chloro-6-[4-(4-methyl-1H-pyrazolo[3,4-b]pyridin-3-yl)piperidin-1-yl]-1,3,5-triazin-2-yl}oxy)methyl]cyclopropanecarbonitrile (I-211) (700 mg, 1.65 mmol) was added to the reaction. The resulting mixture was stirred at room temperature for 12 hr. LCMS showed ~55% amount of (1R,2S)-2-[({4-chloro-6-[4-(4-methyl-1H-pyrazolo[3,4-b]pyridin-3-yl)piperidin-1-yl]-1,3,5-triazin-2-yl}oxy)methyl]cyclopropanecarbonitrile still remained. DMSO (10 mL) was added, and the reaction stirred at room temperature for a further 5 hr. TLC (CH$_2$Cl$_2$/MeOH=10:1, $R_f$=0.3) showed most of (1R,2S)-2-[({4-chloro-6-[4-(4-methyl-1H-pyrazolo[3,4-b]pyridin-3-yl)piperidin-1-yl]-1,3,5-triazin-2-yl}oxy)methyl]cyclopropanecarbonitrile had been consumed. The mixture was filtered and washed with EtOAc (100 mL). The filtrate was concentrated in vacuo to give the crude product. The crude product was purified by column chromatography (on silica gel, CH$_2$Cl$_2$/MeOH=50:1~10:1) to give (4-{[(1S,2R)-2-cyanocyclopropyl]methoxy}-6-[4-(4-methyl-1H-pyrazolo[3,4-b]pyridin-3-yl)piperidin-1-yl]-1,3,5-triazin-2-yl)propanedinitrile (I-212) (710 mg, 93.5%) as a white solid, which was used without further purification. LCMS (APCI), m/z 455.1 [M+H]$^+$.

Step 3—Synthesis of N-(bicyclo[1.1.1]pent-1-yl)-4-{[(1S,2R)-2-cyanocyclopropyl]methoxy}-6-[4-(4-methyl-1H-pyrazolo[3,4-b]pyridin-3-yl)piperidin-1-yl]-1,3,5-triazine-2-carboxamide (Example 135)

To a solution of (4-{[(1S,2R)-2-cyanocyclopropyl]methoxy}-6-[4-(4-methyl-1H-pyrazolo[3,4-b]pyridin-3-yl)piperidin-1-yl]-1,3,5-triazin-2-yl)propanedinitrile (I-212) (400 mg, 1.54 mmol) in MeCN (25 mL) and DMSO (5 mL) was added m-CPBA (536 mg, 85%, 2.64 mmol) at 0° C. The resulting mixture was stirred at room temperature for 30 min. The mixture was then cooled to 0° C. and added bicyclo[1.1.1]pentan-1-amine hydrochloride (421 mg, 3.52 mmol) was added. The resulting mixture was stirred at room temperature for 18 hr. LCMS showed ~30% of (4-{[(1S,2R)-2-cyanocyclopropyl]methoxy}-6-[4-(4-methyl-1H-pyrazolo[3,4-b]pyridin-3-yl) piperidin-1-yl]-1,3,5-triazin-2-yl)propanedinitrile remained and m-CPBA (268 mg, 85%, 1.32 mmol) was added to the reaction mixture. The mixture was then stirred at room temperature for 4 hr. LCMS showed that the reaction was complete. To the mixture was added aqueous saturated NaHCO$_3$ (15 mL), and the reaction was then extracted with EtOAc (3×20 mL). The organic layer was separated, washed with brine (10 mL), dried over Na$_2$SO$_4$ and concentrated in vacuo to give the crude product, which was purified by preparative TLC (CH$_2$Cl$_2$/MeOH=10:1, $R_f$=0.5) to give N-(bicyclo[1.1.1]pent-1-yl)-4-{[(1S,2R)-2-cyanocyclopropyl]methoxy}-6-[4-(4-methyl-1H-pyrazolo[3,4-b]pyridin-3-yl)piperidin-1-yl]-1,3,5-triazine-2-carboxamide (Example 135) (46.6 mg 11%) as a white solid. LCMS (APCI), m/z 500.1 [M+H]$^+$; $^1$H NMR (400 MHz, CD$_3$OD) δ ppm 8.31 (d, J=4.8 Hz, 1 H), 6.98 (d, J=4.8 Hz, 1 H), 5.13-5.16 (m, 1 H), 4.88-4.93 (m, 1 H), 4.77-4.88 (m, 1 H), 4.28-4.31 (m, 1 H), 3.60-3.63 (m, 1 H), 3.24-3.31 (m, 2 H), 2.80 (s, 3 H), 2.48 (s, 1 H), 2.16-2.20 (m, 8 H), 1.85-1.94 (m, 4 H), 1.34-1.36 (m, 1 H), 1.12-1.13 (m, 1 H).

Example 136/137 (Scheme C)
Synthesis of 6-[(3R,4R)-4-{[(4-aminopyrimidin-5-yl)oxy]methyl}-3-fluoropiperidin-1-yl]-N-(bicyclo[1.1.1]pent-1-yl)-2-{[(1S,2R)-2-cyanocyclopropyl]methoxy}pyrimidine-4-carboxamide
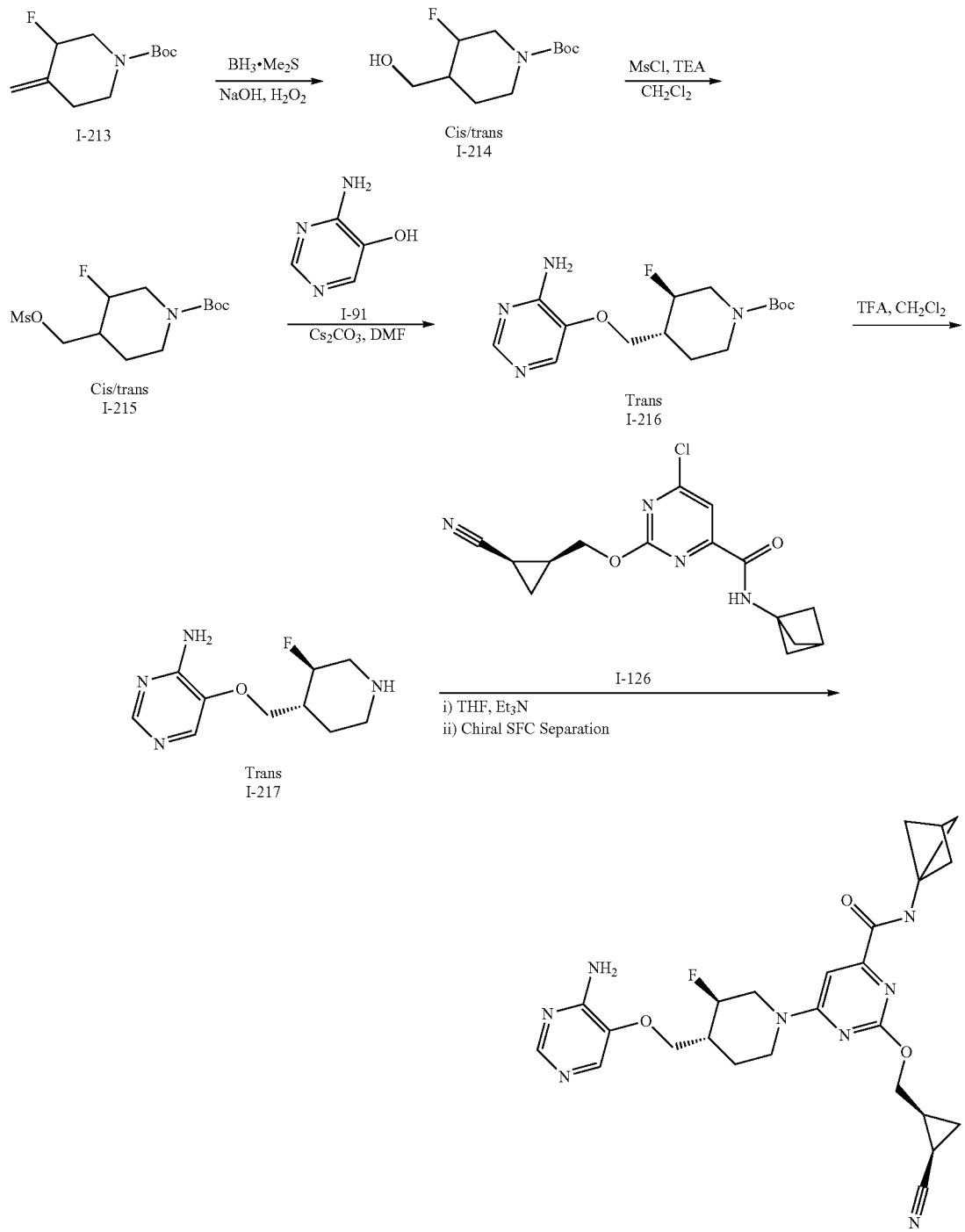
Example 136/137

Step 1—Synthesis of tert-butyl 3-fluoro-4-(hydroxymethyl)piperidine-1-carboxylate (I-214)

To a solution of tert-butyl 3-fluoro-4-methylidenepiperidine-1-carboxylate (I-213) (430 mg, 2 mmol) in dry THF (10 mL) at 0° C. was added $BH_3.Me_2S$ (0.3 mL, 10 M) in a dropwise manner. The mixture was stirred at 0° C. for 1 hr, and then stirred at room temperature overnight. The reaction mixture was cooled to 0° C. and then 1 N NaOH (3.4 mL, 3.4 mmol) and $H_2O_2$ (3 mL, 30%) were added in a dropwise manner. The mixture was stirred at 0° C. for 30 min. TLC ($CH_2Cl_2$:MeOH=20:1) showed there was two new spots. The mixture was stirred at room temperature for 2 hr. TLC ($CH_2Cl_2$:MeOH=20:1) was unchanged. $H_2O$ (30 mL) was added. The mixture was extracted with EtOAc (2×30 mL). The combined organic layers were washed with $H_2O$ (15 mL), brine (15 mL) dried over anhydrous $Na_2SO_4$ and concentrated to give the crude product. The residue was purified by silica gel chromatography ($CH_2Cl_2$:MeOH=100:1 to 50:1) to give a cis/trans mixture of tert-butyl 3-fluoro-4-(hydroxymethyl)piperidine-1-carboxylate (I-214) (320 mg, 69%) as a light yellow oil, which was used directly in the next step.

Step 2—Synthesis of tert-butyl 3-fluoro-4-{[(methylsulfonyl)oxy]methyl}piperidine-1-carboxylate (I-215)

To a solution of the cis/trans mixture of tert-butyl 3-fluoro-4-(hydroxymethyhpiperidine-1-carboxylate (I-214) (320 mg, 1.37 mmol) and TEA (278 mg, 2.74 mmol) in $CH_2Cl_2$ (10 mL) at 0° C. was added dropwise methanesulfonyl chloride (236 mg, 2.06 mmol). The mixture was stirred at 0° C. for 1 hr. TLC ($CH_2Cl_2$:MeOH=20:1) showed the reaction was complete. The mixture was diluted with $CH_2Cl_2$ (15 mL), washed with saturated aq. $NH_4Cl$ (15 mL), saturated aq. $NaHCO_3$ (15 mL), brine (10 mL), dried over anhydrous $Na_2SO_4$ and concentrated to give the cis/trans mixture of tert-butyl 3-fluoro-4-{[(methylsulfonyl)oxy]methyl}piperidine-1-carboxylate (I-215) (380 mg, 94%) as a light yellow oil, which was used without further purification.

Step 3—Synthesis of tert-butyl (trans)-4-{[(4-aminopyrimidin-5-yl)oxy]methyl}-3-fluoropiperidine-1-carboxylate (I-216)

A cis/trans mixture of tert-butyl 3-fluoro-4-{[(methylsulfonyl)oxy]methyl}piperidine-1-carboxylate (I-215) (320 mg, 1.03 mmol), 2-amino-3-hydroxypyrimidine (I-91) (114 mg, 1.03 mmol) and $Cs_2CO_3$ (670 mg, 2.06 mmol) in DMF (3 mL) was stirred at 100° C. for one hr. TLC ($CH_2Cl_2$:MeOH=10:1) showed the reaction was complete. The reaction mixture was filtered and concentrated to give the crude product. The residue was purified by silica gel chromatography ($CH_2Cl_2$:MeOH=50:1 to 10:1) to give a mixture of the trans and cis products. Then, the mixture was separated by preparative TLC ($CH_2Cl_2$:MeOH=10:1) to give tert-butyl (trans)-4-{[(4-aminopyrimidin-5-yl)oxy]methyl}-3-fluoropiperidine-1-carboxylate (I-216) (60 mg, 18%) as a white solid, and a single diastereomer.

Step 4—Synthesis of 5-{[(trans)-3-fluoropiperidin-4-yl]methoxy}pyrimidin-4-amine (I-217)

To a solution of tert-butyl (trans)-4-{[(4-aminopyrimidin-5-yl)oxy]methyl}-3-fluoropiperidine-1-carboxylate (I-216) (60 mg, 0.18 mmol) in $CH_2Cl_2$ (6 mL) at 0° C. was added TFA (2 mL). The mixture was stirred at room temperature for 2 hr. TLC ($CH_2Cl_2$:MeOH=10:1) showed the starting material had been consumed. The reaction mixture was concentrated to give 5-{[(trans)-3-fluoropiperidin-4-yl]methoxy}pyrimidin-4-amine (I-217) (60 mg, TFA salt) as a light yellow oil, which was used directly in the next step.

Step 5—Synthesis of 6-[(3R,4R)-4-{[(4-aminopyrimidin-5-yl)oxy]methyl}-3-fluoropiperidin-1-yl]-N-(bicyclo[1.1.1]pent-1-yl)-2-{[(1S,2R)-2-cyanocyclopropyl]methoxy}pyrimidine-4-carboxamide (Examples 136/137)

A mixture of 5-{[(trans)-3-fluoropiperidin-4-yl]methoxy}pyrimidin-4-amine (I-217) (60 mg, TFA salt, 0.18 mmol), N-(bicyclo[1.1.1]pent-1-yl)-6-chloro-2-{[(1S,2R)-2-cyanocyclopropyl]methoxy}pyrimidine-4-carboxamide (I-126) (63.5 mg, 0.199 mmol) and TEA (91.7 mg, 0.906 mmol) in THF (5 mL) was stirred at 40° C. for 2 hr. TLC ($CH_2Cl_2$:MeOH=10:1) showed the reaction was complete. The mixture was diluted with EtOAc (50 mL), washed with saturated aq. $NH_4Cl$ (25 mL), brine (25 mL), dried over anhydrous $Na_2SO_4$ and concentrated to give the crude product, which was purified by preparative TLC ($CH_2Cl_2$:MeOH=10:1) to give racemic 6-[(trans)-4-{[(4-aminopyrimidin-5-yl)oxy]methyl}-3-fluoropiperidin-1-yl]-N-(bicyclo[1.1.1]pent-1-yl)-2-{[(1S,2R)-2-cyanocyclopropyl]methoxy}pyrimidine-4-carboxamide (42 mg, 92% purity by HPLC) as a white solid.

This material was separated by SFC to afford both enantiomers. The analytical separation by SFC was performed using a Chiralpak OJ-3 column (4.6 mm×150 mm column, 5 micron particle size), which was eluted with 5-40% MeOH (w. 0.05% DEA) in $CO_2$ held at 120 bar. A flow rate of 4 mL/min gave $Rt_{(Peak\ 1)}$=1.62 min and $Rt_{(Peak\ 2)}$=1.94 min.

6-[(3R,4R)-4-{[(4-aminopyrimidin-5-yl)oxy]methyl}-3-fluoropiperidin-1-yl]-N-(bicyclo[1.1.1]pent-1-yl)-2-{[(1S,2R)-2-cyanocyclopropyl]methoxy}pyrimidine-4-carboxamide (Example 136) >99% ee (10.5 mg, 11%) as a white powder. LCMS (APCI), m/z 531.0 [M+Na]$^+$; $^1$H NMR (400 MHz, CDCl$_3$) δ ppm 8.26 (s, 1 H), 8.16 (s, 1 H), 7.90 (s, 1 H), 7.13 (s, 1 H), 5.13 (s, 2 H), 4.85-4.90 (m, 0.5 H), 4.52-4.57 (m, 1.5 H), 4.38-4.43 (m, 2 H), 4.18 (s, 2 H), 3.02-3.07 (m, 2 H), 2.49 (s, 2 H), 2.28-2.32 (m, 1 H), 2.18 (s, 6 H), 2.05-2.08 (m, 1 H), 1.84-1.86 (m, 1 H), 1.68-1.70 (m, 2 H), 1.57-1.59 (m, 1 H), 1.33-1.35 (m, 1 H), 1.13-1.15 (m, 1H).

6-[(3R,4R)-4-{[(4-aminopyrimidin-5-yl)oxy]methyl}-3-fluoropiperidin-1-yl]-N-(bicyclo[1.1.1]pent-1-yl)-2-{[(1S,2R)-2-cyanocyclopropyl]methoxy}pyrimidine-4-carboxamide (Example 137) >99% ee (9.7 mg, 10%) as a white powder. LCMS (APCI), m/z 509.2 [M+H]$^+$; $^1$H NMR (400 MHz, CDCl$_3$) δ ppm 8.26 (s, 1 H), 8.16 (s, 1 H), 7.90 (s, 1 H), 7.13 (s, 1 H), 5.13 (s, 2 H), 4.85-4.90 (m, 0.5 H), 4.52-4.57 (m, 1.5 H), 4.38-4.43 (m, 2 H), 4.18 (s, 2 H), 3.02-3.07 (m, 2 H), 2.49 (s, 2 H), 2.28-2.32 (m, 1 H), 2.18 (s, 6 H), 2.05-2.08 (m, 1 H), 1.84-1.86 (m, 1 H), 1.68-1.70 (m, 2 H), 1.57-1.59 (m, 1 H), 1.33-1.35 (m, 1 H), 1.13-1.15 (m, 1H).

Example 138 (Scheme A)

Synthesis of 6-[4-({[2-amino-5-(1-methyl-1H-1,2,3-triazol-4-yl)pyridin-3-yl]oxy}methyl)piperidin-1-yl]-N-ethyl-2-{[(2R)-1-methoxypropan-2-yl]oxy}pyrimidine-4-carboxamide

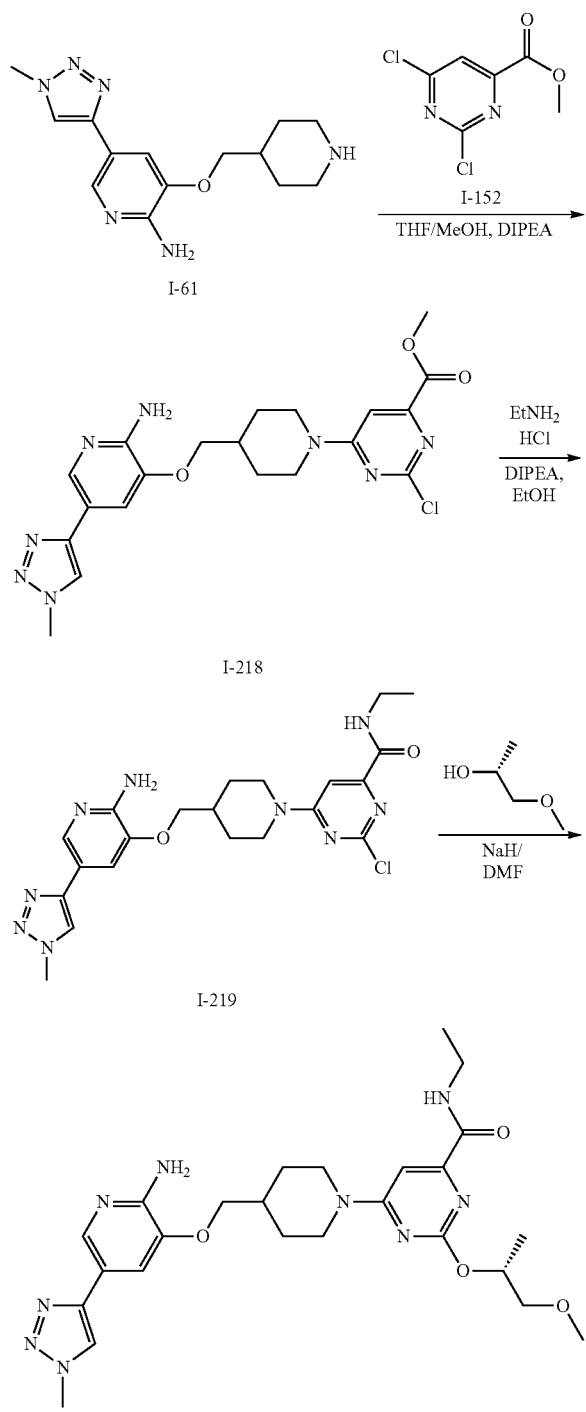

Example 138

Step 1—Synthesis of methyl-6-[4-({[2-amino-5-(1-methyl-1H-1,2,3-triazol-4-yl)pyridin-3-yl]oxy}methyl)piperidin-1-yl]-2-chloropyrimidine-4-carboxylate (I-218)

To a mixture of 5-(1-methyl-1H-1,2,3-triazol-4-yl)-3-(piperidin-4-ylmethoxy)pyridin-2-amine (I-61) (407 mg, 1.13 mmol) and methyl 2,6-dichloropyrimidine-4-carboxylate (I-152) (233 mg, 1.13 mmol) in anhydrous THF (10 mL) and MeOH (20 mL) was added DIPEA (582 mg, 4.52 mml) at 0° C. After the addition was complete, the mixture was stirred at 0° C. for 30 min. LCMS showed the reaction was completed. The mixture was concentrated in vacuo to give the crude product, which was purified by silica gel chromatography ($CH_2Cl_2$/MeOH=20/1 to 10/1) to give the methyl 6-[4-({[2-amino-5-(1-methyl-1H-1,2,3-triazol-4-yl)pyridin-3-yl]oxy}methyl)piperidin-1-yl]-2-chloropyrimidine-4-carboxylate (I-218) (410 mg, 79%) as a white solid, which was used without further purification.

Step 2—Synthesis of 6-[4-({[2-amino-5-(1-methyl-1H-1,2,3-triazol-4-yl)pyridin-3-yl]oxy}methyl)piperidin-1-yl]-2-chloro-N-ethylpyrimidine-4-carboxamide (I-219)

To a mixture of methyl 6-[4-({[2-amino-5-(1-methyl-1H-1,2,3-triazol-4-yl)pyridin-3-yl]oxy}methyl)piperidin-1-yl]-2-chloropyrimidine-4-carboxylate (I-218) (360 mg, 0.784 mmol), ethylamine hydrochloride (640 mg, 7.84 mmol) in anhydrous EtOH (5 mL) was added $Et_3N$ (794 mg, 7.84 mmol). The mixture was stirred at 60° C. for 18 hr. LCMS showed the reaction was complete. The mixture was filtered, and the organic layer was concentrated to dryness to give the product, which was purified by silica gel chromatography ($CH_2Cl_2$/MeOH=20/1 to 10/1) to give 6-[4-({[2-amino-5-(1-methyl-1H-1,2,3-triazol-4-yl)pyridin-3-yl]oxy}methyl)piperidin-1-yl]-2-chloro-N-ethylpyrimidine-4-carboxamide (I-219) (329 mg, 89%) as a white solid, which was used without further purification.

Step 3—Synthesis of 6-[4-({[2-amino-5-(1-methyl-1H-1,2,3-triazol-4-yl)pyridin-3-yl]oxy}methyl)piperidin-1-yl]-N-ethyl-2-{[(2R)-1-methoxypropan-2-yl]oxy}pyrimidine-4-carboxamide (Example 138)

To a solution of (2R)-1-methoxypropan-2-ol (43.0 mg, 0.477 mmol) in DMF (3 mL) was added NaH (50.8 mg, 60% in mineral oil, 1.27 mmol) at 0° C. The mixture was stirred at 0° C. for 30 min, and then 6-[4-({[2-amino-5-(1-methyl-1H-1,2,3-triazol-4-yl)pyridin-3-yl]oxy}methyl)piperidin-1-yl]-2-chloro-N-ethyl pyrimidine-4-carboxamide (I-219) (150 mg, 0.318 mmol) was added. The mixture was stirred at room temperature for 1 hr, and then stirred at 50° C. for 3 hr. LCMS showed the reaction was completed. The mixture was poured into water (10 mL) and extracted with $CH_2Cl_2$/MeOH=10/1 (3×10 mL). The combined organic layers were washed with brine (10 mL), dried over $Na_2SO_4$ and concentrated in vacuo to give the crude product, which was purified by preparative HPLC to give 6-[4-({[2-amino-5-(1-methyl-1H-1,2,3-triazol-4-yl)pyridin-3-yl]oxy}methyl)piperidin-1-yl]-N-ethyl-2-{[(2R)-1-methoxypropan-2-yl]oxy}pyrimidine-4-carboxamide (Example 138) (6.8 mg, 4%) as a white solid. LCMS (APCI), m/z 548.1 [M+H]$^+$; $^1$H NMR (400 MHz, $CDCl_3$) δ ppm 7.96 (s, 1 H), 7.86-7.94 (m, 1 H), 7.71 (s, 1 H), 7.59 (s, 1 H), 7.09 (s, 1 H), 5.33-5.38 (m, 1 H), 4.78 (s, 2 H), 4.44-4.68 (m, 2 H), 4.15 (s, 3 H), 3.98 (d, J=6.4 Hz, 2 H), 3.66-3.70 (m, 1 H), 3.42-3.52 (m, 6 H), 2.92-3.09 (m, 2 H), 2.18-2.31 (m, 1 H), 1.99 (d, J=13.2 Hz, 2 H), 1.34-1.46 (m, 5 H), 1.23 (t, J=7.6 Hz, 3 H).

Example 139 (Scheme C)

Synthesis of 6-(4-{[(2-aminopyridin-3-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide

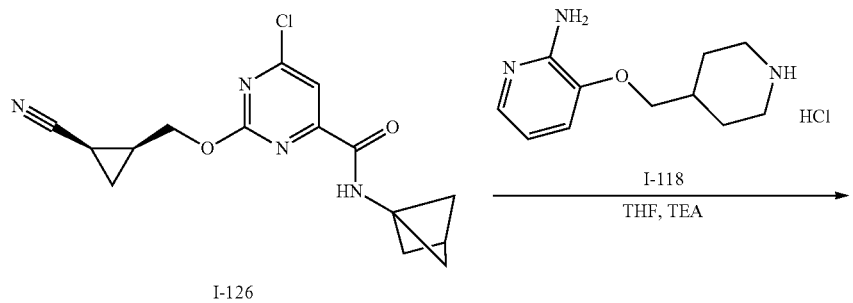

I-126

I-118

THF, TEA

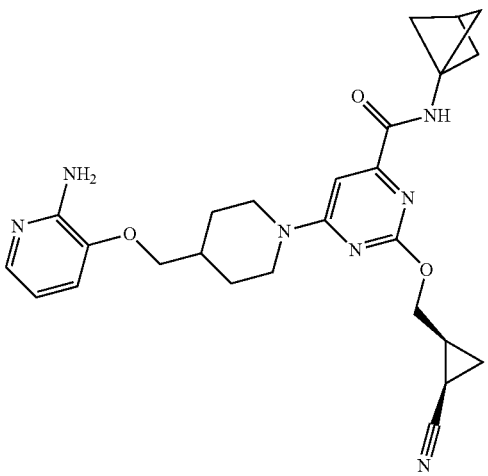

Example 139

Step 1—Synthesis of 6-(4-{[(2-aminopyridin-3-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide (Example 139)

A mixture of 3-(piperidin-4-ylmethoxy)pyridin-2-amine hydrochloride (I-118) (50 mg, 0.21 mmol), N-(bicyclo[1.1.1]pent-1-yl)-6-chloro-2-{[(1S,2R)-2-cyanocyclopropyl]methoxy}pyrimidine-4-carboxamide (I-126) (50 mg, 0.16 mmol) and TEA (95 mg, 0.94 mmol) in dry THF (4 mL) was stirred at 35° C. for 3 hr. TLC (petroleum ether/EtOAc=3/1, $R_f$~0.65) showed 20% of the N-(bicyclo[1.1.1]pent-1-yl)-6-chloro-2-{[(1S,2R)-2-cyanocyclopropyl]methoxy}pyrimidine-4-carboxamide still remained and TLC ($CH_2Cl_2$:MeOH=10:1, $R_f$~0.55) confirmed formation of the product. The mixture was quenched with $H_2O$ (10 mL), and extracted with EtOAc (2×20 mL). The combined organic layers were washed with brine (2×20 mL), dried over $Na_2SO_4$ and concentrated to give a residue, which was purified by preparative. TLC ($CH_2Cl_2$:MeOH=10:1, $R_f$~0.55) to give 6-(4-{[(2-aminopyridin-3-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide (Example 139) (25.3 mg, 33%) as a white solid. LCMS (APCI), m/z 490.1 [M+H]$^+$; $^1$H NMR (400 MHz, DMSO-$d_6$) δ ppm 8.93 (s, 1 H), 7.49 (d, J=4.4 Hz, 1 H), 6.98-7.00 (m, 2 H), 6.48 (d, J=7.6 Hz, 1 H), 5.65 (s, 2 H), 4.30-4.70 (m, 3 H), 4.05 (d, J=12.0 Hz, 1 H), 3.84 (d, J=6.4 Hz, 2 H), 3.01 (br. s., 2 H), 2.46 (s, 1 H), 2.10 (s, 6 H), 1.92-2.02 (m, 3 H), 1.76-1.87 (m, 1 H), 1.24-1.31 (m, 4 H), 1.12-1.14 (m, 1 H).

Example 141 (Scheme A)

Synthesis of 6-[4-({[2-amino-5-(1-methyl-1H-imidazol-5-yl)pyridin-3-yl]oxy}methyl)piperidin-1-yl]-N-ethyl-2-{[(2R)-1-methoxypropan-2-yl]oxy}pyrimidine-4-carboxamide

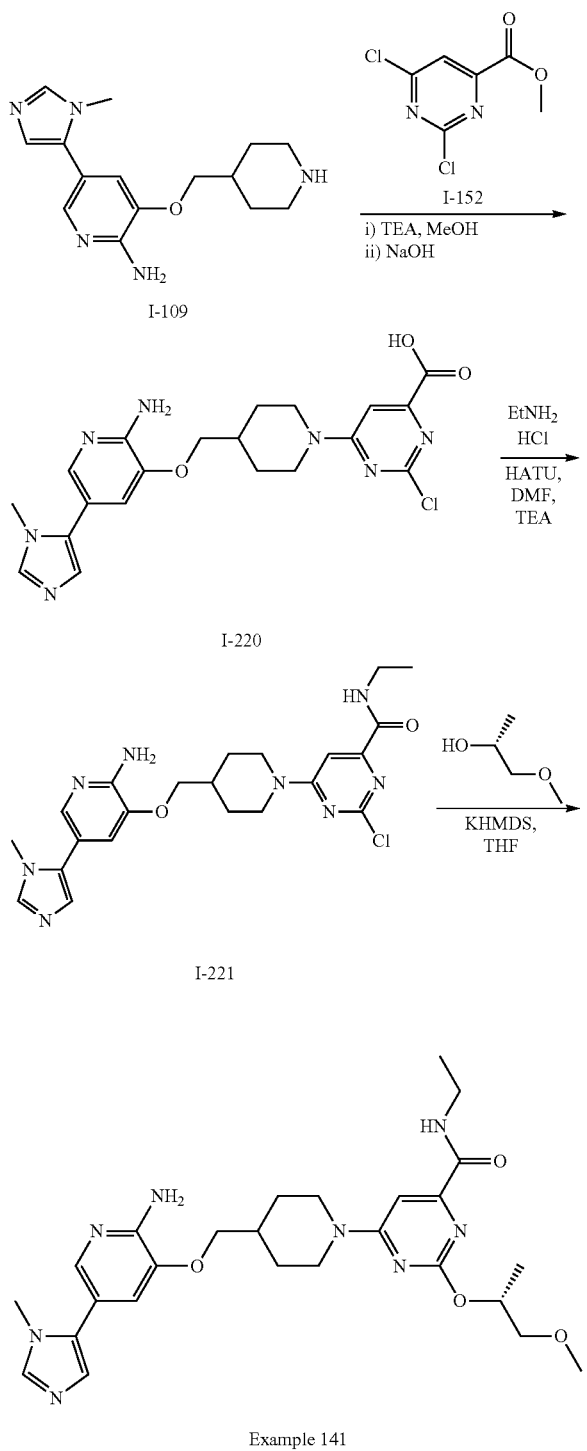

Step 1—Synthesis of 6-[4-({[2-amino-5-(1-methyl-1H-imidazol-5-yl)pyridin-3-yl]oxy}methyl)piperidin-1-yl]-2-chloropyrimidine-4-carboxylic acid (I-220)

To a stirring mixture of 5-(1-methyl-1H-imidazol-5-yl)-3-(piperidin-4-ylmethoxy)pyridin-2-amine (I-109) (88 mg, 0.24 mmol) and methyl 2,6-dichloropyrimidine-4-carboxylate (I-152) (55 mg, 0.26 mmol) in MeOH (3 mL) was added TEA (0.17 mL, 1.22 mmol) at 0° C. The reaction was stirred for 16 hr. LCMS indicated ~35% of the starting material was left, and ~10% of the regioisomer had been formed. A further portion of methyl 2,6-dichloropyrimidine-4-carboxylate (21 mg, 0.1 mmol) was added, and the reaction stirred for 3 hr. LCMS still showed ~10% starting material, and so a further portion of methyl 2,6-dichloropyrimidine-4-carboxylate (12 mg, 0.06 mmol)) was added, and the reaction stirred for 1 hr. LCMS showed the reaction to be complete. NaOH (1.22 mL, 1 M, 1.22 mmol) was added at 0° C., and the reaction stirred at room temperature for 18 hr. A further aliquot of NaOH (0.2 mL, 1M, 0.2 mmol) was added, and the reaction stirred for 6 hr. LCMS indicated the reaction was complete. The volatiles were removed in vacuo, and the remaining crude solid 6-[4-({[2-amino-5-(1-methyl-1H-imidazol-5-yl)pyridin-3-yl]oxy}methyl)piperidin-1-yl]-2-chloropyrimidine-4-carboxylic acid (I-220) dried in the vacuum oven at 60° C. for 24 hr prior to being used directly in the next step.

Step 2—Synthesis of 6-[4-({[2-amino-5-(1-methyl-1H-imidazol-5-yl)pyridin-3-yl]oxy}methyl)piperidin-1-yl]-2-chloro-N-ethylpyrimidine-4-carboxamide (I-221)

To a solution of 6-[4-({[2-amino-5-(1-methyl-1H-imidazol-5-yl)pyridin-3-yl]oxy}methyl)piperidin-1-yl]-2-chloropyrimidine-4-carboxylic acid (I-220) (110 mg, 0.25 mmol) in DMF (2 mL) was added ethylamine hydrochloride (27 mg, 0.32 mmol), TEA (0.173 mL, 1.22 mmol) followed by HATU (113 mg, 0.29 mmol). The resultant mixture was stirred at room temperature for 4 hr. H$_2$O (5 mL) was added, and the reaction extracted with EtOAc (2×10 mL). The organic extracts were dried over Na$_2$SO$_4$, filtered and concentrated in vacuo to afford the crude 6-[4-({[2-amino-5-(1-methyl-1H-imidazol-5-yl)pyridin-3-yl]oxy}methyl)piperidin-1-yl]-2-chloro-N-ethylpyrimidine-4-carboxamide (I-221) (110 mg, 94%) as a yellow oil, which was used directly in the next step without further purification.

Step 3—6-[4-({[2-amino-5-(1-methyl-1H-imidazol-5-yl)pyridin-3-yl]oxy}methyl)piperidin-1-yl]-N-ethyl-2-{[(2R)-1-methoxypropan-2-yl]oxy}pyrimidine-4-carboxamide (Example 141)

To a mixture of 6-[4-({[2-amino-5-(1-methyl-1H-imidazol-5-yl)pyridin-3-yl]oxy}methyl)piperidin-1-yl]-2-chloro-N-ethylpyrimidine-4-carboxamide (I-221) (55 mg, 0.12 mmol) and (2R)-1-methoxypropan-2-ol (42 mg, 0.47 mmol) in THF (2 mL) was added KHMDS (93 mg, 0.47 mmol), and the resulting suspension was stirred at room temperature for 18 hr. LCMS showed the reaction was predominantly starting material, and additional aliquots of both KHMDS (93 mg, 0.47 mmol) and (2R)-1-methoxypropan-2-ol (22 mg, 0.23 mmol) were added. The reaction was stirred for a further 24 hr, before again additional KHMDS (200 mg, 1.01 mmol) and (2R)-1-methoxypropan-2-ol (95 mg, 0.94 mmol) were added. After being stirred for a further 60 hr, LCMS indicated the reaction was complete. H₂O (5 mL) was added, and the reaction extracted with EtOAc (3×10 mL). The organic extracts were dried over Na₂SO₄, filtered and concentrated in vacuo to afford the crude product, which was purified by preparative HPLC to afford 6-[4-({[2-amino-5-(1-methyl-1H-imidazol-5-yl)pyridin-3-yl]oxy}methyl)piperidin-1-yl]-N-ethyl-2-{[(2R)-1-methoxypropan-2-yl]oxy}pyrimidine-4-carboxamide (Example 141) (61 mg, 33%) as a white solid. LCMS (APCI), m/z 525.2 [M+H]⁺; ¹H NMR (600 MHz, DMSO-d₆) δ ppm 8.58 (t, J=6.15 Hz, 1 H), 7.63 (s, 1 H), 7.58 (d, J=1.90 Hz, 1 H), 7.07 (d, J=1.76 Hz, 1 H), 6.95 (s, 1 H), 6.91 (s, 1 H), 5.87 (s, 2 H), 5.33 (quind, J=6.31, 4.17 Hz, 1 H), 3.90 (d, J=6.29 Hz, 3 H), 3.60 (s, 3 H), 3.42-3.52 (m, 1 H), 3.24-3.30 (m, 3 H), 3.01 (br. s., 1 H), 2.07-2.18 (m, 1 H), 1.93 (d, J=12.29 Hz, 3 H), 1.87 (s, 2 H), 1.26-1.32 (m, 2 H), 1.21-1.26 (m, 4 H), 1.04-1.11 (m, 4 H).

Example 161 (Scheme A)

Synthesis of 6-[4-({[2-amino-5-(1-methyl-1H-1,2,3-triazol-5-yl)pyridin-3-yl]oxy}methyl)piperidin-1-yl]-N-ethyl-2-{[(2R)-1-methoxypropan-2-yl]oxy}pyrimidine-4-carboxamide

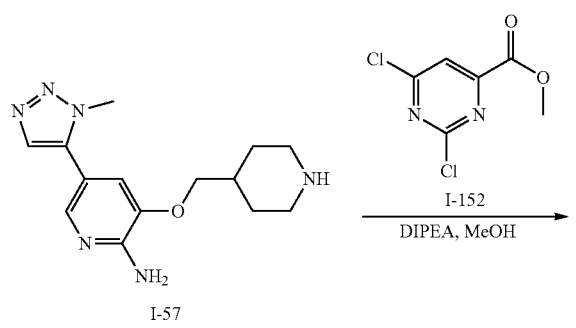

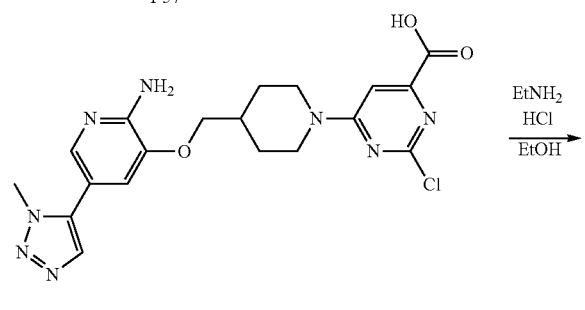

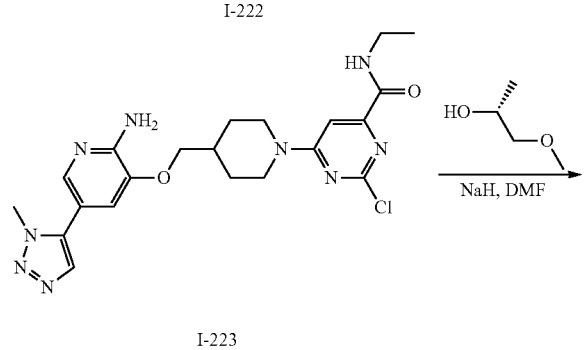

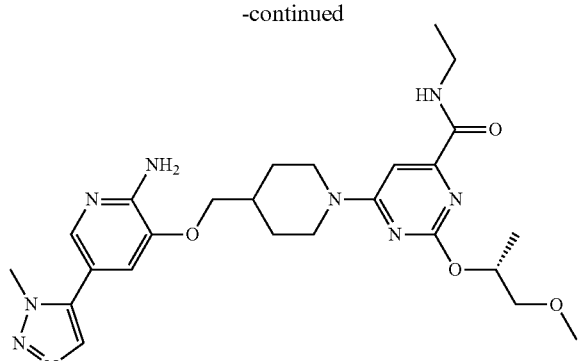

Example 161

Step 1—Synthesis of methyl 6-[4-({[2-amino-5-(1-methyl-1H-1,2,3-triazol-5-yl)pyridin-3-yl]oxy}methyl)piperidin-1-yl]-2-chloropyrimidine-4-carboxylate (I-222)

To a solution of 5-(1-methyl-1H-1,2,3-triazol-5-yl)-3-(piperidin-4-ylmethoxy)pyridin-2-amine (I-57) (310 mg, 1.08 mmol) and methyl 2,6-dichloropyrimidine-4-carboxylate (I-152) (223 mg, 1.08 mmol) in MeOH (4 ml) and THF (4 mL) was added DIPEA (417 mg, 3.23 mmol) at 0° C. Then, the reaction mixture was stirred at 0° C. for 20 min. TLC (EtOAc:MeOH=10:1) showed the reaction was complete. The reaction mixture was concentrated to give the crude product, which was purified by silica gel chromatography (EtOAc:CH₂Cl₂:MeOH=10:10:1) to give methyl 6-[4-({[2-amino-5-(1-methyl-1H-1,2,3-triazol-5-yl)pyridin-3-yl]oxy}methyl)piperidin-1-yl]-2-chloropyrimidine-4-carboxylate (I-222) (290 mg, 59%) as a white solid, which was used without further purification.

Step 2—Synthesis of 6-[4-({[2-amino-5-(1-methyl-1H-1,2,3-triazol-5-yl)pyridin-3-yl]oxy}methyl)piperidin-1-yl]-2-chloro-N-ethylpyrimidine-4-carboxamide (I-223)

To a solution of methyl 6-[4-({[2-amino-5-(1-methyl-1H-1,2,3-triazol-5-yl)pyridin-3-yl]oxy}methyl)piperidin-1-yl]-2-chloropyrimidine-4-carboxylate (I-222) (290 mg, 0.632 mmol) and TEA (639 mg, 6.32 mmol) in EtOH (8 ml) was added ethylamine hydrochloride (515 mg, 6.32 mmol). The reaction mixture was stirred at 50° C. overnight. LCMS showed ~50% of the starting ester still remained, and the reaction mixture was stirred at 50° C. for a further 24 hr. LCMS showed ~20% of the ester still remained. The reaction mixture was concentrated to give the crude product, which was washed with H₂O (20 ml), brine (20 ml), dried over Na₂SO₄ and concentrated to give a residue, which was purified by silica gel chromatography (EtOAc:CH₂Cl₂:MeOH=10:10:1) to give 6-[4-({[2-amino-5-(1-methyl-1H-1,2,3-triazol-5-yl)pyridin-3-yl]oxy}methyl)piperidin-1-yl]-2-chloro-N-ethylpyrimidine-4-carboxamide (I-223), which was used directly without further purification.

Step 3—Synthesis of 6-[4-({[2-amino-5-(1-methyl-1H-1,2,3-triazol-5-yl)pyridin-3-yl]oxy}methyl)piperidin-1-yl]-N-ethyl-2-{[(2R)-1-methoxypropan-2-yl]oxy}pyrimidine-4-carboxamide (Example 161)

To a solution of (2R)-1-methoxypropan-2-ol (84 mg, 0.932 mmol) in DMF (8 mL) was added NaH (67.1 mg, 60% in mineral oil, 2.80 mmol) at 0° C. Then the reaction mixture was stirred at 0° C. for 30 min. Then 6-[4-({[2-amino-5-(1-methyl-1H-1,2,3-triazol-5-yl)pyridin-3-yl]oxy}methyl)piperidin-1-yl]-2-chloro-N-ethylpyrimidine-4-carboxamide (I-223) (220 mg, 0.466 mmol) was added. The reaction mixture was stirred at room temperature for 30 min and then at 50° C. for 2 hr. LCMS showed the reaction was completed. The mixture was poured into water (10 mL) and extracted with CH$_2$Cl$_2$ (3×20 ml). The combined organic layers were washed with brine (10 mL), dried over Na$_2$SO$_4$ and concentrated in vacuo to give the crude product, which was purified by preparative HPLC to give 6-[4-({[2-amino-5-(1-methyl-1H-1,2,3-triazol-5-yl)pyridin-3-yl]oxy}methyl)piperidin-1-yl]-N-ethyl-2-{[(2R)-1-methoxypropan-2-yl]oxy}pyrimidine-4-carboxamide (Example 161) (20 mg, 8%) as a white solid. LCMS (APCI), m/z 526.1 [M+NH]$^+$; $^1$H NMR (400 MHz, CDCl$_3$) δ ppm 7.88 (t, J=5.6 Hz, 1 H), 7.73 (d, J=2.0 Hz, 1 H), 7.68 (s, 1 H), 7.10 (s, 1 H), 6.86 (d, J=1.6 Hz, 1 H), 5.30-5.35 (m, 1 H), 4.96 (s, 2 H), 4.60 (br. s., 2 H), 4.05 (s, 3 H), 3.89-3.91 (m, 2 H), 3.52-3.67 (m, 1 H), 3.47-3.51 (m, 6 H), 3.30-3.42 (m, 2 H), 2.22 (br. s. 1 H), 1.96-1.99 (m, 2 H), 1.38-1.42 (m, 5 H), 1.21-1.23 (m, 3 H).

Example 162 (Scheme A)

Synthesis of 6-[4-({[2-amino-5-(1,5-dimethyl-1H-1,2,3-triazol-4-yl)pyridin-3-yl]oxy}methyl)piperidin-1-yl]-N-ethyl-2-{[(2R)-1-methoxypropan-2-yl]oxy}pyrimidine-4-carboxamide

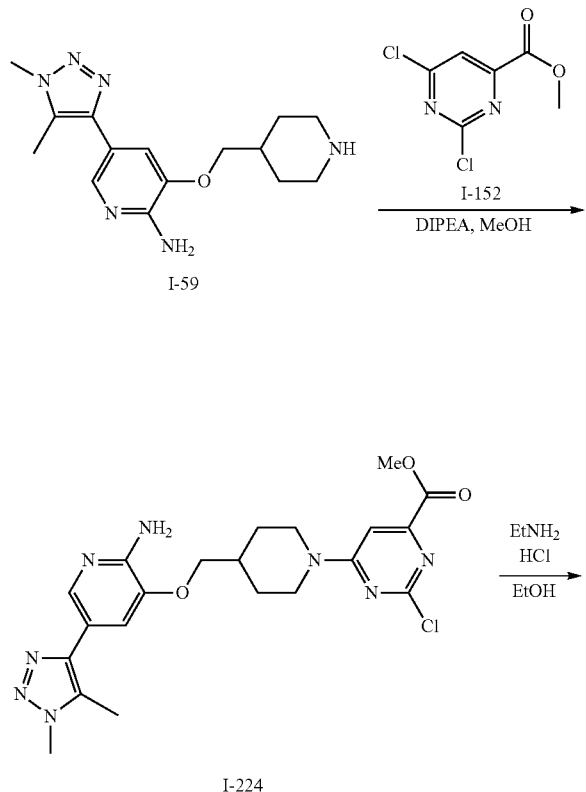

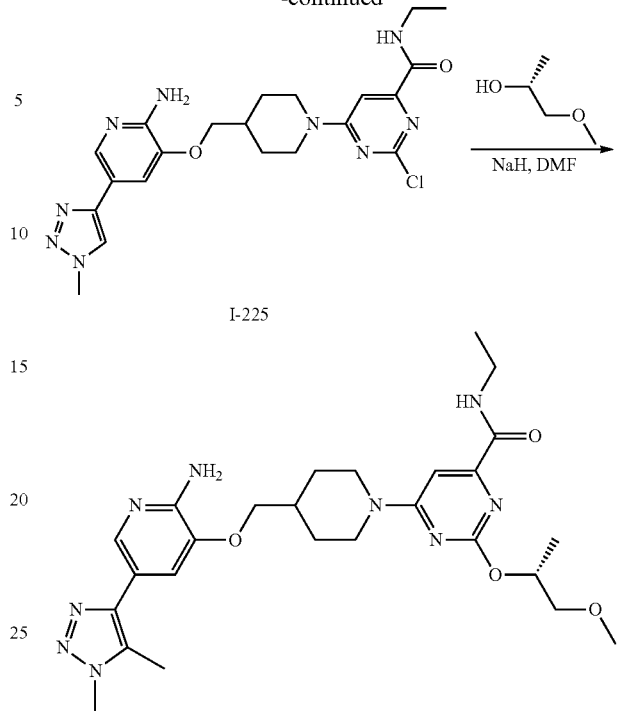

Example 162

Step 1—Synthesis of methyl 6-[4-({[2-amino-5-(1,5-dimethyl-1H-1,2,3-triazol-4-yl)pyridin-3-yl]oxy}methyl)piperidin-1-yl]-2-chloropyrimidine-4-carboxylate (I-224)

To a solution of 5-(1,5-dimethyl-1H-1,2,3-triazol-4-yl)-3-(piperidin-4-ylmethoxy)pyridin-2-amine (I-59) (310 mg, 1.09 mmol) and methyl 2,6-dichloropyrimidine-4-carboxylate (I-152) (226 mg, 1.09 mmol) in THF (10 mL) and MeOH (2 mL) was added DIPEA (423 mg, 3.27 mmol) at 0° C. The reaction was stirred at 0° C. for 30 min. The mixture was concentrated and purified by silica gel chromatography (petroleum Ether:EtOAc=1:1 to 0:1) to give methyl 6-[4-({[2-amino-5-(1,5-dimethyl-1H-1,2,3-triazol-4-yl)pyridin-3-yl]oxy}methyl)piperidin-1-yl]-2-chloropyrimidine-4-carboxylate (I-224) (320 mg, 62%) as a yellow solid, which was used in next step without further purification.

Step 2—Synthesis of 6-[4-({[2-amino-5-(1,5-dimethyl-1H-1,2,3-triazol-4-yl)pyridin-3-yl]oxy}methyl)piperidin-1-yl]-2-chloro-N-ethylpyrimidine-4-carboxamide (I-225)

A mixture of methyl 6-[4-({[2-amino-5-(1,5-dimethyl-1H-1,2,3-triazol-4-yl)pyridin-3-yl]oxy}methyl)piperidin-1-yl]-2-chloropyrimidine-4-carboxylate (I-224) (320 mg, 0.68 mmol), ethylamine hydrochloride (552 mg, 6.77 mmol) in anhydrous EtOH (10 mL) was added TEA (685 mg, 6.77 mmol). The mixture was stirred at 60° C. for 24 hr. The mixture was filtered, and the organic layer was concentrated to dryness to give the 6-[4-({[2-amino-5-(1,5-dimethyl-1H-1,2,3-triazol-4-yl)pyridin-3-yl]oxy}methyl)piperidin-1-yl]-2-chloro-N-ethylpyrimidine-4-carboxamide (I-225) (300 mg, 91%) as a yellow solid, which was used directly in the next step.

Step 3—Synthesis of 6-[4-({[2-amino-5-(1,5-dimethyl-1H-1,2,3-triazol-4-yl)pyridin-3-yl]oxy}methyl)piperidin-1-yl]-N-ethyl-2-{[(2R)-1-methoxypropan-2-yl]oxy}pyrimidine-4-carboxamide (Example 162)

To a suspension of (2R)-1-methoxypropan-2-ol (90.12 mg, 55.6 mmol) in DMF (10 mL) was added NaH (30.9 mg, 60% in mineral oil, 0.77 mmol), the mixture was stirred at room temperature for 30 min, and then 6-[4-({[2-amino-5-(1,5-dimethyl-1H-1,2,3-triazol-4-yl)pyridin-3-yl]oxy}methyl)piperidin-1-yl]-2-chloro-N-ethylpyrimidine-4-carboxamide (I-225) (150 mg, 0.31 mmol) was added at room temperature. The mixture was stirred at room temperature for 1 hr. The reaction was quenched with aqueous NH$_4$Cl (1 mL), and concentrated to remove DMF. The residue was purified by preparative TLC (CH$_2$Cl$_2$/MeOH=10/1) to give 6-[4-({[2-amino-5-(1,5-dimethyl-1H-1,2,3-triazol-4-yl)pyridin-3-yl]oxy}methyl)piperidin-1-yl]-N-ethyl-2-{[(2R)-1-methoxypropan-2-yl]oxy}pyrimidine-4-carboxamide (Example 162) (7 mg, 4%) as a white solid. LCMS (APCI), m/z 562.1 [M+Na]$^+$; $^1$H NMR (400 MHz, CDCl$_3$) δ ppm 7.82-7.88 (m, 1 H), 7.82 (s, 1H), 7.47 (s, 1 H), 7.08 (s, 1 H), 5.30-5.34 (m, 1 H), 4.90 (br. s., 2 H), 4.46-4.76 (m, 1 H), 4.01 (s, 3 H), 3.96 (d, J=6.0 Hz, 2 H), 3.65-3.69 (m, 1 H), 3.41-3.51 (m, 2 H), 3.41 (s 3 H), 2.95-2.99 (m, 2 H), 2.53 (s, 3 H), 2.15-2.25 (m, 1 H), 1.95-1.97 (m, 2 H), 1.30-1.40 (m, 5 H), 1.19-1.20 (m, 3 H).

Example 167 (Scheme E)

Synthesis of 4-{[(1R)-2,2-difluorocyclopropyl]methoxy}-6-[4-(1H-pyrazolo[3,4-b]pyridin-3-yl)piperidin-1-yl]-N-[(2S)-1,1,1-trifluoropropan-2-yl]-1,3,5-triazine-2-carboxamide

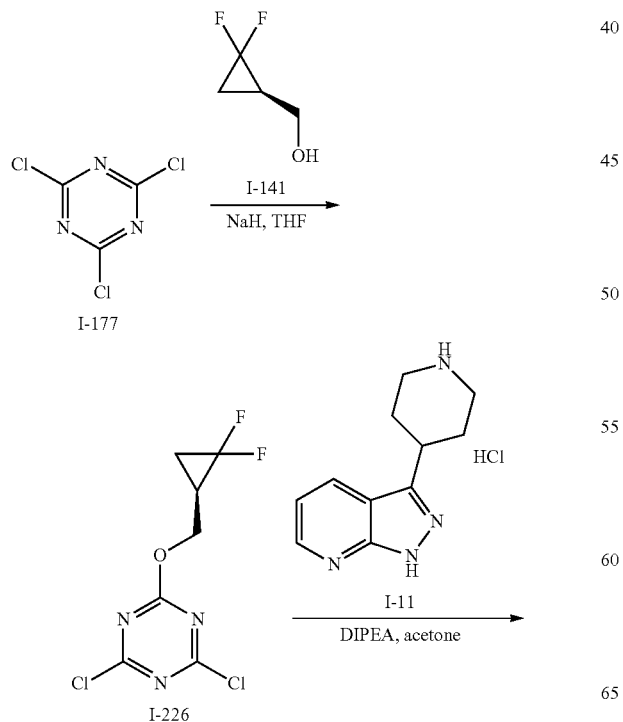

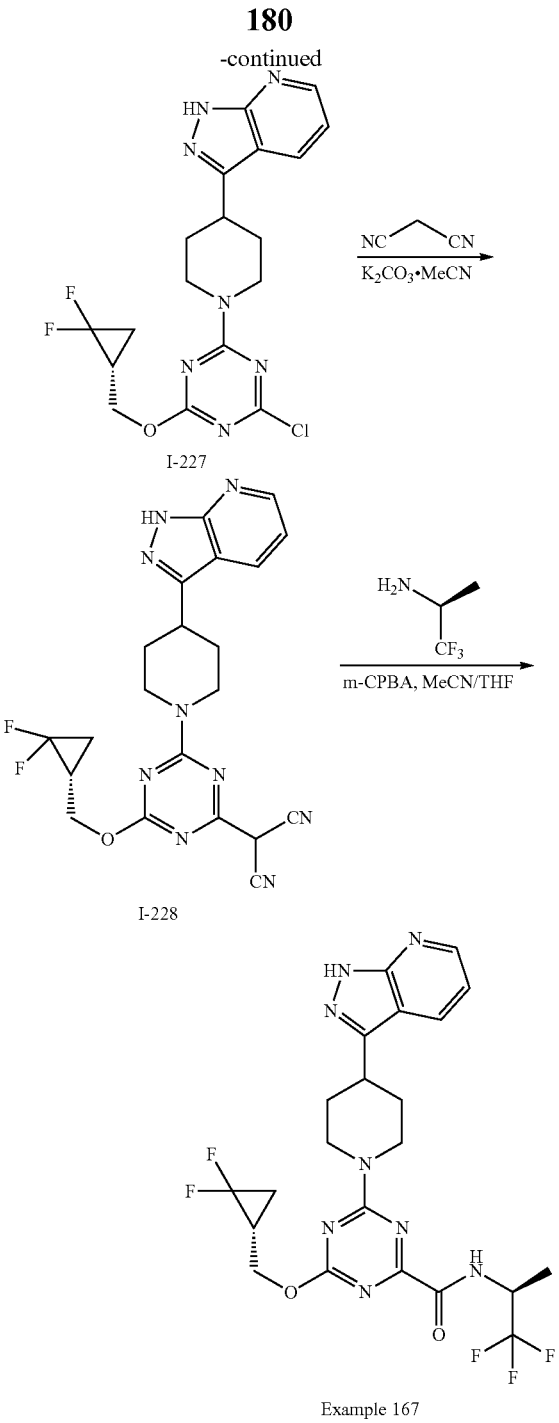

Example 167

Step 1—Synthesis of 2,4-dichloro-6-{[(1R)-2,2-difluorocyclopropyl]methoxy}-1,3,5-triazine (I-226)

To a suspension of cyanuric chloride (I-177) (2.20 g, 11.93 mmol) in anhydrous THF (20 mL) was added [(1R)-2,2-difluorocyclopropyl]methanol (I-141) (1.17 g, 10.8 mmol) at 0° C. followed by the dropwise addition of DIPEA (2.10 g, 16.3 mmol). The resulting colorless mixture was stirred at room temperature (25° C.) for 16 hr. TLC (hexanes:EtOAc=5:1) indicated the starting material had been completely consumed. The resulting white suspension was concentrated and the residue was purified by silica gel chromatography (EtOAc/petroleum ether=0~10%) to give 2,4-dichloro-6-{[(1R)-2,2-difluorocyclopropyl]methoxy}-1,3,5-triazine (I-226) (1.31 g, 43%) as colorless oil, which was used without further purification.

Step 2—Synthesis of 3-[1-(4-chloro-6-{[(1R)-2,2-difluorocyclopropyl]methoxy}-1,3,5-triazin-2-yl)piperidin-4-yl]-1H-pyrazolo[3,4-b]pyridine (I-227)

To a 0° C. cooled suspension of 2,4-dichloro-6-{[(1R)-2,2-difluorocyclopropyl]methoxy}-1,3,5-triazine (I-226) (1.30 g, 5.08 mmol) and 3-(piperidin-4-yl)-1H-pyrazolo[3,4-b]pyridine hydrochloride (I-11) (1.21 g, 5.08 mmol) in anhydrous THF (20 mL) and MeOH (10 mL) was slowly added in a dropwise manner DIPEA (2.62 g, 3.12 mmol). After the addition, the mixture was stirred at 0-20° C. for 2 hr. TLC (petroleum ether/EtOAc=1/1) showed the starting material was consumed completely and a single new spot was formed. The brown reaction mixture was concentrated and the residue was diluted with EtOAc (100 mL). The mixture was washed with water (10 mL), brine (10 mL), dried over $Na_2SO_4$ and concentrated. The residue was purified by silica gel chromatography ($MeOH/CH_2Cl_2$=0~5%) to give 3-[1-(4-chloro-6-{[(1R)-2,2-difluorocyclopropyl]methoxy}-1,3,5-triazin-2-yl)piperidin-4-yl]-1H-pyrazolo[3,4-b]pyridine (I-227) (1.80 g, 84%) as a light yellow solid, which was used without further purification.

Step 3—Synthesis of (4-{[(1R)-2,2-difluorocyclopropyl]methoxy}-6-[4-(1H-pyrazolo[3,4-b]pyridin-3-yl)piperidin-1-yl]-1,3,5-triazin-2-yl)propanedinitrile (I-228)

A suspension of malononitrile (203 mg, 3.07 mmol) and $K_2CO_3$ (424 mg, 3.07 mmol) in MeCN (10 mL) was stirred at room temperature (25° C.) for 10 min. 3-[1-(4-chloro-6-{[(1R)-2,2-difluorocyclopropyl]methoxy}-1,3,5-triazin-2-yl)piperidin-4-yl]-1H-pyrazolo[3,4-b]pyridine (I-227) (300 mg, 0.61 mmol) in MeCN (5 mL) was added in a dropwise manner at room temperature (25° C.) with stirring. The orange suspension obtained was stirred at room temperature (25° C.) for 16 hr. TLC ($CH_2Cl_2$:MeOH=10:1) indicated the start material was consumed, and a single new spot was observed. LCMS also indicated that the reaction was clean and main peak shows the desired product mass (451.9). The obtained light yellow solution of (4-{[(1R)-2,2-difluorocyclopropyl]methoxy}-6-[4-(1H-pyrazolo[3,4-b]pyridin-3-yl)piperidin-1-yl]-1,3,5-triazin-2-yl)propanedinitrile (I-228) (193 mg, 100%, 38.5 mg/mL in MeCN) was used directly in the next reaction.

Step 4—Synthesis of 4-{[(1R)-2,2-difluorocyclopropyl]methoxy}-6-[4-(1H-pyrazolo[3,4-b]pyridin-3-yl)piperidin-1-yl]-N-[(2S)-1,1,1-trifluoropropan-2-yl]-1,3,5-triazine-2-carboxamide (Example 167)

To a solution of (4-{[(1R)-2,2-difluorocyclopropyl]methoxy}-6-[4-(1H-pyrazolo[3,4-b]pyridin-3-yl)piperidin-1-yl]-1,3,5-triazin-2-yl)propanedinitrile (I-228) (1.50 g, 3.4 mmol in 40 mL MeCN) was added (2S)-1,1,1-trifluoropropan-2-amine (1.54 g, 13.6 mmol) at 0° C. followed by the portionwise addition of m-CPBA (5.89 g, 85%, 34.1 mmol). The white suspension obtained was stirred at room temperature (25° C.) for 40 hr. LCMS showed the starting material had been consumed, and the observed main peak shows the mass of the desired product. The light yellow suspension was concentrated and the residue was diluted with EtOAc (100 mL), washed with water (50 mL), saturated $NaHCO_3$ (20 mL) and dried over $Na_2SO_4$. The solvent was evaporated to give a light yellow solid. The crude product was purified by silica gel chromatography (EtOAc/petroleum ether=20-80%) to give 4-{[(1R)-2,2-difluorocyclopropyl]methoxy}-6-[4-(1H-pyrazolo[3,4-b]pyridin-3-yl)piperidin-1-yl]-N-[(2S)-1,1,1-trifluoropropan-2-yl]-1,3,5-triazine-2-carboxamide (1.40 g, 75%) as a light yellow solid, which was further purified by preparative HPLC to give 4-{[(1R)-2,2-difluorocyclopropyl]methoxy}-6-[4-(1H-pyrazolo[3,4-b]pyridin-3-yl)piperidin-1-yl]-N-[(2S)-1,1,1-trifluoropropan-2-yl]-1,3,5-triazine-2-carboxamide (Example 167) (1.06 g, 59% over two steps) as a light yellow solid. LCMS (APCI), m/z 527.2 [M+H]$^+$; $^1$H NMR (400 MHz, CDCl$_3$) δ ppm 11.87 (br. s., 1 H), 8.59 (d, J=3.2 Hz, 1 H), 8.11 (d, J=8.0 Hz, 1 H), 7.91 (d, J=10.0 Hz, 1 H), 7.13-7.16 (m, 1 H), 5.03 (t, J=3.8 Hz, 1 H), 4.83-4.89 (m, 2 H), 4.51-4.53 (m, 1 H), 4.44-4.46 (m, 1 H), 3.40-3.43 (m, 1 H), 3.25-3.28 (m, 2 H), 2.02-2.21 (m, 5 H), 1.59-1.72 (m, 1 H), 1.43 (d, J=6.8 Hz, 3 H), 1.32-1.34 (m, 1H). Chiral analysis. Rt (Peak 1)=8.08 min Chiralcel OJ-H 4.6×250 mm column 5-40% EtOH (w. 0.05% DEA) @ 120 bar CO$_2$, 2.4 mL/min. Retention time of enantiomer (Peak 2—Example 166) is 8.69 min.

Example 173 (Scheme E)

Synthesis of N-(bicyclo[1.1.1]pent-1-yl)-4-{[(1S,2R)-2-cyanocyclopropyl]methoxy}-6-[4-(4-methoxy-1H-pyrazolo[3,4-b]pyridin-3-yl)piperidin-1-yl]-1,3,5-triazine-2-carboxamide

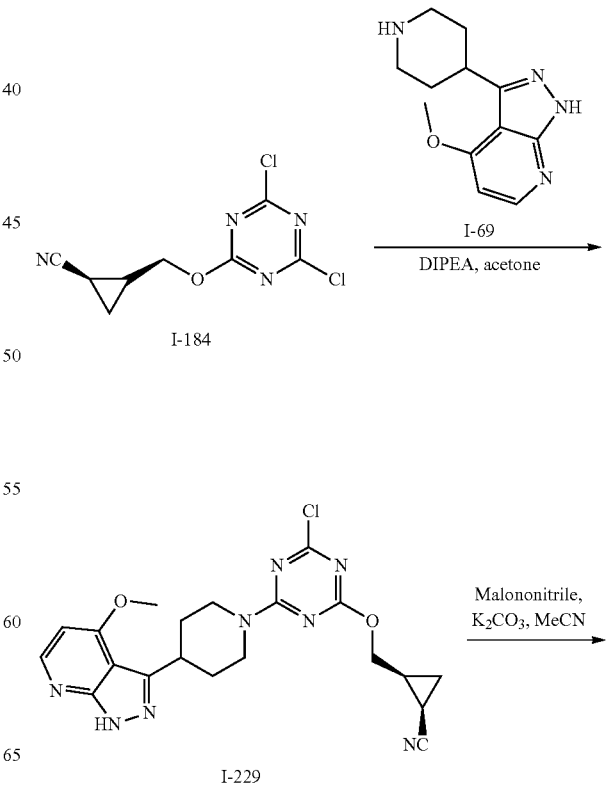

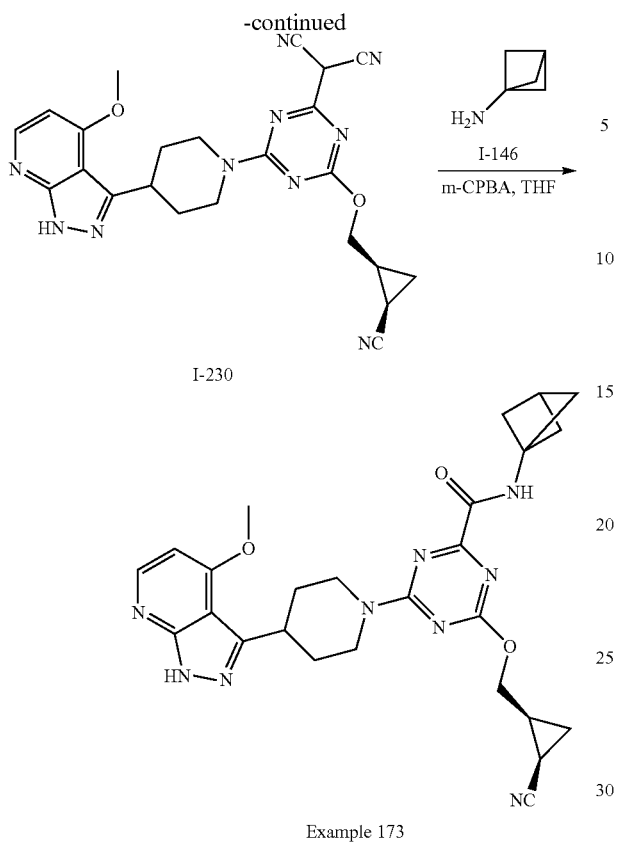

Example 173

Step 1—Synthesis of (1R,2S)-2-[({4-chloro-6-[4-(4-methoxy-1H-pyrazolo[3,4-b]pyridin-3-yl)piperidin-1-yl]-1,3,5-triazin-2-yl}oxy)methyl]cyclopropanecarbonitrile (I-229)

To a stirred mixture of 4-methoxy-3-(piperidin-4-yl)-1H-pyrazolo[3,4-b]pyridine (I-69) (261 mg, 1.12 mmol) and DIPEA (435 mg, 3.37 mmol) in acetone (10 mL) was added (1R,2S)-2-{[(4,6-dichloro-1,3,5-triazin-2-yl)oxy]methyl}cyclopropanecarbonitrile (I-184) (275 mg, 1.12 mmol) at −30° C. under a nitrogen atmosphere. The mixture was stirred at −30° C. for 1 hr. TLC (petroleum ether/EtOAc=1:1) showed that the reaction was completed. The mixture was concentrated at room temperature and purified by silica gel chromatography (CH$_2$Cl$_2$/MeOH=10:1, R$_f$=0.42) to yield (1R,2S)-2-[({4-chloro-6-[4-(4-methoxy-1H-pyrazolo[3,4-b]pyridin-3-yl)piperidin-1-yl]-1,3,5-triazin-2-yl}oxy)methyl]cyclopropanecarbonitrile (I-229) (490 mg, 99%) as yellow syrup, which was used without further purification.

Step 2—Synthesis of (4-{[(1S,2R)-2-cyanocyclopropyl]methoxy}-6-[4-(4-methoxy-1H-pyrazolo[3,4-b]pyridin-3-yl)piperidin-1-yl]-1,3,5-triazin-2-yl)propanedinitrile (I-230)

A mixture of malononitrile (65.9 mg, 0.998 mmol) and K$_2$CO$_3$ (276 mg, 2.0 mmol) in MeCN (10 mL) was stirred at room temperature for 1 hr. Then (1R,2S)-2-[({4-chloro-6-[4-(4-methoxy-1H-pyrazolo[3,4-b]pyridin-3-yl)piperidin-1-yl]-1,3,5-triazin-2-yl}oxy)methyl]cyclopropanecarbonitrile (I-229) (220 mg, 0.499 mmol) was added to the mixture. The resulting mixture was stirred at room temperature for 1 hr. LCMS showed that (1R,2S)-2-[({4-chloro-6-[4-(4-methoxy-1H-pyrazolo[3,4-b]pyridin-3-yl)piperidin-1-yl]-1,3,5-triazin-2-yl}oxy)methyl]cyclopropanecarbonitrile still remained, and DMSO (1 mL) was added to the mixture. The mixture was stirred at room temperature for 24 hr. The mixture was concentrated and purified by silica gel chromatography (CH$_2$Cl$_2$/MeOH, R$_f$=0.42) to yield (4-{[(1S,2R)-2-cyanocyclopropyl]methoxy}-6-[4-(4-methoxy-1H-pyrazolo[3,4-b]pyridin-3-yl)piperidin-1-yl]-1,3,5-triazin-2-yl)propanedinitrile (I-230) (80 mg, 34%) as a light yellow solid, which was used directly in the next step.

Step 3—Synthesis of N-(bicyclo[1.1.1]pent-1-yl)-4-{[(1S,2R)-2-cyanocyclopropyl]methoxy}-6-[4-(4-methoxy-1H-pyrazolo[3,4-b]pyridin-3-yl)piperidin-1-yl]-1,3,5-triazine-2-carboxamide (Example 173)

To a stirred mixture of (4-{[(1S,2R)-2-cyanocyclopropyl]methoxy}-6-[4-(4-methoxy-1H-pyrazolo[3,4-b]pyridin-3-yl)piperidin-1-yl]-1,3,5-triazin-2-yl)propanedinitrile (I-230) (80 mg, 0.17 mmol) in MeCN (5 mL) and THF (5 mL) were added m-CPBA (88 mg, 85%, 0.51 mmol) and bicyclo[1.1.1]pentan-1-amine (I-146) (81.4 mg, 0.68 mmol) at 0° C. The mixture was stirred at room temperature for 18 hr. LCMS showed that (4-{[(1S,2R)-2-cyanocyclopropyl]methoxy}-6-[4-(4-methoxy-1H-pyrazolo[3,4-b]pyridin-3-yl)piperidin-1-yl]-1,3,5-triazin-2-yl)propanedinitrile had almost been consumed. The mixture was quenched by addition of aqueous saturated NaHCO$_3$ (1 mL), and the mixture was dried over Na$_2$SO$_4$, filtered and concentrated. The residue was purified by preparative HPLC (Phenomenex Gemini C-18 column 250×21.2 mm×10 μm. eluting from 33% MeCN/water w. NH$_4$OH to 53% MeCN/water w. NH$_4$OH. Detection wavelength 220 nm). Lyophilization afforded N-(bicyclo[1.1.1]pent-1-yl)-4-{[(1S,2R)-2-cyanocyclopropyl]methoxy}-6-[4-(4-methoxy-1H-pyrazolo[3,4-b]pyridin-3-yl)piperidin-1-yl]-1,3,5-triazine-2-carboxamide (Example 173) (15 mg, 17%) as a white solid. LCMS (APCI), m/z 538.5 [M+H]$^+$; $^1$H NMR (400 MHz, DMSO-d$_6$) δ ppm 13.15 (s, 1 H), 9.17 (s, 1 H), 8.32 (d, J=5.2 Hz, 1 H), 7.17 (d, J=6.4 Hz, 1 H), 4.92-4.95 (m, 1 H), 4.68-4.72 (m, 2 H), 4.04-4.06 (m, 1 H), 3.95 (s, 3 H), 3.32-3.34 (m, 2 H), 3.16-3.20 (m, 2 H), 2.45 (s, 1 H), 2.09 (s, 6 H), 1.99-2.05 (m, 2 H), 1.81-1.83 (m, 3 H), 1.27-1.28 (m, 1 H), 1.16-1.17 (m, 1 H).

Example 189 (Scheme E)

Synthesis of 4-(4-{[(4-aminopyrimidin-5-yl)oxy]methyl}piperidin-1-yl)-6-[(1-cyanocyclopropyl)methoxy]-N-(2,2-dimethylpropyl)-1,3,5-triazine-2-carboxamide

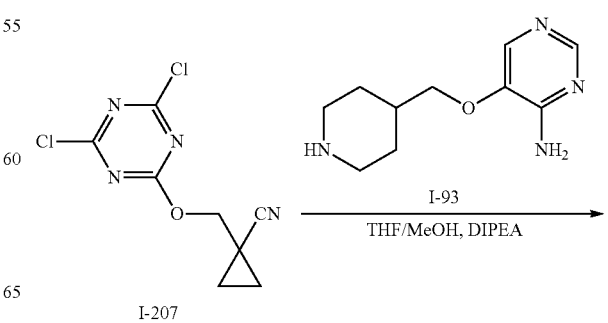

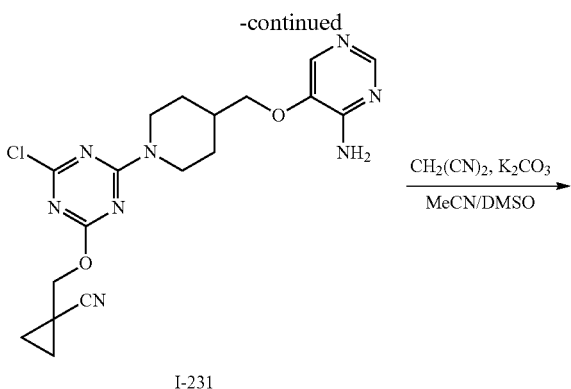

I-231

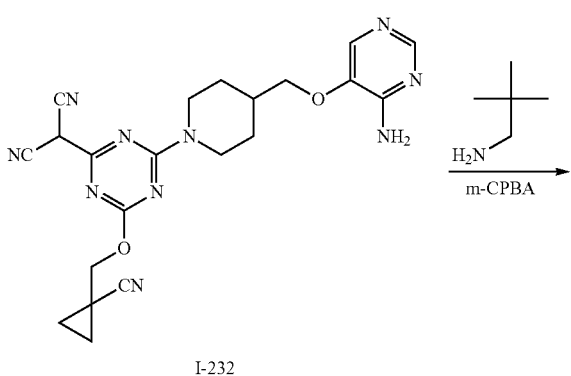

I-232

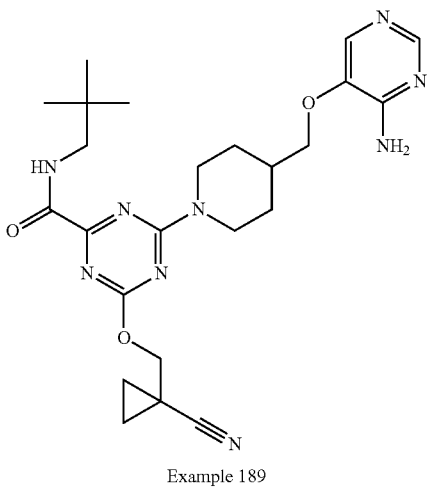

Example 189

Step 1—Synthesis of 1-({[4-(4-{[(4-aminopyrimidin-5-yl)oxy]methyl}piperidin-1-yl)-6-chloro-1,3,5-triazin-2-yl]oxy}methyl)cyclopropanecarbonitrile (I-231)

To a solution of 5-(piperidin-4-ylmethoxy)pyrimidin-4-amine hydrochloride (I-93) (8.0 g, 28.44 mmol, 2 eq HCl) and 1-{[(4,6-dichloro-1,3,5-triazin-2-yl)oxy]methyl}cyclopropanecarbonitrile (I-207) (9.06 g, 37 mmol) in THF (120 mL) and MeOH (30 mL) at 0° C. was added DIPEA (25.3 mL, 142 mmol). The mixture was stirred at 0° C. for 30 min. LCMS indicated that the reaction was complete. The solvent was evaporated, and the residue diluted with EtOAc (100 mL), washed with saturated aq. NH$_4$Cl (3×60 mL), brine (60 mL), dried with anhydrous Na$_2$SO$_4$ and concentrated to give the crude product, which was purified by silica gel chromatography (MeOH:CH$_2$Cl$_2$=8%) to give 1-({[4-(4-{[(4-aminopyrimidin-5-yl)oxy]methyl}piperidin-1-yl)-6-chloro-1,3,5-triazin-2-yl]oxy}methyl)cyclopropanecarbonitrile (I-231) (4.66 g, 39%) as a gray solid. LCMS (APCI), m/z 417.0 [M+H]$^+$; $^1$H NMR (400 MHz, DMSO-d$_6$) δ ppm 7.96 (s, 1 H), 7.77 (s, 1 H), 6.67 (br. s., 2 H), 4.56-4.66 (m, 2 H), 4.31-4.38 (m, 2 H), 3.89 (d, J=6.0 Hz, 2 H), 2.97-3.04 (m, 2 H), 2.08-2.09 (m, 1 H), 1.88-1.91 (m, 2 H), 1.31-1.37 (m, 4 H), 1.19-1.22 (m, 2 H).

Step 2—Synthesis of {4-(4-{[(4-aminopyrimidin-5-yl)oxy]methyl}piperidin-1-yl)-6-[(1-cyanocyclopropyl)methoxy]-1,3,5-triazin-2-yl}propanedinitrile (I-232)

To a solution of malononitrile (31.7 mg 0.48 mmol) in MeCN (5 mL) was added K$_2$CO$_3$ (133 mg, 0.96 mmol). The mixture was stirred at room temperature. (15° C.) for one hr. 1-({[4-(4-{[(4-aminopyrimidin-5-yl)oxy]methyl}piperidin-1-yl)-6-chloro-1,3,5-triazin-2-yl]oxy}methyl)cyclopropanecarbonitrile (I-231) (100 mg, 0.24 mmol) in DMSO (2 mL) was added, and the resulting mixture stirred at room temperature (15° C.) for 16 hr. LCMS showed the reaction was complete. The reaction mixture containing {4-(4-{[(4-aminopyrimidin-5-yl)oxy]methyl}piperidin-1-yl)-6-[(1-cyanocyclopropyl)methoxy]-1,3,5-triazin-2-yl}propanedinitrile (I-232) was used directly in the next step without further purification.

Step 3—Synthesis of 4-(4-{[(4-aminopyrimidin-5-yl)oxy]methyl}piperidin-1-yl)-6-[(1-cyanocyclopropyl)methoxy]-N-(2,2-dimethylpropyl)-1,3,5-triazine-2-carboxamide (Example 189)

To the solution containing {4-(4-{[(4-aminopyrimidin-5-yl)oxy]methyl}piperidin-1-yl)-6-[(1-cyanocyclopropyl)methoxy]-1,3,5-triazin-2-yl}propanedinitrile (I-232) was added 2,2-dimethylpropan-1-amine (83.7 mg, 0.96 mmol) and m-CPBA (331 mg, 85%, 1.92 mmol) at 0° C. MeCN (5 mL) was added, and the resulting mixture was stirred at room temperature (15° C.) for 20 hr. TLC (CH$_2$Cl$_2$:MeOH=12:1) showed the reaction was complete. The reaction mixture was diluted with EtOAc (50 mL), washed with water (40 mL), saturated aq. Na$_2$SO$_3$ (40 mL), saturated aq. NaHCO$_3$ (40 mL), saturated aq. NH$_4$Cl (40 mL), brine (40 mL), dried with anhydrous Na$_2$SO$_4$ and concentrated to give the crude product, which was purified by preparative HPLC to give 4-(4-{[(4-aminopyrimidin-5-yl)oxy]methyl}piperidin-1-yl)-6-[(1-cyanocyclopropyl)methoxy]-N-(2,2-dimethylpropyl)-1,3,5-triazine-2-carboxamide (Example 189) (10.9 mg, 9%) as a white solid. LCMS (APCI), m/z 518.1 [M+Na]$^+$; $^1$H NMR (400 MHz, CDCl$_3$) δ ppm 8.16 (s, 1 H), 7.84 (t, J=6.4 Hz, 1H), 7.74 (s, 1 H), 4.96-5.01 (m, 1 H), 4.81-4.85 (m, 1 H), 4.40 (d, J=12.0 Hz, 1 H), 4.30 (d, J=11.6 Hz, 1 H), 3.86 (d, J=6.4 Hz, 2 H), 3.17-3.19 (m, 2 H), 2.89-2.99 (m, 2 H), 2.10-2.11 (m, 1 H), 1.88-1.91 (m, 2 H), 1.33-1.37 (m, 4 H), 1.11-1.14 (m, 2 H), 0.90 (s, 9 H).

Example 205 (Scheme E)

Synthesis of 4-(4-{[(4-aminopyrimidin-5-yl)oxy]methyl}piperidin-1-yl)-N-(3,3-difluorocyclobutyl)-6-[(2,2-difluorocyclopropyl)methoxy]-1,3,5-triazine-2-carboxamide

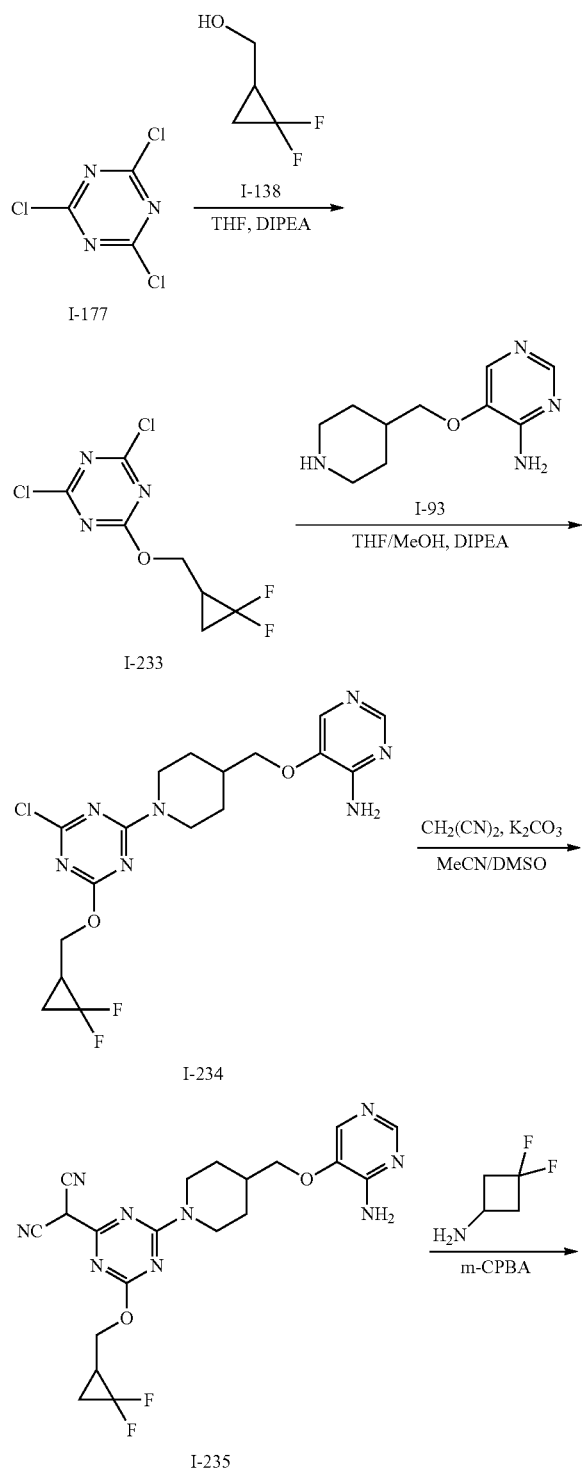

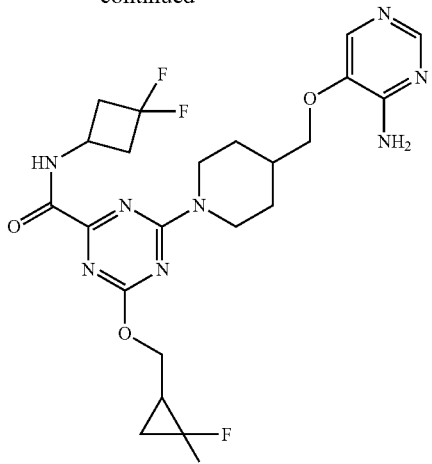

Example 205

Step 1—Synthesis of 2,4-dichloro-6-[(2,2-difluorocyclopropyl)methoxy]-1,3,5-triazine (I-233)

To a mixture of (2,2-difluorocyclopropyl)methanol (I-138) (1.0 g, 9.25 mmol) and cyanuric chloride (I-177) (1.71 g, 9.25 mmol) in anhydrous THF (10 mL) was added slowly in a dropwise manner DIPEA (1.79 g, 13.9 mmol) at 0° C. over 30 min. The mixture was allowed to warm to room temperature and stirred for 16 hr. TLC (petroleum ether/ethyl acetate=10/1, $R_f$=0.7) showed two new spots. The suspension was filtered and the residue concentrated to provide a residue, which was purified by silica gel chromatography (petroleum ether/ethyl acetate=100/0 to 97/3) to give 2,4-dichloro-6-[(2,2-difluorocyclopropyl)methoxy]-1,3,5-triazine (I-233) (1.42 g, 60%) as a colorless oil, which was used without further purification.

Step 2—Synthesis of 5-[(1-{4-chloro-6-[(2,2-difluorocyclopropyl)methoxy]-1,3,5-triazin-2-yl}piperidin-4-yl)methoxy]pyrimidin-4-amine (I-234)

To a suspension of 5-(piperidin-4-ylmethoxy)pyrimidin-4-amine (I-93) (1.16 g, 5.55 mmol) and 2,4-dichloro-6-[(2,2-difluorocyclopropyl)methoxy]-1,3,5-triazine (I-233) (1.42 g, 5.55 mmol) in THF (30 mL) was added slowly in a dropwise manner DIPEA (2.87 g, 22.2 mmol) at 0° C. over 20 min. The suspension was stirred at 0° C. for 30 min. TLC (CH$_2$Cl$_2$/MeOH=10/1, $R_f$=0.65) showed the starting material was completely consumed. MeOH (10 mL) was added, and the reaction became clear. The mixture was concentrated and purified by silica gel chromatography (CH$_2$Cl$_2$/MeOH=100/1 to 50/1) to give 5-[(1-{4-chloro-6-[(2,2-difluorocyclopropyl)methoxy]-1,3,5-triazin-2-yl}piperidin-4-yl)methoxy]pyrimidin-4-amine (I-234) (1.01 g, 42%) as a white solid, which was used without further purification.

Step 3—Synthesis of {4-(4-{[(4-aminopyrimidin-5-yl)oxy]methyl}piperidin-1-yl)-6-[(2,2-difluorocyclopropyl)methoxy]-1,3,5-triazin-2-yl}propanedinitrile (I-235)

To a solution of malononitrile (309 mg 4.67 mmol) in MeCN (20 mL) was added K$_2$CO$_3$ (1.29 g, 9.35 mmol). The mixture was stirred at 15° C. for one hr. 5-[(1-{4-chloro-6-[(2,2-difluorocyclopropyl)methoxy]-1,3,5-triazin-2-yl}piperidin-4-yl)methoxy]pyrimidin-4-amine (I-234) (1.01 g, 2.34 mmol) in MeCN (20 mL) and DMSO (5 mL) was added. The resulting mixture was stirred at 15° C. for 60 hr. LCMS showed the reaction was complete. The reaction mixture was filtered, and the filter cake was washed with MeCN (2×10 mL). The residue was concentrated in vacuo to dryness to give {4-(4-{[(4-aminopyrimidin-5-yl)oxy]methyl}piperidin-1-yl)-6-[(2,2-difluorocyclopropyl)methoxy]-1,3,5-triazin-2-yl}propanedinitrile (I-235), which was used directly in the next step without further purification.

Step 4—Synthesis of 4-(4-{[(4-aminopyrimidin-5-yl)oxy]methyl}piperidin-1-yl)-N-(3,3-difluorocyclobutyl)-6-[(2,2-difluorocyclopropyl)methoxy]-1,3,5-triazine-2-carboxamide (Example 205)

To a solution of {4-(4-{[(4-aminopyrimidin-5-yl)oxy]methyl}piperidin-1-yl)-6-[(2,2-difluorocyclopropyl)methoxy]-1,3,5-triazin-2-yl}propanedinitrile (I-235) (200 mg, 0.44 mmol) in MeCN (20 mL) was added 3,3-difluorocyclobutanamine (140 mg, 1.31 mmol), followed by a single portion of m-CPBA (453 mg, 85%, 2.62 mmol) at 0° C. with stirring. After the addition was completed, the mixture was stirred at ~15° C. for 16 hr. LCMS showed that {4-(4-{[(4-aminopyrimidin-5-yl)oxy]methyl}piperidin-1-yl)-6-[(2,2-difluorocyclopropyl)methoxy]-1,3,5-triazin-2-yl}propanedinitrile was completely consumed. The mixture was poured into water (50 mL), and extracted with EtOAc (3×50 mL). The organic extracts were washed with aq. NaHCO$_3$ (20 mL), aq. Na$_2$SO$_3$ (20 mL), dried over Na$_2$SO$_4$ and concentrated. The residue was purified by silica gel chromatography (CH$_2$Cl$_2$/MeOH=10:1) followed by preparative HPLC (Phenomenex Gemini C18 250×21.2 mm×8 μm eluting with 31% MeCN/water w. NH$_4$OH to 51% MeCN/water w. NH$_4$OH) to give 4-(4-{[(4-aminopyrimidin-5-yl)oxy]methyl}piperidin-1-yl)-N-(3,3-difluorocyclobutyl)-6-[(2,2-difluorocyclopropyl)methoxy]-1,3,5-triazine-2-carboxamide (Example 205) (53.96 mg, 23%) as a colorless solid. LCMS (APCI), m/z 527.2 [M+H]$^+$; $^1$H NMR (400 MHz, DMSO-d$_6$) δ ppm 9.12 (d, J=7.6 Hz, 1 H), 7.99 (s, 1 H), 7.79 (s, 1 H), 6.69 (br. s., 2 H), 4.88 (d, J=12.0 Hz, 1 H), 4.69 (d, J=13.6 Hz, 1 H), 4.53-4.58 (m, 1 H), 4.24-4.29 (m, 2 H), 3.91 (d, J=6.0 Hz, 2 H), 2.97-3.03 (m, 2 H), 2.87-2.92 (m, 4 H) 2.23-2.26 (m, 1 H), 2.08-2.13 (m, 1 H), 1.94 (d, J=12.8 Hz, 2 H), 1.73-1.78 (m, 1 H), 1.52-1.57 (m, 1 H), 1.31-1.34 (m, 2 H).

Example 223 (Scheme E)

Synthesis of 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(2,2-difluoropropyl)-1,3,5-triazine-2-carboxamide

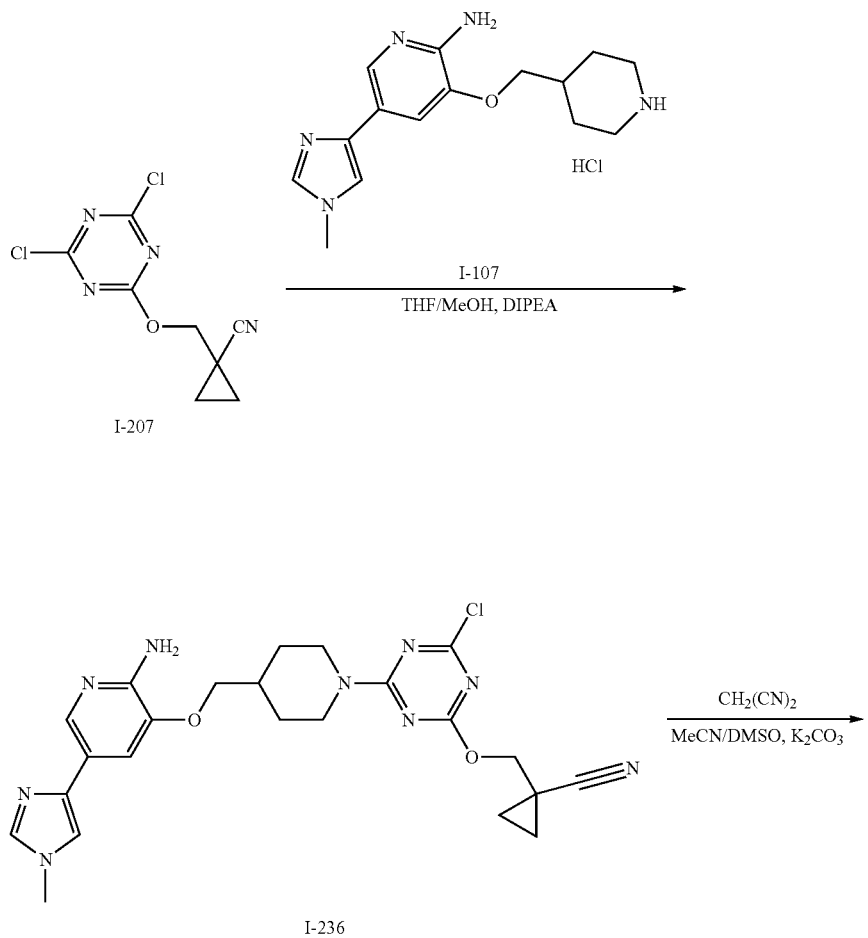

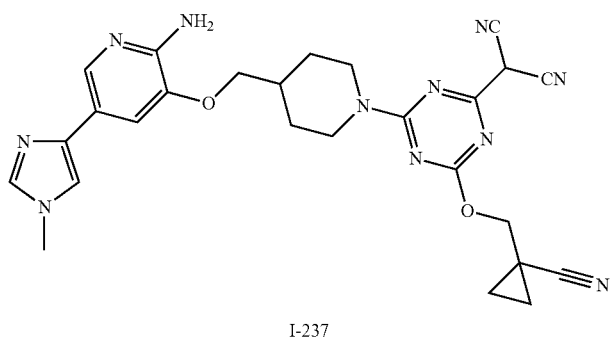

I-237

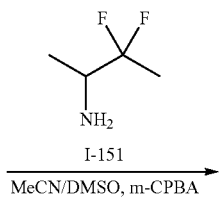

I-151

MeCN/DMSO, m-CPBA

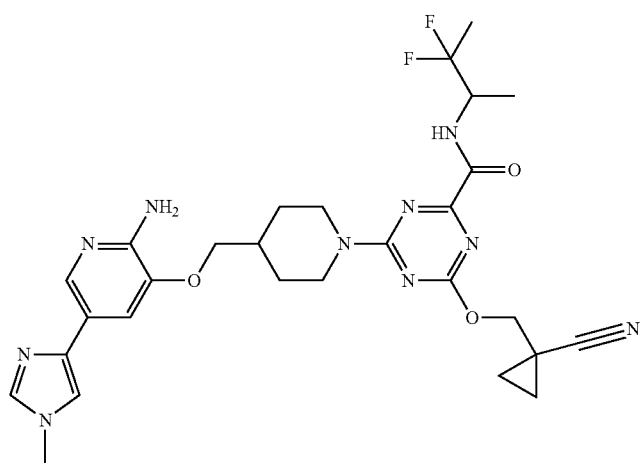

Example 223

Step 1—Synthesis of 1-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-236)

To a solution of 5-(1-methyl-1H-imidazol-4-yl)-3-(piperidin-4-ylmethoxy)pyridin-2-amine hydrochloride (I-107) (2.20 g, 5.54 mmol, 3× HCl salt) and 1-{[(4,6-dichloro-1,3,5-triazin-2-yl)oxy]methyl}cyclopropanecarbonitrile (I-207) (2.04 g, 6.65 mmol) in THF (80 mL) and MeOH (20 mL) at 0° C. was added DIPEA (4.93 mL, 27.7 mmol). The mixture was stirred at 0° C. for 30 min. TLC ($CH_2Cl_2$/MeOH=10:1) showed the reaction was complete. The solvent was evaporated. The reaction mixture was diluted with EtOAc (100 mL), washed with saturated aq. $NH_4Cl$ (60 mL×3), brine (60 mL), dried over anhydrous $Na_2SO_4$, and concentrated to give the crude product, which was purified by silica gel chromatography ($CH_2Cl_2$/MeOH=92:8) to give 1-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-236) (2.01 g, 73%) as a gray solid. LCMS (APCI), m/z 518.2 [M+Na]$^+$; $^1$H NMR (400 MHz, DMSO-$d_6$) δ ppm 7.90 (s, 1 H), 7.55 (s, 1 H), 7.42 (s, 1 H), 7.30 (s, 1 H), 5.61 (s, 2 H), 4.58-4.67 (m, 2 H), 4.31-4.38 (m, 2 H), 3.88 (d, J=6.0 Hz, 2 H), 3.64 (s, 3 H), 3.00-3.06 (m, 2 H), 2.12-2.13 (m, 1 H), 1.93-1.95 (m, 2 H), 1.32-1.37 (m, 4 H), 1.20-1.23 (m, 2 H).

Step 2—Synthesis of {4-[4-({[2-amino-5-(1-methyl-1H-imidazol-4-yl)pyridin-3-yl]oxy}methyl)piperidin-1-yl]-6-[(1-cyanocyclopropyl)methoxy]-1,3,5-triazin-2-yl}propanedinitrile (I-237)

To a colorless solution of malononitrile (320 mg, 4.84 mmol) in MeCN (25 mL) was added $K_2CO_3$ (1.34 g, 9.68 mmol) at 25° C. The white reaction suspension was stirred at 25° C. for one hr. 1-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile (I-236) (1.20 g, 2.42 mmol) in DMSO (40 mL) was added. The resulting brown suspension was stirred at 25° C. for 20 hr. LCMS showed that the 1-[({4-[4-({[2-amino-5-(1-methyl-1H-imidazol-4-yl)pyridin-3-yl]oxy}methyl)piperidin-1-yl]-6-chloro-1,3,5-triazin-2-yl}oxy)methyl]cyclopropanecarbonitrile had been consumed, and the major peak displayed the desired mass of the product. The brown suspension was filtered and concentrated. The residue was purified by silica gel chromatography (MeOH:$CH_2Cl_2$=0% to 15%) to give {4-[4-({[2-amino-5-(1-methyl-1H-imidazol-4-yl)pyridin-3-yl]oxy}methyl)piperidin-1-yl]-6-[(1-cyanocyclopropyl)methoxy]-1,3,5-triazin-2-yl}propanedinitrile (I-237) (1.20 g, 94.%) as a yellow solid, which was used without further purification.

Step 3—Synthesis of 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(3,3-difluorobutan-2-yl)-1,3,5-triazine-2-carboxamide (Example 223)

To a brown suspension of {4-[4-({[2-amino-5-(1-methyl-1H-imidazol-4-yl)pyridin-3-yl]oxy}methyl)piperidin-1-yl]-6-[(1-cyanocyclopropyl)methoxy]-1,3,5-triazin-2-yl}propanedinitrile (I-237) (180 mg, 0.342 mmol) in MeCN (10 mL) and DMSO (1 mL) was added 3,3-difluorobutan-2-amine (I-151) (173 mg, 0.514 mmol) at 25° C. Then m-CPBA (695 mg, 85%, 3.04 mmol) was added at 0° C. The suspension changed to brown solution. The resulting brown solution was stirred at 25° C. for 20 hr. LCMS showed that {4-[4-({[2-amino-5-(1-methyl-1H-imidazol-4-yl)pyridin-3-yl]oxy}methyl)piperidin-1-yl]-6-[(1-cyanocyclopropyl)methoxy]-1,3,5-triazin-2-yl}propanedinitrile had been consumed and the major peak displayed the desired mass of the product. The reaction mixture was diluted with EtOAc (50 mL), washed with water (40 mL), saturated aq. Na$_2$SO$_3$ (40 mL), saturated aq. NaHCO$_3$ (40 mL), saturated aq. NH$_4$Cl (40 mL), brine (40 mL), dried over anhydrous Na$_2$SO$_4$ and concentrated to give the crude product (200 mg, 56% purity in LCMS), which was further purified by preparative HPLC (Agella Durashell C-18 250×21.2 mm×5 μm, eluting with from 24% MeCN/H$_2$O @ pH=10 to 44% MeCN/H$_2$O @ pH=10) to give 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(3,3-difluorobutan-2-yl)-1,3,5-triazine-2-carboxamide (Example 223) (30.28 mg, 15%) as a white solid. LCMS (APCI), m/z 583.3 [M+H]$^+$; $^1$H NMR (400 MHz, DMSO-d$_6$) δ ppm 9.05 (t, J=6.8 Hz, 1 H), 7.90 (d, J=1.2 Hz, 1 H), 7.57 (s, 1 H), 7.43 (s, 1 H), 7.32 (s, 1 H), 5.64 (br. s., 2 H), 4.91 (d, J=12.4 Hz, 1 H), 4.72 (d, J=11.2 Hz, 1 H), 4.38-4.41 (m, 2 H), 3.90 (d, J=5.6 Hz, 2 H), 3.67-3.69 (m, 1 H), 3.64 (s, 3 H), 3.00-3.05 (m, 2 H), 2.14-2.18 (m, 1 H), 1.97 (d, J=12.0 Hz, 2 H), 1.60 (t, J=18.8 Hz, 3 H), 1.35-1.38 (m, 4 H), 1.21-1.24 (m, 2 H).

Example 234 (Scheme E)

Synthesis of 4-[4-({[2-amino-5-(1-methyl-1H-imidazol-4-yl)pyridin-3-yl]oxy}methyl)piperidin-1-yl]-6-[(1-cyanocyclopropyl)methoxy]-N-[(2S)-1,1,1-trifluoropropan-2-yl]-1,3,5-triazine-2-carboxamide

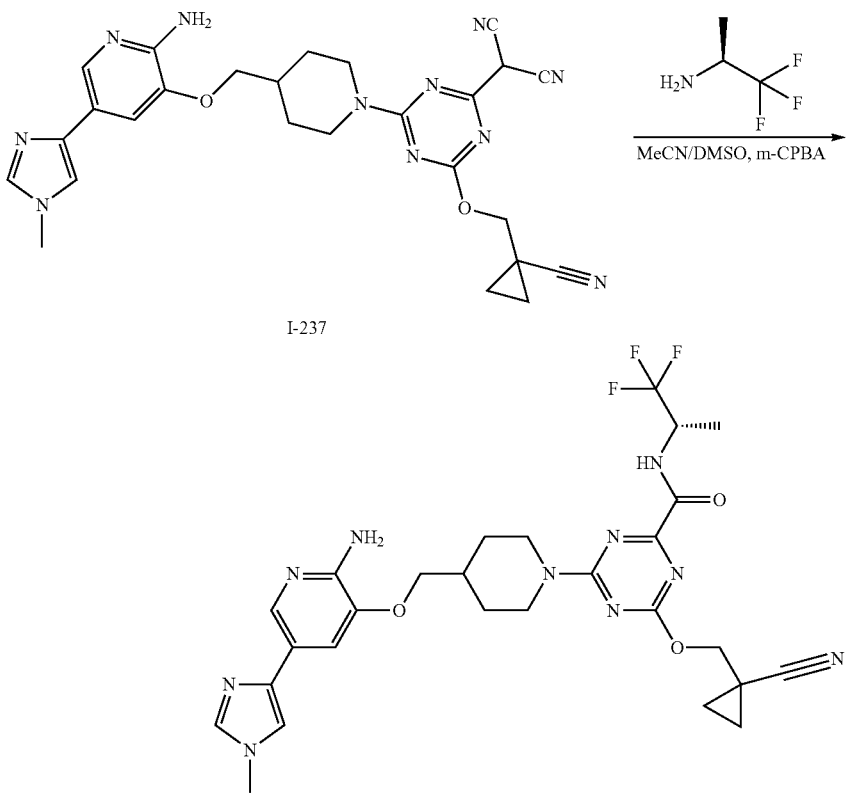

Example 234

Step 1—Synthesis of 4-[4-({[2-amino-5-(1-methyl-1H-imidazol-4-yl)pyridin-3-yl]oxy}methyl)piperidin-1-yl]-6-[(1-cyanocyclopropyl)methoxy]-N-[(2S)-1,1,1-trifluoropropan-2-yl]-1,3,5-triazine-2-carboxamide (Example 234)

To a brown solution of {4-[4-({[2-amino-5-(1-methyl-1H-imidazol-4-yl)pyridin-3-yl]oxy}methyl)piperidin-1-yl]-6-[(1-cyanocyclopropyl)methoxy]-1,3,5-triazin-2-yl}propanedinitrile (I-237) (160 mg, 0.30 mmol) in MeCN (10 mL) and DMSO (1 mL) was added (2S)-1,1,1-trifluoropropan-2-amine (170 mg, 0.913 mmol) at 25° C. Then m-CPBA (618 mg, 85%, 3.04 mmol) was added at 0° C. The solution turned to a brown suspension, which was stirred at 25° C. for 20 hr. LCMS showed that {4-[4-({[2-amino-5-(1-methyl-1H-imidazol-4-yl)pyridin-3-yl]oxy}methyl)piperidin-1-yl]-6-[(1 -cyanocyclopropyl)methoxy]-1,3,5-triazin-2-yl}propanedinitrile had been consumed and the major peak displayed the desired mass of the product. The reaction mixture was diluted with EtOAc (50 mL), washed with water (40 mL), saturated aq. Na$_2$SO$_3$ (40 mL), saturated aq. NaHCO$_3$ (40 mL), saturated aq. NH$_4$Cl (40 mL), brine (40 mL), dried over anhydrous Na$_2$SO$_4$ and concentrated to give the crude product, which was purified by silica gel chromatography (MeOH:CH$_2$Cl$_2$=0%~10% ( ) to give the desired product (90 mg, 57% purity by LCMS), which was further purified by preparative HPLC ((Agella Durashell C-18 250×21.2 mm×5 μm, eluting with from 32% MeCN/H$_2$O @ pH=10 to 52% MeCN/H$_2$O@ pH=10) to give 4-[4-({[2-amino-5-(1-methyl-1H-imidazol-4-yl)pyridin-3-yl]oxy}methyl)piperidin-1-yl]-6-[(1-cyanocyclopropyhmethoxy]-N-[(2S)-1,1,1-trifluoropropan-2-yl]-1,3,5-triazine-2-carboxamide (Example 234) (29.23 mg, 16%) as a white solid. LCMS (APCI), m/z 601.1 [M+H]$^+$; $^1$H NMR (400 MHz, DMSO-d$_6$) δ ppm 9.09 (d, J=9.2 Hz, 1 H), 7.92 (s, 1 H), 7.56 (s, 1 H), 7.44 (s, 1H), 7.32 (s, 1 H), 5.63 (s, 2 H), 4.86 (d, J=10.8 Hz, 1 H), 4.73 (d, J=13.6 Hz, 2 H), 4.42-4.46 (m, 2 H), 3.90-3.92 (m, 2 H), 3.65 (s, 3 H), 3.01-3.09 (m, 2 H), 2.14-2.17 (m, 1 H), 1.99 (d, J=11.6 Hz, 2 H), 1.63 (t, J=19.2 Hz, 3 H), 1.33-1.39 (m, 7 H), 1.23-1.25 (m, 2 H).

Example 244 (Scheme E)

Synthesis of 4-{[(2R)-5,5-dimethyltetrahydrofuran-2-yl]methoxy}-N-[(2R)-1-hydroxypropan-2-yl]-6-[4-(1H-pyrazolo[3,4-b]pyridin-3-yl)piperidin-1-yl]-1,3,5-triazine-2-carboxamide

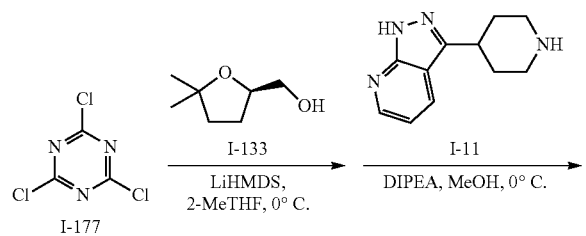

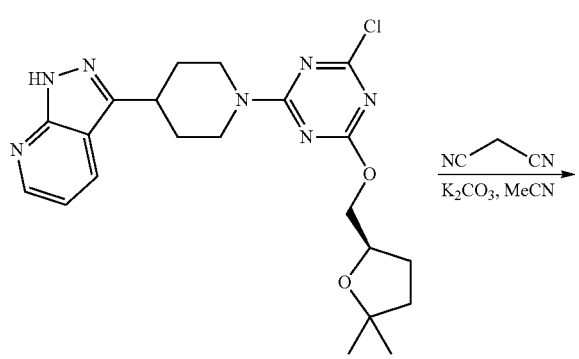

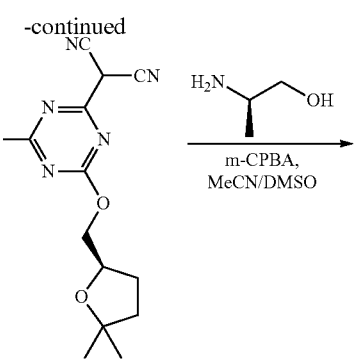

I-239

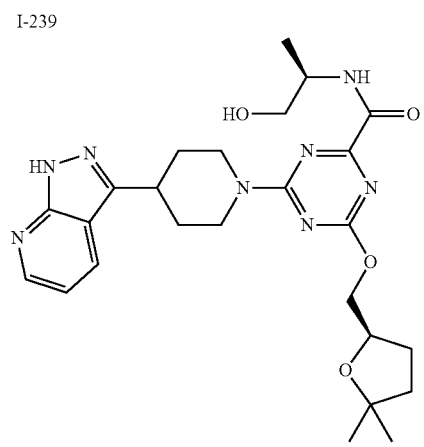

Example 244

Step 1—Synthesis 3-[1-(4-chloro-6-{[(2R)-5,5-dimethyltetrahydrofuran-2-yl]methoxy}-1,3,5-triazin-2-yl)piperidin-4-yl]-1H-pyrazolo[3,4-b]pyridine (I-238)

To a colorless solution of [(2R)-5,5-dimethyltetrahydrofuran-2-yl]methanol (I-133) (150 mg, 1.15 mmol) and cyanuric chloride (I-177) (212 mg, 1.15 mmol) in dry 2-MeTHF (5 mL) was added in a dropwise manner LiHMDS (1.09 mL, 1 M in THF, 1.09 mmol) at 0° C. The reaction mixture turned to give a light yellow solution. The mixture was stirred at 0° C. for one hr. 3-(piperidin-4-yl)-1H-pyrazolo[3,4-b]pyridine dihydrochloride (I-11) (285 mg, 1.04 mmol) was added followed by DIPEA (0.602 mL, 3.46 mmol) and MeOH (2 mL). The reaction mixture turned to a brown suspension. 3-(piperidin-4-yl)-1H-pyrazolo[3,4-b]pyridine dihydrochloride doesn't dissolve completely. After stirring for another hr at 25° C., LCMS showed the major peak to have the desired mass of the product. The solvent was evaporated. The residue was purified by silica gel chromatography (MeOH:CH$_2$Cl$_2$=0%~5%) to give 3-[1-(4-chloro-6-{[(2R)-5,5-dimethyltetrahydrofuran-2-yl]methoxy}-1,3,5-triazin-2-yl)piperidin-4-yl]-1H-pyrazolo[3,4-b]pyridine (I-238) (180 mg, 35%) as a white solid, which was used without further purification.

Step 2—Synthesis of (4-{[(2R)-5,5-dimethyltetrahydrofuran-2-yl]methoxy}-6-[4-(1H-pyrazolo[3,4-b]pyridin-3-yl)piperidin-1-yl]-1,3,5-triazin-2-yl)propanedinitrile (I-239)

To a colorless solution of malononitrile (53.6 mg, 0.81 mmol) in MeCN (3 mL) was added K$_2$CO$_3$ (224 mg, 1.62 mmol) at 25° C. The white suspension was stirred at 25° C. for one hr. 3-[1-(4-chloro-6-{[(2R)-5,5-dimethyltetrahydrofuran-2-yl]methoxy}-1,3,5-triazin-2-yl)piperidin-4-yl]-1H-pyrazolo[3,4-b]pyridine (I-238) (180 mg, 0.41 mmol) in DMSO (5 mL) was added. The resulting brown suspension was stirred at 25° C. for 28 hr. LCMS showed the starting material had been consumed with the major peak displaying the mass of the desired product. The brown suspension was filtered and concentrated to give crude (4-{[(2R)-5,5-dimethyltetrahydrofuran-2-yl]methoxy}-6-[4-(1H-pyrazolo[3,4-b]pyridin-3-yl)piperidin-1-yl]-1,3,5-triazin-2-yl)propanedinitrile (I-239) (220 mg) as a brown gum, which was used in the next step without further purification.

Step 3—Synthesis of 4-{[(2R)-5,5-dimethyltetrahydrofuran-2-yl]methoxy}-N-[(2R)-1-hydroxypropan-2-yl]-6-[4-(1H-pyrazolo[3,4-b]pyridin-3-yl)piperidin-1-yl]-1,3,5-triazine-2-carboxamide To a yellow suspension of (4-{[(2R)-5,5-dimethyltetrahydrofuran-2-yl]methoxy}-6-[4-(1H-pyrazolo[3,4-b]pyridin-3-yl)piperidin-1-yl]-1,3,5-triazin-2-yl)propanedinitrile (I-239) (192 mg, 0.405 mmol) in MeCN (10 mL) and DMSO (1 mL) was added (2R)-2-aminopropan-1-ol (91.4 mg, 1.22 mmol) at 25° C. The reaction mixture turned to give a light yellow solution. m-CPBA (823 mg, 85%, 4.05 mmol) was added at 0° C. The resulting light yellow solution was stirred at 25° C. for 20 hr. LCMS showed the starting material had been consumed with the major peak displaying the mass of the desired product. The reaction mixture was diluted with EtOAc (50 mL), washed with water (40 mL), saturated aq. Na$_2$SO$_3$ (40 mL), saturated aq. NaHCO$_3$ (40 mL), saturated aq. NH$_4$Cl (40 mL), brine (40 mL), dried with anhydrous Na$_2$SO$_4$ and concentrated to give the crude product (210 mg, 86%), which was further purified by preparative HPLC (Agella Durashell C-18 250×21.2 mm×5 μm, eluting with 20% MeCN/H$_2$O @ pH 10 to 40% MeCN/H$_2$O @ pH 10) to give 4-{[(2R)-5,5-dimethyltetrahydrofuran-2-yl]methoxy}-N-[(2R)-1-hydroxypropan-2-yl]-6-[4-(1H-pyrazolo[3,4-b]pyridin-3-yl)piperidin-1-yl]-1,3,5-triazine-2-carboxamide (Example 244) (90.72 mg, 44%) as a white solid. LCMS (APCI), m/z 511.3 [M+H]$^+$; $^1$H NMR (400 MHz, DMSO-d$_6$) δ ppm 13.29 (s, 1 H), 8.48 (d, J=4.4 Hz, 1H), 8.30-8.35 (m, 2 H), 7.14 (t, J=4.4 Hz, 1 H), 4.84-4.91 (m, 2 H), 4.72-4.73 (m, 1 H), 4.23-4.31 (m, 3 H), 3.93-3.95 (m, 1 H), 3.37-3.45 (m, 3 H), 3.12-3.15 (m, 2 H), 2.10-2.14 (m, 3 H), 1.71-1.77 (m, 5 H), 1.18 (d, J=9.6 Hz, 6 H), 1.13 (d, J=6.8 Hz, 3 H).

Example 245 (Scheme E)

Synthesis of 4-{[(2R)-5,5-dimethyltetrahydrofuran-2-yl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide

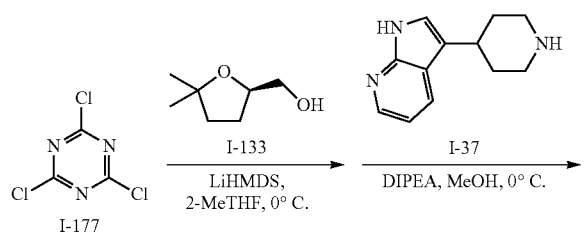

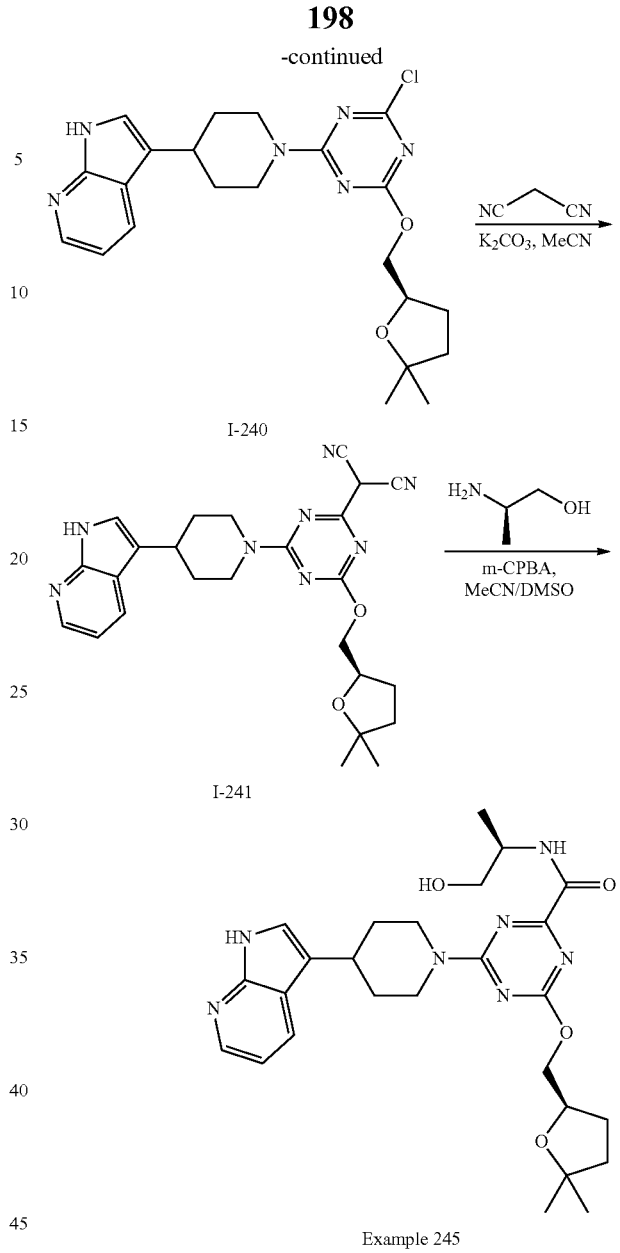

Step 1—Synthesis of 3-[1-(4-chloro-6-{[(2R)-5,5-dimethyltetrahydrofuran-2-yl]methoxy}-1,3,5-triazin-2-yl)piperidin-4-yl]-1H-pyrrolo[2,3-b]pyridine (I-240)

To a colorless solution of [(2R)-5,5-dimethyltetrahydrofuran-2-yl]methanol (I-133) (150 mg, 1.15 mmol) and cyanuric chloride (I-177) (212 mg, 1.15 mmol) in anhydrous 2-MeTHF (5 mL) was added in a dropwise fashion LiHMDS (1.09 mL, 1.0M in THF, 1.09 mmol) at 0° C. The reaction mixture turned to give a light yellow solution. The mixture was stirred at 0° C. for one hr. 3-(piperidin-4-yl)-1H-pyrrolo[2,3-b]pyridine dihydrochloride (I-37) (280 mg, 1.04 mmol) was added followed by DIPEA (0.602 mL, 3.46 mmol) and MeOH (2 mL). The reaction mixture turned to a yellow suspension, and it was observed that the 3-(piperidin-4-yl)-1H-pyrrolo[2,3-b]pyridine dihydrochloride didn't dissolve completely. The reaction mixture was stirred at 0° C. for a further hr. LCMS showed the starting material had been consumed with the major peak displaying the mass of the desired product. The solvent was evaporated. The residue was purified by silica gel chromatography (MeOH:CH$_2$Cl$_2$=0%~5%) to give 3-[1-(4-chloro-6-{[(2R)-5,5-dimethyltetrahydrofuran-2-yl]methoxy}-1,3,5-triazin-2-yl)piperidin-4-yl]-1H-pyrrolo[2,3-b]pyridine (I-240) (150 mg, 29%) as a white solid.

Step 2—Synthesis of (4-{[(2R)-5,5-dimethyltetrahydrofuran-2-yl]methoxy}-6-[4-(1H-pyrrolo[2,3-b]pyridin-3-yl)piperidin-1-yl]-1,3,5-triazin-2-yl)propanedinitrile (I-241)

To a colorless solution of malononitrile (44.7 mg, 0.61 mmol) in MeCN (3 mL) was added K$_2$CO$_3$ (187 mg, 1.21 mmol) at 25° C. The resulting white suspension was stirred at 25° C. for one hr. 3-[1-(4-chloro-6-{[(2R)-5,5-dimethyltetrahydrofuran-2-yl]methoxy}-1,3,5-triazin-2-yl)piperidin-4-yl]-1H-pyrrolo[2,3-b]pyridine (I-240) (150 mg, 0.34 mmol) in DMSO (5 mL) was added. The resulting brown suspension was stirred at 25° C. for 28 hr. LCMS showed the starting material had been consumed with the major peak displaying the mass of the desired product. The brown suspension was filtered and concentrated to give the crude (4-{[(2R)-5,5-dimethyltetrahydrofuran-2-yl]methoxy}-6-[4-(1H-pyrrolo[2,3-b]pyridin-3-yl)piperidin-1-yl]-1,3,5-triazin-2-yl)propanedinitrile (I-241) (180 mg) as brown gum, which was used in the next step without further purification.

Step 3—Synthesis of 4-{[(2R)-5,5-dimethyltetrahydrofuran-2-yl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide (Example 245)

To a brown suspension of (4-{[(2R)-5,5-dimethyltetrahydrofuran-2-yl]methoxy}-6-[4-(1H-pyrrolo[2,3-b]pyridin-3-yl)piperidin-1-yl]-1,3,5-triazin-2-yl)propanedinitrile (I-241) (160 mg, 0.34 mmol) in MeCN (10 mL) and DMSO (1 mL) was added (2R)-2-aminopropan-1-ol (76.3 mg, 1.02 mmol) at 25° C. The reaction mixture turned to give a brown solution. Then m-CPBA (687 mg, 85%, 3.39 mmol) was added at 0° C. The resulting light yellow solution was stirred at 25° C. for 20 hr. LCMS showed the starting material had been consumed with the major peak displaying the mass of the desired product. The reaction mixture was diluted with EtOAc (50 mL), washed with water (40 mL), saturated aq. Na$_2$SO$_3$ (40 mL), saturated aq. NaHCO$_3$ (40 mL), saturated aq. NH$_4$Cl (40 mL), brine (40 mL), dried over anhydrous Na$_2$SO$_4$ and concentrated to give crude product (152 mg, 55% purity in LCMS), which was purified by preparative HPLC (Agella Durashell C-18 250×21.2 mm×5 μm, eluting with 26% MeCN/H$_2$O @ pH 10 to 46% MeCN/H$_2$O @ pH 10) to give 4-{[(2R)-5,5-dimethyltetrahydrofuran-2-yl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide (Example 245) (41.55 mg, 24%) as a white solid. LCMS (APCI), m/z 532.2 [M+Na]; $^1$H NMR (400 MHz, DMSO-d$_6$) δ ppm 11.38 (s, 1 H), 8.31 (d, J=8.4 Hz, 1 H), 8.19 (d, J=3.6 Hz, 1 H), 8.04 (d, J=7.6 Hz, 1 H), 7.26 (s, 1 H), 7.03 (t, J=4.8 Hz, 1 H), 4.90-4.93 (m, 1 H), 4.83-4.86 (m, 2 H), 4.24-4.31 (m, 3 H), 3.93-3.95 (m, 1 H), 3.37-3.45 (m, 2 H), 3.12-3.15 (m, 3 H), 2.07-2.09 (m, 3 H), 1.66-1.77 (m, 5 H), 1.19 (d, J=10.0 Hz, 6 H), 1.13 (d, J=6.8 Hz, 3 H).

Example 272 (Scheme D)

Synthesis of 6-[4-({[2-amino-5-(1-methyl-1H-imidazol-4-yl)pyridin-3-yl]oxy}methyl)piperidin-1-yl]-N-[(2R)-1-hydroxypropan-2-yl]-2-[(2R)-tetrahydrofuran-2-ylmethoxy]pyrimidine-4-carboxamide

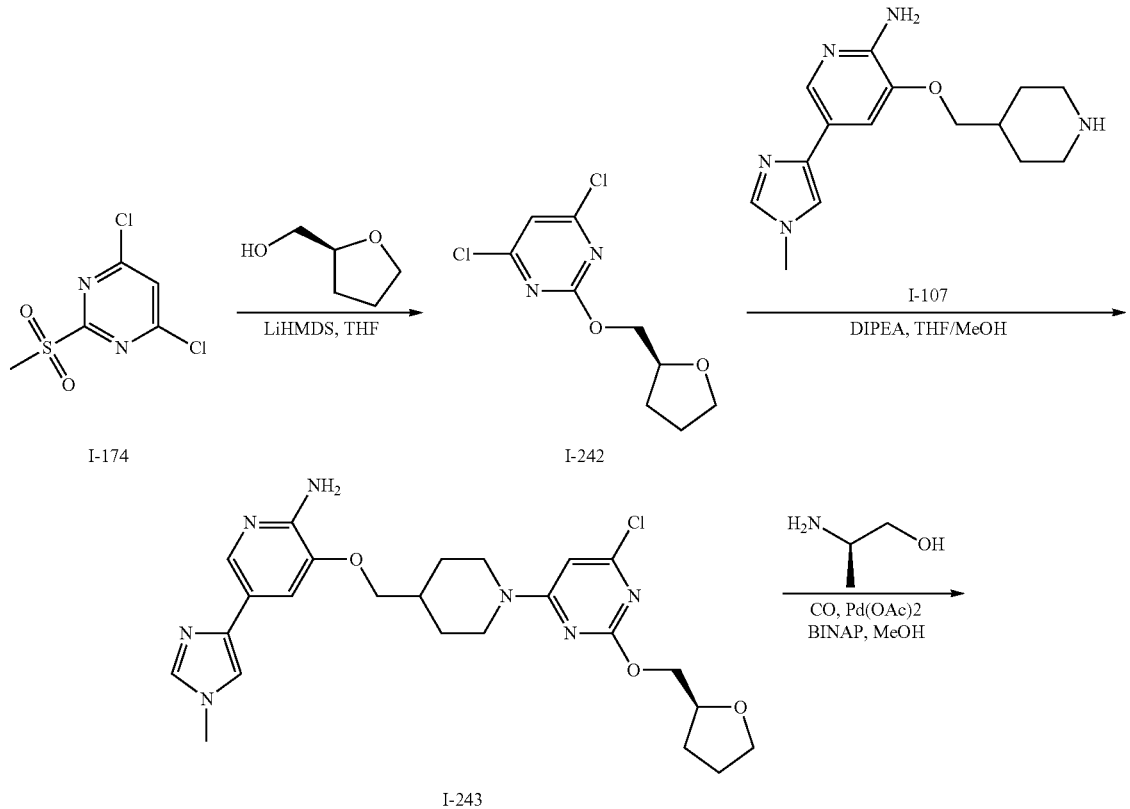

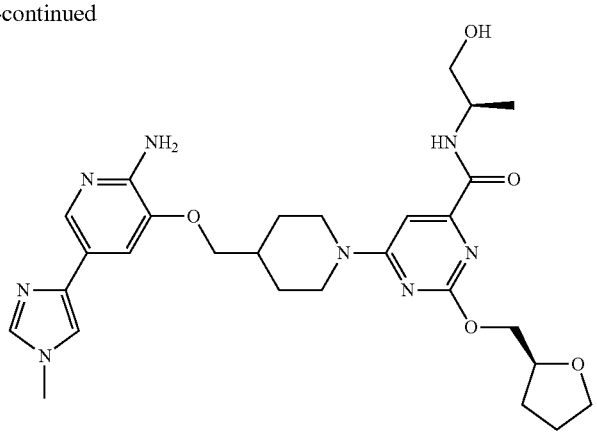

Example 272

Step 1—Synthesis of 4,6-dichloro-2-[(2R)-tetrahydrofuran-2-ylmethoxy]pyrimidine (I-242)

To an ice-bath cooled clear solution of 2,4-dichloro-6-(methylsulfonyl)pyrimidine (I-174) (200 mg, 0.88 mmol) and (2R)-tetrahydrofuran-2-ylmethanol (90 mg, 0.88 mmol) in THF (5 mL) was added in a dropwise fashion LiHMDS (0.969 mL, 1M in THF, 0.97 mmol) over 1 minute. The resultant light yellow suspension was allowed to stir at 0° C. for an additional 10 min. The ice-bath was removed and the mixture was allowed to warm to room temperature (25° C.), and stirred for 2 hr. TLC (hexanes:EtOAc=5:1) indicated the starting material had been completely consumed. The mixture was concentrated and taken up in EtOAc (20 mL), washed with sat aq. NH$_4$Cl (10 mL), and brine (10 mL). The organic layer was dried over Na$_2$SO$_4$, filtered and concentrated to give 4,6-dichloro-2-[(2R)-tetrahydrofuran-2-ylmethoxy]pyrimidine (I-242) (120 mg, 55%) as light yellow oil, which was used without further purification.

Step 2—Synthesis of 3-[(1-{6-chloro-2-[(2R)-tetrahydrofuran-2-ylmethoxy]pyrimidin-4-yl}piperidin-4-yl)methoxy]-5-(1-methyl-1H-imidazol-4-yl)pyridin-2-amine (I-243)

To a light yellow suspension of 4,6-dichloro-2-[(2R)-tetrahydrofuran-2-ylmethoxy]pyrimidine (I-242) (120 mg, 0.48 mmol) and 5-(1-methyl-1H-imidazol-4-yl)-3-(piperidin-4-ylmethoxy)pyridin-2-amine dihydrochloride (I-107) (176 mg, 0.484 mmol) in MeOH (5 mL) was added slowly DIPEA (217 mg, 1.68 mmol) at 0° C. The clear light yellow reaction mixture was stirred at room temperature (25° C.) for 16 hr. TLC (hexanes:EtOAc=5:1) showed the starting material had been consumed completely. The mixture was concentrated in vacuo and diluted with 20 mL EtOAc. The organic extract was washed with sat.aq.NH$_4$Cl (10 mL), H$_2$O (10 mL) and brine (10 mL), dried over Na$_2$SO$_4$ and concentrated. The light yellow residue was purified by silica gel chromatography (MeOH/CH$_2$Cl$_2$=0~10%, 20 CV) to give 3-[(1-{6-chloro-2-[(2R)-tetrahydrofuran-2-ylmethoxy]pyrimidin-4-yl}piperidin-4-yl)methoxy]-5-(1-methyl-1H-imidazol-4-yl)pyridin-2-amine (I-243) (140 mg, 58%) as a light yellow solid.

Step 3—Synthesis of 6-[4-({[2-amino-5-(1-methyl-1H-imidazol-4-yl)pyridin-3-yl]oxy}methyl)piperidin-1-yl]-N-[(2R)-1-hydroxypropan-2-yl]-2-[(2R)-tetrahydrofuran-2-ylmethoxy]pyrimidine-4-carboxamide (Example 272)

To a solution of 3-[(1-{6-chloro-2-[(2R)-tetrahydrofuran-2-ylmethoxy]pyrimidin-4-yl}piperidin-4-yl)methoxy]-5-(1-methyl-1H-imidazol-4-yl)pyridin-2-amine (I-243) (160 mg, 0.32 mmol), (2R)-2-aminopropan-1-ol (179 mg, 1.6 mmol), DIPEA (207 mg, 1.6 mmol) in MeOH (10 mL placed in a 50 mL stainless steel vessel was added Pd(OAc)$_2$ (3.6 mg, 0.016 mmol) and BINAP (19.9 mg, 0.0320 mmol). Stirring was initiated (900 rpm), and the mixture was purged with Ar (2 Bar) three times followed by CO (1 MPa) three times. The reaction mixture was stirred under 2 MPa of CO pressure and heated to 100° C. for 18 hr. Yellow solids were observed in the reaction mixture, and LCMS indicated that ca. 10% of the starting material was remained and 64% of a product with the desired mass had been formed. The reaction mixture was filtered through a plug of Celite and the filtrate was concentrated. The light yellow crude residue was purified by preparative HPLC to give 6-[4-({[2-amino-5-(1-methyl-1H-imidazol-4-yl)pyridin-3-yl]oxy}methyl)piperidin-1-yl]-N-[(2R)-1-hydroxypropan-2-yl]-2-[(2R)-tetrahydrofuran-2-ylmethoxy]pyrimidine-4-carboxamide (Example 272) (82 mg, 45%) as a white solid. LCMS (APCI), m/z 567.1 [M+H]$^+$; $^1$H NMR (400 MHz, DMSO-d$_6$) δ ppm 8.15 (d, J=8.4 Hz, 1 H), 7.92 (d, J=1.2 Hz, 1 H), 7.55 (s, 1 H), 7.43 (s, 1 H), 7.32 (s, 1 H), 6.99 (s, 1 H), 5.57 (br. s., 2 H), 4.86 (t, J=5.6 Hz, 1 H), 4.35-4.65 (m, 1 H), 4.25-4.38 (m, 2 H), 4.11-4.18 (m, 1 H), 3.92-4.05 (m, 1 H), 3.90 (d, J=6.4 Hz, 2 H), 3.72-3.85 (m, 1 H), 3.60-3.72 (m, 4 H), 3.35-3.48 (m, 2 H), 2.98-3.06 (m, 3 H), 2.08-2.18 (m, 1 H), 1.91-2.05 (m, 2 H), 1.73-1.91 (m, 3 H), 1.62-1.72 (m, 1 H), 1.20-1.38 (m, 2 H), 1.12 (d, J=6.8 Hz, 3 H).

Example 286 (Scheme D)

Synthesis of 6-[4-({[2-amino-5-(1-methyl-1H-imidazol-4-yl)pyridin-3-yl]oxy}methyl)piperidin-1-yl]-N-[(2R)-1-hydroxypropan-2-yl]-2-{[(2R)-1-methoxypropan-2-yl]oxy}pyrimidine-4-carboxamide

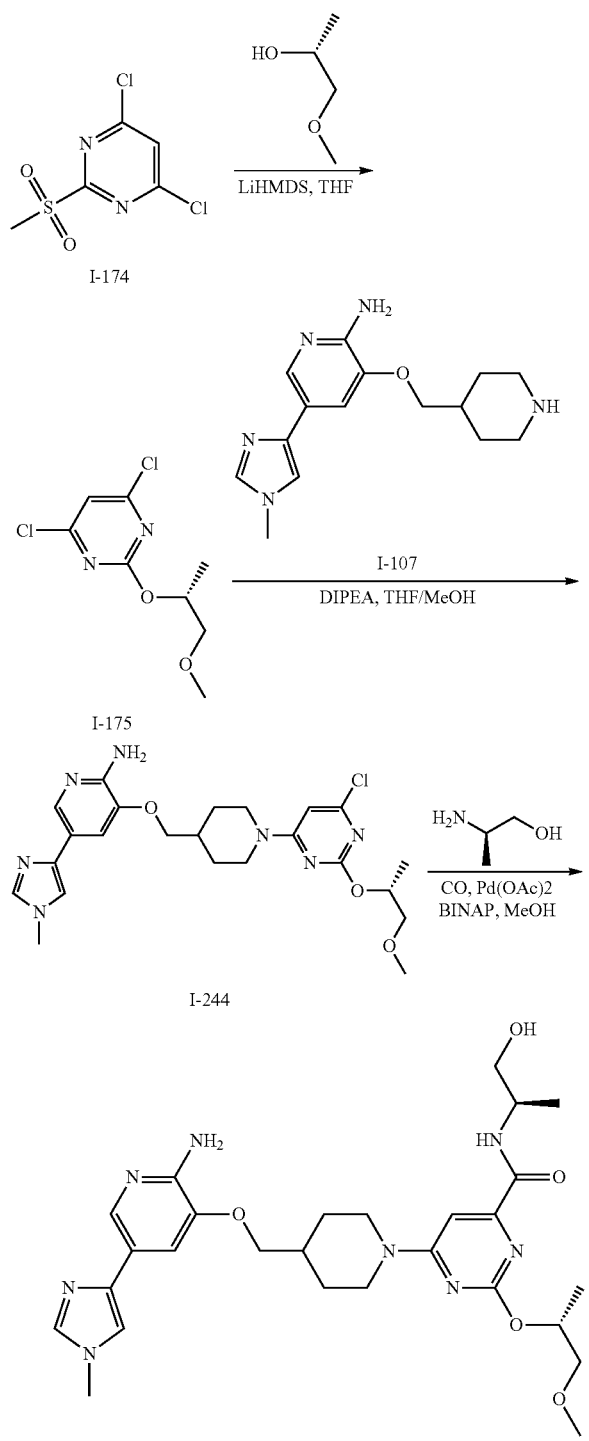

Example 286

Step 1—Synthesis of 4,6-dichloro-2-{[(2R)-1-methoxypropan-2-yl]oxy}pyrimidine (I-175)

To a clear solution of 2,4-dichloro-6-(methylsulfonyl)pyrimidine (I-174) (200 mg, 0.88 mmol) and (2R)-1-methoxypropan-2-ol (79.4 mg, 0.88 mmol) in THF (5 mL) cooled to 0° C. using an ice bath was added in a dropwise manner LiHMDS (0.97 mL, 1M in THF, 0.97 mmol) over 1 minute. The resultant light yellow suspension was allowed to stir at 0° C. for an additional 10 min. The ice-bath was removed and the mixture was allowed to warm to room temperature (25° C.), and stirred for 2 hr. TLC (hexane:EtOAc=5:1) indicated that the 2,4-dichloro-6-(methylsulfonyl)pyrimidine had been completely consumed. The mixture was concentrated, and taken up in EtOAc (20 mL), washed with sat aq. NH$_4$Cl (10 mL) and brine (10 mL). The organic layer was dried over Na$_2$SO$_4$, filtered and concentrated to give 4,6-dichloro-2-{[(2R)-1-methoxypropan-2-yl]oxy}pyrimidine (I-175) (110 mg, 53%) as a light yellow oil, which was used without further purification.

Step 2—Synthesis of 3-{[1-(6-chloro-2-{[(2R)-1-methoxypropan-2-yl]oxy}pyrimidin-4-yl)piperidin-4-yl]methoxy}-5-(1-methyl-1H-imidazol-4-yl)pyridin-2-amine (I-244)

To a light yellow suspension of 4,6-dichloro-2-{[(2R)-1-methoxypropan-2-yl]oxy}pyrimidine (I-175) (110 mg, 0.46 mmol) and 5-(1-methyl-1H-imidazol-4-yl)-3-(piperidin-4-ylmethoxy)pyridin-2-amine dihydrochloride (I-107) (171 mg, 0.46 mmol) in MeOH (5 mL) was slowly added DIPEA (247 mg, 1.91 mmol) at 0° C. Then, the clean light yellow reaction mixture was stirred at room temperature (25° C.) for 16 hr. TLC (hexane:EtOAc=10:1) showed the 4,6-dichloro-2-{[(2R)-1-methoxypropan-2-yl]oxy}pyrimidine had been consumed completely. The mixture was concentrated in vacuo and diluted with EtOAc (20 mL), washed with sat. aq. NH$_4$Cl (10 mL), H$_2$O (10 mL) and brine (10 mL), dried over Na$_2$SO$_4$ and concentrated. The light yellow residue was purified by silica gel chromatography (MeOH/CH$_2$Cl$_2$=0-10%) to give 3-{[1-(6-chloro-2-{[(2R)-1-methoxypropan-2-yl]oxy}pyrimidin-4-yl)piperidin-4-yl]methoxy}-5-(1-methyl-1H-imidazol-4-yl)pyridin-2-amine (I-244) (150 mg, 66%) as a light yellow solid.

Step 3—Synthesis of 44[(2R)-5,5-dimethyltetrahydrofuran-2-yl]methoxy)-N-[(2R)-1-hydroxypropan-2-yl]-6-[4-(1H-pyrrolo[2,3-b]pyridin-3-yl)piperidin-1-yl]-1,3,5-triazine-2-carboxamide (Example 286)

To a solution of 3-{[1-(6-chloro-2-{[(2R)-1-methoxypropan-2-yl]oxy}pyrimidin-4-yl)piperidin-4-yl]methoxy}-5-(1-methyl-1H-imidazol-4-yl)pyridin-2-amine (I-244) (80 mg, 0.16 mmol), (2R)-2-aminopropan-1-ol (61.6 mg, 0.82 mmol), DIPEA (102 mg, 0.164 mmol) in MeOH (10 mL) placed in a 50 mL stainless steel vessel was added Pd(OAc)$_2$ (3.68 mg, 0.0164 mmol) and BINAP (20.4 mg, 0.0328 mmol). Stirring was initiated (900 rpm), and the mixture was purged with Ar (2 Bar) three times followed by CO (1 MPa) three times. The reaction mixture was stirred under 2 MPa of CO pressure and heated to 100° C. for 18 hr. Upon opening the vessel, some yellow solids were observed in the reaction mixture. The reaction mixture was filtered through a plug of Celite and the filtrate was concentrated. The light yellow residue was purified by preparative HPLC to give 6-[4-({[2-amino-5-(1-methyl-1H-imidazol-4-yl)pyridin-3-yl]oxy}methyl)piperidin-1-yl]- N-[(2R)-1-hydroxypropan- 2-yl]-2-{[(2R)-1-methoxypropan-2-yl]oxy}pyrimidine-4-carboxamide (Example 286) (10 mg, 11%) as a white solid. LCMS (APCI), m/z 555.1 [M+H]$^+$; $^1$H NMR (400 MHz, CDCl$_3$) δ ppm 7.94-7.96 (m, 2 H), 7.45 (s, 1 H), 7.09 (s, 1 H), 7.06 (s, 1 H), 5.28-5.34 (m, 1 H), 4.48-4.88 (br. s., 4 H), 4.18-4.21 (m, 1 H), 3.95 (d, J=6.4 Hz, 2 H), 3.55-3.74 (m, 6 H), 3.45-3.55 (m, 1 H), 3.41 (s, 1 H), 2.96-3.03 (m, 2 H), 2.16-2.23 (m, 1 H), 1.93-1.98 (m, 2 H), 1.34-1.41 (m, 5 H), 1.26 (d, J=6.8 Hz, 3 H).

Example 293 (Scheme E)

Synthesis of (1R,2S)-2-[({4-[(3,3-difluoroazetidin-1-yl)carbonyl]-6-[4-(1H-pyrazolo[3,4-b]pyridin-3-yl)piperidin-1-yl]-1,3,5-triazin-2-yl}oxy)methyl]cyclopropanecarbonitrile

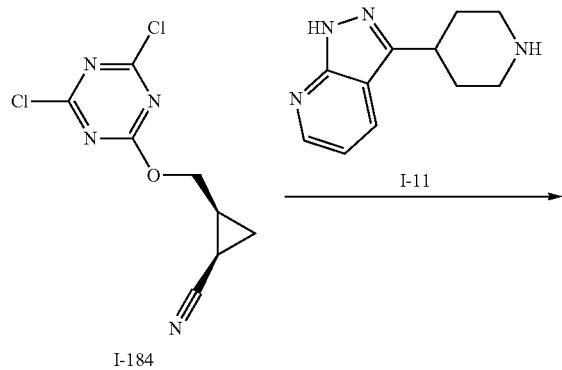

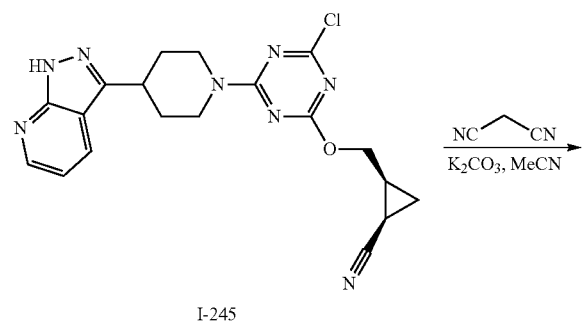

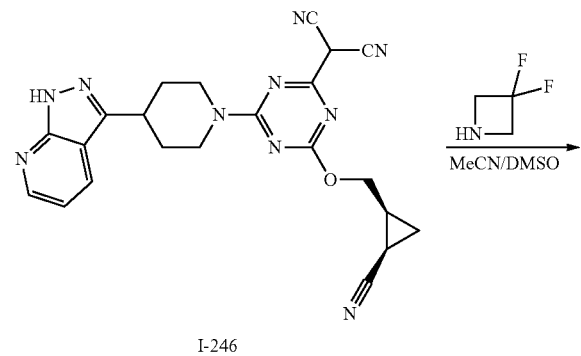

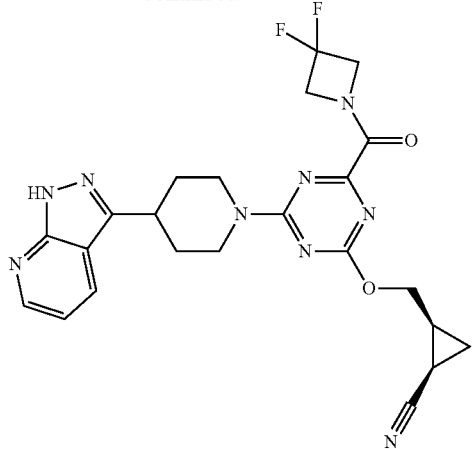

Example 293

Step 1—Synthesis of (1R,2S)-2-[({4-chloro-6-[4-(1H-pyrazolo[3,4-b]pyridin-3-yl)piperidin-1-yl]-1,3,5-triazin-2-yl}oxy)methyl]cyclopropanecarbonitrile (I-245)

To a light yellow ice-bath cooled suspension of (1R,2S)-2-{[(4,6-dichloro-1,3,5-triazin-2-yl)oxy]methyl}cyclopropanecarbonitrile (I-184) (1 g, 85% purity, 3.0 mmol) and 3-(piperidin-4-yl)-1H-pyrazolo[3,4-b]pyridine dihydrochloride (I-11) (955 mg, 3.47 mmol) in THF (10 mL) was added DIPEA (2.24 g, 17.3 mmol). Then MeOH (1 mL) was added, and the reaction mixture was stirred in an ice-water bath for 3 hr. The reaction mixture became a yellow color. TLC (EtOAc/MeOH=10:1, R$_f$~0.5) showed the reaction was complete. The reaction mixture was concentrated, diluted with CH$_2$Cl$_2$ (300 mL), washed with aq NH$_4$Cl (100 mL), brine (100 mL), dried over Na$_2$SO4, and concentrated to give the crude product, which was purified by silica gel chromatography (EtOAc) to give compound (1R,2S)-2-[({4-chloro-6-[4-(1H-pyrazolo[3,4-b]pyridin-3-yl)piperidin-1-yl]-1,3,5-triazin-2-yl}oxy)methyl]cyclopropanecarbonitrile (I-245) (1.1 g, 80%) as a white solid.

Step 2—Synthesis of (4-{[(1S,2R)-2-cyanocyclopropyl]methoxy}-6-[4-(1H-pyrazolo[3,4-b]pyridin-3-yl)piperidin-1-yl]-1,3,5-triazin-2-yl)propanedinitrile (I-246)

To a solution of malononitrile (322 mg, 4.87 mmol) in MeCN (10 mL) was added K$_2$CO$_3$ (1.35 g, 9.74 mmol) at room temperature (25° C.). The white suspension was stirred at room temperature (25° C.) for 1 hr. (1R,2S)-2-[({4-chloro-6-[4-(1H-pyrazolo[3,4-b]pyridin-3-yl)piperidin-1-yl]-1,3,5-triazin-2-yl}oxy)methyl]cyclopropanecarbonitrile (I-245) (1 g, 2 mmol) in DMSO (1.5 mL) was added to the reaction mixture. Upon addition, the reaction mixture immediately gave a pink solution. The reaction mixture was stirred at room temperature (22-26° C.) for 20 hr leading to a pink suspension. TLC (EtOAc/MeOH=10:1, R$_f$~0.1) showed the reaction was completed. The reaction mixture was filtered, and the filtrate was concentrated under high vacuum to give the crude product, which was purified by silica gel chromatography (EtOAc/MeOH=1:0 to 10:1) to give (4-{[(1S,2R)-2-cyanocyclopropyl]methoxy}-6-[4-(1H-pyrazolo[3,4-b]pyridin-3-yl)piperidin-1-yl]-1,3,5-triazin-2- yl)propanedinitrile (I-246) (670 mg, 60%) as a pink solid, which was used without further purification.

Step 3—Synthesis of (1R,2S)-2-[({4-[(3,3-difluoro-azetidin-1-yl)carbonyl]-6-[4-(1H-pyrazolo[3,4-b]pyridin-3-yl)piperidin-1-yl]-1,3,5-triazin-2-yl}oxy)methyl]cyclopropanecarbonitrile (Example 293)

To a cooled (ice-EtOH bath) light yellow suspension of (4-{[(1S,2R)-2-cyanocyclopropyl]methoxy}-6-[4-(1H-pyrazolo[3,4-b]pyridin-3-yl)piperidin-1-yl]-1,3,5-triazin-2-yl)propanedinitrile (I-246) (100 mg, 0.23 mmol) and 3,3-difluoroazetidine (63.4 mg, 0.68 mmol) in MeCN (7 mL) and DMSO (1 mL) was added m-CPPA (392 mg, 85%, 2.27 mmol). The reaction mixture was slowly warmed to room temperature (25° C.), and stirred for 20 hr leading to a slightly yellow suspension. LCMS indicated that the starting material had been completely consumed. The reaction mixture was diluted with EtOAc (60 mL) and washed with aq Na$_2$SO$_3$ (2×20 mL), brine (20 mL), dried over Na$_2$SO$_4$ and concentrated to give the crude product. The residue was purified by silica gel chromatography (EtOAc) to give a yellow solid, which was further purified by preparative HPLC (Agella Durashell C-18 250×21.2 mm×5 μm, eluting with 26% MeCN/H$_2$O @ pH 10 to 46% MeCN/H$_2$O @ pH 10). After concentration in vacuo to remove organic solvents, the residual solution was lyophilized to give (1R,2S)-2-[({4-[(3,3-difluoroazetidin-1-yl)carbonyl]-6-[4-(1H-pyrazolo[3,4-b]pyridin-3-yl)piperidin-1-yl]-1,3,5-triazin-2-yl}oxy)methyl]cyclopropanecarbonitrile (Example 293) (16 mg, 14%) as a white solid. LCMS (APCI), m/z 496.0 [M+H]$^+$; $^1$H NMR (400 MHz, CD$_3$OD) δ ppm 8.50 (d, J=3.6 Hz, 1 H), 8.34 (d, J=7.2 Hz, 1 H), 7.18-7.21 (m, 1 H), 5.04 (t, J=8.4 Hz, 2 H), 4.89-4.93 (m, 2 H), 4.73-4.76 (m, 1 H), 4.54 (t, J=12.0 Hz, 2 H), 4.32-4.33 (m, 1 H), 3.48-3.54 (m, 1 H), 3.37 (s, 1 H), 3.29 (s, 1 H), 2.19-2.22 (m, 2 H), 1.88-2.00 (m, 4 H), 1.36-1.38 (m, 1 H), 1.14-1.16 (m, 1 H).

Example 326 (Scheme D)

Synthesis of 2-{[(2R)-1-methoxypropan-2-yl]oxy}-N-methyl-6-[4-(1H-pyrazolo[3,4-b]pyridin-3-yl)piperidin-1-yl]pyrimidine-4-carboxamide

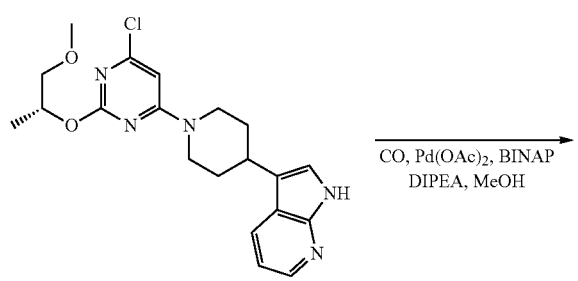

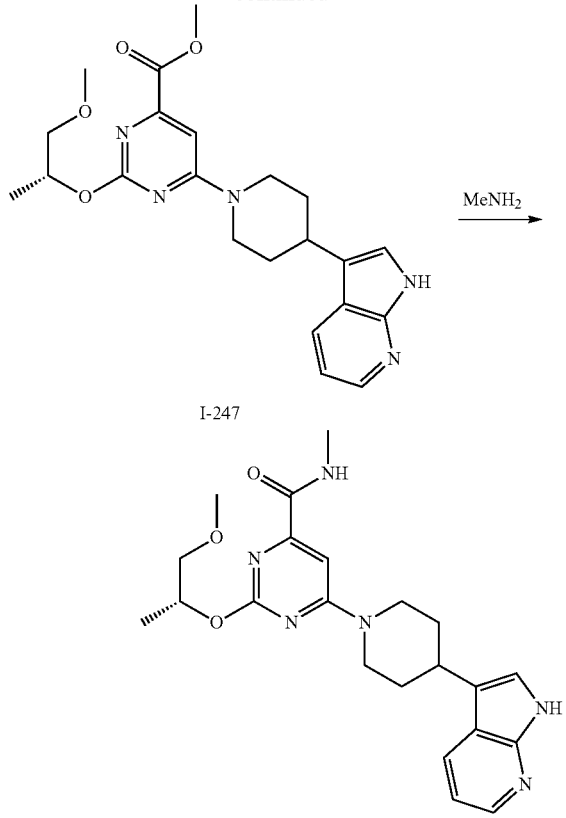

Example 326

Step 1—Synthesis of methyl 2-{[(2R)-1-methoxypropan-2-yl]oxy}-6-[4-(1H-pyrrolo[2,3-b]pyridin-3-yl)piperidin-1-yl]pyrimidine-4-carboxylate (I-247)

To 3-[1-(6-chloro-2-{[(2R)-1-methoxypropan-2-yl]oxy}pyrimidin-4-yl)piperidin-4-yl]-1H-pyrrolo[2,3-b]pyridine (I-181) (5.02 g, 12.5 mmol) in a 100 mL stainless steel vessel was added MeOH (50 mL), DIPEA (4.85 g, 37.5 mmol), racemic BINAP (234 mg, 0.375 mmol) and Pd(OAc)$_2$ trimer (84.2 mg, 0.375 mmol). The vessel was sealed, stirring was initiated (900 rpm) and after three 1.5 to 4 bar purges of nitrogen, the reaction was pressurized under 8 Bar of CO and was left for 18 h at 100° C. After 18 h, the chamber was de-pressurized and purged with three 1.5 to 4 bar purges of nitrogen the reaction was filtered through celite, concentrated and purified by chromatography on silica gel (2% EtOH in EtOAc) to give methyl 2-{[(2R)-1-methoxypropan-2-yl]oxy}-6-[4-(1H-pyrrolo[2,3-b]pyridin-3-yl)piperidin-1-yl]pyrimidine-4-carboxylate (I-247) (2.84 g, 54%) as a yellow foam. LCMS (APCI), m/z 425.8 [M+H]$^+$; $^1$H NMR (400 MHz, DMSO-d$_6$) δ ppm 11.34 (br. s., 1 H), 8.18 (dd, J=4.52, 1.34 Hz, 1 H), 8.02 (d, J=7.70 Hz, 1 H), 7.25 (d, J=2.32 Hz, 1 H), 6.97-7.08 (m, 2 H), 5.19-5.30 (m, 1 H), 4.53 (br. s., 2 H), 3.85 (s, 3 H), 3.41-3.55 (m, 2 H), 3.29 (s, 3 H), 3.08-3.21 (m, 3 H), 2.06 (d, J=11.49 Hz, 2 H), 1.64 (qd, J=12.43, 3.55 Hz, 2 H), 1.25 (d, J=6.36 Hz, 3 H).

Step 2—Synthesis of 2-{[(2R)-1-methoxypropan-2-yl]oxy}-N-methyl-6-[4-(1H-pyrazolo[3,4-b]pyridin-3-yl)piperidin-1-yl]pyrimidine-4-carboxamide (Example 326)

Methylamine (5.59 mL, 0.5 M in MeOH, 11.2 mmol) was added to methyl 2-{[(2R)-1-methoxypropan-2-yl]oxy}-6-

[4-(1H-pyrrolo[2,3-b]pyridin-3-yl)piperidin-1-yl]pyrimidine-4-carboxylate (I-247) (476 mg, 1.12 mmol) and the vial sealed and heated to 65° C. for 18 h. The reaction was concentrated and the residue purified by chromatography on silica gel (0-10% EtOH/EtOAc) to give 2-{[(2R)-1-methoxypropan-2-yl]oxy}-N-methyl-6-[4-(1H-pyrazolo[3,4-b]pyridin-3-yl)piperidin-1-yl]pyrimidine-4-carboxamide (Example 326) (340 mg, 72%) as a white solid 340 mg. LCMS (APCI), m/z 425.3 [M+H]$^+$; $^1$H NMR (400 MHz, DMSO-d$_6$) δ ppm 11.33 (br. s., 1 H), 8.57 (d, J=4.77 Hz, 1 H), 8.18 (d, J=4.52 Hz, 1 H), 8.02 (d, J=7.58 Hz, 1 H), 7.25 (d, J=2.08 Hz, 1 H), 6.94-7.06 (m, 2 H), 5.32-5.44 (m, 1 H), 4.53 (br. s., 2 H), 3.42-3.56 (m, 2 H), 3.29 (s, 3 H), 3.08-3.21 (m, 3 H), 2.79 (d, J=4.77 Hz, 3 H), 2.07 (d, J=12.96 Hz, 2 H), 1.56-1.70 (m, 2 H), 1.25 (d, J=6.36 Hz, 3 H).

Example 345 (Scheme E)

Synthesis of 4-[4-({[2-amino-5-(1-methyl-1H-imidazol-4-yl)pyridin-3-yl]oxy}methyl)piperidin-1-yl]-N-[(2R)-3-hydroxy-3-methylbutan-2-yl]-6-{[(2R)-1-methoxypropan-2-yl]oxy}-1,3,5-triazine-2-carboxamide

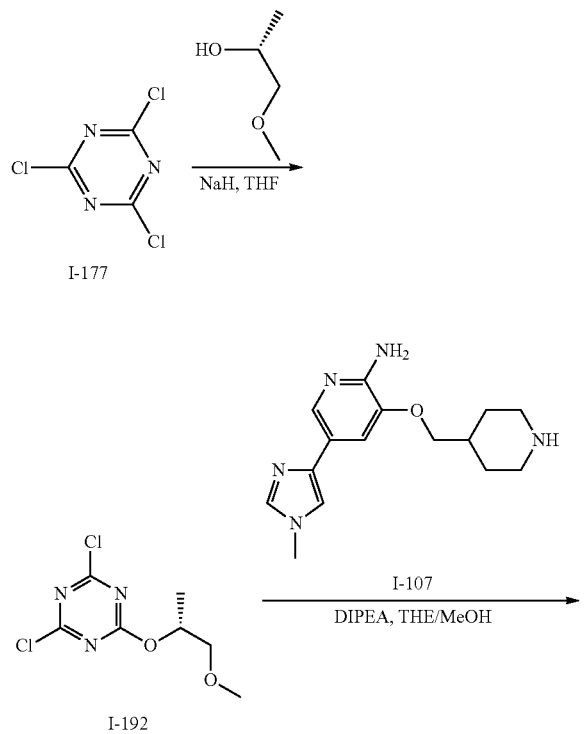

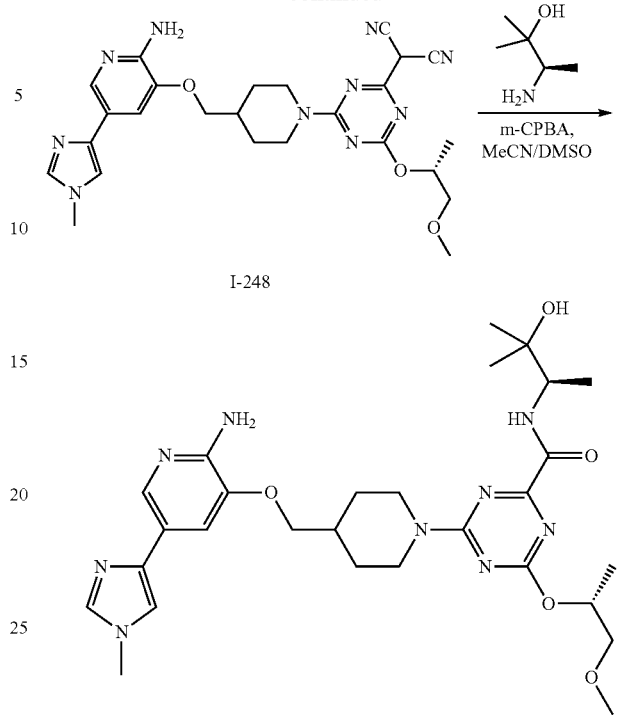

Example 345

Step 1—Synthesis of 2,4-dichloro-6-{[(2R)-1-methoxypropan-2-yl]oxy}-1,3,5-triazine (I-192)

To a solution of (2R)-1-methoxypropan-2-ol (489 mg, 5.42 mmol) in dry THF (10 mL) under a nitrogen atmosphere was added NaH (260 mg, 60% in mineral oil, 6.51 mmol) in portions at 0~10° C. After stirred at room temperature (25° C.) for 10 min, the grey suspension was cooled to 0° C. and cyanuric chloride (I-177) (1.00 g, 5.42 mmol) was added in portions over 10 min while maintaining the temperature below 10° C. The obtained grey suspension was stirred at room temperature (25° C.) for 2 hr. TLC (hexanes: EtOAc=5:1) indicated the that two new main spots had been formed. The light yellow suspension was cooled to 0° C., and diluted with water (20 mL). The mixture was extracted with EtOAc (3×20 mL). The combined organic layers were dried over Na$_2$SO$_4$ and concentrated. The residue was purified by silica gel chromatography (EtOAc/petroleum ether=0~15%) to give 2,4-dichloro-6-{[(2R)-1-methoxypropan-2-yl]oxy}-1,3,5-triazine (I-192) (500 mg, 39%) as colorless oil, which was used without further purification.

Step 2—Synthesis of 3-{[1-(4-chloro-6-{[(2R)-1-methoxypropan-2-yl]oxy}-1,3,5-triazin-2-yl)piperidin-4-yl]methoxy}-5-(1-methyl-1H-imidazol-4-yl)pyridin-2-amine (I-247)

To a suspension of 2,4-dichloro-6-{[(2R)-1-methoxypropan-2-yl]oxy}-1,3,5-triazine (I-192) (200 mg, 0.84 mmol) and 5-(1-methyl-1H-imidazol-4-yl)-3-(piperidin-4-ylmethoxy)pyridin-2-amine dihydrochloride (I-107) (303 mg, 0.84 mmol) in dry THF (10 mL) was added DIPEA (380 mg, 2.94 mmol) in a dropwise manner at 0° C. The light yellow suspension was stirred at 0° C. for 5 min before dropwise addition of MeOH (2 mL). The cloudy yellow mixture was stirred at room temperature (25° C.) for 2 hr. TLC (CH₂Cl₂/MeOH=10:1) indicated a new spot had been formed, and LCMS showed that the major peak had the mass of the desired product. The light yellow mixture was concentrated and the residue was purified by silica gel chromatography (MeOH/CH₂Cl₂=0~8%) to give 3-{[1-(4-chloro-6-{[(2R)-1-methoxypropan-2-yl]oxy}-1,3,5-triazin-2-yl)piperidin-4-yl]methoxy}-5-(1-methyl-1H-imidazol-4-yl)pyridin-2-amine (I-247) (300 mg, 73%) as a light yellow solid.

Step 3—Synthesis of (4-[4-({[2-amino-5-(1-methyl-1H-imidazol-4-yl)pyridin-3-yl]oxy}methyl)piperidin-1-yl]-6-{[(2R)-1-methoxypropan-2-yl]oxy}-1,3,5-triazin-2-yl)propanedinitrile (I-248)

A suspension of malononitrile (203 mg, 3.07 mmol) and K₂CO₃ (424 mg, 3.07 mmol) in MeCN (10 mL) was stirred at room temperature (25° C.) for 10 min. 3-{[1-(4-chloro-6-{[(2R)-1-methoxypropan-2-yl]oxy}-1,3,5-triazin-2-yl)piperidin-4-yl]methoxy}-5-(1-methyl-1H-imidazol-4-yl)pyridin-2-amine (I-247) (300 mg, 0.61 mmol) in MeCN (5 mL) was added in a dropwise manner at room temperature (25° C.) with stirring. The orange suspension was stirred at room temperature (25° C.) for 16 hr. TLC (CH₂Cl₂:MeOH=10:1) indicated the starting material had been consumed, and a new spot formed. The light yellow mixture was filtered and the filtrate was concentrated. The light yellow residue was purified by silica gel chromatography (MeOH/CH₂Cl₂=0~10%) to give (4-[4-({[2-amino-5-(1-methyl-1H-imidazol-4-yl)pyridin-3-yl]oxy}methyl)piperidin-1-yl]-6-{[(2R)-1-methoxypropan-2-yl]oxy}-1,3,5-triazin-2-yl)propanedinitrile (I-248) (200 mg, 63%) as a light yellow solid, which was used directly in the next step.

Step 4—Synthesis of (1R,2S)-2-[({4-[(3,3-difluoroazetidin-1-yl)carbonyl]-6-[4-(1H-pyrazolo[3,4-b]pyridin-3-yl)piperidin-1-yl]-1,3,5-triazin-2-yl}oxy)methyl]cyclopropanecarbonitrile (Example 345)

To a light yellow suspension of (4-[4-({[2-amino-5-(1-methyl-1H-imidazol-4-yl)pyridin-3-yl]oxy}methyl)piperidin-1-yl]-6-{[(2R)-1-methoxypropan-2-yl]oxy}-1,3,5-triazin-2-yl)propanedinitrile (I-248) (70 mg, 0.13 mmol) and (3R)-3-amino-2-methylbutan-2-ol (151 mg, 1.08 mmol) in MeCN (5 mL) and DMSO (0.2 mL) was added DIPEA (87.2 mg, 0.675 mmol) at room temperature (25° C.). After the addition, m-CPBA (274 mg, 85%, 1.35 mmol) was added to the light brown solution in portions at 0~10° C. with stirring (note—exothermic). The red brown clear solution was stirred at room temperature (25° C.) for 2 hr. LCMS showed that the starting material was consumed completely, and that the major peak had the mass of the desired product. The red brown mixture was concentrated and the residue was purified by silica gel chromatography (MeOH/CH₂Cl₂=0~10%) to give the product with ~80% purity as a light brown solid. This crude product was further purified by preparative HPLC to give 4-[4-({[2-amino-5-(1-methyl-1H-imidazol-4-yl)pyridin-3-yl]oxy}methyl)piperidin-1-yl]-N-[(2R)-3-hydroxy-3-methylbutan-2-yl]-6-{[(2R)-1-methoxypropan-2-yl]oxy}-1,3,5-triazine-2-carboxamide (Example 345) (18 mg, 23%) as a white solid. LCMS (APCI), m/z 583.9 [M+H]⁺; ¹H NMR (400 MHz, CDCl₃) δ ppm 8.30 (d, J=9.6 Hz, 1 H), 7.96 (s, 1 H), 7.43-7.47 (m, 2 H), 7.10 (s, 1 H), 5.38-5.46 (m, 1 H), 5.06 (d, J=12.8 Hz, 1 H), 4.85 (d, J=10.8 Hz, 1 H), 4.70 (br. S., 2 H), 4.02-4.08 (m, 1 H), 3.93-4.02 (m, 2 H), 3.72 (s, 3 H), 3.66-3.71 (m, 1 H), 3.48-3.55 (m, 1 H), 3.41 (s, 3 H), 2.95-3.08 (m, 1 H), 2.15-2.25 (m, 1 H), 1.92-2.02 (m, 2 H), 1.32-1.43 (m, 5 H), 1.18-1.25 (m, 9 H).

Example 348/349 (Scheme I)

Synthesis of 2-[(1-cyanocyclopropyl)methoxy]-N-(3-hydroxy-3-methylbutan-2-yl)-6-[4-(1H-pyrrolo[2,3-b]pyridin-3-yl)piperidin-1-yl]pyrimidine-4-carboxamide

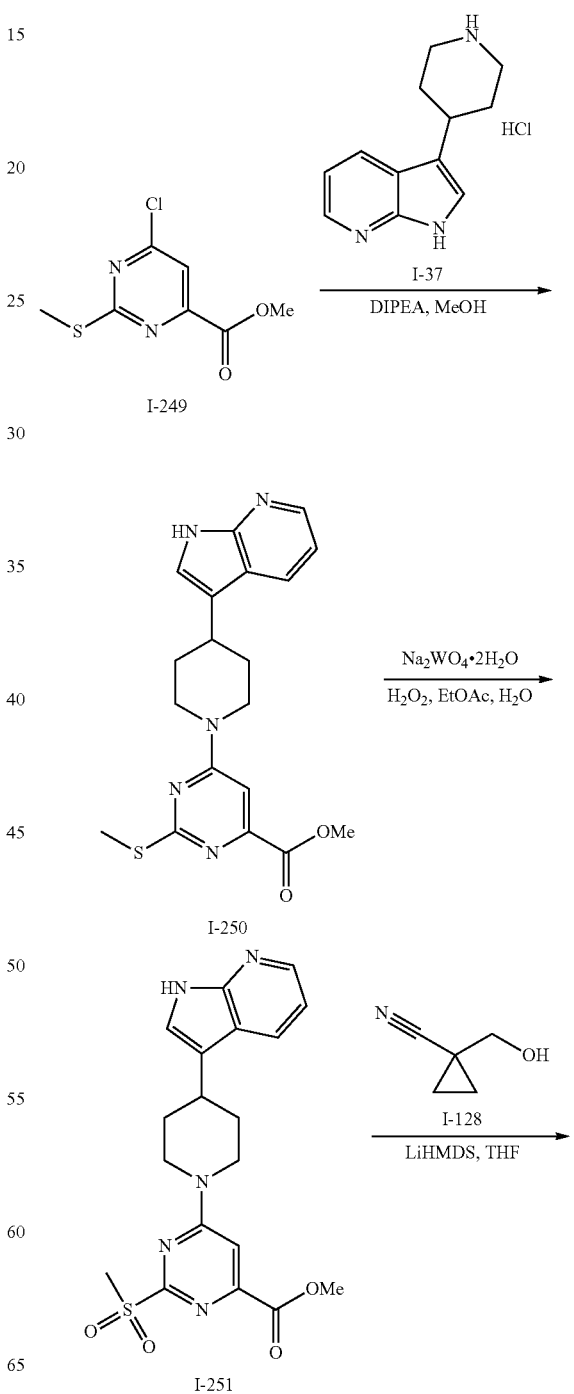

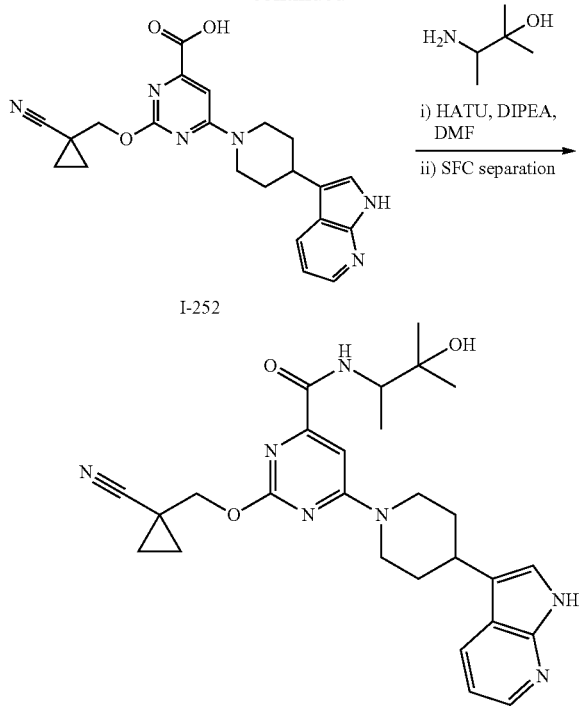

Examples 348/349

Step 1—Synthesis of methyl 2-(methylsulfanyl)-6-[4-(1H-pyrrolo[2,3-b]pyridin-3-yl)piperidin-1-yl]pyrimidine-4-carboxylate (I-250)

Methyl 6-chloro-2-(methylsulfanyl)pyrimidine-4-carboxylate (I-249) (193 mg, 0.883 mmol) and 3-(piperidin-4-yl)-1H-pyrrolo[2,3-b]pyridine hydrochloride (I-37) (238 mg, 0.883 mmol) were combined in MeOH (10 mL), and DIPEA (0.538 mL, 3.09 mmol) was added. The reaction was then allowed to stir at room temperature for 14 hr. The solvent was removed to afford methyl 2-(methylsulfanyl)-6-[4-(1H-pyrrolo[2,3-b]pyridin-3-yl)piperidin-1-yl]pyrimidine-4-carboxylate (I-250) as a tan solid, which was used directly in the next step without further purification. LCMS (APCI), m/z 384.2 [M+H]+

Step 2—Synthesis of methyl 2-(methylsulfonyl)-6-[4-(1H-pyrrolo[2,3-b]pyridin-3-yl)piperidin-1-yl]pyrimidine-4-carboxylate (I-251)

To a solution of methyl 2-(methylsulfanyl)-6-[4-(1H-pyrrolo[2,3-b]pyridin-3-yl)piperidin-1-yl]pyrimidine-4-carboxylate (I-250) (338 mg, 0.881 mmol) and $Na_2WO_4.2H_2O$ (29.1 mg, 0.0881 mmol) in EtOAc (12.8 mL) and water (0.5 mL) was added hydrogen peroxide (0.254 mL, 30%, 2.64 mmol), and the reaction was allowed to stir at room temperature for 2 h. LCMS indicated no reaction, and a further aliquot of hydrogen peroxide (0.4 mL) was added and the reaction stirred for 14 hr. LCMS indicated that ~20% of the desired product had been former, and a further 0.3 mL of hydrogen peroxide was added, and the reaction stirred for 3 h. The reaction was now shown by LCMS to be ~50% complete. 0.6 mL of hydrogen peroxide wad added, and the reaction stirred for 14 h. LCMS now showed only the desired product with no over-oxidation to the N-oxide. The reaction was diluted with saturated $Na_2SO_3$ (10 mL) at 0° C., and extracted with EtOAc (25 mL). The organic extracts were dried over $MgSO_4$, filtered and concentrated to afford methyl 2-(methylsulfonyl)-6-[4-(1H-pyrrolo[2,3-b]pyridin-3-yl)piperidin-1-yl]pyrimidine-4-carboxylate (I-251) (297 mg, 81%) as an off-white solid, which was used directly in the next step. LCMS (APCI), m/z 416.2 [M+H]+

Step 3—Synthesis of 2-[(1-cyanocyclopropyl)methoxy]-6-[4-(1H-pyrrolo[2,3-b]pyridin-3-yl)piperidin-1-yl]pyrimidine-4-carboxylic acid (I-252)

To a cooled 0° C. solution of methyl 2-(methylsulfonyl)-6-[4-(1H-pyrrolo[2,3-b]pyridin-3-yl)piperidin-1-yl]pyrimidine-4-carboxylate (I-151) (234 mg, 0.563 mmol) and 1-(hydroxymethyl)cyclopropanecarbonitrile (I-128) (82 mg, 0.845 mmol) in THF (10 mL) was added in a dropwise manner LiHMDS (1.18 mL, 1 M in THF, 1.18 mmol) over 20 min. The reaction was allowed to stir at 0° C. for 30 min before being allowed to warm to room temperature and stirred for 12 hr. LCMS indicated that only the acid product had been formed (M+H=419) with ~25% starting material remaining. A further aliquot of LiHMDS (0.5 mL) was added, and 0° C., and the reaction allowed to warm back to room temperature and stirred for 3 hr. The reaction was concentrated, and the residue re-suspended in EtOAc. The organic layer was washed with saturated NH4Cl, saturated brine, dried over Na2SO4, filtered and concentrated to afford the product as a yellow oil. LCMS indicated that product was till in the aqueous layer, which was acidified to pH~6 with 1 N HCl, extracted with EtOAc (3×25 mL). The organics were dried over Na2SO4, filtered, concentrated and combined with the oil obtained previously to afford 2-[(1-cyanocyclopropyl)methoxy]-6-[4-(1H-pyrrolo[2,3-b]pyridin-3-yl)piperidin-1-yl]pyrimidine-4-carboxylic acid (I-252) (69 mg, 29%) as a yellow solid, which was used in the next step. Some solid residues still remained which contained both product, and an unidentified product of higher MW (652/653). LCMS (APCI), m/z 419.2 [M+H]+

Step 4—Synthesis of 2-[(1-cyanocyclopropyl)methoxy]-N-(3-hydroxy-3-methylbutan-2-yl)-6-[4-(1H-pyrrolo[2,3-b]pyridin-3-yl)piperidin-1-yl]pyrimidine-4-carboxamide To a solution of 2-[(1-cyanocyclopropyl)methoxy]-6-[4-(1H-pyrrolo[2,3-b]pyridin-3-yl)piperidin-1-yl]pyrimidine-4-carboxylic acid (I-252) (69 mg, 0.16 mmol) and 3-amino-2-methylbutan-2-ol (23.8 mg, 0.231 mmol) in DMF (3.5 mL) was added DIPEA (0.09 mL, 0.495 mmol) followed by a solution of HATU (87.8 mg, 0.231 mmol) in DMF (2 mL). The reaction was allowed to stir for 15 hr at room temperature. Removal of the solvent afforded the crude residue, which was subjected to chiral separation by SFC to afford both enantiomers. The analytical chiral separation by SFC was performed using a ChiralCel OJ-3 (4.6 mm×1000 mm column, 3 micron particle size), which was eluted with 10% MeOH in $CO_2$ held at 120 bar. A flow rate of 4.0 mL/min gave $Rt_{(Peak\ 1)}$=1.80 min and $Rt_{(Peak\ 2)}$=2.48 min.

2-[(1-Cyanocyclopropyhmethoxy]-N-(3-hydroxy-3-methylbutan-2-yl)-6-[4-(1H-pyrrolo[2,3-b]pyridin-3-yl)piperidin-1-yl]pyrimidine-4-carboxamide (Example 348) (Peak 1): 10.62 mg, ~99% ee. (+). LCMS (APCI), m/z 504.0 [M+H]+; $^1$H NMR (700 MHz, DMSO-$d_6$) δ ppm 11.31 (br. s., 1 H), 8.09-8.22 (m, 2 H), 8.01 (br. s., 1 H), 7.22 (br. s., 1 H), 6.96-7.07 (m, 2 H), 4.78 (s, 1 H), 4.29-4.39 (m, 2 H), 3.84 (d, J=2.73 Hz, 1 H), 3.45-3.57 (m, 3 H), 3.15 (br. s., 1

H), 2.05 (d, J=11.61 Hz, 2 H), 1.62 (d, J=11.27 Hz, 2 H), 1.35 (br. s., 3 H), 1.03-1.16 (m, 11 H).

2-[(1-Cyanocyclopropyl)methoxy]-N-(3-hydroxy-3-methylbutan-2-yl)-6-[4-(1H-pyrrolo[2,3-b]pyridin-3-yl)piperidin-1-yl]pyrimidine-4-carboxamide (Example 349) (Peak 2): 9.57 mg, ~98% ee. (−). LCMS (APCI), m/z 504.0 [M+H]⁺; ¹H NMR (700 MHz, DMSO-$d_6$) δ ppm 11.30 (br. s., 1 H), 8.08-8.22 (m, 2 H), 8.01 (d, J=6.49 Hz, 1 H), 7.21 (br. s., 1 H), 6.96-7.07 (m, 2 H), 4.78 (d, J=10.25 Hz, 1 H), 4.26-4.38 (m, 2 H), 3.84 (dd, J=9.31, 6.58 Hz, 1 H), 3.47 (d, J=4.27 Hz, 3 H), 3.15 (br. s., 1 H), 2.05 (d, J=11.96 Hz, 2 H), 1.61 (d, J=12.13 Hz, 2 H), 1.30-1.39 (m, 3 H), 1.03-1.15 (m, 11 H).

Example 375 (Scheme D)

Synthesis of N-(2-methoxyethyl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide

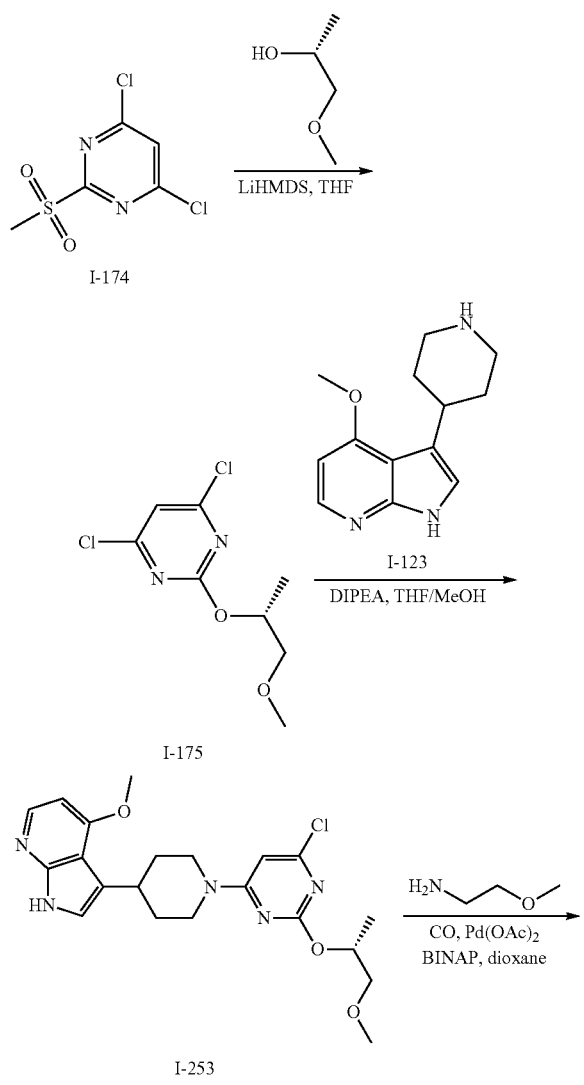

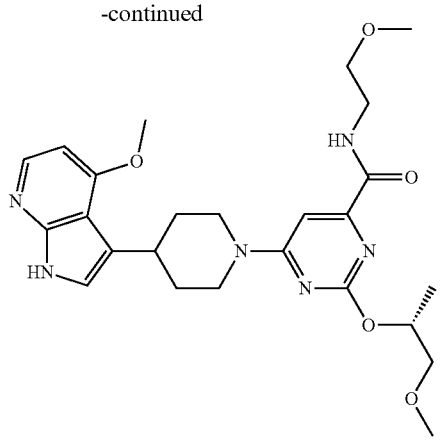

Example 375

Step 1—Synthesis of 4,6-dichloro-2-{[(2R)-1-methoxypropan-2-yl]oxy}pyrimidine (I-175)

To a clear solution of 2,4-dichloro-6-(methylsulfonyl)pyrimidine (I-174) (13.0 g, 57.3 mmol) and (2R)-1-methoxypropan-2-ol (5.16 g, 57.3 mmol) in THF (5 mL) cooled to 0° C. using an ice bath was added in a dropwise manner LiHMDS (63 mL, 1M in THF, 63 mmol) over 10 min. The resultant light yellow suspension was allowed to stir at 0° C. for an additional 30 min. The ice-bath was removed and the mixture was allowed to warm to room temperature (25° C.), and stirred for 2 hr. TLC (hexane:EtOAc=5:1) indicated that the 2,4-dichloro-6-(methylsulfonyl)pyrimidine had been completely consumed. The mixture was concentrated, and taken up in EtOAc (20 mL), washed with sat aq. NH₄Cl (10 mL) and brine (10 mL). The organic layer was dried over Na₂SO₄, filtered and concentrated to give 4,6-dichloro-2-{[(2R)-1-methoxypropan-2-yl]oxy}pyrimidine (I-175) (13.0 g, 96%) as a light yellow oil, which was used without further purification.

Step 2—Synthesis of 3-[1-(6-chloro-2-{[(2R)-1-methoxypropan-2-yl]oxy}pyrimidin-4-yl)piperidin-4-yl]-4-methoxy-1H-pyrrolo[2,3-b]pyridine (I-253)

To a light yellow suspension of 4,6-dichloro-2-{[(2R)-1-methoxypropan-2-yl]oxy}pyrimidine (I-175) (300 mg, 1.27 mmol) and 4-methoxy-3-(piperidin-4-yl)-1H-pyrrolo[2,3-b]pyridine dihydrochloride (I-123) (565 mg, 1.27 mmol) in THF/MeOH (10 mL/5 mL) was slowly added DIPEA (2.18 g, 16.9 mmol) at 0° C. Then, the clean light yellow reaction mixture was stirred at room temperature (25° C.) for 30 min. LCMS showed the 4,6-dichloro-2-{[(2R)-1-methoxypropan-2-yl]oxy}pyrimidine had been consumed completely. The mixture was concentrated in vacuo and the light yellow residue was purified by silica gel chromatography (EtOAc/petroleum ether 0-80%) to give 3-[1-(6-chloro-2-{[(2R)-1-methoxypropan-2-yl]oxy}pyrimidin-4-yl)piperidin-4-yl]-4-methoxy-1H-pyrrolo[2,3-b]pyridine (I-253) (410 mg, 75%) as a light yellow solid.

Step 3—Synthesis of N-(2-methoxyethyl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide (Example 375)

To a solution of 3-[1-(6-chloro-2-{[(2R)-1-methoxypropan-2-yl]oxy}pyrimidin-4-yl)piperidin-4- yl]-4-methoxy- 1H-pyrrolo[2,3-b]pyridine (I-253) (100 mg, 0.23 mmol), 2-methoxyethanamine (34.4 mg, 0.46 mmol), DIPEA (104 mg, 0.82 mmol) in dioxane (5 mL) placed in a 50 mL stainless steel vessel was added Pd(OAc)$_2$ (7.72 mg, 0.0344 mmol) and BINAP (28.5 mg, 0.0458 mmol). Stirring was initiated (900 rpm), and the mixture was purged with Ar (2 Bar) three times followed by CO (1 MPa) three times. The reaction mixture was stirred under 2 MPa of CO pressure and heated to 120° C. for 16 hr. The reaction mixture was filtered through a plug of Celite and the filtrate was concentrated. The light yellow residue was purified by preparative HPLC to give N-(2-methoxyethyl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide (Example 375) (36 mg, 32%) as a white solid. LCMS (APCI), m/z 499.1 [M+H]$^+$; (400 MHz, DMSO-d$_6$) δ ppm 11.25 (s, 1 H), 8.52 (d, J=5.6 Hz, 1 H), 8.07 (d, J=5.6 Hz, 1 H), 7.03 (d, J=2.0 Hz, 1 H) 6.99 (s, 1 H), 6.60 (d, J=5.6 Hz, 1 H), 5.31-5.35 (m, 1 H), 4.28-4.72 (m, 2 H), 3.88-3.93 (m, 3 H), 3.43-3.57 (m, 6 H), 3.21-3.32 (m, 6 H), 3.04-3.17 (m, 2 H), 2.42-2.47 (m, 1 H), 2.03 (d, J=13.2 Hz, 2 H), 1.56-1.64 (m, 2 H), 1.27 (d, J=6.4 Hz, 3 H).

Synthetic examples of compounds of the invention are summarized in Table 1 below by showing compound number (which includes the method/scheme of preparation and numbered example for that method, the chemical structure, the chemical name, and $^1$H NMR data.

TABLE 1

| Ex. # | Structure | Compound Name | LRMS m/z (M + H)$^+$; and $^1$H NMR |
|---|---|---|---|
| 1** (A) | 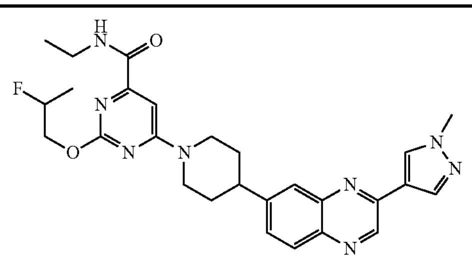 | N-ethyl-2-(2-fluoropropoxy)-6-{4-[3-(1-methyl-1H-pyrazol-4-yl)quinoxalin-6-yl]piperidin-1-yl}pyrimidine-4-carboxamide | 519.2; (400 MHz, CDCl$_3$) δ ppm 9.01 (s, 1 H), 8.18 (s, 1 H), 8.14 (s, 1 H), 8.01 (d, J = 8.67 Hz, 1 H), 7.88 (br. s., 1 H), 7.83 (d, J = 1.88 Hz, 1 H), 7.56 (dd, J = 8.57, 1.98 Hz, 1 H), 7.18 (s, 1 H), 4.99 (td, J = 6.50, 3.58 Hz, 1 H), 4.71 (br. s., 1 H), 4.30-4.57 (m, 2 H), 4.03 (s, 3 H), 3.41-3.55 (m, 2 H), 3.11 (d, J = 12.81 Hz, 3 H), 2.12 (d, J = 12.81 Hz, 2 H), 1.81-1.93 (m, 1 H), 1.77 (d, J = 4.33 Hz, 1 H), 1.53 (d, J = 6.40 Hz, 2 H), 1.41-1.48 (m, 2 H), 1.20-1.31 (m, 4 H). |
| 2 (A) | 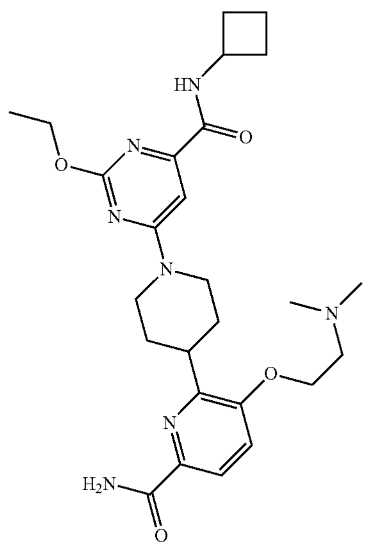 [SMILES: CCOc1nc(C(=O)NC2CCC2)cc(N2CCC(c3nc(C(N)=O)ccc3OCCN(C)C)CC2)n1] | 6-(4-{6-carbamoyl-3-[2-(dimethylamino)ethoxy]pyridin-2-yl}piperidin-1-yl)-N-cyclobutyl-2-ethoxypyrimidine-4-carboxamide | 512.2; (400 MHz, DMSO-d6) δ ppm 8.57 (d, J = 8.59 Hz, 1 H), 7.85 (d, J = 8.34 Hz, 1 H), 7.79-7.83 (m, 1 H), 7.51 (d, J = 8.84 Hz, 1 H), 7.35-7.39 (m, 1 H), 6.95 (s, 1 H), 4.38-4.45 (m, 1 H), 4.34 (q, J = 6.99 Hz, 3 H), 4.18 (t, J = 5.68 Hz, 2 H), 3.39-3.44 (m, 2 H), 3.01-3.13 (m, 2 H), 2.68 (t, J = 5.68 Hz, 2 H), 2.24 (s, 6 H), 2.10-2.20 (m, 4 H), 1.81-1.89 (m, 4 H), 1.59-1.70 (m, 2 H), 1.31 (t, J = 7.07 Hz, 3 H). |
| 3** | 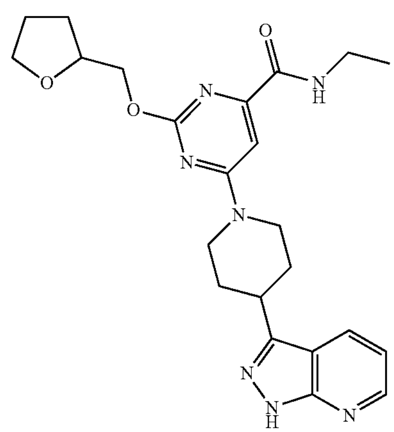 [SMILES: CCNC(=O)c1cc(N2CCC(c3n[nH]c4ncccc34)CC2)nc(OCC2CCCO2)n1] | N-ethyl-6-[4-(1H-pyrazolo[3,4-b]pyridin-3-yl)piperidin-1-yl]-2-(tetrahydrofuran-2-ylmethoxy)pyrimidine-4-carboxamide | 452.0; (400 MHz, CDCl$_3$) δ ppm 10.35 (br. s., 1 H), 8.55 (dd, J = 4.67, 1.39 Hz, 1 H), 8.09 (dd, J = 8.08, 1.52 Hz, 1 H), 7.91 (t, J = 5.94 Hz, 1 H), 7.08-7.20 (m, 2 H), 4.62 (br. s., 2 H), 4.37-4.45 (m, 1 H), 4.21-4.36 (m, 2 H), 3.89-4.02 (m, 1 H), 3.75-3.88 (m, 1 H), 3.32-3.52 (m, 3 H), 3.11-3.29 (m, 2 H), 1.88-2.35 (m, 7 H), 1.71-1.86 (m, 1 H), 1.25 (t, J = 7.33 Hz, 3 H). |

TABLE 1-continued

| Ex. # | Structure | Compound Name | LRMS m/z (M + H)+; and 1H NMR |
|---|---|---|---|
| 4* | 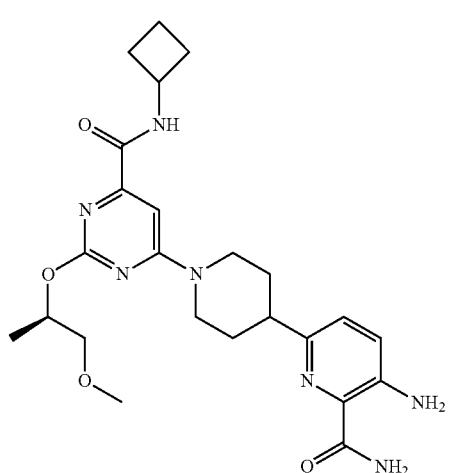 [SMILES: COC[C@@H](C)Oc1nc(C(=O)NC2CCC2)cc(N2CCC(c3ccc(N)c(C(N)=O)n3)CC2)n1] | 6-[4-(5-amino-6-carbamoylpyridin-2-yl)piperidin-1-yl]-N-cyclobutyl-2-{[(2R)-1-methoxypropan-2-yl]oxy}pyrimidine-4-carboxamide | 484.2; (400 MHz, CDCl$_3$) δ ppm 8.02 (d, J = 7.83 Hz, 1 H), 7.85 (s, 1 H), 7.04-7.14 (m, 2 H), 6.98 (d, J = 8.59 Hz, 1 H), 5.85 (s, 2 H), 5.21-5.42 (m, 2 H), 4.56-4.89 (m, 2 H), 4.50-4.57 (m, 1 H), 3.69 (dd, J = 9.85, 6.32 Hz, 1 H), 3.53 (dd, J = 9.98, 4.67 Hz, 1 H), 3.43 (s, 3 H), 2.96-3.18 (m, 2 H), 2.83-2.95 (m, 1 H), 2.30-2.45 (m, 2 H), 1.93-2.08 (m, 4 H), 1.70-1.83 (m, 4 H), 1.40 (d, J = 6.32 Hz, 3 H). |
| 5*** | 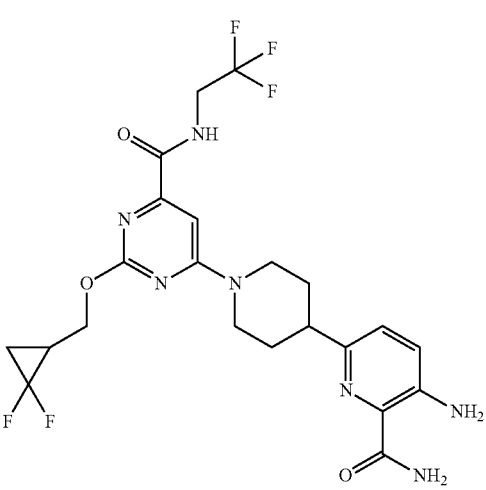 [SMILES: NC(=O)c1nc(C2CCN(c3cc(C(=O)NCC(F)(F)F)nc(OCC4CC4(F)F)n3)CC2)ccc1N] | 6-[4-(5-amino-6-carbamoylpyridin-2-yl)piperidin-1-yl]-2-[(2,2-difluoro-cyclopropyl)methoxy]-N-(2,2,2-trifluoroethyl)pyrimidine-4-carboxamide | 530.2; (400 MHz, CDCl$_3$) δ ppm 8.16 (t, J = 6.57 Hz, 1 H), 7.84 (br. s., 1 H), 7.16 (s, 1 H), 7.09 (d, J = 7.0 Hz, 1 H), 6.99 (d, J = 8.59 Hz, 1 H), 5.85 (br. s, 2 H), 5.30 (br. s., 1 H), 4.46-4.53 (m, 1 H), 4.31-4.38 (m, 1 H), 4.24-4.96 (m, 2 H), 4.03-4.12 (m, 2 H), 3.00-3.23 (m, 2 H), 2.86-2.97 (m, 1 H), 2.08-2.20 (m, 1 H), 2.00-2.08 (m, 2 H), 1.70-1.83 (m, 2 H), 1.22-1.41 (m, 2 H). |
| 6* | 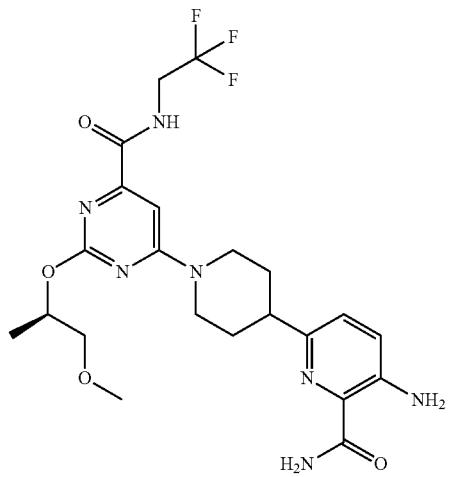 [SMILES: COC[C@@H](C)Oc1nc(C(=O)NCC(F)(F)F)cc(N2CCC(c3ccc(N)c(C(N)=O)n3)CC2)n1] | 6-[4-(5-amino-6-carbamoylpyridin-2-yl)piperidin-1-yl]-2-{[(2R)-1-methoxypropan-2-yl]oxy}-N-(2,2,2-trifluoroethyl)pyrimidine-4-carboxamide | 512.2; (400 MHz, CDCl$_3$) δ ppm 8.21 (t, J = 5.81 Hz, 1 H), 7.85 (s, 1 H), 7.11 (s, 1 H), 7.08 (d, J = 8.59 Hz, 1 H), 6.99 (d, J = 8.34 Hz, 1 H), 5.85 (s, 2 H), 5.27-5.39 (m, 2 H), 4.64 (s, 2H), 4.00-4.10 (m, 2 H), 3.68 (dd, J = 9.85, 6.32 Hz, 1 H), 3.51 (dd, J = 9.98, 4.42 Hz, 1 H), 3.42 (s, 3 H), 3.08 (t, J = 11.87 Hz, 2 H), 2.90 (t, J = 11.75 Hz, 1 H), 1.96-2.06 (m, 2 H), 1.68-1.83 (m, 2 H), 1.39 (d, J = 6.32 Hz, 3 H). |

| Ex. # | Structure | Compound Name | LRMS m/z (M + H)+; and 1H NMR |
|---|---|---|---|
| 7* | 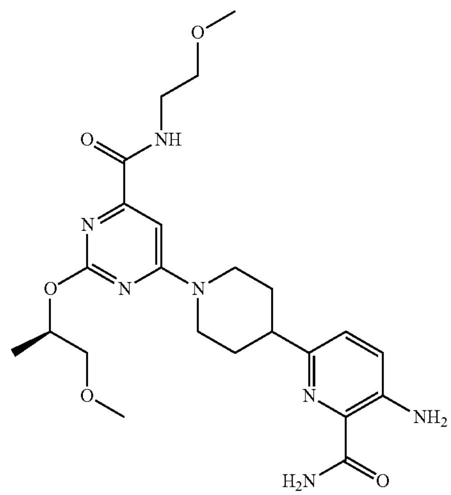 [SMILES: COCCNC(=O)c1cc(N2CCC(c3ccc(N)c(C(N)=O)n3)CC2)nc(O[C@H](C)COC)n1] | 6-[4-(5-amino-6-carbamoylpyridin-2-yl)piperidin-1-yl]-N-(2-methoxyethyl)-2-{[(2R)-1-methoxypropan-2-yl]oxy}pyrimidine-4-carboxamide | 488.2; (400 MHz, CDCl$_3$) δ ppm 8.13 (t, J = 5.43 Hz, 1 H), 7.86 (s, 1 H), 7.11 (s, 1 H), 7.08 (d, J = 5.62 Hz, 1 H), 6.99 (d, J = 5.41 Hz, 1 H), 5.84 (s, 2 H), 5.31-5.38 (m, 1 H), 5.28 (s, 1 H), 4.63 (br. s., 2 H), 3.68 (dd, J = 9.98, 6.19 Hz, 1 H), 3.62 (q, J = 5.22 Hz, 2 H), 3.48-3.56 (m, 3 H), 3.42 (s, 3 H), 3.38 (s, 3 H), 3.06 (t, J = 13.39 Hz, 2 H), 2.89 (t, J = 13.40 Hz, 1 H), 2.00 (d, J = 12.63 Hz, 2 H), 1.68-1.81 (m, 2 H), 1.39 (d, J = 6.32 Hz, 3 H). |
| 8* | 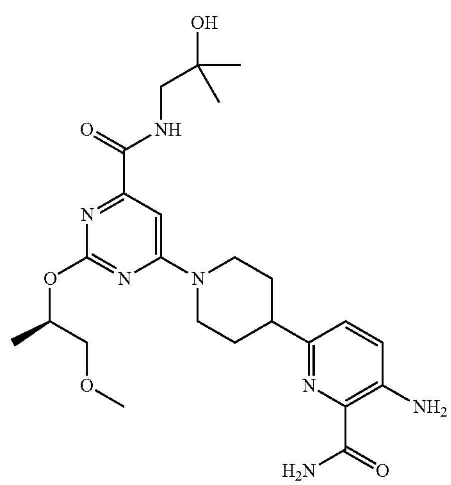 [SMILES: COC[C@@H](C)Oc1nc(C(=O)NCC(C)(C)O)cc(N2CCC(c3ccc(N)c(C(N)=O)n3)CC2)n1] | 6-[4-(5-amino-6-carbamoylpyridin-2-yl)piperidin-1-yl]-N-(2-hydroxy-2-methylpropyl)-2-{[(2R)-1-methoxypropan-2-yl]oxy}pyrimidine-4-carboxamide | 502.2; (400 MHz, CDCl$_3$) δ ppm 8.27 (t, J = 6.32 Hz, 1 H), 7.85 (s, 1 H), 7.12 (s, 1 H), 7.08 (d, J = 6.32 Hz, 1 H), 6.99 (d, J = 8.34 Hz, 1 H), 5.85 (s, 2 H), 5.26-5.40 (m, 2 H), 4.63 (br. s., 2 H), 3.68 (dd, J = 10.11, 6.32 Hz, 1 H), 3.51 (dd, J = 10.11, 4.80 Hz, 1 H), 3.42-3.45 (m, 2 H), 3.42 (s, 3 H), 3.07 (t, J = 11.62 Hz, 2 H), 2.90 (tt, J = 11.78, 3.60, 3.41 Hz, 1 H), 2.70 (br. s., 1 H), 2.00 (d, J = 12.13 Hz, 2 H), 1.68-1.81 (m, 2 H), 1.39 (d, J = 6.57 Hz, 3 H), 1.27 (s, 6 H). |
| 9* | 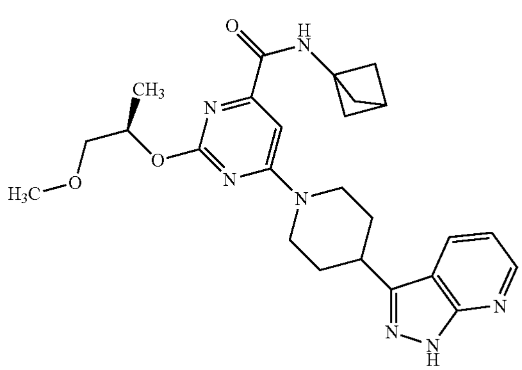 [SMILES: COC[C@@H](C)Oc1nc(C(=O)NC23CC(C2)C3)cc(N2CCC(c3n[nH]c4ncccc34)CC2)n1] | N-(bicyclo[1.1.1]pent-1-yl)-2-{[(2R)-1-methoxypropan-2-yl]oxy}-6-[4-(1H-pyrazolo[3,4-b]pyridin-3-yl)piperidin-1-yl]pyrimidine-4-carboxamide | 478.2; (400 MHz, CDCl$_3$) δ ppm 10.35 (br. s., 1 H), 8.55 (dd, J = 4.55, 1.52 Hz, 1 H), 8.25 (s, 1 H), 8.09 (dd, J = 8.08, 1.52 Hz, 1 H), 7.14 (dd, J = 8.08, 4.55 Hz, 1 H), 7.11 (s, 1 H), 5.18-5.57 (m, 1 H), 4.58 (br. s., 2 H), 3.68 (dd, J = 10.11, 6.32 Hz, 1 H), 3.50 (dd, J = 9.85, 4.80 Hz, 1 H), 3.34-3.46 (m, 4 H), 3.07-3.31 (m, 2 H), 2.49 (s, 1 H), 2.10-2.26 (m, 8 H), 1.83-2.10 (m, 2 H), 1.39 (d, J = 6.57 Hz, 3H). |

TABLE 1-continued

| Ex. # | Structure | Compound Name | LRMS m/z (M + H)+; and 1H NMR |
|---|---|---|---|
| 10* | 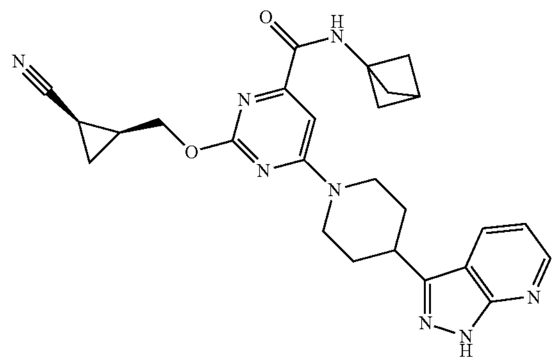 [SMILES: N#C[C@@H]1C[C@@H]1COc1nc(C(=O)NC23CC(C2)C3)cc(N2CCC(c3n[nH]c4ncccc34)CC2)n1] | N-(bicyclo[1.1.1]pent-1-yl)-2-{[(1S,2R)-2-cyanocyclopropyl]methoxy}-6-[4-(1H-pyrazolo[3,4-b]pyridin-3-yl)piperidin-1-yl]pyrimidine-4-carboxamide | 485.2; (400 MHz, CDCl$_3$) δ ppm 12.15 (br. s., 1 H), 8.47-8.48 (m, 1 H), 8.60-8.61 (m, 1 H), 8.21 (s, 1 H), 8.11-8.13 (m, 1 H), 7.13-7.16 (m, 2 H), 4.43-4.53 (m, 4 H), 3.40-3.45 (m, 1 H), 3.24 (t, J = 11.4 Hz, 2 H), 2.49 (s, 1 H), 2.05-2.22 (m, 8 H), 2.00-2.10 (m, 2 H), 1.86-1.88 (m, 1 H), 1.67-1.69 (m, 1 H), 1.33-1.34 (m, 1 H), 1.13-1.15 (m, 1 H). |
| 11* | 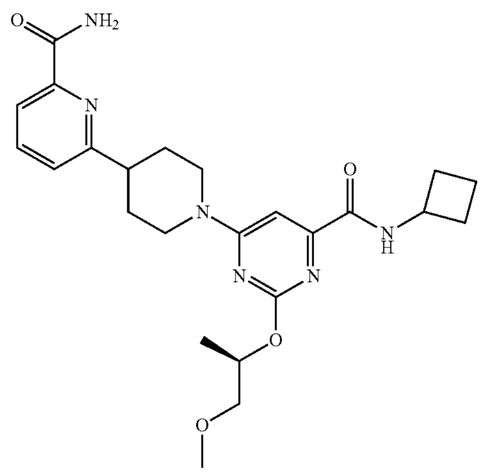 [SMILES: COC[C@@H](C)Oc1nc(C(=O)NC2CCC2)cc(N2CCC(c3cccc(C(N)=O)n3)CC2)n1] | 6-[4-(6-carbamoylpyridin-2-yl)piperidin-1-yl]-N-cyclobutyl-2-{[(2R)-1-methoxypropan-2-yl]oxy}pyrimidine-4-carboxamide | 469.2; (400 MHz, CDCl$_3$) δ ppm 8.04-8.11 (m, 1 H), 8.02 (d, J = 8.34 Hz, 1 H), 7.77-7.88 (m, 2 H), 7.30-7.38 (m, 1 H), 7.11 (s, 1 H), 5.54 (d, J = 2.02 Hz, 1 H), 5.34 (td, J = 6.32, 4.80 Hz, 1 H), 4.72 (br. s., 2 H), 4.48-4.59 (m, 1 H), 3.69 (dd, J = 10.11, 6.32 Hz, 1 H), 3.52 (dd, J = 9.98, 4.67 Hz, 1 H), 3.36-3.45 (m, 3 H), 3.01-3.19 (m, 3 H), 2.32-2.50 (m, 2 H), 1.97-2.13 (m, 4 H), 1.69-1.91 (m, 4 H), 1.40 (d, J = 6.32 Hz, 3 H). |
| 12* | 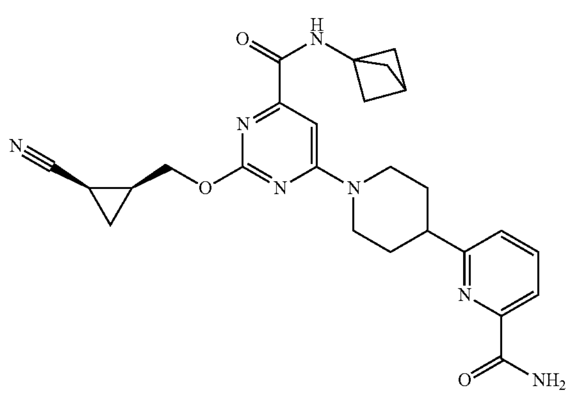 [SMILES: N#C[C@@H]1C[C@@H]1COc1nc(C(=O)NC23CC(C2)C3)cc(N2CCC(c3cccc(C(N)=O)n3)CC2)n1] | N-(bicyclo[1.1.1]pent-1-yl)-6-[4-(6-carbamoylpyridin-2-yl)piperidin-1-yl]-2-{[(1S,2R)-2-cyanocyclopropyl]methoxy}pyrimidine-4-carboxamide | 488.2; (400 MHz, CDCl$_3$) δ ppm 8.19 (s, 1 H), 8.07 (dd, J = 7.71, 0.88 Hz, 1 H), 7.74-7.98 (m, 2 H), 7.31-7.39 (m, 1 H), 7.15 (s, 1 H), 5.53 (br. s., 1 H), 4.65 (br. s., 2 H), 4.27-4.56 (m, 2 H), 2.95-3.25 (m, 3 H), 2.50 (s, 1 H), 2.20 (s, 6 H), 2.07 (d, J = 15.16 Hz, 2 H), 1.77-1.93 (m, 3 H), 1.69 (td, J = 8.34, 5.56 Hz, 1 H), 1.35 (td, J = 8.46, 5.56 Hz, 1H), 1.10-1.19 (m, 1H). |

TABLE 1-continued

| Ex. # | Structure | Compound Name | LRMS m/z (M + H)+; and 1H NMR |
|---|---|---|---|
| 13* | 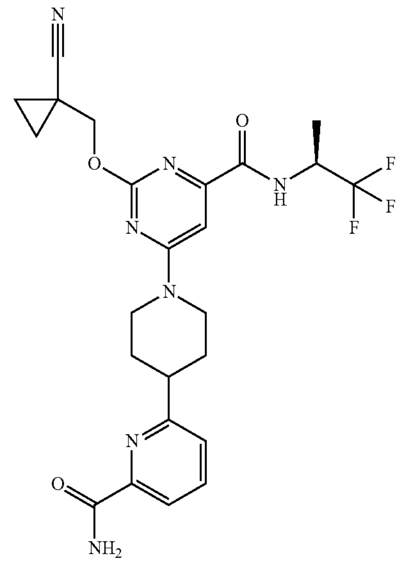 [SMILES: C[C@H](NC(=O)c1cc(N2CCC(c3cccc(C(N)=O)n3)CC2)nc(OCC2(C#N)CC2)n1)C(F)(F)F] | 6-[4-(6-carbamoylpyridin-2-yl)piperidin-1-yl]-2-[(1-cyanocyclopropyl)methoxy]-N-[(2S)-1,1,1-trifluoropropan-2-yl]pyrimidine-4-carboxamide | 518.2; (400 MHz, CDCl$_3$) δ ppm 8.08 (d, J = 6.82 Hz, 1 H), 8.00 (d, J = 10.11 Hz, 1 H), 7.82 (t, J = 7.71 Hz, 2 H), 7.34 (d, J = 7.07 Hz, 1 H), 7.19 (s, 1 H), 5.52 (br. s., 1 H), 4.69-4.90 (m, 1 H), 5.05 (br. s., 2 H), 4.46 (d, J = 12.13 Hz, 1 H), 4.32 (d, J = 11.87 Hz, 1 H), 3.01-3.23 (m, 3 H), 2.04-2.14 (m, 2 H), 1.80-1.95 (m, 2 H), 1.38-1.48 (m, 5 H), 1.17-1.24 (m, 2 H). |
| 14* | 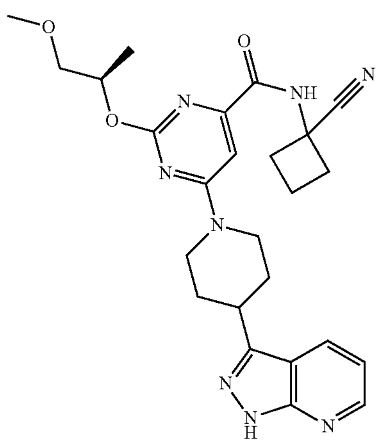 [SMILES: COC[C@@H](C)Oc1nc(C(=O)NC2(C#N)CCC2)cc(N2CCC(c3n[nH]c4ncccc34)CC2)n1] | N-(1-cyanocyclobutyl)-2-{[(2R)-1-methoxypropan-2-yl]oxy}-6-[4-(1H-pyrazolo[3,4-b]pyridin-3-yl)piperidin-1-yl]pyrimidine-4-carboxamide | 491.2; (400 MHz, CDCl$_3$) δ ppm 10.40 (br. s., 1 H), 8.56 (d, J = 4.29 Hz, 1 H), 8.21 (s, 1 H), 8.10 (d, J = 8.08 Hz, 1 H), 7.06-7.19 (m, 2 H), 5.20-5.41 (m, 1 H), 4.59 (br. s., 2 H), 3.68 (dd, J = 9.98, 6.44 Hz, 1 H), 3.52 (dd, J = 9.98, 4.42 Hz, 1 H), 3.34-3.47 (m, 4 H), 3.26 (t, J = 12.00 Hz, 2 H), 2.81-2.92 (m, 2 H), 2.39-2.61 (m, 2 H), 1.86-2.37 (m, 6 H), 1.40 (d, J = 6.32 Hz, 3 H). |
| 15** | 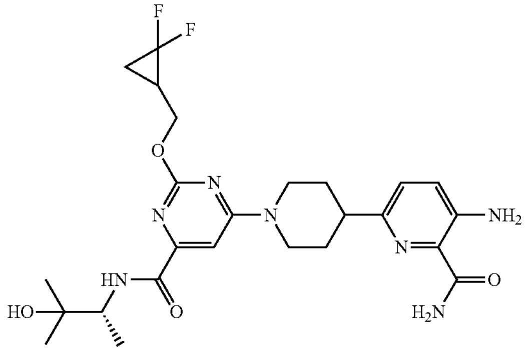 [SMILES: C[C@@H](NC(=O)c1cc(N2CCC(c3ccc(N)c(C(N)=O)n3)CC2)nc(OCC2CC2(F)F)n1)C(C)(C)O] | 6-[4-(5-amino-6-carbamoylpyridin-2-yl)piperidin-1-yl]-2-[(2,2-difluorocyclopropyl)methoxy]-N-[(2R)-3-hydroxy-3-methylbutan-2-yl]pyrimidine-4-carboxamide | 534.2; (400 MHz, CDCl$_3$) δ ppm 8.02 (d, J = 9.09 Hz, 1H), 7.85 (br. s., 1 H), 7.16 (s, 1 H), 7.09 (d, J = 8.34 Hz, 1 H), 6.94-7.03 (m, 1 H), 5.85 (br. s., 2 H), 5.34 (br. s., 1 H), 4.64 (br. s., 1 H), 4.43-4.54 (m, 1 H), 4.29-4.42 (m, 1 H), 4.00-4.13 (m, 1 H), 3.00-3.19 (m, 2 H), 2.91 (tt, J = 11.84, 3.69 Hz, 1 H), 2.49 (br. s., 1 H), 2.11-2.25 (m, 1 H), 2.02 (d, J = 11.12 Hz, 2 H), 1.75 (dd, J = 12.51, 3.41 Hz, 2 H), 1.30-1.39 (m, 1 H), 1.23-1.29 (m, 9 H). |

TABLE 1-continued

| Ex. # | Structure | Compound Name | LRMS m/z (M + H)+; and 1H NMR |
|---|---|---|---|
| 16** | 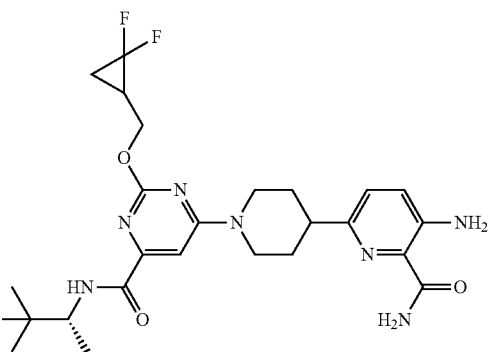 | 6-[4-(5-amino-6-carbamoylpyridin-2-yl)piperidin-1-yl]-2-[(2,2-difluoro-cyclopropyl)methoxy]-N-[(2R)-3-hydroxy-3-methylbutan-2-yl]pyrimidine-4-carboxamide | 534.2; (400 MHz, CDCl$_3$) δ ppm 8.02 (d, J = 9.09 Hz, 1H), 7.85 (br. s., 1 H), 7.16 (s, 1 H), 7.09 (d, J = 8.34 Hz, 1 H), 6.94-7.03 (m, 1 H), 5.85 (br. s., 2 H), 5.34 (br. s., 1 H), 4.64 (br. s., 1 H), 4.43-4.54 (m, 1 H), 4.29-4.42 (m, 1 H), 4.00-4.13 (m, 1 H), 3.00-3.19 (m, 2 H), 2.91 (tt, J = 11.84, 3.69 Hz, 1 H), 2.49 (br. s., 1 H), 2.11-2.25 (m, 1 H), 2.02 (d, J = 11.12 Hz, 2H), 1.75 (dd, J = 12.51, 3.41 Hz, 2 H), 1.30-1.39 (m, 1 H), 1.23-1.29 (m, 9 H). |
| 17*** | 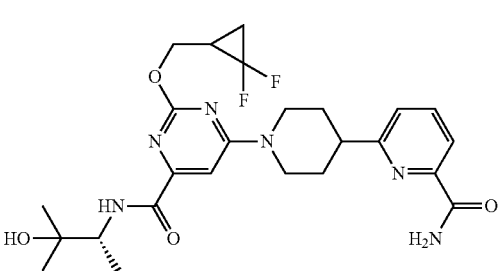 [SMILES: C[C@@H](NC(=O)c1cc(N2CCC(c3cccc(C(N)=O)n3)CC2)nc(OCC2CC2(F)F)n1)C(C)(C)O] | 6-[4-(6-carbamoylpyridin-2-yl)piperidin-1-yl]-2-[(2,2-difluoro-cyclopropyl)methoxy]-N-[(2R)-3-hydroxy-3-methylbutan-2-yl]pyrimidine-4-carboxamide | 519.2; (400 MHz, CDCl$_3$) δ ppm 8.08 (d, J = 7.58 Hz, 1 H), 8.02 (s, 1 H), 7.82 (t, J = 7.83 Hz, 2 H), 7.34 (d, J = 7.58 Hz, 1 H), 7.18 (s, 1 H), 5.53 (br. s., 1 H), 4.67 (br. s., 2 H), 4.44-4.56 (m, 1 H), 4.31-4.44 (m, 1 H), 4.01-4.14 (m, 1 H), 2.99-3.23 (m, 3 H), 2.11-2.24 (m, 1 H), 2.02-2.11 (m, 2 H), 1.85 (d, J = 8.84 Hz, 2 H), 1.28-1.40 (m, 2 H), 1.20-1.28 (m, 9 H). |
| 18* | 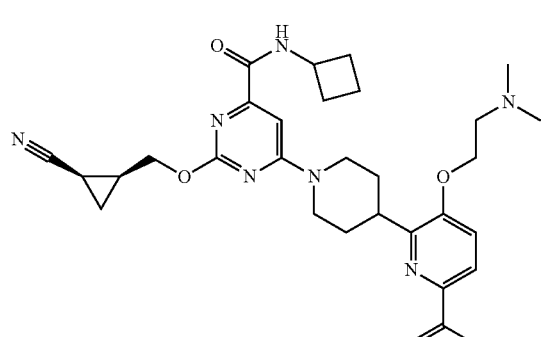 | 6-(4-{6-carbamoyl-3-[2-(dimethylamino)ethoxy]pyridin-2-yl}piperidin-1-yl)-2-{[(1S,2R)-2-cyanocyclopropyl]methoxy}-N-cyclobutyl-pyrimidine-4-carboxamide | 563.2; (400 MHz, DMSO-d$_6$) δ ppm 8.62 (d, J = 8.34 Hz, 1 H), 7.86 (d, J = 8.34 Hz, 1 H), 7.83 (d, J = 2.27 Hz, 1 H), 7.52 (d, J = 8.59 Hz, 1 H), 7.38 (d, J = 2.27 Hz, 1 H), 7.00 (s, 1 H), 4.68 (dd, J = 11.87, 5.31 Hz, 1 H), 4.37-4.46 (m, 1 H), 4.23 (t, J = 5.43 Hz, 2 H), 4.07 (dd, J = 11.87, 9.35 Hz, 1 H), 3.04-3.17 (m, 3 H), 2.81-2.89 (m, 2 H), 2.36 (s, 6 H), 2.14-2.22 (m, 5 H), 1.95-2.03 (m, 1 H), 1.81-1.90 (m, 5 H), 1.62-1.71 (m, 2 H), 1.23-1.33 (m, 1 H), 1.09-1.16 (m, 1 H). |
| 19 | 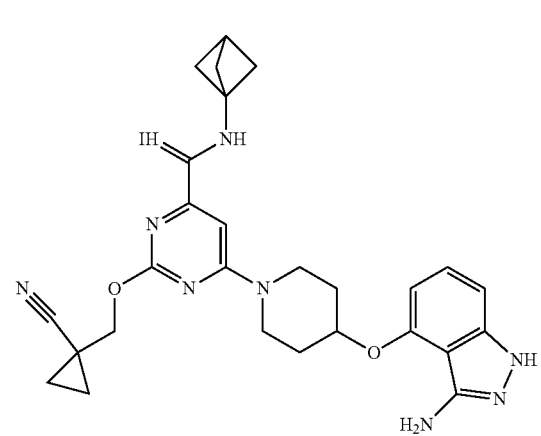 | 6-{4-[(3-amino-1H-indazol-4-yl)oxy]piperidin-1-yl}-N-(bicyclo[1.1.1]pent-1-yl)-2-[(1-cyanocyclopropyl)methoxy]pyrimidine-4-carboxamide | 515.2; (400 MHz, CDCl$_3$) δ ppm 8.22 (s, 1 H), 7.15 (s, 1 H), 6.92 (d, J = 8.08 Hz, 1 H), 6.42 (d, J = 7.07 Hz, 1 H), 4.81 (s, 1 H), 4.37 (s, 2 H), 3.91-4.10 (m, 2 H), 3.67-3.87 (m, 2 H), 3.06-3.18 (m, 2 H), 2.50 (s, 1 H), 2.20 (s, 6 H), 2.11-2.16 (m, 2 H), 1.95-2.03 (m, 2 H), 1.40-1.46 (m, 4 H), 1.16-1.21 (m, 2 H). |

TABLE 1-continued

| Ex. # | Structure | Compound Name | LRMS m/z (M + H)+; and 1H NMR |
|---|---|---|---|
| 20 | 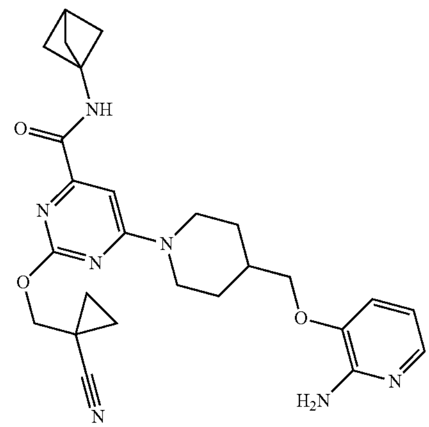 [SMILES: N#CC1(COc2nc(C(=O)NC34CC(C3)C4)cc(N3CCC(COc4cccnc4N)CC3)n2)CC1] | 6-(4-{[(2-aminopyridin-3-yl)oxy]methyl}piperidin-1-yl)-N-(bicyclo[1.1.1]pent-1-yl)-2-[(1-cyanocyclopropyl)methoxy]pyrimidine-4-carboxamide | 490.2; (400 MHz, CDCl$_3$) δ ppm 8.21 (s, 1 H), 7.64 (d, J = 4.55 Hz, 1 H), 7.12 (s, 1 H), 6.90 (d, J = 7.58 Hz, 1 H), 6.61 (dd, J = 7.58, 5.31 Hz, 1 H), 4.91 (s, 2 H), 4.46 (s, 2 H), 4.36 (br. s., 2 H), 3.87 (d, J = 6.32 Hz, 2 H), 2.96-3.10 (m, 2 H), 2.50 (s, 1 H), 2.20 (s, 6 H), 2.12-2.18 (m, 1 H), 1.97 (d, J = 12.63 Hz, 2 H), 1.32-1.46 (m, 4 H), 1.16-1.22 (m, 2 H). |
| 21* | 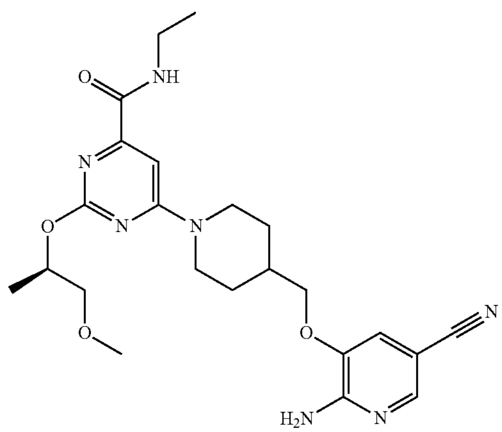 [SMILES: CCNC(=O)c1cc(N2CCC(COc3cc(C#N)cnc3N)CC2)nc(O[C@H](C)COC)n1] | 6-(4-{[(2-amino-5-cyanopyridin-3-yl)oxy]methyl}piperidin-1-yl)-N-ethyl-2-{[(2R)-1-methoxypropan-2-yl]oxy}pyrimidine-4-carboxamide | 470.2; (400 MHz, CDCl$_3$) δ ppm 8.00 (br. s., 2 H), 7.17 (br. s., 1 H), 7.00 (s, 1 H), 5.29-5.42 (m, 3 H), 4.63 (br. s., 2 H), 3.91 (d, J = 5.8 Hz, 2 H), 3.68 (dd, J = 9.9, 6.3, 1 H), 3.39-3.52 (m, 6 H), 3.02 (t, J = 11.7 Hz, 2 H), 2.22 (br. s., 1 H), 1.74-2.04 (m, 5 H), 1.32-1.46 (m, 5 H), 1.24 (t, J = 7.2 Hz, 3H). |
| 22* | 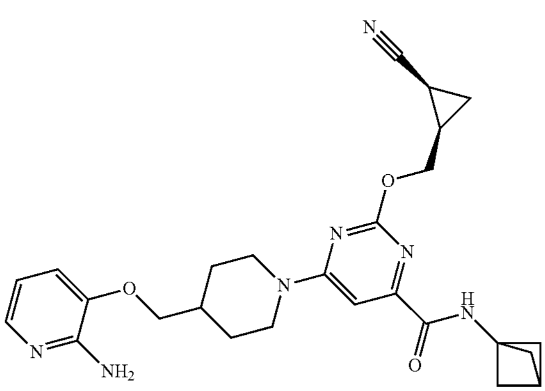 [SMILES: N#C[C@H]1C[C@H]1COc1nc(C(=O)NC23CC(C2)C3)cc(N2CCC(COc3cccnc3N)CC2)n1] | 6-(4-{[(2-aminopyridin-3-yl)oxy]methyl}piperidin-1-yl)-N-(bicyclo[1.1.1]pent-1-yl)-2-{[(1R,2S)-2-cyanocyclopropyl]methoxy}pyrimidine-4-carboxamide | 490.2; (400 MHz, CDCl$_3$) δ ppm 8.18 (s, 1 H), 7.63 (d, J = 5.05 Hz, 1 H), 7.11 (s, 1 H), 6.91 (d, J = 7.58 Hz, 1 H), 6.61 (dd, J = 7.58, 5.31 Hz, 1 H), 5.03 (br. s., 2H), 4.41-4.53 (m, 2 H), 4.48 (br. s, 2 H), 3.87 (d, J = 6.32 Hz, 2 H), 3.01 (t, J = 11.87 Hz, 2 H), 2.50 (s, 1 H), 2.19 (s, 6 H), 1.97 (d, J = 12.13 Hz, 2 H), 1.83-1.91 (m, 1 H), 1.65-1.71 (m, 2 H), 1.33-1.43 (m, 3 H), 1.14 (q, J = 5.64 Hz, 1 H). |

TABLE 1-continued

| Ex. # | Structure | Compound Name | LRMS m/z (M + H)+; and 1H NMR |
|---|---|---|---|
| 23* | 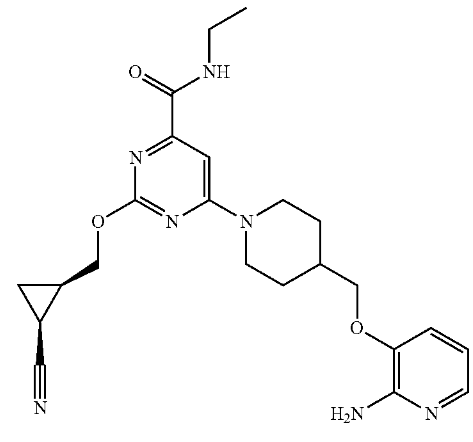 [SMILES: CCNC(=O)c1cc(N2CCC(COc3cccnc3N)CC2)nc(OC[C@@H]2C[C@@H]2C#N)n1] | 6-(4-{[(2-aminopyridin-3-yl)oxy]methyl}piperidin-1-yl)-2-{[(1R,2S)-2-cyanocyclopropyl]methoxy}-N-ethylpyrimidine-4-carboxamide | 452.2; (400 MHz, CDCl$_3$) δ ppm 7.86 (t, J = 5.68 Hz, 1 H), 7.65 (d, J = 4.04 Hz, 1 H), 7.14 (s, 1 H), 6.91 (d, J = 7.83 Hz, 1 H), 6.62 (dd, J = 7.58, 5.31 Hz, 1 H), 4.87 (s, 2 H), 4.44-4.53 (m, 2 H), 4.49 (br. s., 2 H), 3.87 (d, J = 6.32 Hz, 2 H), 3.41-3.53 (m, 2 H), 2.90-3.15 (m, 2 H), 2.12-2.29 (m, 1 H), 1.98 (d, J = 12.38 Hz, 2 H), 1.82-1.93 (m, 1 H), 1.70-1.76 (m, 1 H), 1.31-1.46 (m, 3 H), 1.24 (t, J = 7.33 Hz, 3 H), 1.10-1.19 (m, 1 H). |
| 24* | 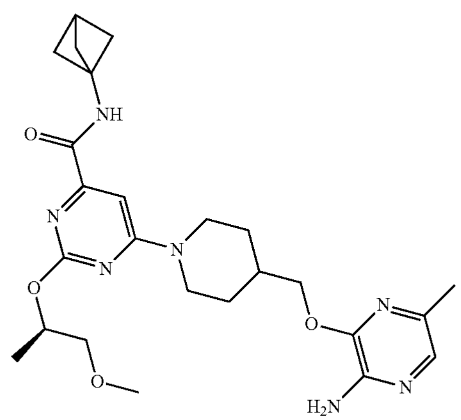 [SMILES: COC[C@@H](C)Oc1nc(C(=O)NC23CC(C2)C3)cc(N2CCC(COc3nc(C)cnc3N)CC2)n1] | 6-(4-{[(3-amino-6-methylpyrazin-2-yl)oxy]methyl}piperidin-1-yl)-N-(bicyclo[1.1.1]pent-1-yl)-2-{[(2R)-1-methoxypropan-2-yl]oxy}pyrimidine-4-carboxamide | 498.2; (400 MHz, CDCl$_3$) δ ppm 8.23 (s, 1 H), 7.40 (s, 1 H), 7.06 (s, 1 H), 5.25-5.41 (m, 1 H), 4.57 (s, 2 H), 4.24 (d, J = 6.32 Hz, 2 H), 4.35 (br. s., 2 H), 3.67 (dd, J = 9.85, 6.32 Hz, 1 H), 3.49 (dd, J = 10.11, 4.80 Hz, 1 H), 3.41 (s, 3 H), 2.99 (t, J = 12.25 Hz, 2 H), 2.49 (s, 1 H), 2.29 (s, 3 H), 2.19 (s, 6 H), 2.07-2.23 (m, 1 H), 1.93 (d, J = 12.88 Hz, 2 H), 1.38 (d, J = 6.32 Hz, 3 H), 1.29-1.43 (m, 2 H). |
| 25* | 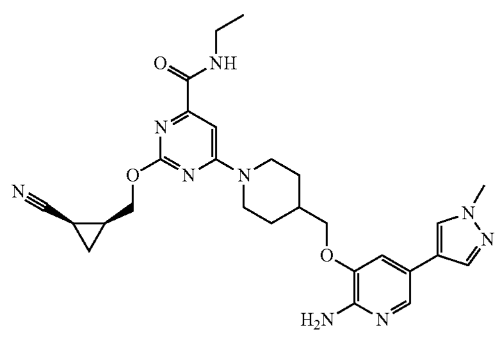 [SMILES: CCNC(=O)c1cc(N2CCC(COc3cc(-c4cnn(C)c4)cnc3N)CC2)nc(OC[C@H]2C[C@H]2C#N)n1] | 6-[4-({[2-amino-5-(1-methyl-1H-pyrazol-4-yl)pyridin-3-yl]oxy}methyl)piperidin-1-yl]-2-{[(1S,2R)-2-cyanocyclopropyl]methoxy}-N-ethylpyrimidine-4-carboxamide | 532.2; (400 MHz, CDCl$_3$) δ ppm 7.86 (t, J = 5.56 Hz, 1 H), 7.72 (s, 1 H), 7.65 (s, 1 H), 7.53 (s, 1 H), 7.15 (s, 1 H), 6.99 (s, 1 H), 5.37 (s, 2 H), 4.42-4.57 (m, 2 H), 4.49 (br. s., 2 H), 3.95 (s, 3 H), 3.92 (d, J = 6.32 Hz, 2 H), 3.43-3.51 (m, 2 H), 3.03 (t, J = 12.63 Hz, 2 H), 2.11-2.37 (m, 1 H), 2.00 (d, J = 13.89 Hz, 2 H), 1.84-1.91 (m, 1 H), 1.30-1.49 (m, 4 H), 1.25 (t, J = 7.20 Hz, 3 H), 1.15 (q, J = 5.64 Hz, 1 H). |
| 26* | 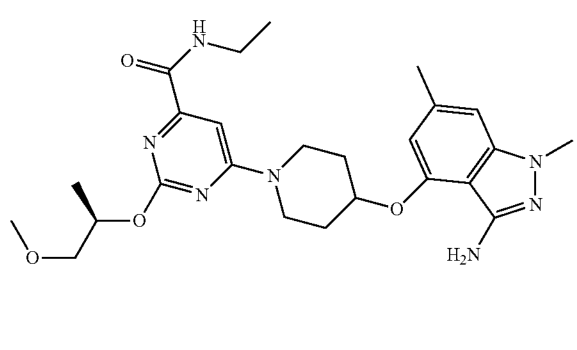 | 6-{4-[(3-amino-1,6-dimethyl-1H-indazol-4-yl)oxy]piperidin-1-yl}-N-ethyl-2-{[(2R)-1-methoxypropan-2-yl]oxy}pyrimidine-4-carboxamide | 484.4; (400 MHz, CD$_3$OD) δ ppm 7.10 (s, 1 H), 6.65 (s, 1 H), 6.35 (s, 1 H), 5.40-5.44 (m, 1 H), 4.07 (s, 2 H), 3.78 (s, 2 H), 3.50-3.68 (m, 2 H), 3.41-3.46 (m, 5 H), 2.41 (s, 3 H), 2.46 (s, 2 H), 1.97 (s, 2 H), 1.36 (d, J = 6.4 Hz, 3 H), 1.25 (t, J = 7.6 Hz, 3 H). |

TABLE 1-continued

| Ex. # | Structure | Compound Name | LRMS m/z (M + H)+; and 1H NMR |
|---|---|---|---|
| 27* | 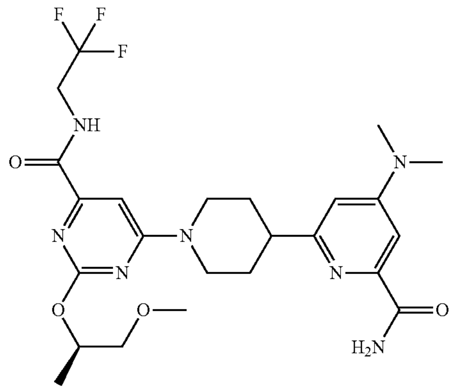 [SMILES: COC[C@@H](C)Oc1nc(C(=O)NCC(F)(F)F)cc(N2CCC(c3cc(N(C)C)cc(C(N)=O)n3)CC2)n1] | 6-{4-[6-carbamoyl-4-(dimethylamino)pyridin-2-yl]piperidin-1-yl}-2-{[(2R)-1-methoxypropan-2-yl]oxy}-N-(2,2,2-trifluoroethyl)pyrimidine-4-carboxamide | 540.3; (400 MHz, CD$_3$OD) δ ppm 7.21-7.29 (m, 1 H), 7.12 (s, 1 H), 6.62-6.65 (m, 1 H), 5.35-5.45 (m, 1 H), 4.10 (q, J = 6.6 Hz, 2 H), 3.45-3.65 (m, 3 H), 3.39 (s, 3 H), 3.15-3.20 (m, 2 H), 3.06 (s, 3 H), 2.95-3.02 (m, 1 H), 1.95-2.05 (m, 2 H), 1.82-1.97 (m, 2 H), 1.35 (d, J = 6.4 Hz, 3 H). |
| 28 | 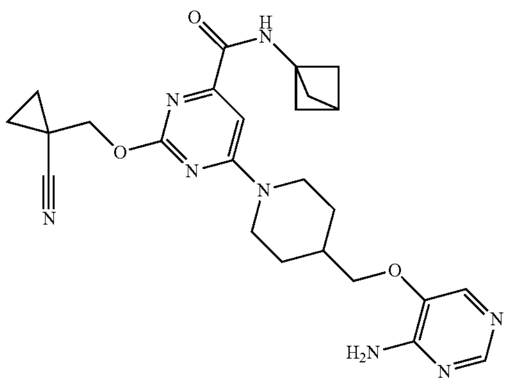 [SMILES: N#CC1(COc2nc(C(=O)NC34CC(C3)C4)cc(N3CCC(COc4cncnc4N)CC3)n2)CC1] | 6-(4-{[(4-aminopyrimidin-5-yl)oxy]methyl}piperidin-1-yl)-N-(bicyclo[1.1.1]pent-1-yl)-2-[(1-cyanocyclopropyl)methoxy]pyrimidine-4-carboxamide | 491.2; (400 MHz, CDCl$_3$) δ ppm 8.23 (d, J = 11.87 Hz, 2 H), 7.82 (s, 1 H), 7.13 (s, 1 H), 5.13 (s, 2 H), 4.36 (s, 2 H), 4.46 (br. s., 2 H), 3.93 (d, J = 6.06 Hz, 2 H), 3.02 (t, J = 13.01 Hz, 2 H), 2.50 (s, 1 H), 2.19 (s, 6 H), 2.13-2.20 (m, 1 H), 1.95 (d, J = 11.87 Hz, 2 H), 1.35-1.47 (m, 4 H), 1.14-1.22 (m, 2 H). |
| 29* | 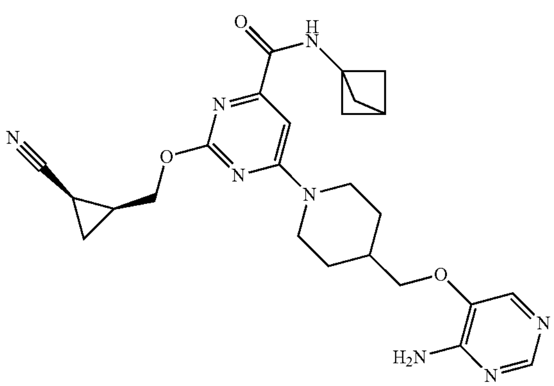 [SMILES: N#C[C@@H]1C[C@@H]1COc1nc(C(=O)NC23CC(C2)C3)cc(N2CCC(COc3cncnc3N)CC2)n1] | 6-(4-{[(4-aminopyrimidin-5-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide | 491.0; (400 MHz, CDCl$_3$) δ ppm 8.24 (s, 1 H), 8.18 (s, 1 H), 7.81 (s, 1 H), 7.11 (s, 1 H), 5.13 (s, 2 H), 4.40-4.52 (m, 4 H), 3.92 (d, J = 6.0 Hz, 2 H), 3.00 (m, 2 H), 2.49 (s, 1 H), 2.18 (s, 7 H), 1.93-1.96 (m, 2 H), 1.84-1.86 (m, 1 H), 1.68-1.75 (m, 2H), 1.32-1.40 (m, 3H), 1.12-1.17 (m, 1 H). |
| 30* | 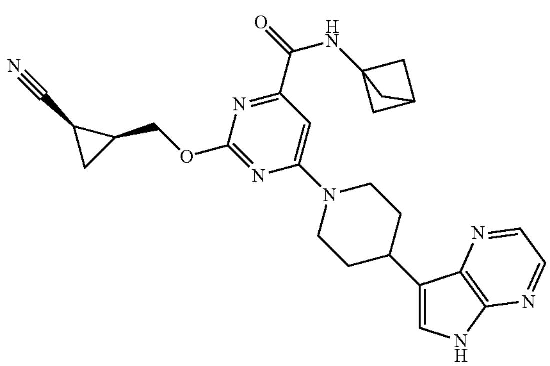 [SMILES: N#C[C@@H]1C[C@@H]1COc1nc(C(=O)NC23CC(C2)C3)cc(N2CCC(c3c[nH]c4nccnc34)CC2)n1] | N-(bicyclo[1.1.1]pent-1-yl)-2-{[(1S,2R)-2-cyanocyclopropyl]methoxy}-6-[4-(5H-pyrrolo[2,3-b]pyrazin-7-yl)piperidin-1-yl]pyrimidine-4-carboxamide | 485.2; (400 MHz, CDCl$_3$) δ ppm 8.49 (br. s., 1 H), 8.44 (d, J = 2.78 Hz, 1 H), 8.25 (d, J = 2.53 Hz, 1 H), 8.19 (s, 1 H), 7.33 (d, J = 2.78 Hz, 1 H), 7.14 (s, 1 H), 4.28-5.13 (m, 4 H), 3.31-3.45 (m, 1 H), 3.18 (t, J = 12.88 Hz, 2 H), 2.50 (s, 1 H), 2.28 (d, J = 13.39 Hz, 2 H), 2.19 (s, 6 H), 1.73-1.94 (m, 3 H), 1.68 (td, J = 8.34, 5.56 Hz, 1 H), 1.34 (td, J = 8.53, 5.68 Hz, 1 H), 1.09-1.18 (m, 1 H). |

TABLE 1-continued

| Ex. # | Structure | Compound Name | LRMS m/z (M + H)+; and 1H NMR |
|---|---|---|---|
| 31 | 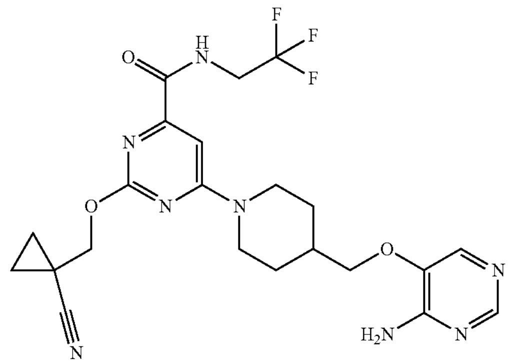 [SMILES: N#CC1(COc2nc(C(=O)NCC(F)(F)F)cc(N3CCC(COc4cncnc4N)CC3)n2)CC1] | 6-(4-{[(4-aminopyrimidin-5-yl)oxy]methyl}piperidin-1-yl)-2-[(1-cyanocyclopropyl)methoxy]-N-(2,2,2-trifluoroethyl)pyrimidine-4-carboxamide | 507.2; (400 MHz, CD$_3$OD) δ ppm 8.04 (s, 1 H), 7.79 (s, 1 H), 7.16 (s, 1 H), 4.59 (br. s., 2 H), 4.45 (s, 2 H), 4.10 (q, J = 9.09 Hz, 2 H), 4.00 (d, J = 6.06 Hz, 2 H), 3.11 (t, J = 11.62 Hz, 2 H), 2.19-2.35 (m, 1 H), 2.04 (d, J = 12.38 Hz, 2 H), 1.36-1.52 (m, 4 H), 1.19-1.29 (m, 2 H). |
| 32* | 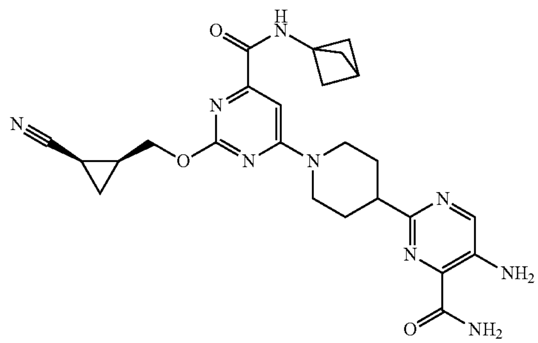 [SMILES: N#C[C@@H]1C[C@@H]1COc1nc(C(=O)NC23CC(C2)C3)cc(N2CCC(c3ncc(N)c(C(N)=O)n3)CC2)n1] | 6-[4-(5-amino-4-carbamoylpyrimidin-2-yl)piperidin-1-yl]-N-(bicyclo[1.1.1]pent-1-yl)-2-{[(1S,2R)-2-cyanocyclopropyl]methoxy}pyrimidine-4-carboxamide | 504.2 (400 MHz, CDCl$_3$) δ ppm 8.32 (s, 1 H), 8.19 (s, 1 H), 7.80 (br. s., 1 H), 7.13 (s, 1 H), 5.77 (s, 2 H), 5.46 (br. s., 1 H), 4.30-5.04 (m, 4 H), 2.91-3.28 (m, 3 H), 2.50 (s, 1 H), 2.19 (s, 6 H), 2.07-2.15 (m, 2 H), 1.74-1.93 (m, 3 H), 1.68 (td, J = 8.21, 5.56 Hz, 1 H), 1.34 (td, J = 8.53, 5.68 Hz, 1 H), 1.14 (q, J = 5.81 Hz, 1 H). |
| 33* | 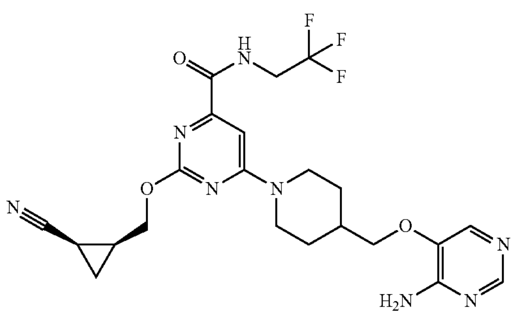 [SMILES: N#C[C@@H]1C[C@@H]1COc1nc(C(=O)NCC(F)(F)F)cc(N2CCC(COc3cncnc3N)CC2)n1] | 6-(4-{[(4-aminopyrimidin-5-yl)oxy]methyl}piperidin-1-yl)-2-{[(1S,2R)-2-cyanocyclopropyl]methoxy}-N-(2,2,2-trifluoroethyl)pyrimidine-4-carboxamide | 507.2; (400 MHz, CDCl$_3$) δ ppm 8.24 (s, 1 H), 8.18 (t, J = 6.44 Hz, 1 H), 7.82 (s, 1 H), 7.14 (s, 1 H), 5.12 (s, 2 H), 4.43-4.56 (m, 2 H), 4.49 (br. s., 2 H), 4.02-4.12 (m, 2 H), 3.94 (d, J = 6.06 Hz, 2 H), 3.03 (t, J = 10.99 Hz, 2 H), 2.13-2.28 (m, 1 H), 1.97 (d, J = 12.38 Hz, 2 H), 1.83-1.91 (m, 1 H), 1.69-1.72 (m, 1 H), 1.32-1.45 (m, 3 H), 1.15 (q, J = 5.64 Hz, 1 H). |
| 34*** | 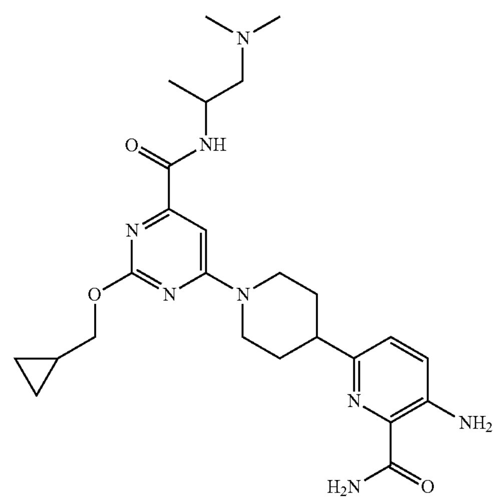 [SMILES: CC(CN(C)C)NC(=O)c1cc(N2CCC(c3ccc(N)c(C(N)=O)n3)CC2)nc(OCC2CC2)n1] | 6-[4-(5-amino-6-carbamoylpyridin-2-yl)piperidin-1-yl]-2-(cyclopropylmethoxy)-N-[1-(dimethylamino)propan-2-yl]pyrimidine-4-carboxamide | 497.2; (400 MHz, CD$_3$OD) δ ppm 8.31 (s, 1 H), 7.09 (d, J = 8.8 Hz, 1 H), 7.02 (d, J = 8.8 Hz, 1 H), 6.94 (s, 1 H), 4.40-4.42 (m, 3 H), 4.10 (d, J = 7.2 Hz, 2 H), 3.06-3.07 (m, 3 H), 3.02-3.03 (m, 1 H), 2.76 (s, 6 H), 1.91-1.94 (m, 2 H), 1.64-1.68 (m, 2 H), 1.20 (d, J = 6.4 Hz, 4 H), 0.49-0.51 (m, 2 H), 0.25-0.27 (m, 2 H). |

_US 9,593,097 B2_

TABLE 1-continued

| Ex. # | Structure | Compound Name | LRMS m/z (M + H)+; and 1H NMR |
|---|---|---|---|
| 35* | 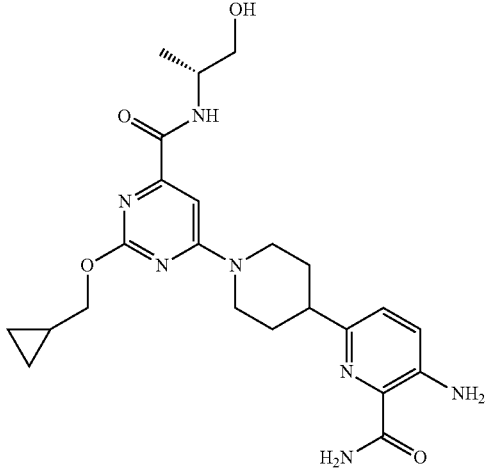 [SMILES: C[C@H](CO)NC(=O)c1cc(N2CCC(c3ccc(N)c(C(N)=O)n3)CC2)nc(OCC2CC2)n1] | 6-[4-(5-amino-6-carbamoylpyridin-2-yl)piperidin-1-yl]-2-(cyclopropyl-methoxy)-N-[(2R)-1-hydroxypropan-2-yl]pyrimidine-4-carboxamide | 470.2; (400 MHz, DMSO-d6) δ ppm 8.14 (d, J = 8.6 Hz, 1 H), 7.82 (d, J = 2.8 Hz, 1 H), 7.21 (d, J = 2.8 Hz, 1 H), 7.15-7.20 (m, 1 H), 7.09 (d, J = 8.6 Hz, 1 H), 6.98 (s, 1 H), 6.65 (s, 2 H), 4.84 (t, J = 5.3 Hz, 1 H), 4.50 (br. s., 2 H), 4.11 (d, J = 7.3 Hz, 2 H), 3.89-4.02 (m, 1 H), 3.43 (qd, J = 5.5, 11.2 Hz, 2 H), 3.06 (t, J = 12.2 Hz, 2 H), 2.88 (t, J = 11.8 Hz, 1 H), 1.92 (dd, J = 2.1, 12.7 Hz, 2H), 1.66 (dq, J = 4.2, 12.5 Hz, 2 H), 1.17-1.27 (m, 1 H), 1.13 (d, J = 6.8 Hz, 3H), 0.48-0.64 (m, 2 H), 0.27-0.38 (m, 2H). |
| 36** | 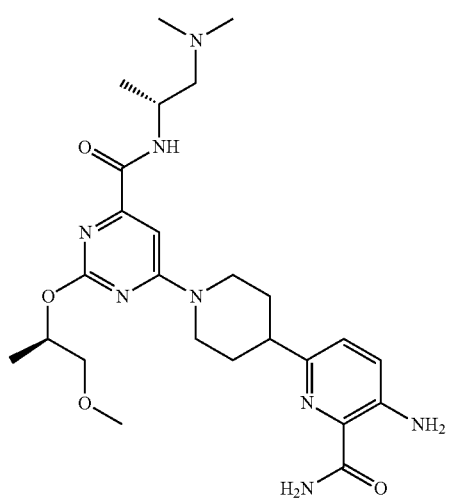 [SMILES: COC[C@@H](C)Oc1nc(C(=O)N[C@H](C)CN(C)C)cc(N2CCC(c3ccc(N)c(C(N)=O)n3)CC2)n1] | 6-[4-(5-amino-6-carbamoylpyridin-2-yl)piperidin-1-yl]-N-[(2R)-1-(dimethylamino)propan-2-yl]-2-{[(2R)-1-methoxypropan-2-yl]oxy}pyrimidine-4-carboxamide | 515.3; (400 MHz, CD3OD) δ ppm 8.53 (s, 1 H), 7.19 (d, J = 8.4 Hz, 1 H), 7.12 (d, J = 8.4 Hz, 1 H), 7.04 (s, 1 H), 5.37-5.38 (m, 1 H), 4.40-4.42 (m, 2 H), 4.39-4.40 (m, 1 H), 3.51-3.62 (m, 2 H), 3.38 (s, 3 H), 3.10-3.16 (m, 2 H), 2.92-3.00 (m, 2 H), 2.75-2.80 (m, 1 H), 2.59 (s, 6 H), 2.03 (d, J = 12.0 Hz, 2 H), 1.74-1.77 (m, 2 H), 1.34 (d, J = 7.2 Hz, 3 H), 1.28 (d, J = 6.8 Hz, 3H). |
| 37* | 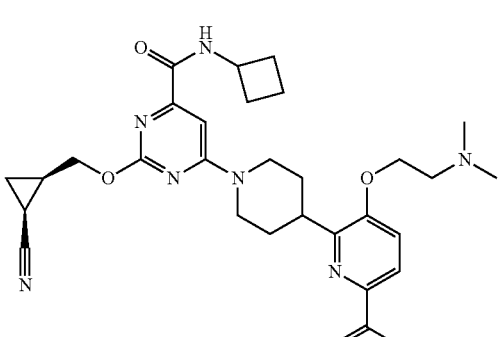 | 6-(4-{6-carbamoyl-3-[2-(dimethylamino)ethoxy]pyridin-2-yl}piperidin-1-yl)-2-{[(1R,2S)-2-cyanocyclopropyl]methoxy}-N-cyclobutyl-pyrimidine-4-carboxamide | 563.2; (400 MHz, CDCl3) δ ppm 8.05 (d, J = 8.59 Hz, 1 H), 7.98 (d, J = 8.34 Hz, 1 H), 7.64 (d, J = 4.04 Hz, 1 H), 7.24 (d, J = 8.59 Hz, 1 H), 7.15 (s, 1 H), 5.45 (d, J = 4.29 Hz, 1 H), 4.34-5.11 (m, 5 H), 4.19 (t, J = 5.68 Hz, 2 H), 3.47 (tt, J = 11.40, 3.88 Hz, 1 H), 3.12 (t, J = 10.48 Hz, 2 H), 2.85 (t, J = 5.68 Hz, 2 H), 2.32-2.52 (m, 8 H), 1.68-2.11 (m, 10 H, partially obscured by water), 1.35 (td, J = 8.46, 5.56 Hz, 1 H), 1.13-1.19 (m, 1 H). |

TABLE 1-continued

| Ex. # | Structure | Compound Name | LRMS m/z (M + H)+; and 1H NMR |
|---|---|---|---|
| 38* | 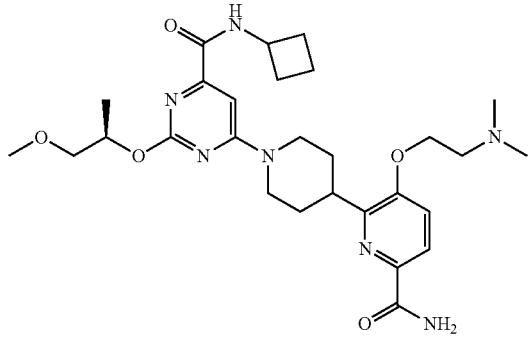 | 6-(4-{6-carbamoyl-3-[2-(dimethylamino)ethoxy]pyridin-2-yl}piperidin-1-yl)-N-cyclobutyl-2-{[(2R)-1-methoxypropan-2-yl]oxy}pyrimidine-4-carboxamide | 556.3; (400 MHz, CDCl$_3$) δ ppm 8.01-8.05 (m, 2 H), 7.63 (d, J = 4.0 Hz, 1 H), 7.22 (d, J = 8.0 Hz, 1 H), 7.09 (s, 1 H), 5.48 (d, J = 4.0 Hz, 1 H), 5.31-5.35 (m, 1 H), 5.51-5.53 (m, 3 H), 4.13 (t, J = 5.6 Hz, 2 H), 3.66-3.69 (m, 1 H), 3.42-3.52 (m, 5 H), 3.09-3.11 (m, 2 H), 2.80 (t, J = 5.6 Hz, 2 H), 2.36-2.38 (m, 8 H), 1.93-2.00 (m, 8 H, partially obscured by water), 1.40-1.38 (d, J = 6.4 Hz, 3 H). |
| 39*** | 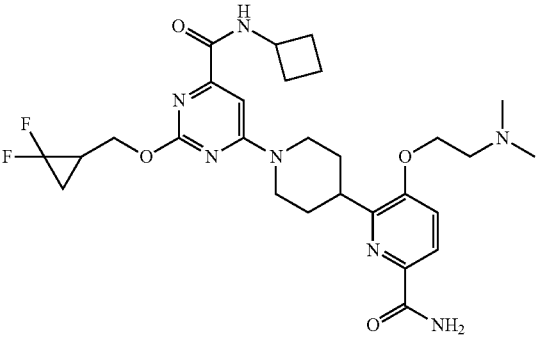 [SMILES: CN(C)CCOc1ccc(C(N)=O)nc1C1CCN(c2cc(C(=O)NC3CCC3)nc(OCC3CC3(F)F)n2)CC1] | 6-(4-{6-carbamoyl-3-[2-(dimethylamino)ethoxy]pyridin-2-yl}piperidin-1-yl)-N-cyclobutyl-2-[(2,2-difluorocyclopropyl)methoxy]pyrimidine-4-carboxamide | 574.2; (400 MHz, CDCl$_3$) δ ppm 8.05 (d, J = 8.08 Hz 1 H), 7.98 (d, J = 8.08 Hz, 1 H), 7.63 (d, J = 4.29 Hz, 1 H), 7.24 (d, J = 8.59 Hz, 1 H), 7.15 (s, 1 H), 5.44 (d, J = 4.04 Hz, 1 H), 4.43-4.97 (m, 4 H), 4.28-4.40 (m, 1 H), 4.17 (t, J = 5.68 Hz, 2 H), 3.46 (tt, J = 11.49, 3.66 Hz, 1 H), 3.12 (t, J = 12.51 Hz, 2 H), 2.82 (t, J = 5.68 Hz, 2 H), 2.32-2.49 (m, 8 H), 1.93-2.25 (m, 5 H), 1.72-1.93 (m, 4 H), 1.53-1.60 (m, 1 H, partially obscured by water), 1.34 (m, 1 H). |
| 40* | 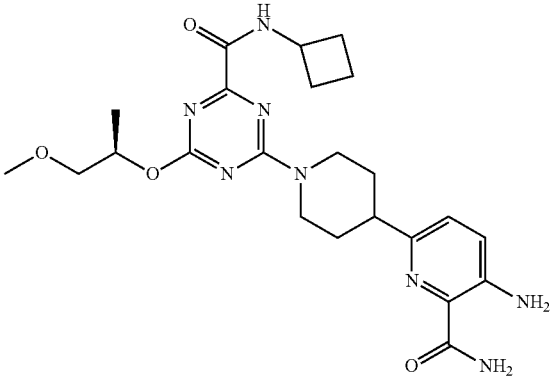 [SMILES: COC[C@@H](C)Oc1nc(C(=O)NC2CCC2)nc(N2CCC(c3ccc(N)c(C(N)=O)n3)CC2)n1] | 4-[4-(5-amino-6-carbamoylpyridin-2-yl)piperidin-1-yl]-N-cyclobutyl-6-{[(2R)-1-methoxypropan-2-yl]oxy}-1,3,5-triazine-2-carboxamide | 485.2; (400 MHz, CDCl$_3$) δ ppm 7.94 (d, J = 7.8 Hz, 1 H), 7.86 (br. s., 1 H), 7.04-7.15 (m, 1 H), 6.93-7.05 (m, 1 H), 5.84 (s, 2 H), 5.36-5.50 (m, 1 H), 5.30 (br. s., 1 H), 5.15 (d, J = 12.13 Hz, 1 H), 4.90 (d, J = 12.38 Hz, 1 H), 4.44-4.62 (m, 1 H), 3.65 (dd, J = 10.36, 6.57 Hz, 1 H), 3.52 (dd, J = 10.36, 4.29 Hz, 1 H), 3.42 (s, 3 H), 2.99-3.17 (m, 2 H), 2.89 (tt, J = 11.87, 3.66 Hz, 1 H), 2.34-2.51 (m, 2 H), 1.94-2.07 (m, 4 H), 1.68-1.86 (m, 4 H), 1.39 (d, J = 6.32 Hz, 3 H). |
| 41 | 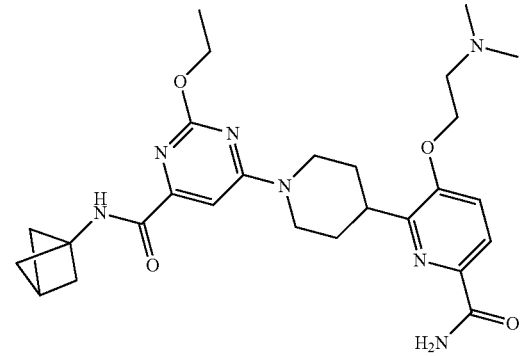 [SMILES: CCOc1nc(C(=O)NC23CC(C2)C3)cc(N2CCC(c3nc(C(N)=O)ccc3OCCN(C)C)CC2)n1] | N-(bicyclo[1.1.1]pent-1-yl)-6-(4-{6-carbamoyl-3-[2-(dimethylamino)ethoxy]pyridin-2-yl}piperidin-1-yl)-2-ethoxypyrimidine-4-carboxamide | 524.2; (400 MHz, DMSO-d$_6$) δ ppm 8.85 (s, 1 H), 7.81-7.85 (m, 2 H), 7.50 (d, J = 8.4 Hz, 1 H), 7.37-7.38 (m, 1 H), 6.94 (s, 1 H), 4.33 (q, J = 6.8 Hz, 2 H), 4.16-4.19 (m, 2 H), 3.32-3.40 (m, 3 H), 3.07 (br. s., 2 H), 2.67-2.69 (m, 2 H), 2.43 (s, 1 H), 2.23 (s, 6 H), 2.07 (s, 6 H), 1.84 (s, 4 H), 1.29 (t, J = 7.2 Hz, 3H). |

TABLE 1-continued

| Ex. # | Structure | Compound Name | LRMS m/z (M + H)+; and 1H NMR |
|---|---|---|---|
| 42* | 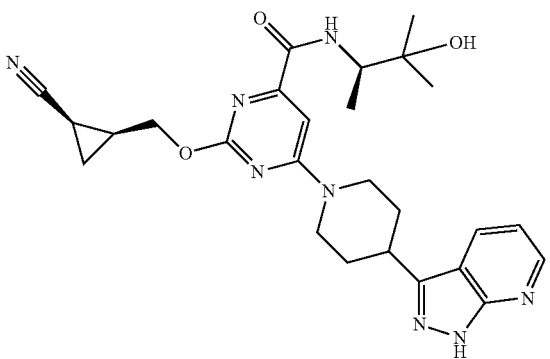 [SMILES: C[C@@H](NC(=O)c1cc(N2CCC(c3n[nH]c4ncccc34)CC2)nc(OC[C@H]2C[C@H]2C#N)n1)C(C)(C)O] | 2-{[(1S,2R)-2-cyanocyclopropyl]methoxy}-N-[(2R)-3-hydroxy-3-methylbutan-2-yl]-6-[4-(1H-pyrazolo[3,4-b]pyridin-3-yl)piperidin-1-yl]pyrimidine-4-carboxamide | 505.1; (600 MHz, DMSO-$d_6$) δ ppm 8.47 (dd, J = 4.39, 1.17 Hz, 1 H), 8.31 (d, J = 8.05 Hz, 1 H), 8.14 (d, J = 9.51 Hz, 1 H), 7.14 (dd, J = 8.05, 4.54 Hz, 1 H), 7.06 (s, 1 H), 4.75 (s, 1 H), 4.60 (dd, J = 11.78, 5.63 Hz, 1 H), 4.08 (dd, J = 11.78, 9.15 Hz, 1 H), 3.84 (dd, J = 9.29, 6.81 Hz, 2 H), 2.11 (d, J = 10.83 Hz, 3 H), 1.98 (td, J = 8.09, 5.78 Hz, 1 H), 1.77-1.89 (m, 4 H), 1.28 (td, J = 8.45, 5.05 Hz, 1 H), 1.13-1.15 (m, 5 H), 1.12 (s, 2 H), 1.11 (s, 2H), 1.07 (s, 4 H). |
| 43* | 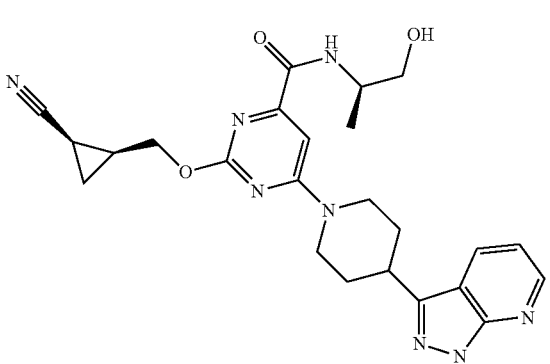 | 2-{[(1S,2R)-2-cyanocyclopropyl]methoxy}-N-[(2R)-1-hydroxypropan-2-yl]-6-[4-(1H-pyrazolo[3,4-b]pyridin-3-yl)piperidin-1-yl]pyrimidine-4-carboxamide | 477.1; (600 MHz, DMSO-$d_6$) δ ppm 8.47 (dd, J = 4.39, 1.46 Hz, 1 H), 8.31 (dd, J = 8.12, 1.39 Hz, 1 H), 8.19 (d, J = 8.49 Hz, 1 H), 7.13 (dd, J = 8.05, 4.54 Hz, 1 H), 7.05 (s, 1 H), 4.65 (dd, J = 11.85, 5.41 Hz, 1 H), 4.06 (dd, J = 11.85, 9.22 Hz, 1 H), 3.94-4.00 (m, 1 H), 3.33-3.48 (m, 5 H), 2.11 (d, J = 10.68 Hz, 2 H), 1.98 (td, J = 8.12, 5.71 Hz, 1 H), 1.77-1.88 (m, 5 H), 1.28 (td, J = 8.52, 4.90 Hz, 1 H), 1.23 (s, 2 H), 1.10-1.16 (m, 4 H). |
| 44* | 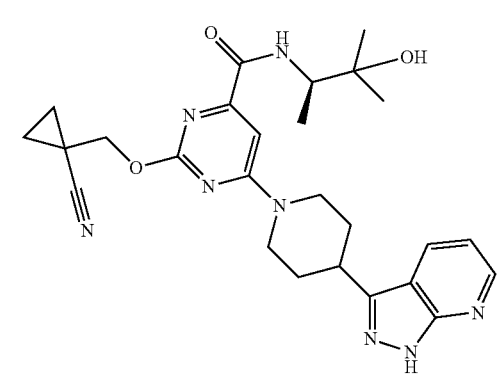 [SMILES: C[C@@H](NC(=O)c1cc(N2CCC(c3n[nH]c4ncccc34)CC2)nc(OCC2(C#N)CC2)n1)C(C)(C)O] | 2-[(1-cyanocyclopropyl)methoxy]-N-[(2R)-3-hydroxy-3-methylbutan-2-yl]-6-[4-(1H-pyrazolo[3,4-b]pyridin-3-yl)piperidin-1-yl]pyrimidine-4-carboxamide | 505.1; (700 MHz, DMSO-$d_6$) δ ppm 8.46-8.51 (m, 1 H), 8.28-8.34 (m, 1 H), 8.10-8.16 (m, 1 H), 7.11-7.18 (m, 1 H), 7.05-7.10 (m, 1 H), 4.67-4.76 (m, 1 H), 4.27-4.41 (m, 3 H), 3.81-3.91 (m, 1 H), 3.45 (d, J = 3.93 Hz, 1 H), 2.11 (br. s., 2 H), 1.83 (br. s., 2 H), 1.36 (d, J = 3.25 Hz, 2 H), 1.19-1.27 (m, 3 H), 1.09-1.18 (m, 8 H), 1.02-1.11 (m, 4 H). |
| 45*** | 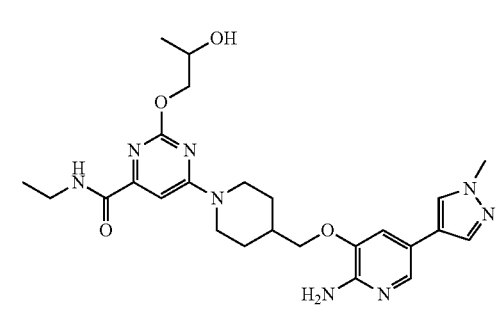 [SMILES: CCNC(=O)c1cc(N2CCC(COc3cc(-c4cnn(C)c4)cnc3N)CC2)nc(OCC(C)O)n1] | 6-[4-({[2-amino-5-(1-methyl-1H-pyrazol-4-yl)pyridin-3-yl]oxy}methyl)piperidin-1-yl]-N-ethyl-2-(2-hydroxypropoxy)pyrimidine-4-carboxamide | 511.2; (700 MHz, DMSO-$d_6$) δ ppm 8.56 (t, J = 6.06 Hz, 1 H), 7.99 (s, 1 H), 7.72-7.77 (m, 2 H), 7.18 (d, J = 1.71 Hz, 1 H), 6.98 (s, 1 H), 5.58 (s, 2 H), 4.29-4.97 (m, 1 H), 4.17 (dd, J = 10.76, 6.15 Hz, 1 H), 4.10 (dd, J = 10.76, 5.12 Hz, 1 H), 3.92-3.97 (m, 1 H), 3.91 (d, J = 6.49 Hz, 2 H), 3.82 (s, 3 H), 3.28 (quin, J = 6.88 Hz, 1 H), 3.02 (br. s., 1 H), 2.10-2.19 (m, 1 H), 1.95 (d, J = 11.44 Hz, 2 H), 1.29 (dq, J = 4.01, 12.33 Hz, 2 H), 1.20-1.25 (m, 1 H), 1.14 (d, J = 6.32 Hz, 3 H), 1.10 (t, J = 7.17 Hz, 3 H) |

TABLE 1-continued

| Ex. # | Structure | Compound Name | LRMS m/z (M + H)+; and 1H NMR |
|---|---|---|---|
| 46*** | 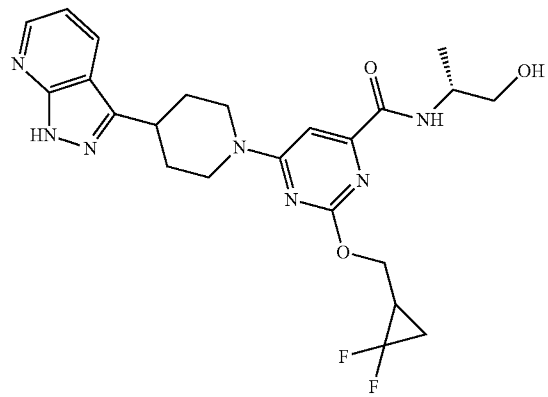 [SMILES: C[C@H](CO)NC(=O)c1cc(N2CCC(c3n[nH]c4ncccc34)CC2)nc(OCC2CC2(F)F)n1] | 2-[(2,2-difluoro-cyclopropyl)methoxy]-N-[(2R)-1-hydroxypropan-2-yl]-6-[4-(1H-pyrazolo[3,4-b]pyridin-3-yl)piperidin-1-yl]pyrimidine-4-carboxamide | 488.5; (400 MHz, CD$_3$OD) δ ppm 8.31-8.32 (m, 1 H) 8.29-8.30 (m, 1 H) 7.31-7.32 (m, 1 H) 7.18 (s, 1 H) 4.10 (d, J = 8.0 Hz, 2 H) 4.52-4.63 (m, 1 H) 4.19-4.28 (m, 1 H) 3.60-3.65 (m, 2 H) 3.40 (s, 1 H) 3.30-3.31 (m, 4 H) 2.15-2.18 (m, 3 H) 1.79-2.00 (m, 2 H) 1.58-1.71 (m, 1 H) 1.31-1.42 (m, 1 H) 1.30 (d, J = 7.2 Hz, 3 H). |
| 47* | 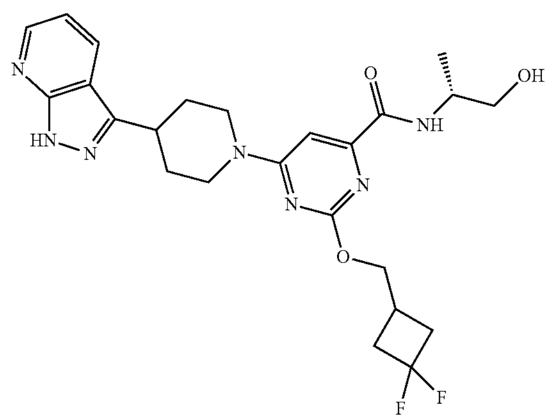 [SMILES: C[C@H](CO)NC(=O)c1cc(N2CCC(c3n[nH]c4ncccc34)CC2)nc(OCC2CC(F)(F)C2)n1] | 2-[(3,3-difluoro-cyclobutyl)methoxy]-N-[(2R)-1-hydroxypropan-2-yl]-6-[4-(1H-pyrazolo[3,4-b]pyridin-3-yl)piperidin-1-yl]pyrimidine-4-carboxamide | 502.1; (400 MHz, CD$_3$OD) δ ppm 8.49-8.50 (m, 1 H), 8.33 (d, J = 6.4 Hz, 1 H), 7.18-7.21 (m, 1 H), 7.12 (s, 1 H), 4.43 (s, 1 H), 4.42 (d, J = 6.4 Hz, 2 H), 4.10-4.14 (m, 1 H), 3.33-3.63 (m, 1 H), 3.27-3.32 (m, 1 H), 2.71-3.01 (m, 4 H), 2.68-2.69 (m, 3 H), 2.49-2.53 (m, 2 H), 2.20-2.21 (m, 2 H), 1.93-2.03 (m, 2 H), 1.25 (d, J = 6.8 Hz, 4 H). |
| 48* | 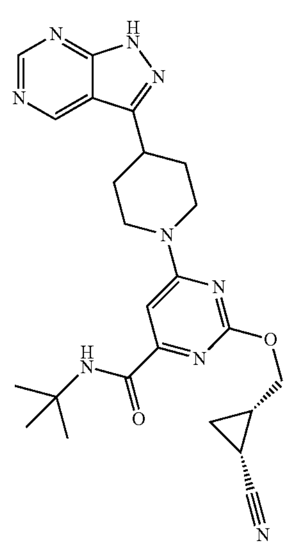 [SMILES: CC(C)(C)NC(=O)c1cc(N2CCC(c3n[nH]c4ncncc34)CC2)nc(OC[C@H]2C[C@H]2C#N)n1] | N-tert-butyl-2-{[(1S,2R)-2-cyanocyclopropyl]methoxy}-6-[4-(1H-pyrazolo[3,4-d]pyrimidin-3-yl)piperidin-1-yl]pyrimidine-4-carboxamide | 476.1; (400 MHz, CDCl$_3$) δ ppm 11.21 (br. s., 1 H), 9.23 (s, 1 H), 9.05 (s, 1 H), 7.76 (s, 1 H), 7.18 (s, 1 H), 4.53-4.70 (m, 1 H), 4.43-4.53 (m, 2 H), 3.42-3.49 (m, 1 H), 3.24 (t, J = 12.3 Hz, 2 H), 2.22-2.25 (m, 2 H), 1.95-2.04 (m, 2 H), 1.83-1.91 (m, 1 H), 1.68-1.71 (m, 2 H), 1.47 (s, 9 H), 1.31-1.37 (m, 1 H), 1.13-1.17 (m, 1H). |

TABLE 1-continued

| Ex. # | Structure | Compound Name | LRMS m/z (M + H)+; and 1H NMR |
|---|---|---|---|
| 49* | 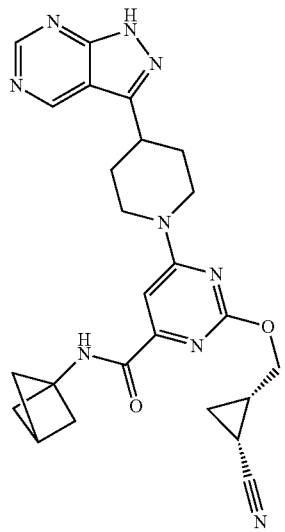 [SMILES: N#C[C@@H]1C[C@@H]1COc1nc(C(=O)NC23CC(C2)C3)cc(N2CCC(c3n[nH]c4ncncc34)CC2)n1] | N-(bicyclo[1.1.1]pent-1-yl)-2-{[(1S,2R)-2-cyanocyclopropyl]methoxy}-6-[4-(1H-pyrazolo[3,4-d]pyrimidin-3-yl)piperidin-1-yl]pyrimidine-4-carboxamide | 486.2; (400 MHz, CD$_3$OD) δ ppm 9.37 (s, 1 H), 8.92 (s, 1 H), 7.10 (s, 1 H), 4.71-4.75 (m, 1 H), 4.25-4.30 (m, 1 H), 3.54-3.61 (m, 1 H), 3.32-3.33 (m, 2 H), 2.50 (s, 1 H), 2.25-2.28 (m, 2 H), 2.21 (s, 7 H), 1.84-2.04 (m, 5 H), 1.33-1.39 (m, 1 H), 1.11-1.15 (m, 1 H). |
| 50* | 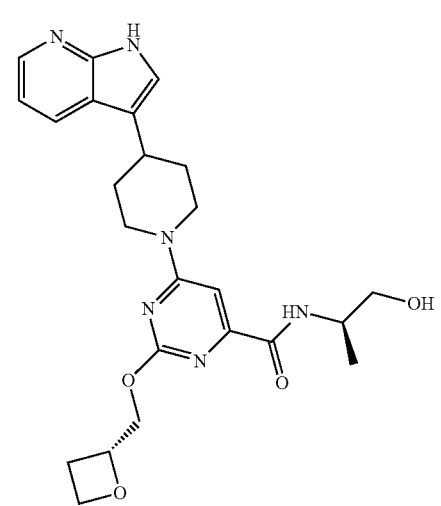 [SMILES: C[C@H](CO)NC(=O)c1cc(N2CCC(c3c[nH]c4ncccc34)CC2)nc(OC[C@H]2CCO2)n1] | N-[(2R)-1-hydroxypropan-2-yl]-2-[(2R)-oxetan-2-ylmethoxy]-6-[4-(1H-pyrrolo[2,3-b]pyridin-3-yl)piperidin-1-yl]pyrimidine-4-carboxamide | 489.1; (400 MHz, CDCl$_3$) δ ppm 8.96 (s, 1 H), 8.22 (s, 1 H), 7.99 (d, J = 7.6 Hz 1 H), 7.90 (d, J = 8.0 Hz, 1 H), 7.06 (s, 1 H), 7.01-7.04 (m, 2 H), 5.09-5.11 (m, 1 H), 4.59-4.65 (m, 3 H), 4.50-4.53 (m, 1 H), 4.41-4.49 (m, 1 H), 4.12-4.22 (m, 1 H), 3.66-3.69 (m, 1 H), 3.57-3.59 (m, 1 H), 3.07-3.11 (m, 3 H), 2.71-2.74 (m, 1 H), 2.60-2.62 (m, 1 H), 2.08 (d, J = 11.6 Hz, 2 H), 1.66-1.73 (m, 3 H), 1.22 (d, J = 6.4 Hz, 3 H). |
| 51* | 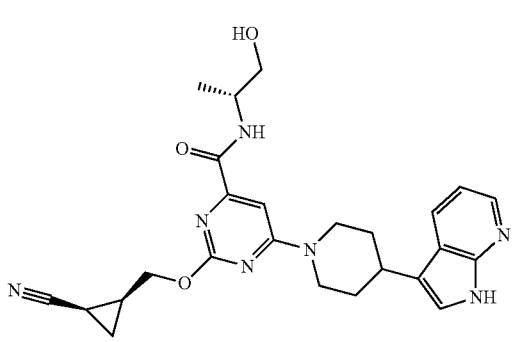 [SMILES: C[C@H](CO)NC(=O)c1cc(N2CCC(c3c[nH]c4ncccc34)CC2)nc(OC[C@H]2C[C@H]2C#N)n1] | 2-{[(1S,2R)-2-cyanocyclopropyl]methoxy}-N-[(2R)-1-hydroxypropan-2-yl]-6-[4-(1H-pyrrolo[2,3-b]pyridin-3-yl)piperidin-1-yl]pyrimidine-4-carboxamide | 476.3; (400 MHz, CDCl$_3$) δ ppm 8.82 (s, 1H), 8.30 (d, J = 5.2 Hz 1 H), 7.95 (d, J = 3.6 Hz, 2 H), 7.17 (s, 1 H), 7.07-7.10 (m, 2 H), 4.51-4.53 (m, 2 H), 4.23-4.24 (m, 1 H), 3.74-3.77 (m, 1 H), 3.62-3.67 (m, 1 H), 3.12-3.18 (m, 3 H), 2.17 (d, J = 13.2 Hz, 2 H), 1.67-1.87 (m, 7 H), 1.34-1.35 (m, 1 H), 1.15 (d, J = 6.4 Hz, 3 H), 1.13-1.18 (m, 1 H). |

TABLE 1-continued

| Ex. # | Structure | Compound Name | LRMS m/z (M + H)+; and 1H NMR |
|---|---|---|---|
| 52* | 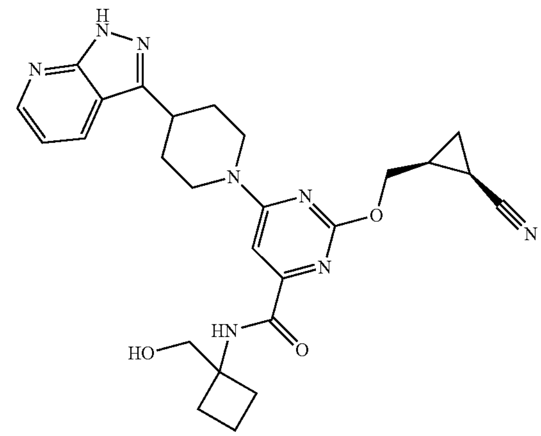 [SMILES: N#C[C@@H]1C[C@@H]1COc1nc(C(=O)NC2(CO)CCC2)cc(N2CCC(c3n[nH]c4ncccc34)CC2)n1] | 2-{[(1S,2R)-2-cyanocyclopropyl]methoxy}-N-[1-(hydroxymethyl)cyclobutyl]-6-[4-(1H-pyrazolo[3,4-b]pyridin-3-yl)piperidin-1-yl]pyrimidine-4-carboxamide | 503.1; (400 MHz, CDCl$_3$) δ ppm 10.90 (br. s., 1 H), 8.56 (d, J = 3.6 Hz, 1 H), 8.20 (s, 1 H), 8.11 (d, J = 6.8 Hz, 1 H), 7.13-7.16 (m, 2 H), 4.45-4.60 (m, 3 H), 3.89 (s, 2 H), 3.41-3.42 (m, 1 H), 3.26 (t, J = 11.6 Hz, 2 H), 2.15-2.40 (m, 6 H), 1.80-2.10 (m, 5 H), 1.63-1.70 (m, 1 H), 1.25-1.40 (m, 2 H), 1.15-1.17 (m, 1 H), 0.85-0.89 (m, 1 H). |
| 53* | 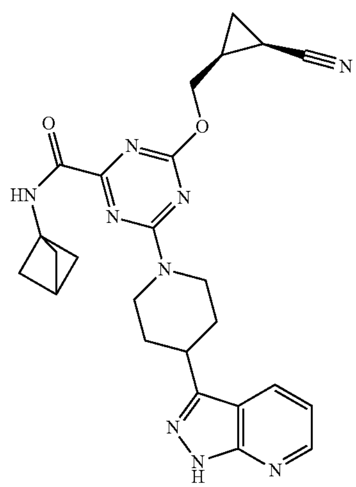 [SMILES: N#C[C@@H]1C[C@@H]1COc1nc(C(=O)NC23CC(C2)C3)nc(N2CCC(c3n[nH]c4ncccc34)CC2)n1] | N-(bicyclo[1.1.1]pent-1-yl)-4-{[(1S,2R)-2-cyanocyclopropyl]methoxy}-6-[4-(1H-pyrazolo[3,4-b]pyridin-3-yl)piperidin-1-yl]-1,3,5-triazine-2-carboxamide | 486.2; (600 MHz, DMSO-d6) δ ppm 9.07 (s, 1 H), 7.93 (s, 1 H), 7.72 (br. s., 1 H), 6.60 (br. s., 1 H), 4.82 (d, J = 12.73 Hz, 1 H), 4.63 (dd, J = 5.27, 11.27 Hz, 2 H), 4.04 (dd, J = 9.37, 11.71 Hz, 1 H), 3.85 (d, J = 4.98 Hz, 2 H), 3.42 (br. s., 1 H), 2.94 (t, J = 12.07 Hz, 2 H), 2.49 (s, 2 H), 2.03 (s, 6 H), 1.89-1.94 (m, 1 H), 1.86 (br. s., 2 H), 1.74-1.80 (m, 1 H), 1.20-1.29 (m, 3 H), 1.09 (br. s., 1 H). |
| 54* | 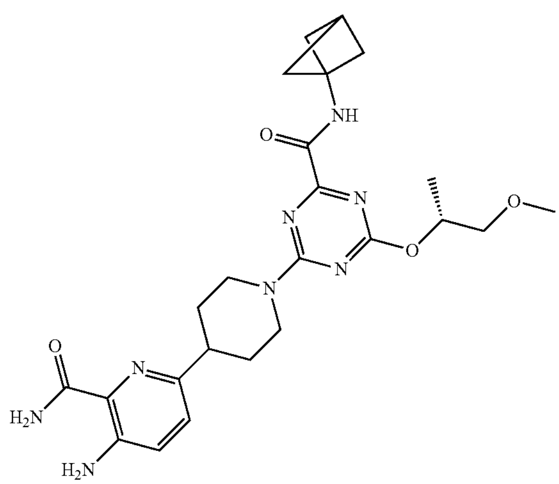 [SMILES: COC[C@@H](C)Oc1nc(C(=O)NC23CC(C2)C3)nc(N2CCC(c3ccc(N)c(C(N)=O)n3)CC2)n1] | 4-[4-(5-amino-6-carbamoylpyridin-2-yl)piperidin-1-yl]-N-(bicyclo[1.1.1]pent-1-yl)-6-{[(2R)-1-methoxypropan-2-yl]oxy}-1,3,5-triazine-2-carboxamide | 497.1; (700 MHz, DMSO-d$_6$) δ ppm 9.11 (br. s., 1 H), 7.89 (br. s., 1 H), 7.17 (d, J = 8.54 Hz, 1 H), 7.03-7.12 (m, 2 H), 6.53 (br. s., 1 H), 5.34 (td, J = 6.28, 3.67 Hz, 1 H), 4.89 (d, J = 12.98 Hz, 1 H), 4.67 (d, J = 12.13 Hz, 1 H), 3.40-3.50 (m, 2 H), 3.23 (s, 3 H), 3.01 (t, J = 12.73 Hz, 2 H), 2.86 (t, J = 11.79 Hz, 1 H), 2.42 (s, 1 H), 2.05 (s, 6 H), 1.88 (br. s., 2 H), 1.51-1.63 (m, 2 H), 1.20 (d, J = 6.49 Hz, 3 H). |

TABLE 1-continued

| Ex. # | Structure | Compound Name | LRMS m/z (M + H)+; and 1H NMR |
|---|---|---|---|
| 55* | 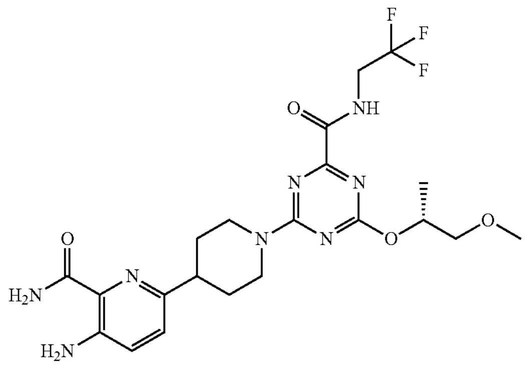 [SMILES: COC[C@@H](C)Oc1nc(C(=O)NCC(F)(F)F)nc(N2CCC(c3ccc(N)c(C(N)=O)n3)CC2)n1] | 4-[4-(5-amino-6-carbamoylpyridin-2-yl)piperidin-1-yl]-6-{[(2R)-1-methoxypropan-2-yl]oxy}-N-(2,2,2-trifluoroethyl)-1,3,5-triazine-2-carboxamide | 513.1; (700 MHz, DMSO-d6) δ ppm 9.31 (t, J = 6.66 Hz, 1 H), 7.87-7.96 (m, 1 H), 7.19 (d, J = 8.54 Hz, 1 H), 7.06-7.12 (m, 2 H), 6.55 (br. s., 2 H), 5.37 (td, J = 6.15, 4.10 Hz, 1 H), 4.92 (d, J = 12.81 Hz, 1 H), 4.70 (d, J = 12.13 Hz, 1 H), 3.42-3.53 (m, 2 H), 3.25 (s, 3 H), 3.05 (t, J = 12.81 Hz, 2 H), 2.89 (t, J = 11.70 Hz, 1 H), 1.86-1.95 (m, 2 H), 1.57-1.69 (m, 2 H), 1.23 (dd, J = 6.41, 1.11 Hz, 3 H). |
| 56* | 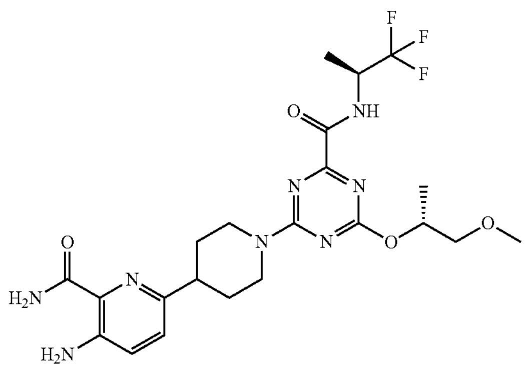 [SMILES: COC[C@@H](C)Oc1nc(C(=O)N[C@@H](C)C(F)(F)F)nc(N2CCC(c3ccc(N)c(C(N)=O)n3)CC2)n1] | 4-[4-(5-amino-6-carbamoylpyridin-2-yl)piperidin-1-yl]-6-{[(2R)-1-methoxypropan-2-yl]oxy}-N-[(2S)-1,1,1-trifluoropropan-2-yl]-1,3,5-triazine-2-carboxamide | 527.1; (600 MHz, DMSO-d6) δ ppm 8.98 (d, J = 9.22 Hz, 1 H), 7.84-7.95 (m, 1 H), 7.16 (d, J = 8.34 Hz, 1 H), 7.07 (d, J = 8.63 Hz, 1 H), 7.03 (br. s., 1 H), 6.48 (br. s., 1 H), 5.33 (d, J = 4.54 Hz, 1 H), 4.82-4.89 (m, 1 H), 4.63-4.73 (m, 2 H), 3.39-3.49 (m, 2 H), 3.22 (s, 3 H), 3.02 (t, J = 12.51 Hz, 2 H), 2.86 (t, J = 3.37 Hz, 1 H), 1.83-1.92 (m, 2 H), 1.59 (t, J = 12.07 Hz, 2 H), 1.32 (d, J = 7.17 Hz, 3 H), 1.20 (dd, J = 6.44, 1.02 Hz, 3 H). |
| 57* | 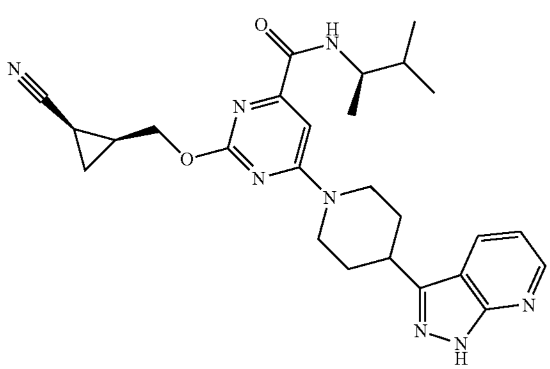 [SMILES: CC(C)[C@@H](C)NC(=O)c1cc(N2CCC(c3n[nH]c4ncccc34)CC2)nc(OC[C@H]2C[C@H]2C#N)n1] | 2-{[(1S,2R)-2-cyanocyclopropyl]methoxy}-N-[(2R)-3-methylbutan-2-yl]-6-[4-(1H-pyrazolo[3,4-b]pyridin-3-yl)piperidin-1-yl]pyrimidine-4-carboxamide | 489.1; (600 MHz, DMSO-d6) δ ppm 8.41-8.46 (m, 1 H), 8.23-8.30 (m, 1 H), 8.10 (d, J = 9.37 Hz, 1 H), 7.14 (dd, J = 8.05, 4.54 Hz, 1 H), 7.00 (s, 1 H), 4.62 (dd, J = 11.93, 5.34 Hz, 1 H), 4.06-4.10 (m, 6 H), 3.68-3.76 (m, 1 H), 3.42 (br. s., 1 H), 3.21 (d, J = 0.88 Hz, 1 H), 2.07 (d, J = 12.00 Hz, 2 H), 1.84-1.88 (m, 1 H), 1.82 (d, J = 8.05 Hz, 1 H), 1.69-1.76 (m, 3 H), 1.26 (dd, J = 8.49, 3.37 Hz, 1 H), 1.08 (d, J = 6.73 Hz, 3 H), 0.79-0.84 (m, 6 H). |
| 58* | 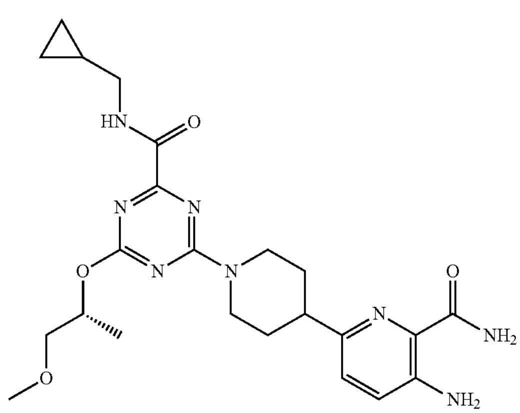 [SMILES: COC[C@@H](C)Oc1nc(C(=O)NCC2CC2)nc(N2CCC(c3ccc(N)c(C(N)=O)n3)CC2)n1] | 4-[4-(5-amino-6-carbamoylpyridin-2-yl)piperidin-1-yl]-N-(cyclopropylmethyl)-6-{[(2R)-1-methoxypropan-2-yl]oxy}-1,3,5-triazine-2-carboxamide | 485.1; (600 MHz, DMSO-d6) δ ppm 8.83 (t, J = 6.15 Hz, 1 H), 7.90 (br. s., 1 H), 7.16 (d, J = 8.63 Hz, 1 H), 7.07 (d, J = 8.63 Hz, 1 H), 7.02 (br. s., 1 H), 6.47 (br. s., 2 H), 5.34 (dt, J = 6.37, 3.66 Hz, 1 H), 4.89 (d, J = 12.59 Hz, 1 H), 4.67 (d, J = 12.15 Hz, 1 H), 3.38-3.50 (m, 2 H), 3.22 (s, 3 H), 2.97-3.10 (m, 4 H), 2.82-2.90 (m, 1 H), 1.87 (d, J = 12.15 Hz, 2 H), 1.51-1.64 (m, 2 H), 1.19 (d, J = 6.29 Hz, 3 H), 0.91-1.01 (m, 1 H), 0.33-0.41 (m, 2 H), 0.14-0.22 (m, 2 H). |

TABLE 1-continued

| Ex. # | Structure | Compound Name | LRMS m/z (M + H)+; and ¹H NMR |
|---|---|---|---|
| 59 | 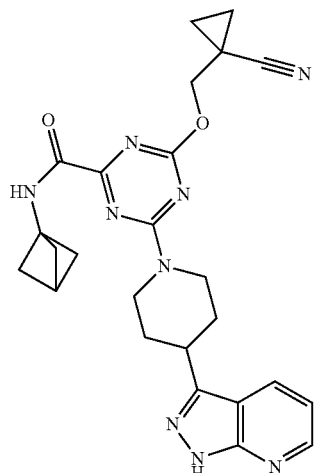 | N-(bicyclo[1.1.1]pent-1-yl)-4-[(1-cyanocyclopropyl)methoxy]-6-[4-(1H-pyrazolo[3,4-b]pyridin-3-yl)piperidin-1-yl]-1,3,5-triazine-2-carboxamide | 486.2; (600 MHz, DMSO-$d_6$) δ ppm 8.47 (dd, J = 4.54, 1.46 Hz, 1 H), 8.32 (dd, J = 8.05, 1.46 Hz, 1 H), 7.13 (dd, J = 8.05, 4.54 Hz, 1 H), 4.91 (d, J = 13.02 Hz, 1 H), 4.74 (d, J = 13.17 Hz, 1 H), 4.35-4.44 (m, 2 H), 3.43 (tt, J = 11.45, 3.55 Hz, 1 H), 3.17-3.27 (m, 1 H), 2.45 (s, 1 H), 2.05-2.15 (m, 9 H), 1.78-1.87 (m, 2 H), 1.34-1.40 (m, 2 H), 1.20-1.27 (m, 3 H). |
| 60* | 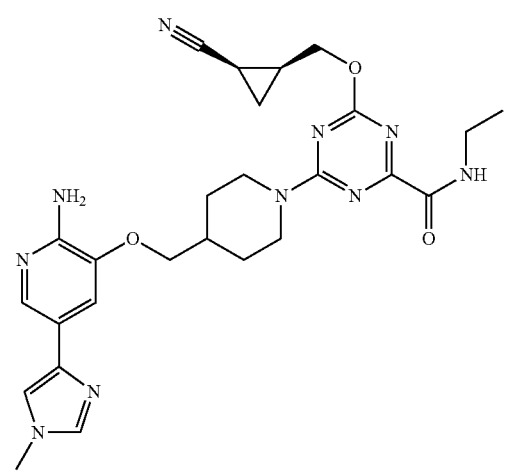 [SMILES: CCNC(=O)c1nc(OC[C@H]2C[C@H]2C#N)nc(N2CCC(COc3cc(-c4cn(C)cn4)cnc3N)CC2)n1] | 6-[4-({[2-amino-5-(1-methyl-1H-imidazol-4-yl)pyridin-3-yl]oxy}methyl)piperidin-1-yl]-2-{[(1S,2R)-2-cyanocyclopropyl]methoxy}-N-ethylpyrimidine-4-carboxamide | 532.1; (400 MHz, CDCl$_3$) δ ppm 7.96 (s, 1 H), 7.84-7.87 (m, 1 H), 7.45 (s, 1 H), 7.13 (s, 1 H), 7.10 (s, 1 H), 4.68 (s, 2 H), 4.43-4.52 (m, 2 H), 3.96 (d, J = 6.0 Hz, 2 H), 3.72 (s, 3 H), 3.42-3.49 (m, 2 H), 3.01-3.04 (m, 2 H), 2.19-2.21 (m, 1 H), 1.96-1.99 (m, 2 H), 1.86-1.88 (m, 1 H), 1.32-1.36 (m, 3 H), 1.22-1.25 (m, 4 H), 1.13-1.15 (m, 1H). |
| 61* | 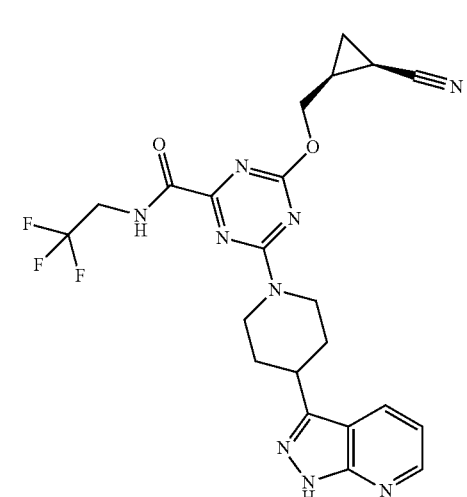 | 4-{[(1S,2R)-2-cyanocyclopropyl]methoxy}-6-[4-(1H-pyrazolo[3,4-b]pyridin-3-yl)piperidin-1-yl]-N-(2,2,2-trifluoroethyl)-1,3,5-triazine-2-carboxamide | 502.1; (600 MHz, DMSO-d6) δ ppm 8.48 (dd, J = 4.46, 1.39 Hz, 1 H), 8.29-8.36 (m, 1 H), 7.13 (dd, J = 8.05, 4.39 Hz, 1 H), 4.95 (d, J = 13.17 Hz, 1 H), 4.68-4.80 (m, 2 H), 4.15 (dt, J = 11.78, 8.74 Hz, 1 H), 3.98-4.08 (m, 2 H), 3.40-3.47 (m, 1 H), 3.38 (br. s., 1 H), 3.26 (d, J = 8.63 Hz, 1 H), 2.13 (d, J = 11.56 Hz, 2 H), 1.93-2.01 (m, 1 H), 1.80-1.88 (m, 3 H), 1.29 (td, J = 8.49, 4.98 Hz, 1 H), 1.13-1.19 (m, 1 H). |

TABLE 1-continued

| Ex. # | Structure | Compound Name | LRMS m/z (M + H)+; and 1H NMR |
|---|---|---|---|
| 62*** | 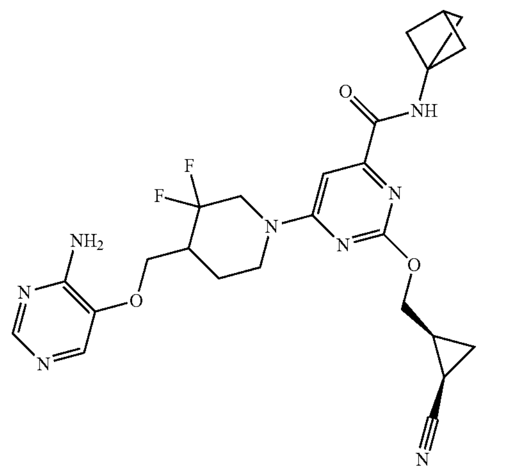 [SMILES: N#C[C@@H]1C[C@@H]1COc1nc(C(=O)NC23CC(C2)C3)cc(N2CCC(COc3cncnc3N)C(F)(F)C2)n1] | 6-(4-{[(4-aminopyrimidin-5-yl)oxy]methyl}-3,3-difluoropiperidin-1-yl)-N-(bicyclo[1.1.1]pent-1-yl)-2-{[(1S,2R)-2-cyanocyclopropyl]methoxy}pyrimidine-4-carboxamide | 527.1; (400 MHz, CDCl$_3$) δ ppm 8.26 (s, 1 H), 8.16 (s, 1 H), 7.86 (s, 1 H), 7.15 (s, 1 H), 5.13 (s, 2 H), 4.39-5.13 (m, 3 H), 4.05-4.09 (m, 1 H), 3.07-3.28 (m, 2 H), 2.50-2.61 (m, 1 H), 2.49 (s, 1 H), 2.10-2.19 (m, 1 H), 2.18 (s, 6 H), 1.78-1.85 (m, 1 H), 1.32-1.36 (m, 2 H), 1.14-1.17 (m, 1 H), 0.84-0.88 (m, 3 H). |
| 63*** | 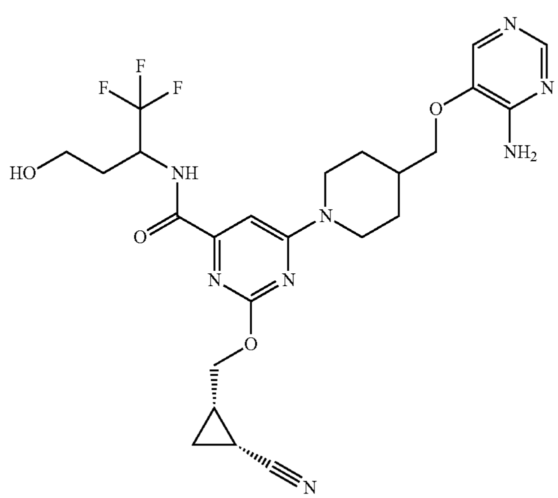 [SMILES: N#C[C@@H]1C[C@@H]1COc1nc(C(=O)NC(CCO)C(F)(F)F)cc(N2CCC(COc3cncnc3N)CC2)n1] | 6-(4-{[(4-aminopyrimidin-5-yl)oxy]methyl}piperidin-1-yl)-2-{[(1S,2R)-2-cyanocyclopropyl]methoxy}-N-(1,1,1-trifluoro-4-hydroxybutan-2-yl)pyrimidine-4-carboxamide | 551.1; (400 MHz, DMSO-d$_6$) δ ppm 8.88 (d, J = 7.6 Hz, 1 H), 7.99 (s, 1 H), 7.78 (s, 1 H), 7.02 (s, 1 H), 6.62-6.74 (m, 2 H), 4.83-4.85 (m, 1 H), 4.65-4.69 (m, 2 H), 4.25-4.50 (m, 2 H), 4.04-4.06 (m, 1H), 3.88 (d, J = 6.0 Hz, 2 H), 3.50-3.53 (m, 2 H), 2.99-3.02 (m, 2 H), 2.08-2.11 (m, 2 H), 1.84-1.98 (m, 5 H), 1.26-1.30 (m, 3 H), 1.12-1.14 (m, 1 H). |
| 64* | 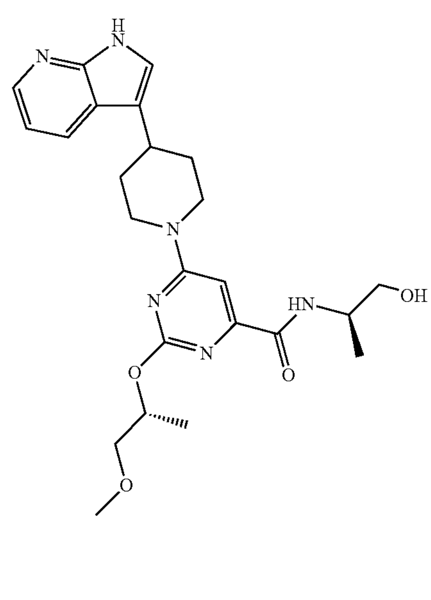 [SMILES: COC[C@@H](C)Oc1nc(C(=O)N[C@H](C)CO)cc(N2CCC(c3c[nH]c4ncccc34)CC2)n1] | N-[(2R)-1-hydroxypropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide | 469.1; (400 MHz, CDCl$_3$) δ ppm 9.69 (s, 1 H), 8.30 (d, J = 4.4 Hz, 1 H), 7.93-7.98 (m, 2 H), 7.06-7.11 (m, 3 H), 5.30-5.35 (m, 1 H), 4.58 (br. s., 2 H), 4.21-4.23 (m, 1 H), 3.65-3.72 (m, 3 H), 3.49-3.52 (m, 2 H), 3.41 (s, 3 H), 3.13-3.15 (m, 4 H), 2.14 (s, 3 H), 1.68-1.77 (m, 2 H), 1.38 (d, J = 6.4 Hz, 3 H), 1.27 (d, J = 6.4 Hz, 3H). |

| Ex. # | Structure | Compound Name | LRMS m/z (M + H)+; and 1H NMR |
|---|---|---|---|
| 65* | 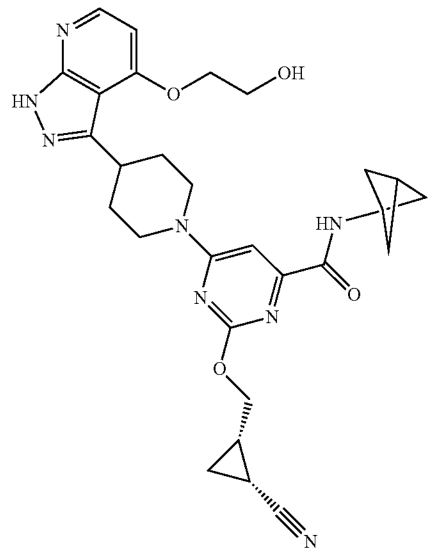 [SMILES: N#C[C@@H]1C[C@@H]1COc1nc(C(=O)NCCC2CCC2)cc(N2CCC(c3n[nH]c4nccc(OCCO)c34)CC2)n1] | N-(bicyclo[1.1.1]pent-1-yl)-2-{[(1S,2R)-2-cyanocyclopropyl]methoxy}-6-{4-[4-(2-hydroxyethoxy)-1H-pyrazolo[3,4-b]pyridin-3-yl]piperidin-1-yl}pyrimidine-4-carboxamide | 545.1; (400 MHz, CDCl$_3$) δ ppm 11.65 (br. s., 1 H), 8.37 (d, J = 4.8 Hz, 1 H), 8.20 (s, 1 H), 7.14 (s, 1 H), 6.51-6.52 (d, J = 5.2 Hz, 1 H), 4.51-4.56 (m, 2 H), 4.40-4.42 (m, 1 H), 4.22-4.24 (m, 2 H), 3.84-3.85 (m, 2 H), 3.44-3.45 (m, 1 H), 3.15-3.17 (m, 2 H), 2.50 (s, 1 H), 2.07-2.49 (m, 11 H), 1.86-1.88 (m, 1 H), 1.64-1.68 (m, 1 H), 1.35-1.37 (m, 1 H), 1.10-1.12 (m, 1 H). |
| 66* | 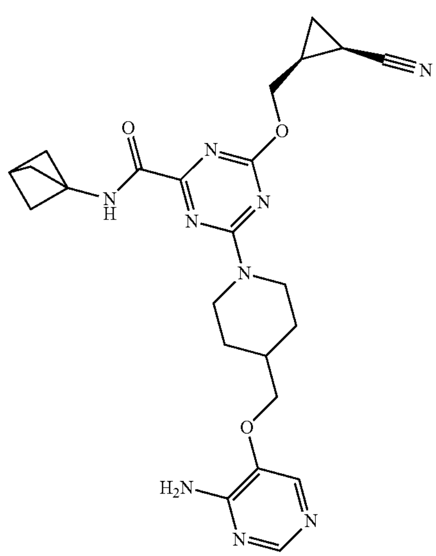 [SMILES: N#C[C@@H]1C[C@@H]1COc1nc(C(=O)NC23CC(C2)C3)nc(N2CCC(COc3cncnc3N)CC2)n1] | 4-(4-{[(4-aminopyrimidin-5-yl)oxy]methyl}piperidin-1-yl)-N-(bicyclo[1.1.1]pent-1-yl)-6-{[(1S,2R)-2-cyanocyclopropyl]methoxy}-1,3,5-triazine-2-carboxamide | 492.1; (600 MHz, DMSO-d$_6$) δ ppm 9.07 (s, 1 H), 7.93 (s, 1 H), 7.72 (br. s., 1 H), 6.60 (br. s., 1 H), 4.82 (d, J = 12.73 Hz, 1 H), 4.63 (dd, J = 11.27, 5.27 Hz, 2 H), 4.04 (dd, J = 11.71, 9.37 Hz, 1 H), 3.85 (d, J = 4.98 Hz, 2 H), 3.42 (br. s. 1 H), 2.94 (t, J = 12.07 Hz, 2 H), 2.49 (s, 2 H), 2.03 (s, 6 H), 1.89-1.94 (m, 1 H), 1.86 (br. s., 2 H), 1.74-1.80 (m, 1 H), 1.20-1.29 (m, 3 H), 1.09 (br. s., 1 H). |

TABLE 1-continued

| Ex. # | Structure | Compound Name | LRMS m/z (M + H)+; and 1H NMR |
|---|---|---|---|
| 67* | 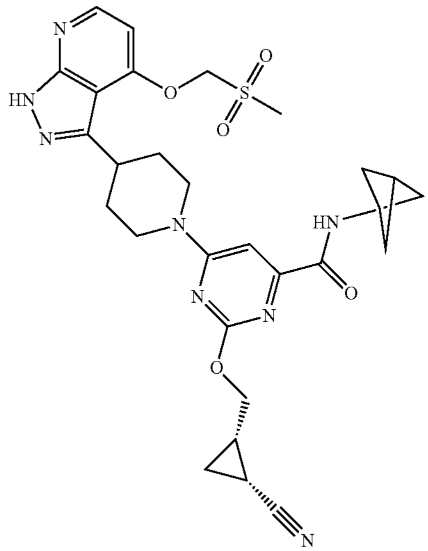 [SMILES: CS(=O)(=O)COc1ccnc2[nH]nc(C3CCN(c4cc(C(=O)NCCC5CCC5)nc(OC[C@H]5C[C@H]5C#N)n4)CC3)c12] | N-(bicyclo[1.1.1]pent-1-yl)-2-{[(1S,2R)-2-cyanocyclopropyl]methoxy}-6-(4-{4-[(methylsulfonyl)methoxy]-1H-pyrazolo[3,4-b]pyridin-3-yl}piperidin-1-yl)pyrimidine-4-carboxamide | 615.2 [M + Na]+; (400 MHz, CDCl$_3$) δ ppm 11.65 (br. s., 1 H), 8.48 (br. s., 1 H), 8.19 (s, 1 H), 7.26 (s, 1 H), 6.61-6.62 (m, 1 H), 5.14 (s, 2 H), 4.51-4.56 (m, 3 H), 3.49-3.51 (m, 1 H), 3.20-3.22 (m, 2 H), 3.02-3.05 (m, 3 H), 2.49 (s, 1 H), 2.15-2.18 (m, 8 H), 1.98-2.05 (m, 3 H), 1.60-1.82 (m, 2 H), 1.20-1.40 (m, 2 H). |
| 68* | 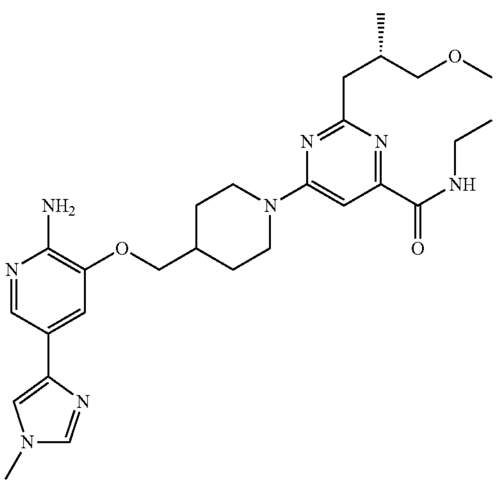 | 6-[4-({[2-amino-5-(1-methyl-1H-imidazol-4-yl)pyridin-3-yl]oxy}methyl)piperidin-1-yl]-N-ethyl-2-{[(2R)-1-methoxypropan-2-yl]oxy}pyrimidine-4-carboxamide | 525.1; (400 MHz, CDCl$_3$) δ ppm 7.94 (s, 1 H), 7.89 (br. s., 1 H), 7.46 (s, 2 H), 7.09 (d, J = 6.8 Hz, 1 H), 5.30-5.34 (m, 1 H), 4.56-4.89 (m, 4 H), 3.96 (d, J = 6.4 Hz, 2 H), 3.72 (s, 3 H), 3.65-3.67 (m, 1 H), 3.41-3.52 (m, 6 H), 2.97-3.41 (m, H), 2.19-2.20 (m, 1 H), 1.95-1.98 (m, 2 H), 1.33-1.39 (m, 5 H), 1.22 (t, J = 7.2 Hz, 3H). |
| 69* | 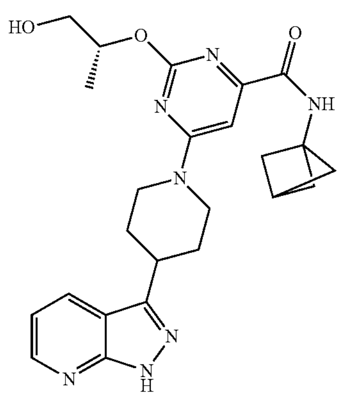 [SMILES: C[C@H](CO)Oc1nc(C(=O)NC23CC(C2)C3)cc(N2CCC(c3n[nH]c4ncccc34)CC2)n1] | N-(bicyclo[1.1.1]pent-1-yl)-2-{[(2R)-1-hydroxypropan-2-yl]oxy}-6-[4-(1H-pyrazolo[3,4-b]pyridin-3-yl)piperidin-1-yl]pyrimidine-4-carboxamide | 464.3; (400 MHz, CDCl$_3$) δ ppm 8.57 (br. s., 1 H), 8.40 (br. s., 1 H), 8.12 (d, J = 7.95 Hz, 1 H), 7.12-7.23 (m, 2 H), 5.30 (d, J = 3.79 Hz, 1 H), 4.38-4.81 (m, 2 H), 3.77-3.88 (m, 2 H), 3.44 (br. s., 1 H), 3.29 (t, J = 12.10 Hz, 2 H), 2.50 (s, 1 H), 2.20 (s, 8 H), 2.04 (d, J = 10.27 Hz, 2 H), 1.39 (d, J = 6.36 Hz, 3 H). |

TABLE 1-continued

| Ex. # | Structure | Compound Name | LRMS m/z (M + H)+; and 1H NMR |
|---|---|---|---|
| 70* | 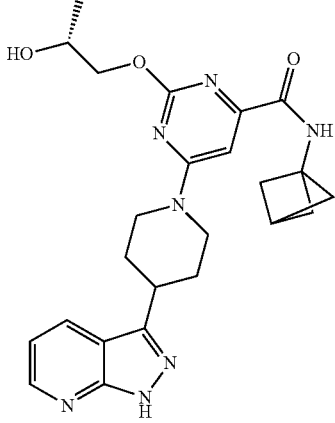 [SMILES: C[C@@H](O)COc1nc(C(=O)NC23CC(C2)C3)cc(N2CCC(c3n[nH]c4ncccc34)CC2)n1] | N-(bicyclo[1.1.1]pent-1-yl)-2-[(2R)-2-hydroxypropoxy]-6-[4-(1H-pyrazolo[3,4-b]pyridin-3-yl)piperidin-1-yl]pyrimidine-4-carboxamide | 464.3; (400 MHz, CDCl$_3$) δ ppm 8.57 (br. s., 1 H), 8.27 (br. s., 1 H), 8.11 (d, J = 8.07 Hz, 1 H), 7.10-7.20 (m, 2 H), 4.40-4.83 (m, 2 H), 4.34 (d, J = 7.70 Hz, 1 H), 4.20-4.27 (m, 2 H), 3.43 (br. s., 1 H), 3.27 (t, J = 12.04 Hz, 2 H), 2.51 (s, 1 H), 2.21 (s, 8 H), 2.04 (d, J = 13.08 Hz, 2 H), 1.31 (d, J = 5.87 Hz, 3 H). |
| 71* | 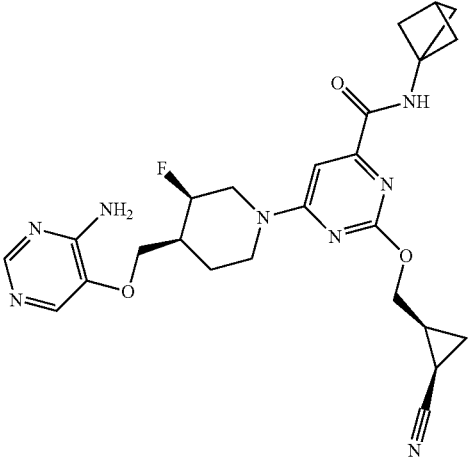 [SMILES: N#C[C@@H]1C[C@@H]1COc1nc(C(=O)NC23CC(C2)C3)cc(N2CC[C@@H](COc3cncnc3N)[C@@H](F)C2)n1] | 6-[(3R,4S)-4-{[(4-aminopyrimidin-5-yl)oxy]methyl}-3-fluoropiperidin-1-yl]-N-(bicyclo[1.1.1]pent-1-yl)-2-{[(1S,2R)-2-cyanocyclopropyl]methoxy}pyrimidine-4-carboxamide | 509.1; (400 MHz, CDCl$_3$) δ ppm 8.27 (s, 1 H), 8.17 (s, 1 H), 7.88 (s, 1 H), 7.15 (s, 1 H), 5.29 (s, 2 H), 4.90-5.05 (m, 1 H), 4.46-4.49 (m, 2 H), 4.13-4.18 (m, 1 H), 3.97-4.00 (m, 1 H), 3.06-3.19 (m, 2 H), 2.49 (s, 1 H), 2.10-2.19 (m, 1 H), 2.18 (s, 6 H), 1.74-1.87 (m, 5 H), 1.35-1.36 (m, 3 H). |
| 72* | 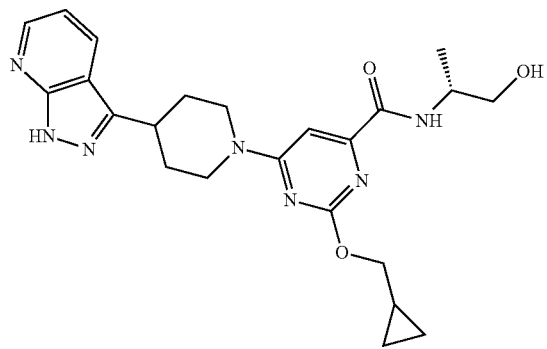 [SMILES: C[C@H](CO)NC(=O)c1cc(N2CCC(c3n[nH]c4ncccc34)CC2)nc(OCC2CC2)n1] | 2-(cyclopropylmethoxy)-N-[(2R)-1-hydroxypropan-2-yl]-6-[4-(1H-pyrazolo[3,4-b]pyridin-3-yl)piperidin-1-yl]pyrimidine-4-carboxamide | 452.5; (400 MHz, CD$_3$OD) δ ppm 8.50 (d, J = 3.2 Hz, 1 H) 8.33 (d, J = 6.8 Hz, 1 H) 7.19-7.22 (m, 1 H) 7.11 (s, 1 H) 4.22 (d, J = 7.2 Hz, 2 H), 4.13-4.15 (m, 1 H) 3.63 (d, J = 5.2 Hz, 3 H) 3.28-3.32 (m, 4 H) 2.20 (d, J = 10.8 Hz, 2 H) 1.96-2.00 (m, 2 H) 1.27 (d, J = 6.8 Hz, 4 H) 0.61-0.63 (m, 2 H) 0.39 (d, J = 5.6 Hz, 2 H). |

TABLE 1-continued

| Ex. # | Structure | Compound Name | LRMS m/z (M + H)+; and 1H NMR |
|---|---|---|---|
| 73* | 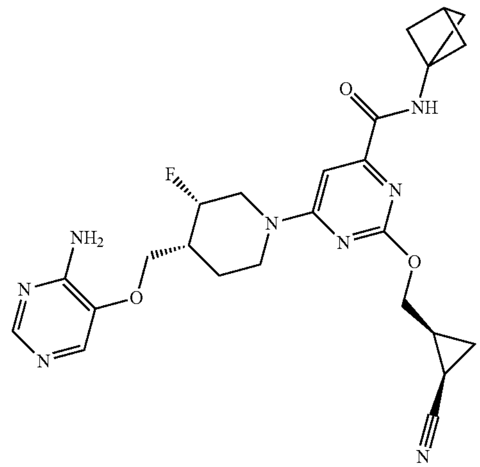 [SMILES: N#C[C@@H]1C[C@@H]1COc1nc(C(=O)NC23CC(C2)C3)cc(N2CC[C@H](COc3cncnc3N)[C@H](F)C2)n1] | 6-[(3S,4R)-4-{[(4-aminopyrimidin-5-yl)oxy]methyl}-3-fluoropiperidin-1-yl]-N-(bicyclo[1.1.1]pent-1-yl)-2-{[(1S,2K)-2-cyanocyclopropyl]methoxy}pyrimidine-4-carboxamide | 509.1 (400 MHz, DMSO-d$_6$) δ ppm 8.94 (s, 1 H), 8.07 (s, 1 H), 7.85 (s, 1 H), 7.03 (s, 1 H), 5.18-5.29 (s, 1 H), 4.66-4.71 (m, 1 H), 3.95-4.09 (m, 3 H), 3.06-3.08 (m, 2 H), 2.40-2.45 (m, 4 H), 2.10 (s, 6 H), 1.96-1.99 (m, 1 H), 1.79-1.81 (m, 2 H), 1.46-1.48 (m, 1 H), 1.26-1.29 (m, 1 H), 1.12-1.26 (m, 1 H). |
| 74** | 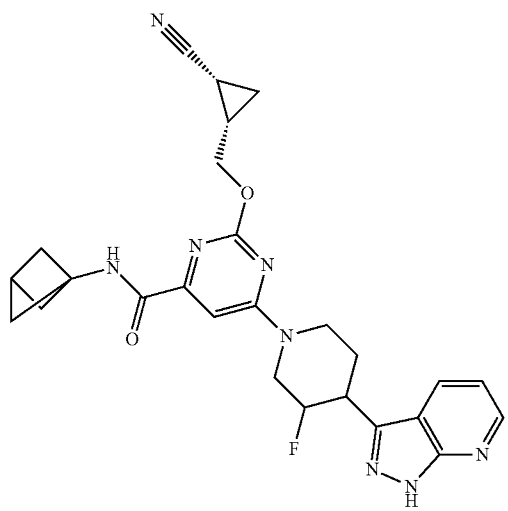 [SMILES: N#C[C@@H]1C[C@@H]1COc1nc(C(=O)NC23CC(C2)C3)cc(N2CCC(c3n[nH]c4ncccc34)C(F)C2)n1] | N-(bicyclo[1.1.1]pent-1-yl)-2-{[(1S,2R)-2-cyanocyclopropyl]methoxy}-6-[3-fluoro-4-(1H-pyrazolo[3,4-b]pyridin-3-yl)piperidin-1-yl]pyrimidine-4-carboxamide | 525.1 [M + Na]+; (400 MHz, DMSO-d$_6$) δ ppm 13.42 (s, 1 H), 8.97 (s, 1 H), 8.49 (d, J = 4.4 Hz, 1 H), 8.31 (d, J = 8.0 Hz, 1 H), 7.14-7.17 (m, 1 H), 7.07 (s, 1 H), 5.17-5.29 (m, 1 H), 4.69-4.73 (m, 1 H), 4.04-4.11 (m, 1 H), 3.66-3.78 (m, 1 H), 2.46 (s, 1 H), 2.28-2.38 (m, 2 H), 2.11 (s, 6 H), 1.96-2.06 (m, 3 H), 1.81-1.88 (m, 1 H), 1.21-1.32 (m, 3 H), 1.12-1.17 (m, 1 H). |
| 75** | 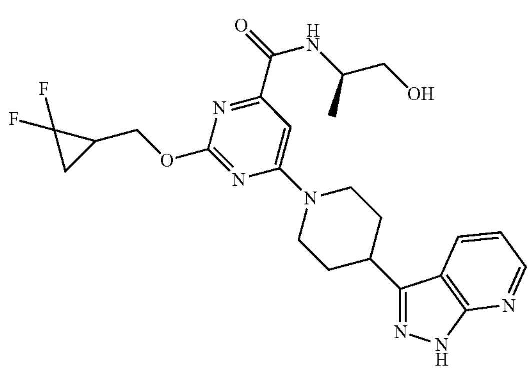 [SMILES: C[C@H](CO)NC(=O)c1cc(N2CCC(c3n[nH]c4ncccc34)CC2)nc(OCC2CC2(F)F)n1] | 2-[(2,2-difluorocyclopropyl)methoxy]-N-[(2R)-1-hydroxypropan-2-yl]-6-[4-(1H-pyrazolo[3,4-b]pyridin-3-yl)piperidin-1-yl]pyrimidine-4-carboxamide | 488.3; (600 MHz, DMSO-d$_6$) δ ppm 8.46 (dd, J = 4.54, 0.88 Hz, 1 H), 8.29 (dd, J = 8.05, 1.17 Hz, 1 H), 8.17 (d, J = 8.63 Hz, 1 H), 7.12 (dd, J = 8.05, 4.54 Hz, 1 H), 7.03 (s, 1 H), 4.43-4.50 (m, 1 H), 4.18-4.25 (m, 1 H), 3.92-4.00 (m, 1 H), 3.39-3.46 (m, 1 H), 3.16-3.25 (m, 1 H), 2.87-2.92 (m, 1 H), 2.21 (d, J = 7.02 Hz, 1 H), 2.09 (d, J = 12.88 Hz, 2 H), 1.74-1.84 (m, 2 H), 1.64-1.72 (m, 2 H), 1.49 (dd, J = 13.24, 3.88 Hz, 2 H), 1.19-1.25 (m, 2 H), 1.13 (d, J = 6.73 Hz, 5 H). |

TABLE 1-continued

| Ex. # | Structure | Compound Name | LRMS m/z (M + H)+; and 1H NMR |
|---|---|---|---|
| 76** | 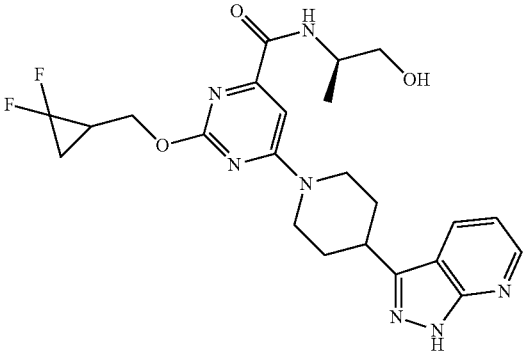 [SMILES: C[C@H](CO)NC(=O)c1cc(N2CCC(c3n[nH]c4ncccc34)CC2)nc(OCC2CC2(F)F)n1] | 2-[(2,2-difluorocyclopropyl)methoxy]-N-[(2R)-1-hydroxypropan-2-yl]-6-[4-(1H-pyrazolo[3,4-b]pyridin-3-yl)piperidin-1-yl]pyrimidine-4-carboxamide | 488.3; (600 MHz, DMSO-d$_6$) δ ppm 8.73 (dd, J = 4.54, 1.46 Hz, 1 H), 8.56 (dd, J = 8.05, 1.46 Hz, 1 H), 8.44 (d, J = 8.49 Hz, 1 H), 7.39 (dd, J = 8.05, 4.54 Hz, 1 H), 7.28-7.34 (m, 1 H), 5.11 (t, J = 5.49 Hz, 1 H), 4.69-4.78 (m, 2 H), 4.45-4.53 (m, 1 H), 4.18-4.28 (m, 1 H), 3.65-3.74 (m, 3 H), 3.44-3.52 (m, 2 H), 2.44-2.52 (m, 1 H), 2.37 (d, J = 10.68 Hz, 2 H), 2.01-2.13 (m, 2 H), 1.91-2.01 (m, 1 H), 1.70-1.81 (m, 1 H), 1.49 (s, 1 H), 1.36-1.44 (m, 4 H). |
| 77* | 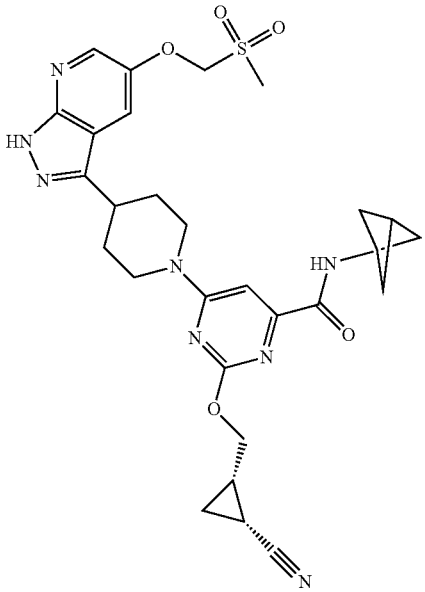 [SMILES: CS(=O)(=O)COc1cnc2[nH]nc(C3CCN(c4cc(C(=O)NCCC5CCC5)nc(OC[C@H]5C[C@H]5C#N)n4)CC3)c2c1] | N-(bicyclo[1.1.1]pent-1-yl)-2-{[(1S,2R)-2-cyanocyclopropyl]methoxy}-6-(4-{5-[(methylsulfonyl)methoxy]-1H-pyrazolo[3,4-b]pyridin-3-yl}piperidin-1-yl)pyrimidine-4-carboxamide | 593.3; (400 MHz, CDCl$_3$) δ ppm 10.71 (br. s., 1 H), 8.45 (s, 1 H), 8.20 (s, 1 H), 7.81 (s, 1 H), 7.15-7.27 (m, 1 H), 5.06 (s, 2 H), 4.38-4.48 (m, 3 H), 3.09-3.36 (m, 6 H), 2.49 (s, 1 H), 2.19 (s, 8 H), 1.89-1.97 (m, 3 H), 1.34-1.45 (m, 2 H), 1.14-1.19 (m, 2 H). |
| 78** | 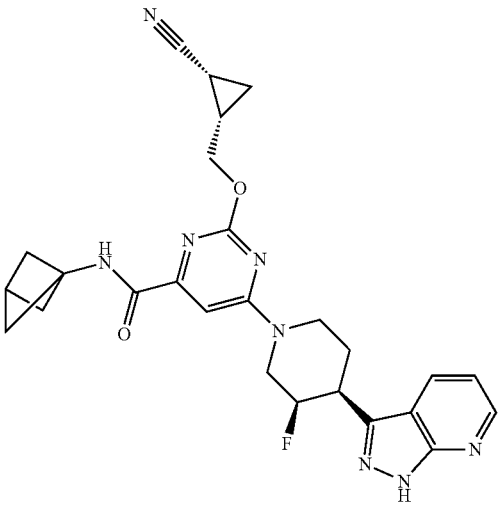 [SMILES: N#C[C@@H]1C[C@@H]1COc1nc(C(=O)NC23CC(C2)C3)cc(N2CC[C@@H](c3n[nH]c4ncccc34)[C@@H](F)C2)n1] | N-(bicyclo[1.1.1]pent-1-yl)-2-{[(1S,2R)-2-cyanocyclopropyl]methoxy}-6-[(3R,4S)-3-fluoro-4-(1H-pyrazolo[3,4-b]pyridin-3-yl)piperidin-1-yl]pyrimidine-4-carboxamide | 503.3; (600 MHz, DMSO-d$_6$) δ ppm 8.94 (s, 1 H), 8.49 (dd, J = 4.54, 1.32 Hz, 1 H), 8.30 (d, J = 8.20 Hz, 1 H), 7.15 (dd, J = 8.05, 4.39 Hz, 1 H), 7.06 (s, 1 H), 5.16-5.30 (m, 1 H), 4.70 (dd, J = 11.85, 5.27 Hz, 1 H), 4.07 (dd, J = 11.63, 9.59 Hz, 1 H), 3.64-3.81 (m, 1 H), 2.45 (s, 1 H), 2.35 (br. s., 1 H), 2.10 (s, 7 H), 1.95-2.06 (m, 2 H), 1.84 (d, J = 8.34 Hz, 1 H), 1.21-1.32 (m, 2 H), 1.13 (q, J = 5.41 Hz, 1 H). |

TABLE 1-continued

| Ex. # | Structure | Compound Name | LRMS m/z (M + H)⁺; and ¹H NMR |
|---|---|---|---|
| 79** | 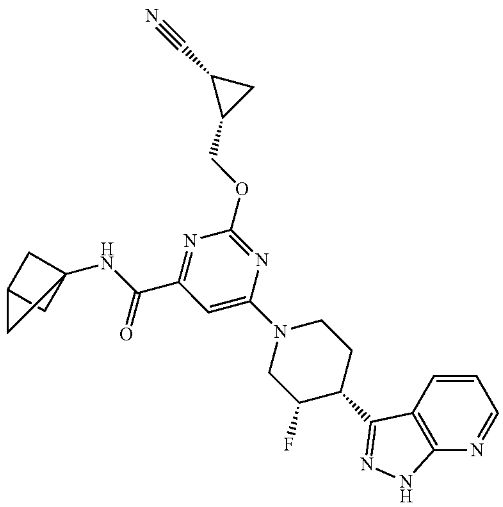 [SMILES: N#C[C@@H]1C[C@@H]1COc1nc(C(=O)NC23CC(C2)C3)cc(N2CC[C@H](c3n[nH]c4ncccc34)[C@H](F)C2)n1] | N-(bicyclo[1.1.1]pent-1-yl)-2-{[(1S,2R)-2-cyanocyclopropyl]methoxy}-6-[(3S,4R)-3-fluoro-4-(1H-pyrazolo[3,4-b]pyridin-3-yl)piperidin-1-yl]pyrimidine-4-carboxamide | 503.3; (600 MHz, DMSO-d$_6$) δ ppm 8.94 (s, 1 H), 8.44-8.51 (m, 1H), 8.29 (d, J = 8.05 Hz, 1 H), 7.15 (dd, J = 8.05, 4.54 Hz, 1 H), 7.06 (s, 1 H), 5.13-5.29 (m, 1 H), 4.70 (dd, J = 11.93, 5.34 Hz, 1 H), 4.03-4.13 (m, 1 H), 3.64-3.80 (m, 1 H), 2.45 (s, 1 H), 2.27-2.39 (m, 1 H), 2.10 (s, 7 H), 1.95-2.06 (m, 2 H), 1.83 (d, J = 7.61 Hz, 1 H), 1.20-1.32 (m, 2 H), 1.13 (q, J = 5.32 Hz, 1 H). |
| 80* | 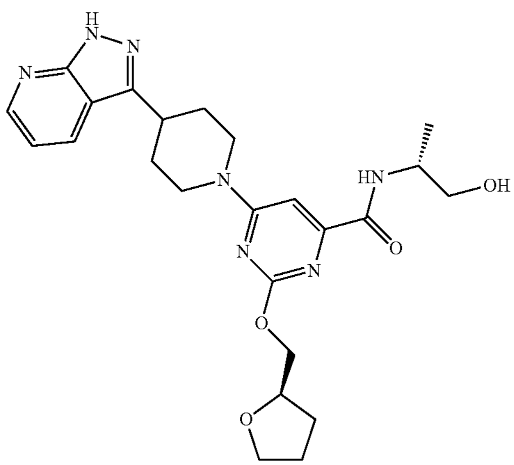 [SMILES: C[C@H](CO)NC(=O)c1cc(N2CCC(c3n[nH]c4ncccc34)CC2)nc(OC[C@H]2CCCO2)n1] | N-[(2R)-1-hydroxypropan-2-yl]-6-[4-(1H-pyrazolo[3,4-b]pyridin-3-yl)piperidin-1-yl]-2-[(2R)-tetrahydrofuran-2-ylmethoxy]pyrimidine-4-carboxamide | 482.2; (400 MHz, DMSO-d$_6$) δ ppm 13.29 (br. s., 1 H), 8.48-8.49 (m, 1 H), 8.31 (d, J = 8.0 Hz, 1 H), 8.18 (d, J = 8.8 Hz, 1 H), 7.13-7.16 (m, 1 H), 7.04 (s, 1 H), 4.89 (t, J = 5.5 Hz, 1 H), 4.50 (br. s., 1 H), 4.26 (d, J = 5.5 Hz, 2 H), 4.12-4.18 (m, 1 H), 4.03-4.04 (m, 1 H), 3.77-3.82 (m, 1 H), 3.65-3.70 (m, 1 H), 3.42-3.47 (m, 3 H), 3.16-3.23 (m, 2 H), 3.00 (br. s., 1 H), 2.12 (d, J = 11 Hz, 2 H), 1.96-2.04 (m, 1 H), 1.81-1.88 (m, 4 H), 1.62-1.71 (m, 1 H), 1.15 (d, J = 6.5 Hz, 3 H). |
| 81* | 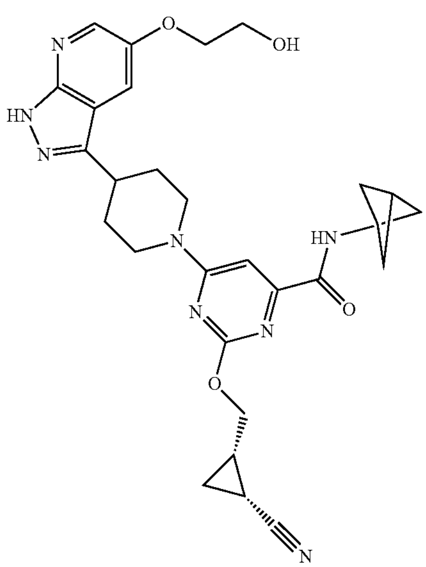 [SMILES: N#C[C@@H]1C[C@@H]1COc1nc(C(=O)NCCC2CCC2)cc(N2CCC(c3n[nH]c4ncc(OCCO)cc34)CC2)n1] | N-(bicyclo[1.1.1]pent-1-yl)-2-{[(1S,2R)-2-cyanocyclopropyl]methoxy}-6-{4-[5-(2-hydroxyethoxy)-1H-pyrazolo[3,4-b]pyridin-3-yl]piperidin-1-yl}pyrimidine-4-carboxamide | 567.3; [M + Na]⁺; (400 MHz, CDCl$_3$) δ ppm 10.31 (br. s., 1 H), 8.36 (s, 1 H), 8.20 (s, 1 H), 7.45 (d, J = 2.8 Hz, 1 H), 7.15 (s, 1 H), 4.46-4.53 (m, 2 H), 4.16-4.18 (m, 2 H), 4.04 (s, 2 H), 3.23-3.35 (m, 4 H), 2.52 (s, 1 H), 2.10-2.19 (m, 8 H), 1.89-2.10 (m, 2 H), 1.80-1.89 (m, 1 H), 1.59-1.71 (m, 2 H), 1.33-1.35 (m, 1 H), 1.25-1.34 (m, 1 H). |

TABLE 1-continued

| Ex. # | Structure | Compound Name | LRMS m/z (M + H)+; and 1H NMR |
|---|---|---|---|
| 82 | 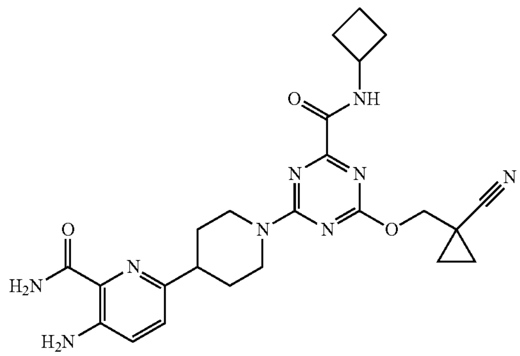 [SMILES: N#CC1(COc2nc(C(=O)NC3CCC3)nc(N3CCC(c4ccc(N)c(C(N)=O)n4)CC3)n2)CC1] | 4-[4-(5-amino-6-carbamoylpyridin-2-yl)piperidin-1-yl]-6-[(1-cyanocyclopropyl)methoxy]-N-cyclobutyl-1,3,5-triazine-2-carboxamide | 492.1; (600 MHz, DMSO-d6) δ ppm 7.84 (d, J = 3.22 Hz, 1 H), 7.23 (br. s., 1 H), 7.17 (s, 1 H), 7.05-7.11 (m, 1 H), 6.65 (br. s., 1 H), 6.30 (br. s., 1 H), 4.93 (d, J = 13.46 Hz, 1 H), 4.75 (d, J = 12.88 Hz, 1 H), 4.29-4.43 (m, 3 H), 3.04-3.08 (m, 2 H), 2.85-2.91 (m, 1 H), 2.10-2.18 (m, 2 H), 2.02 (s, 2 H), 1.91 (br. s., 2 H), 1.66-1.71 (m, 3 H), 1.30-1.38 (m, 2 H), 1.15-1.26 (m, 3 H). |
| 83* | 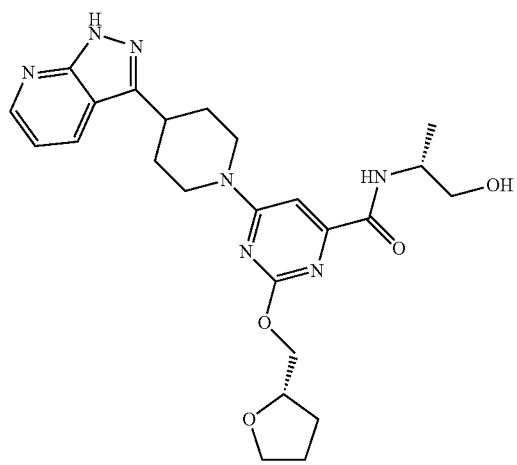 [SMILES: C[C@H](CO)NC(=O)c1cc(N2CCC(c3n[nH]c4ncccc34)CC2)nc(OC[C@@H]2CCCO2)n1] | N-[(2R)-1-hydroxypropan-2-yl]-6-[4-(1H-pyrazolo[3,4-b]pyridin-3-yl)piperidin-1-yl]-2-[(2S)-tetrahydrofuran-2-ylmethoxy]pyrimidine-4-carboxamide | 504.2 [M + Na]+; (600 MHz, DMSO-d6) δ ppm 13.29 (br. s., 1 H), 8.48-8.49 (m, 1 H), 8.31 (6, J = 8.2 Hz, 1 H), 8.18 (d, J = 8.4 Hz, 1 H), 7.13-7.16 (m, 1 H), 7.04 (s, 1 H), 4.90 (t, J = 5.6 Hz, 1 H), 4.50 (br. s., 1 H), 4.26 (d, J = 5.5 Hz, 2 H), 4.12-4.18 (m, 1 H), 3.95-4.01 (m, 1 H), 3.76-3.81 (m, 1 H), 3.64-3.70 (m, 1 H), 3.44-3.49 (m, 3 H), 3.18-3.25 (m, 3 H), 2.12 (d, J = 8.4 Hz, 2 H), 1.96-2.02 (m, 1 H), 1.78-1.89 (m, 4 H), 1.64-1.70 (m, 1 H), 1.15 (d, J = 6.8 Hz, 3 H). |
| 84* | 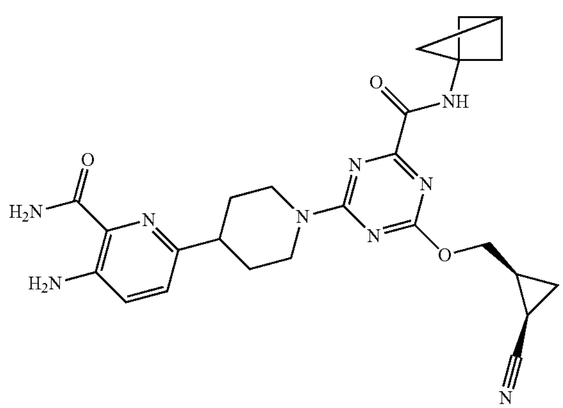 [SMILES: N#C[C@@H]1C[C@@H]1COc1nc(C(=O)NC23CC(C2)C3)nc(N2CCC(c3ccc(N)c(C(N)=O)n3)CC2)n1] | 4-[4-(5-amino-6-carbamoylpyridin-2-yl)piperidin-1-yl]-N-(bicyclo[1.1.1]pent-1-yl)-6-{[(1S,2R)-2-cyanocyclopropyl]methoxy}-1,3,5-triazine-2-carboxamide | 504.2; (600 MHz, DMSO-d6) δ ppm 7.86 (d, J = 3.07 Hz, 1 H), 7.20-7.26 (m, 1 H), 7.18 (d, J = 8.63 Hz, 1 H), 7.09 (d, J = 8.63 Hz, 1 H), 6.66 (br. s., 2 H), 4.95 (d, J = 12.88 Hz, 1 H), 4.75 (d, J = 12.73 Hz, 1 H), 4.68 (dd, J = 11.85, 5.56 Hz, 1 H), 4.11 (dd, J = 11.78, 9.29 Hz, 1 H), 3.05 (t, J = 13.02 Hz, 2 H), 2.82-2.92 (m, 1 H), 2.45 (s, 1 H), 2.08 (s, 6 H), 1.99 (dt, J = 8.12, 5.56 Hz, 1 H), 1.91 (d, J = 11.41 Hz, 2 H), 1.79-1.87 (m, 1 H), 1.64-1.72 (m, 2 H), 1.27 (dt, J = 8.49, 4.98 Hz, 1 H), 1.11-1.20 (m, 1 H). |

TABLE 1-continued

| Ex. # | Structure | Compound Name | LRMS m/z (M + H)⁺; and ¹H NMR |
|---|---|---|---|
| 85* | 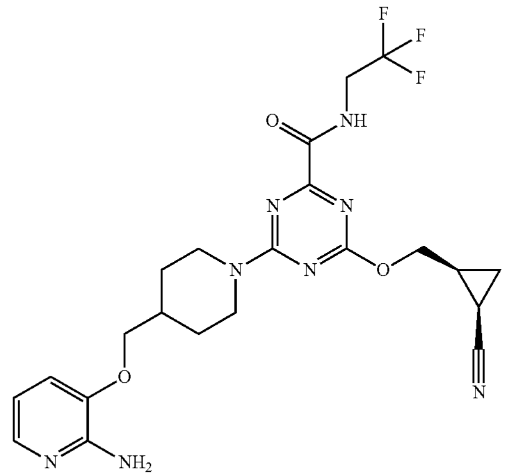 [SMILES: N#C[C@@H]1C[C@@H]1COc1nc(C(=O)NCC(F)(F)F)nc(N2CCC(COc3cccnc3N)CC2)n1] | 4-(4-{[(2-aminopyridin-3-yl)oxy]methyl}piperidin-1-yl)-6-{[(1S,2R)-2-cyanocyclopropyl]methoxy}-N-(2,2,2-trifluoroethyl)-1,3,5-triazine-2-carboxamide | 507.1; (600 MHz, DMSO-d₆) δ ppm 7.48 (d, J = 4.98 Hz, 1 H), 6.98 (d, J = 7.76 Hz, 1 H), 6.47 (dd, J = 7.68, 5.05 Hz, 1 H), 5.61 (s, 2 H), 4.91 (d, J = 13.32 Hz, 1 H), 4.65-4.75 (m, 2 H), 4.13 (t, J = 10.46 Hz, 1 H), 4.03 (d, J = 7.76 Hz, 2 H), 3.84 (dd, J = 5.93, 3.15 Hz, 2 H), 2.12 (br. s., 1 H), 1.96-2.03 (m, 1 H), 1.91-1.96 (m, 2 H), 1.84 (d, J = 8.34 Hz, 1 H), 1.27-1.36 (m, 3 H), 1.13-1.21 (m, 1 H). |
| 86* | 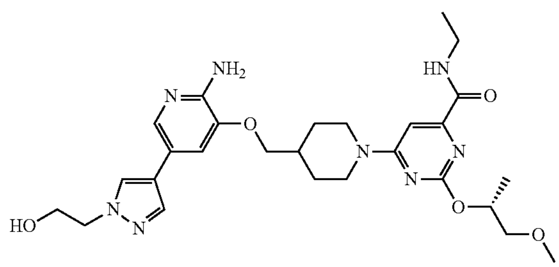 [SMILES: CCNC(=O)c1cc(N2CCC(COc3cc(-c4cnn(CCO)c4)cnc3N)CC2)nc(O[C@H](C)COC)n1] | 6-{4-[({2-amino-5-[1-(2-hydroxyethyl)-1H-pyrazol-4-yl]pyridin-3-yl}oxy)methyl]piperidin-1-yl}-N-ethyl-2-{[(2R)-1-methoxypropan-2-yl]oxy}pyrimidine-4-carboxamide | 555.3; (400 MHz, DMSO-d₆) δ ppm 8.61 (t, J = 6.0 Hz, 1 H), 8.02 (s, 1 H), 7.77 (d, J = 3.6 Hz, 1 H), 7.20 (s, 1 H), 6.97 (s, 1 H), 5.60 (s, 2 H), 5.30-5.35 (m, 1 H), 4.91-4.94 (m, 2 H), 4.25-4.60 (m, 2 H), 4.10-4.14 (m, 2 H), 3.71-3.75 (m, 2 H), 3.26-3.37 (m, 5 H), 2.95-3.11 (m, 2 H), 2.09-2.22 (m, 1 H), 1.94-1.97 (m, 2 H), 1.24-1.34 (m, 5 H), 1.09 (t, J = 7.2 Hz, 3 H). |
| 87* | 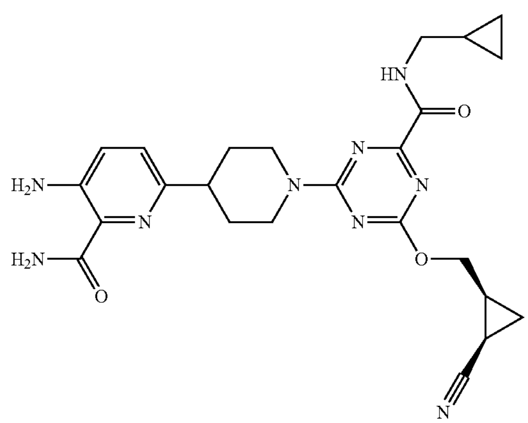 [SMILES: N#C[C@@H]1C[C@@H]1COc1nc(C(=O)NCC2CC2)nc(N2CCC(c3ccc(N)c(C(N)=O)n3)CC2)n1] | 4-[4-(5-amino-6-carbamoylpyridin-2-yl)piperidin-1-yl]-6-{[(1S,2R)-2-cyanocyclopropyl]methoxy}-N-(cyclopropylmethyl)-1,3,5-triazine-2-carboxamide | 49.2; (400 MHz, CD₃OD) δ ppm 7.22 (d, J = 8.8 Hz, 1 H), 7.14 (d, J = 8.4 Hz, 1 H), 5.16 (d, J = 14.4 Hz, 1 H), 4.76-4.84 (m, 2 H), 3.30-3.35 (m, 1 H), 3.27 (d, J = 7.2 Hz, 2 H), 3.16 (t, J = 12.4 Hz, 2 H), 2.96-2.99 (m, 1 H), 2.04 (d, J = 7.2 Hz, 2 H), 1.80-1.92 (m, 4 H), 1.31-1.38 (m, 1 H), 1.13-1.16 (m, 2 H), 0.54 (d, J = 4.4 Hz, 2 H), 0.33 (d, J = 5.2 Hz, 2 H). |
| 88* | 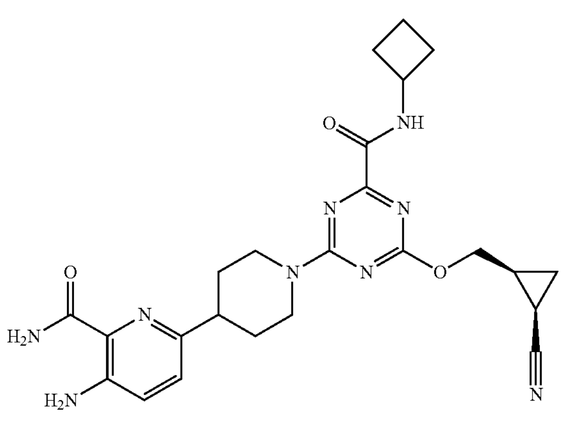 [SMILES: N#C[C@@H]1C[C@@H]1COc1nc(C(=O)NC2CCC2)nc(N2CCC(c3ccc(N)c(C(N)=O)n3)CC2)n1] | 4-[4-(5-amino-6-carbamoylpyridin-2-yl)piperidin-1-yl]-6-{[(1S,2R)-2-cyanocyclopropyl]methoxy}-N-cyclobutyl-1,3,5-triazine-2-carboxamide | 492.2; (400 MHz, DMSO-d₆) δ ppm 8.80 (d, J = 8.07 Hz, 1 H), 7.85 (br. s., 1 H), 7.18-7.26 (m, 2 H), 7.09 (d, J = 8.56 Hz, 1 H), 6.67 (br. s., 2 H), 6.26 (br. s., 1 H), 4.95 (d, J = 12.72 Hz, 1 H), 4.76 (d, J = 14.06 Hz, 1 H), 4.69 (dd, J = 5.38, 11.98 Hz, 1 H), 4.31-4.42 (m, 1 H), 4.08-4.17 (m, 1 H), 3.03-3.10 (m, 2 H), 2.88 (t, J = 11.86 Hz, 1 H), 2.11-2.21 (m, 4 H), 1.89-2.04 (m, 3 H), 1.61-1.71 (m, 4H), 1.21-1.32 (m, 2 H), 1.12-1.21 (m, 1 H). |

TABLE 1-continued

| Ex. # | Structure | Compound Name | LRMS m/z (M + H)+; and 1H NMR |
|---|---|---|---|
| 89* | 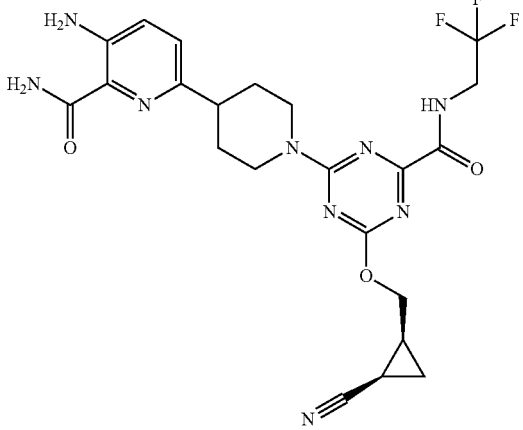 | 4-[4-(5-amino-6-carbamoylpyridin-2-yl)piperidin-1-yl]-6-{[(1S,2R)-2-cyanocyclopropyl]methoxy}-N-(2,2,2-trifluoroethyl)-1,3,5-triazine-2-carboxamide | 520.1; (400 MHz, DMSO-$d_6$) δ ppm 9.34 (t, J = 6.8 Hz, 1 H), 7.89 (s, 1 H), 7.26 (s, 1 H), 7.21 (d, J = 8.8 Hz, 1 H), 7.10 (d, J = 8.4 Hz, 1 H), 6.68 (br. s., 2 H), 5.00 (d, J = 14.8 Hz, 1 H), 4.70-4.80 (m, 2 H), 4.02-4.16 (m, 3 H), 3.09 (t, J = 13.2 Hz, 2 H), 2.89-2.92 (m, 1 H), 1.81-2.01 (m, 3 H), 1.70-1.73 (m, 2 H), 1.17-1.30 (m, 3 H). |
| 90 | 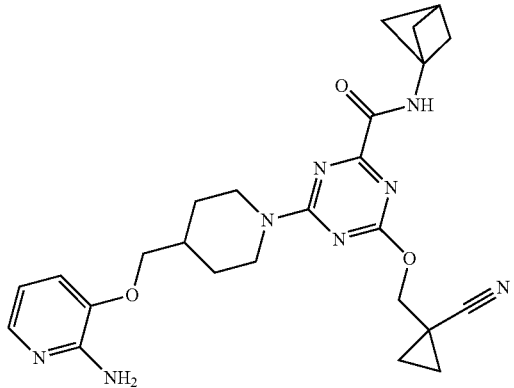 [SMILES: N#CC1(COc2nc(C(=O)NC34CC(C3)C4)nc(N3CCC(COc4cccnc4N)CC3)n2)CC1] | 4-(4-{[(2-aminopyridin-3-yl)oxy]methyl}piperidin-1-yl)-N-(bicyclo[1.1.1]pent-1-yl)-6-[(1-cyanocyclopropyl)methoxy]-1,3,5-triazine-2-carboxamide | 491.2; (600 MHz, DMSO-$d_6$) δ ppm 9.13 (s, 1 H), 7.48 (d, J = 5.27 Hz, 1 H), 7.05 (d, J = 7.61 Hz, 1 H), 6.52 (dd, J = 7.61, 5.27 Hz, 1 H), 4.88 (d, J = 12.88 Hz, 1 H), 4.68 (t, J = 11.34 Hz, 2 H), 4.35-4.44 (m, 2 H), 4.33 (d, J = 6.15 Hz, 1 H), 3.81-3.93 (m, 2 H), 2.91-3.04 (m, 2 H), 2.45 (s, 1 H), 2.04-2.16 (m, 6 H), 1.87-1.98 (m, 2 H), 1.26-1.40 (m, 5 H). |
| 91 | 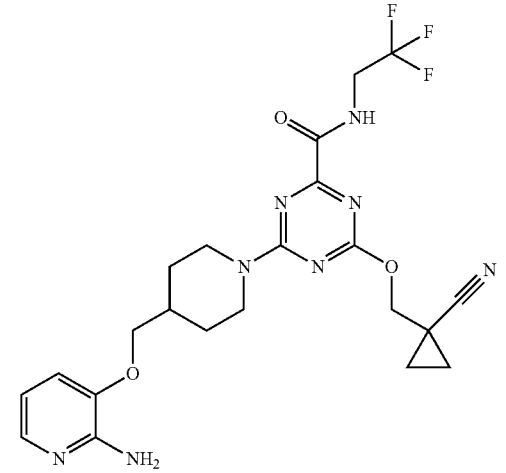 [SMILES: N#CC1(COc2nc(C(=O)NCC(F)(F)F)nc(N3CCC(COc4cccnc4N)CC3)n2)CC1] | 4-(4-{[(2-aminopyridin-3-yl)oxy]methyl}piperidin-1-yl)-6-[(1-cyanocyclopropyl)methoxy]-N-(2,2,2-trifluoroethyl)-1,3,5-triazine-2-carboxamide | 507.1; (600 MHz, DMSO-$d_6$) δ ppm 7.48 (d, J = 4.98 Hz, 1 H), 6.98 (d, J = 7.61 Hz, 1 H), 6.47 (dd, J = 7.68, 5.05 Hz, 1 H), 5.56-5.65 (m, 2 H), 4.90 (d, J = 13.02 Hz, 1 H), 4.71 (d, J = 13.02 Hz, 1 H), 4.38-4.45 (m, 2 H), 3.98-4.07 (m, 2 H), 3.80-3.86 (m, 2 H), 2.98-3.08 (m, 2 H), 2.08-2.16 (m, 1H), 1.93 (d, J = 12.15 Hz, 2 H), 1.29-1.37 (m, 5 H), 1.12-1.20 (m, 1 H). |

TABLE 1-continued

| Ex. # | Structure | Compound Name | LRMS m/z (M + H)+; and 1H NMR |
|---|---|---|---|
| 92* | 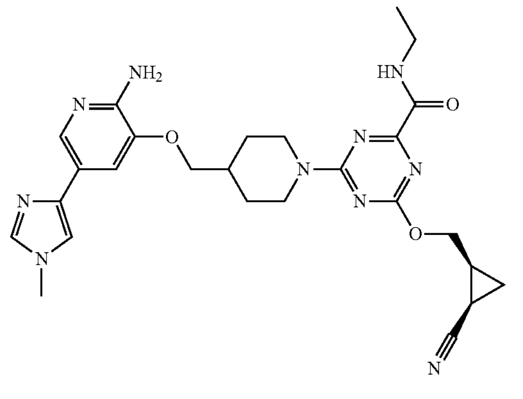 [SMILES: CCNC(=O)c1nc(OC[C@H]2C[C@H]2C#N)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-6-{[(1S,2R)-2-cyanocyclopropyl]methoxy}-N-ethyl-1,3,5-triazine-2-carboxamide | 533.1; (400 MHz, CDCl$_3$) δ ppm 7.95 (s, 1 H), 7.61-7.72 (m, 1 H), 7.45 (s, 2 H), 7.10 (s, 1 H), 5.04-5.13 (m, 1 H), 4.81-4.90 (m, 1 H), 4.71 (s, 1 H), 4.56-4.61 (m, 1 H), 4.45-4.50 (m, 1 H), 3.96-3.97 (m, 2 H), 3.45-3.49 (m, 2 H), 2.96-3.06 (m, 1 H), 2.18-2.20 (m, 1 H), 1.80-1.97 (m, 2 H), 1.40-1.45 (m, 2 H), 1.20-1.35 (m, 6 H), 0.80-0.88 (m, 1 H). |
| 93* | 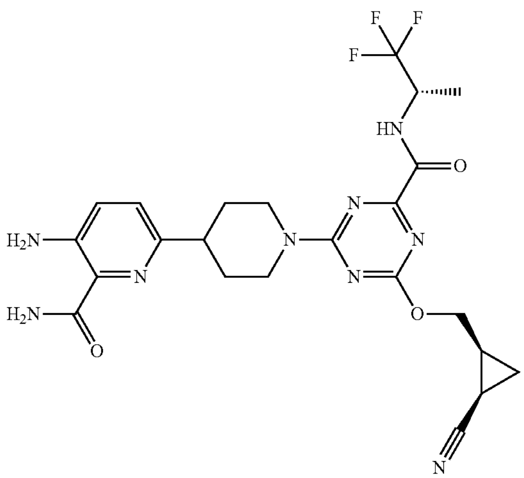 [SMILES: C[C@H](NC(=O)c1nc(OC[C@H]2C[C@H]2C#N)nc(N2CCC(c3ccc(N)c(C(N)=O)n3)CC2)n1)C(F)(F)F] | 4-[4-(5-amino-6-carbamoylpyridin-2-yl)piperidin-1-yl]-6-{[(1S,2R)-2-cyanocyclopropyl]methoxy}-N-[(2S)-1,1,1-trifluoropropan-2-yl]-1,3,5-triazine-2-carboxamide | 534.1; (400 MHz, DMSO-d$_6$) δ ppm 9.06 (d, J = 9.2 Hz, 1 H), 7.88 (s, 1 H), 7.21-7.25 (m, 2 H), 7.10 (d, J = 8.4 Hz, 1 H), 6.68 (s, 2 H), 4.95 (d, J = 13.6 Hz, 1 H), 4.69-4.80 (m, 3 H), 4.11-4.16 (m, 1 H), 3.09 (t, J = 12.8 Hz, 2 H), 2.91 (t, J = 10.7 Hz, 1 H), 1.81-2.01 (m, 4 H), 1.70-1.72 (m, 2 H), 1.38 (d, J = 7.2 Hz, 3 H), 1.28-1.30 (m, 1 H), 1.17-1.19 (m, 1 H). |
| 94* | 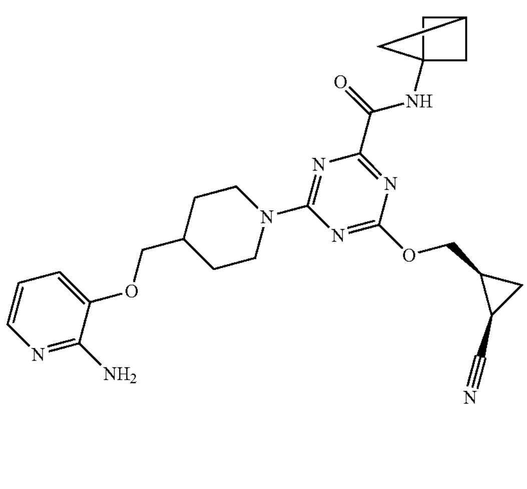 [SMILES: N#C[C@@H]1C[C@@H]1COc1nc(C(=O)NC23CC(C2)C3)nc(N2CCC(COc3cccnc3N)CC2)n1] | 4-(4-{[(2-aminopyridin-3-yl)oxy]methyl}piperidin-1-yl)-N-(bicyclo[1.1.1]pent-1-yl)-6-{[(1S,2R)-2-cyanocyclopropyl]methoxy}-1,3,5-triazine-2-carboxamide | 491.2; (600 MHz, DMSO-d$_6$) δ ppm 7.48 (d, J = 4.98 Hz, 1 H), 6.98 (d, J = 7.76 Hz, 1 H), 6.47 (dd, J = 7.68, 5.05 Hz, 1 H), 5.60 (s, 2 H), 4.88 (d, J = 12.88 Hz, 1 H), 4.63-4.73 (m, 2 H), 4.12 (d, J = 10.10 Hz, 1 H), 3.84 (dd, J = 6.07, 3.00 Hz, 2 H), 2.98-3.05 (m, 2 H), 2.45 (s, 1 H), 2.05-2.16 (m, 6 H), 1.89-2.02 (m, 3 H), 1.83 (d, J = 8.63 Hz, 1 H), 1.25-1.35 (m, 3 H), 1.16 (dd, J = 5.56, 3.22 Hz, 1 H). |

TABLE 1-continued

| Ex. # | Structure | Compound Name | LRMS m/z (M + H)+; and 1H NMR |
|---|---|---|---|
| 95** | 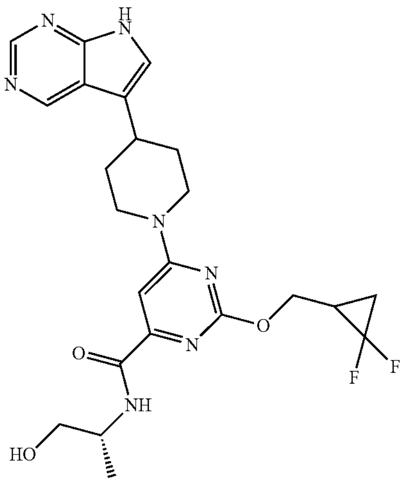 [SMILES: C[C@H](CO)NC(=O)c1cc(N2CCC(c3c[nH]c4ncncc34)CC2)nc(OCC2CC2(F)F)n1] | 2-[(2,2-difluoro-cyclopropyl)methoxy]-N-[(2R)-1-hydroxypropan-2-yl]-6-[4-(7H-pyrrolo[2,3-d]pyrimidin-5-yl)piperidin-1-yl]pyrimidine-4-carboxamide | 488.2; (400 MHz, CDCl$_3$) δ ppm 9.48 (br. s., 1 H), 9.03 (s, 1 H), 9.05 (s, 1 H), 8.88 (s, 1 H), 7.93 (d, J = 7.8 Hz, 1 H), 7.16 (s, 1 H), 7.09 (d, J = 2.0 Hz, 1 H), 4.56-4.82 (m, 1 H), 4.44-4.53 (m, 1 H), 4.33-4.37 (m, 1 H), 4.19-4.26 (m, 1 H), 3.75-3.77 (m, 1 H), 3.64-3.68 (m, 1 H), 3.12-3.22 (m, 3 H), 2.30 (br. s., 1 H), 2.10-2.20 (m, 3 H), 1.73-1.81 (m, 2 H), 1.54-1.61 (m, 1 H), 1.25-1.36 (m, 5 H). |
| 96** | 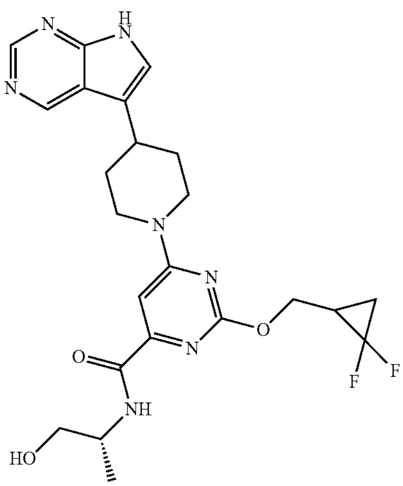 [SMILES: C[C@H](CO)NC(=O)c1cc(N2CCC(c3c[nH]c4ncncc34)CC2)nc(OCC2CC2(F)F)n1] | 2-[(2,2-difluoro-cyclopropyl)methoxy]-N-[(2R)-1-hydroxypropan-2-yl]-6-[4-(7H-pyrrolo[2,3-d]pyrimidin-5-yl)piperidin-1-yl]pyrimidine-4-carboxamide | 488.2; (400 MHz, CDCl$_3$) δ ppm 9.48 (br. s., 1 H), 9.03 (s, 1 H), 9.05 (s, 1 H), 8.88 (s, 1 H), 7.93 (d, J = 7.8 Hz, 1 H), 7.16 (s, 1 H), 7.09 (d, J = 2.0 Hz, 1 H), 4.56-4.82 (m, 1 H), 4.44-4.53 (m, 1 H), 4.33-4.37 (m, 1 H), 4.19-4.26 (m, 1 H), 3.75-3.77 (m, 1 H), 3.64-3.68 (m, 1 H), 3.12-3.22 (m, 3 H), 2.30 (br. s., 1 H), 2.10-2.20 (m, 3 H), 1.73-1.81 (m, 2 H), 1.54-1.61 (m, 1 H), 1.25-1.36 (m, 5 H). |
| 97* | 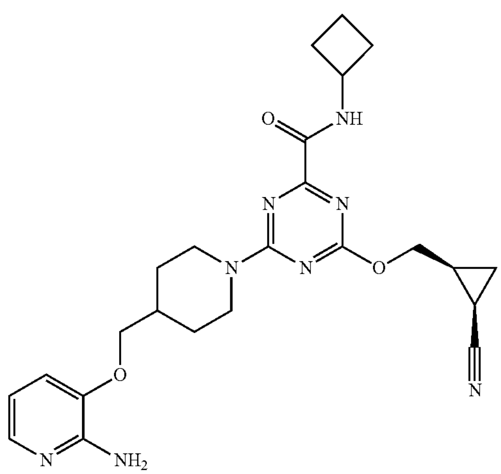 [SMILES: N#C[C@@H]1C[C@@H]1COc1nc(C(=O)NC2CCC2)nc(N2CCC(COc3cccnc3N)CC2)n1] | 4-(4-{[(2-aminopyridin-3-yl)oxy]methyl}piperidin-1-yl)-6-{[(1S,2R)-2-cyanocyclopropyl]methoxy}-N-cyclobutyl-1,3,5-triazine-2-carboxamide | 479.2; (600 MHz, DMSO-d$_6$) δ ppm 8.76 (d, J = 8.05 Hz, 1 H), 7.43 (d, J = 4.54 Hz, 1 H), 6.93 (d, J = 7.61 Hz, 1 H), 6.42 (dd, J = 7.68, 5.05 Hz, 1 H), 5.55 (s, 2 H), 4.83 (d, J = 12.59 Hz, 1 H), 4.60-4.68 (m, 2 H), 4.25-4.35 (m, 1 H), 4.03-4.09 (m, 1 H), 3.76-3.84 (m, 2 H), 2.96 (t, J = 12.73 Hz, 2 H), 2.04-2.15 (m, 5 H), 1.73-1.81 (m, 3 H), 1.59-1.65 (m, 2 H), 1.19-1.31 (m, 3 H). |

TABLE 1-continued

| Ex. # | Structure | Compound Name | LRMS m/z (M + H)+; and 1H NMR |
|---|---|---|---|
| 98* | 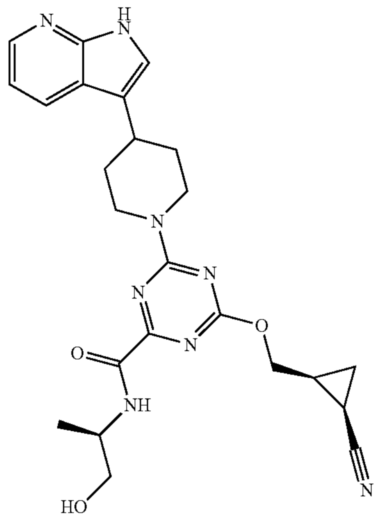 [SMILES: C[C@H](CO)NC(=O)c1nc(OC[C@H]2C[C@H]2C#N)nc(N2CCC(c3c[nH]c4ncccc34)CC2)n1] | 4-{[(1S,2R)-2-cyanocyclopropyl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide | 477.1; (400 MHz, CD$_3$OD) δ ppm 8.17 (d, J = 4.8 Hz, 1 H), 8.11 (d, J = 6.4 Hz, 1 H), 7.21 (s, 1 H), 7.09-7.12 (m, 1 H), 5.16 (d, J = 10.8 Hz, 1 H), 4.97 (d, J = 12.8 Hz, 1 H), 4.76-4.79 (m, 1 H), 4.32 (t, J = 10.7 Hz, 1 H), 4.16 (d, J = 6.8 Hz, 1 H), 3.64 (d, J = 5.2 Hz, 2 H), 3.22 (t, J = 12.8 Hz, 2 H), 2.20 (d, J = 13.6 Hz, 2 H), 1.90-1.93 (m, 2 H), 1.79 (d, J = 12.4 Hz, 2 H), 1.36 (d, J = 6.8 Hz, 3 H), 1.27 (d, J = 6.8 Hz, 3 H). |
| 99* | 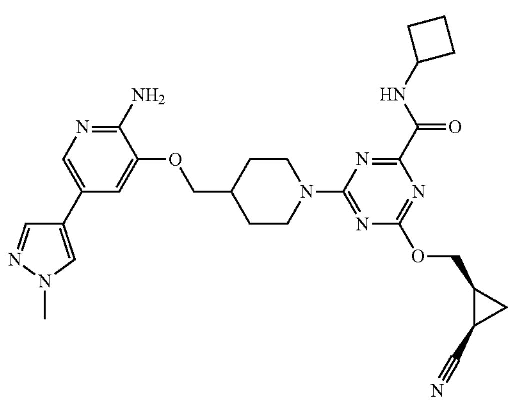 [SMILES: Cn1cc(-c2cnc(N)c(OCC3CCN(c4nc(OC[C@H]5C[C@H]5C#N)nc(C(=O)NC5CCC5)n4)CC3)c2)cn1] | 4-[4-({[2-amino-5-(1-methyl-1H-imidazol-4-yl)pyridin-3-yl]oxy}methyl)piperidin-1-yl]-6-{[(1S,2R)-2-cyanocyclopropyl]methoxy}-N-cyclobutyl-1,3,5-triazine-2-carboxamide | 581.3; (400 MHz, CD$_3$OD) δ ppm 7.88 (s, 1 H), 7.64 (s, 1 H), 7.37 (s, 1 H), 7.30 (s, 1 H), 5.06-5.13 (m, 1 H), 4.75-4.78 (m, 1 H), 4.71 (s, 1 H), 4.47-4.51 (m, 1 H), 4.31 (t, J = 7.20 Hz, 1 H), 4.02 (d, J = 6.4 Hz, 2 H), 3.76 (s, 3 H), 3.09 (t, J = 7.2 Hz, 2 H), 2.30-2.35 (m, 2 H), 2.18-2.20 (m, 2 H), 2.06-2.08 (m, 2 H), 1.80-1.90 (m, 4 H), 1.30-1.45 (m, 5 H), 1.10-1.15 (m, 1 H), 0.88-0.90 (m, 1 H). |
| 100 | 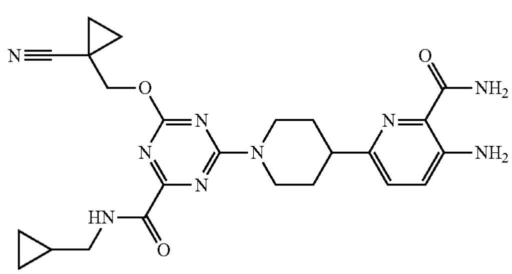 [SMILES: N#CC1(COc2nc(C(=O)NCC3CC3)nc(N3CCC(c4ccc(N)c(C(N)=O)n4)CC3)n2)CC1] | 4-[4-(5-amino-6-carbamoylpyridin-2-yl)piperidin-1-yl]-6-[(1-cyanocyclopropyl)methoxy]-N-(cyclopropylmethyl)-1,3,5-triazine-2-carboxamide | 492.2; (400 MHz, DMSO-d$_6$) δ ppm 8.89 (t, J = 8.2 Hz, 1 H), 7.87 (s, 1 H), 7.09-7.27 (m, 3 H), 6.69 (s, 2 H), 4.97 (d, J = 11.8 Hz, 1 H), 4.78 (d, J = 11.6 Hz 1 H), 4.42 (s, 2 H), 3.11-3.21 (m, 4 H), 2.90 (s, 1 H), 1.93 (d, J = 15.6 Hz, 2 H), 1.66-1.72 (m, 2 H), 1.38 (s, 2 H), 1.26 (s, 2 H), 1.04 (s, 1 H), 0.42 (d, J = 7.8 Hz, 2 H), 0.24 (d, J = 3.6 Hz, 2H). |

TABLE 1-continued

| Ex. # | Structure | Compound Name | LRMS m/z (M + H)+; and 1H NMR |
|---|---|---|---|
| 101* | 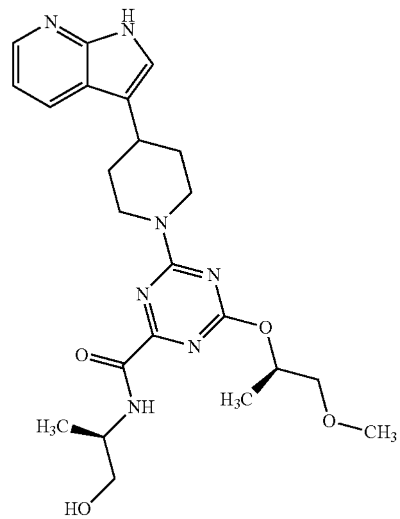 [SMILES: COC[C@@H](C)Oc1nc(C(=O)N[C@H](C)CO)nc(N2CCC(c3c[nH]c4ncccc34)CC2)n1] | N-[(2R)-1-hydroxypropan-2-yl]-4-{[(2R)-1-methoxypropan-2-yl]oxy}-6-[4-(1H-pyrrolo[2,3-b]pyridin-3-yl)piperidin-1-yl]-1,3,5-triazine-2-carboxamide | 470.1; (400 MHz, CD$_3$OD) δ ppm 8.18 (d, J = 4.8 Hz, 1 H), 8.11 (d, J = 6.4 Hz, 1 H), 7.22 (s, 1 H), 7.09-7.12 (m, 1 H), 5.46-5.50 (m, 1 H), 5.15 (d, J = 10.8 Hz, 1 H), 4.92-4.96 (m, 1 H), 4.15-4.16 (m, 1 H), 3.57-3.65 (m, 4 H), 3.40 (s, 3 H), 3.19-3.25 (m, 3 H), 2.21 (d, J = 13.6 Hz, 2 H), 1.76-1.79 (m, 2 H), 1.37 (d, J = 6.8 Hz 3 H), 1.7 (d, J = 6.8 Hz, 3 H). |
| 102* | 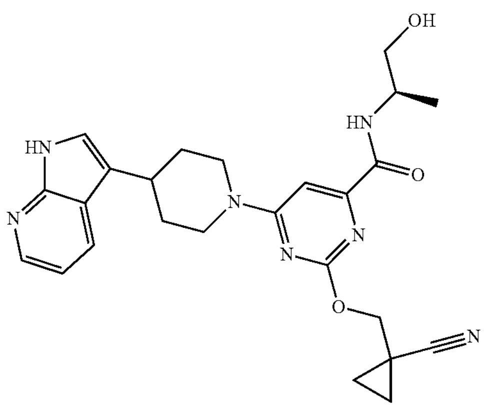 [SMILES: C[C@H](CO)NC(=O)c1cc(N2CCC(c3c[nH]c4ncccc34)CC2)nc(OCC2(C#N)CC2)n1] | 2-[(1-cyanocyclopropyl)methoxy]-N-[(2R)-1-hydroxypropan-2-yl]-6-[4-(1H-pyrrolo[2,3-b]pyridin-3-yl)piperidin-1-yl]pyrimidine-4-carboxamide | 476.2; (400 MHz, DMSO-d$_6$) δ ppm 11.36 (s, 1 H), 8.18-8.22 (m, 2 H), 8.01-8.03 (m, 1 H), 7.24 (d, J = 5.6 Hz, 1 H), 7.03-7.06 (m, 2 H), 4.86-4.89 (m, 1 H), 4.70 (br. s., 1 H), 4.36 (s, 2 H), 3.98-4.00 (m, 1 H), 3.43-3.47 (m, 3 H), 3.13-3.40 (m, 3 H), 2.05-2.09 (m, 2 H), 1.62-1.65 (m, 2 H), 1.37-1.39 (m, 2 H), 1.22-1.24 (m, 2 H), 1.14-1.16 (m, 3 H). |
| 103* | 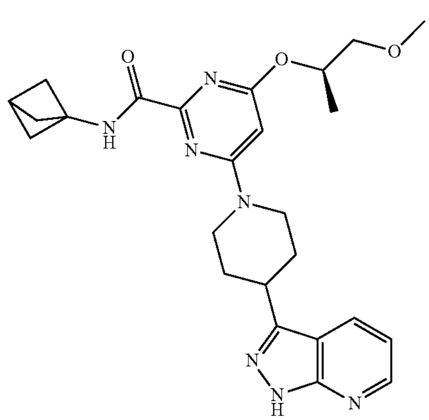 [SMILES: COC[C@@H](C)Oc1cc(N2CCC(c3n[nH]c4ncccc34)CC2)nc(C(=O)NC23CC(C2)C3)n1] | N-(bicyclo[1.1.1]pent-1-yl)-4-{[(2R)-1-methoxypropan-2-yl]oxy}-6-[4-(1H-pyrazolo[3,4-b]pyridin-3-yl)piperidin-1-yl]pyrimidine-2-carboxamide | 478.2; (400 MHz, DMSO-d6) δ ppm 13.25 (br. s., 1 H), 8.85 (s, 1 H), 8.47 (dd, J = 4.5, 1.5 Hz, 1 H), 8.30 (dd, J = 8.1, 1.5 Hz, 1 H), 7.13 (dd, J = 8.1, 4.5 Hz, 1 H), 6.17 (s, 1 H), 5.42-5.52 (m, 1 H), 4.53 (d, J = 10.8 Hz, 2 H), 3.42-3.52 (m, 2H), 3.37 (d, J = 11.6 Hz, 1 H), 3.28 (br. s., 3 H), 3.11 (t, J = 11.6 Hz, 2 H), 2.45 (s, 1H), 2.02-2.17 (m, 8 H), 1.71-1.92 (m, 2H), 1.23 (d, J = 6.3 Hz, 3H). |

TABLE 1-continued

| Ex. # | Structure | Compound Name | LRMS m/z (M + H)+; and 1H NMR |
|---|---|---|---|
| 104 | 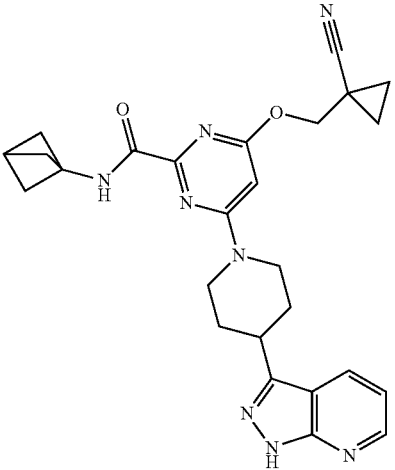 [SMILES: N#CC1(COc2cc(N3CCC(c4n[nH]c5ncccc45)CC3)nc(C(=O)NC34CC(C3)C4)n2)CC1] | N-(bicyclo[1.1.1]pent-1-yl)-4-[(1-cyanocyclopropyl)methoxy]-6-[4-(1H-pyrazolo[3,4-b]pyridin-3-yl)piperidin-1-yl]pyrimidine-2-carboxamide | 485.2; (400 MHz, DMSO-d6) δ ppm 13.25 (s, 1 H), 8.89 (s, 1 H), 8.48 (dd, J = 4.53, 1.51 Hz, 1 H), 8.31 (d, J = 6.80 Hz, 1 H), 7.14 (dd, J = 8.06, 4.53 Hz, 1 H), 6.32 (s, 1 H), 4.56 (br. s., 2 H), 4.40 (s, 2 H), 3.36-3.48 (m, 2 H), 3.09-3.21 (m, 2 H), 2.46 (s, 1 H), 2.10 (s, 7 H), 1.75-1.88 (m, 2 H), 1.33-1.39 (m, 2 H), 1.21-1.28 (m, 2 H). |
| 105 | 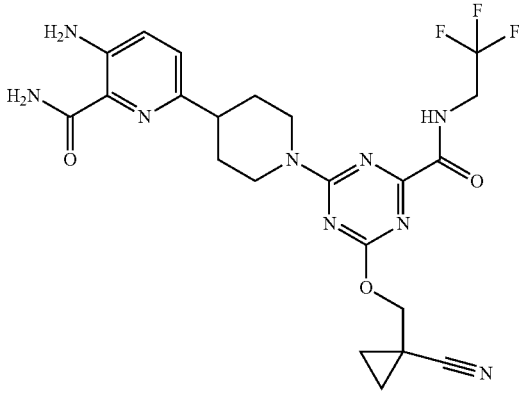 [SMILES: N#CC1(COc2nc(C(=O)NCC(F)(F)F)nc(N3CCC(c4ccc(N)c(C(N)=O)n4)CC3)n2)CC1] | 4-[4-(5-amino-6-carbamoylpyridin-2-yl)piperidin-1-yl]-6-[(1-cyanocyclopropyl)methoxy]-N-(2,2,2-trifluoroethyl)-1,3,5-triazine-2-carboxamide | 520.1; (400 MHz, DMSO-d6) δ ppm 9.35 (t, J = 6.0 Hz, 1 H), 7.86 (s, 1 H), 7.27 (s, 1 H), 7.08-7.20 (m, 2 H), 6.68 (s, 2 H), 4.97 (d, J = 12.4 Hz, 1 H), 4.77 (d, J = 12.4 Hz, 1 H), 4.38-4.44 (m, 2 H), 4.01 (t, J = 9.6 Hz, 2 H), 3.08 (s, 2 H), 2.89 (s, 1 H), 1.90 (d, J = 13.6 Hz, 2 H), 1.71-1.74 (m, 2 H), 1.36-1.39 (m, 2 H), 1.22-1.25 (m, 2 H). |
| 106* | 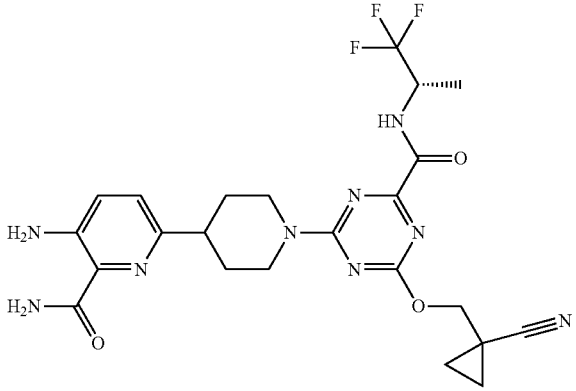 [SMILES: C[C@H](NC(=O)c1nc(OCC2(C#N)CC2)nc(N2CCC(c3ccc(N)c(C(N)=O)n3)CC2)n1)C(F)(F)F] | 4-[4-(5-amino-6-carbamoylpyridin-2-yl)piperidin-1-yl]-6-[(1-cyanocyclopropyl)methoxy]-N-[(2S)-1,1,1-trifluoropropan-2-yl]-1,3,5-triazine-2-carboxamide | 534.1; (400 MHz, DMSO-d6) δ ppm 9.08 (d, J = 9.6 Hz, 1 H), 7.86 (s, 1 H), 7.27 (s, 1 H), 7.20 (d, J = 8.8 Hz, 1H) 7.08 (d, J = 8.8 Hz, 1 H), 6.68 (s, 2 H), 4.93 (d, J = 13.6 Hz, 1 H), 4.78 (d, J = 14.4 Hz, 2 H), 4.37-4.45 (m, 2 H), 3.08 (s, 2 H), 2.89 (s, 1 H), 1.92 (d, J = 11.6 Hz, 2 H), 1.68-1.71 (m, 2 H), 1.37-1.38 (m, 5 H), 1.22-1.25 (m, 2 H). |

TABLE 1-continued

| Ex. # | Structure | Compound Name | LRMS m/z (M + H)+; and 1H NMR |
|---|---|---|---|
| 107* | 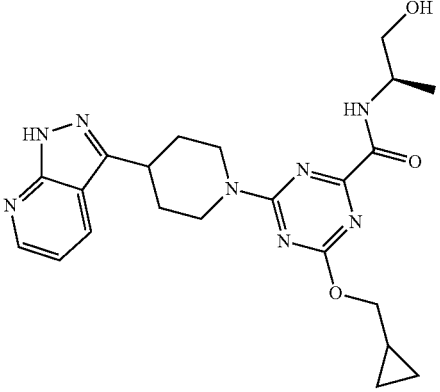 [SMILES: C[C@H](CO)NC(=O)c1nc(OCC2CC2)nc(N2CCC(c3n[nH]c4ncccc34)CC2)n1] | 4-(cyclopropylmethoxy)-N-[(2R)-1-hydroxypropan-2-yl]-6-[4-(1H-pyrazolo[3,4-b]pyridin-3-yl)piperidin-1-yl]-1,3,5-triazine-2-carboxamide | 453.1; (400 MHz, DMSO-d6) δ ppm 13.35 (s, 1 H), 8.47-8.48 (m, 1 H), 8.30-8.34 (m, 2 H), 7.12-7.15 (m, 1 H), 4.86-4.90 (m, 2 H), 4.72-4.75 (m, 1 H), 4.18-4.19 (m, 2 H), 3.85-3.95 (m, 2 H), 3.40-3.44 (m, 2 H), 3.21-3.23 (m, 2 H), 2.10-2.14 (m, 2 H), 1.80-1.83 (m, 2 H), 1.23-1.25 (m, 2 H), 1.11-1.13 (m, 3 H), 0.54-0.57 (m, 2 H), 0.33-0.37 (m, 2 H). |
| 108* | 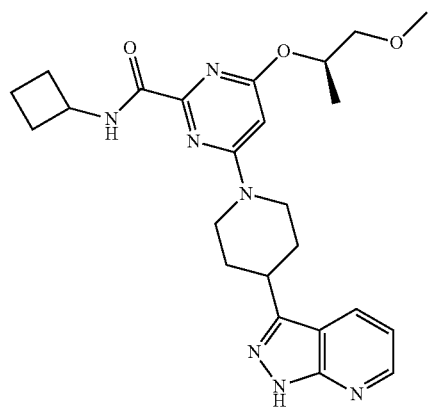 [SMILES: COC[C@@H](C)Oc1cc(N2CCC(c3n[nH]c4ncccc34)CC2)nc(C(=O)NC2CCC2)n1] | N-cyclobutyl-4-{[(2R)-1-methoxypropan-2-yl]oxy}-6-[4-(1H-pyrazolo[3,4-b]pyridin-3-yl)piperidin-1-yl]pyrimidine-2-carboxamide | 466.3; (600 MHz, DMSO-d6) δ ppm 8.56 (d, J = 8.2 Hz, 1 H), 8.47 (dd, J = 4.5, 1.0 Hz, 1 H), 8.30 (dd, J = 8.0, 1.0 Hz, 1 H), 7.13 (dd, J = 8.0, 4.5 Hz, 1 H), 6.17 (s, 1H), 5.42-5.51 (m, 1 H), 4.53 (br. s., 2 H), 4.37 (sxt, J = 8.3 Hz, 1 H), 3.46-3.52 (m, 1 H), 3.34-3.46 (m, 2 H), 3.11 (t, J = 11.9 Hz, 2 H), 2.52-2.55 (m, 3 H), 2.16-2.22 (m, 2 H), 2.13 (t, J = 9.4 Hz, 2 H), 2.07 (d, J = 11.4 Hz, 2 H), 1.74-1.86 (m, 2 H), 1.61-1.69 (m, 2 H), 1.23 (d, J = 6.4 Hz, 3 H). |
| 109 | 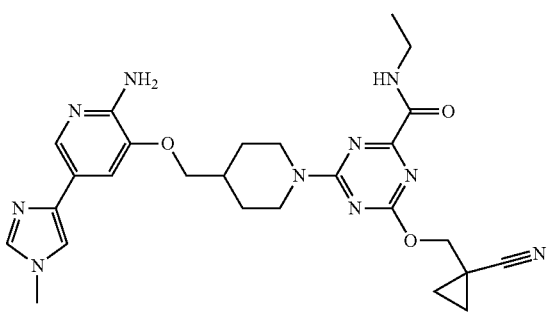 | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-ethyl-1,3,5-triazine-2-carboxamide | 533.2; (400 MHz, CD3OD) δ ppm 7.55 (s, 1H), 7.43 (s, 1 H), 7.38 (s, 1 H), 7.32 (s, 1 H), 5.05-5.11 (m, 1 H), 4.38-4.49 (m, 2 H), 3.97 (d, J = 6.0 Hz, 2 H), 3.74 (s, 3 H), 3.42 (q, J = 7.2 Hz, 2 H), 3.09-3.11 (m, 2 H), 2.21-2.23 (m, 1 H), 1.98-2.11 (m, 2 H), 1.19-1.35 (m, 11 H). |
| 110* | 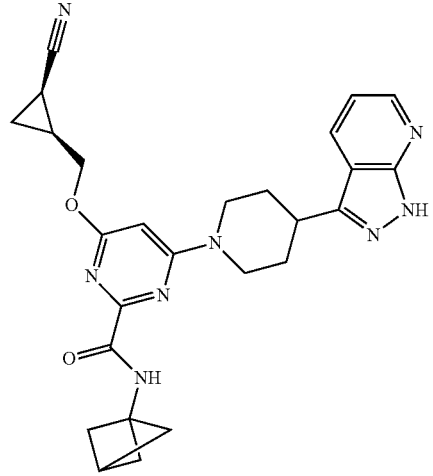 [SMILES: N#C[C@@H]1C[C@@H]1COc1cc(N2CCC(c3n[nH]c4ncccc34)CC2)nc(C(=O)NC23CC(C2)C3)n1] | N-(bicyclo[1.1.1]pent-1-yl)-4-{[(1S,2R)-2-cyanocyclopropyl]methoxy}-6-[4-(1H-pyrazolo[3,4-b]pyridin-3-yl)piperidin-1-yl]pyrimidine-2-carboxamide | 485.1; (600 MHz, DMSO-d6) δ ppm 8.47 (dd, J = 4.4, 1.5 Hz, 1 H), 8.30 (dd, J = 8.0, 1.5 Hz, 1 H), 7.13 (dd, J = 8.0, 4.4 Hz, 1 H), 6.27 (s, 1 H), 4.68 (dd, J = 11.8, 5.5 Hz, 1 H), 4.55 (br. s., 2 H), 4.08 (dd, J = 11.7, 9.1 Hz, 1 H), 3.12 (t, J = 11.9 Hz, 2 H), 2.45 (s, 1 H), 2.07 (br. s., 9 H), 1.93-2.01 (m, 1 H), 1.74-1.89 (m, 3 H), 1.28 (dt, J = 8.5, 5.0 Hz, 1 H), 1.13 (q, J = 5.5 Hz, 1 H). |

TABLE 1-continued

| Ex. # | Structure | Compound Name | LRMS m/z (M + H)+; and 1H NMR |
|---|---|---|---|
| 111* | 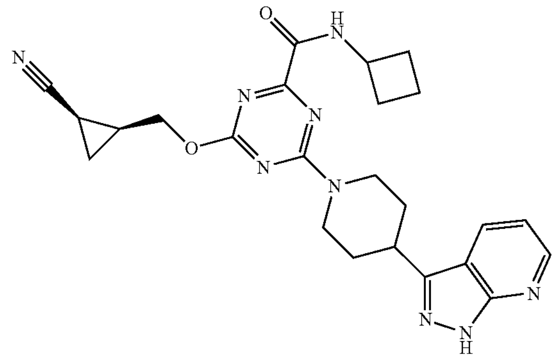 [SMILES: N#C[C@@H]1C[C@@H]1COc1nc(C(=O)NC2CCC2)nc(N2CCC(c3n[nH]c4ncccc34)CC2)n1] | 4-{[(1S,2R)-2-cyanocyclopropyl]methoxy}-N-cyclobutyl-6-[4-(1H-pyrazolo[3,4-b]pyridin-3-yl)piperidin-1-yl]-1,3,5-triazine-2-carboxamide | 474.1; (400 MHz, CD3OD) δ ppm 8.47-8.50 (m, 1 H), 8.34-8.36 (m, 1 H), 7.19-7.22 (m, 1 H), 5.13-5.16 (m, 1 H), 4.89-4.96 (m, 2 H), 4.75-4.77 (m, 1 H), 4.50-4.52 (m, 1 H), 4.31-4.35 (m, 1 H), 3.51-3.54 (m, 1 H), 3.25-3.27 (m, 1 H), 2.35-2.37 (m, 2 H), 2.19-2.22 (m, 4 H), 1.80-1.88 (m, 6 H), 1.38-1.39 (m, 1 H), 1.14-1.15 (m, 1 H). |
| 112 | 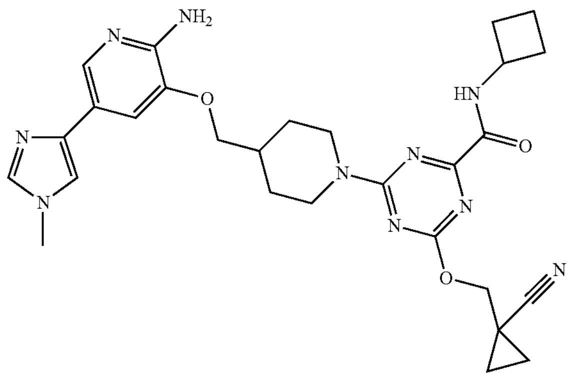 [SMILES: Cn1cnc(-c2cnc(N)c(OCC3CCN(c4nc(OCC5(C#N)CC5)nc(C(=O)NC5CCC5)n4)CC3)c2)c1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-cyclobutyl-1,3,5-triazine-2-carboxamide | 581.4 [M + Na]+; (400 MHz, CD3OD) δ ppm 7.88 (s, 1 H), 7.64 (s, 1 H), 7.37 (s, 1 H), 7.30 (s, 1 H), 5.10-5.13 (m, 1 H), 4.46-4.49 (m, 4 H), 4.02 (d, J = 6.0 Hz, 2 H), 3.76 (s, 3 H), 3.10-3.16 (m, 2 H), 2.30-2.38 (m, 3 H), 2.20-2.24 (m, 2 H), 2.06-2.10 (m, 2 H), 1.76-1.80 (m, 2 H), 1.38-1.46 (m, 4 H), 1.28-1.30 (m, 2 H) |
| 113* | 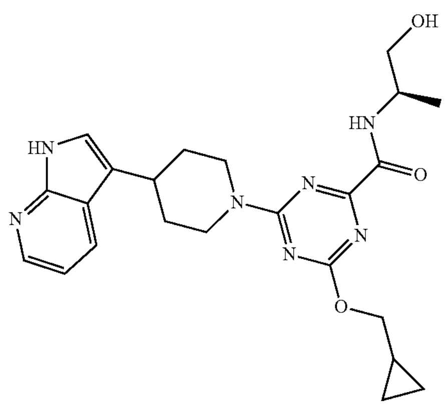 [SMILES: C[C@H](CO)NC(=O)c1nc(OCC2CC2)nc(N2CCC(c3c[nH]c4ncccc34)CC2)n1] | 4-(cyclopropylmethoxy)-N-[(2R)-1-hydroxypropan-2-yl]-6-[4-(1H-pyrrolo[2,3-b]pyridin-3-yl)piperidin-1-yl]-1,3,5-triazine-2-carboxamide | 452.2; (400 MHz, CD3OD) δ ppm 8.18 (d, J = 4.0 Hz, 1 H), 8.02 (dd, J = 7.6, 1.2 Hz, 1 H), 7.21 (s, 1 H), 7.09-7.12 (m, 1 H), 5.15 (d, J = 14.0 Hz, 1 H), 4.96 (s, 1 H), 4.27 (d, J = 6.8 Hz, 2 H), 4.14-4.18 (m, 1 H), 3.64 (d, J = 4.0 Hz, 2 H), 3.17-3.26 (m, 3 H), 2.17-2.20 (m, 2 H), 1.74-1.78 (m, 2 H), 1.27-1.33 (m, 4 H), 0.65 (d, J = 4.8 Hz, 2 H), 0.40 (d, J = 4.4 Hz, 2 H). |
| 114* | 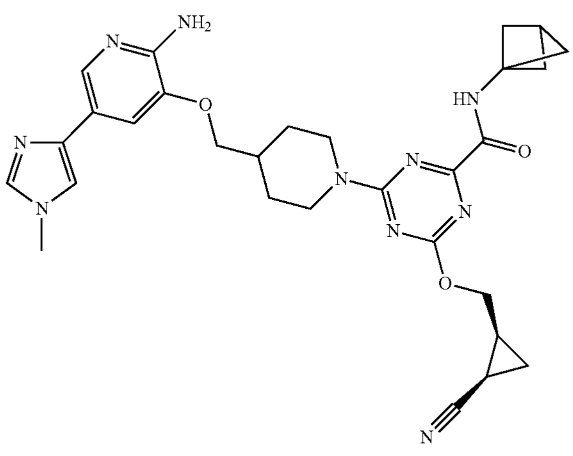 [SMILES: Cn1cnc(-c2cnc(N)c(OCC3CCN(c4nc(OC[C@H]5C[C@H]5C#N)nc(C(=O)NC56CC(C5)C6)n4)CC3)c2)c1] | 4-[4-({[2-amino-5-(1-methyl-1H-imidazol-4-yl)pyridin-3-yl]oxy}methyl)piperidin-1-yl]-N-(bicyclo[1.1.1]pent-1-yl)-6-{[(1S,2R)-2-cyanocyclopropyl]methoxy}-1,3,5-triazine-2-carboxamide | 571.3; (400 MHz, CD3OD) δ ppm 7.88 (s, 1 H), 7.64 (s, 1 H), 7.42 (s, 1 H), 7.37 (s, 1 H), 5.07-5.15 (m, 2 H), 4.75 (d, J = 3.2 Hz, 2 H), 4.28-4.31 (m, 1 H), 4.02 (d, J = 6.4 Hz, 2 H), 3.76 (s, 3 H), 3.05-3.11 (m, 2 H), 2.49 (s, 1 H), 2.28-2.30 (m, 1 H), 2.21 (s, 6 H), 2.05-2.10 (d, 2 H), 1.86-1.92 (m, 2 H), 1.35-1.45 (m, 3 H), 1.12-1.15 (m, 1 H). |

TABLE 1-continued

| Ex. # | Structure | Compound Name | LRMS m/z (M + H)+; and 1H NMR |
|---|---|---|---|
| 115* | 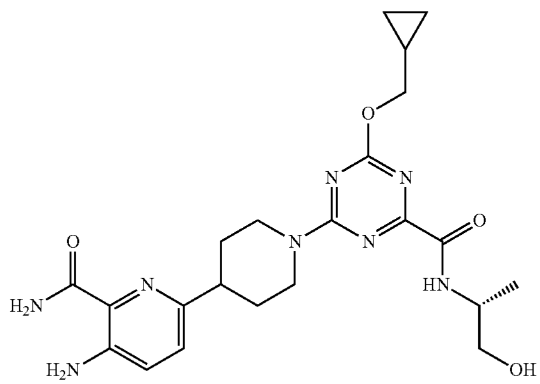 [SMILES: C[C@H](CO)NC(=O)c1nc(OCC2CC2)nc(N2CCC(c3ccc(N)c(C(N)=O)n3)CC2)n1] | 4-[4-(5-amino-6-carbamoylpyridin-2-yl)piperidin-1-yl]-6-(cyclopropylmethoxy)-N-[(2R)-1-hydroxypropan-2-yl]-1,3,5-triazine-2-carboxamide | 471.2; (400 MHz, DMSO-$d_6$) δ ppm 8.29-8.31 (m, 1 H), 7.87 (s, 1 H), 7.26 (s, 1 H), 7.19 (d, J = 8.6 Hz, 1 H), 7.09 (d, J = 8.6 Hz, 1 H), 6.68 (s, 2 H), 4.85-4.90 (m, 2 H), 4.74-4.77 (m, 1 H), 4.16-4.18 (m, 2 H), 3.88-3.95 (m, 1 H), 3.40-3.44 (m, 1 H), 3.02-3.05 (m, 2 H), 2.87-2.90 (m, 1 H), 1.90-1.93 (m, 2 H), 1.66-1.69 (m, 2 H), 1.23-1.25 (m, 1 H), 1.11-1.13 (m, 3 H), 0.55-0.58 (m, 2 H), 0.34-0.36 (m, 2 H). |
| 116* | 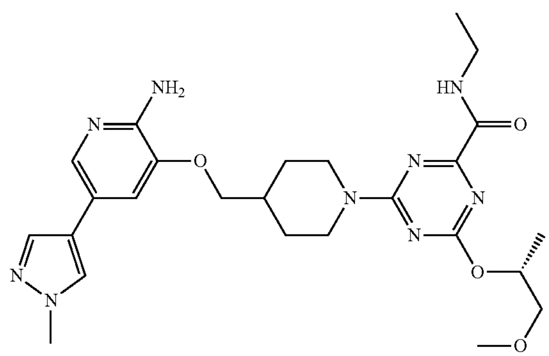 [SMILES: CCNC(=O)c1nc(O[C@H](C)COC)nc(N2CCC(COc3cc(-c4cnn(C)c4)cnc3N)CC2)n1] | 4-[4-({[2-amino-5-(1-methyl-1H-imidazol-4-yl)pyridin-3-yl]oxy}methyl)piperidin-1-yl]-N-ethyl-6-{[(2R)-1-methoxypropan-2-yl]oxy}-1,3,5-triazine-2-carboxamide | 526.2; (400 MHz, CDCl$_3$) δ ppm 7.97 (s, 1 H), 7.80-7.82 (m, 1 H), 7.45 (s, 2 H), 7.10 (s, 1 H), 5.43-5.48 (m, 1 H), 5.08-5.10 (m, 1 H), 4.83-4.85 (m, 1 H), 4.62 (s, 2 H), 3.95 (t, J = 4.8 Hz, 2 H), 3.71 (s, 3 H), 3.61-3.64 (m, 1 H), 3.44-3.47 (m, 3 H), 3.40 (s, 3 H), 2.95-3.05 (m, 2 H), 2.19-2.21 (m, 1 H), 1.95-1.98 (m, 2 H), 1.28-1.38 (m, 5 H), 1.22 (t, J = 7.2 Hz, 3 H). |
| 117 | 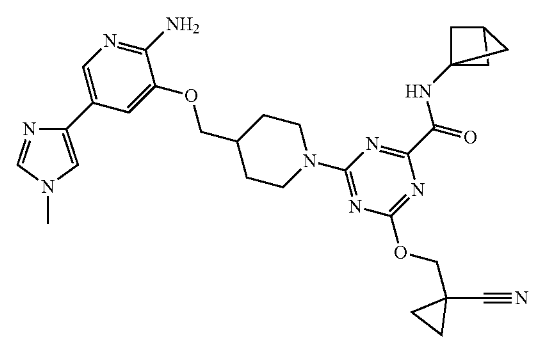 [SMILES: Cn1cnc(-c2cnc(N)c(OCC3CCN(c4nc(OCC5(C#N)CC5)nc(C(=O)NC56CC(C5)C6)n4)CC3)c2)c1] | 4-[4-({[2-amino-5-(1-methyl-1H-imidazol-4-yl)pyridin-3-yl]oxy}methyl)piperidin-1-yl]-N-(bicyclo[1.1.1]pent-1-yl)-6-[(1-cyanocyclopropyl)methoxy]-1,3,5-triazine-2-carboxamide | 571.2; (400 MHz, CD$_3$OD) δ ppm 7.88 (s, 1 H), 7.74 (s, 1 H), 7.50 (s, 1 H), 7.44 (s, 1 H), 5.10-5.11 (br. s., 1 H), 4.44-4.50 (m, 2 H), 4.03-4.05 (m, 2 H), 3.78 (s, 3 H), 3.10-3.12 (m, 2 H), 2.50 (s, 1 H), 2.00-2.30 (m, 10 H), 1.35-1.45 (m, 4 H), 1.24 (s, 2 H). |
| 118*** | 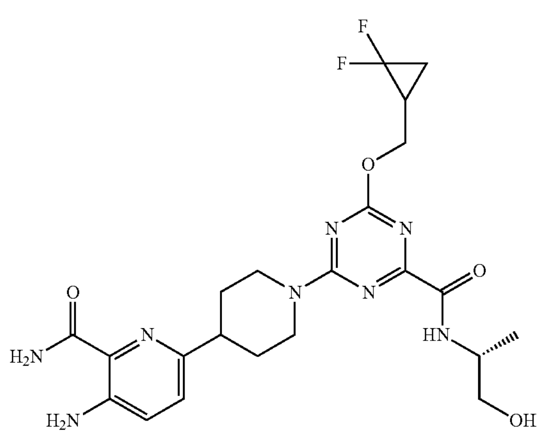 [SMILES: C[C@H](CO)NC(=O)c1nc(OCC2CC2(F)F)nc(N2CCC(c3ccc(N)c(C(N)=O)n3)CC2)n1] | 4-[4-(5-amino-6-carbamoylpyridin-2-yl)piperidin-1-yl]-6-[(2,2-difluorocyclopropyl)methoxy]-N-[(2R)-1-hydroxypropan-2-yl]-1,3,5-triazine-2-carboxamide | 507.2; (400 MHz, DMSO-$d_6$) δ ppm 8.31-8.33 (m, 1 H), 7.87 (s, 1 H), 7.26 (s, 1 H), 7.19 (d, J = 8.8 Hz, 1 H), 7.09 (d, J = 8.8 Hz, 1 H), 6.69 (s, 2 H), 4.85-4.86 (m, 2 H), 4.74-4.79 (m, 1 H), 4.22-4.30 (m, 1 H), 3.90-3.95 (m, 1 H), 3.85-3.90 (m, 1H), 3.22-3.44 (m, 5 H), 3.05-3.10 (m, 2 H), 1.91-1.93 (m, 2 H), 1.65-1.75 (m, 2 H), 1.23-1.27 (m, 2 H), 1.11-1.13 (m, 3 H). |

TABLE 1-continued

| Ex. # | Structure | Compound Name | LRMS m/z (M + H)+; and 1H NMR |
|---|---|---|---|
| 119 | 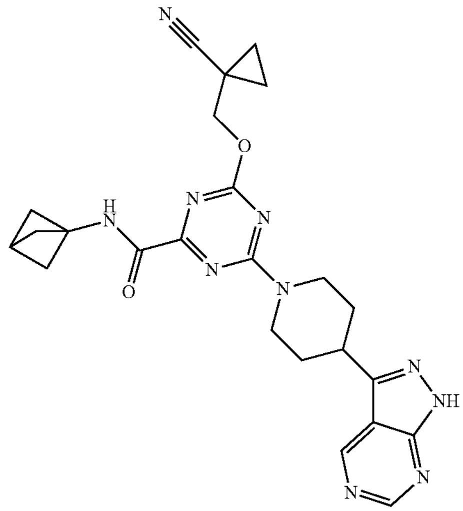 [SMILES: N#CC1(COc2nc(C(=O)NC34CC(C3)C4)nc(N3CCC(c4n[nH]c5ncncc45)CC3)n2)CC1] | N-(bicyclo[1.1.1]pent-1-yl)-4-[(1-cyanocyclopropyl)methoxy]-6-[4-(1H-pyrazolo[3,4-d]pyrimidin-3-yl)piperidin-1-yl]-1,3,5-triazine-2-carboxamide | 487.2; (400 MHz, CD$_3$OD) δ ppm 9.38 (s, 1 H), 8.93 (s, 1 H), 5.13-5.16 (m, 1 H), 4.45-4.63 (m, 3 H), 3.57-3.60 (m, 1 H), 3.20-3.23 (m, 1 H), 2.50 (s, 1 H), 2.21-2.28 (m, 8 H), 2.00-2.03 (m, 2 H), 1.38-1.41 (m, 2 H), 1.25-1.28 (m, 3 H). |
| 120* | 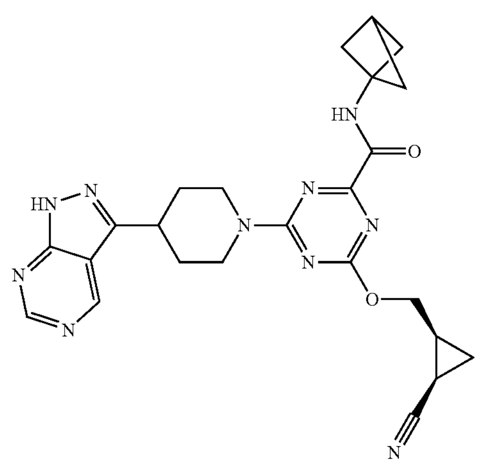 [SMILES: N#C[C@@H]1C[C@@H]1COc1nc(C(=O)NC23CC(C2)C3)nc(N2CCC(c3n[nH]c4ncncc34)CC2)n1] | N-(bicyclo[1.1.1]pent-1-yl)-4-{[(1S,2R)-2-cyanocyclopropyl]methoxy}-6-[4-(1H-pyrazolo[3,4-d]pyrimidin-3-yl)piperidin-1-yl]-1,3,5-triazine-2-carboxamide | 487.2; (400 MHz, CD$_3$OD) δ ppm 9.41 (s, 1 H), 8.95 (s, 1 H), 5.13-5.16 (m, 1 H), 4.76-4.84 (m, 2 H), 4.29-4.36 (m, 1 H), 3.58-3.61 (m, 1 H), 3.20-3.28 (m, 1 H), 2.49 (s, 1 H), 2.21-2.28 (m, 8 H), 1.87-1.91 (m, 4 H), 1.31-1.37 (m, 2 H), 1.12-1.14 (m, 1 H). |
| 121* | 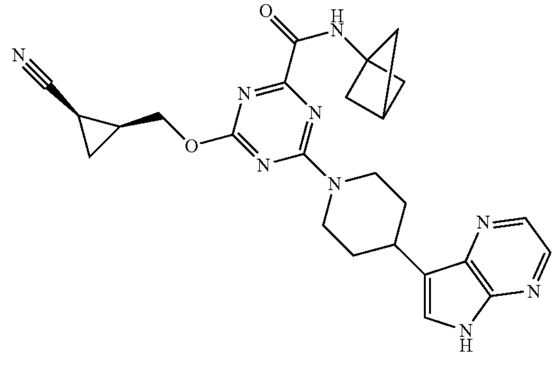 [SMILES: N#C[C@@H]1C[C@@H]1COc1nc(C(=O)NC23CC(C2)C3)nc(N2CCC(c3c[nH]c4nccnc34)CC2)n1] | N-(bicyclo[1.1.1]pent-1-yl)-4-{[(1S,2R)-2-cyanocyclopropyl]methoxy}-6-[4-(5H-pyrrolo[2,3-b]pyrazin-7-yl)piperidin-1-yl]-1,3,5-triazine-2-carboxamide | 486.2; (400 MHz, CD$_3$OD) δ ppm 8.35 (s, 1 H), 8.24 (s, 1 H), 7.61 (s, 1 H), 5.16-5.20 (m, 1 H), 4.56-4.62 (m, 2 H), 4.29-4.36 (m, 1 H), 3.19-3.25 (m, 1 H), 2.49 (s, 1 H), 1.95-2.21 (m, 8 H), 1.87-1.92 (m, 4 H), 1.34-1.37 (m, 2 H), 1.14-1.15 (m, 1 H). |

TABLE 1-continued

| Ex. # | Structure | Compound Name | LRMS m/z (M + H)+; and 1H NMR |
|---|---|---|---|
| 122 | 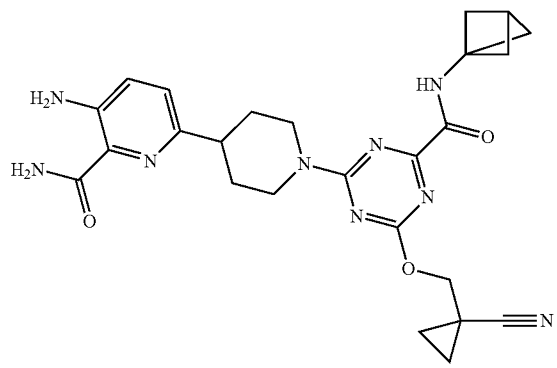 [SMILES: N#CC1(COc2nc(C(=O)NC34CC(C3)C4)nc(N3CCC(c4ccc(N)c(C(N)=O)n4)CC3)n2)CC1] | 4-[4-(5-amino-6-carbamoylpyridin-2-yl)piperidin-1-yl]-N-(bicyclo[1.1.1]pent-1-yl)-6-[(1-cyanocyclopropyl)methoxy]-1,3,5-triazine-2-carboxamide | 504.2; (400 MHz, $CD_3OD$) δ ppm 7.17 (d, J = 8.4 Hz, 1 H), 7.09 (d, J = 8.4 Hz, 1 H), 5.12 (d, J = 9.6 Hz, 1 H), 4.82 (d, J = 4.0 Hz, 1 H), 4.39-4.46 (m, 2 H), 3.11 (t, J = 12.8 Hz, 2 H), 2.91-2.94 (m, 1 H), 2.46 (s, 1 H), 2.17 (s, 6 H), 1.97-2.00 (m, 2 H), 1.75-1.81 (m, 2 H), 1.34-1.37 (m, 2 H), 1.20-1.23 (m, 2 H). |
| 123* | 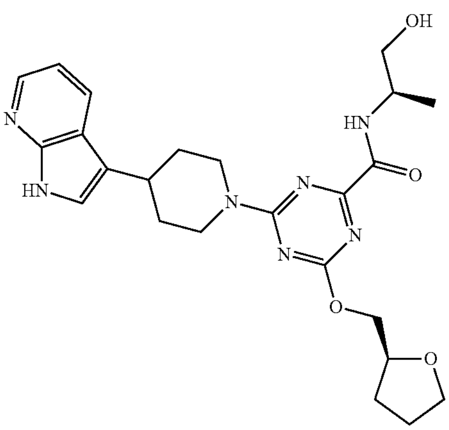 [SMILES: C[C@H](CO)NC(=O)c1nc(OC[C@@H]2CCCO2)nc(N2CCC(c3c[nH]c4ncccc34)CC2)n1] | N-[(2R)-1-hydroxypropan-2-yl]-4-[4-(1H-pyrrolo[2,3-b]pyridin-3-yl)piperidin-1-yl]-6-[(2S)-tetrahydrofuran-2-ylmethoxy]-1,3,5-triazine-2-carboxamide | 482.2; (400 MHz, $CDCl_3$) δ ppm 9.55 (s, 1 H), 8.29 (d, J = 4.4 Hz, 1 H), 7.93-8.00 (m, 2 H), 7.06-7.09 (m, 2 H), 5.09 (d, J = 12.4 Hz, 1 H), 4.92 (d, J = 12.4 Hz, 1H), 4.28-4.39 (m, 4 H), 3.92-3.94 (m, 1 H), 3.79-3.83 (m, 2 H), 3.69-3.76 (m, 1 H), 3.08-3.14 (m, 3 H), 2.08-2.13 (m, 4 H), 1.95-2.07 (m, 2 H), 1.70-1.76 (m, 3 H), 1.29 (d, J = 6.8 Hz, 3 H). |
| 134* | 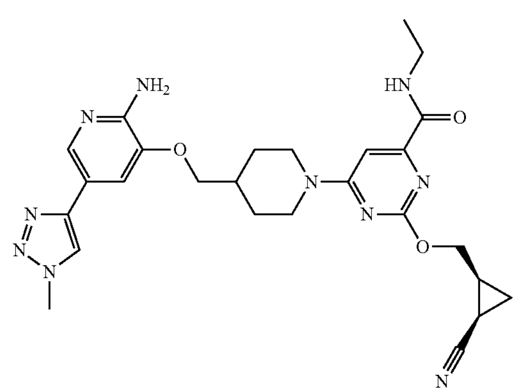 [SMILES: CCNC(=O)c1cc(N2CCC(COc3cc(-c4cn(C)nn4)cnc3N)CC2)nc(OC[C@H]2C[C@H]2C#N)n1] | 6-[4-({[2-amino-5-(1-methyl-1H-1,2,3-triazol-4-yl)pyridin-3-yl]oxy}methyl)piperidin-1-yl]-2-{[(1S,2R)-2-cyanocyclopropyl]methoxy}-N-ethylpyrimidine-4-carboxamide | 533.2; (400 MHz, $CDCl_3$) δ ppm 7.96 (s, 1 H), 7.83-7.93 (m, 1 H), 7.71 (s, 1 H), 7.60 (s, 1 H), 7.14 (s, 1 H), 4.88-5.02 (m, 2 H), 4.49 (t, J = 6.4 Hz, 2 H), 4.15 (s, 3 H), 3.99 (d, J = 6.0 Hz, 2 H), 3.44-3.49 (m, 2 H), 2.94-3.09 (m, 2 H), 2.14-2.28 (m, 1 H), 1.98-2.01 (m, 2 H), 1.85-1.87 (m, 1 H), 1.68-1.70 (m, 2 H), 1.34-1.36 (m, 3 H), 1.24 (t, J = 7.2 Hz, 4 H), 1.14-1.16 (m, 1H). |

TABLE 1-continued

| Ex. # | Structure | Compound Name | LRMS m/z (M + H)+; and 1H NMR |
|---|---|---|---|
| 135* | 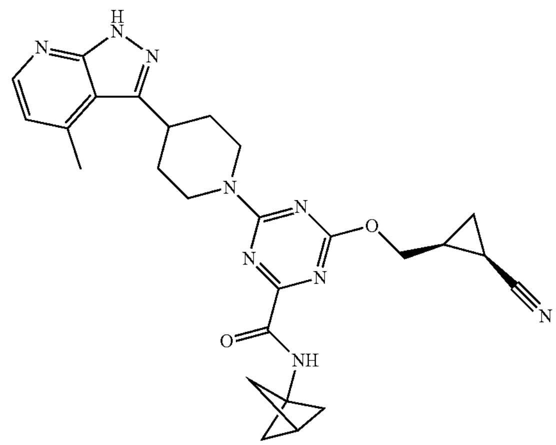 [SMILES: Cc1ccnc2[nH]nc(C3CCN(c4nc(OC[C@H]5C[C@H]5C#N)nc(C(=O)NC56CC(C5)C6)n4)CC3)c12] | N-(bicyclo[1.1.1]pent-1-yl)-4-{[(1S,2R)-2-cyanocyclopropyl]methoxy}-6-[4-(4-methyl-1H-pyrazolo[3,4-b]pyridin-3-yl)piperidin-1-yl]-1,3,5-triazine-2-carboxamide | 500.1; (400 MHz, CD$_3$OD) δ ppm 8.31 (d, J = 4.8 Hz, 1 H), 6.98 (d, J = 4.8 Hz, 1 H), 5.13-5.16 (m, 1 H), 4.88-4.93 (m, 1 H), 4.77-4.88 (m, 1 H), 4.28-4.31 (m, 1 H), 3.60-3.63 (m, 1 H), 3.24-3.31 (m, 2 H), 2.80 (s, 3 H), 2.48 (s, 1 H), 2.16-2.20 (m, 8 H), 1.85-1.94 (m, 4 H), 1.34-1.36 (m, 1 H), 1.12-1.13 (m, 1 H). |
| 136** | 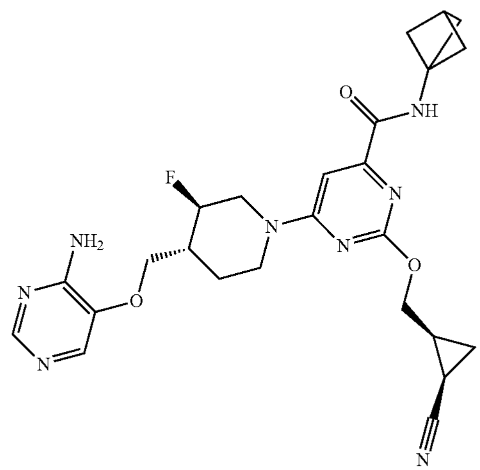 [SMILES: N#C[C@@H]1C[C@@H]1COc1nc(C(=O)NC23CC(C2)C3)cc(N2CC[C@H](COc3cncnc3N)[C@@H](F)C2)n1] | 6-[(3R,4R)-4-{[(4-aminopyrimidin-5-yl)oxy]methyl}-3-fluoropiperidin-1-yl]-N-(bicyclo[1.1.1]pent-1-yl)-2-{[(1S,2R)-2-cyanocyclopropyl]methoxy}pyrimidine-4-carboxamide | 531.0 [M + Na]+; (400 MHz, CDCl$_3$) δ ppm 8.26 (s, 1 H), 8.16 (s, 1 H), 7.90 (s, 1 H), 7.13 (s, 1 H), 5.13 (s, 2 H), 4.85-4.90 (m, 0.5 H), 4.52-4.57 (m, 1.5 H), 4.38-4.43 (m, 2 H), 4.18 (s, 2 H), 3.02-3.07 (m, 2 H), 2.49 (s, 2 H), 2.28-2.32 (m, 1 H), 2.18 (s, 6 H), 2.05-2.08 (m, 1 H), 1.84-1.86 (m, 1 H), 1.68-1.70 (m, 2 H), 1.57-1.59 (m, 1 H), 1.33-1.35 (m, 1 H), 1.13-1.15 (m, 1H). |
| 137** | 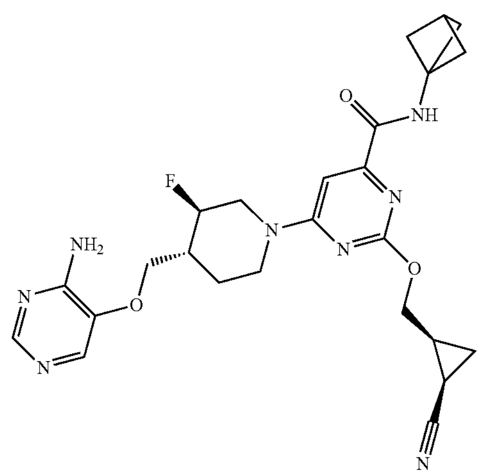 [SMILES: N#C[C@@H]1C[C@@H]1COc1nc(C(=O)NC23CC(C2)C3)cc(N2CC[C@H](COc3cncnc3N)[C@@H](F)C2)n1] | 6-[(3R,4R)-4-{[(4-aminopyrimidin-5-yl)oxy]methyl}-3-fluoropiperidin-1-yl]-N-(bicyclo[1.1.1]pent-1-yl)-2-{[(1S,2R)-2-cyanocyclopropyl]methoxy}pyrimidine-4-carboxamide | 509.2; (400 MHz, CDCl$_3$) δ ppm 8.26 (s, 1 H), 8.16 (s, 1 H), 7.90 (s, 1 H), 7.13 (s, 1 H), 5.13 (s, 2 H), 4.85-4.90 (m, 0.5 H), 4.52-4.57 (m, 1.5 H), 4.38-4.43 (m, 2 H), 4.18 (s, 2 H), 3.02-3.07 (m, 2 H), 2.49 (s, 2 H), 2.28-2.32 (m, 1 H), 2.18 (s, 6 H), 2.05-2.08 (m, 1 H), 1.84-1.86 (m, 1 H), 1.68-1.70 (m, 2 H), 1.57-1.59 (m, 1 H), 1.33-1.35 (m, 1 H), 1.13-1.15 (m, 1H). |

TABLE 1-continued

| Ex. # | Structure | Compound Name | LRMS m/z (M + H)+; and 1H NMR |
|---|---|---|---|
| 138* | 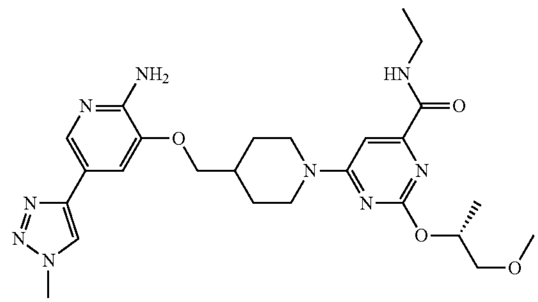 [SMILES: CCNC(=O)c1cc(N2CCC(COc3cc(-c4cn(C)nn4)cnc3N)CC2)nc(O[C@H](C)COC)n1] | 6-[4-({[2-amino-5-(1-methyl-1H-1,2,3-triazol-4-yl)pyridin-3-yl]oxy}methyl)piperidin-1-yl]-N-ethyl-2-{[(2R)-1-methoxypropan-2-yl]oxy}pyrimidine-4-carboxamide | 548.1; (400 MHz, CDCl$_3$) δ ppm 7.96 (s, 1 H), 7.86-7.94 (m, 1 H), 7.71 (s, 1 H), 7.59 (s, 1 H), 7.09 (s, 1 H), 5.33-5.38 (m, 1 H), 4.78 (s, 2 H), 4.44-4.68 (m, 2 H), 4.15 (s, 3 H), 3.98 (d, J = 6.4 Hz, 2 H), 3.66-3.70 (m, 1 H), 3.42-3.52 (m, 6 H), 2.92-3.09 (m, 2 H), 2.18-2.31 (m, 1 H), 1.99 (d, J = 13.2 Hz, 2 H), 1.34-1.46 (m, 5 H), 1.23 (t, J = 7.6 Hz, 3 H). |
| 139* | 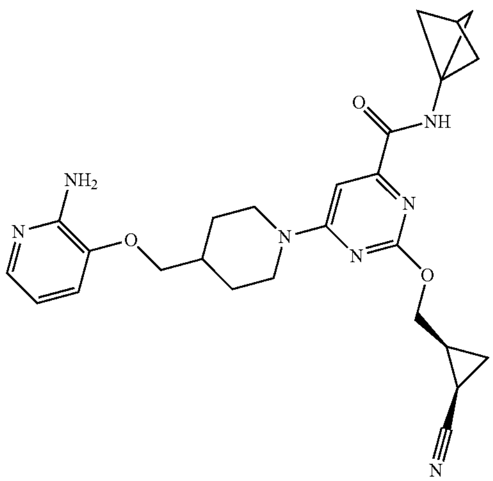 [SMILES: N#C[C@@H]1C[C@@H]1COc1nc(C(=O)NC23CC(C2)C3)cc(N2CCC(COc3cccnc3N)CC2)n1] | 6-(4-{[(2-aminopyridin-3-yl)oxy]methyl}piperidin-1-yl)-N-(bicyclo[1.1.1]pent-1-yl)-2-{[(1S,2R)-2-cyanocyclopropyl]methoxy}pyrimidine-4-carboxamide | 490.1; (400 MHz, DMSO-d$_6$) δ ppm 8.93 (s, 1 H), 7.49 (d, J = 4.4 Hz, 1 H), 6.98-7.00 (m, 2 H), 6.48 (d, J = 7.6 Hz, 1 H), 5.65 (s, 2 H), 4.30-4.70 (m, 3 H), 4.05 (d, J = 12.0 Hz, 1 H), 3.84 (d, J = 6.4 Hz, 2 H), 3.01 (br. s., 2 H), 2.46 (s, 1 H), 2.10 (s, 6 H), 1.92-2.02 (m, 3 H), 1.76-1.87 (m, 1 H), 1.24-1.31 (m, 4 H), 1.12-1.14 (m, 1 H). |
| 140* | 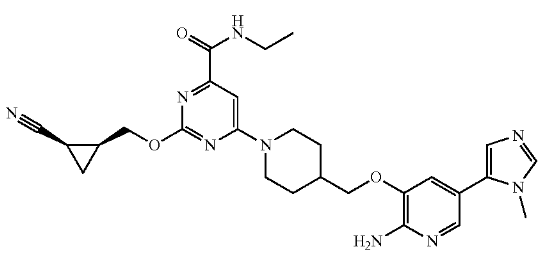 [SMILES: CCNC(=O)c1cc(N2CCC(COc3cc(-c4cncn4C)cnc3N)CC2)nc(OC[C@H]2C[C@H]2C#N)n1] | 6-[4-({[2-amino-5-(1-methyl-1H-imidazol-5-yl)pyridin-3-yl]oxy}methyl)piperidin-1-yl]-2-{[(1S,2R)-2-cyanocyclopropyl]methoxy}-N-ethylpyrimidine-4-carboxamide | 532.2; (700 MHz, DMSO-d6) δ ppm 8.56 (t, J = 6.06 Hz, 1 H), 7.57 (s, 1 H), 7.51 (d, J = 1.88 Hz, 1 H), 7.00 (d, J = 1.54 Hz, 1 H), 6.93 (s, 1 H), 6.85 (s, 1 H), 5.81 (s, 2 H), 4.59 (dd, J = 11.96, 5.30 Hz, 1 H), 3.99 (dd, J = 11.87, 9.48 Hz, 1 H), 3.83 (d, J = 6.32 Hz, 3 H), 3.17-3.23 (m, 1 H), 2.96 (br. s., 1 H), 2.04-2.12 (m, 1 H), 1.81-1.93 (m, 4 H), 1.73-1.78 (m, 1 H), 1.19-1.27 (m, 4 H), 1.00-1.06 (m, 6 H). |
| 141* | 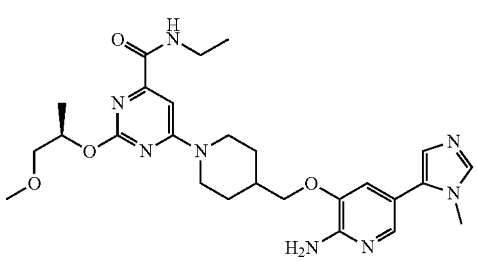 [SMILES: CCNC(=O)c1cc(N2CCC(COc3cc(-c4cncn4C)cnc3N)CC2)nc(O[C@H](C)COC)n1] | 6-[4-({[2-amino-5-(1-methyl-1H-imidazol-5-yl)pyridin-3-yl]oxy}methyl)piperidin-1-yl]-N-ethyl-2-{[(2R)-1-methoxypropan-2-yl]oxy}pyrimidine-4-carboxamide | 525.2; (600 MHz, DMSO-d6) δ ppm 8.58 (t, J = 6.15 Hz, 1 H), 7.63 (s, 1 H), 7.58 (d, J = 1.90 Hz, 1 H), 7.07 (d, J = 1.76 Hz, 1 H), 6.95 (s, 1 H), 6.91 (s, 1 H), 5.87 (s, 2 H), 5.33 (quind, J = 6.31, 4.17 Hz, 1 H), 3.90 (d, J = 6.29 Hz, 3 H), 3.60 (s, 3 H), 3.42-3.52 (m, 1 H), 3.24-3.30 (m, 3 H), 3.01 (br. s., 1 H), 2.07-2.18 (m, 1 H), 1.93 (d, J = 12.29 Hz, 3 H), 1.87 (s, 2 H), 1.26-1.32 (m, 2 H), 1.21-1.26 (m, 4 H), 1.04-1.11 (m, 4 H). |

TABLE 1-continued

| Ex. # | Structure | Compound Name | LRMS m/z (M + H)+; and 1H NMR |
|---|---|---|---|
| 142* | 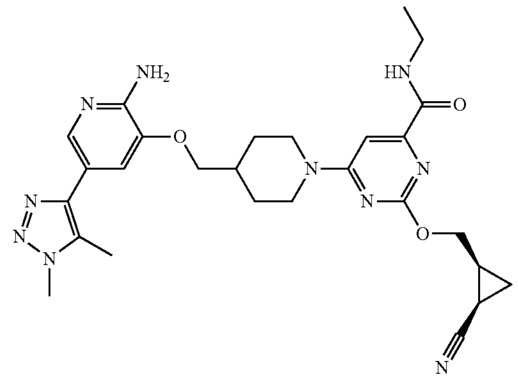 [SMILES: CCNC(=O)c1cc(N2CCC(COc3cc(-c4nnn(C)c4C)cnc3N)CC2)nc(OC[C@H]2C[C@H]2C#N)n1] | 6-[4-({[2-amino-5-(1,5-dimethyl-1H-1,2,3-triazol-4-yl)pyridin-3-yl]oxy}methyl)piperidin-1-yl]-2-{[(1S,2R)-2-cyanocyclopropyl]methoxy}-N-ethylpyrimidine-4-carboxamide | 569.0 [M + Na]+; (400 MHz, CDCl$_3$) δ ppm 7.82-7.88 (m, 1 H), 7.80 (s, 1 H), 7.47 (s, 1 H), 7.13 (s, 1 H), 4.93 (br. s., 2 H), 4.43-4.52 (m, 2 H), 4.00 (s, 3 H), 3.98 (d, J = 6.4 Hz, 2 H), 3.43-3.50 (m, 2 H), 2.93-3.25 (m, 2 H), 2.45 (s, 3 H), 2.19-2.20 (m, 1 H), 1.97 (d, J = 11.2 Hz, 2 H), 1.91-1.95 (m, 1 H), 1.65-1.69 (m, 1 H), 1.30-1.34 (m, 4 H), 1.24 (t, J = 7.2 Hz, 3 H) 1.14-1.15 (m, 2 H). |
| 143** | 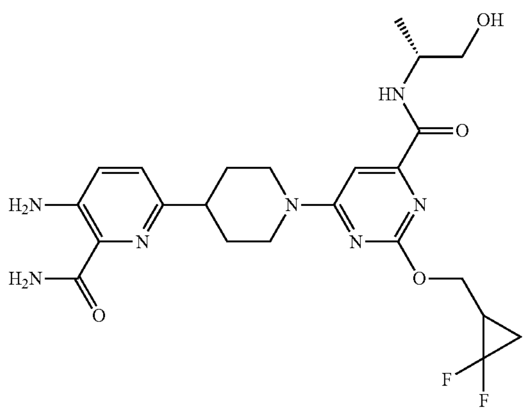 [SMILES: C[C@H](CO)NC(=O)c1cc(N2CCC(c3ccc(N)c(C(N)=O)n3)CC2)nc(OCC2CC2(F)F)n1] | 6-[4-(5-amino-6-carbamoylpyridin-2-yl)piperidin-1-yl]-2-[(2,2-difluorocyclopropyl)methoxy]-N-[(2R)-1-hydroxypropan-2-yl]pyrimidine-4-carboxamide | 506.2; (400 MHz, CD$_3$OD) δ ppm 7.20-7.22 (m, 1 H), 7.12-7.14 (m, 2 H), 4.54-4.56 (m, 2 H), 4.31-4.36 (m, 1 H), 4.14-4.15 (m, 1 H), 3.62 (d, J = 4.8 Hz, 2 H), 3.14-3.17 (m, 2 H), 2.97-3.00 (m, 1 H), 2.20-2.21 (m, 1 H), 2.02-2.05 (m, 2 H), 1.81-1.84 (m, 2 H), 1.62-1.64 (m, 1 H), 1.36-1.39 (m, 2 H), 1.26 (d, J = 6.4 Hz, 3 H). |
| 160* | 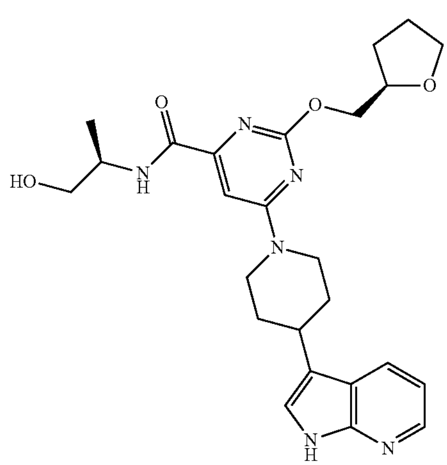 [SMILES: C[C@H](CO)NC(=O)c1cc(N2CCC(c3c[nH]c4ncccc34)CC2)nc(OC[C@H]2CCCO2)n1] | N-[(2R)-1-hydroxypropan-2-yl]-6-[4-(1H-pyrrolo[2,3-b]pyridin-3-yl)piperidin-1-yl]-2-[{2R}-tetrahydrofuran-2-ylmethoxy]pyrimidine-4-carboxamide | 481.3; (700 MHz, DMSO-d6) δ ppm 11.33 (br. s., 1 H), 11.29-11.36 (m, 1 H), 8.11-8.20 (m, 2 H), 8.01 (d, J = 7.86 Hz, 1 H), 7.23 (d, J = 1.02 Hz, 1 H), 6.96-7.04 (m, 2 H), 4.24 (d, J = 5.64 Hz, 3 H), 4.10-4.18 (m, 1 H), 3.90-3.99 (m, 1 H), 3.77 (q, J = 7.00 Hz, 1 H), 3.61-3.69 (m, 1 H), 3.33-3.52 (m, 1 H), 3.09-3.17 (m, 1 H), 1.99-2.10 (m, 3 H), 1.94-2.00 (m, 1 H), 1.85-1.90 (m, 1 H), 1.79-1.85 (m, 1 H), 1.56-1.69 (m, 4 H), 1.23 (s, 1 H), 1.13 (d, J = 6.83 Hz, 4 H). |
| 161* | 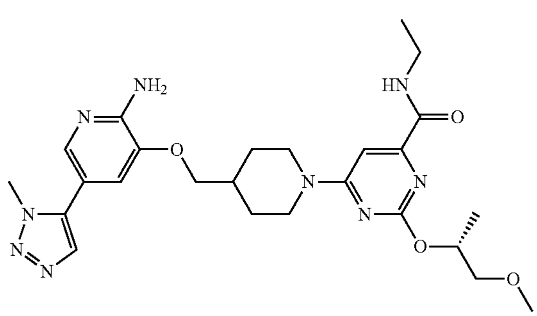 | 6-[4-({[2-amino-5-(1-methyl-1H-1,2,3-triazol-5-yl)pyridin-3-yl]oxy}methyl)piperidin-1-yl]-N-ethyl-2-{[(2R)-1-methoxypropan-2-yl]oxy}pyrimidine-4-carboxamide | 526.1; (400 MHz, CDCl$_3$) δ ppm 7.88 (t, J = 5.6 Hz, 1 H), 7.73 (d, J = 2.0 Hz, 1 H), 7.68 (s, 1 H), 7.10 (s, 1 H), 6.86 (d, J = 1.6 Hz, 1 H), 5.30-5.35 (m, 1 H), 4.96 (s, 2 H), 4.60 (br. s., 2 H), 4.05 (s, 3 H), 3.89-3.91 (m, 2 H), 3.52-3.67 (m, 1 H), 3.47-3.51 (m, 6 H), 3.30-3.42 (m, 2 H), 2.22 (br. s. 1 H), 1.96-1.99 (m, 2 H), 1.38-1.42 (m, 5 H), 1.21-1.23 (m, 3 H). |

TABLE 1-continued

| Ex. # | Structure | Compound Name | LRMS m/z (M + H)+; and 1H NMR |
|---|---|---|---|
| 162* | 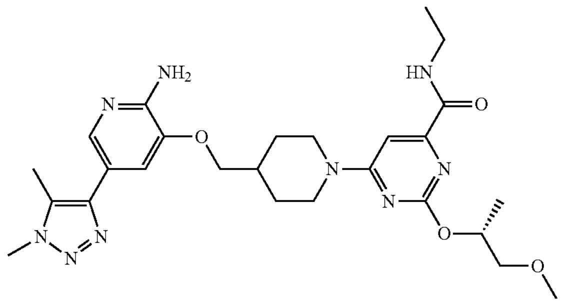 | 6-[4-({[2-amino-5-(1,5-dimethyl-1H-1,2,3-triazol-4-yl)pyridin-3-yl]oxy}methyl)piperidin-1-yl]-N-ethyl-2-{[(2R)-1-methoxypropan-2-yl]oxy}pyrimidine-4-carboxamide | 562.1 [M + Na]+; (400 MHz, CDCl$_3$) δ ppm 7.82-7.88 (m, 1 H), 7.82 (s, 1H), 7.47 (s, 1 H), 7.08 (s, 1 H), 5.30-5.34 (m, 1 H), 4.90 (br. s., 2 H), 4.46-4.76 (m, 1 H), 4.01 (s, 3 H), 3.96 (d, J = 6.0 Hz, 2 H), 3.65-3.69 (m, 1 H), 3.41-3.51 (m, 2 H), 3.41 (s 3 H), 2.95-2.99 (m, 2 H), 2.53 (s, 3 H), 2.15-2.25 (m, 1 H), 1.95-1.97 (m, 2 H), 1.30-1.40 (m, 5 H), 1.19-1.20 (m, 3 H). |
| 163** | 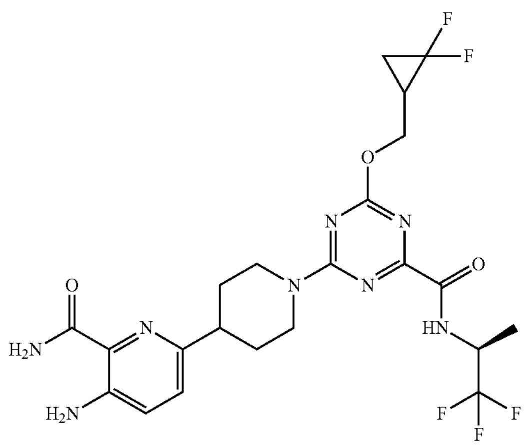 [SMILES: C[C@H](NC(=O)c1nc(OCC2CC2(F)F)nc(N2CCC(c3ccc(N)c(C(N)=O)n3)CC2)n1)C(F)(F)F] | 4-[4-(5-amino-6-carbamoylpyridin-2-yl)piperidin-1-yl]-6-[(2,2-difluorocyclopropyl)methoxy]-N-[(2S)-1,1,1-trifluoropropan-2-yl]-1,3,5-triazine-2-carboxamide | 545.0; (400 MHz, CDCl$_3$) δ ppm 7.86-7.91 (m, 2 H), 7.09 (d, J = 8.4 Hz, 1 H), 7.01 (d, J = 8.4 Hz, 1 H), 5.86 (br. s., 2 H), 5.32 (s, 1 H), 5.09-5.12 (m, 1 H), 4.85-4.92 (m, 2 H), 4.45-4.53 (m, 2 H), 3.05-3.15 (m, 2 H), 2.90-2.92 (m, 1 H), 2.10-2.20 (m, 1 H), 2.02-2.05 (m, 2 H), 1.76-1.81 (m, 2 H), 1.59-1.63 (m, 1 H), 1.42-1.44 (m, 3 H), 1.34-1.39 (m, 1 H). |
| 164** | 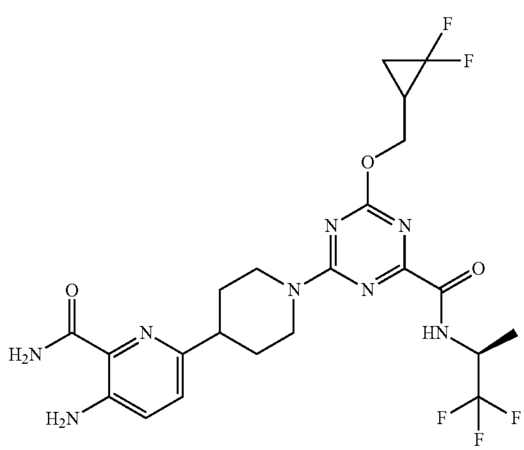 [SMILES: C[C@H](NC(=O)c1nc(OCC2CC2(F)F)nc(N2CCC(c3ccc(N)c(C(N)=O)n3)CC2)n1)C(F)(F)F] | 4-[4-(5-amino-6-carbamoylpyridin-2-yl)piperidin-1-yl]-6-[(2,2-difluorocyclopropyl)methoxy]-N-[(2S)-1,1,1-trifluoropropan-2-yl]-1,3,5-triazine-2-carboxamide | 545.0; (400 MHz, CDCl$_3$) δ ppm 7.89-7.91 (m, 2 H), 7.09-7.11 (d, J = 8.4 Hz, 1 H), 7.01 (d, J = 8.4 Hz, 1 H), 5.66 (br. s., 1 H), 5.09-5.12 (m, 1 H), 4.85-4.92 (m, 2 H), 4.43-4.53 (m, 2 H), 3.08-3.12 (m, 2 H), 2.85-2.90 (m, 1 H), 2.10-2.20 (m, 1 H), 2.02-2.05 (m, 2 H), 1.74-1.80 (m, 2 H), 1.61-1.63 (m, 1 H), 1.42-1.44 (m, 3 H), 1.33-1.35 (m, 1H). |

TABLE 1-continued

| Ex. # | Structure | Compound Name | LRMS m/z (M + H)⁺; and ¹H NMR |
|---|---|---|---|
| 165* | 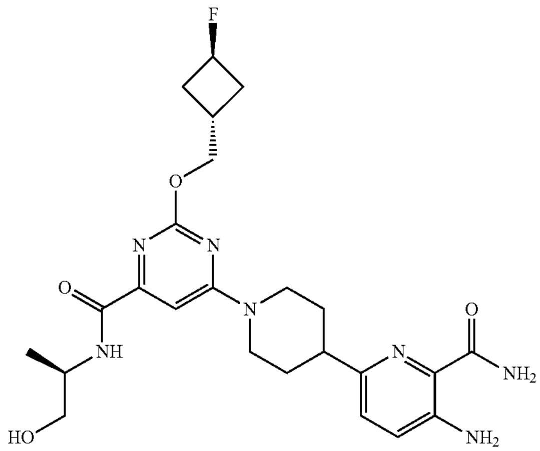 [SMILES: C[C@H](CO)NC(=O)c1cc(N2CCC(c3ccc(N)c(C(N)=O)n3)CC2)nc(OC[C@H]2C[C@H](F)C2)n1] | 6-[4-(5-amino-6-carbamoylpyridin-2-yl)piperidin-1-yl]-2-[{trans-3-fluorocyclobutyl)methoxy]-N-[(2R)-1-hydroxypropan-2-yl]pyrimidine-4-carboxamide | 524.2 [M + Na]⁺; (400 MHz, DMSO-d₆) δ ppm 8.16 (d, J = 8.4 Hz, 1 H), 7.85 (s, 1 H), 7.28 (s, 1 H), 7.19 (d, J = 8.8 Hz, 1 H), 7.09 (d, J = 8.8 Hz, 1 H), 7.00 (s, 1 H), 6.69 (br. s., 1 H), 5.16-5.33 (m, 1 H), 4.89 (br. s., 1 H), 4.48 (br. s., 1 H), 4.28 (d, J = 7.2 Hz, 2 H), 3.93-4.02 (m, 1 H), 3.41-3.46 (m, 2 H), 2.98-3.12 (m, 2 H), 2.82-2.95 (m, 1 H), 2.66-2.70 (m, 2 H), 2.32-2.36 (m, 2 H), 2.24-2.32 (m, 3 H), 1.92 (d, J = 12.0 Hz, 2 H), 1.62-1.74 (m, 2 H), 1.14 (d, J = 6.8 Hz, 3 H). |
| 166* | 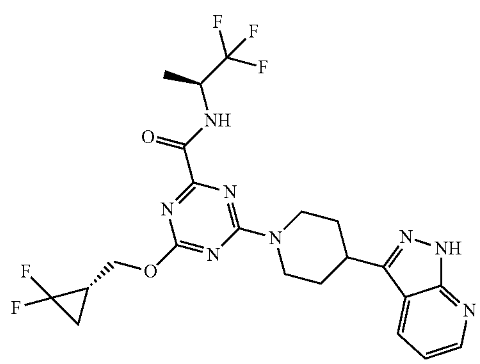 [SMILES: C[C@H](NC(=O)c1nc(OC[C@@H]2CC2(F)F)nc(N2CCC(c3n[nH]c4ncccc34)CC2)n1)C(F)(F)F] | 4-{[(1S)-2,2-difluoro-cyclopropyl]methoxy}-6-[4-(1H-pyrazolo[3,4-b]pyridin-3-yl)piperidin-1-yl]-N-[(2S)-1,1,1-trifluoropropan-2-yl]-1,3,5-triazine-2-carboxamide | 527.0; (400 MHz, CDCl₃) δ ppm 11.59 (br. s., 1 H), 8.59 (d, J = 4.0 Hz, 1 H), 8.10-8.12 (m, 1 H), 7.90 (d, J = 9.6 Hz, 1 H), 7.13-7.16 (m, 1 H), 5.03 (d, J = 3.8 Hz, 1 H), 4.85-4.89 (m, 2 H), 4.51-4.53 (m, 1 H), 4.44-4.46 (m, 1 H), 3.43 (d, J = 3.6 Hz, 1 H), 3.22-3.32 (m, 2 H), 2.03-2.21 (m, 5 H), 1.60-1.63 (m, 1 H), 1.42 (d, J = 6.8 Hz, 3 H), 1.33-1.36 (m, 1 H). |
| 167* | 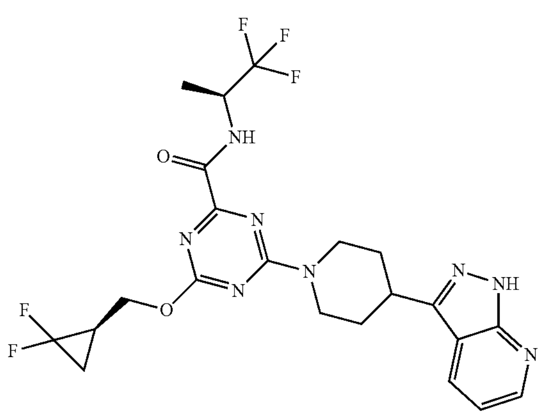 [SMILES: C[C@H](NC(=O)c1nc(OC[C@H]2CC2(F)F)nc(N2CCC(c3n[nH]c4ncccc34)CC2)n1)C(F)(F)F] | 4-{[(1R)-2,2-difluoro-cyclopropyl]methoxy}-6-[4-(1H-pyrazolo[3,4-b]pyridin-3-yl)piperidin-1-yl]-N-[(2S)-1,1,1-trifluoropropan-2-yl]-1,3,5-triazine-2-carboxamide | 527.2; (400 MHz, CDCl₃) δ ppm 11.87 (br. s., 1 H), 8.59 (d, J = 3.2 Hz, 1 H), 8.11 (d, J = 8.0 Hz, 1 H), 7.91 (d, J = 10.0 Hz, 1 H), 7.13-7.16 (m, 1 H), 5.03 (t, J = 3.8 Hz, 1 H), 4.83-4.89 (m, 2 H), 4.51-4.53 (m, 1 H), 4.44-4.46 (m, 1 H), 3.40-3.43 (m, 1 H), 3.25-3.28 (m, 2 H), 2.02-2.21 (m, 5 H), 1.59-1.72 (m, 1 H), 1.43 (d, J = 6.8 Hz, 3 H), 1.32-1.34 (m, 1H). |

TABLE 1-continued

| Ex. # | Structure | Compound Name | LRMS m/z (M + H)+; and 1H NMR |
|---|---|---|---|
| 168** | 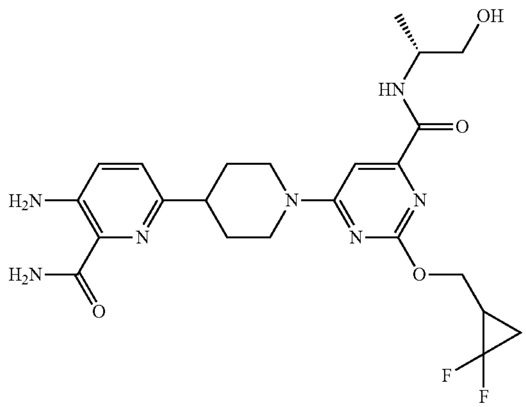 [SMILES: C[C@H](CO)NC(=O)c1cc(N2CCC(c3ccc(N)c(C(N)=O)n3)CC2)nc(OCC2CC2(F)F)n1] | 6-[4-(5-amino-6-carbamoylpyridin-2-yl)piperidin-1-yl]-2-[(2,2-difluorocyclopropyl)methoxy]-N-[(2R)-1-hydroxypropan-2-yl]pyrimidine-4-carboxamide | 528.2 [M + Na]+; (400 MHz, CD$_3$OD) δ ppm 7.20-7.22 (m, 1 H), 7.12-7.14 (m, 2 H), 4.54-4.56 (m, 2 H), 4.31-4.36 (m, 1 H), 4.14-4.15 (m, 1H), 3.62 (d, J = 4.8 Hz, 2 H), 3.14-3.17 (m, 2 H), 2.97-3.00 (m, 1 H), 2.20-2.21 (m, 1 H), 2.02-2.05 (m, 2 H), 1.77-1.81 (m, 2 H), 1.62-1.64 (m, 1 H), 1.36-1.39 (m, 2 H), 1.27 (d, J = 6.4 Hz, 3 H). |
| 169*** | 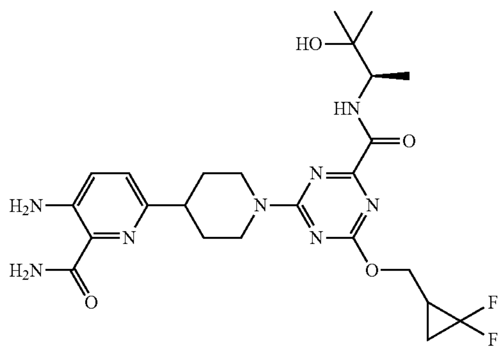 [SMILES: C[C@@H](NC(=O)c1nc(OCC2CC2(F)F)nc(N2CCC(c3ccc(N)c(C(N)=O)n3)CC2)n1)C(C)(C)O] | 4-[4-(5-amino-6-carbamoylpyridin-2-yl)piperidin-1-yl]-6-[(2,2-difluorocyclopropyl)methoxy]-N-[(2R)-3-hydroxy-3-methylbutan-2-yl]-1,3,5-triazine-2-carboxamide | 535.1; (400 MHz, CDCl$_3$) δ ppm 8.01-8.03 (m, 1 H), 7.86 (br. s., 1 H), 7.09 (d, J = 8.4 Hz, 1 H), 6.99 (d, J = 8.4 Hz, 1 H), 5.86 (br. s., 2 H), 5.33-5.35 (m, 1 H), 5.09-5.13 (m, 1 H), 4.89-4.93 (m, 1 H), 4.44-4.54 (m, 2 H), 4.06-4.10 (m, 1 H), 3.07-3.11 (m, 2 H), 2.90-2.92 (m, 1 H), 2.02-2.22 (m, 4 H), 1.74-1.80 (m, 2 H), 1.33-1.35 (m, 1 H), 1.26-1.28 (m, 9 H). |
| 170* | 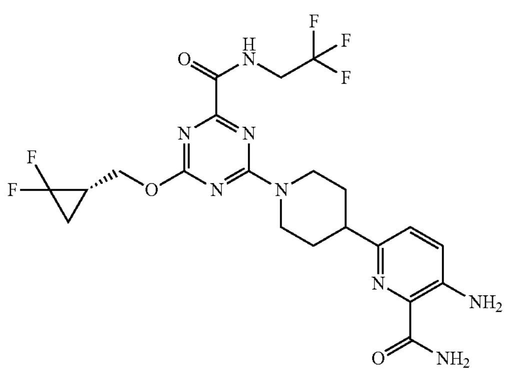 [SMILES: NC(=O)c1nc(C2CCN(c3nc(OC[C@@H]4CC4(F)F)nc(C(=O)NCC(F)(F)F)n3)CC2)ccc1N] | 4-[4-(5-amino-6-carbamoylpyridin-2-yl)piperidin-1-yl]-6-{[(1S)-2,2-difluorocyclopropyl]methoxy}-N-(2,2,2-trifluoroethyl)-1,3,5-triazine-2-carboxamide | 531.1; (400 MHz, CDCl$_3$) δ ppm 8.07-8.08 (m, 1 H), 7.85 (br. s., 1 H), 7.09 (d, J = 8.4 Hz, 1 H), 6.99 (d, J = 8.4 Hz, 1 H), 5.86 (br. s., 2 H), 5.33-5.35 (m, 1 H), 5.08-5.11 (m, 1 H), 4.89-4.92 (m, 1 H), 4.44-4.51 (m, 2 H), 4.07-4.12 (m, 2 H), 3.08-3.14 (m, 2 H), 2.91-2.92 (m, 1 H), 2.02-2.20 (m, 3 H), 1.74-1.80 (m, 2 H), 1.60-1.62 (m, 1 H), 1.32-1.34 (m, 1 H). |
| 171* | 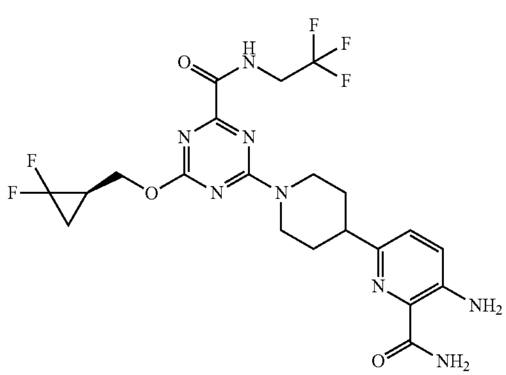 [SMILES: NC(=O)c1nc(C2CCN(c3nc(OC[C@H]4CC4(F)F)nc(C(=O)NCC(F)(F)F)n3)CC2)ccc1N] | 4-[4-(5-amino-6-carbamoylpyridin-2-yl)piperidin-1-yl]-6-{[(1R)-2,2-difluorocyclopropyl]methoxy}-N-(2,2,2-trifluoroethyl)-1,3,5-triazine-2-carboxamide | 531.1; (400 MHz, CDCl$_3$) δ ppm 8.07-8.10 (m, 1 H), 7.85 (br. s., 1 H), 7.09 (d, J = 8.4 Hz, 1 H), 6.99 (d, J = 8.4 Hz, 1 H), 5.86 (br. s., 2 H), 5.33-5.35 (m, 1 H), 5.09-5.12 (m, 1 H), 4.89-4.93 (m, 1 H), 4.45-4.53 (m, 2 H), 4.04-4.12 (m, 2 H), 3.08-3.15 (m, 2 H), 2.91-2.95 (m, 1 H), 2.03-2.20 (m, 3 H), 1.75-1.81 (m, 2 H), 1.61-1.63 (m, 1 H), 1.33-1.36 (m, 1H). |

TABLE 1-continued

| Ex. # | Structure | Compound Name | LRMS m/z (M + H)+; and 1H NMR |
|---|---|---|---|
| 172* | 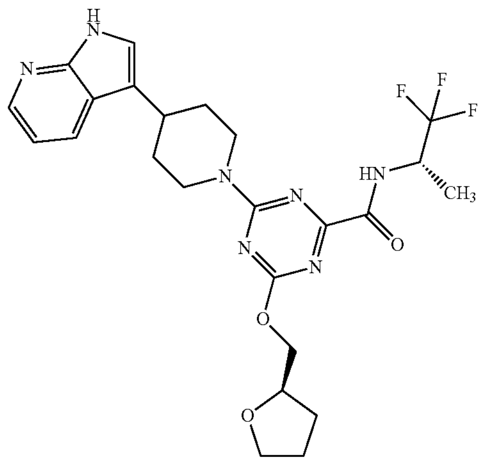 [SMILES: C[C@H](NC(=O)c1nc(OC[C@H]2CCCO2)nc(N2CCC(c3c[nH]c4ncccc34)CC2)n1)C(F)(F)F] | 4-[4-(1H-pyrrolo[2,3-b]pyridin-3-yl)piperidin-1-yl]-6-[(2R)-tetrahydrofuran-2-ylmethoxy]-N-[(2S)-1,1,1-trifluoropropan-2-yl]-1,3,5-triazine-2-carboxamide | 520.1; (400 MHz, CD$_3$OD) δ ppm 8.65-8.67 (m, 1 H), 8.35-8.36 (m, 1 H), 7.44-7.47 (m, 2 H), 5.18-5.22 (m, 1 H), 4.97-5.00 (m, 1 H), 4.84-4.87 (m, 1 H), 4.43-4.45 (m, 2 H), 4.28-4.30 (m, 1 H), 3.81-3.92 (m, 2 H), 3.20-3.26 (m, 3 H), 1.87-2.22 (m, 8 H), 1.47 (d, J = 7.2 Hz, 3 H). |
| 173* | 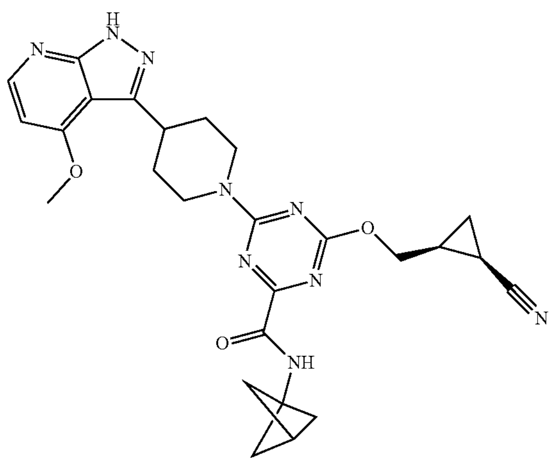 [SMILES: COc1ccnc2[nH]nc(C3CCN(c4nc(OC[C@H]5C[C@H]5C#N)nc(C(=O)NC56CC(C5)C6)n4)CC3)c12] | N-(bicyclo[1.1.1]pent-1-yl)-4-{[(1S,2R)-2-cyanocyclopropyl]methoxy}-6-[4-(4-methoxy-1H-pyrazolo[3,4-b]pyridin-3-yl)piperidin-1-yl]-1,3,5-triazine-2-carboxamide | 538.5; (400 MHz, DMSO-d$_6$) δ ppm 13.15 (s, 1 H), 9.17 (s, 1 H), 8.32 (d, J = 5.2 Hz, 1 H), 7.17 (d, J = 6.4 Hz, 1 H), 4.92-4.95 (m, 1 H), 4.68-4.72 (m, 2 H), 4.04-4.06 (m, 1 H), 3.95 (s, 3 H), 3.32-3.34 (m, 2 H), 3.16-3.20 (m, 2 H), 2.45 (s, 1 H), 2.09 (s, 6 H), 1.99-2.05 (m, 2 H), 1.81-1.83 (m, 3H), 1.27-1.28 (m, 1 H), 1.16-1.17 (m, 1 H). |
| 174* | 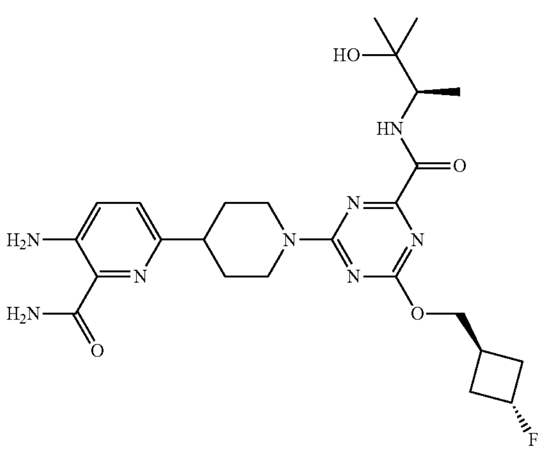 [SMILES: C[C@@H](NC(=O)c1nc(OC[C@H]2C[C@H](F)C2)nc(N2CCC(c3ccc(N)c(C(N)=O)n3)CC2)n1)C(C)(C)O] | 4-[4-(5-amino-6-carbamoylpyridin-2-yl)piperidin-1-yl]-6-[(trans-3-fluorocyclobutyl)methoxy]-N-[(2R)-3-hydroxy-3-methylbutan-2-yl]-1,3,5-triazine-2-carboxamide | 541.1; (400 MHz, CD$_3$OD) δ ppm 7.21 (d, J = 8.4 Hz, 1 H), 7.15 (d, J = 8.4 Hz 1 H), 5.09-5.28 (m, 3 H), 4.43 (d, J = 6.8 Hz, 2 H), 4.01-4.05 (m, 1 H), 3.11-3.15 (m, 2 H), 2.98-3.10 (m, 1 H), 2.78-2.80 (m, 1 H), 2.42-2.46 (m, 4 H), 2.02-2.05 (m, 2 H), 1.80-1.83 (m, 2 H), 1.22-1.27 (m, 9 H). |

TABLE 1-continued

| Ex. # | Structure | Compound Name | LRMS m/z (M + H)+; and 1H NMR |
|---|---|---|---|
| 175* | 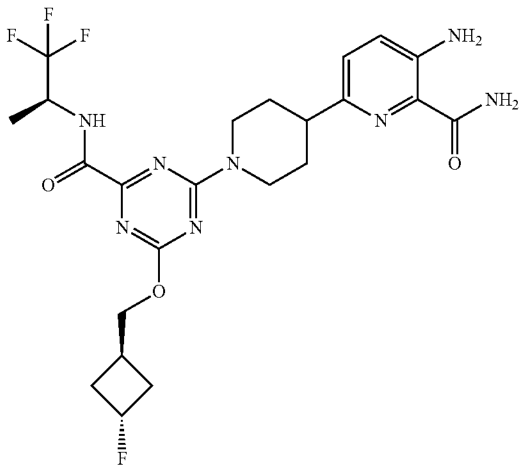 [SMILES: C[C@H](NC(=O)c1nc(OC[C@H]2C[C@H](F)C2)nc(N2CCC(c3ccc(N)c(C(N)=O)n3)CC2)n1)C(F)(F)F] | 4-[4-(5-amino-6-carbamoylpyridin-2-yl)piperidin-1-yl]-6-[(trans-3-fluorocyclobutyl)methoxy]-N-[(2S)-1,1,1-trifluoropropan-2-yl]-1,3,5-triazine-2-carboxamide | 541.1; (400 MHz, CD$_3$OD) δ ppm 7.21 (d, J = 8.4 Hz, 1 H), 7.14 (d, J = 8.8 Hz 1 H), 5.14-5.28 (m, 3 H), 4.44 (d, J = 5.2 Hz, 2 H), 3.11-3.14 (m, 2 H), 2.98-3.11 (m, 1 H), 2.78-2.80 (m, 1 H), 2.42-2.46 (m, 5 H), 2.02-2.05 (m, 2 H), 1.80-1.83 (m, 2 H), 1.47 (d, J = 7.6 Hz, 3 H). |
| 176** | 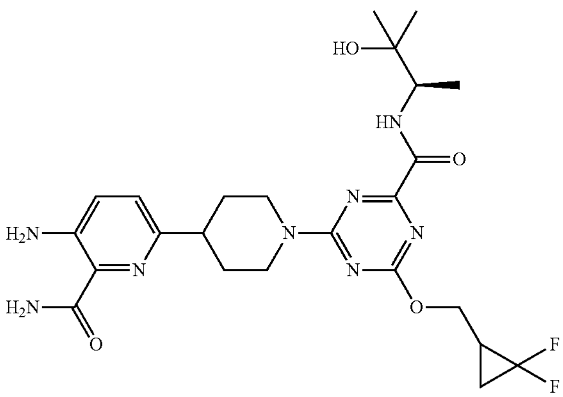 [SMILES: C[C@@H](NC(=O)c1nc(OCC2CC2(F)F)nc(N2CCC(c3ccc(N)c(C(N)=O)n3)CC2)n1)C(C)(C)O] | 4-[4-(5-amino-6-carbamoylpyridin-2-yl)piperidin-1-yl]-6-[(2,2-difluorocyclopropyl)methoxy]-N-[(2R)-3-hydroxy-3-methylbutan-2-yl]-1,3,5-triazine-2-carboxamide | 535.3; (700 MHz DMSO-d$_6$) δ ppm 8.16 (d, J = 9.6 Hz, 1 H), 7.86 (d, J = 2.6 Hz, 1 H), 7.17-7.19 (m, 2 H), 7.09 (d, J = 8.5 Hz, 1 H), 6.63 (br. s., 2 H), 4.86 (d, J = 12.7 Hz, 1 H), 4.73-4.78 (m, 1 H), 4.50-4.54 (m, 1 H), 4.26 (t, J = 10.2 Hz, 1 H), 3.8 (dd, J = 9.2, 6.7 Hz, 1 H), 3.04-3.09 (m, 2 H), 2.85-2.89 (m, 1 H), 2.23 (td, J = 12.2, 7.8 Hz, 1 H), 1.91 (d, J = 11.9 Hz, 2 H), 1.61-1.74 (m, 3 H), 1.47-1.54 (m, 1 H), 1.12 (s, 3 H), 1.09 (d, J = 6.5 Hz, 3 H), 1.07 (s, 3 H). |
| 177** | 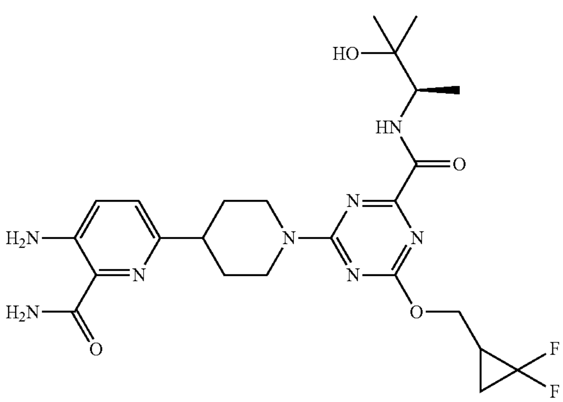 [SMILES: C[C@@H](NC(=O)c1nc(OCC2CC2(F)F)nc(N2CCC(c3ccc(N)c(C(N)=O)n3)CC2)n1)C(C)(C)O] | 4-[4-(5-amino-6-carbamoylpyridin-2-yl)piperidin-1-yl]-6-[(2,2-difluorocyclopropyl)methoxy]-N-[(2R)-3-hydroxy-3-methylbutan-2-yl]-1,3,5-triazine-2-carboxamide | 535.3; (700 MHz DMSO-d$_6$) δ ppm 8.16 (d, J = 9.2 Hz, 1 H), 7.86 (br. s., 1 H), 7.17-7.19 (m, 2 H), 7.09 (d, J = 8.5 Hz, 1 H), 6.63 (br. s., 2 H), 4.86 (d, J = 12.1 Hz, 1 H), 4.72-4.78 (m, 1 H), 4.50-4.56 (m, 1 H), 4.25 (t, J = 10.2 Hz, 1 H), 3.52-3.90 (m, 1 H), 3.07 (q, J = 11.5 Hz, 2 H), 2.88 (t, J = 11.5 Hz, 1 H), 2.21-2.25 (m, 1 H), 1.91 (d, J = 11.9 Hz, 2 H), 1.62-1.74 (m, 3 H), 1.48-1.55 (m, 1 H), 1.12 (s, 3 H), 1.09 (d, J = 6.6 Hz, 3 H), 1.08 (s, 3 H). |
| 178 | 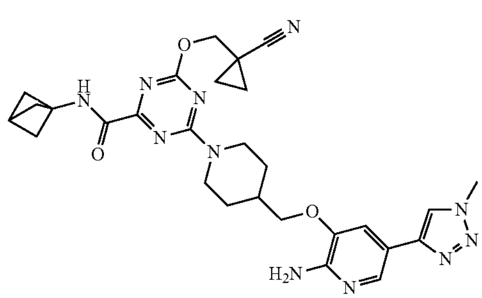 [SMILES: Cn1cc(-c2cnc(N)c(OCC3CCN(c4nc(OCC5(C#N)CC5)nc(C(=O)NC56CC(C5)C6)n4)CC3)c2)nn1] | 4-[4-({[2-amino-5-(1-methyl-1H-1,2,3-triazol-4-yl)pyridin-3-yl]oxy}methyl)piperidin-1-yl]-N-(bicyclo[1.1.1]pent-1-yl)-6-[(1-cyanocyclopropyl)methoxy]-1,3,5-triazine-2-carboxamide | 572.2; (700 MHz, DMSO-d$_6$) δ ppm 8.29 (s, 1 H), 7.95 (s, 1 H), 7.39 (s, 1 H), 5.79 (s, 2 H), 4.86 (d, J = 12.98 Hz, 1 H), 4.67 (d, J = 12.47 Hz, 1 H), 4.37 (q, J = 11.84 Hz, 2 H), 4.03 (s, 3 H), 3.91 (d, J = 6.15 Hz, 2 H), 2.95-3.06 (m, 3 H), 2.15 (br. s., 1 H), 2.06 (s, 6 H), 1.94 (d, J = 12.30 Hz, 2 H), 1.32-1.37 (m, 3 H), 1.29 (d, J = 6.15 Hz, 1 H), 1.16-1.21 (m, 3 H). |

TABLE 1-continued

| Ex. # | Structure | Compound Name | LRMS m/z (M + H)+; and 1H NMR |
|---|---|---|---|
| 179* | 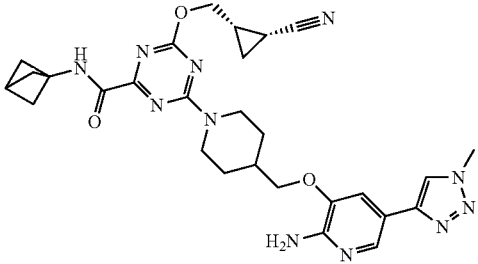 [SMILES: Cn1cc(-c2cnc(N)c(OCC3CCN(c4nc(OC[C@H]5C[C@H]5C#N)nc(C(=O)NC56CC(C5)C6)n4)CC3)c2)nn1] | 4-[4-({[2-amino-5-(1-methyl-1H-1,2,3-triazol-4-yl)pyridin-3-yl]oxy}methyl)piperidin-1-yl]-N-(bicyclo[1.1.1]pent-1-yl)-6-{[(1S,2R)-2-cyanocyclopropyl]methoxy}-1,3,5-triazine-2-carboxamide | 572.3; (700 MHz, DMSO-d$_6$) δ ppm 9.14 (s, 1 H), 8.28 (s, 1 H), 7.94 (br. s., 1 H), 7.39 (br. s., 1H), 5.78 (s, 3 H), 4.86 (d, J = 12.47 Hz, 1 H), 4.67 (t, J = 13.07 Hz, 3 H), 4.01-4.08 (m, 5 H), 3.91 (br. s., 1 H), 2.99 (t, J = 12.73 Hz, 3 H), 2.43 (d, J = 2.39 Hz, 1 H), 2.14 (br. s., 2 H), 1.93 (d, J = 7.17 Hz, 5 H), 1.82 (d, J = 5.81 Hz, 1 H), 1.23-1.35 (m, 4 H). |
| 180* | 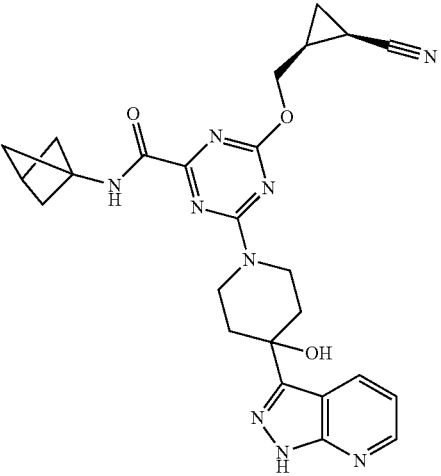 [SMILES: N#C[C@@H]1C[C@@H]1COc1nc(C(=O)NC23CC(C2)C3)nc(N2CCC(O)(c3n[nH]c4ncccc34)CC2)n1] | N-(bicyclo[1.1.1]pent-1-yl)-4-{[(1S,2R)-2-cyanocyclopropyl]methoxy}-6-[4-hydroxy-4-(1H-pyrazolo[3,4-b]pyridin-3-yl)piperidin-1-yl]-1,3,5-triazine-2-carboxamide | 502.2; (400 MHz, DMSO-d6) δ ppm 13.32 (br. s., 1 H), 9.11 (br. s., 1 H), 8.36-8.54 (m, 2 H), 7.09-7.24 (m, 1 H), 5.75 (s, 1 H), 5.63 (br. s., 1 H), 4.61-4.77 (m, 1 H), 4.56 (d, J = 12.23 Hz, 1 H), 4.40 (d, J = 13.20 Hz, 1 H), 4.13 (d, J = 8.56 Hz, 1 H), 3.63 (d, J = 11.00 Hz, 2 H), 1.92-2.18 (m, 11 H), 1.84 (d, J = 7.34 Hz, 1 H), 1.21-1.33 (m, 1 H), 1.16 (br. s., 1 H). |
| 181* | 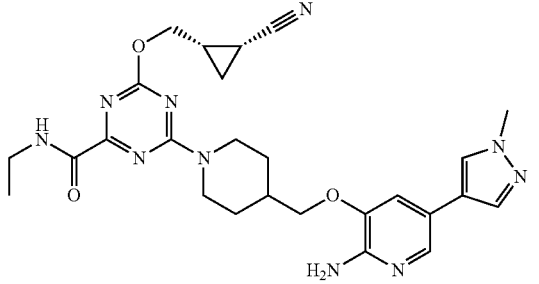 [SMILES: CCNC(=O)c1nc(OC[C@H]2C[C@H]2C#N)nc(N2CCC(COc3cc(-c4cnn(C)c4)cnc3N)CC2)n1] | 4-[4-({[2-amino-5-(1-methyl-1H-pyrazol-4-yl)pyridin-3-yl]oxy}methyl)piperidin-1-yl]-6-{[(1S,2R)-2-cyanocyclopropyl]methoxy}-N-ethyl-1,3,5-triazine-2-carboxamide | 533.2; (700 MHz, DMSO-d6) δ ppm 8.83 (t, J = 6.06 Hz, 1 H), 7.91 (s, 1 H), 7.71 (s, 1 H), 7.66 (s, 1 H), 7.16 (d, J = 1.02 Hz, 1 H), 5.46 (s, 2 H), 4.84 (d, J = 12.81 Hz, 1 H), 4.66-4.73 (m, 1 H), 4.63 (d, J = 12.47 Hz, 1 H), 3.88 (d, J = 6.15 Hz, 1 H), 3.78 (s, 3 H), 3.23 (t, J = 7.09 Hz, 2 H), 2.97 (t, J = 12.64 Hz, 2 H), 2.07-2.15 (m, 1 H), 1.88 (dd, J = 14.60, 7.09 Hz, 3 H), 1.82 (d, J = 7.86 Hz, 1 H), 1.19-1.30 (m, 4 H), 0.98-1.10 (m, 5 H). |
| 182*** | 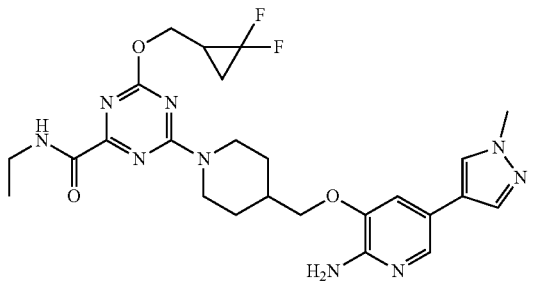 [SMILES: CCNC(=O)c1nc(OCC2CC2(F)F)nc(N2CCC(COc3cc(-c4cnn(C)c4)cnc3N)CC2)n1] | 4-[4-({[2-amino-5-(1-methyl-1H-pyrazol-4-yl)pyridin-3-yl]oxy}methyl)piperidin-1-yl]-6-[(2,2-difluorocyclopropyl)methoxy]-N-ethyl-1,3,5-triazine-2-carboxamide | 544.2; (700 MHz, DMSO-d6) δ ppm 7.99 (s, 1 H), 7.71-7.77 (m, 2 H), 7.18 (d, J = 1.37 Hz, 1 H), 5.60 (s, 2 H), 4.90 (d, J = 12.81 Hz, 1 H), 4.69 (d, J = 12.81 Hz, 1 H), 4.50-4.57 (m, 1 H), 4.23-4.31 (m, 1 H), 3.88-3.95 (m, 3 H), 3.25 (t, J = 7.17 Hz, 1 H), 2.95-3.07 (m, 3 H), 2.23 (td, J = 12.26, 7.60 Hz, 2 H), 2.11-2.16 (m, 1 H), 1.96 (br. s., 3 H), 1.70-1.75 (m, 1 H), 1.54 (d, J = 8.03 Hz, 1 H), 1.27-1.34 (m, 3H), 1.09 (t, J = 7.17 Hz, 3 H). |

TABLE 1-continued

| Ex. # | Structure | Compound Name | LRMS m/z (M + H)+; and 1H NMR |
|---|---|---|---|
| 183* | 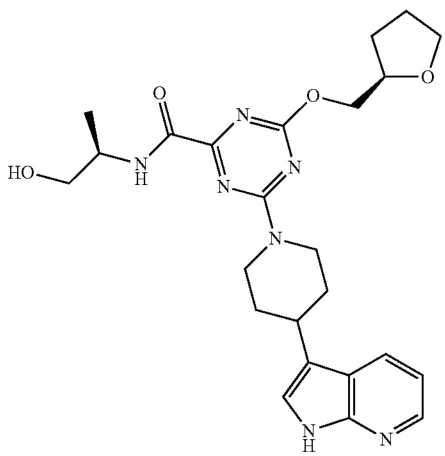 [SMILES: C[C@H](CO)NC(=O)c1nc(OC[C@H]2CCCO2)nc(N2CCC(c3c[nH]c4ncccc34)CC2)n1] | N-[(2R)-1-hydroxypropan-2-yl]-4-[4-(1H-pyrrolo[2,3-b]pyridin-3-yl)piperidin-1-yl]-6-[(2R)-tetrahydrofuran-2-ylmethoxy]-1,3,5-triazine-2-carboxamide | 482.2; (700 MHz, DMSO-d6) δ ppm 7.99 (s, 1 H), 7.71-7.77 (m, 2 H), 7.18 (d, J = 1.37 Hz, 1 H), 5.60 (s, 2 H), 4.90 (d, J = 12.81 Hz, 1 H), 4.69 (d, J = 12.81 Hz, 1 H), 4.50-4.57 (m, 1 H), 4.23-4.31 (m, 1 H), 3.88-3.95 (m, 3 H), 3.25 (t, J = 7.17 Hz, 1 H), 2.95-3.07 (m, 3 H), 2.23 (td, J = 12.26, 7.60 Hz, 2 H), 2.11-2.16 (m, 1 H), 1.96 (br. s., 3 H), 1.70-1.75 (m, 1 H), 1.54 (d, J = 8.03 Hz, 1 H), 1.27-1.34 (m, 3H), 1.09 (t, J = 7.17 Hz, 3 H). |
| 184* | 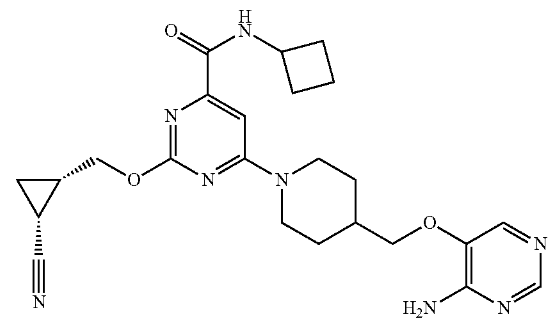 [SMILES: N#C[C@@H]1C[C@@H]1COc1nc(C(=O)NC2CCC2)cc(N2CCC(COc3cncnc3N)CC2)n1] | 6-(4-{[(4-aminopyrimidin-5-yl)oxy]methyl}piperidin-1-yl)-2-{[(1S,2R)-2-cyanocyclopropyl]methoxy}-N-cyclobutyl-pyrimidine-4-carboxamide | 479.3; (400 MHz, DMSO-d6) δ ppm 8.59 (d, J = 8.44 Hz, 1 H), 7.99 (s, 1 H), 7.78 (s, 1 H), 6.97 (s, 1 H), 6.66 (br. s., 2 H), 4.66 (dd, J = 11.92, 5.44 Hz, 1 H), 4.35-4.45 (m, 1 H), 4.01-4.12 (m, 1 H), 3.89 (d, J = 6.24 Hz, 2 H), 3.00 (t, J = 12.10 Hz, 2 H), 2.06-2.22 (m, 5 H), 1.89-2.02 (m, 4 H), 1.78-1.89 (m, 1 H), 1.59-1.71 (m, 2 H), 1.22-1.35 (m, 4 H), 1.13 (q, J = 5.42 Hz, 1 H). |
| 185 | 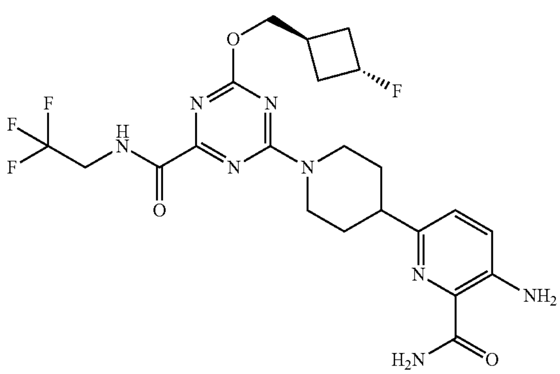 [SMILES: NC(=O)c1nc(C2CCN(c3nc(OC[C@H]4C[C@H](F)C4)nc(C(=O)NCC(F)(F)F)n3)CC2)ccc1N] | 4-[4-(5-amino-6-carbamoylpyridin-2-yl)piperidin-1-yl]-6-[(trans-3-fluorocyclobutyl)methoxy]-N-(2,2,2-trifluoroethyl)-1,3,5-triazine-2-carboxamide | 526.7; (600 MHz, DMSO-d6) δ ppm 7.86 (d, J = 2.93 Hz, 1 H), 7.24 (d, J = 2.78 Hz, 1 H), 7.19 (d, J = 8.49 Hz, 1 H), 7.09 (d, J = 8.63 Hz, 1 H), 6.67 (br. s., 2 H), 5.13-5.31 (m, 1 H), 4.97 (d, J = 13.02 Hz, 1 H), 4.76 (d, J = 12.88 Hz, 1 H), 4.36 (d, J = 7.17 Hz, 2 H), 3.97-4.06 (m, 2 H), 3.33-3.44 (m, 1 H), 3.00-3.11 (m, 2 H), 2.88 (tt, J = 11.74, 3.40 Hz, 1 H), 2.66-2.73 (m, 1 H), 2.22-2.36 (m, 4 H), 1.92 (d, J = 11.85 Hz, 2 H), 1.64-1.74 (m, 2 H). |
| 186 | 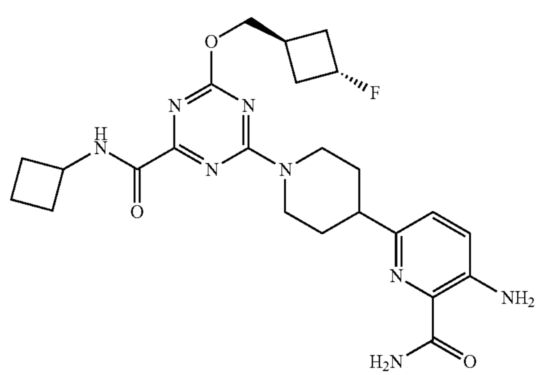 [SMILES: NC(=O)c1nc(C2CCN(c3nc(OC[C@H]4C[C@H](F)C4)nc(C(=O)NC4CCC4)n3)CC2)ccc1N] | 4-[4-(5-amino-6-carbamoylpyridin-2-yl)piperidin-1-yl]-N-cyclobutyl-6-[{trans-3-fluorocyclobutyl}methoxy]-1,3,5-triazine-2-carboxamide | 499.3; (700 MHz, DMSO-d6) δ ppm 8.77 (d, J = 8.20 Hz, 1 H), 7.86 (d, J = 2.05 Hz, 1 H), 7.25 (br. s., 1 H), 7.19 (d, J = 8.54 Hz, 1 H), 7.09 (d, J = 8.54 Hz, 1 H), 6.67 (br. s., 2 H), 5.14-5.30 (m, 1H), 4.94 (d, J = 13.15 Hz, 1 H), 4.75 (d, J = 12.98 Hz, 1 H), 4.30-4.37 (m, 3 H), 3.05 (t, J = 12.90 Hz, 2 H), 2.87 (tt, J = 11.74, 3.29 Hz, 1 H), 2.68 (ddt, J = 9.86, 6.45, 3.20 Hz, 1 H), 2.23-2.37 (m, 5 H), 2.09-2.18 (m, 5 H), 1.62-1.71 (m, 4 H). |

TABLE 1-continued

| Ex. # | Structure | Compound Name | LRMS m/z (M + H)+; and 1H NMR |
|---|---|---|---|
| 187* | 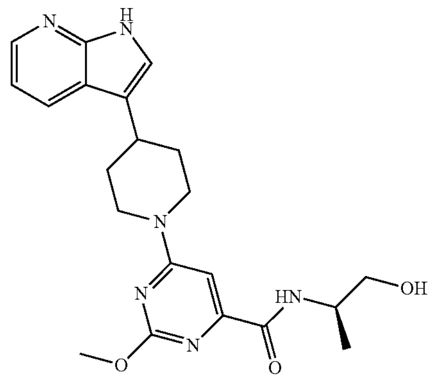 [SMILES: COc1nc(C(=O)N[C@H](C)CO)cc(N2CCC(c3c[nH]c4ncccc34)CC2)n1] | N-[(2R)-1-hydroxypropan-2-yl]-2-methoxy-6-[4-(1H-pyrrolo[2,3-b]pyridin-3-yl)piperidin-1-yl]pyrimidine-4-carboxamide | 411.1; (400 MHz, CDCl$_3$) δ ppm 8.78 (s, 1 H), 8.30 (d, J = 4.4 Hz, 1 H), 7.94-7.96 (m, 2 H), 7.14 (s, 1 H), 7.06-7.13 (m, 2 H), 4.23-4.24 (m, 1 H), 3.98 (s, 3 H), 3.74-3.77 (m, 1 H), 3.63-3.67 (m, 1 H), 3.13-3.17 (m, 3 H), 2.16 (d, J = 12.8 Hz, 2 H), 1.73-1.75 (m, 4 H), 1.29 (d, J = 6.8 Hz, 3 H). |
| 188* | 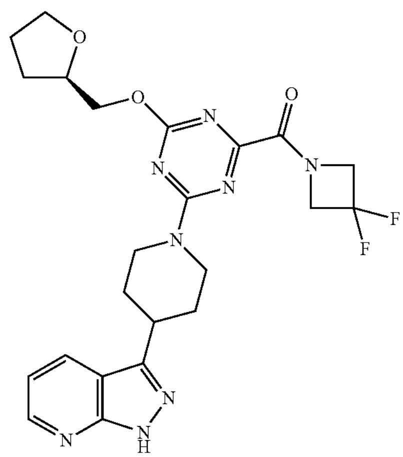 [SMILES: O=C(c1nc(OC[C@H]2CCCO2)nc(N2CCC(c3n[nH]c4ncccc34)CC2)n1)N1CC(F)(F)C1] | (3,3-difluoroazetidin-1-yl){6-[4-(1H-pyrazolo[3,4-b]pyridin-3-yl)piperidin-1-yl]-2-[(2R)-tetrahydrofuran-2-ylmethoxy]pyrimidin-4-yl}methanone | 500.1; (700 MHz, DMSO-d6) δ ppm 8.41 (d, J = 4.18 Hz, 1 H), 8.23 (d, J = 7.92 Hz, 1 H), 7.07 (dd, J = 7.92, 4.40 Hz, 1 H), 6.95 (s, 1 H), 4.94 (t, J = 12.43 Hz, 2 H), 4.41 (t, J = 12.43 Hz, 2 H), 4.03-4.17 (m, 3 H), 3.71 (q, J = 7.19 Hz, 1 H), 3.60 (q, J = 7.41 Hz, 1 H), 3.34-3.39 (m, 2 H), 3.20-3.22 (m, 1 H), 3.13 (br. s., 2 H), 2.03 (d, J = 11.66 Hz, 2 H), 1.91 (td, J = 12.65, 7.70 Hz, 1 H), 1.78-1.85 (m, 1 H), 1.68-1.78 (m, 3 H), 1.57-1.63 (m, 1 H). |
| 189 | 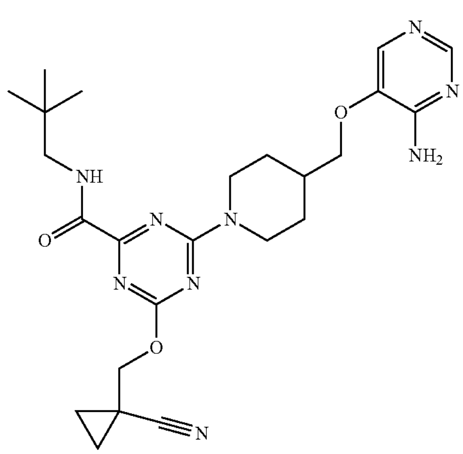 [SMILES: CC(C)(C)CNC(=O)c1nc(OCC2(C#N)CC2)nc(N2CCC(COc3cncnc3N)CC2)n1] | 4-(4-{[(4-aminopyrimidin-5-yl)oxy]methyl}piperidin-1-yl)-6-[(1-cyanocyclopropyl)methoxy]-N-(2,2-dimethylpropyl)-1,3,5-triazine-2-carboxamide | 518.1 [M + Na]+; (400 MHz, CDCl$_3$) δ ppm 8.16 (s, 1 H), 7.84 (t, J = 6.4 Hz, 1H), 7.74 (s, 1 H), 4.96-5.01 (m, 1 H), 4.81-4.85 (m, 1 H), 4.40 (d, J = 12.0 Hz, 1 H), 4.30 (d, J = 11.6 Hz, 1 H), 3.86 (d, J = 6.4 Hz, 2 H), 3.17-3.19 (m, 2 H), 2.89-2.99 (m, 2 H), 2.10-2.11 (m, 1 H), 1.88-1.91 (m, 2 H), 1.33-1.37 (m, 4 H), 1.11-1.14 (m, 2 H), 0.90 (s, 9 H). |

TABLE 1-continued

| Ex. # | Structure | Compound Name | LRMS m/z (M + H)+; and 1H NMR |
|---|---|---|---|
| 190 | 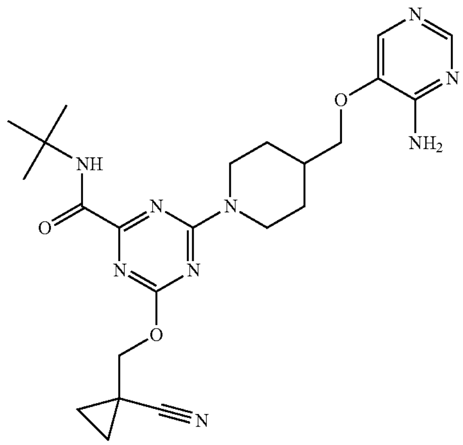 [SMILES: CC(C)(C)NC(=O)c1nc(OCC2(C#N)CC2)nc(N2CCC(COc3cncnc3N)CC2)n1] | 4-(4-{[(4-aminopyrimidin-5-yl)oxy]methyl}piperidin-1-yl)-N-tert-butyl-6-[(1-cyanocyclopropyl)methoxy]-1,3,5-triazine-2-carboxamide | 482.1; (400 MHz, CDCl$_3$) δ ppm 8.20 (s, 1 H), 7.82 (s, 1 H), 7.63 (s, 1 H), 5.46 (s, 2 H), 5.04 (d, J = 13.6 Hz, 1 H), 4.82 (d, J = 14.0 Hz, 1 H), 4.42 (d, J = 12.0 Hz, 1 H), 4.26 (d, J = 11.6 Hz, 1 H), 3.89 (d, J = 5.6 Hz, 2 H), 2.88-2.98 (m, 2 H), 2.10-2.11 (m, 1 H), 1.86-1.89 (m, 2 H), 1.35-1.39 (m, 13 H), 1.11-1.12 (m, 2 H). |
| 191*** | 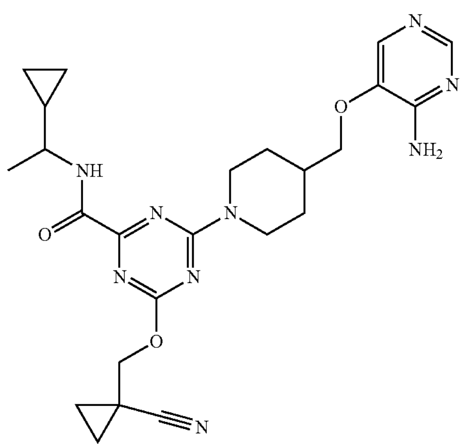 [SMILES: CC(NC(=O)c1nc(OCC2(C#N)CC2)nc(N2CCC(COc3cncnc3N)CC2)n1)C1CC1] | 4-(4-{[(4-aminopyrimidin-5-yl)oxy]methyl}piperidin-1-yl)-6-[(1-cyanocyclopropyl)methoxy]-N-(1-cyclopropylethyl)-1,3,5-triazine-2-carboxamide | 494.1; (400 MHz, DMSO-d$_6$) δ ppm 8.58 (d, J = 8.8 Hz, 1 H), 8.00 (s, 1 H), 7.79 (s, 1 H), 6.71 (br. s., 2 H), 4.88 (d, J = 12.8 Hz, 1 H), 4.72 (d, J = 13.2 Hz, 1 H), 4.41 (s, 2 H), 3.91 (d, J = 6.0 Hz, 2H), 2.98-3.05 (m, 2 H), 2.10-2.12 (m, 1 H), 1.92-1.95 (m, 2 H), 1.35-1.40 (m, 7 H), 1.24 (d, J = 7.6 Hz, 3 H), 1.04-1.06 (m, 1 H), 0.38-0.46 (m, 2 H), 0.21-0.25 (m, 2 H). |
| 192 | 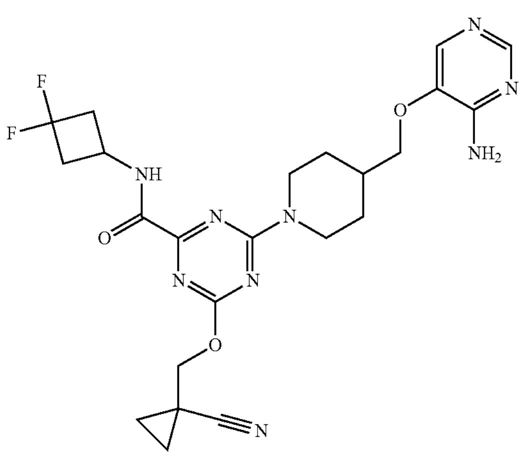 [SMILES: N#CC1(COc2nc(C(=O)NC3CC(F)(F)C3)nc(N3CCC(COc4cncnc4N)CC3)n2)CC1] | 4-(4-{[(4-aminopyrimidin-5-yl)oxy]methyl}piperidin-1-yl)-6-[(1-cyanocyclopropyl)methoxy]-N-(3,3-difluorocyclobutyl)-1,3,5-triazine-2-carboxamide | 516.2; (400 MHz, DMSO-d$_6$) δ ppm 9.15 (d, J = 6.8 Hz, 1 H), 7.99 (s, 1 H), 7.79 (s, 1 H), 6.70 (br. s., 2 H), 4.89 (d, J = 13.2 Hz, 1 H), 4.71 (d, J = 14.0 Hz, 1 H), 4.37-4.44 (m, 2 H), 3.91 (d, J = 6.0 Hz, 2 H), 2.98-3.06 (m, 2 H), 2.89-2.92 (m, 3 H), 2.10-2.11 (m, 1 H), 1.92-1.95 (m, 2 H), 1.24-1.38 (m, 8 H). |

TABLE 1-continued

| Ex. # | Structure | Compound Name | LRMS m/z (M + H)+; and 1H NMR |
|---|---|---|---|
| 193 | 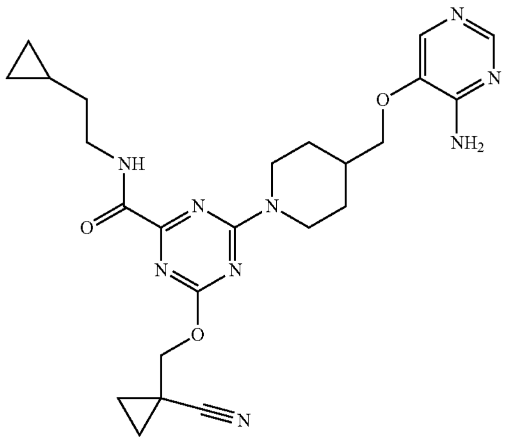 [SMILES: N#CC1(COc2nc(C(=O)NCCC3CC3)nc(N3CCC(COc4cncnc4N)CC3)n2)CC1] | 4-(4-{[(4-aminopyrimidin-5-yl)oxy]methyl}piperidin-1-yl)-6-[(1-cyanocyclopropyl)methoxy]-N-(2-cyclopropylethyl)-1,3,5-triazine-2-carboxamide | 494.1; (400 MHz, DMSO-d$_6$) δ ppm 8.79 (t, J = 6.0 Hz, 1 H), 7.99 (s, 1 H), 7.79 (s, 1 H), 6.71 (br. s., 2 H), 4.90 (d, J = 13.2 Hz, 1 H), 4.70 (d, J = 13.2 Hz, 1 H), 4.37-4.43 (m, 2 H), 3.91 (d, J = 6.0 Hz, 2 H), 3.27-3.32 (m, 2 H), 3.00-3.02 (m, 2 H), 2.10-2.12 (m, 1 H), 1.91-1.94 (m, 2 H), 1.21-1.43 (m, 8 H), 0.67-0.69 (m, 1 H), 0.39-0.41 (m, 2 H), 0.04-0.05 (m, 2 H). |
| 194 | 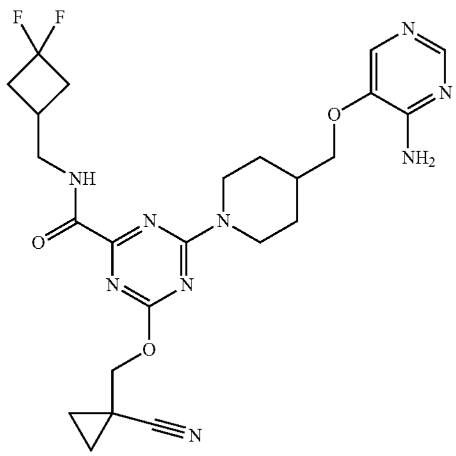 [SMILES: N#CC1(COc2nc(C(=O)NCC3CC(F)(F)C3)nc(N3CCC(COc4cncnc4N)CC3)n2)CC1] | 4-(4-{[(4-aminopyrimidin-5-yl)oxy]methyl}piperidin-1-yl)-6-[(1-cyanocyclopropyl)methoxy]-N-[(3,3-difluorocyclobutyl)methyl]-1,3,5-triazine-2-carboxamide | 530.0; (400 MHz, DMSO-d$_6$, 80° C.) δ ppm 8.80 (t, J = 5.6 Hz, 1 H), 8.02 (s, 1 H), 7.82 (s, 1 H), 6.48 (br. s., 2 H), 4.91 (d, J = 12.0 Hz, 1 H), 4.71 (d, J = 12.0 Hz, 1 H), 4.43-4.44 (m, 2 H), 3.95 (d, J = 5.6 Hz, 2 H), 3.35-3.41 (m, 2 H), 3.04-3.06 (m, 2 H), 2.59-2.63 (m, 2 H), 2.26-2.41 (m, 4 H), 1.93-1.96 (m, 2 H), 1.25-1.37 (m, 6 H). |
| 195* | 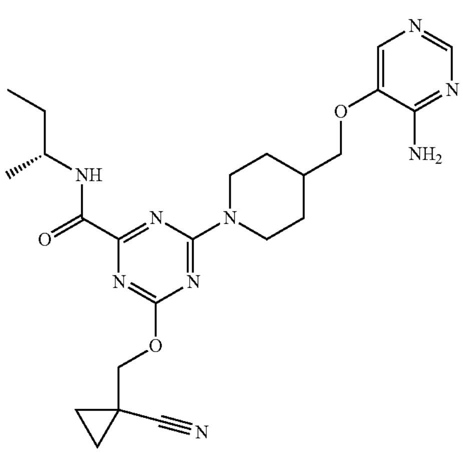 [SMILES: CC[C@@H](C)NC(=O)c1nc(OCC2(C#N)CC2)nc(N2CCC(COc3cncnc3N)CC2)n1] | 4-(4-{[(4-aminopyrimidin-5-yl)oxy]methyl}piperidin-1-yl)-N-[(2R)-butan-2-yl]-6-[(1-cyano-cyclopropyl)methoxy]-1,3,5-triazine-2-carboxamide | 482.2; (400 MHz, DMSO-d$_6$) δ ppm 8.37 (d, J = 8.4 Hz, 1 H), 7.99 (s, 1 H), 7.79 (s, 1 H), 6.70 (br. s., 2 H), 4.87 (d, J = 13.2 Hz, 1 H), 4.71 (d, J = 14.0 Hz, 1 H), 4.36-4.44 (m, 2 H), 3.91 (d, J = 6.0 Hz, 2 H), 3.83-3.86 (m, 1 H), 2.97-3.01 (m, 2 H), 2.10-2.12 (m, 1 H), 1.92-1.95 (m, 2 H), 1.48-1.53 (m, 2 H), 1.24-1.37 (m, 6 H), 1.13 (d, J = 4.4 Hz, 3 H), 0.84 (t, J = 7.6 Hz, 3 H). |

TABLE 1-continued

| Ex. # | Structure | Compound Name | LRMS m/z (M + H)+; and 1H NMR |
|---|---|---|---|
| 196* | 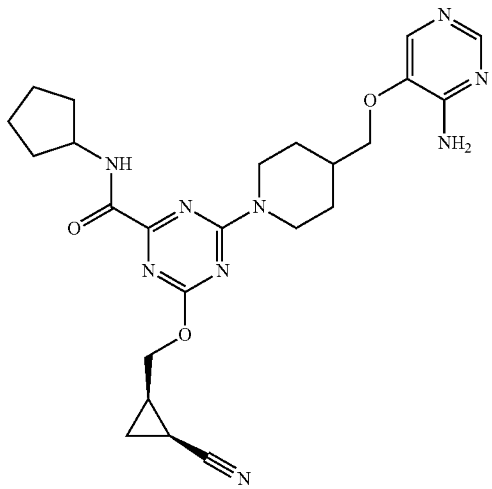 [SMILES: N#C[C@H]1C[C@H]1COc1nc(C(=O)NC2CCCC2)nc(N2CCC(COc3cncnc3N)CC2)n1] | 4-(4-{[(4-aminopyrimidin-5-yl)oxy]methyl}piperidin-1-yl)-6-{[(1R,2S)-2-cyanocyclopropyl]methoxy}-N-cyclopentyl-1,3,5-triazine-2-carboxamide | 516.1 [M + Na]+; (400 MHz, CDCl3) δ ppm 8.24 (s, 1 H), 7.82 (s, 1 H), 7.71 (d, J = 7.6 Hz, 1 H), 5.06-5.16 (m, 3 H), 4.85-4.92 (m, 1 H), 4.56-4.59 (m, 1 H), 4.46-4.51 (m, 1 H), 4.32-4.36 (m, 1 H), 3.94 (d, J = 6.0 Hz, 2 H), 2.95-3.03 (m, 2 H), 2.15-2.20 (m, 1 H), 2.06-2.15 (m, 2 H), 1.95-2.06 (m, 2 H), 1.87-1.95 (m, 1 H), 1.62-1.85 (m, 4 H), 1.48-1.57 (m, 3 H), 1.27-1.48 (m, 3 H), 1.13-1.16 (m, 1 H). |
| 197* | 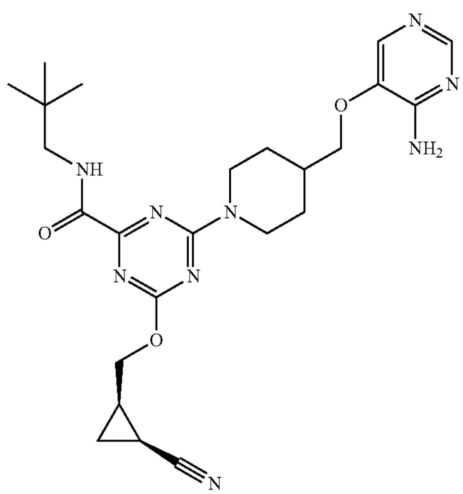 [SMILES: CC(C)(C)CNC(=O)c1nc(OC[C@@H]2C[C@@H]2C#N)nc(N2CCC(COc3cncnc3N)CC2)n1] | 4-(4-{[(4-aminopyrimidin-5-yl)oxy]methyl}piperidin-1-yl)-6-{[(1R,2S)-2-cyanocyclopropyl]methoxy}-N-(2,2-dimethylpropyl)-1,3,5-triazine-2-carboxamide | 518.2 [M + Na]+; (400 MHz, CDCl3) δ ppm 8.24 (s, 1 H), 7.89-7.95 (m, 1 H), 7.82 (s, 1 H), 5.06-5.13 (m, 3 H), 4.85-4.92 (m, 1 H), 4.55-4.62 (m, 1 H), 4.46-4.51 (m, 1 H), 3.94 (d, J = 6.0 Hz, 2 H), 3.22-3.27 (m, 2 H), 2.93-3.06 (m, 2 H), 2.15-2.19 (m, 1 H), 1.94-1.99 (m, 2 H), 1.82-1.94 (m, 1 H), 1.66-1.75 (m, 1 H), 1.26-1.44 (m, 3 H), 1.13-1.16 (m, 1 H), 0.97 (s, 9 H). |
| 198* | 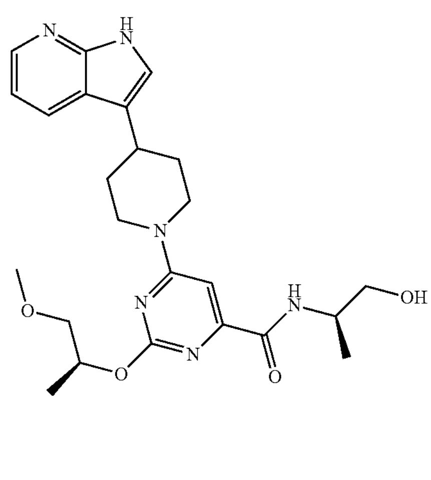 [SMILES: COC[C@H](C)Oc1nc(C(=O)N[C@H](C)CO)cc(N2CCC(c3c[nH]c4ncccc34)CC2)n1] | N-[(2R)-1-hydroxypropan-2-yl]-2-{[(2S)-1-methoxypropan-2-yl]oxy}-6-[4-(1H-pyrrolo[2,3-b]pyridin-3-yl)piperidin-1-yl]pyrimidine-4-carboxamide | 469.2; (400 MHz, CDCl3) δ ppm 9.30 (br. s., 1 H), 8.30 (s, 1 H), 7.93-7.98 (m, 2 H), 7.07-7.12 (m, 3 H), 5.31-5.32 (m, 1 H), 4.64 (br. s., 1 H), 4.21-4.22 (m, 1 H), 3.64-3.72 (m, 3 H), 3.49-3.52 (m, 1 H), 3.42 (d, J = 4.0 Hz, 3 H), 3.13-3.15 (m, 4 H), 2.14 (d, J = 12.4 Hz, 2 H), 1.69-1.75 (m, 2 H), 1.38-1.40 (m, 3 H), 1.26-1.28 (m, 3 H). |

TABLE 1-continued

| Ex. # | Structure | Compound Name | LRMS m/z (M + H)+; and 1H NMR |
|---|---|---|---|
| 199*** | 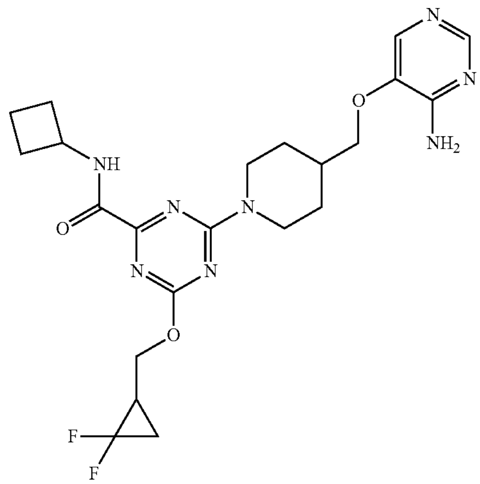 [SMILES: Nc1ncncc1OCC1CCN(c2nc(OCC3CC3(F)F)nc(C(=O)NC3CCC3)n2)CC1] | 4-(4-{[(4-aminopyrimidin-5-yl)oxy]methyl}piperidin-1-yl)-N-cyclobutyl-6-[(2,2-difluorocyclopropyl)methoxy]-1,3,5-triazine-2-carboxamide | 491.1; (400 MHz, CDCl$_3$) δ ppm 8.25 (s, 1 H), 7.89 (d, J = 8.4 Hz, 1 H), 7.83 (s, 1 H), 5.09-5.14 (m, 3 H), 4.88 (d, J = 14.8 Hz, 1 H), 4.44-4.56 (m, 3 H), 3.94 (d, J = 5.6 Hz, 2 H), 2.99-3.02 (m, 2 H), 2.41-2.44 (m, 2 H), 2.14-2.18 (m, 2 H), 1.96-2.04 (m, 4 H), 1.75-1.80 (m, 2 H), 1.56-1.58 (m, 1 H), 1.32-1.40 (m, 3 H). |
| 200*** | 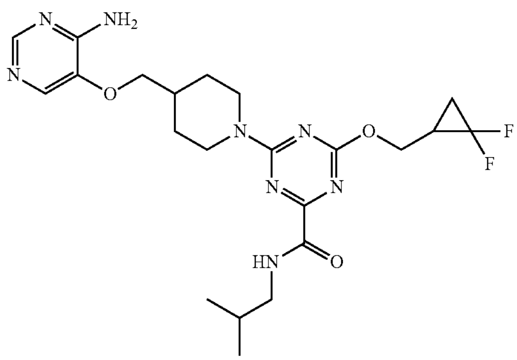 [SMILES: CC(C)CNC(=O)c1nc(OCC2CC2(F)F)nc(N2CCC(COc3cncnc3N)CC2)n1] | 4-(4-{[(4-aminopyrimidin-5-yl)oxy]methyl}piperidin-1-yl)-6-[(2,2-difluorocyclopropyl)methoxy]-N-(2-methylpropyl)-1,3,5-triazine-2-carboxamide | 493.1; (400 MHz, CDCl$_3$) δ ppm 8.25 (s, 1 H), 7.83-7.86 (m, 2 H), 5.07-5.13 (m, 3 H), 4.89 (d, J = 13.2 Hz, 1 H), 4.44-4.52 (m, 2 H), 3.95 (d, J = 6.4 Hz, 2 H), 3.27 (t, J = 6.8 Hz, 2 H), 2.99-3.03 (m, 2 H), 2.12-2.19 (m, 2 H), 1.89-2.00 (m, 3 H), 1.61 (s, 1 H), 1.32-1.44 (m, 3 H), 0.97 (d, J = 6.8 Hz, 6 H). |
| 201* | 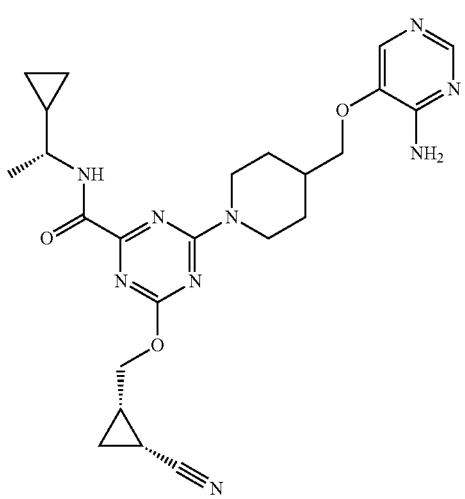 [SMILES: C[C@@H](NC(=O)c1nc(OC[C@H]2C[C@H]2C#N)nc(N2CCC(COc3cncnc3N)CC2)n1)C1CC1] | 4-(4-{[(4-aminopyrimidin-5-yl)oxy]methyl}piperidin-1-yl)-6-{[(1S,2R)-2-cyanocyclopropyl]methoxy}-N-[(1R)-1-cyclopropylethyl]-1,3,5-triazine-2-carboxamide | 494.0; (400 MHz, CDCl$_3$) δ ppm 8.30 (s, 1 H), 7.88 (s, 1 H), 7.85 (s, 1 H), 5.17-5.22 (m, 1 H), 5.12 (br. s, 2 H), 4.92-4.97 (m, 1 H), 4.62-4.68 (m, 1 H), 4.53-4.58 (m, 1 H), 3.95 (d, J = 6.0 Hz, 2 H), 3.53-3.62 (m, 1 H), 3.02-3.12 (m, 1 H), 2.15-2.31 (m, 1 H), 1.98-2.06 (m, 1 H), 1.88-1.98 (m, 1 H), 1.74-1.78 (m, 1 H), 1.42-1.53 (m, 3 H), 1.40 (d, J = 5.6 Hz, 3 H), 1.18-1.25 (m, 1H), 0.95-1.04 (m, 1 H), 0.43-0.62 (m, 3 H), 0.28-0.36 (m, 1 H). |

TABLE 1-continued

| Ex. # | Structure | Compound Name | LRMS m/z (M + H)+; and 1H NMR |
|---|---|---|---|
| 202* | 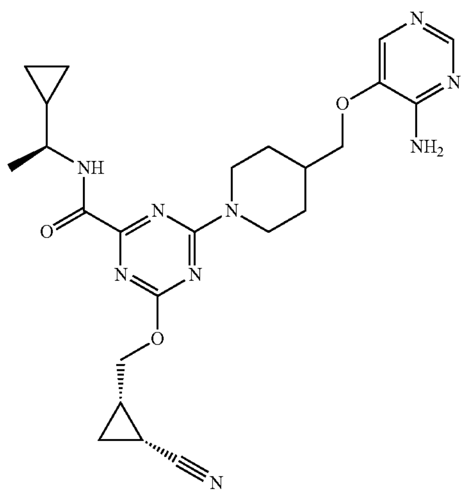 [SMILES: C[C@H](NC(=O)c1nc(OC[C@H]2C[C@H]2C#N)nc(N2CCC(COc3cncnc3N)CC2)n1)C1CC1] | 4-(4-{[(4-aminopyrimidin-5-yl)oxy]methyl}piperidin-1-yl)-6-{[(1S,2R)-2-cyanocyclopropyl]methoxy}-N-[(1S)-1-cyclopropylethyl]-1,3,5-triazine-2-carboxamide | 516.0 [M + Na]+; (400 MHz, CDCl$_3$) δ ppm 8.30 (s, 1 H), 7.88 (s, 1 H), 7.85 (s, 1 H), 5.20 (d, J = 12.0 Hz, 1 H), 5.12 (br. s., 2 H), 4.95 (m, d, J = 12.0 Hz, 1 H), 4.62-4.68 (m, 1 H), 4.53-4.58 (m, 1 H), 4.00 (d, d, J = 6.0 Hz, 2 H), 3.53-3.62 (m, 1 H), 3.02-3.12 (m, 1 H), 2.15-2.31 (m, 1 H), 1.98-2.06 (m, 1 H), 1.88-1.98 (m, 1 H), 1.74-1.78 (m, 1 H), 1.42-1.53 (m, 3 H), 1.40 (d, J = 5.6 Hz, 3 H), 1.18-1.25 (m, 1 H), 0.95-1.04 (m, 1 H), 0.43-0.62 (m, 3 H), 0.28-0.36 (m, 1 H). |
| 203*** | 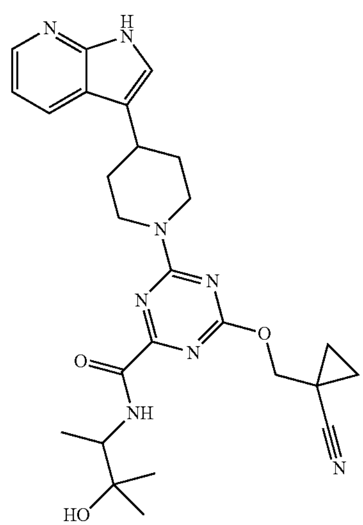 [SMILES: CC(NC(=O)c1nc(OCC2(C#N)CC2)nc(N2CCC(c3c[nH]c4ncccc34)CC2)n1)C(C)(C)O] | 4-[(1-cyanocyclopropyl)methoxy]-N-(3-hydroxy-3-methylbutan-2-yl)-6-[4-(1H-pyrrolo[2,3-b]pyridin-3-yl)piperidin-1-yl]-1,3,5-triazine-2-carboxamide | 527.1 [M + Na]+; (400 MHz, DMSO-d$_6$) δ ppm 11.37 (s, 1 H), 8.17-8.20 (m, 2 H), 8.04 (d, J = 8.0 Hz, 1 H), 7.26 (s, 1 H), 7.02 (t, J = 3.2 Hz, 1 H), 4.90 (d, J = 12.0 Hz, 1H), 4.80 (d, J = 10.8 Hz, 1 H), 4.68 (s, 1 H), 4.37-4.44 (m, 2 H), 3.81-3.85 (m, 1 H), 3.12-3.21 (m, 3 H), 2.07-2.19 (m, 2 H), 1.66-1.67 (m, 2 H), 1.36-1.38 (m, 2 H), 1.23-1.26 (m, 2 H), 1.08-1.14 (m, 9 H). |
| 204*** | 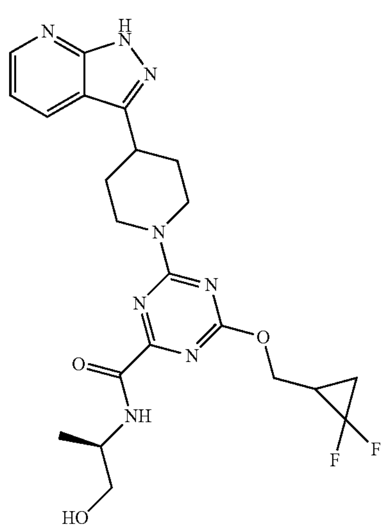 [SMILES: C[C@H](CO)NC(=O)c1nc(OCC2CC2(F)F)nc(N2CCC(c3n[nH]c4ncccc34)CC2)n1] | 4-[(2,2-difluorocyclopropyl)methoxy]-N-[(2R)-1-hydroxypropan-2-yl]-6-[4-(1H-pyrazolo[3,4-b]pyridin-3-yl)piperidin-1-yl]-1,3,5-triazine-2-carboxamide | 489.1; (400 MHz, CDCl$_3$) δ ppm 8.57 (s, 1 H), 8.10 (d, J = 6.8 Hz, 1 H), 7.94 (s, 1 H), 7.15 (s, 1 H), 5.06 (d, J = 14.4 Hz, 1 H), 4.89 (d, J = 12.8 Hz, 1 H), 4.45-4.53 (m, 2 H), 4.23 (s, 1 H), 3.69-3.77 (m, 2 H), 3.24-3.41 (m, 3 H), 2.02-2.20 (m, 5 H), 1.30-1.32 (m, 4 H). |

TABLE 1-continued

| Ex. # | Structure | Compound Name | LRMS m/z (M + H)+; and 1H NMR |
|---|---|---|---|
| 205*** | 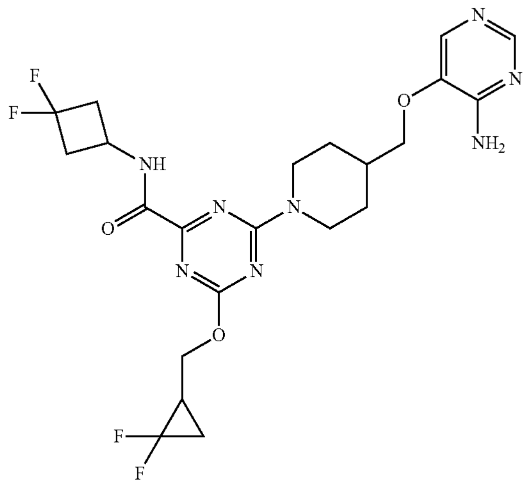 [SMILES: Nc1ncncc1OCC1CCN(c2nc(OCC3CC3(F)F)nc(C(=O)NC3CC(F)(F)C3)n2)CC1] | 4-(4-{[(4-aminopyrimidin-5-yl)oxy]methyl}piperidin-1-yl)-N-(3,3-difluorocyclobutyl)-6-[(2,2-difluorocyclopropyl)methoxy]-1,3,5-triazine-2-carboxamide | 527.2; (400 MHz, DMSO-d$_6$) δ ppm 9.12 (d, J = 7.6 Hz, 1 H), 7.99 (s, 1 H), 7.79 (s, 1 H), 6.69 (br. s., 2 H), 4.88 (d, J = 12.0 Hz, 1 H), 4.69 (d, J = 13.6 Hz, 1 H), 4.53-4.58 (m, 1 H), 4.24-4.29 (m, 2 H), 3.91 (d, J = 6.0 Hz, 2 H), 2.97-3.03 (m, 2 H), 2.87-2.92 (m, 4 H) 2.23-2.26 (m, 1 H), 2.08-2.13 (m, 1 H), 1.94 (d, J = 12.8 Hz, 2 H), 1.73-1.78 (m, 1 H), 1.52-1.57 (m, 1 H), 1.31-1.34 (m, 2 H). |
| 206*** | 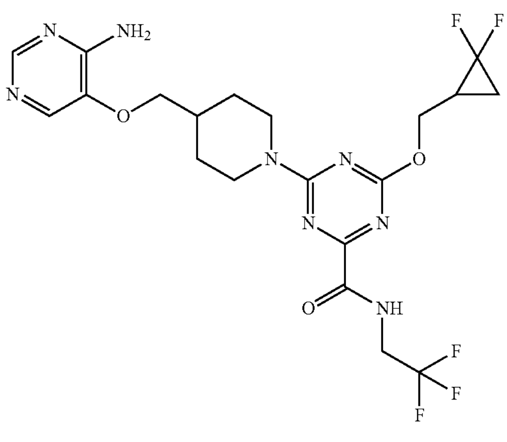 [SMILES: Nc1ncncc1OCC1CCN(c2nc(OCC3CC3(F)F)nc(C(=O)NCC(F)(F)F)n2)CC1] | 4-(4-{[(4-aminopyrimidin-5-yl)oxy]methyl}piperidin-1-yl)-6-[(2,2-difluorocyclopropyl)methoxy]-N-(2,2,2-trifluoroethyl)-1,3,5-triazine-2-carboxamide | 519.2; (400 MHz, DMSO-d$_6$) δ ppm 9.32 (t, J = 6.0 Hz, 1 H), 7.99 (s, 1 H), 7.79 (s, 1 H), 6.69 (s, 2 H), 4.91 (d, J = 12.4 Hz, 1 H), 4.68-4.71 (m, 1 H), 4.53-4.56 (m, 1 H), 4.27 (t, J = 9.2 Hz, 1 H), 4.03 (t, J = 8.4 Hz, 2 H), 3.91 (d, J = 5.2 Hz, 2 H), 2.98-3.06 (m, 2 H), 2.23-2.27 (m, 1 H), 2.11-2.17 (m, 1 H), 1.92 (d, J = 11.2 Hz, 2 H), 1.73-1.78 (m, 1 H), 1.54-1.57 (m, 1 H), 1.32-1.41 (m, 2H). |
| 207*** | 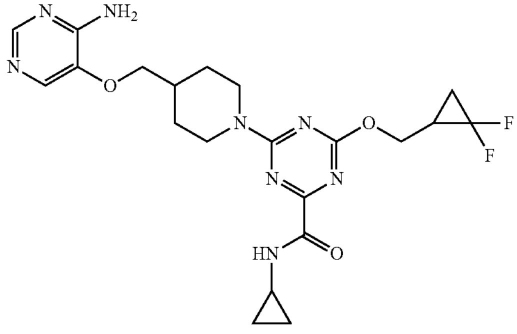 [SMILES: Nc1ncncc1OCC1CCN(c2nc(OCC3CC3(F)F)nc(C(=O)NC3CC3)n2)CC1] | 4-(4-{[(4-aminopyrimidin-5-yl)oxy]methyl}piperidin-1-yl)-N-cyclopropyl-6-[(2,2-difluorocyclopropyl)methoxy]-1,3,5-triazine-2-carboxamide | 477.1; (400 MHz, DMSO-d$_6$) δ ppm 8.67 (d, J = 4.8 Hz, 1 H), 8.00 (s, 1 H), 7.79 (s, 1 H), 6.69 (br. s., 2 H), 4.87 (d, J = 12.8 Hz, 1 H), 4.69 (d, J = 11.2 Hz, 1 H), 4.52-4.54 (m, 1 H), 4.28 (t, J = 10.4 Hz, 1 H), 3.90 (d, J = 5.2 Hz, 2 H), 3.00 (t, J = 12.0 Hz, 2 H), 2.80 (d, J = 4.4 Hz, 1 H), 2.11-2.24 (m, 2 H), 1.93 (d, J = 12.8 Hz, 2 H), 1.72-1.75 (m, 1 H), 1.52-1.57 (m, 1 H), 1.30-1.33 (m, 2 H), 0.63-0.71 (m, 4 H). |

TABLE 1-continued

| Ex. # | Structure | Compound Name | LRMS m/z (M + H)+; and ¹H NMR |
|---|---|---|---|
| 208*** | 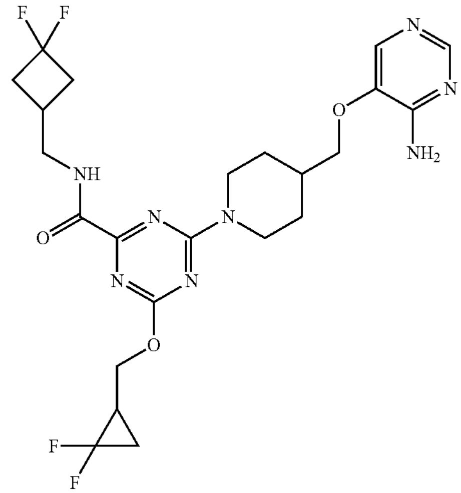 [SMILES: Nc1ncncc1OCC1CCN(c2nc(OCC3CC3(F)F)nc(C(=O)NCC3CC(F)(F)C3)n2)CC1] | 4-(4-{[(4-aminopyrimidin-5-yl)oxy]methyl}piperidin-1-yl)-N-[(3,3-difluorocyclobutyl)methyl]-6-[(2,2-difluorocyclopropyl)methoxy]-1,3,5-triazine-2-carboxamide | 541.2; (400 MHz, DMSO-d₆) δ ppm 8.96-8.97 (m, 1 H), 8.00 (s, 1 H), 7.79 (s, 1 H), 6.70 (br. s., 2 H), 4.90 (d, J = 12.0 Hz, 1 H), 4.68-4.71 (m, 1 H), 4.53-4.58 (m, 1 H), 4.28 (t, J = 12.0 Hz, 1 H), 3.91 (d, J = 6.4 Hz, 2 H), 2.98-3.01 (m, 2 H), 2.61-2.63 (m, 2 H), 2.12-2.39 (m, 7 H), 1.94 (d, J = 12.0 Hz, 2 H), 1.73-1.78 (m, 1 H), 1.54-1.62 (m, 1 H), 1.32-1.36 (m, 2H). |
| 209*** | 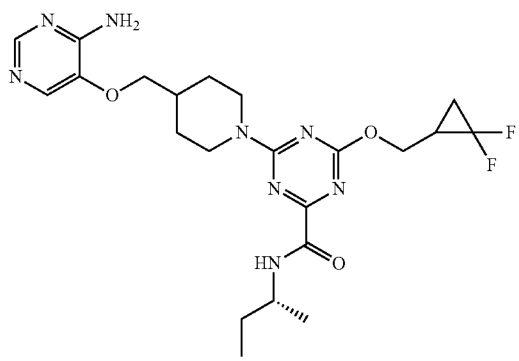 [SMILES: CC[C@@H](C)NC(=O)c1nc(OCC2CC2(F)F)nc(N2CCC(COc3cncnc3N)CC2)n1] | 4-(4-{[(4-aminopyrimidin-5-yl)oxy]methyl}piperidin-1-yl)-N-[(2R)-butan-2-yl]-6-[(2,2-difluorocyclopropyl)methoxy]-1,3,5-triazine-2-carboxamide | 493.1; (400 MHz, CDCl₃) δ ppm 8.25 (s, 1 H), 7.83 (s, 1 H), 7.60 (d, J = 8.8 Hz, 1 H), 5.03-5.14 (m, 3 H), 4.88 (d, J = 13.2 Hz, 1 H), 4.43-4.52 (m, 2 H), 4.06-4.12 (m, 1 H), 3.95 (d, J = 6.4 Hz, 2 H), 2.96-3.02 (m, 2 H), 2.13-2.24 (m, 2 H), 1.96-1.99 (m, 2 H), 1.59-1.64 (m, 2 H), 1.36-1.44 (m, 3 H), 1.23-1.27 (m, 4 H), 0.95 (t, J = 7.6 Hz, 3 H). |
| 210* | 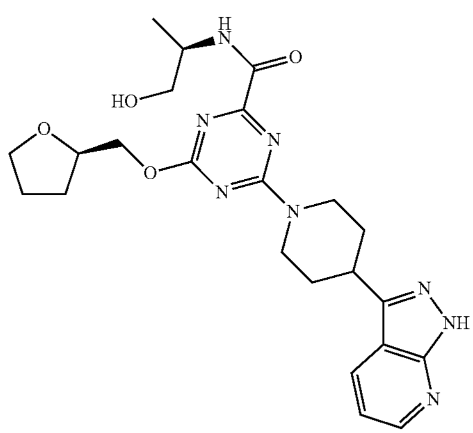 [SMILES: C[C@H](CO)NC(=O)c1nc(OC[C@H]2CCCO2)nc(N2CCC(c3n[nH]c4ncccc34)CC2)n1] | N-[(2R)-1-hydroxypropan-2-yl]-4-[4-(1H-pyrazolo[3,4-b]pyridin-3-yl)piperidin-1-yl]-6-[(2R)-tetrahydrofuran-2-ylmethoxy]-1,3,5-triazine-2-carboxamide | 483.2; (600 MHz, DMSO-d₆) δ ppm 8.45-8.49 (m, 1 H), 8.26-8.35 (m, 2 H), 7.16 (td, J = 4.5, 7.6 Hz, 1 H), 4.88 (br. s., 1 H), 4.73 (br. s., 1 H), 4.28-4.32 (m, 2 H), 4.15 (d, J = 5.1 Hz, 1 H), 3.94 (d, J = 6.5 Hz, 1 H), 3.77 (t, J = 6.9 Hz, 1 H), 3.62-3.69 (m, 1 H), 3.44 (br. s., 1 H), 3.23 (br. s., 1 H), 2.12 (br. s., 2 H), 1.95-2.01 (m, 1 H), 1.77-1.91 (m, 5 H), 1.58-1.68 (m, 2H), 1.13 (t, J = 7.0 Hz, 3 H). |

TABLE 1-continued

| Ex. # | Structure | Compound Name | LRMS m/z (M + H)+; and 1H NMR |
|---|---|---|---|
| 211* | 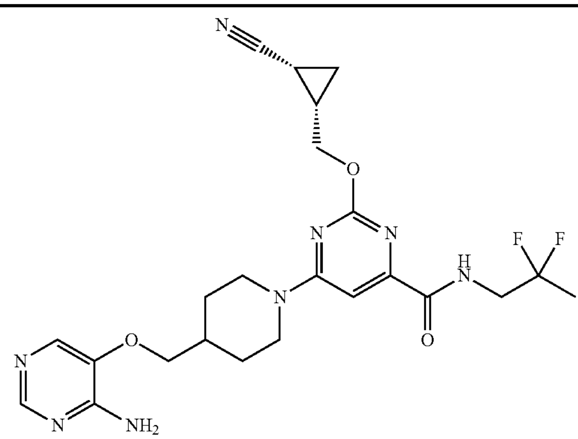 | 6-(4-{[(4-aminopyrimidin-5-yl)oxy]methyl}piperidin-1-yl)-2-{[(1S,2R)-2-cyanocyclopropyl]methoxy}-N-(2,2-difluoropropyl)pyrimidine-4-carboxamide | 525.1 [M + Na]+; (400 MHz, CD$_3$OD) δ ppm 8.08 (br. s., 1 H), 7.80 (br. s., 1 H), 7.13 (s, 1 H), 4.70-4.75 (m, 3 H), 4.24-4.29 (m, 1 H), 3.99 (d, J = 6.4 Hz, 2 H), 3.81 (t, J = 14.0 Hz, 2 H), 3.11-3.12 (m, 2 H), 2.56 (br. s., 1H), 2.04 (d, J = 12.4 Hz, 2 H), 1.86-1.88 (m, 2 H), 1.65 (t, J = 14.4 Hz, 3 H), 1.36-1.44 (m, 3 H), 1.12-1.14 (m, 1 H). |
| 212* | 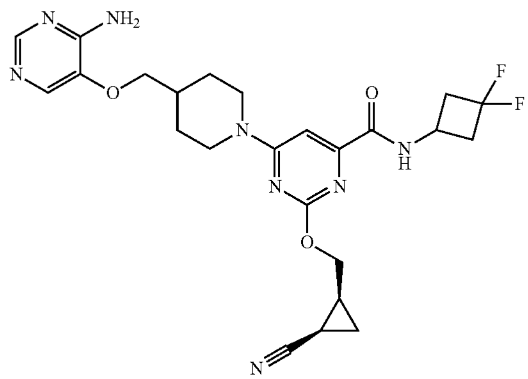 [SMILES: N#C[C@@H]1C[C@@H]1COc1nc(C(=O)NC2CC(F)(F)C2)cc(N2CCC(COc3cncnc3N)CC2)n1] | 6-(4-{[(4-aminopyrimidin-5-yl)oxy]methyl}piperidin-1-yl)-2-{[(1S,2R)-2-cyanocyclopropyl]methoxy}-N-(3,3-difluorocyclobutyl)pyrimidine-4-carboxamide | 537.1 [M + Na]+; (400 MHz, CD$_3$OD) δ ppm 8.05 (br. s., 1 H), 7.78 (br. s., 1 H), 7.07 (s, 1 H), 4.72-4.76 (m, 3 H), 4.24-4.36 (m, 2 H), 3.99 (d, J = 6.0 Hz, 2 H), 2.95-3.09 (m, 4 H), 2.79-2.81 (m, 2 H), 2.04 (br. s., 1 H), 1.91 (d, J = 8.0 Hz, 2H), 1.86-1.89 (m, 2 H), 1.36-1.44 (m, 3 H), 1.12-1.14 (m, 1 H). |
| 213* | 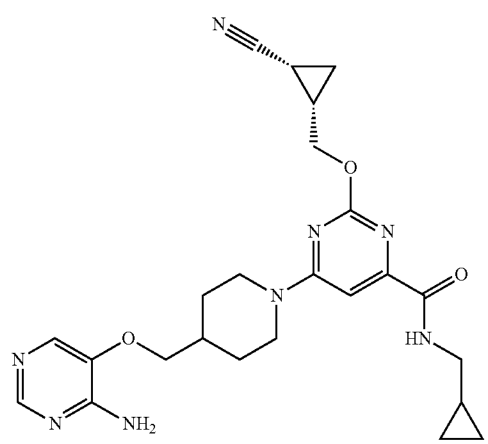 [SMILES: N#C[C@@H]1C[C@@H]1COc1nc(C(=O)NCC2CC2)cc(N2CCC(COc3cncnc3N)CC2)n1] | 6-(4-{[(4-aminopyrimidin-5-yl)oxy]methyl}piperidin-1-yl)-2-{[(1S,2R)-2-cyanocyclopropyl]methoxy}-N-(cyclopropylmethyl)pyrimidine-4-carboxamide | 479.0; (400 MHz, CD$_3$OD) δ ppm 8.03 (s, 1 H), 7.78 (s, 1 H), 7.10 (s, 1 H), 4.62-4.74 (m, 3 H), 4.24-4.29 (m, 1 H), 3.99 (d, J = 6.0 Hz, 2 H), 3.27-3.26 (d, J = 6.4 Hz, 2 H), 3.10 (t, J = 12.4 Hz, 2 H), 2.26 (br. s., 1 H), 2.03 (d, J = 11.2 Hz, 2 H), 1.87-1.90 (m, 2 H), 1.36-1.44 (m, 3 H), 1.11-1.14 (m, 2 H), 0.57 (d, J = 5.6 Hz, 2H), 0.31 (d, J = 4.4 Hz, 2 H). |
| 214*** | 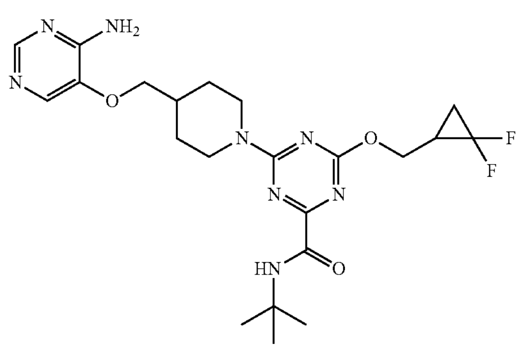 [SMILES: CC(C)(C)NC(=O)c1nc(OCC2CC2(F)F)nc(N2CCC(COc3cncnc3N)CC2)n1] | 4-(4-{[(4-aminopyrimidin-5-yl)oxy]methyl}piperidin-1-yl)-N-tert-butyl-6-[(2,2-difluorocyclopropyl)methoxy]-1,3,5-triazine-2-carboxamide | 493.2; (400 MHz, CDCl$_3$) δ ppm 8.25 (s, 1 H), 7.83 (s, 1 H), 7.71 (s, 1 H), 5.07-5.11 (m, 3 H), 4.88 (d, J = 12.0 Hz, 1 H), 4.44-4.50 (m, 2 H), 3.94 (d, J = 6.0 Hz, 2 H), 2.95-3.05 (m, 2 H), 2.13-2.24 (m, 2 H), 1.96-1.99 (m, 2 H), 1.58 (br. s., 1 H), 1.27-1.47 (m, 12 H). |

TABLE 1-continued

| Ex. # | Structure | Compound Name | LRMS m/z (M + H)+; and 1H NMR |
|---|---|---|---|
| 215* | 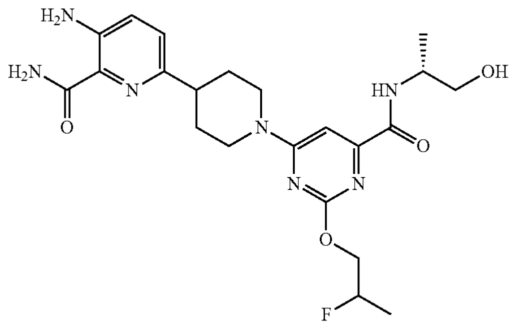 [SMILES: CC(F)COc1nc(C(=O)N[C@H](C)CO)cc(N2CCC(c3ccc(N)c(C(N)=O)n3)CC2)n1] | 6-[4-(5-amino-6-carbamoylpyridin-2-yl)piperidin-1-yl]-2-(2-fluoropropoxy)-N-[(2R)-1-hydroxypropan-2-yl]pyrimidine-4-carboxamide | 498.2 [M + Na]+; (400 MHz, DMSO-$d_6$) δ ppm 8.17-8.19 (m, 1 H), 7.85 (s, 1 H), 7.27 (s, 1 H), 7.18-7.20 (m, 1 H), 7.08-7.10 (m, 1 H), 7.02 (s, 1 H), 6.68 (s, 2 H), 4.88-5.08 (m, 2 H), 4.30-4.49 (m, 3 H), 3.96-3.99 (m, 1 H), 3.42-3.48 (m, 3 H), 3.00-3.16 (m, 2 H), 2.86-2.91 (m, 1 H), 1.90-1.94 (m, 2 H), 1.66-1.71 (m, 2 H), 1.33-1.41 (m, 3 H), 1.13-1.24 (m, 3 H). |
| 216*** | 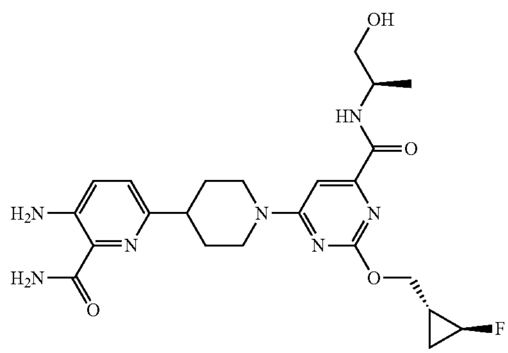 [SMILES: C[C@H](CO)NC(=O)c1cc(N2CCC(c3ccc(N)c(C(N)=O)n3)CC2)nc(OC[C@H]2C[C@@H]2F)n1] | 6-[4-(5-amino-6-carbamoylpyridin-2-yl)piperidin-1-yl]-2-{[(1R,2S)-2-fluorocyclopropyl]methoxy}-N-[(2R)-1-hydroxypropan-2-yl]pyrimidine-4-carboxamide | 488.1; (400 MHz, CDCl$_3$) δ ppm 7.92 (d, J = 8.0 Hz, 1 H), 7.84 (s, 1 H), 7.12 (s, 1H), 7.08 (d, J = 8.8 Hz, 1 H), 6.98 (d, J = 8.8 Hz, 1 H), 5.85 (s, 2 H), 5.35 (s, 1 H), 4.52-4.67 (m, 3 H), 4.10-4.20 (m, 3 H), 3.62-3.76 (m, 2 H), 3.02-3.07 (m, 2 H), 2.82-2.92 (m, 2 H), 1.98-2.02 (m, 2 H), 1.62-1.82 (m, 3 H), 1.20-1.29 (m, 4 H), 0.73-0.78 (m, 1 H). |
| 217*** | 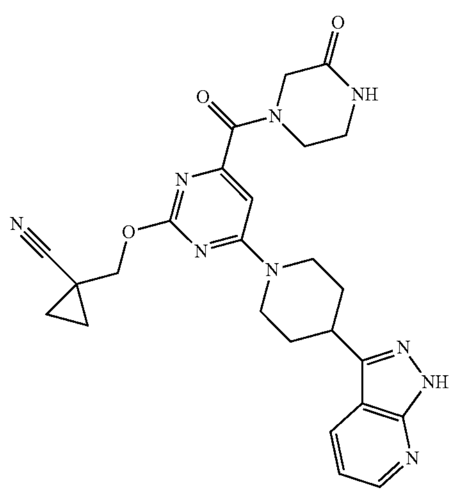 [SMILES: N#CC1(COc2nc(C(=O)N3CCNC(=O)C3)cc(N3CCC(c4n[nH]c5ncccc45)CC3)n2)CC1] | 1-[({4-[(3-oxopiperazin-1-yl)carbonyl]-6-[4-(1H-pyrazolo[3,4-b]pyridin-3-yl)piperidin-1-yl]pyrimidin-2-yl}oxy)methyl]cyclopropanecarbonitrile | 502.2; (700 MHz, DMSO-$d_6$) δ ppm 8.47 (d, J = 4.4 Hz, 1 H), 8.28-8.32 (m, 1 H), 8.13 (br. s., 1 H), 7.14 (dd, J = 7.9, 4.5 Hz, 1 H), 6.69-6.74 (m, 1 H), 4.24-4.26 (m, 2 H), 4.07 (s, 1 H), 4.00 (s, 1 H), 3.74 (t, J = 5.4 Hz, 1 H), 3.58 (t, J = 5.2 Hz, 1 H), 3.19-3.26 (m, 2 H), 2.08 (d, J = 12.0 Hz, 2 H), 1.75-1.84 (m, 2 H), 1.32-1.34 (m, 2H), 1.17-1.19 (m, 2H). |
| 218 | 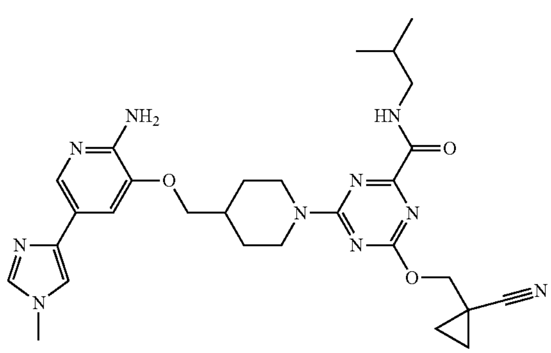 [SMILES: CC(C)CNC(=O)c1nc(OCC2(C#N)CC2)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(2-methylpropyl)-1,3,5-triazine-2-carboxamide | 561.2; (400 MHz, DMSO-$d_6$) δ ppm 8.73-8.76 (m, 1 H), 7.90 (s, 1 H), 7.56 (s, 1 H), 7.43 (s, 1 H), 7.32 (s, 1 H), 5.62 (s, 2 H), 4.88-4.91 (m, 1 H), 4.69-4.72 (m, 1 H), 4.40 (s, 2 H), 3.89-3.90 (m, 2 H), 3.64 (s, 3 H), 3.03-3.06 (m, 4 H), 2.32-2.33 (m, 1 H), 1.94-1.97 (m, 2 H), 1.82-1.87 (m, 1 H), 1.35-1.38 (m, 4 H), 1.21-1.24 (m, 2 H), 0.86 (d, J = 6.8 Hz, 6H). |

| Ex. # | Structure | Compound Name | LRMS m/z (M + H)+; and 1H NMR |
|---|---|---|---|
| 219 | 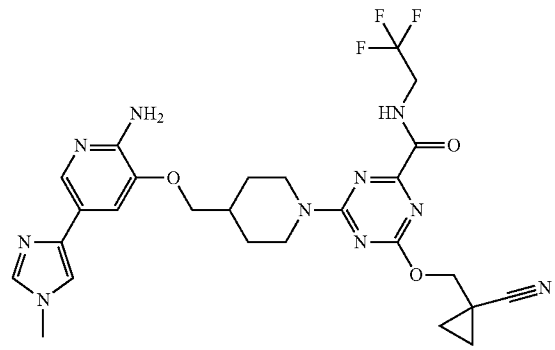 [SMILES: Cn1cnc(-c2cnc(N)c(OCC3CCN(c4nc(OCC5(C#N)CC5)nc(C(=O)NCC(F)(F)F)n4)CC3)c2)c1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(2,2,2-trifluoroethyl)-1,3,5-triazine-2-carboxamide | 587.1; (400 MHz, DMSO-$d_6$) δ ppm 9.33-9.36 (m, 1 H), 7.91 (s, 1 H), 7.56 (s, 1 H), 7.43 (s, 1 H), 7.32 (s, 1 H), 5.62 (s, 2 H), 4.91-4.94 (m, 1 H), 4.71-4.74 (m, 1 H), 4.38-4.45 (m, 2 H), 4.02-4.06 (m, 2 H), 3.90-3.91 (m, 2 H), 3.65 (s, 3 H), 3.01-3.09 (m, 2 H), 2.14-2.16 (m, 1 H), 1.91-1.99 (m, 2 H), 1.22-1.37 (m, 6 H). |
| 220* | 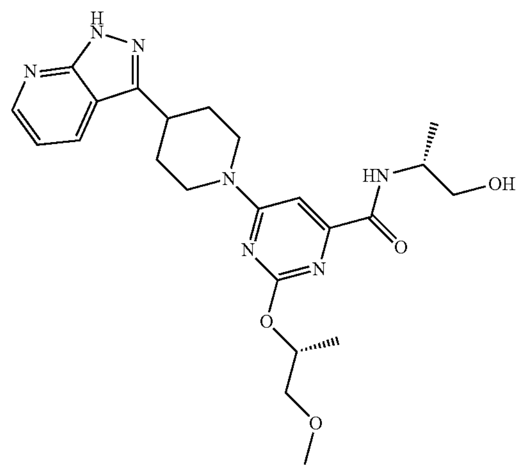 [SMILES: COC[C@@H](C)Oc1nc(C(=O)N[C@H](C)CO)cc(N2CCC(c3n[nH]c4ncccc34)CC2)n1] | N-[(2R)-1-hydroxypropan-2-yl]-2-{[(2R)-1-methoxypropan-2-yl]oxy}-6-[4-(1H-pyrazolo[3,4-b]pyridin-3-yl)piperidin-1-yl]pyrimidine-4-carboxamide | 470.1; (400 MHz, CDCl$_3$) δ ppm 11.86 (br. s., 1 H), 8.58 (s, 1 H), 8.10 (d, J = 8.0 Hz, 1 H), 7.98 (d, J = 7.6 Hz, 1 H), 7.13-7.15 (m, 2 H), 5.29-5.35 (m, 1 H), 4.58 (br. s., 2 H), 4.22-4.23 (m, 1 H), 3.65-3.72 (m, 3 H), 3.51-3.52 (m, 1 H), 3.41-3.49 (m, 4 H), 3.22-3.25 (m, 3 H), 2.19 (d, J = 12.4 Hz, 2 H), 1.97-2.05 (m, 2H), 1.38 (d, J = 6.4 Hz, 3 H), 1.28 (d, J = 6.8 Hz, 3 H). |
| 221 | 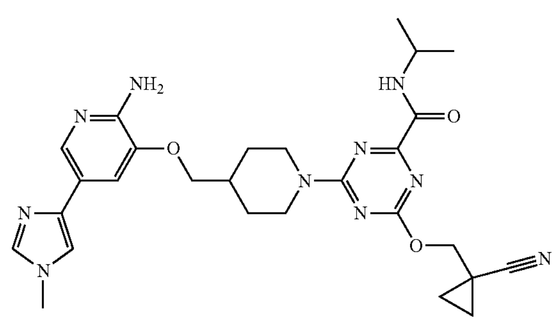 | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(propan-2-yl)-1,3,5-triazine-2-carboxamide | 569.1 [M + Na]+; (400 MHz, DMSO-$d_6$) δ ppm 8.41 (d, J = 8.4 Hz, 1 H), 7.90 (s, 1 H), 7.56 (s, 1 H), 7.43 (s, 1 H), 7.31 (s, 1 H), 5.61 (d, J = 5.2 Hz, 2 H), 4.87 (d, J = 12.8 Hz, 1 H), 4.72 (d, J = 12.4 Hz, 1 H), 4.36-4.42 (m, 2 H), 4.00-4.05 (m, 1 H), 3.89-3.90 (m, 2 H), 3.64 (s, 3 H), 3.01-3.03 (m, 2 H), 2.14-2.18 (m, 1 H), 1.95-1.98 (m, 2 H), 1.28-1.36 (m, 4 H), 1.21-1.24 (m, 2 H), 1.16 (d, J = 6.8 Hz, 6 H). |
| 222 | 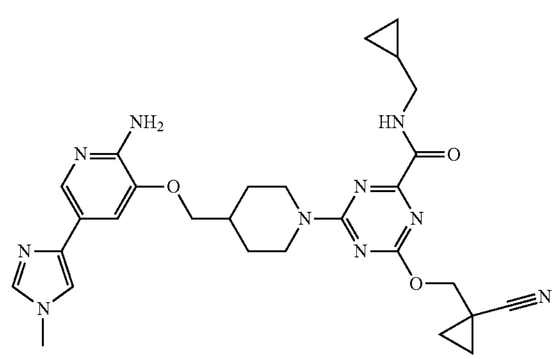 [SMILES: Cn1cnc(-c2cnc(N)c(OCC3CCN(c4nc(OCC5(C#N)CC5)nc(C(=O)NCC5CC5)n4)CC3)c2)c1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(cyclopropylmethyl)-1,3,5-triazine-2-carboxamide | 581.1 [M + Na]+; (400 MHz, DMSO-$d_6$) δ ppm 8.86 (t, J = 5.6 Hz, 1 H), 7.90 (s, 1 H), 7.59 (s, 1 H), 7.45 (s, 1 H), 7.33 (s, 1 H), 5.66 (s, 2 H), 4.89 (d, J = 12.4 Hz, 1 H), 4.72 (d, J = 12.0 Hz, 1 H), 4.38-4.44 (m, 2 H), 3.91 (d, J = 6.0 Hz, 2 H), 3.66 (s, 3 H), 3.03-3.13 (m, 4 H), 2.14-2.08 (m, 1 H), 1.96-1.99 (m, 2 H), 1.29-1.38 (m, 4 H), 1.22-1.25 (m, 2 H), 1.03-1.04 (m, 1 H), 0.41-0.43 (m, 2 H), 0.22-0.24 (m, 2H). |

| Ex. # | Structure | Compound Name | LRMS m/z (M + H)+; and 1H NMR |
|---|---|---|---|
| 223 | 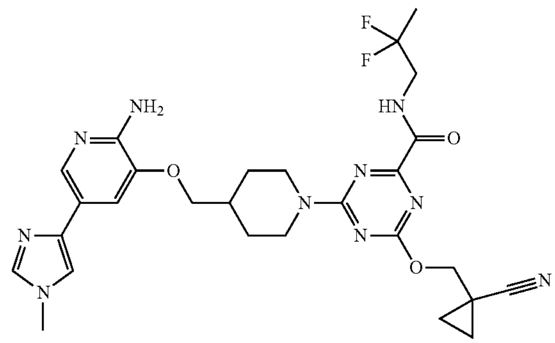 [SMILES: Cn1cnc(-c2cnc(N)c(OCC3CCN(c4nc(OCC5(C#N)CC5)nc(C(=O)NCC(C)(F)F)n4)CC3)c2)c1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(2,2-difluoropropyl)-1,3,5-triazine-2-carboxamide | 583.3; (400 MHz, DMSO-d$_6$) δ ppm 9.05 (t, J = 6.8 Hz, 1 H), 7.90 (d, J = 1.2 Hz, 1 H), 7.57 (s, 1 H), 7.43 (s, 1 H), 7.32 (s, 1 H), 5.64 (br. s., 2 H), 4.91 (d, J = 12.4 Hz, 1 H), 4.72 (d, J = 11.2 Hz, 1 H), 4.38-4.41 (m, 2 H), 3.90 (d, J = 5.6 Hz, 2 H), 3.67-3.69 (m, 1 H), 3.64 (s, 3 H), 3.00-3.05 (m, 2 H), 2.14-2.18 (m, 1 H), 1.97 (d, J = 12.0 Hz, 2 H), 1.60 (t, J = 18.8 Hz, 3 H), 1.35-1.38 (m, 4 H), 1.21-1.24 (m, 2 H). |
| 224*** | 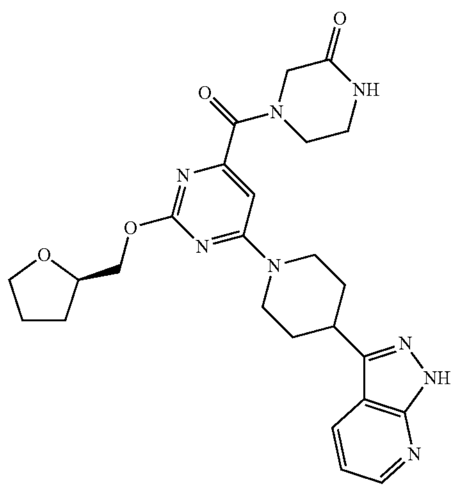 [SMILES: O=C1CN(C(=O)c2cc(N3CCC(c4n[nH]c5ncccc45)CC3)nc(OC[C@H]3CCCO3)n2)CCN1] | 4-({6-[4-(1H-pyrazolo[3,4-b]pyridin-3-yl)piperidin-1-yl]-2-[(2R)-tetrahydrofuran-2-ylmethoxy]pyrimidin-4-yl}carbonyl)piperazin-2-one | 506.2; (700 MHz, DMSO-d$_6$) δ ppm 8.43 (d, J = 4.4 Hz, 1 H), 8.25-8.28 (m, 1 H), 8.05-8.11 (m, 1 H), 7.09 (dd, J = 4.5, 7.9 Hz, 1 H), 6.65-6.67 (m, 1 H), 4.12-4.17 (m, 2 H), 4.05-4.10 (m, 1 H), 4.03 (s, 1 H), 3.97 (s, 1 H), 3.68-3.75 (m, 2 H), 3.61 (q, J = 7.5 Hz, 1 H), 3.08-3.42 (m, 8 H), 2.05 (d, J = 11.6 Hz, 2 H), 1.90-1.96 (m, 1 H), 1.71-1.86 (m, 5H), 1.56-1.62 (m, 1 H). |
| 225* | 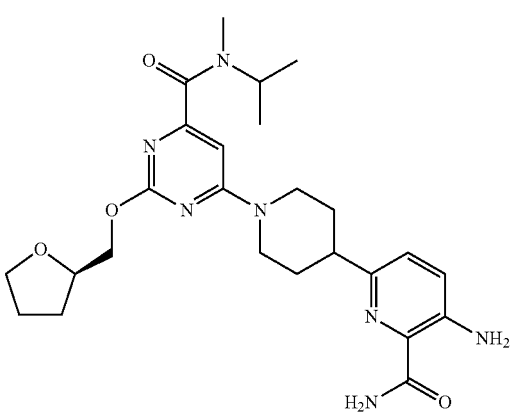 [SMILES: CC(C)N(C)C(=O)c1cc(N2CCC(c3ccc(N)c(C(N)=O)n3)CC2)nc(OC[C@H]2CCCO2)n1] | 6-[4-(5-amino-6-carbamoylpyridin-2-yl)piperidin-1-yl]-N-methyl-N-(propan-2-yl)-2-[(2R)-tetrahydrofuran-2-ylmethoxy]pyrimidine-4-carboxamide | 498.1; (700 MHz, DMSO-d$_6$) δ ppm 7.84 (br. s., 1 H), 7.24 (br. s., 1 H), 7.18 (d, J = 8.7 Hz, 1 H), 7.09 (d, J = 8.5 Hz, 1 H), 6.66 (br. s., 2 H), 6.52-6.54 (m, 1 H), 4.63-4.67 (m, 1 H), 4.09-4.17 (m, 3 H), 3.83 (dt, J = 13.2, 6.6 Hz, 1 H), 3.74-3.76 (m, 1 H), 3.65 (q, J = 7.3 Hz, 1 H), 2.99 (br. s., 1 H), 2.83-2.87 (m, 1 H), 2.78 (s, 2 H), 2.71 (s, 1 H), 1.93-1.98 (m, 1 H), 1.79-1.88 (m, 4 H), 1.60-1.66 (m, 3 H), 1.11-1.13 (m, 6 H). |

TABLE 1-continued

| Ex. # | Structure | Compound Name | LRMS m/z (M + H)+; and 1H NMR |
|---|---|---|---|
| 226*** | 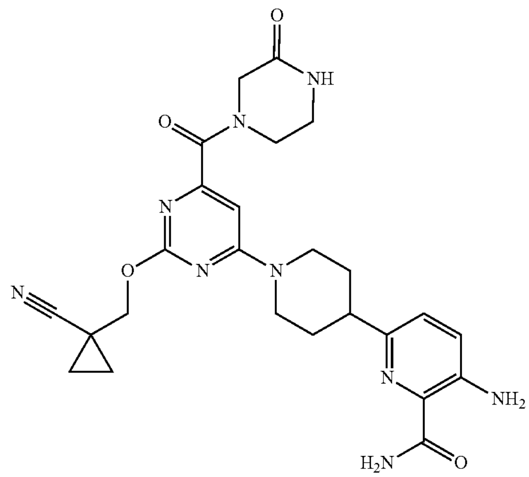 [SMILES: N#CC1(COc2nc(C(=O)N3CCNC(=O)C3)cc(N3CCC(c4ccc(N)c(C(N)=O)n4)CC3)n2)CC1] | 3-amino-6-(1-{2-[(1-cyanocyclopropyl)methoxy]-6-[(3-oxopiperazin-1-yl)carbonyl]pyrimidin-4-yl}piperidin-4-yl)pyridine-2-carboxamide | 520.2; (700 MHz, DMSO-d$_6$) δ ppm 8.12 (br. s., 1 H), 7.82-7.86 (m, 1 H), 7.21-7.25 (m, 1 H), 7.17 (d, J = 6.7 Hz, 1 H), 7.09 (br. s., 1 H), 6.63-6.72 (m, 3 H), 4.24 (br. s., 2 H), 4.05-4.06 (m, 1 H), 3.98 (d, J = 3.1 Hz, 1 H), 3.71-3.74 (m, 1 H), 3.57 (br. s., 1 H), 3.35 (d, J = 10.8 Hz, 1 H), 3.19-3.25 (m, 1 H), 2.85-2.87 (m, 1 H), 2.53-2.55 (m, 1 H), 1.88 (br. s., 4 H), 1.66 (br. s., 4 H), 1.34 (d, J = 3.8 Hz, 4 H), 1.16-1.24 (m, 6 H). |
| 227*** | 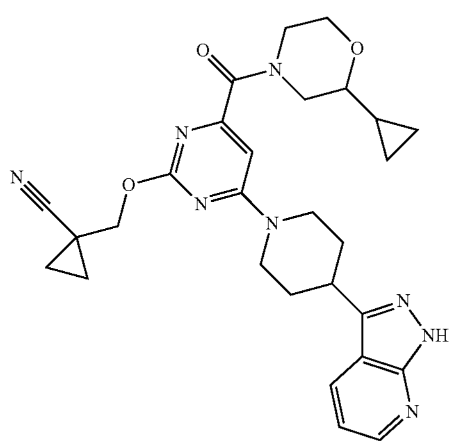 [SMILES: N#CC1(COc2nc(C(=O)N3CCOC(C4CC4)C3)cc(N3CCC(c4n[nH]c5ncccc45)CC3)n2)CC1] | 1-[({4-[(2-cyclopropylmorpholin-4-yl)carbonyl]-6-[4-(1H-pyrazolo[3,4-b]pyridin-3-yl)piperidin-1-yl]pyrimidin-2-yl}oxy)methyl]cyclopropanecarbonitrile | 529.1; (700 MHz, DMSO-d$_6$) δ ppm 8.48 (d, J = 3.2 Hz, 1 H), 8.31 (J = 8.0 Hz, 1 H), 7.14 (dd, J = 8.0, 4.4 Hz, 1 H), 6.69 (d, J = 1.5 Hz, 1 H), 4.15-4.34 (m, 3 H), 3.90 (d, J = 11.3 Hz, 0.5 H), 3.77 (d, J = 11.8 Hz, 0.5 H), 3.63 (d, J = 13.0 Hz, 0.5 H), 3.53 (d, J = 13.8 Hz, 0.5 H), 3.39-3.44 (m, 0.5 H), 3.17 (d, J = 11.3 Hz, 1 H), 3.02-3.05 (m, 0.5 H), 2.90-2.93 (m, 0.5 H), 2.74-2.81 (m, 2 H), 2.09 (d, J = 12 Hz, 2 H), 1.79-1.84 (m, 2 H), 1.34 (d, J = 4.6 Hz, 2 H), 1.19 (J = 1.4 Hz, 2 H), 0.90 (d, J = 5.0 Hz, 0.5 H), 0.80 (d, J = 5.3 Hz, 0.5 H), 0.49 (d, J = 8.0 Hz, 1 H), 0.26-0.43 (m, 3 H), 0.10 (d, J = 4.4 Hz, 0.5 H). |
| 228 | 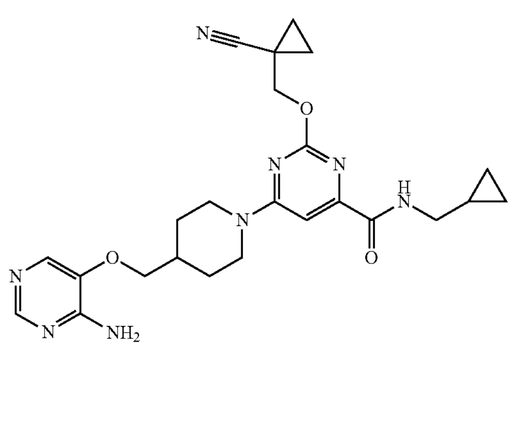 [SMILES: N#CC1(COc2nc(C(=O)NCC3CC3)cc(N3CCC(COc4cncnc4N)CC3)n2)CC1] | 6-(4-{[(4-aminopyrimidin-5-yl)oxy]methyl}piperidin-1-yl)-2-[(1-cyanocyclopropyl)methoxy]-N-(cyclopropylmethyl)pyrimidine-4-carboxamide | 479.1; (400 MHz, CDCl$_3$) δ ppm 8.24 (s, 1 H), 8.00 (t, J = 5.6 Hz, 1 H), 7.81 (s, 1 H), 7.15 (s, 1 H), 5.09 (s, 2 H), 4.65 (br. s., 2 H), 4.37 (s, 2 H), 3.93 (d, J = 6.4 Hz, 2 H), 3.29 (t, J = 6.0 Hz, 2 H), 2.95-3.01 (m, 2 H), 2.17-2.19 (m, 1 H), 1.96 (d, J = 12.4 Hz, 2 H), 1.39-1.44 (m, 4 H), 1.17-1.20 (m, 2 H), 1.02-1.06 (m, 1 H), 0.52-0.55 (m, 2 H), 0.27-0.30 (m, 2 H). |

TABLE 1-continued

| Ex. # | Structure | Compound Name | LRMS m/z (M + H)+; and 1H NMR |
|---|---|---|---|
| 229*** | 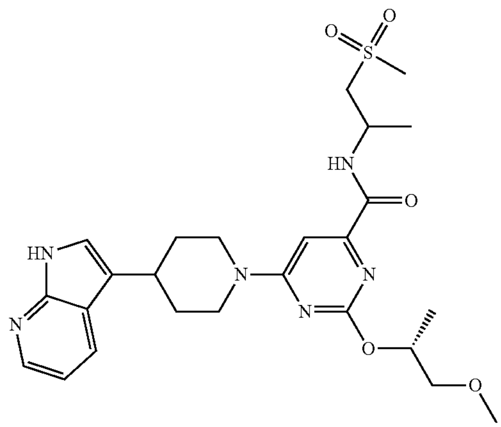 [SMILES: COC[C@@H](C)Oc1nc(C(=O)NC(C)CS(C)(=O)=O)cc(N2CCC(c3c[nH]c4ncccc34)CC2)n1] | 2-{[(2R)-1-methoxypropan-2-yl]oxy}-N-[1-(methylsulfonyl)propan-2-yl]-6-[4-(1H-pyrrolo[2,3-b]pyridin-3-yl)piperidin-1-yl]pyrimidine-4-carboxamide | 553.3 [M + Na]+; (400 MHz, CDCl$_3$) δ ppm 8.87 (s, 1 H), 8.29 (d, J = 4.4 Hz, 1 H), 8.13 (6, J = 5.2 Hz, 1 H), 7.95 (d, J = 7.6 Hz, 1 H), 7.06-7.10 (m, 3 H), 5.29-5.35 (m, 1 H), 4.56 (br. s., 2 H), 3.65-3.67 (m, 1 H), 3.49-3.53 (m, 3 H), 3.41 (s, 3 H), 3.11-3.15 (m, 4 H), 3.03 (s, 3 H), 2.16 (d, J = 12.8 Hz, 2 H), 1.75-1.76 (m, 2 H), 1.53 (d, J = 6.8 Hz, 3 H), 1.39 (d, J = 6.8 Hz, 3 H). |
| 230*** | 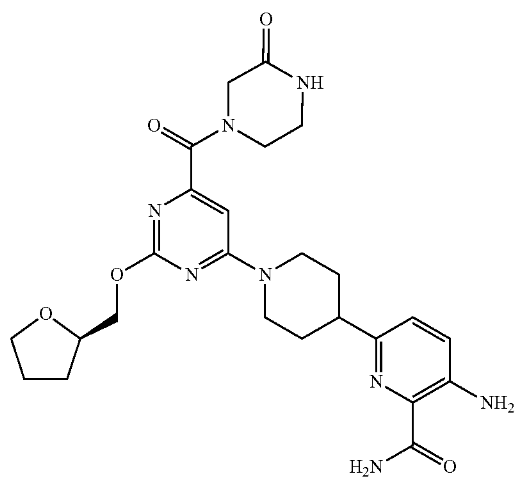 [SMILES: NC(=O)c1nc(C2CCN(c3cc(C(=O)N4CCNC(=O)C4)nc(OC[C@H]4CCCO4)n3)CC2)ccc1N] | 3-amino-6-(1-{6-[(3-oxopiperazin-1-yl)carbonyl]-2-[(2R)-tetrahydrofuran-2-ylmethoxy]pyrimidin-4-yl}piperidin-4-yl)pyridine-2-carboxamide | 525.2; (700 MHz, DMSO-d$_6$) δ ppm 8.13 (br. s., 1 H), 7.83-7.86 (m, 1 H), 7.25 (br. s., 1 H), 7.18 (d, J = 8.5 Hz, 1 H), 7.09 (d, J = 8.5 Hz, 1 H), 6.64-6.67 (m, 2 H), 4.09-4.17 (m, 3 H), 4.07 (s, 1 H), 4.00 (s, 1 H), 3.73-3.76 (m, 2 H), 3.65 (q, J = 7.1 Hz, 1 H), 3.58 (br. s., 1 H), 3.21-3.26 (m, 1 H), 3.00 (br. s., 1 H), 2.86 (t, J = 11.2 Hz, 1 H), 1.60-1.98 (m, 11 H), 1.23 (br. s., 1 H). |
| 231*** | 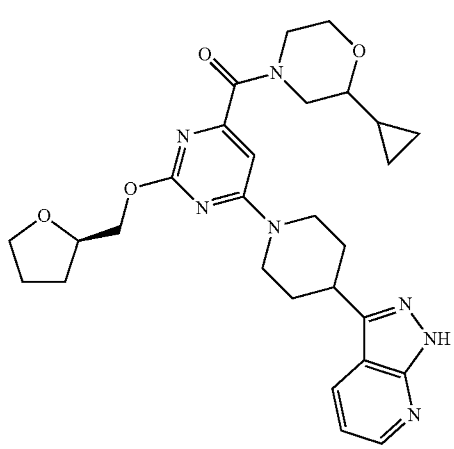 [SMILES: O=C(c1cc(N2CCC(c3n[nH]c4ncccc34)CC2)nc(OC[C@H]2CCCO2)n1)N1CCOC(C2CC2)C1] | (2-cyclopropylmorpholin-4-yl){6-[4-(1H-pyrazolo[3,4-b]pyridin-3-yl)piperidin-1-yl]-2-[(2R)-tetrahydrofuran-2-ylmethoxy]pyrimidin-4-yl}methanone | 533.8; (600 MHz, DMSO-d$_6$) δ ppm 8.46-8.48 (m, 1 H), 8.30 (dd, J = 8.0, 1.5 Hz, 1 H), 7.13 (dd, J = 8.0, 4.5 Hz, 1 H), 6.64-6.66 (m, 1 H), 4.32 (d, J = 10.2 Hz, 0.5 H), 4.09-4.21 (m, 4 H), 3.90 (d, J = 11.4 Hz, 0.5 H), 3.74-3.78 (m, 2 H), 3.63-3.67 (m, 2 H), 3.53 (d, J = 13.3 Hz, 0.5 H), 3.13-3.17 (m, 1 H), 3.02 (dd, J = 13.0, 10.3 Hz, 0.5 H), 2.89-2.94 (m, 0.5 H), 2.71-2.79 (m, 2 H), 2.05-2.09 (m, 2 H), 1.95-1.97 (m, 1 H), 1.76-1.88 (m, 5 H), 1.62-1.65 (m, 1 H), 1.22 (br. s., 1 H), 0.88-0.91 (m, 0.5 H), 0.78-0.81 (m, 0.5 H), 0.25-0.49 (m, 5 H), 0.06-0.10 (m, 0.5 H). |

TABLE 1-continued

| Ex. # | Structure | Compound Name | LRMS m/z (M + H)+; and 1H NMR |
|---|---|---|---|
| 232 | 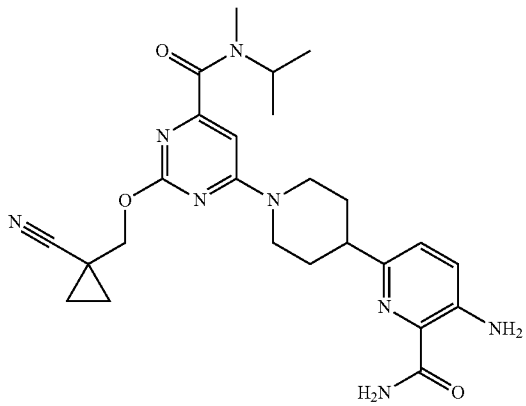 [SMILES: CC(C)N(C)C(=O)c1cc(N2CCC(c3ccc(N)c(C(N)=O)n3)CC2)nc(OCC2(C#N)CC2)n1] | 6-[4-(5-amino-6-carbamoylpyridin-2-yl)piperidin-1-yl]-2-[(1-cyanocyclopropyl)methoxy]-N-methyl-N-(propan-2-yl)pyrimidine-4-carboxamide | 493.2; (600 MHz, DMSO-$d_6$) δ ppm 7.82 (d, J = 3.1 Hz, 1 H), 7.22 (br s, 1 H), 7.17 (d, J = 8.6 Hz, 1 H), 7.08 (d, J = 8.5 Hz, 1 H), 6.64 (br. s., 2 H), 6.55-6.57 (m, 1 H), 4.64-4.67 (m, 1 H), 4.22-4.23 (m, 2 H), 3.81 (quin, J = 6.6 Hz, 1 H), 3.36-3.51 (m, 4 H), 2.99 (br. s., 1 H), 2.85 (tt, J = 11.5, 3.5 Hz, 1 H), 2.77 (s, 2 H), 2.48-2.49 (m, 2 H), 1.87 (d, J = 12.4 Hz, 2 H), 1.63 (qd, J = 12.5, 3.9 Hz, 2 H), 1.31-1.33 (m, 2 H), 1.16-1.18 (m, 2 H), 1.09-1.11 (m, 6 H). |
| 233*** | 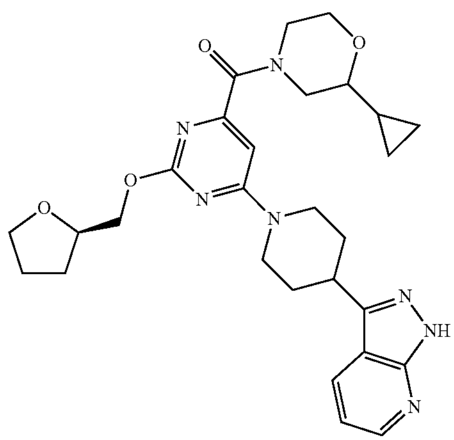 [SMILES: O=C(c1cc(N2CCC(c3n[nH]c4ncccc34)CC2)nc(OC[C@H]2CCCO2)n1)N1CCOC(C2CC2)C1] | (2-cyclopropylmorpholin-4-yl){6-[4-(1H-pyrazolo[3,4-b]pyridin-3-yl)piperidin-1-yl]-2-[(2R)-tetrahydrofuran-2-ylmethoxy]pyrimidin-4-yl}methanone | 533.8; (600 MHz, DMSO-$d_6$) δ ppm 8.47 (d, J = 4.4, 1.5 Hz, 1 H), 8.29-8.31 (m, 1 H), 7.13 (dd, J = 8.0, 4.5 Hz, 1H), 6.64-6.65 (m, 1H), 4.32 (d, J = 10.5 Hz, 0.5 H), 4.10-4.21 (m, 4 H), 3.89-3.91 (m, 0.5 H), 3.74-3.78 (m, 2 H), 3.63-3.66 (m, 2 H), 3.53 (d, J = 13.0 Hz, 0.5 H), 3.13-3.17 (m, 1 H), 3.02 (dd, J = 13.0, 10.2 Hz, 0.5H), 2.89-2.94 (m, 0.5 H), 2.72-2.80 (m, 2 H), 2.08 (d, J = 13.0 Hz, 2 H), 1.93-1.98 (m, 1 H), 1.76-1.88 (m, 5 H), 1.60-1.66 (m, 1 H), 1.23 (s, 1 H), 0.88-0.91 (m, 0.5 H), 0.77-0.81 (m, 0.5 H), 0.25-0.49 (m, 5 H), 0.09 (dd, J = 9.1, 4.1 Hz, 0.5 H). |
| 234* | 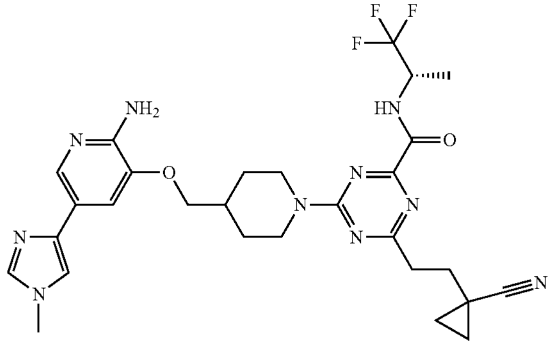 [SMILES: C[C@H](NC(=O)c1nc(CCC2(C#N)CC2)nc(N2CCC(COc3cc(-c4cn(C)cn4)cnc3N)CC2)n1)C(F)(F)F] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-[(2S)-1,1,1-trifluoropropan-2-yl]-1,3,5-triazine-2-carboxamide | 601.1; (400 MHz, DMSO-$d_6$) δ ppm 9.09 (d, J = 9.2 Hz, 1 H), 7.92 (s, 1 H), 7.56 (s, 1 H), 7.44 (s, 1H), 7.32 (s, 1 H), 5.63 (s, 2 H), 4.86 (d, J = 10.8 Hz, 1 H), 4.73 (d, J = 13.6 Hz, 2 H), 4.42-4.46 (m, 2 H), 3.90-3.92 (m, 2 H), 3.65 (s, 3 H), 3.01-3.09 (m, 2 H), 2.14-2.17 (m, 1 H), 1.99 (d, J = 11.6 Hz, 2 H), 1.63 (t, J = 19.2 Hz, 3 H), 1.33-1.39 (m, 7 H), 1.23-1.25 (m, 2 H). |

TABLE 1-continued

| Ex. # | Structure | Compound Name | LRMS m/z (M + H)+; and 1H NMR |
|---|---|---|---|
| 235** | 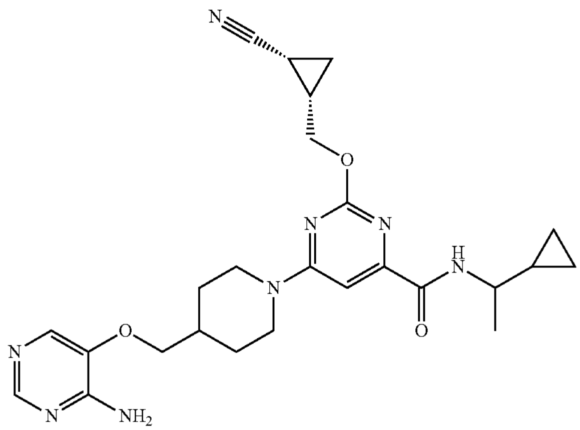 [SMILES: CC(NC(=O)c1cc(N2CCC(COc3cncnc3N)CC2)nc(OC[C@H]2C[C@H]2C#N)n1)C1CC1] | 6-(4-{[(4-aminopyrimidin-5-yl)oxy]methyl}piperidin-1-yl)-2-{[(1S,2R)-2-cyanocyclopropyl]methoxy}-N-(1-cyclopropylethyl)pyrimidine-4-carboxamide | 493.1; (400 MHz, CDCl$_3$) δ ppm 8.24 (s, 1 H), 7.81-7.86 (m, 2 H), 7.14 (s, 1 H), 5.10 (s, 2 H), 4.43-4.54 (m, 4 H), 3.93 (d, J = 6.4 Hz, 2 H), 3.46-3.54 (m, 1 H), 3.01-3.04 (m, 2 H), 2.19 (br. s., 1 H), 1.87-1.97 (m, 3 H), 1.35-1.40 (m, 7 H), 1.30-1.34 (m, 1 H), 0.92-0.94 (m, 1 H), 0.38-0.47 (m, 2 H), 0.26-0.28 (m, 2 H). |
| 236** | 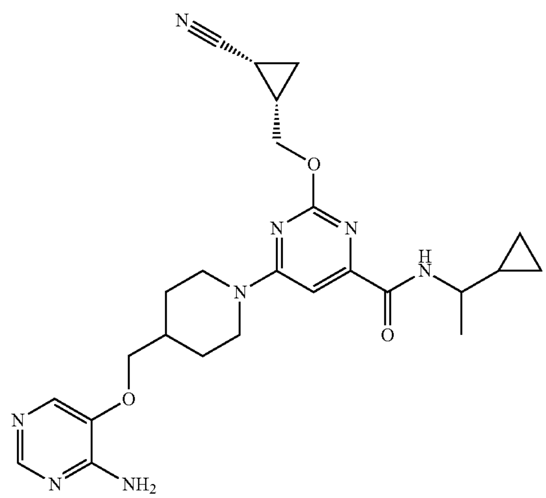 [SMILES: CC(NC(=O)c1cc(N2CCC(COc3cncnc3N)CC2)nc(OC[C@H]2C[C@H]2C#N)n1)C1CC1] | 6-(4-{[(4-aminopyrimidin-5-yl)oxy]methyl}piperidin-1-yl)-2-{[(1S,2R)-2-cyanocyclopropyl]methoxy}-N-(1-cyclopropylethyl)pyrimidine-4-carboxamide | 515.1 [M + Na]+; (400 MHz, CDCl$_3$) δ ppm 8.24 (s, 1 H), 7.81-7.86 (m, 2 H), 7.14 (s, 1 H), 5.10 (s, 2 H), 4.43-4.54 (m, 4 H), 3.93 (d, J = 6.4 Hz, 2 H), 3.46-3.54 (m, 1 H), 3.01-3.04 (m, 2 H), 2.19 (br. s., 1 H), 1.87-1.97 (m, 3 H), 1.35-1.40 (m, 7 H), 1.30-1.34 (m, 1 H), 0.92-0.94 (m, 1 H), 0.38-0.47 (m, 2 H), 0.26-0.28 (m, 2 H). |
| 237 | 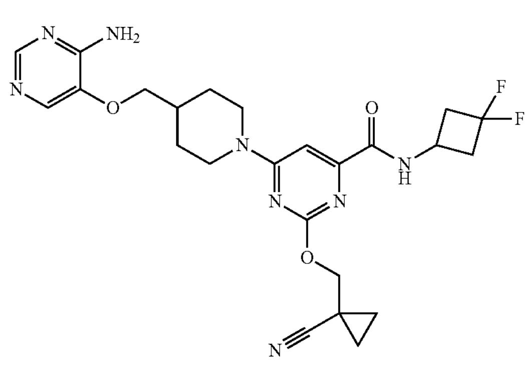 [SMILES: N#CC1(COc2nc(C(=O)NC3CC(F)(F)C3)cc(N3CCC(COc4cncnc4N)CC3)n2)CC1] | 6-(4-{[(4-aminopyrimidin-5-yl)oxy]methyl}piperidin-1-yl)-2-[(1-cyanocyclopropyl)methoxy]-N-(3,3-difluorocyclobutyl)pyrimidine-4-carboxamide | 537.1 [M + Na]+; (400 MHz, CD$_3$OD) δ ppm 8.03 (s, 1 H), 7.76 (s, 1 H), 7.08 (s, 1 H), 4.61 (br. s., 2 H), 4.42 (s, 2 H), 4.33-4.35 (m, 1 H), 3.97 (d, J = 6.0 Hz, 2 H), 2.96-3.08 (m, 4 H), 2.78-2.82 (m, 2 H), 2.24-2.28 (m, 1 H), 2.03 (d, J = 8.8 Hz, 2 H), 1.36-1.45 (m, 4 H), 1.23-1.24 (m, 2 H). |

TABLE 1-continued

| Ex. # | Structure | Compound Name | LRMS m/z (M + H)+; and 1H NMR |
|---|---|---|---|
| 238 | 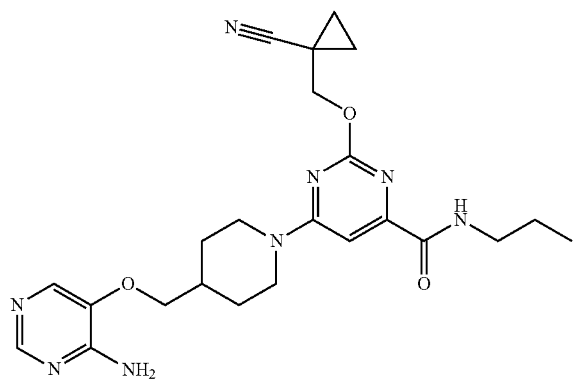 [SMILES: CCCNC(=O)c1cc(N2CCC(COc3cncnc3N)CC2)nc(OCC2(C#N)CC2)n1] | 6-(4-{[(4-aminopyrimidin-5-yl)oxy]methyl}piperidin-1-yl)-2-[(1-cyanocyclopropyl)methoxy]-N-propylpyrimidine-4-carboxamide | 489.1 [M + Na]+; (400 MHz, CDCl$_3$) δ ppm 8.25 (s, 1 H), 7.93 (t, J = 4.0 Hz, 1 H), 7.82 (s, 1 H), 7.16 (s, 1 H), 5.07 (s, 2 H), 4.58 (br. s., 2 H), 4.37 (s, 2 H), 3.94 (d, J = 6.4 Hz, 2 H), 3.37-3.39 (q, J = 6.8 Hz, 2 H), 2.94-3.02 (m, 2 H), 2.09-2.19 (m, 1 H), 1.96 (d, J = 11.6 Hz, 2 H), 1.62-1.67 (m, 2 H), 1.41-1.43 (m, 4 H), 1.19 (t, J = 2.0 Hz, 2 H), 0.98 (t, J = 11.6 Hz, 3 H). |
| 239* | 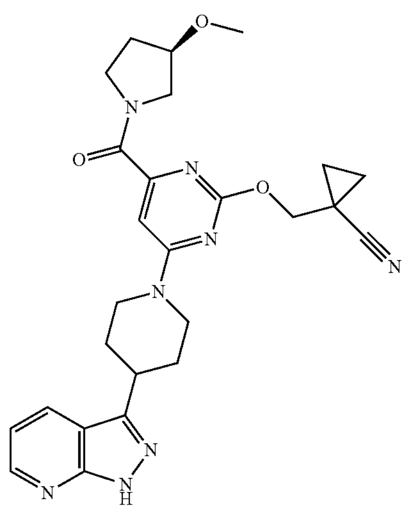 [SMILES: CO[C@@H]1CCN(C(=O)c2cc(N3CCC(c4n[nH]c5ncccc45)CC3)nc(OCC3(C#N)CC3)n2)C1] | 1-{[(4-{[(3R)-3-methoxypyrrolidin-1-yl]carbonyl}-6-[4-(1H-pyrazolo[3,4-b]pyridin-3-yl)piperidin-1-yl]pyrimidin-2-yl)oxy]methyl}cyclopropanecarbonltrile | 503.2; (700 MHz, DMSO-d$_6$) δ ppm 8.47 (dd, J = 3.8, 2.1 Hz, 1 H), 8.29-8.31 (m, 1 H), 7.13 (ddd, J = 7.8, 4.7, 2.6 Hz, 1 H), 6.73-6.76 (m, 1 H), 4.22-4.29 (m, 2 H), 3.95-4.00 (m, 1 H), 3.61-3.68 (m, 1 H), 3.52-3.58 (m, 1 H), 3.24-3.26 (m, 1 H), 3.16-3.20 (m, 2 H), 2.08 (d, J = 12.0 Hz, 2 H), 1.96-2.03 (m, 2 H), 1.91 (br. s., 1 H), 1.75-1.83 (m, 3 H), 1.67 (br. s., 9 H), 1.34 (d, J = 2.6 Hz, 2 H), 1.19 (d, J = 2.0 Hz, 2 H). |
| 240 | 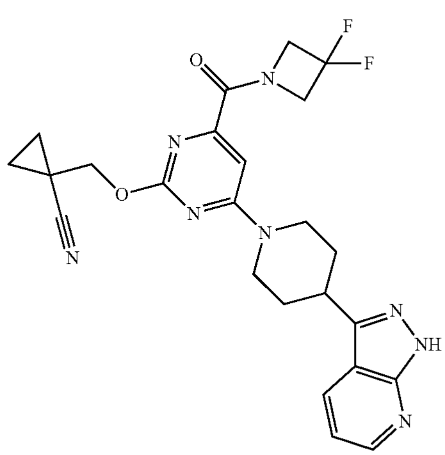 [SMILES: N#CC1(COc2nc(C(=O)N3CC(F)(F)C3)cc(N3CCC(c4n[nH]c5ncccc45)CC3)n2)CC1] | 1-[({4-[(3,3-difluoroazetidin-1-yl)carbonyl]-6-[4-(1H-pyrazolo[3,4-b]pyridin-3-yl)piperidin-1-yl]pyrimidin-2-yl}oxy)methyl]cyclopropanecarbonitrile | 495.1; (700 MHz, DMSO-d6) δ ppm 8.48 (dd, J = 4.18, 2.82 Hz, 1 H), 8.30 (br. s., 1 H), 7.11-7.17 (m, 1 H), 7.06 (d, J = 8.88 Hz, 1 H), 5.03 (d, J = 9.91 Hz, 2 H), 4.48 (d, J = 9.91 Hz, 2 H), 4.27 (d, J = 8.71 Hz, 2 H), 3.37-3.47 (m, 4 H), 2.47-2.56 (m, 2 H), 2.10 (br. s., 2 H), 1.81 (d, J = 8.54 Hz, 2 H), 1.36 (d, J = 4.27 Hz, 2 H), 1.16-1.25 (m, 2 H). |

TABLE 1-continued

| Ex. # | Structure | Compound Name | LRMS m/z (M + H)+; and 1H NMR |
|---|---|---|---|
| 241* | 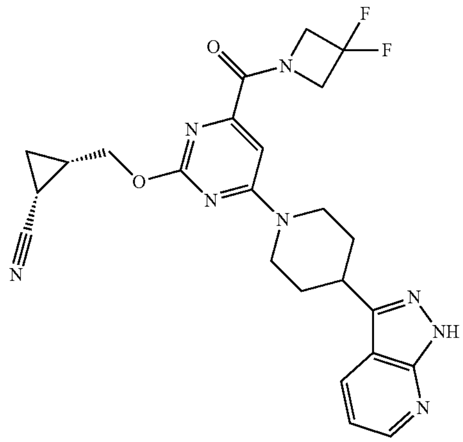 [SMILES: N#C[C@@H]1C[C@@H]1COc1nc(C(=O)N2CC(F)(F)C2)cc(N2CCC(c3n[nH]c4ncccc34)CC2)n1] | (1R,2S)-2-[({4-[(3,3-difluoroazetidin-1-yl)carbonyl]-6-[4-(1H-pyrazolo[3,4-b]pyridin-3-yl)piperidin-1-yl]pyrimidin-2-yl}oxy)methyl]cyclopropanecarbonitrile | 495.1; (700 MHz, DMSO-d6) δ ppm 8.42-8.52 (m, 1 H), 8.31 (br. s., 1 H), 7.09-7.19 (m, 1 H), 6.97-7.09 (m, 1 H), 5.02 (d, J = 11.10 Hz, 2 H), 4.40-4.59 (m, 5 H), 4.06 (d, J = 9.05 Hz, 1 H), 3.31-3.46 (m, 1 H), 2.10 (br. s., 3 H), 1.91-2.03 (m, 1 H), 1.81 (d, J = 8.03 Hz, 4 H), 1.21-1.31 (m, 2 H), 1.11-1.19 (m, 1 H). |
| 242*** | 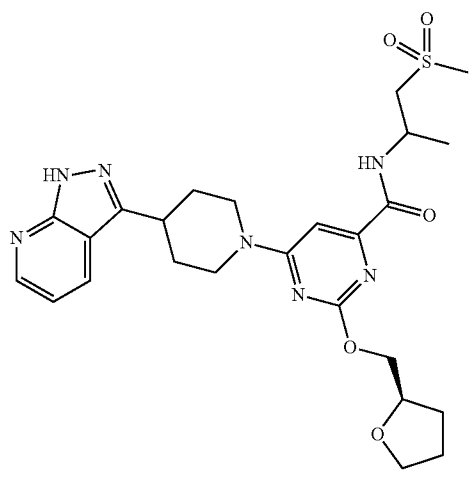 [SMILES: CC(CS(C)(=O)=O)NC(=O)c1cc(N2CCC(c3n[nH]c4ncccc34)CC2)nc(OC[C@H]2CCCO2)n1] | N-[1-(methylsulfonyl)propan-2-yl]-6-[4-(1H-pyrazolo[3,4-b]pyridin-3-yl)piperidin-1-yl]-2-[(2R)-tetrahydrofuran-2-ylmethoxy]pyrimidine-4-carboxamide | 544.3; (400 MHz, CDCl3) δ ppm 8.12-8.17 (m, 2 H), 7.15-7.19 (m, 1 H), 7.09 (s, 1 H), 4.53-4.56 (m, 2 H), 4.27-4.37 (m, 3 H), 3.93-3.95 (m, 1 H), 3.81-3.83 (m, 1 H), 3.43-3.49 (m, 2 H), 3.13-3.17 (m, 3 H), 3.03 (s, 3 H), 1.75-2.20 (m, 9 H), 1.54 (d, J = 6.8 Hz, 3 H). |
| 243 | 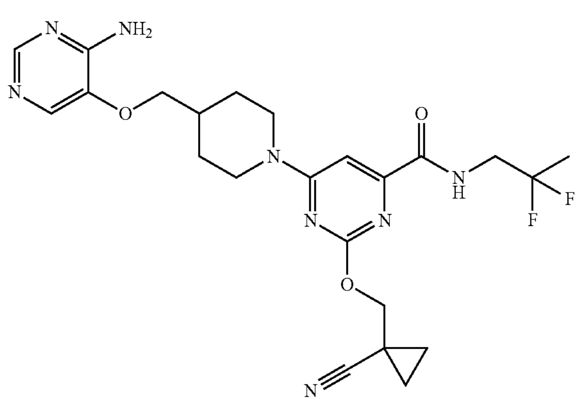 [SMILES: CC(F)(F)CNC(=O)c1cc(N2CCC(COc3cncnc3N)CC2)nc(OCC2(C#N)CC2)n1] | 6-(4-{[(4-aminopyrimidin-5-yl)oxy]methyl}piperidin-1-yl)-2-[(1-cyanocyclopropyl)methoxy]-N-(2,2-difluoropropyl)pyrimidine-4-carboxamide | 503.0; (400 MHz, CD3OD) δ ppm 8.42 (s, 1 H), 7.91 (s, 1 H), 7.28 (s, 1 H), 4.64 (br. s., 2 H), 4.52 (s, 2 H), 4.08 (d, J = 6.4 Hz, 2 H), 3.86 (t, J = 13.6 Hz, 2 H), 3.22-3.32 (m, 2 H), 2.32-2.36 (m, 1 H), 2.08 (d, J = 11.6 Hz, 2 H), 1.66 (t, J = 18.8 Hz, 3 H), 1.41-1.52 (m, 2 H), 1.29-1.30 (m, 2 H), 1.28-1.29 (m, 2 H). |

TABLE 1-continued

| Ex. # | Structure | Compound Name | LRMS m/z (M + H)+; and 1H NMR |
|---|---|---|---|
| 244* | 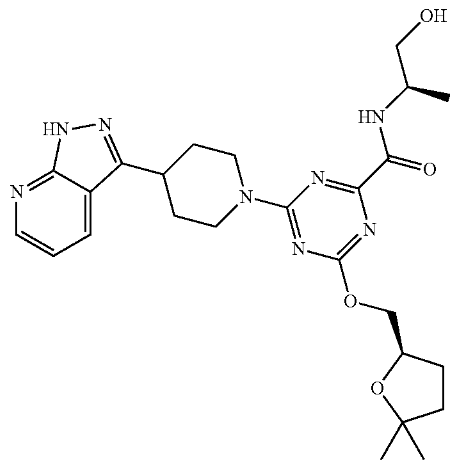 [SMILES: C[C@H](CO)NC(=O)c1nc(OC[C@H]2CCC(C)(C)O2)nc(N2CCC(c3n[nH]c4ncccc34)CC2)n1] | 4-{[(2R)-5,5-dimethyltetrahydro-furan-2-yl]methoxy}-N-[(2R)-1-hydroxypropan-2-yl]-6-[4-(1H-pyrazolo[3,4-b]pyridin-3-yl)piperidin-1-yl]-1,3,5-triazine-2-carboxamide | 511.3; (400 MHz, DMSO-d6) δ ppm 13.29 (s, 1 H), 8.48 (d, J = 4.4 Hz, 1H), 8.30-8.35 (m, 2 H), 7.14 (t, J = 4.4 Hz, 1 H), 4.84-4.91 (m, 2 H), 4.72-4.73 (m, 1 H), 4.23-4.31 (m, 3 H), 3.93-3.95 (m, 1 H), 3.37-3.45 (m, 3 H), 3.12-3.15 (m, 2 H), 2.10-2.14 (m, 3 H), 1.71-1.77 (m, 5 H), 1.18 (d, J = 9.6 Hz, 6 H), 1.13 (d, J = 6.8 Hz, 3 H). |
| 245* | 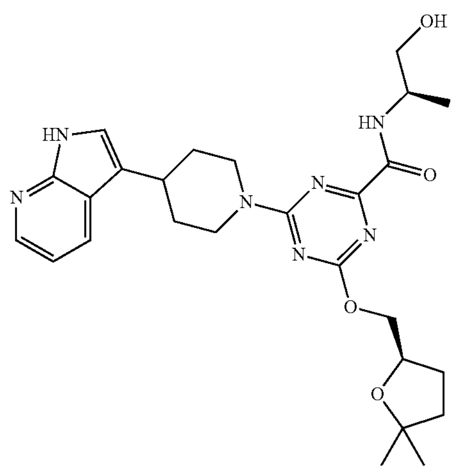 [SMILES: C[C@H](CO)NC(=O)c1nc(OC[C@H]2CCC(C)(C)O2)nc(N2CCC(c3c[nH]c4ncccc34)CC2)n1] | 4-{[(2R)-5,5-dimethyltetrahydro-furan-2-yl]methoxy}-N-[(2R)-1-hydroxypropan-2-yl]-6-[4-(1H-pyrrolo[2,3-b]pyridin-3-yl)piperidin-1-yl]-1,3,5-triazine-2-carboxamide | 532.2 [M + Na]+; (400 MHz, DMSO-d6) δ ppm 11.38 (s, 1 H), 8.31 (d, J = 8.4 Hz, 1 H), 8.19 (d, J = 3.6 Hz, 1 H), 8.04 (d, J = 7.6 Hz, 1 H), 7.26 (s, 1 H), 7.03 (t, J = 4.8 Hz, 1 H), 4.90-4.93 (m, 1 H), 4.83-4.86 (m, 2 H), 4.24-4.31 (m, 3 H), 3.93-3.95 (m, 1 H), 3.37-3.45 (m, 2 H), 3.12-3.15 (m, 3 H), 2.07-2.09 (m, 3 H), 1.66-1.77 (m, 5H), 1.19 (d, J = 10.0 Hz, 6 H), 1.13 (d, J = 6.8 Hz, 3 H). |
| 246*** | 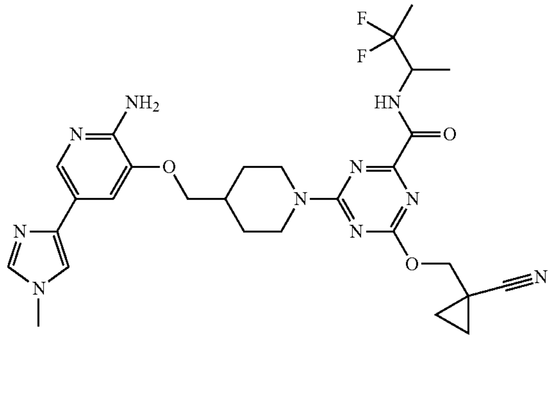 | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(3,3-difluorobutan-2-yl)-1,3,5-triazine-2-carboxamide | 597.0; (400 MHz, DMSO-d6) δ ppm 8.67 (d, J = 9.2 Hz, 1 H), 7.91 (s, 1H), 7.56 (s, 1 H), 7.44 (s, 1 H), 7.32 (s, 1 H), 5.62 (s, 2 H), 4.86 (d, J = 10.8 Hz, 1 H), 4.73 (d, J = 13.6 Hz, 1 H), 4.41-4.43 (m, 3 H), 3.91 (d, J = 6.0 Hz, 2 H), 3.65 (s, 3 H), 3.01-3.04 (m, 2 H), 2.14-2.16 (m, 1 H), 1.98-2.01 (m, 2 H), 1.65 (t, J = 19.6 Hz, 3 H), 1.23-1.40 (m, 9 H). |

| Ex. # | Structure | Compound Name | LRMS m/z (M + H)+; and 1H NMR |
|---|---|---|---|
| 247* | 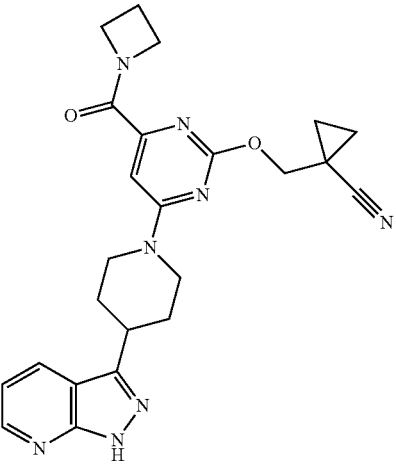 [SMILES: N#CC1(COc2nc(C(=O)N3CCC3)cc(N3CCC(c4n[nH]c5ncccc45)CC3)n2)CC1] | 1-[({4-(azetidin-1-ylcarbonyl)-6-[4-(1H-pyrazolo[3,4-b]pyridin-3-yl)piperidin-1-yl]pyrimidin-2-yl}oxy)methyl]cyclopropanecarbonitrile | 459.1; (700 MHz, DMSO-d6) δ ppm 8.47 (br. s., 1 H), 8.29 (br. s., 1 H), 7.13 (br. s., 1 H), 6.96 (br. s., 1 H), 4.39-4.62 (m, 2 H), 4.26 (br. s., 1 H), 4.03 (br. s., 2 H), 2.25 (br. s., 2 H), 2.09 (br. s., 2 H), 1.79 (br. s., 2 H), 1.35 (br. s., 2 H), 1.20 (br. s., 3 H). |
| 248 | 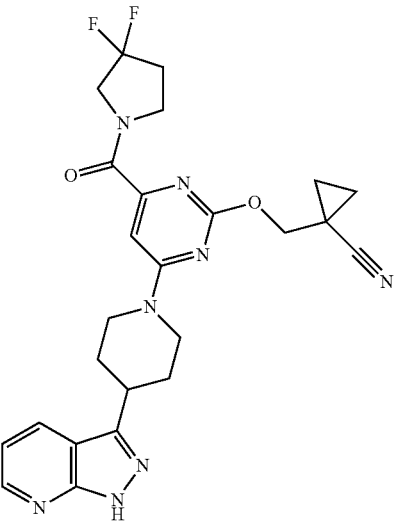 [SMILES: N#CC1(COc2nc(C(=O)N3CCC(F)(F)C3)cc(N3CCC(c4n[nH]c5ncccc45)CC3)n2)CC1] | 1-({4-[(3,3-difluoropyrrolidin-1-yl)carbonyl]-6-[4-(1H-pyrazolo[3,4-b]pyridin-3-yl)piperidin-1-yl]pyrimidin-2-yl}oxy)methyl]cyclopropanecarbonitrlie | 509.2; (700 MHz, DMSO-d6) δ ppm 8.47 (d, J = 4.6 Hz, 1 H), 8.30 (d, J = 8.0 Hz, 1 H), 7.13 (dd, J = 7.9, 4.5 Hz, 1 H), 6.84 (d, J = 17.4 Hz, 1 H), 4.27 (d, J = 9.4 Hz, 2 H), 4.11 (t, J = 12.8 Hz, 1 H), 3.85-3.98 (m, 2 H), 3.69 (t, J = 7.6 Hz, 1 H), 2.42-2.47 (m, 2 H), 2.09 (d, J = 11.6 Hz, 2 H), 1.80 (q, J = 12.4 Hz, 2 H), 1.34-1.36 (m, 2 H), 1.19-1.20 (m, 2 H). |
| 249*** | 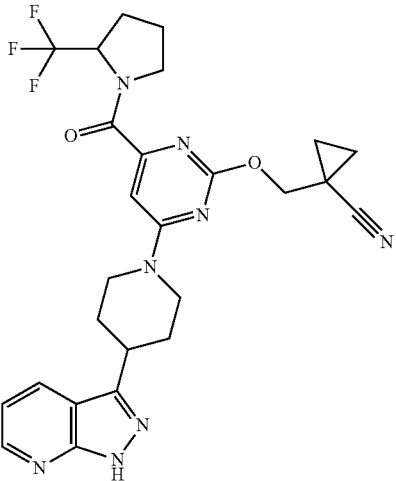 [SMILES: N#CC1(COc2nc(C(=O)N3CCCC3C(F)(F)F)cc(N3CCC(c4n[nH]c5ncccc45)CC3)n2)CC1] | 1-{[(4-[4-(1H-pyrazolo[3,4-b]pyridin-3-yl)piperidin-1-yl]-6-{[2-(trifluoromethyl)pyrrolidin-1-yl]carbonyl}pyrimidin-2-yl)oxy]methyl}cyclopropanecarbonitrile | 541.2; (700 MHz, DMSO-d6) δ ppm 8.46-8.50 (m, 1 H), 8.30 (d, J = 6.7 Hz, 1 H), 7.14 (br. s., 1 H), 6.76-6.84 (m, 1 H), 5.65 (br. s., 1 H), 4.95 (br. s., 1 H), 4.21-4.38 (m, 3 H), 3.70 (br. s., 1 H), 3.37-3.58 (m, 1 H), 3.20 (br. s., 1 H), 2.35 (br. s., 1 H), 2.10 (br. s., 3 H), 1.75-2.05 (m, 6 H), 1.34 (br. s., 2 H), 1.17-1.27 (m, 3 H). |

TABLE 1-continued

| Ex. # | Compound Name | LRMS m/z (M + H)+; and 1H NMR |
|---|---|---|
| 250 | 6-(4-{[(4-aminopyrimidin-5-yl)oxy]methyl}piperidin-1-yl)-2-[(1-cyanocyclopropyl)methoxy]-N-cyclopropylpyrimidine-4-carboxamide | 464.2; (400 MHz, CD$_3$OD) δ ppm 8.03 (s, 1 H), 7.78 (s, 1 H), 7.11 (s, 1 H), 4.62 (br. s., 2 H), 4.40 (s, 2 H), 3.99 (d, J = 6.0 Hz, 2 H), 3.05-3.09 (m, 2 H), 2.86-2.90 (m, 1 H), 2.23-2.26 (m, 1 H), 2.03 (d, J = 12.0 Hz, 2 H), 1.37-1.38 (m, 4 H), 1.23-1.25 (m, 2 H), 0.83-0.85 (m, 2 H), 0.69-0.70 (m, 2 H). |
| 251*** | 6-(4-{[(4-aminopyrimidin-5-yl)oxy]methyl}piperidin-1-yl)-2-[(2,2-difluorocyclopropyl)methoxy]-N-[(1R,5S,6r)-3-oxabicyclo[3.1.0]hex-6-yl]pyrimidine-4-carboxamide | 518.1; (400 MHz, DMSO-d$_6$) δ ppm 8.57 (d, J = 3.6 Hz, 1 H), 8.00 (s, 1 H), 7.79 (s, 1 H), 6.98 (s, 1 H), 6.63-6.74 (m, 2 H), 4.18-4.68 (m, 4 H), 3.84-3.91 (m, 4 H), 3.63 (d, J = 8.4 Hz, 2 H), 2.93-3.08 (m, 2 H), 2.58-2.63 (m, 1 H), 2.06-2.24 (m, 2 H), 1.87-2.02 (m, 4 H), 1.66-1.77 (m, 1 H), 1.46-1.54 (m, 1 H), 1.23-1.36 (m, 2 H). |
| 252* | 1-((4-(4-(1H-pyrazolo[3,4-b]pyridin-3-yl)piperidin-1-yl)-6-((3S,4S)-3,4-difluoropyrrolidine-1-carbonyl)pyrimidin-2-yloxy)methyl)cyclopropanecarbonitrile | 509.1; (700 MHz, DMSO-d$_6$) δ ppm 8.46-8.48 (m, 1 H), 8.30 (dd, J = 8.0. 1.4 Hz, 1 H), 7.13 (dd, J = 8.0. 4.4 Hz, 1 H), 6.87 (s, 1 H), 5.41-5.43 (m, 1 H), 5.35 (d, J = 15.4 Hz, 1 H), 4.27-4.31 (m, 2 H), 3.98-4.06 (m, 2 H), 3.75-3.89 (m, 2 H), 2.09 (d, J = 12.8 Hz, 2 H), 1.78-1.83 (m, 2 H), 1.34-1.36 (m, 2 H), 1.19-1.21 (m, 2 H). |

TABLE 1-continued

| Ex. # | Structure | Compound Name | LRMS m/z (M + H)+; and 1H NMR |
|---|---|---|---|
| 253** | 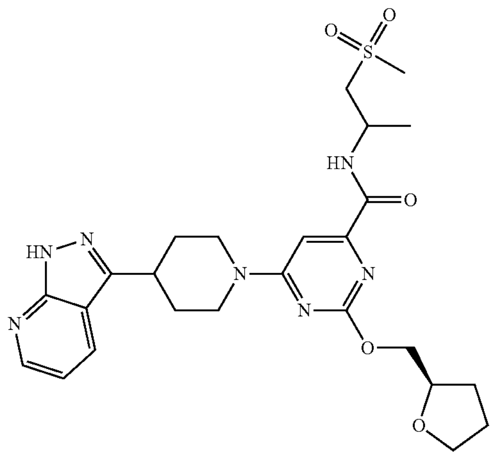 [SMILES: CC(CS(C)(=O)=O)NC(=O)c1cc(N2CCC(c3n[nH]c4ncccc34)CC2)nc(OC[C@H]2CCCO2)n1] | N-[1-(methylsulfonyl)propan-2-yl]-6-[4-(1H-pyrazolo[3,4-b]pyridin-3-yl)piperidin-1-yl]-2-[(2R)-tetrahydrofuran-2-ylmethoxy]pyrimidine-4-carboxamide | 544.1; (400 MHz, CDCl$_3$) δ ppm 10.86 (br. s., 1 H), 8.56 (s, 1 H), 8.16 (d, J = 7.2 Hz, 1 H), 8.10 (d, J = 8.0 Hz, 1 H), 7.13-7.16 (m, 1 H), 7.09 (s, 1 H), 4.53-4.56 (m, 2 H), 4.31-4.37 (m, 3 H), 3.93-3.95 (m, 1 H), 3.81-3.83 (m, 1 H), 3.48-3.50 (m, 2 H), 3.15-3.23 (m, 3 H), 3.02 (s, 3 H), 1.75-2.20 (m, 9 H), 1.54 (d, J = 7.2 Hz, 3 H). |
| 254** | 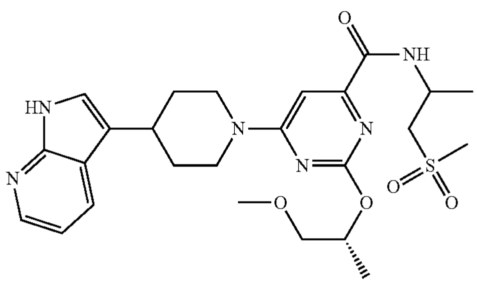 [SMILES: COC[C@@H](C)Oc1nc(C(=O)NC(C)CS(C)(=O)=O)cc(N2CCC(c3c[nH]c4ncccc34)CC2)n1] | 2-{[(2R)-1-methoxypropan-2-yl]oxy}-N-[1-(methylsulfonyl)propan-2-yl]-6-[4-(1H-pyrrolo[2,3-b]pyridin-3-yl)piperidin-1-yl]pyrimidine-4-carboxamide | 553.3; [M + Na]+; (400 MHz, CDCl$_3$) δ ppm 8.99 (s, 1 H), 8.31 (d, J = 4.4 Hz, 1 H), 8.11 (d, J = 8.4 Hz, 1 H), 7.94 (d, J = 7.6 Hz, 1 H), 7.07-7.10 (m, 3 H), 5.31-5.35 (m, 1 H), 4.50-4.56 (m, 3 H), 3.65-3.67 (m, 1 H), 3.49-3.52 (m, 2 H), 3.41 (s, 3 H), 3.09-3.15 (m, 4 H), 3.03 (s, 3 H), 2.15 (d, J = 12.8 Hz, 2 H), 1.75-1.76 (m, 2 H), 1.53 (d, J = 6.8 Hz, 3 H), 1.39 (d, J = 6.0 Hz, 3 H). |
| 255** | 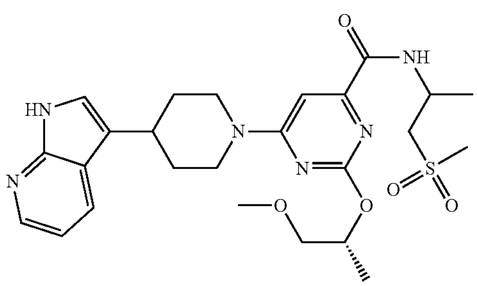 [SMILES: COC[C@@H](C)Oc1nc(C(=O)NC(C)CS(C)(=O)=O)cc(N2CCC(c3c[nH]c4ncccc34)CC2)n1] | 2-{[(2R)-1-methoxypropan-2-yl]oxy}-N-[1-(methylsulfonyl)propan-2-yl]-6-[4-(1H-pyrrolo[2,3-b]pyridin-3-yl)piperidin-1-yl]pyrimidine-4-carboxamide | 553.3 [M + Na]+; (400 MHz, CDCl$_3$) δ ppm 9.08 (s, 1H), 8.31 (d, J = 4.4 Hz, 1 H), 8.11 (d, J = 8.4 Hz, 1 H), 7.96 (d, J = 7.6 Hz, 1 H), 7.07-7.10 (m, 3 H), 5.31-5.35 (m, 1 H), 4.54-4.59 (m, 3 H), 3.65-3.67 (m, 1 H), 3.50-3.53 (m, 2 H), 3.41 (s, 3 H), 3.11-3.16 (m, 4 H), 3.02 (s, 3 H), 2.16 (d, J = 12.8 Hz, 2 H), 1.75-1.78 (m, 2 H), 1.53 (d, J = 6.8 Hz, 3 H), 1.39 (d, J = 6.0 Hz, 3 H). |
| 256 | 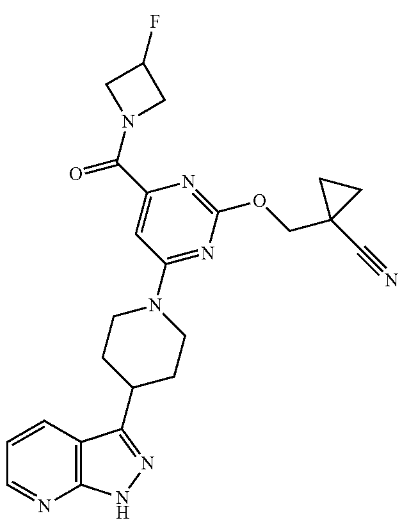 [SMILES: N#CC1(COc2nc(C(=O)N3CC(F)C3)cc(N3CCC(c4n[nH]c5ncccc45)CC3)n2)CC1] | 1-[({4-[(3-fluoroazetidin-1-yl)carbonyl]-6-[4-(1H-pyrazolo[3,4-b]pyridin-3-yl)piperidin-1-yl]pyrimidin-2-yl}oxy)methyl]cyclopropanecarbonitrile | 477.1; (700 MHz, DMSO-d6) δ ppm 8.46-8.48 (m, 1 H), 8.29 (dd, J = 7.9, 1.3 Hz, 1 H), 7.18 (dd, J = 8.0, 4.4 Hz, 1 H), 7.0 (s, 1 H), 5.45-5.48 (m, 0.5 H), 5.37-5.39 (m, 0.5 H), 4.87-4.93 (m, 1 H), 4.60-4.66 (m, 1 H), 4.34-4.40 (m, 1 H), 4.26 (s, 2 H), 4.04-4.10 (m, 1 H), 2.09 (d, J = 11.6 Hz, 2 H), 1.79 (q, J = 12.0 Hz, 2 H), 1.35-1.36 (m, 2 H), 1.19-1.22 (m, 2 H). |

TABLE 1-continued

| Ex. # | Structure | Compound Name | LRMS m/z (M + H)+; and 1H NMR |
|---|---|---|---|
| 257 | 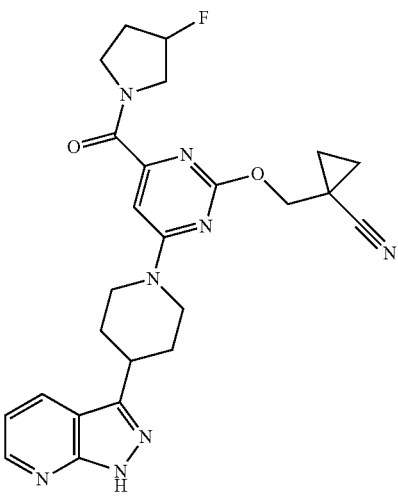 [SMILES: N#CC1(COc2nc(C(=O)N3CCC(F)C3)cc(N3CCC(c4n[nH]c5ncccc45)CC3)n2)CC1] | 1-[({4-[(3-fluoropyrrolidin-1-yl)carbonyl]-6-[4-(1H-pyrazolo[3,4-b]pyridin-3-yl)piperidin-1-yl]pyrimidin-2-yl}oxy)methyl]cyclopropanecarbonitrile | 491.1; (700 MHz, DMSO-d6) δ ppm 8.47 (dd, J = 4.5, 1.5 Hz, 1 H), 8.30 (dd, J = 8.0, 1.4 Hz, 1 H), 7.13 (dd, J = 8.0, 4.4 Hz, 1 H), 6.8 (d, J = 12 Hz, 1 H), 5.29-5.40 (m, 1 H), 4.23-4.36 (m, 2 H), 4.60-4.66 (m, 1 H), 3.62-3.88 (m, 3 H), 2.02-2.20 (m, 4 H), 1.77-1.82 (m, 2 H), 1.33-1.35 (m, 2 H), 1.18-1.21 (m, 2 H). |
| 258** | 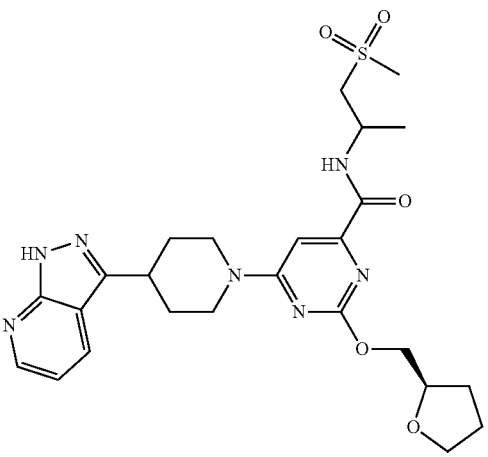 [SMILES: CC(CS(C)(=O)=O)NC(=O)c1cc(N2CCC(c3n[nH]c4ncccc34)CC2)nc(OC[C@H]2CCCO2)n1] | N-[1-(methylsulfonyl)propan-2-yl]-6-[4-(1H-pyrazolo[3,4-b]pyridin-3-yl)piperidin-1-yl]-2-[(2R)-tetrahydrofuran-2-ylmethoxy]pyrimidine-4-carboxamide | 544.1; (400 MHz, CDCl3) δ ppm 10.68 (br. s., 1 H), 8.56 (s, 1 H), 8.15 (d, J = 7.2 Hz, 1 H), 8.09 (d, J = 8.0 Hz, 1 H), 7.12-7.16 (m, 1 H), 7.09 (s, 1 H), 4.53-4.56 (m, 2 H), 4.27-4.37 (m, 3 H), 3.93-3.95 (m, 1 H), 3.81-3.83 (m, 1 H), 3.47-3.51 (m, 2 H), 3.15-3.27 (m, 3 H), 3.02 (s, 3 H), 1.75-2.20 (m, 9 H), 1.54 (d, J = 7.2 Hz, 3 H). |
| 259 | 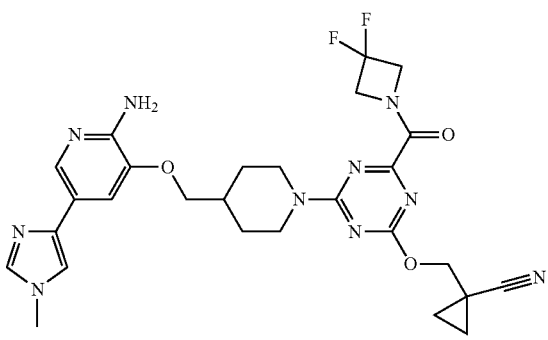 [SMILES: Cn1cnc(-c2cnc(N)c(OCC3CCN(c4nc(OCC5(C#N)CC5)nc(C(=O)N5CC(F)(F)C5)n4)CC3)c2)c1] | 1-[({4-[4-({[2-amino-5-(1-methyl-1H-imidazol-4-yl)pyridin-3-yl]oxy}methyl)piperidin-1-yl]-6-[(3,3-difluoroazetidin-1-yl)carbonyl]-1,3,5-triazin-2-yl}oxy)methyl]cyclopropanecarbonitrile | 581.3; (400 MHz, DMSO-d6) δ ppm 7.91 (s, 1 H), 7.56 (s, 1 H), 7.44 (s, 1 H), 7.32 (s, 1 H), 5.60 (s, 2 H), 4.88-4.95 (m, 2 H), 4.71-4.73 (m, 2 H), 4.46-4.52 (m, 2 H), 4.37 (d, J = 2.8 Hz, 2 H), 3.89-3.91 (m, 2 H), 3.65 (s, 3 H), 3.01-3.04 (m, 2 H), 2.14-2.16 (m, 1 H), 1.97-1.99 (m, 2 H), 1.24-1.37 (m, 6 H). |

TABLE 1-continued

| Ex. # | Structure | Compound Name | LRMS m/z (M + H)+; and 1H NMR |
|---|---|---|---|
| 260 | 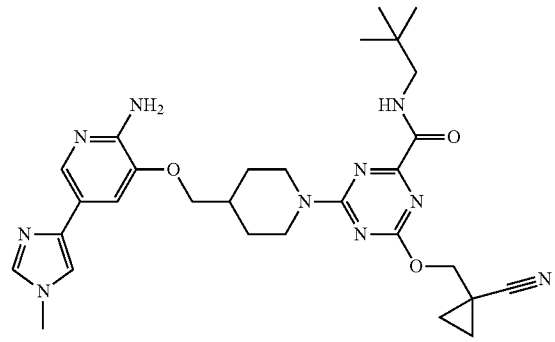 [SMILES: Cn1cnc(-c2cnc(N)c(OCC3CCN(c4nc(OCC5(C#N)CC5)nc(C(=O)NCC(C)(C)C)n4)CC3)c2)c1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(2,2-dimethylpropyl)-1,3,5-triazine-2-carboxamide | 575.1; (400 MHz, CDCl$_3$) δ ppm 7.98 (s, 1 H), 7.91 (d, J = 1.6 Hz, 1 H), 7.45 (s, 2 H), 7.10 (s, 1 H), 5.04 (d, J = 10.0 Hz, 1 H), 4.87 (d, J = 12.8 Hz, 1 H), 4.61 (s, 2 H), 4.42 (s, 2 H), 3.97 (d, J = 6.4 Hz, 2 H), 3.72 (s, 3 H), 3.26 (t, J = 4.8 Hz, 2 H), 2.97-3.08 (m, 2 H), 2.19-2.21 (m, 1 H), 2.00 (d, J = 13.6 Hz, 2 H), 1.38-1.44 (m, 4 H). 1.18-1.21 (m, 2 H), 0.98 (s, 9 H). |
| 261* | 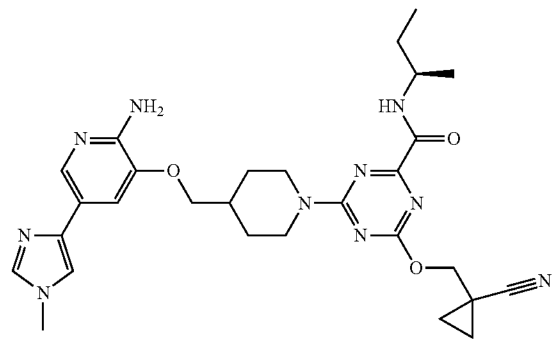 [SMILES: CC[C@@H](C)NC(=O)c1nc(OCC2(C#N)CC2)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-N-[(2R)-butan-2-yl]-6-[(1-cyanocyclopropyl)methoxy]-1,3,5-triazine-2-carboxamide | 561.0; (400 MHz, CDCl$_3$) δ ppm 7.90 (s, 1 H), 7.53 (d, J = 8.8 Hz, 1 H), 7.38 (s, 2 H), 7.03 (s, 1H), 4.99 (d, J = 14.0 Hz, 1 H), 4.78 (d, J = 14.0 Hz, 1 H), 4.60 (s, 2 H), 4.34 (s, 2 H), 3.96-4.04 (m, 1 H), 3.90 (d, J = 6.8 Hz, 2 H), 3.65 (s, 3 H), 2.90-3.00 (m, 1 H), 2.10-2.12 (m, 1 H), 1.92 (d, J = 12.0 Hz, 2 H), 1.50-1.53 (m, 2 H), 1.34-1.36 (m, 4 H), 1.12-1.16 (m, 5 H), 0.88 (t, J = 7.2 Hz, 3 H). |
| 262* | 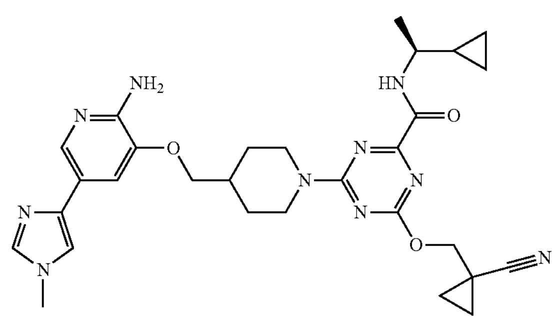 [SMILES: C[C@H](NC(=O)c1nc(OCC2(C#N)CC2)nc(N2CCC(COc3cc(-c4cn(C)cn4)cnc3N)CC2)n1)C1CC1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-[(1S)-1-cyclopropylethyl]-1,3,5-triazine-2-carboxamide | 573.2; (400 MHz, CDCl$_3$) δ ppm 7.97 (s, 1 H), 7.81 (d, J = 8.8 Hz, 1 H), 7.45 (s, 2 H), 7.11 (s, 1 H), 5.08 (d, J = 13.2 Hz, 1 H), 4.86 (d, J = 13.2 Hz, 1 H), 4.68 (s, 2 H), 4.42 (s, 2 H), 3.98 (d, J = 6.4 Hz, 2 H), 3.72 (s, 3 H), 3.48-3.54 (m, 1 H), 2.97-3.08 (m, 2 H), 2.18-2.20 (m, 1 H), 2.00 (d, J = 12.4 Hz, 2 H), 1.39-1.43 (m, 4 H), 1.31 (d, J = 6.8 Hz, 3 H), 1.20-1.21 (m, 2 H), 0.90-0.92 (m, 1 H), 0.40-0.53 (m, 3 H), 0.27-0.29 (m, 1 H). |
| 263* | 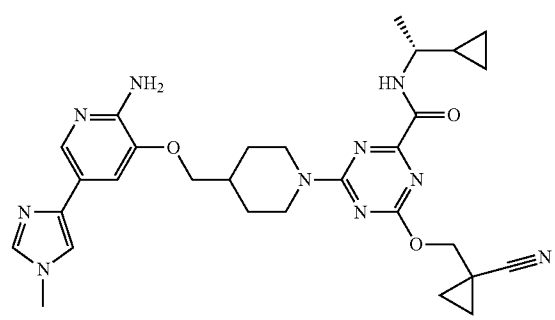 [SMILES: C[C@@H](NC(=O)c1nc(OCC2(C#N)CC2)nc(N2CCC(COc3cc(-c4cn(C)cn4)cnc3N)CC2)n1)C1CC1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-[(1R)-1-cyclopropylethyl]-1,3,5-triazine-2-carboxamide | 573.0; (400 MHz, CDCl$_3$) δ ppm 7.97 (s, 1 H), 7.80 (d, J = 8.8 Hz, 1 H), 7.45 (s, 2 H), 7.11 (s, 1 H), 5.07 (d, J = 13.2 Hz, 1 H), 4.86 (d, J = 13.2 Hz, 1 H), 4.63 (s, 2 H), 4.41 (s, 2 H), 3.98 (d, J = 6.4 Hz, 2 H), 3.72 (s, 3 H), 3.48-3.54 (m, 1 H), 2.97-3.08 (m, 2 H), 2.18-2.20 (m, 1 H), 2.00 (d, J = 12.4 Hz, 2 H), 1.39-1.45 (m, 4 H), 1.31 (d, J = 6.8 Hz, 3 H), 1.20-1.21 (m, 2 H), 0.90-0.92 (m, 1 H), 0.40-0.53 (m, 3 H), 0.27-0.29 (m, 1 H). |

TABLE 1-continued

| Ex. # | Structure | Compound Name | LRMS m/z (M + H)+; and 1H NMR |
|---|---|---|---|
| 264 | 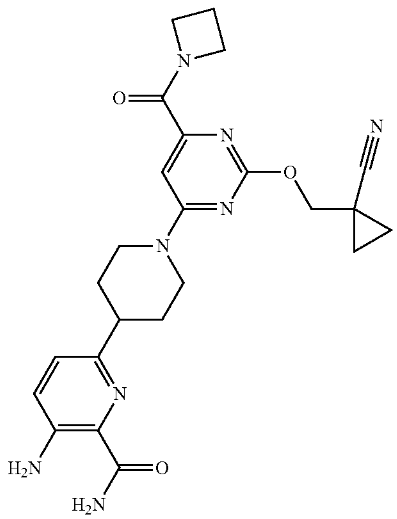 [SMILES: N#CC1(COc2nc(C(=O)N3CCC3)cc(N3CCC(c4ccc(N)c(C(N)=O)n4)CC3)n2)CC1] | 3-amino-6-(1-{6-(azetidin-1-ylcarbonyl)-2-[(1-cyanocyclopropyl)methoxy]pyrimidin-4-yl}piperidin-4-yl)pyridine-2-carboxamide | 477.1; (700 MHz, DMSO-d6) δ ppm 7.83 (br. s., 1 H), 7.22 (d, J = 2.9 Hz, 1 H), 7.17 (d, J = 8.5 Hz, 1 H), 7.09 (d, J = 8.5 Hz, 1 H), 6.92 (s, 1 H), 6.65 (br. s., 2 H), 4.55 (t, J = 7.7 Hz, 2 H), 4.24 (s, 2 H), 4.02 (t, J = 7.8 Hz, 2 H), 3.42-3.46 (m, 2 H), 3.03 (br. s., 1 H), 2.87 (t, J = 11.7 Hz, 1 H), 2.25 (quin, J = 7.8 Hz, 2 H), 1.90 (d, J = 12.0 Hz, 2 H), 1.58-1.66 (m, 3 H), 1.33-1.35 (m, 2 H), 1.18-1.19 (m, 2 H). |
| 265 | 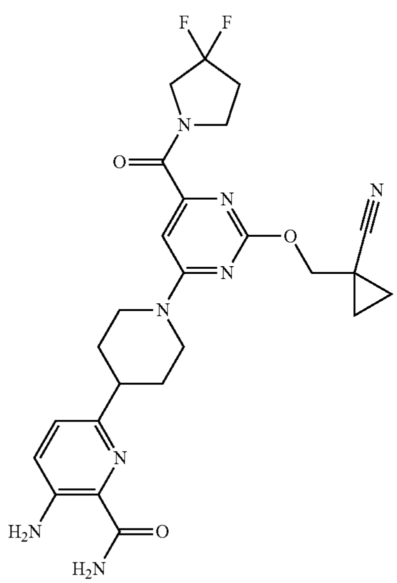 [SMILES: N#CC1(COc2nc(C(=O)N3CCC(F)(F)C3)cc(N3CCC(c4ccc(N)c(C(N)=O)n4)CC3)n2)CC1] | 3-amino-6-(1-{2-[(1-cyanocyclopropyl)methoxy]-6-[(3,3-difluoropyrrolidin-1-yl)carbonyl]pyrimidin-4-yl}piperidin-4-yl)pyridine-2-carboxamide | 527.2; (700 MHz, DMSO-d6) δ ppm 7.84 (br. s., 1 H), 7.24 (br. s., 1 H), 7.16-7.19 (m, 1 H), 7.08-7.11 (m, 1 H), 6.77-6.84 (m, 1 H), 6.66 (br. s., 2 H), 4.25-4.27 (m, 2 H), 4.06-4.12 (m, 1 H), 3.44-3.48 (m, 2 H), 3.69 (d, J = 7.3 Hz, 1 H), 3.36-3.46 (m, 1 H), 3.03 (br. s., 1 H), 2.83-2.92 (m, 1 H), 2.39-2.48 (m, 2 H), 1.90 (br. s., 2 H), 1.60-1.69 (m, 2 H), 1.34 (dd, J = 4.8, 2.4 Hz, 2 H), 1.19 (d, J = 3.4 Hz, 2 H). |

TABLE 1-continued

| Ex. # | Structure | Compound Name | LRMS m/z (M + H)+; and 1H NMR |
|---|---|---|---|
| 266*** | 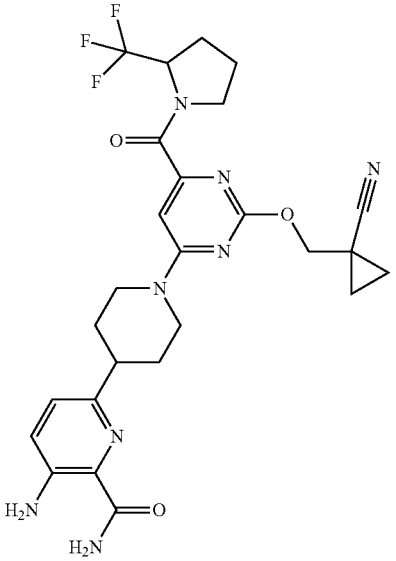 [SMILES: N#CC1(COc2nc(C(=O)N3CCCC3C(F)(F)F)cc(N3CCC(c4ccc(N)c(C(N)=O)n4)CC3)n2)CC1] | 3-amino-6-[1-(2-[(1-cyanocyclopropyl)methoxy]-6-{[2-(trifluoromethyl)pyrrolidin-1-yl]carbonyl}pyrimidin-4-yl)piperidin-4-yl]pyridine-2-carboxamide | 559.2; (700 MHz, DMSO-d6) δ ppm 7.84 (br. s., 1 H), 7.23 (br. s., 1 H), 7.18 (d, J = 8.5 Hz, 1 H), 7.09 (d, J = 8.7 Hz, 1 H), 6.79 (br. s., 0.3 H), 6.71 (br. s., 0.7 H), 6.65 (br. s., 2 H), 5.61-5.67 (m, 0.3 H), 4.94 (t, J = 7.4 Hz, 0.7 H), 4.28-4.34 (m, 1 H), 4.18-4.24 (m, 1 H), 3.65-3.72 (m, 1 H), 3.43-3.57 (m, 2 H), 3.03 (br. s., 1 H), 2.87 (t, J = 11.7 Hz, 1 H), 2.09-2.17 (m, 1 H), 1.86-2.03 (m, 5 H), 1.61-1.69 (m, 2 H), 1.34 (br. s., 2 H), 1.16-1.21 (m, 2 H). |
| 267** | 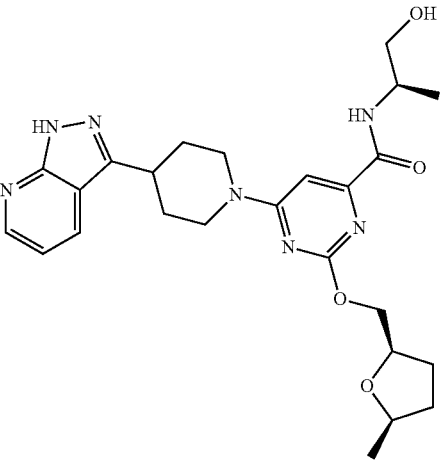 [SMILES: C[C@H](CO)NC(=O)c1cc(N2CCC(c3n[nH]c4ncccc34)CC2)nc(OC[C@H]2CC[C@@H](C)O2)n1] | N-[{2R)-1-hydroxypropan-2-yl]-2-{[(2R,5R)-5-methyl-tetrahydrofuran-2-yl]methoxy}-6-[4-(1H-pyrazolo[3,4-b]pyridin-3-yl)piperidin-1-yl]pyrimidine-4-carboxamide | 518.2 [M + Na]+; (400 MHz, CD3OD) δ ppm 8.47-8.48 (m, 1 H), 8.30-8.33 (m, 1 H), 7.17-7.20 (m, 1 H), 7.11 (s, 1H), 4.59 (s, 1 H), 4.11-4.37 (m, 5 H), 3.60 (d, J = 5.2 Hz, 2 H), 3.43-3.51 (m, 1 H), 3.26-3.30 (m, 3 H), 1.94-2.19 (m, 7 H), 1.49-1.54 (m, 1 H), 1.21-1.28 (m, 6 H). |
| 268** | 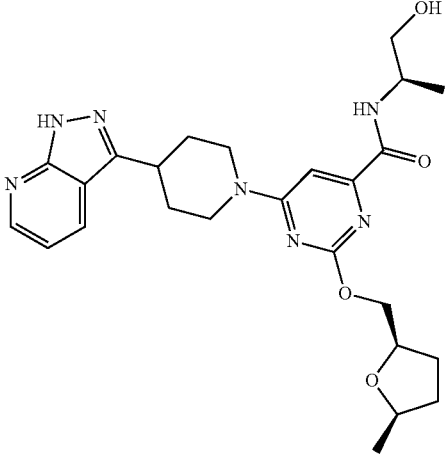 [SMILES: C[C@H](CO)NC(=O)c1cc(N2CCC(c3n[nH]c4ncccc34)CC2)nc(OC[C@H]2CC[C@@H](C)O2)n1] | N-[(2R)-1-hydroxypropan-2-yl]-2-{[(2R,5R)-5-methyltetrahydrofuran-2-yl]methoxy}-6-[4-(1H-pyrazolo[3,4-b]pyridin-3-yl)piperidin-1-yl]pyrimidine-4-carboxamide | 518.2 [M + Na]+; (400 MHz, CD3OD) δ ppm 8.47-8.49 (m, 1 H), 8.31-8.33 (m, 1 H), 7.17-7.20 (m, 1 H), 7.11 (s, 1 H), 4.61 (s, 1 H), 4.34-4.37 (m, 2 H), 4.25-4.26 (m, 1 H), 4.13-4.14 (m, 1 H), 4.04-4.06 (m, 1 H), 3.61 (d, J = 5.2 Hz, 2 H), 3.49-3.51 (m, 1 H), 3.26-3.31 (m, 3 H), 2.25-2.31 (m, 2 H), 1.88-2.07 (m, 5 H), 1.50-1.62 (m, 1 H), 1.24-1.26 (m, 6 H). |

TABLE 1-continued

| Ex. # | Structure | Compound Name | LRMS m/z (M + H)+; and 1H NMR |
|---|---|---|---|
| 269 | 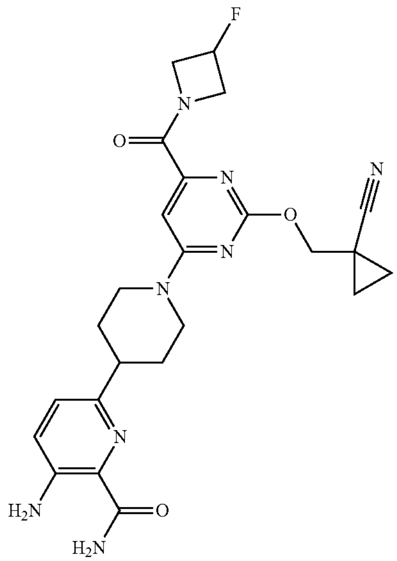 [SMILES: N#CC1(COc2nc(C(=O)N3CC(F)C3)cc(N3CCC(c4ccc(N)c(C(N)=O)n4)CC3)n2)CC1] | 3-amino-6-(1-{2-[(1-cyanocyclopropyl)methoxy]-6-[(3-fluoroazetidin-1-yl)carbonyl]pyrimidin-4-yl}piperidin-4-yl)pyridine-2-carboxamide | 495.1; (700 MHz, DMSO-d$_6$) δ ppm 7.83 (br. s., 1 H), 7.22 (br. s., 1 H), 7.18 (dt, J = 8.5, 2.0 Hz, 1 H), 7.09 (d5, J = 8.5, 2.2 Hz, 1 H), 6.96-6.98 (m, 1 H), 6.65 (br. s., 2 H), 5.46 (d, J = 2.9 Hz, 0.5 H), 5.36-5.38 (m, 0.5 H), 4.86-4.92 (m, 1 H), 4.59-4.64 (m, 1 H), 4.34-4.39 (m, 1 H), 4.24-4.25 (m, 2 H), 4.04-4.09 (m, 1 H), 3.04 (br. s., 1 H), 1.90 (d, J = 12.6 Hz, 2 H), 1.59-1.67 (m, 2 H), 1.35 (d, J = 1.9 Hz, 2 H), 1.20 (d, J = 1.7 Hz, 2 H), |
| 270 | 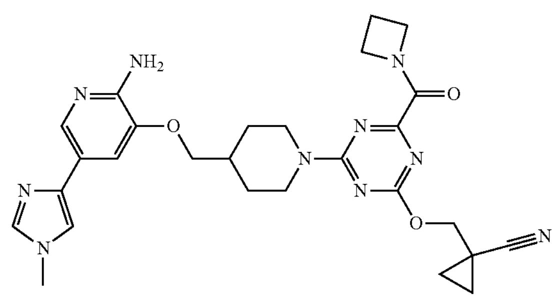 [SMILES: Cn1cnc(-c2cnc(N)c(OCC3CCN(c4nc(OCC5(C#N)CC5)nc(C(=O)N5CCC5)n4)CC3)c2)c1] | 1-[({4-[4-({[2-amino-5-(1-methyl-1H-imidazol-4-yl)pyridin-3-yl]oxy}methyl)piperidin-1-yl]-6-(azetidin-1-ylcarbonyl)-1,3,5-triazin-2-yl}oxy)methyl]cyclopropanecarbonitrile | 567.2 [M + Na]+; (400 MHz, CDCl$_3$) δ ppm 7.94 (s, 1 H), 7.47 (d, J = 8.0 Hz, 2 H), 7.12 (s, 1 H), 4.83-4.97 (m, 4 H), 4.51-4.55 (m, 2 H), 4.39-4.40 (m, 2 H), 4.20-4.24 (m, 2 H), 3.97-3.98 (m, 2 H), 3.72 (s, 3 H), 2.96-3.03 (m, 2 H), 2.31-2.39 (m, 2 H), 2.19-2.21 (m, 1 H), 1.97-1.99 (m, 2 H), 1.36-1.42 (m, 4 H), 1.15-1.19 (m, 2 H). |
| 271* | 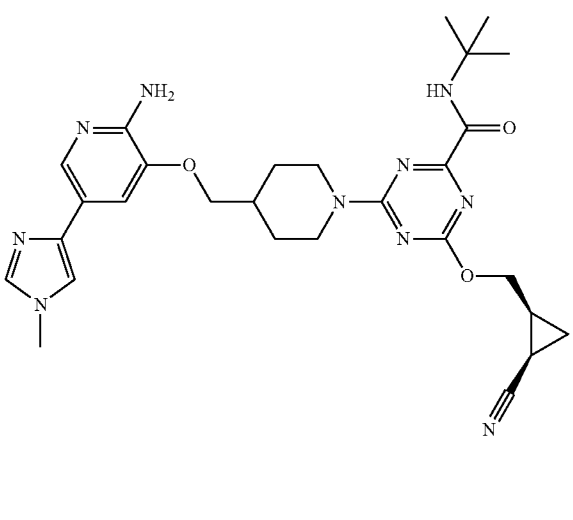 [SMILES: Cn1cnc(-c2cnc(N)c(OCC3CCN(c4nc(OC[C@H]5C[C@H]5C#N)nc(C(=O)NC(C)(C)C)n4)CC3)c2)c1] | 4-[4-({[2-amino-5-(1-methyl-1H-imidazol-4-yl)pyridin-3-yl]oxy}methyl)piperidin-1-yl]-N-tert-butyl-6-{[(1S,2R)-2-cyanocyclopropyl]methoxy}-1,3,5-triazine-2-carboxamide | 561.3; (400 MHz, CDCl$_3$) δ ppm 7.95 (s, 1 H), 7.70 (s, 1 H), 7.45 (s, 2 H), 7.10 (s, 1 H), 5.04 (d, J = 12.4 Hz, 1 H), 4.85 (d, J = 12.4 Hz, 1 H), 4.73 (s, 2 H), 4.56-4.58 (m, 1 H), 4.45-4.47 (m, 1 H), 3.95-3.97 (m, 2 H), 3.71 (s, 3 H), 2.94-3.05 (m, 2 H), 2.17-2.18 (m, 1 H), 1.85-1.89 (m, 2 H), 1.70-1.72 (m, 1 H), 1.33-1.45 (m, 13 H), 1.12-1.14 (m, 2 H). |

TABLE 1-continued

| Ex. # | Structure | Compound Name | LRMS m/z (M + H)+; and 1H NMR |
|---|---|---|---|
| 272* | 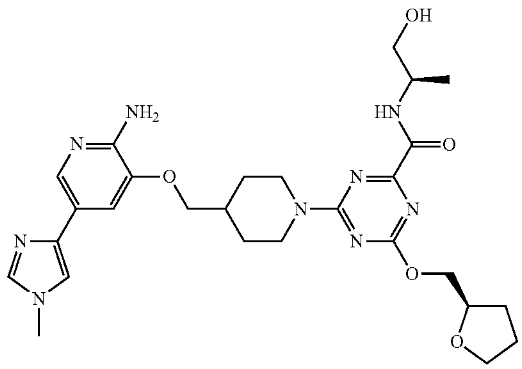 [SMILES: C[C@H](CO)NC(=O)c1nc(OC[C@H]2CCCO2)nc(N2CCC(COc3cc(-c4cn(C)cn4)cnc3N)CC2)n1] | 6-[4-({[2-amino-5-(1-methyl-1H-imidazol-4-yl)pyridin-3-yl]oxy}methyl)piperidin-1-yl]-N-[(2R)-1-hydroxypropan-2-yl]-2-[(2R)-tetrahydrofuran-2-ylmethoxy]pyrimidine-4-carboxamide | 567.1; (400 MHz, DMSO-d$_6$) δ ppm 8.15 (d, J = 8.4 Hz, 1 H), 7.92 (d, J = 1.2 Hz, 1 H), 7.55 (s, 1 H), 7.43 (s, 1 H), 7.32 (s, 1 H), 6.99 (s, 1 H), 5.57 (br. s., 2 H), 4.86 (t, J = 5.6 Hz, 1 H), 4.35-4.65 (m, 1 H), 4.25-4.38 (m, 2 H), 4.11-4.18 (m, 1 H), 3.92-4.05 (m, 1 H), 3.90 (d, J = 6.4 Hz, 2 H), 3.72-3.85 (m, 1 H), 3.60-3.72 (m, 4 H), 3.35-3.48 (m, 2 H), 2.98-3.06 (m, 3 H), 2.08-2.18 (m, 1 H), 1.91-2.05 (m, 2 H), 1.73-1.91 (m, 3 H), 1.62-1.72 (m, 1 H), 1.20-1.38 (m, 2 H), 1.12 (d, J = 6.8 Hz, 3 H). |
| 273* | 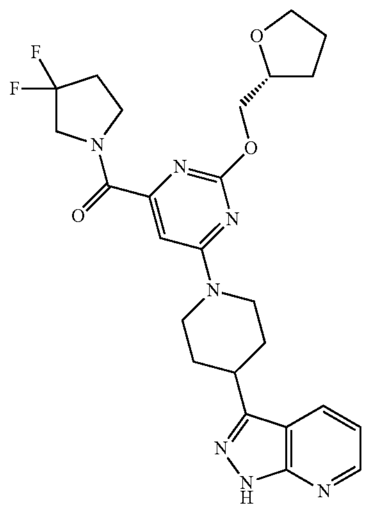 [SMILES: O=C(c1cc(N2CCC(c3n[nH]c4ncccc34)CC2)nc(OC[C@H]2CCCO2)n1)N1CCC(F)(F)C1] | (3,3-difluoropyrrolidin-1-yl){6-[4-(1H-pyrazolo[3,4-b]pyridin-3-yl)piperidin-1-yl]-2-[(2R)-tetrahydrofuran-2-ylmethoxy]pyrimidin-4-yl}methanone | 514.1; (700 MHz, DMSO-d6) δ ppm 8.45 (dd, J = 4.4, 1.5 Hz, 1 H), 8.30 (dd, J = 8.0, 1.5 Hz, 1 H), 7.13 (dd, J = 8.0, 1.5 Hz, 1 H), 6.79-6.83 (m, 1 H), 4.18-4.22 (m, 2 H), 4.11-4.15 (m, 2 H), 3.86-3.89 (m, 2 H), 3.75-3.78 (m, 1 H), 3.64-3.71 (m, 2 H), 2.42-2.46 (m, 2 H), 2.09 (d, J = 10.8 Hz, 2 H), 1.95-1.98 (m, 1 H), 1.77-1.89 (m, 4 H), 1.61-1.66 (m, 1 H). |
| 274* | 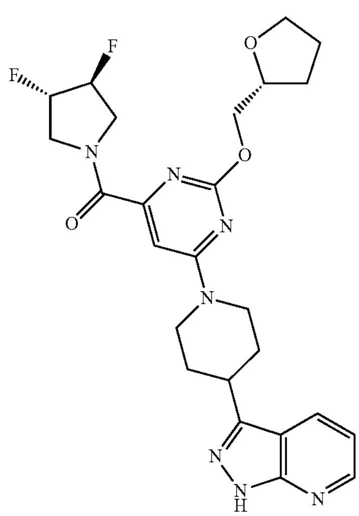 [SMILES: O=C(c1cc(N2CCC(c3n[nH]c4ncccc34)CC2)nc(OC[C@H]2CCCO2)n1)N1C[C@H](F)[C@@H](F)C1] | [(3S,4S)-3,4-difluoropyrrolidin-1-yl]{6-[4-(1H-pyrazolo[3,4-b]pyridin-3-yl)piperidin-1-yl]-2-[(2R)-tetrahydrofuran-2-ylmethoxy]pyrimidin-4-yl}methanone | 514.2; (700 MHz, DMSO-d$_6$) δ ppm 8.47 (d, J = 4.4 Hz, 1 H), 8.31 (d, J = 8.0 Hz, 1 H), 7.13 (dd, J = 8.0, 4.4 Hz, 1 H), 6.83 (s, 1 H), 5.43 (br. s., 1 H), 5.36 (br. s., 1 H), 4.16-4.23 (m, 2 H), 4.13-4.15 (m, 1 H), 3.96-4.09 (m, 2 H), 3.76-3.89 (m, 3 H), 3.66 (q, J = 7.4 Hz, 1 H), 2.09 (d, J = 12.3 Hz, 2 H), 1.95-1.99 (m, 1 H), 1.77-1.89 (m, 5 H), 1.62-1.67 (m, 1 H). |

TABLE 1-continued

| Ex. # | Structure | Compound Name | LRMS m/z (M + H)+; and 1H NMR |
|---|---|---|---|
| 275* | 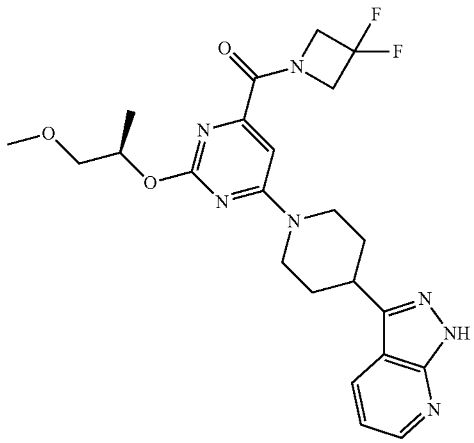 [SMILES: COC[C@@H](C)Oc1nc(C(=O)N2CC(F)(F)C2)cc(N2CCC(c3n[nH]c4ncccc34)CC2)n1] | (3,3-difluoroazetidin-1-yl)(2-{[(2R)-1-methoxypropan-2-yl]oxy}-6-[4-(1H-pyrazolo[3,4-b]pyridin-3-yl)piperidin-1-yl]pyrimidin-4-yl)methanone | 488.1; (700 MHz, DMSO-d6) δ ppm 8.47 (d, J = 1.20 Hz, 1 H), 8.30 (d, J = 6.49 Hz, 1 H), 7.10-7.16 (m, 1 H), 6.96-7.03 (m, 1 H), 5.13-5.22 (m, 1 H), 4.98 (t, J = 12.21 Hz, 2 H), 4.47 (t, J = 11.96 Hz, 3 H), 3.47-3.54 (m, 1 H), 3.44 (d, J = 10.42 Hz, 1 H), 3.25-3.30 (m, 1 H), 2.46-2.52 (m, 6 H), 2.09 (d, J = 12.81 Hz, 2 H), 1.73-1.81 (m, 2 H), 1.20-1.28 (m, 4 H). |
| 276* | 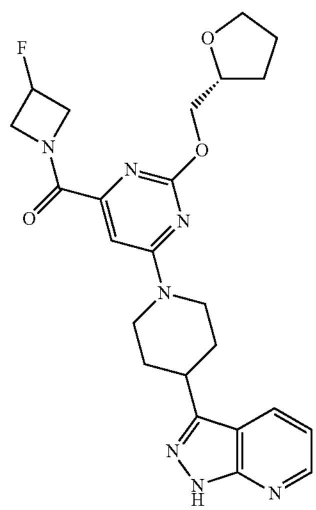 [SMILES: O=C(c1cc(N2CCC(c3n[nH]c4ncccc34)CC2)nc(OC[C@H]2CCCO2)n1)N1CC(F)C1] | (3-fluoroazetidin-1-yl){6-[4-(1H-pyrazolo[3,4-b]pyridin-3-yl)piperidin-1-yl]-2-[(2R)-tetrahydrofuran-2-ylmethoxy]pyrimidin-4-yl}methanone | 482.2; (700 MHz, DMSO-d6) δ ppm 8.47 (td, J = 3.9, 1.3 Hz, 1 H), 8.28-8.30 (m, 1 H), 7.12-7.14 (m, 1 H), 6.97-6.98 (m, 1 H), 5.47 (br. s., 0.5 H), 5.39 (br. s., 0.5 H), 4.87-4.93 (m, 1 H), 4.59-4.64 (m, 1 H), 4.34-4.39 (m, 1 H), 4.05-4.21 (m, 4 H), 3.76-3.79 (m, 1 H), 3.64-3.67 (m, 1 H), 3.16-3.18 (m, 1 H), 2.09 (d, J = 12.8 Hz, 2 H), 1.96-1.99 (m, 1 H), 1.75-1.91 (m, 4 H), 1.62-1.66 (m, 1 H). |
| 277* | 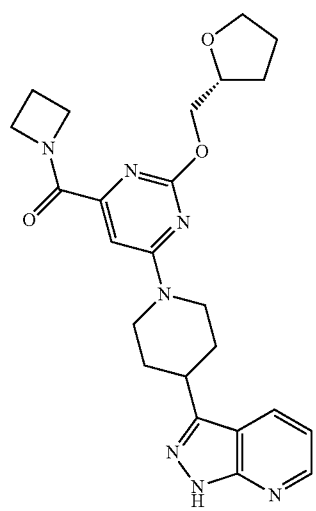 [SMILES: O=C(c1cc(N2CCC(c3n[nH]c4ncccc34)CC2)nc(OC[C@H]2CCCO2)n1)N1CCC1] | Azetidin-1-yl{6-[4-(1H-pyrazolo[3,4-b]pyridin-3-yl)piperidin-1-yl]-2-[(2R)-tetrahydrofuran-2-ylmethoxy]pyrimidin-4-yl}methanone | 464.1; (700 MHz, DMSO-d6) δ ppm 8.46-8.48 (m, 1 H), 8.29-8.30 (m, 1 H), 7.13 (dd, J = 8.0, 4.4 Hz, 1 H), 6.93 (s, 1 H), 4.57 (t, J = 7.7 Hz, 2 H), 4.13-4.20 (m, 3 H), 4.03 (t, J = 7.7 Hz, 2 H), 3.77 (q, J = 7.1 Hz, 2 H), 3.66 (q, J = 7.3 Hz, 1 H), 2.26 (quin, J = 7.7 Hz, 2 H), 2.08 (d, J = 11.4 Hz, 2 H), 1.95-1.98 (m, 1 H), 1.75-1.87 (m, 5 H), 1.59-1.64 (m, 2 H). |

TABLE 1-continued

| Ex. # | Structure | Compound Name | LRMS m/z (M + H)+; and 1H NMR |
|---|---|---|---|
| 278* | 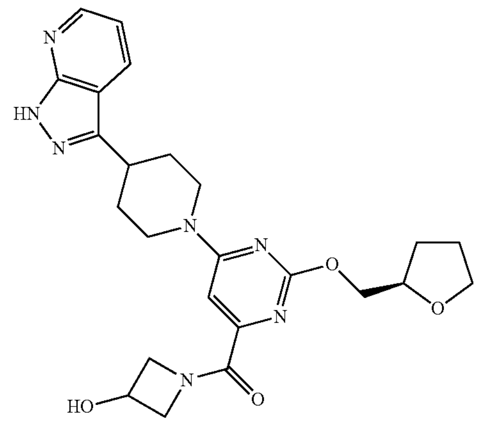 [SMILES: O=C(c1cc(N2CCC(c3n[nH]c4ncccc34)CC2)nc(OC[C@H]2CCCO2)n1)N1CC(O)C1] | (3-hydroxyazetidin-1-yl){6-[4-(1H-pyrazolo[3,4-b]pyridin-3-yl)piperidin-1-yl]-2-[(2R)-tetrahydrofuran-2-ylmethoxy]pyrimidin-4-yl}methanone | 480.0; (400 MHz, CD$_3$OD) δ ppm 8.50 (d, J = 4.4 Hz, 1 H), 8.33 (d, J = 8.0 Hz, 1 H), 7.19-7.22 (m, 1 H), 7.01 (s, 1 H), 4.47-4.64 (m, 3 H), 4.28-4.39 (m, 5 H), 3.91-3.95 (m, 2 H), 3.81-3.82 (m, 1 H), 3.33-3.50 (m, 2 H), 3.26-3.29 (m, 2 H), 2.09-2.20 (m, 3 H), 1.97-2.02 (m, 4 H), 1.81-1.94 (m, 1 H). |
| 279* | 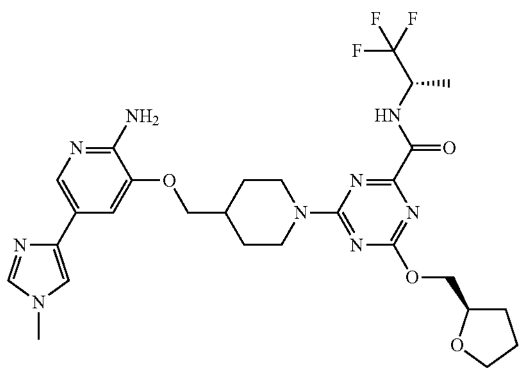 [SMILES: C[C@H](NC(=O)c1nc(OC[C@H]2CCCO2)nc(N2CCC(COc3cc(-c4cn(C)cn4)cnc3N)CC2)n1)C(F)(F)F] | 4-[4-({[2-amino-5-(1-methyl-1H-imidazol-4-yl)pyridin-3-yl]oxy}methyl)piperidin-1-yl]-6-[(2R)-tetrahydrofuran-2-ylmethoxy]-N-[(2S)-1,1,1-trifluoropropan-2-yl]-1,3,5-triazine-2-carboxamide | 606.1; (400 MHz, CD$_3$OD) δ ppm 7.88 (s, 1 H), 7.63 (s, 1 H), 7.44 (s, 1 H), 7.36 (s, 1 H), 5.10 (d, J = 15.2 Hz, 2 H), 4.44-4.57 (m, 1 H), 4.41-4.43 (m, 2 H), 4.28-4.29 (m, 1 H), 4.02 (d, J = 8.0 Hz, 2 H), 3.90-3.92 (m, 2 H), 3.76 (s, 3 H), 3.10-3.13 (m, 2 H), 2.23-2.29 (m, 1 H), 1.96-2.11 (m, 5 H), 1.70-1.82 (m, 1 H), 1.44-1.47 (m, 5 H). |
| 280* | 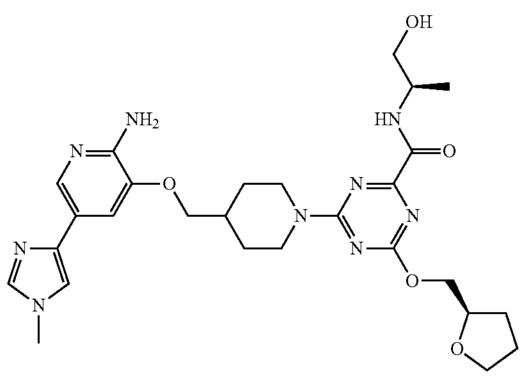 [SMILES: C[C@H](CO)NC(=O)c1nc(OC[C@H]2CCCO2)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-N-[(2R)-1-hydroxypropan-2-yl]-6-[(2R)-tetrahydrofuran-2-ylmethoxy]-1,3,5-triazine-2-carboxamide | 568.1; (400 MHz, CD$_3$OD) δ ppm 7.88 (s, 1 H), 7.63 (s, 1 H), 7.44 (s, 1 H), 7.36 (s, 1 H), 5.07-5.10 (m, 2 H), 4.41-4.43 (m, 2 H), 4.14-4.26 (m, 2 H), 4.01-4.03 (m, 2 H), 3.91 (d, J = 8.0 Hz, 2 H), 3.76 (s, 3 H), 3.63 (d, J = 5.2 Hz, 2 H), 3.06-3.09 (m, 2 H), 2.23-2.28 (m, 1 H), 1.82-2.11 (m, 6 H), 1.42-1.45 (m, 2 H), 1.27 (d, J = 6.6 Hz, 3 H). |
| 281* | 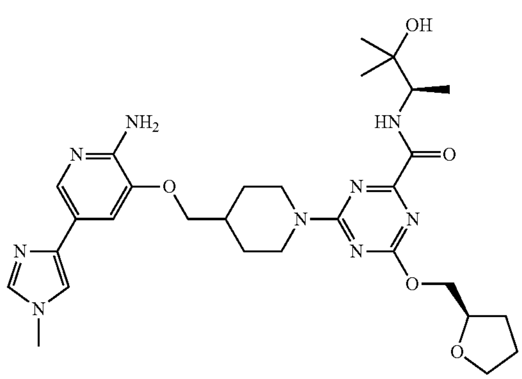 [SMILES: C[C@@H](NC(=O)c1nc(OC[C@H]2CCCO2)nc(N2CCC(COc3cc(-c4cn(C)cn4)cnc3N)CC2)n1)C(C)(C)O] | 4-[4-({[2-amino-5-(1-methyl-1H-imidazol-4-yl)pyridin-3-yl]oxy}methyl)piperidin-1-yl]-N-[(2R)-3-hydroxy-3-methylbutan-2-yl]-6-[(2R)-tetrahydrofuran-2-ylmethoxy]-1,3,5-triazine-2-carboxamide | 596.1; (400 MHz, CD$_3$OD) δ ppm 7.88 (s, 1 H), 7.63 (s, 1 H), 7.44 (s, 1 H), 7.36 (s, 1 H), 5.09 (d, J = 12.4 Hz, 2 H), 4.54-4.57 (m, 1 H), 4.41-4.43 (m, 2 H), 4.28-4.29 (m, 1 H), 4.02 (d, J = 6.8 Hz, 2 H), 3.90-3.92 (m, 1 H), 3.80-3.81 (s, 1 H), 3.76 (s, 3 H), 3.08-3.13 (m, 2 H), 2.23-2.28 (m, 1 H), 1.96-2.11 (m, 5 H), 1.77-1.83 (m, 1 H), 1.43-1.46 (m, 2 H) 1.22-1.27 (m, 8 H). |

TABLE 1-continued

| Ex. # | Structure | Compound Name | LRMS m/z (M + H)+; and 1H NMR |
|---|---|---|---|
| 282* | 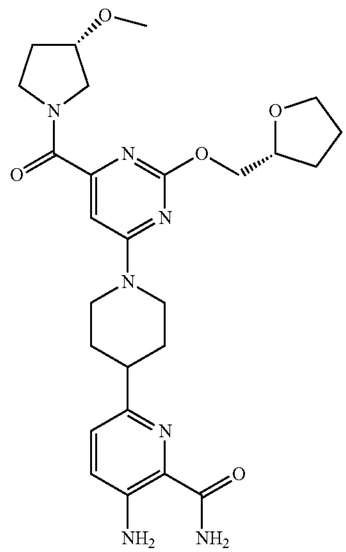 [SMILES: CO[C@H]1CCN(C(=O)c2cc(N3CCC(c4ccc(N)c(C(N)=O)n4)CC3)nc(OC[C@H]3CCCO3)n2)C1] | 3-amino-6-[1-(6-{[(3S)-3-methoxypyrrolidin-1-yl]carbonyl}-2-[(2R)-tetrahydrofuran-2-ylmethoxy]pyrimidin-4-yl)piperidin-4-yl]pyridine-2-carboxamide | 526.2; (700 MHz, DMSO-d$_6$) δ ppm 7.84 (br. s., 1 H), 7.24 (br. s., 1 H), 7.18 (dd, J = 8.6, 2.3 Hz, 1 H), 7.09 (dt, J = 8.5, 2.2 Hz, 1 H), 6.63-6.69 (m, 3 H), 4.09-4.20 (m, 3 H), 3.94-4.00 (m, 1 H), 3.74-3.77 (m, 1 H), 3.48-3.66 (m, 4 H), 3.08-3.22 (m, 2 H), 3.00 (br. s., 1 H), 2.84-2.87 (m, 1 H), 1.76-2.03 (m, 7 H), 1.64 (d, J = 8.7 Hz, 3 H). |
| 283* | 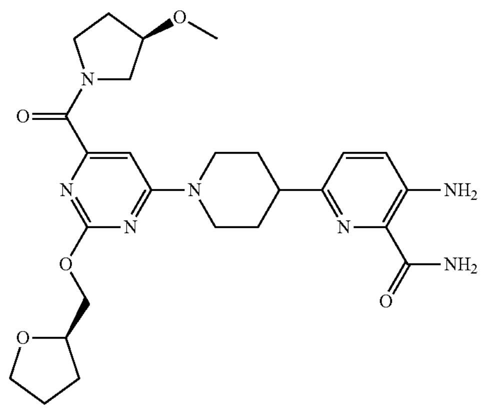 [SMILES: CO[C@@H]1CCN(C(=O)c2cc(N3CCC(c4ccc(N)c(C(N)=O)n4)CC3)nc(OC[C@H]3CCCO3)n2)C1] | 3-amino-6-[1-(6-{[(3R)-3-methoxypyrrolidin-1-yl]carbonyl}-2-[(2R)-tetrahydrofuran-2-ylmethoxy]pyrimidin-4-yl)piperidin-4-yl]pyridine-2-carboxamide | 526.2; (700 MHz, DMSO-d$_6$) δ ppm 7.84 (d, J = 2.9 Hz, 1 H), 7.24 (d, J = 3.1 Hz, 1 H), 7.18 (d, J = 8.5 Hz, 1 H), 7.09 (d, J = 8.5 Hz, 1 H), 6.63-6.70 (m, 3 H), 4.16-4.19 (m, 2 H), 4.09-4.14 (m, 1 H), 3.95-3.99 (m, 1 H), 3.76 (q, J = 7.1 Hz, 1 H), 3.48-3.67 (m, 4 H), 3.24-3.25 (m, 1 H), 3.18-3.19 (m, 1 H), 3.00 (br. s., 1 H), 2.86 (tt, J = 11.7, 3.7 Hz, 1 H), 1.78-2.01 (m, 7 H), 1.60-1.67 (m, 3 H). |
| 284* | 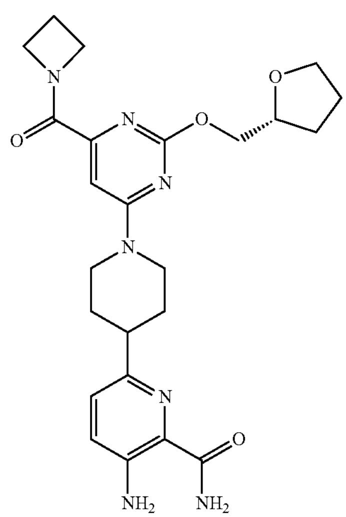 [SMILES: NC(=O)c1nc(C2CCN(c3cc(C(=O)N4CCC4)nc(OC[C@H]4CCCO4)n3)CC2)ccc1N] | 3-amino-6-(1-{6-(azetidin-1-ylcarbonyl)-2-[(2R)-tetrahydrofuran-2-ylmethoxy]pyrimidin-4-yl}piperidin-4-yl)pyridine-2-carboxamide | 483.1; (700 MHz, DMSO-d$_6$) δ ppm 7.83 (br. s., 1 H), 7.24 (br. s., 1 H), 7.17 (d, J = 8.5 Hz, 1 H), 7.09 (d, J = 8.5 Hz, 1 H), 6.90 (s, 1 H), 6.67 (br. s., 2 H), 4.56 (t, J = 7.6 Hz, 2 H), 4.10-4.19 (m, 3 H), 4.02 (t, J = 7.8 Hz, 2 H), 3.75-3.78 (m, 1 H), 3.64-3.67 (m, 1 H), 3.01 (br. s., 1 H), 2.82-2.88 (m, 1 H), 2.26 (quin, J = 7.7 Hz, 2 H), 1.97 (td, J = 12.7, 7.7 Hz, 1 H), 1.81-1.90 (m, 5 H), 1.59-1.66 (m, 4 H). |

TABLE 1-continued

| Ex. # | Structure | Compound Name | LRMS m/z (M + H)+; and 1H NMR |
|---|---|---|---|
| 285* | 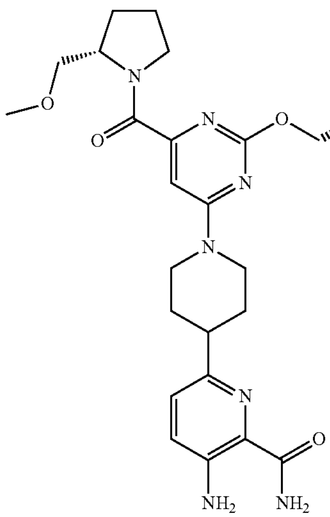 | 3-amino-6-[1-(6-{[(2S)-2-(methoxymethyl)pyrrolidin-1-yl]carbonyl}-2-[(2R)-tetrahydrofuran-2-ylmethoxy]pyrimidin-4-yl)piperidin-4-yl]pyridine-2-carboxamide | 540.2; (700 MHz, DMSO-d$_6$) δ ppm 7.81-7.84 (m, 1 H), 7.25 (br. s., 1 H), 7.17-7.19 (m, 1 H), 7.09 (d, J = 8.5 Hz, 1 H), 6.63-6.68 (m, 3 H), 4.44 (d, J = 4.4 Hz, 1 H), 4.10-4.19 (m, 4 H), 3.76 (q, J = 7.2 Hz, 1 H), 3.64-3.67 (m, 1 H), 3.46-3.56 (m, 2 H), 3.11-3.13 (m, 1 H), 3.00 (br. s., 1 H), 2.84-2.87 (m, 1 H), 1.75-1.98 (m, 11 H), 1.61-1.67 (m, 4 H). |
| 286* | 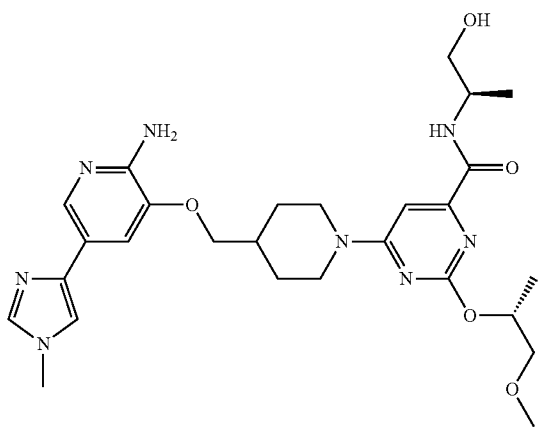 [SMILES: COC[C@@H](C)Oc1nc(C(=O)N[C@H](C)CO)cc(N2CCC(COc3cc(-c4cn(C)cn4)cnc3N)CC2)n1] | 6-[4-({[2-amino-5-(1-methyl-1H-imidazol-4-yl)pyridin-3-yl]oxy}methyl)piperidin-1-yl]-N-[(2R)-1-hydroxypropan-2-yl]-2-{[(2R)-1-methoxypropan-2-yl]oxy}pyrimidine-4-carboxamide | 555.1; (400 MHz, CDCl$_3$) δ ppm 7.94-7.96 (m, 2 H), 7.45 (s, 1 H), 7.09 (s, 1 H), 7.06 (s, 1 H), 5.28-5.34 (m, 1 H), 4.48-4.88 (br. s., 4 H), 4.18-4.21 (m, 1 H), 3.95 (d, J = 6.4 Hz, 2 H), 3.55-3.74 (m, 6 H), 3.45-3.55 (m, 1 H), 3.41 (s, 1 H), 2.96-3.03 (m, 2 H), 2.16-2.23 (m, 1 H), 1.93-1.98 (m, 2 H), 1.34-1.41 (m, 5 H), 1.26 (d, J = 6.8 Hz, 3H). |
| 287 | 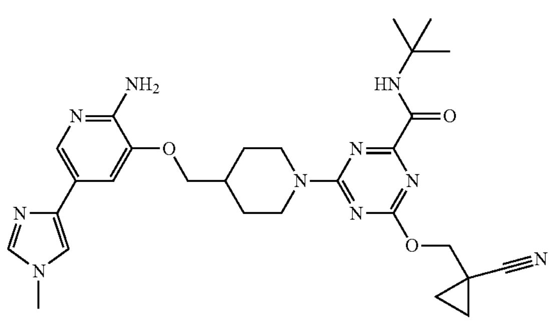 [SMILES: Cn1cnc(-c2cnc(N)c(OCC3CCN(c4nc(OCC5(C#N)CC5)nc(C(=O)NC(C)(C)C)n4)CC3)c2)c1] | 4-[4-({[2-amino-5-(1-methyl-1H-imidazol-4-yl)pyridin-3-yl]oxy}methyl)piperidin-1-yl]-N-tert-butyl-6-[(1-cyanocyclopropyl)methoxy]-1,3,5-triazine-2-carboxamide | 561.1; (400 MHz, CDCl$_3$) δ ppm 7.95 (s, 1 H), 7.70 (s, 1 H), 7.46 (s, 2 H), 7.10 (s, 1 H), 5.05 (d, J = 14.0 Hz, 1 H), 4.85 (d, J = 12.8 Hz, 1 H), 4.75 (s, 2 H), 4.40 (d, J = 4.4 Hz, 2 H), 3.96-3.97 (m, 2 H), 3.72 (s, 3 H), 2.99-3.03 (m, 2 H), 2.17-2.19 (m, 1 H), 1.98-2.00 (m, 2 H), 1.39-1.46 (m, 13 H), 1.18-1.20 (m, 2 H). |

| Ex. # | Structure | Compound Name | LRMS m/z (M + H)+; and 1H NMR |
|---|---|---|---|
| 288* | 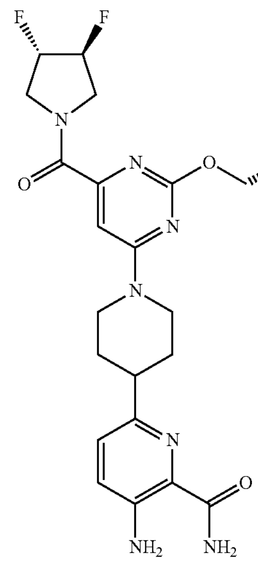 | 3-amino-6-[1-(6-{[(3S,4S)-3,4-difluoropyrrolidin-1-yl]carbonyl}-2-[(2R)-tetrahydrofuran-2-ylmethoxy]pyrimidin-4-yl]piperidin-4-yl)pyridine-2-carboxamide | 532.2; (700 MHz, DMSO-d$_6$) δ ppm 7.77 (br. s., 1 H), 7.18 (d, J = 2.2 Hz, 1 H), 7.11 (dd, J = 8.6, 2.1 Hz, 1 H), 7.02 (dd, J = 8.5, 2.4 Hz, 1 H), 6.73 (d, J = 1.9 Hz, 1 H), 6.60 (br. s., 2 H), 5.36 (br. s., 1 H), 5.29 (br. s., 1 H), 3.88-4.15 (m, 6 H), 3.67-3.82 (m, 3 H), 3.58-3.61 (m, 1 H), 2.95 (br. s., 1 H), 2.80 (t, J = 11.8 Hz, 1 H), 1.73-1.93 (m, 6 H), 1.55-1.62 (m, 4 H). |
| 289* | 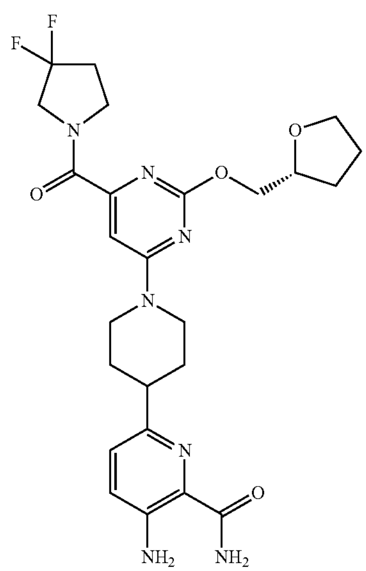 [SMILES: NC(=O)c1nc(C2CCN(c3cc(C(=O)N4CCC(F)(F)C4)nc(OC[C@H]4CCCO4)n3)CC2)ccc1N] | 3-amino-6-(1-{6-[(3,3-difluoropyrrolidin-1-yl)carbonyl]-2-[(2R)-tetrahydrofuran-2-ylmethoxy]pyrimidin-4-yl}piperidin-4-yl)pyridine-2-carboxamide | 532.2; (700 MHz, DMSO-d$_6$) δ ppm 7.84 (d, J = 3.1 Hz, 1 H), 7.25 (d, J = 2.9 Hz, 1 H), 7.18 (d, J = 8.7 Hz, 1 H), 7.09 (d, J = 8.5 Hz, 1 H), 6.79 (s, 0.5 H, 6.75 (s, 0.5 H), 6.67 (br. s., 2 H), 4.16-4.20 (m, 2 H), 4.10-4.14 (m, 2 H), 3.85-3.89 (m, 2 H), 3.75-3.78 (m, 1 H), 3.64-3.70 (m, 2 H), 3.02 (br. s., 1 H), 2.85-2.88 (m, 1 H), 2.42-2.48 (m, 2 H), 1.93-1.98 (m, 1 H), 1.80-1.91 (m, 4 H), 1.62-1.68 (m, 3 H). |
| 290* | 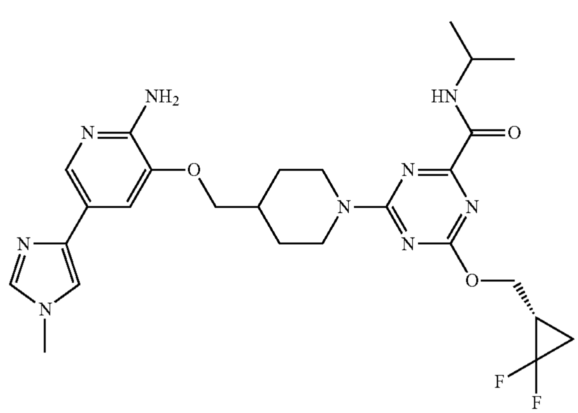 [SMILES: CC(C)NC(=O)c1nc(OC[C@@H]2CC2(F)F)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-6-{[(1S)-2,2-difluorocyclopropyl]methoxy}-N-(propan-2-yl)-1,3,5-triazine-2-carboxamide | 580.1; [M + Na]+; (400 MHz, CDCl$_3$) δ ppm 8.38 (s, 1 H), 7.85 (s, 1 H), 7.63 (d, J = 8.8 Hz, 1 H), 7.50 (d, J = 5.6 Hz, 2 H), 7.11 (s, 1 H), 5.67 (s, 2 H), 5.10 (d, J = 14.0 Hz, 1 H), 4.86 (d, J = 12.0 Hz, 1 H), 4.40-4.55 (m, 2 H), 4.22-4.26 (m, 1 H), 3.95-4.05 (m, 2 H), 3.74 (s, 3 H), 2.97-3.08 (m, 2 H), 2.05 (d, J = 11.2 Hz, 4 H), 1.55-1.65 (m, 1 H), 1.32-1.41 (m, 3 H), 1.26 (d, d, J = 10.0 Hz, 6 H). |

TABLE 1-continued

| Ex. # | Structure | Compound Name | LRMS m/z (M + H)+; and 1H NMR |
|---|---|---|---|
| 291* | 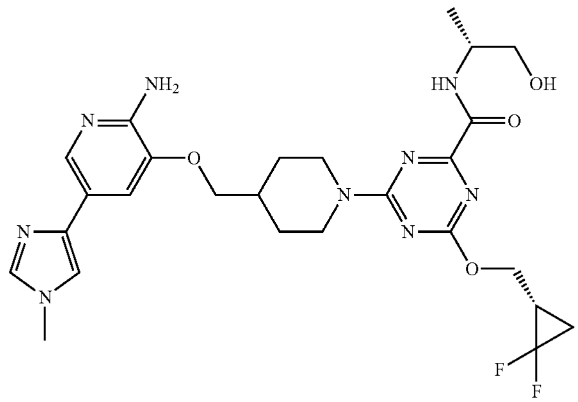 [SMILES: C[C@H](CO)NC(=O)c1nc(OC[C@@H]2CC2(F)F)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-6-{[(1S)-2,2-difluorocyclopropyl]methoxy}-N-[(2R)-1-hydroxypropan-2-yl]-1,3,5-triazine-2-carboxamide | 596.2 [M + Na]+; (400 MHz, CDCl$_3$) δ ppm 7.96 (s, 1 H), 7.90 (d, J = 11.6 Hz, 1 H), 7.48 (d, J = 5.2 Hz, 2 H), 7.12 (s, 1 H), 5.05 (d, J = 12.8 Hz, 1 H), 4.83-4.87 (m, 1 H), 4.80 (br. s., 2 H), 4.40-4.55 (m, 2 H), 4.15-4.25 (m, 1 H), 3.99 (t, J = 3.2 Hz, 2 H), 3.75-3.77 (m, 1 H), 3.73 (s, 3 H), 3.64-3.69 (m, 1 H), 2.95-3.05 (m, 2 H), 2.10-2.25 (m, 2 H), 1.98-2.02 (m, 2 H), 1.59-1.62 (m, 2 H), 1.34-1.45 (m, 3 H), 1.30 (d, J = 6.8 Hz, 6 H). |
| 292* | 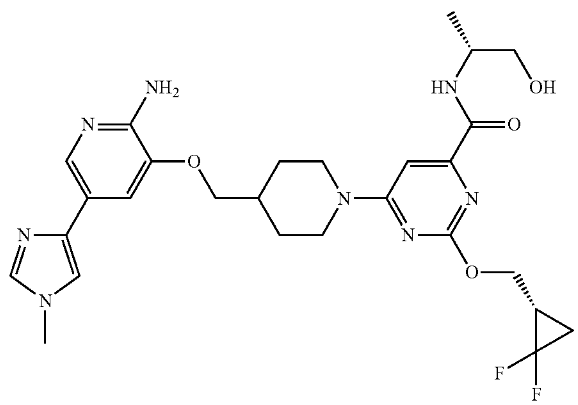 [SMILES: C[C@H](CO)NC(=O)c1cc(N2CCC(COc3cc(-c4cn(C)cn4)cnc3N)CC2)nc(OC[C@@H]2CC2(F)F)n1] | 6-[4-({[2-amino-5-(1-methyl-1H-imidazol-4-yl)pyridin-3-yl]oxy}methyl)piperidin-1-yl]-2-{[(1S)-2,2-difluorocyclopropyl]methoxy}-N-[(2R)-1-hydroxypropan-2-yl]pyrimidine-4-carboxamide | 595.2 [M + Na]+; (400 MHz, CDCl$_3$) δ ppm (Formate salt) 7.89-7.93 (m, 2 H), 7.49 (d, J = 5.2 Hz, 2 H), 7.12 (d, J = 5.2 Hz, 2 H), 5.32 (s, 2 H), 4.46-4.60 (m, 2 H), 4.35-4.38 (m, 1 H), 4.15-4.25 (m, 1 H), 3.98 (d, J = 6.4 Hz, 2 H), 3.74-3.77 (m, 1 H), 3.73 (s, 3 H), 3.64-3.67 (m, 1 H), 2.95-3.10 (m, 2 H), 1.98-2.05 (m, 4 H), 1.58-1.60 (m, 1 H), 1.28-1.40 (m, 7 H). |
| 293* | 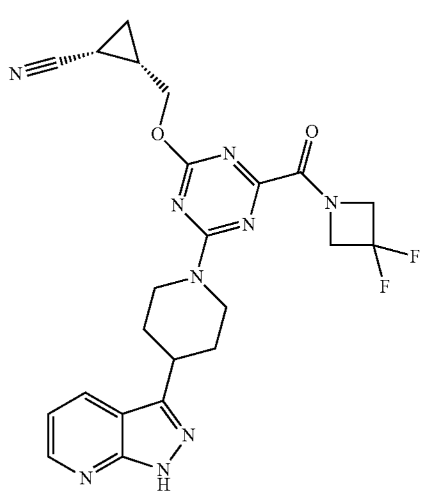 [SMILES: N#C[C@@H]1C[C@@H]1COc1nc(C(=O)N2CC(F)(F)C2)nc(N2CCC(c3n[nH]c4ncccc34)CC2)n1] | (1R,2S)-2-[({4-[(3,3-difluoroazetidin-1-yl)carbonyl]-6-[4-(1H-pyrazolo[3,4-b]pyridin-3-yl)piperidin-1-yl]-1,3,5-triazin-2-yl}oxy)methyl]cyclopropanecarbonitrile | 496.0; (400 MHz, CD$_3$OD) δ ppm 8.50 (d, J = 3.6 Hz, 1 H), 8.34 (d, J = 7.2 Hz, 1 H), 7.18-7.21 (m, 1 H), 5.04 (t, J = 8.4 Hz, 2 H), 4.89-4.93 (m, 2 H), 4.73-4.76 (m, 1 H), 4.54 (t, J = 12.0 Hz, 2 H), 4.32-4.33 (m, 1 H), 3.48-3.54 (m, 1 H), 3.37 (s, 1 H), 3.29 (s, 1 H), 2.19-2.22 (m, 2 H), 1.88-2.00 (m, 4 H), 1.36-1.38 (m, 1 H), 1.14-1.16 (m, 1 H). |

TABLE 1-continued

| Ex. # | Structure | Compound Name | LRMS m/z (M + H)+; and 1H NMR |
|---|---|---|---|
| 294* | 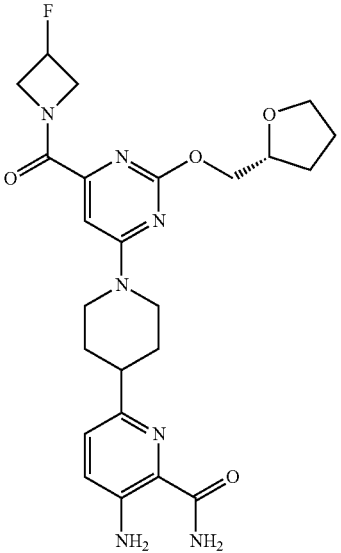 [SMILES: NC(=O)c1nc(C2CCN(c3cc(C(=O)N4CC(F)C4)nc(OC[C@H]4CCCO4)n3)CC2)ccc1N] | 3-amino-6-(1-{6-[(3-fluoroazetidin-1-yl)carbonyl]-2-[(2R)-tetrahydrofuran-2-ylmethoxy]pyrimidin-4-yl}piperidin-4-yl)pyridine-2-carboxamide | 500.2; (700 MHz, DMSO-d$_6$) δ ppm 7.83 (br. s., 1 H), 7.24 (br. s., 1 H), 7.16-7.18 (m, 1 H), 7.08-7.10 (m, 1 H), 6.94-6.95 (m, 1 H), 6.66 (br. s., 2 H), 5.47 (br. s., 0.5 H), 5.39 (br. s., 0.5 H), 4.87-4.93 (m, 1 H), 4.57-4.63 (m, 1 H), 4.04-4.20 (m, 4 H), 3.75-3.79 (m, 1 H), 3.65-3.68 (m, 1 H), 3.03 (br. s., 1 H), 2.87 (br. s., 1 H), 1.79-1.99 (m, 5 H), 1.58-1.65 (m, 3 H). |
| 295* | 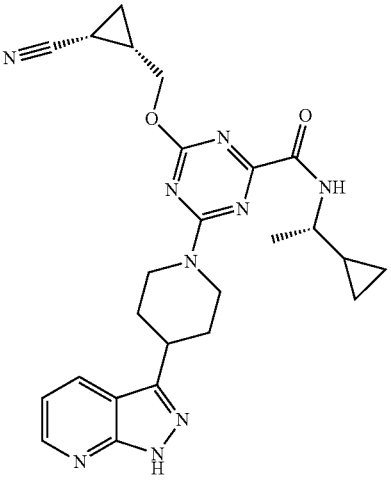 [SMILES: C[C@H](NC(=O)c1nc(OC[C@H]2C[C@H]2C#N)nc(N2CCC(c3n[nH]c4ncccc34)CC2)n1)C1CC1] | 4-{[(1S,2R)-2-cyanocyclopropyl]methoxy}-N-[(1S)-1-cyclopropylethyl]-6-[4-(1H-pyrazolo[3,4-b]pyridin-3-yl)piperidin-1-yl]-1,3,5-triazine-2-carboxamide | 488.0; (400 MHz, CDCl$_3$) δ ppm 12.39 (s, 1 H), 8.59 (d, J = 4.0 Hz, 1 H), 8.09 (d, J = 8.0 Hz, 1 H), 7.85 (d, J = 8.4 Hz, 1 H), 7.10-7.13 (m, 1 H), 5.05 (s, 1 H), 4.87 (d, J = 11.6 Hz, 1 H), 4.60-4.62 (m, 1 H), 4.46-4.50 (m, 1 H), 3.51-3.53 (m, 1 H), 3.37-3.39 (m, 1 H), 3.20-3.22 (m, 2 H), 2.05-2.17 (m, 4 H), 1.86-1.88 (m, 1 H), 1.68-1.70 (m, 1 H), 1.31-1.35 (m, 4 H), 1.29-1.30 (m, 1 H), 1.13-1.15 (m, 1 H), 0.40-0.52 (m, 3 H), 0.26-0.27 (m, 1 H). |
| 296* | 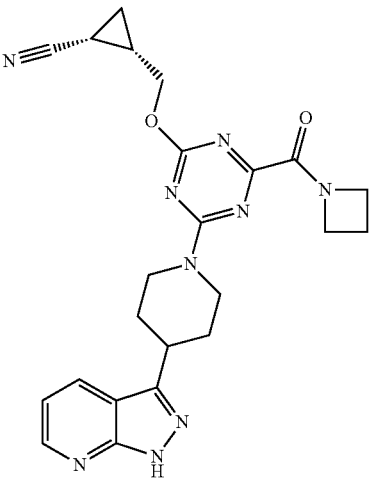 [SMILES: N#C[C@@H]1C[C@@H]1COc1nc(C(=O)N2CCC2)nc(N2CCC(c3n[nH]c4ncccc34)CC2)n1] | (1R,2S)-2-[({4-(azetidin-1-ylcarbonyl)-6-[4-(1H-pyrazolo[3,4-b]pyridin-3-yl)piperidin-1-yl]-1,3,5-triazin-2-yl}oxy)methyl]cyclopropanecarbonitrile | 460.1; (400 MHz, CDCl$_3$) δ ppm 12.23 (br. s., 1 H), 8.59 (d, J = 4.4 Hz, 1 H), 8.11 (d, J = 8.0 Hz, 1 H), 7.11-7.15 (m, 1 H), 4.85-4.94 (m, 2 H), 4.52-4.56 (m, 3 H), 4.44-4.47 (m, 1 H), 4.21-4.25 (m, 2 H), 3.39-3.42 (m, 1 H), 3.19-3.21 (m, 2 H), 2.32-2.36 (m, 2 H), 2.13-2.17 (m, 2 H), 2.00-2.04 (m, 2 H), 1.67-1.85 (m, 1 H), 1.65-1.66 (m, 1 H), 1.31-1.32 (m, 1 H), 1.10-1.12 (m, 1 H). |

TABLE 1-continued

| Ex. # | Structure | Compound Name | LRMS m/z (M + H)+; and 1H NMR |
|---|---|---|---|
| 297* | 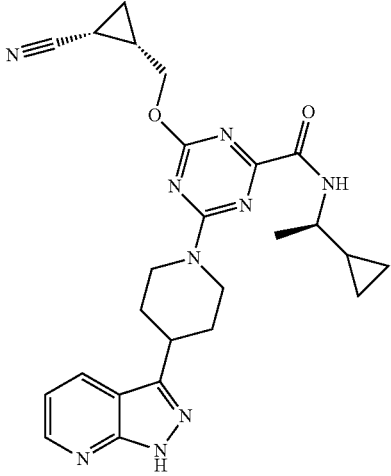 [SMILES: C[C@@H](NC(=O)c1nc(OC[C@H]2C[C@H]2C#N)nc(N2CCC(c3n[nH]c4ncccc34)CC2)n1)C1CC1] | 4-{[(1S,2R)-2-cyanocyclopropyl]methoxy}-N-[(1R)-1-cyclopropylethyl]-6-[4-(1H-pyrazolo[3,4-b]pyridin-3-yl)piperidin-1-yl]-1,3,5-triazine-2-carboxamide | 488.0; (400 MHz, CDCl$_3$) δ ppm 12.74 (s, 1 H), 8.59 (d, J = 4.0 Hz, 1 H), 8.08 (d, J = 8.0 Hz, 1 H), 7.87 (d, J = 8.4 Hz, 1 H), 7.09-7.12 (m, 1 H), 5.05 (s, 1 H), 4.88 (d, J = 11.6 Hz, 1 H), 4.58-4.61 (m, 1 H), 4.44-4.47 (m, 1 H), 3.50-3.52 (m, 1 H), 3.38-3.39 (m, 1 H), 3.19-3.21 (m, 2 H), 2.16-2.35 (m, 4 H), 1.69-1.85 (m, 1 H), 1.68-1.70 (m, 1 H), 1.32-1.33 (m, 4 H), 1.28-1.30 (m, 1 H), 1.11-1.13 (m, 1 H), 0.45-0.52 (m, 3 H), 0.26-0.39 (m, 1 H). |
| 298* | 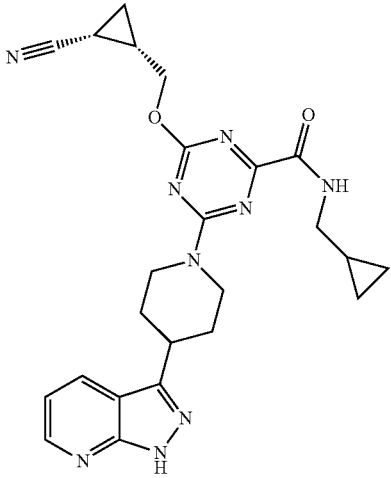 [SMILES: N#C[C@@H]1C[C@@H]1COc1nc(C(=O)NCC2CC2)nc(N2CCC(c3n[nH]c4ncccc34)CC2)n1] | 4-{[(1S,2R)-2-cyanocyclopropyl]methoxy}-N-(cyclopropylmethyl)-6-[4-(1H-pyrazolo[3,4-b]pyridin-3-yl)piperidin-1-yl]-1,3,5-triazine-2-carboxamide | 496.0 [M + Na]+; (400 MHz, CDCl$_3$) δ ppm 11.60 (br. s., 1 H), 8.57 (s, 1 H), 8.11 (d, J = 8.0 Hz, 1 H), 7.94 (d, J = 6.0 Hz, 1 H), 7.12-7.15 (m, 1 H), 5.08 (d, J = 9.2 Hz, 1 H), 4.89 (d, J = 11.2 Hz, 1 H), 4.49-4.62 (m, 2 H), 3.23-3.42 (m, 5 H), 1.69-2.18 (m, 4 H), 1.14-1.36 (m, 5 H), 0.55 (d, J = 8.0 Hz, 2 H), 0.29 (t, J = 5.2 Hz, 2 H). |
| 299* | 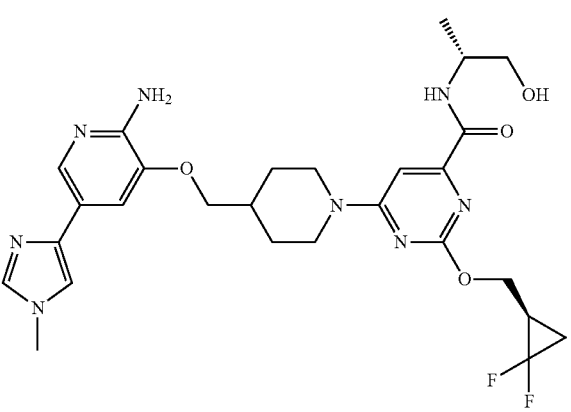 [SMILES: C[C@H](CO)NC(=O)c1cc(N2CCC(COc3cc(-c4cn(C)cn4)cnc3N)CC2)nc(OC[C@H]2CC2(F)F)n1] | 6-[4-({[2-amino-5-(1-methyl-1H-imidazol-4-yl)pyridin-3-yl]oxy}methyl)piperidin-1-yl]-2-{[(1R)-2,2-difluorocyclopropyl]methoxy}-N-[(2R)-1-hydroxypropan-2-yl]pyrimidine-4-carboxamide | 573.0; (400 MHz, CDCl$_3$) δ ppm 7.96 (s, 1 H), 7.93 (d, J = 7.6 Hz, 1 H), 7.45 (s, 2 H), 7.08-7.13 (m, 2H), 4.73 (br. s., 2 H), 4.42-4.52 (m, 2 H), 4.28-4.38 (m, 1 H), 4.15-4.25 (m, 1 H), 3.96 (d, J = 6.0 Hz, 2 H), 3.68-3.78 (m, 4 H), 3.58-3.68 (m, 1 H), 2.95-3.08 (m, 2 H), 2.08-2.20 (m, 2 H), 1.95-2.02 (m, 2 H), 1.55-1.65 (m, 2 H), 1.25-1.45 (m, 7 H). |

TABLE 1-continued

| Ex. # | Structure | Compound Name | LRMS m/z (M + H)+; and 1H NMR |
|---|---|---|---|
| 300* | 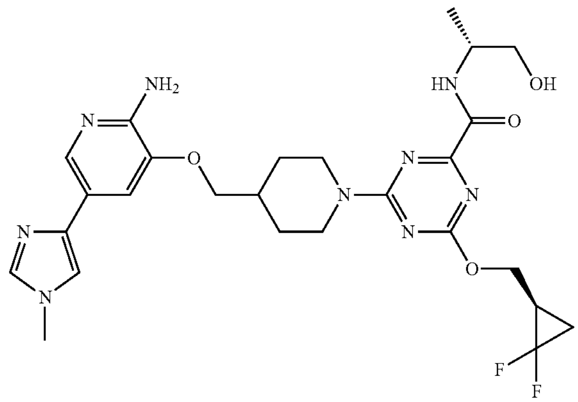 [SMILES: C[C@H](CO)NC(=O)c1nc(OC[C@H]2CC2(F)F)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-6-{[(1R)-2,2-difluoro-cyclopropyl]methoxy}-N-[(2R)-1-hydroxypropan-2-yl]-1,3,5-triazine-2-carboxamide | 574.2; (400 MHz, CDCl$_3$) δ ppm 7.97 (d, J = 2.0 Hz, 1 H), 7.89 (d, J = 7.6 Hz, 1 H), 7.47 (d, J = 1.6 Hz, 2 H), 7.11 (s, 1 H), 5.06 (d, J = 12.4 Hz, 1 H), 4.84 (d, J = 14.4 Hz, 1 H), 4.68 (br. s., 2 H), 4.38-4.55 (m, 2 H), 4.12-4.25 (m, 1 H), 3.95-4.05 (m, 2 H), 3.74-3.77 (m, 1 H), 3.71 (s, 3 H), 3.62-3.68 (m, 1 H), 2.95-3.07 (m, 2 H), 2.05-2.22 (m, 2 H), 1.96-2.05 (m, 2 H), 1.35-1.42 (m, 4 H), 1.31 (d, J = 6.8 Hz, 3 H). |
| 301* | 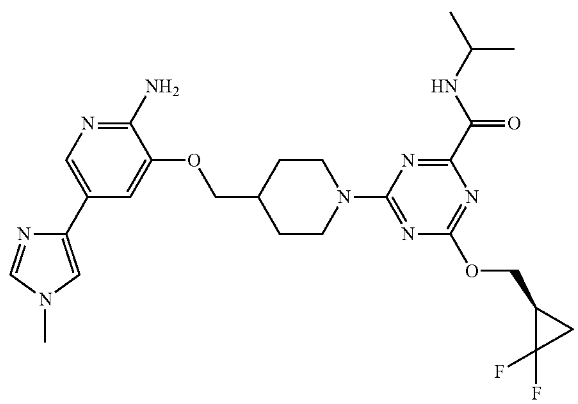 [SMILES: CC(C)NC(=O)c1nc(OC[C@H]2CC2(F)F)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-6-{[(1R)-2,2-difluoro-cyclopropyl]methoxy}-N-(propan-2-yl)-1,3,5-triazine-2-carboxamide | 558.2; (400 MHz, CDCl$_3$) δ ppm 7.97 (s, 1 H), 7.60 (d, J = 2.0 Hz, 1 H), 7.46 (d, J = 4.0 Hz, 2 H), 7.11 (s, 1 H), 5.07 (d, J = 13.2 Hz, 1 H), 4.86 (d, J = 12.8 Hz, 1 H), 4.69 (br. s., 2 H), 4.38-4.57 (m, 2 H), 4.15-4.28 (m, 1 H), 3.98 (t, J = 4.4 Hz, 2 H), 3.72 (s, 3 H), 2.95-3.08 (m, 2 H), 2.08-2.22 (m, 2 H), 1.96-2.05 (m, 2 H), 1.27-1.42 (m, 4 H), 1.26 (d, J = 6.4 Hz, 6 H). |
| 302* | 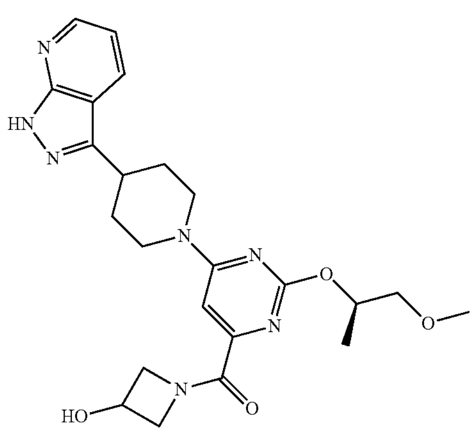 [SMILES: COC[C@@H](C)Oc1nc(C(=O)N2CC(O)C2)cc(N2CCC(c3n[nH]c4ncccc34)CC2)n1] | (3-hydroxyazetidin-1-yl)(2-{[(2R)-1-methoxypropan-2-yl]oxy}-6-[4-(1H-pyrazolo[3,4-b]pyridin-3-yl)piperidin-1-yl]pyrimidin-4-yl)methanone | 468.2; (400 MHz, CD$_3$OD) δ ppm 8.48 (d, J = 3.2 Hz, 1 H), 8.32 (d, J = 8.4 Hz, 1 H), 7.17-7.20 (m, 1 H), 6.98 (s, 1 H), 5.29-5.32 (m, 1 H), 4.59-4.63 (m, 3 H), 4.40-4.44 (m, 2 H), 3.87-3.93 (m, 1 H), 3.54-3.61 (m, 1 H), 3.51-3.53 (m, 2 H), 3.38 (s, 3 H), 3.24-3.31 (m, 3 H), 2.14-2.18 (m, 2 H), 1.93-2.00 (m, 2 H), 1.34 (d, J = 6.0 Hz, 3 H). |

TABLE 1-continued

| Ex. # | Structure | Compound Name | LRMS m/z (M + H)+; and 1H NMR |
|---|---|---|---|
| 303* | 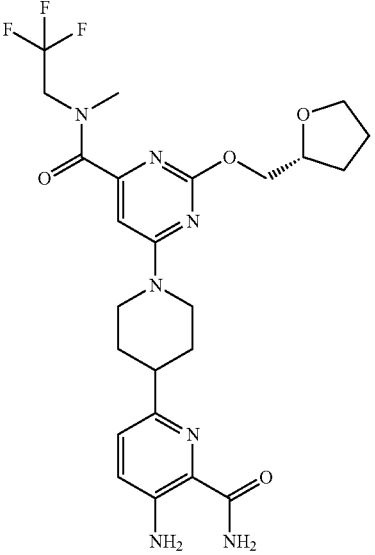 [SMILES: CN(CC(F)(F)F)C(=O)c1cc(N2CCC(c3ccc(N)c(C(N)=O)n3)CC2)nc(OC[C@H]2CCCO2)n1] | 6-[4-(5-amino-6-carbamoylpyridin-2-yl)piperidin-1-yl]-N-methyl-2-[(2R)-tetrahydrofuran-2-ylmethoxy]-N-(2,2,2-trifluoroethyl)pyrimidine-4-carboxamide | 538.2; (700 MHz, DMSO-d$_6$) δ ppm 7.84 (br. s., 1 H), 7.24 (br. s., 1 H), 7.17-7.19 (m, 1 H), 7.09 (dd, J = 8.5, 2.1 Hz, 1 H), 6.67 (br. s., 2 H), 6.60 (d, J = 1.9 Hz, 1 H), 4.52 (d, J = 9.1 Hz, 1 H), 4.31 (d, J = 9.2 Hz, 1 H), 4.11-4.37 (m, 3 H), 3.75 (t, J = 6.7 Hz, 1 H), 3.65 (t, J = 7.2 Hz, 1 H), 2.98-3.06 (m, 3 H), 2.86 (br. s., 1 H), 1.78-1.97 (m, 5 H), 1.58-1.68 (m, 3 H). |
| 344* | 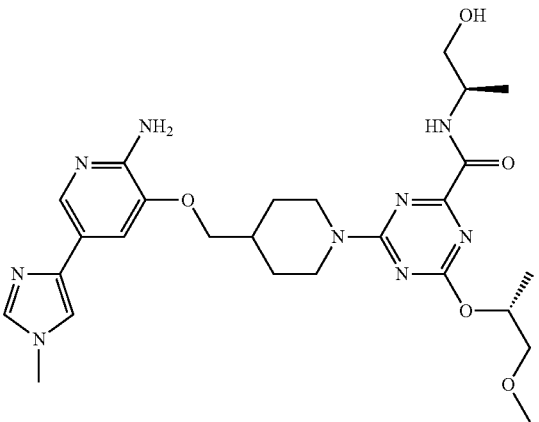 [SMILES: COC[C@@H](C)Oc1nc(C(=O)N[C@H](C)CO)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-N-[(2R)-1-hydroxypropan-2-yl]-6-{[(2R)-1-methoxypropan-2-yl]oxy}-1,3,5-triazine-2-carboxamide | 578.3 [M + Na]+; (400 MHz, CDCl$_3$) δ ppm 7.96 (s, 1 H), 7.93 (d, J = 8.0 Hz, 1 H), 7.45 (s, 2 H), 7.10 (s, 1 H), 5.38-5.46 (m, 1 H), 5.04 (d, J = 14.0 Hz, 1 H), 4.83 (d, J = 12.4 Hz, 1 H), 4.69 (br. s., 2 H), 4.15-4.23 (m, 1 H), 3.85-4.02 (m, 2 H), 3.58-3.75 (m, 6 H), 3.48-3.55 (m, 1 H), 3.40 (s, 3 H), 2.93-3.08 (m, 1 H), 2.15-2.25 (m, 1 H), 1.92-2.02 (m, 2 H), 1.37 (d, J = 6.0 Hz, 5 H), 1.27 (d, J = 6.4 Hz, 3 H). |
| 345* | 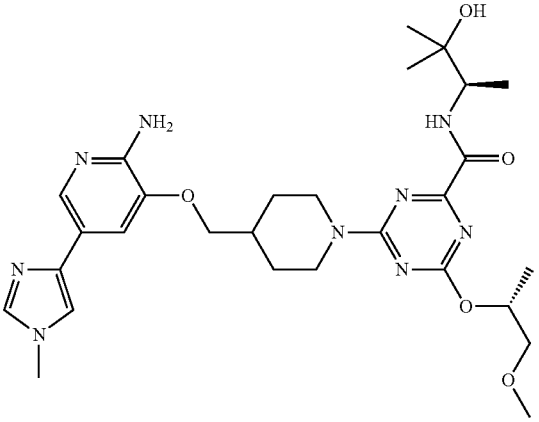 [SMILES: COC[C@@H](C)Oc1nc(C(=O)N[C@H](C)C(C)(C)O)nc(N2CCC(COc3cc(-c4cn(C)cn4)cnc3N)CC2)n1] | 4-[4-({[2-amino-5-(1-methyl-1H-imidazol-4-yl)pyridin-3-yl]oxy}methyl)piperidin-1-yl]-N-[(2R)-3-hydroxy-3-methylbutan-2-yl]-6-{[(2R)-1-methoxypropan-2-yl]oxy}-1,3,5-triazine-2-carboxamide | 583.9; (400 MHz, CDCl$_3$) δ ppm 8.30 (d, J = 9.6 Hz, 1 H), 7.96 (s, 1 H), 7.43-7.47 (m, 2 H), 7.10 (s, 1 H), 5.38-5.46 (m, 1 H), 5.06 (d, J = 12.8 Hz, 1 H), 4.85 (d, J = 10.8 Hz, 1 H), 4.70 (br. s., 2 H), 4.02-4.08 (m, 1 H), 3.93-4.02 (m, 2 H), 3.72 (s, 3 H), 3.66-3.71 (m, 1 H), 3.48-3.55 (m, 1 H), 3.41 (s, 3 H), 2.95-3.08 (m, 1 H), 2.15-2.25 (m, 1 H), 1.92-2.02 (m, 2 H), 1.32-1.43 (m, 5 H), 1.18-1.25 (m, 9 H). |

TABLE 1-continued

| Ex. # | Structure | Compound Name | LRMS m/z (M + H)+; and 1H NMR |
|---|---|---|---|
| 346 | 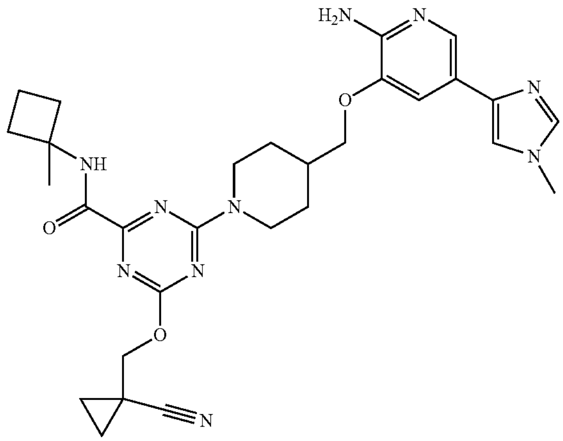 [SMILES: Cn1cnc(-c2cnc(N)c(OCC3CCN(c4nc(OCC5(C#N)CC5)nc(C(=O)NC5(C)CCC5)n4)CC3)c2)c1] | 4-[4-({[2-amino-5-(1-methyl-1H-imidazol-4-yl)pyridin-3-yl]oxy}methyl)piperidin-1-yl]-6-[(1-cyanocyclopropyl)methoxy]-N-(1-methylcyclobutyl)-1,3,5-triazine-2-carboxamide | 573.1; (400 MHz, CDCl$_3$) δ ppm 7.96 (s, 1 H), 7.88 (s, 1 H), 7.44 (s, 2 H), 7.10 (s, 1 H), 5.06 (d, J = 13.2 Hz, 1 H), 4.84 (d, J = 12.8 Hz, 1 H), 4.65 (s, 2 H), 4.40 (m, 2 H), 3.96-3.97 (m, 2 H), 3.71 (s, 3 H), 2.99-3.06 (m, 2 H), 2.41-2.46 (m, 2 H), 1.96-2.01 (m, 3 H), 1.79-1.89 (m, 6 H), 1.41-1.43 (m, 4 H), 1.18-1.20 (m, 2 H). |
| 347* | 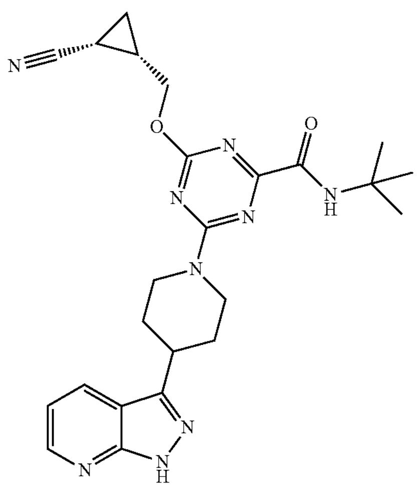 [SMILES: CC(C)(C)NC(=O)c1nc(OC[C@H]2C[C@H]2C#N)nc(N2CCC(c3n[nH]c4ncccc34)CC2)n1] | N-tert-butyl-4-{[(1S,2R)-2-cyanocyclopropyl]methoxy}-6-[4-(1H-pyrazolo[3,4-b]pyridin-3-yl)piperidin-1-yl]-1,3,5-triazine-2-carboxamide | 498.2 [M + Na]+; (400 MHz, CDCl$_3$) δ ppm 11.75 (br. s., 1 H), 8.59 (d, J = 3.2 Hz, 1 H), 8.11 (d, J = 8.0 Hz, 1 H), 7.73 (s, 1 H), 7.12-7.15 (m, 1 H), 5.09 (d, J = 11.6 Hz, 1 H), 4.89 (d, J = 13.6 Hz, 1 H), 4.59-4.62 (m, 1 H), 4.48-4.51 (m, 1 H), 3.38-3.44 (m, 1 H), 3.19-3.29 (m, 2 H), 2.16-2.19 (m, 2 H), 2.02-2.05 (m, 2 H), 1.78-1.87 (m, 1 H), 1.69-1.70 (m, 1 H), 1.47 (s, 9 H), 1.34-1.36 (m, 1 H), 1.14-1.26 (m, 1H). |
| 348** | 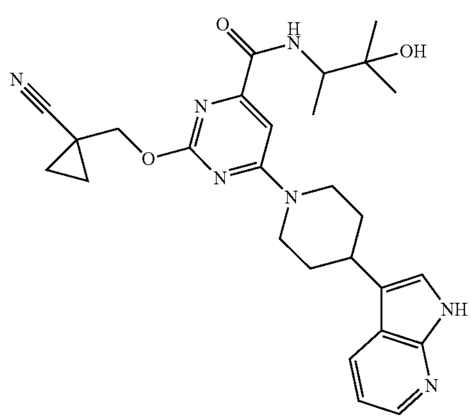 [SMILES: CC(NC(=O)c1cc(N2CCC(c3c[nH]c4ncccc34)CC2)nc(OCC2(C#N)CC2)n1)C(C)(C)O] | 2-[(1-cyanocyclopropyl)methoxy]-N-(3-hydroxy-3-methylbutan-2-yl)-6-[4-(1H-pyrrolo[2,3-b]pyridin-3-yl)piperidin-1-yl]pyrimidine-4-carboxamide | 504.0; (700 MHz, DMSO-d$_6$) δ ppm 11.31 (br. s., 1 H), 8.09-8.22 (m, 2 H), 8.01 (br. s., 1 H), 7.22 (br. s., 1 H), 6.96-7.07 (m, 2 H), 4.78 (s, 1 H), 4.29-4.39 (m, 2 H), 3.84 (d, J = 2.73 Hz, 1 H), 3.45-3.57 (m, 3 H), 3.15 (br. s., 1 H), 2.05 (d, J = 11.61 Hz, 2 H), 1.62 (d, J = 11.27 Hz, 2 H), 1.35 (br. s., 3 H), 1.03-1.16 (m, 11 H). |

TABLE 1-continued

| Ex. # | Structure | Compound Name | LRMS m/z (M + H)⁺; and ¹H NMR |
|---|---|---|---|
| 349** | 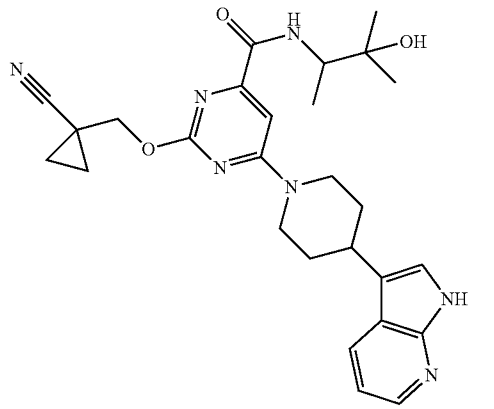 [SMILES: CC(NC(=O)c1cc(N2CCC(c3c[nH]c4ncccc34)CC2)nc(OCC2(C#N)CC2)n1)C(C)(C)O] | 2-[(1-cyanocyclopropyl)methoxy]-N-(3-hydroxy-3-methylbutan-2-yl)-6-[4-(1H-pyrrolo[2,3-b]pyridin-3-yl)piperidin-1-yl]pyrimidine-4-carboxamide | 504.0; (700 MHz, DMSO-d$_6$) δ ppm 11.30 (br. s., 1 H), 8.08-8.22 (m, 2 H), 8.01 (d, J = 6.49 Hz, 1 H), 7.21 (br. s., 1 H), 6.96-7.07 (m, 2 H), 4.78 (d, J = 10.25 Hz, 1 H), 4.26-4.38 (m, 2 H), 3.84 (dd, J = 9.31, 6.58 Hz, 1 H), 3.47 (d, J = 4.27 Hz, 3 H), 3.15 (br. s., 1 H), 2.05 (d, J = 11.96 Hz, 2 H), 1.61 (d, J = 12.13 Hz, 2 H), 1.30-1.39 (m, 3 H), 1.03-1.15 (m, 11 H). |
| 350 | 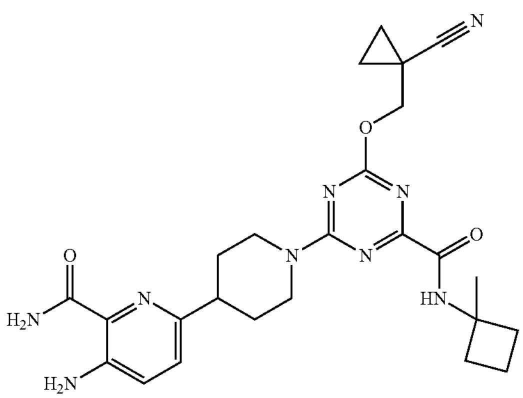 [SMILES: CC1(NC(=O)c2nc(OCC3(C#N)CC3)nc(N3CCC(c4ccc(N)c(C(N)=O)n4)CC3)n2)CCC1] | 4-[4-(5-amino-6-carbamoylpyridin-2-yl)piperidin-1-yl]-6-[(1-cyanocyclopropyl)methoxy]-N-(1-methylcyclobutyl)-1,3,5-triazine-2-carboxamide | 528.3; [M + Na]⁺; (400 MHz, CDCl$_3$) δ ppm 7.87 (br. s., 2 H), 7.07 (d, J = 8.4 Hz, 1 H), 6.98 (d, J = 8.4 Hz, 1 H), 5.84 (s, 2H), 5.33 (s, 1 H), 5.12 (d, J = 13.2 Hz, 1 H), 4.90 (d, J = 12.0 Hz, 1 H), 4.37-4.46 (m, 2 H), 3.02-3.12 (m, 2 H), 2.87-2.89 (m, 1 H), 2.41-2.46 (m, 2 H), 2.10-2.11 (m, 2 H), 1.99-2.02 (m, 2 H), 1.87-1.90 (m, 4 H), 1.55 (s, 3 H), 1.42-1.42 (m, 2 H), 1.19-1.20 (m, 2 H). |
| 351* | 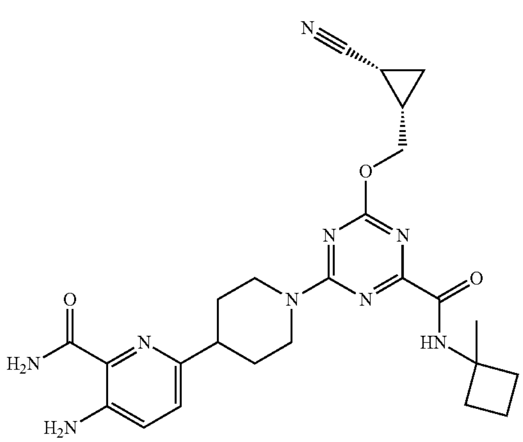 [SMILES: CC1(NC(=O)c2nc(OC[C@H]3C[C@H]3C#N)nc(N3CCC(c4ccc(N)c(C(N)=O)n4)CC3)n2)CCC1] | 4-[4-(5-amino-6-carbamoylpyridin-2-yl)piperidin-1-yl]-6-{[(1S,2R)-2-cyanocyclopropyl]methoxy}-N-(1-methylcyclobutyl)-1,3,5-triazine-2-carboxamide | 528.3; [M + Na]⁺; (400 MHz, CDCl$_3$) δ ppm 7.87 (br. s., 2 H), 7.09 (d, J = 8.4 Hz, 1 H), 6.98 (d, J = 8.8 Hz, 1 H), 5.87 (s, 2 H), 5.31 (s, 1 H), 5.12-5.16 (m, 1 H), 4.88-4.92 (m, 1 H), 4.57-4.59 (m, 1 H), 4.45-4.48 (m, 1 H), 3.02-3.12 (m, 2 H), 2.87-2.89 (m, 1 H), 2.43-2.46 (m, 2 H), 2.10-2.12 (m, 2 H), 1.99-2.03 (m, 2 H), 1.85-1.89 (m, 6 H), 1.55 (s, 3 H), 1.32-1.34 (m, 1 H), 1.13-1.15 (m, 1 H). |

TABLE 1-continued

| Ex. # | Structure | Compound Name | LRMS m/z (M + H)+; and 1H NMR |
|---|---|---|---|
| 352* | 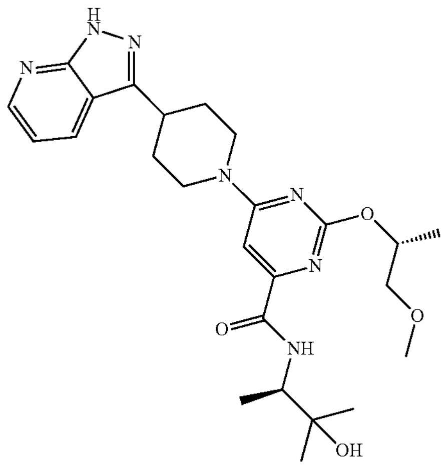 [SMILES: COC[C@@H](C)Oc1nc(C(=O)N[C@H](C)C(C)(C)O)cc(N2CCC(c3n[nH]c4ncccc34)CC2)n1] | N-[(2R)-3-hydroxy-3-methylbutan-2-yl]-2-{[(2R)-1-methoxypropan-2-yl]oxy}-6-[4-(1H-pyrazolo[3,4-b]pyridin-3-yl)piperidin-1-yl]pyrimidine-4-carboxamide | 498.3; (400 MHz, DMSO-d$_6$) δ ppm 13.29 (s, 1 H), 8.49 (d, J = 1.6 Hz, 1 H), 8.32 (d, J = 8.4 Hz, 1 H), 8.14 (d, J = 8.4 Hz, 1 H), 7.13-7.16 (m, 1 H), 7.03 (s, 1 H), 5.23-5.27 (m, 1 H), 4.74 (s, 1 H), 4.39-4.68 (m, 1 H), 3.82-3.84 (m, 1 H), 3.53-3.54 (m, 1 H), 3.42-3.48 (m, 2 H), 3.24-3.29 (m, 5 H), 2.44-2.47 (m, 1 H), 2.10-2.13 (m, 2 H), 1.81-1.83 (m, 2 H), 1.28 (d, J = 6.4 Hz, 3 H); 1.08-1.15 (m, 9 H). |
| 353* | 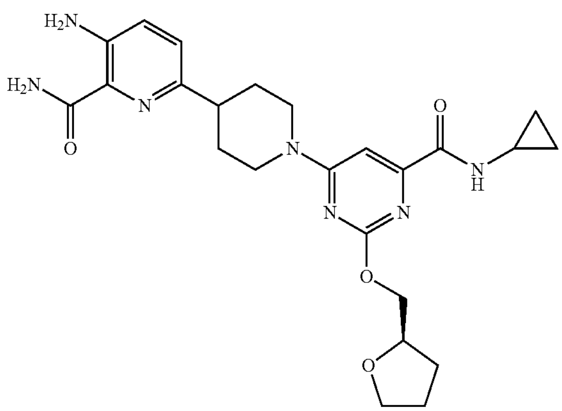 [SMILES: NC(=O)c1nc(C2CCN(c3cc(C(=O)NC4CC4)nc(OC[C@H]4CCCO4)n3)CC2)ccc1N] | 6-[4-(5-amino-6-carbamoylpyridin-2-yl)piperidin-1-yl]-N-cyclopropyl-2-[(2R)-tetrahydrofuran-2-ylmethoxy]pyrimidine-4-carboxamide | 482.2; (700 MHz, DMSO-d$_6$) δ ppm 8.41 (d, J = 4.83 Hz, 1 H), 7.83 (d, J = 2.93 Hz, 1 H), 7.20 (d, J = 2.63 Hz, 1 H), 7.17 (d, J = 8.49 Hz, 1 H), 7.08 (dd, J = 8.63, 0.88 Hz, 1 H), 6.95 (s, 1 H), 6.64 (br. s., 1 H), 4.22 (d, J = 5.41 Hz, 2 H), 4.09 (quin, J = 6.18 Hz, 1 H), 3.71-3.77 (m, 1 H), 3.64 (q, J = 7.07 Hz, 1 H), 3.56 (br. s., 1 H), 3.03 (br. s., 2 H), 2.78-2.89 (m, 2 H), 1.80-1.99 (m, 6 H), 1.57-1.68 (m, 3 H), 0.65-0.70 (m, 2 H), 0.60-0.64 (2 H). |
| 354*** | 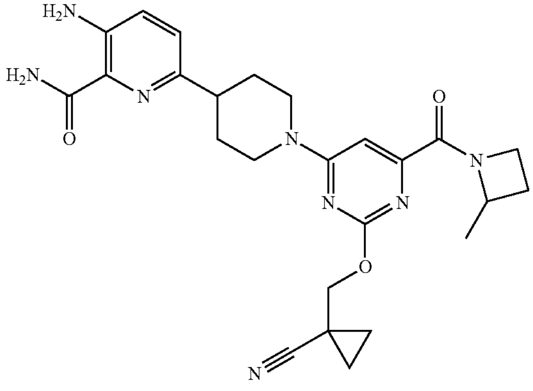 [SMILES: CC1CCN1C(=O)c1cc(N2CCC(c3ccc(N)c(C(N)=O)n3)CC2)nc(OCC2(C#N)CC2)n1] | 3-amino-6-(1-{2-[(1-cyanocyclopropyl)methoxy]-6-[(2-methylazetidin-1-yl)carbonyl]pyrimidin-4-yl}piperidin-4-yl)pyridine-2-carboxamide | 491.2; (700 MHz, DMSO-d$_6$) δ ppm 7.85 (d, J = 2.9 Hz, 1 H), 7.17 (d, J = 8.5 Hz, 1 H), 7.13 (br. s., 1 H), 7.08 (d, J = 8.5 Hz, 1 H), 6.88 (s, 1 H), 6.58 (br. s., 1 H), 4.50-4.54 (m, 1 H), 4.44-4.47 (m, 1 H), 4.35-4.38 (m, 1 H), 4.20-4.25 (m, 2 H), 3.02 (br. s., 1 H), 2.86 (t, J = 11.7 Hz, 1 H), 2.39-2.43 (m, 1 H), 1.89 (d, J = 12.5 Hz, 2 H), 1.76-1.82 (m, 3 H), 1.56-1.64 (m, 2 H), 1.40 (d, J = 6.3 Hz, 2 H), 1.31-1.33 (m, 2 H), 1.27 (d, J = 6.1 Hz, 1 H), 1.15-1.17 (m, 2 H). |

TABLE 1-continued

| Ex. # | Structure | Compound Name | LRMS m/z (M + H)+; and 1H NMR |
|---|---|---|---|
| 355 | 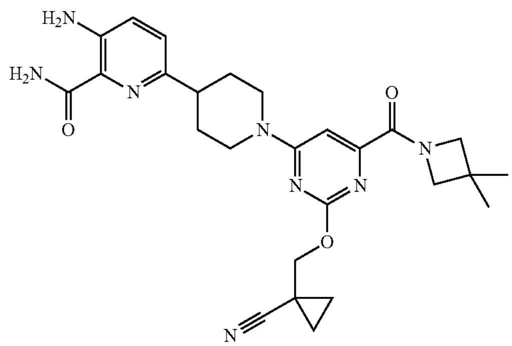 [SMILES: CC1(C)CN(C(=O)c2cc(N3CCC(c4ccc(N)c(C(N)=O)n4)CC3)nc(OCC3(C#N)CC3)n2)C1] | 3-amino-6-(1-{2-[(1-cyanocyclopropyl)methoxy]-6-[(3,3-dimethylazetidin-1-yl)carbonyl]pyrimidin-4-yl}piperidin-4-yl)pyridine-2-carboxamide | 505.2; (700 MHz, DMSO-d$_6$) δ ppm 7.85 (br. s., 1 H), 7.17 (dd, J = 8.54, 3.07 Hz, 1 H), 7.13 (br. s., 1 H), 7.08 (dd, J = 8.63, 3.16 Hz, 1 H), 6.90 (d, J = 3.25 Hz, 1 H), 6.58 (br. s., 1 H), 4.21 (dd, J = 16.65, 1.96 Hz, 4 H), 3.75 (s, 5 H), 3.68 (br. s., 1 H), 3.02 (br. s., 1 H), 2.83-2.90 (m, 1 H), 1.89 (d, J = 12.47 Hz, 2 H), 1.60 (q, J = 12.41 Hz, 2 H), 1.15-1.35 (m, 10 H). |
| 356*** | 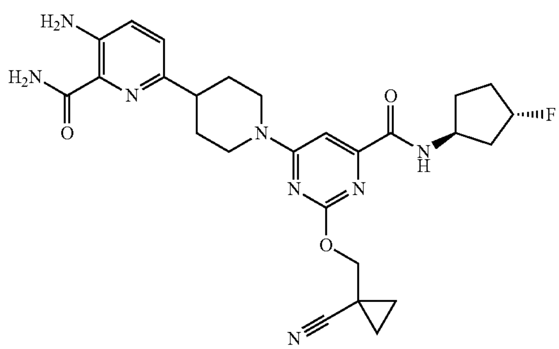 [SMILES: N#CC1(COc2nc(C(=O)N[C@H]3CC[C@H](F)C3)cc(N3CCC(c4ccc(N)c(C(N)=O)n4)CC3)n2)CC1] | 6-[4-(5-amino-6-carbamoylpyridin-2-yl)piperidin-1-yl]-2-[(1-cyanocyclopropyl)methoxy]-N-[(1S,3S)-3-fluorocyclopentyl]pyrimidine-4-carboxamide | 523.2; (700 MHz, DMSO-d$_6$) δ ppm 8.48 (d, J = 8.2 Hz, 1 H), 7.85 (d, J = 2.7 Hz, 1 H), 7.17 (d, J = 8.4 Hz, 1 H), 7.13 (br. s., 1 H), 7.08 (d, J = 8.5 Hz, 1 H), 6.99 (s, 1 H), 6.58 (br. s., 2 H), 5.23-5.25 (m, 0.5 H), 5.14-5.16 (m, 0.5 H), 4.40-4.45 (m, 1 H), 4.32 (s, 2 H), 3.06 (br. s., 1 H), 2.85-2.89 (m, 1 H), 2.01-2.17 (m, 4 H), 1.76-1.93 (m, 4 H), 1.58-1.66 (m, 4 H), 1.32-1.34 (m, 2 H), 1.16-1.20 (m, 3 H). |
| 357*** | 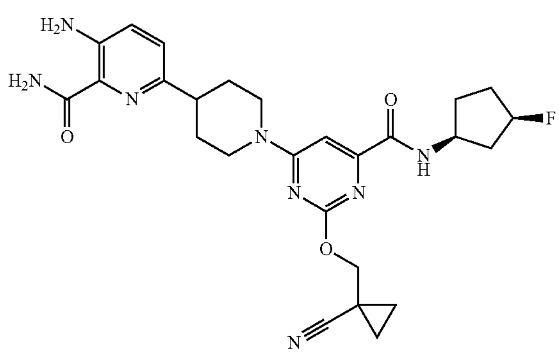 [SMILES: N#CC1(COc2nc(C(=O)N[C@H]3CC[C@@H](F)C3)cc(N3CCC(c4ccc(N)c(C(N)=O)n4)CC3)n2)CC1] | 6-[4-(5-amino-6-carbamoylpyridin-2-yl)piperidin-1-yl]-2-[(1-cyanocyclopropyl)methoxy]-N-[(1S,3R)-3-fluorocyclopentyl]pyrimidine-4-carboxamide | 523.2; (700 MHz, DMSO-d$_6$) δ ppm 7.17 (d, J = 8.5 Hz, 1 H), 7.08 (d, J = 8.5 Hz, 1 H), 7.00 (s, 1 H), 6.57 (br. s., 2 H), 5.20-5.24 (m, 0.5 H), 5.13-5.16 (m, 0.5 H), 4.26-4.34 (m, 3 H), 3.05 (br. s., 1 H), 2.85-2.91 (m, 1 H), 2.18-2.27 (m, 1 H), 1.72-2.00 (m, 8 H), 1.57-1.65 (m, 3 H), 1.32-1.34 (m, 2 H), 1.16-1.20 (m, 3 H). |
| 358* | 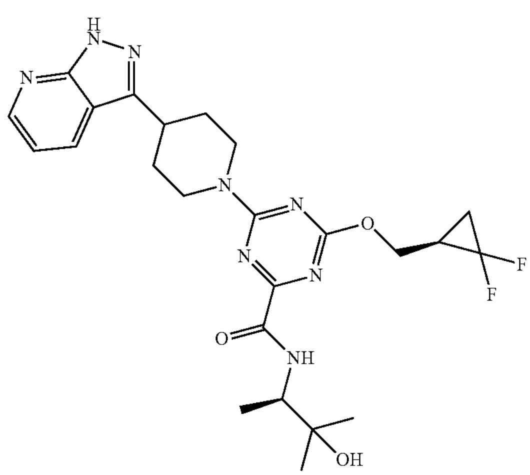 [SMILES: C[C@@H](NC(=O)c1nc(OC[C@H]2CC2(F)F)nc(N2CCC(c3n[nH]c4ncccc34)CC2)n1)C(C)(C)O] | 4-{[(1R)-2,2-difluoro-cyclopropyl]methoxy}-N-[(2R)-3-hydroxy-3-methylbutan-2-yl]-6-[4-(1H-pyrazolo[3,4-b]pyridin-3-yl)piperidin-1-yl]-1,3,5-triazine-2-carboxamide | 517.3; (400 MHz, DMSO-d$_6$) δ ppm 13.30 (s, 1 H), 8.49 (d, J = 2.8 Hz, 1 H), 8.35 (d, J = 5.6 Hz, 1 H), 8.18 (d, J = 6.4 Hz, 1 H), 7.13-7.16 (m, 1 H), 4.84-4.87 (m, 1 H), 4.75-4.78 (m, 1 H), 4.68 (s, 1 H), 4.53-4.58 (m, 1 H), 4.26-4.33 (m, 1 H), 3.84-3.88 (m, 1 H), 3.44-3.45 (m, 1 H), 3.24-3.26 (m, 1 H), 2.24-2.29 (m, 1 H), 2.13-2.18 (m, 2 H), 1.72-1.88 (m, 3 H), 1.52-1.59 (m, 1 H), 1.09-1.14 (m, 10 H). |

TABLE 1-continued

| Ex. # | Structure | Compound Name | LRMS m/z (M + H)+; and 1H NMR |
|---|---|---|---|
| 359* | 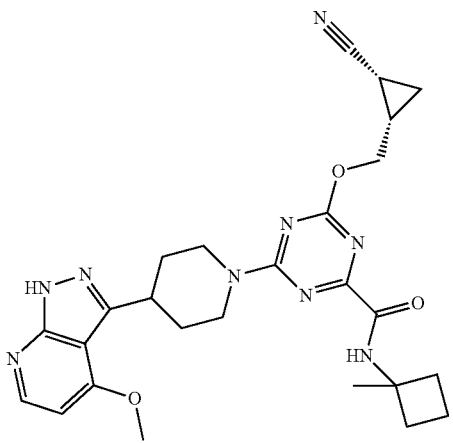 [SMILES: COc1ccnc2[nH]nc(C3CCN(c4nc(OC[C@H]5C[C@H]5C#N)nc(C(=O)NC5(C)CCC5)n4)CC3)c12] | 4-{[(1S,2R)-2-cyano-cyclopropyl]methoxy}-6-[4-(4-methoxy-1H-pyrazolo[3,4-b]pyridin-3-yl)piperidin-1-yl]-N-(1-methylcyclobutyl)-1,3,5-triazine-2-carboxamide | 518.0; (400 MHz, CDCl$_3$) δ ppm 11.35 (br. s., 1 H), 8.42 (s, 2 H), 7.90 (s, 1 H), 6.51 (d, J = 5.2 Hz, 1 H), 5.06 (d, J = 15.2 Hz, 1 H), 4.86 (d, J = 12.4 Hz, 1 H), 4.47-4.61 (m, 2 H), 4.01 (s, 3 H), 3.47-3.49 (m, 1 H), 3.24-3.27 (m, 2 H), 2.43-2.46 (m, 2 H), 2.10-2.17 (m, 4 H), 1.85-1.99 (m, 5 H), 1.69-1.71 (m, 1 H), 1.55 (s, 3 H), 1.32-1.34 (m, 1 H), 1.13-1.15 (m, 1 H). |
| 360* | 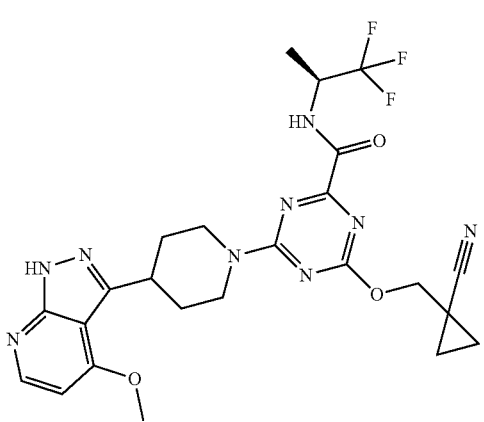 [SMILES: COc1ccnc2[nH]nc(C3CCN(c4nc(OCC5(C#N)CC5)nc(C(=O)N[C@@H](C)C(F)(F)F)n4)CC3)c12] | 4-[(1-cyano-cyclopropyl)methoxy]-6-[4-(4-methoxy-1H-pyrazolo[3,4-b]pyridin-3-yl)piperidin-1-yl]-N-[(2S)-1,1,1-trifluoropropan-2-yl]-1,3,5-triazine-2-carboxamide | 546.0; (400 MHz, CD$_3$OD) δ ppm 8.33 (d, J = 5.6 Hz, 1 H), 6.71 (d, J = 6.0 Hz, 1 H), 5.13 (d, J = 14.0 Hz, 2 H), 4.82-4.84 (m, 1 H), 4.48 (s, 2 H), 4.03 (s, 3 H), 3.55 (s, 1 H), 3.24-3.28 (m, 2 H), 2.15 (d, J = 13.6 Hz, 2 H), 1.94-2.00 (m, 2 H), 1.46 (d, J = 7.2 Hz, 3 H), 1.39-1.40 (m, 2 H), 1.25-1.27 (m, 2H). |
| 361* | 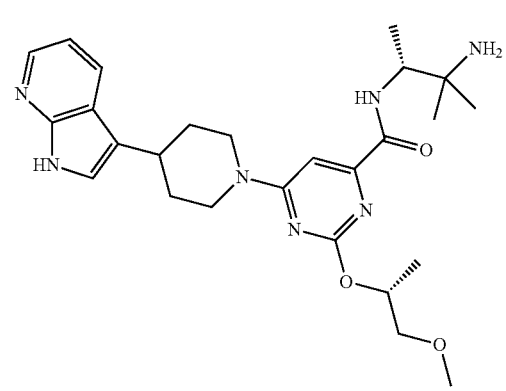 [SMILES: COC[C@@H](C)Oc1nc(C(=O)N[C@H](C)C(C)(C)N)cc(N2CCC(c3c[nH]c4ncccc34)CC2)n1] | N-[(2R)-3-amino-3-methylbutan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide | 518.3 [M + Na]+; (700 MHz, DMSO-d$_6$) δ ppm 11.41 (br. s., 1 H), 8.35 (d, J = 9.6 Hz, 1 H), 8.19 (d, J = 4.4 Hz, 1 H), 8.02 (d, J = 8.0 Hz, 1 H), 7.26 (d, J = 2.0 Hz, 1 H), 7.01-7.05 (m, 2 H), 5.22-5.26 (m, 1 H), 4.48-4.65 (m, 2 H), 3.74-3.76 (m, 1 H), 3.45-3.56 (m, 2 H), 3.30 (s, 3 H), 3.18-3.23 (m, 3 H), 2.05-2.08 (m, 2 H), 1.53-1.65 (m, 4 H), 1.27 (d, J = 6.4 Hz, 3 H), 1.09 (s, 6 H), 0.98 (s, 3 H). |

TABLE 1-continued

| Ex. # | Structure | Compound Name | LRMS m/z (M + H)+; and 1H NMR |
|---|---|---|---|
| 362* | 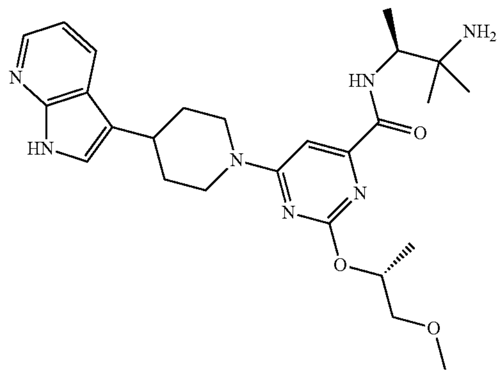 [SMILES: COC[C@@H](C)Oc1nc(C(=O)N[C@@H](C)C(C)(C)N)cc(N2CCC(c3c[nH]c4ncccc34)CC2)n1] | N-[(2S)-3-amino-3-methylbutan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide | 518.3 [M + Na]+; (400 MHz, DMSO-d$_6$) δ ppm 11.36 (br. s., 1 H), 8.33 (d, J = 9.6 Hz, 1 H), 8.20 (d, J = 4.4 Hz, 1 H), 8.02 (d, J = 8.0 Hz, 1 H), 7.26 (d, J = 2.0 Hz, 1 H), 7.01-7.04 (m, 2 H), 5.22-5.26 (m, 1 H), 4.48-4.65 (m, 2 H), 3.74-3.76 (m, 1 H), 3.45-3.55 (m, 2 H), 3.30 (s, 3 H), 3.16-3.23 (m, 3 H), 2.05-2.08 (m, 2 H), 1.53-1.65 (m, 4 H), 1.26-1.28 (m, 3 H), 1.09 (s, 6 H), 0.98 (s, 3 H). |
| 363* | 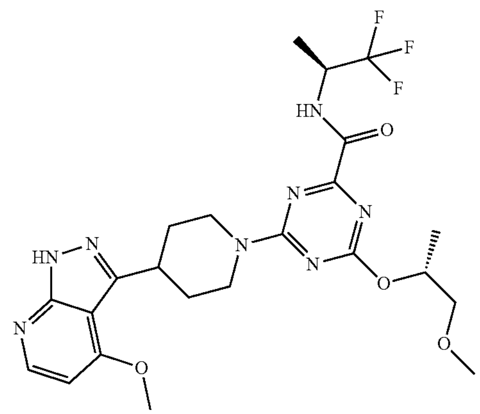 [SMILES: COC[C@@H](C)Oc1nc(C(=O)N[C@@H](C)C(F)(F)F)nc(N2CCC(c3n[nH]c4nccc(OC)c34)CC2)n1] | 4-{[(2R)-1-methoxypropan-2-yl]oxy}-6-[4-(4-methoxy-1H-pyrazolo[3,4-b]pyridin-3-yl)piperidin-1-yl]-N-[(2S)-1,1,1-trifluoropropan-2-yl]-1,3,5-triazine-2-carboxamide | 539.1; (400 MHz, CD$_3$OD) δ ppm 8.35 (d, J = 6.0 Hz, 1 H), 6.73 (d, J = 5.6 Hz, 1 H), 5.48-5.51 (m, 1 H), 4.95-5.14 (m, 1 H), 4.61-4.63 (m, 2 H), 4.06 (s, 3 H), 3.58-3.63 (m, 3 H), 3.41 (d, J = 2.8 Hz, 3 H), 3.22-3.33 (m, 2 H), 2.15-2.18 (m, 2 H), 1.97-2.03 (m, 2 H), 1.47 (d, J = 7.2 Hz, 3 H), 1.38 (d, J = 6.0 Hz, 3H). |
| 364* | 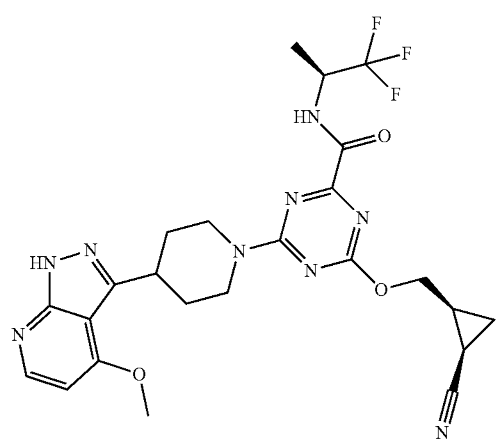 [SMILES: COc1ccnc2[nH]nc(C3CCN(c4nc(OC[C@H]5C[C@H]5C#N)nc(C(=O)N[C@@H](C)C(F)(F)F)n4)CC3)c12] | 4-{[(1S,2R)-2-cyanocyclopropyl]methoxy}-6-[4-(4-methoxy-1H-pyrazolo[3,4-b]pyridin-3-yl)piperidin-1-yl]-N-[(2S)-1,1,1-trifluoropropan-2-yl]-1,3,5-triazine-2-carboxamide | 568.0 [M + Na]+; (400 MHz, CDCl$_3$) δ ppm 10.59 (br. s., 1 H), 8.39 (d, J = 5.2 Hz, 1 H), 7.90 (d, J = 7.6 Hz, 1 H), 6.52 (d, J = 5.6 Hz, 1 H), 5.03 (d, J = 12.8 Hz, 1 H), 4.83-4.95 (m, 2 H), 4.47-4.62 (m, 2 H), 4.02 (s, 3 H), 3.46-3.55 (m, 1 H), 3.19-3.28 (m, 2 H), 2.15-2.24 (m, 1 H), 1.95-2.08 (m, 2 H), 1.83-1.95 (m, 1 H), 1.68-1.75 (m, 1 H), 1.43 (d, J = 7.2 Hz, 3 H), 1.33-1.41 (m, 1 H), 1.11-1.20 (m, 1H). |

TABLE 1-continued

| Ex. # | Structure | Compound Name | LRMS m/z (M + H)+; and 1H NMR |
|---|---|---|---|
| 365* | 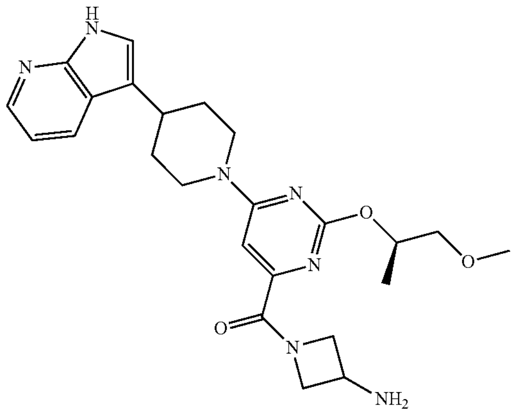 [SMILES: COC[C@@H](C)Oc1nc(C(=O)N2CC(N)C2)cc(N2CCC(c3c[nH]c4ncccc34)CC2)n1] | (3-aminoazetidin-1-yl)(2-{[(2R)-1-methoxypropan-2-yl]oxy}-6-[4-(1H-pyrrolo[2,3-b]pyridin-3-yl)piperidin-1-yl]pyrimidin-4-yl)methanone | 465.9; (400 MHz, CD$_3$OD) δ ppm 8.17 (d, J = 4.0 Hz, 1 H), 8.08 (d, J = 8.0 Hz, 1 H), 7.20 (s, 1 H), 7.08-7.11 (m, 1 H), 6.97 (s, 1 H), 5.29-5.34 (m, 1 H), 4.34-4.41 (m, 2 H), 3.85-3.87 (m, 2 H), 3.60-3.63 (m, 1 H), 3.53-3.54 (m, 1 H), 3.40 (s, 3 H), 3.18-3.33 (m, 3 H), 2.16 (d, J = 12.0 Hz, 2 H), 1.72-1.78 (m, 2 H), 1.35 (d, J = 6.0 Hz, 3 H). |
| 366 | 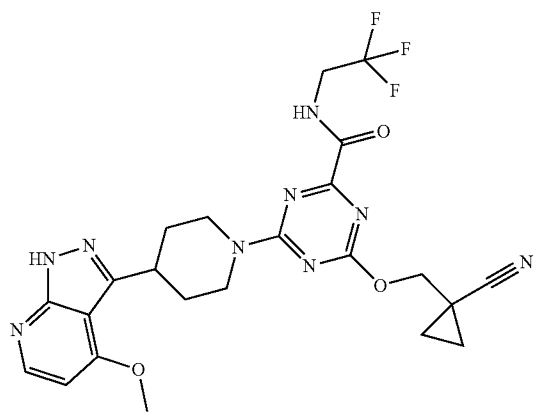 [SMILES: COc1ccnc2[nH]nc(C3CCN(c4nc(OCC5(C#N)CC5)nc(C(=O)NCC(F)(F)F)n4)CC3)c12] | 4-[(1-cyanocyclopropyl)methoxy]-6-[4-(4-methoxy-1H-pyrrolo[2,3-b]pyridin-3-yl)piperidin-1-yl]-N-(2,2,2-trifluoroethyl)-1,3,5-triazine-2-carboxamide | 531.1; (400 MHz, DMSO-d$_6$) δ ppm 11.27 (br. s., 1 H), 9.32-9.36 (m, 1 H), 8.06 (d, J = 5.6 Hz, 1 H), 7.03 (s, 1 H), 6.62 (d, J = 5.6 Hz, 1 H), 5.00 (d, J = 13.2 Hz, 1 H), 4.80 (d, J = 12.0 Hz, 1 H), 4.42-4.46 (m, 2 H), 4.04-4.06 (m, 2 H), 3.92 (s, 3 H), 3.24-3.26 (m, 1 H), 3.09-3.14 (m, 2 H), 2.07-2.10 (m, 2 H), 1.57-1.60 (m, 1 H), 1.36-1.37 (m, 2 H), 1.23-1.26 (m, 2H). |
| 367* | 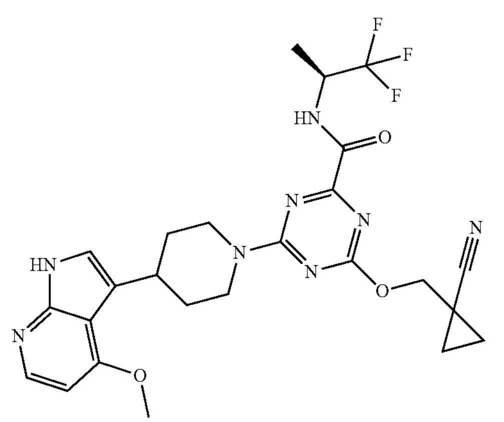 [SMILES: COc1ccnc2[nH]cc(C3CCN(c4nc(OCC5(C#N)CC5)nc(C(=O)N[C@@H](C)C(F)(F)F)n4)CC3)c12] | 4-[(1-cyanocyclopropyl)methoxy]-6-[4-(4-methoxy-1H-pyrrolo[2,3-b]pyridin-3-yl)piperidin-1-yl]-N-[(2S)-1,1,1-trifluoropropan-2-yl]-1,3,5-triazine-2-carboxamide | 567.1 [M + Na]+; (400 MHz, CDCl$_3$) δ ppm 9.00 (br. s., 1 H), 8.17 (d, J = 5.6 Hz, 1 H), 7.91 (d, J = 9.6 Hz, 1 H), 6.88 (s, 1 H), 6.53 (d, J = 5.6 Hz, 1 H), 5.08 (d, J = 12.0 Hz, 1 H), 4.82-4.92 (m, 2 H), 4.41-4.43 (m, 2 H), 3.98 (s, 3 H), 3.29-3.35 (m, 1 H), 3.07-3.16 (m, 2 H), 2.19-2.22 (m, 2 H), 1.42-1.44 (m, 5 H), 1.18-1.21 (m, 2H). |

TABLE 1-continued

| Ex. # | Structure | Compound Name | LRMS m/z (M + H)+; and 1H NMR |
|---|---|---|---|
| 368* | 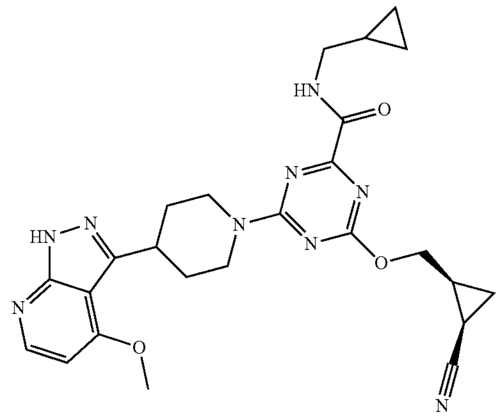 [SMILES: COc1ccnc2[nH]nc(C3CCN(c4nc(OC[C@H]5C[C@H]5C#N)nc(C(=O)NCC5CC5)n4)CC3)c12] | 4-{[(1S,2R)-2-cyanocyclopropyl]methoxy}-N-(cyclopropylmethyl)-6-[4-(4-methoxy-1H-pyrazolo[3,4-b]pyridin-3-yl)piperidin-1-yl]-1,3,5-triazine-2-carboxamide | 504.3; (400 MHz, CDCl$_3$) δ ppm 10.84 (br. s., 1 H), 8.40 (d, J = 5.6 Hz, 1 H), 7.91 (t, J = 2.9 Hz, 1 H), 6.52 (d, J = 5.6 Hz, 1 H), 5.06 (d, J = 13.2 Hz, 1 H), 4.86 (d, J = 12.8 Hz, 1 H), 4.46-4.65 (m, 2 H), 4.02 (s, 3 H), 3.46-3.57 (m, 1 H), 3.14-3.34 (m, 4 H), 2.16 (d, J = 13.2 Hz, 1 H), 1.92-2.08 (m, 2 H), 1.81-1.92 (m, 1 H), 1.65-1.73 (m, 1 H), 1.30-1.43 (m, 1 H), 1.11-1.18 (m, 1 H), 1.01-1.11 (m, 1 H), 0.48-0.57 (m, 2 H), 0.25-0.32 (m, 2 H). |
| 369* | 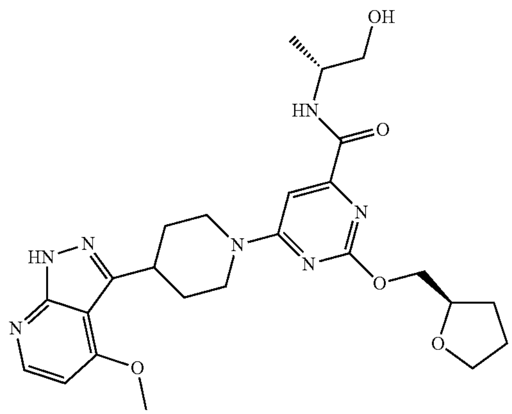 [SMILES: COc1ccnc2[nH]nc(C3CCN(c4cc(C(=O)N[C@H](C)CO)nc(OC[C@H]5CCCO5)n4)CC3)c12] | N-[(2R)-1-hydroxypropan-2-yl]-6-[4-(4-methoxy-1H-pyrazolo[3,4-b]pyridin-3-yl)piperidin-1-yl]-2-[{2R}-tetrahydrofuran-2-ylmethoxy]pyrimidine-4-carboxamide | 512.1; (400 MHz, CD$_3$OD) δ ppm 8.34 (d, J = 6.0 Hz, 1 H), 7.12 (s, 1 H), 6.71 (d, J = 5.6 Hz, 1 H), 5.18 (m, 1 H), 4.62-4.83 (m, 2 H), 4.32-4.38 (m, 3 H), 4.14-4.15 (m, 1 H), 4.00 (s, 3 H), 3.91-3.93 (m, 1 H), 3.82-3.83 (m, 1 H), 3.62-3.63 (m, 3 H), 3.21-3.24 (m, 2 H), 1.79-2.13 (m, 8 H), 1.27 (d, J = 6.8 Hz, 3 H). |
| 370* | 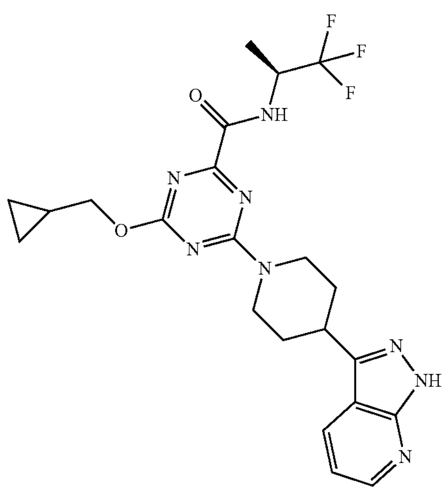 [SMILES: C[C@H](NC(=O)c1nc(OCC2CC2)nc(N2CCC(c3n[nH]c4ncccc34)CC2)n1)C(F)(F)F] | 4-(cyclopropylmethoxy)-6-[4-(1H-pyrazolo[3,4-b]pyridin-3-yl)piperidin-1-yl]-N-[(2S)-1,1,1-trifluoropropan-2-yl]-1,3,5-triazine-2-carboxamide | 491.1; (400 MHz, DMSO-d$_6$) δ ppm 13.29 (br. s., 1 H), 9.02-9.06 (m, 1 H), 8.48 (d, J = 2.8 Hz, 1 H), 8.31-8.34 (m, 1 H), 7.13-7.16 (m, 1 H), 4.89-4.91 (m, 1 H), 4.74-4.75 (m, 2 H), 4.19-4.22 (m, 2 H), 3.39-3.43 (m, 1 H), 3.23-3.25 (m, 2 H), 2.11-2.13 (m, 2 H), 1.83-1.84 (m, 2 H), 1.37-1.39 (m, 3 H), 1.23-1.25 (m, 1 H), 0.55-0.56 (m, 2 H), 0.33-0.35 (m, 2 H). |

TABLE 1-continued

| Ex. # | Structure | Compound Name | LRMS m/z (M + H)+; and 1H NMR |
|---|---|---|---|
| 371* | 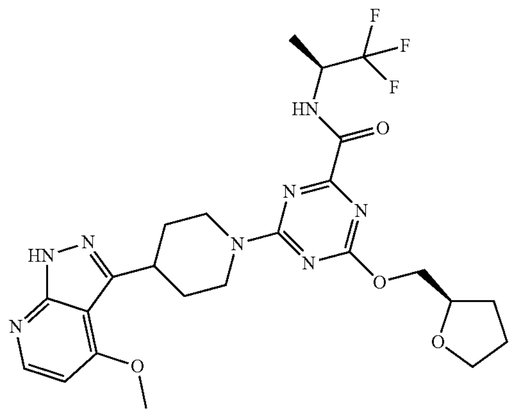 [SMILES: COc1ccnc2[nH]nc(C3CCN(c4nc(OC[C@H]5CCCO5)nc(C(=O)N[C@@H](C)C(F)(F)F)n4)CC3)c12] | 4-[4-(4-methoxy-1H-pyrazolo[3,4-b]pyridin-3-yl)piperidin-1-yl]-6-[(2R)-tetrahydrofuran-2-ylmethoxy]-N-[(2S)-1,1,1-trifluoropropan-2-yl]-1,3,5-triazine-2-carboxamide | 555.1; (400 MHz, CDCl$_3$) δ ppm 8.41 (d, J = 3.6 Hz, 1 H), 7.95 (d, J = 9.2 Hz, 1 H), 6.52 (d, J = 5.6 Hz, 1 H), 4.89-5.00 (m, 1 H), 4.86-4.87 (m, 2 H), 4.38-4.41 (m, 2 H), 4.29-4.31 (m, 1 H), 4.02 (s, 3 H), 3.93-3.95 (m, 1 H), 3.82-3.83 (m, 1 H), 3.48 (m, 1 H), 3.19-3.24 (m, 2 H), 2.03-2.18 (m, 3 H), 1.94-2.01 (m, 4 H), 1.61-1.79 (m, 1 H), 1.41 (d, J = 7.2 Hz, 3 H). |
| 372** | 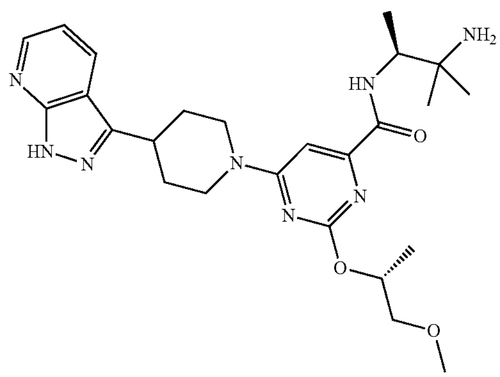 [SMILES: COC[C@@H](C)Oc1nc(C(=O)N[C@@H](C)C(C)(C)N)cc(N2CCC(c3n[nH]c4ncccc34)CC2)n1] | N-[(2S)-3-amino-3-methylbutan-2-yl]-2-{[(2R)-1-methoxypropan-2-yl]oxy}-6-[4-(1H-pyrazolo[3,4-b]pyridin-3-yl)piperidin-1-yl]pyrimidine-4-carboxamide | 497.0; (400 MHz, DMSO-d$_6$) δ ppm 13.41 (br. s., 1 H), 8.48 (d, J = 4.4 Hz, 1 H), 8.30-8.35 (m, 2 H), 7.10-7.15 (m, 1 H), 7.02 (s, 1 H), 5.22-5.26 (m, 1 H), 4.48-4.65 (m, 2 H), 3.74-3.75 (m, 1 H), 3.45-3.56 (m, 3 H), 3.30 (s, 3 H), 3.18-3.23 (m, 2 H), 2.05-2.08 (m, 2 H), 1.53-1.65 (m, 2 H), 1.47 (s, 2 H), 1.27 (d, J = 6.0 Hz, 3 H), 1.09 (s, 6 H), 0.98 (s, 3 H). |
| 373* | 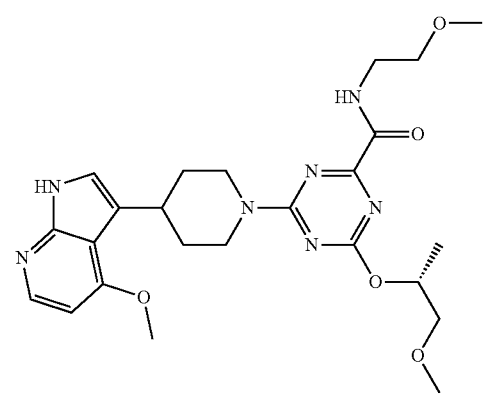 [SMILES: COCCNC(=O)c1nc(O[C@H](C)COC)nc(N2CCC(c3c[nH]c4nccc(OC)c34)CC2)n1] | N-(2-methoxyethyl)-4-{[(2R)-1-methoxypropan-2-yl]oxy}-6-[4-(4-methoxy-1H-pyrrolo[2,3-b]pyridin-3-yl)piperidin-1-yl]-1,3,5-triazine-2-carboxamide | 500.1; (400 MHz, DMSO-d$_6$) δ ppm 11.28 (br. s., 1 H), 8.74 (d, J = 6.0 Hz, 1 H), 8.06 (d, J = 5.2 Hz, 1 H), 7.04 (s, 1 H), 6.62 (d, J = 5.6 Hz, 1 H), 5.37-5.41 (m, 1 H), 4.97 (d, J = 12.4 Hz, 1 H), 4.75 (d, J = 12.0 Hz, 1 H), 3.91 (s, 3 H), 3.38-3.48 (m, 6 H), 3.26-3.29 (m, 7 H), 3.08-3.09 (m, 2 H), 2.05-2.08 (m, 2 H), 1.56-1.59 (m, 1 H), 1.27 (d, J = 6.4 Hz, 3 H). |
| 374* | 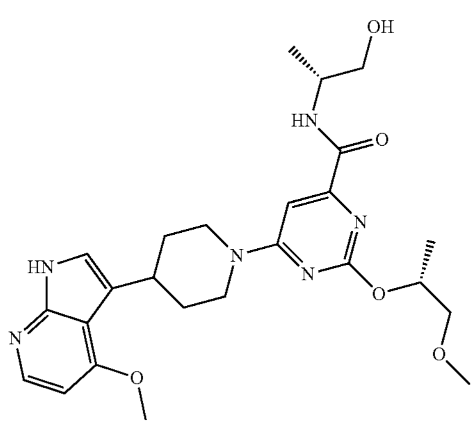 [SMILES: COC[C@@H](C)Oc1nc(C(=O)N[C@H](C)CO)cc(N2CCC(c3c[nH]c4nccc(OC)c34)CC2)n1] | N-[(2R)-1-hydroxypropan-2-yl]-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 499.1; (400 MHz, DMSO-d$_6$) δ ppm 11.24 (s, 1 H), 8.17 (d, J = 8.8 Hz, 1 H), 8.05 (d, J = 4.8 Hz, 1 H), 7.01 (d, J = 12.4 Hz, 2 H), 6.60 (d, J = 5.2 Hz, 1 H), 5.27 (s, 1 H), 4.89 (s, 1 H), 4.33-4.68 (m, 2 H), 3.93-3.97 (m, 2 H), 3.86 (s, 3 H), 3.50-3.52 (m, 2 H), 3.10-3.28 (m, 8 H), 2.03 (d, J = 12.0 Hz, 2 H), 1.58-1.61 (m, 2 H), 1.26 (d, J = 6.0 Hz, 3 H), 1.14 (d, J = 6.4 Hz, 3 H). |

TABLE 1-continued

| Ex. # | Structure | Compound Name | LRMS m/z (M + H)+; and 1H NMR |
|---|---|---|---|
| 375* | 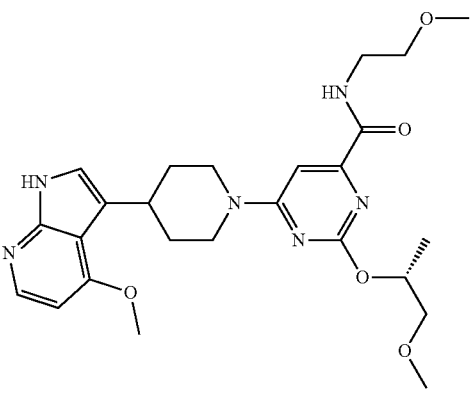 [SMILES: COCCNC(=O)c1cc(N2CCC(c3c[nH]c4nccc(OC)c34)CC2)nc(O[C@H](C)COC)n1] | N-(2-methoxyethyl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 499.1; (400 MHz, DMSO-$d_6$) δ ppm 11.25 (s, 1 H), 8.52 (d, J = 5.6 Hz, 1 H), 8.07 (d, J = 5.6 Hz, 1 H), 7.03 (d, J = 2.0 Hz, 1 H) 6.99 (s, 1 H), 6.60 (d, J = 5.6 Hz, 1 H), 5.31-5.35 (m, 1 H), 4.28-4.72 (m, 2 H), 3.88-3.93 (m, 3 H), 3.43-3.57 (m, 6 H), 3.21-3.32 (m, 6 H), 3.04-3.17 (m, 2 H), 2.42-2.47 (m, 1 H), 2.03 (d, J = 13.2 Hz, 2 H), 1.56-1.64 (m, 2 H), 1.27 (d, J = 6.4 Hz, 3 H). |
| 376** | 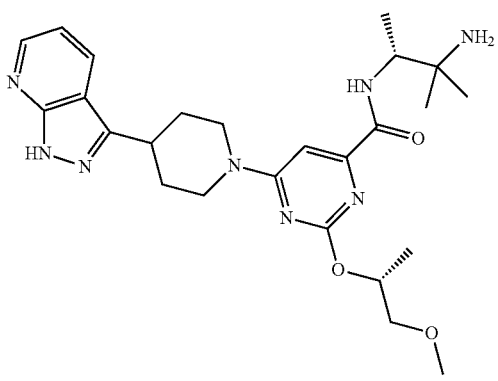 [SMILES: COC[C@@H](C)Oc1nc(C(=O)N[C@H](C)C(C)(C)N)cc(N2CCC(c3n[nH]c4ncccc34)CC2)n1] | N-[(2R)-3-amino-3-methylbutan-2-yl]-2-{[(2R)-1-methoxypropan-2-yl]oxy}-6-[4-(1H-pyrazolo[3,4-b]pyridin-3-yl)piperidin-1-yl]pyrimidine-4-carboxamide | 497.1; (400 MHz, DMSO-$d_6$) δ ppm 8.48 (d, J = 4.4 Hz, 1 H), 8.31-8.33 (m, 2 H), 7.12-7.16 (m, 1 H), 7.02 (s, 1 H), 5.22-5.26 (m, 1 H), 4.48-4.65 (m, 2 H), 3.74-3.75 (m, 1 H), 3.45-3.56 (m, 3 H), 3.30 (s, 3 H), 3.18-3.23 (m, 2 H), 2.11 (d, J = 10.4 Hz, 2 H), 1.81-1.86 (m, 2 H), 1.47 (s, 2 H), 1.27 (d, J = 6.0 Hz, 3 H), 1.10 (s, 6 H), 0.99 (s, 3 H). |
| 377* | 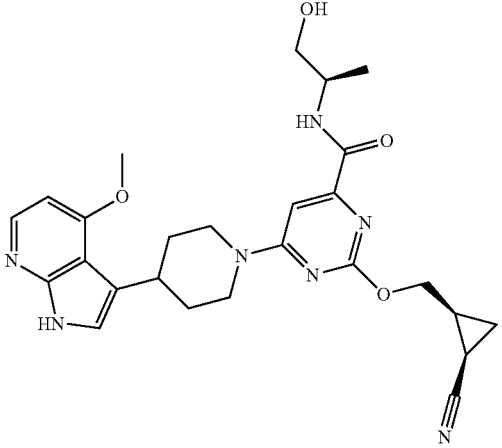 | 2-{[(1S,2R)-2-cyanocyclopropyl]methoxy}-N-[(2R)-1-hydroxypropan-2-yl]-6-[4-(4-methoxy-1H-pyrrolo[2,3-b]pyridin-3-yl)piperidin-1-yl]pyrimidine-4-carboxamide | 506.3; (400 MHz, DMSO-$d_6$) δ ppm 11.26 (s, 1 H), 8.20 (d, J = 8.4 Hz, 1 H), 8.05 (d, J = 5.6 Hz, 1 H), 7.04 (d, J = 4.8 Hz, 2 H), 6.60 (d, J = 5.6 Hz, 1 H), 4.90 (t, J = 5.6 Hz, 1 H), 4.26-4.67 (m, 2 H), 3.98-4.08 (m, 2 H), 3.87 (s, 3 H), 3.44-3.52 (m, 3 H), 3.04-3.28 (m, 3 H), 2.02-2.06 (m, 3 H), 1.82-1.88 (m, 1 H), 1.58-1.61 (m, 2 H), 1.27-1.30 (m, 1 H), 1.13-1.16 (m, 4 H). |

TABLE 1-continued

| Ex. # | Structure | Compound Name | LRMS m/z (M + H)+; and 1H NMR |
|---|---|---|---|
| 378* | 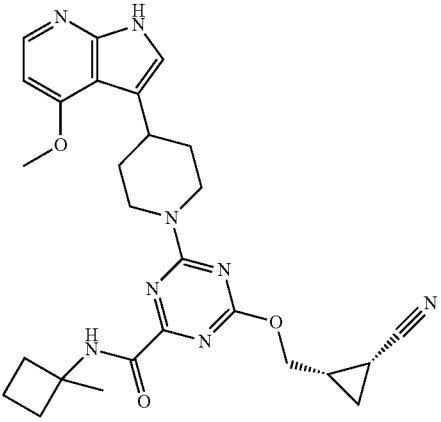 [SMILES: COc1ccnc2[nH]cc(C3CCN(c4nc(OC[C@H]5C[C@H]5C#N)nc(C(=O)NC5(C)CCC5)n4)CC3)c12] | 4-{[(1S,2R)-2-cyanocyclopropyl]methoxy}-6-[4-(4-methoxy-1H-pyrrolo[2,3-b]pyridin-3-yl)piperidin-1-yl]-N-(1-methylcyclobutyl)-1,3,5-triazine-2-carboxamide | 539.0 [M + Na]+; (400 MHz, DMSO-d$_6$) δ ppm 11.26 (s, 1 H), 8.52 (s, 1 H), 8.06 (d, J = 5.6 Hz, 1 H), 7.03 (s, 1), 6.62 (d, J = 5.6 Hz, 1 H), 4.96 (d, J = 11.6 Hz, 1 H), 4.75 (d, J = 14.8 Hz, 1 H), 4.66-4.69 (m, 1 H), 4.11-4.16 (m, 1 H), 3.91 (s, 3 H), 3.24-3.26 (m, 1 H), 3.08-3.12 (m, 2 H), 2.33-2.36 (m, 2 H), 2.07-2.10 (m, 2 H), 1.97-2.01 (m, 3 H), 1.80-1.83 (m, 3H), 1.56-1.59 (m, 1 H), 1.45 (s, 3 H), 1.28-1.29 (m, 1 H), 1.17-1.18 (m, 1 H). |
| 379* | 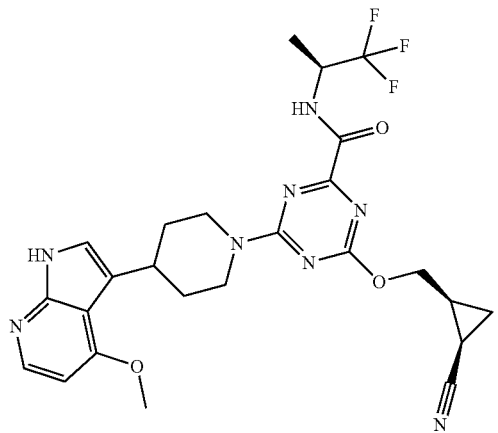 [SMILES: COc1ccnc2[nH]cc(C3CCN(c4nc(OC[C@H]5C[C@H]5C#N)nc(C(=O)N[C@@H](C)C(F)(F)F)n4)CC3)c12] | 4-{[(1S,2R)-2-cyanocyclopropyl]methoxy}-6-[4-(4-methoxy-1H-pyrrolo[2,3-b]pyridin-3-yl)piperidin-1-yl]-N-[(2S)-1,1,1-trifluoropropan-2-yl]-1,3,5-triazine-2-carboxamide | 567.1 [M + Na]+; (400 MHz, DMSO-d$_6$) δ ppm 11.26 (s, 1 H), 9.06 (d, J = 9.2 Hz, 1 H), 8.06 (d, J = 5.6 Hz, 1 H), 7.03 (s, 1 H), 6.62 (d, J = 6.0 Hz, 1 H), 4.85-4.95 (m, 1 H), 4.69-4.80 (m, 2 H), 4.12-4.17 (m, 1 H), 3.91 (s, 3 H), 3.24-3.26 (m, 1 H), 3.08-3.12 (m, 2 H), 2.08-2.11 (m, 2 H), 2.00-2.01 (m, 1 H), 1.80-1.83 (m, 1 H), 1.56-1.59 (m, 1 H), 1.38 (d, J = 7.2 Hz, 3 H), 1.28-1.30 (m, 1H), 1.17-1.18 (m, 1H). |
| 380* | 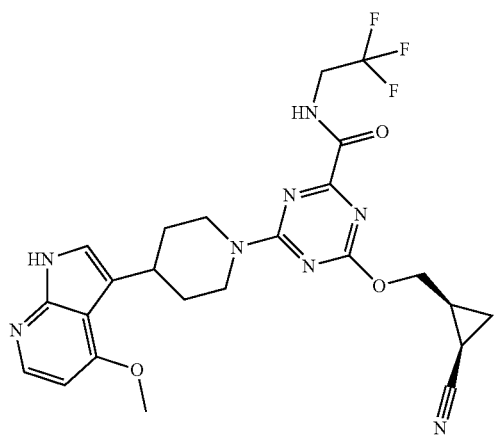 [SMILES: COc1ccnc2[nH]cc(C3CCN(c4nc(OC[C@H]5C[C@H]5C#N)nc(C(=O)NCC(F)(F)F)n4)CC3)c12] | 4-{[(1S,2R)-2-cyanocyclopropyl]methoxy}-6-[4-(4-methoxy-1H-pyrrolo[2,3-b]pyridin-3-yl)piperidin-1-yl]-N-(2,2,2-trifluoroethyl)-1,3,5-triazine-2-carboxamide | 531.0; (400 MHz, DMSO-d$_6$) δ ppm 11.27 (br. s., 1 H), 9.31-9.34 (m, 1 H), 8.06 (d, J = 5.6 Hz, 1 H), 7.03 (s, 1 H), 6.62 (d, J = 5.6 Hz, 1 H), 4.99 (d, J = 11.6 Hz, 1 H), 4.78 (d, J = 14.8 Hz, 1 H), 4.69-4.73 (m, 1 H), 4.12-4.18 (m, 1 H), 4.01-4.04 (m, 2 H), 3.91 (s, 3 H), 3.24-3.26 (m, 1 H), 3.09-3.14 (m, 2 H), 2.07-2.14 (m, 2 H), 2.00-2.01 (m, 1 H), 1.84-1.86 (m, 1 H), 1.58-1.60 (m, 2 H), 1.28-1.30 (m, 1 H), 1.17-1.18 (m, 1H). |

TABLE 1-continued

| Ex. # | Structure | Compound Name | LRMS m/z (M + H)+; and 1H NMR |
|---|---|---|---|
| 381* | 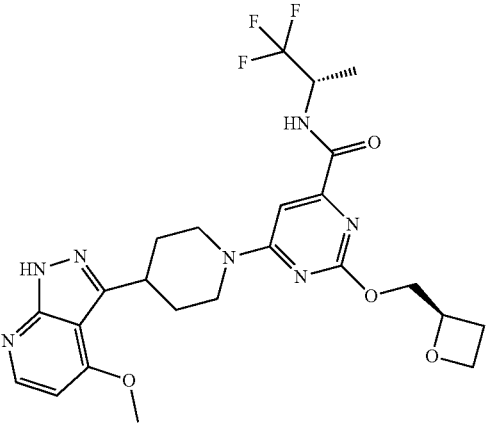 [SMILES: COc1ccnc2[nH]nc(C3CCN(c4cc(C(=O)N[C@@H](C)C(F)(F)F)nc(OC[C@H]5CCO5)n4)CC3)c12] | 6-[4-(4-methoxy-1H-pyrazolo[3,4-b]pyridin-3-yl)piperidin-1-yl]-2-[(2R)-oxetan-2-ylmethoxy]-N-[(2S)-1,1,1-trifluoropropan-2-yl]pyrimidine-4-carboxamide | 536.1; (400 MHz, CD$_3$OD) δ ppm 8.34 (d, J = 5.6 Hz, 1 H), 7.16 (s, 1 H), 6.71 (d, J = 5.6 Hz, 1 H), 5.14-5.18 (m, 1 H), 4.81-4.54 (m, 8 H), 4.01 (s, 3 H), 3.53-3.56 (m, 1 H), 3.23-3.26 (m, 2 H), 2.71-2.79 (m, 2 H), 1.98-2.14 (m, 4 H), 1.46 (d, J = 7.2 Hz, 3 H). |
| 382* | 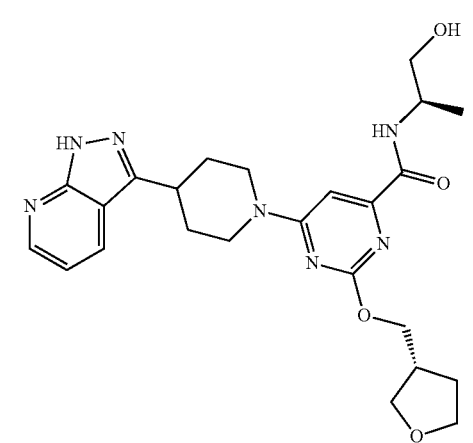 [SMILES: C[C@H](CO)NC(=O)c1cc(N2CCC(c3n[nH]c4ncccc34)CC2)nc(OC[C@@H]2CCOC2)n1] | N-[(2R)-1-hydroxypropan-2-yl]-6-[4-(1H-pyrazolo[3,4-b]pyridin-3-yl)piperidin-1-yl]-2-[(3R)-tetrahydrofuran-3-ylmethoxy]pyrimidine-4-carboxamide | 482.1; (400 MHz, CD$_3$OD) δ ppm 8.48 (dd, J = 3.2, 1.2 Hz, 1 H), 8.32 (d, J = 6.8 Hz, 1 H), 7.18-7.21 (m, 1 H), 7.12 (s, 1 H), 4.54-4.60 (m, 2 H), 4.29-4.36 (m, 2 H), 4.12-4.15 (m, 1 H), 3.89-3.93 (m, 2 H), 3.71-3.79 (m, 2 H), 3.62 (d, J = 5.2 Hz, 2 H), 3.50-3.52 (m, 1 H), 3.20-3.27 (m, 2 H), 2.77 (m, 1 H), 2.15-2.21 (m, 3 H), 2.00-2.03 (m, 2 H), 1.73-1.80 (m, 1 H), 1.27 (d, J = 6.8 Hz, 3 H). |
| 383* | 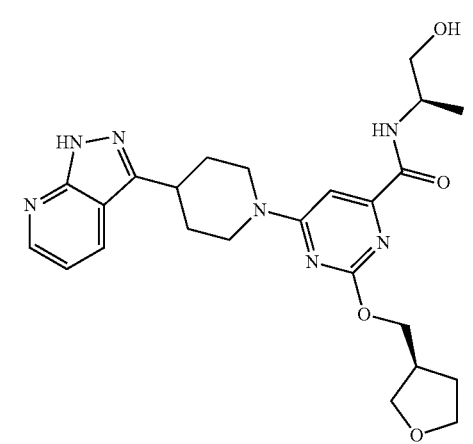 [SMILES: C[C@H](CO)NC(=O)c1cc(N2CCC(c3n[nH]c4ncccc34)CC2)nc(OC[C@H]2CCOC2)n1] | N-[(2R)-1-hydroxypropan-2-yl]-6-[4-(1H-pyrazolo[3,4-b]pyridin-3-yl)piperidin-1-yl]-2-[(3S)-tetrahydrofuran-3-ylmethoxy]pyrimidine-4-carboxamide | 482.1; (400 MHz, CD$_3$OD) δ ppm 8.49 (d, J = 3.2 Hz, 1 H), 8.32 (dd, J = 6.8, 1.2 Hz, 1 H), 7.18-7.21 (m, 1 H), 7.12 (s, 1 H), 4.54-4.60 (m, 2 H), 4.29-4.36 (m, 2 H), 4.12-4.15 (m, 1 H), 3.89-3.93 (m, 2 H), 3.71-3.79 (m, 2 H), 3.62 (d, J = 5.2 Hz, 2 H), 3.50-3.52 (m, 1 H), 3.20-3.27 (m, 2 H), 2.73-2.77 (m, 1 H), 2.15-2.21 (m, 3 H), 2.00-2.03 (m, 2 H), 1.76-1.80 (m, 1 H), 1.29 (d, J = 6.8 Hz, 3 H). |

TABLE 1-continued

| Ex. # | Structure | Compound Name | LRMS m/z (M + H)+; and 1H NMR |
|---|---|---|---|
| 384* | 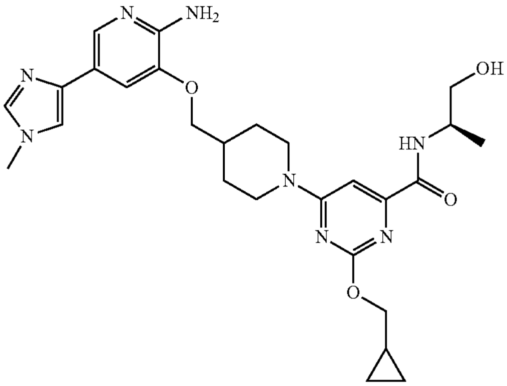 [SMILES: C[C@H](CO)NC(=O)c1cc(N2CCC(COc3cc(-c4cn(C)cn4)cnc3N)CC2)nc(OCC2CC2)n1] | 6-[4-({[2-amino-5-(1-methyl-1H-imidazol-4-yl)pyridin-3-yl]oxy}methyl)piperidin-1-yl]-2-(cyclopropylmethoxy)-N-[(2R)-1-hydroxypropan-2-yl]pyrimidine-4-carboxamide | 437.3; (400 MHz, DMSO-d$_6$) δ ppm 8.17 (d, J = 8.8 Hz, 1 H), 7.92 (s, 1 H), 7.56 (s, 1 H), 7.43 (s, 1 H), 7.32 (s, 1 H), 6.98 (s, 1 H), 5.60 (s, 2 H), 4.90 (t, J = 5.6 Hz, 1 H), 4.45-4.56 (br. s., 1 H), 4.12 (d, J = 7.2 Hz, 2 H), 3.94-3.97 (m, 1 H), 3.89 (d, J = 6.4 Hz, 2 H), 3.65 (s, 3 H), 3.02-3.17 (m, 2 H), 2.10-2.25 (m, 1 H), 1.95-1.98 (m, 2 H), 1.23-1.35 (m, 3 H), 1.14 (d, J = 6.8 Hz, 3 H), 0.54-0.57 (m, 2 H), 0.33-0.36 (m, 2 H). |
| 385* (E) | 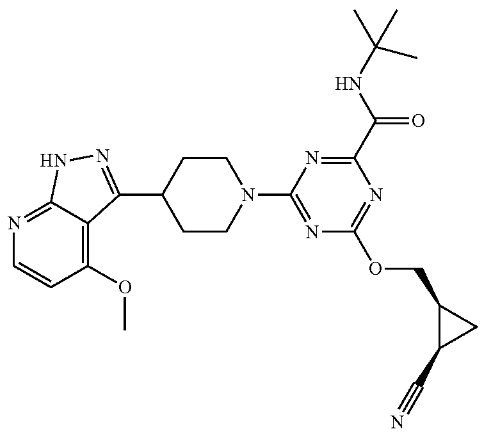 [SMILES: COc1ccnc2[nH]nc(C3CCN(c4nc(OC[C@H]5C[C@H]5C#N)nc(C(=O)NC(C)(C)C)n4)CC3)c12] | N-tert-butyl-4-{[(1S,2R)-2-cyanocyclopropyl]methoxy}-6-[4-(4-methoxy-1H-pyrazolo[3,4-b]pyridin-3-yl)piperidin-1-yl]-1,3,5-triazine-2-carboxamide | 506.2; (400 MHz, CDCl$_3$) δ ppm 10.76 (br s, 1 H), 8.39 (d, J = 5.2 Hz, 1 H), 7.73 (s, 1 H), 6.51 (d, J = 5.6 Hz, 1 H), 5.06 (d, J = 13.2 Hz, 1 H), 4.85 (d, J = 14.4 Hz, 1 H), 4.45-4.62 (m, 2 H), 4.01 (s, 3 H), 3.42-3.53 (m, 1 H), 3.13-3.29 (m, 2 H), 2.11-2.20 (m, 1 H), 1.93-2.05 (m, 2 H), 1.83-1.93 (m, 1 H), 1.65-1.75 (m, 1 H), 1.46 (s, 9 H), 1.28-1.41 (m, 1 H), 1.11-1.20 (m, 1 H). |
| 386* (E) | 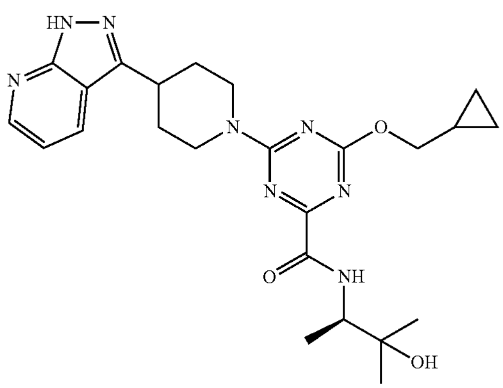 [SMILES: C[C@@H](NC(=O)c1nc(OCC2CC2)nc(N2CCC(c3n[nH]c4ncccc34)CC2)n1)C(C)(C)O] | 4-(cyclopropylmethoxy)-N-[(2R)-3-hydroxy-3-methylbutan-2-yl]-6-[4-(1H-pyrazolo[3,4-b]pyridin-3-yl)piperidin-1-yl]-1,3,5-triazine-2-carboxamide | 481.1; (400 MHz, DMSO-d$_6$) δ ppm 13.29 (s, 1 H), 8.48 (d, J = 4.4 Hz, 1 H), 8.34 (d, J = 8.0 Hz, 1 H), 8.17 (d, J = 9.2 Hz, 1 H), 7.14 (dd, J = 4.8, 3.6 Hz, 1 H), 4.85 (d, J = 11.6 Hz, 1 H), 4.73 (d, J = 11.6 Hz, 1 H), 4.72 (d, J = 5.2 Hz, 1 H), 4.67 (s, 1 H), 4.19 (d, J = 7.2 Hz, 1 H), 3.80-3.84 (m, 2 H), 3.42-3.43 (m, 1 H), 3.24-3.26 (m, 2 H), 2.11-2.13 (m, 2 H), 1.81-1.84 (m, 2 H), 1.23-1.27 (m, 1 H), 1.08-1.14 (m, 9 H), 0.55-0.58 (m, 2 H), 0.35-0.37 (m, 2 H). |
| 387* (D) | 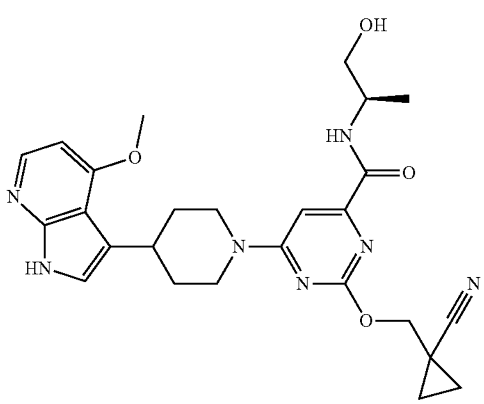 [SMILES: COc1ccnc2[nH]cc(C3CCN(c4cc(C(=O)N[C@H](C)CO)nc(OCC5(C#N)CC5)n4)CC3)c12] | 2-[(1-cyanocyclopropyl)methoxy]-N-[(2R)-1-hydroxypropan-2-yl]-6-[4-(4-methoxy-1H-pyrrolo[2,3-b]pyridin-3-yl)piperidin-1-yl]pyrimidine-4-carboxamide | 506.3; (400 MHz, DMSO-d$_6$) δ ppm 11.27 (s, 1 H), 8.22 (d, J = 8.4 Hz, 1 H), 8.05 (d, J = 5.2, Hz 1 H), 7.04 (d, J = 10.4, Hz 2 H), 6.61 (d, J = 6.0, Hz, 1 H), 4.89 (t, J = 5.6 Hz 1 H), 4.54-4.74 (m, 1 H), 4.36 (s, 2 H), 3.96-4.03 (m, 1 H), 3.89 (s, 3 H), 3.44-3.49 (m, 3 H), 3.24-3.37 (m, 3 H), 2.03-2.06 (m, 2 H), 1.54-1.63 (m, 2 H), 1.36-1.38 (m, 2 H), 1.20-1.23 (m, 2 H), 1.15 (d, J = 6.4 Hz, 3 H). |

TABLE 1-continued

| Ex. # | Structure | Compound Name | LRMS m/z (M + H)+; and 1H NMR |
|---|---|---|---|
| 388** (D) | 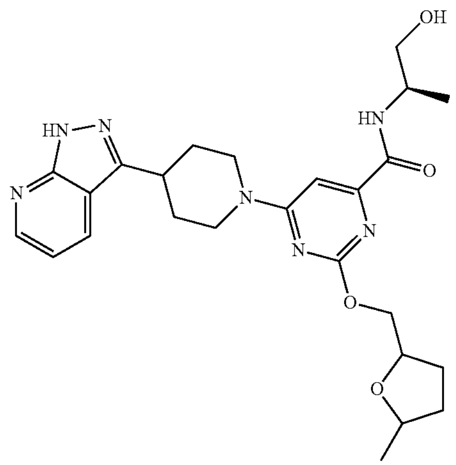 [SMILES: CC1CCC(COc2nc(C(=O)N[C@H](C)CO)cc(N3CCC(c4n[nH]c5ncccc45)CC3)n2)O1] | (trans)-N-[(2R)-1-hydroxypropan-2-yl]-2-[(5-methyl-tetrahydrofuran-2-yl)methoxy]-6-[4-(1H-pyrazolo[3,4-b]pyridin-3-yl)piperidin-1-yl]pyrimidine-4-carboxamide | 495.9; (400 MHz, CD$_3$OD) δ ppm 8.50 (d, J = 3.2 Hz, 1 H), 8.34 (d, J = 6.4 Hz, 1 H), 7.21 (dd, J = 4.4, 3.6 Hz, 1 H), 7.13 (s, 1 H), 4.59-4.63 (m, 3 H), 4.36-4.44 (m, 3 H), 4.14-4.21 (m, 2 H), 3.63 (d, J = 5.2 Hz, 2 H), 3.51-3.52 (m, 1 H), 3.24-3.31 (m, 1 H), 2.15-2.21 (m, 4 H), 1.87-2.00 (m, 3 H), 1.52-1.61 (m, 1 H), 1.23-1.28 (m, 6 H). |
| 389** (D) | 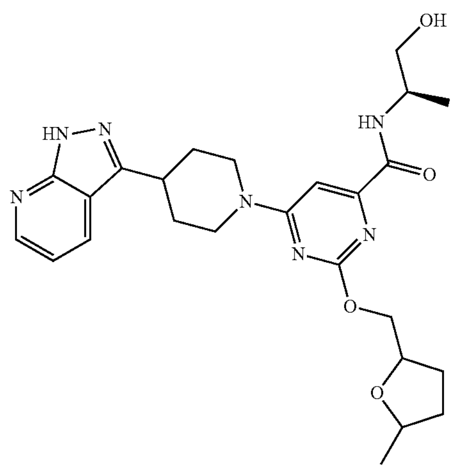 [SMILES: CC1CCC(COc2nc(C(=O)N[C@H](C)CO)cc(N3CCC(c4n[nH]c5ncccc45)CC3)n2)O1] | (trans)-N-[(2R)-1-hydroxypropan-2-yl]-2-[(5-methyl-tetrahydrofuran-2-yl)methoxy]-6-[4-(1H-pyrazolo[3,4-b]pyridin-3-yl)piperidin-1-yl]pyrimidine-4-carboxamide | 495.9; (400 MHz, CD$_3$OD) δ ppm 8.50 (d, J = 3.2 Hz, 1 H), 8.34 (d, J = 6.4 Hz, 1 H), 7.21 (dd, J = 4.4, 3.6 Hz, 1 H), 7.13 (s, 1 H), 4.59-4.63 (m, 3 H), 4.36-4.44 (m, 3 H), 4.14-4.21 (m, 2 H), 3.63 (d, J = 5.2 Hz, 2 H), 3.51-3.52 (m, 1 H), 3.24-3.31 (m, 1 H), 2.15-2.21 (m, 4 H), 1.87-2.00 (m, 3 H), 1.52-1.61 (m, 1 H), 1.23-1.28 (m, 6 H). |
| 390* (D) | 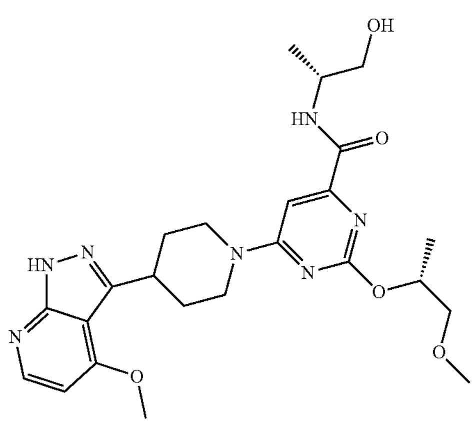 [SMILES: COC[C@@H](C)Oc1nc(C(=O)N[C@H](C)CO)cc(N2CCC(c3n[nH]c4nccc(OC)c34)CC2)n1] | N-[(2R)-1-hydroxypropan-2-yl]-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 500.0; (400 MHz, CDCl$_3$) δ ppm 11.77 (br s, 1 H), 8.41 (d, J = 5.6 Hz, 1 H), 7.98 (d, J = 7.6 Hz, 1 H), 7.13 (s, 1 H), 6.51 (d, J = 5.6 Hz, 1 H), 5.30-5.37 (m, 1 H), 4.56 (br s, 2 H), 4.21-4.23 (m, 1 H), 3.97 (s, 3 H), 3.50-3.70 (m, 5 H), 3.49 (s, 3 H), 3.17-3.41 (m, 2 H), 1.76-2.13 (m, 4 H), 1.38 (d, J = 6.4 Hz, 3 H), 1.28 (d, J = 6.8 Hz, 3 H). |

TABLE 1-continued

| Ex. # | Structure | Compound Name | LRMS m/z (M + H)+; and 1H NMR |
|---|---|---|---|
| 391* (E) | 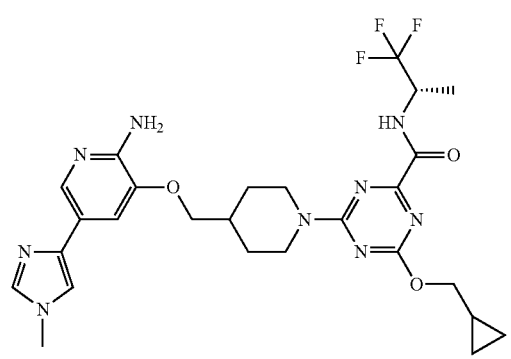 [SMILES: C[C@H](NC(=O)c1nc(OCC2CC2)nc(N2CCC(COc3cc(-c4cn(C)cn4)cnc3N)CC2)n1)C(F)(F)F] | 4-[4-({[2-amino-5-(1-methyl-1H-imidazol-4-yl)pyridin-3-yl]oxy}methyl)piperidin-1-yl]-6-(cyclopropylmethoxy)-N-[(2S)-1,1,1-trifluoropropan-2-yl]-1,3,5-triazine-2-carboxamide | 576.1; (400 MHz, DMSO-$d_6$) δ ppm 9.02 (d, J = 8.8 Hz, 1 H), 7.91 (s, 1 H), 7.56 (s, 1 H), 7.43 (s, 1 H), 7.32 (s, 1 H), 5.60 (s, 2 H), 4.87 (d, J = 14.4 Hz, 1 H), 4.69-4.77 (m, 2 H), 4.19 (d, J = 7.6 Hz, 2 H), 3.91 (d, J = 5.6 Hz, 2 H), 3.65 (s, 3 H), 3.03-3.06 (m, 2 H), 2.15-2.16 (m, 1 H), 1.96-2.00 (m, 2 H), 1.24-1.38 (m, 6 H), 0.57 (d, J = 6.4 Hz, 2 H), 0.36 (d, J = 4.8 Hz, 2 H). |
| 392* (D) | 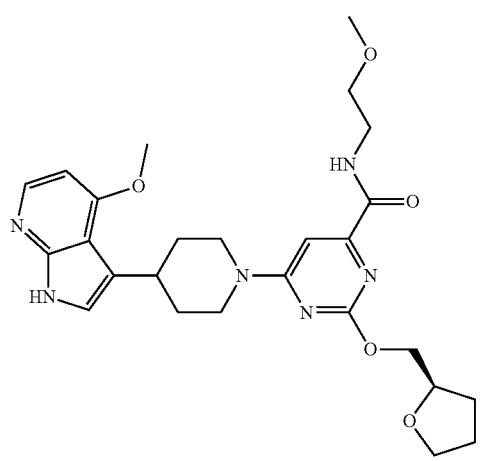 [SMILES: COCCNC(=O)c1cc(N2CCC(c3c[nH]c4nccc(OC)c34)CC2)nc(OC[C@H]2CCCO2)n1] | N-(2-methoxyethyl)-6-[4-(4-methoxy-1H-pyrrolo[2,3-b]pyridin-3-yl)piperidin-1-yl]-2-[(2R)-tetrahydrofuran-2-ylmethoxy]pyrimidine-4-carboxamide | 511.0; (400 MHz, DMSO-$d_6$) δ ppm 11.26 (s, 1 H), 8.53 (s, 1 H), 8.05 (d, J = 5.2 Hz, 1 H), 7.02 (s, 2 H), 6.60 (d, J = 5.2 Hz, 1 H), 4.26-4.58 (m, 4 H), 4.13-4.18 (m, 1 H), 3.88 (s, 3 H), 3.64-3.78 (m, 2 H), 3.44 (s, 4 H), 3.08-3.27 (m, 6 H), 1.84-2.05 (m, 5 H), 1.57-1.62 (m, 3 H). |
| 393* (D) | 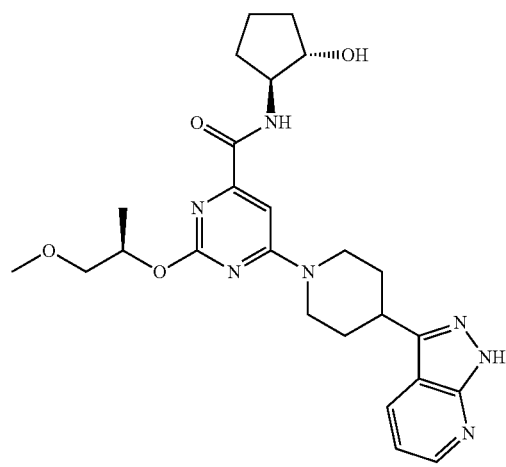 [SMILES: COC[C@@H](C)Oc1nc(C(=O)N[C@H]2CCC[C@@H]2O)cc(N2CCC(c3n[nH]c4ncccc34)CC2)n1] | N-[(1S,2S)-2-hydroxycyclopentyl]-2-{[(2R)-1-methoxypropan-2-yl]oxy}-6-[4-(1H-pyrazolo[3,4-b]pyridin-3-yl)piperidin-1-yl]pyrimidine-4-carboxamide | 496.3; (400 MHz, DMSO-$d_6$) δ ppm 13.29 (s, 1 H), 8.49 (d, J = 1.6 Hz, 1 H), 8.31 (d, J = 6.8 Hz, 1 H), 8.21 (d, J = 8.0 Hz, 1 H), 7.13-7.16 (m, 1 H), 7.03 (s, 1 H), 5.31-5.33 (m, 1 H), 4.84 (d, J = 4.4 Hz, 1 H), 4.39-4.68 (m, 1 H), 3.92-4.02 (m, 2 H), 3.44-3.52 (m, 3 H); 3.23-3.29 (m, 5 H); 2.12 (d, J = 13.6 Hz, 2 H), 1.94-1.98 (m, 1 H), 1.79-1.86 (m, 3 H), 1.63-1.72 (m, 2 H), 1.44-1.58 (m, 2 H), 1.25 (d, J = 6.0 Hz, 3 H). |

TABLE 1-continued

| Ex. # | Structure | Compound Name | LRMS m/z (M + H)+; and 1H NMR |
|---|---|---|---|
| 394* (D) | 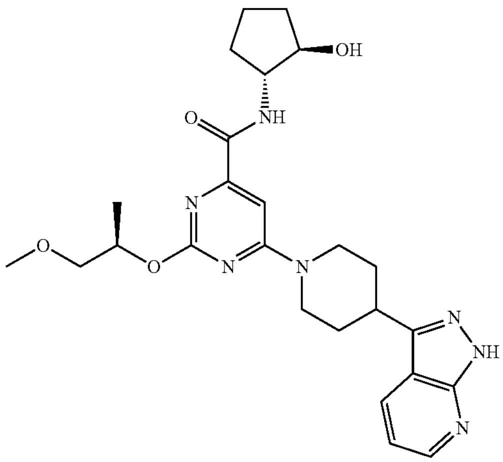 [SMILES: COC[C@@H](C)Oc1nc(C(=O)N[C@@H]2CCC[C@H]2O)cc(N2CCC(c3n[nH]c4ncccc34)CC2)n1] | N-[1R,2R)-2-hydroxy-cyclopentyl]-2-{[(2R)-1-methoxypropan-2-yl]oxy}-6-[4-(1H-pyrazolo[3,4-b]pyridin-3-yl)piperidin-1-yl]pyrimidine-4-carboxamide | 496.3; (400 MHz, DMSO-$d_6$) δ ppm 13.29 (s, 1 H), 8.49 (d, J = 1.6 Hz, 1 H), 8.31 (d, J = 6.8 Hz, 1 H), 8.21 (d, J = 8.0 Hz, 1 H), 7.13-7.16 (m, 1 H), 7.03 (s, 1 H), 5.31-5.33 (m, 1 H), 4.84 (d, J = 4.4 Hz, 1 H), 4.39-4.68 (m, 1 H), 3.92-4.02 (m, 2 H), 3.44-3.52 (m, 3 H); 3.23-3.29 (m, 5 H); 2.12 (d, J = 13.6 Hz, 2 H), 1.94-1.98 (m, 1 H), 1.79-1.86 (m, 3 H), 1.63-1.72 (m, 2 H), 1.44-1.58 (m, 2 H), 1.25 (d, J = 6.0 Hz, 3 H). |
| 395** (D) | 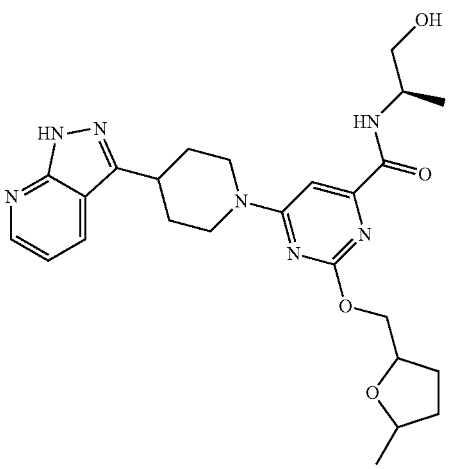 [SMILES: CC1CCC(COc2nc(C(=O)N[C@H](C)CO)cc(N3CCC(c4n[nH]c5ncccc45)CC3)n2)O1] | (Cis)-N-[(2R)-1-hydroxypropan-2-yl]-2-[(5-methyl-tetrahydrofuran-2-yl)methoxy]-6-[4-(1H-pyrazolo[3,4-b]pyridin-3-yl)piperidin-1-yl]pyrimidine-4-carboxamide | 496.3; (400 MHz, CD$_3$OD) δ ppm 8.50 (d, J = 4.4 Hz, 1 H), 8.34 (d, J = 6.8 Hz, 1 H), 7.19-7.22 (m, 1 H), 7.13 (s, 1 H), 4.55-4.61 (m, 1 H), 4.37-4.40 (m, 2 H), 4.26-4.29 (m, 1 H), 4.13-4.15 (m, 1 H), 4.02-4.08 (m, 1 H), 3.64 (d, J = 5.2 Hz, 2 H), 3.49-3.51 (m, 1 H), 3.26-3.31 (m, 3 H), 1.91-2.22 (m, 7 H), 1.50-1.61 (m, 1 H), 1.26-1.28 (m, 6 H). |
| 396** (D) | 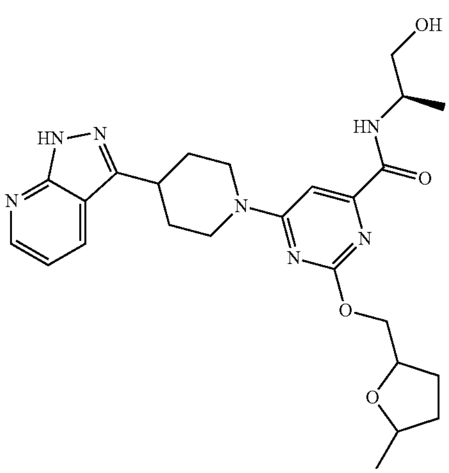 [SMILES: CC1CCC(COc2nc(C(=O)N[C@H](C)CO)cc(N3CCC(c4n[nH]c5ncccc45)CC3)n2)O1] | (Cis)-N-[(2R)-1-hydroxypropan-2-yl]-2-[(5-methyl-tetrahydrofuran-2-yl)methoxy]-6-[4-(1H-pyrazolo[3,4-b]pyridin-3-yl)piperidin-1-yl]pyrimidine-4-carboxamide | 496.3; (400 MHz, CD$_3$OD) δ ppm 8.50 (d, J = 4.4 Hz, 1 H), 8.34 (d, J = 6.8 Hz, 1 H), 7.19-7.22 (m, 1 H), 7.13 (s, 1 H), 4.55-4.61 (m, 1 H), 4.37-4.40 (m, 2 H), 4.26-4.29 (m, 1 H), 4.13-4.15 (m, 1 H), 4.02-4.08 (m, 1 H), 3.64 (d, J = 5.2 Hz, 2 H), 3.49-3.51 (m, 1 H), 3.26-3.31 (m, 3 H), 1.91-2.22 (m, 7 H), 1.50-1.61 (m, 1 H), 1.26-1.28 (m, 6 H). |

TABLE 1-continued

| Ex. # | Structure | Compound Name | LRMS m/z (M + H)+; and 1H NMR |
|---|---|---|---|
| 397* (D) | 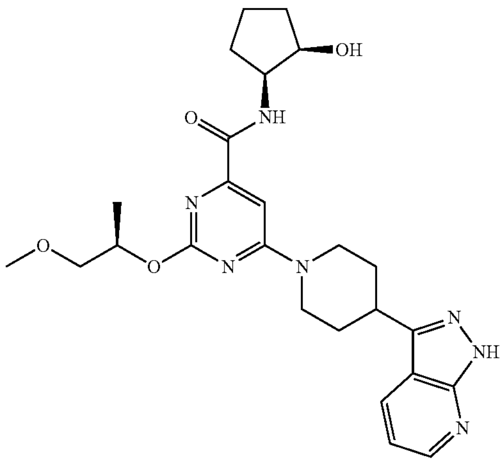 [SMILES: COC[C@@H](C)Oc1nc(C(=O)N[C@H]2CCC[C@H]2O)cc(N2CCC(c3n[nH]c4ncccc34)CC2)n1] | N-[(1S,2R)-2-hydroxy-cyclopentyl]-2-{[(2R)-1-methoxypropan-2-yl]oxy}-6-[4-(1H-pyrazolo[3,4-b]pyridin-3-yl)piperidin-1-yl]pyrimidine-4-carboxamide | 518.2 [M + Na]+; (400 MHz, DMSO-d$_6$) δ ppm 13.28 (s, 1 H), 8.48 (d, J = 1.2 Hz, 1 H), 8.28 (t, J = 8.4 Hz, 2 H), 7.11-7.16 (m, 1 H), 7.03 (s, 1 H), 5.21-5.25 (m, 1 H), 5.17 (d, J = 6.4 Hz, 1 H), 4.40 (br s, 2 H), 3.91-4.07 (m, 2 H), 3.35-3.62 (m, 2 H), 3.12-3.25 (m, 5 H), 2.03-2.15 (m, 2 H), 1.65-1.96 (m, 5 H), 1.42-1.65 (m, 3 H), 1.26 (d, J = 6.4 Hz, 3 H). |
| 398* (D) | 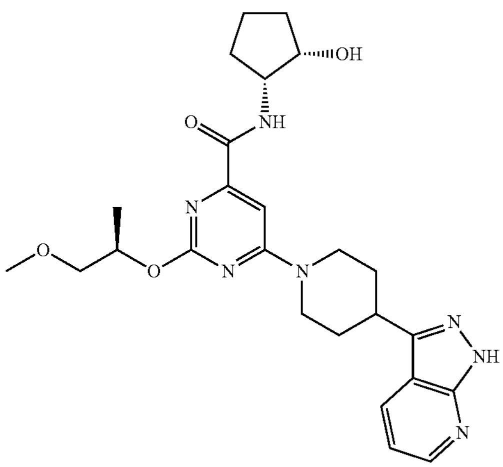 [SMILES: COC[C@@H](C)Oc1nc(C(=O)N[C@@H]2CCC[C@@H]2O)cc(N2CCC(c3n[nH]c4ncccc34)CC2)n1] | N-[(1R,2S)-2-hydroxy-cyclopentyl]-2-{[(2R)-1-methoxypropan-2-yl]oxy}-6-[4-(1H-pyrazolo[3,4-b]pyridin-3-yl)piperidin-1-yl]pyrimidine-4-carboxamide | 518.2 [M + Na]+; (400 MHz, DMSO-d$_6$) δ ppm 13.28 (s, 1 H), 8.48 (d, J = 4.0 Hz, 1 H), 8.28 (t, J = 8.8 Hz, 2 H), 7.11-7.16 (m, 1 H), 7.03 (s, 1 H), 5.21-5.25 (m, 1 H), 5.17 (d, J = 4.4 Hz, 1 H), 4.40 (br s, 2 H), 3.91-4.07 (m, 2 H), 3.35-3.62 (m, 2 H), 3.12-3.25 (m, 5 H), 2.03-2.15 (m, 2 H), 1.65-1.96 (m, 5 H), 1.42-1.65 (m, 3 H), 1.26 (d, J = 6.4 Hz, 3 H). |
| 399* (D) | 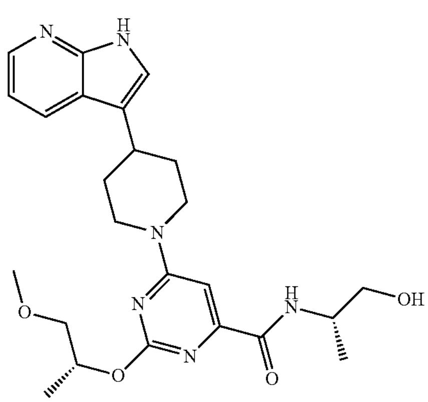 [SMILES: COC[C@@H](C)Oc1nc(C(=O)N[C@@H](C)CO)cc(N2CCC(c3c[nH]c4ncccc34)CC2)n1] | N-[(2S)-1-hydroxypropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide | 491.1 [M + Na]+; (400 MHz, DMSO-d$_6$) δ ppm 11.36 (br s, 1 H), 8.16-8.19 (m, 2 H), 8.02 (d, J = 6.8 Hz, 1 H), 7.25 (s, 1 H), 7.01-7.04 (m, 2 H), 5.27-5.31 (m, 1 H), 4.89 (t, J = 5.6 Hz, 1 H), 4.54 (br s, 2 H), 3.96-3.99 (m, 1 H), 3.51-3.52 (m, 1 H), 3.43-3.47 (m, 3 H), 3.29 (s, 3 H), 3.13-3.16 (m, 3 H), 2.06 (d, J = 10.8 Hz, 2 H), 1.59-1.68 (m, 2 H), 1.27 (d, J = 6.4 Hz, 3 H), 1.14 (d, J = 6.8 Hz, 3 H). |

TABLE 1-continued

| Ex. # | Structure | Compound Name | LRMS m/z (M + H)+; and 1H NMR |
|---|---|---|---|
| 400* (D) | 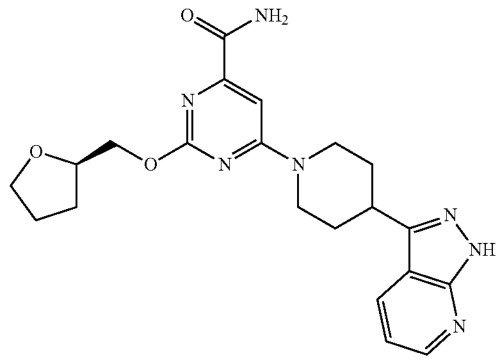 [SMILES: NC(=O)c1cc(N2CCC(c3n[nH]c4ncccc34)CC2)nc(OC[C@H]2CCCO2)n1] | 6-[4-(1H-pyrazolo[3,4-b]pyridin-3-yl)piperidin-1-yl]-2-[{2R)-tetrahydrofuran-2-ylmethoxy]pyrimidine-4-carboxamide | 424.1; (600 MHz DMSO-d$_6$) δ ppm 13.27 (s, 1 H), 8.48 (dd, J = 4.52, 1.59 Hz, 1 H), 8.31 (dd, J = 8.07, 1.47 Hz, 1 H), 7.96 (d, J = 2.20 Hz, 1 H), 7.66 (br. s., 1 H), 7.14 (dd, J = 8.07, 4.52 Hz, 1 H), 7.04 (s, 1 H), 4.51 (br s, 2 H), 4.22-4.33 (m, 2 H), 4.10-4.20 (m, 1 H), 3.74-3.83 (m, 1 H), 3.64-3.72 (m, 1 H), 3.38-3.50 (m, 1 H), 3.22 (t, J = 12.17 Hz, 2 H), 2.06-2.16 (m, 2 H), 1.94-2.04 (m, 1 H), 1.75-1.93 (m, 4 H), 1.60-1.71 (m, 1 H). |
| 401* (D) | 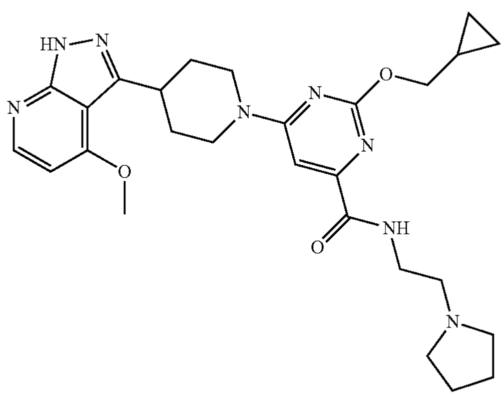 [SMILES: COc1ccnc2[nH]nc(C3CCN(c4cc(C(=O)NCCN5CCCC5)nc(OCC5CC5)n4)CC3)c12] | 2-(cyclopropylmethoxy)-6-[4-(4-methoxy-1H-pyrazolo[3,4-b]pyridin-3-yl)piperidin-1-yl]-N-[2-(pyrrolidin-1-yl)ethyl]pyrimidine-4-carboxamide | 521.0; (400 MHz, CDCl$_3$) δ ppm 12.37 (s, 1 H), 8.42-8.43 (m, 1 H), 8.24-8.25 (m, 1 H), 7.12 (s, 1 H), 6.48-6.49 (m, 1 H), 4.58 (br s, 2 H), 4.14 (d, J = 6.4 Hz, 2 H), 3.96 (s, 3 H), 3.53-3.56 (m, 3 H), 3.10-3.16 (m, 2 H), 2.58-2.70 (m, 6 H), 1.99-2.28 (m, 6 H), 1.24-1.33 (m, 2 H), 0.60 (d, J = 6.0 Hz, 2 H), 0.34-0.35 (m, 2 H). |
| 402* (D) | 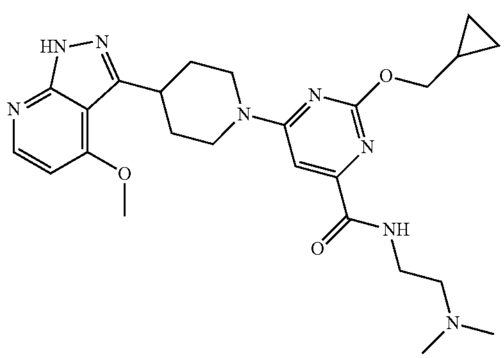 [SMILES: COc1ccnc2[nH]nc(C3CCN(c4cc(C(=O)NCCN(C)C)nc(OCC5CC5)n4)CC3)c12] | 2-(cyclopropylmethoxy)-N-[2-(dimethylamino)ethyl]-6-[4-(4-methoxy-1H-pyrazolo[3,4-b]pyridin-3-yl)piperidin-1-yl]pyrimidine-4-carboxamide | 494.4; (400 MHz, CDCl$_3$) δ ppm 8.40 (d, J = 5.6 Hz, 1 H), 8.18-8.21 (m, 1 H), 7.12 (s, 1 H), 6.50 (d, J = 5.6 Hz, 1 H), 4.58 (br s, 2 H), 4.16 (d, J = 7.2 Hz, 2 H), 3.96 (s, 3 H), 3.47-3.54 (m, 3 H), 3.17 (t, J = 11.2 Hz, 2 H), 2.51 (t, J = 6.4 Hz, 2 H), 2.28 (s, 6 H), 2.09-2.12 (m, 4 H), 1.34-1.36 (m, 1 H), 0.59-0.64 (m, 2 H), 0.34-0.38 (m, 2 H). |
| 403* (D) | 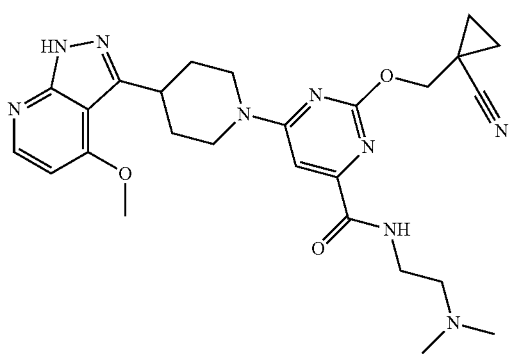 [SMILES: COc1ccnc2[nH]nc(C3CCN(c4cc(C(=O)NCCN(C)C)nc(OCC5(C#N)CC5)n4)CC3)c12] | 2-[(1-cyanocyclopropyl)methoxy]-N-[2-(dimethylamino)ethyl]-6-[4-(4-methoxy-1H-pyrazolo[3,4-b]pyridin-3-yl)piperidin-1-yl]pyrimidine-4-carboxamide | 520.0; (400 MHz, CD$_3$OD) δ ppm 8.34 (d, J = 5.6 Hz, 1 H), 7.15 (s, 1 H), 6.70 (d, J = 6.0 Hz, 1 H), 4.63 (br s, 2 H), 4.44 (s, 2 H), 4.01 (s, 3 H), 3.67 (t, J = 6.0 Hz, 1H), 3.55-3.66 (m, 2 H), 3.21-3.25 (m, 2 H), 2.95 (t, J = 6.4 Hz, 2 H), 2.61 (s, 6 H), 1.95-2.13 (m, 4 H), 1.37-1.39 (m, 2 H), 1.23-1.26 (m, 2 H). |

TABLE 1-continued

| Ex. # | Structure | Compound Name | LRMS m/z (M + H)⁺; and ¹H NMR |
|---|---|---|---|
| 404* (D) | 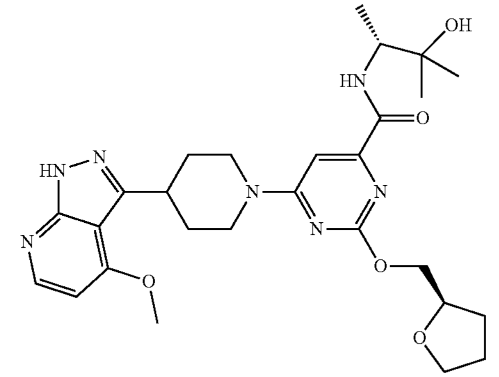 [SMILES: COc1ccnc2[nH]nc(C3CCN(c4cc(C(=O)N[C@H](C)C(C)(C)O)nc(OC[C@H]5CCCO5)n4)CC3)c12] | N-[(2R)-3-hydroxy-3-methylbutan-2-yl]-6-[4-(4-methoxy-1H-pyrazolo[3,4-b]pyridin-1-yl)piperidin-1-yl]-2-[(2R)-tetrahydrofuran-2-ylmethoxy]pyrimidine-4-carboxamide | 540.0; (400 MHz, CDCl$_3$) δ ppm 11.3 (br s, 1 H), 8.41 (d, J = 5.6 Hz, 1 H), 8.09 (d, J = 8.8 Hz, 1 H), 7.14 (s, 1 H), 6.51 (d, J = 5.2 Hz, 2 H), 4.54 (br s, 2 H), 4.37-4.39 (m, 3 H), 4.04-4.08 (m, 1 H), 3.83 (s, 3 H), 3.94 (s, 3 H), 3.79-3.83 (m, 1 H), 3.44-3.50 (m, 1 H), 3.19-3.25 (m, 1 H), 2.79 (br s, 1 H), 1.95-2.14 (m, 7 H), 1.75-1.77 (m, 1 H), 1.24-1.26 (m, 9 H). |
| 405* (D) | 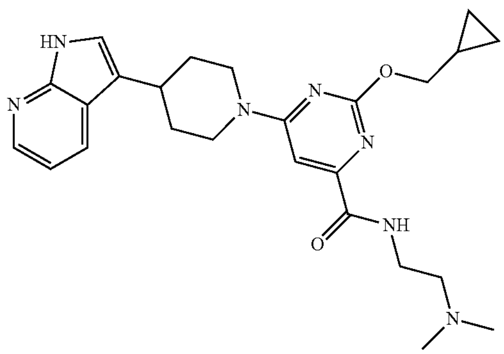 [SMILES: CN(C)CCNC(=O)c1cc(N2CCC(c3c[nH]c4ncccc34)CC2)nc(OCC2CC2)n1] | 2-(cyclopropylmethoxy)-N-[2-(dimethylamino)ethyl]-6-[4-(1H-pyrrolo[2,3-b]pyridin-3-yl)piperidin-1-yl]pyrimidine-4-carboxamide | 464.3; (400 MHz, DMSO-d$_6$) δ ppm 11.36 (s, 1 H), 8.49 (t, J = 6.0 Hz, 1 H), 8.18 (d, J = 3.6 Hz, 1 H), 8.02 (d, J = 7.2 Hz, 1 H), 7.24 (d, J = 4.8 Hz, 1 H), 7.01-7.05 (m, 2 H), 4.38-4.42 (m, 2 H), 4.14 (d, J = 7.2 Hz, 2 H), 3.08-3.31 (m, 5 H), 2.45 (t, J = 6.0 Hz, 2 H), 2.22 (s, 6 H), 2.05 (d, J = 11.6 Hz, 2 H), 1.61-1.67 (m, 2 H), 1.22-1.28 (m, 1 H), 0.56 (d, J = 6.4 Hz, 2 H), 0.34 (d, J = 5.2 Hz, 2 H). |
| 406* (D) | 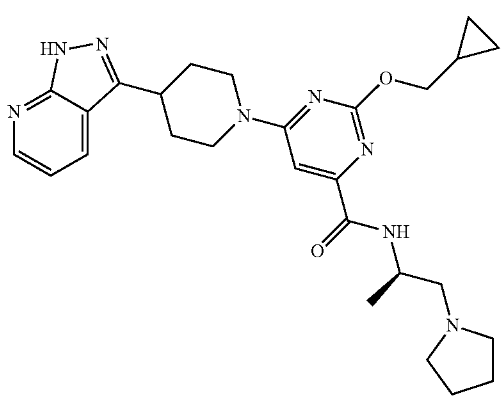 [SMILES: C[C@H](CN1CCCC1)NC(=O)c1cc(N2CCC(c3n[nH]c4ncccc34)CC2)nc(OCC2CC2)n1] | 2-(cyclopropylmethoxy)-N-[(2R)-1-(pyrrolidin-1-yl)propan-2-yl]-6-[4-(1H-pyrrolo[2,3-b]pyridin-3-yl)piperidin-1-yl]pyrimidine-4-carboxamide | 504.3; (400 MHz, DMSO-d$_6$) δ ppm 11.34 (s, 1 H), 8.25 (d, J = 8.0 Hz, 1 H), 8.18 (d, J = 4.4 Hz, 1 H), 8.02 (d, J = 8.0 Hz, 1 H), 7.24 (s, 1 H), 7.00-7.04 (m, 2 H), 4.42-4.68 (m, 2 H), 4.03-4.14 (m, 3 H), 3.12-3.23 (m, 3 H), 2.62-2.68 (m, 1 H), 2.29-2.47 (m, 5 H), 2.08 (d, J = 8.8 Hz, 2 H), 1.58-1.74 (m, 6 H), 1.14-1.29 (m, 4 H), 0.60 (d, J = 8.0 Hz, 2 H), 0.35 (d, J = 5.2 Hz, 2 H). |
| 407* (D) | 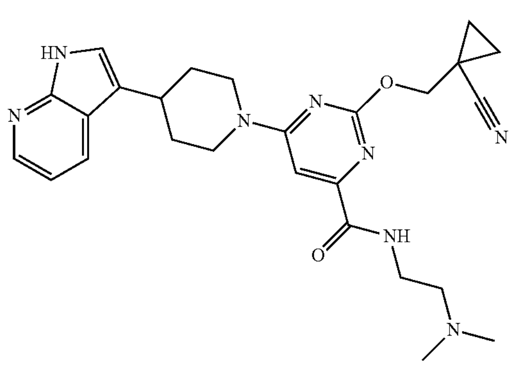 [SMILES: CN(C)CCNC(=O)c1cc(N2CCC(c3c[nH]c4ncccc34)CC2)nc(OCC2(C#N)CC2)n1] | 2-[(1-cyanocyclopropyl)methoxy]-N-[2-(dimethylamino)ethyl]-6-[4-(1H-pyrrolo[2,3-b]pyridin-3-yl)piperidin-1-yl]pyrimidine-4-carboxamide | 511.2 [M + Na]⁺; (400 MHz, CDCl$_3$) δ ppm 9.17 (s, 1 H), 8.30 (d, J = 4.0 Hz, 1 H), 8.15 (t, J = 5.2 Hz, 1 H), 7.94 (d, J = 6.8 Hz, 1 H), 7.16 (s, 1 H), 7.04-7.10 (m, 2 H), 4.21-5.10 (m, 4 H), 3.53 (q, J = 6.4 Hz 2 H), 3.06-3.22 (m, 3 H), 2.53 (t, J = 6.4 Hz, 2 H), 2.29 (s, 6 H), 2.11-2.20 (m, 2 H), 1.67-1.80 (m, 2 H, overlapped by H$_2$O peak), 1.37-1.44 (m, 2 H), 1.15-1.22 (m, 2H). |

TABLE 1-continued

| Ex. # | Structure | Compound Name | LRMS m/z (M + H)+; and 1H NMR |
|---|---|---|---|
| 408* (D) | 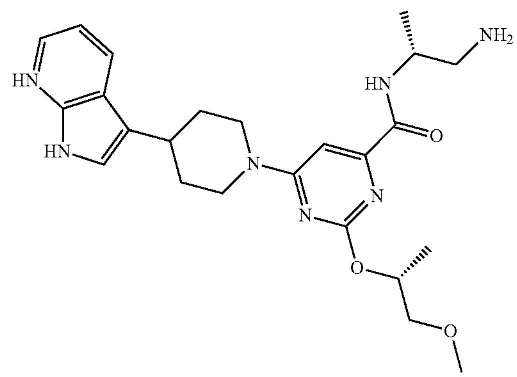 [SMILES: COC[C@@H](C)Oc1nc(C(=O)N[C@H](C)CN)cc(N2CCC(c3c[nH]c4ncccc34)CC2)n1] | N-[(2R)-1-aminopropan-2-yl]-2-{[(2R)-1-methoxypropan-2-yl]oxy}-6-[4-(1H-pyrrolo[2,3-b]pyridin-3-yl)piperidin-1-yl]pyrimidine-4-carboxamide | 468.1; (400 MHz, CD₃OD) δ ppm 11.36 (s, 1 H), 8.25 (d, J = 3.6 Hz, 1 H), 8.09 (d, J = 4.2 Hz 1 H), 7.21 (s, 1 H), 7.05-7.18 (m, 2 H), 5.31-5.45 (m, 1 H), 4.55 (br s, 2 H), 4.35-4.45 (m, 1 H), 3.55-3.65 (m, 2 H), 3.41 (s, 3 H); 3.02-3.33 (m, 5 H), 2.21 (d, J = 12.0 Hz, 2 H), 1.70-1.84 (m, 2 H), 1.32-1.38 (m, 6 H). |
| 409* (D) | 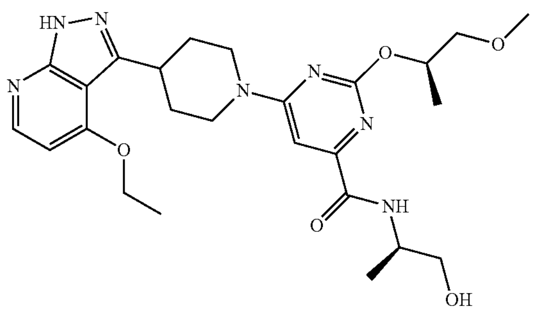 [SMILES: CCOc1ccnc2[nH]nc(C3CCN(c4cc(C(=O)N[C@H](C)CO)nc(O[C@H](C)COC)n4)CC3)c12] | 6-[4-(4-ethoxy-1H-pyrazolo[3,4-b]pyridin-3-yl)piperidin-1-yl]-N-[(2R)-1-hydroxypropan-2-yl]-2-{[(2R)-1-methoxypropan-2-yl]oxy}pyrimidine-4-carboxamide | 514.0; (400 MHz, CD₃OD) δ ppm 8.30 (d, J = 5.6 Hz, 1 H), 7.11 (s, 1 H), 6.66 (d, J = 5.6 Hz, 1 H), 5.36-5.40 (m, 1 H), 4.29-4.46 (m, 2 H), 4.24-4.29 (m, 2 H), 4.13-4.15 (m, 1 H), 3.52-3.63 (m, 5 H), 3.40 (s, 3 H), 3.22 (br s, 2 H), 2.07 (br s, 4 H), 1.34-1.37 (m, 6 H), 1.26 (d, J = 6.8 Hz, 3 H). |
| 410* (D) | 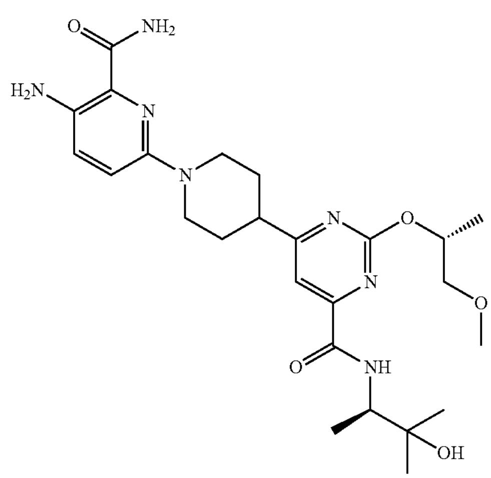 [SMILES: COC[C@@H](C)Oc1nc(C(=O)N[C@H](C)C(C)(C)O)cc(C2CCN(c3ccc(N)c(C(N)=O)n3)CC2)n1] | 6-[4-(5-amino-6-carbamoylpyridin-2-yl)piperidin-1-yl]-N-[(2R)-3-hydroxy-3-methylbutan-2-yl]-2-{[(2R)-1-methoxypropan-2-yl]oxy}pyrimidine-4-carboxamide | 538.3 [M + Na]+; (400 MHz, DMSO-d₆) δ ppm 8.12 (d, J = 8.4 Hz, 1 H), 7.87 (s, 1 H), 7.28 (br s, 1 H), 7.20 (d, J = 8.4 Hz, , 1 H0, 7.10 (d, J = 8.4 Hz, , 1 H), 7.04 (s, 1 H), 6.69 (s, 2 H), 5.23 (s, 1 H), 4.75 (s, 1 H), 3.82-3.88 (m, 1 H), 3.44-3.57 (m, 2 H), 3.27-3.29 (m, 3 H), 3.07-3.12 (m, 3 H), 2.87-2.93 (m, 1 H), 1.92-1.97 (m, 2 H), 1.64-1.73 (m, 2 H), 1.29 (d, J = 6.0 Hz, 3 H), 1.04-1.17 (m, 9 H). |

TABLE 1-continued

| Ex. # | Structure | Compound Name | LRMS m/z (M + H)+; and 1H NMR |
|---|---|---|---|
| 411** (D) | 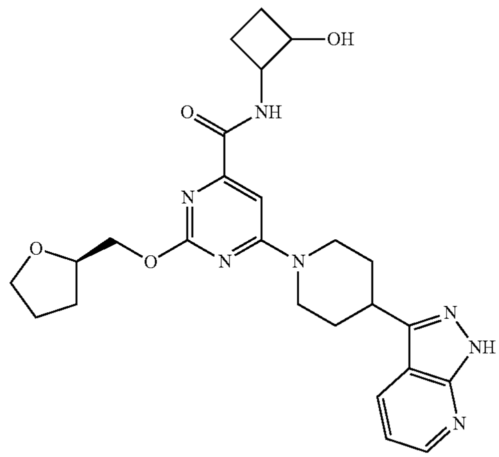 [SMILES: O=C(NC1CCC1O)c1cc(N2CCC(c3n[nH]c4ncccc34)CC2)nc(OC[C@H]2CCCO2)n1] | (trans)-N-(2-hydroxycyclobutyl)-6-[4-(1H-pyrazolo[3,4-b]pyridin-3-yl)piperidin-1-yl]-2-[(2R)-tetrahydrofuran-2-ylmethoxy]pyrimidine-4-carboxamide | 493.9; (600 MHz, DMSO-d$_6$) δ ppm 13.21 (br s, 1 H), 8.59 (d, J = 8.4 Hz, 1 H), 8.41 (d, J = 3.5 Hz, 1 H), 8.29 (d, J = 7.9 Hz, 1 H), 7.07 (dd, J = 7.4, 4.5 Hz, 1 H), 6.94 (br s, 1 H), 5.22 (d, J = 6.4 Hz, 1 H), 4.21 (d, J = 5.1 Hz, 2 H), 4.02-4.15 (m, 3 H), 3.71 (q, J = 7.3 Hz, 1 H), 3.60 (q, J = 7.0 Hz, 1 H), 3.34-3.41 (m, 1 H, partially obscured by H$_2$O peak), 3.11-3.21 (m, 3 H), 2.04 (d, J = 12.3 Hz, 2 H), 1.71-1.95 (m, 7 H), 1.57-1.62 (m, 1 H), 1.32-1.43 (m, 2 H). |
| 412** (D) | 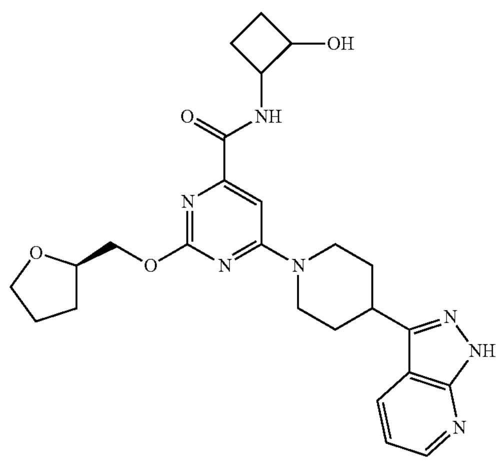 [SMILES: O=C(NC1CCC1O)c1cc(N2CCC(c3n[nH]c4ncccc34)CC2)nc(OC[C@H]2CCCO2)n1] | (trans)-N-(2-hydroxycyclobutyl)-6-[4-(1H-pyrazolo[3,4-b]pyridin-3-yl)piperidin-1-yl]-2-[(2R)-tetrahydrofuran-2-ylmethoxy]pyrimidine-4-carboxamide | 493.9; (600 MHz, DMSO-d$_6$) δ ppm 13.24 (br s, 1 H), 8.68 (d, J = 8.4 Hz, 1 H), 8.48 (d, J = 3.5 Hz, 1 H), 8.31 (d, J = 7.9 Hz, 1 H), 7.12-7.15 (m, 1 H), 7.01 (br s, 1 H), 5.29 (d, J = 6.5 Hz, 1 H), 4.26-4.32 (m, 2 H), 4.10-4.17 (m, 4 H), 3.76-3.81 (m, 1 H), 3.65-3.69 (m, 1 H), 3.11-3.21 (m, 3 H), 2.09-2.14 (m, 2 H), 1.77-2.03 (m, 7 H), 1.64-1.70 (m, 1 H), 1.40-1.49 (m, 2 H). |
| 413* (D) | 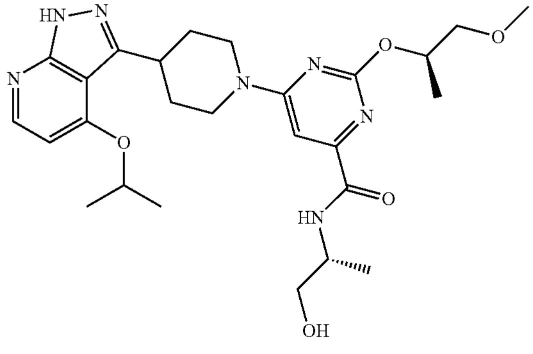 [SMILES: COC[C@@H](C)Oc1nc(C(=O)N[C@H](C)CO)cc(N2CCC(c3n[nH]c4nccc(OC(C)C)c34)CC2)n1] | N-[(2R)-1-hydroxypropan-2-yl]-2-{[(2R)-1-methoxypropan-2-yl]oxy}-6-{4-[4-(propan-2-yloxy)-1H-pyrazolo[3,4-b]pyridin-3-yl]piperidin-1-yl}pyrimidine-4-carboxamide | 528.3; (400 MHz, CD$_3$OD) δ ppm 8.28 (d, J = 5.6 Hz, 1 H), 7.10 (s, 1 H), 6.67 (d, J = 5.6 Hz, 1 H), 5.35-5.39 (m, 1 H), 4.95-4.96 (m, 1 H), 4.52-4.73 (m, 2 H), 4.10-4.15 (m, 1 H), 3.62-3.64 (m, 3 H), 3.56-3.60 (m, 2 H), 3.40 (s, 3 H), 3.10-3.30 (m, 2 H), 2.06-2.08 (m, 4 H), 1.35 (d, J = 6.0 Hz, 9 H), 1.25 (d, J = 6.8 Hz, 3 H). |

TABLE 1-continued

| Ex. # | Structure | Compound Name | LRMS m/z (M + H)+; and 1H NMR |
|---|---|---|---|
| 414* (D) | 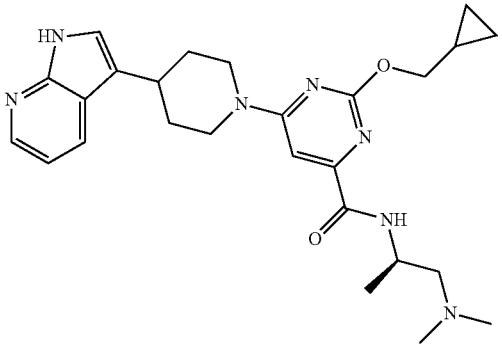 [SMILES: C[C@H](CN(C)C)NC(=O)c1cc(N2CCC(c3c[nH]c4ncccc34)CC2)nc(OCC2CC2)n1] | 2-(cyclo-propylmethoxy)-N-[(2R)-1-(dimethylamino)propan-2-yl]-6-[4-(1H-pyrrolo[2,3-b]pyridin-3-yl)piperidin-1-yl]pyrimidine-4-carboxamide | 478.2; (400 MHz, DMSO-d$_6$) δ ppm 11.37 (s, 1 H), 8.25 (d, J = 8.4 Hz, 1 H), 8.19 (d, J = 4.4 Hz, 1 H), 8.05 (d, J = 7.6 Hz, 1 H), 7.27 (s, 1 H), 7.01-7.07 (m, 2 H), 4.32-4.81 (m, 2 H), 4.03-4.41 (m, 3 H), 3.01-3.21 (m, 3 H), 2.44-2.48 (m, 1 H), 2.14-2.26 (m, 7 H), 2.05 (d, J = 15.2 Hz, 2 H), 1.56-1.66 (m, 2 H), 1.21-1.31 (m, 2 H), 1.31 (d, J = 5.6 Hz, 2 H), 0.58 (d, J = 8.0 Hz, 2 H), 0.35 (d, J = 5.2 Hz, 2 H). |
| 415* (D) | 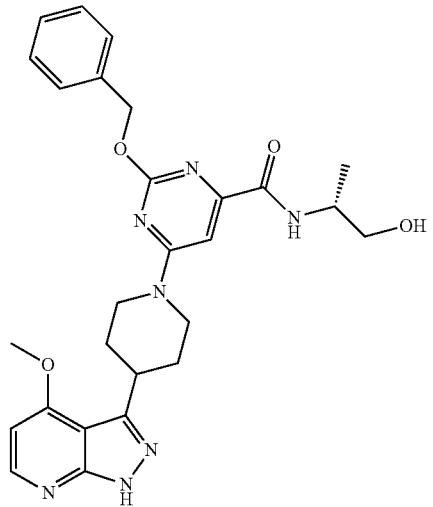 [SMILES: COc1ccnc2[nH]nc(C3CCN(c4cc(C(=O)N[C@H](C)CO)nc(OCc5ccccc5)n4)CC3)c12] | 2-(benzyloxy)-N-[(2R)-1-hydroxypropan-2-yl]-6-[4-(4-methoxy-1H-pyrazolo[3,4-b]pyridin-3-yl)piperidin-1-yl]pyrimidine-4-carboxamide | 538.3; (400 MHz, DMSO-d$_6$) δ ppm 13.13 (s, 1 H), 8.36 (d, J = 5.2 Hz, 1 H), 8.18 (d, J = 8.4 Hz, 1 H), 7.50 (d, J = 7.6 Hz, 2 H), 7.26-7.39 (m, 3 H), 7.03 (s, 1 H), 6.65 (d, J = 5.6 Hz, 1 H), 5.38 (s, 2 H), 4.88-4.92 (m, 1 H), 4.26-4.48 (m, 2 H); 3.94-4.02 (m, 1 H), 3.88 (s, 3 H), 3.42-3.48 (m, 3 H), 3.12-3.21 (m, 2 H), 1.97-2.01 (m, 2 H), 1.73-1.82 (m, 2 H), 1.14 (d, J = 6.8 Hz, 3 H). |
| 416* (D) | 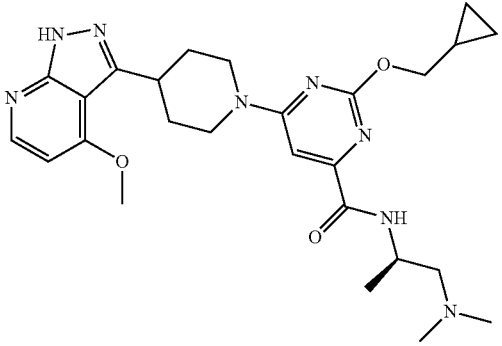 [SMILES: COc1ccnc2[nH]nc(C3CCN(c4cc(C(=O)N[C@H](C)CN(C)C)nc(OCC5CC5)n4)CC3)c12] | 2-(cyclo-propylmethoxy)-N-[(2R)-1-(dimethylamino)propan-2-yl]-6-[4-(4-methoxy-1H-pyrazolo[3,4-b]pyridin-3-yl)piperidin-1-yl]pyrimidine-4-carboxamide | 509.2 (400 MHz, CD$_3$OD) δ ppm 8.33 (d, J = 5.6 Hz, 1 H), 7.11 (s, 1 H), 6.71 (d, J = 5.6 Hz, 1 H), 4.61 (br s, 2 H), 4.18-4.28 (m, 3 H), 4.01 (s, 3 H), 3.55-3.58 (m, 1 H), 3.24-3.27 (m, 2 H), 2.60-2.63 (m, 1 H), 2.37-2.39 (m, 1H), 2.30 (s, 6 H), 1.97-2.13 (m, 4 H), 1.29-1.32 (m, 2 H), 1.28 (d, J = 6.8 Hz, 2 H), 0.62 (d, J = 8.0 Hz, 2 H), 0.39 (d, J = 4.8 Hz, 2 H). |

TABLE 1-continued

| Ex. # | Structure | Compound Name | LRMS m/z (M + H)+; and 1H NMR |
|---|---|---|---|
| 417* (D) | 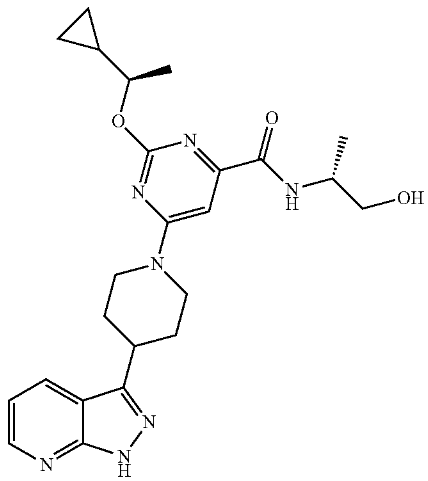 [SMILES: C[C@H](CO)NC(=O)c1cc(N2CCC(c3n[nH]c4ncccc34)CC2)nc(O[C@H](C)C2CC2)n1] | 2-[(1R)-1-cyclopropylethoxy]-N-[(2R)-1-hydroxypropan-2-yl]-6-[4-(1H-pyrazolo[3,4-b]pyridin-3-yl)piperidin-1-yl]pyrimidine-4-carboxamide | 466.1; (400 MHz, CD3OD) δ ppm 8.49 (d, J = 3.2 Hz, 1 H), 8.33 (d, J = 8.0 Hz, 1 H), 7.19-7.20 (m, 1 H), 7.08 (s, 1 H), 4.58-4.71 (m, 3 H), 4.11-4.16 (m, 1H), 3.62 (d, J = 5.2 Hz, 2 H), 3.48-3.51 (m, 1 H), 3.21-3.24 (m, 1 H), 2.18-2.21 (m, 2 H), 1.97-2.02 (m, 2 H), 1.44 (d, J = 6.4 Hz, 3 H), 1.27 (d, J = 6.8 Hz, 3 H), 1.15-1.17 (m, 1 H), 0.46-0.58 (m, 3 H), 0.36-0.37 (m, 1 H). |
| 418* (D) | 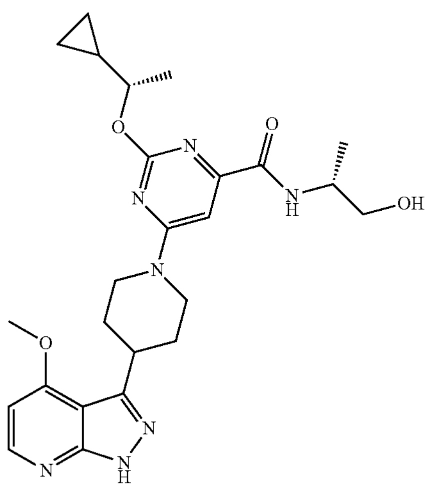 [SMILES: COc1ccnc2[nH]nc(C3CCN(c4cc(C(=O)N[C@H](C)CO)nc(O[C@@H](C)C5CC5)n4)CC3)c12] | 2-[(1S)-1-cyclopropylethoxy]-N-[(2R)-1-hydroxypropan-2-yl]-6-[4-(1H-pyrazolo[3,4-b]pyridin-3-yl)piperidin-1-yl]pyrimidine-4-carboxamide | 466.1; (400 MHz, CD3OD) δ ppm 8.49 (d, J = 3.2 Hz, 1 H), 8.33 (d, J = 8.0 Hz, 1 H), 7.19-7.20 (m, 1 H), 7.08 (s, 1 H), 4.58-4.71 (m, 3 H), 4.11-4.16 (m, 1H), 3.62 (d, J = 5.2 Hz, 2 H), 3.48-3.51 (m, 1 H), 3.21-3.24 (m, 1 H), 2.18-2.21 (m, 2 H), 1.97-2.02 (m, 2 H), 1.44 (d, J = 6.4 Hz, 3 H), 1.27 (d, J = 6.8 Hz, 3 H), 1.15-1.17 (m, 1 H), 0.46-0.58 (m, 3 H), 0.36-0.37 (m, 1 H). |
| 419* (D) | 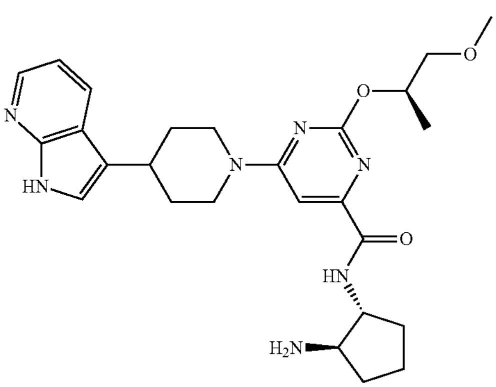 [SMILES: COC[C@@H](C)Oc1nc(C(=O)N[C@@H]2CCC[C@H]2N)cc(N2CCC(c3c[nH]c4ncccc34)CC2)n1] | N-[(1R,2R)-2-aminocyclopentyl]-2-{[(2R)-1-methoxypropan-2-yl]oxy}-6-[4-(1H-pyrrolo[2,3-b]pyridin-3-yl)piperidin-1-yl]pyrimidine-4-carboxamide | 494.1; (400 MHz, CD3OD) δ ppm 8.17 (d, J = 4.8 Hz, 1 H), 8.09 (d, J = 8.0 Hz, 1 H), 7.21 (s, 1 H), 7.09-7.10 (m, 2 H), 5.37-5.41 (m, 1 H), 4.75 (br s, 2 H), 3.97-3.99 (m, 1 H), 3.56-3.63 (m, 2 H), 3.56 (s, 3 H), 3.41 (s, 3 H), 3.19-3.32 (m, 4 H), 2.19 (d, J = 13.2 Hz, 1 H), 2.07-2.16 (m, 2 H), 1.74-1.82 (m, 5 H), 1.65-1.67 (m, 1 H), 1.36 (d, J = 6.4 Hz, 3 H). |

TABLE 1-continued

| Ex. # | Structure | Compound Name | LRMS m/z (M + H)+; and 1H NMR |
|---|---|---|---|
| 420* (D) | 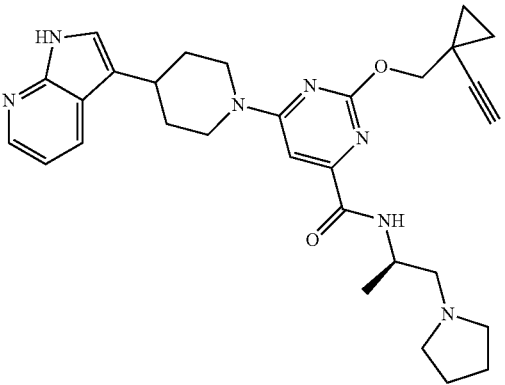 [SMILES: C#CC1(COc2nc(C(=O)N[C@H](C)CN3CCCC3)cc(N3CCC(c4c[nH]c5ncccc45)CC3)n2)CC1] | 2-[(1-cyanocyclopropyl)methoxy]-N-[(2R)-1-(pyrrolidin-1-yl)propan-2-yl]-6-[4-(1H-pyrrolo[2,3-b]pyridin-3-yl)piperidin-1-yl]pyrimidine-4-carboxamide | 529.1; (400 MHz, CD$_3$OD) δ ppm 8.17 (br s, 1 H), 8.07 (d, J = 8.4 Hz, 1 H), 7.19 (s, 1 H), 7.12 (s, 1 H), 7.07-7.08 (m, 1 H), 4.54 (br s, 1 H), 4.49 (1, J = 12.0 Hz, 2 H),, 3.35-3.50 (m, 3 H), 3.13-3.28 (m, 4 H), 2.18 (d, J = 12.0 Hz, 2 H), 1.97-2.11 (m, 4 H), 1.67-1.82 (m, 2 H), 1.20-1.41 (m, 11 H). |
| 421* (D) | 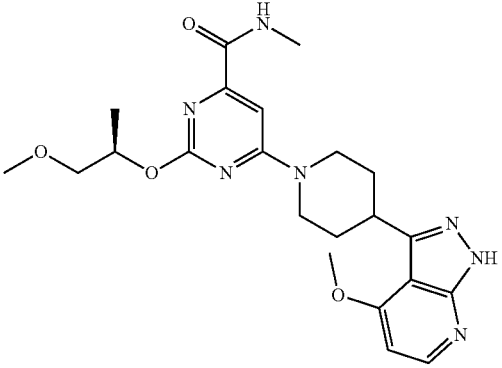 [SMILES: CNC(=O)c1cc(N2CCC(c3n[nH]c4nccc(OC)c34)CC2)nc(O[C@H](C)COC)n1] | 2-{[(2R)-1-methoxypropan-2-yl]oxy}-6-[4-(4-methoxy-1H-pyrazolo[3,4-b]pyridin-3-yl)piperidin-1-yl]-N-methylpyrimidine-4-carboxamide | 456.1; (400 MHz, CDCl$_3$) δ ppm 10.98 (br s, 1 H), 8.40 (d, J = 5.6 Hz, 1 H), 7.90 (d, J = 5.6 Hz, 1 H), 7.13 (s, 1 H), 6.51 (d, J = 5.6 Hz, 1 H), 5.33-5.42 (m, 1 H), 4.56 (br s, 2 H), 3.97 (s, 3 H), 3.66-3.72 (m, 1 H), 3.48-3.54 (m, 2 H), 3.42 (s, 3 H), 3.09-3.27 (m, 2 H), 2.95 (d, J = 5.2 Hz, 3 H), 2.11 (d, J = 12.4 Hz, 2 H), 1.96-2.11 (m, 2 H); 1.38 (d, J = 8.4 Hz, 3 H). |
| 422* (D) | 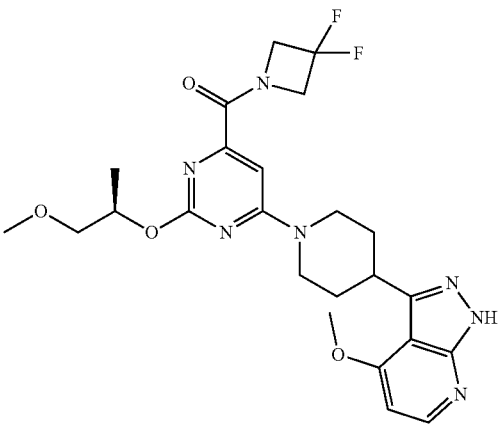 [SMILES: COC[C@@H](C)Oc1nc(C(=O)N2CC(F)(F)C2)cc(N2CCC(c3n[nH]c4nccc(OC)c34)CC2)n1] | (3,3-difluoroazetidin-1-yl)(2-{[(2R)-1-methoxypropan-2-yl]oxy}-6-[4-(4-methoxy-1H-pyrazolo[3,4-b]pyridin-3-yl)piperidin-1-yl]pyrimidin-4-yl)methanone | 456.1; (400 MHz, DMSO-d$_6$) δ ppm 13.14 (s, 1 H), 8.32 (d, J = 5.6 Hz, 1 H), 7.01 (s, 1 H), 6.66 (d, J = 5.6 Hz, 1 H), 5.18-5.27 (m, 1 H), 5.02 (t, J = 12.4 Hz, 2 H), 4.78 (br s, 2 H), 4.48 (t, J = 12.4 Hz, 2 H), 3.91 (s, 3 H), 3.44-3.58 (m, 2 H), 3.24-3.26 (m, 3 H), 3.12-3.18 (m, 3 H), 2.00 (d, J = 10.8 Hz, 2 H), 1.77-1.79 (m, 2 H), 1.26 (d, J = 6.8 Hz, 3 H). |

TABLE 1-continued

| Ex. # | Structure | Compound Name | LRMS m/z (M + H)$^+$; and $^1$H NMR |
|---|---|---|---|
| 423* (D) | 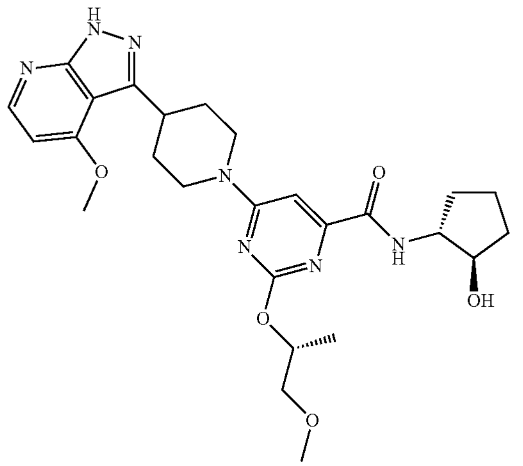 [SMILES: COC[C@@H](C)Oc1nc(C(=O)N[C@@H]2CCC[C@H]2O)cc(N2CCC(c3n[nH]c4nccc(OC)c34)CC2)n1] | N-[1R,2R)-2-hydroxycyclopentyl]-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 526.2; (400 MHz, DMSO-d$_6$) δ ppm 13.14 (s, 1 H), 8.32 (d, J = 5.2 Hz, 1 H), 8.23 (d, J = 8.0 Hz, 1 H), 7.00 (s, 1 H), 6.67 (d, J = 5.2 Hz, 1 H), 5.29-5.33 (m, 1 H), 4.83 (d, J = 6.0 Hz, 1 H), 4.31-4.69 (m, 2 H), 3.91-4.01 (m, 5 H), 3.44-3.52 (m, 2 H), 3.20-3.31 (m, 6 H), 1.99-2.03 (m, 3 H), 1.83-1.86 (m, 3 H), 1.62-1.69 (m, 2 H), 1.43-1.52 (m, 2 H), 1.26 (d, J = 6.4 Hz, 3 H). |
| 424* (D) | 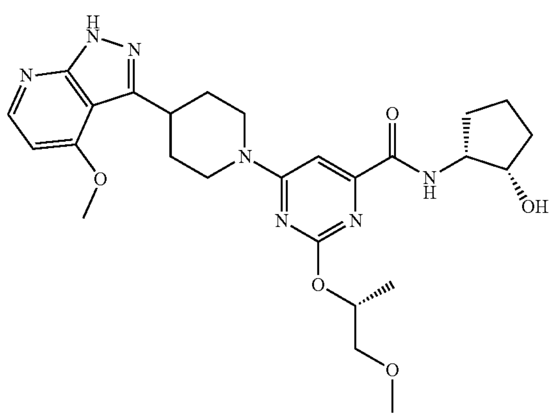 [SMILES: COC[C@@H](C)Oc1nc(C(=O)N[C@@H]2CCC[C@@H]2O)cc(N2CCC(c3n[nH]c4nccc(OC)c34)CC2)n1] | N-[(1R,2S)-2-hydroxycyclopentyl]-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 526.1; (400 MHz, CDCl$_3$) δ ppm 11.37 (br s, 1H), 8.40 (d, J = 5.6 Hz, 1 H), 8.16 (d, J = 7.6 Hz, 1 H), 7.12 (s, 1 H), 6.49 (d, J = 5.6 Hz, 2 H), 5.30-5.36 (m, 1 H), 4.62 (br s, 4 H), 3.96 (s, 3 H), 3.65-3.72 (m, 1 H), 3.41-3.52 (m, 2 H), 3.40 (s, 3 H), 3.15-3.25 (m, 2 H), 2.08 (br s, 1 H), 1.85-2.12 (m, 7 H), 1.65-1.78 (m, 2 H), 1.38 (d, J = 6.4 Hz, 3 H). |
| 425* (D) | 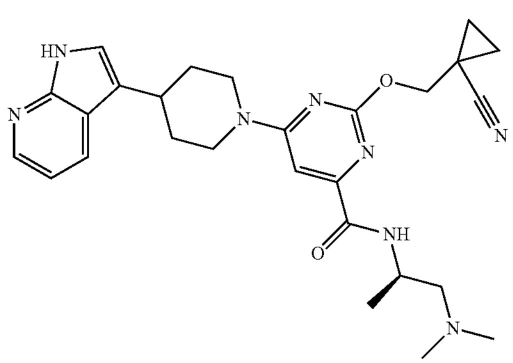 [SMILES: C[C@H](CN(C)C)NC(=O)c1cc(N2CCC(c3c[nH]c4ncccc34)CC2)nc(OCC2(C#N)CC2)n1] | 2-[(1-cyanocyclopropyl)methoxy]-N-[(2R)-1-(dimethylamino)propan-2-yl]-6-[4-(1H-pyrrolo[2,3-b]pyridin-3-yl)piperidin-1-yl]pyrimidine-4-carboxamide | 525.1 [M + Na]$^+$; (400 MHz, CDCl$_3$) δ ppm 9.15 (s, 1 H), 8.31 (s, 1 H), 7.92 (t, J = 8.0 Hz, 2 H), 7.17 (s, 1 H), 7.04-7.12 (m, 2 H), 4.51-4.64 (m, 2 H) 4.41 (q, J = 12.0 Hz, 2 H), 4.19-4.22 (m, 1 H), 3.12 (t, J = 12.4 Hz, 3 H), 2.45-2.55 (m, 1 H), 2.27 (s, 6 H), 2.15 (d, J = 11.6 Hz, 2 H), 1.67-1.80 (m, 2 H, overlapped by H$_2$O peak), 1.37-1.44 (m, 2 H), 1.27 (d, J = 4.8 Hz, 3 H), 1.13-1.22 (m, 2 H). |

TABLE 1-continued

| Ex. # | Structure | Compound Name | LRMS m/z (M + H)+; and 1H NMR |
|---|---|---|---|
| 426* (D) | 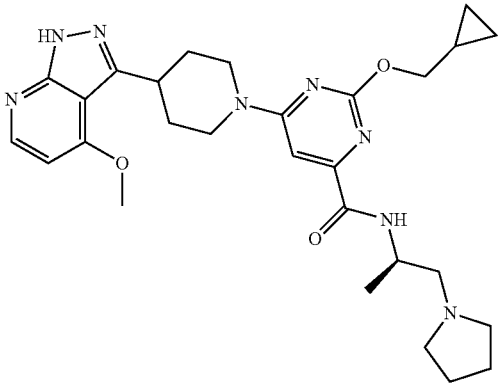 [SMILES: COc1ccnc2[nH]nc(C3CCN(c4cc(C(=O)N[C@H](C)CN5CCCC5)nc(OCC5CC5)n4)CC3)c12] | 2-(cyclopropylmethoxy)-6-[4-(4-methoxy-1H-pyrazolo[3,4-b]pyridin-3-yl)piperidin-1-yl]-N-[(2R)-1-(pyrrolidin-1-yl)propan-2-yl]pyrimidine-4-carboxamide | 535.2; (400 MHz, CD$_3$OD) δ ppm 8.33 (d, J = 5.6 Hz, 1 H), 7.11 (s, 1 H), 6.70 (d, J = 5.2 Hz, 1 H), 4.65 (br s, 2 H), 4.21-4.28 (m, 3 H), 4.00 (s, 3 H), 3.52-3.58 (m, 1 H), 3.23-3.26 (m, 2 H), 2.54-2.79 (m, 6 H), 1.97-2.12 (m, 4 H), 1.79-1.81 (m, 4 H), 1.28-1.32 (m, 4 H), 0.62-0.64 (m, 2 H), 0.39 (d, J = 5.2 Hz, 2 H). |
| 427* (D) | 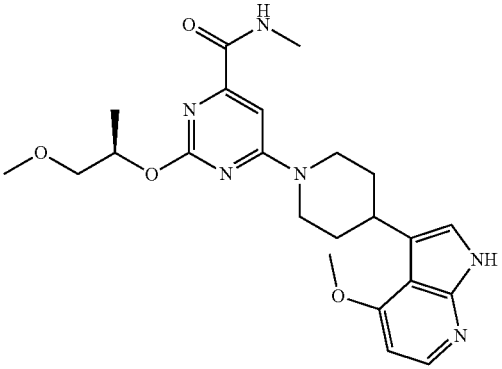 [SMILES: CNC(=O)c1cc(N2CCC(c3c[nH]c4nccc(OC)c34)CC2)nc(O[C@H](C)COC)n1] | 2-{[(2R)-1-methoxypropan-2-yl]oxy}-6-[4-(4-methoxy-1H-pyrrolo[2,3-b]pyridin-3-yl)piperidin-1-yl]-N-methylpyrimidine-4-carboxamide | 477.1 [M + Na]+; (400 MHz, CDCl$_3$) δ ppm 8.92 (br s, 1 H), 8.17 (d, J = 5.2 Hz, 1 H), 7.91 (d, J = 5.2 Hz, 1 H), 7.12 (s, 1 H), 6.87 (s, 1H), 6.54 (d, J = 5.6 Hz, 1 H), 5.32-5.36 (m, 1 H), 4.25-4.85 (br s, 2 H), 3.95 (s, 3 H), 3.64-3.84 (m, 1 H), 3.46-3.52 (m, 1 H), 3.41 (s, 3 H), 3.33-3.40 (m, 1 H), 3.02-3.15 (m, 2 H), 2.96 (d, J = 5.2 Hz, 3 H), 2.14 (d, J = 12.8 Hz, 2 H), 1.65-1.71 (m, 2 H), 1.37 (d, J = 6.0 Hz, 3 H). |
| 428* (D) | 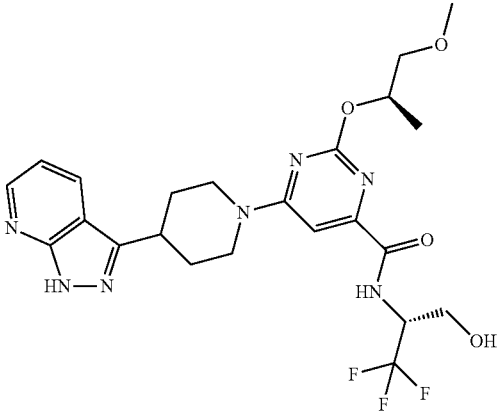 [SMILES: COC[C@@H](C)Oc1nc(C(=O)N[C@H](CO)C(F)(F)F)cc(N2CCC(c3n[nH]c4ncccc34)CC2)n1] | 2-{[(2R)-1-methoxypropan-2-yl]oxy}-6-[4-(1H-pyrazolo[3,4-b]pyridin-3-yl)piperidin-1-yl]-N-[(2R)-1,1,1-trifluoro-3-hydroxypropan-2-yl]pyrimidine-4-carboxamide | 524.1; (400 MHz, CDCl$_3$) δ ppm 11.03 (s, 1 H), 8.57 (d, J = 1.6 Hz, 1 H), 8.39 (d, J = 9.6 Hz, 1 H), 8.11 (d, J = 8.0 Hz, 1 H), 7.14-7.17 (m, 2 H), 5.30-5.34 (m, 1 H), 4.20-4.83 (m, 3 H), 3.99-4.01 (m, 2 H), 3.66-3.70 (m, 1 H), 3.51-3.53 (m, 1 H), 3.42-3.50 (m, 4 H), 3.25 (t, J = 5.2 Hz, 2 H), 2.47 (s, 1 H), 2.20 (d, J = 10.8 Hz, 2 H), 1.98-2.06 (m, 2 H), 1.41 (d, J = 6.0 Hz, 3H). |

TABLE 1-continued

| Ex. # | Structure | Compound Name | LRMS m/z (M + H)+; and 1H NMR |
|---|---|---|---|
| 429* (D) | 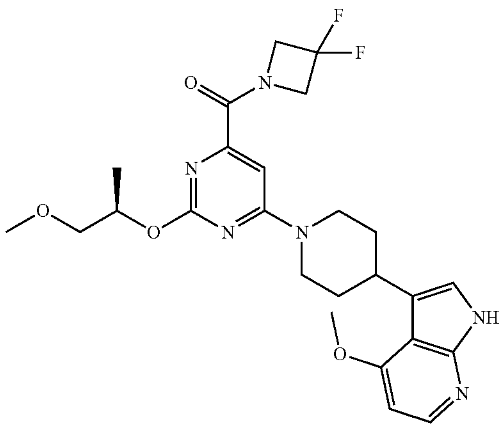 [SMILES: COC[C@@H](C)Oc1nc(C(=O)N2CC(F)(F)C2)cc(N2CCC(c3c[nH]c4nccc(OC)c34)CC2)n1] | (3,3-difluoroazetidin-1-yl)(2-{[(2R)-1-methoxypropan-2-yl]oxy}-6-[4-(4-methoxy-1H-pyrrolo[2,3-b]pyridin-3-yl)piperidin-1-yl]pyrimidin-4-yl)methanone | 539.1 [M + Na]+; (400 MHz, CDCl3) δ ppm 9.45 (br, 1 H), 8.17 (d, J = 5.6 Hz, 1 H), 7.07 (s, 1 H), 6.88 (s, 1 H), 6.52 (d, J = 5.6 Hz, 1 H), 5.20-5.25 (m, 1 H), 5.03 (dt, J = 12.0, 4.0 Hz, 2 H), 4.25-4.75 (m, 4 H), 3.96 (s, 3 H), 3.64-3.68 (m, 1 H), 3.46-3.51 (m, 1 H), 3.46 (s, 3 H), 3.32 (t, J = 5.2 Hz, 1 H), 3.02-3.15 (m, 2 H), 2.13 (d, J = 12.4 Hz, 2 H), 1.58-1.65 (m, 2 H), 1.36 (d, J = 6.0 Hz, 3 H). |
| 430** (D) | 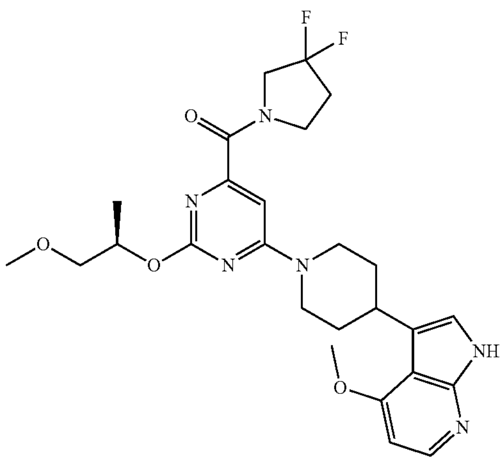 [SMILES: COC[C@@H](C)Oc1nc(C(=O)N2CCC(F)(F)C2)cc(N2CCC(c3c[nH]c4nccc(OC)c34)CC2)n1] | (3,3-difluoropyrrolidin-1-yl)(2-{[(2R)-1-methoxypropan-2-yl]oxy}-6-[4-(4-methoxy-1H-pyrrolo[2,3-b]pyridin-3-yl)piperidin-1-yl]pyrimidin-4-yl)methanone | 531.1; (400 MHz, CD3OD) δ ppm 9.03 (br, 1 H), 8.17 (d, J = 5.6 Hz, 1 H), 6.77-6.87 (m, 1 H), 6.53 (d, J = 5.6 Hz, 1H), 5.28-5.30 (m, 1 H), 4.25-4.75 (m, 2 H), 4.25 (t, J = 12.4 Hz, 1 H), 4.11-4.15 (m, 1 H), 3.96 (s, 3 H), 3.83-3.90 (m, 1 H), 3.63-3.67 (m, 1 H), 3.48-3.52 (m, 1 H), 3.47 (s, 3 H), 3.35 (t, J = 5.6 Hz, 1 H), 3.02-3.15 (m, 2 H), 2.35-2.48 (m, 2 H), 2.14 (d, J = 12.8 Hz, 2 H), 1.68-1.75 (m, 2 H), 1.36-1.38 (m, 3 H). |
| 431* (D) | 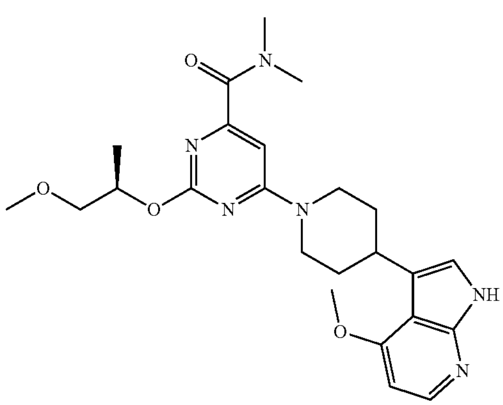 [SMILES: COC[C@@H](C)Oc1nc(C(=O)N(C)C)cc(N2CCC(c3c[nH]c4nccc(OC)c34)CC2)n1] | 2-{[(2R)-1-methoxypropan-2-yl]oxy}-6-[4-(4-methoxy-1H-pyrrolo[2,3-b]pyridin-3-yl)piperidin-1-yl]-N,N-dimethylpyrimidine-4-carboxamide | 469.1; (400 MHz, CDCl3) δ ppm 8.16 (d J = 4.8 Hz, 1 H), 6.90 (s, 1 H), 6.46-6.51 (m, 2 H), 5.27-5.32 (m, 1 H), 4.25-4.85 (br s, 2 H), 3.93 (s, 3 H), 3.59-3.66 (m, 1 H), 3.85-3.95 (m, 1 H), 3.37 (s, 3 H), 3.18-3.35 (m, 1 H), 2.95-3.15 (m, 8 H), 2.09 (d, J = 12.0 Hz, 2 H), 1.57-1.65 (m, 2 H), 1.32 (d, J = 6.0 Hz, 3 H). |

| Ex. # | Structure | Compound Name | LRMS m/z (M + H)+; and 1H NMR |
|---|---|---|---|
| 432** (D) | 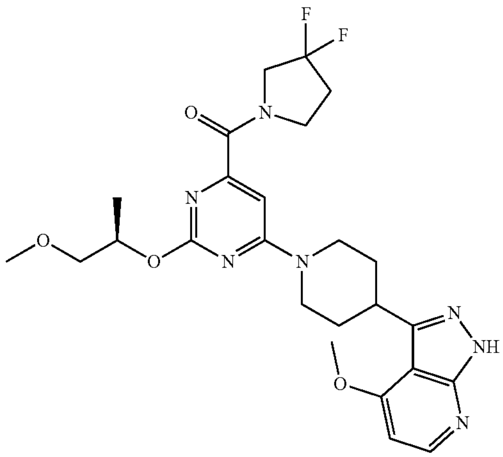 [SMILES: COC[C@@H](C)Oc1nc(C(=O)N2CCC(F)(F)C2)cc(N2CCC(c3n[nH]c4nccc(OC)c34)CC2)n1] | (3,3-difluoropyrrolidin-1-yl)(2-{[(2R)-1-methoxypropan-2-yl]oxy}-6-[4-(4-methoxy-1H-pyrazolo[3,4-b]pyridin-3-yl)piperidin-1-yl]pyrimidin-4-yl)methanone | 532.1; (400 MHz, CDCl$_3$) δ ppm 11.22 (s, 1 H), 8.40 (d, J = 5.2 Hz, 1 H), 6.77-6.87 (m, 1 H), 6.51 (d, J = 5.6 Hz, 1 H), 5.28-5.30 (m, 1 H), 4.37-4.75 (m, 2 H), 4.29 (t, J = 8.4 Hz, 1 H), 4.16 (t, J = 5.6 Hz, 1 H), 3.96-4.03 (m, 4 H), 3.83-3.88 (m, 1 H), 3.62-3.67 (m, 1 H), 3.44-3.54 (m, 5 H), 3.19 (t, J = 4.4 Hz, 2 H), 2.36-2.42 (m, 2 H), 1.93-2.15 (m, 4 H), 1.35 (d, J = 4.0 Hz, 3 H). |
| 433** (D) | 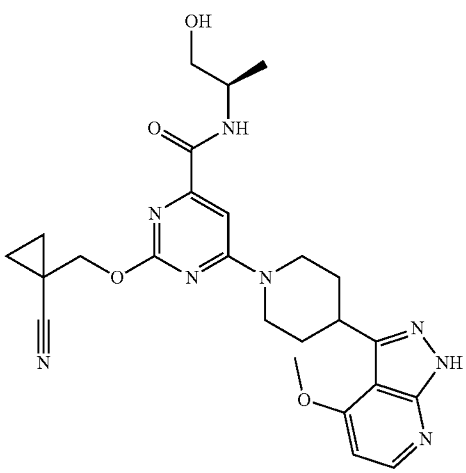 [SMILES: COc1ccnc2[nH]nc(C3CCN(c4cc(C(=O)N[C@H](C)CO)nc(OCC5(C#N)CC5)n4)CC3)c12] | 2-[(1-cyanocyclopropyl)methoxy]-N-[(2R)-1-hydroxypropan-2-yl]-6-[4-(4-methoxy-1H-pyrazolo[3,4-b]pyridin-3-yl)piperidin-1-yl]pyrimidine-4-carboxamide | 507.1; (400 MHz, CD$_3$OD) δ ppm, 8.34 (d, J = 5.6 Hz, 1 H), 7.16 (s, 1 H), 6.71 (d, J = 5.6 Hz, 1 H), 4.77-4.83 (m, 2 H), 4.43 (s, 2 H), 4.15-4.17 (m, 1 H), 4.00 (s, 3 H), 3.63 (d, J = 5.2 Hz, 2 H), 3.55-3.58 (m, 1 H), 3.25-3.27 (m, 2 H), 2.12 (d, J = 11.2 Hz, 2 H), 1.98-2.00 (m, 2 H), 1.37-1.41 (m, 2 H), 1.24-1.28 (m, 5 H). |
| 434* (D) | 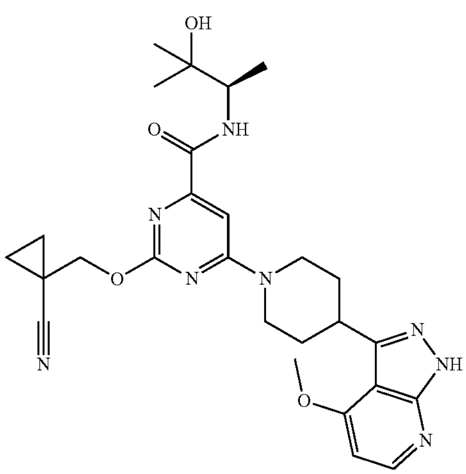 [SMILES: COc1ccnc2[nH]nc(C3CCN(c4cc(C(=O)N[C@H](C)C(C)(C)O)nc(OCC5(C#N)CC5)n4)CC3)c12] | 2-[(1-cyanocyclopropyl)methoxy]-N-[(2R)-3-hydroxy-3-methylbutan-2-yl]-6-[4-(4-methoxy-1H-pyrazolo[3,4-b]pyridin-3-yl)piperidin-1-yl]pyrimidine-4-carboxamide | 535.1; (400 MHz, CD$_3$OD) δ ppm 8.34 (d, J = 5.6 Hz, 1 H), 7.16 (s, 1 H), 6.70 (d, J = 5.6 Hz, 1 H), 4.62 (br s, 2 H), 4.42 (s, 2 H), 4.04-4.06 (m, 1 H), 4.00 (s, 3 H), 3.55-3.57 (m, 1 H), 2.12 (d. J = 10.8 Hz, 2 H), 1.97-2.08 (m, 2 H), 1.37-1.40 (m, 2 H), 1.23-1.27 (m, 10 H). |

TABLE 1-continued

| Ex. # | Structure | Compound Name | LRMS m/z (M + H)+; and 1H NMR |
|---|---|---|---|
| 435* (D) | 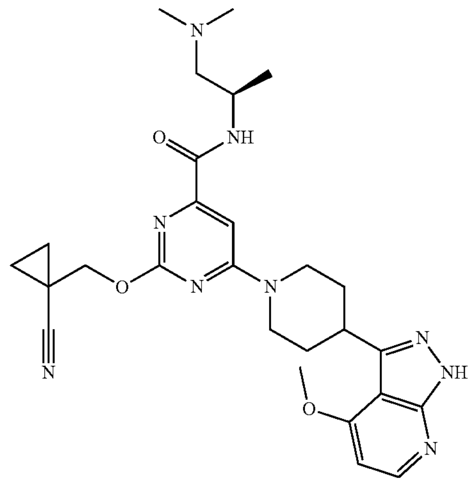 [SMILES: COc1ccnc2[nH]nc(C3CCN(c4cc(C(=O)N[C@H](C)CN(C)C)nc(OCC5(C#N)CC5)n4)CC3)c12] | 2-[(1-cyanocyclopropyl)methoxy]-N-[(2R)-1-(dimethylamino)propan-2-yl]-6-[4-(4-methoxy-1H-pyrazolo[3,4-b]pyridin-3-yl)piperidin-1-yl]pyrimidine-4-carboxamide | 534.1; (400 MHz, CD$_3$OD) δ ppm 8.34 (d, J = 5.2 Hz, 1 H), 7.16 (s, 1 H), 6.71 (d, J = 5.6 Hz, 1 H), 4.63 (br s, 2 H), 4.44 (s, 2 H), 4.28-4.30 (m, 1 H), 4.00 (s, 3 H), 3.53-3.55 (m, 1 H), 3.18-3.24 (m, 2 H), 2.65-2.68 (t, J = 12.0 Hz, 1 H), 2.21-2.31 (m, 7 H), 1.97-2.13 (m, 4 H), 1.38 (br s, 2 H), 1.25-1.27 (m, 5 H). |
| 436** (D) | 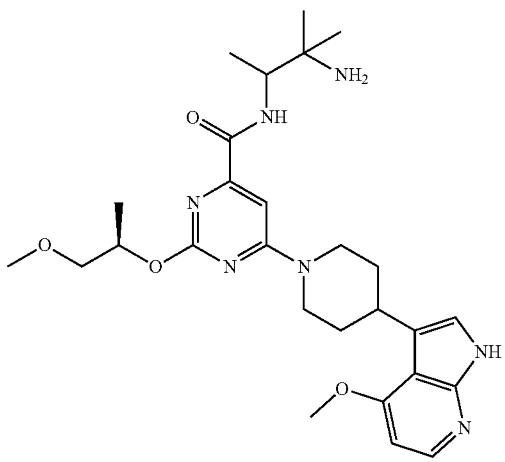 [SMILES: COC[C@@H](C)Oc1nc(C(=O)NC(C)C(C)(C)N)cc(N2CCC(c3c[nH]c4nccc(OC)c34)CC2)n1] | N-(3-amino-3-methylbutan-2-yl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 526.1; (400 MHz, CD$_3$OD) δ ppm 8.06 (d, J = 5.6 Hz, 1 H), 7.09 (s, 1 H), 6.99 (s, 1 H), 6.67 (d, J = 5.6 Hz, 1 H), 5.36-5.40 (m, 1 H), 4.61 (br s, 2 H), 4.24-4.25 (m, 1 H), 3.97 (s, 3 H), 3.61-3.65 (m, 2 H), 3.40 (s, 3 H), 3.19-3.22 (m, 3 H), 2.17 (d, J = 12.8 Hz, 2 H), 1.70-1.77 (m, 2 H), 1.30-1.39 (m, 12 H). |
| 437** (D) | 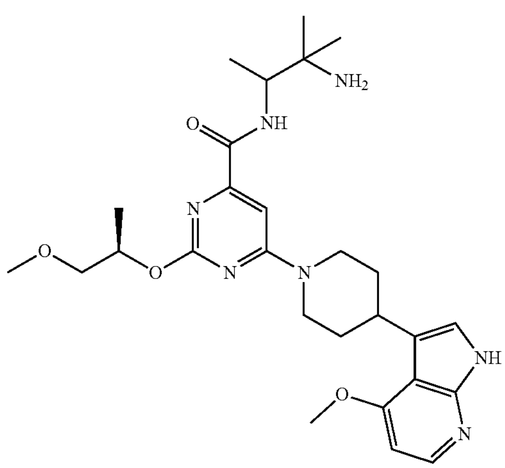 [SMILES: COC[C@@H](C)Oc1nc(C(=O)NC(C)C(C)(C)N)cc(N2CCC(c3c[nH]c4nccc(OC)c34)CC2)n1] | N-(3-amino-3-methylbutan-2-yl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 526.1; (400 MHz, CD$_3$OD) δ ppm 8.06 (d, J = 5.6 Hz, 1 H), 7.09 (s, 1 H), 6.99 (s, 1 H), 6.67 (d, J = 6.0 Hz, 1 H), 5.36-5.40 (m, 1 H), 4.61 (br s, 2 H), 4.24-4.25 (m, 1 H), 3.97 (s, 3 H), 3.61-3.65 (m, 2 H), 3.40 (s, 3 H), 3.19-3.22 (m, 3 H), 2.17 (d, J = 12.8 Hz, 2 H), 1.70-1.77 (m, 2 H), 1.29 (d, J = 2.4 Hz, 3 H) 1.27-1.29 (m, 9 H). |

TABLE 1-continued

| Ex. # | Structure | Compound Name | LRMS m/z (M + H)+; and 1H NMR |
|---|---|---|---|
| 438* (E) | 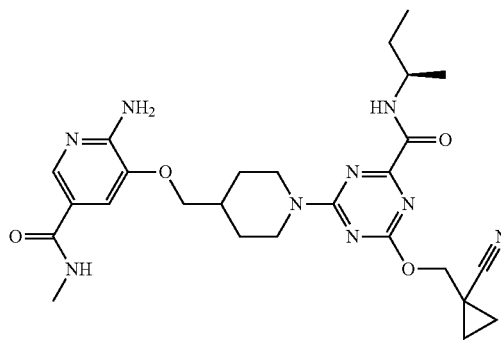 | 4-[4-({[2-amino-5-(methylcarbamoyl)pyridin-3-yl]oxy}methyl)piperidin-1-yl]-N-[(2R)-butan-2-yl]-6-[(1-cyanocyclopropyl)methoxy]-1,3,5-triazine-2-carboxamide | 538.2; (400 MHz, CDCl$_3$) δ ppm 8.00 (s, 1 H), 7.61 (d, J = 8.4 Hz, 1 H), 7.44 (s, 1 H), 6.10 (br s, 1 H), 5.07 (d, J = 13.6 Hz, 1 H), 4.98 (s, 2 H), 4.87 (d, J = 12.8 Hz, 1 H), 4.42 (q, J = 10.4 Hz, 2 H), 4.05-4.09 (m, 1 H), 3.94 (d, J = 6.4 Hz, 2H), 2.95-3.05 (m, 5 H), 2.18 (br s, 1 H), 1.96 (d, J = 12.8 Hz, 2 H), 1.52-1.58 (m, 2 H), 1.41-1.43 (m, 4 H), 1.19-1.23 (m, 5 H), 0.94 (t, J = 7.6 Hz, 3H). |
| 439* (E) | 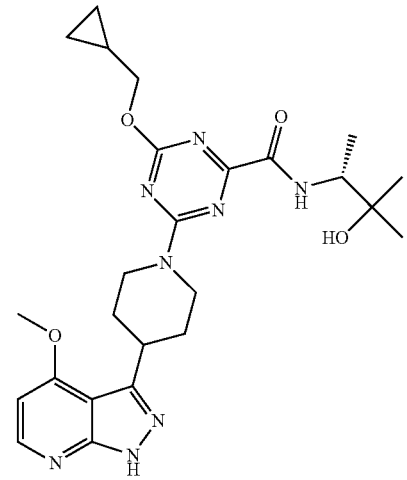 [SMILES: COc1ccnc2[nH]nc(C3CCN(c4nc(OCC5CC5)nc(C(=O)N[C@H](C)C(C)(C)O)n4)CC3)c12] | 4-(cyclopropylmethoxy)-N-[(2R)-3-hydroxy-3-methylbutan-2-yl]-6-[4-(4-methoxy-1H-pyrazolo[3,4-b]pyridin-3-yl)piperidin-1-yl]-1,3,5-triazine-2-carboxamide | 511.1; (400 MHz, CDCl$_3$) δ ppm 11.89 (br s, 1 H), 8.42 (d, J = 5.6 Hz, 1 H), 8.06 (d, J = 5.2 Hz, 1 H), 6.51 (d, J = 5.6 Hz, 1H), 5.03 (d, J = 12.8 Hz, 1 H), 4.87 (d, J = 12.8 Hz, 1 H), 4.23 (d, J = 7.2 Hz, 2 H), 4.05-4.09 (m, 1 H), 4.00 (s, 3 H), 3.46-3.48 (m, 1 H), 3.12-3.20 (m, 2H), 2.42 (br s, 1 H), 2.13 (d, J = 13.2 Hz, 2 H), 1.96-2.00 (m, 2 H), 1.24-1.33 (m, 10 H), 0.63 (q, J = 5.6 Hz, 2 H), 0.38 (q, J = 4.8 Hz, 2 H). |
| 440* (D) | 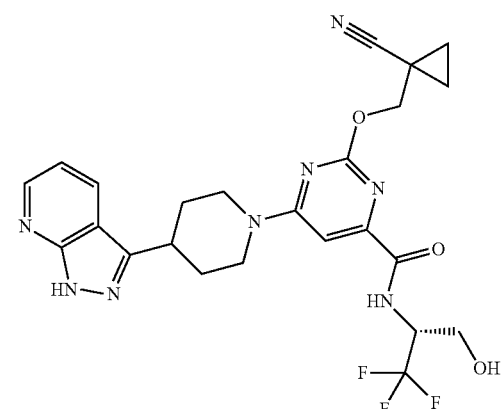 | 2-[(1-cyanocyclopropyl)methoxy]-6-[4-(1H-pyrazolo[3,4-b]pyridin-3-yl)piperidin-1-yl]-N-[(2R)-1,1,1-trifluoro-3-hydroxypropan-2-yl]pyrimidine-4-carboxamide | 531.1; (400 MHz, CDCl$_3$) δ ppm 11.48 (s, 1 H), 8.59 (d, J = 4.4 Hz, 1 H), 8.32 (d, J = 5.2 Hz, 1 H), 8.12 (d, J = 7.6 Hz, 1 H), 7.26 (d, J = 9.6 Hz, 1 H), 7.14-7.17 (m, 1 H), 4.20-4.94 (m, 4 H), 3.91-4.05 (m, 3 H), 3.41-3.47 (m, 1 H), 3.27 (br s, 2 H), 3.12 (br s, 1 H), 2.22 (d, J = 11.6 Hz, 2 H), 2.03-2.05 (m, 2 H), 1.41-1.45 (m, 2 H), 1.29-1.31 (m, 1 H), 1.21-1.22 (m, 1 H). |

TABLE 1-continued

| Ex. # | Structure | Compound Name | LRMS m/z (M + H)$^+$; and $^1$H NMR |
|---|---|---|---|
| 441** (D) | 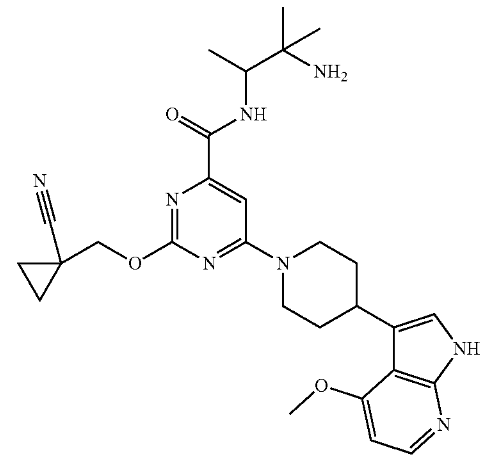 [SMILES: COc1ccnc2[nH]cc(C3CCN(c4cc(C(=O)NC(C)C(C)(C)N)nc(OCC5(C#N)CC5)n4)CC3)c12] | N-(3-amino-3-methylbutan-2-yl)-2-[(1-cyanocyclopropyl)methoxy]-6-[4-(4-methoxy-1H-pyrrolo[2,3-b]pyridin-3-yl)piperidin-1-yl]pyrimidine-4-carboxamide | 533.1; (400 MHz, CD$_3$OD) δ ppm 8.06 (d, J = 5.6 Hz, 1 H), 7.14 (s, 1 H), 6.99 (s, 1 H), 6.65 (d, J = 5.2 Hz, 1 H), 4.71 (br s, 2 H), 4.43 (q, J = 11.2 Hz, 2 H), 4.05-4.10 (m, 1 H), 3.97 (s, 3 H), 3.38 (br s, 1 H), 3.17 (br s, 2 H), 2.16 (d, J = 12.0 Hz, 2 H), 1.70-1.71 (m, 2 H), 1.38-1.41 (m, 2 H), 1.25-1.27 (m, 5 H), 1.16 (d, J = 8.8 Hz, 6 H). |
| 442** (D) | 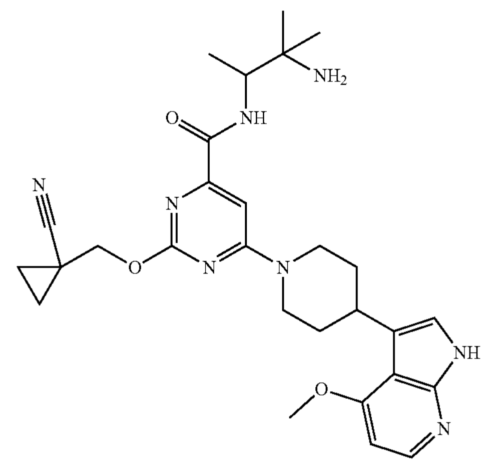 [SMILES: COc1ccnc2[nH]cc(C3CCN(c4cc(C(=O)NC(C)C(C)(C)N)nc(OCC5(C#N)CC5)n4)CC3)c12] | N-(3-amino-3-methylbutan-2-yl)-2-[(1-cyanocyclopropyl)methoxy]-6-[4-(4-methoxy-1H-pyrrolo[2,3-b]pyridin-3-yl)piperidin-1-yl]pyrimidine-4-carboxamide | 533.1; (400 MHz, CD$_3$OD) δ ppm 8.06 (d, J = 5.6 Hz, 1 H), 7.14 (s, 1 H), 6.99 (s, 1 H), 6.65 (d, J = 5.6 Hz, 1 H), 4.71 (br s, 2 H), 4.43 (q, J = 12.0 Hz, 2 H), 4.05-4.10 (m, 1 H), 3.97 (s, 3 H), 3.38 (br s, 1 H), 3.17 (br s, 2 H), 2.16 (d, J = 12.0 Hz, 2 H), 1.70-1.71 (m, 2 H), 1.38-1.41 (m, 2 H), 1.25-1.27 (m, 5 H), 1.16 (d, J = 9.2 Hz, 6 H). |
| 443* (E) | 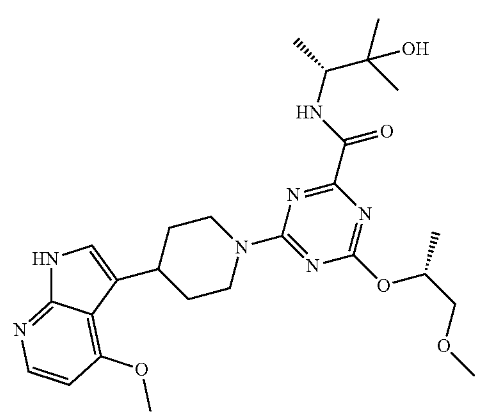 [SMILES: COC[C@@H](C)Oc1nc(C(=O)N[C@H](C)C(C)(C)O)nc(N2CCC(c3c[nH]c4nccc(OC)c34)CC2)n1] | N-[(2R)-3-hydroxy-3-methylbutan-2-yl]-4-{[(2R)-1-methoxypropan-2-yl]oxy}-6-[4-(4-methoxy-1H-pyrrolo[2,3-b]pyridin-3-yl)piperidin-1-yl]-1,3,5-triazine-2-carboxamide | 528.1; (400 MHz, CDCl$_3$) δ ppm 9.26 (s, 1 H), 8.17 (d, J = 5.6 Hz, 1 H), 8.06 (d, J = 8.8 Hz, 1 H), 6.88 (s, 1 H), 6.53 (d, J = 5.2 Hz, 1 H), 5.40-5.45 (m, 1 H), 5.11 (d, J = 12.8 Hz, 1 H), 4.91 (d, J = 12.8 Hz, 1 H), 4.07-4.09 (m, 1 H), 3.97 (s, 3 H), 3.62-3.66 (m, 1 H), 3.50-3.53 (m, 1 H), 3.40 (s, 3 H), 3.32-3.35 (m, 1 H), 3.06-3.09 (m, 2 H), 2.15 (d, J = 10.4 Hz, 2 H), 1.59-1.66 (m, 2 H), 1.39 (d, J = 4.4 Hz, 3 H), 1.24-1.26 (m, 9 H). |

TABLE 1-continued

| Ex. # | Structure | Compound Name | LRMS m/z (M + H)+; and 1H NMR |
|---|---|---|---|
| 444* (E) | 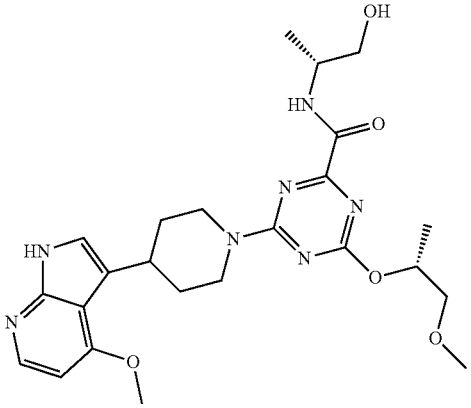 [SMILES: COC[C@@H](C)Oc1nc(C(=O)N[C@H](C)CO)nc(N2CCC(c3c[nH]c4nccc(OC)c34)CC2)n1] | N-[(2R)-1-hydroxypropan-2-yl]-4-{[(2R)-1-methoxypropan-2-yl]oxy}-6-[4-(4-methoxy-1H-pyrrolo[2,3-b]pyridin-3-yl)piperidin-1-yl]-1,3,5-triazine-2-carboxamide | 500.1; (400 MHz, CDCl$_3$) δ ppm 9.75 (s, 1 H), 8.16 (d, J = 5.6 Hz, 1 H), 7.97 (d, J = 7.6 Hz, 1 H), 6.88 (s, 1 H), 6.51 (d, J = 5.6 Hz, 1 H), 5.40-5.44 (m, 1 H), 5.09 (d, J = 13.6 Hz, 1 H), 4.88 (d, J = 13.6 Hz, 1 H), 4.20-4.21 (m, 1 H), 3.96 (d, J = 5.6 Hz, 3 H), 3.72-3.74 (m, 1 H), 3.61-3.66 (m, 2 H), 3.50-3.52 (m, 1 H), 3.40 (s, 3 H), 3.34 (t, J = 6.0 Hz, 1 H), 3.08 (q, J = 7.6 Hz, 2 H), 2.11 (t, J = 13.2 Hz, 2 H), 1.58-1.64 (m, 2 H), 1.36-1.38 (m, 3 H), 1.27 (d, J = 6.8 Hz, 3 H). |
| 445** (D) | 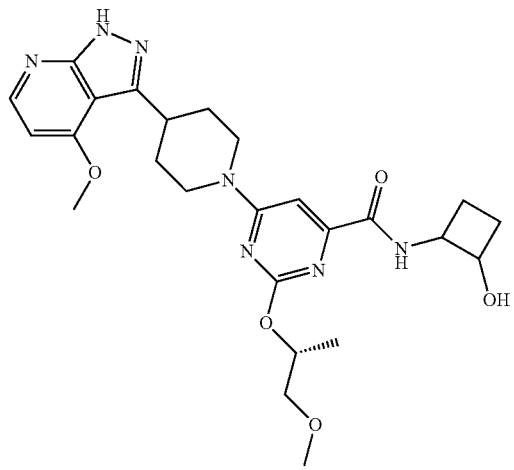 [SMILES: COC[C@@H](C)Oc1nc(C(=O)NC2CCC2O)cc(N2CCC(c3n[nH]c4nccc(OC)c34)CC2)n1] | (trans)-N-(2-hydroxy-cyclobutyl)-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 512.1; (400 MHz, CDCl$_3$) δ ppm 11.42 (s, 1 H), 8.41 (d, J = 5.6 Hz, 1 H), 8.15 (d, J = 8.4 Hz, 1 H), 7.11 (s, 1 H), 6.51 (d, J = 5.2 Hz, 1 H), 5.32-5.36 (m, 1 H), 3.72-4.82 (m, 1 H), 3.94-4.17 (m, 5 H), 3.64-3.78 (m, 2 H), 3.48-3.54 (m, 2 H), 3.42 (s, 3 H), 3.14-3.24 (m, 2 H), 2.01-2.18 (m, 6 H), 1.66-1.75 (m, 1 H), 1.38-1.40 (m, 1 H), 1.39 (d, J = 7.2 Hz, 3 H). |
| 446** (D) | 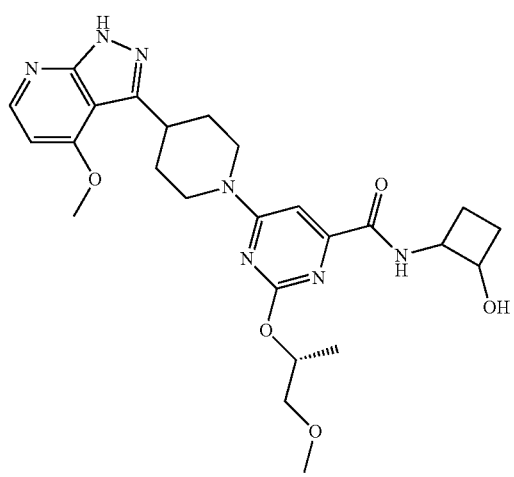 [SMILES: COC[C@@H](C)Oc1nc(C(=O)NC2CCC2O)cc(N2CCC(c3n[nH]c4nccc(OC)c34)CC2)n1] | (trans)-N-(2-hydroxy-cyclobutyl)-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 512.1; (400 MHz, CDCl$_3$) δ ppm 11.05 (s, 1 H), 8.41 (d, J = 5.2 Hz, 1H), 8.15 (d, J = 8.4 Hz, 1 H), 7.11 (s, 1 H), 6.51 (d, J = 5.6 Hz, 1 H), 5.32-5.36 (m, 1 H), 3.72-4.82 (m, 1 H), 3.94-4.17 (m, 5 H), 3.64-3.78 (m, 2 H), 3.48-3.54 (m, 2 H), 3.42 (s, 3 H), 3.14-3.24 (m, 2 H), 2.01-2.18 (m, 6 H), 1.66-1.75 (m, 1 H), 1.38-1.40 (m, 1 H), 1.39 (d, J = 6.4 Hz, 3 H). |

TABLE 1-continued

| Ex. # | Structure | Compound Name | LRMS m/z (M + H)⁺; and ¹H NMR |
|---|---|---|---|
| 447* (D) | 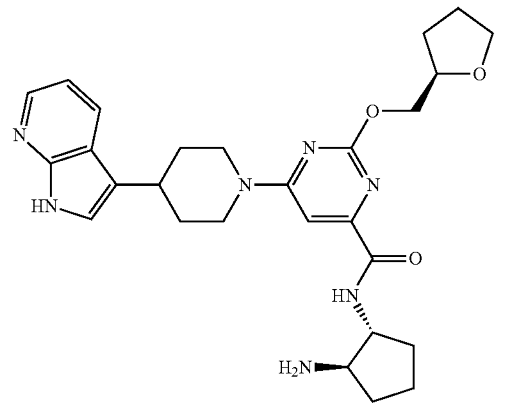 [SMILES: N[C@@H]1CCC[C@H]1NC(=O)c1cc(N2CCC(c3c[nH]c4ncccc34)CC2)nc(OC[C@H]2CCCO2)n1] | N-[(1R,2R)-2-aminocyclopentyl]-6-[4-(1H-pyrrolo[2,3-b]pyridin-3-yl)piperidin-1-yl]-2-[(2R)-tetrahydrofuran-2-ylmethoxy]pyrimidine-4-carboxamide | 506.2; (400 MHz, CDCl₃) δ ppm 9.27 (br s, 1 H), 8.32 (br s, 1 H), 7.94 (d, J = 8.0 Hz, 1 H), 7.88 (br s, 1 H), 7.07-7.13 (m, 3 H), 4.66 (br s, 1 H), 4.32-4.39 (m, 4 H), 4.27-4.31 (m, 3 H), 3.81-3.95 (m, 1 H), 3.02-3.13 (m, 4 H), 1.47-2.17 (m, 14 H). |
| 448* (D) | 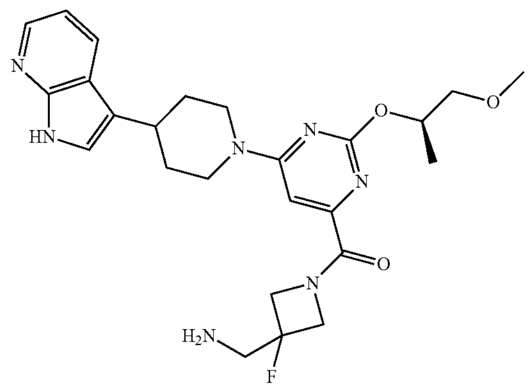 [SMILES: COC[C@@H](C)Oc1nc(C(=O)N2CC(F)(CN)C2)cc(N2CCC(c3c[nH]c4ncccc34)CC2)n1] | [3-(Aminomethyl)-3-fluoroazetidin-1-yl](2-{[(2R)-1-methoxypropan-2-yl]oxy}-6-[4-(1H-pyrrolo[2,3-b]pyridin-3-yl)piperidin-1-yl]pyrimidin-4-yl)methanone | 498.1; (400 MHz, CDCl₃) δ ppm 8.90 (br s, 1 H), 8.38 (br s, 1 H), 7.94 (d, J = 7.6 Hz, 1 H), 7.06-7.07 (m, 2 H), 5.26 (br s, 1 H), 4.76 (d, J = 19.6 Hz, 2 H), 4.52 (br s, 1 H), 4.19-4.24 (m, 2 H), 3.67-3.68 (m, 1 H), 3.47-3.48 (m, 1 H), 3.46 (s, 3 H), 3.09-3.12 (m, 4 H), 2.13 (d, J = 13.2 Hz, 2 H), 1.39-1.74 (m, 2 H), 1.37 (d, J = 2.0 Hz, 3 H). |
| 449* (D) | 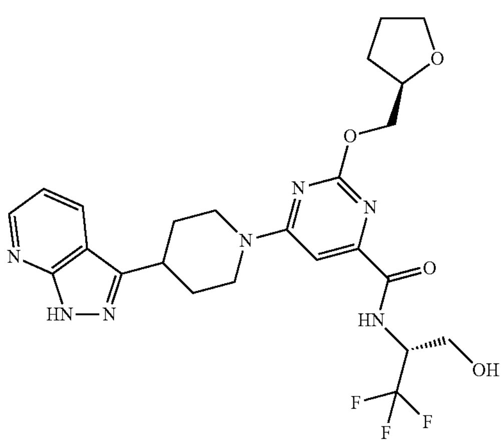 [SMILES: O=C(N[C@H](CO)C(F)(F)F)c1cc(N2CCC(c3n[nH]c4ncccc34)CC2)nc(OC[C@H]2CCCO2)n1] | 6-[4-(1H-pyrazolo[3,4-b]pyridin-3-yl)piperidin-1-yl]-2-[(2R)-tetrahydrofuran-2-ylmethoxy]-N-[(2R)-1,1,1-trifluoro-3-hydroxypropan-2-yl]pyrimidine-4-carboxamide | 536.01; (400 MHz, CDCl₃) δ ppm 11.77 (br s, 1 H), 8.57 (d, J = 7.6 Hz, 1 H), 8.40 (d, J = 7.6 Hz, 1 H), 8.11 (d, J = 7.6 Hz, 1 H), 7.11-7.16 (m, 2 H), 4.84 (br s, 1 H), 4.50 (br s, 1 H), 4.29-4.33 (m, 3 H), 3.95-4.04 (m, 3 H), 3.82-3.93 (m, 1 H), 3.23-3.42 (m, 4 H), 1.86-2.20 (m, 9 H). |

TABLE 1-continued

| Ex. # | Structure | Compound Name | LRMS m/z (M + H)+; and 1H NMR |
|---|---|---|---|
| 450* (E) | 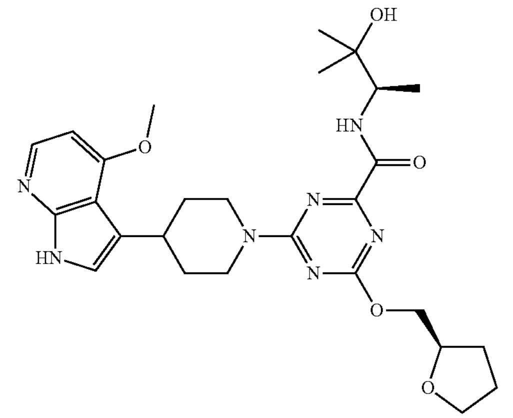 [SMILES: COc1ccnc2[nH]cc(C3CCN(c4nc(OC[C@H]5CCCO5)nc(C(=O)N[C@H](C)C(C)(C)O)n4)CC3)c12] | N-[(2R)-3-hydroxy-3-methylbutan-2-yl]-4-[4-(4-methoxy-1H-pyrrolo[2,3-b]pyridin-3-yl)piperidin-1-yl]-6-[(2R)-tetrahydrofuran-2-ylmethoxy]-1,3,5-triazine-2-carboxamide | 540.1; (400 MHz, CDCl$_3$) δ ppm 9.27 (br s, 1 H), 8.17 (d, J = 5.6 Hz, 1 H), 8.07 (d, J = 8.8 Hz, 1 H), 6.87 (s, 1 H), 6.52 (d, J = 5.6 Hz, 1H), 5.09 (d, J = 13.6 Hz, 1 H), 4.89 (d, J = 13.6 Hz, 1 H), 4.29-4.40 (m, 3 H), 4.06-4.08 (m, 1 H), 3.92-3.97 (m, 4 H), 3.81-3.82 (m, 1 H), 3.28 (t, J = 12.8 Hz, 1 H), 3.05 (q, J = 13.2 Hz, 2 H), 2.07-2.17 (m, 3 H), 1.93-1.98 (m, 2 H), 1.76-1.79 (m, 1 H), 1.60-1.63 (m, 2 H), 1.24-1.27 (m, 9 H). |
| 451* (E) | 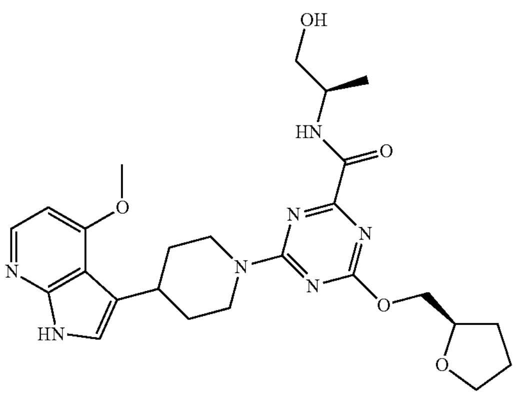 [SMILES: COc1ccnc2[nH]cc(C3CCN(c4nc(OC[C@H]5CCCO5)nc(C(=O)N[C@H](C)CO)n4)CC3)c12] | N-[(2R)-1-hydroxypropan-2-yl]-4-[4-(4-methoxy-1H-pyrrolo[2,3-b]pyridin-3-yl)piperidin-1-yl]-6-[(2R)-tetrahydrofuran-2-ylmethoxy]-1,3,5-triazine-2-carboxamide | 512.0; (400 MHz, CDCl$_3$) δ ppm 9.55 (br s, 1 H), 8.16 (d, J = 5.6 Hz, 1 H), 7.99 (d, J = 7.6 Hz, 1 H), 6.88 (s, 1 H), 6.52 (d, J = 5.2 Hz, 1 H), 5.07 (d, J = 12.8 Hz, 1 H), 4.91 (d, J = 12.4 Hz, 1 H), 4.28-4.38 (m, 4 H), 3.92-3.96 (m, 4 H), 3.74-3.82 (m, 2 H), 3.66-3.68 (m, 1 H), 3.27 (t, J = 12.8 Hz, 1 H), 3.06 (q, J = 12.4 Hz, 2 H), 2.07-2.18 (m, 3 H), 1.94-1.98 (m, 2 H), 1.75-1.78 (m, 1 H), 1.59-1.61 (m, 2 H), 1.28 (d, J = 6.8 Hz, 3 H). |
| 452* (D) | 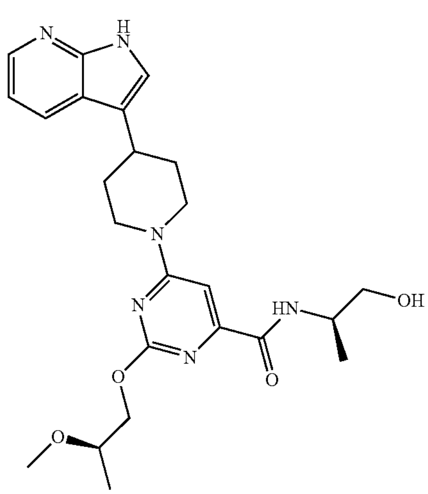 [SMILES: CO[C@H](C)COc1nc(C(=O)N[C@H](C)CO)cc(N2CCC(c3c[nH]c4ncccc34)CC2)n1] | N-[(2R)-1-hydroxypropan-2-yl]-2-[(2R)-2-methoxypropoxy]-6-[4-(1H-pyrrolo[2,3-b]pyridin-3-yl)piperidin-1-yl]pyrimidine-4-carboxamide | 491.2 [M + Na]+; (400 MHz, CDCl$_3$) δ ppm 9.09 (br s, 1H), 8.31 (d, J = 4.4 Hz, 1 H), 7.93-7.98 (m, 2 H), 7.13 (s, 1 H), 7.07-7.08 (m, 2 H), 4.61 (br s, 2 H), 4.34-4.36 (m, 1 H), 4.22-4.26 (m, 2 H), 3.73-3.78 (m, 2 H), 3.66-3.67 (m, 1 H), 3.45 (s, 3 H), 3.10-3.14 (m, 4 H), 2.16 (d, J = 12.6 Hz, 2 H), 1.73-1.79 (m, 2 H), 1.29 (d, J = 5.2 Hz, 6 H). |

TABLE 1-continued

| Ex. # | Structure | Compound Name | LRMS m/z (M + H)+; and 1H NMR |
|---|---|---|---|
| 453* (D) | 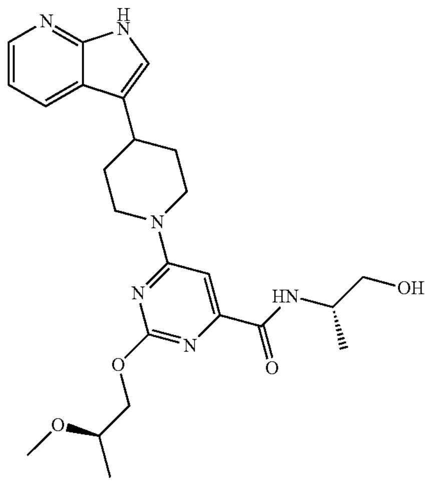 [SMILES: CO[C@H](C)COc1nc(C(=O)N[C@@H](C)CO)cc(N2CCC(c3c[nH]c4ncccc34)CC2)n1] | N-[(2S)-1-hydroxypropan-2-yl]-2-[(2R)-2-methoxypropoxy]-6-[4-(1H-pyrrolo[2,3-b]pyridin-3-yl)piperidin-1-yl]pyrimidine-4-carboxamide | 491.2 [M + Na]+; (400 MHz, CDCl$_3$) δ ppm 9.01 (br s, 1 H), 8.31 (d, J = 4.8 Hz, 1 H), 7.93-7.98 (m, 2 H), 7.13 (s, 1 H), 7.06-7.09 (m, 2 H), 4.61 (br s, 2 H), 4.35-4.36 (m, 1 H), 4.22-4.26 (m, 2 H), 3.73-3.78 (m, 2 H), 3.66-3.67 (m, 1 H), 3.45 (s, 3 H), 3.10-3.14 (m, 4 H), 2.15 (d, J = 8.8 Hz, 2 H), 1.70-1.79 (m, 2 H), 1.29 (d, J = 5.2 Hz, 6 H). |
| 454* (D) | 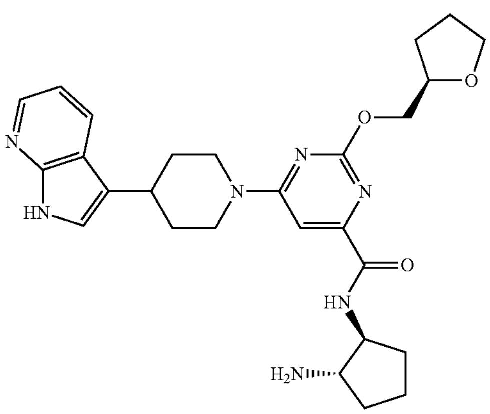 [SMILES: N[C@H]1CCC[C@@H]1NC(=O)c1cc(N2CCC(c3c[nH]c4ncccc34)CC2)nc(OC[C@H]2CCCO2)n1] | N-[(1S,2S)-2-aminocyclopentyl]-6-[4-(1H-pyrrolo[2,3-b]pyridin-3-yl)piperidin-1-yl]-2-[(2R)-tetrahydrofuran-2-ylmethoxy]pyrimidine-4-carboxamide | 528.3 [M + Na]+; (400 MHz, CD$_3$OD) δ ppm 8.17 (d, J = 4.4 Hz, 1 H), 8.09 (d, J = 8.0 Hz, 1 H), 7.20 (s, 1 H), 7.08-7.11 (m, 2 H), 4.41 (br s, 2 H), 4.37 (d, J = 4.8 Hz, 2 H), 4.27-4.29 (m, 1 H), 3.91-3.99 (m, 2 H), 3.82-3.89 (m, 1 H), 3.21-3.25 (m, 4 H), 2.18 (d, J = 13.2 Hz, 2 H), 1.51-2.09 (m, 12 H). |
| 455* (D) | 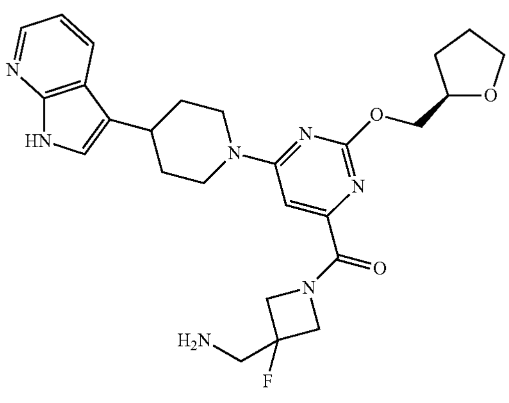 [SMILES: NCC1(F)CN(C(=O)c2cc(N3CCC(c4c[nH]c5ncccc45)CC3)nc(OC[C@H]3CCCO3)n2)C1] | [3-(aminomethyl)-3-fluoroazetidin-1-yl]{6-[4-(1H-pyrrolo[2,3-b]pyridin-3-yl)piperidin-1-yl]-2-[(2R)-tetrahydrofuran-2-ylmethoxy]pyrimidn-4-yl}methanone | 532.2 [M + Na]+; (400 MHz, CDCl$_3$) δ ppm 8.74 (br s, 1 H), 8.30 (d, J = 4.0 Hz, 1 H), 7.94 (d, J = 7.6 Hz, 1 H), 7.06-7.09 (m, 3 H), 4.78 (d, J = 12.4 Hz, 2 H), 4.65 (br s, 2 H), 4.27-4.44 (m, 5 H), 3.87-3.92 (m, 1 H), 3.76-3.84 (m, 1 H), 3.51 (br s, 1 H), 3.01-3.09 (m, 5 H), 2.09-2.15 (m, 3 H), 1.72-1.98 (m, 2 H), 1.63-1.71 (m, 3 H). |

TABLE 1-continued

| Ex. # | Structure | Compound Name | LRMS m/z (M + H)+; and 1H NMR |
|---|---|---|---|
| 456* (D) | 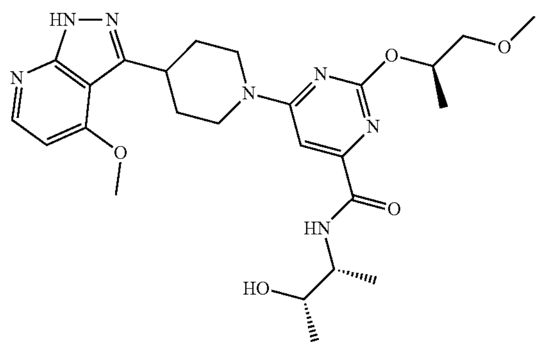 [SMILES: COC[C@@H](C)Oc1nc(C(=O)N[C@H](C)[C@H](C)O)cc(N2CCC(c3n[nH]c4nccc(OC)c34)CC2)n1] | N-[{2R,3S)-3-hydroxybutan-2-yl]-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 513.2; (400 MHz, CD$_3$OD) δ ppm 8.32 (d, J = 5.6 Hz, 1 H), 7.10 (s, 1 H), 6.70 (d, J = 7.2 Hz, 1 H), 5.34-5.38 (m, 1 H), 4.60 (br s, 2 H), 3.98-4.01 (m, 4 H), 3.75-3.90 (m, 1 H), 3.55-3.61 (m, 3 H), 3.39 (s, 3 H), 3.21-3.31 (m, 2 H), 2.10 (d, J = 10.4 Hz, 2 H), 1.94-2.05 (m, 4 H), 1.35 (d, J = 6.0 Hz, 3 H), 1.19-1.29 (m, 6 H). |
| 457** (D) | 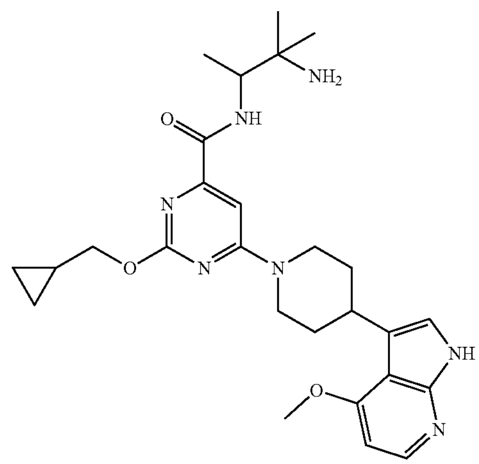 [SMILES: COc1ccnc2[nH]cc(C3CCN(c4cc(C(=O)NC(C)C(C)(C)N)nc(OCC5CC5)n4)CC3)c12] | N-(3-amino-3-methylbutan-2-yl)-2-(cyclopropylmethoxy)-6-[4-(4-methoxy-1H-pyrrolo[2,3-b]pyridin-3-yl)piperidin-1-yl]pyrimidine-4-carboxamide | 508.1 (400 MHz, CD$_3$OD) δ ppm 8.05 (d, J = 5.6 Hz, 1 H), 7.09 (s, 1 H), 6.99 (s, 1 H), 6.66 (d, J = 5.6 Hz, 1 H), 4.82 (br s, 2 H), 4.21 (d, J = 9.2 Hz, 2 H), 4.05 (q, J = 8.0 Hz, 1 H), 3.97 (s, 3 H), 3.38 (br s, 1 H), 3.15-3.17 (m, 2 H), 2.16 (d, J = 12.8 Hz, 2 H), 1.70-1.72 (m, 2 H), 1.31-1.34 (m, 2 H), 1.30 (d, J = 8.8 Hz, 3 H), 1.21 (d, J = 8.0 Hz, 6 H), 0.61-0.63 (m, 2 H), 0.39-0.40 (m, 2 H). |
| 458** (D) | 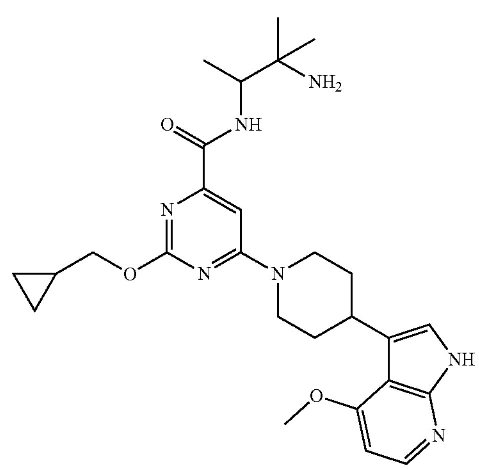 [SMILES: COc1ccnc2[nH]cc(C3CCN(c4cc(C(=O)NC(C)C(C)(C)N)nc(OCC5CC5)n4)CC3)c12] | N-(3-amino-3-methylbutan-2-yl)-2-(cyclopropylmethoxy)-6-[4-(4-methoxy-1H-pyrrolo[2,3-b]pyridin-3-yl)piperidin-1-yl]pyrimidine-4-carboxamide | 508.1; (400 MHz, CD$_3$OD) δ ppm 8.05 (d, J = 5.6 Hz, 1 H), 7.09 (s, 1 H), 6.99 (s, 1 H), 6.66 (d, J = 5.6 Hz, 1 H), 4.82 (br s, 2 H), 4.23 (d, J = 8.4 Hz, 2 H), 4.06 (q, J = 6.8 Hz, 1 H), 3.97 (s, 3 H), 3.38 (s, 1 H), 3.17 (br s, 2 H), 2.15 (d, J = 12.8 Hz, 2 H), 1.70-1.72 (m, 2 H), 1.31-1.34 (m, 2 H), 1.30 (d, J = 6.8 Hz, 3 H), 1.21 (d, J = 6.8 Hz, 6 H), 0.61-0.63 (m, 2 H), 0.39-0.40 (m, 2 H). |

TABLE 1-continued

| Ex. # | Structure | Compound Name | LRMS m/z (M + H)+; and 1H NMR |
|---|---|---|---|
| 459* (D) | 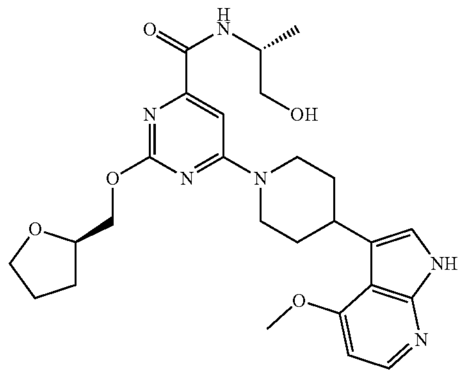 [SMILES: COc1ccnc2[nH]cc(C3CCN(c4cc(C(=O)N[C@H](C)CO)nc(OC[C@H]5CCCO5)n4)CC3)c12] | N-[(2R)-1-hydroxypropan-2-yl]-6-[4-(4-methoxy-1H-pyrrolo[2,3-b]pyridin-3-yl)piperidin-1-yl]-2-[(2R)-tetrahydrofuran-2-ylmethoxy]pyrimidine-4-carboxamide | 511.1; (400 MHz, DMSO-d$_6$) δ ppm 11.26 (s, 1 H), 8.17 (d, J = 8.4 Hz, 1 H), 8.05 (d, J = 5.2 Hz, 1 H), 7.02 (d, J = 5.2 Hz, 2 H), 6.60 (d, J = 5.2 Hz, 1 H), 4.86 (t, J = 5.2 Hz, 1 H), 4.34-4.78 (m, 2 H), 4.25 (d, J = 5.6 Hz, 2 H), 4.13-4.18 (m, 1 H), 3.93-3.98 (m, 1 H), 3.87 (s, 3 H), 3.74-3.78 (m, 1 H), 3.63-3.67 (m, 1 H), 3.42-3.47 (m, 2 H), 3.20-3.27 (m, 1 H), 3.03-3.18 (m, 2 H), 2.02-2.07 (m, 3 H), 1.83-1.86 (m, 2 H), 1.54-1.66 (m, 3 H), 1.14 (d, J = 6.8 Hz, 3 H). |
| 460* (D) | 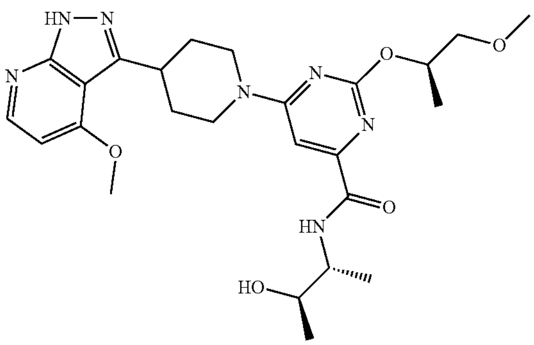 [SMILES: COC[C@@H](C)Oc1nc(C(=O)N[C@H](C)[C@@H](C)O)cc(N2CCC(c3n[nH]c4nccc(OC)c34)CC2)n1] | N-[(2R,3R)-3-hydroxybutan-2-yl]-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 513.0; (400 MHz, CDCl$_3$) δ ppm 11.31 (br s, 1 H), 8.41 (d, J = 5.6 Hz, 1 H), 8.02 (d, J = 8.4 Hz, 1 H), 7.14 (s, 1 H), 6.52 (d, J = 5.6 Hz, 1 H), 5.31-5.36 (m, 1 H), 4.58 (br s, 2 H), 4.02-4.14 (m, 4 H), 3.83-3.98 (m, 1 H), 3.67-3.68 (m, 1 H), 3.51-3.53 (m, 2 H), 3.42 (s, 3 H), 3.19 (br s, 2 H), 1.99-2.26 (m, 5 H), 1.41 (d, J = 6.4 Hz, 3 H), 1.29 (d, J = 6.8 Hz, 3 H), 1.21 (d, J = 6.4 Hz, 3 H). |
| 461* (D) | 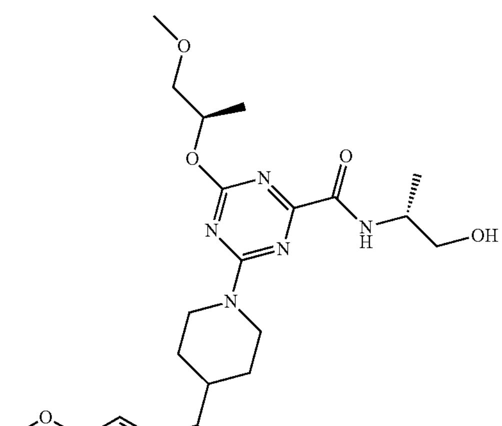 | N-[(2R)-1-hydroxypropan-2-yl]-2-{[(2R)-1-methoxypropan-2-yl]oxy}-6-[4-(5-methoxy-1H-pyrrolo[2,3-b]pyridin-3-yl)piperidin-1-yl]pyrimidine-4-carboxamide | 499.1; (400 MHz, CDCl$_3$) δ ppm 8.78 (br s, 1 H), 8.09 (d, J = 2.4 Hz, 1 H), 7.98 (d, J = 6.8 Hz, 1 H), 7.40 (d, J = 2.4 Hz, 1 H), 7.11 (s, 1 H), 7.05 (s, 1 H), 5.31-5.35 (m, 1 H), 4.44-4.96 (m, 2 H), 4.20-4.21 (m, 1 H), 3.91 (s, 3 H), 3.66-3.72 (m, 3 H), 3.50-3.52 (m, 1 H), 3.42 (s, 3 H), 3.09-3.14 (m, 4 H), 2.14 (d, J = 12.4 Hz, 2 H), 1.70-1.73 (m, 2 H), 1.39 (d, J = 6.4 Hz, 3 H), 1.28 (d, J = 6.8 Hz, 3 H). |

TABLE 1-continued

| Ex. # | Structure | Compound Name | LRMS m/z (M + H)+; and 1H NMR |
|---|---|---|---|
| 462* (D) | 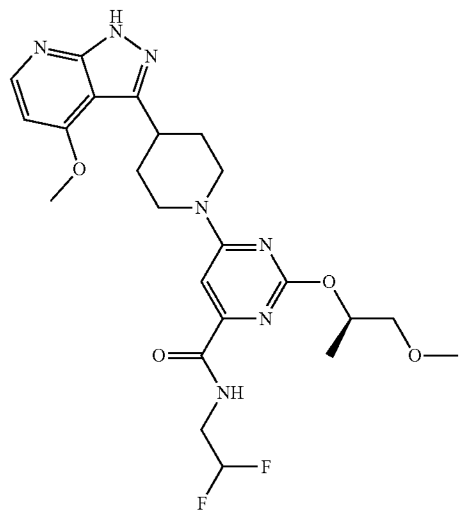 [SMILES: COC[C@@H](C)Oc1nc(C(=O)NCC(F)F)cc(N2CCC(c3n[nH]c4nccc(OC)c34)CC2)n1] | N-(2,2-difluoroethyl)-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 528.2 [M + Na]+; (400 MHz, CDCl$_3$) δ ppm 8.40-8.41 (m, 1 H), 8.14-8.15 (m, 1 H), 7.12 (s, 1 H), 6.52 (d, J = 6.0 Hz, 1 H), 5.91 (t, J = 56.0 Hz, 1 H), 5.33-5.37 (m, 1 H), 4.52 (br s, 2 H), 3.98 (s, 3 H), 3.66-3.79, m, 2 H), 3.59-3.63 (m, 1 H), 3.51-3.54 (m, 2 H), 3.41 (s, 3 H), 3.11-3.22 (m, 2 H), 1.99-2.17 (m, 4 H), 1.39 (d, J = 10.8 Hz, 2 H). |
| 463* (D) | 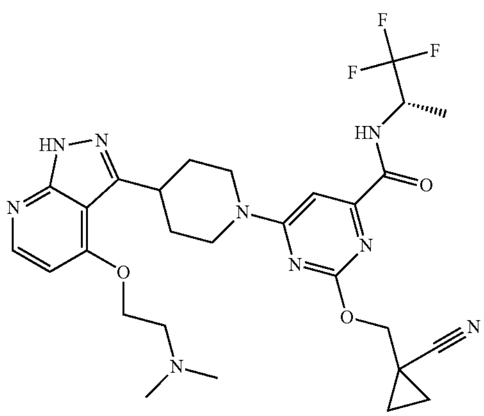 [SMILES: C[C@H](NC(=O)c1cc(N2CCC(c3n[nH]c4nccc(OCCN(C)C)c34)CC2)nc(OCC2(C#N)CC2)n1)C(F)(F)F] | 2-[(1-cyanocyclopropyl)methoxy]-6-(4-{2-[2-(dimethylamino)ethoxy]-1H-pyrazolo[3,4-b]pyridin-3-yl}piperidin-1-yl)-N-[(2S)-1,1,1-trifluoropropan-2-yl]pyrimidine-4-carboxamide | 624.2 [M + Na]+; (400 MHz, CD$_3$OD) δ ppm 8.34 (d, J = 5.2 Hz, 1 H), 7.20 (s, 1 H), 6.73 (d, J = 5.2 Hz, 1 H), 4.78-4.92 (m, 2 H), 4.32-4.50 (m, 5 H), 3.52-3.58 (m, 1 H), 3.12-3.25 (m, 2 H), 2.22-2.28 (m, 1 H), 2.34 (s, 6 H), 1.98-2.15 (m, 4 H), 1.48 (d, J = 4.4 Hz, 3 H), 1.35-1.45 (m, 2 H), 1.15-1.25 (m, 2 H). |
| 464* (D) | 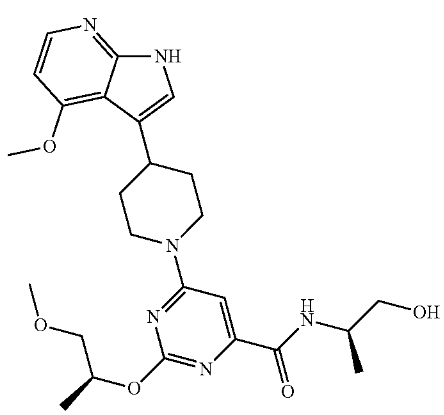 [SMILES: COC[C@H](C)Oc1nc(C(=O)N[C@H](C)CO)cc(N2CCC(c3c[nH]c4nccc(OC)c34)CC2)n1] | N-[(2R)-1-hydroxypropan-2-yl]-2-{[(2S)-1-methoxypropan-2-yl]oxy}-6-[4-(4-methoxy-1H-pyrrolo[2,3-b]pyridin-3-yl)piperidin-1-yl]pyrimidine-4-carboxamide | 521.3 [M + Na]+; (400 MHz, DMSO-d$_6$) δ ppm 11.26 (s, 1 H), 8.16 (d, J = 8.0 Hz, 1 H), 8.04 (d, J = 5.2 Hz, 1 H), 7.01 (d, J = 13.2 Hz, 2 H), 6.60 (d, J = 5.2 Hz, 1 H), 5.28 (d, J = 4.4 Hz, 1 H), 4.87-4.89 (m, 1H), 4.56 (br s, 2 H), 3.96 (br s, 1 H), 3.86 (s, 3 H), 3.50-3.54 (m, 1 H), 3.43-3.45 (m, 3 H), 3.27-3.33 (m, 4 H), 3.22 (br s, 2 H), 2.02 (d, J = 12.4 Hz, 2 H), 1.54-1.63 (m, 2 H), 1.25 (d, J = 6.0 Hz, 3 H), 1.13 (d, J = 6.8 Hz, 3 H). |

TABLE 1-continued

| Ex. # | Structure | Compound Name | LRMS m/z (M + H)⁺; and ¹H NMR |
|---|---|---|---|
| 465* (D) | 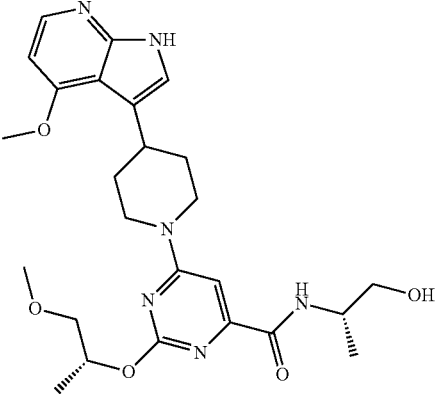 [SMILES: COC[C@@H](C)Oc1nc(C(=O)N[C@@H](C)CO)cc(N2CCC(c3c[nH]c4nccc(OC)c34)CC2)n1] | N-[(2S)-1-hydroxypropan-2-yl]-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 521.2; [M + Na]⁺; (400 MHz, DMSO-$d_6$) δ ppm 11.26 (s, 1 H), 8.16 (d, J = 5.2 Hz, 1 H), 8.04 (d, J = 5.6 Hz, 1 H), 7.01 (d, J = 13.2 Hz, 2 H), 6.59 (d, J = 5.6 Hz, 1 H), 5.27-5.28 (m, 1 H), 4.87-4.88 (m, 1 H), 4.54 (br s, 2 H), 3.96 (br s, 1 H), 3.86 (s, 3 H), 3.50-3.53 (m, 1 H), 3.44-3.45 (m, 3 H), 3.27-3.33 (m, 4 H), 3.22 (br s, 2 H), 2.02 (d, J = 11.6 Hz, 2 H), 1.57-1.63 (m, 2 H), 1.26 (d, J = 6.4 Hz, 3 H), 1.13 (d, J = 6.4 Hz, 3 H). |
| 466* (D) | 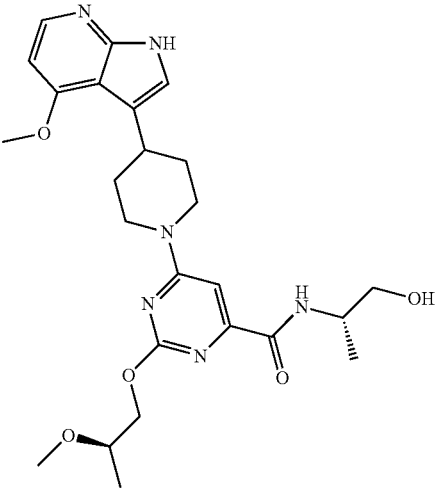 [SMILES: COc1ccnc2[nH]cc(C3CCN(c4cc(C(=O)N[C@@H](C)CO)nc(OC[C@@H](C)OC)n4)CC3)c12] | N-[(2S)-1-hydroxypropan-2-yl]-2-[(2R)-2-methoxypropoxy]-6-[4-(4-methoxy-1H-pyrrolo[2,3-b]pyridin-3-yl)piperidin-1-yl]pyrimidine-4-carboxamide | 499.2; (400 MHz, CDCl₃) δ ppm 9.21 (br s, 1 H), 8.18 (d, J = 5.6 Hz, 1 H), 7.98 (d, J = 7.6 Hz, 1 H), 7.12 (s, 1 H), 6.88 (s, 1 H), 6.53 (d, J = 5.6 Hz, 1 H), 5.02 (br s, 2 H), 4.35-4.38 (m, 1 H), 4.22-4.26 (m, 2 H), 3.96 (s, 3 H), 3.73-3.78 (m, 2 H), 3.66 (t, J = 8.8 Hz, 1 H), 3.45 (s, 3 H), 3.30-3.31 (m, 1 H), 3.09-3.10 (m, 2 H), 2.16 (d, J = 12.8 Hz, 2 H), 1.65 (q, J = 3.6 Hz, 2 H), 1.29 (d, J = 4.4 Hz, 6 H). |
| 467* (D) | 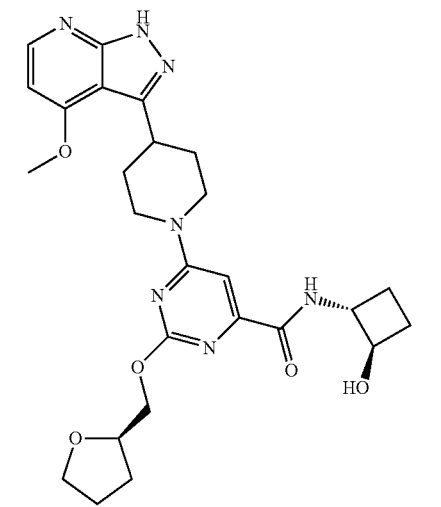 [SMILES: COc1ccnc2[nH]nc(C3CCN(c4cc(C(=O)N[C@@H]5CC[C@H]5O)nc(OC[C@H]5CCCO5)n4)CC3)c12] | N-[(1R,2R)-2-hydroxy-cyclobutyl]-6-[4-(4-methoxy-1H-pyrazolo[3,4-b]pyridin-3-yl)piperidin-1-yl]-2-[(2R)-tetrahydrofuran-2-ylmethoxy]pyrimidine-4-carboxamide | 524.1; (400 MHz, CDCl₃) δ ppm 11.65 (br s, 1 H), 8.49 (d, J = 5.6 Hz, 1 H), 8.16 (d, J = 4.4 Hz, 1 H), 7.12 (s, 1 H), 6.51 (d, J = 5.6 Hz, 1 H), 4.31-4.39 (m, 3 H), 4.10-4.25 (m, 2 H), 3.98 (s, 3 H), 3.89-3.96 (m, 1 H), 3.76-3.88 (m, 1 H), 3.19-3.25 (m, 2 H), 1.98-2.10 (m, 10 H), 1.69-1.78 (m, 2 H), 1.51-1.54 (m, 1 H). |

TABLE 1-continued

| Ex. # | Structure | Compound Name | LRMS m/z (M + H)+; and 1H NMR |
|---|---|---|---|
| 458* (D) | 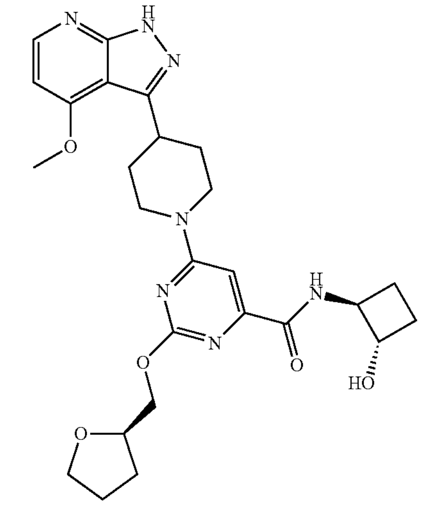 [SMILES: COc1ccnc2[nH]nc(C3CCN(c4cc(C(=O)N[C@H]5CC[C@@H]5O)nc(OC[C@H]5CCCO5)n4)CC3)c12] | N-[(1S,2S)-2-hydroxycyclobutyl]-6-[4-(4-methoxy-1H-pyrazolo[3,4-b]pyridin-3-yl)piperidin-1-yl]-2-[(2R)-tetrahydrofuran-2-ylmethoxy]pyrimidine-4-carboxamide | 524.1; (400 MHz, CDCl$_3$) δ ppm 11.34 (br s, 1 H), 8.41 (d, J = 4.4 Hz, 1 H), 8.16 (d, J = 4.8 Hz, 1 H), 7.12 (s, 1 H), 6.51 (d, J = 5.2 Hz, 1 H), 4.31-4.39 (m, 3 H), 4.10-4.25 (m, 2 H), 3.98 (s, 3 H), 3.89-3.96 (m, 1 H), 3.76-3.88 (m, 1 H), 3.19-3.25 (m, 2 H), 1.98-2.10 (m, 10 H), 1.69-1.78 (m, 2 H), 1.51-1.54 (m, 1 H). |
| 469* (D) | 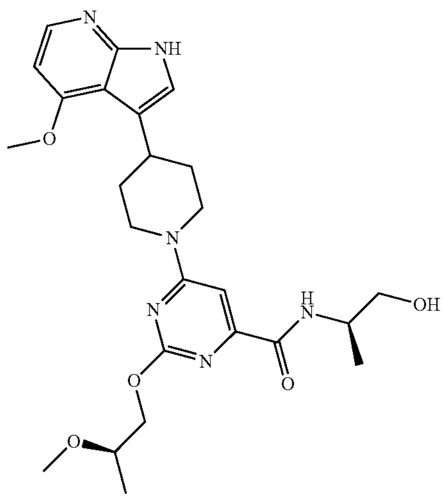 [SMILES: COc1ccnc2[nH]cc(C3CCN(c4cc(C(=O)N[C@H](C)CO)nc(OC[C@@H](C)OC)n4)CC3)c12] | N-[(2R)-1-hydroxypropan-2-yl]-2-[(2R)-2-methoxypropoxy]-6-[4-(4-methoxy-1H-pyrrolo[2,3-b]pyridin-3-yl)piperidin-1-yl]pyrimidine-4-carboxamide | 499.0; (400 MHz, CDCl$_3$) δ ppm 9.39 (br s, 1 H), 8.17 (d, J = 5.6 Hz, 1 H), 7.98 (d, J = 7.6 Hz, 1 H), 7.12 (s, 1 H), 6.88 (s, 1 H), 6.53 (d, J = 5.6 Hz, 1 H), 5.02 (br s, 2 H), 4.35-4.38 (m, 1 H), 4.22-4.26 (m, 2 H), 3.96 (s, 3 H), 3.73-3.78 (m, 2 H), 3.66-3.68 (m, 1 H), 3.45 (s, 3 H), 3.31 (t, J = 7.2 Hz, 1 H), 3.09-3.10 (m, 2H), 2.16 (d, J = 12.8 Hz, 2 H), 1.65 (q, J = 5.2 Hz, 2 H), 1.29 (d, J = 6.4 Hz, 6 H). |
| 470* (D) | 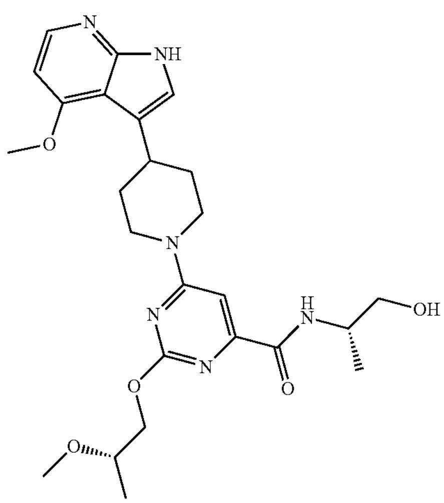 [SMILES: COc1ccnc2[nH]cc(C3CCN(c4cc(C(=O)N[C@@H](C)CO)nc(OC[C@H](C)OC)n4)CC3)c12] | N-[(2S)-1-hydroxypropan-2-yl]-2-[(2S)-2-methoxypropoxy]-6-[4-(4-methoxy-1H-pyrrolo[2,3-b]pyridin-3-yl)piperidin-1-yl]pyrimidine-4-carboxamide | 499.1; (400 MHz, CDCl$_3$) δ ppm 10.36 (br, 1H), 8.17 (d, J = 4.8 Hz, 1 H), 7.98 (d, J = 8.0 Hz, 1 H), 7.11 (s, 1 H), 6.91 (s, 1 H), 6.51 (d, J = 5.6 Hz, 1 H), 5.02 (br s, 2 H), 4.35-4.38 (m, 1 H), 4.22-4.26 (m, 2 H), 3.96 (s, 3 H), 3.73-3.83 (m, 2 H), 3.66-3.68 (m, 1 H), 3.45 (s, 3 H), 3.31 (q, J = 6.2 Hz, 1 H), 3.09-3.10 (m, 2 H), 2.16 (d, J = 11.6 Hz, 2 H), 1.62-1.71 (m, 2 H), 1.28-1.29 (m, 6 H). |

TABLE 1-continued

| Ex. # | Structure | Compound Name | LRMS m/z (M + H)+; and 1H NMR |
|---|---|---|---|
| 471* (D) | 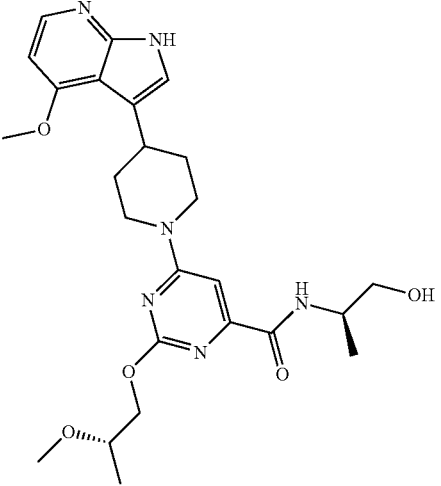 [SMILES: COc1ccnc2[nH]cc(C3CCN(c4cc(C(=O)N[C@H](C)CO)nc(OC[C@H](C)OC)n4)CC3)c12] | N-[(2R)-1-hydroxypropan-2-yl]-2-[(2S)-2-methoxypropoxy]-6-[4-(4-methoxy-1H-pyrrolo[2,3-b]pyridin-3-yl)piperidin-1-yl]pyrimidine-4-carboxamide | 499.1; (400 MHz, CDCl$_3$) δ ppm 9.85 (br s, 1 H), 8.17 (d, J = 5.6 Hz, 1 H), 7.98 (d, J = 7.6 Hz, 1 H), 7.12 (s, 1 H), 6.88 (s, 1 H), 6.52 (d, J = 5.6 Hz, 1 H), 5.02 (br s, 2 H), 4.35-4.38 (m, 1 H), 4.22-4.26 (m, 2 H), 3.96 (s, 3 H), 3.73-3.78 (m, 2 H), 3.66-3.68 (m, 1 H), 3.45 (s, 3 H), 3.31 (t, J = 7.2 Hz, 1 H), 3.09-3.10 (m, 2 H), 2.16 (d, J = 13.4 Hz, 2 H), 1.65 (q, J = 3.2 Hz, 2 H), 1.28-1.29 (m, 6 H). |
| 472* (D) | 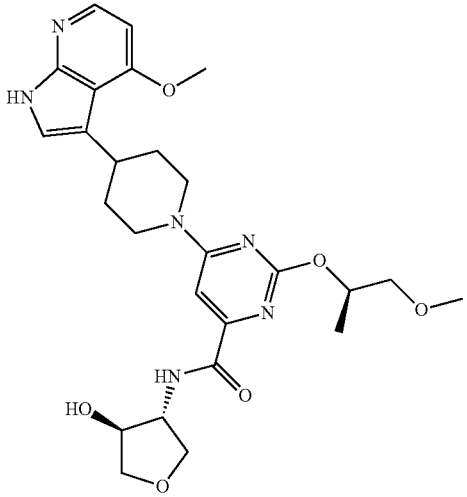 [SMILES: COC[C@@H](C)Oc1nc(C(=O)N[C@@H]2COC[C@H]2O)cc(N2CCC(c3c[nH]c4nccc(OC)c34)CC2)n1] | N-[(3R,4S)-4-hydroxytetrahydrofuran-3-yl]-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 527.3; (400 MHz, CDCl$_3$) δ ppm 11.03 (br s, 1 H), 8.39 (s, 1 H), 8.05 (d, J = 6.8 Hz, 1 H), 7.09 (s, 1 H), 6.93 (s, 1 H), 6.58 (d, J = 4.8 Hz, 1 H), 5.29-5.33 (m, 1 H), 4.89 (br s, 2 H), 4.34-4.37 (m, 1 H), 4.21-4.22 (m, 1 H), 4.21-4.21 (m, 1 H), 4.00 (s, 3 H), 3.80-3.81 (m, 2 H), 3.75-3.77 (m, 1 H), 3.51-3.53 (m, 1 H), 3.41 (s, 3 H), 3.26-3.27 (m, 1 H), 3.09 (br s, 2 H), 2.13 (d, J = 12.6 Hz, 2 H), 1.66 (d, J = 8.0 Hz, 2 H), 1.38 (d, J = 6.0 Hz, 3 H). |
| 473*** (D) | 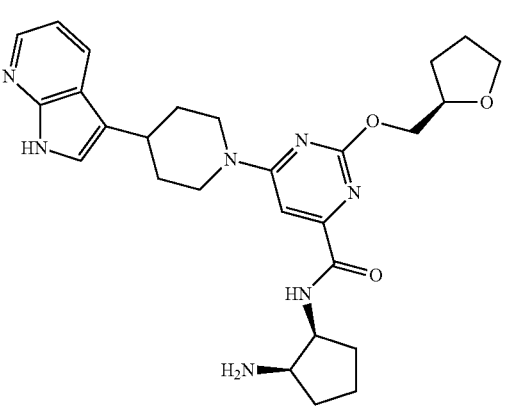 [SMILES: N[C@@H]1CCC[C@@H]1NC(=O)c1cc(N2CCC(c3c[nH]c4ncccc34)CC2)nc(OC[C@H]2CCCO2)n1] | N-[(cis)-2-aminocyclopentyl]-6-[4-(1H-pyrrolo[2,3-b]pyridin-3-yl)piperidin-1-yl]-2-[(2R)-tetrahydrofuran-2-ylmethoxy]pyrimidine-4-carboxamide | 506.1; (400 MHz, CD$_3$OD) δ ppm 8.17 (d, J = 3.6 Hz, 1 H), 8.09 (d, J = 6.4 Hz, 1 H), 7.21 (s, 1 H), 7.07-7.12 (m, 2 H), 4.38 (br s, 1 H), 4.27-4.39 (m, 4 H), 3.81-3.95 (m, 2 H), 3.45-3.46 (m, 1 H), 3.24 (br s, 3 H), 1.31-2.21 (m, 14 H). |

TABLE 1-continued

| Ex. # | Structure | Compound Name | LRMS m/z (M + H)+; and 1H NMR |
|---|---|---|---|
| 474* (E) | 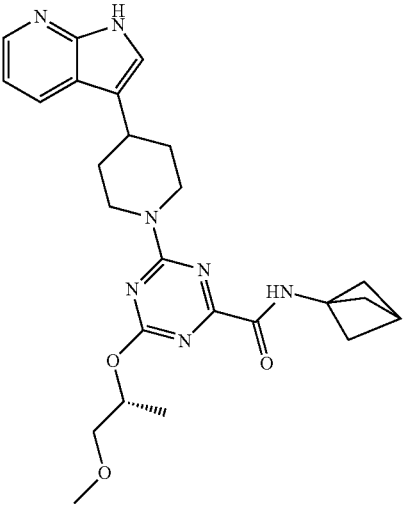 [SMILES: COC[C@@H](C)Oc1nc(C(=O)NC23CC(C2)C3)nc(N2CCC(c3c[nH]c4ncccc34)CC2)n1] | N-(bicyclo[1.1.1]pent-1-yl)-4-{[(2R)-1-methoxypropan-2-yl]oxy}-6-[4-(1H-pyrrolo[2,3-b]pyridin-3-yl)piperidin-1-yl]-1,3,5-triazine-2-carboxamide | 478.1; (400 MHz, CDCl$_3$) δ ppm 8.84 (s, 1 H), 8.31 (d, J = 4.4 Hz, 1 H), 8.17 (s, 1 H), 7.95 (d, J = 7.2 Hz, 1 H), 7.06-7.09 (m, 2 H), 5.42-5.44 (m, 1 H), 5.16 (d, J = 13.8 Hz, 1 H), 4.92 (d, J = 14.0 Hz, 1 H), 3.61-3.66 (m, 1 H), 3.49-3.52 (m, 1 H), 3.40 (s, 3 H), 3.09-3.12 (m, 3 H), 2.48 (s, 1 H), 2.13-2.17 (m, 8 H), 1.70-1.74 (m, 2 H), 1.38 (d, J = 6.4 Hz, 3H). |
| 475* (E) | 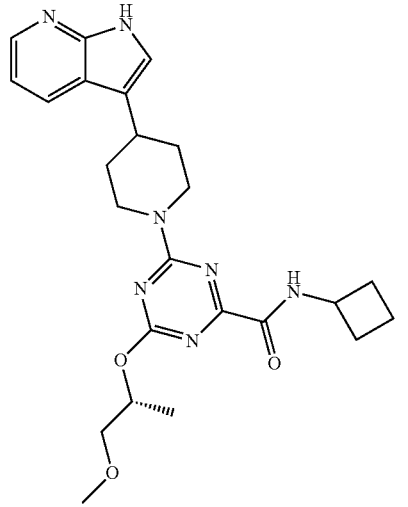 [SMILES: COC[C@@H](C)Oc1nc(C(=O)NC2CCC2)nc(N2CCC(c3c[nH]c4ncccc34)CC2)n1] | N-cyclobutyl-4-{[(2R)-1-methoxypropan-2-yl]oxy}-6-[4-(1H-pyrrolo[2,3-b]pyridin-3-yl)piperidin-1-yl]-1,3,5-triazine-2-carboxamide | 488.1 [M + Na]+; (400 MHz, CDCl$_3$) δ ppm 9.28 (s, 1 H), 8.31 (d, J = 4.4 Hz, 1 H), 7.94 (d, J = 7.2 Hz, 1 H), 7.06-7.09 (m, 2 H), 5.42 (d, J = 4.8 Hz, 1 H), 5.15 (d, J = 13.2 Hz, 1 H), 4.92 (d, J = 12.2 Hz, 1 H), 4.51-4.57 (m, 1 H), 3.63-3.65 (m, 1 H), 3.50-3.53 (m, 1 H), 3.41 (s, 3 H), 3.09-3.12 (m, 3 H), 2.38 (br s, 2 H), 2.12-2.17 (m, 2 H), 1.97-2.00 (m, 2 H), 1.70-1.78 (m, 4 H), 1.39 (d, J = 6.4 Hz, 3 H). |
| 476* (E) | 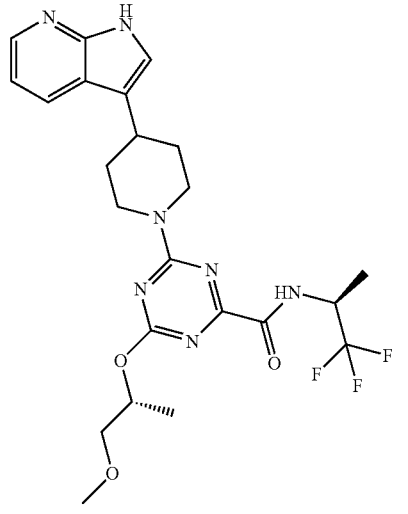 [SMILES: COC[C@@H](C)Oc1nc(C(=O)N[C@@H](C)C(F)(F)F)nc(N2CCC(c3c[nH]c4ncccc34)CC2)n1] | 4-{[(2R)-1-methoxypropan-2-yl]oxy}-6-[4-(1H-pyrrolo[2,3-b]pyridin-3-yl)piperidin-1-yl]-N-[(2S)-1,1,1-trifluoropropan-2-yl]-1,3,5-triazine-2-carboxamide | 508.0; (400 MHz, CDCl$_3$) δ ppm 9.48 (s, 1 H), 8.32 (d, J = 3.6 Hz, 1 H), 7.95 (d, J = 5.6 Hz, 2 H), 7.06-7.09 (m, 2 H), 5.42-5.43 (m, 1 H), 5.12 (d, J = 12.8 Hz, 1 H), 4.84-4.93 (m, 2 H), 3.62-3.67 (m, 1 H), 3.52-3.54 (m, 1 H), 3.41 (s, 3 H), 3.11-3.17 (m, 3 H), 2.14 (br s, 2 H), 1.72-1.77 (m, 2 H), 1.41 (d, J = 7.2 Hz, 6 H). |

TABLE 1-continued

| Ex. # | Structure | Compound Name | LRMS m/z (M + H)+; and 1H NMR |
|---|---|---|---|
| 477* (E) | 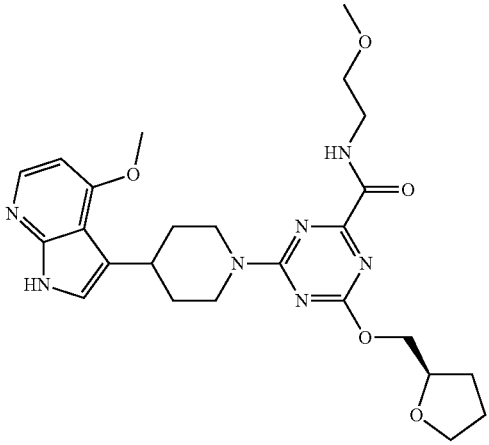 [SMILES: COCCNC(=O)c1nc(OC[C@H]2CCCO2)nc(N2CCC(c3c[nH]c4nccc(OC)c34)CC2)n1] | N-(2-methoxyethyl)-4-[4-(4-methoxy-1H-pyrrolo[2,3-b]pyridin-3-yl)piperidin-1-yl]-6-[(2R)-tetrahydrofuran-2-ylmethoxy]-1,3,5-triazine-2-carboxamide | 512.0; (400 MHz, CDCl$_3$) δ ppm 8.90 (br s, 1 H), 8.18 (d, J = 5.2 Hz, 1 H), 8.10-8.11 (m, 1 H), 6.88 (s, 1 H), 6.53 (d, J = 5.6 Hz, 1 H), 5.10 (d, J = 13.6 Hz, 1 H), 4.92 (d, J = 13.2 Hz, 1 H), 4.36-4.41 (m, 3 H), 3.97 (s, 3 H), 3.61-3.82 (m, 3 H), 3.53-3.58 (m, 2 H), 3.38 (s, 3 H), 3.25-3.31 (m, 1 H), 3.09 (q, J = 8.0 Hz, 2 H), 1.95-2.19 (m, 5 H), 1.61-1.79 (m, 3 H). |
| 478* (D) | 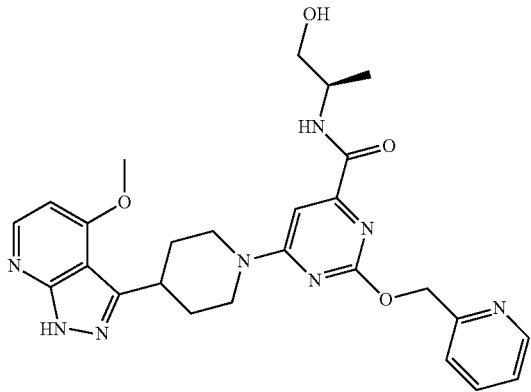 [SMILES: COc1ccnc2[nH]nc(C3CCN(c4cc(C(=O)N[C@H](C)CO)nc(OCc5ccccn5)n4)CC3)c12] | N-[(2R)-1-hydroxypropan-2-yl]-6-[4-(4-methoxy-1H-pyrazolo[3,4-b]pyridin-3-yl)piperidin-1-yl]-2-(pyridin-2-ylmethoxy)pyrimidine-4-carboxamide | 519.1; (400 MHz, CDCl$_3$) δ ppm 12.01 (br s, 1 H), 8.56 (d, J = 4.0 Hz, 1 H), 8.43 (br s, 1 H), 8.01 (d, J = 3.6 Hz, 1 H), 7.70 (t, J = 3.6 Hz, 1 H), 7.65 (d, J = 3.6 Hz, 1 H), 7.18-7.19 (m, 1 H), 7.12 (s, 1 H), 6.49 (d, J = 5.2 Hz, 1 H), 5.51 (s, 2 H), 4.51 (br s, 1 H), 4.18-4.0 (m, 1 H), 3.96 (s, 3 H), 3.67-3.75 (m, 3 H), 3.36-3.45 (m, 1 H), 3.09-3.17 (m, 2 H), 1.92-2.09 (m, 4 H), 1.27 (t, J = 6.4 Hz, 3 H). |
| 479* (E) | 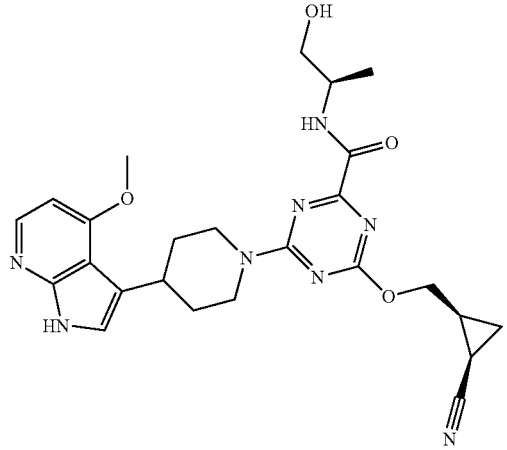 [SMILES: COc1ccnc2[nH]cc(C3CCN(c4nc(OC[C@H]5C[C@H]5C#N)nc(C(=O)N[C@H](C)CO)n4)CC3)c12] | 4-{[(1S,2R)-2-cyanocyclopropyl]methoxy}-N-[(2R)-1-hydroxypropan-2-yl]-6-[4-(4-methoxy-1H-pyrrolo[2,3-b]pyridin-3-yl)piperidin-1-yl]-1,3,5-triazine-2-carboxamide | 507.1; (400 MHz, CDCl$_3$) δ ppm 9.19 (br s, 1 H), 8.17 (d, J = 5.2 Hz, 1 H), 7.93 (d, J = 8.0 Hz, 1 H), 6.38 (s, 1 H), 6.53 (d, J = 5.6 Hz, 1 H), 5.10 (d, J = 11.6 Hz, 1 H), 4.89 (d, J = 12.8 Hz, 1 H), 4.50-4.58 (m, 2 H), 4.19-4.22 (m, 1 H), 3.97 (s, 3 H), 3.76-3.78 (m, 1 H), 3.67-3.69 (m, 1 H), 3.29-3.38 (m, 1 H), 3.07 (q, J = 12.8 Hz, 2 H), 2.09-2.18 (m, 2 H), 1.85-1.89 (m, 1 H), 1.55-1.73 (m, 3 H), 1.32-1.34 (m, 1 H), 1.31 (d, J = 6.8 Hz, 3 H), 1.13-1.15 (m, 1 H). |

TABLE 1-continued

| Ex. # | Structure | Compound Name | LRMS m/z (M + H)+; and 1H NMR |
|---|---|---|---|
| 480* (E) | 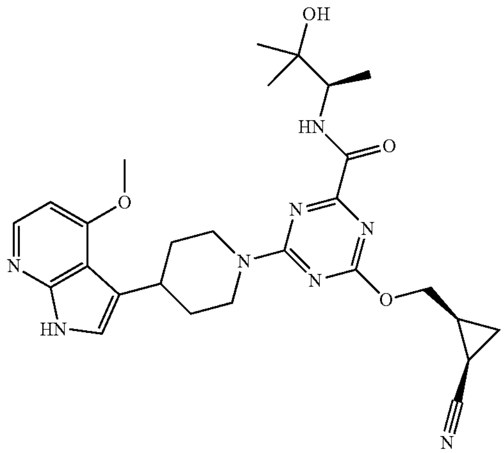 [SMILES: COc1ccnc2[nH]cc(C3CCN(c4nc(OC[C@H]5C[C@H]5C#N)nc(C(=O)N[C@H](C)C(C)(C)O)n4)CC3)c12] | 4-{[(1S,2R)-2-cyanocyclopropyl]methoxy}-N-[(2R)-3-hydroxy-3-methylbutan-2-yl]-6-[4-(4-methoxy-1H-pyrrolo[2,3-b]pyridin-3-yl)piperidin-1-yl]-1,3,5-triazine-2-carboxamide | 535.1; (400 MHz, CDCl$_3$) δ ppm 9.10 (s, 1 H), 8.17 (d, J = 5.2 Hz, 1 H), 8.03 (d, J = 8.8 Hz, 1 H), 6.88 (s, 1 H), 6.56 (d, J = 5.6 Hz, 1 H), 5.11 (d, J = 12.4 Hz, 1 H), 4.93 (d, J = 14.0 Hz, 1 H), 4.52-4.61 (m, 2 H), 4.10-4.14 (m, 1 H), 3.98 (s, 3 H), 3.30 (t, J = 11.2 Hz, 1 H), 3.12 (q, J = 14.0 Hz, 2 H), 2.18-2.23 (m, 2 H), 1.65-1.83 (m, 4 H), 1.34-1.35 (m, 1 H), 1.26 (t, J = 6.4 Hz, 9 H), 1.13-1.15 (m, 1 H). |
| 481* (D) | 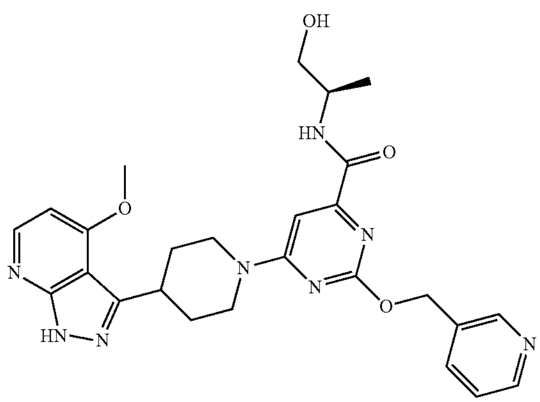 [SMILES: COc1ccnc2[nH]nc(C3CCN(c4cc(C(=O)N[C@H](C)CO)nc(OCc5cccnc5)n4)CC3)c12] | N-[(2R)-1-hydroxypropan-2-yl]-6-[4-(4-methoxy-1H-pyrazolo[3,4-b]pyridin-3-yl)piperidin-1-yl]-2-(pyridin-3-ylmethoxy)pyrimidine-4-carboxamide | 519.2; (400 MHz, CDCl$_3$) δ ppm 11.82 (br s, 1 H), 8.75 (d, J = 2.0 Hz, 1 H), 8.54 (d, J = 5.6 Hz, 1 H), 8.41 (d, J = 5.2 Hz, 1 H), 7.90 (d, J = 7.6 Hz, 1 H), 7.84 (d, J = 8.0 Hz, 1 H), 7.28-7.33 (m, 1 H), 7.14 (s, 1 H), 6.49 (d, J = 5.6 Hz, 1 H), 5.40 (s, 2 H), 4.48 (br s, 1 H), 4.20-4.22 (m, 1 H), 3.96 (s, 3 H), 3.50-3.73 (m, 4 H), 3.15-3.26 (m, 2 H), 1.94-2.13 (m, 4 H), 1.29 (d, J = 6.8 Hz, 3 H). |
| 482* (E) | 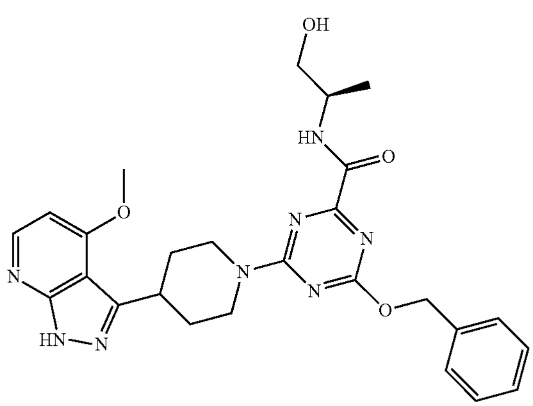 [SMILES: COc1ccnc2[nH]nc(C3CCN(c4nc(OCc5ccccc5)nc(C(=O)N[C@H](C)CO)n4)CC3)c12] | 4-(benzyloxy)-N-[(2R)-1-hydroxypropan-2-yl]-6-[4-(4-methoxy-1H-pyrazolo[3,4-b]pyridin-3-yl)piperidin-1-yl]-1,3,5-triazine-2-carboxamide | 519.2; (400 MHz, DMSO-d$_6$) δ ppm 13.18 (s, 1 H), 8.32 (d, J = 4.8 Hz, 1 H), 7.35-7.61 (m, 5 H), 6.68 (d, J = 4.8 Hz, 1 H), 5.44 (s, 2 H), 4.74-4.85 (m, 3 H), 3.42-3.46 (m, 3 H), 3.23-3.41 (m, 2 H), 2.07 (d, J = 11.6 Hz, 2 H), 1.74-1.83 (m, 2 H), 1.13 (d, J = 6.8 Hz, 3 H). |

TABLE 1-continued

| Ex. # | Structure | Compound Name | LRMS m/z (M + H)⁺; and ¹H NMR |
|---|---|---|---|
| 483* (E) | 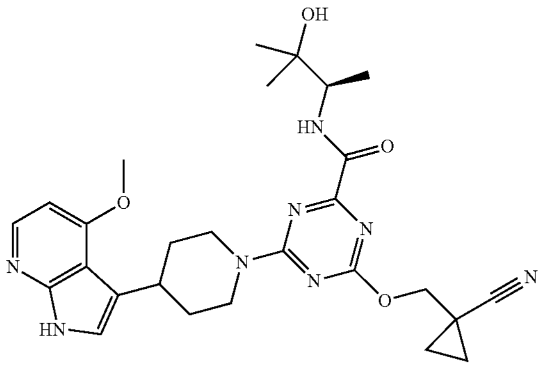 [SMILES: COc1ccnc2[nH]cc(C3CCN(c4nc(OCC5(C#N)CC5)nc(C(=O)N[C@H](C)C(C)(C)O)n4)CC3)c12] | 4-[(1-cyanocyclopropyl)methoxy]-N-[(2R)-3-hydroxy-3-methylbutan-2-yl]-6-[4-(4-methoxy-1H-pyrrolo[2,3-b]pyridin-3-yl)piperidin-1-yl]-1,3,5-triazine-2-carboxamide | 535.1; (400 MHz, CDCl$_3$) δ ppm 8.99 (br s, 1 H), 8.17 (d, J = 5.6 Hz, 1 H), 8.03 (d, J = 8.4 Hz, 1 H), 6.88 (s, 1 H), 6.53 (d, J = 5.6 Hz, 1 H), 5.10 (d, J = 11.6 Hz, 1 H), 4.75 (d, J = 11.4 Hz, 1 H), 4.51 (d, J = 3.2 Hz, 1 H), 4.48 (d, J = 2.8 Hz, 1 H), 4.09-4.10 (m, 1 H), 3.98 (s, 3 H), 3.29-3.35 (m, 1 H), 3.06-3.16 (m, 2 H), 2.20 (d, J = 12.8 Hz, 2 H), 1.42-1.67 (m, 2 H), 1.41-1.42 (m, 2 H), 1.27-1.28 (m, 9 H), 1.19-1.21 (m, 2 H). |
| 484* (E) | 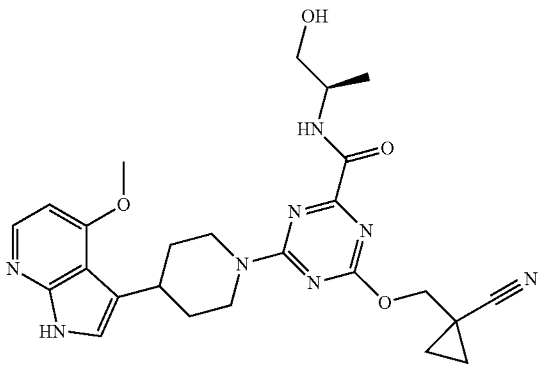 [SMILES: COc1ccnc2[nH]cc(C3CCN(c4nc(OCC5(C#N)CC5)nc(C(=O)N[C@H](C)CO)n4)CC3)c12] | 4-[(1-cyanocyclopropyl)methoxy]-N-[(2R)-1-hydroxypropan-2-yl]-6-[4-(4-methoxy-1H-pyrrolo[2,3-b]pyridin-3-yl)piperidin-1-yl]-1,3,5-triazine-2-carboxamide | 507.0; (400 MHz, CDCl$_3$) δ ppm 9.40 (br s, 1 H), 8.16 (d, J = 5.6 Hz, 1 H), 7.95 (d, J = 6.8 Hz, 1 H), 6.88 (s, 1 H), 6.52 (d, J = 5.6 Hz, 1 H), 5.10 (d, J = 12.8 Hz, 1 H, 4.90 (d, J = 12.8 Hz, 1 H), 4.46-4.49 (m, 1 H), 4.35 (d, J = 11.6 Hz, 1 H), 4.28 (br s, 1 H), 3.97 (s, 3 H, 3.69-3.76 (m, 2 H), 3.31-3.34 (m, 1 H), 3.05-3.14 (m, 2 H), 2.18-2.21 (m, 2 H), 1.63-1.66 (m, 2 H), 1.30 (d, J = 6.8 Hz, 3 H), 1.19-1.21 (m, 2 H). |
| 485* (E) | 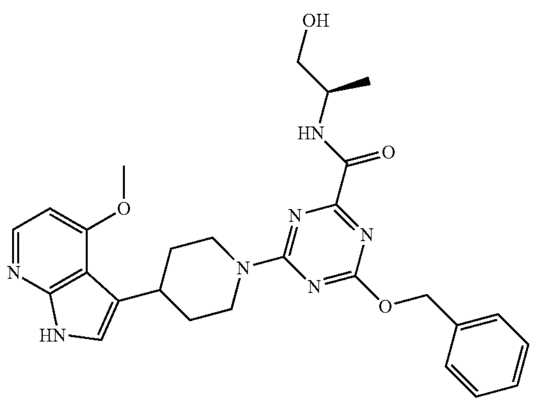 [SMILES: COc1ccnc2[nH]cc(C3CCN(c4nc(OCc5ccccc5)nc(C(=O)N[C@H](C)CO)n4)CC3)c12] | 4-(benzyloxy)-N-[(2R)-1-hydroxypropan-2-yl]-6-[4-(4-methoxy-1H-pyrrolo[2,3-b]pyridin-3-yl)piperidin-1-yl]-1,3,5-triazine-2-carboxamide | 518.2; (400 MHz, DMSO-d$_6$) δ ppm 11.28 (s, 1 H), 8.31 (d, J = 8.4 Hz, 1 H), 8.05 (d, J = 5.6 Hz, 1 H), 7.34-7.48 (m, 5 H), 7.03 (s, 1 H), 5.60 (d, J = 5.6 Hz, 1 H), 5.42 (s, 2 H), 4.82-4.88 (m, 3 H), 3.89-3.95 (m, 1 H), 3.45 (s, 3 H), 3.34-3.45 (m, 3 H), 3.13 (t, J = 12.0 Hz, 2 H), 2.06-2.09 (m, 2 H), 1.52-1.60 (m, 2 H), 1.12 (d, J = 6.4 Hz, 3 H). |
| 486** (D) | 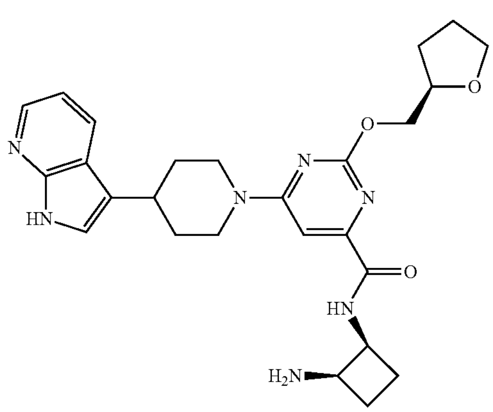 [SMILES: N[C@@H]1CC[C@@H]1NC(=O)c1cc(N2CCC(c3c[nH]c4ncccc34)CC2)nc(OC[C@H]2CCCO2)n1] | N-[(cis)-2-aminocyclobutyl]-6-[4-(1H-pyrrolo[2,3-b]pyridin-3-yl)piperidin-1-yl]-2-[(2R)-tetrahydrofuran-2-ylmethoxy]pyrimidine-4-carboxamide | 491.9; (400 MHz, CD$_3$OD) δ ppm (HCl salt) 8.90 (d, J = 7.6 Hz, 1 H), 8.45 (d, J = 5.6 Hz, 1 H), 7.77 (br s, 1 H), 7.61 (br s, 2 H), 4.53-4.62 (m, 2 H), 4.33 (br s, 1 H), 4.07 (br s, 1 H), 3.91-3.93 (m, 2 H), 3.50 (br s, 2 H), 1.80-2.51 (m, 13 H). |

TABLE 1-continued

| Ex. # | Structure | Compound Name | LRMS m/z (M + H)+; and ¹H NMR |
|---|---|---|---|
| 487** (D) | 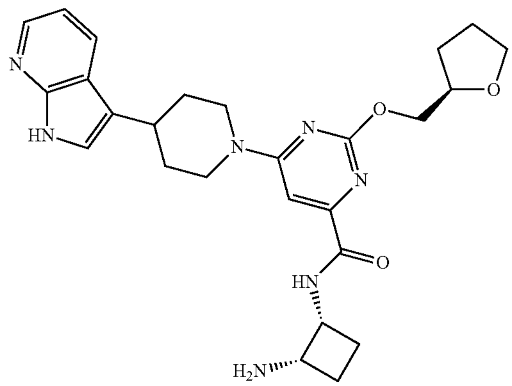 [SMILES: N[C@H]1CC[C@H]1NC(=O)c1cc(N2CCC(c3c[nH]c4ncccc34)CC2)nc(OC[C@H]2CCCO2)n1] | N-[(cis)-2-aminocyclobutyl]-6-[4-(1H-pyrrolo[2,3-b]pyridin-3-yl)piperidin-1-yl]-2-[(2R)-tetrahydrofuran-2-ylmethoxy]pyrimidine-4-carboxamide | 492.0; (400 MHz, CD₃OD) δ ppm (HCl salt) 8.93 (br s, 1 H), 8.44 (d, J = 5.6 Hz, 1 H), 7.90 (br s, 1 H), 7.62 (br s, 2 H), 5.21 (br s, 1 H), 4.56-4.59 (m, 2 H), 4.33 (br s, 1 H), 4.06 (br s, 1 H), 3.82-3.91 (m, 2 H), 3.52-3.63 (m, 3 H), 1.79-2.39 (m, 12 H). |
| 488* (D) | 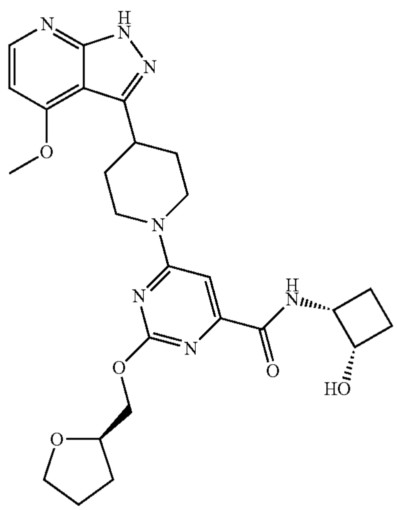 [SMILES: COc1ccnc2[nH]nc(C3CCN(c4cc(C(=O)N[C@@H]5CC[C@@H]5O)nc(OC[C@H]5CCCO5)n4)CC3)c12] | N-[(1R,2S)-2-hydroxycyclobutyl]-6-[4-(4-methoxy-1H-pyrazolo[3,4-b]pyridin-3-yl)piperidin-1-yl]-2-[(2R-tetrahydrofuran-2-ylmethoxy]pyrimidine-4-carboxamide | 524.1; (400 MHz, CDCl₃) δ ppm 11.22 (br s, 1 H), 8.36-8.40 (m, 2 H), 7.12 (s, 1 H), 6.50 (d, J = 5.6 Hz, 1 H), 4.41-4.59 (m, 2 H), 4.27-4.40 (m, 3 H), 3.97 (s, 3 H), 3.93-3.96 (m, 1 H), 3.81-3.84 (m, 1 H), 3.42-3.48 (m, 1 H), 3.08-3.19 (m, 1 H), 1.63-2.23 (m, 12 H). |
| 489* (D) | 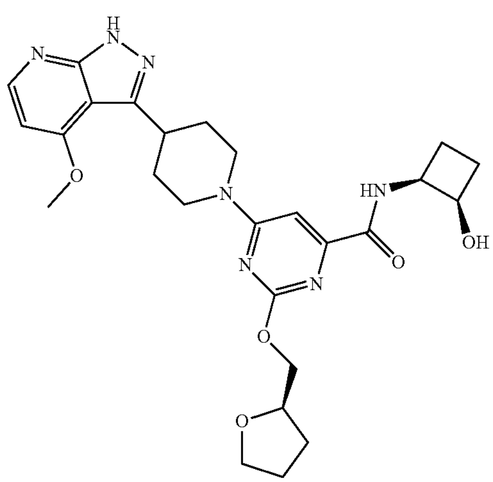 [SMILES: COc1ccnc2[nH]nc(C3CCN(c4cc(C(=O)N[C@H]5CC[C@H]5O)nc(OC[C@H]5CCCO5)n4)CC3)c12] | N-[(1S,2R)-2-hydroxycyclobutyl]-6-[4-(4-methoxy-1H-pyrazolo[3,4-b]pyridin-3-yl)piperidin-1-yl]-2-[(2R)-tetrahydrofuran-2-ylmethoxy]pyrimidine-4-carboxamide | 524.1; (400 MHz, CDCl₃) δ ppm 11.39 (br s, 1 H), 8.35-8.41 (m, 2 H), 7.12 (s, 1 H), 6.49 (d, J = 5.6 Hz, 1 H), 4.51-4.59 (m, 1 H), 4.38-4.41 (m, 1 H), 4.30-4.37 (m, 2 H), 3.96 (s, 3 H), 3.94-3.96 (m, 1 H), 3.81-3.82 (m, 1 H), 3.43-3.47 (m, 1 H), 3.16-3.18 (m, 1 H), 2.92 (br s, 1 H), 1.67-2.28 (m, 13 H). |

TABLE 1-continued

| Ex. # | Structure | Compound Name | LRMS m/z (M + H)+; and 1H NMR |
|---|---|---|---|
| 490* (D) | 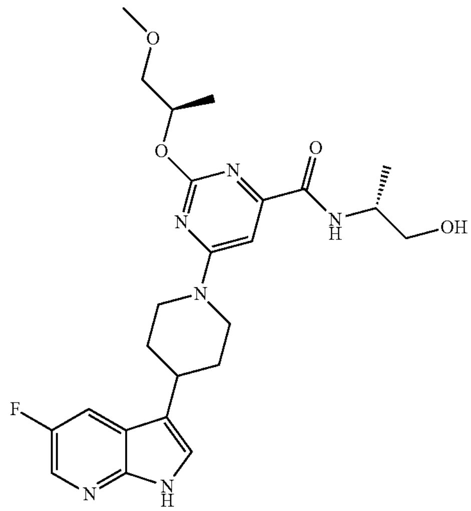 [SMILES: COC[C@@H](C)Oc1nc(C(=O)N[C@H](C)CO)cc(N2CCC(c3c[nH]c4ncc(F)cc34)CC2)n1] | 6-[4-(5-fluoro-1H-pyrrolo[2,3-b]pyridin-3-yl)piperidin-1-yl]-N-[(2R)-1-hydroxypropan-2-yl]-2-{[(2R)-1-methoxypropan-2-yl]oxy}pyrimidine-4-carboxamide | 487.1; (400 MHz, CDCl$_3$) δ ppm 8.85 (br s, 1 H), 8.19 (s, 1 H), 7.97 (d, J = 7.2 Hz, 1 H), 7.62 (d, J = 6.4 Hz, 1 H), 7.14 (s, 2 H), 5.31-5.35 (m, 1 H), 4.71 (br s, 1 H), 4.20-4.22 (m, 1 H), 3.66-3.70 (m, 3 H), 3.51-3.55 (m, 1 H), 3.50 (s, 3 H), 3.08-3.42 (m, 4 H), 2.13 (d, J = 12.8 Hz, 2 H), 1.55-1.76 (m, 2 H), 1.39 (d, J = 6.4 Hz, 3 H), 1.27 (d, J = 7.2 Hz, 3 H). |
| 491* (D) | 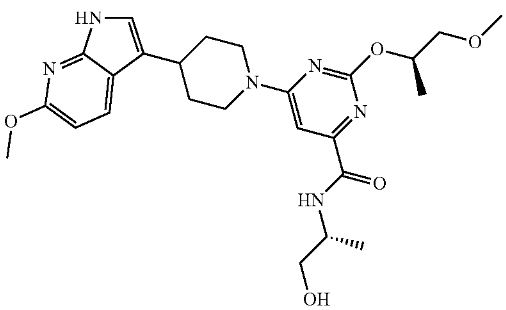 | N-[(2R)-1-hydroxypropan-2-yl]-2-{[(2R)-1-methoxypropan-2-yl]oxy}-6-[4-(6-methoxy-1H-pyrrolo[2,3-b]pyridin-3-yl)piperidin-1-yl]pyrimidine-4-carboxamide | 499.2; (400 MHz, CDCl$_3$) δ ppm 8.36 (br s, 1 H), 7.96 (d, J = 4.0 Hz, 1 H), 7.79 (d, J = 8.4 Hz, 1 H), 7.10 (s, 1 H), 6.81 (d, J = 1.6 Hz, 1 H), 6.56 (d, J = 8.8 Hz, 1 H), 5.29-5.35 (m, 1 H), 4.63 (br s, 2 H), 4.21-4.23 (m, 1H), 3.95 (s, 3 H), 3.64-3.72 (m, 3 H), 3.51-3.52 (m, 1 H), 3.42 (s, 3 H), 3.07-3.10 (m, 3 H), 2.92 (br s, 1 H), 2.12 (d, J = 12.8 Hz, 2 H), 1.69-1.75 (m, 2 H), 1.38 (d, J = 6.4 Hz, 3 H), 1.27 (d, J = 6.4 Hz, 3 H). |
| 492* (D) | 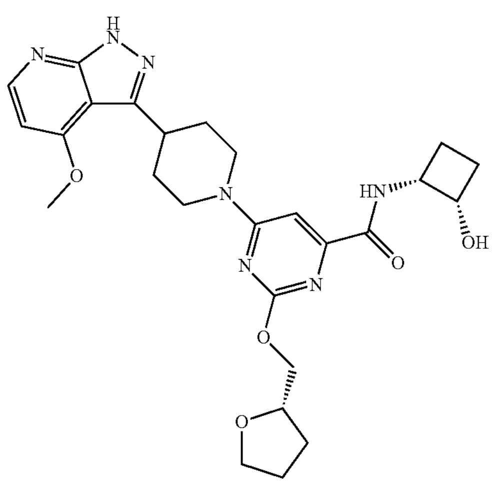 [SMILES: COc1ccnc2[nH]nc(C3CCN(c4cc(C(=O)N[C@@H]5CC[C@@H]5O)nc(OC[C@@H]5CCCO5)n4)CC3)c12] | N-[(1R,2S)-2-hydroxycyclobutyl]-6-[4-(4-methoxy-1H-pyrazolo[3,4-b]pyridin-3-yl)piperidin-1-yl]-2-[(2S)-tetrahydrofuran-2-ylmethoxy]pyrimidine-4-carboxamide | 524.1; (400 MHz, CDCl$_3$) δ ppm 10.76 (br s, 1 H), 8.35-8.40 (m, 2 H), 7.12 (s, 1 H), 6.50 (d, J = 5.6 Hz, 1 H), 4.29-4.58 (m, 4 H), 3.97 (s, 3 H), 3.81-3.95 (m, 2 H), 3.46-3.49 (m, 1 H), 3.17-3.22 (m, 2 H), 1.59-2.43 (m, 11 H). |

TABLE 1-continued

| Ex. # | Structure | Compound Name | LRMS m/z (M + H)+; and 1H NMR |
|---|---|---|---|
| 493* (D) | 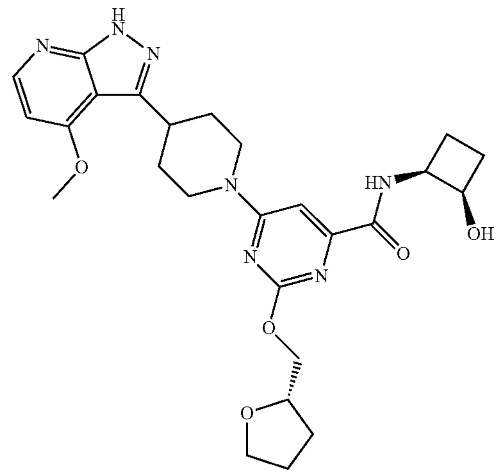 [SMILES: COc1ccnc2[nH]nc(C3CCN(c4cc(C(=O)N[C@H]5CC[C@H]5O)nc(OC[C@@H]5CCCO5)n4)CC3)c12] | N-[(1S,2R)-2-hydroxycyclobutyl]-6-[4-(4-methoxy-1H-pyrazolo[3,4-b]pyridin-3-yl)piperidin-1-yl]-2-[(2S)-tetrahydrofuran-2-ylmethoxy]pyrimidine-4-carboxamide | 524.1; (400 MHz, CDCl$_3$) δ ppm 10.82 (br s, 1 H), 8.37-8.40 (m, 2 H), 7.10 (s, 1 H), 6.48 (d, J = 5.6 Hz, 1 H), 4.28-4.58 (m, 4 H), 3.98 (s, 3 H), 3.81-3.93 (m, 2 H), 3.46-3.49 (m, 1 H), 3.17-3.22 (m, 2 H), 1.26-2.26 (m, 11 H). |
| 494* (D) | 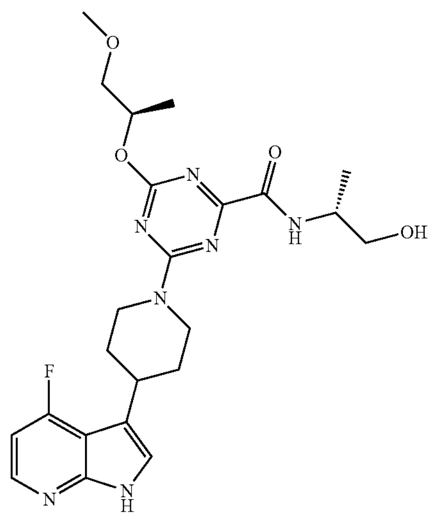 [SMILES: COC[C@@H](C)Oc1nc(C(=O)N[C@H](C)CO)nc(N2CCC(c3c[nH]c4nccc(F)c34)CC2)n1] | 6-[4-(4-fluoro-1H-pyrrolo[2,3-b]pyridin-3-yl)piperidin-1-yl]-N-[(2R)-1-hydroxypropan-2-yl]-2-{[(2R)-1-methoxypropan-2-yl]oxy}pyrimidine-4-carboxamide | 487.1; (400 MHz, CDCl$_3$) δ ppm 8.82 (br s, 1 H), 8.22-8.23 (m, 1 H), 7.96 (d, J = 8.4 Hz, 1 H), 7.11 (s, 1 H), 7.00 (s, 1 H), 6.76-6.78 (m, 1 H), 5.31-5.35 (m, 1 H), 4.62 (br s, 2 H), 4.17-4.19 (m, 1 H), 3.66-3.72 (m, 3 H), 3.52-3.53 (m, 1 H), 3.49 (s, 3 H), 3.22-3.49 (m, 3 H), 2.88-289 (m, 1 H), 2.17 (d, J = 13.2 Hz, 2 H), 1.66-1.69 (m, 2 H), 1.38 (d, J = 6.4 Hz, 3 H), 1.26 (d, J = 6.2 Hz, 3 H). |
| 495*** (D) | 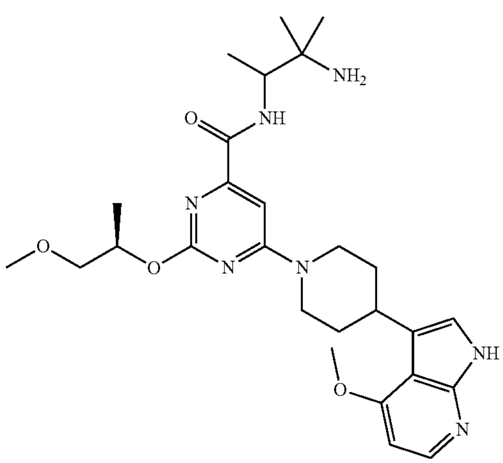 [SMILES: COC[C@@H](C)Oc1nc(C(=O)NC(C)C(C)(C)N)cc(N2CCC(c3c[nH]c4nccc(OC)c34)CC2)n1] | N-(3-amino-3-methylbutan-2-yl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 526.1; (400 MHz, CD$_3$OD) δ ppm 8.66 (d, J = 6.0 Hz, 1 H), 7.10 (s, 1 H), 6.99 (s, 1 H), 6.66 (d, J = 6.0 Hz, 1 H), 5.36-5.40 (m, 1 H), 4.61 (br s, 2 H), 4.12-4.14 (m, 1 H), 3.96 (s, 3 H), 3.58-3.64 (m, 3 H), 3.41 (s, 3 H), 3.17-3.23 (m, 2 H), 2.16 (d, J = 11.2 Hz, 2 H), 1.72-1.78 (m, 2 H), 1.26 (d, J = 6.8 Hz, 3 H), 1.21-1.25 (m, 6 H). |

TABLE 1-continued

| Ex. # | Structure | Compound Name | LRMS m/z (M + H)+; and 1H NMR |
|---|---|---|---|
| 496** (D) | 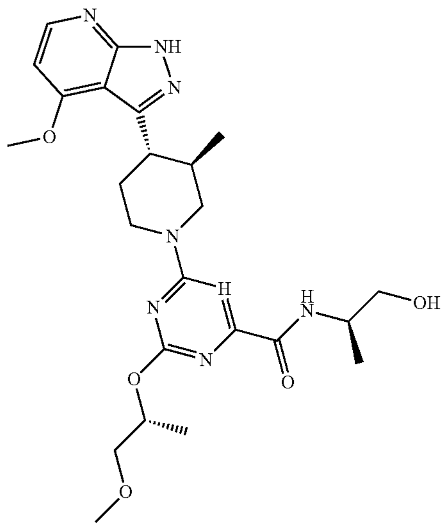 | N-[(2R)-1-hydroxypropan-2-yl]-2-{[(2R)-1-methoxypropan-2-yl]oxy}-6-[(3R,4S)-4-(4-methoxy-1H-pyrazolo[3,4-b]pyridin-3-yl)-3-methylpiperidin-1-yl]pyrimidine-4-carboxamide | 514.1; (400 MHz, DMSO-$d_6$) δ ppm 13.17 (br s, 1 H), 8.31 (d, J = 5.6 Hz, 1 H), 8.19 (d, J = 8.8 Hz, 1 H), 7.04 (s, 1 H), 6.63 (d, J = 5.6 Hz, 1 H), 5.26-5.31 (m, 1 H), 4.87-4.89 (m, 1 H), 3.96-3.98 (m, 1H), 3.78 (s, 3 H), 3.47-3.54 (m, 5 H), 3.43 (s, 3 H), 2.81-3.11 (m, 3 H), 2.13-2.14 (m, 1 H), 1.89-1.92 (m, 2 H), 1.26 (d, J = 6.4 Hz, 1 H), 1.14 (d, J = 6.8 Hz, 1 H), 0.74 (d, J = 6.4 Hz, 1 H). |
| 497** (D) | 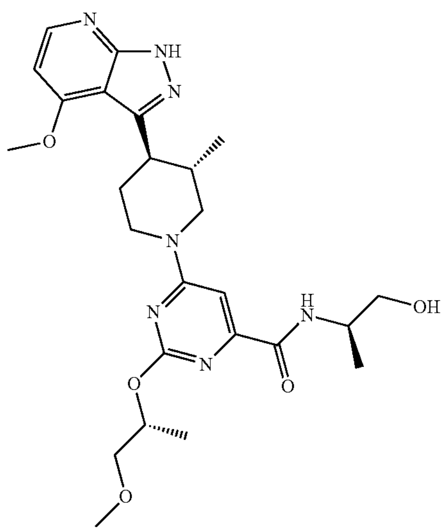 [SMILES: COC[C@@H](C)Oc1nc(C(=O)N[C@H](C)CO)cc(N2CC[C@@H](c3n[nH]c4nccc(OC)c34)[C@H](C)C2)n1] | N-[(2R)-1-hydroxypropan-2-yl]-2-{[(2R)-1-methoxypropan-2-yl]oxy}-6-[(3S,4R)-4-(4-methoxy-1H-pyrazolo[3,4-b]pyridin-3-yl)-3-methylpiperidin-1-yl]pyrimidine-4-carboxamide | 514.1; (400 MHz, DMSO-$d_6$) δ ppm 13.18 (br s, 1 H), 8.31 (d, J = 5.6 Hz, 1 H), 8.18 (d, J = 8.8 Hz, 1 H), 7.04 (s, 1 H), 6.63 (d, J = 5.6 Hz, 1 H), 5.26-5.29 (m, 1 H), 4.87-4.90 (m, 1 H), 3.97-3.99 (m, 1H), 3.78 (s, 3 H), 3.47-3.54 (m, 5 H), 3.46 (s, 3 H), 2.81-3.11 (m, 3 H), 2.13-2.15 (m, 1 H), 1.89-1.92 (m, 2 H), 1.26 (d, J = 6.4 Hz, 1 H), 1.14 (d, J = 6.8 Hz, 1 H), 0.74 (d, J = 6.4 Hz, 1 H). |
| 498** (D) | 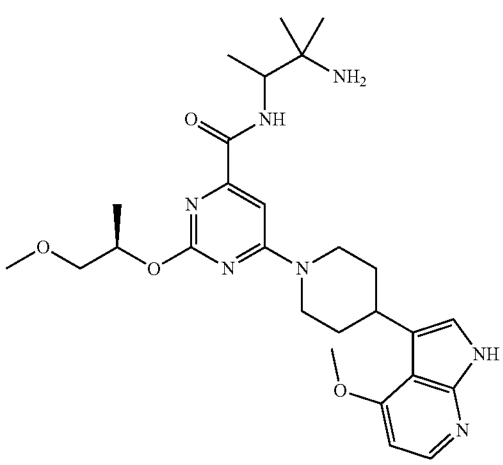 [SMILES: COC[C@@H](C)Oc1nc(C(=O)NC(C)C(C)(C)N)cc(N2CCC(c3c[nH]c4nccc(OC)c34)CC2)n1] | N-(3-amino-3-methylbutan-2-yl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 526.3; (400 MHz, CD$_3$OD) δ ppm 8.05 (d, J = 6.0 Hz, 1 H), 7.10 (s, 1 H), 6.99 (s, 1 H), 6.65 (d, J = 5.6 Hz, 1 H), 5.36-5.42 (m, 1 H), 4.66 (br s, 2 H), 4.04-4.06 (m, 1 H), 3.96 (s, 3 H), 3.62-3.70 (m, 3 H), 3.41 (s, 3 H), 3.18-3.23 (m, 2 H), 2.15 (d, J = 12.0 Hz, 2 H), 1.71 (q, J = 8.8 Hz, 2 H), 1.37 (d, J = 6.4 Hz, 3 H), 1.24 (d, J = 6.8 Hz, 3 H), 1.15 (d, J = 7.2 Hz, 3 H). |

TABLE 1-continued

| Ex. # | Structure | Compound Name | LRMS m/z (M + H)+; and 1H NMR |
|---|---|---|---|
| 499** (D) | 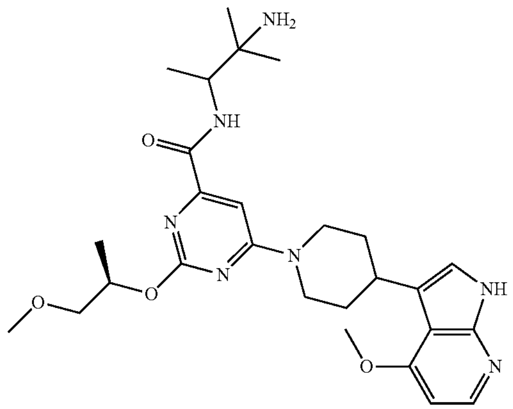 [SMILES: COC[C@@H](C)Oc1nc(C(=O)NC(C)C(C)(C)N)cc(N2CCC(c3c[nH]c4nccc(OC)c34)CC2)n1] | N-(3-amino-3-methylbutan-2-yl)-2-{[(2R)-1-methoxypropan-2-yl]oxy}-6-[4-(4-methoxy-1H-pyrrolo[2,3-b]pyridin-3-yl)piperidin-1-yl]pyrimidine-4-carboxamide | 526.3; (400 MHz, CD$_3$OD) δ ppm 8.05 (d, J = 5.6 Hz, 1 H), 7.10 (s, 1 H), 6.99 (s, 1 H), 6.66 (d, J = 6.0 Hz, 1 H), 5.36-5.42 (m, 1 H), 4.66 (br s, 2 H), 4.04-4.06 (m, 1 H), 3.96 (s, 3 H), 3.62-3.70 (m, 3 H), 3.41 (s, 3 H), 3.18-3.23 (m, 2 H), 2.15 (d, J = 13.4 Hz, 2 H), 1.68-1.77 (m, 2 H), 1.38 (d, J = 6.4 Hz, 3 H), 1.28-1.32 (m, 6 H). |
| 500** (D) | 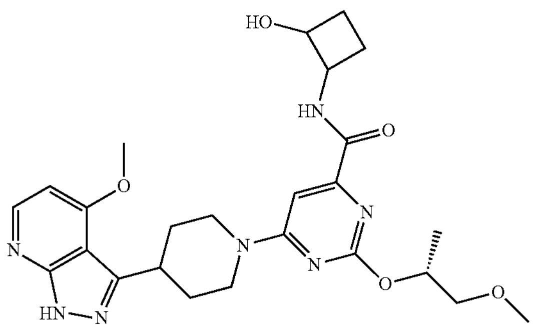 [SMILES: COC[C@@H](C)Oc1nc(C(=O)NC2CCC2O)cc(N2CCC(c3n[nH]c4nccc(OC)c34)CC2)n1] | (Trans)-N-(2-hydroxycyclobutyl)-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 512.3; (400 MHz, CDCl$_3$) δ ppm 11.94 (br s, 1 H), 8.42 (d, J = 5.2 Hz, 1 H), 8.15 (d, J = 4.4 Hz, 1 H), 7.11 (s, 1 H), 6.51 (d, J = 4.8 Hz, 1 H), 5.29-5.37 (m, 1 H), 4.42 (br s, 2 H), 3.99-4.05 (m, 1 H), 3.97 (s, 3 H), 3.66-3.67 (m, 1 H) 3.51-3.53 (m, 2 H), 3.49 (s, 3 H), 3.21-3.24 (m, 2 H), 1.99-2.14 (m, 6 H) 1.72-1.74 (m, 1 H), 1.44-1.48 (m, 1 H), 1.39 (d, J = 6.4 Hz, 3 H). |
| 501* (E) | 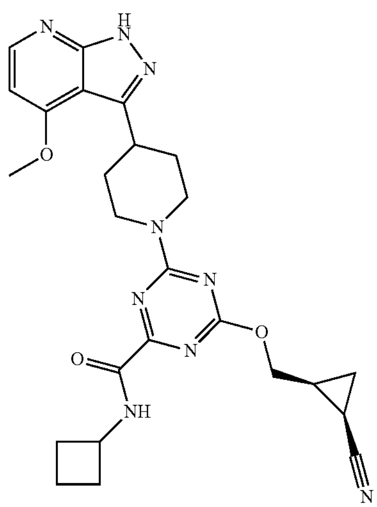 [SMILES: COc1ccnc2[nH]nc(C3CCN(c4nc(OC[C@H]5C[C@H]5C#N)nc(C(=O)NC5CCC5)n4)CC3)c12] | 4-{[(1S,2R)-2-cyanocyclopropyl]methoxy}-N-cyclobutyl-6-[4-(4-methoxy-1H-pyrazolo[3,4-b]pyridin-3-yl)piperidin-1-yl]-1,3,5-triazine-2-carboxamide | 503.0; (400 MHz, CDCl$_3$) δ ppm 8.40 (d, J = 5.2 Hz, 1 H), 7.79 (d, J = 7.6 Hz, 1 H), 6.51 (d, J = 5.2 Hz, 1 H), 5.05 (d, J = 15.2 Hz, 1 H), 4.85 (d, J = 14.0 Hz, 1 H), 4.50-4.61 (m, 3 H), 4.02 (s, 3 H), 3.48-3.51 (m, 1 H), 3.24 (q, J = 9.6 Hz, 2 H), 2.39-2.41 (m, 2 H), 1.71-2.14 (m, 10 H), 1.32-1.34 (m 1 H), 1.13-1.15 (m, 1 H). |

TABLE 1-continued

| Ex. # | Structure | Compound Name | LRMS m/z (M + H)+; and 1H NMR |
|---|---|---|---|
| 502* (E) | 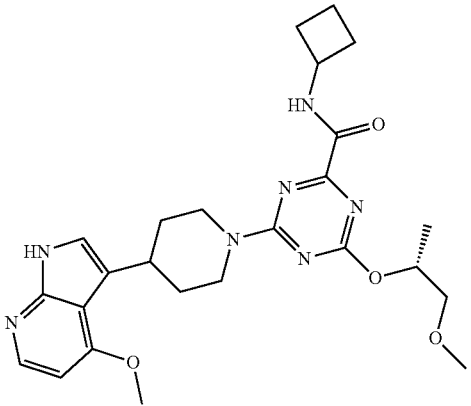 [SMILES: COC[C@@H](C)Oc1nc(C(=O)NC2CCC2)nc(N2CCC(c3c[nH]c4nccc(OC)c34)CC2)n1] | N-cyclobutyl-4-{[(2R)-1-methoxypropan-2-yl]oxy}-6-[4-(4-methoxy-1H-pyrrolo[2,3-b]pyridin-3-yl)piperidin-1-yl]-1,3,5-triazine-2-carboxamide | 496.2; (400 MHz, CDCl$_3$) δ ppm 9.09 (br s, 1 H), 8.18 (d, J = 5.6 Hz, 1 H), 7.95 (d, J = 8.0 Hz, 1 H), 6.88 (s, 1 H), 6.53 (d, J = 5.6 Hz, 1 H), 5.42-5.45 (m, 1 H), 5.13 (d, J = 12.4 Hz, 1 H), 4.91 (d, J = 12.8 Hz, 1 H), 4.51-4.58 (m, 1 H), 3.98 (s, 3 H), 3.61-3.63 (m, 1 H), 3.52-3.54 (m, 1 H), 3.42 (s, 3 H), 3.32 (t, J = 7.6 Hz, 1 H), 3.14 (q, J = 9.6 Hz, 2 H), 2.45-2.49 (m, 2 H), 2.23 (d, J = 11.6 Hz, 2 H), 1.98-2.03 (m, 2 H), 1.67-1.75 (m, 4 H), 1.38 (d, J = 5.2 Hz, 3 H). |
| 503* (E) | 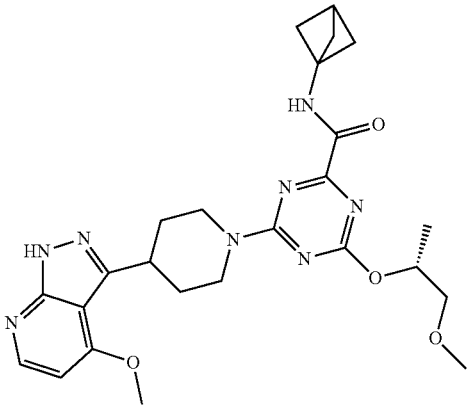 [SMILES: COC[C@@H](C)Oc1nc(C(=O)NC23CC(C2)C3)nc(N2CCC(c3n[nH]c4nccc(OC)c34)CC2)n1] | N-(bicyclo[1.1.1]pent-1-yl)-4-{[(2R)-1-methoxypropan-2-yl]oxy}-6-[4-(4-methoxy-1H-pyrazolo[3,4-b]pyridin-3-yl)piperidin-1-yl]-1,3,5-triazine-2-carboxamide | 509.2; (400 MHz, CDCl$_3$) δ ppm 8.40 (d, J = 5.6 Hz, 1 H), 8.18 (s, 1 H), 6.51 (d, J = 6.4 Hz, 1 H), 5.42-5.46 (m, 1 H), 5.05 (d, J = 14.0 Hz, 1 H), 4.85 (d, J = 13.4 Hz, 1 H), 4.02 (s, 3 H), 3.64-3.66 (m, 1H), 3.41-3.60 (m, 2 H), 3.50 (s, 3 H), 3.17-3.21 (m, 2 H), 2.48 (s, 1 H), 2.12 (s, 8 H), 1.6-1.99 (m, 2 H), 1.42-1.43 (m, 3 H). |
| 504* (E) | 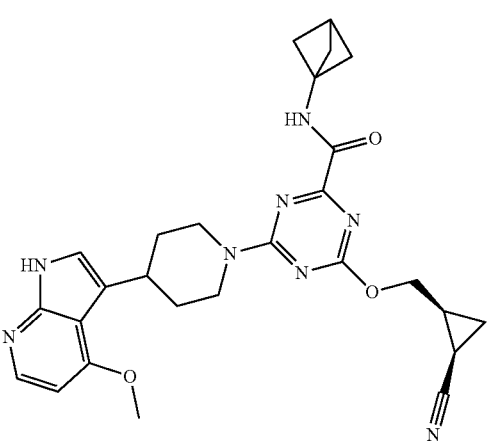 [SMILES: COc1ccnc2[nH]cc(C3CCN(c4nc(OC[C@H]5C[C@H]5C#N)nc(C(=O)NC56CC(C5)C6)n4)CC3)c12] | N-(bicyclo[1.1.1]pent-1-yl)-4-{[(1S,2R)-2-cyanocyclopropyl]methoxy}-6-[4-(4-methoxy-1H-pyrrolo[2,3-b]pyridin-3-yl)piperidin-1-yl]-1,3,5-triazine-2-carboxamide | 515.2; (400 MHz, CDCl$_3$) δ ppm 9.02 (br s, 1 H), 8.18 (d, J = 5.6 Hz, 1 H), 8.13 (s, 1 H), 6.88 (s, 1 H), 6.53 (d, J = 5.6 Hz, 1 H), 5.15 (d, J = 14.0 Hz, 1 H), 4.87 (d, J = 13.2 Hz, 1 H), 4.47-4.58 (m, 2 H), 3.98 (s, 3 H), 3.28-3.34 (m, 1 H), 3.14 (q, J = 9.6 Hz, 2 H), 2.49 (s, 1 H), 2.19 (s, 8 H), 1.71-1.76 (m, 1 H), 1.62-1.70 (m, 3 H), 1.34-1.36 (m, 1 H), 1.13-1.15 (m, 1 H). |

TABLE 1-continued

| Ex. # | Structure | Compound Name | LRMS m/z (M + H)+; and 1H NMR |
|---|---|---|---|
| 505* (E) | 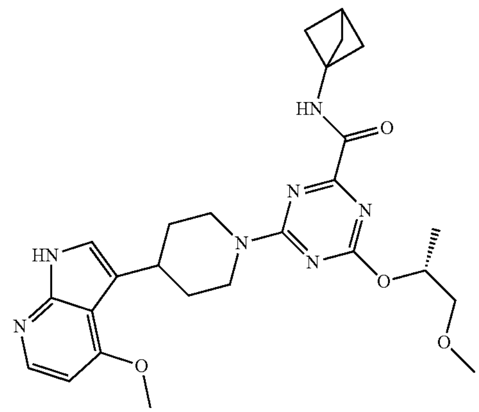 [SMILES: COC[C@@H](C)Oc1nc(C(=O)NC23CC(C2)C3)nc(N2CCC(c3c[nH]c4nccc(OC)c34)CC2)n1] | N-(bicyclo[1.1.1]pent-1-yl)-4-{[(2R)-1-methoxypropan-2-yl]oxy}-6-[4-(4-methoxy-1H-pyrrolo[2,3-b]pyridin-3-yl)piperidin-1-yl]-1,3,5-triazine-2-carboxamide | 508.2; (400 MHz, CDCl$_3$) δ ppm 9.04 (br s, 1 H), 8.18 (d, J = 5.6 Hz, 1 H), 6.88 (s, 1 H), 6.53 (d, J = 5.6 Hz, 1 H), 5.43-5.45 (m, 1 H), 5.15 (d, J = 12.8 Hz, 1 H), 4.90 (d, J = 12.8 Hz, 1 H), 3.98 (s, 3 H), 3.65-3.66 (m, 1 H), 3.53-3.54 (m, 1 H), 3.41 (s, 3 H), 3.38-3.40 (m, 1 H), 3.09 (q, J = 9.6 Hz, 2 H), 2.48 (s, 1 H), 2.18 (s, 8 H), 1.61-1.66 (m, 2 H), 1.38 (d, J = 6.4 Hz, 3 H). |
| 506* (E) | 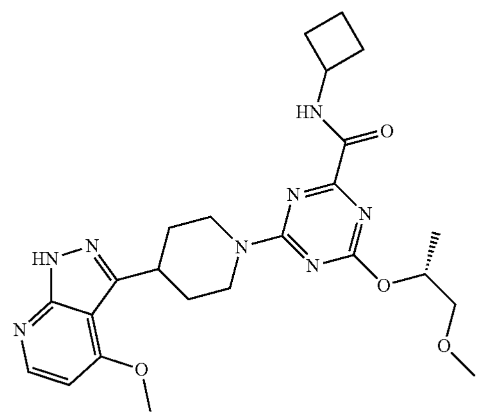 [SMILES: COC[C@@H](C)Oc1nc(C(=O)NC2CCC2)nc(N2CCC(c3n[nH]c4nccc(OC)c34)CC2)n1] | N-cyclobutyl-4-{[(2R)-1-methoxypropan-2-yl]oxy}-6-[4-(4-methoxy-1H-pyrazolo[3,4-b]pyridin-3-yl)piperidin-1-yl]-1,3,5-triazine-2-carboxamide | 497.2; (400 MHz, CDCl$_3$) δ ppm 8.40 (d, J = 5.6 Hz, 1 H), 7.95 (d, J = 8.8 Hz, 1 H), 6.51 (d, J = 5.6 Hz, 1 H), 5.42-5.46 (m, 1 H), 5.05 (d, J = 14.0 Hz, 1 H), 4.87 (d, J = 14.0 Hz, 1 H), 4.51-4.55 (m, 1 H), 4.01 (s, 3 H), 3.65-3.66 (m, 1 H), 3.53-3.54 (m, 2 H), 3.42 (s, 3 H), 3.21-3.30 (m, 2 H), 2.38-2.40 (m, 2 H), 1.98-2.12 (m, 5 H), 1.75-1.78 (m, 2 H), 1.38-1.39 (m, 3 H). |
| 507** (D) | 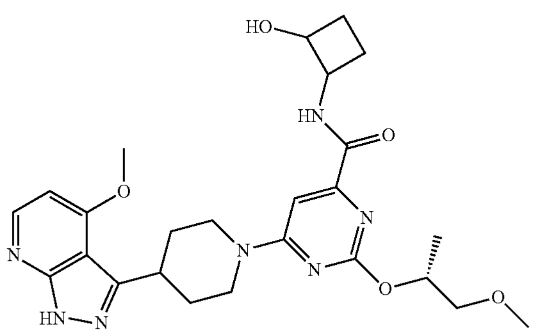 [SMILES: COC[C@@H](C)Oc1nc(C(=O)NC2CCC2O)cc(N2CCC(c3n[nH]c4nccc(OC)c34)CC2)n1] | (Cis)-N-(2-hydroxycyclobutyl)-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 534.1 [M + Na]+; (400 MHz, CDCl$_3$) δ ppm 12.02 (br s, 1 H), 8.41 (d, J = 5.6 Hz, 1 H), 8.15 (d, J = 4.8 Hz, 1 H), 7.11 (s, 1 H), 6.49 (d, J = 5.6 Hz, 1 H), 5.29-5.37 (m, 1 H), 4.61 (br s, 2 H), 4.07-4.09 (m, 2 H), 3.97 (s, 3 H), 3.64-3.67 (m, 1 H), 3.40-3.51 (m, 2 H), 3.40 (s, 3 H), 3.10-3.21 (m, 2 H), 1.41-2.14 (m, 9 H), 1.37 (d, J = 6.0 Hz, 3 H). |
| 508* (D) | 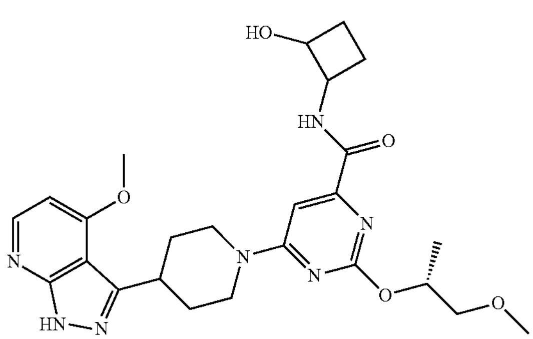 [SMILES: COC[C@@H](C)Oc1nc(C(=O)NC2CCC2O)cc(N2CCC(c3n[nH]c4nccc(OC)c34)CC2)n1] | (Cis)-N-(2-hydroxycyclobutyl)-2-{[(2R)-1-methoxypropan-2-yl]oxy}-6-[4-(4-methoxy-1H-pyrazolo[3,4-b]pyridin-3-yl)piperidin-1-yl]pyrimidine-4-carboxamide | 534.1 [M + Na]+; (400 MHz, CDCl$_3$) δ ppm 11.43 (br s, 1 H), 8.41 (d, J = 5.6 Hz, 1 H), 8.15 (d, J = 4.8 Hz, 1 H), 7.11 (s, 1 H), 6.49 (d, J = 5.6 Hz, 1 H), 5.29-5.37 (m, 1 H), 4.55 (br s, 2 H), 4.07-4.11 (m, 2 H), 3.97 (s, 3 H), 3.64-3.67 (m, 1 H), 3.40-3.51 (m, 2 H), 3.40 (s, 3 H), 3.10-3.21 (m, 2 H), 1.82-2.14 (m, 6 H), 1.41-1.75 (m, 3 H), 1.38 (d, J = 6.0 Hz, 3 H). |

TABLE 1-continued

| Ex. # | Structure | Compound Name | LRMS m/z (M + H)+; and 1H NMR |
|---|---|---|---|
| 509* (D) | 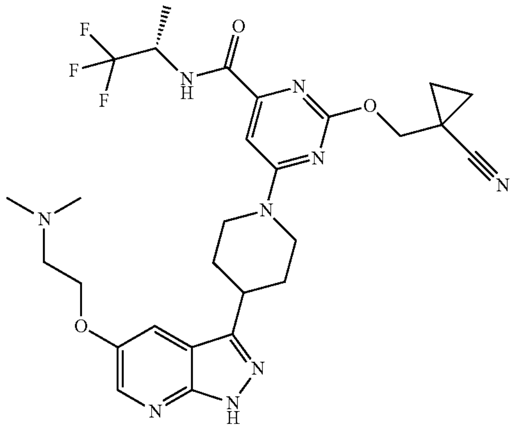 [SMILES: C[C@H](NC(=O)c1cc(N2CCC(c3n[nH]c4ncc(OCCN(C)C)cc34)CC2)nc(OCC2(C#N)CC2)n1)C(F)(F)F] | 2-[(1-cyanocyclopropyl)methoxy]-6-(4-{5-[2-(dimethylamino)ethoxy]-1H-pyrazolo[3,4-b]pyridin-3-yl}piperidin-1-yl)-N-[(2S)-1,1,1-trifluoropropan-2-yl]pyrimidine-4-carboxamide | 602.2; (400 MHz, DMSO-$d_6$) δ ppm 8.32 (d, J = 6.4 Hz, 1 H), 7.79 (d, J = 6.8 Hz, 1 H), 7.19 (s, 1 H), 4.64-4.86 (m, 4 H), 4.49 (q, J = 8.4 Hz, 2 H), 4.21-4.23 (m, 2 H), 3.47-3.48 (m, 1H), 3.26-3.29 (m, 1 H), 2.84-2.86 (m, 2 H), 2.39 (s, 6 H), 2.17-2.19 (m, 2 H), 2.00-2.04 (m, 2 H), 1.39 (d, J = 4.4 Hz, 3 H), 1.26-1.27 (m, 2 H), 1.24-1.25 (m, 2 H). |

*Compounds are single enantiomers with known absolute stereochemistry is unknown.
**Compounds are single enantiomers with unknown absolute stereochemistry.
***Compounds are racemates, or known mixtures of diastereomers.

Additional examples of compounds of the invention are summarized in Table 2 below (Schemes indicated in parentheses).

TABLE 2

| Ex. # | Structure | Compound Name | Observed MW; and RT (min) | Method |
|---|---|---|---|---|
| 124* (E) | 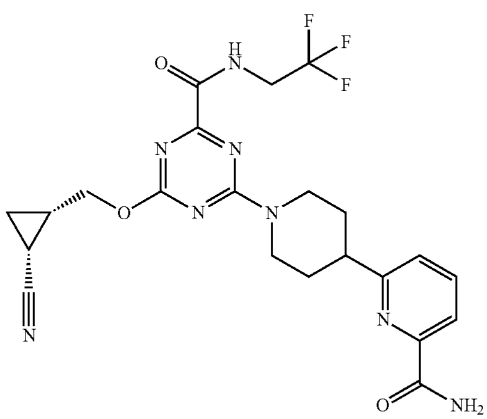 [SMILES: N#C[C@@H]1C[C@@H]1COc1nc(C(=O)NCC(F)(F)F)nc(N2CCC(c3cccc(C(N)=O)n3)CC2)n1] | 4-[4-(6-carbamoylpyridin-2-yl)piperidin-1-yl]-6-{[(1S,2R)-2-cyanocyclopropyl]methoxy}-N-(2,2,2-trifluoroethyl)-1,3,5-triazine-2-carboxamide | 505; 2.953 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 125* (E) | 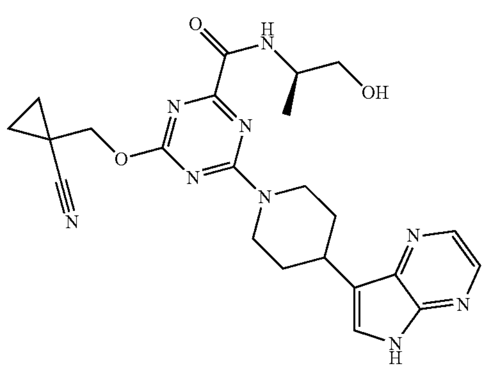 [SMILES: C[C@H](CO)NC(=O)c1nc(OCC2(C#N)CC2)nc(N2CCC(c3c[nH]c4nccnc34)CC2)n1] | 4-[(1-cyanocyclopropyl)methoxy]-N-[(2R)-1-hydroxypropan-2-yl]-6-[4-(5H-pyrrolo[2,3-b]pyrazin-7-yl)piperidin-1-yl]-1,3,5-triazine-2-carboxamide | 478; 2.567 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 126 * (E) | 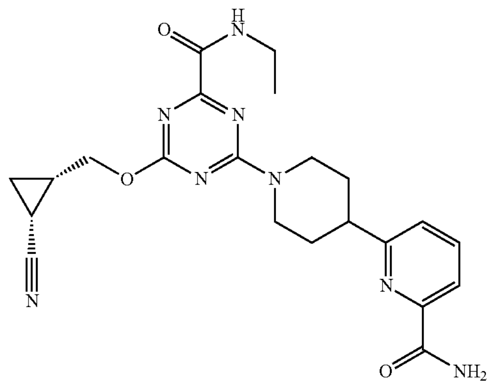 [SMILES: CCNC(=O)c1nc(OC[C@H]2C[C@H]2C#N)nc(N2CCC(c3cccc(C(N)=O)n3)CC2)n1] | 4-[4-(6-carbamoylpyridin-2-yl)piperidin-1-yl]-6-{[(1S,2R)-2-cyanocyclopropyl]methoxy}-N-ethyl-1,3,5-triazine-2-carboxamide | 451; 2.732 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 127 * (E) | 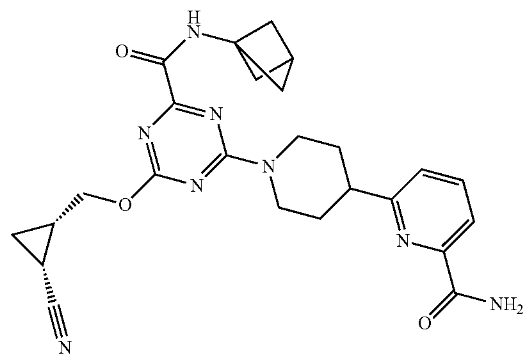 [SMILES: N#C[C@@H]1C[C@@H]1COc1nc(C(=O)NC23CC(C2)C3)nc(N2CCC(c3cccc(C(N)=O)n3)CC2)n1] | N-(bicyclo[1.1.1]pent-1-yl)-4-[4-(6-carbamoylpyridin-2-yl)piperidin-1-yl]-6-{[(1S,2R)-2-cyanocyclopropyl]methoxy}-1,3,5-triazine-2-carboxamide | 489; 3.004 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 128 * (E) | 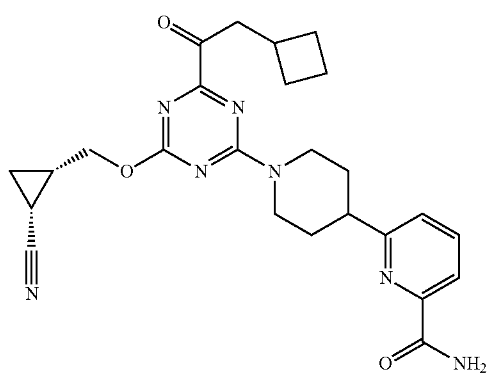 [SMILES: N#C[C@@H]1C[C@@H]1COc1nc(C(=O)CC2CCC2)nc(N2CCC(c3cccc(C(N)=O)n3)CC2)n1] | 4-[4-(6-carbamoylpyridin-2-yl)piperidin-1-yl)-6-{[(1S,2R)-2-cyanocyclopropyl]methoxy}-N-cyclobutyl-1,3,5-triazine-2-carboxamide | 477; 2.918 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 129 * (E) | 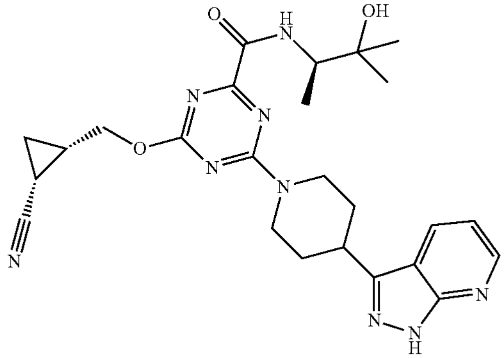 [SMILES: C[C@@H](NC(=O)c1nc(OC[C@H]2C[C@H]2C#N)nc(N2CCC(c3n[nH]c4ncccc34)CC2)n1)C(C)(C)O] | 4-{[(1S,2R)-2-cyanocyclopropyl]methoxy}-N-[(2R)-3-hydroxy-3-methylbutan-2-yl]-6-[4-(1H-pyrazolo[3,4-b]pyridin-3-yl)piperidin-1-yl]-1,3,5-triazine-2-carboxamide | 506; 2.671 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 130 *** (E) | 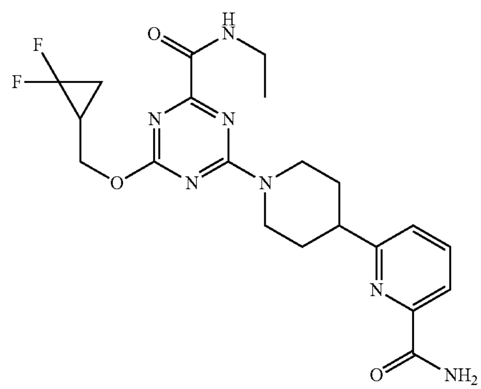 [SMILES: CCNC(=O)c1nc(OCC2CC2(F)F)nc(N2CCC(c3cccc(C(N)=O)n3)CC2)n1] | 4-[4-(6-carbamoylpyridin-2-yl)piperidin-1-yl]-6-[(2,2-difluorocyclopropyl)methoxy]-N-ethyl-1,3,5-triazine-2-carboxamide | 462; 2.951 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 131 (E) | 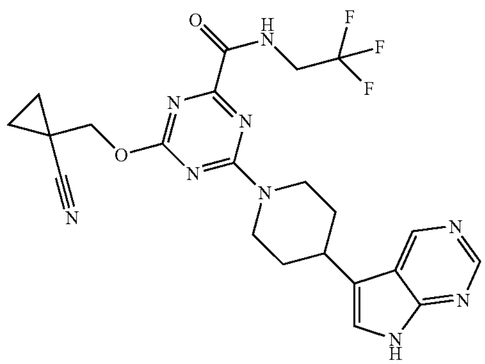 [SMILES: N#CC1(COc2nc(C(=O)NCC(F)(F)F)nc(N3CCC(c4c[nH]c5ncncc45)CC3)n2)CC1] | 4-[(1-cyanocyclopropyl)methoxy]-6-[4-(7H-pyrrolo(2,3-d]pyrimidin-5-yl)piperidin-1-yl]-N-(2,2,2-trifluoroethyl)-1,3,5-triazine-2-carboxamide | 502; 2.581 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 132 (E) | 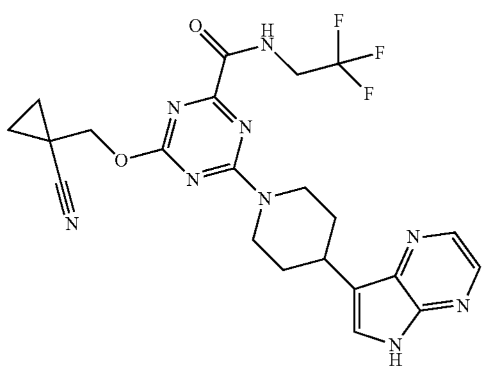 [SMILES: N#CC1(COc2nc(C(=O)NCC(F)(F)F)nc(N3CCC(c4c[nH]c5nccnc45)CC3)n2)CC1] | 4-(4-(5H-pyrrolo[2,3-b]pyrazin-7-yl)piperidin-1-yl)-6-((1-cyanocyclopropyl)methoxy)-N-(2,2,2-trifluoroethyl)-1,3,5-triazine-2-carboxamide | 502; 2.910 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 133 (E) | 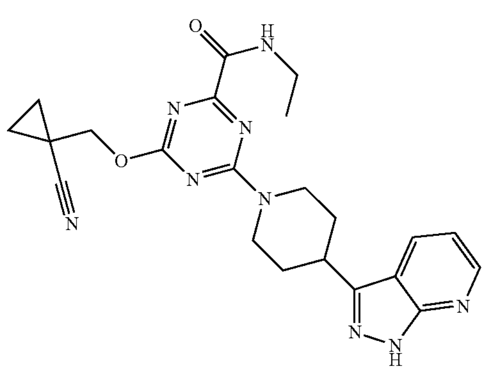 [SMILES: CCNC(=O)c1nc(OCC2(C#N)CC2)nc(N2CCC(c3n[nH]c4ncccc34)CC2)n1] | 4-(4-(1H-pyrazolo[3,4-b]pyridin-3-yl)piperidin-1-yl)-6-((1-cyanocyclopropyl)methoxy)-N-ethyl-1,3,5-triazine-2-carboxamide | 448; 2.723 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 144 * (E) | 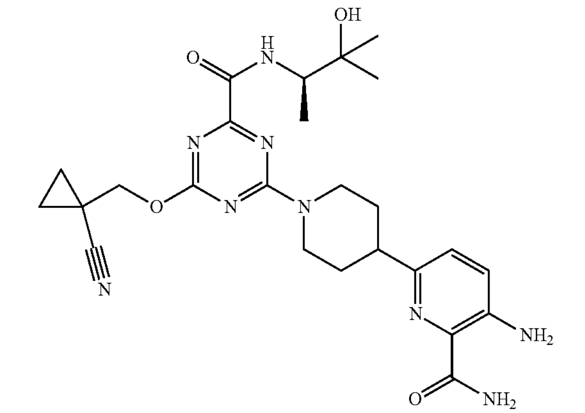 [SMILES: C[C@@H](NC(=O)c1nc(OCC2(CN)CC2)nc(N2CCC(c3ccc(N)c(C(N)=O)n3)CC2)n1)C(C)(C)O] | 4-[4-(5-amino-6-carbamoylpyridin-2-yl)piperidin-1-yl]-6-[(1-cyanocyclopropyl)methoxy]-N-[(2R)-3-hydroxy-3-methylbutan-2-yl]-1,3,5-triazine-2-carboxamide | 524; 2.235 | Xbridge C18 2.1 × 50 mm (5 μm). 40° C. Mobile phase A: 0.05% NH4OH in water. B: MeCN. 5% B over 0.5 mins to 100% B after 3.4 mins. Flow rate 0.8 mL/min. API-ES positive |
| 145 * (E) | 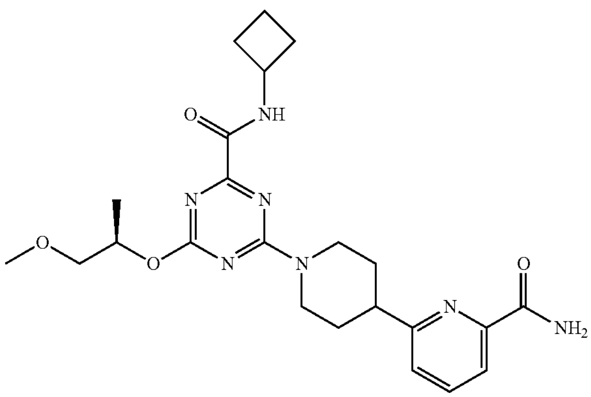 [SMILES: COC[C@@H](C)Oc1nc(C(=O)NC2CCC2)nc(N2CCC(c3cccc(C(N)=O)n3)CC2)n1] | 4-[4-(6-carbamoylpyridin-2-yl)piperidin-1-yl]-N-cyclobutyl-6-{[(2R)-1-methoxypropan-2-yl]oxy}-1,3,5-triazine-2-carboxamide | 470; 2.457 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 146 * (E) | 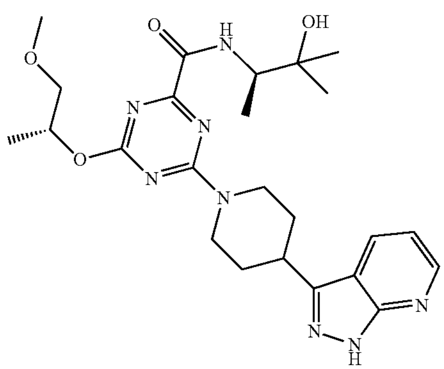 [SMILES: COC[C@@H](C)Oc1nc(C(=O)N[C@H](C)C(C)(C)O)nc(N2CCC(c3n[nH]c4ncccc34)CC2)n1] | N-[(2R)-3-hydroxy-3-methylbutan-2-yl]-4-{[(2R)-1-methoxypropan-2-yl]oxy}-6-[4-(1H-pyrazolo[3,4-b]pyridin-3-yl)piperidin-1-yl]-1,3,5-triazine-2-carboxamide | 499; 2.427 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 147 * (E) | 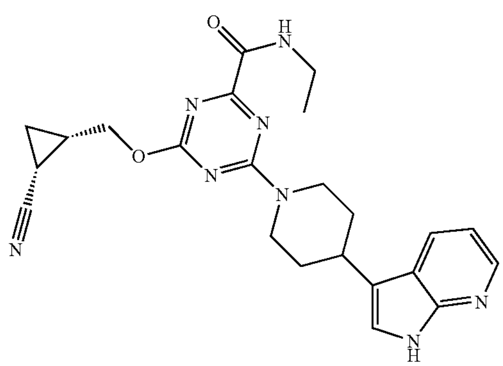 [SMILES: CCNC(=O)c1nc(OC[C@H]2C[C@H]2C#N)nc(N2CCC(c3c[nH]c4ncccc34)CC2)n1] | 4-{[(1S,2R)-2-cyanocyclopropyl]methoxy}-N-ethyl-6-[4-(1H-pyrrolo[2,3-b]pyridin-3-yl)piperidin-1-yl]-1,3,5-triazine-2-carboxamide | 447; 2.211 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 148 * (E) | 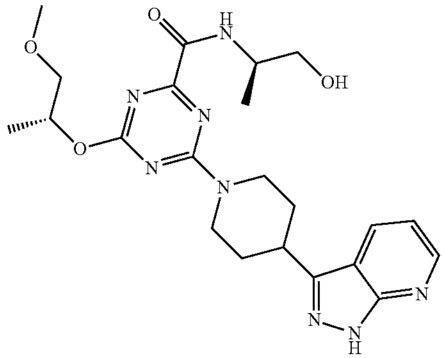 [SMILES: COC[C@@H](C)Oc1nc(C(=O)N[C@H](C)CO)nc(N2CCC(c3n[nH]c4ncccc34)CC2)n1] | N-[(2R)-1-hydroxypropan-2-yl]-4-{[(2R)-1-methoxypropan-2-yl]oxy}-6-[4-(1H-pyrazolo[3,4-b]pyridin-3-yl)piperidin-1-yl]-1,3,5-triazine-2-carboxamide | 471; 2.313 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 149 * (E) | 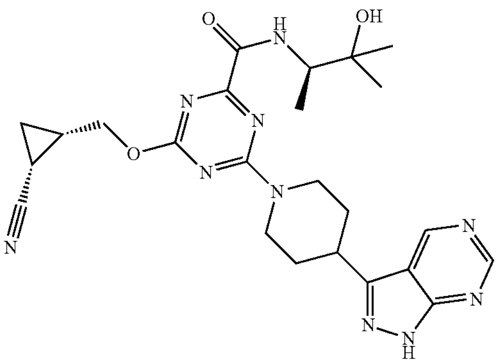 [SMILES: C[C@@H](NC(=O)c1nc(OC[C@H]2C[C@H]2C#N)nc(N2CCC(c3n[nH]c4ncncc34)CC2)n1)C(C)(C)O] | 4-{[(1S,2R)-2-cyanocyclopropyl]methoxy}-N-[(2R)-3-hydroxy-3-methylbutan-2-yl]-6-[4-(1H-pyrazolo[3,4-d]pyrimidin-3-yl)piperidin-1-yl]-1,3,5-triazine-2-carboxamide | 507; 2.418 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 150 * (E) | 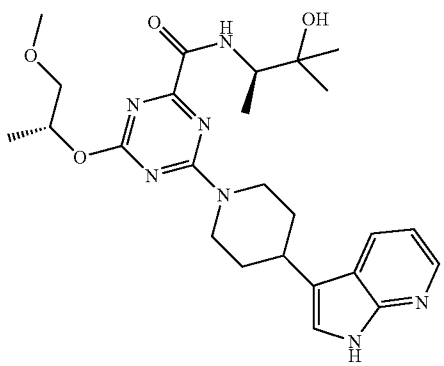 [SMILES: COC[C@@H](C)Oc1nc(C(=O)N[C@H](C)C(C)(C)O)nc(N2CCC(c3c[nH]c4ncccc34)CC2)n1] | N-[(2R)-3-hydroxy-3-methylbutan-2-yl]-4-{[(2R)-1-methoxypropan-2-yl]oxy}-6-[4-(1H-pyrrolo[2,3-b]pyridin-3-yl)piperidin-1-yl]-1,3,5-triazine-2-carboxamide | 498; 2.252 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 151 * (E) | 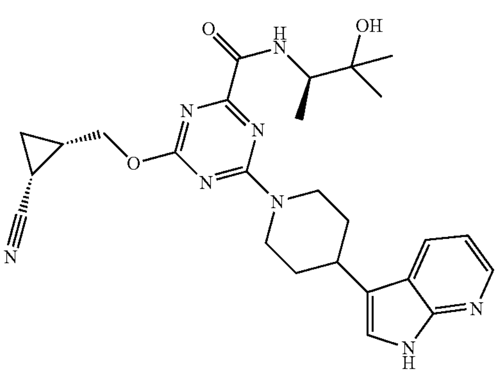 [SMILES: C[C@@H](NC(=O)c1nc(OC[C@H]2C[C@H]2C#N)nc(N2CCC(c3c[nH]c4ncccc34)CC2)n1)C(C)(C)O] | 4-{[(1S,2R)-2-cyanocyclopropyl]methoxy}-N-[(2R)-3-hydroxy-3-methylbutan-2-yl]-6-[4-(1H-pyrrolo[2,3-b]pyridin-3-yl)piperidin-1-yl]-1,3,5-triazine-2-carboxamide | 505; 2.218 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 152 * (E) | 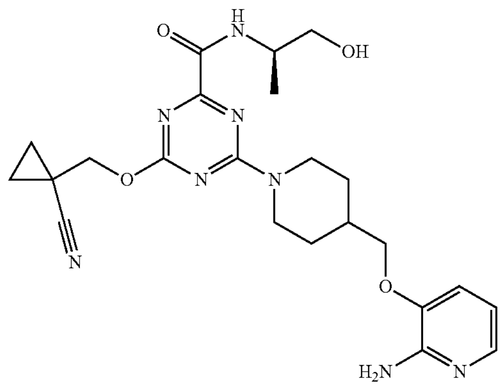 [SMILES: C[C@H](CO)NC(=O)c1nc(OCC2(C#N)CC2)nc(N2CCC(COc3cccnc3N)CC2)n1] | 4-(4-{[(2-aminopyridin-3-yl)oxy]methyl}piperidin-1-yl)-6-[(1-cyanocyclopropyl)methoxy]-N-[(2R)-1-hydroxypropan-2-yl]-1,3,5-triazine-2-carboxamide | 483; 2.094 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 153 * (E) | 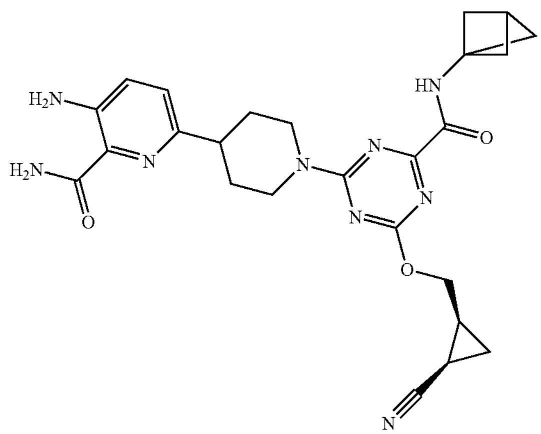 [SMILES: N#C[C@@H]1C[C@@H]1COc1nc(C(=O)NC23CC(C2)C3)nc(N2CCC(c3ccc(N)c(C(N)=O)n3)CC2)n1] | 4-[4-(5-amino-6-carbamoylpyridin-2-yl)piperidin-1-yl]-N-(bicyclo[1.1.1]pent-1-yl)-6-{[(1S,2R)-2-cyanocyclopropyl]methoxy}-1,3,5-triazine-2-carboxamide | 504; 2.725 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 154 * (E) | 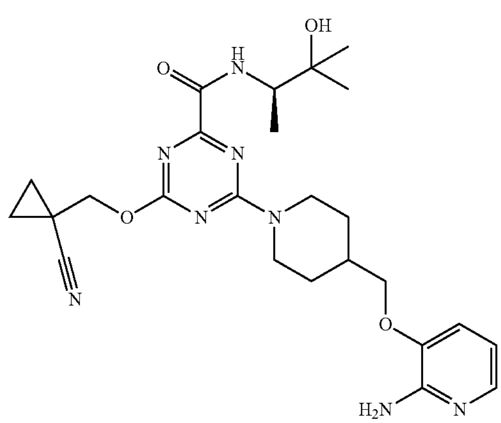 [SMILES: C[C@@H](NC(=O)c1nc(OCC2(C#N)CC2)nc(N2CCC(COc3cccnc3N)CC2)n1)C(C)(C)O] | 4-(4-{[(2-aminopyridin-3-yl)oxy]methyl}piperidin-1-yl)-6-[(1-cyanocyclopropyl)methoxy]-N-[(2R)-3-hydroxy-3-methylbutan-2-yl]-1,3,5-triazine-2-carboxamide | 511; 2.190 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 155 * (E) | 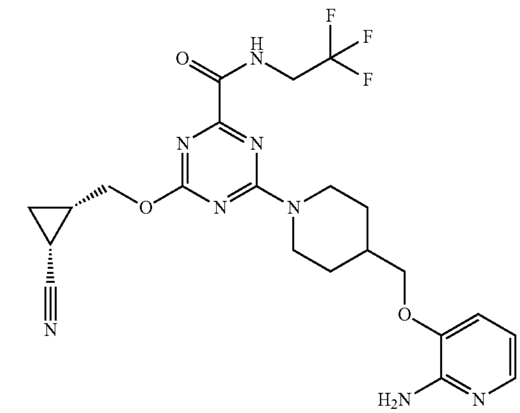 [SMILES: N#C[C@@H]1C[C@@H]1COc1nc(C(=O)NCC(F)(F)F)nc(N2CCC(COc3cccnc3N)CC2)n1] | 4-(4-{[(2-aminopyridin-3-yl)oxy]methyl}piperidin-1-yl)-6-{[(1S,2R)-2-cyanocyclopropyl]methoxy}-N-(2,2,2-trifluoroethyl)-1,3,5-triazine-2-carboxamide | 507; 2.603 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 156 * (E) | 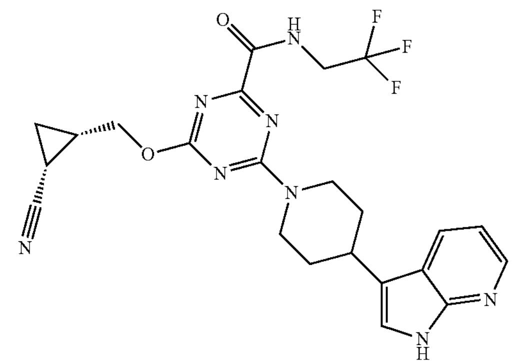 [SMILES: N#C[C@@H]1C[C@@H]1COc1nc(C(=O)NCC(F)(F)F)nc(N2CCC(c3c[nH]c4ncccc34)CC2)n1] | 4-{[(1S,2R)-2-cyanocyclopropyl]methoxy}-6-[4-(1H-pyrrolo[2,3-b]pyridin-3-yl)piperidin-1-yl]-N-(2,2,2-trifluoroethyl)-1,3,5-triazine-2-carboxamide | 501; 2.389 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 157 * (E) | 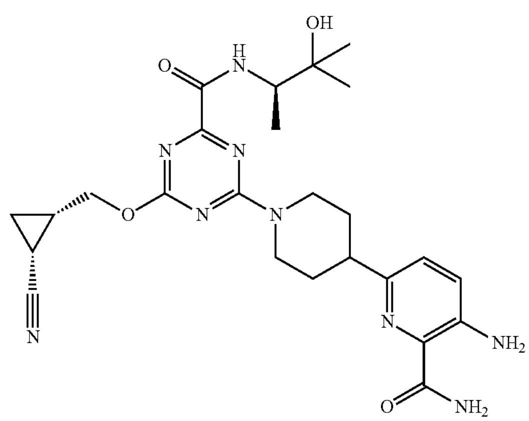 [SMILES: C[C@@H](NC(=O)c1nc(OC[C@H]2C[C@H]2C#N)nc(N2CCC(c3ccc(N)c(C(N)=O)n3)CC2)n1)C(C)(C)O] | 4-[4-(5-amino-6-carbamoylpyridin-2-yl)piperidin-1-yl]-6-{[(1S,2R)-2-cyanocyclopropyl]methoxy}-N-[(2R)-3-hydroxy-3-methylbutan-2-yl]-1,3,5-triazine-2-carboxamide | 524; 2.433 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 158 * (E) | 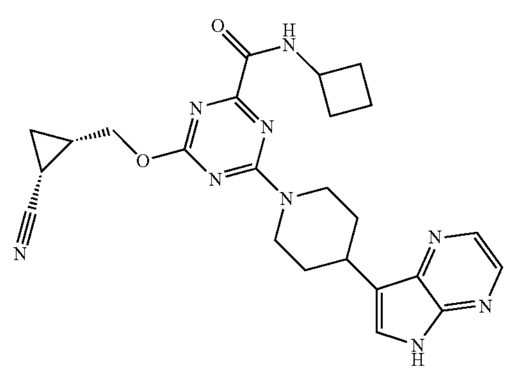 [SMILES: N#C[C@@H]1C[C@@H]1COc1nc(C(=O)NC2CCC2)nc(N2CCC(c3c[nH]c4nccnc34)CC2)n1] | 4-{[(1S,2R)-2-cyanocyclopropyl]methoxy}-N-cyclobutyl-6-[4-(5H-pyrrolo[2,3-b]pyrazin-7-yl)piperidin-1-yl]-1,3,5-triazine-2-carboxamide | 474; 2.558 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 159 (E) | 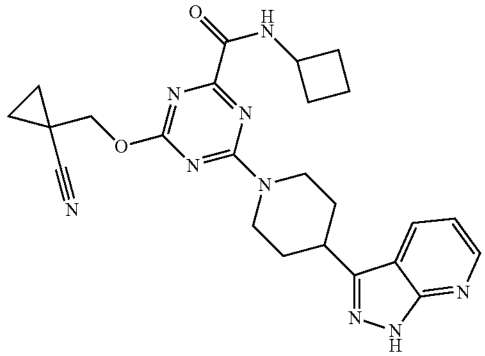 [SMILES: N#CC1(COc2nc(C(=O)NC3CCC3)nc(N3CCC(c4n[nH]c5ncccc45)CC3)n2)CC1] | 4-[(1-cyanocyclopropyl)methoxy]-N-cyclobutyl-6-[4-(1H-pyrazolo[3,4-b]pyridin-3-yl)piperidin-1-yl]-1,3,5-triazine-2-carboxamide | 474; 2.623 | Xbridge C18 2.1 × 50 mm (5 µm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 304 * (E) | 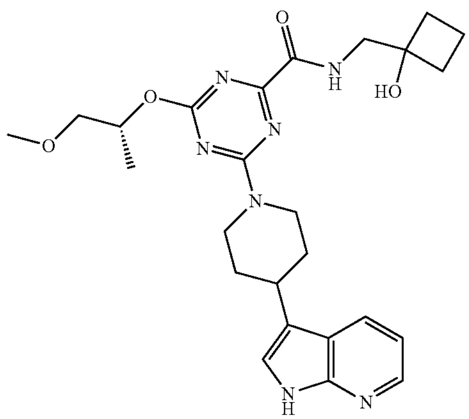 [SMILES: COC[C@@H](C)Oc1nc(C(=O)NCC2(O)CCC2)nc(N2CCC(c3c[nH]c4ncccc34)CC2)n1] | N-[(1-hydroxycyclobutyl)methyl]-4-{[(2R)-1-methoxypropan-2-yl]oxy}-6-[4-(1H-pyrrolo[2,3-b]pyridin-3-yl)piperidin-1-yl]-1,3,5-triazine-2-carboxamide | 496; 2.465 | Xbridge C18 2.1 × 50 mm (5 µm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 305 * (E) | 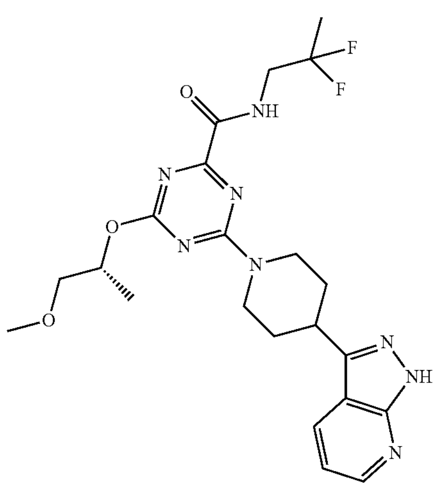 [SMILES: COC[C@@H](C)Oc1nc(C(=O)NCC(C)(F)F)nc(N2CCC(c3n[nH]c4ncccc34)CC2)n1] | N-(2,2-difluoropropyl)-4-{[(2R)-1-methoxypropan-2-yl]oxy}-6-[4-(1H-pyrazolo[3,4-b]pyridin-3-yl)piperidin-1-yl]-1,3,5-triazine-2-carboxamide | 491; 2.873 | Xbridge C18 2.1 × 50 mm (5 µm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 306 * (E) | 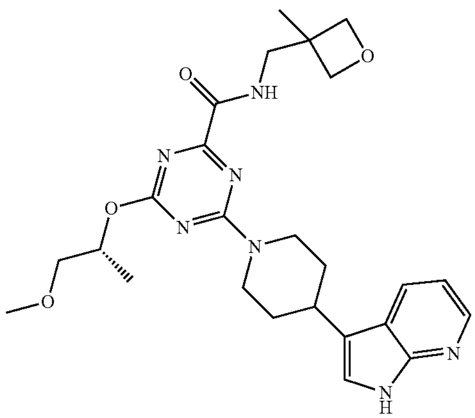 [SMILES: COC[C@@H](C)Oc1nc(C(=O)NCC2(C)COC2)nc(N2CCC(c3c[nH]c4ncccc34)CC2)n1] | 4{[(2R)-1-methoxypropan-2-yl]oxy}-N-[(3-methyloxetan-3-yl)methyl]-6-[4-(1H-pyrrolo[2,3-b]pyridin-3-yl)piperidin-1-yl]-1,3,5-triazine-2-carboxamide | 496; 2.464 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 307 * (E) | 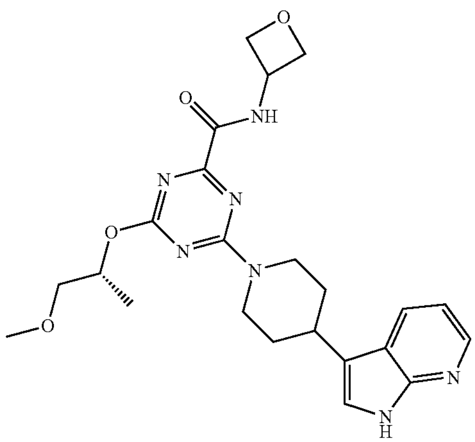 [SMILES: COC[C@@H](C)Oc1nc(C(=O)NC2COC2)nc(N2CCC(c3c[nH]c4ncccc34)CC2)n1] | 4-{[(2R)-1-methoxypropan-2-yl]oxy}-N-(oxetan-3-yl)-6-[4-(1H-pyrrolo[2,3-b]pyridin-3-yl)piperidin-1-yl]-1,3,5-triazine-2-carboxamlde | 468; 2.374 | Xbrige C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 308 * (E) | 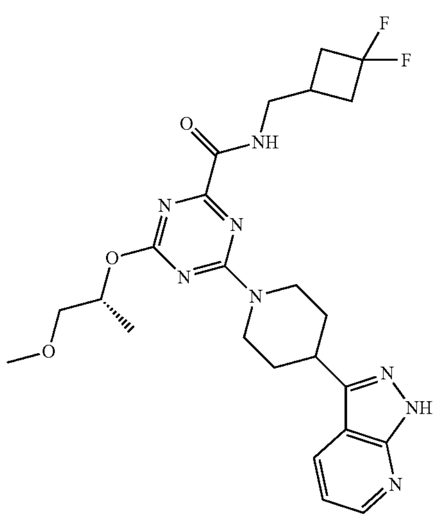 [SMILES: COC[C@@H](C)Oc1nc(C(=O)NCC2CC(F)(F)C2)nc(N2CCC(c3n[nH]c4ncccc34)CC2)n1] | N-[(3,3-difluorocyclobutyl)methyl]-4-{[(2R)-1-methoxypropan-2-yl]oxy}-6-[4-(1H-pyrazolo[3,4-b]pyridin-3-yl)piperidin-1-yl]-1,3,5-triazine-2-carboxamide | 517; 2.978 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 309 * (E) | 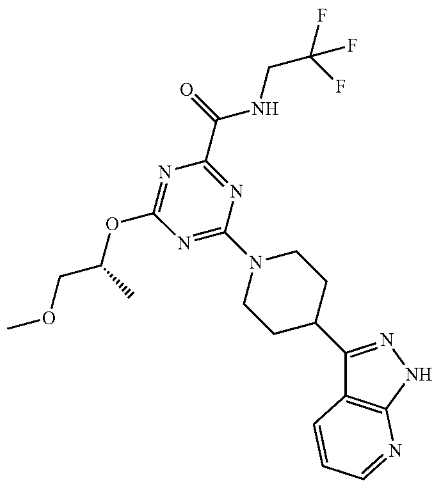 [SMILES: COC[C@@H](C)Oc1nc(C(=O)NCC(F)(F)F)nc(N2CCC(c3n[nH]c4ncccc34)CC2)n1] | 4-{[(2R)-1-methoxypropan-2-yl]oxy}-6-[4-(1H-pyrazolo[3,4-b]pyridin-3-yl)piperidin-1-yl]-N-(2,2,2-trifluoroethyl)-1,3,5-triazine-2-carboxamide | 495; 2.918 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 310 * (E) | 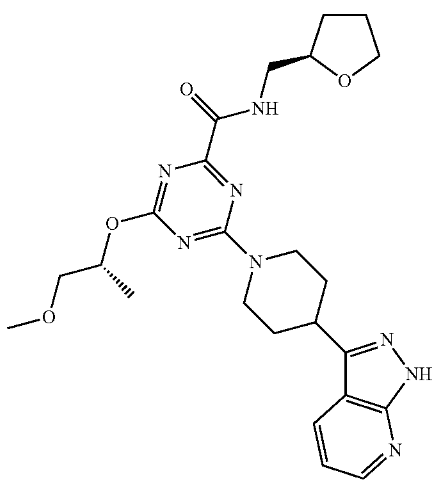 [SMILES: COC[C@@H](C)Oc1nc(C(=O)NC[C@H]2CCCO2)nc(N2CCC(c3n[nH]c4ncccc34)CC2)n1] | 4-{[(2R)-1-methoxypropan-2-yl]oxy}-6-[4-(1H-pyrazolo[3,4-b]pyridin-3-yl)piperidin-1-yl]-N-[(2R)-tetrahydrofuran-2-ylmethyl]-1,3,5-triazine-2-carboxamide | 497; 2.737 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 311 * (E) | 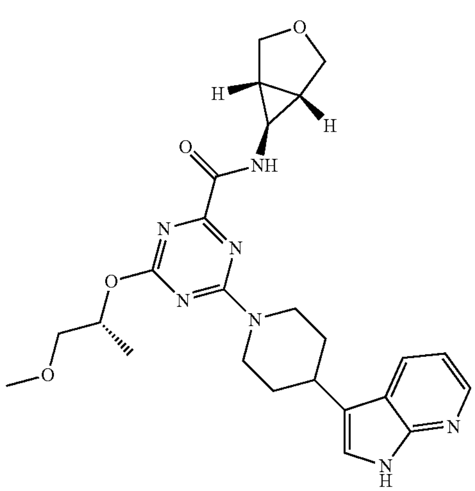 [SMILES: COC[C@@H](C)Oc1nc(C(=O)N[C@H]2[C@@H]3COC[C@@H]32)nc(N2CCC(c3c[nH]c4ncccc34)CC2)n1] | 4-{[(2R)-1-methoxypropan-2-yl]oxy}-N-[(1R,5S,6r)-3-oxabicyclo[3.1.0]hex-6-yl]-6-[4-(1H-pyrrolo[2,3-b]pyridin-3-yl)piperidin-1-yl]-1,3,5-triazine-2-carboxamide | 494; 2.458 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 312 * (D) | 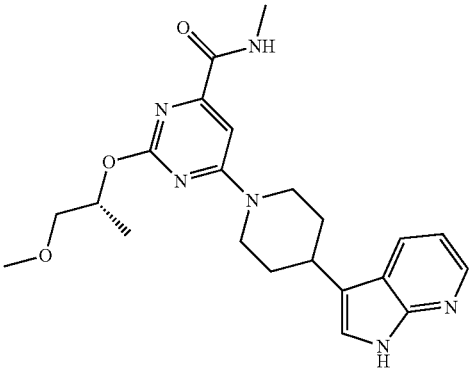 [SMILES: CNC(=O)c1cc(N2CCC(c3c[nH]c4ncccc34)CC2)nc(O[C@H](C)COC)n1] | 2-{[(2R)-1-methoxypropan-2-yl]oxy}-N-methyl-6-[4-(1H-pyrrolo[2,3-b]pyridin-3-yl)piperidin-1-yl]pyrimidine-4-carboxamide | 425; 2.362 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 313 * (E) | 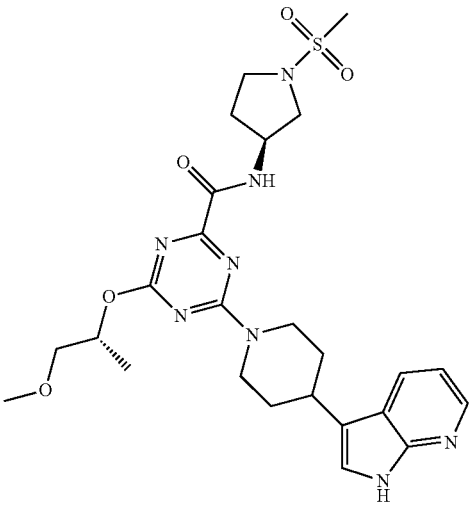 [SMILES: COC[C@@H](C)Oc1nc(C(=O)N[C@H]2CCN(S(C)(=O)=O)C2)nc(N2CCC(c3c[nH]c4ncccc34)CC2)n1] | 4-{[(2R)-1-methoxypropan-2-yl]oxy}-N-[(3S)-1-(methylsulfonyl)pyrrolidin-3-yl]-6-[4-(1H-pyrrolo[2,3-b]pyridin-3-yl)piperidin-1-yl]-1,3,5-triazine-2-carboxamide | 559; 2.471 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 314 *** (E) | 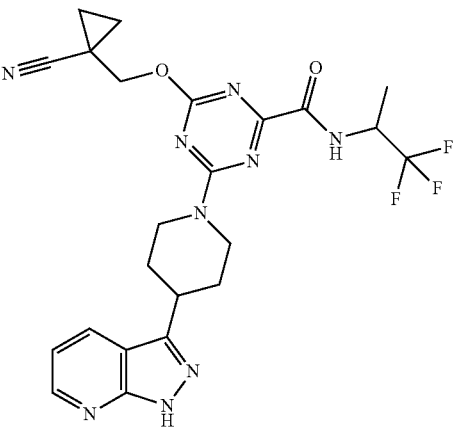 [SMILES: CC(NC(=O)c1nc(OCC2(C#N)CC2)nc(N2CCC(c3n[nH]c4ncccc34)CC2)n1)C(F)(F)F] | 4-[(1-cyanocyclopropyl)methoxy]-6-[4-(1H-pyrazolo[3,4-b]pyridin-3-yl)piperidin-1-yl]-N-(1,1,1-trifluoropropan-2-yl)-1,3,5-triazine-2-carboxamide | 516; 3.023 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 315 * (D) | 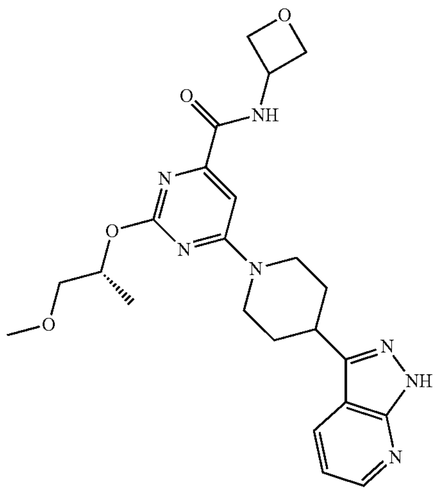 [SMILES: COC[C@@H](C)Oc1nc(C(=O)NC2COC2)cc(N2CCC(c3n[nH]c4ncccc34)CC2)n1] | 2-{[(2R)-1-methoxypropan-2-yl]oxy}-N-(oxetan-3-yl)-6-[4-(1H-pyrazolo[3,4-b]pyridin-3-yl)piperidin-1-yl]pyrimidine-4-carboxamide | 468; 2.528 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 316 * (D) | 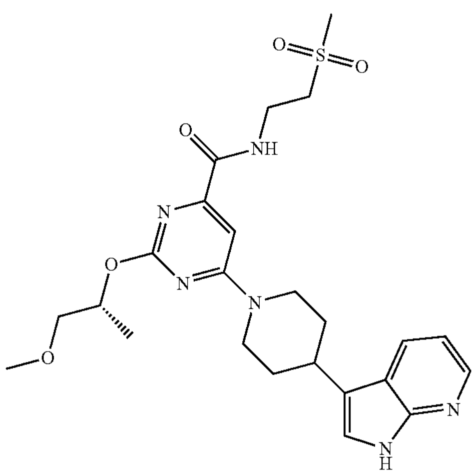 [SMILES: COC[C@@H](C)Oc1nc(C(=O)NCCS(C)(=O)=O)cc(N2CCC(c3c[nH]c4ncccc34)CC2)n1] | 2-{[(2R)-1-methoxypropan-2-yl]oxy}-N-2-(methylsulfonyl)ethyl]-6-[4-(1H-pyrrolo[2,3-b]pyridin-3-yl)piperidin-1-yl]pyrimidine-4-carboxamide | 517; 2.392 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 317 * (E) | 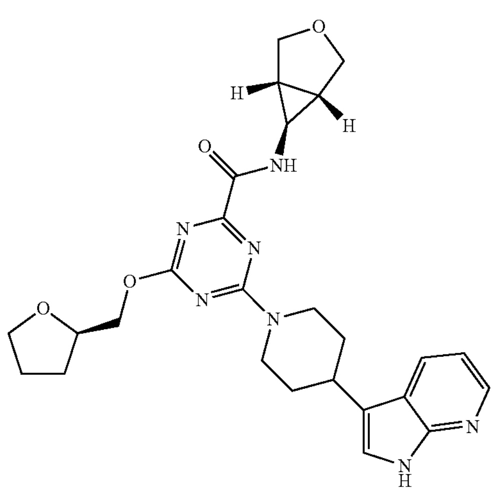 [SMILES: O=C(N[C@H]1[C@@H]2COC[C@@H]21)c1nc(OC[C@H]2CCCO2)nc(N2CCC(c3c[nH]c4ncccc34)CC2)n1] | N-[(1R,5S,6r)-3-oxabicyclo[3.1.0]hex-6-yl]-4-[4-(1H-pyrrolo[2,3-b]pyridin-3-yl)piperidin-1-yl]-6-[(2R)-tetrahydrofuran-2-ylmethoxy]-1,3,5-triazine-2-carboxamide | 506; 2.440 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 318 * (D) | 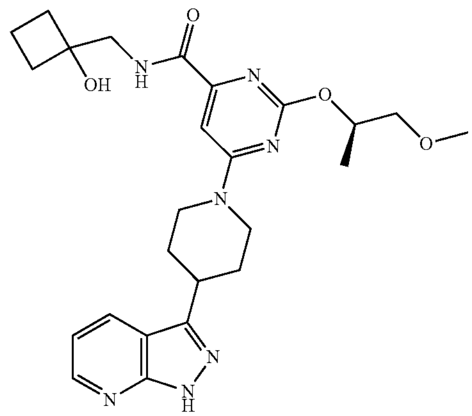 [SMILES: COC[C@@H](C)Oc1nc(C(=O)NCC2(O)CCC2)cc(N2CCC(c3n[nH]c4ncccc34)CC2)n1] | N-[(1-hydroxycyclobutyl)methyl]-2-{[(2R)-1-methoxypropan-2-yl]oxy}-6-[4-(1H-pyrazolo[3,4-b]pyridin-3-yl)piperidin-1-yl]pyrimidine-4-carboxamide | 496; 2.653 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 319 * (E) | 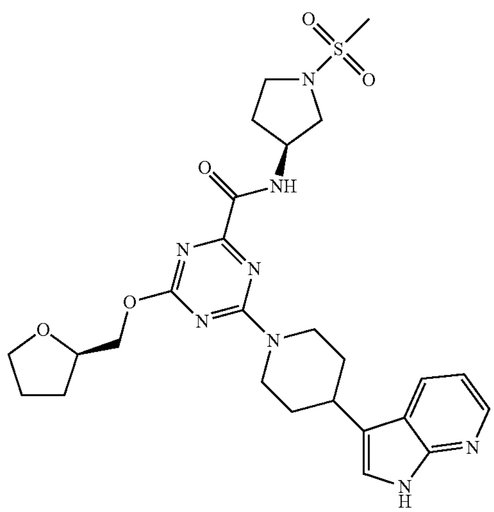 [SMILES: CS(=O)(=O)N1CC[C@H](NC(=O)c2nc(OC[C@H]3CCCO3)nc(N3CCC(c4c[nH]c5ncccc45)CC3)n2)C1] | N-[(3S)-1-(methylsulfonyl)pyrrolidin-3-yl]-4-[4-(1H-pyrrolo[2,3-b]pyridin-3-yl)piperidin-1-yl]-6-[(2R)-tetrahydrofuran-2-ylmethoxy]-1,3,5-triazine-2-carboxamide | 571; 2.468 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 320 * (D) | 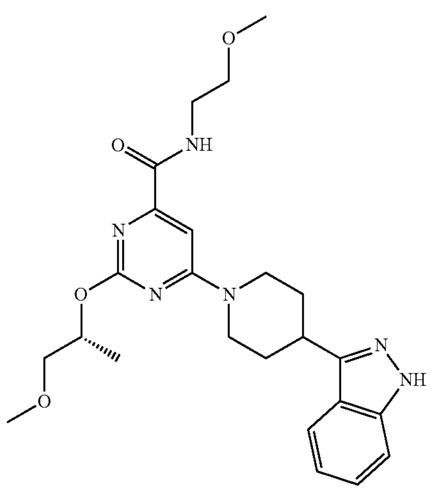 [SMILES: COCCNC(=O)c1cc(N2CCC(c3n[nH]c4ccccc34)CC2)nc(O[C@H](C)COC)n1] | N-(2-methoxyethyl)-2-{[(2R)-1-methoxypropan-2-yl]oxy}-6-[4-(1H-pyrazolo[3,4-b]pyridin-3-yl)piperidin-1-yl]pyrimidine-4-carboxamide | 470; 2.622 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 321 * (D) | 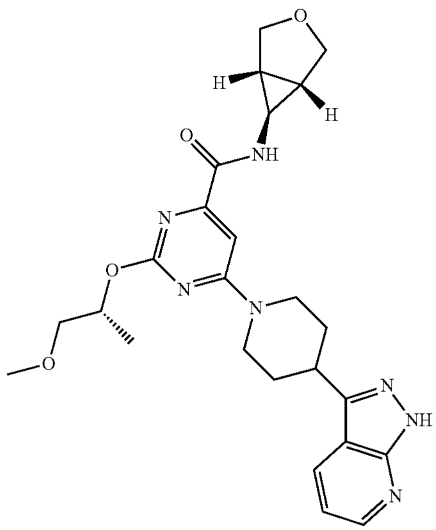 [SMILES: COC[C@@H](C)Oc1nc(C(=O)N[C@H]2[C@@H]3COC[C@@H]32)cc(N2CCC(c3n[nH]c4ncccc34)CC2)n1] | 2-{[(2R)-1-methoxypropan-2-yl]oxy}-N-[(1R,5S,6r)-3-oxabicyclo[3.1.0]hex-6-yl]-6-[4-(1H-pyrazolo[3,4-b]pyridin-3-yl)piperidin-1-yl]pyrimidine-4-carboxamide | 494; 2.610 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 322 *** (E) | 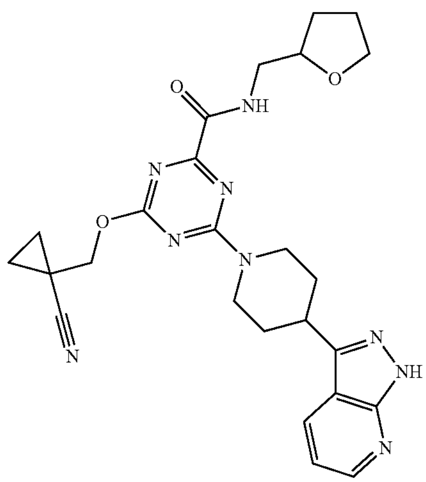 [SMILES: N#CC1(COc2nc(C(=O)NCC3CCCO3)nc(N3CCC(c4n[nH]c5ncccc45)CC3)n2)CC1] | 4-[(1-cyanocyclopropyl)methoxy]-6-[4-(1H-pyrazolo[3,4-b]pyridin-3-yl)piperidin-1-yl]-N-(tetrahydrofuran-2-ylmethyl)-1,3,5-triazine-2-carboxamide | 504; 2.650 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 323 * (D) | 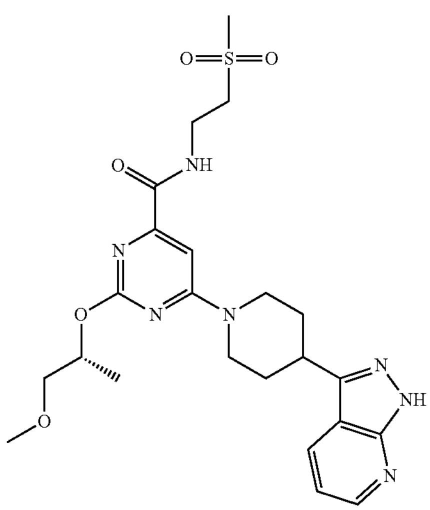 [SMILES: COC[C@@H](C)Oc1nc(C(=O)NCCS(C)(=O)=O)cc(N2CCC(c3n[nH]c4ncccc34)CC2)n1] | 2-{[(2R)-1-methoxypropan-2-yl]oxy}-N-[2-(methylsulfonyl)ethyl]-6-[4-(1H-pyrazolo[3,4-b]pyridin-3-yl)piperidin-1-yl]pyrimidine-4-carboxamide | 518; 2.557 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 324 * (E) | 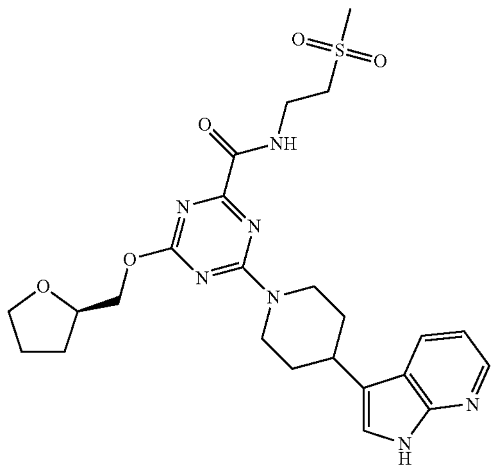 [SMILES: CS(=O)(=O)CCNC(=O)c1nc(OC[C@H]2CCCO2)nc(N2CCC(c3c[nH]c4ncccc34)CC2)n1] | N-[2-(methylsulfonyl)ethyl]-4-[4-(1H-pyrrolo[2,3-b]pyridin-3-yl)piperidin-1-yl]-6-[(2R)-tetrahydrofuran-2-ylmethoxy]-1,3,5-triazine-2-carboxamide | 530; 2.374 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 325 * (E) | 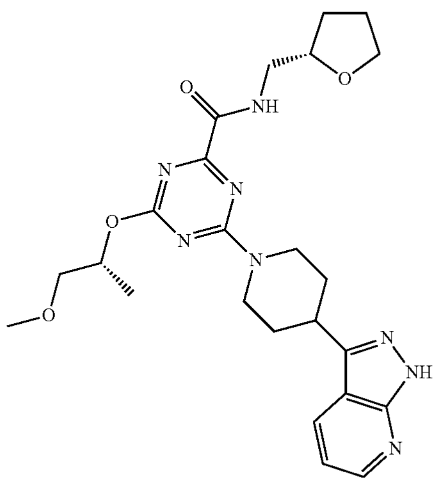 [SMILES: COC[C@@H](C)Oc1nc(C(=O)NC[C@@H]2CCCO2)nc(N2CCC(c3n[nH]c4ncccc34)CC2)n1] | 4-{[(2R)-1-methoxypropan-2-yl]oxy}-6-[4-(1H-pyrazolo[3,4-b]pyridin-3-yl)piperidin-1-yl]-N-[(2S)-tetrahydrofuran-2-ylmethyl]-1,3,5-triazine-2-carboxamide | 497; 2.737 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 326 * (D) | 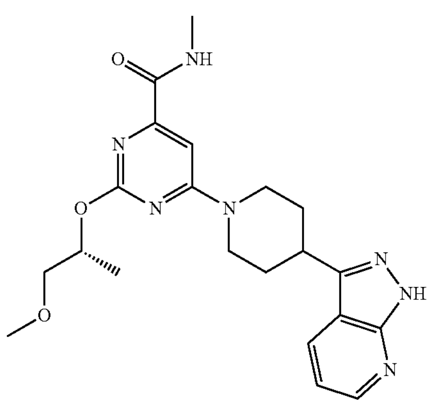 [SMILES: CNC(=O)c1cc(N2CCC(c3n[nH]c4ncccc34)CC2)nc(O[C@H](C)COC)n1] | 2-{[(2R)-1-methoxypropan-2-yl]oxy}-N-methyl-6-[4-(1H-pyrazolo[3,4-b]pyridin-3-yl)piperidin-1-yl]pyrimidine-4-carboxamide | 426; 2.524 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 327 * (E) | 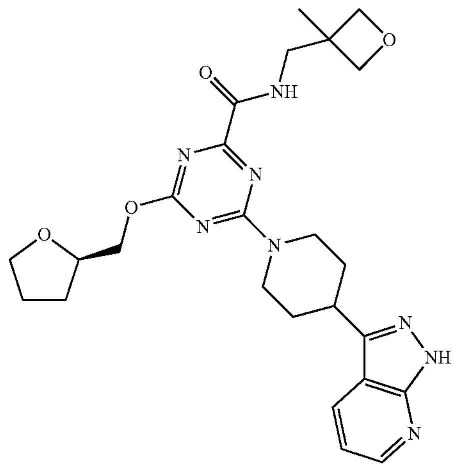 [SMILES: CC1(CNC(=O)c2nc(OC[C@H]3CCCO3)nc(N3CCC(c4n[nH]c5ncccc45)CC3)n2)COC1] | N-[(3-methyloxetan-3-yl)methyl]-4-[4-(1H-pyrazolo[3,4-b]pyridin-3-yl)piperidin-1-yl]-6-[(2R)-tetrahydrofuran-2-ylmethoxy]-1,3,5-triazine-2-carboxamide | 509; 2.643 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 328 * (E) | 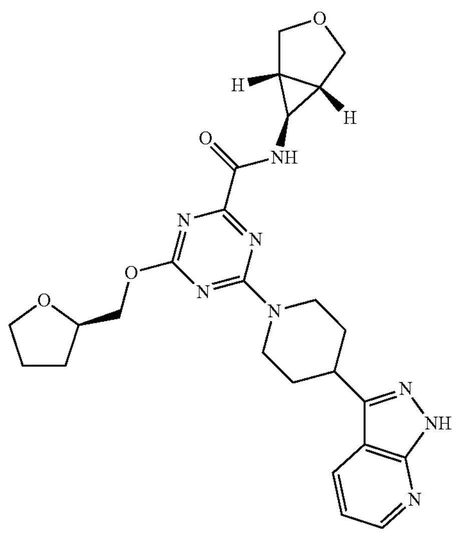 [SMILES: O=C(N[C@H]1[C@@H]2COC[C@@H]21)c1nc(OC[C@H]2CCCO2)nc(N2CCC(c3n[nH]c4ncccc34)CC2)n1] | N-[(1R,5S,6r)-3-oxabicyclo[3.1.0]hex-6-yl]-4-[4-(1H-pyrazolo[3,4-b]pyridin-3-yl)piperdin-1-yl]-6-[(2R)-tetrahydrofuran-2-ylmethoxy]-1,3,5-triazine-2-carboxamide | 495; 2.610 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 329 * (E) | 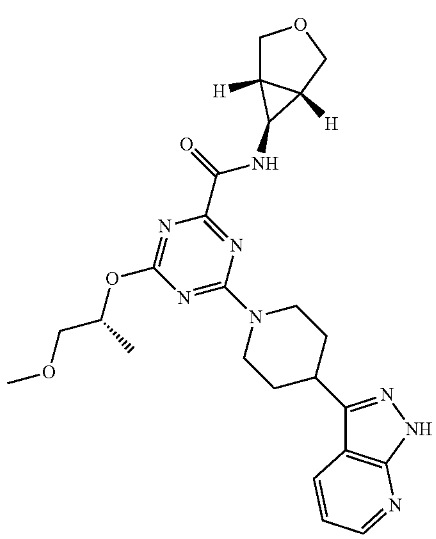 [SMILES: COC[C@@H](C)Oc1nc(C(=O)N[C@H]2[C@@H]3COC[C@@H]32)nc(N2CCC(c3n[nH]c4ncccc34)CC2)n1] | 4-(4-(1H-pyrazolo[3,4-b]pyridin-3-yl)piperidin-1-yl)-N-((1R,5S,6r)-3-oxabicyclo[3.1.0]hexan-6-yl)-6-((R)-1-methoxypropan-2-yloxy)-1,3,5-triazine-2-carboxamide | 507; 2.637 | Xbrldge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 330 * (D) | 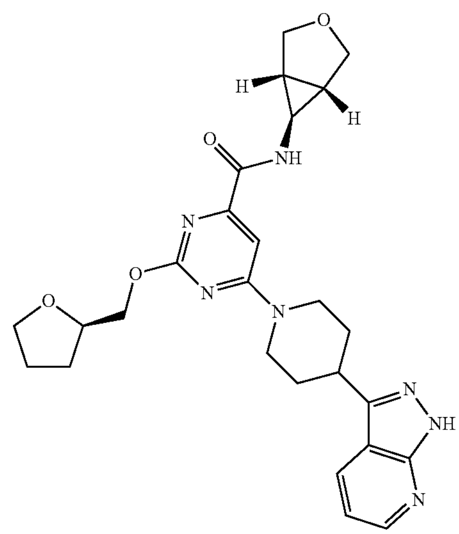 [SMILES: O=C(N[C@H]1[C@@H]2COC[C@@H]21)c1cc(N2CCC(c3n[nH]c4ncccc34)CC2)nc(OC[C@H]2CCCO2)n1] | 4-{[(2R)-1-methoxypropan-2-yl]oxy}-N-[(1R,5S,6r)-3-oxabicyclo[3.1.0]hex-6-yl]-6-[4-(1H-pyrazolo[3,4-b]pyridin-3-yl)piperidin-1-yl]-1,3,5-triazine-2-carboxamide | 506; 2.620 | Xbridge C18 2.1 × 50 mm (5 µm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 331 * (D) | 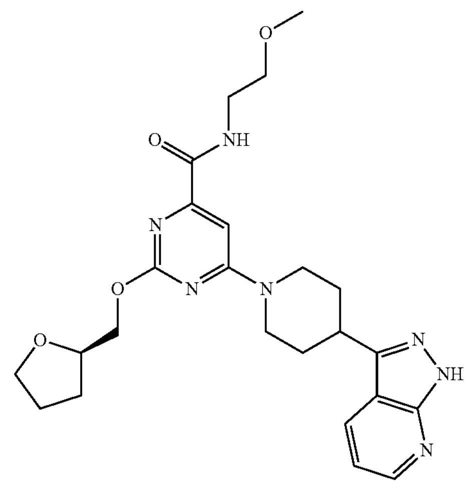 [SMILES: COCCNC(=O)c1cc(N2CCC(c3n[nH]c4ncccc34)CC2)nc(OC[C@H]2CCCO2)n1] | N-(2-methoxyethyl)-6-[4-(1H-pyrazolo[3,4-b]pyridin-3-yl)piperidin-1-yl]-2-[(2R)-tetrahydrofuran-2-ylmethoxy]pyrimidine-4-carboxamide | 482; 2.619 | Xbridge C18 2.1 × 50 mm (5 µm ). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 332 * (D) | 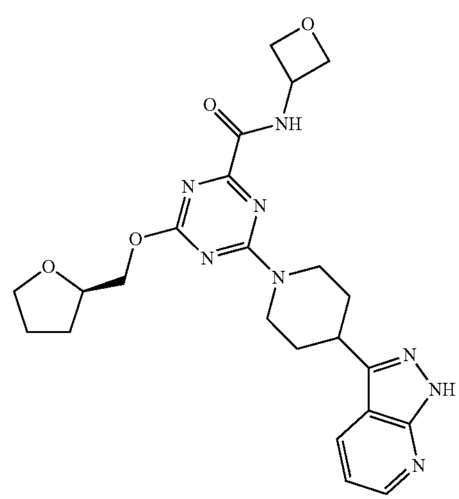 [SMILES: O=C(NC1COC1)c1nc(OC[C@H]2CCCO2)nc(N2CCC(c3n[nH]c4ncccc34)CC2)n1] | N-(oxetan-3-yl)-4-[4-(1H-pyrazolo[3,4-b]pyridin-3-yl)piperidin-1-yl]-6-[(2R)-tetrahydrofuran-2-ylmethoxy]-1,3,5-triazine-2-carboxamide | 481; 2.551 | Xbridge C18 2.1 × 50 mm (5 µm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 333 * (D) | 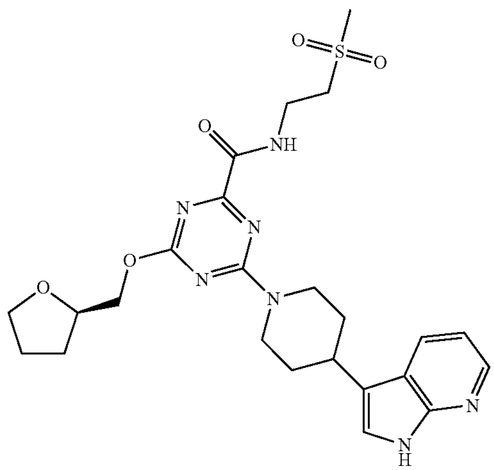 [SMILES: CS(=O)(=O)CCNC(=O)c1nc(OC[C@H]2CCCO2)nc(N2CCC(c3c[nH]c4ncccc34)CC2)n1] | N-[2-(methylsulfonyl)ethyl]-6-[4-(1H-pyrrolo[2,3-b]pyridin-3-yl)piperidin-1-yl]-2-[(2R)-tetrahydrofuran-2-ylmethoxy]pyrimidine-4-carboxamide | 530; 2.374 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 334 * (E) | 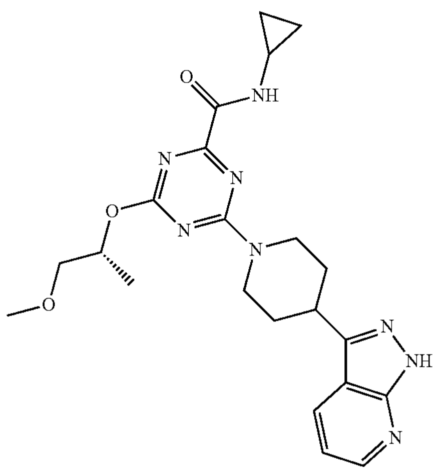 [SMILES: COC[C@@H](C)Oc1nc(C(=O)NC2CC2)nc(N2CCC(c3n[nH]c4ncccc34)CC2)n1] | N-cyclopropyl-4-{[(2R)-1-methoxypropan-2-yl]oxy}-6-[4-(1H-pyrazolo[3,4-b]pyridin-3-yl)piperidin-1-yl]-1,3,5-triazine-2-carboxamide | 453; 2.677 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 335 *** (E) | 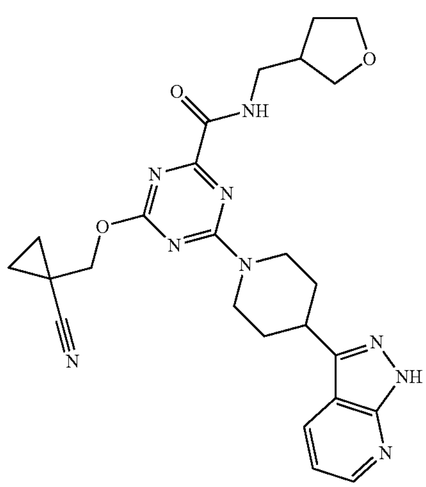 [SMILES: N#CC1(COc2nc(C(=O)NCC3CCOC3)nc(N3CCC(c4n[nH]c5ncccc45)CC3)n2)CC1] | 4-[(1-cyanocyclopropyl)methoxy]-6-[4-(1H-pyrazolo[3,4-b]pyridin-3-yl)piperidin-1-yl]-N-(tetrahydrofuran-3-ylmethyl)-1,3,5-triazine-2-carboxamide | 504; 2.650 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 336 * (E) | 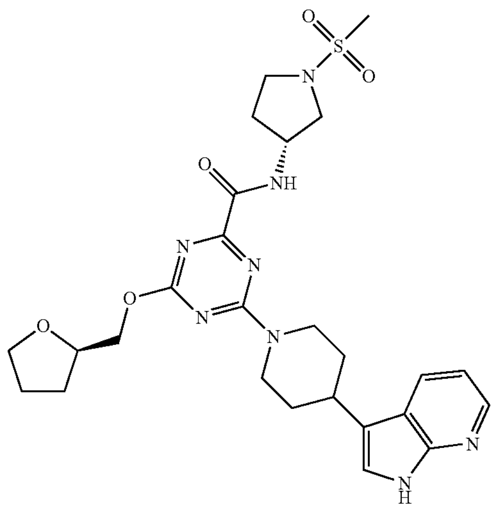 [SMILES: CS(=O)(=O)N1CC[C@@H](NC(=O)c2nc(OC[C@H]3CCCO3)nc(N3CCC(c4c[nH]c5ncccc45)CC3)n2)C1] | N-[(3R)-1-(methylsulfonyl)pyrrolidin-3-yl]-4-[4-(1H-pyrrolo[2,3-b]pyridin-3-yl)piperidin-1-yl]-6-[(2R)-tetrahydrofuran-2-ylmethoxy]-1,3,5-triazine-2-carboxamide | 571; 2.468 | Xbridge C18 2.1 × 50 mm (5 μm). 40° C. Mobile phase A: Water (W. 0.375% TFA). B: MeCN (w. 0.1875% TFA). 1 to 5% B over 0.6 mins to 100% B after 4 mins. Flow rate 0.8 mL/min. API-ES positive |
| 337 * (E) | 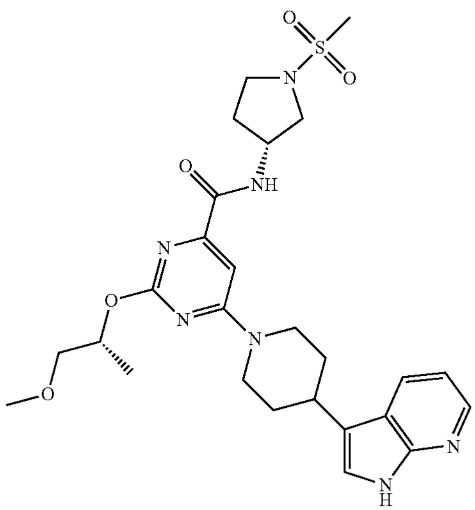 [SMILES: COC[C@@H](C)Oc1nc(C(=O)N[C@@H]2CCN(S(C)(=O)=O)C2)cc(N2CCC(c3c[nH]c4ncccc34)CC2)n1] | 2-{[(2R)-1-methoxypropan-2-yl]oxy}-N-[(3R)-1-(methylsulfonyl)pyrrolidin-3-yl]-6-[4-(1H-pyrrolo[2,3-b]pyridin-3-yl)piperidin-1-yl]pyrimidine-4-carboxamide | 558; 2.544 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 338 * (E) | 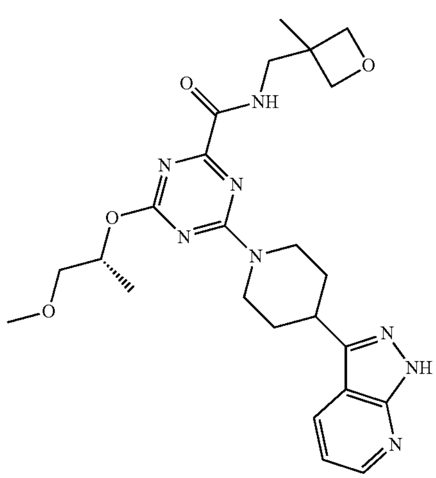 [SMILES: COC[C@@H](C)Oc1nc(C(=O)NCC2(C)COC2)nc(N2CCC(c3n[nH]c4ncccc34)CC2)n1] | 4-{[(2R)-1-methoxypropan-2-yl]oxy}-N-[(3-methyloxetan-3-yl)methyl]-6-(4-(1H-pyrazolo[3,4-b]pyridin-3-yl)piperidin-1-yl]-1,3,5-triazine-2-carboxamide | 497; 2.666 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 339 * (D) | 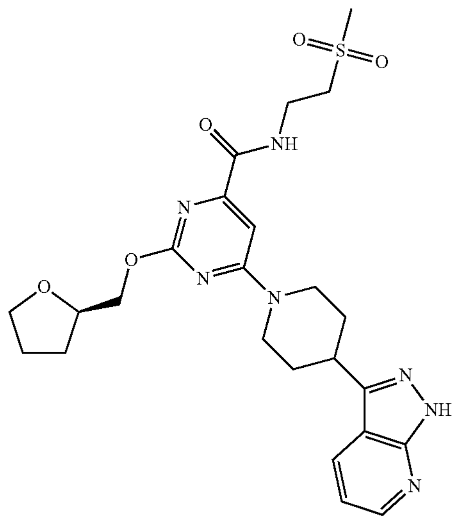 [SMILES: CS(=O)(=O)CCNC(=O)c1cc(N2CCC(c3n[nH]c4ncccc34)CC2)nc(OC[C@H]2CCCO2)n1] | 4-{[(2R)-1-methoxypropan-2-yl]oxy}-N-[(3-methyloxetan-3-yl)methyl]-6-[4-(1H-pyrazolo[3,4-b]pyridin-3-yl)piperidin-1-yl]-1,3,5-triazine-2-carboxamide | 530; 2.552 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 340 * (E) | 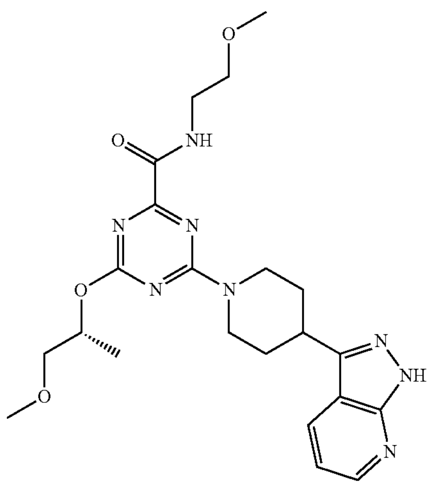 [SMILES: COCCNC(=O)c1nc(O[C@H](C)COC)nc(N2CCC(c3n[nH]c4ncccc34)CC2)n1] | N-(2-methoxyethyl)-4-{[(2R)-1-methoxypropan-2-yl]oxy}-6-[4-(1H-pyrazolo[3,4-b]pyridin-3-yl)piperidin-1-yl]-1,3,5-triazine-2-carboxamide | 471; 2.647 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 341 * (D) | 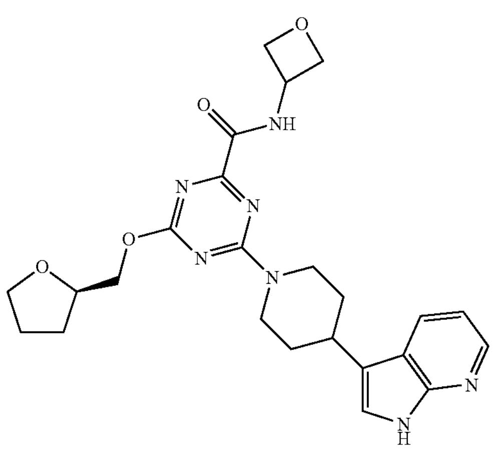 [SMILES: O=C(NC1COC1)c1nc(OC[C@H]2CCCO2)nc(N2CCC(c3c[nH]c4ncccc34)CC2)n1] | N-(oxetan-3-yl)-4-[4-(1H-pyrrolo[2,3-b]pyridin-3-yl)piperidin-1-yl]-6-[(2R)-tetrahydrofuran-2-ylmethoxy]-1,3,5-triazine-2-carboxamide | 480; 2.385 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

TABLE 2-continued

| Ex. # | Structure | Compound Name | Observed MW; and RT (min) | Method |
|---|---|---|---|---|
| 342 * (E) | 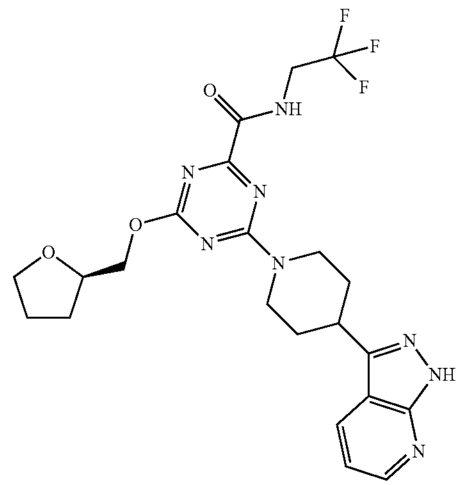 [SMILES: O=C(NCC(F)(F)F)c1nc(OC[C@H]2CCCO2)nc(N2CCC(c3n[nH]c4ncccc34)CC2)n1] | 4-[4-(1H-pyrazolo[3,4-b]pyridin-3-yl)piperidin-1-yl]-6-[(2R)-tetrahydrofuran-2-ylmethoxy]-N-(2,2,2-trifluoroethyl)-1,3,5-triazine-2-carboxamide | 507; 2.932 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |
| 343 * (E) | 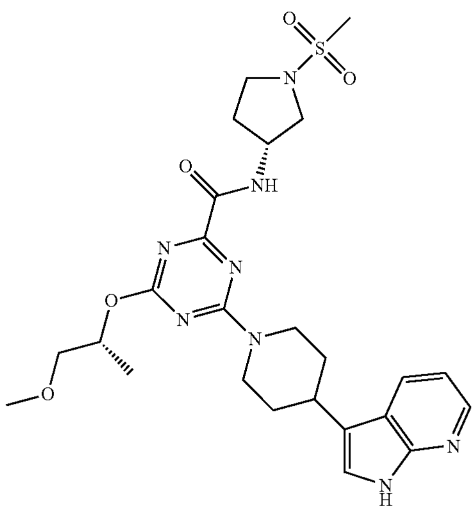 [SMILES: COC[C@@H](C)Oc1nc(C(=O)N[C@@H]2CCN(S(C)(=O)=O)C2)nc(N2CCC(c3c[nH]c4ncccc34)CC2)n1] | 4-{[(2R)-1-methoxypropan-2-yl]oxy}-N-((3R)-1-(methylsulfonyl)pyrrolidin-3-yl]-6-[4-(1H-pyrrolo(2,3-b]pyridin-3-yl)piperidin-1-yl]-1,3,5-triazine-2-carboxamide | 559; 2.471 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive |

* Compounds are single enantiomers with known absolute stereochemistry is unknown.
** Compounds are single enantiomers with unknown absolute stereochemistry.
*** Compounds are racemates, or known mixtures of diastereomers.

Chiral Separation Conditions
General Method for Chiral Purification

Chiral method development was performed using a Berger Analytical SFC/MS system (Waters SFC, Inc., Milford, Mass., USA) equipped with analytical scale supercritical fluid chromatograph coupled to a single quadrupole LC/MSD VL mass spectrometer with a multimode source (Agilent, Palo Alto, Calif., USA). A 1 mg/mL solution of sample was prepared in MeOH, and 15 μL was injected onto a selection of chiral stationary phases. Separation of the enantiomers was achieved for the relevant examples utilizing the conditions specified in Table 3. For purification, a Berger Multigram II semi-preparative SFC system was used, with UV-triggered fraction collection capability. Approximately 10 mg/mL of the sample was dissolved in MeOH. If complete solvation was not achieved, a co-solvent such as dichloromethane or DMSO was then added to the solution to give a final concentration of the solution of ~11 mg/mL. Injection volume of the sample solution was 0.3 mL, and semi-preparative chiral columns were utilized as described in Table 3 with typical flow rates of 50-70 mL/min with UV detection of peaks enabled at 240 nm. If full resolution of the enantiomers did not occur, a subsequent purification attempt was carried out under the same SFC conditions. All purified fractions were checked by analytical SFC-MS, evaporated and lyophilized.

Chiral separation of the compounds disclosed herein are summarized in Table 3:

TABLE 3

| Example No. (Scheme) | Chiral Separation Conditions (SFC) |
|---|---|
| 1** (Scheme A) | Rt(Peak 1) = 15.77 minutes Regis Whelk-O1 (R, R) 4.6 × 250 mm column 35% MeOH (w 0.1% DEA) @ 140 bar $CO_2$, 2.5 mL/min. |
| 3** (Scheme A) | Rt(Peak 2) = 9.63 minutes Chiralcel OJ-H 4.6 × 250 mm column 15% MeOH @ 140 bar $CO_2$, 3.0 mL/min. |
| 15** (Scheme A) | Rt(Peak 1) = 4.24 minutes Chiralcel AD-H 4.6 × 250 mm column 60% MeOH @ 100 bar $CO_2$, 3.0 mL/min. |
| 16** (Scheme A) | Rt(Peak 2) = 6.51 minutes Chiralcel AD-H 4.6 × 250 mm column 60% MeOH @ 100 bar $CO_2$, 3.0 mL/min. |
| 36** (Scheme A) | Rt(Peak 2) = 10.85 minutes Chiralcel OD-H 4.6 × 250 mm column 5 - 40% EtOH (w. 0.05% DEA) @ 120 bar $CO_2$, 2.35 mL/min. |
| 42* (Scheme A) | Rt(Peak 2) = 8.71 minutes Chiralcel OJ-H 4.6 × 250 mm column 15% MeOH @ 140 bar $CO_2$, 3.0 mL/min. |
| 44* (Scheme A) | Rt(Peak 2) = 8.58 minutes Chiralcel OJ-H 4.6 × 250 mm column 15% MeOH (w. 0.1% DEA) @ 140 bar $CO_2$, 3.0 mL/min. |
| 62** (Scheme C) | Rt(Peak 2) = 4.10 minutes Chiralcel AS-H 4.6 × 150 mm column 5 - 40% MeOH (w. 0.05% DEA) @ 120 bar $CO_2$, 3.0 mL/min. |
| 69* (Scheme B) | Rt(Peak 1) = 2.91 minutes Chiralcel OD-H 4.6 × 150 mm column 5 - 20% MeOH (w. 0.1% DEA) @ 120 bar $CO_2$, 4.0 mL/min. |
| 70* (Scheme B) | Rt(Peak 2) = 3.53 minutes Chiralcel OD-H 4.6 × 150 mm column 5 - 20% MeOH (w. 0.1% DEA) @ 120 bar $CO_2$, 4.0 mL/min. |
| 75** (Scheme A) | Rt(Peak 2) = 6.04 minutes Regis Whelk-O1 (S, S) 4.6 × 100 mm column 20% MeOH (w. 0.1% DEA) @ 120 bar $CO_2$, 4.0 mL/min. |
| 76** (Scheme A) | Rt(Peak 1) = 5.74 minutes Regis Whelk-O1 (S, S) 4.6 × 100 mm column 20% MeOH (w. 0.1% DEA) @ 120 bar $CO_2$, 4.0 mL/min. |
| 78** (Scheme C) | Rt(Peak 1) = 1.20 minutes Chiralcel OJ-H 4.6 × 150 mm column 40% MeOH @ 120 bar $CO_2$, 4.0 mL/min. |
| 79** (Scheme C) | Rt(Peak 2) = 2.34 minutes Chiralcel OJ-H 4.6 × 150 mm column 40% MeOH @ 120 bar $CO_2$, 4.0 mL/min. |
| 95** (Scheme B) | Rt(Peak 2) = 8.78 minutes Regis-Whelk O1 (S, S) 4.6 × 100 mm column 20% MeOH @ 120 bar $CO_2$, 4.0 mL/min. |
| 96** (Scheme B) | Rt(Peak 1) = 8.41 minutes Regis-Whelk O1 (S, S) 4.6 × 100 mm column 20% MeOH @ 120 bar $CO_2$, 4.0 mL/min. |
| 136** (Scheme C) | Rt(Peak 1) = 1.62 minutes Chiralcel OJ-3 4.6 × 50 mm column 5 - 40% MeOH (w. 0.05% DEA) @ 120 bar $CO_2$, 4.0 mL/min. |
| 137** (Scheme C) | Rt(Peak 2) = 1.94 minutes Chiralcel OJ-3 4.6 × 50 mm column 5 - 40% MeOH (w. 0.05% DEA) @ 120 bar $CO_2$, 4.0 mL/min. |
| 143** (Scheme A) | Rt(Peak 1) = 4.94 minutes Chiralcel AD-3 4.6 × 150 mm column 50% MeOH (w. 0.05% DEA) @ 120 bar $CO_2$, 2.0 mL/min. |
| 163** (Scheme E) | Rt(Peak 2) = 8.39 minutes Chiralcel AD-3 4.6 × 150 mm column 40% IPA (w. 0.05% DEA) @ 120 bar $CO_2$, 2.5 mL/min. |
| 164** (Scheme E) | Rt(Peak 1) = 7.68 minutes Chiralcel AD-3 4.6 × 150 mm column 40% IPA (w. 0.05% DEA) @ 120 bar $CO_2$, 2.5 mL/min. |
| 166* (Scheme E) | Rt(Peak 2) = 8.69 minutes Chiralcel OJ-H 4.6 × 250 mm column 5 - 40% EtOH (w. 0.05% DEA) @ 120 bar $CO_2$, 2.4 mL/min. |
| 167* (Scheme E) | Rt(Peak 1) = 8.08 minutes Chiralcel OJ-H 4.6 × 250 mm column 5 - 40% EtOH (w. 0.05% DEA) @ 120 bar $CO_2$, 2.4 mL/min. |
| 168** (Scheme A) | Rt(Peak 2) = 6.76 minutes Chiralcel AD-3 4.6 × 150 mm column 50% MeOH (w. 0.05% DEA) @ 120 bar $CO_2$, 2.0 mL/min. |
| 170* (Scheme E) | Rt(Peak 1) = 11.50 minutes Chiralcel AS-H 4.6 × 250 mm column 20% EtOH (w. 0.05% DEA) @ 120 bar $CO_2$, 2.35 mL/min. |
| 171* (Scheme E) | Rt(Peak 2) = 13.15 minutes Chiralcel AS-H 4.6 × 250 mm column 20% EtOH (w. 0.05% DEA) @ 120 bar $CO_2$, 2.35 mL/min. |
| 176** (Scheme E) | Rt(Peak 2) = 11.10 minutes Lux Cellulose-4 4.6 × 100 mm column 25% MeOH @ 120 bar $CO_2$, 4.0 mL/min. |
| 177** (Scheme E) | Rt(Peak 1) = 9.87 minutes Lux Cellulose-4 4.6 × 100 mm column 25% MeOH @ 120 bar $CO_2$, 4.0 mL/min. |
| 198* (Scheme A) | Rt(Peak 2) = 6.08 minutes ChiralCel AD-H 4.6 × 250 mm column 40% EtOH (w. 0.05% DEA) @ 120 bar $CO_2$, 2.35 mL/min. |
| 231** (Scheme D) | Rt(Peak 1) = 4.10 minutes Lux Cellulose 4.6 × 100 mm column 25% MeOH @ 120 bar $CO_2$, 4 mL/min. |
| 233** (Scheme D) | Rt(Peak 2) = 4.61 minutes Lux Cellulose 4.6 × 100 mm column 25% MeOH @ 120 bar $CO_2$, 4 mL/min. |
| 235** (Scheme D) | Rt(Peak 2) = 6.18 minutes ChiralCel AD-H 4.6 × 250 mm column 40% IPA (w. 0.05% DEA) @ 120 bar $CO_2$, 2.5 mL/min. |
| 236** (Scheme D) | Rt(Peak 1) = 5.58 minutes ChiralCel AD-H 4.6 × 250 mm column 40% IPA (w. 0.05% DEA) @ 120 bar $CO_2$, 2.5 mL/min. |
| 253** (Scheme D) | Rt(Peak 2) = 6.50 minutes Chiralcel OJ-3 4.6 × 150 mm column 5 - 40% MeOH (w. 0.05% DEA) @ 120 bar $CO_2$, 2.5 mL/min. |
| 254** (Scheme D) | Rt(Peak 1) = 8.60 minutes IC 4.6 × 250 mm column 60% IPA (w. 0.05% DEA) @ 120 bar $CO_2$, 2.0 mL/min. |
| 255** (Scheme D) | Rt(Peak2) = 10.19 minutes IC 4.6 × 250 mm column 60% IPA (w. 0.05% DEA) @ 120 bar $CO_2$, 2.0 mL/min. |
| 258** (Scheme D) | Rt(Peak 1) = 6.22 minutes Chiralcel OJ-3 4.6 × 150 mm column 5 - 40% MeOH (w. 0.05% DEA) @ 120 bar $CO_2$, 2.5 mL/min. |
| 267** (Scheme D) | Rt(Peak 2) = 12.34 minutes ChiralCel AD-H 4.6 × 250 mm column 40% EtOH (w. 0.05% DEA) @ 120 bar $CO_2$, 2.35 mL/min. |
| 268** | Rt(Peak 1) = 10.66 minutes ChiralCel AD-H 4.6 × 250 mm column |

TABLE 3-continued

| Example No. (Scheme) | Chiral Separation Conditions (SFC) |
|---|---|
| (Scheme D) | 40% EtOH (w. 0.05% DEA) @ 120 bar CO$_2$, 2.35 mL/min. |
| 348** (Scheme I) | Rt(Peak 1) = 1.80 minutes ChiralCel OJ-3 4.6 × 100 mm column 10% MeOH @ 120 bar CO$_2$, 4.00 mL/min. |
| 349** (Scheme I) | Rt(Peak 2) = 2.48 minutes ChiralCel OJ-3 4.6 × 100 mm column 10% MeOH @ 120 bar CO$_2$, 4.00 mL/min. |
| 361* (Scheme D) | Rt(Peak 1) = 6.46 minutes ChiralCel OJ-H 4.6 × 250 mm column 5 - 40% MeOH (w. 0.05% DEA) @ 120 bar CO$_2$, 2.35 mL/min. |
| 362* (Scheme D) | Rt(Peak 2) = 7.09 minutes ChiralCel OJ-H 4.6 × 250 mm column 5 - 40% MeOH (w. 0.05% DEA) @ 120 bar CO$_2$, 2.35 mL/min. |
| 372** (Scheme D) | Rt(Peak 1) = 5.58 minutes ChiralCel OJ-H 4.6 × 250 mm column 5 - 40% MeOH (w. 0.05% DEA) @ 120 bar CO$_2$, 2.5 mL/min. |
| 376** (Scheme D) | Rt(Peak 2) = 5.70 minutes ChiralCel OJ-H 4.6 × 250 mm column 5 - 40% MeOH (w. 0.05% DEA) @ 120 bar CO$_2$, 2.5 mL/min. |
| 388** (Scheme D) | Rt(Peak 1) = 3.57 minutes ChiralCel AD-3, 4.6 × 250 mm column 40% EtOH (w. 0.05% DEA) @ 120 bar CO$_2$, 2.5 mL/min. |
| 389** (Scheme D) | Rt(Peak 2) = 3.88 minutes ChiralCel AD-3, 4.6 × 250 mm column 40% EtOH (w. 0.05% DEA) @ 120 bar CO$_2$, 2.5 mL/min. |
| 395** (Scheme D) | Rt(Peak 1) = 10.29 minutes Chiralcel AD-H 4.6 × 250 mm column 40% EtOH @ 100 bar CO$_2$, 2.35 mL/min. |
| 396** (Scheme D) | Rt(Peak 2) = 11.94 minutes ChiralCel AD-H 4.6 × 250 mm column 40% EtOH @ 100 bar CO$_2$, 2.35 mL/min. |
| 411** (Scheme D) | Rt(Peak 1) = 3.28 minutes Lux Cellulose-4 4.6 × 100 mm column 50% MeOH @ 120 bar CO$_2$, 4 mL/min. |
| 412** (Scheme D) | Rt(Peak 2) = 4.43 minutes Lux Cellulose-4 4.6 × 100 mm column 50% MeOH @ 120 bar CO$_2$, 4 mL/min. |
| 430** (Scheme D) | Rt(Peak 2) = 1.09 minutes ChiralCel OJ-3 4.6 × 50 mm column 5 - 40% MeOH (w. 0.05% DEA) @ 100 bar CO$_2$, 4 mL/min. |
| 432** (Scheme D) | Rt(Peak 1) = 0.98 minutes ChiralCel OJ-3 4.6 × 50 mm column 5 - 40% MeOH (w. 0.05% DEA) @ 100 bar CO$_2$, 4 mL/min. |
| 436** (Scheme D) | Rt(Peak 2) = 17.90 minutes ChiralCel IC 4.6 × 250 mm column 40% EtOH (w. 0.05% DEA) @ 100 bar CO$_2$, 2.35 mL/min. |
| 437** (Scheme D) | Rt(Peak 1) = 14.80 minutes ChiralCel IC 4.6 × 250 mm column 40% EtOH (w. 0.05% DEA) @ 100 bar CO$_2$, 2.35 mL/min. |
| 441** (Scheme D) | Rt(Peak 2) = 31.10 minutes ChiralCel IC-3 4.6 × 150 mm column 40% MeOH (w. 0.05% DEA) @ 100 bar CO$_2$, 2.5 mL/min. |
| 442** (Scheme D) | Rt(Peak 1) = 24.89 minutes ChiralCel IC-3 4.6 × 150 mm column 40% MeOH (w. 0.05% DEA) @ 100 bar CO$_2$, 2.5 mL/min. |
| 445** (Scheme D) | Rt(Peak 1) = 0.83 minutes ChiralCel AD-3 4.6 × 50 mm column 40% IPA (w. 0.05% DEA) @ 100 bar CO$_2$, 4 mL/min. |
| 446** (Scheme D) | Rt(Peak 2) = 1.51 minutes ChiralCel AD-3 4.6 × 50 mm column 40% EtOH (w. 0.05% DEA) @ 100 bar CO$_2$, 4 mL/min. |
| 457** (Scheme D) | Rt(Peak 1) = 1.46 minutes ChiralCel AD-3 4.6 × 50 mm column 40% IPA (w. 0.05% DEA) @ 100 bar CO$_2$, 4 mL/min. |
| 458** (Scheme D) | Rt(Peak 2) = 1.98 minutes ChiralCel AD-3 4.6 × 50 mm column 40% EtOH (w. 0.05% DEA) @ 100 bar CO$_2$, 4 mL/min. |
| 486** (Scheme D) | Rt(Peak 1) = 3.64 minutes ChiralCel OJ-3 4.6 × 50 mm column 5 - 40% MeOH (w. 0.05% DEA) @ 100 bar CO$_2$, 2.8 mL/min. |
| 487** (Scheme D) | Rt(Peak 2) = 3.85 minutes ChiralCel OJ-3 4.6 × 50 mm column 5 - 40% MeOH (w. 0.05% DEA) @ 100 bar CO$_2$, 2.8 mL/min. |
| 497** (Scheme D) | Rt(Peak 1) = 1.97 minutes Chiralcel AD-3 4.6 × 100 mm column 40% IPA (w. 0.05% DEA) @ 100 bar CO$_2$, 2.8 mL/min. |
| 497** (Scheme D) | Rt(Peak 2) = 2.46 minutes Chiralcel AD-3 4.6 × 100 mm column 40% IPA (w. 0.05% DEA) @ 100 bar CO$_2$, 2.8 mL/min. |
| 498** (Scheme D) | Rt(Peak 1) = 21.98 minutes Chiralcel IC-3 4.6 × 150 mm column 40% EtOH (w. 0.05% DEA) @ 120 bar CO$_2$, 2.5 mL/min. |
| 499** (Scheme D) | Rt(Peak 1) = 32.92 minutes Chiralcel IC-3 4.6 × 150 mm column 40% EtOH (w. 0.05% DEA) @ 120 bar CO$_2$, 2.5 mL/min. |
| 500** (Scheme D) | Rt(Peak 2) = 3.09 minutes Chiralcel AD-3 4.6 × 50 mm column 40% IPA (w. 0.05% DEA) @ 100 bar CO$_2$, 4 mL/min. |
| 507** (Scheme D) | Rt(Peak 1) = 1.65 minutes Chiralcel AD-3 4.6 × 50 mm column 40% IPA (w. 0.05% DEA) @ 100 bar CO$_2$, 4 mL/min. |
| 508** (Scheme D) | Rt(Peak 2) = 3.09 minutes Chiralcel AD-3 4.6 × 50 mm column 40% IPA (w. 0.05% DEA) @ 100 bar CO$_2$, 4 mL/min. |

*Compounds are single enantiomers with known absolute stereochemistry is unknown.
**Compounds are single enantiomers with unknown absolute stereochemistry.
*** Compounds are racemates, or known mixtures of diastereomers.

Biological Examples

Results for biological examples are summarized in Table 4 and shown as KI and/or IC$_{50}$ values in μM.

Recombinant AXL Enzyme Assay

AXL enzyme inhibition (% inhibition, K$_{iapp}$ and K$_i$ values) by small molecule inhibitors was evaluated using a fluorescence-based microfluidic mobility shift assay. AXL catalyzes the production of ADP from ATP that accompanies the phosphoryl transfer to the substrate peptide FL-Peptide-30 (5-FAM-KKKKEEIYFFF-CONH$_2$, CPC Scientific, Sunnyvale, Calif.). The mobility shift assay electrophoretically separates the fluorescently labeled peptides (substrate and phosphorylated product) following the kinase reaction.

Both substrate and product are measured and the ratio of these values is used to generate % conversion of substrate to product by the LabChip EZ Reader. Human wild-type receptor tyrosine kinase protein Axl comprising residues 505-811 was produced in-house using the baculoviral expression vector system that incorporated a hexahistidine affinity tag into the protein (LJIC-1916B1.1). The enzyme was preactivated by auto-phosphorylation of 34 uM non-activated enzyme in the presence of 2 mM ATP, 4 mM $MgCl_2$, 50 mM NaCl and 1 mM TCEP in 20 mM HEPES, pH 7.3 at 4° C. for 30 minutes. Typical reaction solutions (50 μL final reaction volume) contained 2% DMSO (±inhibitor), 10 mM $MgCl_2$, 1 mM DTT, 120 μM ATP (ATP $K_m$=70.4 μM), 0.01% Tween-20, 3 μM FL-Peptide-30, and 0.5 nM phosphorylated AXL enzyme in 100 mM HEPES buffer at pH 7.3. The assay was initiated with the addition of ATP, following a fifteen minutes pre-incubation of enzyme and inhibitor at room temperature in the reaction mixture. The reaction was stopped after 30 minutes at 25° C. by the addition of 50 μL of 200 mM EDTA, pH 7.5. The $K_i$ values were determined from the fit of the data to the Morrison tight-binding competitive inhibition equation with the enzyme concentration as a variable. (See, Morrison, J. F. (1969) Kinetics of the reversible inhibition of enzyme-catalysed reactions by tight-binding inhibitors, *Biochimica et biophysica acta* 185, 269-286; and Murphy, D. J. (2004) Determination of accurate KI values for tight-binding enzyme inhibitors: an in silico study of experimental error and assay design, *Analytical biochemistry* 327, 61-67.)

Cellular Axl Phosphorylation ELISA Assay

293MSR-AxlWT6 cells were seeded at density 40,000 cells/well in 96-well plates, in DMEM medium supplemented with 1% penicillin and streptomycin, 0.5 mg/mL G418, 10 μg/mL blasticidin and 10% fetal bovine serum (FBS). After 6-7 hrs in tissue culture incubator at 37° C. 5% $CO_2$, medium was removed, serum-free medium was added (with 0.04% bovine serum albumin) and plates were returned to incubator where they remained overnight. After 20 hrs in the tissue culture incubator, the medium was removed and cells were cultured in serum-free medium at 37° C. in the presence of a compound of the invention at designated compound concentrations ranging from 0.0024 uM to 10 uM or controls for 1 h. After incubation with a compound of the invention, cells were stimulated with 200 ng/ml human recombinant Gas6 (R&D Systems) and 0.5× Phosphatase Inhibitor Cocktail in starvation media for 20 min at 37° C. 5% $CO_2$. Media was then removed and lysis buffer was added to wells and shaken at 4° C. for 30 min to generate protein lysates. Subsequently, phosphorylation of Axl was assessed by a sandwich ELISA method using a DuoSet IC Human Phospho-Axl ELISA assay kit (R&D System), an immobilized mouse anti-human Axl antibody and an anti-phospho-tyrosine-HRP antibody as a detection antibody. Antibody-coated plates were (a) incubated in presence of protein lysates at room temperature for 2 hrs, (b) washed seven times in 0.1% Tween 20 in PBS, (c) incubated with secondary antibody (a horseradish peroxidase-conjugated antiphospho-Axl antibody) for 2 hrs, (d) washed seven times again, (e) TMB peroxidase substrate (Bio-Rad) was added to initiate a colorimetric reaction and stopped by adding 0.2 N $H2SO4$, and (f) measured at OD 450 nm using a spectrophotometer. $IC_{50}$ values were calculated by concentration-response curve fitting using a four-parameter analytic method and reported in μM.

TABLE 4A

| Ex. # | ENZYME AXL KI (μM) | CELL AXL IC50 (μM) |
|---|---|---|
| 1 | 0.00009 | 0.00101 |
| 2 |  | 0.24566 |
| 3 | 0.003138 | 0.02191 |
| 4 |  | 0.00283 |
| 5 |  | 0.01245 |
| 6 |  | 0.02915 |
| 7 |  | 0.01486 |
| 8 |  | 0.07785 |
| 9 | 0.000126 | 0.0011 |
| 10 | 0.000063 | 0.00031 |
| 11 |  | 0.01015 |
| 12 | 0.002485 | 0.00996 |
| 13 |  | 0.05903 |
| 14 |  | 0.01241 |
| 15 |  | 0.00836 |
| 16 |  | 0.0126 |
| 17 |  | 0.03987 |
| 18 |  | 0.06494 |
| 19 |  | 0.02473 |
| 20 | 0.000075 | 0.00165 |
| 21 |  | 0.03701 |
| 22 | 0.000131 | 0.00358 |
| 23 | 0.003982 | 0.0578 |
| 24 |  | 0.00192 |
| 25 |  | 0.00178 |
| 26 | 0.001136 | 0.0279 |
| 27 | 0.000219 | 0.0089 |
| 28 | 0.000367 | 0.01052 |
| 29 | 0.000311 | 0.00495 |
| 30 | 0.000125 | 0.00253 |
| 31 |  | 0.01263 |
| 32 | 0.002429 | 0.01985 |
| 33 |  | 0.02342 |
| 34 |  | 0.03052 |
| 35 | 0.000909 | 0.01037 |
| 36 |  | 0.08737 |
| 37 |  | 0.24167 |
| 38 | 0.009583 | 0.01054 |
| 39 |  | 0.08385 |
| 40 |  | 0.00577 |
| 41 |  | 0.12416 |
| 42 | 0.000337 | 0.01334 |
| 43 |  | 0.13127 |
| 44 | 0.000276 | 0.00629 |
| 45 |  | 0.23542 |
| 46 | 0.000504 | 0.00397 |
| 47 |  | 0.00384 |
| 48 |  | 0.03812 |
| 49 | 0.000953 | 0.01235 |
| 50 |  | 0.01555 |
| 51 |  | 0.00789 |
| 52 | 0.001425 | 0.0313 |
| 53 | 0.000316 | 0.0034 |
| 54 |  | 0.00527 |
| 55 | 0.001813 | 0.01697 |
| 56 | 0.000518 | 0.01079 |
| 57 | 0.000215 | 0.00461 |
| 58 |  | 0.02381 |
| 59 |  | 0.00274 |
| 60 |  | 0.00665 |
| 61 | 0.003256 | 0.08593 |
| 62 |  | 0.03868 |
| 63 |  | 0.45539 |
| 64 | 0.000173 | 0.00101 |
| 65 |  | 0.00186 |
| 66 |  | 0.06176 |
| 67 |  | 0.01875 |
| 68 |  | 0.00294 |
| 69 |  | 0.22823 |
| 70 |  | 0.04078 |
| 71 |  | 0.01203 |
| 72 |  | 0.00431 |
| 73 |  | 0.22842 |
| 74 |  | 0.01549 |
| 75 |  | 0.00854 |
| 76 |  | 0.01916 |

TABLE 4A-continued

| Ex. # | ENZYME AXL KI (μM) | CELL AXL IC50 (μM) |
|---|---|---|
| 77 |  | 0.04282 |
| 78 |  | 0.00842 |
| 79 |  | 0.0564 |
| 80 | 0.00032 | 0.00766 |
| 81 |  | 0.00521 |
| 82 | 0.001502 | 0.01103 |
| 83 |  | 0.03329 |
| 84 |  | 0.02943 |
| 85 |  | 0.1895 |
| 86 |  | 0.0167 |
| 87 |  | 0.06604 |
| 88 | 0.001526 | 0.0158 |
| 89 |  | 0.13375 |
| 90 |  | 0.00698 |
| 91 |  | 0.06489 |
| 92 | 0.000807 | 0.46129 |
| 93 | 0.001735 | 0.01223 |
| 94 | 0.000104 | 0.00377 |
| 95 | 0.000726 | 0.0284 |
| 96 | 0.003086 | 0.08639 |
| 97 | 0.013152 |  |
| 98 | 0.002403 | 0.31442 |
| 99 | 0.000053 | 0.01853 |
| 100 | 0.001878 | 0.0406 |
| 101 | 0.000936 | 0.02676 |
| 102 | 0.00014 | 0.00079 |
| 103 | 0.026548 | 0.1369 |
| 104 | 0.002347 | 0.01862 |
| 105 | 0.00463 | 0.05399 |
| 106 | 0.00107 | 0.01281 |
| 107 | 0.002355 | 0.05975 |
| 108 | 0.022478 | 0.18998 |
| 109 | 0.000172 | 0.07394 |
| 110 | 0.01492 | 0.13966 |
| 111 | 0.000823 | 0.00906 |
| 112 | 0.000016 | 0.00338 |
| 113 | 0.000438 | 0.007 |
| 114 | 0.000028 | 0.00136 |
| 115 | 0.003995 | 0.11638 |
| 116 | 0.000487 | 0.03805 |
| 117 | 0.00001 | 0.00059 |
| 118 | 0.007941 | 0.35112 |
| 119 | 0.00529 | 0.10708 |
| 120 | 0.005573 | 0.17034 |
| 121 | 0.00097 | 0.0066 |
| 122 | 0.000319 | 0.00358 |
| 123 | 0.001005 | 0.11083 |
| 124 | 0.04523 | 1.15388 |
| 125 | 0.010664 | 5.1323 |
| 126 | 0.208601 | 7.80667 |
| 127 | 0.002512 | 0.05451 |
| 128 | 0.013868 | 0.34261 |
| 129 | 0.003338 | 1.38513 |
| 130 | 0.066775 | 1.0325 |
| 131 | 0.010469 | 0.70056 |
| 132 |  | 0.23077 |
| 133 |  | 0.28486 |
| 134 | 0.000264 | 0.00626 |
| 135 | 0.000415 | 0.00426 |
| 136 | 0.007081 | 0.06711 |
| 137 | 0.000247 | 0.0029 |
| 138 | 0.000372 | 0.0056 |
| 139 | 0.000079 | 0.00232 |
| 140 | 0.001951 | 0.20876 |
| 141 | 0.003032 | 0.03456 |
| 142 | 0.000168 | 0.02479 |
| 143 | 0.000607 | 0.00339 |
| 144 | 0.002415 | 0.50494 |
| 145 | 0.003012 | 0.01877 |
| 146 | 0.003848 | 0.13832 |
| 147 | 0.002444 | 0.01163 |
| 148 | 0.003293 | 0.45803 |
| 149 | 0.010719 | 9.78842 |
| 150 | 0.001416 | 0.00988 |
| 151 | 0.000986 | 0.02623 |
| 152 | 0.00507 | 1.51236 |
| 153 | 0.000587 | 0.0022 |
| 154 | 0.003355 | 0.25518 |
| 155 | 0.010438 | 0.02813 |
| 156 | 0.001495 | 0.0046 |
| 157 | 0.004819 | 0.84062 |
| 158 | 0.003155 | 0.02712 |
| 159 | 0.000663 | 0.00609 |
| 160 | 0.00009 | 0.00064 |
| 161 | 0.003464 | 0.07118 |
| 162 | 0.0003 | 0.01285 |
| 163 | 0.000453 | 0.00171 |
| 164 | 0.001786 | 0.00348 |
| 165 | 0.001143 | 0.0051 |
| 166 | 0.000838 | 0.0034 |
| 167 | 0.00021 | 0.00052 |
| 168 | 0.003111 | 0.01478 |
| 169 | 0.001413 | 0.02318 |
| 170 | 0.005729 | 0.0262 |
| 171 | 0.001256 | 0.00526 |
| 172 | 0.000097 | 0.00054 |
| 173 | 0.00003 | 0.00026 |
| 174 | 0.001496 | 0.01916 |
| 175 | 0.000742 | 0.00203 |
| 176 | 0.001026 | 0.02525 |
| 177 | 0.00344 | 0.08604 |
| 178 | 0.000098 | 0.00067 |
| 179 | 0.000085 | 0.00119 |
| 180 | 0.037935 | 0.32664 |
| 181 | 0.000369 | 0.02508 |
| 182 | 0.000211 | 0.00102 |
| 183 | 0.000351 | 0.01554 |
| 184 | 0.001911 | 0.01289 |
| 185 | 0.002375 | 0.00669 |
| 186 | 0.000543 | 0.00227 |
| 187 | 0.052695 | 0.36206 |
| 188 | 0.001665 | 0.0038 |
| 189 | 0.004825 | 0.08484 |
| 190 | 0.005214 | 0.03868 |
| 191 | 0.005493 | 0.07417 |
| 192 | 0.028389 | 1.33598 |
| 193 | 0.022188 | 0.29525 |
| 194 | 0.052695 | 2.00576 |
| 195 | 0.010816 | 0.22819 |
| 196 | 0.009244 | 0.15938 |
| 197 | 0.010657 | 0.16406 |
| 198 | 0.002208 | 0.02577 |
| 199 | 0.00205 | 0.0163 |
| 200 | 0.006253 | 0.03494 |
| 201 | 0.007559 | 0.23587 |
| 202 | 0.011089 | 0.31465 |
| 203 | 0.000526 | 0.01305 |
| 204 | 0.00148 | 0.05674 |
| 205 | 0.015449 | 0.0848 |
| 206 | 0.009318 | 0.06699 |
| 207 | 0.015211 | 0.1941 |
| 208 | 0.022234 | 0.12057 |
| 209 | 0.009029 | 0.02302 |
| 210 | 0.004129 | 1.46178 |
| 211 | 0.011046 | 0.08632 |
| 212 | 0.023777 | 0.14147 |
| 213 | 0.006005 | 0.03014 |
| 214 | 0.0042 | 0.01369 |
| 215 | 0.012533 | 0.07593 |
| 216 | 0.001631 | 0.00948 |
| 217 | 0.052695 | 10 |
| 218 | 0.000056 | 0.00275 |
| 219 | 0.000039 | 0.00395 |
| 220 | 0.000712 | 0.00703 |
| 221 | 0.000042 | 0.00354 |
| 222 | 0.000032 | 0.00223 |
| 223 | 0.000091 | 0.00732 |
| 224 | 0.052695 | 10 |
| 225 | 0.052695 | 1.4926 |
| 226 | 0.052695 | 3.73402 |
| 227 | 0.052695 | 0.23582 |
| 228 | 0.003585 | 0.01747 |

TABLE 4A-continued

| Ex. # | ENZYME AXL KI (μM) | CELL AXL IC50 (μM) |
|---|---|---|
| 229 | 0.003028 | 0.01032 |
| 230 | 0.040546 | 10 |
| 231 | 0.033862 | 0.22799 |
| 232 | 0.052695 | 3.73097 |
| 233 | 0.02633 | 0.10142 |
| 234 | 0.000083 | 0.00053 |
| 235 | 0.004953 | 0.01491 |
| 236 | 0.003805 | 0.00852 |
| 237 | 0.0239 | 0.09042 |
| 238 | 0.006285 | 0.03744 |
| 239 | 0.052695 | 0.65742 |
| 240 | 0.003832 | 0.04887 |
| 241 | 0.004851 | 0.02019 |
| 242 | 0.002403 | 0.07139 |
| 243 | 0.009341 | 0.05285 |
| 244 | 0.006865 | 0.4862 |
| 245 | 0.000823 | 0.01338 |
| 246 | 0.00004 | 0.00137 |
| 247 | 0.023456 | |
| 248 | 0.006464 | 0.03347 |
| 249 | 0.008307 | 0.03659 |
| 250 | 0.003026 | 0.04093 |
| 251 | 0.052695 | 0.41771 |
| 252 | 0.014442 | |
| 253 | 0.001951 | 0.02161 |
| 254 | 0.001913 | 0.00971 |
| 255 | 0.030176 | 0.10005 |
| 256 | 0.006436 | 0.03683 |
| 257 | 0.019371 | |
| 258 | 0.052695 | 1.40385 |
| 259 | 0.000876 | 0.13543 |
| 260 | 0.000028 | 0.00085 |
| 261 | 0.000026 | 0.00134 |
| 262 | 0.000068 | 0.00127 |
| 263 | 0.000019 | 0.0011 |
| 264 | 0.003842 | 0.78046 |
| 265 | 0.022308 | |
| 266 | 0.03151 | |
| 267 | 0.000635 | 0.00541 |
| 268 | 0.004067 | 0.03383 |
| 269 | 0.044671 | |
| 270 | 0.003647 | 1.32072 |
| 271 | 0.000021 | 0.00151 |
| 272 | 0.000012 | 0.00267 |
| 273 | 0.004014 | 0.0118 |
| 274 | 0.01231 | |
| 275 | 0.00185 | 0.00575 |
| 276 | 0.002733 | 0.0104 |
| 277 | 0.014467 | |
| 278 | 0.034389 | 0.44515 |
| 279 | 0.000016 | 0.00026 |
| 280 | 0.000068 | 0.03545 |
| 281 | 0.000034 | 0.01284 |
| 282 | 0.052695 | 0.9114 |
| 283 | 0.052695 | 0.93049 |
| 284 | 0.047786 | 0.09752 |
| 285 | 0.052695 | 0.27692 |
| 286 | 0.000089 | 0.00329 |
| 287 | 0.00002 | 0.00083 |
| 288 | 0.028547 | 0.08467 |
| 289 | 0.012077 | 0.03453 |
| 290 | 0.000086 | 0.00119 |
| 291 | 0.000157 | 0.00383 |
| 292 | 0.000033 | 0.00086 |
| 293 | 0.017649 | 0.30299 |
| 294 | 0.012828 | 0.06198 |
| 295 | 0.002003 | 0.01111 |
| 296 | 0.052695 | 4.33031 |
| 297 | 0.000938 | 0.00426 |
| 298 | 0.002147 | 0.01641 |
| 299 | 0.000093 | |
| 300 | 0.000029 | 0.01591 |
| 301 | 0.000015 | 0.00026 |
| 302 | 0.018592 | 0.94532 |
| 303 | 0.052695 | 0.45963 |
| 304 | 0.00184 | 0.01182 |
| 305 | 0.003054 | 0.01285 |
| 306 | 0.005748 | 0.01779 |
| 307 | 0.011385 | |
| 308 | 0.00781 | 0.01983 |
| 309 | 0.002575 | 0.00883 |
| 310 | 0.01123 | 0.06854 |
| 311 | 0.008774 | 0.02971 |
| 312 | 0.002113 | 0.00658 |
| 313 | 0.04725 | |
| 314 | 0.000995 | 0.00419 |
| 315 | 0.009907 | |
| 316 | 0.007682 | 0.06768 |
| 317 | 0.004109 | 0.01786 |
| 318 | 0.003273 | 0.01409 |
| 319 | 0.018814 | |
| 320 | 0.006341 | 0.02038 |
| 321 | 0.012517 | |
| 322 | 0.012211 | |
| 323 | 0.03239 | |
| 324 | 0.008661 | 1.24263 |
| 325 | 0.010357 | 0.05992 |
| 326 | 0.007962 | 0.02265 |
| 327 | 0.00696 | 0.16597 |
| 328 | 0.023395 | |
| 329 | 0.031246 | |
| 330 | 0.008378 | 0.02427 |
| 331 | 0.002355 | 0.00891 |
| 332 | 0.014953 | |
| 333 | 0.002817 | 0.02375 |
| 334 | 0.005902 | 0.01902 |
| 335 | 0.02011 | |
| 336 | 0.006059 | 0.26784 |
| 337 | 0.002761 | 0.00996 |
| 338 | 0.019733 | |
| 339 | 0.030394 | |
| 340 | 0.022174 | |
| 341 | 0.006845 | 0.05064 |
| 342 | 0.00171 | 0.01069 |
| 343 | 0.008632 | 0.19354 |
| 344 | 0.000157 | 0.10231 |
| 345 | 0.000142 | 0.02819 |
| 346 | 0.000012 | 0.00028 |
| 347 | 0.001317 | 0.00653 |
| 348 | 0.0006 | 0.00362 |
| 349 | 0.000078 | 0.00074 |
| 350 | 0.000788 | 0.00287 |
| 351 | 0.000835 | 0.00573 |
| 352 | 0.001104 | 0.008 |
| 353 | 0.001589 | 0.01402 |
| 354 | 0.025264 | 0.23599 |
| 355 | 0.00613 | 0.05669 |
| 356 | 0.005621 | 0.04458 |
| 357 | 0.003695 | 0.02169 |
| 358 | 0.000952 | 0.0073 |
| 359 | 0.000083 | 0.00074 |
| 360 | 0.000056 | 0.00044 |
| 361 | 0.052695 | 0.11787 |
| 362 | 0.002055 | 0.01346 |
| 363 | 0.000075 | 0.00023 |
| 364 | 0.000078 | 0.00067 |
| 365 | 0.021181 | 0.25109 |
| 366 | 0.000048 | 0.0005 |
| 367 | 0.000021 | 0.00071 |
| 368 | 0.000088 | 0.00322 |
| 369 | 0.000015 | 0.00097 |
| 370 | 0.000254 | 0.00133 |
| 371 | 0.000057 | 0.00022 |
| 372 | 0.052695 | 0.77712 |
| 373 | 0.000138 | 0.00142 |
| 374 | | 0.00018 |
| 375 | 0.000088 | 0.001 |
| 376 | 0.004582 | 0.12254 |
| 377 | | 0.0004 |
| 378 | | 0.00024 |
| 379 | | 0.0002 |
| 380 | | 0.00072 |

TABLE 4A-continued

| Ex. # | ENZYME AXL KI (μM) | CELL AXL IC50 (μM) |
|---|---|---|
| 381 | | 0.00077 |
| 382 | | 0.154 |
| 383 | | 0.11958 |
| 384 | | 0.00036 |

For Table 4B, $IC_{50}$ values were calculated by concentration-response curve fitting using a four-parameter analytic method and reported in nM.

TABLE 4B

| Ex. # | ENZYME AXL KI (nM) | CELL AXL IC50 (nM) |
|---|---|---|
| 385 | 0.109 | 1.461 |
| 386 | 0.824 | 4.15 |
| 387 | <0.018 | 0.152 |
| 388 | 0.711 | 4.08 |
| 389 | 4.392 | 67.024 |
| 390 | 0.056 | 0.755 |
| 391 | <0.013 | 0.143 |
| 392 | 0.016 | 0.137 |
| 393 | 18.654 | 69.686 |
| 394 | 0.087 | 0.937 |
| 395 | 2.809 | 33.992 |
| 396 | 0.401 | 4.079 |
| 397 | 4.728 | 16.963 |
| 398 | 0.144 | 0.615 |
| 399 | 9.414 | 36.122 |
| 400 | 6.238 | 70.752 |
| 401 | 11.115 | 24.754 |
| 402 | 4.086 | 7.305 |
| 403 | 21.974 | 59.395 |
| 404 | 0.05 | 0.248 |
| 405 | 6.514 | 11.458 |
| 406 | 1.027 | 8.791 |
| 407 | 18.543 | 32.266 |
| 408 | 0.979 | 31.9 |
| 409 | 0.054 | 0.744 |
| 410 | 3.639 | 37.656 |
| 411 | 0.098 | 0.999 |
| 412 | 4.246 | 38.304 |
| 413 | 0.223 | 1.79 |
| 414 | 0.717 | 7.403 |
| 415 | <0.013 | 0.052 |
| 416 | 0.293 | 1.396 |
| 417 | 0.507 | 2.132 |
| 418 | 0.103 | 0.634 |
| 419 | 0.056 | 1.622 |
| 420 | 3.65 | 30.029 |
| 421 | 0.435 | 2.796 |
| 422 | 0.105 | 0.364 |
| 423 | 0.08 | 0.071 |
| 424 | 0.109 | 0.138 |
| 425 | 1.075 | 9.282 |
| 426 | 0.476 | 1.951 |
| 427 | 0.081 | 0.495 |
| 428 | 6.906 | 32.324 |
| 429 | 0.018 | 0.161 |
| 430 | 0.07 | 0.523 |
| 431 | 15.482 | 49.629 |
| 432 | 0.389 | 3.114 |
| 433 | 0.049 | 5.057 |
| 434 | 0.055 | 0.865 |
| 435 | 1.397 | 39.811 |
| 436 | 2.798 | 40.541 |
| 437 | 0.034 | 1.256 |
| 438 | 0.17 | 76.695 |
| 439 | 0.053 | 0.685 |
| 440 | 3.229 | 33.267 |
| 441 | 1.931 | 22.065 |
| 442 | 0.04 | 2.974 |
| 443 | 0.038 | 0.584 |
| 444 | 0.028 | 1.883 |
| 445 | 0.049 | 0.403 |
| 446 | 0.879 | 15.498 |
| 447 | 0.058 | 4.209 |
| 448 | 0.48 | 11.149 |
| 449 | 4.224 | 22.202 |
| 450 | 0.02 | 0.441 |
| 451 | 0.03 | 1.003 |
| 452 | 0.181 | 1.808 |
| 453 | 4.008 | 20.807 |
| 454 | 0.97 | 99.975 |
| 455 | 0.474 | 19.401 |
| 456 | 0.111 | 0.725 |
| 457 | <0.013 | 1.185 |
| 458 | 0.75 | 14.103 |
| 459 | <0.013 | 0.272 |
| 460 | 0.08 | 0.98 |
| 461 | 0.083 | 0.41 |
| 462 | 0.093 | 0.694 |
| 463 | 5.93 | 33.073 |
| 464 | 0.239 | 4.631 |
| 465 | 0.61 | 4.143 |
| 466 | 0.244 | 1.669 |
| 467 | 0.034 | 0.19 |
| 468 | 0.334 | 3.757 |
| 469 | 0.014 | 0.078 |
| 470 | 0.765 | 3.759 |
| 471 | 0.02 | 0.196 |
| 472 | 0.048 | 1.576 |
| 473 | 0.164 | 6.736 |
| 474 | 0.119 | 0.863 |
| 475 | 0.068 | 0.5 |
| 476 | 0.158 | 0.958 |
| 477 | 0.051 | 0.499 |
| 478 | 0.162 | 4.629 |
| 479 | 0.035 | 4.941 |
| 480 | 0.032 | 1.892 |
| 481 | 0.187 | 11.47 |
| 482 | 0.037 | 0.868 |
| 483 | 0.038 | 0.981 |
| 484 | 0.03 | 3.449 |
| 485 | 0.025 | 0.287 |
| 486 | 4.876 | 5.693 |
| 487 | 0.111 | 0.493 |
| 488 | 0.042 | 0.354 |
| 489 | 0.319 | 2.892 |
| 490 | 0.534 | 1.973 |
| 491 | 3.363 | 5.783 |
| 492 | <0.206 | 0.461 |
| 493 | 1.219 | 6.721 |
| 494 | 0.119 | 0.602 |
| 495 | 1.593 | 14.693 |
| 496 | 4.995 | 4.326 |
| 497 | >52.695 | 90.785 |
| 498 | 0.088 | 0.927 |
| 499 | 8.42 | 6.631 |
| 500 | 3.021 | 20.864 |
| 501 | <0.412 | 1.066 |
| 502 | <0.082 | 0.132 |
| 503 | 0.227 | 0.186 |
| 504 | <0.082 | 0.125 |
| 505 | <0.082 | 0.409 |
| 506 | 0.021 | 0.299 |
| 507 | 0.041 | 0.389 |
| 508 | 1.396 | 8.8 |
| 509 | 0.658 | 9.754 |

We claim:
1. A compound of formula (I):

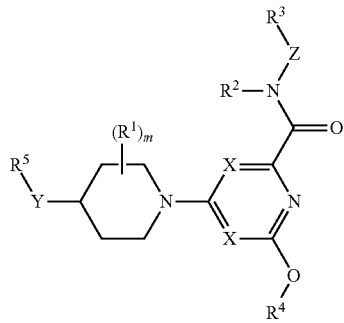

wherein:
each X is N or CR$^6$, where at least one X is N, where each R$^6$ is independently selected from the group consisting of hydrogen, halogen, (C$_1$-C$_8$)alkyl, (C$_2$-C$_8$)alkenyl, (C$_1$-C$_8$)alkynyl, (C$_1$-C$_8$)haloalkyl, —(C$_1$-C$_4$)alkylene-R$^7$, —OR$^7$, —CN, —NO$_2$ and —NR$^7$R$^7$, where each R$^7$ is independently selected from the group consisting of hydrogen and (C$_1$-C$_8$)alkyl, and where each said (C$_1$-C$_8$)alkyl in R$^6$ is optionally substituted by one or more substituents independently selected from the group consisting of halogen, hydroxyl and (C$_1$-C$_8$) alkoxy;

Y is Y$^1$-Y$^2$ or Y$^2$-Y$^1$, where Y$^1$ is absent or is selected from the group consisting of (C$_1$-C$_8$)alkylene, (C$_2$-C$_8$) alkenylene, (C$_1$-C$_8$)haloalkylene, (C$_1$-C$_8$)heteroalkylene, and (C$_2$-C$_8$)heteroalkenylene, and where Y$^1$ is optionally substituted with one or more R$^8$ where each R$^8$ is independently selected from the group consisting of halogen, (C$_1$-C$_{10}$)alkyl, —CN, =O, —R$^9$—OR$^9$, —SR$^9$ and —NO$_2$, and where each R$^9$ is independently selected from the group consisting of hydrogen, (C$_1$-C$_8$)alkyl, (C$_3$-C$_{10}$)cycloalkyl, 3-12 membered heterocyclyl, (C$_6$-C$_{12}$)aryl and 5-12 membered heteroaryl, and where Y$^2$ is absent or oxygen;

Z is Z$^1$-Z$^2$, where each of Z$^1$ and Z$^2$ is independently absent or selected from the group consisting of (C$_1$-C$_8$)alkylene, (C$_2$-C$_8$)alkenylene, (C$_3$-C$_{10}$)cycloalkyl, 3-12 membered heterocyclyl and (C$_1$-C$_8$)heteroalkylene, where Z is optionally independently substituted with one or more R$^{10}$ where each R$^{10}$ is independently selected from the group consisting of halogen, (C$_1$-C$_8$) alkyl, —CN, =O, —OR$^{11}$ and —NO$_2$, and where each R$^{11}$ is independently selected from the group consisting of hydrogen, (C$_1$-C$_8$)alkyl, (C$_3$-C$_{10}$)cycloalkyl, 3-12 membered heterocyclyl, (C$_6$-C$_{12}$)aryl and 5-12 membered heteroaryl;

each R$^1$ is independently selected from the group consisting of hydrogen, halogen, (C$_1$-C$_8$)alkyl, (C$_1$-C$_8$)haloalkyl, —(C$_1$-C$_4$alkyl)R$^7$, —OR$^7$, —CN, —C(O)R$^7$, —CO$_2$R$^7$, —C(O)NR$^7$R$^7$, —SR$^7$, —SOR$^7$, —SO$_2$R$^7$, —SO$_2$NR$^7$R$^7$, —NO$_2$, —NR$^7$R$^7$, —NR$^7$C(O)R$^7$, —NR$^7$C(O)NR$^7$R$^7$, —NR$^7$C(O)OR$^7$, —NR$^7$SO$_2$R$^7$, —NR$^7$SO$_2$NR$^7$R$^7$, —OC(O)R$^7$ and —OC(O)NR$^7$R$^7$; where any set of two R$^1$ on the same or different piperidine carbons optionally join to form a spirocyclic, fused or bridged ring system comprising 1-4 non-piperidine members and 1-2 heteroatoms selected from N, O and S, and where any set of two R$^1$ on adjacent piperidine carbons optionally join to form a carbon-carbon bond;

R$^2$ and R$^3$ are each independently selected from the group consisting of hydrogen, halogen, (C$_1$-C$_8$)alkyl, (C$_1$-C$_8$) haloalkyl, (C$_3$-C$_{10}$)cycloalkyl, 3-12 membered heterocyclyl, —OR$^{13}$, —NR$^{14}$R$^{14}$, —C(O)NR$^{14}$R$^{14}$, —SO$_2$NR$^{14}$R$^{14}$, —NR$^{14}$SO$_2$R$^{14}$, —SO$_2$R$^{14}$, (C$_6$-C$_{12}$) aryl and 5-12 membered heteroaryl, where each R$^{13}$ is independently selected from the group consisting of hydrogen, (C$_1$-C$_4$)alkyl, (C$_1$-C$_4$)haloalkyl, (C$_3$-C$_{10}$)cycloalkyl, 3-12 membered heterocyclyl, (C$_6$-C$_{12}$)aryl and 5-12 membered heteroaryl, where each R$^{14}$ is independently selected from the group consisting of hydrogen, (C$_1$-C$_8$)alkyl, (C$_3$-C$_{10}$)cycloalkyl, 3-12 membered heterocyclyl, (C$_6$-C$_{12}$)aryl and 5-12 membered heteroaryl, or two R$^{14}$ together with the N atom to which they are attached to form a 3-12 membered heterocyclyl or 5-12 membered heteroaryl, each optionally containing 1, 2 or 3 additional heteroatoms selected from O, N and S, and where R$^2$, R$^3$ or both R$^2$ and R$^3$ is optionally substituted with one or more substituents independently selected from halogen, (C$_1$-C$_8$)alkyl, hydroxyl, (C$_1$-C$_4$)alkoxy, —CN, NH$_2$, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$)aryl and 5-12 membered heteroaryl;

or R$^2$ and R$^3$ join to form a heterocyclic ring selected from azetidinyl, pyrrolidinyl, piperidinyl, piperazinyl, piperadinonyl, piperazinonyl and morpholinyl, optionally substituted with one or more substituents independently selected from the group consisting of R$^{15}$ and (C$_1$-C$_4$)alkylene-R$^{15}$, where R$^{15}$ is independently selected from the group consisting of halogen, (C$_1$-C$_4$) alkyl, (C$_1$-C$_4$)haloalkyl, hydroxyl, (C$_1$-C$_4$)alkoxy, CN, NH$_2$, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$)aryl and 5-12 membered heteroaryl;

R$^4$ is selected from the group consisting of (C$_1$-C$_8$)alkyl, (C$_1$-C$_8$)haloalkyl, (C$_3$-C$_{10}$)cycloalkyl, 3-12 membered heterocyclyl and —C(O)NR$^{14}$R$^{14}$, where R$^4$ is optionally substituted with one or more R$^{12}$ independently selected from halogen, hydroxyl, (C$_1$-C$_4$)alkoxy, —CN, NH$_2$, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$) aryl and 5-12 membered heteroaryl, and where, when R$^{12}$ is (C$_1$-C$_4$)alkoxy, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$)aryl or 5-12 membered heteroaryl, it is optionally substituted by one or more substituents independently selected from halogen, hydroxyl, (C$_1$-C$_4$)alkoxy, —CN, NH$_2$, NH(C$_1$-C$_4$alkyl), N(C$_1$-C$_4$alkyl)$_2$, (C$_3$-C$_{10}$)cycloalkyl, 3-12 membered heterocyclyl, (C$_6$-C$_{12}$)aryl and 5-12 membered heteroaryl;

R$^5$ is a mono- or bi-cyclic aryl or a mono- or bi-cyclic heteroaryl, optionally substituted with one or more substituents independently selected from the group consisting of (C$_1$-C$_8$)alkyl, halogen, (C$_1$-C$_8$)haloalkyl, (C$_3$-C$_{10}$)cycloalkyl, 3-12 membered heterocyclyl, —OR$^{13}$, —NR$^{14}$R$^{14}$, —C(O)NR$^{14}$R$^{14}$, —SO$_2$NR$^{14}$R$^{14}$, —SO$_2$R$^{14}$, —NR$^{14}$SO$_2$R$^{14}$, CN, mono- or bi-cyclic aryl and mono- or bi-cyclic heteroaryl, said one or more optional substituents being further optionally substituted with one or more substituents selected from the group consisting of (C$_1$-C$_8$) alkyl, (C$_1$-C$_8$)alkylene-OH, (C$_1$-C$_8$)haloalkyl, (C$_3$-C$_{10}$) cycloalkyl, 3-12 membered heterocyclyl, —OR$^{13}$, —NR¹⁴R¹⁴, —C(O)NR¹⁴R¹⁴, —SO₂NR¹⁴R¹⁴, —SO₂R¹⁴, —NR¹⁴SO₂R¹⁴ and CN;
and m is 1-9,
or a pharmaceutically acceptable salt thereof.

2. A compound of formula (II):

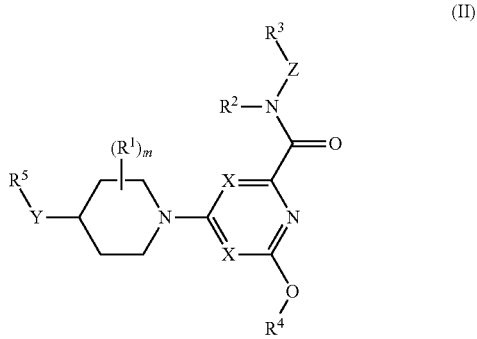

(II)

wherein:
each X is N or CR⁶, where at least one X is N, and where each R⁶ is independently selected from the group consisting of hydrogen, halogen and (C₁-C₈)alkyl;
Y is Y¹-Y² or Y²-Y¹, where Y¹ is absent or is selected from the group consisting of (C₁-C₈)alkylene and (C₁-C₈)haloalkylene, and where Y¹ is optionally substituted with one or more R⁸ where each R⁸ is independently selected from the group consisting of halogen, (C₁-C₁₀) alkyl and —CN, and where Y² is absent or oxygen;
Z is Z¹-Z², where each of Z¹ and Z² is independently absent or selected from the group consisting of (C₁-C₈)alkylene, (C₃-C₁₀)cycloalkyl and 3-12 membered heterocyclyl, where Z is optionally substituted with one or more R¹⁰ where each R¹⁰ is independently selected from the group consisting of halogen, (C₁-C₈)alkyl and —CN;
each R¹ is independently selected from the group consisting of hydrogen, halogen, (C₁-C₈)alkyl, (C₁-C₈)haloalkyl, —(C₁-C₄alkyl)R⁷, —OR⁷ and —CN;
R² and R³ are each independently selected from the group consisting of hydrogen, (C₁-C₈)alkyl, (C₁-C₈)haloalkyl, (C₃-C₁₀)cycloalkyl, 3-12 membered heterocyclyl, —OR¹³ and —SO₂R¹⁴, where each R¹³ is independently selected from the group consisting of hydrogen, (C₁-C₄)alkyl and (C₁-C₄)haloalkyl, where each R¹⁴ is independently selected from the group consisting of hydrogen and (C₁-C₈)alkyl, and where R², R³ or both R² and R³ is optionally substituted with one or more substituents independently selected from halogen, (C₁-C₈)alkyl, hydroxyl, (C₁-C₄)alkoxy, —CN, NH₂, NH(C₁-C₄alkyl), N(C₁-C₄alkyl)₂;
or R² and R³ join to form a heterocyclic ring selected from azetidinyl, pyrrolidinyl, piperidinyl, piperazinyl, piperadinonyl, piperazinonyl and morpholinyl, optionally substituted with one or more substituents independently selected from the group consisting of R¹⁵ and (C₁-C₄)alkylene-R¹⁵, where R¹⁵ is independently selected from the group consisting of halogen, (C₁-C₄) alkyl, (C₁-C₄)haloalkyl, hydroxyl, (C₁-C₄)alkoxy, CN, NH₂, NH(C₁-C₄alkyl), N(C₁-C₄alkyl)₂ and (C₃-C₁₀) cycloalkyl;
R⁴ is selected from the group consisting of (C₁-C₈)alkyl and (C₁-C₈)haloalkyl, where R⁴ is optionally substituted with one or more R¹² independently selected from halogen, hydroxyl, (C₁-C₄)alkoxy, —CN, NH₂, NH(C₁-C₄alkyl), N(C₁-C₄alkyl)₂, (C₃-C₁₀)cycloalkyl, and 3-12 membered heterocyclyl, and where, when R¹² is (C₁-C₄)alkoxy, NH(C₁-C₄alkyl), N(C₁-C₄alkyl)₂, (C₃-C₁₀)cycloalkyl or 3-12 membered heterocyclyl, it is optionally substituted by one or more substituents independently selected from halogen, hydroxyl, (C₁-C₄)alkoxy, —CN, NH₂, NH(C₁-C₄alkyl) and N(C₁-C₄alkyl)₂;
R⁵ is a mono- or bi-cyclic aryl or a mono- or bi-cyclic heteroaryl, optionally substituted with one or more substituents independently selected from the group consisting of (C₁-C₈)alkyl, (C₁-C₈)haloalkyl, —OR¹³, —NR¹⁴R¹⁴, —C(O)NR¹⁴R¹⁴, CN, mono- or bi-cyclic aryl and mono- or bi-cyclic heteroaryl, said one or more optional substituents being further optionally substituted with one or more substituents selected from the group consisting of (C₁-C₈)alkyl, (C₁-C₈)alkylene-OH, (C₁-C₈)haloalkyl, —OR¹³, —NR¹⁴R¹⁴ and —SO₂R¹⁴;
and m is 1-9
or a pharmaceutically acceptable salt thereof.

3. A compound of formula (III):

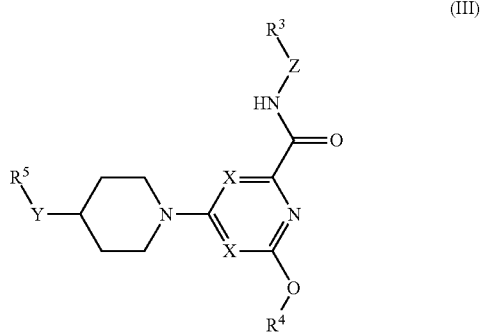

(III)

wherein:
X is N or CR⁶, where R⁶ is selected from the group consisting of hydrogen, halogen and (C₁-C₈)alkyl;
Y is absent, (C₁-C₈)alkylene, O—(C₁-C₈)alkylene or (C₁-C₈)alkylene-O;
Z is Z¹-Z², where each of Z¹ and Z² is independently absent or C₁-C₈alkylene, where Z is optionally substituted with one or more R¹⁰ where each R¹⁰ is independently selected from the group consisting of halogen and (C₁-C₈)alkyl;
R³ is selected from the group consisting of hydrogen, (C₁-C₈)alkyl and —OR¹³, where R¹³ is selected from the group consisting of hydrogen and (C₁-C₄)alkyl;
R⁴ is (C₁-C₈)alkyl optionally substituted by one or more R¹² independently selected from halogen, hydroxyl, (C₁-C₄)alkoxy, —(C₃-C₁₀)cycloalkyl, and 3-12 membered heterocyclyl, where one or more carbons on R¹², if present, are optionally substituted by one or more substituents independently selected from halogen, hydroxyl and (C₁-C₄)alkoxy; and
R⁵ is a mono- or bi-cyclic heteroaryl, optionally substituted with one or more substituents independently selected from the group consisting of (C₁-C₈)alkyl and —OR¹³;
or a pharmaceutically acceptable salt thereof.

4. The compound or pharmaceutically acceptable salt of claim 1 or 2, wherein —Z—R³ is straight or branched (C₁-C₈)alkylene-OH, or straight or branched (C₁-C₈)alkylene-O—(C₁-C₄)alkyl.

5. The compound or pharmaceutically acceptable salt of claim 1 or 2, wherein —$R^4$ is straight or branched $(C_1-C_8)$ alkyl substituted with hydroxyl, $(C_1-C_4)$alkoxy, $(C_3-C_{10})$ cycloalkyl or 3-12 membered heterocyclyl.

6. The compound or pharmaceutically acceptable salt of claim 1 or 2, wherein Y is absent or $(C_1-C_8)$alkylene, and $R^5$ is selected from pyrrolopyrimidine, pyrazolopyrimidine and pyridine, optionally substituted with one or more substituents independently selected from the group consisting of $(C_1-C_8)$alkyl, $(C_1-C_8)$haloalkyl, —$OR^{13}$, —$NR^{14}R^{14}$, mono- or bi-cyclic aryl and mono- or bi-cyclic heteroaryl, said aryl or heteroaryl being further optionally substituted with one or more substituents selected from the group consisting of $(C_1-C_8)$alkyl.

7. The compound or pharmaceutically acceptable salt of any of claims 1, 2 or 3, wherein $R^5$ is selected from:

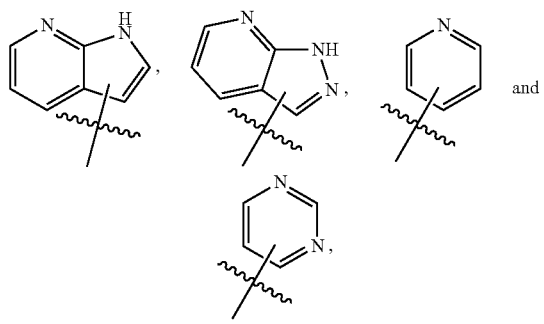

wherein R5 is optionally substituted with one or more substituents independently selected from the group consisting of $(C_1-C_8)$alkyl and —$OR^{13}$.

8. The compound or pharmaceutically acceptable salt of any of claims 1, 2 or 3, wherein Y is —$CH_2$—O— or —O—$CH_2$—.

9. The compound or pharmaceutically acceptable salt of claim 3, wherein X is N.

10. The compound or pharmaceutically acceptable salt of claim 3, wherein X is CH.

11. A compound selected from:

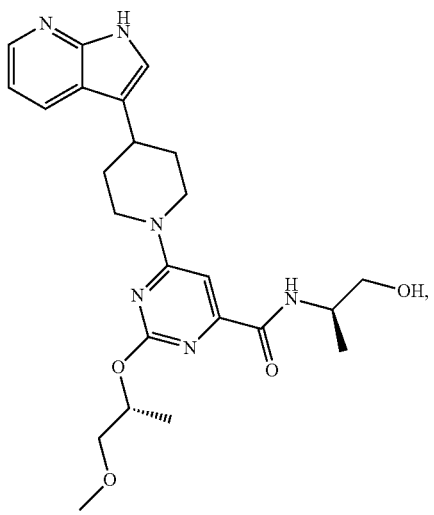

-continued

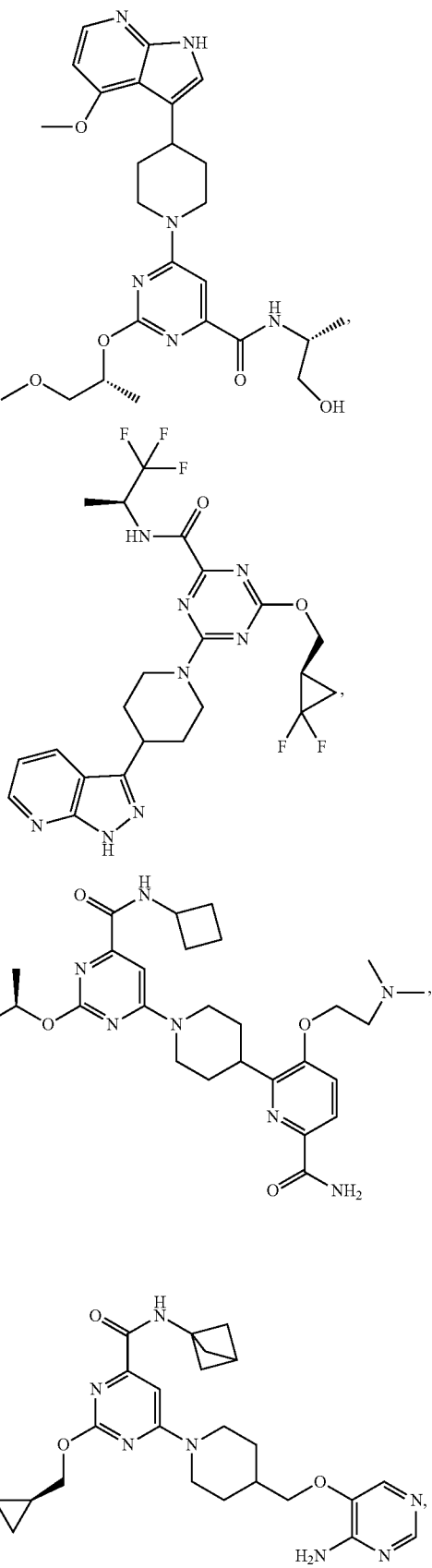

553
-continued
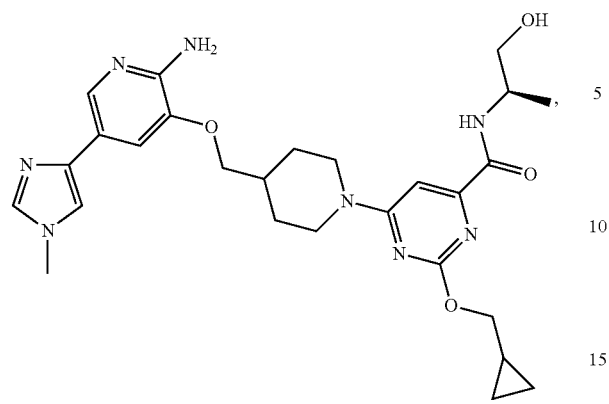
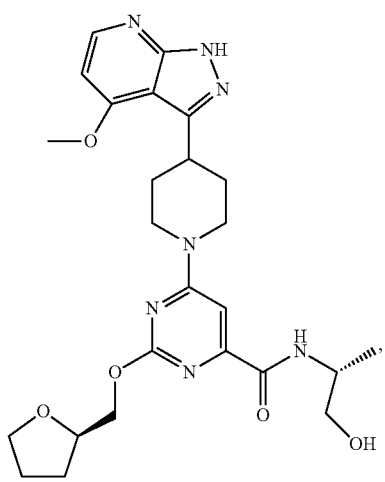
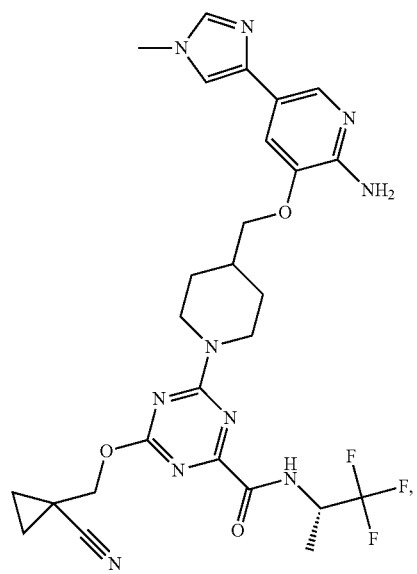
554
-continued
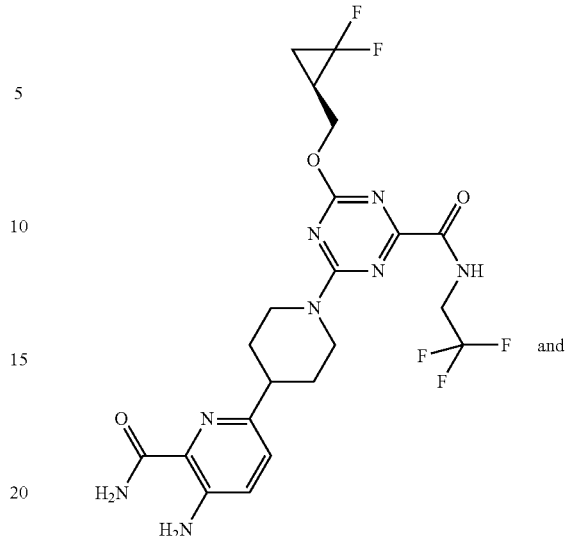
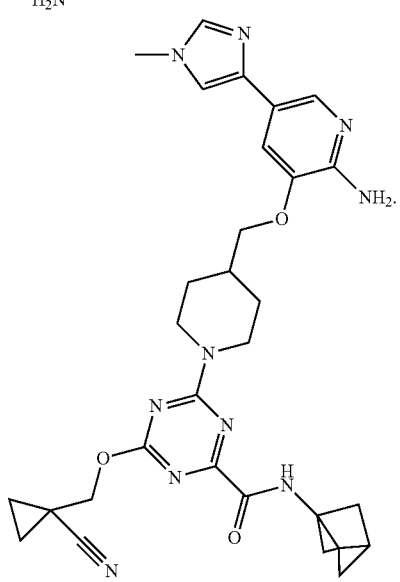
or a pharmaceutically acceptable salt thereof.
12. A pharmaceutical composition comprising a compound according to claim 1, or a pharmaceutically acceptable salt thereof, and a pharmaceutically acceptable carrier.
13. A compound selected from:
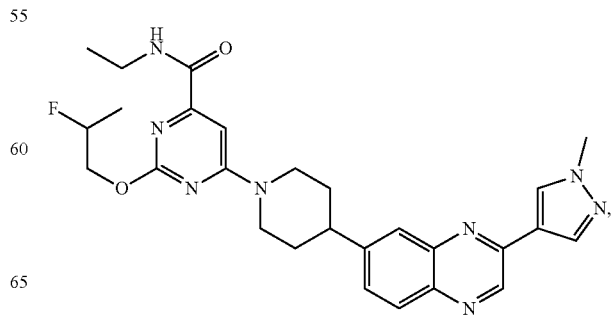

555
-continued
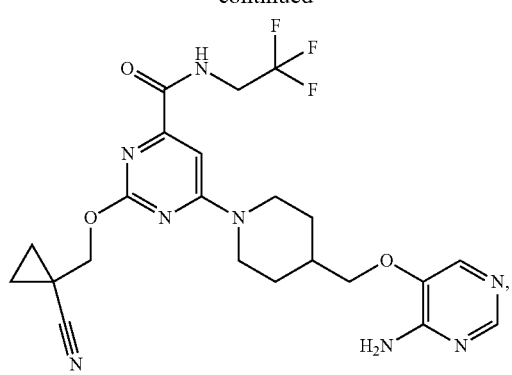
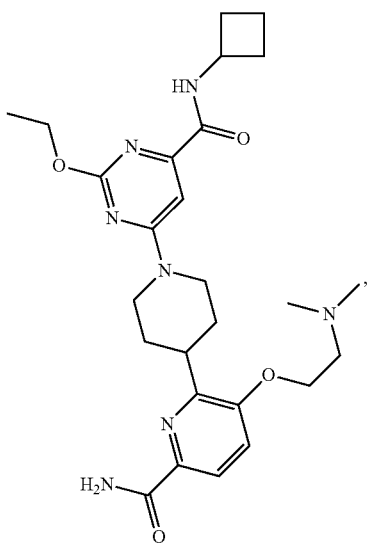
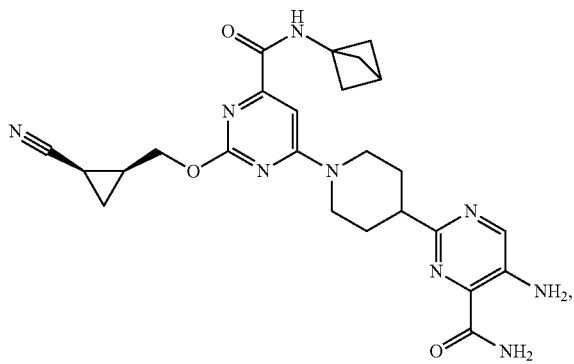
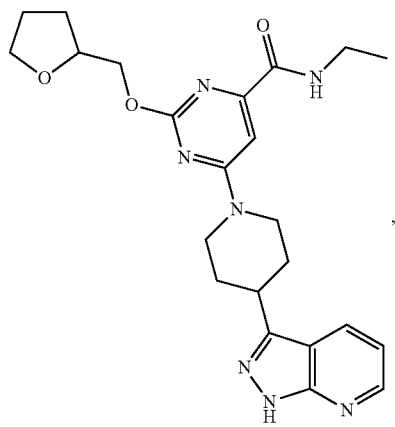
556
-continued
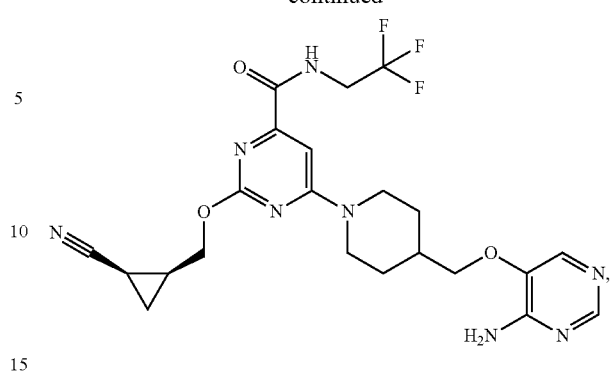
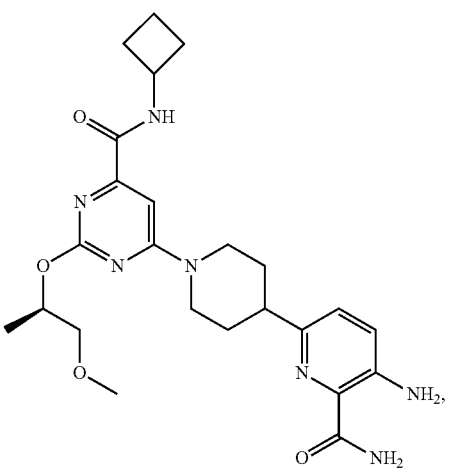
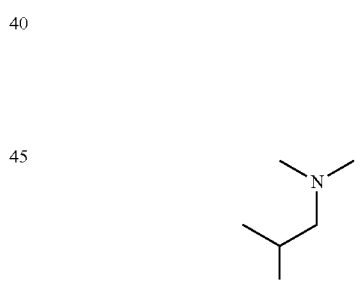
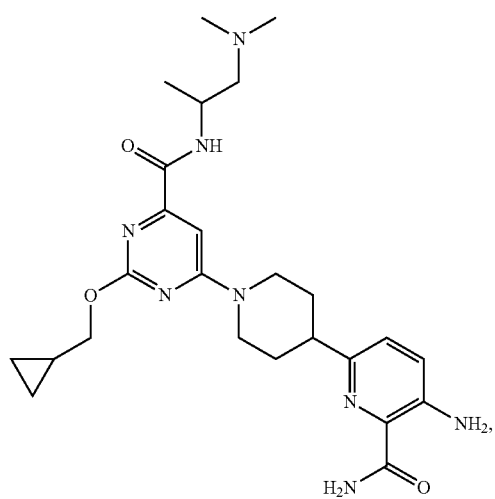

557
-continued
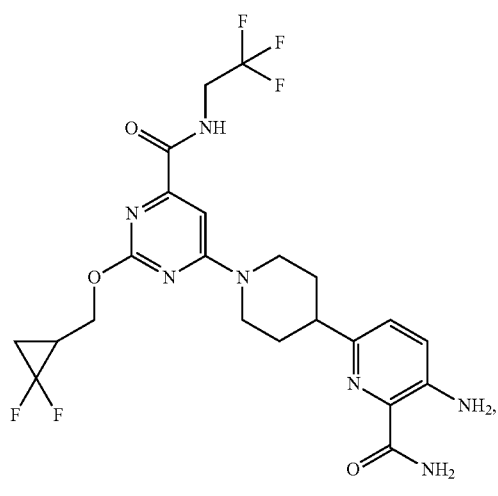
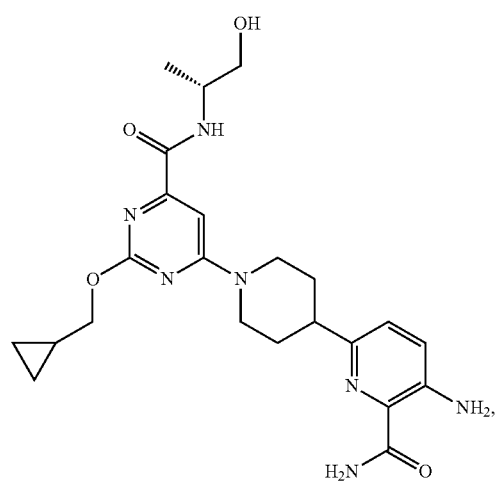
558
-continued
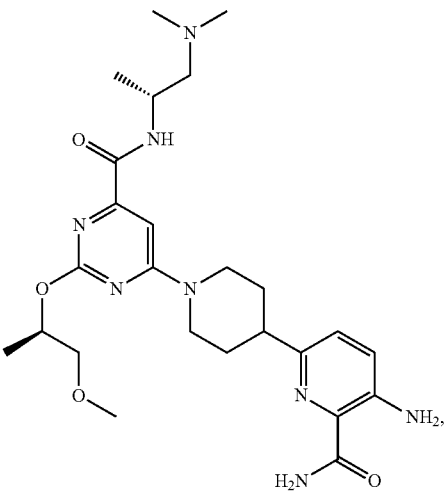
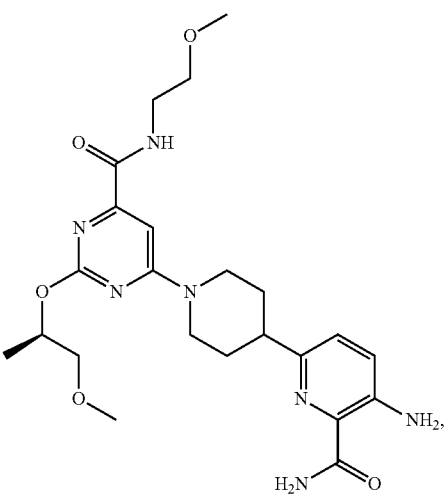
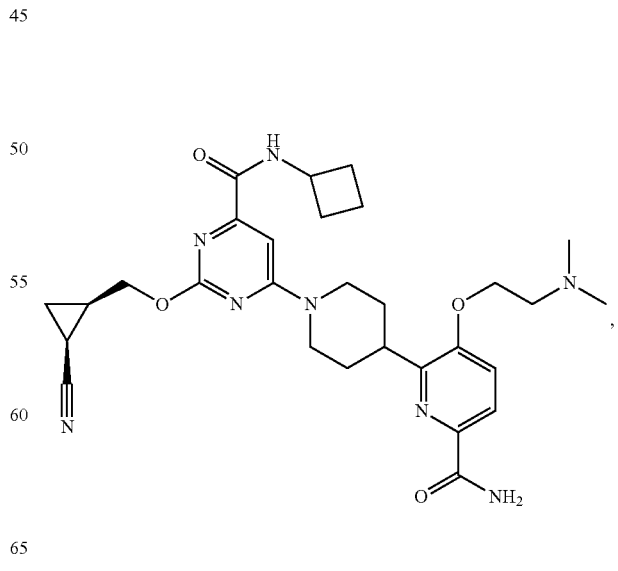

559
-continued
560
-continued
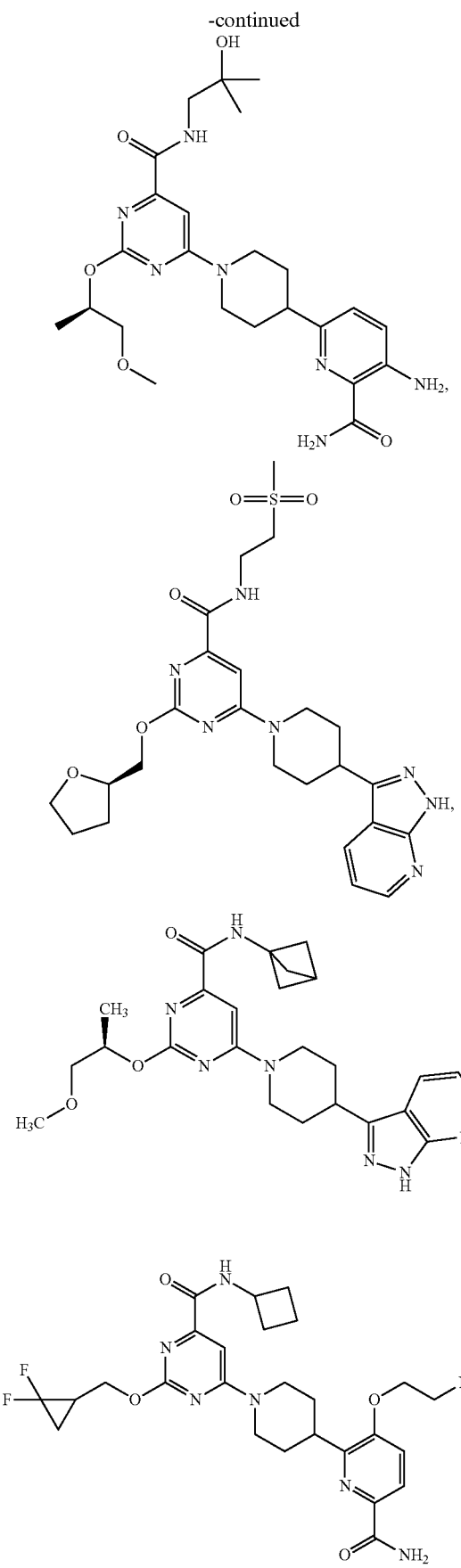
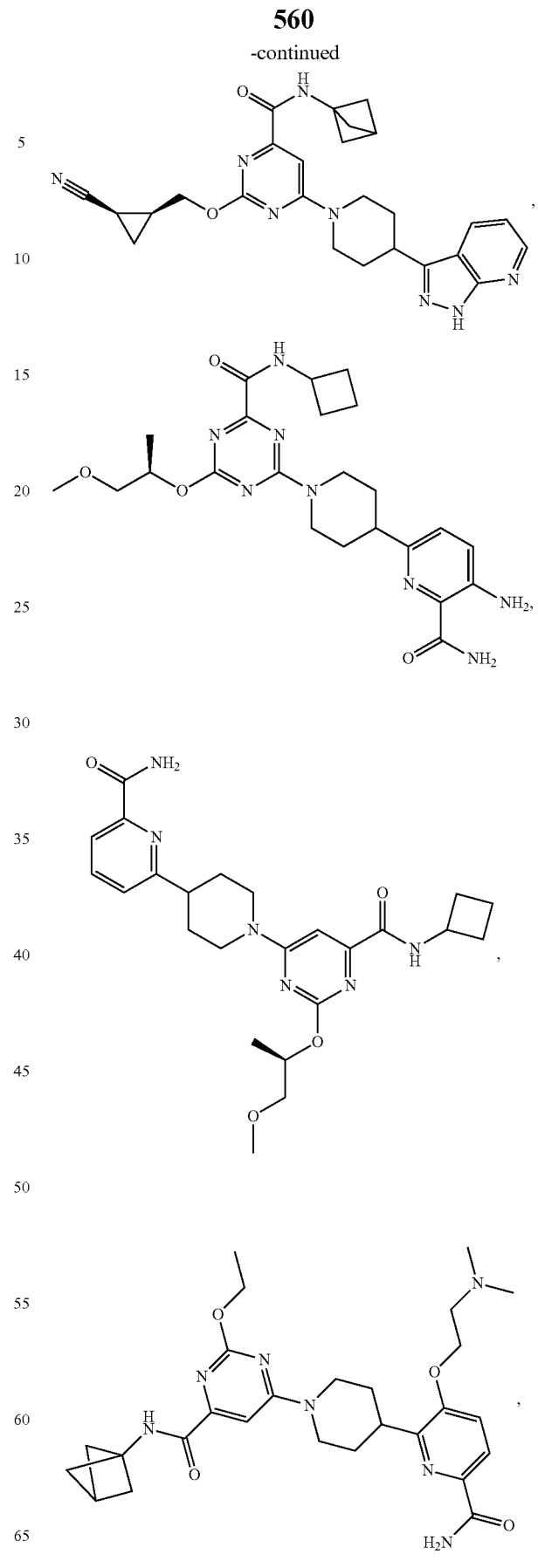

561
-continued
562
-continued
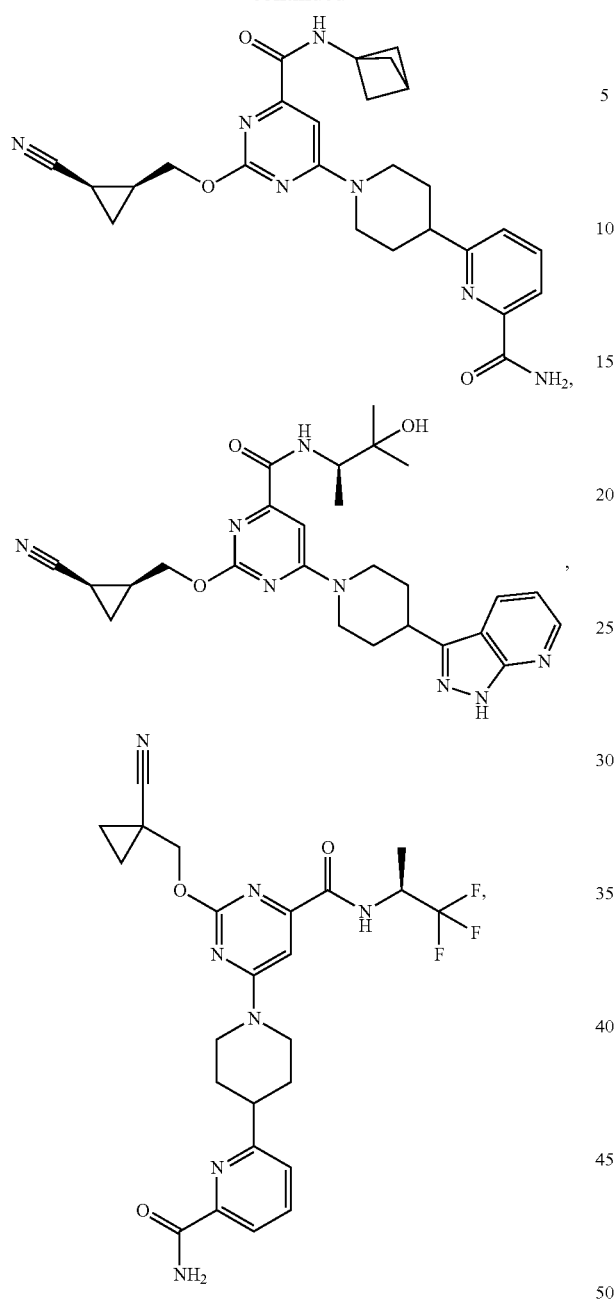
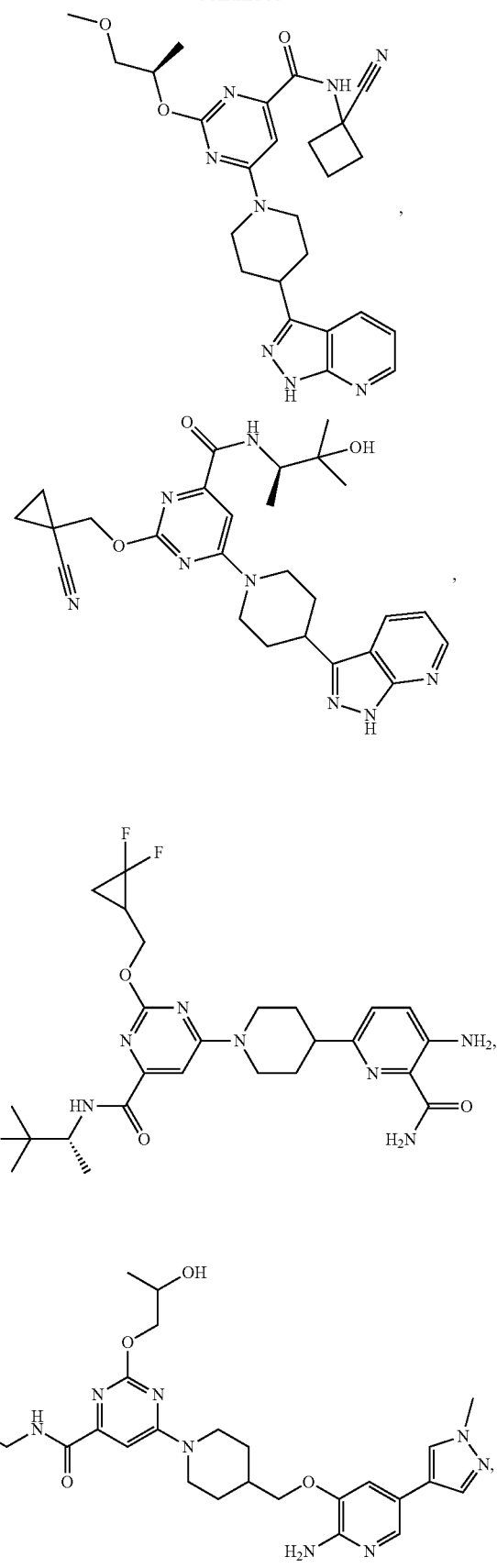

563
-continued
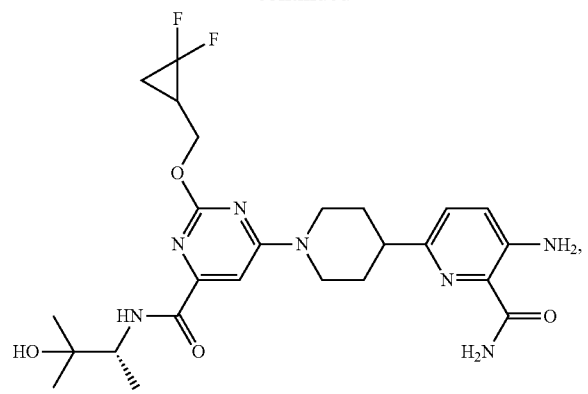
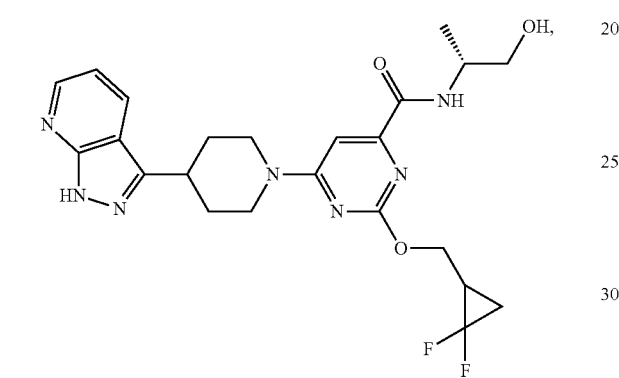
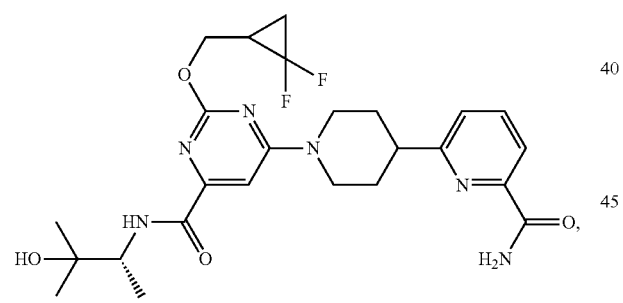
564
-continued
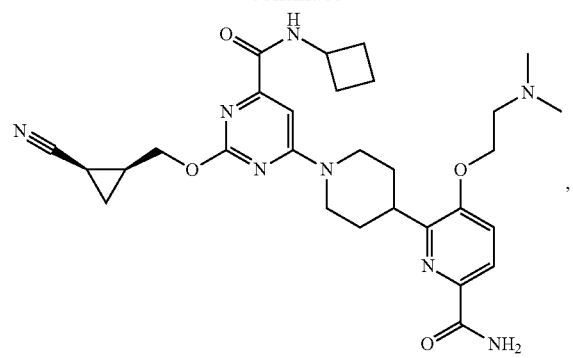
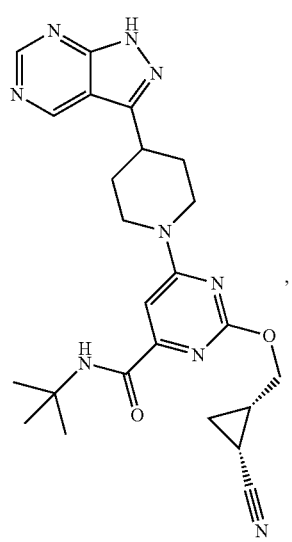
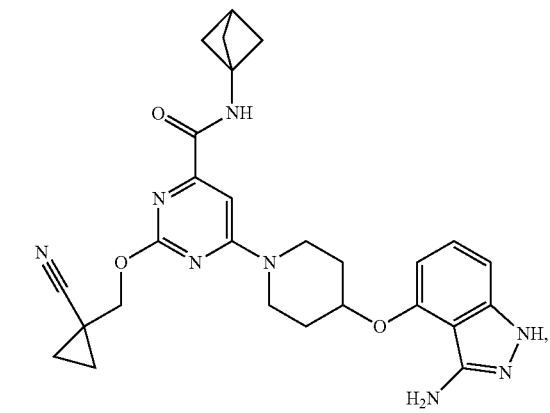

565
-continued
566
-continued
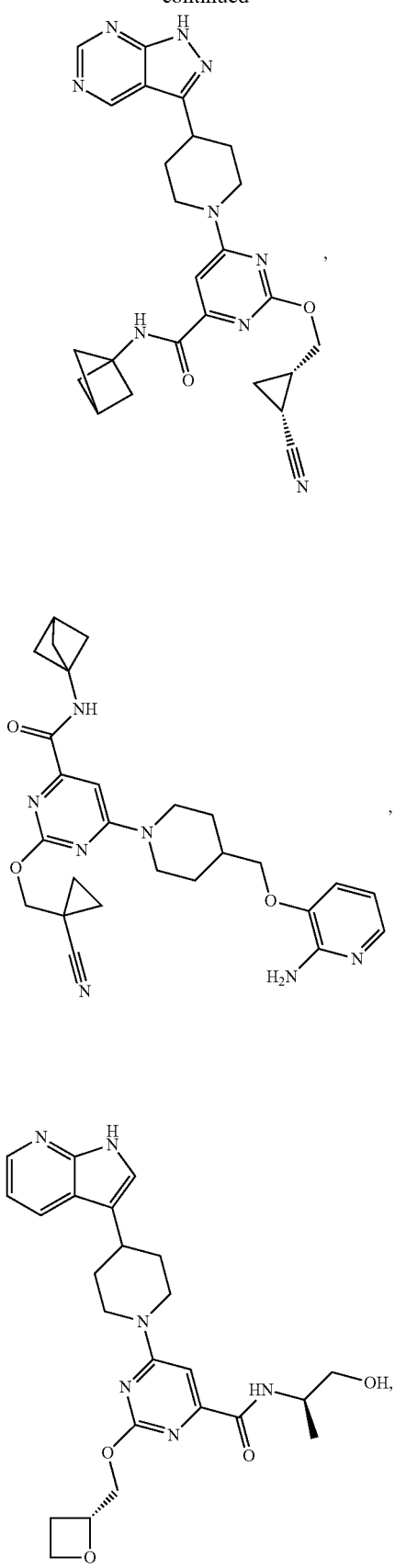
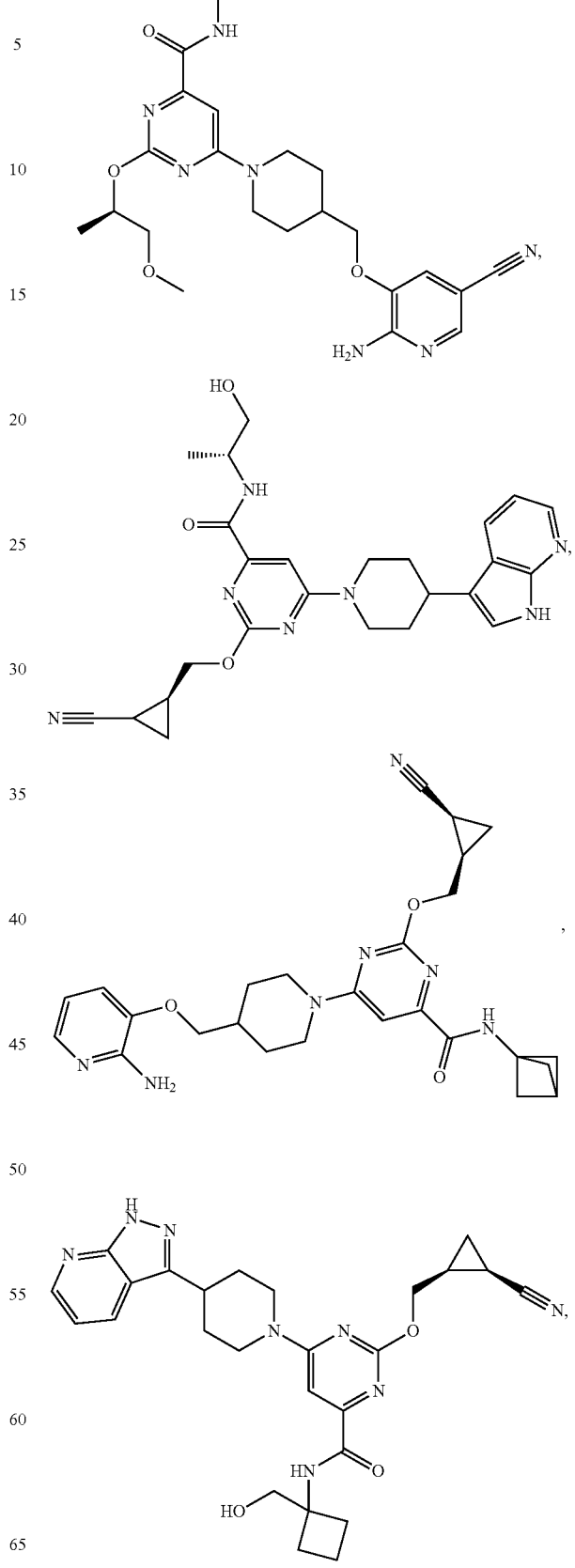

567
-continued
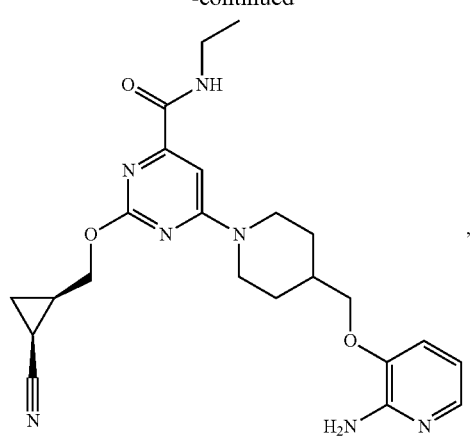
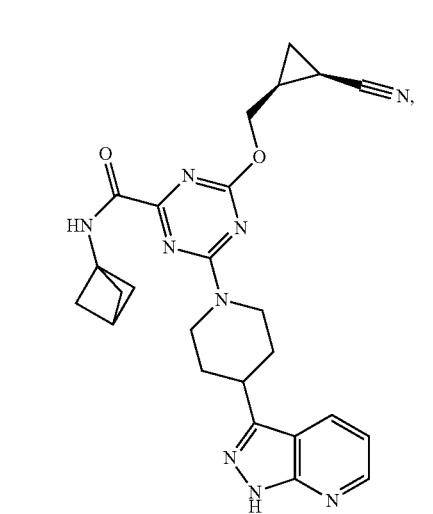
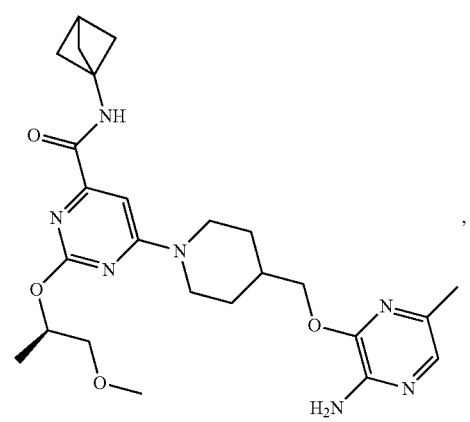
568
-continued
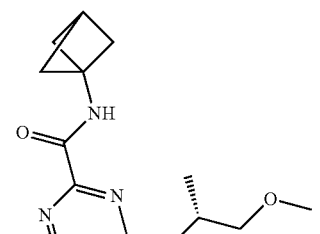
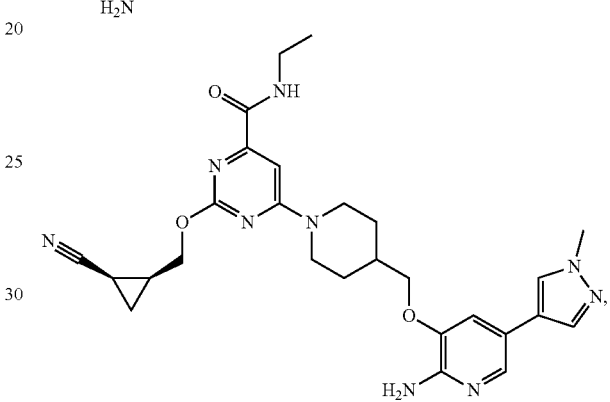
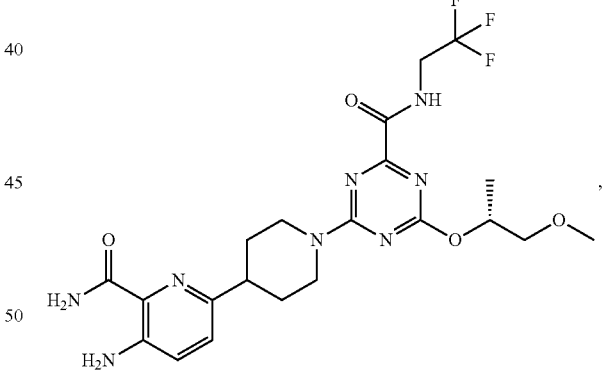
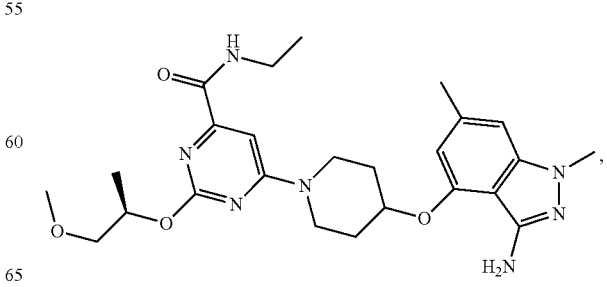

569
-continued
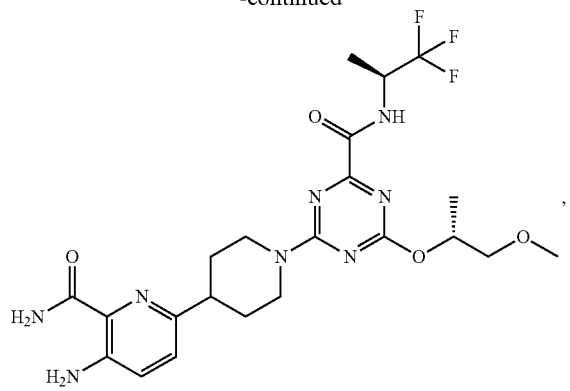
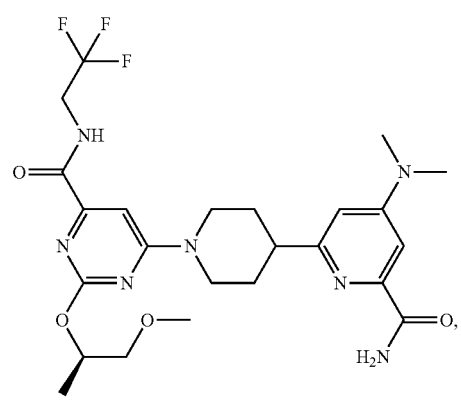
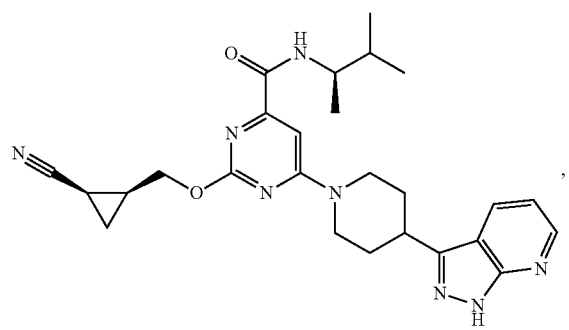
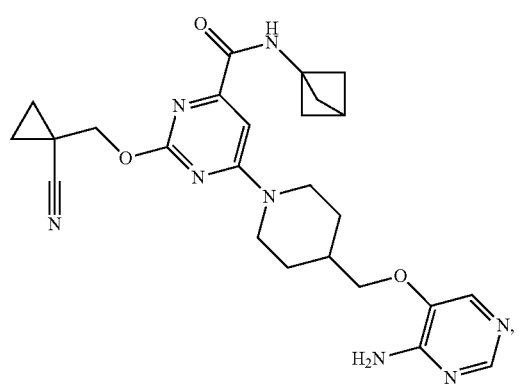
570
-continued
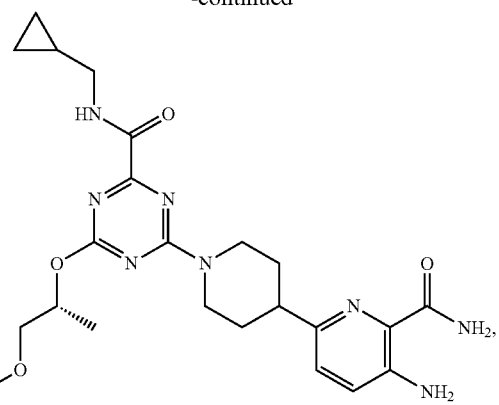
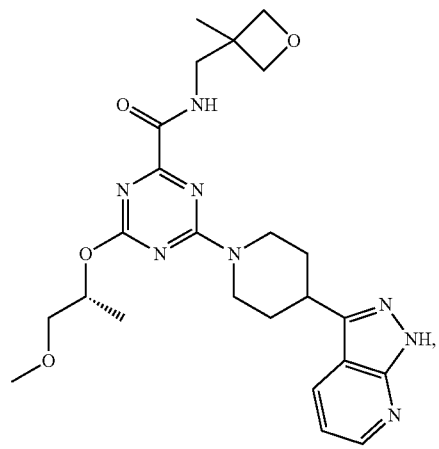
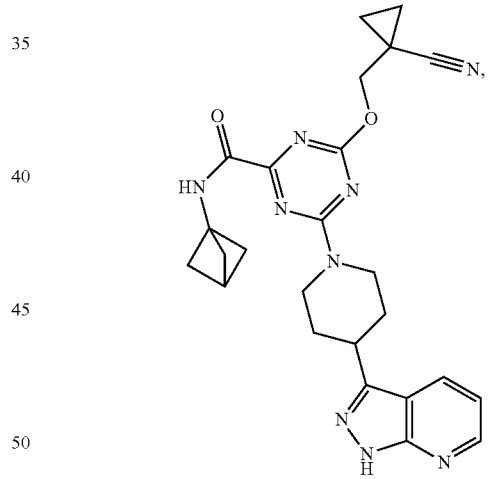
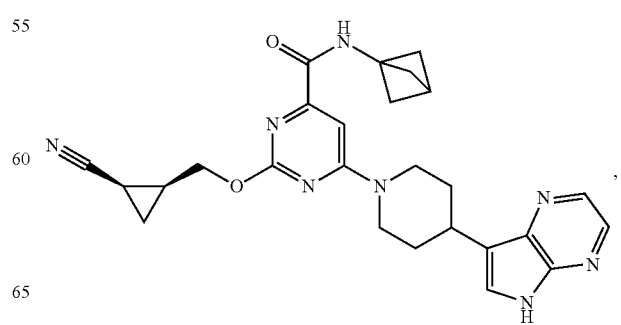

571
-continued
572
-continued
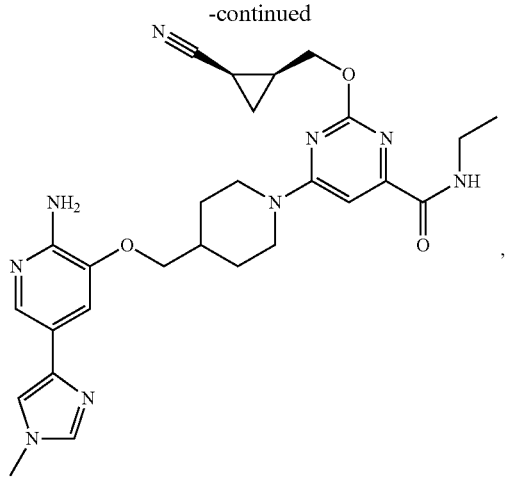
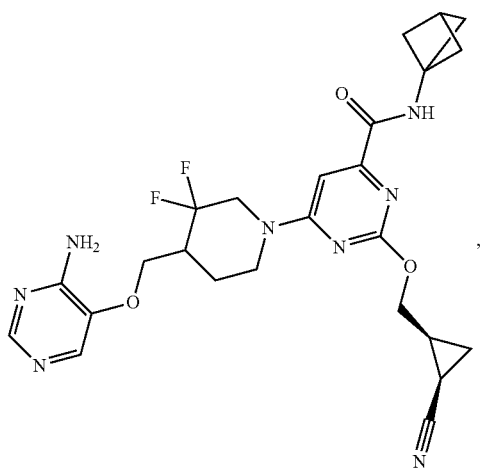
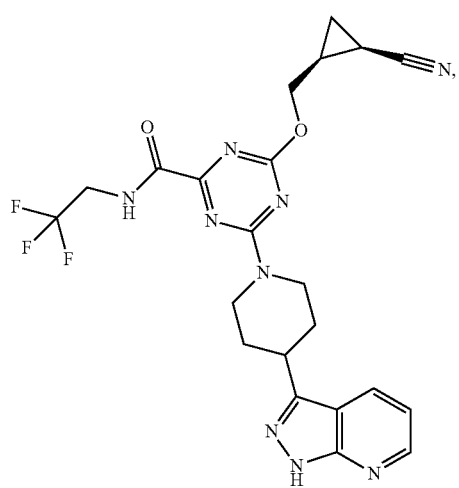
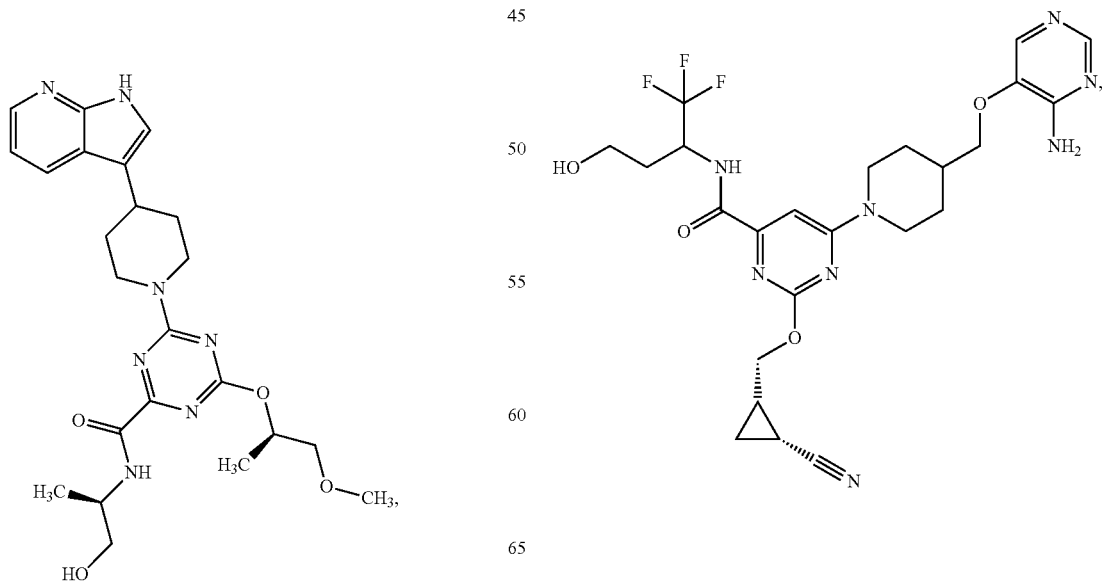

573
-continued
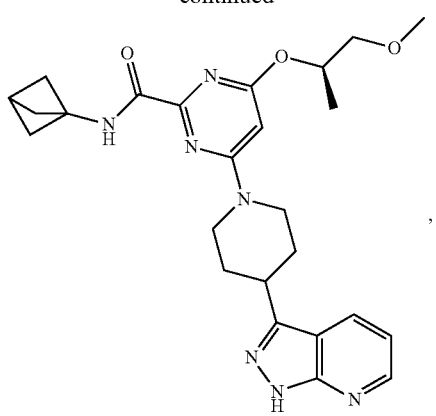
,
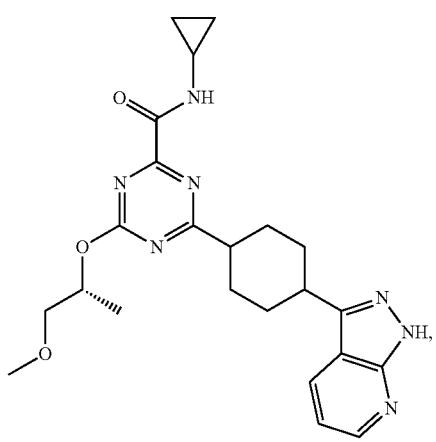
,
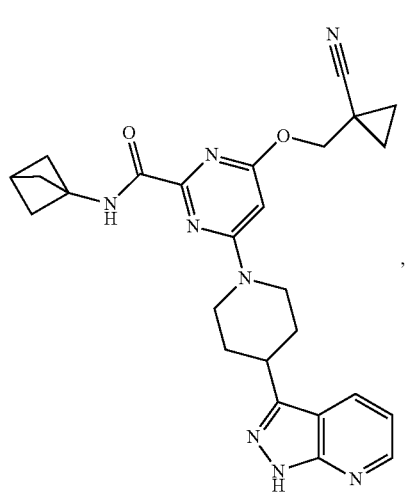
,
574
-continued
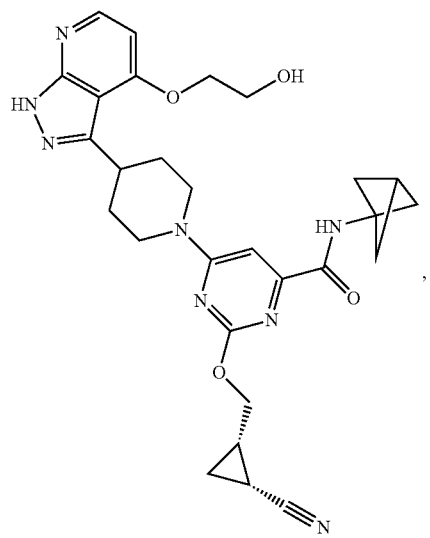
,
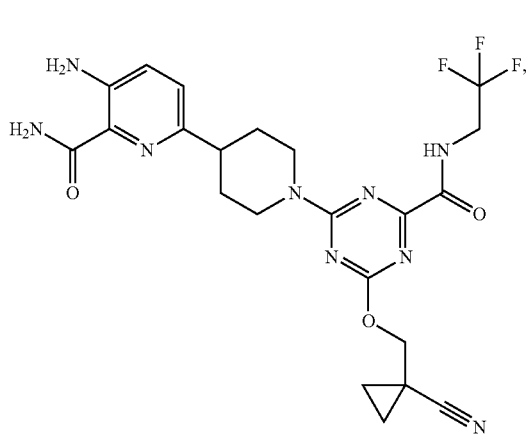
,
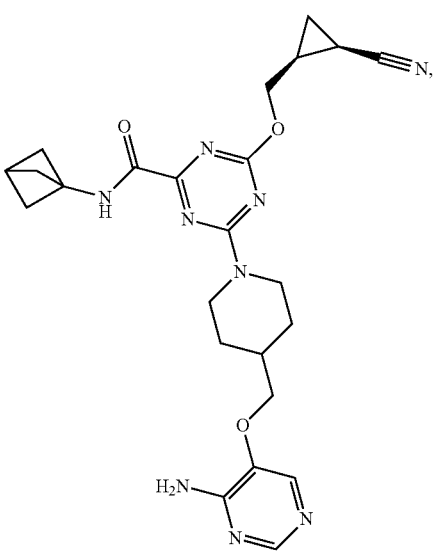

575
-continued
576
-continued
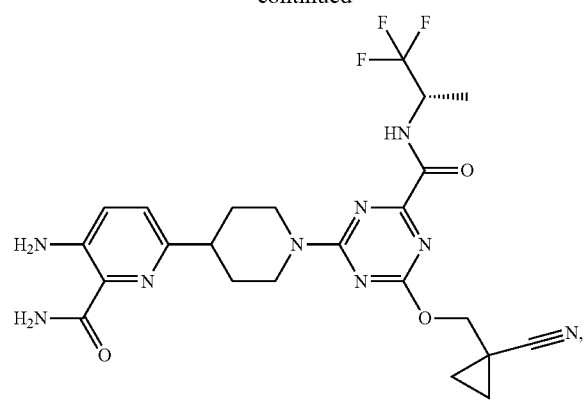
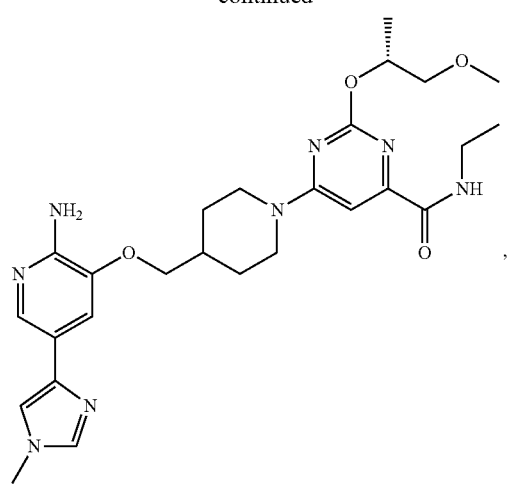
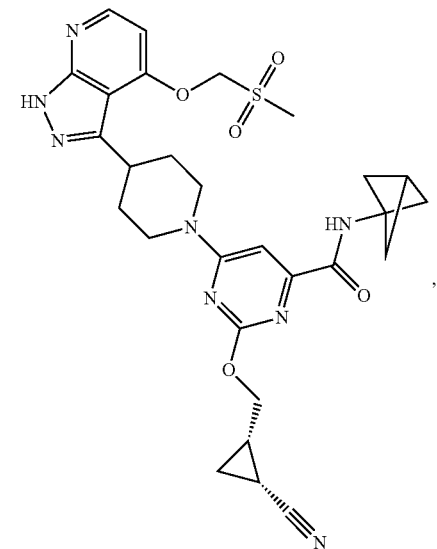
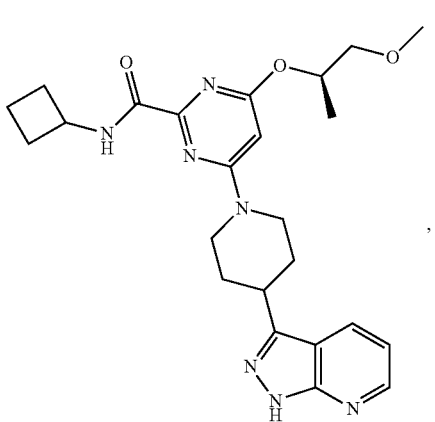
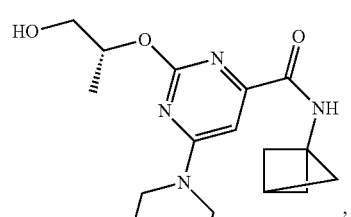
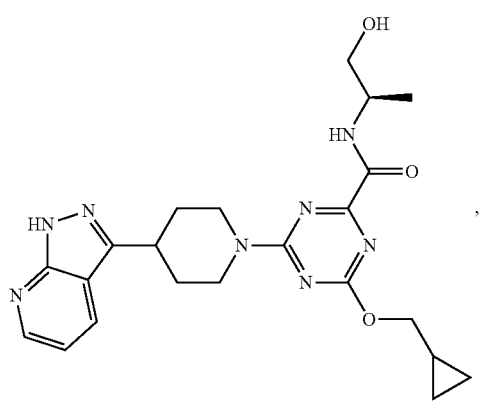
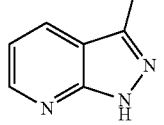
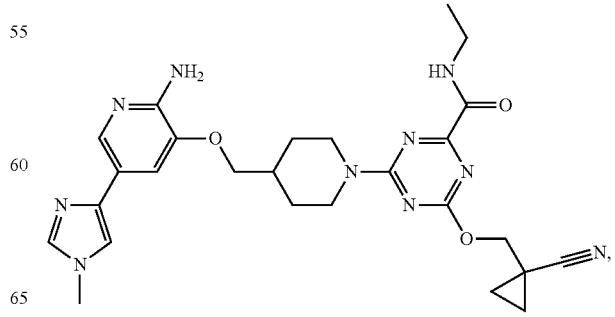

577
-continued
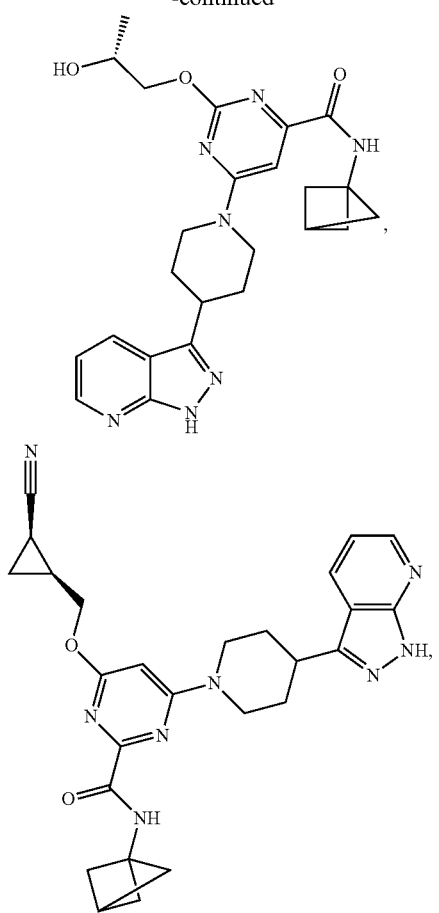
578
-continued
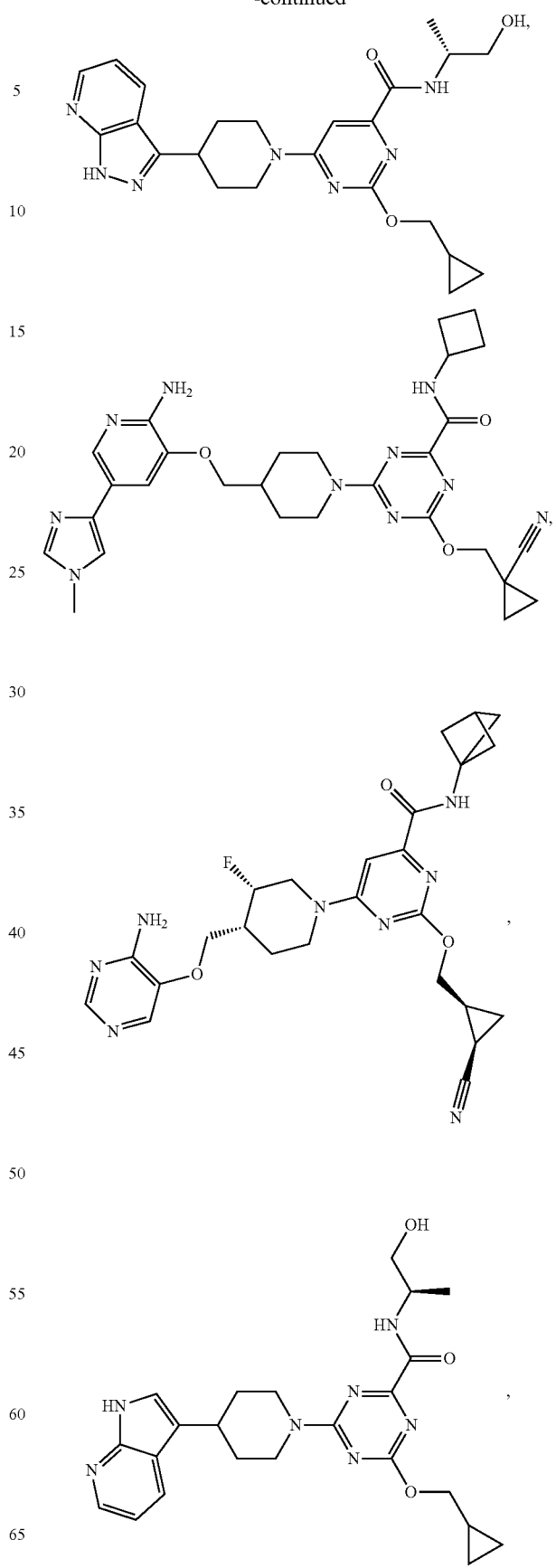

579
-continued
580
-continued
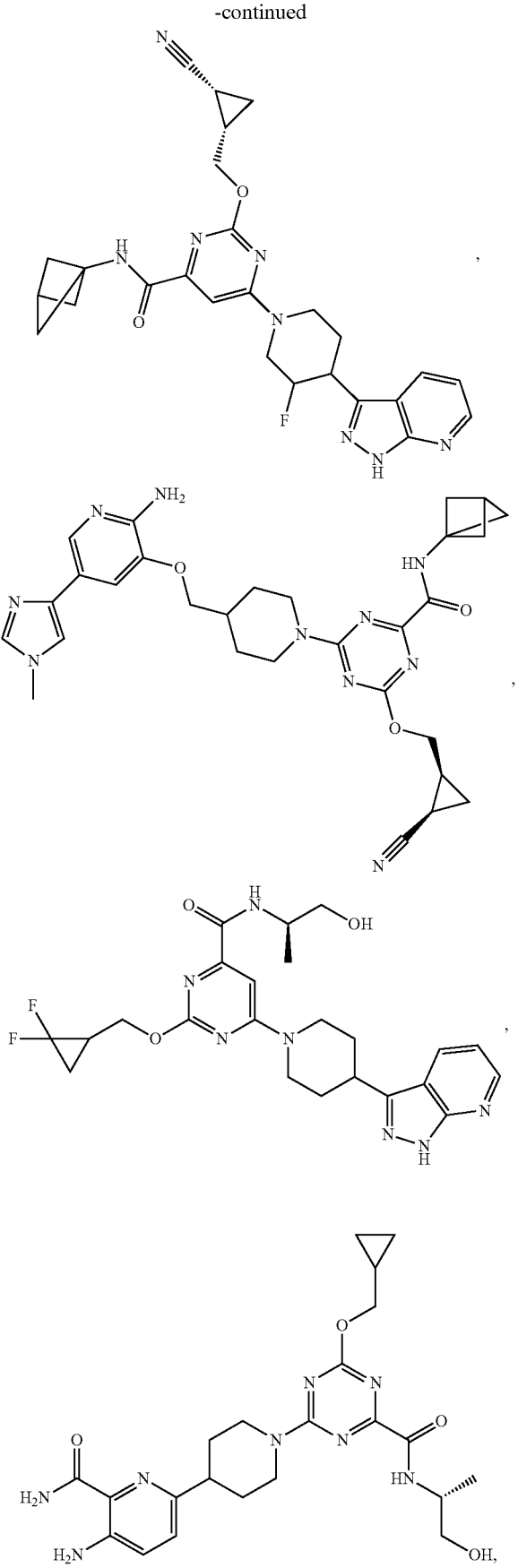
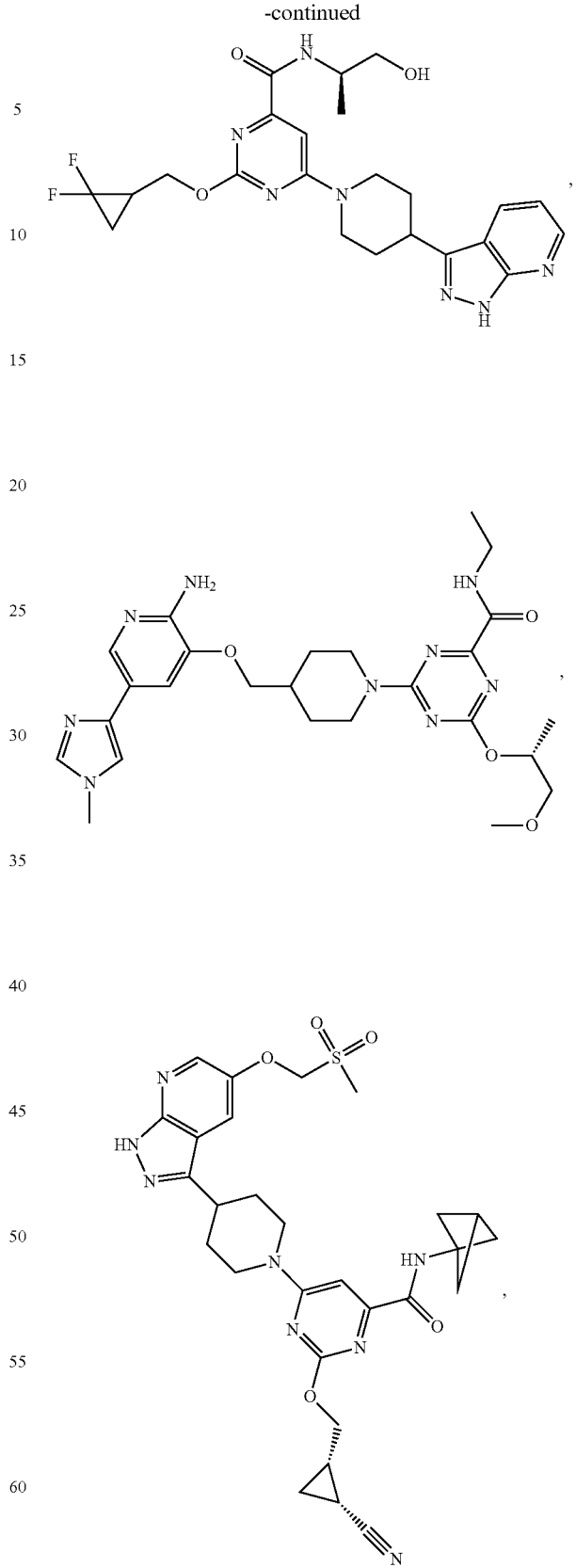

581
-continued
582
-continued
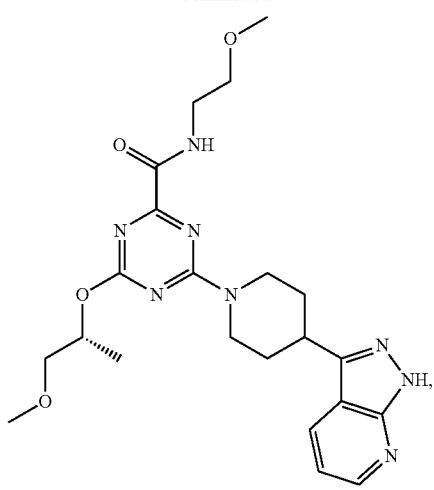
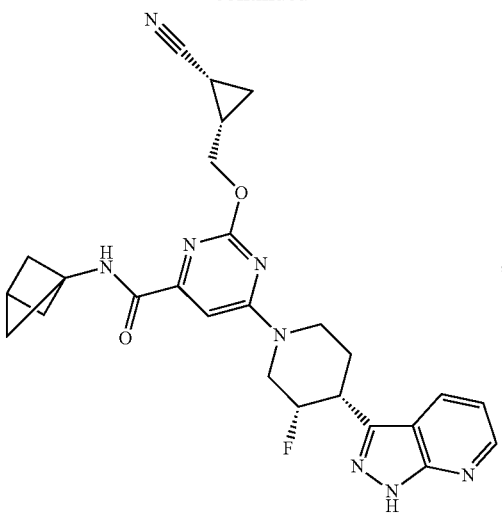
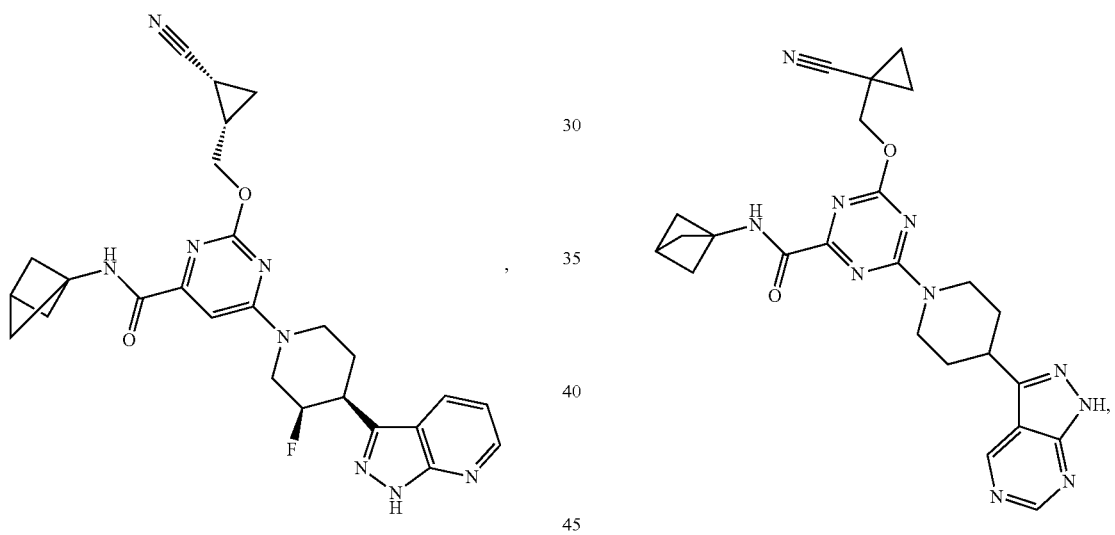
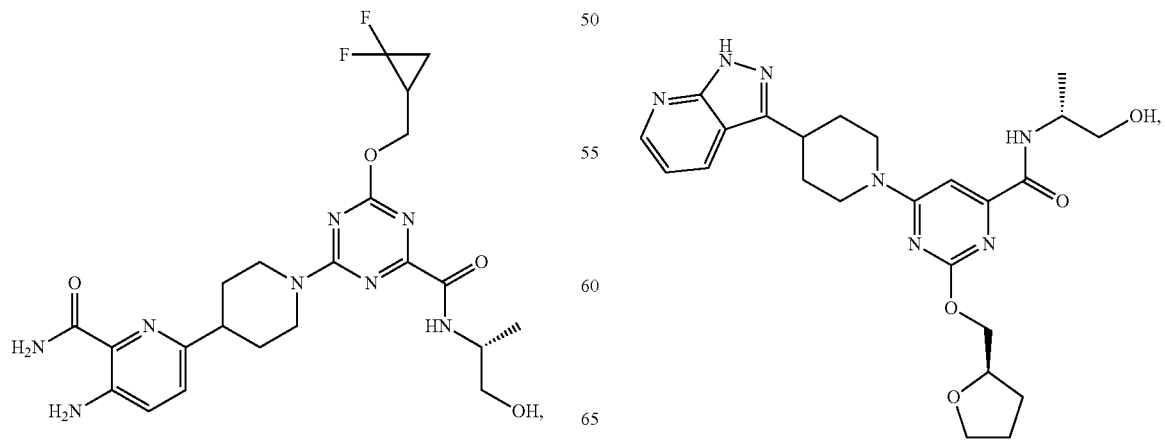

583
-continued
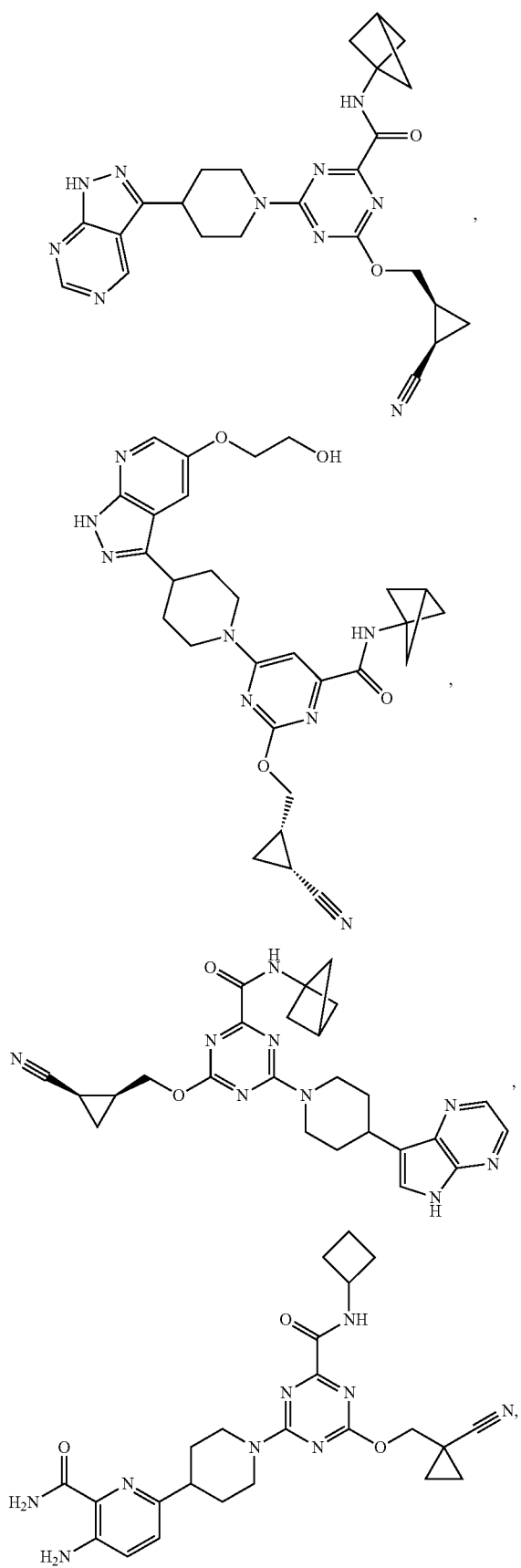
584
-continued
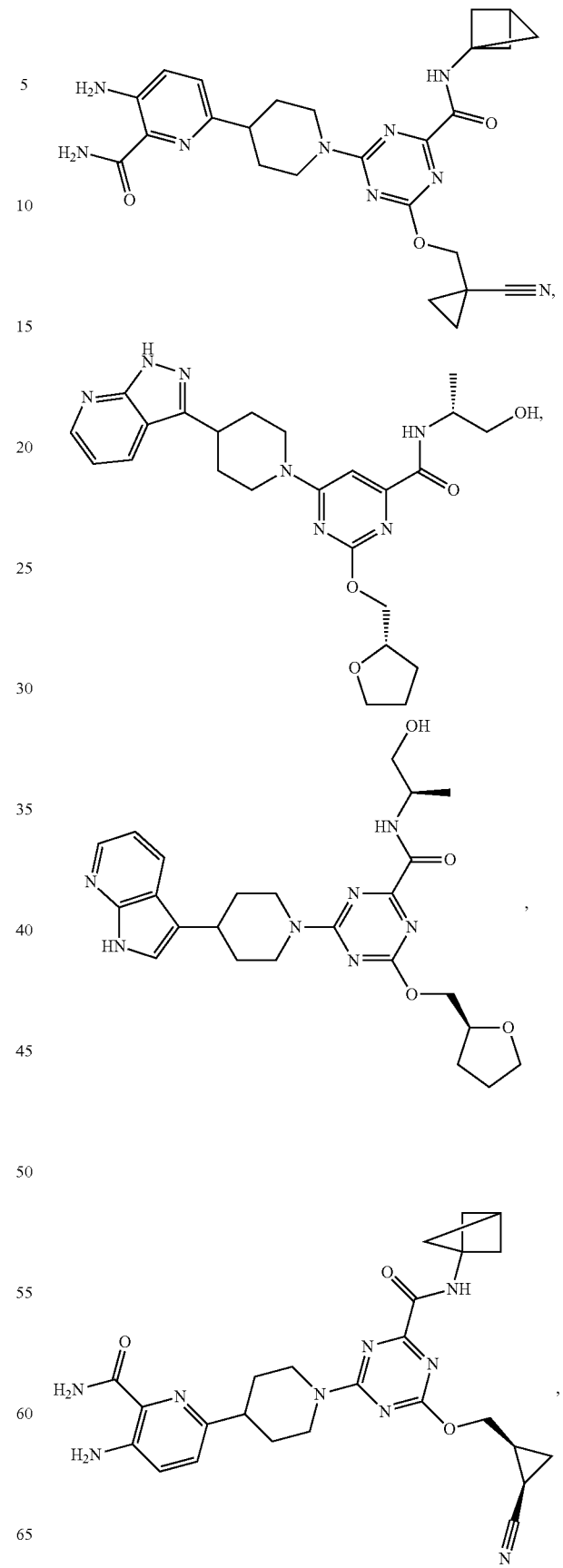

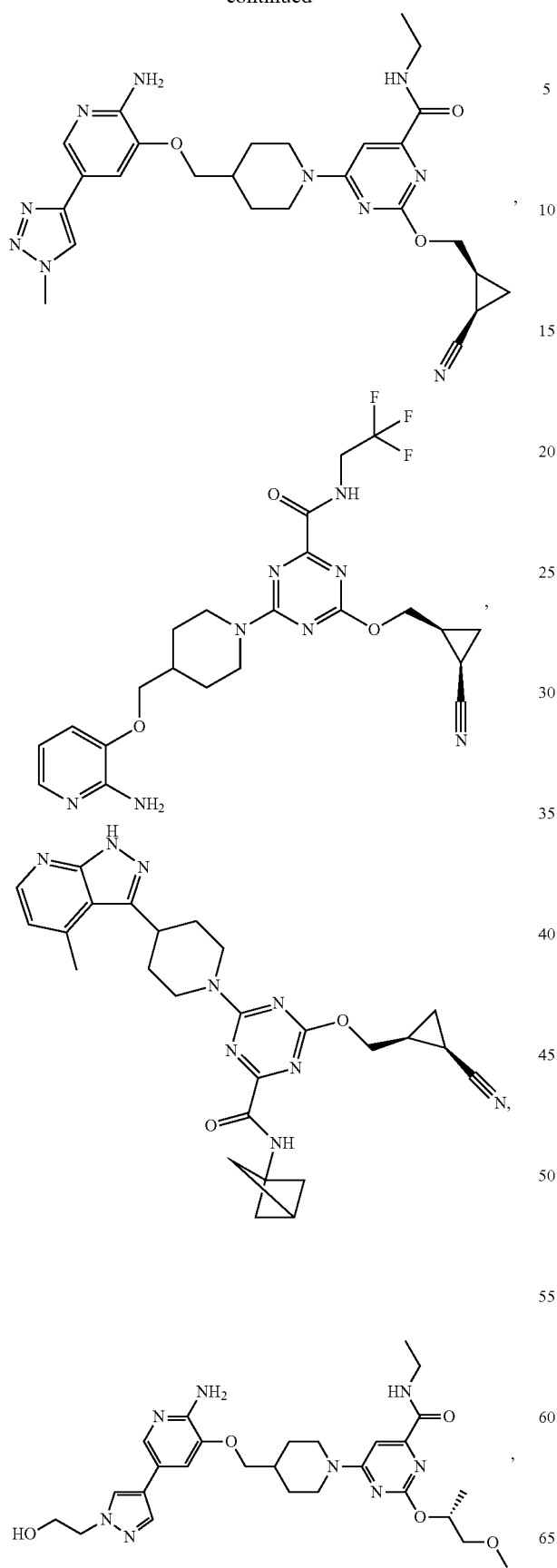
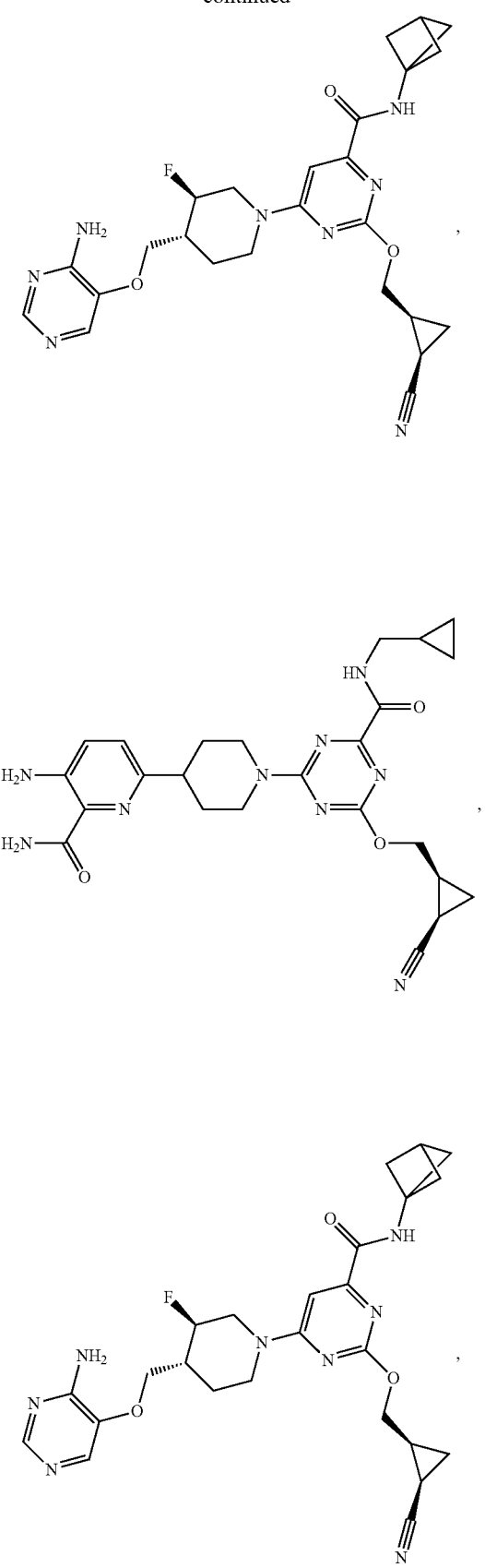

587
-continued
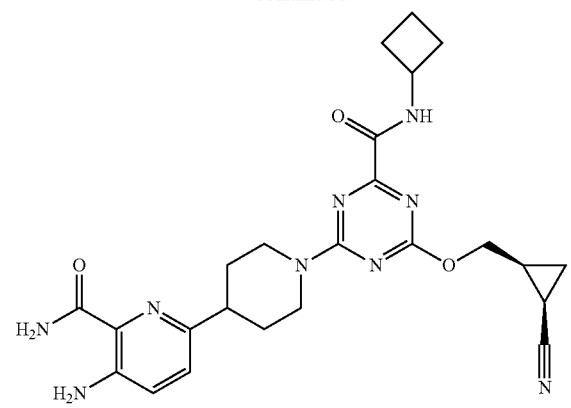
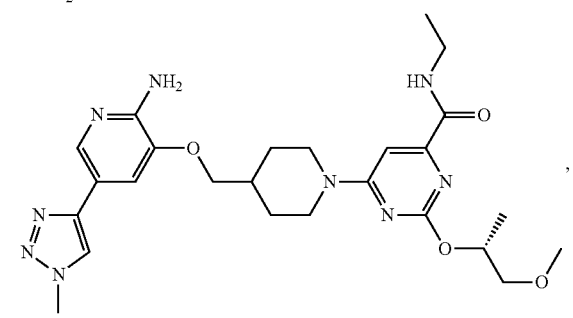
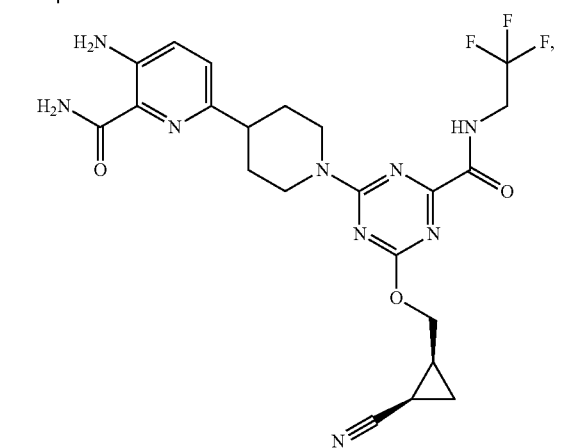
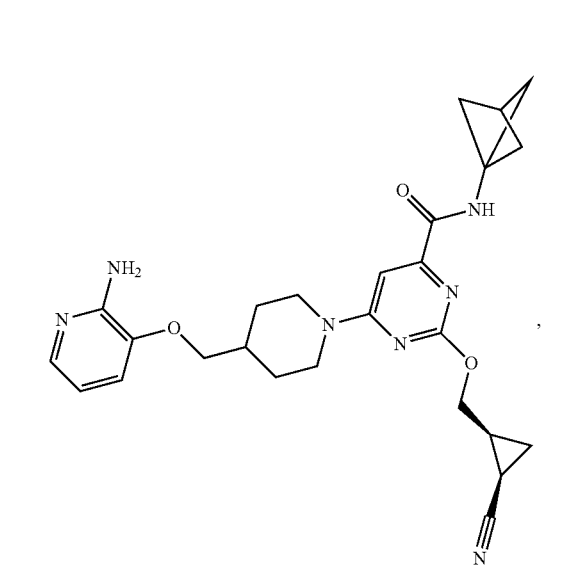
588
-continued
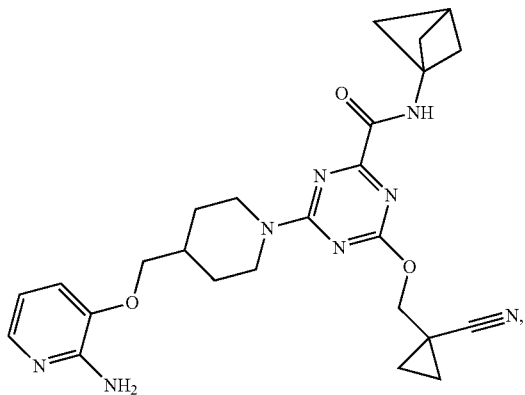

589
-continued
590
-continued
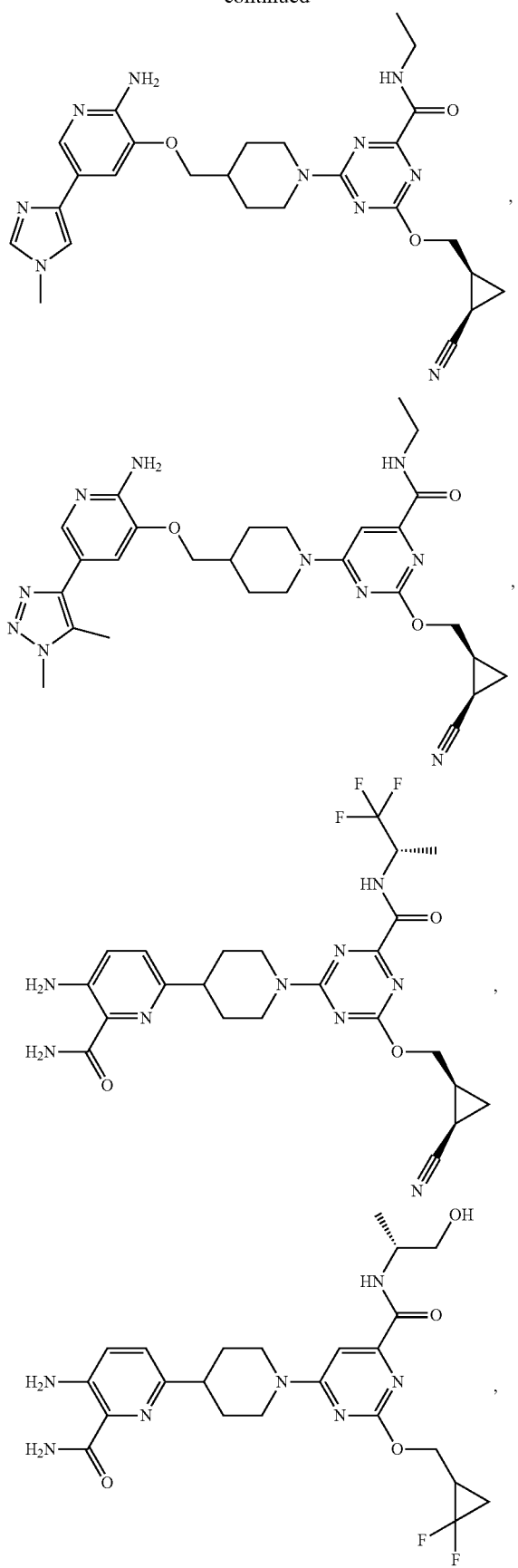
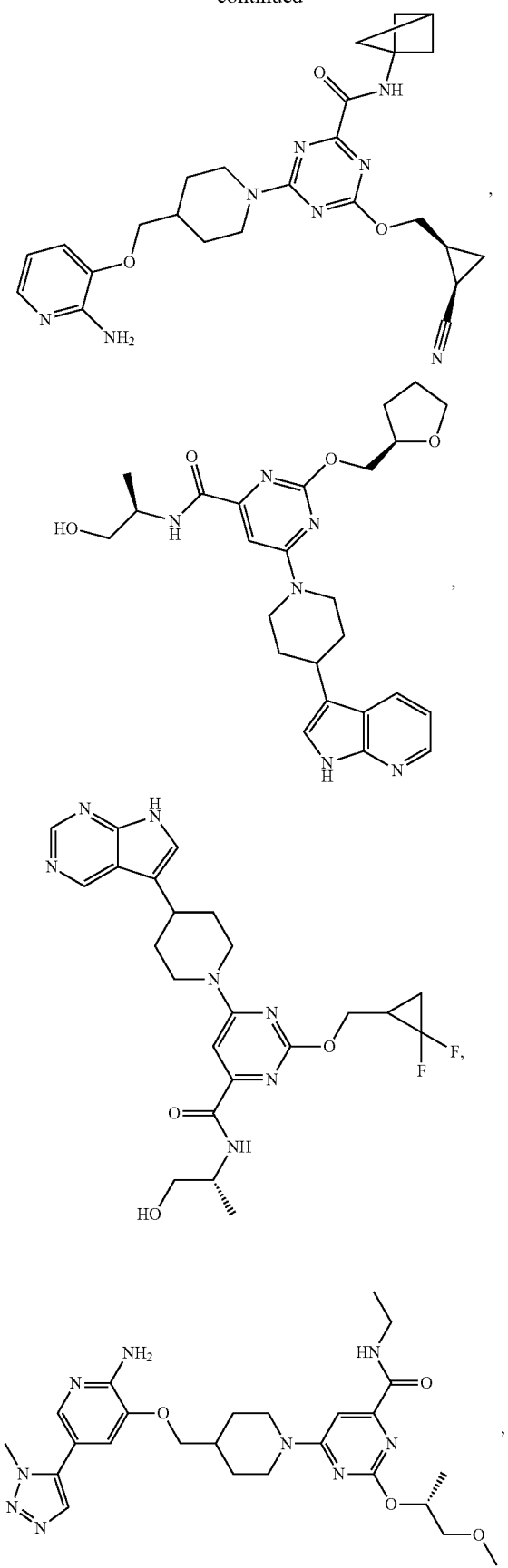

591
-continued
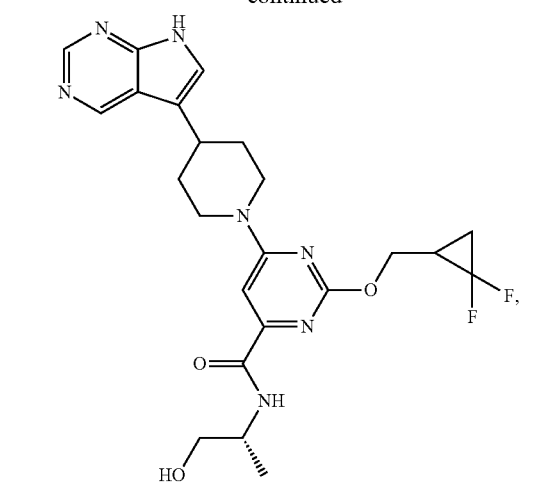
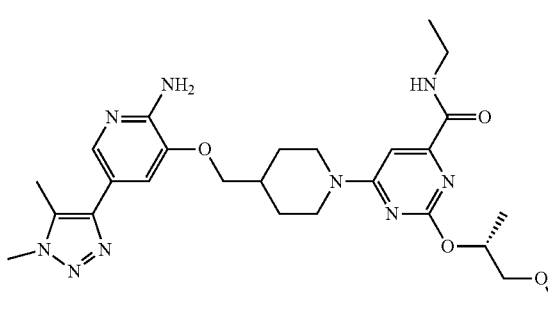
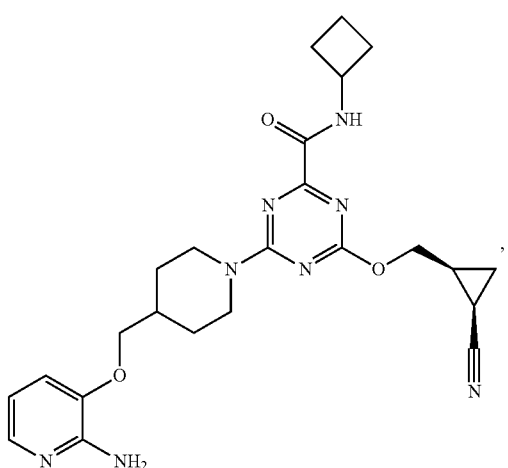
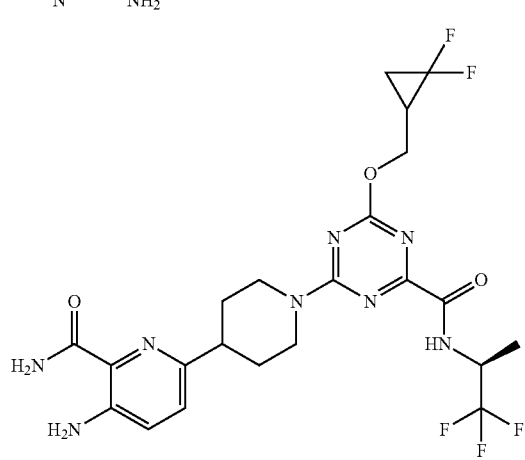
592
-continued
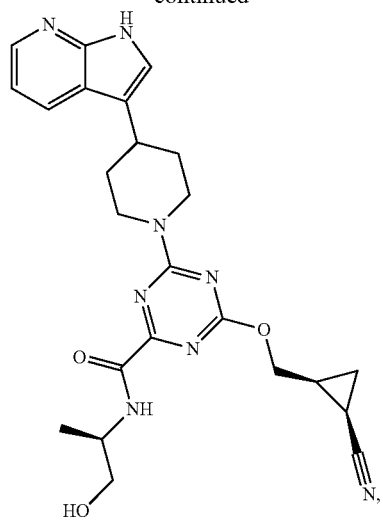
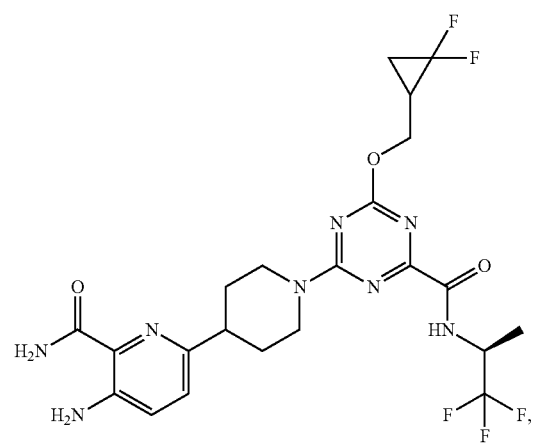
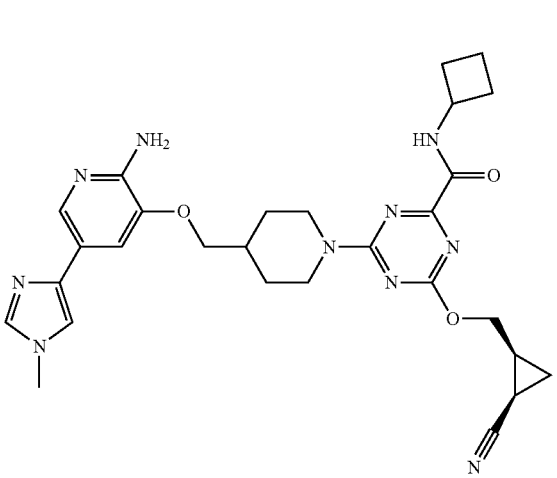

593
-continued
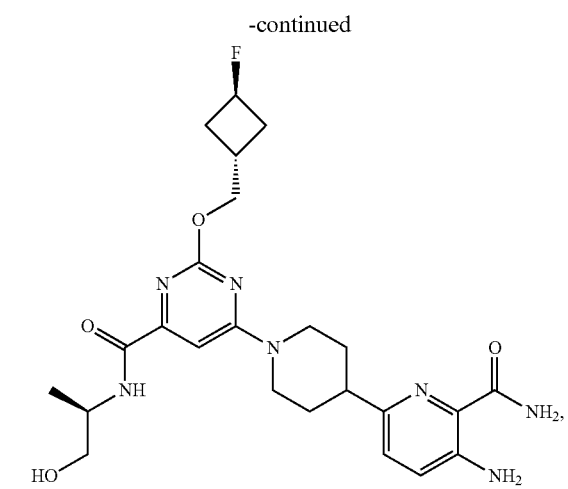
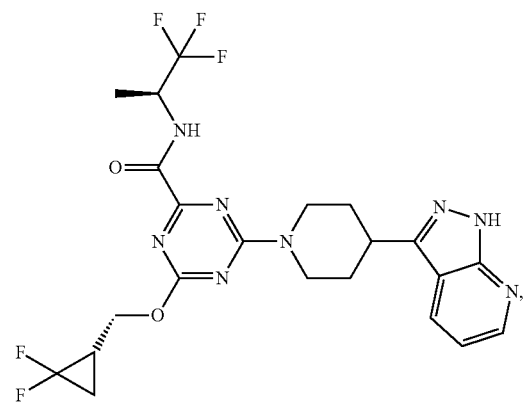
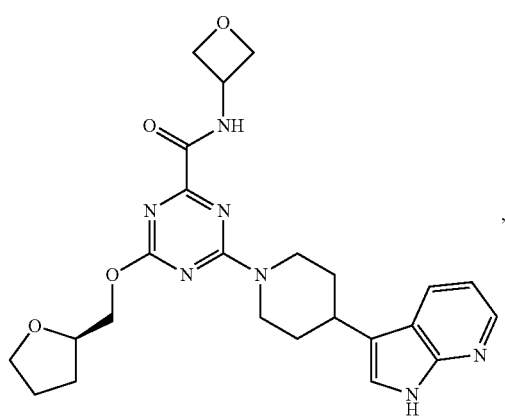
594
-continued
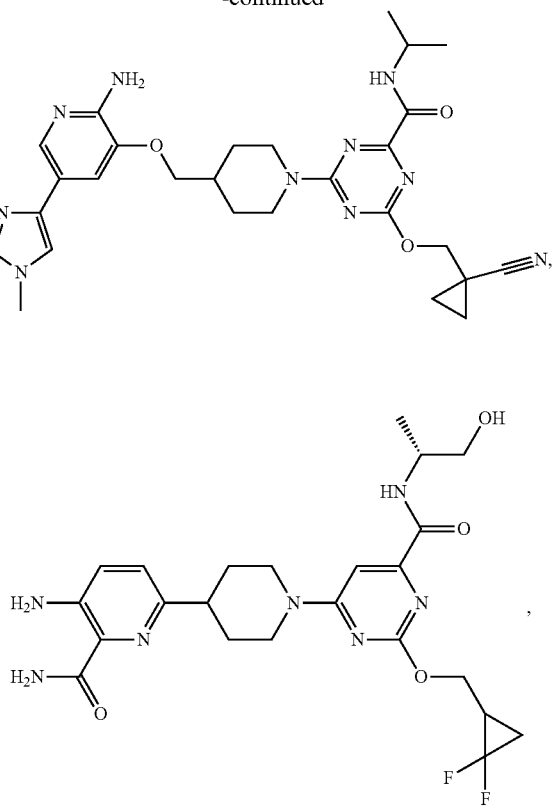
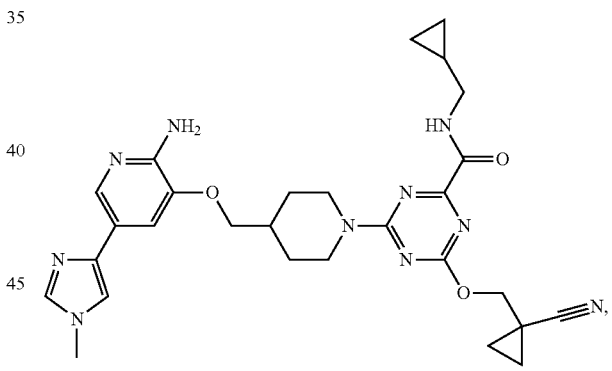

595
-continued
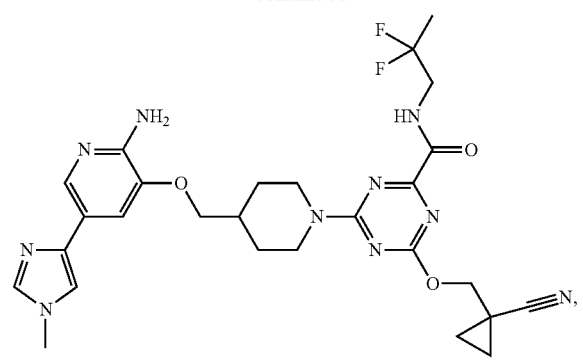
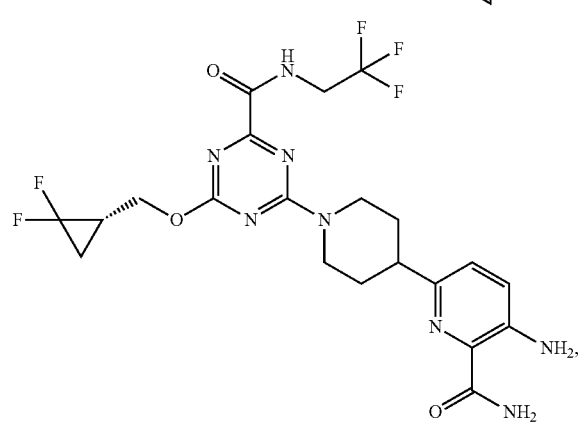
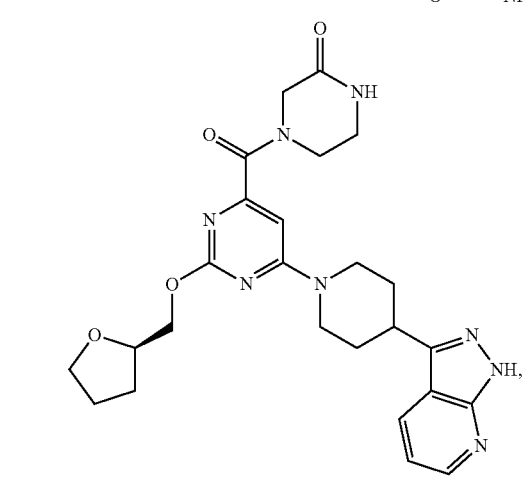
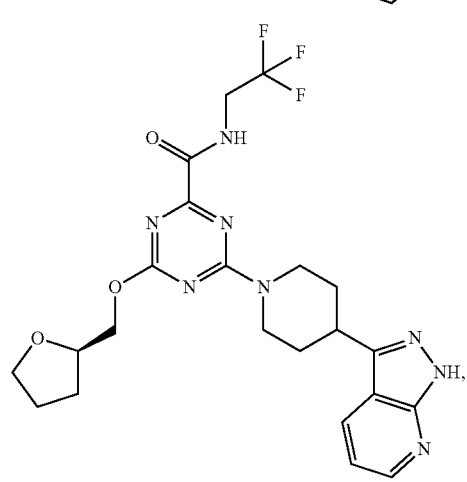
596
-continued
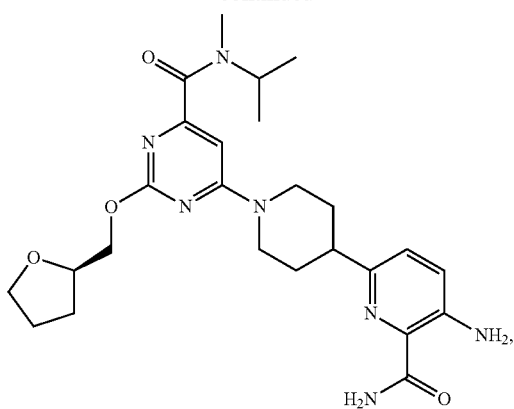
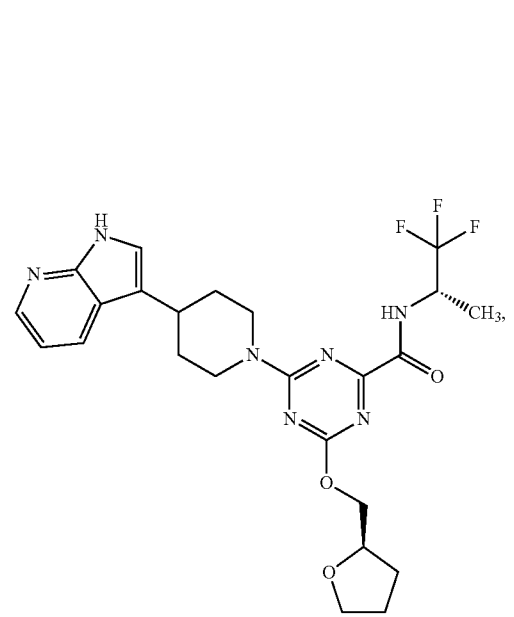
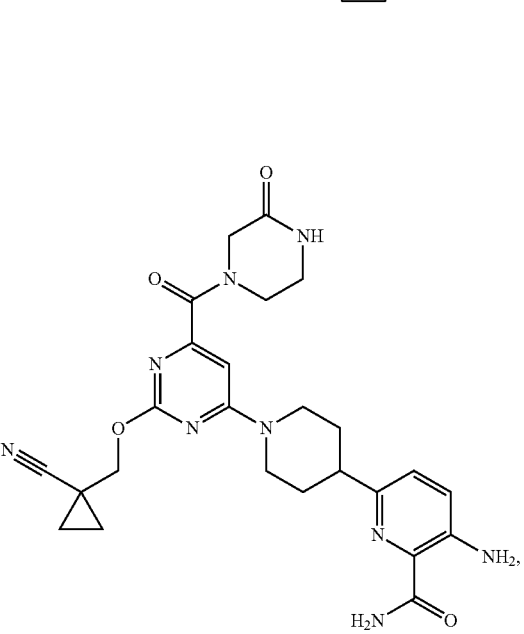

597
-continued
598
-continued
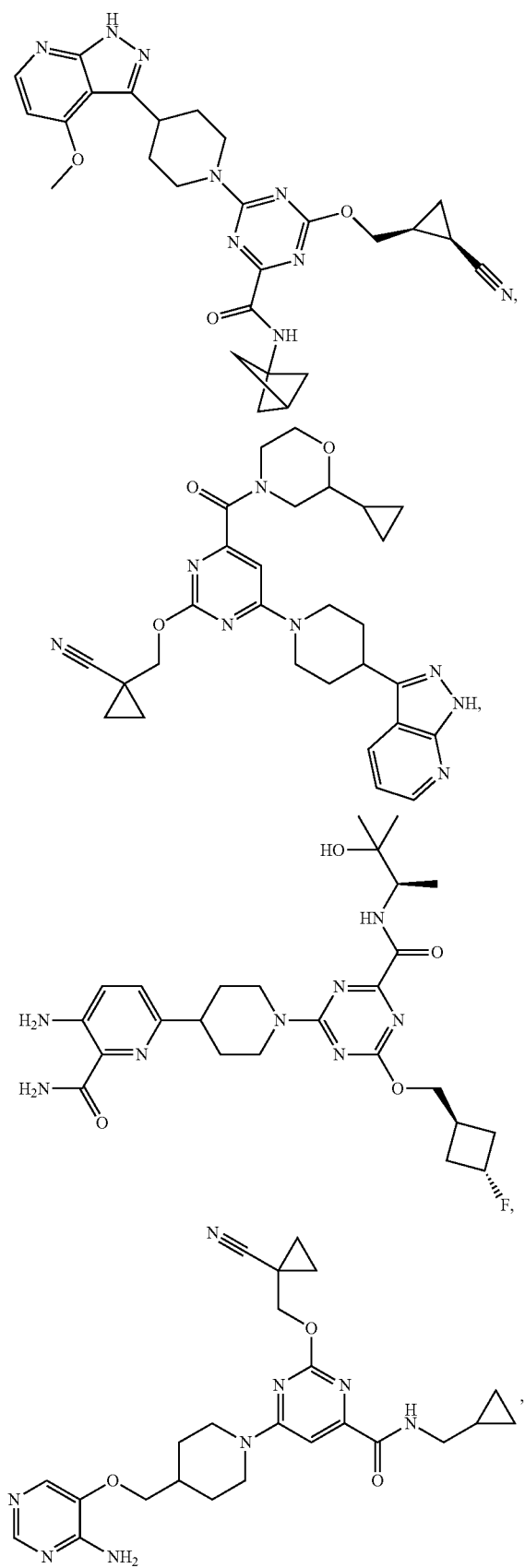
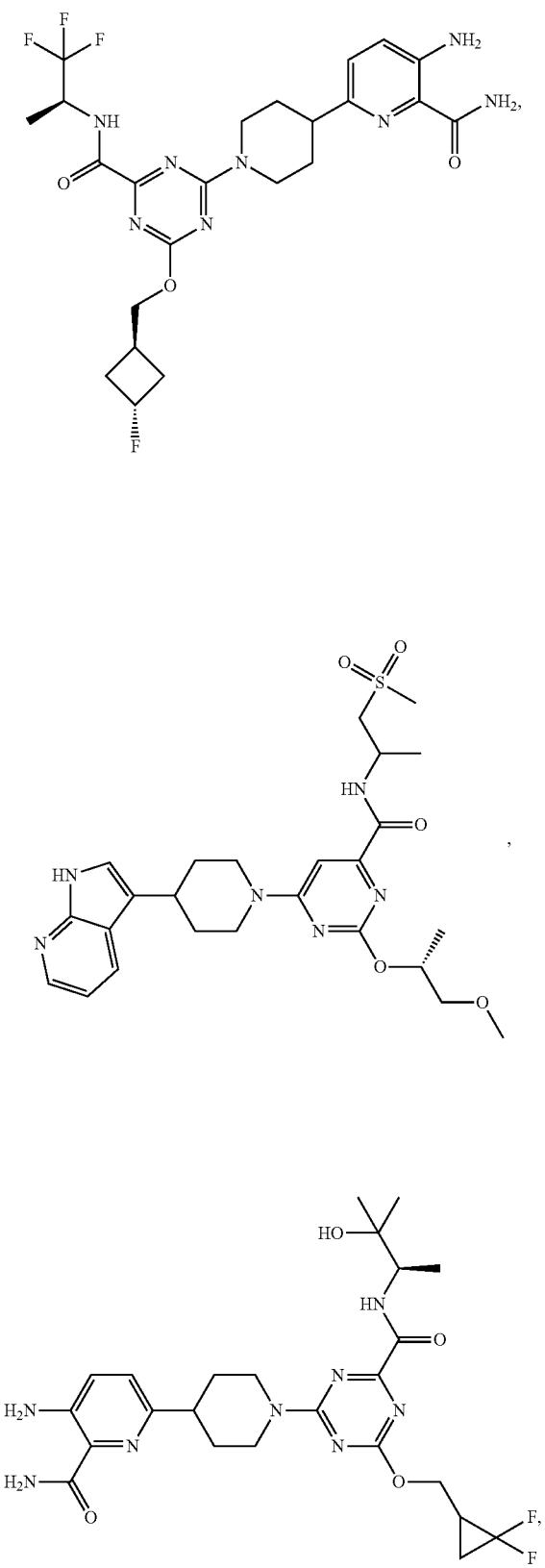

599
-continued
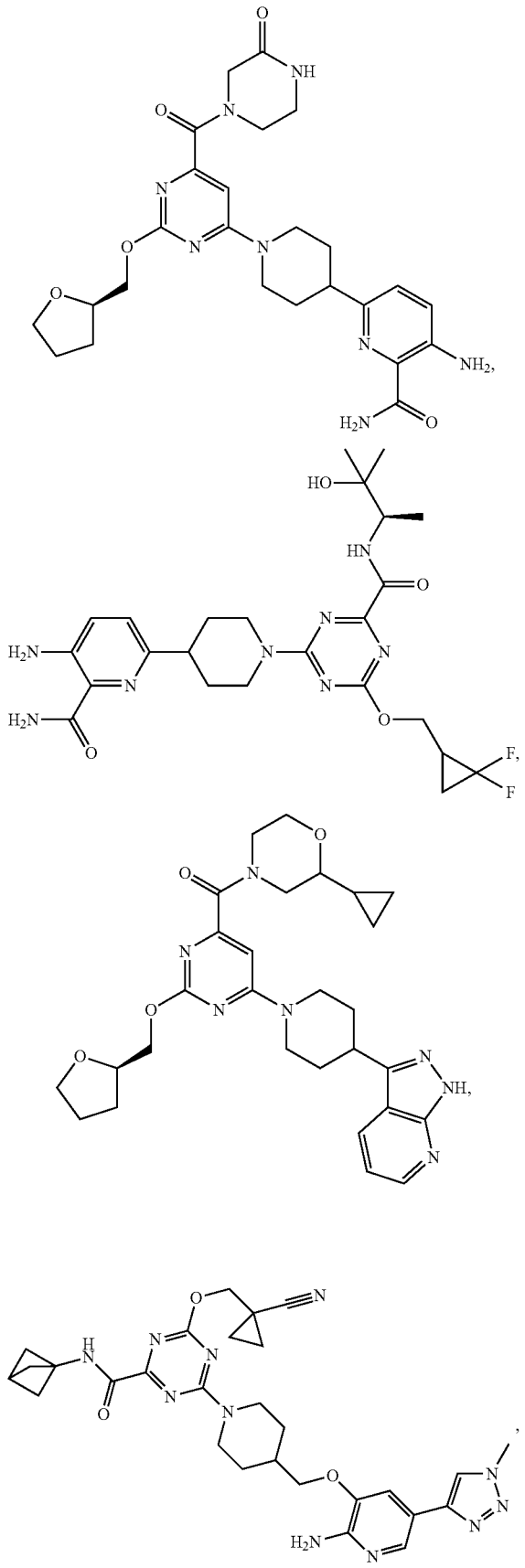
600
-continued
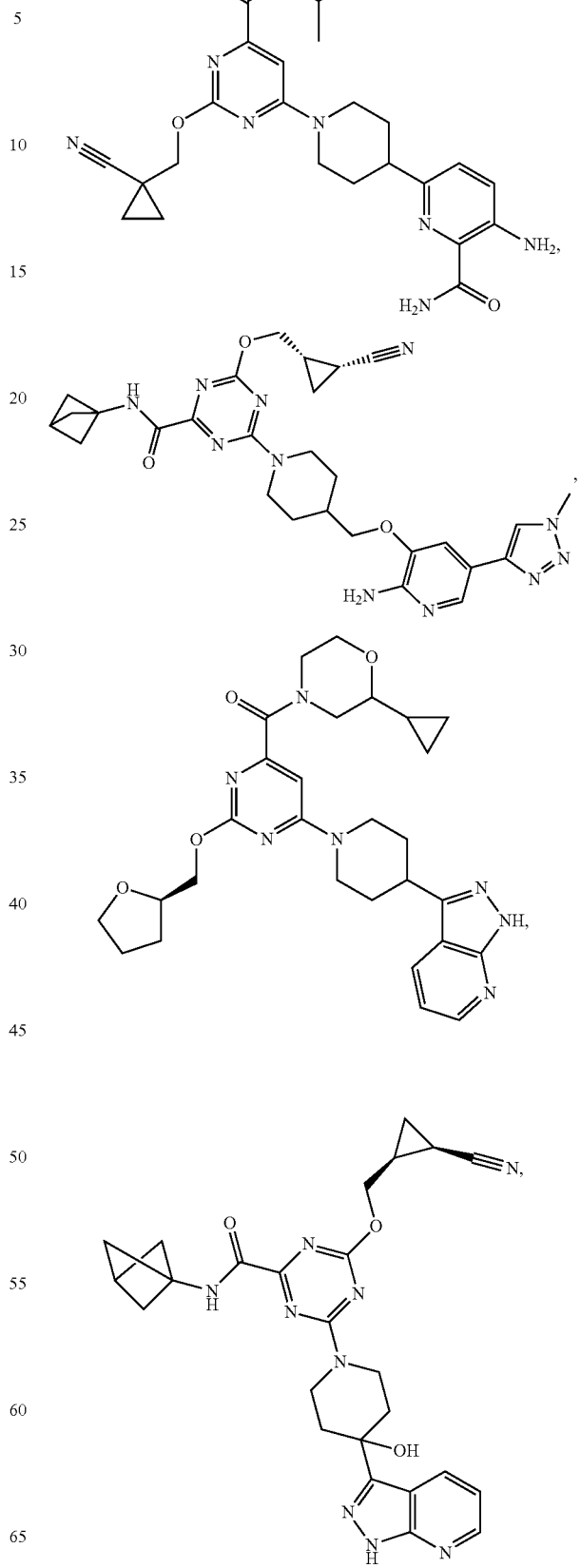

601
-continued
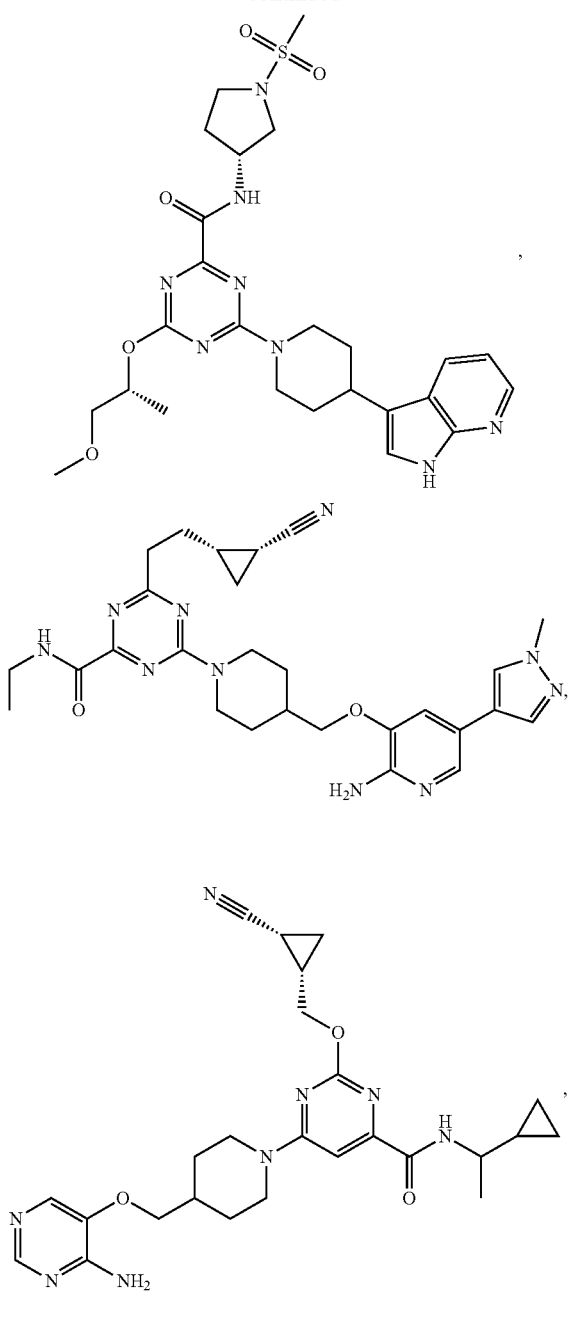
602
-continued
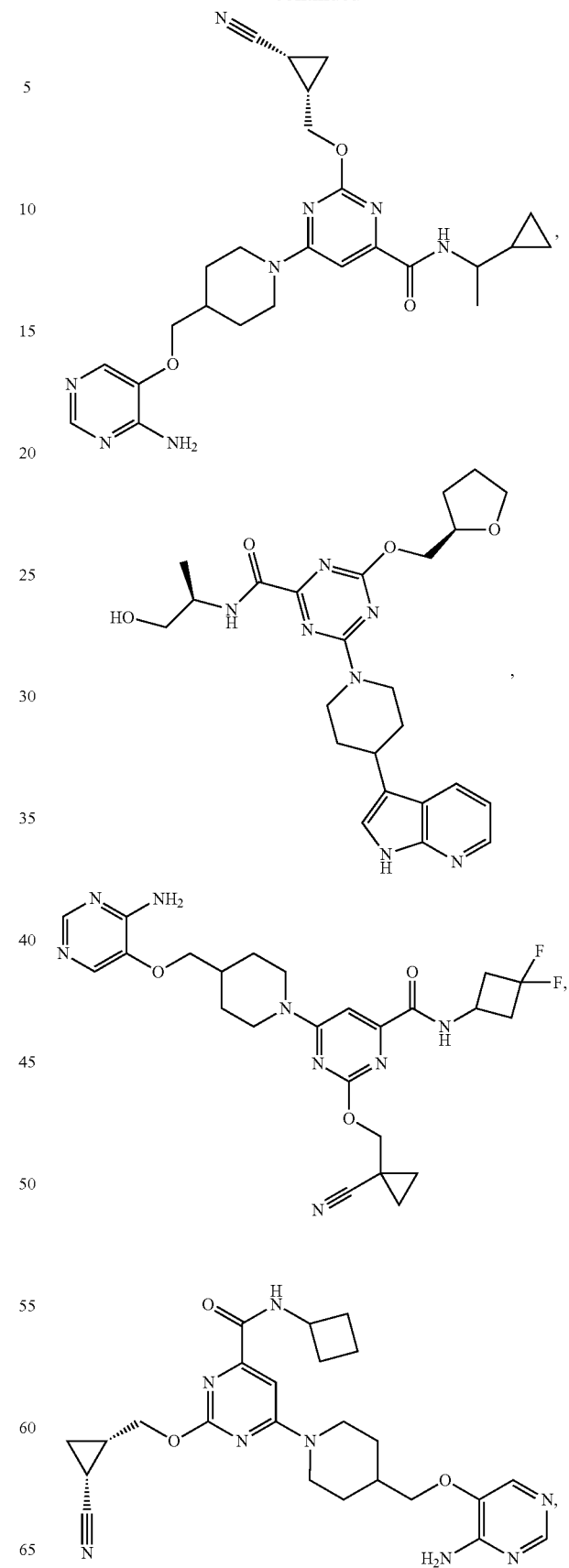

603
-continued
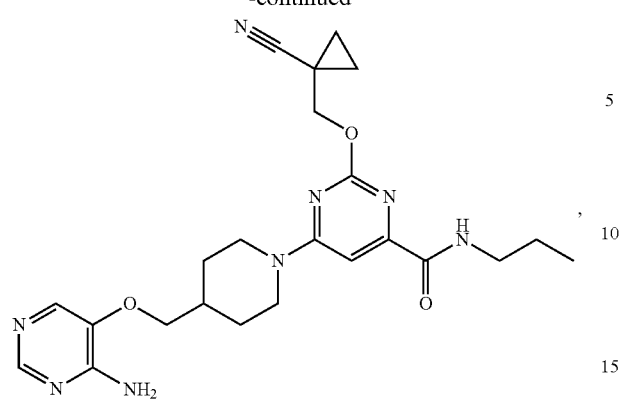
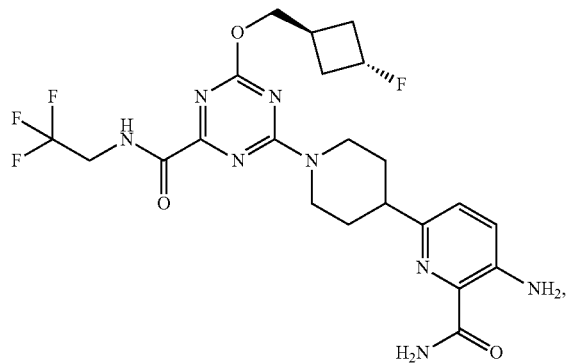
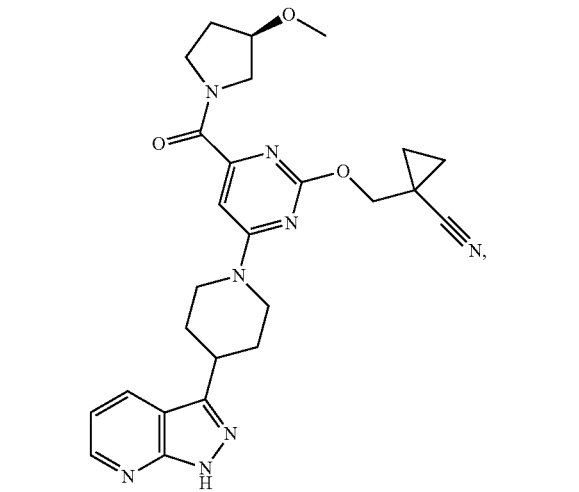
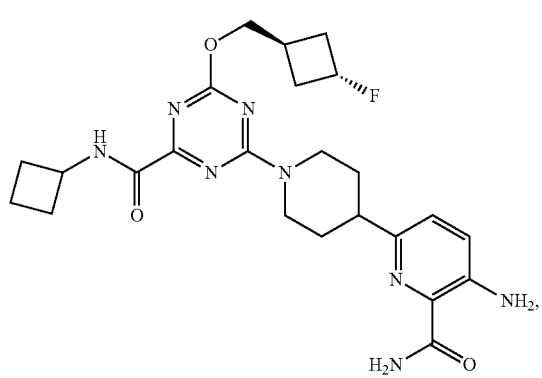
604
-continued
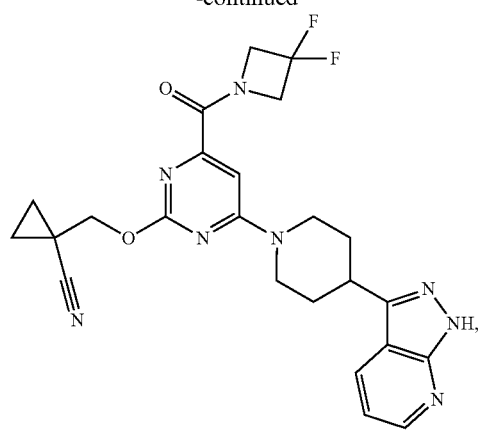
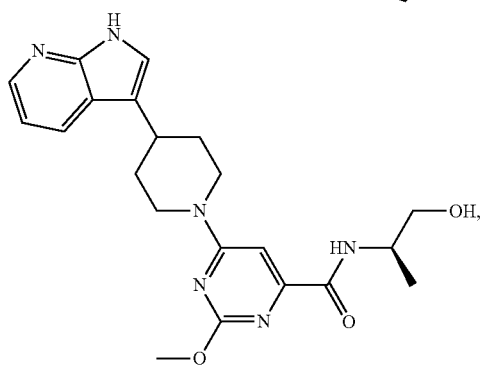
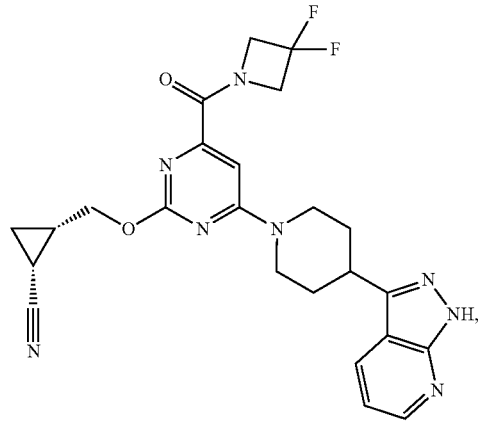
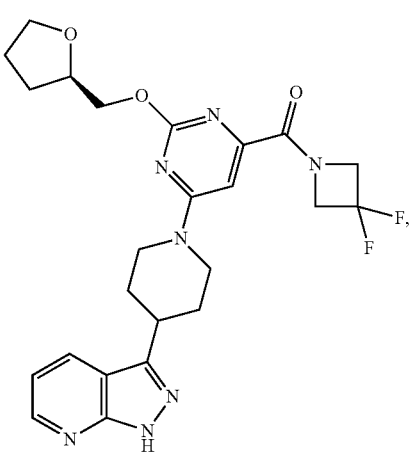

605
-continued
606
-continued
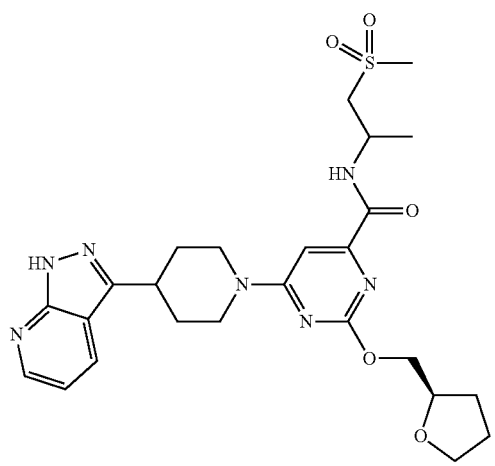
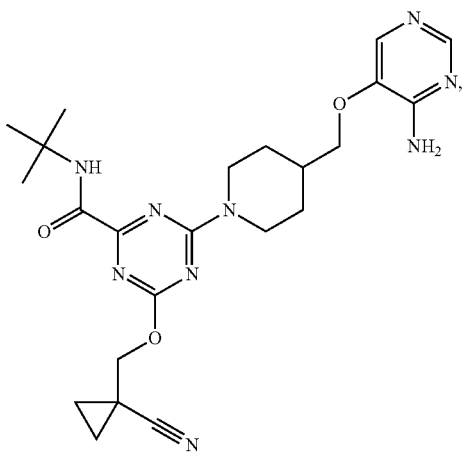
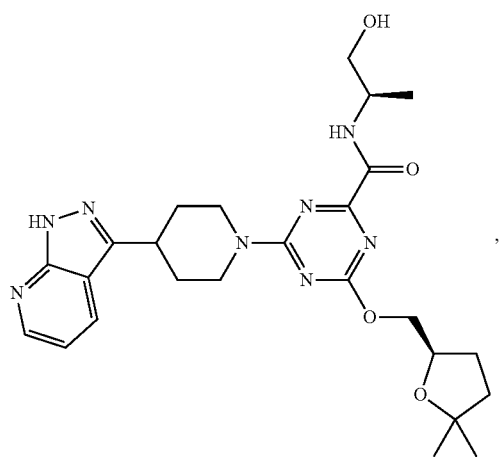
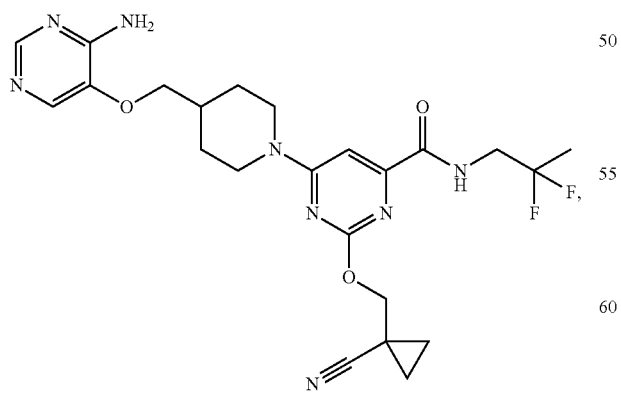
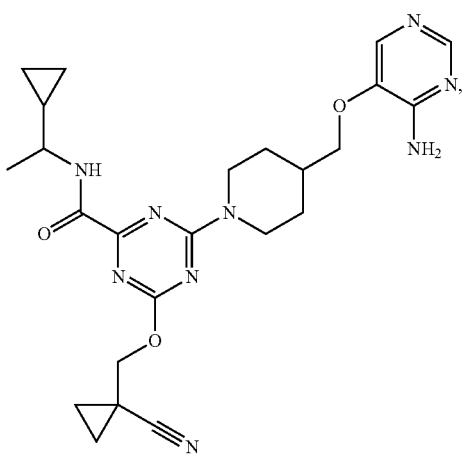

607
-continued
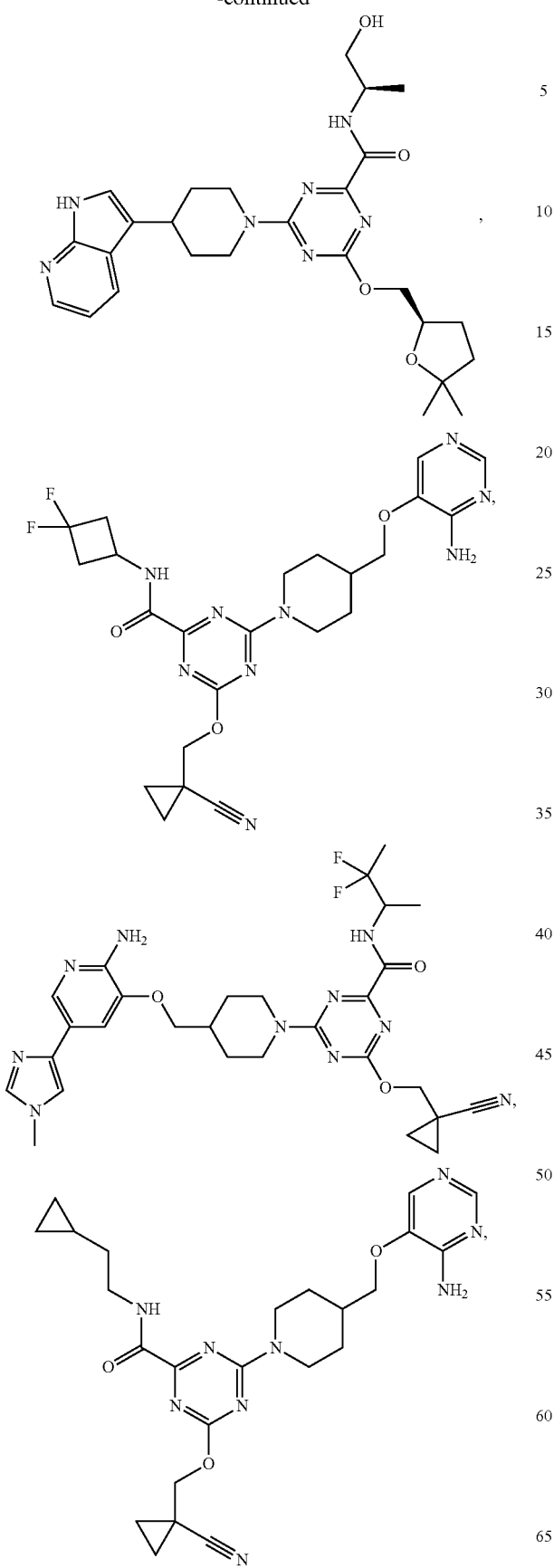
608
-continued
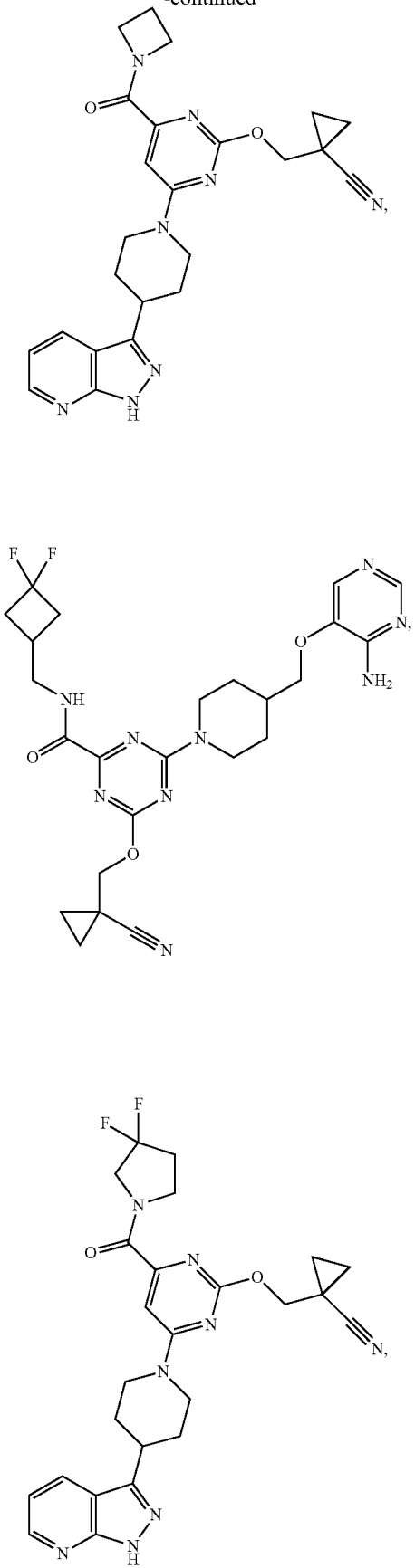

609
-continued
610
-continued
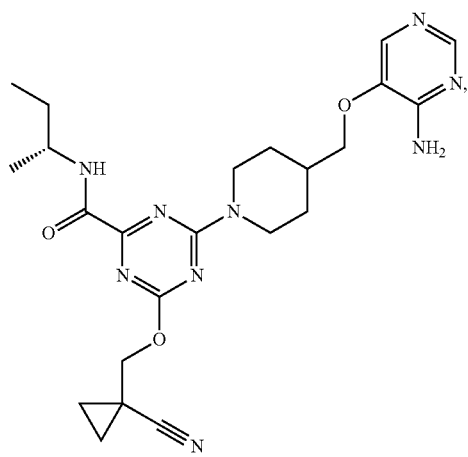
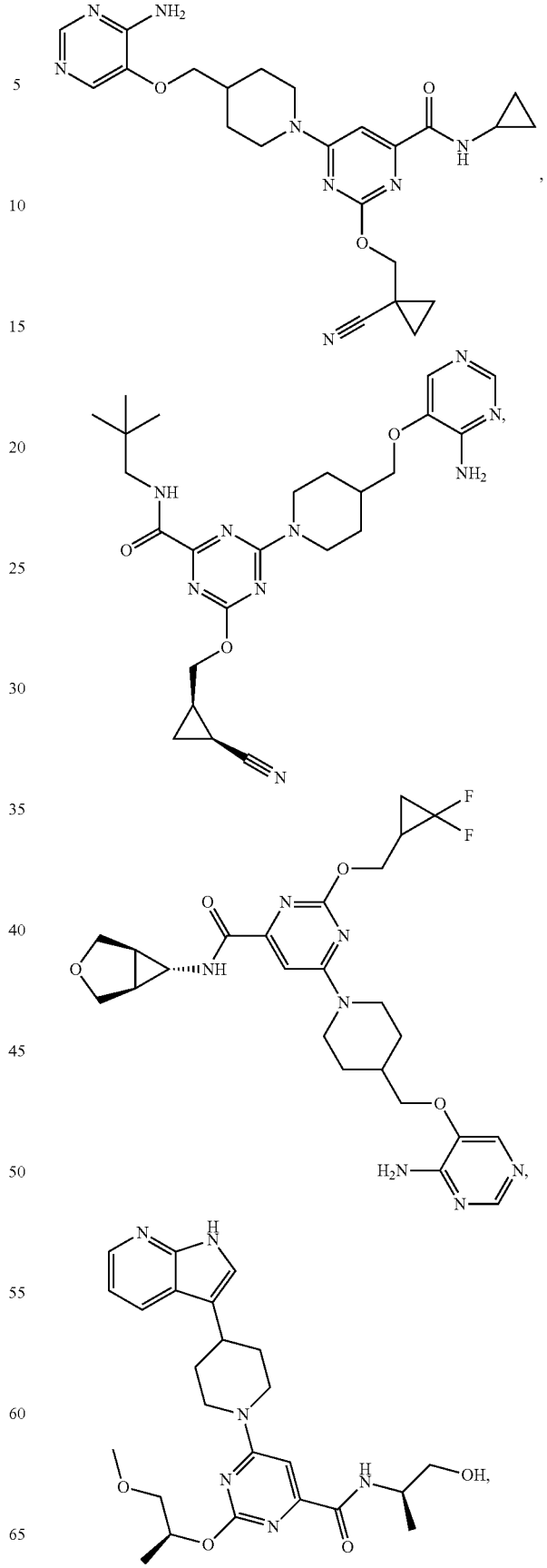

611
-continued
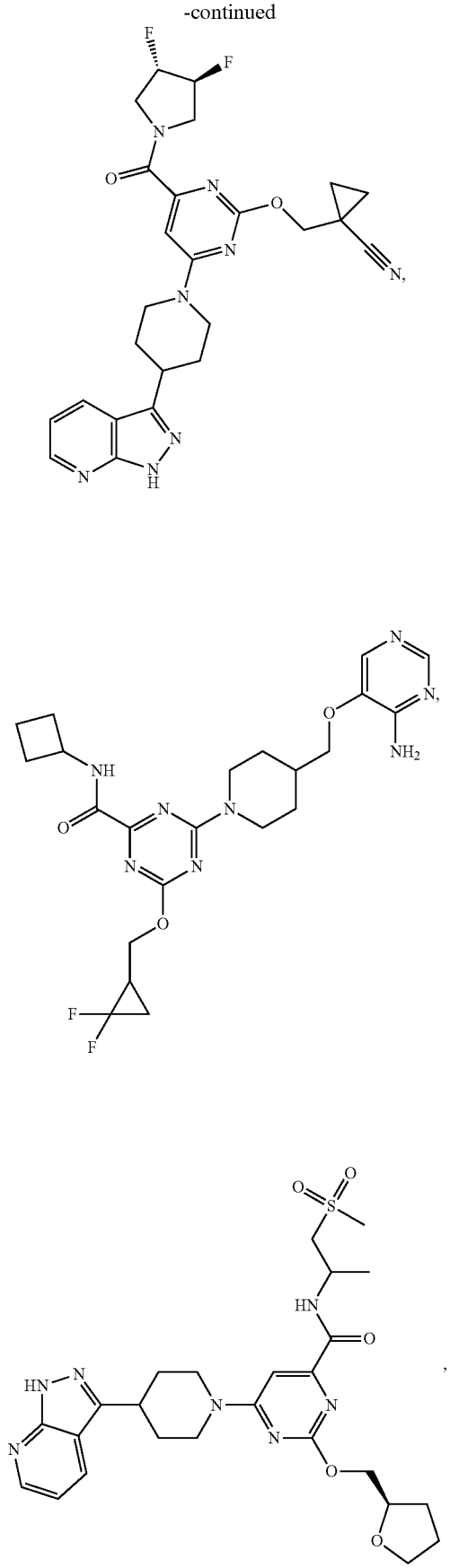
612
-continued
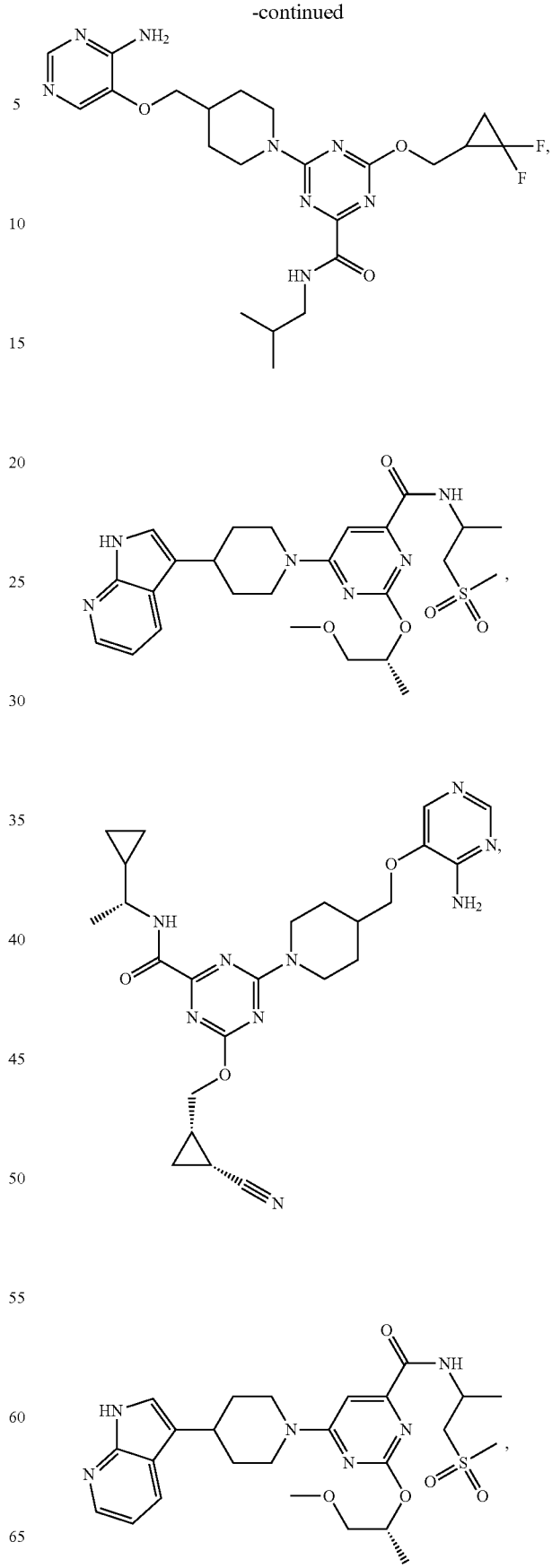

613
-continued
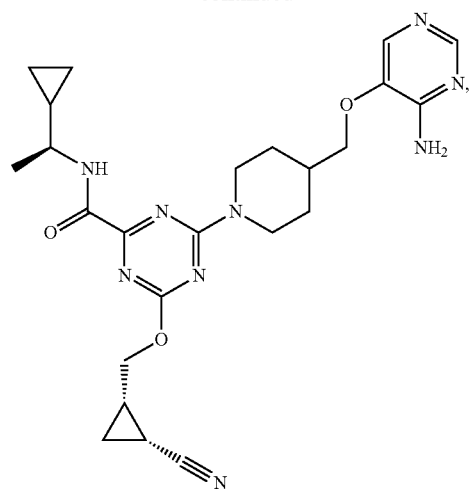
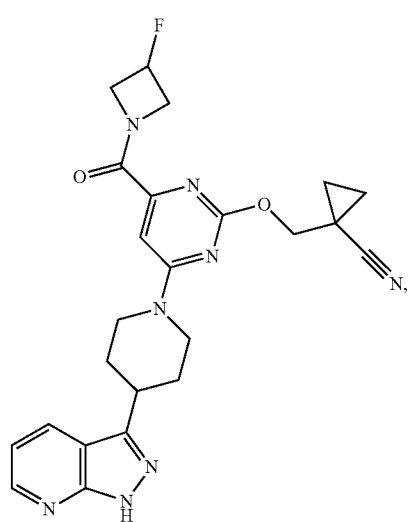
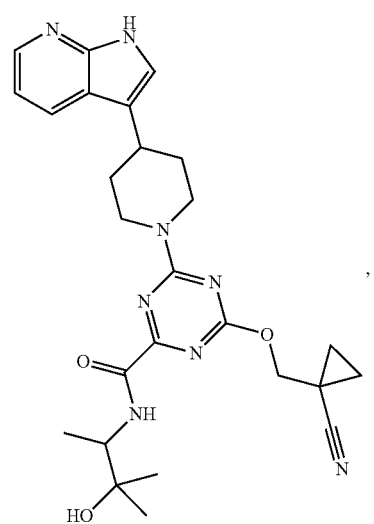
614
-continued
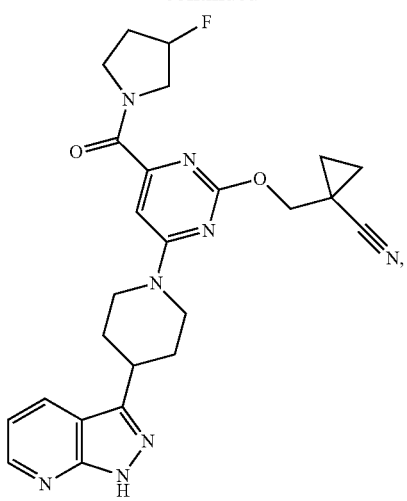
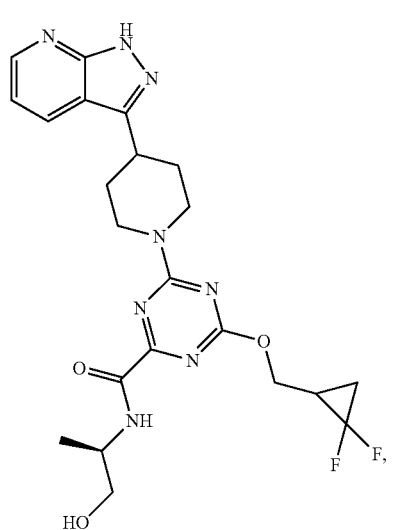
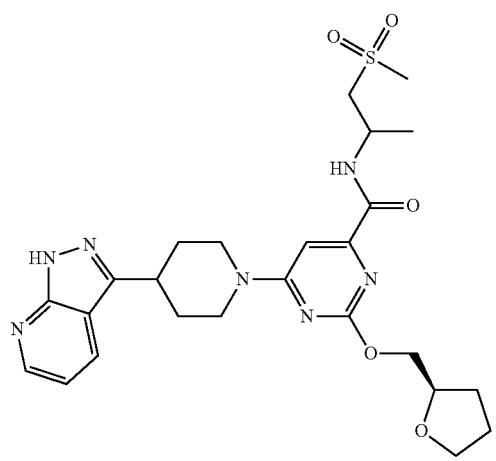

615
-continued
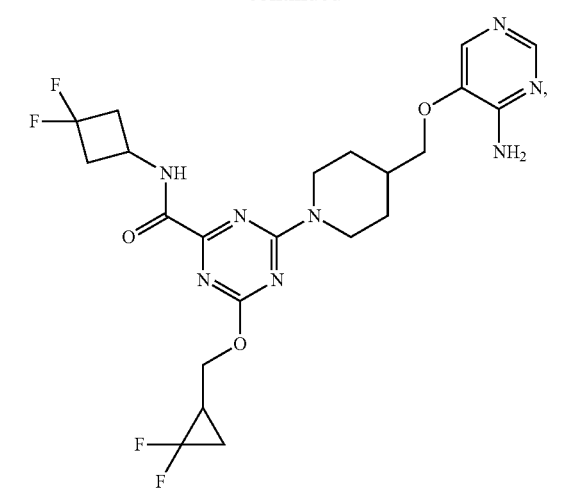
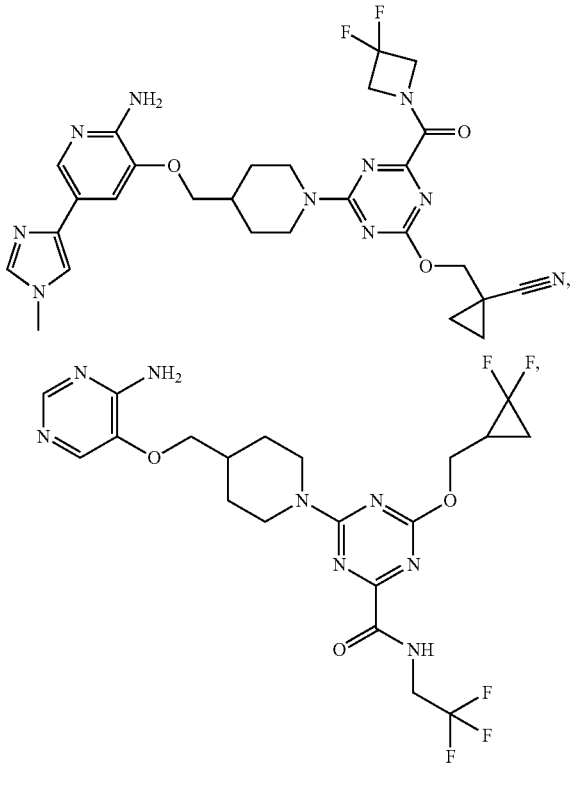
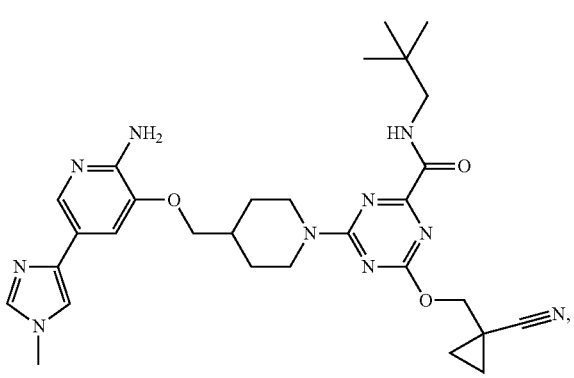
616
-continued
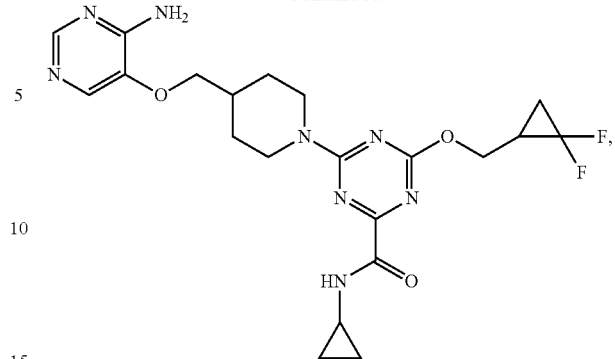
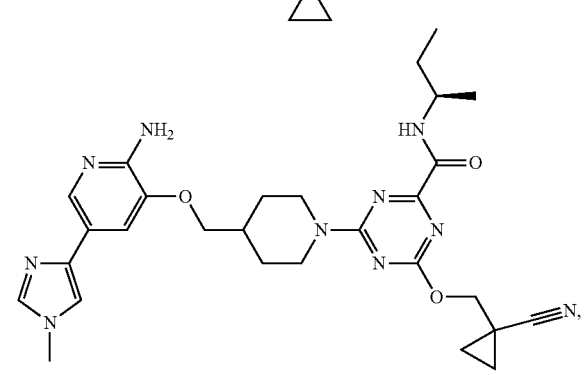
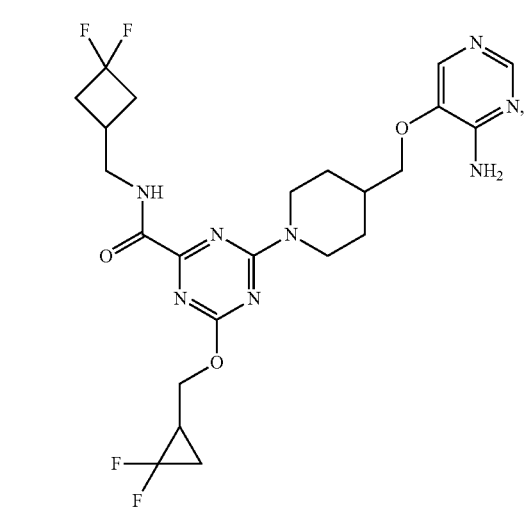
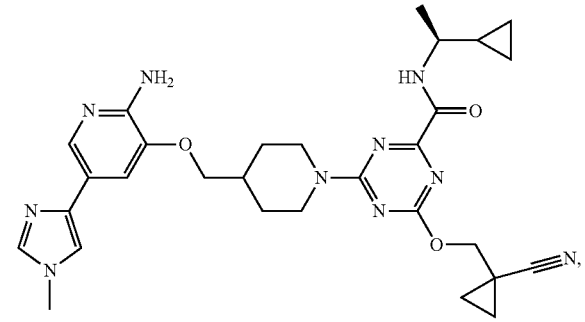

617
-continued
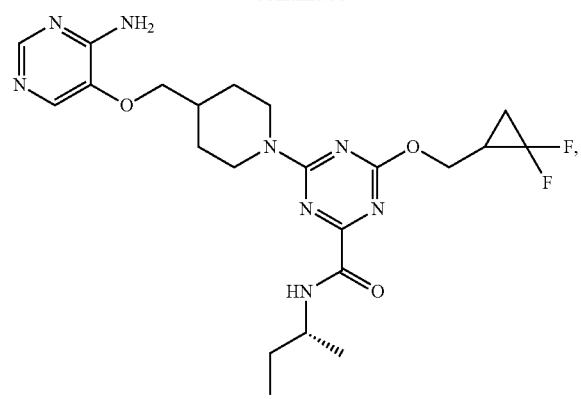
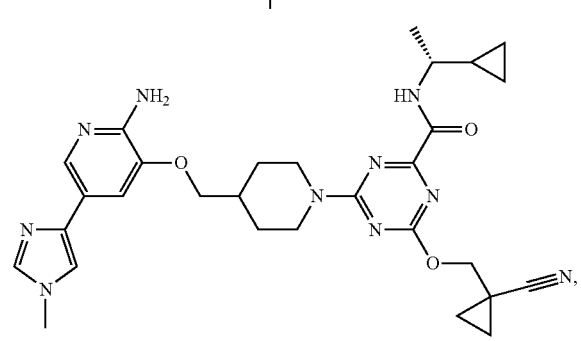
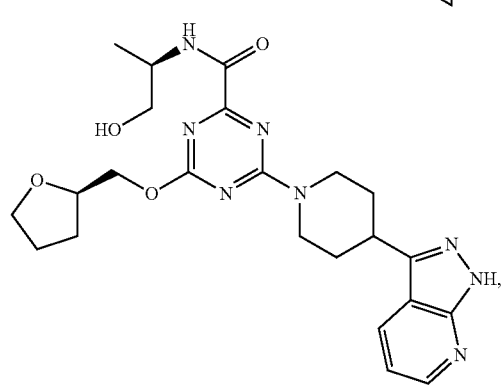
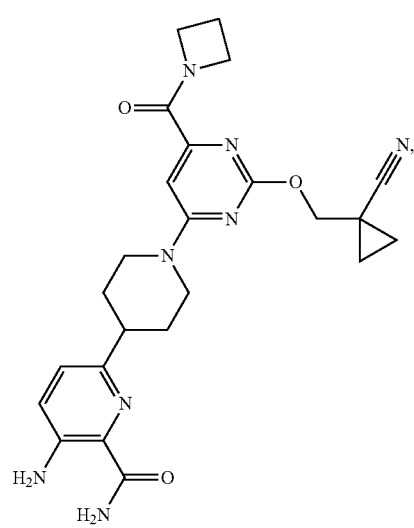
618
-continued
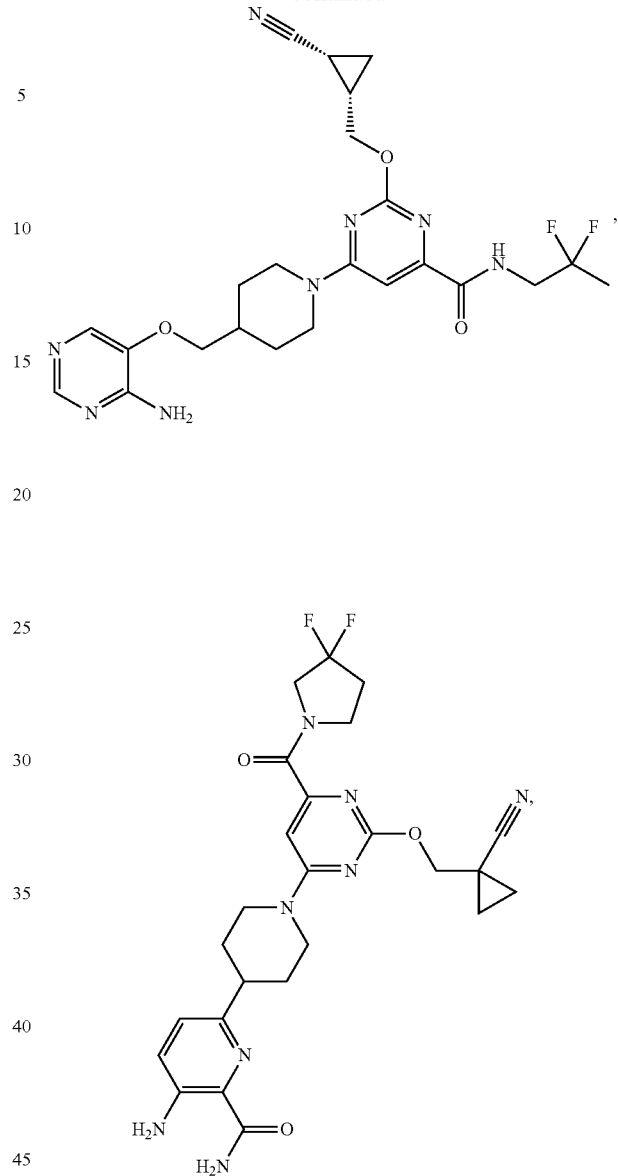
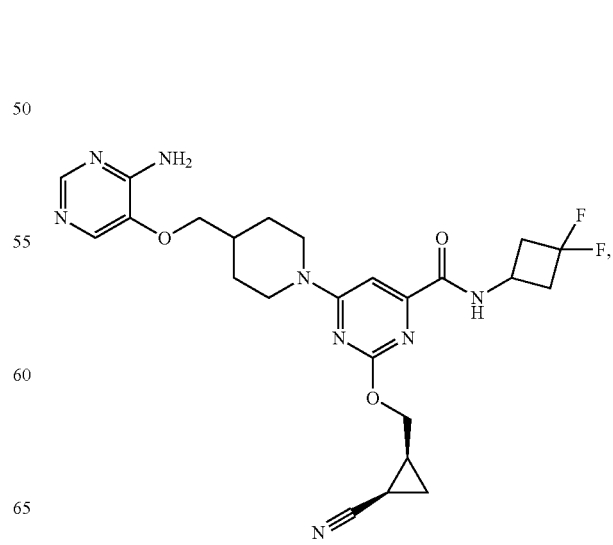

619
-continued
620
-continued
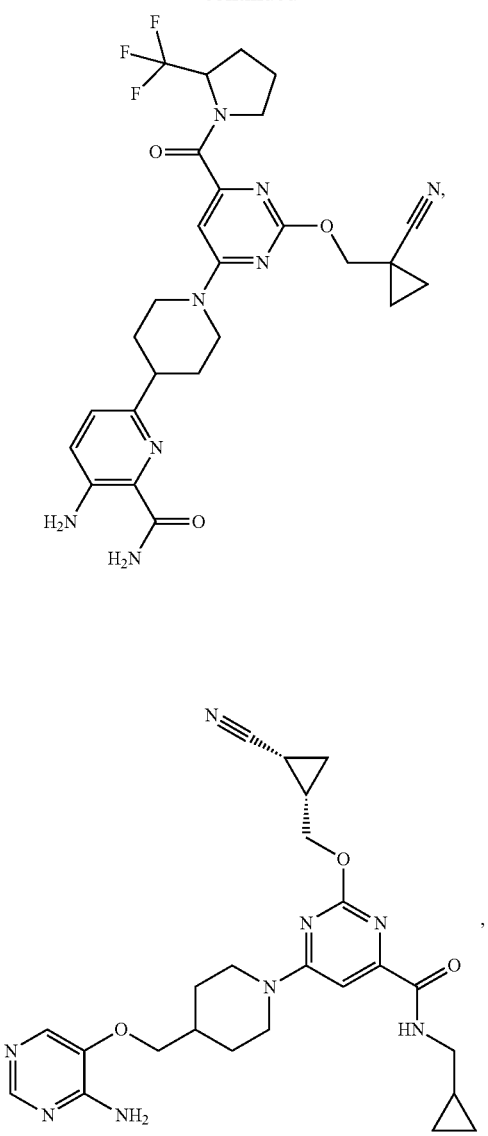
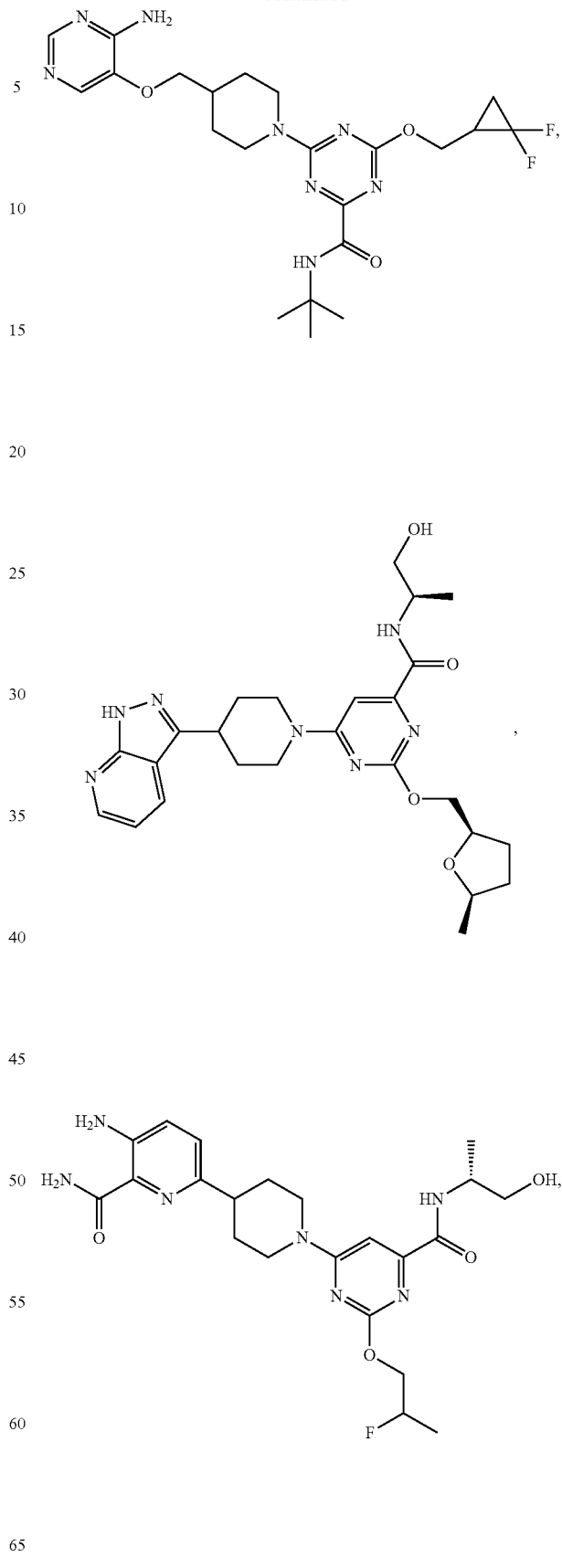

621
-continued
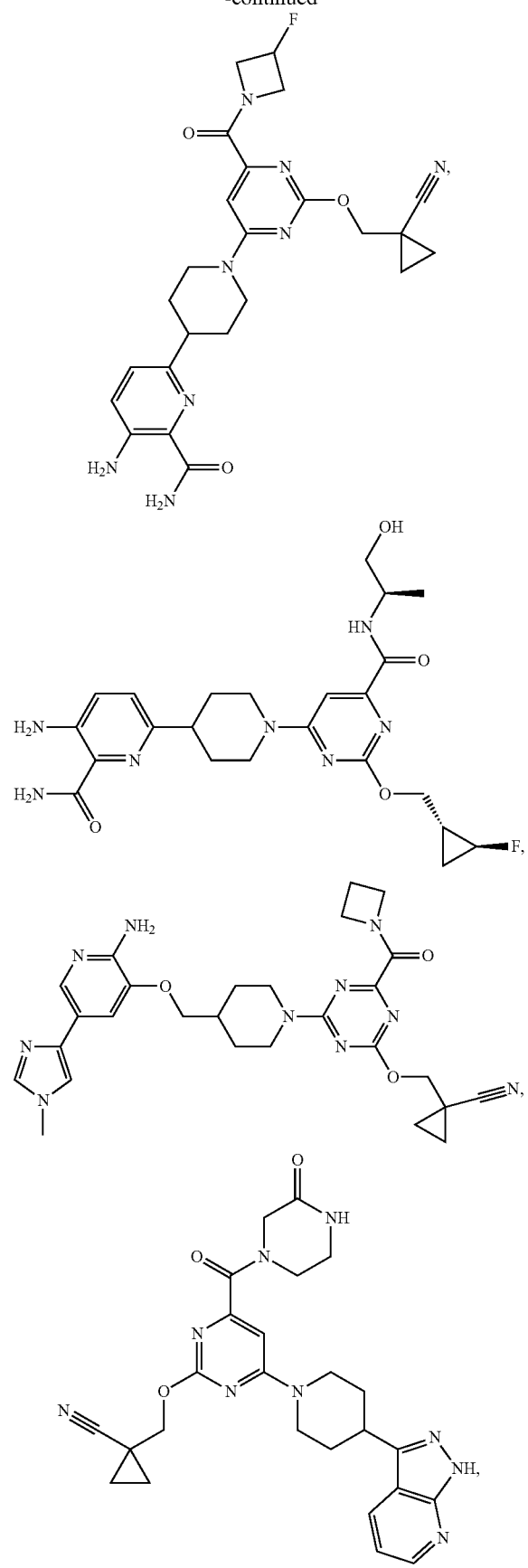
622
-continued
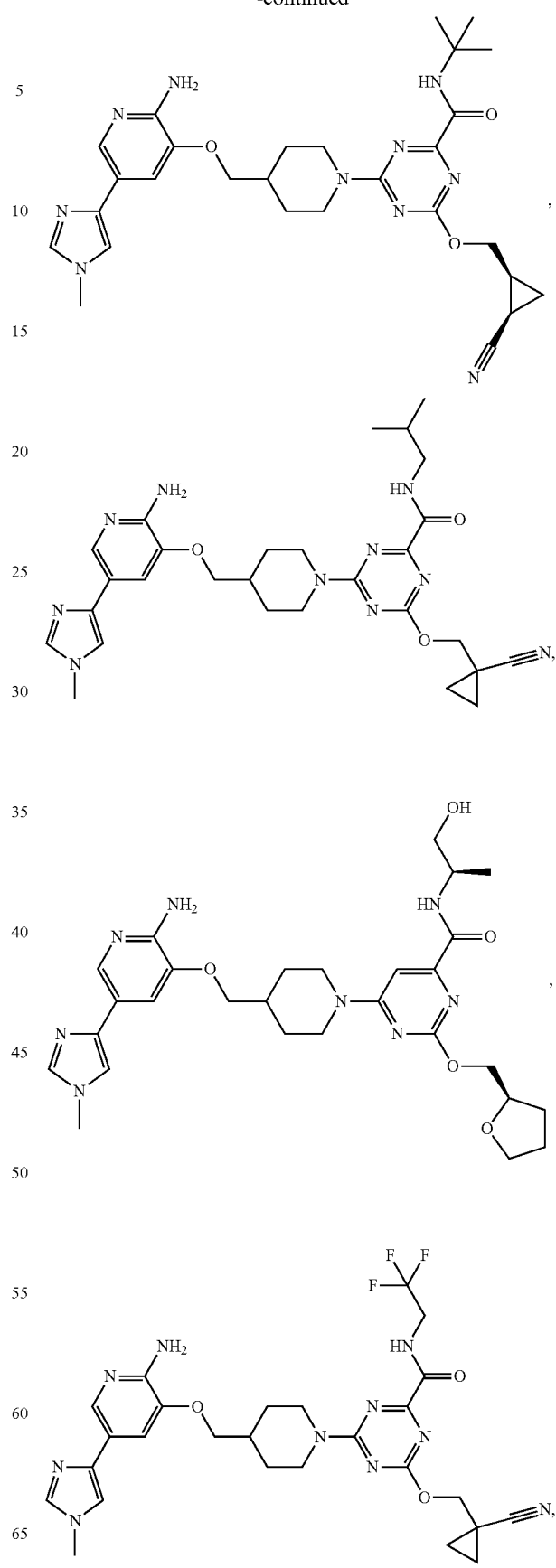

623
-continued
624
-continued
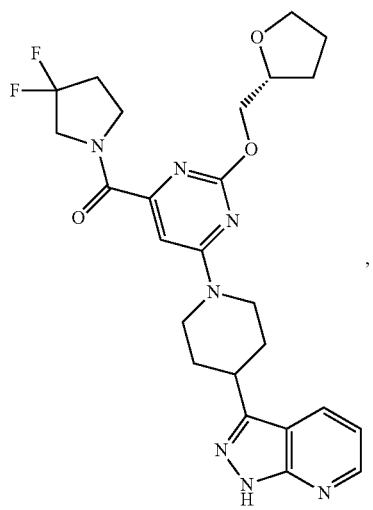
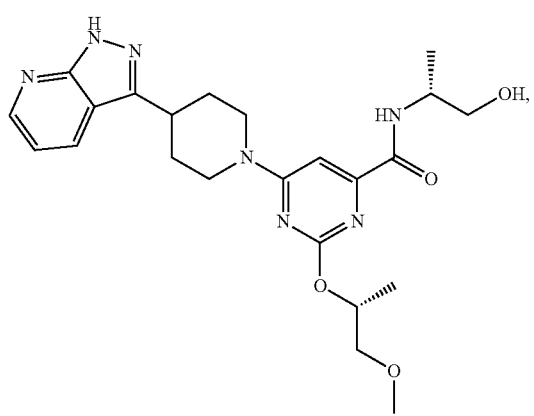
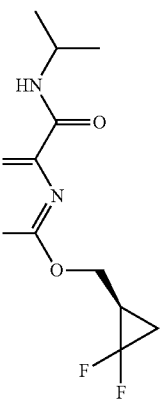
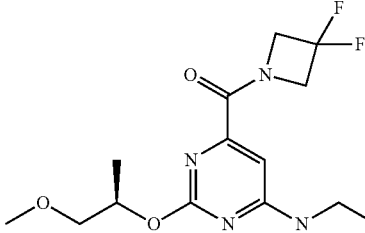
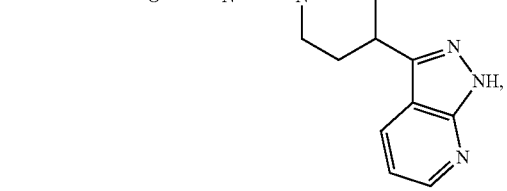
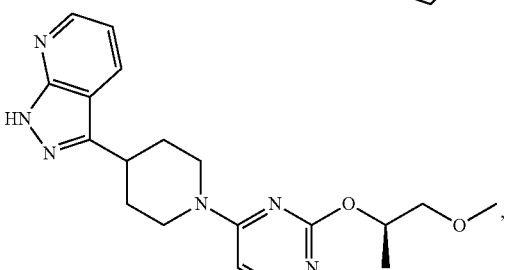
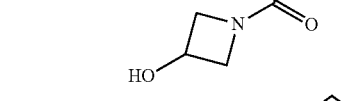
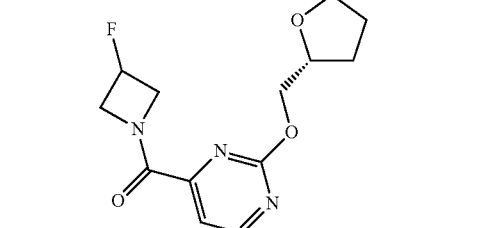
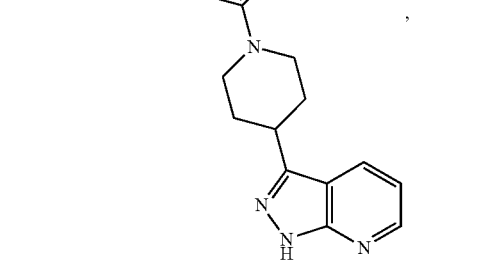

625
-continued
626
-continued
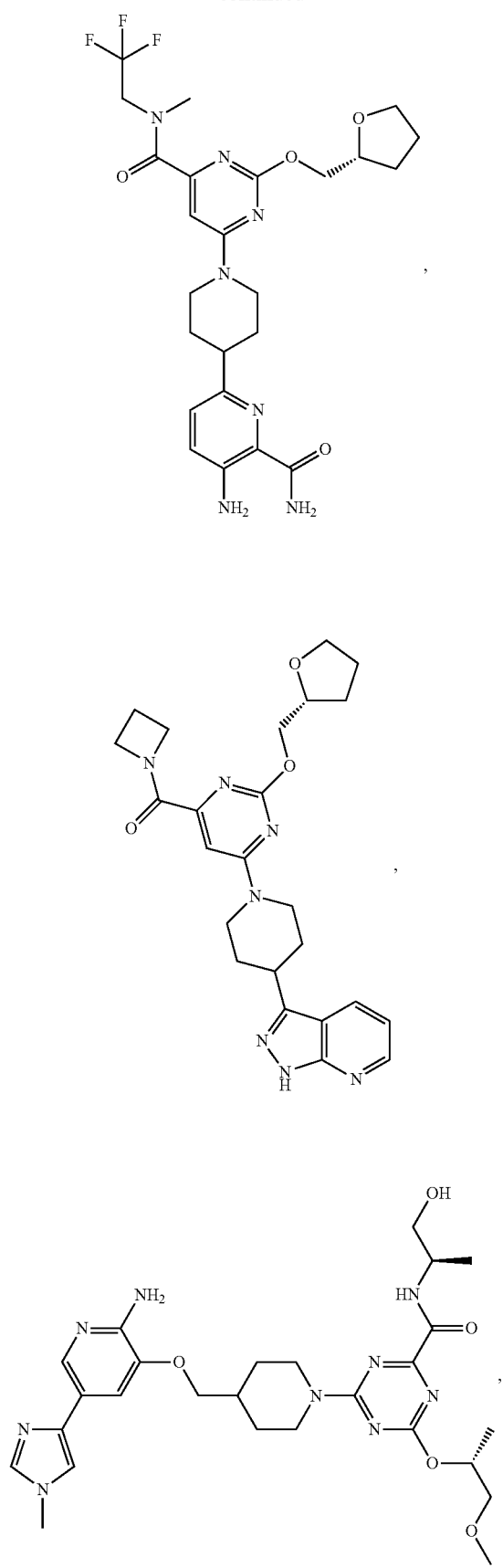
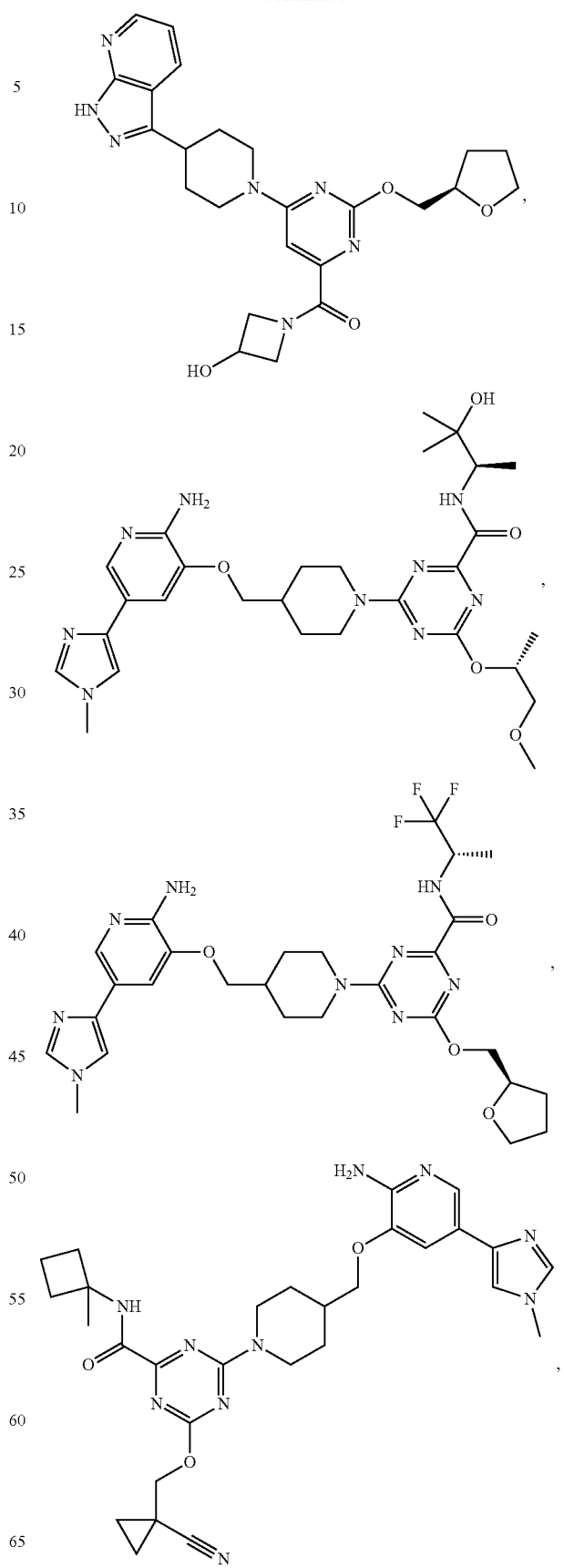

627
-continued
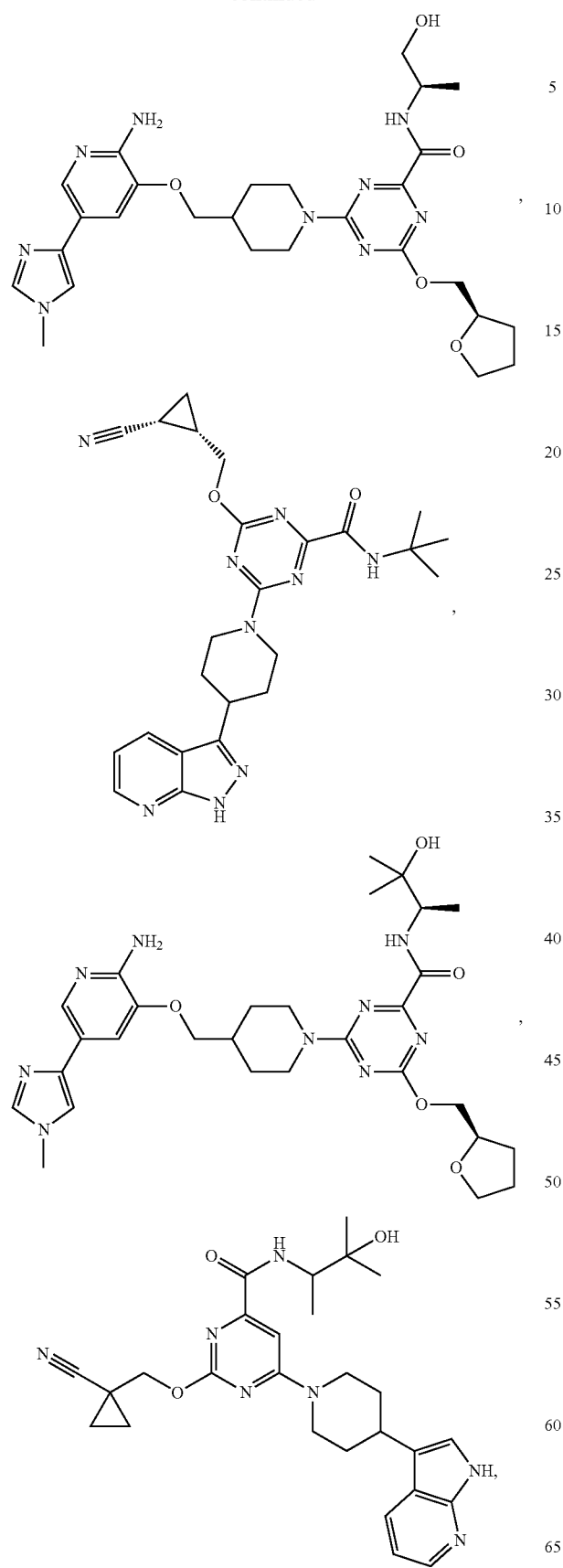
628
-continued
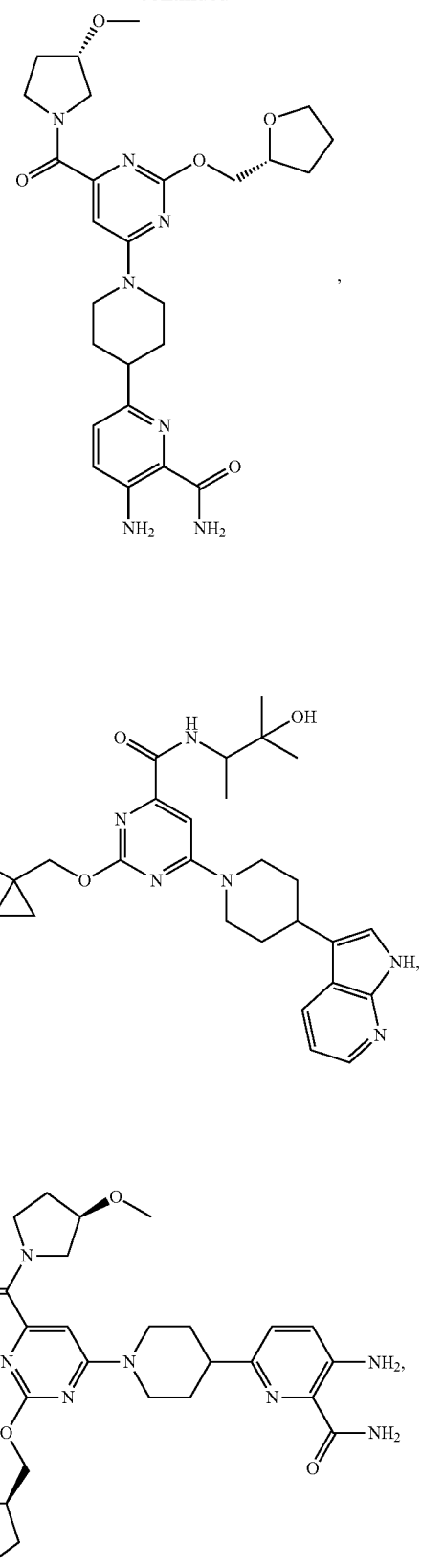

629
-continued
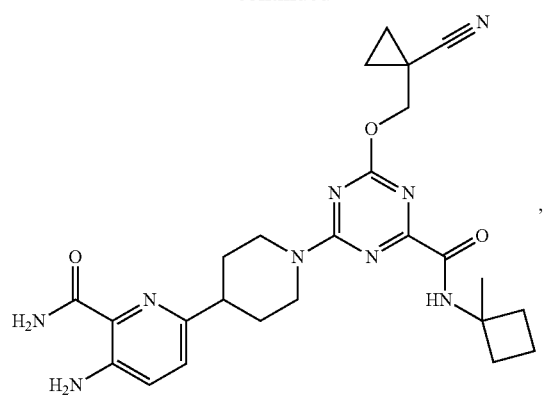
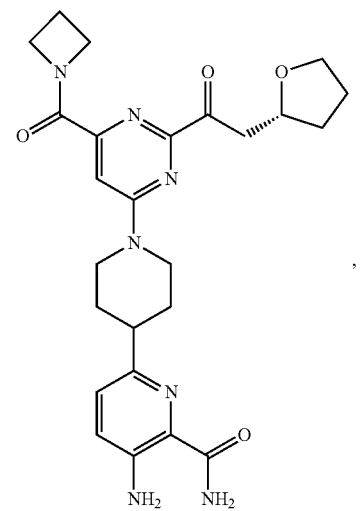
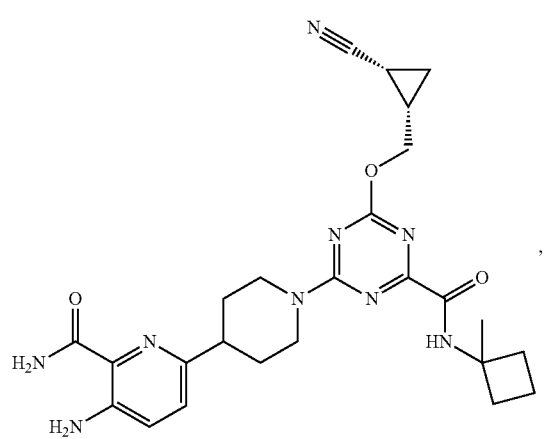
630
-continued
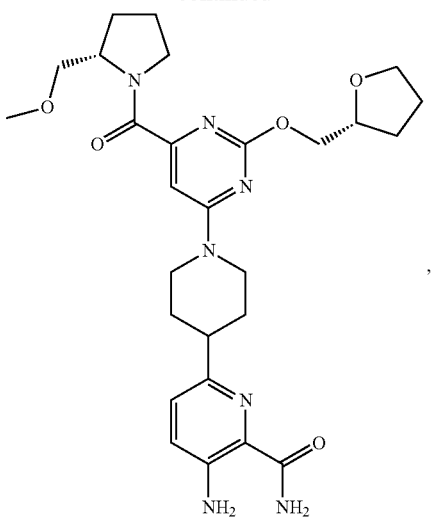
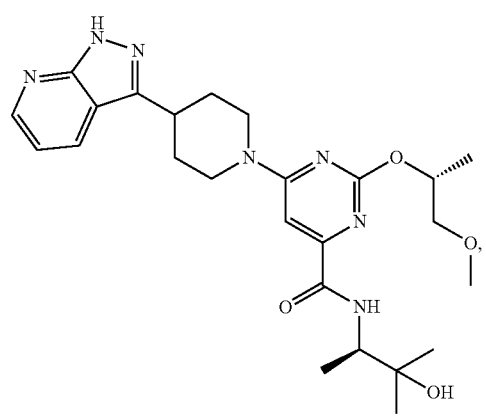
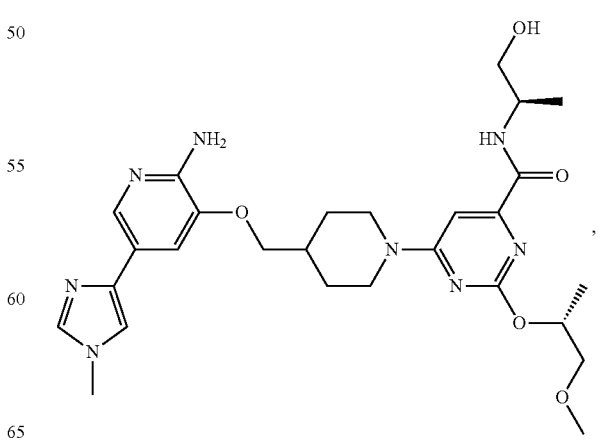

631
-continued
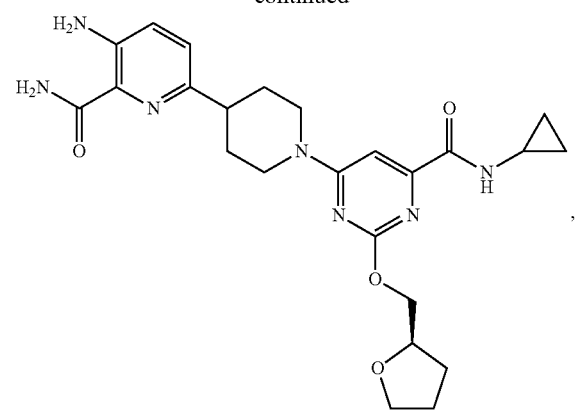
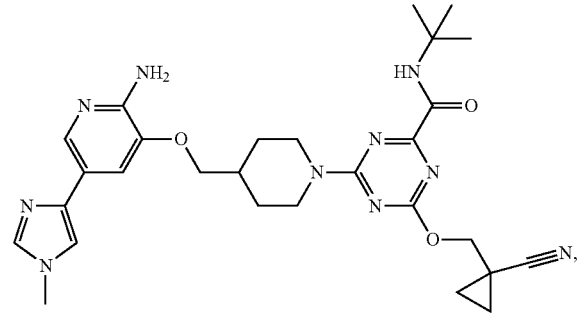
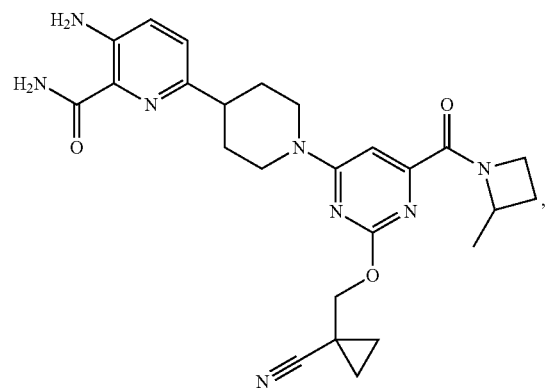
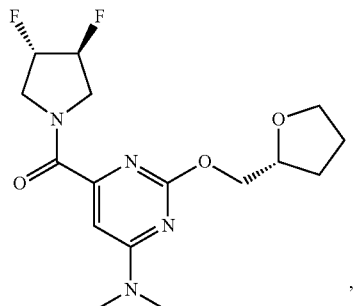
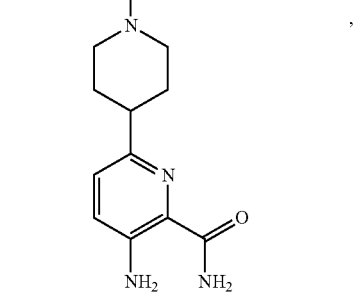
632
-continued
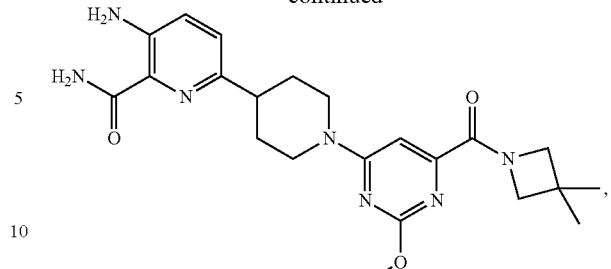
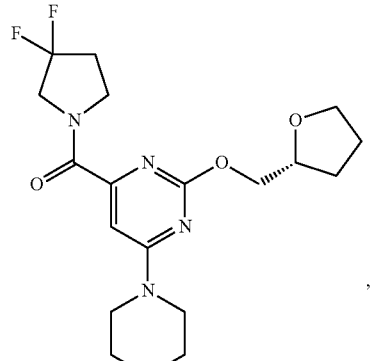
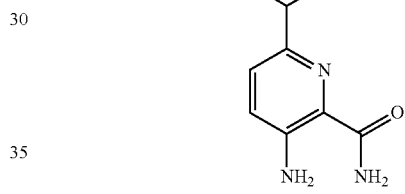
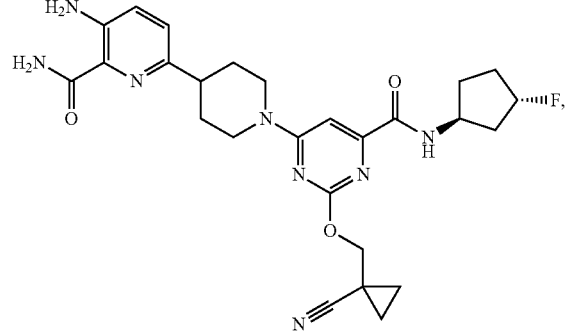
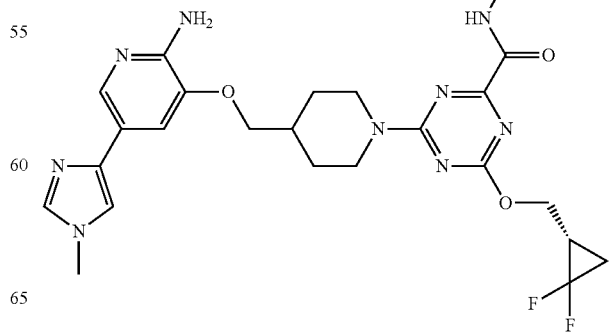

633
-continued
634
-continued
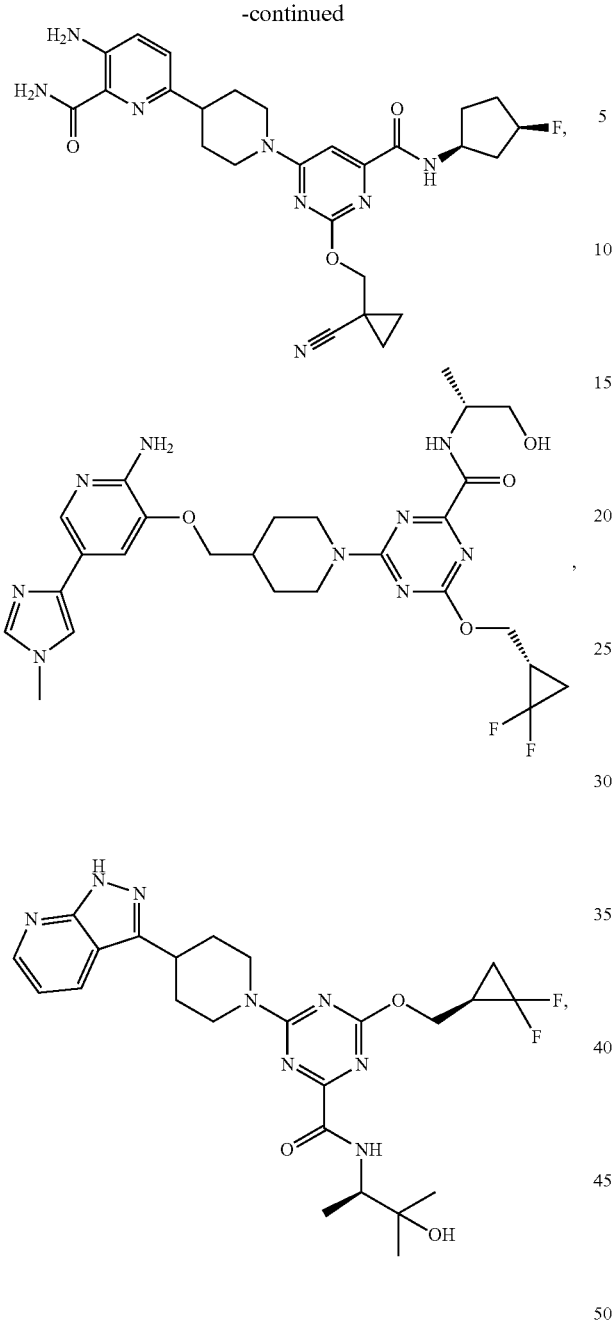
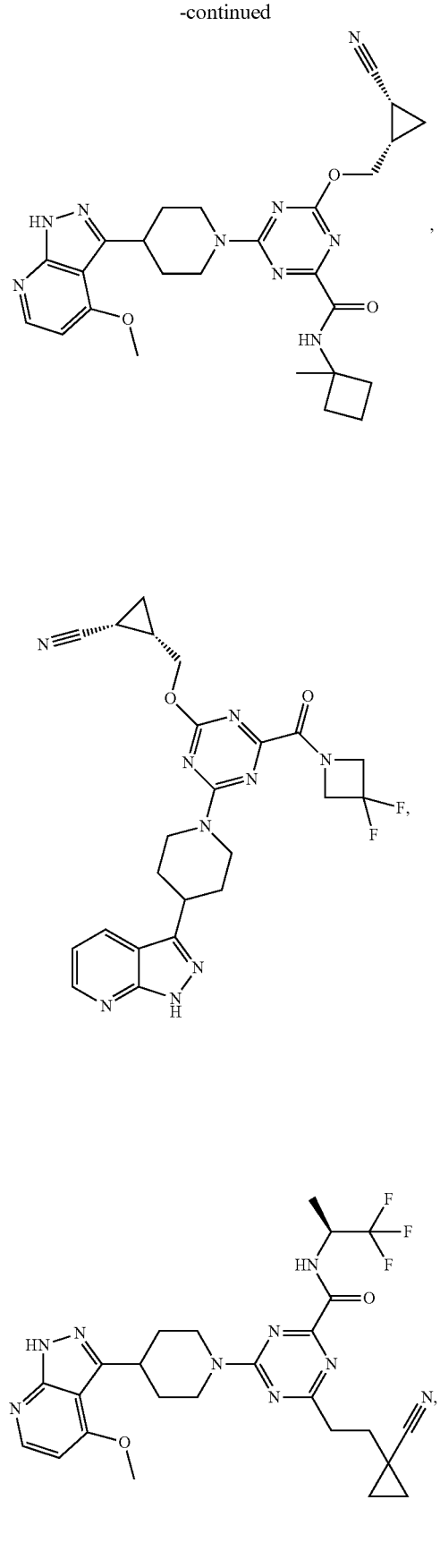

635
-continued
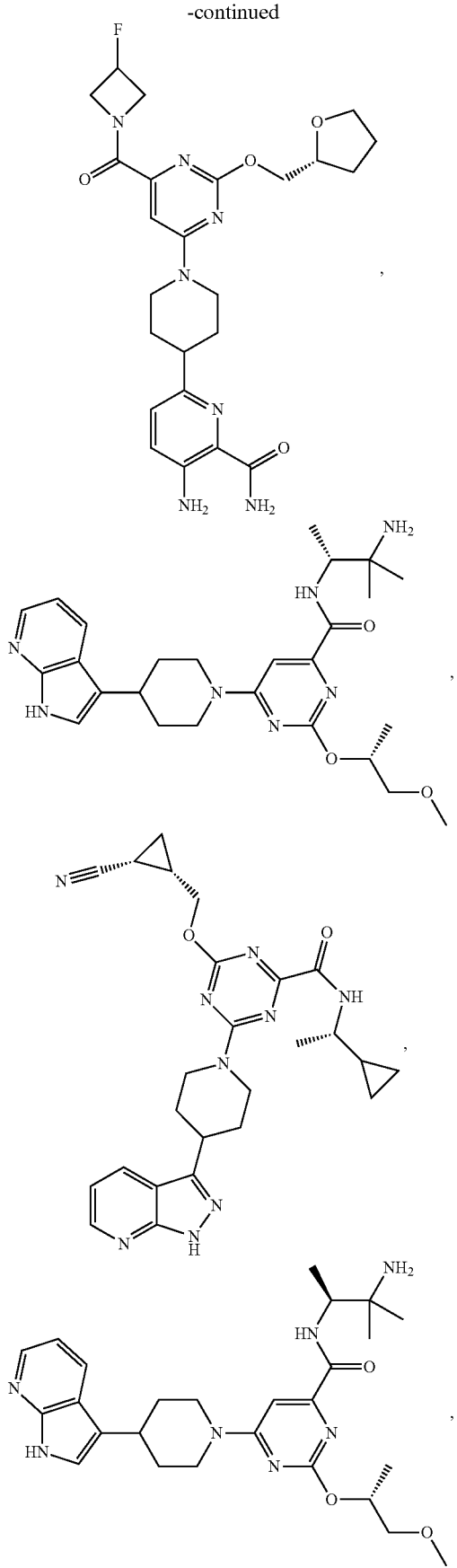
636
-continued
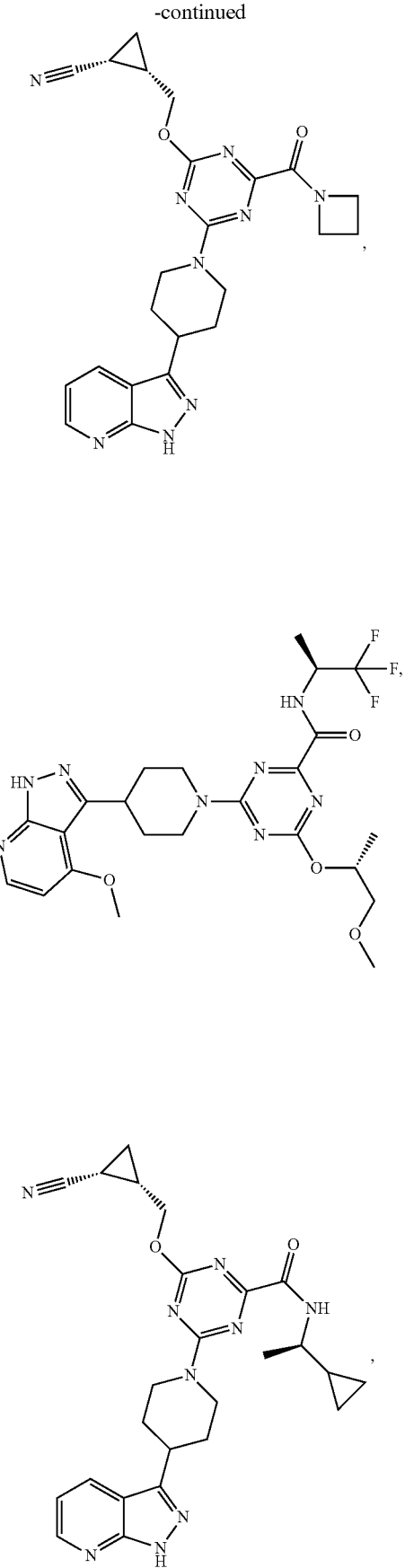

637
-continued
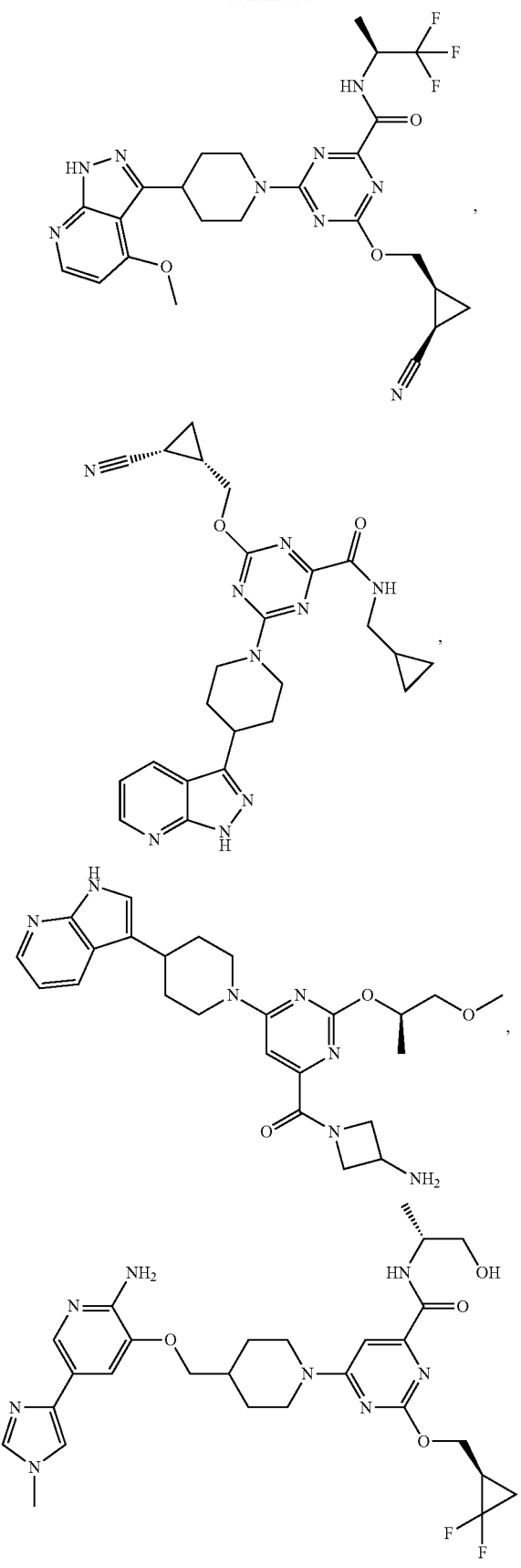
638
-continued
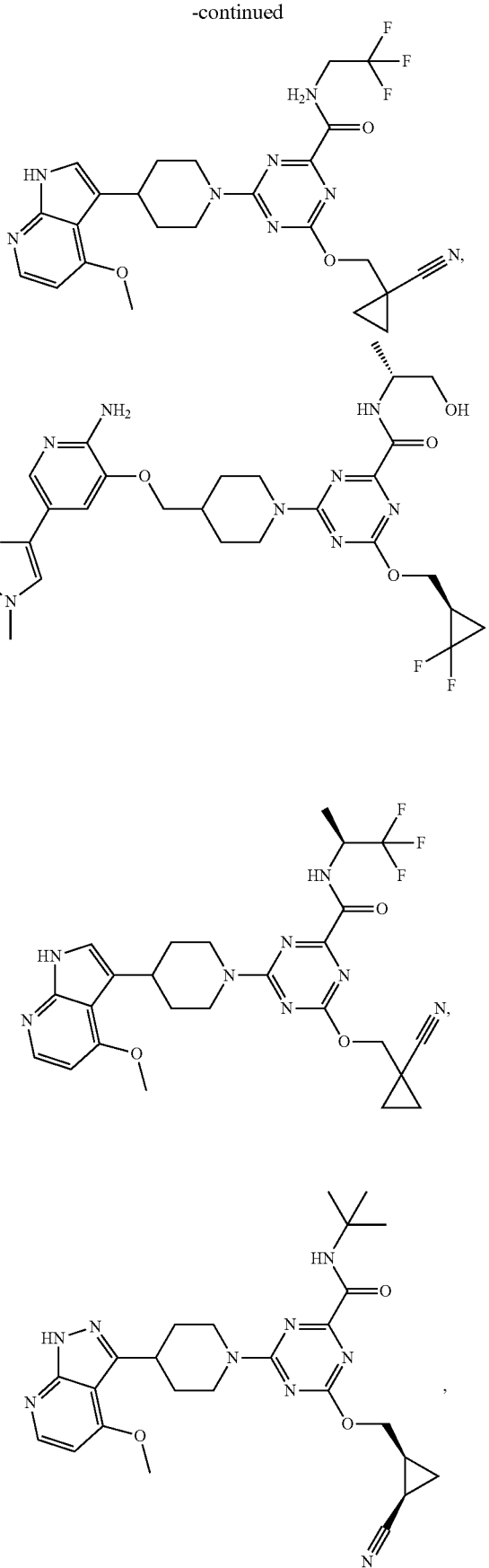

639
-continued
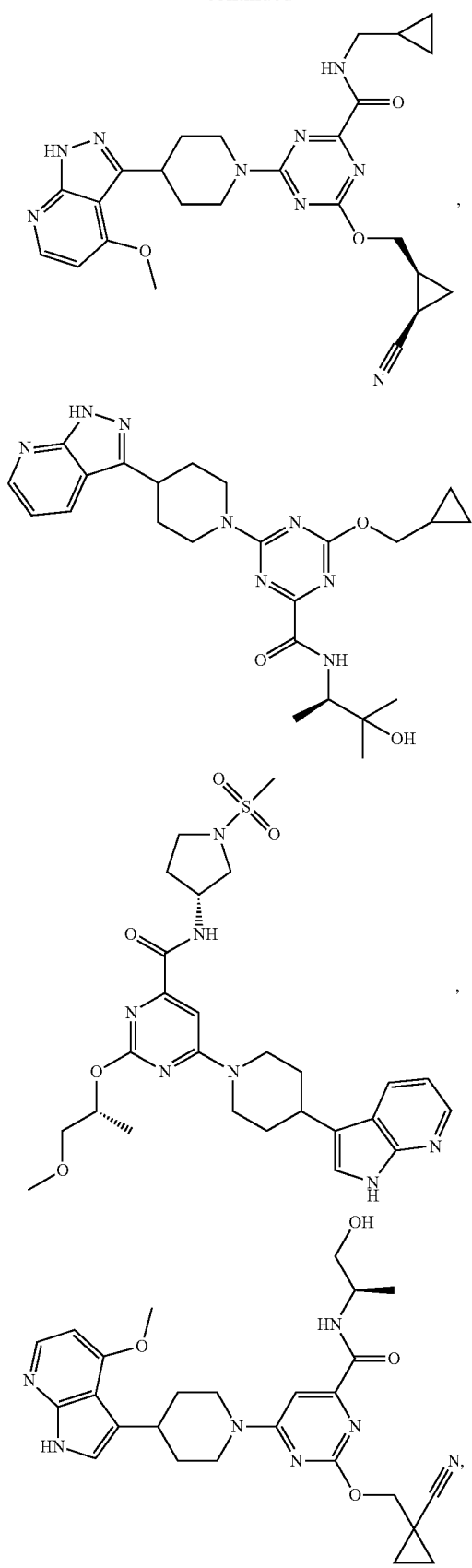
640
-continued
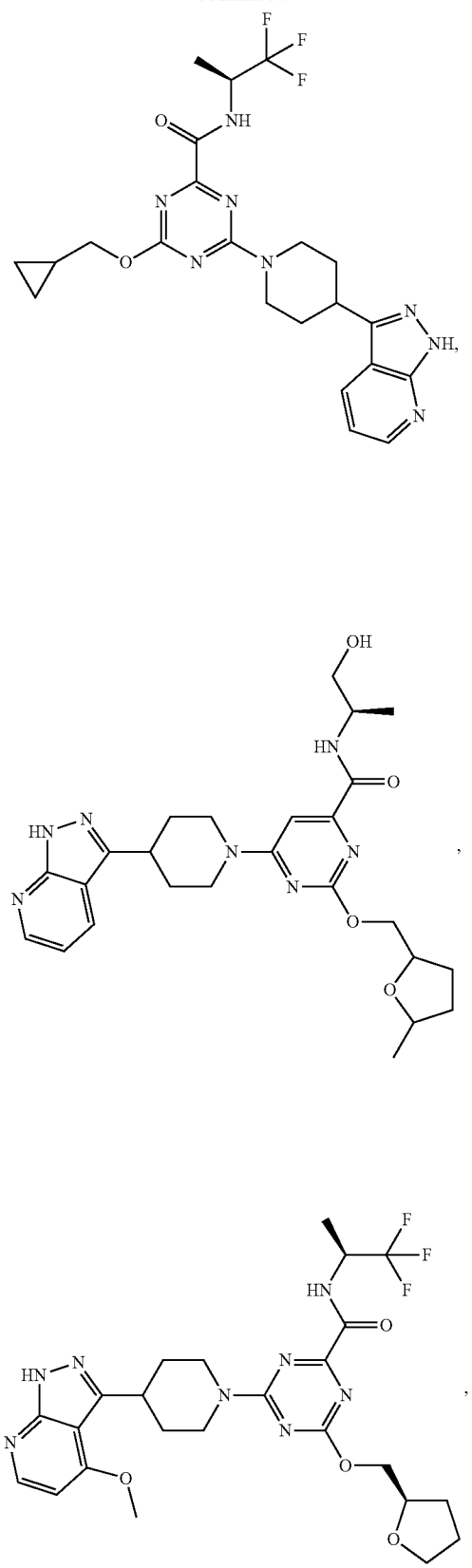

641
-continued
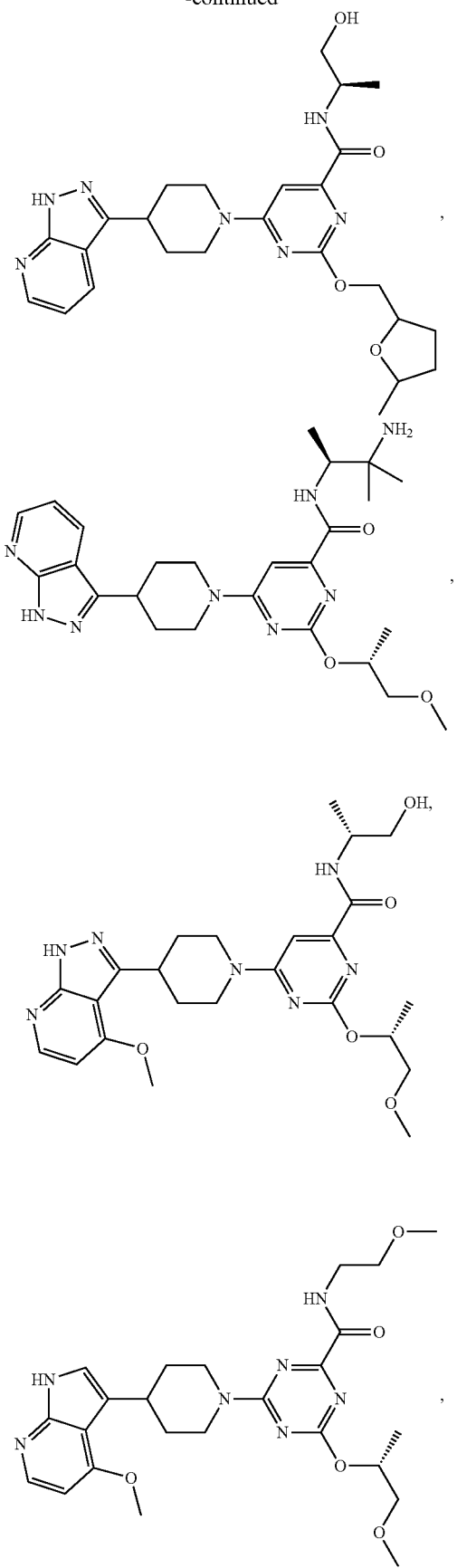
642
-continued
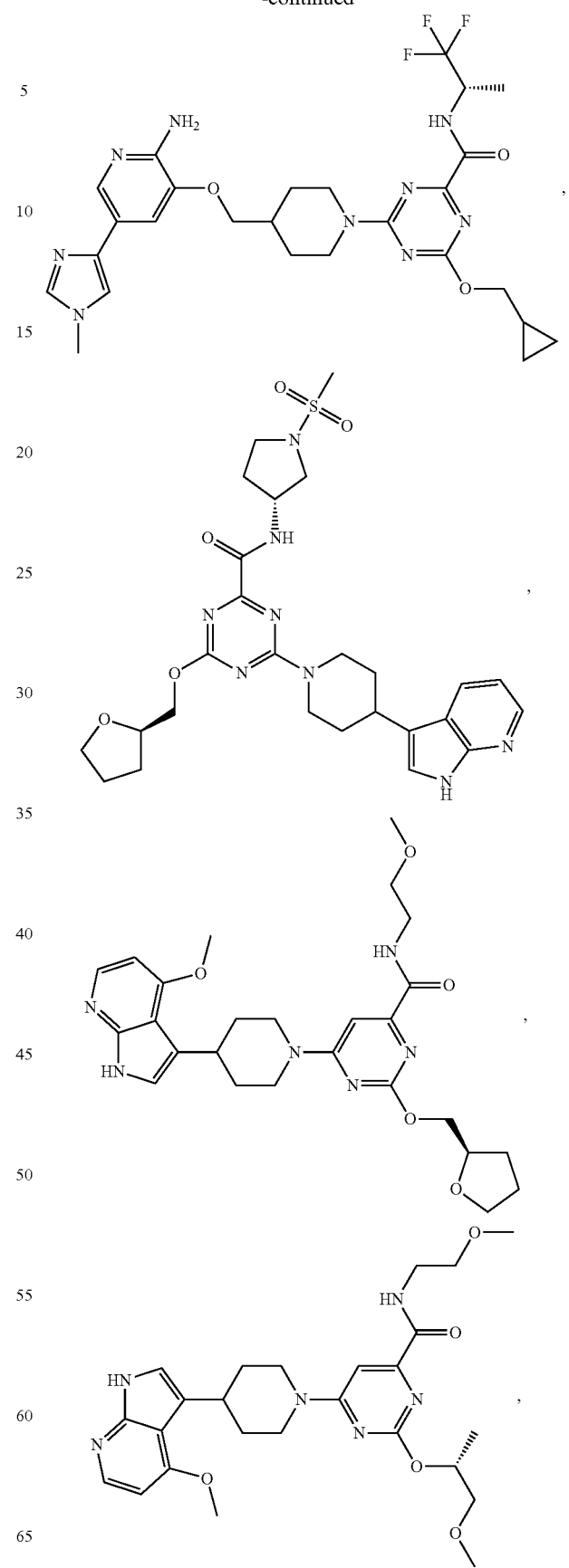

643
-continued
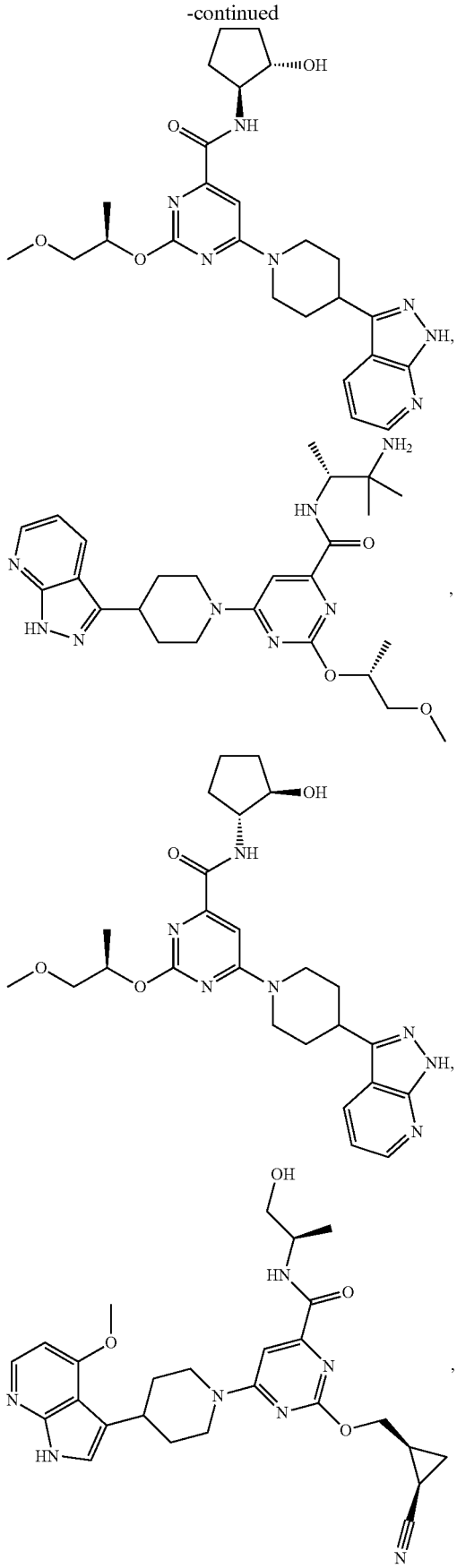
644
-continued
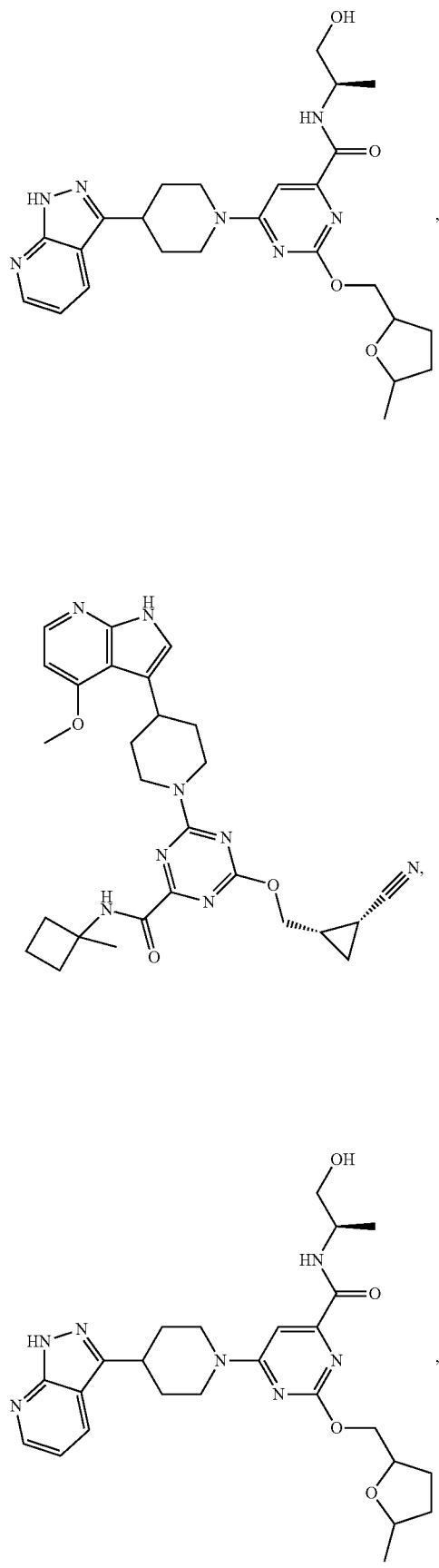

645
-continued
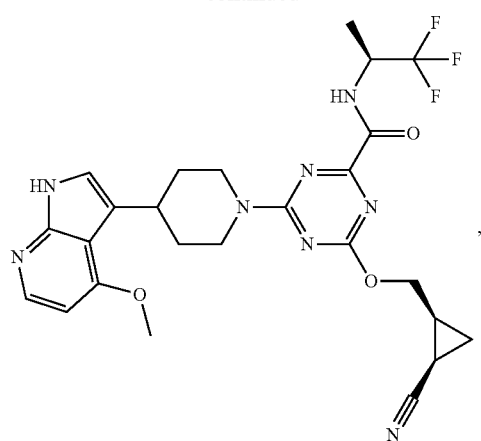
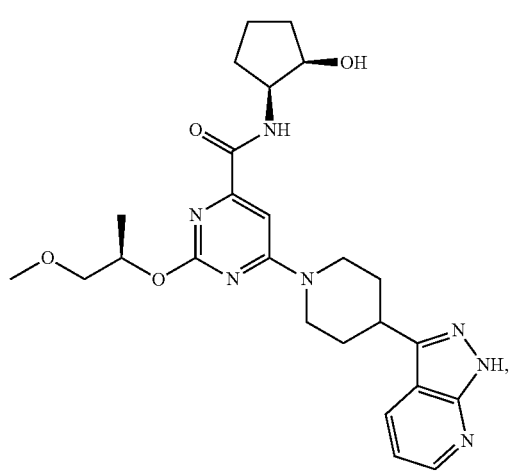
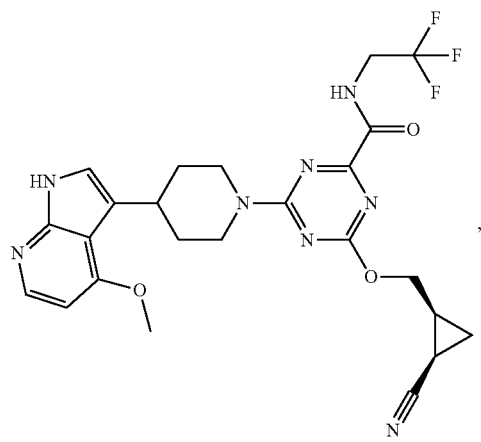
646
-continued
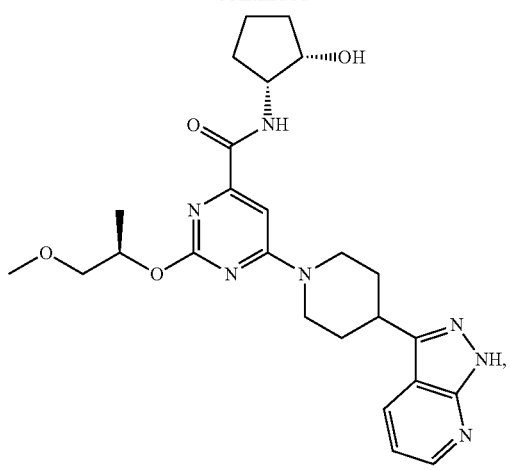
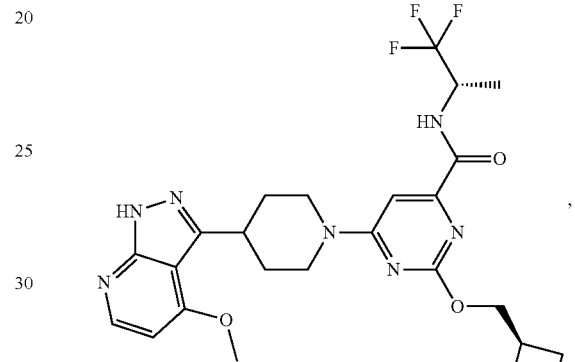
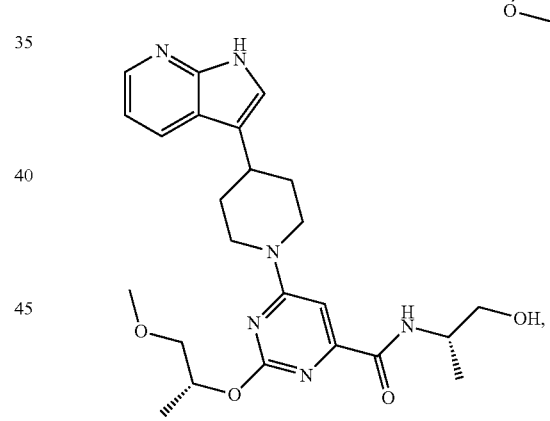
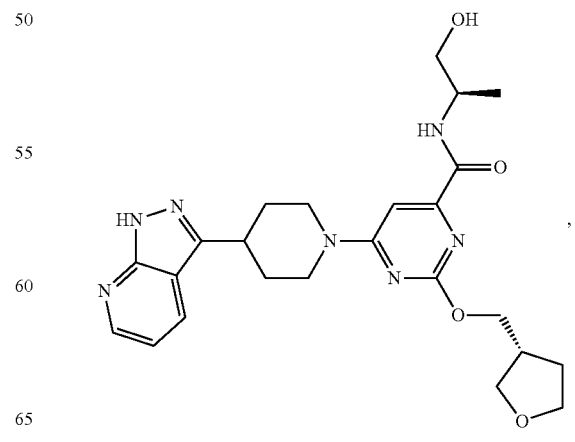

647
-continued
648
-continued
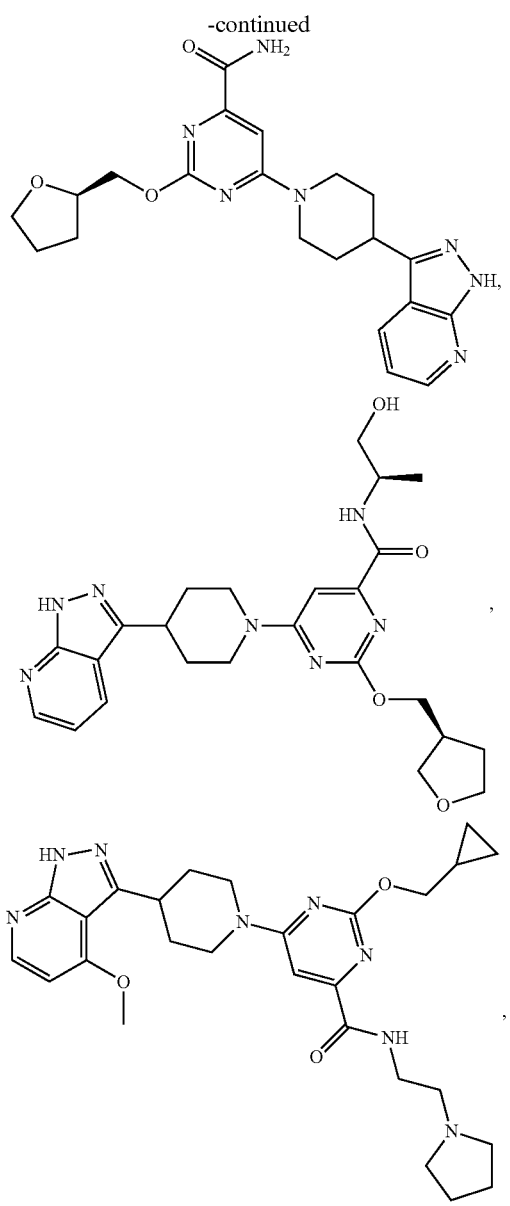
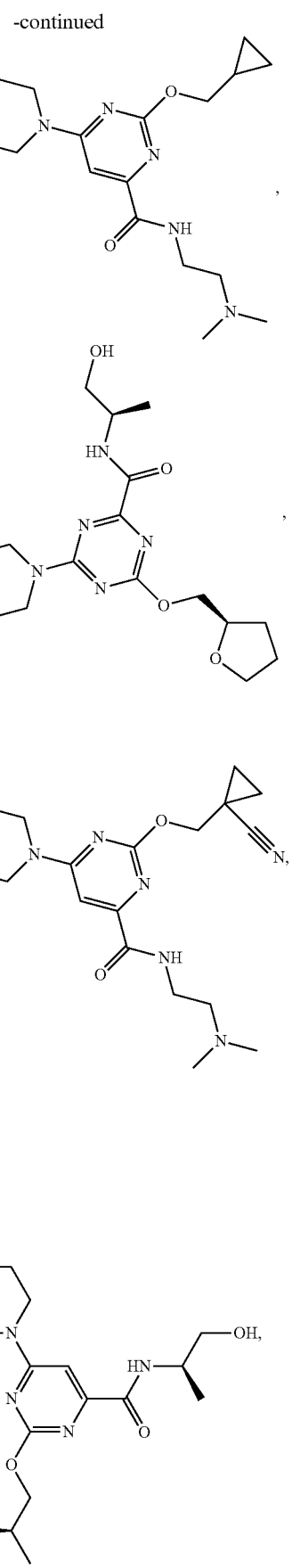

649
-continued
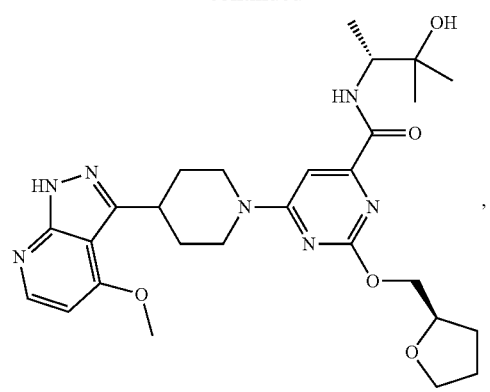
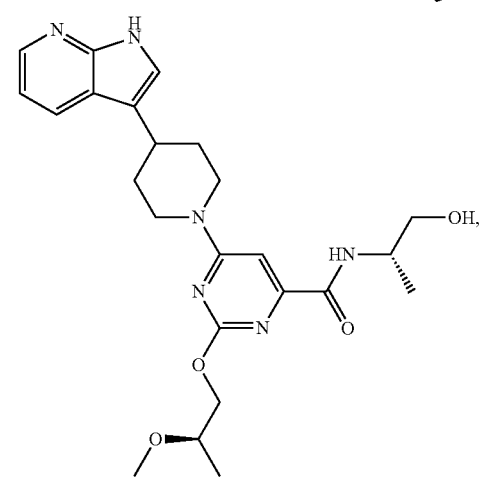
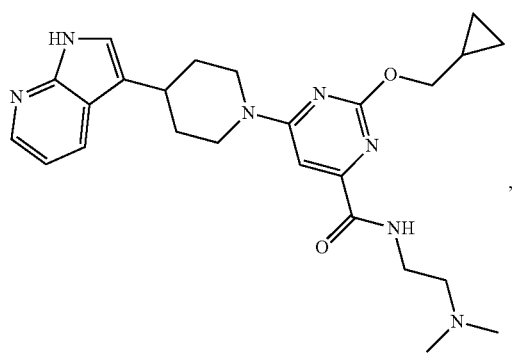
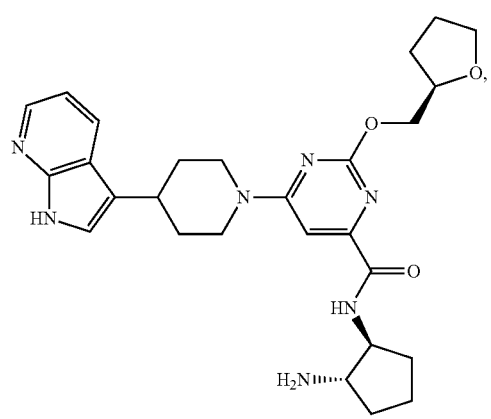
650
-continued
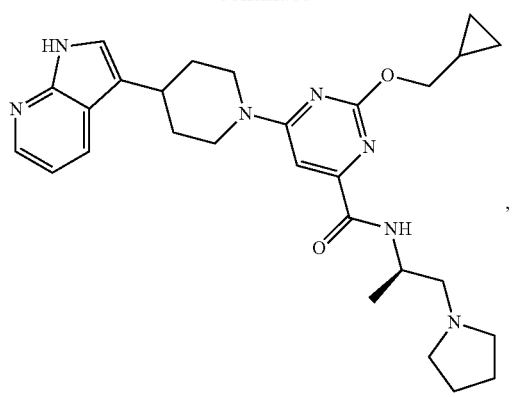
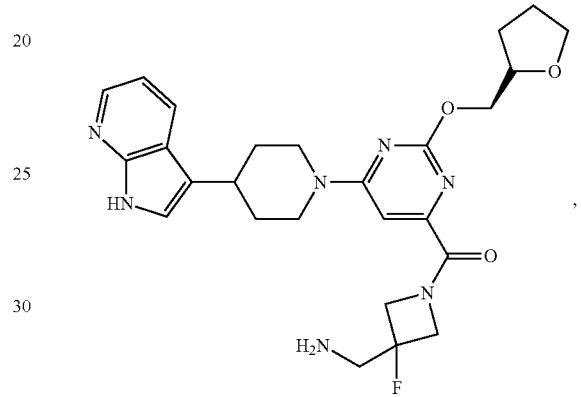
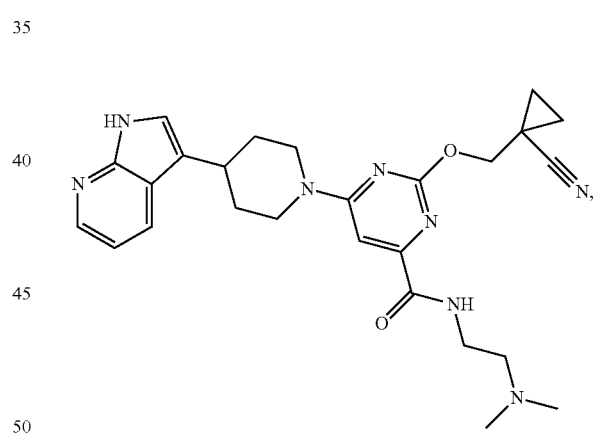
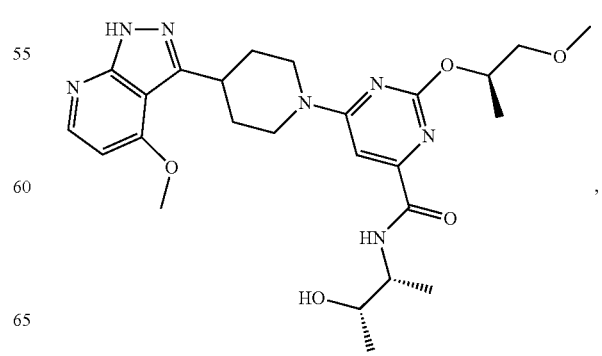

-continued
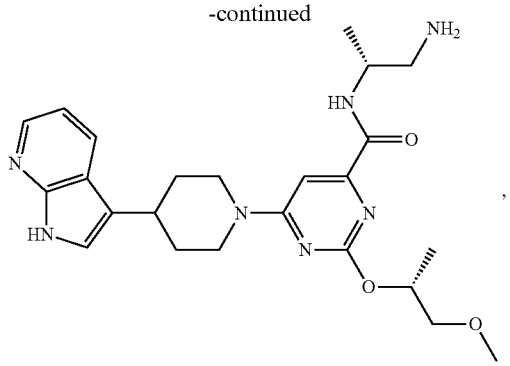
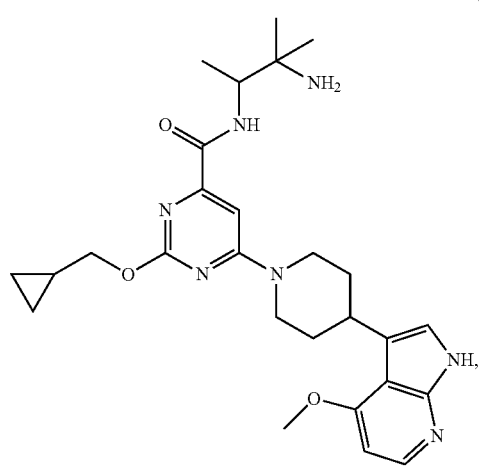
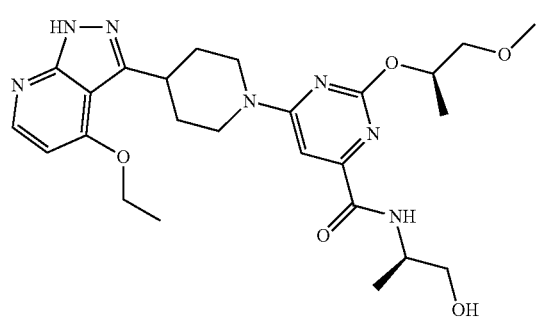
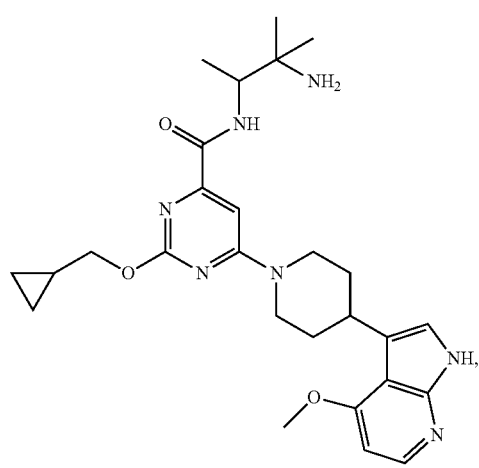
-continued
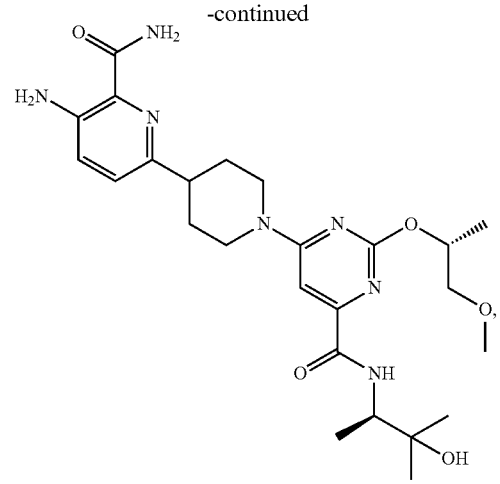
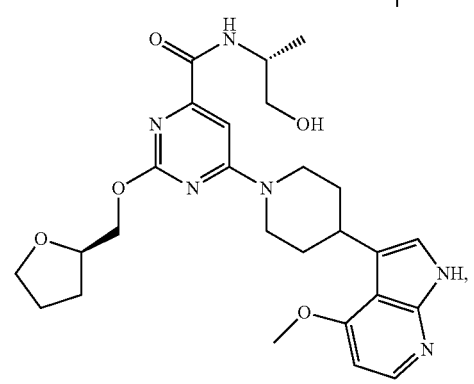
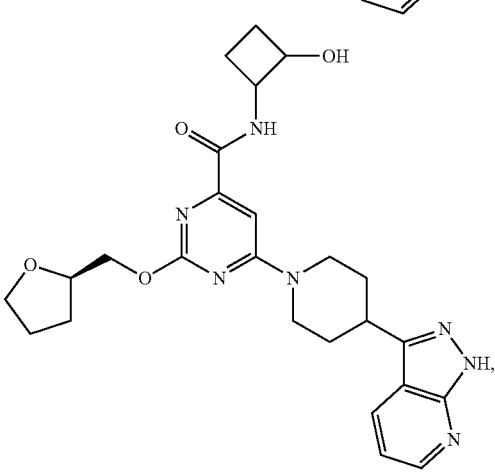
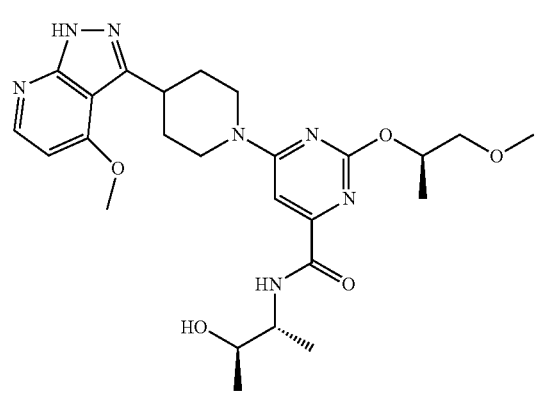

653
-continued
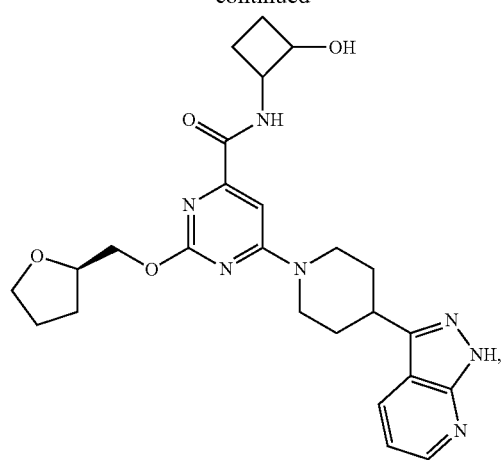
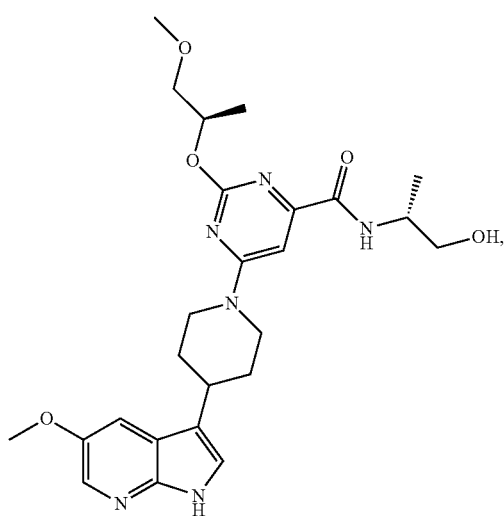
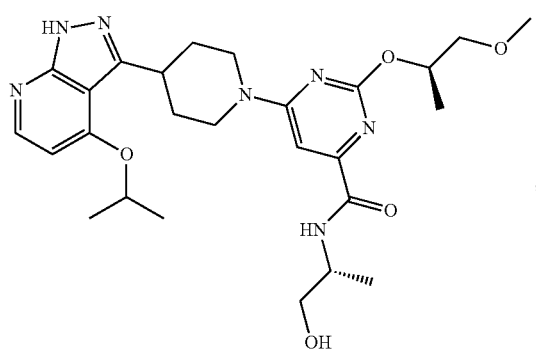
654
-continued
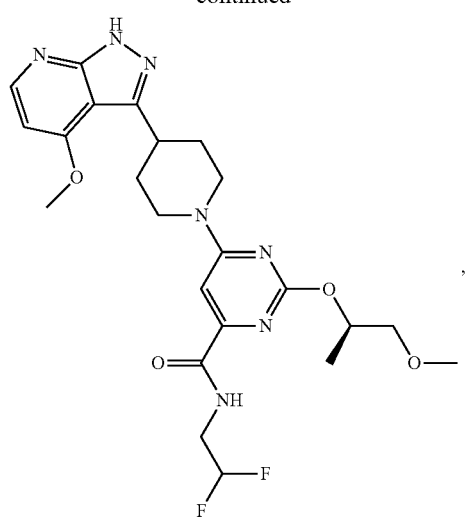
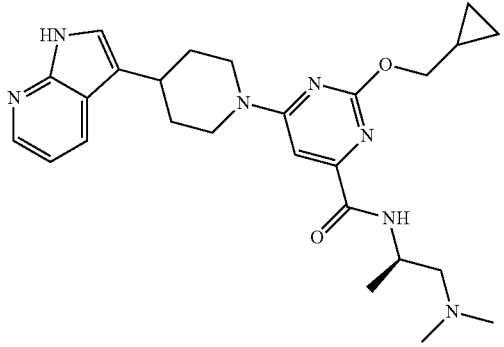
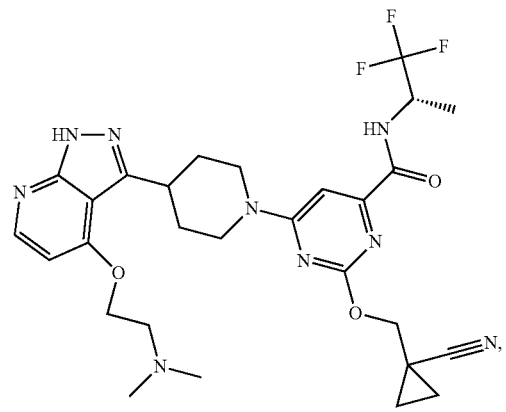

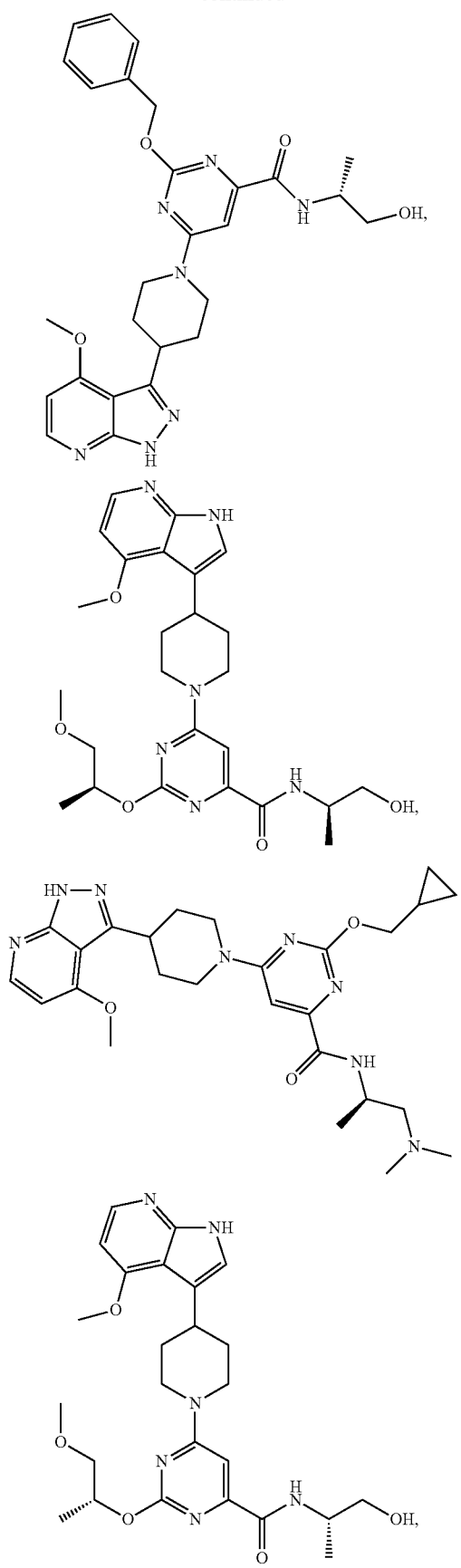
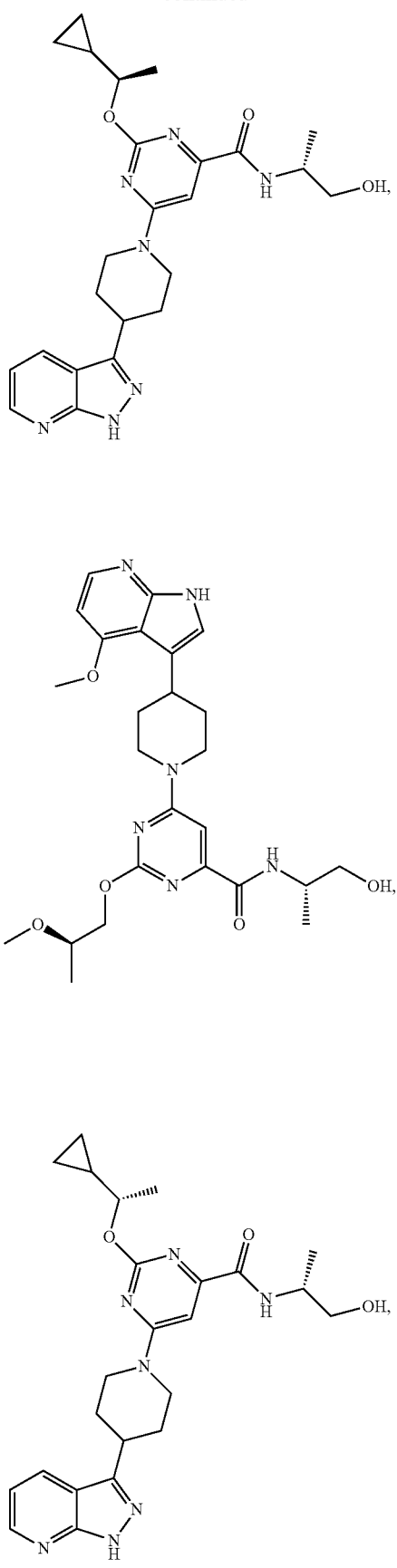

657
-continued
658
-continued
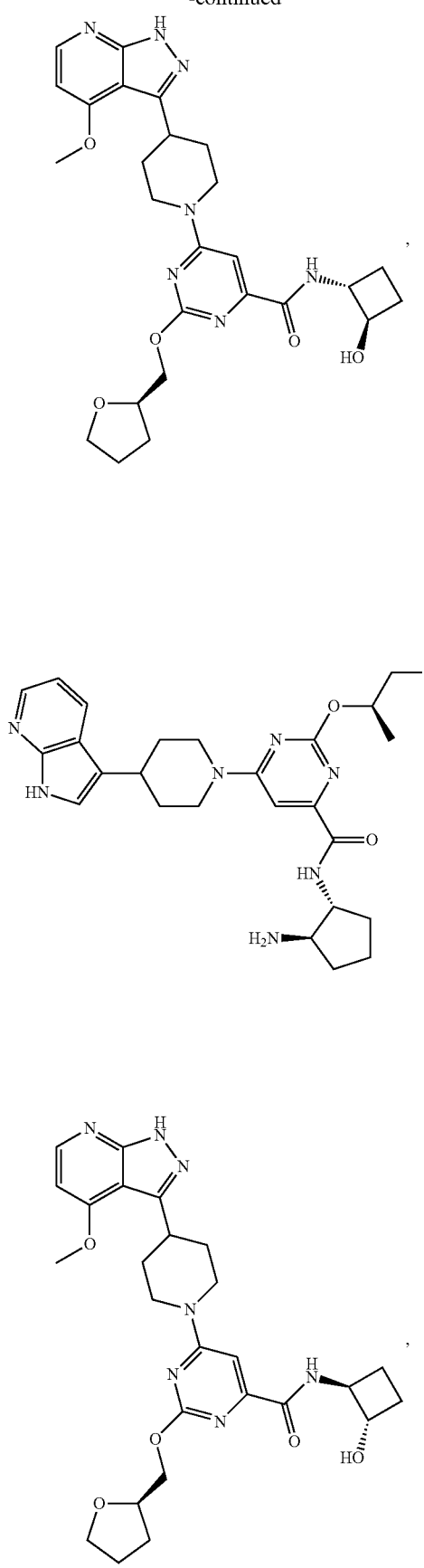
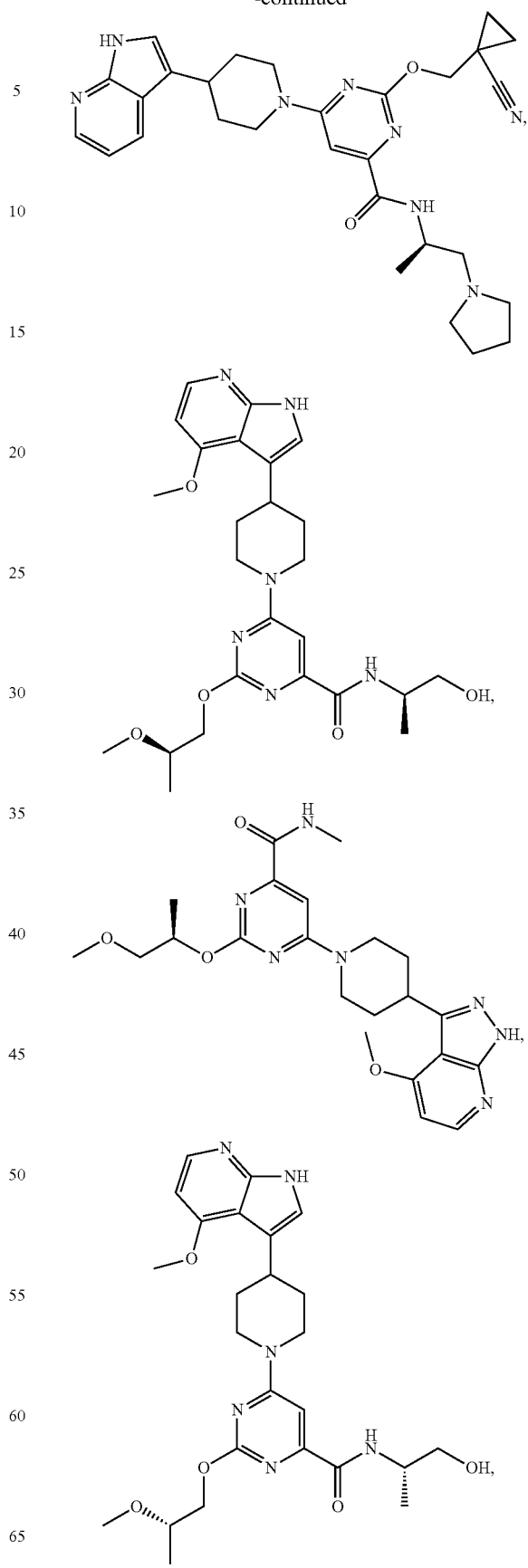

659
-continued
660
-continued
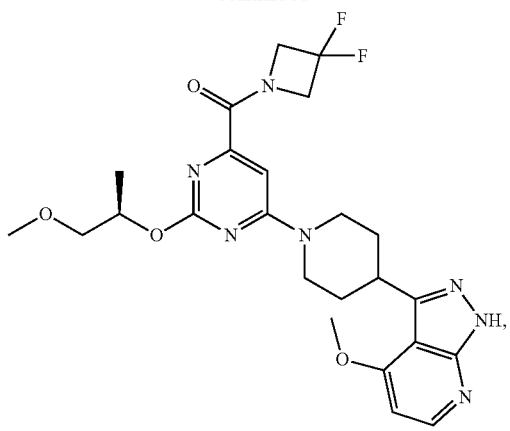
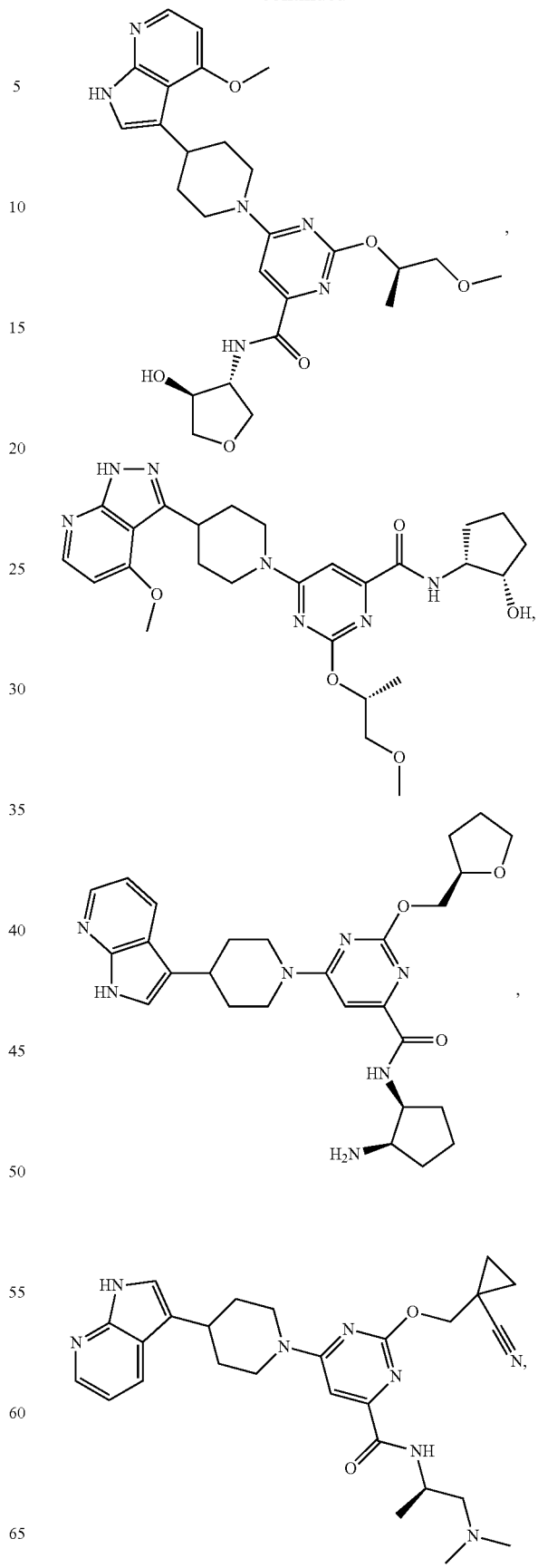

661
-continued
662
-continued
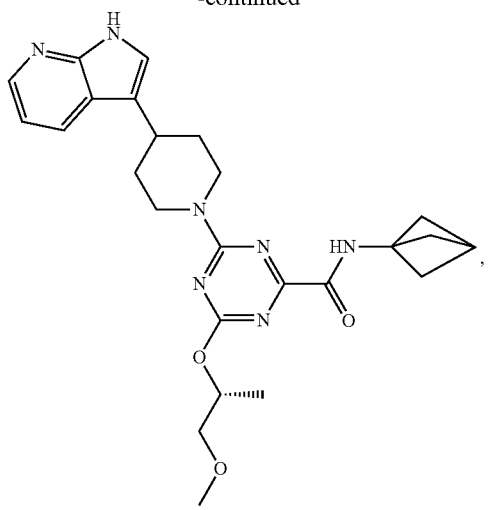
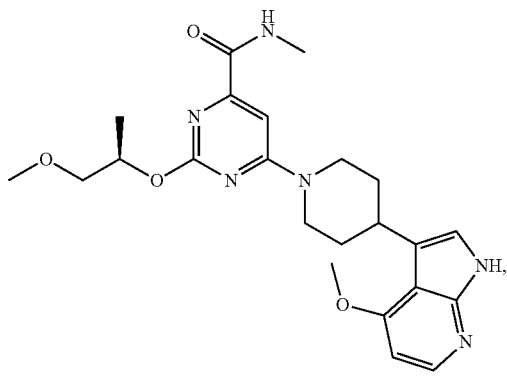
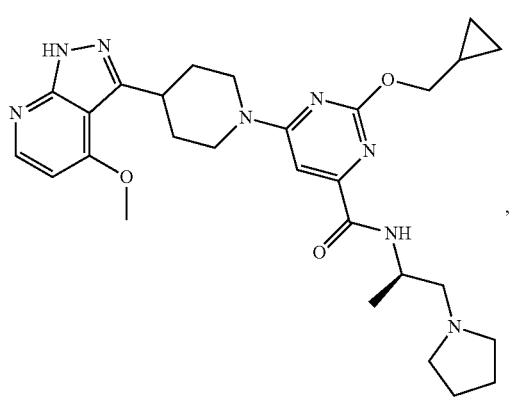
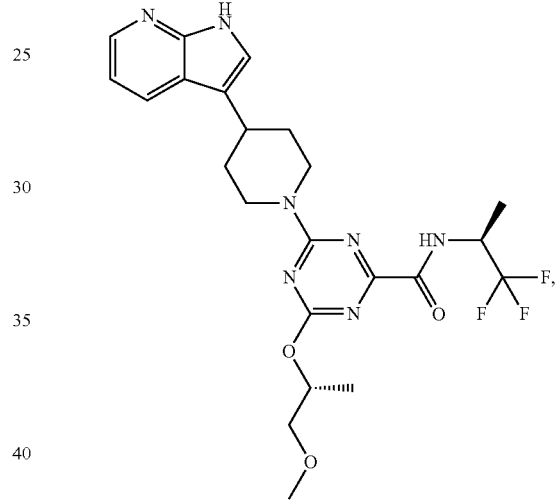
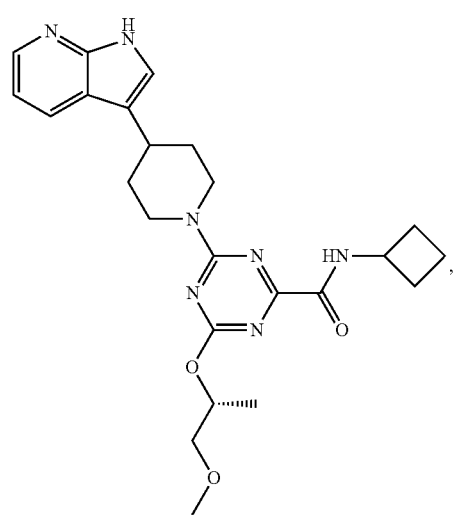
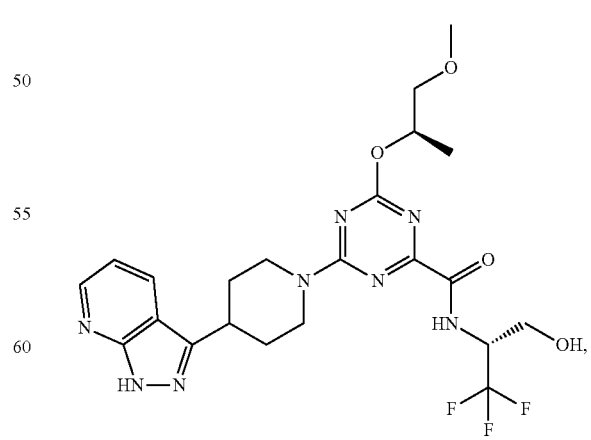

663
-continued
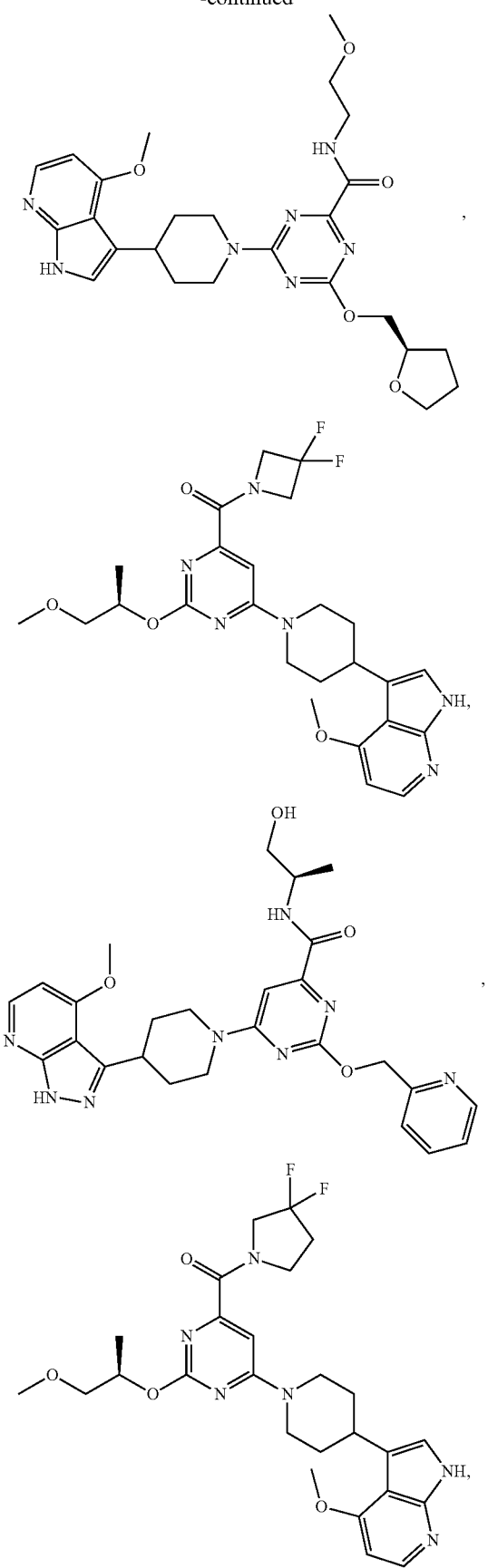
664
-continued
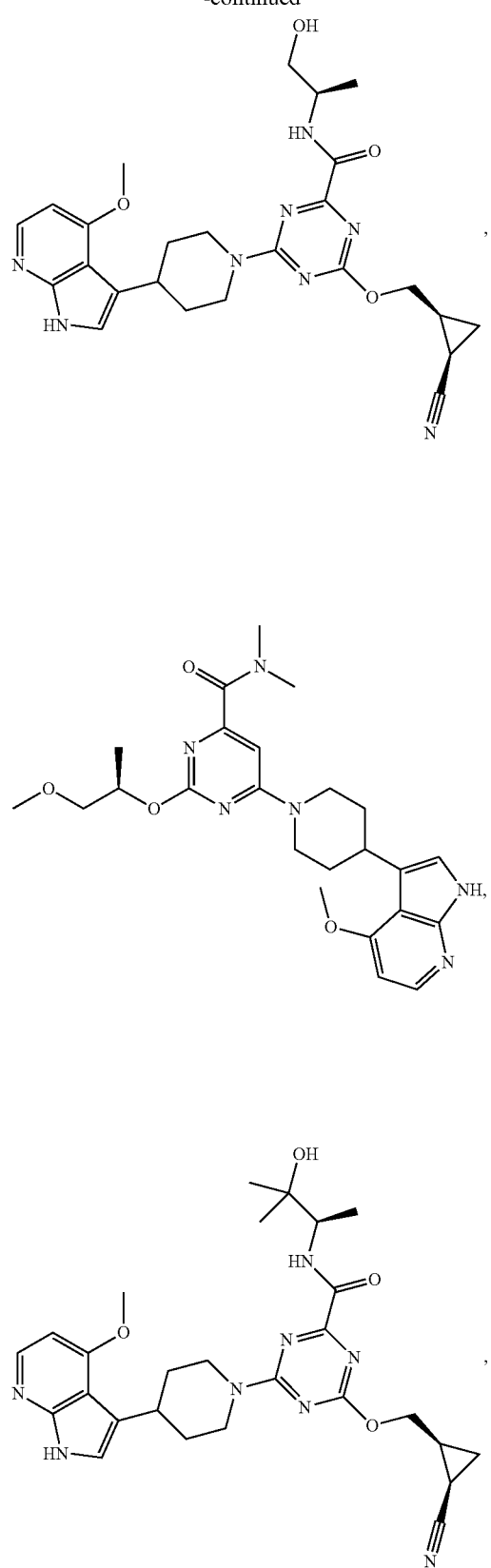

665
-continued
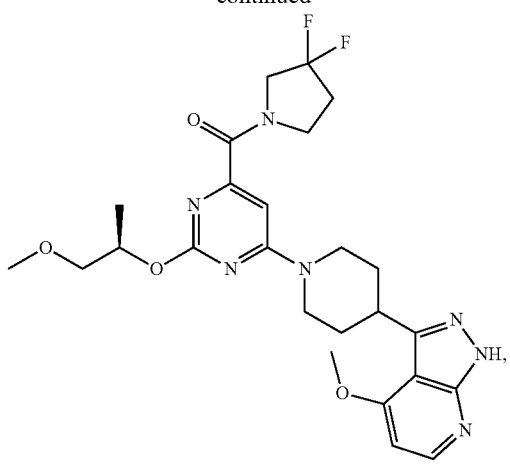
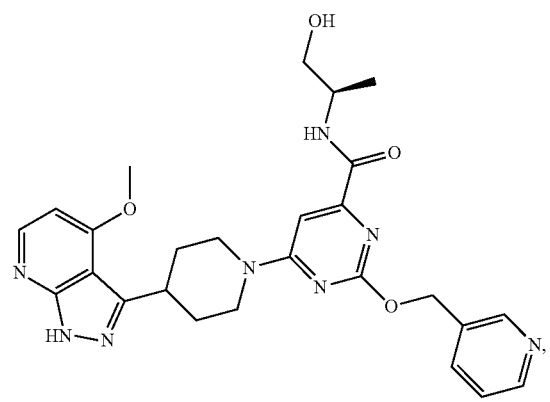
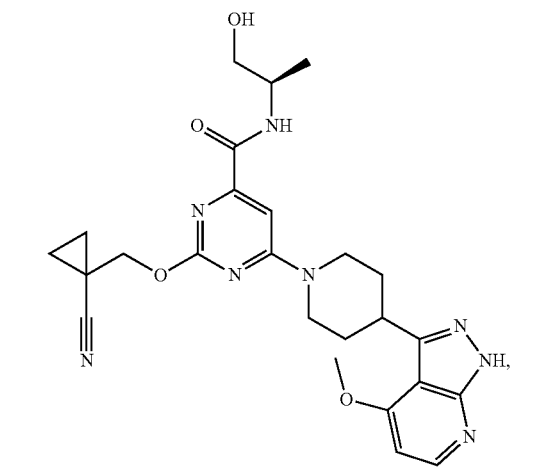
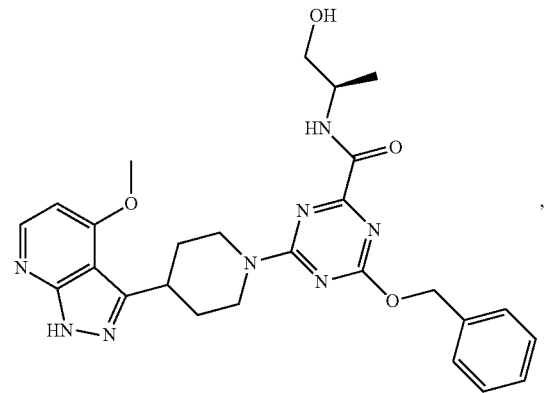
666
-continued
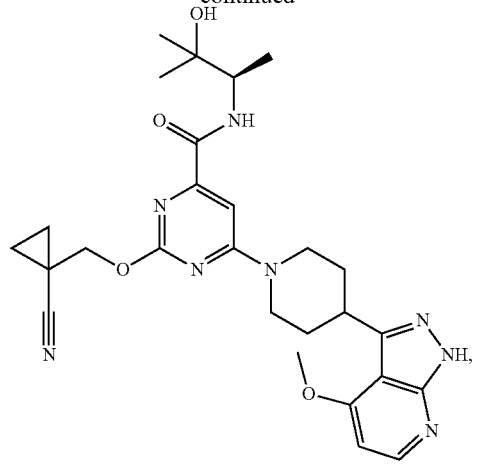
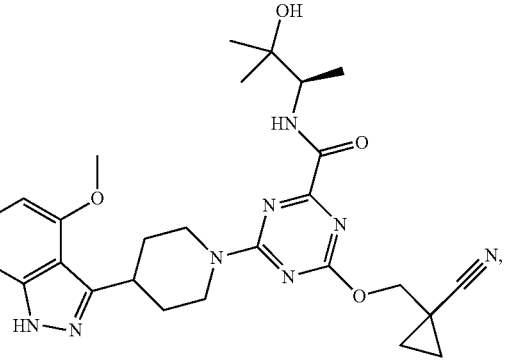
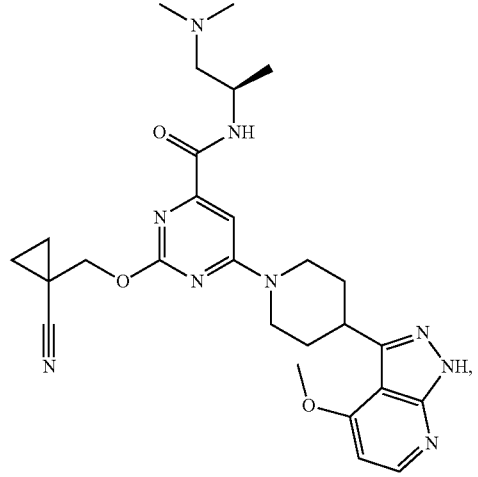
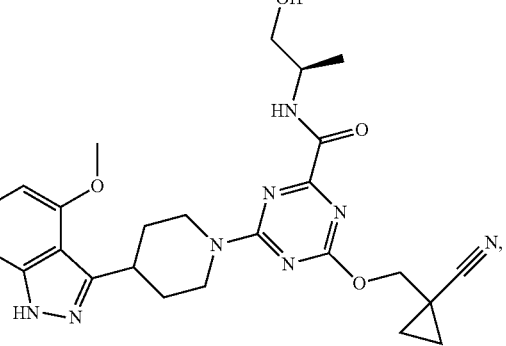

667
-continued
668
-continued
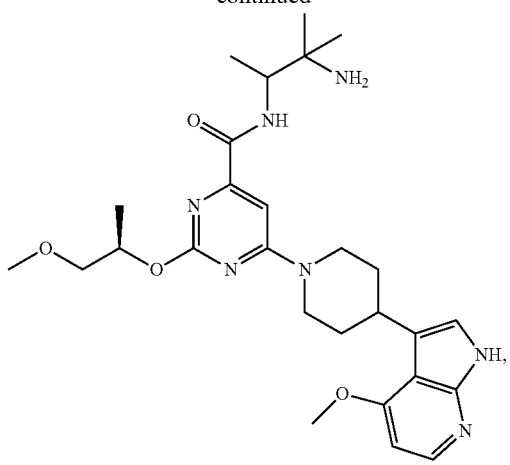
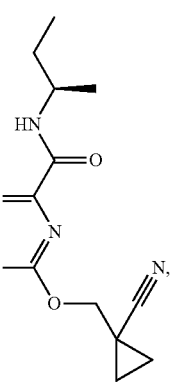
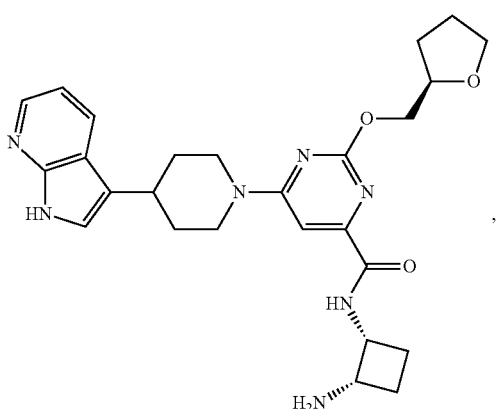
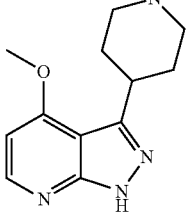

669
-continued
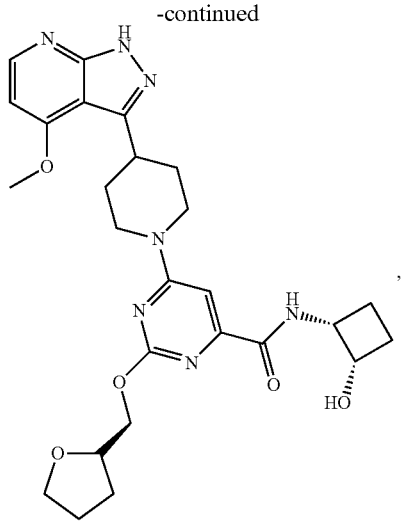
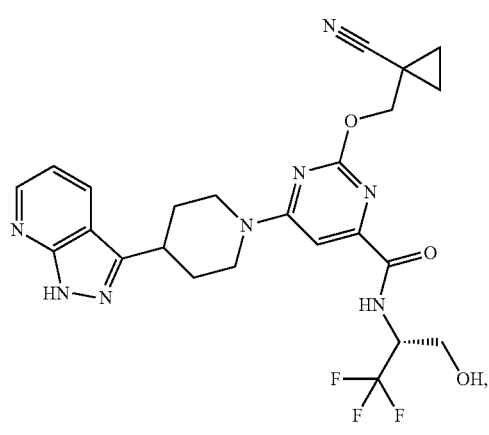
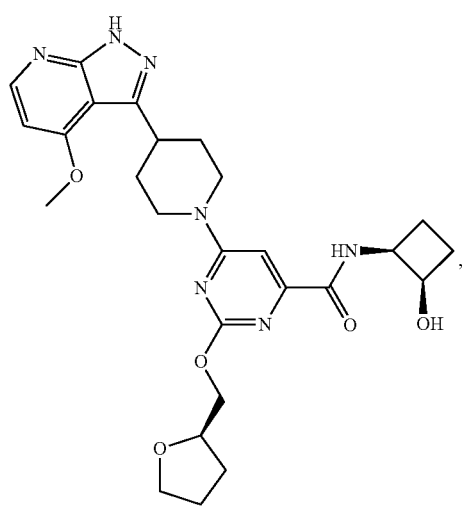
670
-continued
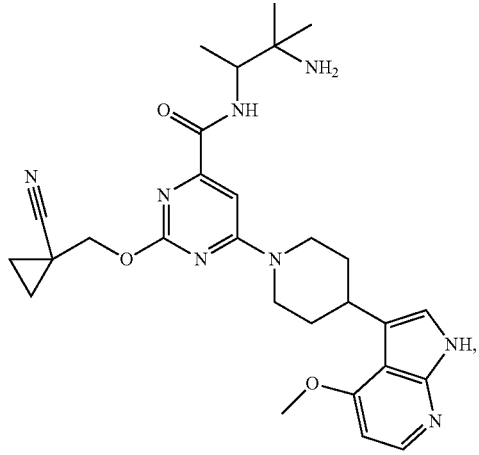
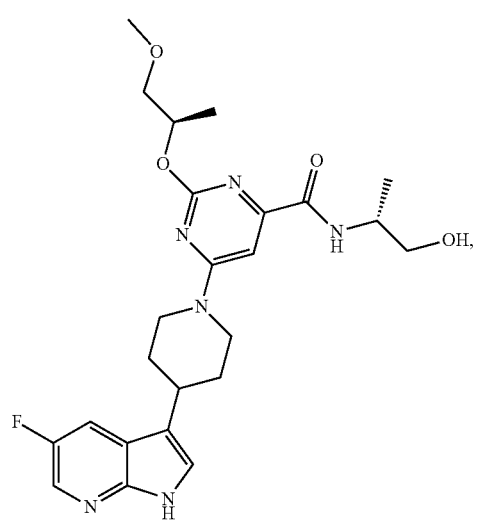
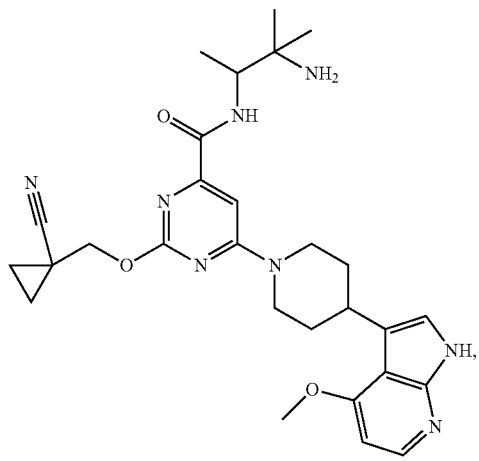

671
-continued
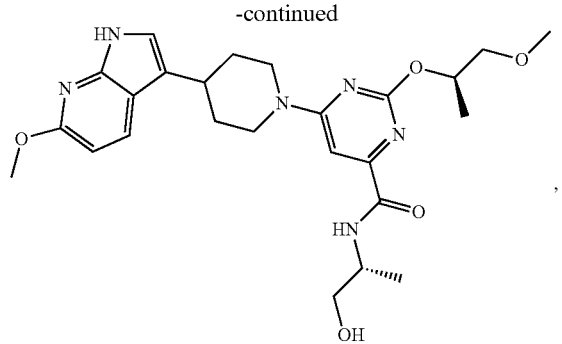
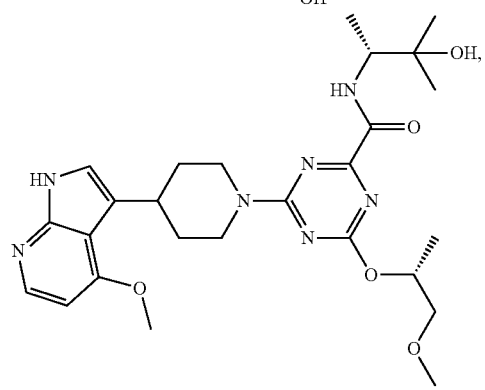
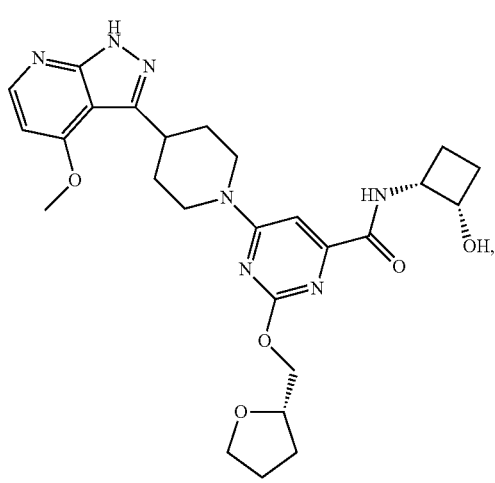
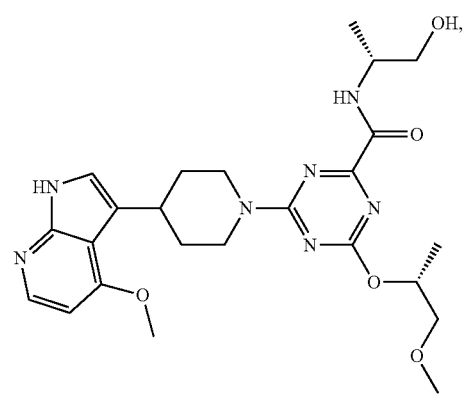
672
-continued
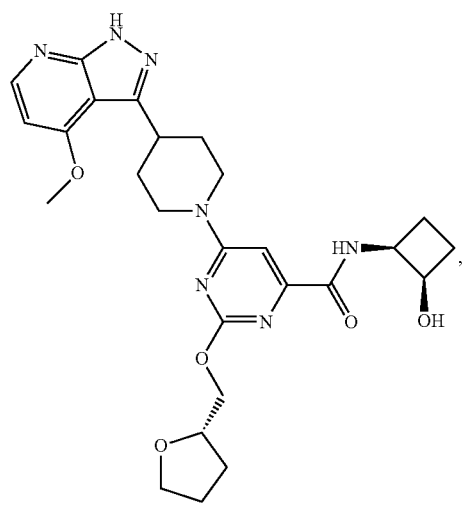
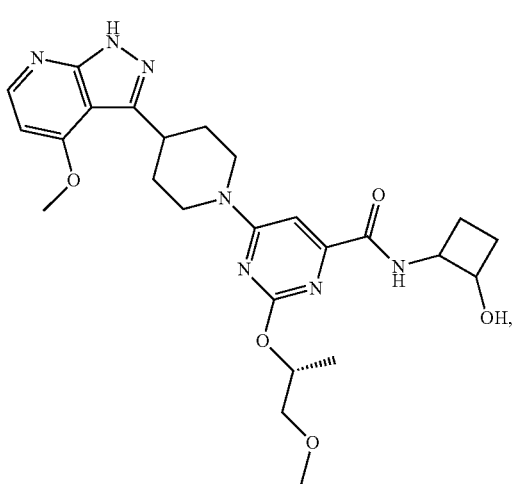
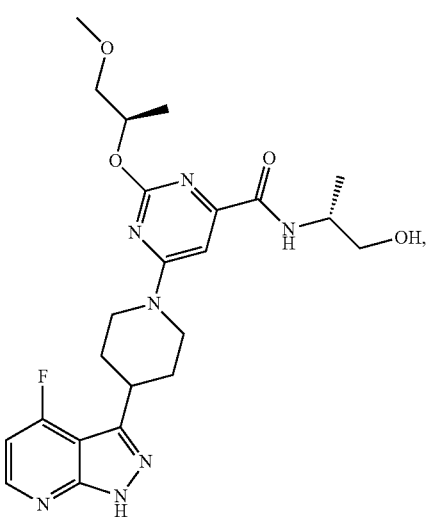

673
-continued
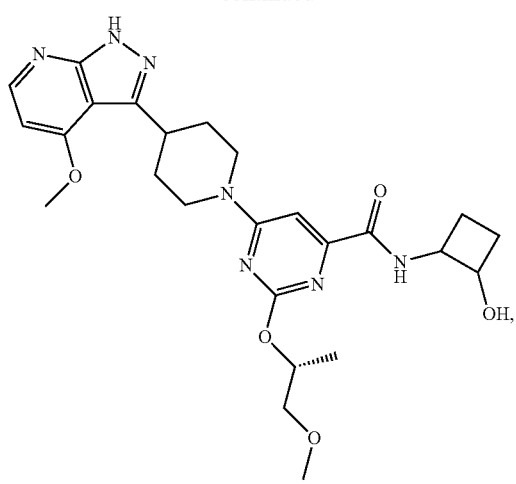
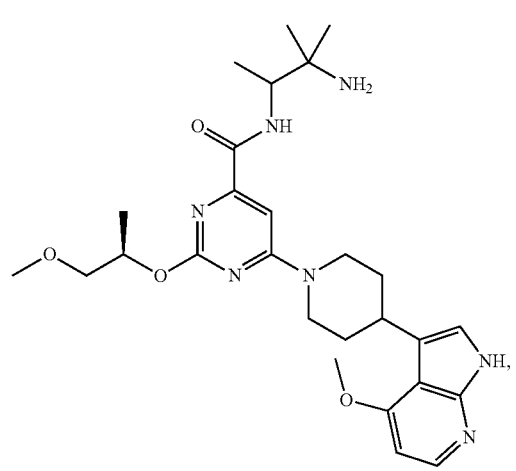
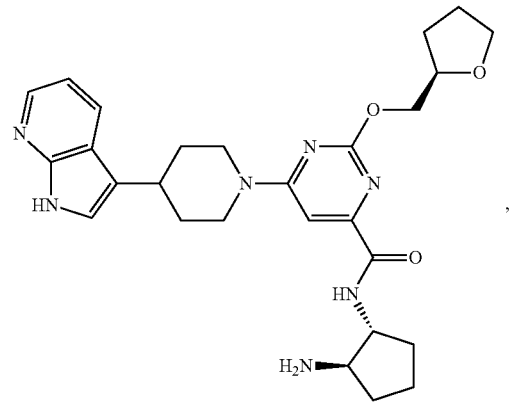
674
-continued
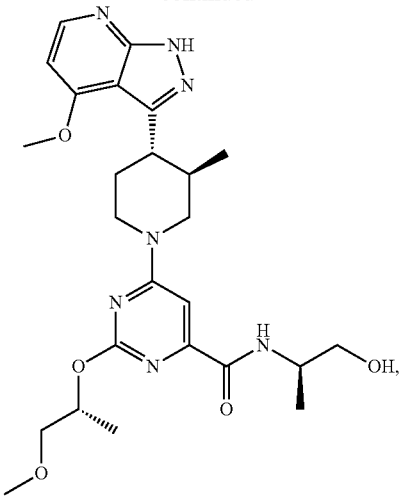
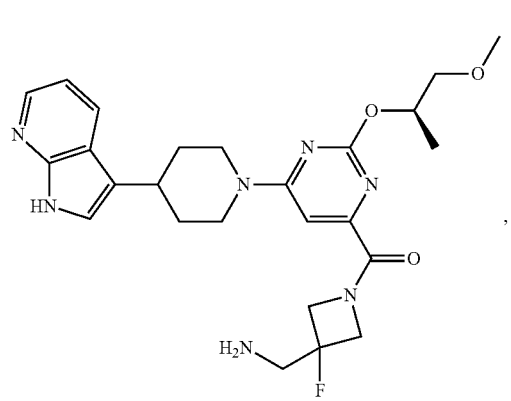
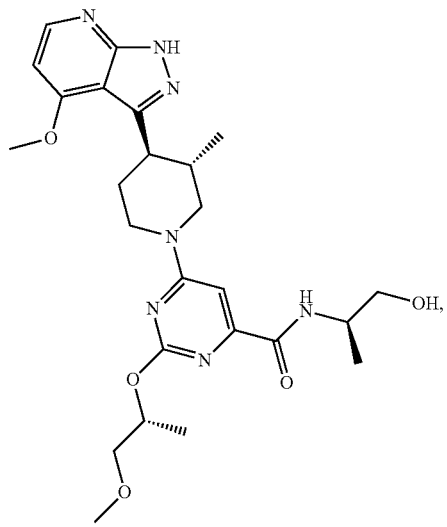

675
-continued
676
-continued
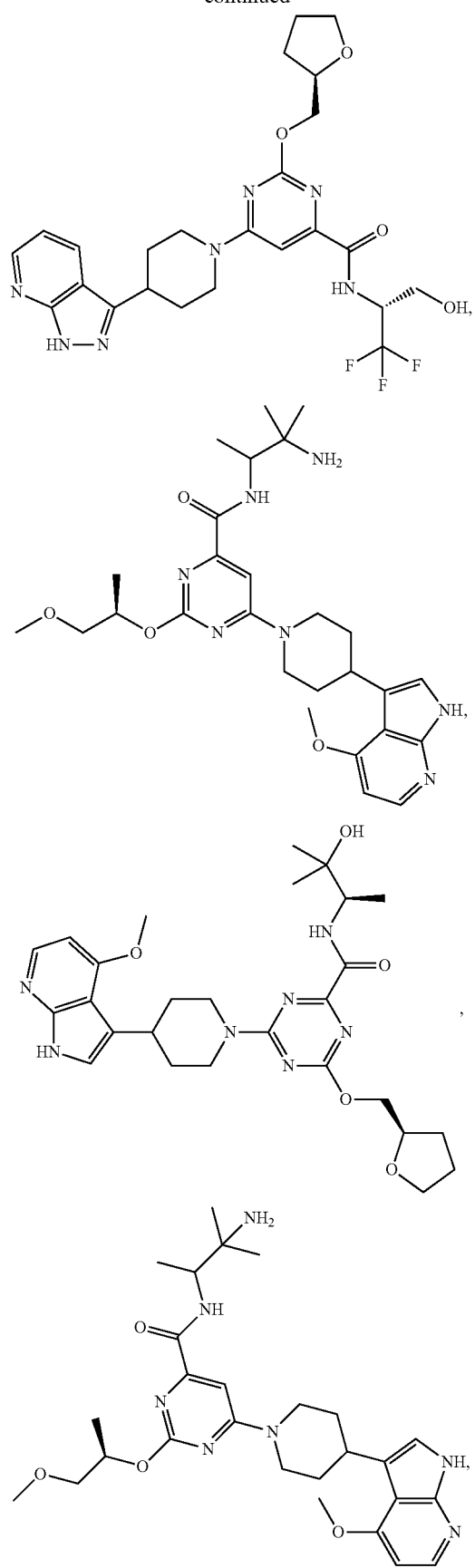
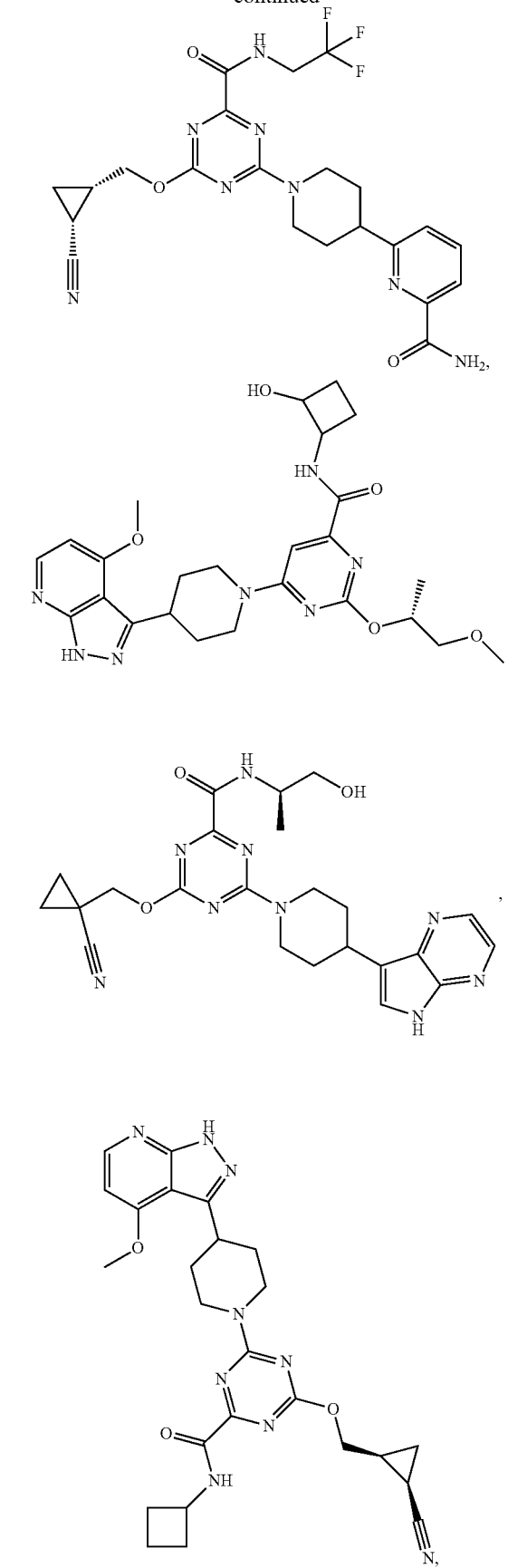

677
-continued
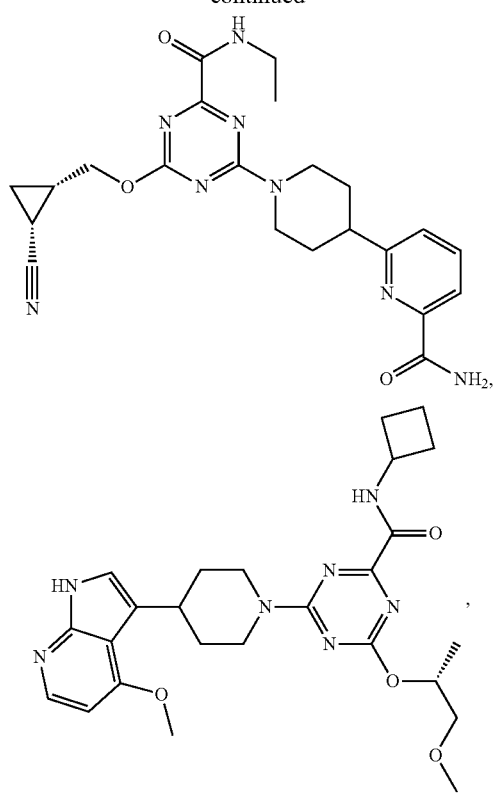
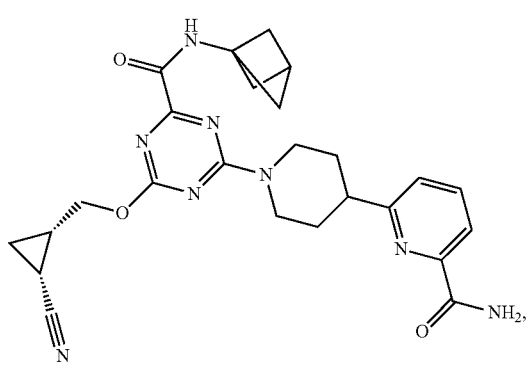
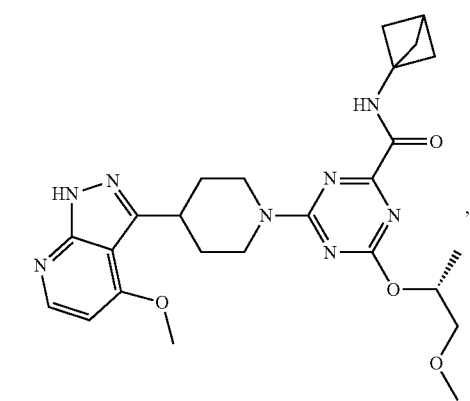
678
-continued
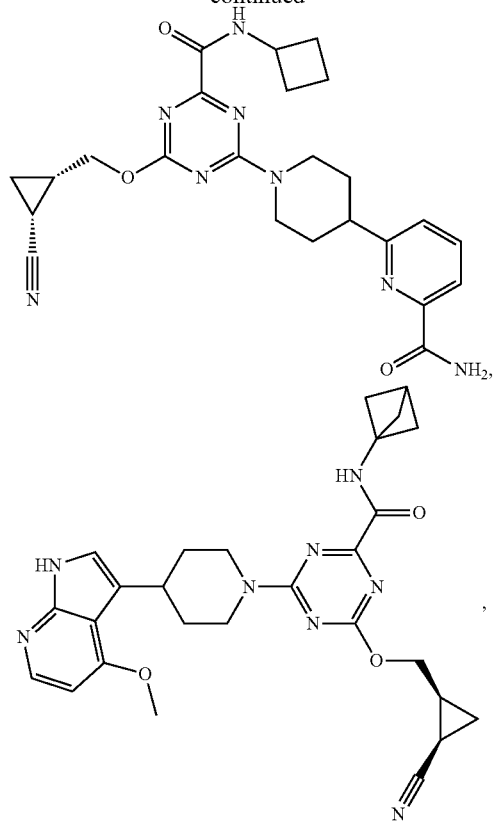
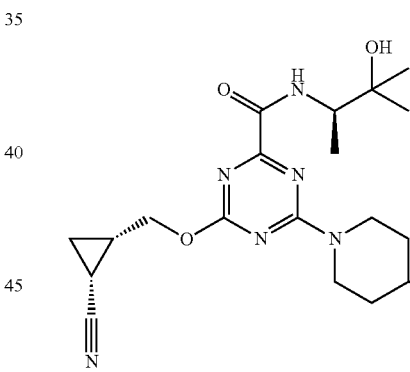
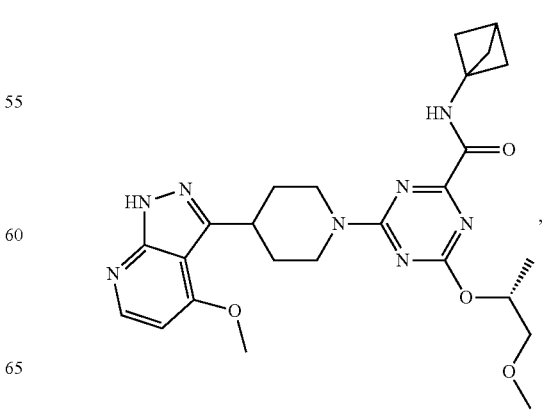

679
-continued
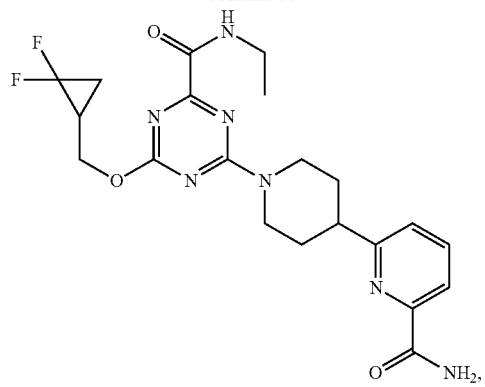
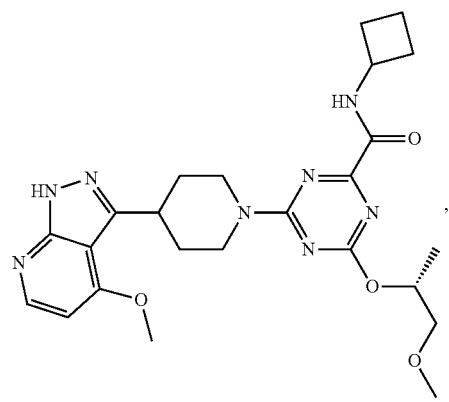
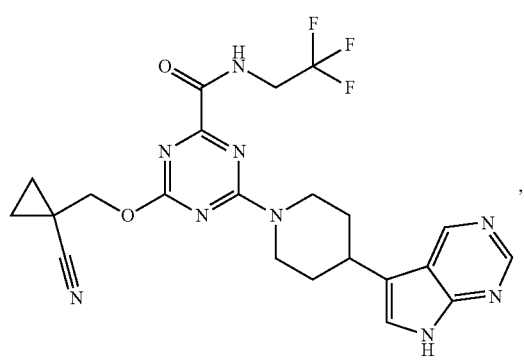
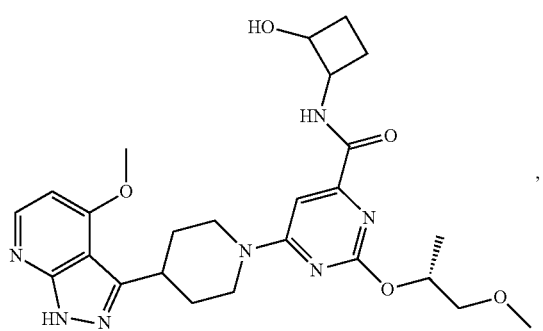
680
-continued
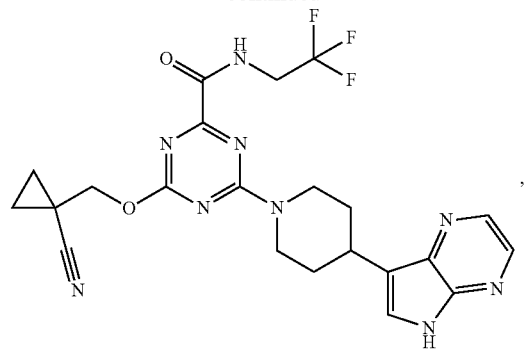
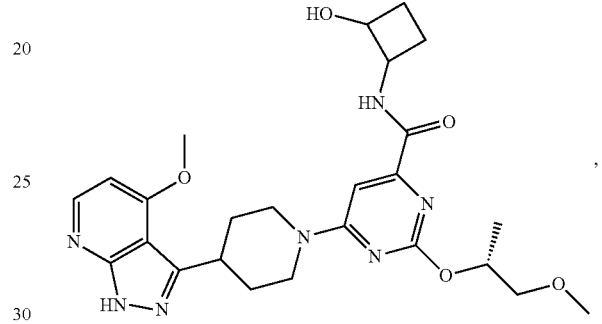
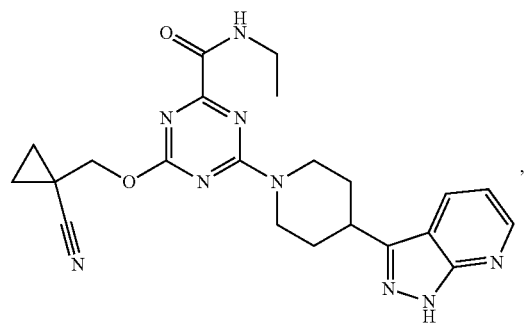
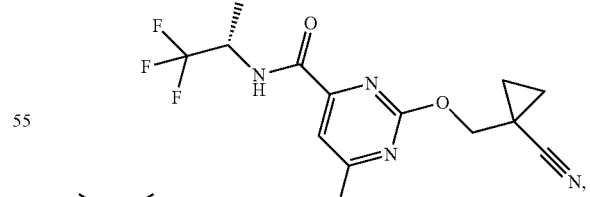
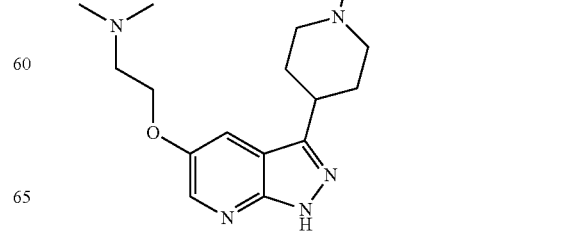

681 -continued

682 -continued

683
-continued
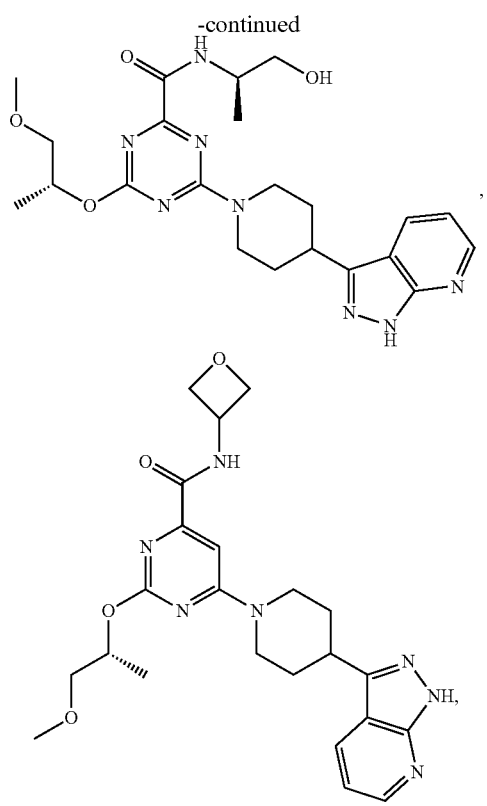
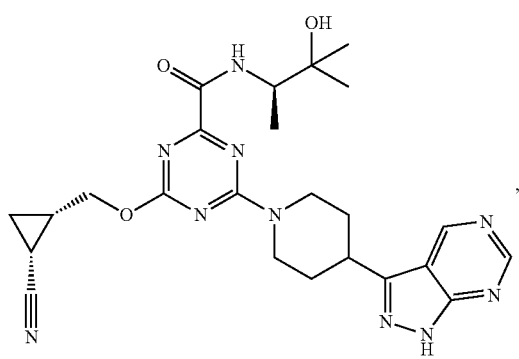
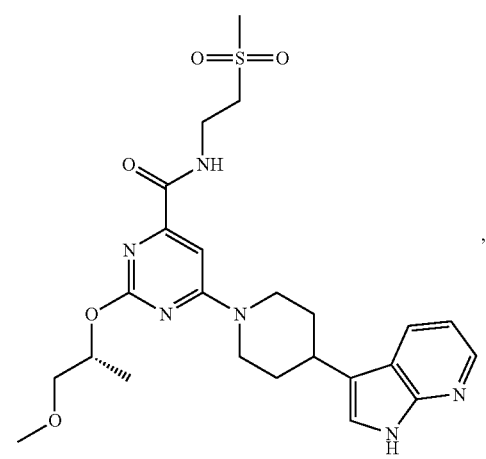
684
-continued
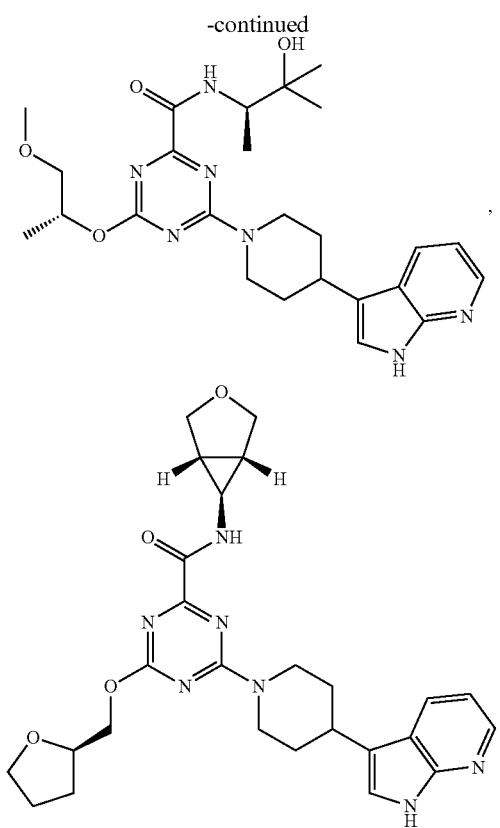
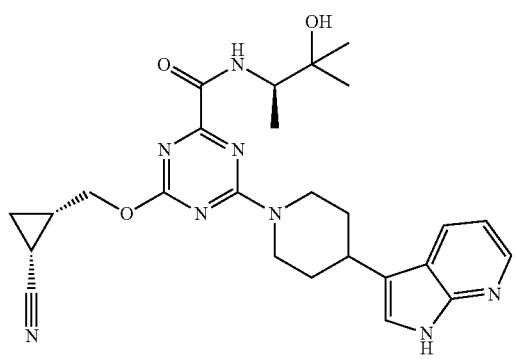
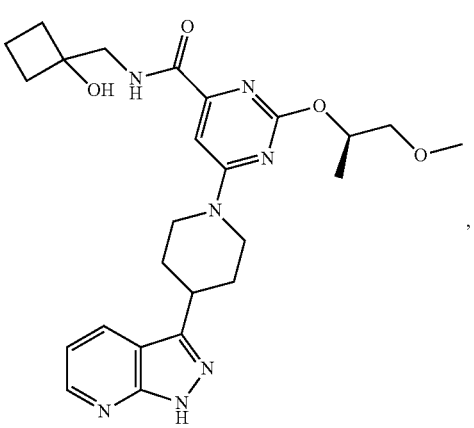

685
-continued
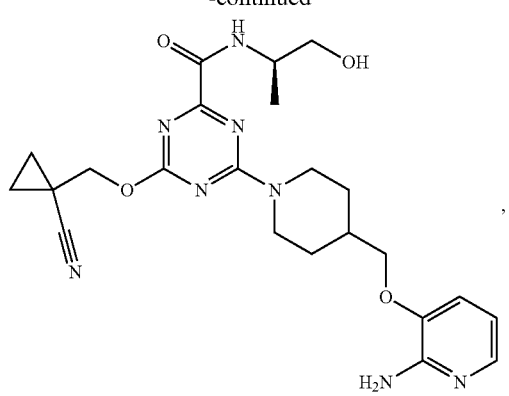
,
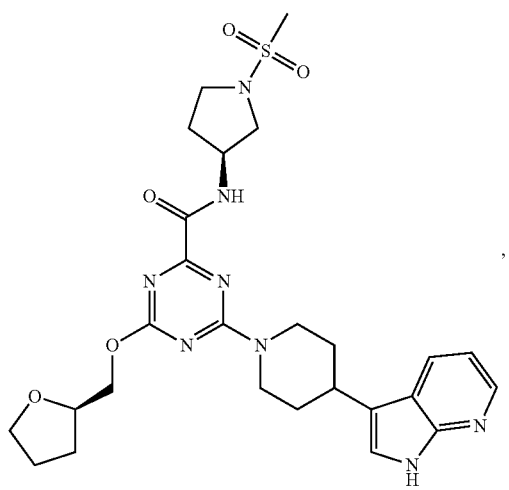
,
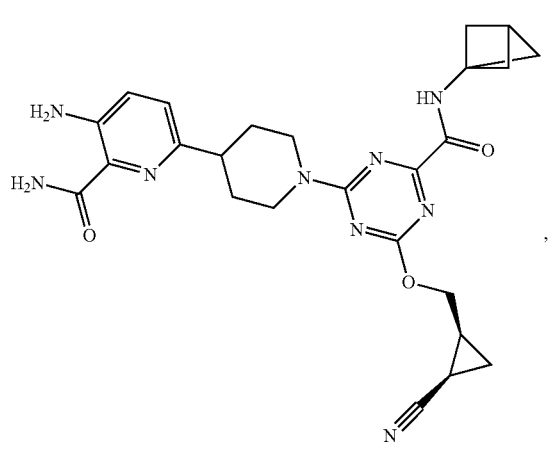
,
686
-continued
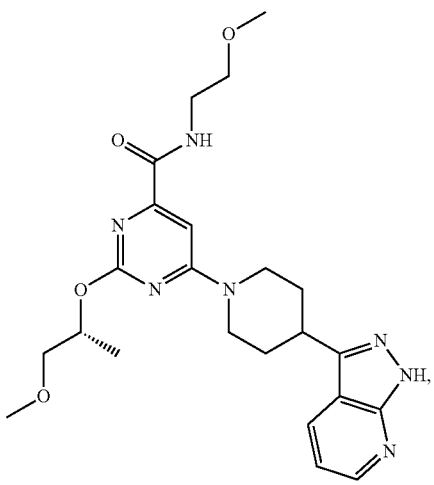
,
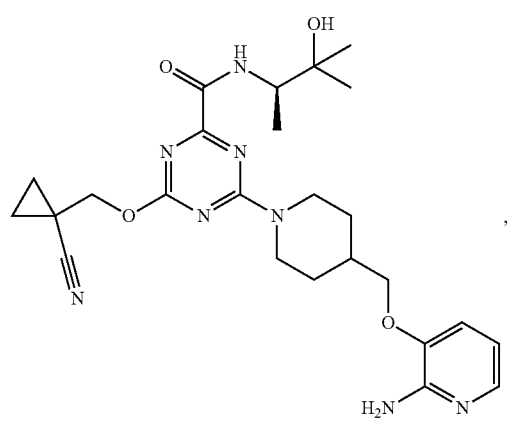
,
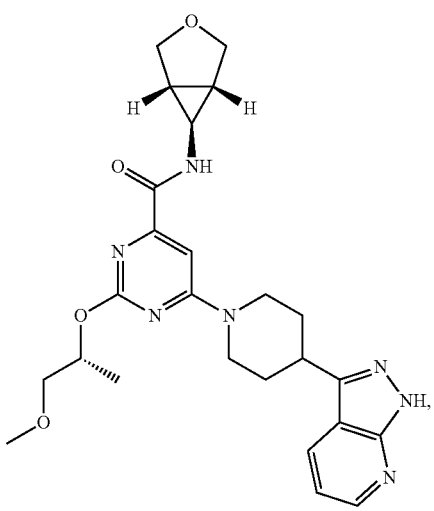

687
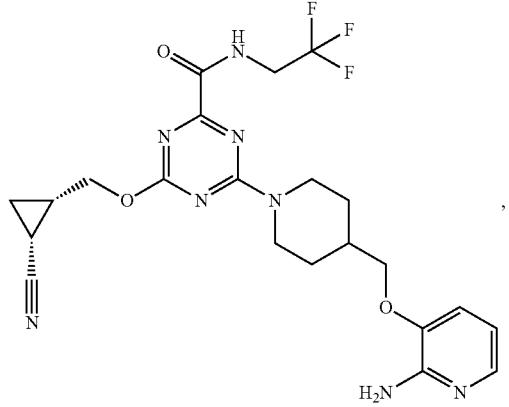
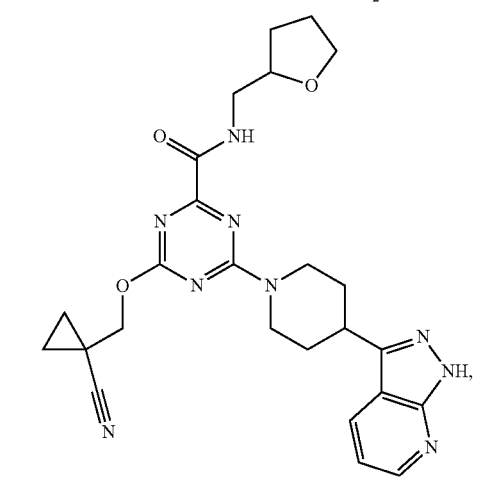
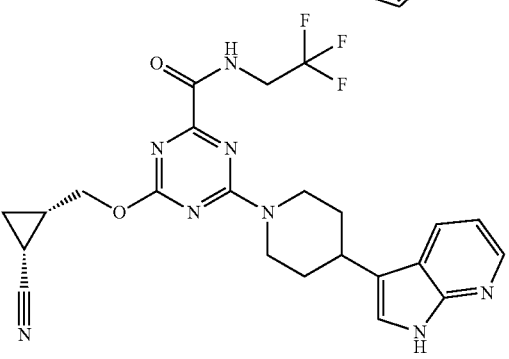
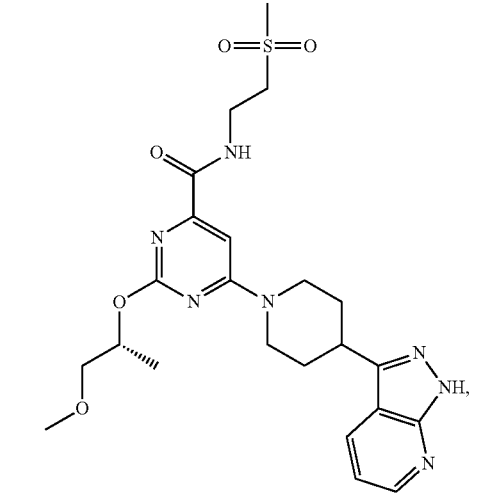
688
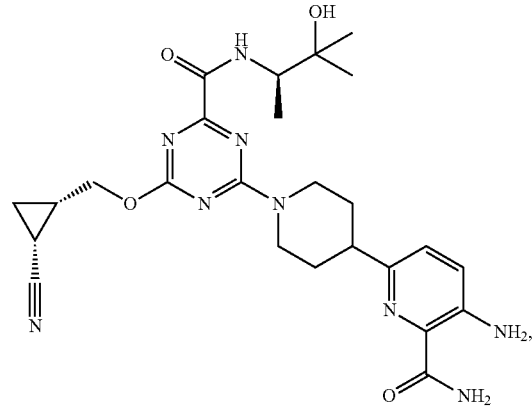
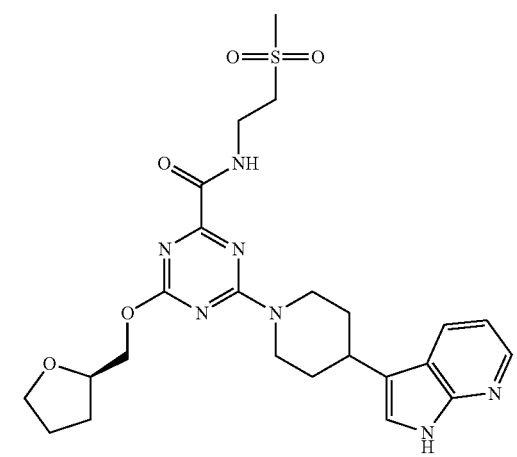
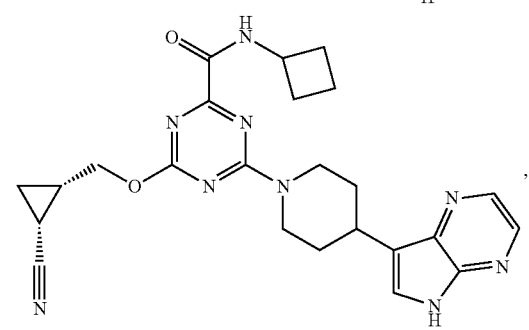
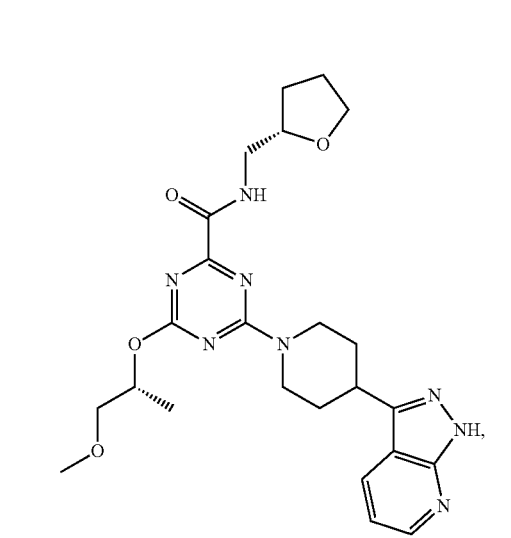

689
-continued
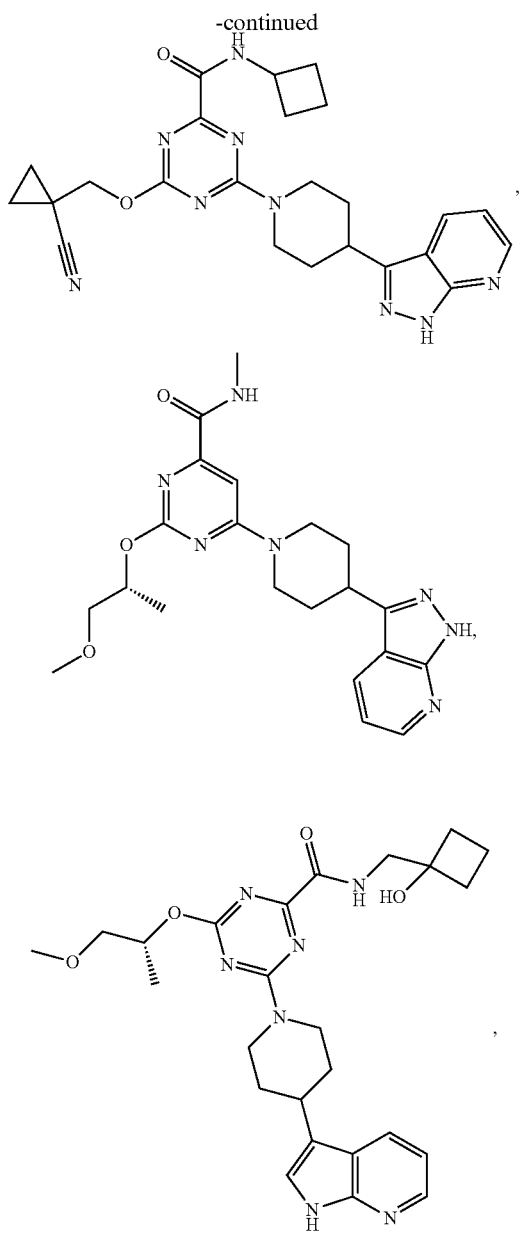
690
-continued
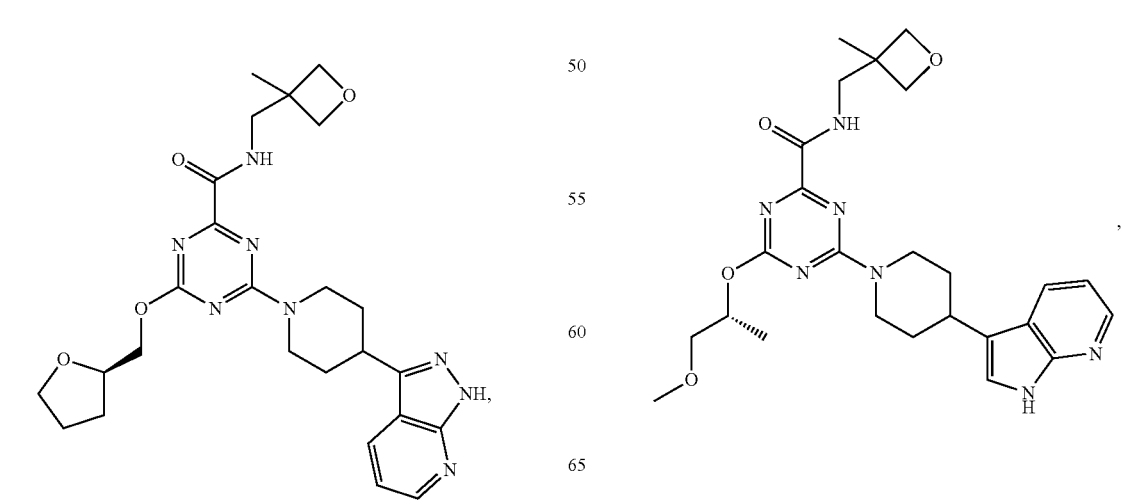

691
-continued
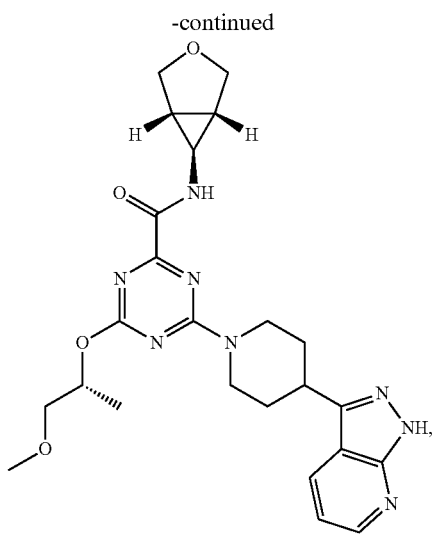
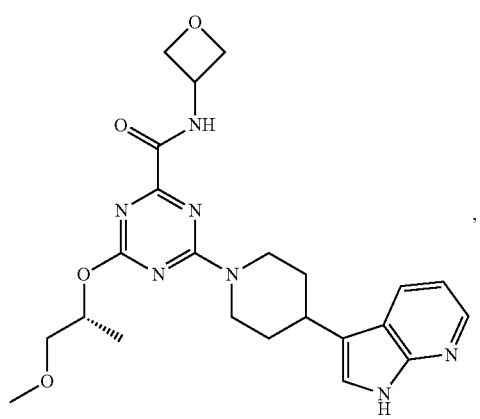
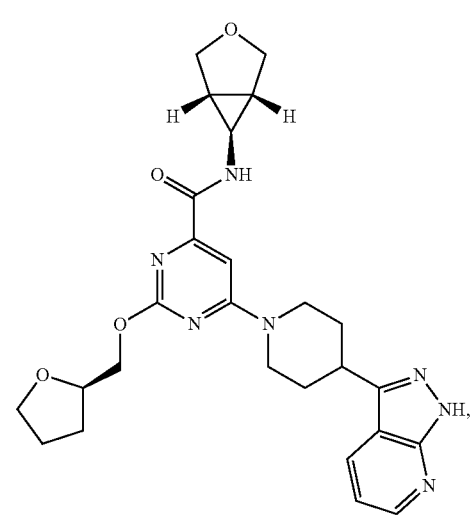
692
-continued
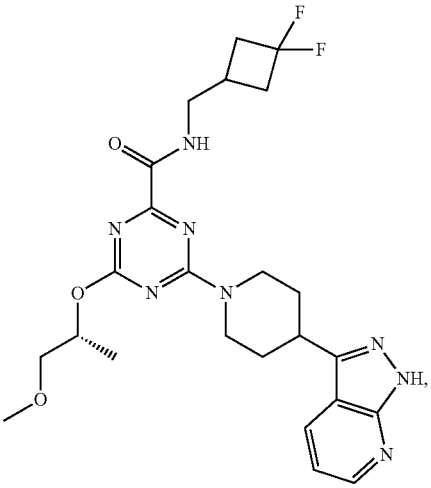
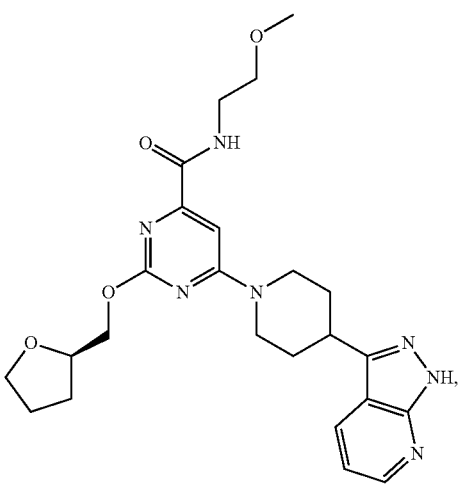
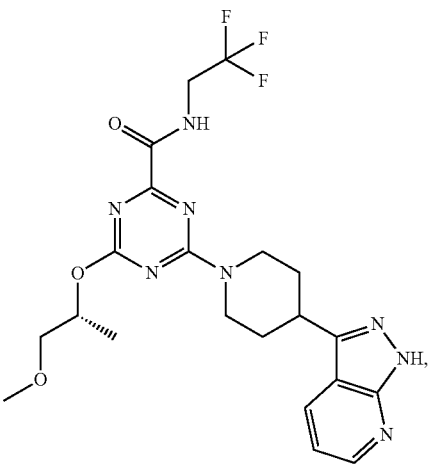

693
-continued
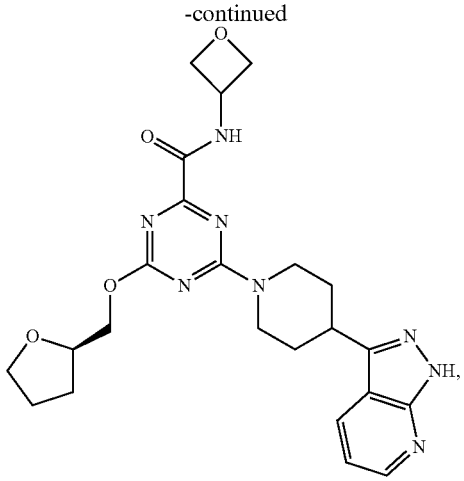
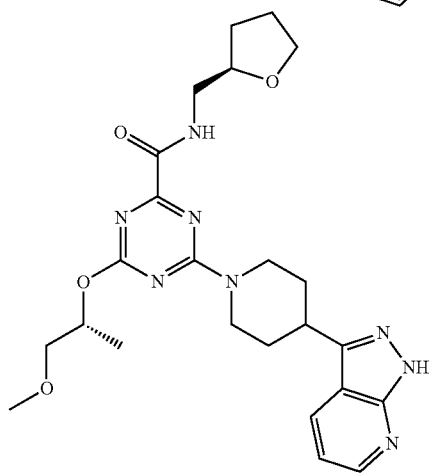
and
694
-continued
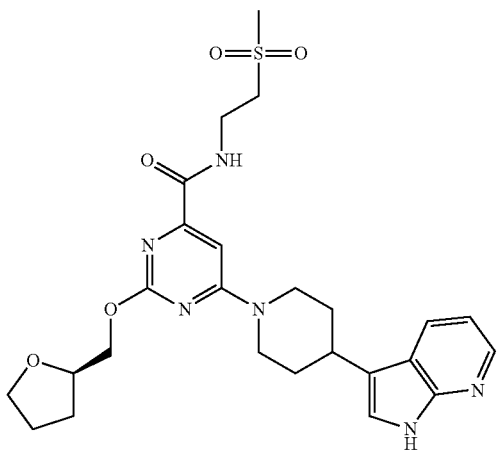
or a pharmaceutically acceptable salt thereof.
* * * * *